(12) United States Patent
Lewis et al.

(10) Patent No.: US 12,084,472 B2
(45) Date of Patent: *Sep. 10, 2024

(54) SUBSTITUTED 4-PHENYL PYRIDINE COMPOUNDS AS NON-SYSTEMIC TGR5 AGONISTS

(71) Applicant: Ardelyx, Inc., Fremont, CA (US)

(72) Inventors: Jason G. Lewis, Fremont, CA (US); Michael Robert Leadbetter, Fremont, CA (US); Jeremy Caldwell, Fremont, CA (US); Dean Dragoli, Fremont, CA (US); Noah Bell, Fremont, CA (US); Jeffrey W. Jacobs, Fremont, CA (US); Patricia Finn, Fremont, CA (US); Rakesh Jain, Fremont, CA (US); Tao Chen, Fremont, CA (US); Matthew Siegel, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 578 days.

This patent is subject to a terminal disclaimer.

(21) Appl. No.: 17/185,653

(22) Filed: Feb. 25, 2021

(65) Prior Publication Data
US 2022/0306672 A1 Sep. 29, 2022

Related U.S. Application Data

(63) Continuation-in-part of application No. 16/456,661, filed on Jun. 28, 2019, now Pat. No. 10,968,246, (Continued)

(51) Int. Cl.
*A61K 31/444* (2006.01)
*A61K 31/4418* (2006.01)
(Continued)

(52) U.S. Cl.
CPC ......... *C07H 15/26* (2013.01); *A61K 31/4418* (2013.01); *A61K 31/4425* (2013.01); *A61K 31/4427* (2013.01); *A61K 31/443* (2013.01); *A61K 31/4433* (2013.01); *A61K 31/4436* (2013.01); *A61K 31/4439* (2013.01); *A61K 31/444* (2013.01); *A61K 31/4545* (2013.01); *A61K 31/496* (2013.01); *A61K 31/506* (2013.01); *A61K 31/5377* (2013.01); *A61K 31/551* (2013.01); *A61K 31/553* (2013.01); *A61K 31/706* (2013.01); *A61K 45/06* (2013.01); *C07B 59/002* (2013.01); *C07C 409/12* (2013.01); *C07D 213/30* (2013.01); *C07D 213/38* (2013.01); *C07D 213/80* (2013.01); *C07D 213/81* (2013.01); *C07D 401/12* (2013.01); *C07D 405/04* (2013.01); *C07D 405/12* (2013.01); *C07D 409/12* (2013.01); *C07D 413/12* (2013.01); *C07D 471/04* (2013.01); *C07D 487/08* (2013.01);
(Continued)

(58) Field of Classification Search
CPC .............. A61K 31/4439; A61K 31/444; A61K 31/4545; A61K 31/5377
See application file for complete search history.

(56) References Cited

U.S. PATENT DOCUMENTS 4,916,145 A 4/1990 Tilley et al.
4,927,838 A 5/1990 Guthrie et al.
(Continued)

FOREIGN PATENT DOCUMENTS

CN 103864754 A 6/2014
DE 10008042 A1 8/2000
(Continued)

OTHER PUBLICATIONS

Gilchrist, T , "Six-membered ring compounds with two or more heteroatoms", Heterocyclic Chemistry, Chapter 7, p. 257 (1997).
Taiwan Office Action , for TW Application No. 105141875, with English Translation, 23 pages, dated Dec. 14, 2020.
Zhou, C , et al., "Identification of new non-steroidal TGR5 agonists using virtual screening with combined pharmacophore models", Med Chem Res 24(6), 2561-2572 (2015).
Zhu, J , et al., "Design, synthesis and biological evaluation of a novel class of potent TGR5 agonists based on a 4-phenyl pyridine scaffold", European Journal of Medicinal Chemistry 6, 55-68 (2013).

*Primary Examiner* — Sikarl A Witherspoon
(74) *Attorney, Agent, or Firm* — Wolf, Greenfield & Sacks, P.C.

(57) ABSTRACT

The invention relates to non-systemic TGR5 agonist useful in the treatment of chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS), and other TGR5 associated diseases and disorders, having the Formula:

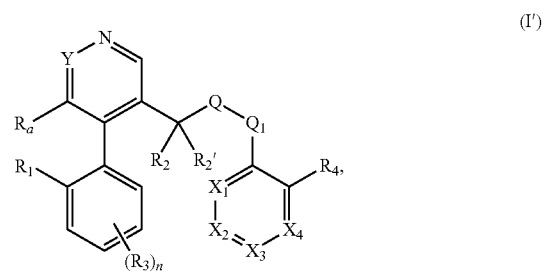

where $R_1$, $R_2$, $R_{2'}$, $R_3$, $R_4$, $X_1$, $X_2$, $X_3$, $X_4$, Q, and n are described herein.

54 Claims, 15 Drawing Sheets

Related U.S. Application Data which is a continuation of application No. 15/382,872, filed on Dec. 19, 2016, now Pat. No. 10,392,413.

(60) Provisional application No. 62/419,939, filed on Nov. 9, 2016, provisional application No. 62/269,804, filed on Dec. 18, 2015.

(51) Int. Cl.

| | | |
|---|---|---|
| *A61K 31/4425* | (2006.01) | |
| *A61K 31/4427* | (2006.01) | |
| *A61K 31/443* | (2006.01) | |
| *A61K 31/4433* | (2006.01) | |
| *A61K 31/4436* | (2006.01) | |
| *A61K 31/4439* | (2006.01) | |
| *A61K 31/4545* | (2006.01) | |
| *A61K 31/496* | (2006.01) | |
| *A61K 31/506* | (2006.01) | |
| *A61K 31/5377* | (2006.01) | |
| *A61K 31/551* | (2006.01) | |
| *A61K 31/553* | (2006.01) | |
| *A61K 31/706* | (2006.01) | |
| *A61K 45/06* | (2006.01) | |
| *C07B 59/00* | (2006.01) | |
| *C07C 409/12* | (2006.01) | |
| *C07D 213/30* | (2006.01) | |
| *C07D 213/38* | (2006.01) | |
| *C07D 213/80* | (2006.01) | |
| *C07D 213/81* | (2006.01) | |
| *C07D 401/12* | (2006.01) | |
| *C07D 405/04* | (2006.01) | |
| *C07D 405/12* | (2006.01) | |
| *C07D 409/12* | (2006.01) | |
| *C07D 413/12* | (2006.01) | |
| *C07D 471/04* | (2006.01) | |
| *C07D 487/08* | (2006.01) | |
| *C07H 15/04* | (2006.01) | |
| *C07H 15/18* | (2006.01) | |
| *C07H 15/234* | (2006.01) | |
| *C07H 15/26* | (2006.01) | |

(52) U.S. Cl.
CPC ............. *C07H 15/04* (2013.01); *C07H 15/18* (2013.01); *C07H 15/234* (2013.01); *C07B 2200/05* (2013.01)

(56) References Cited

U.S. PATENT DOCUMENTS

| | | | |
|---|---|---|---|
| 5,283,057 A | 2/1994 | Shinoda | |
| 5,344,843 A | 9/1994 | Guthrie et al. | |
| 5,700,810 A | 12/1997 | Natsugari et al. | |
| 6,030,972 A | 2/2000 | Boehm et al. | |
| 6,194,581 B1 | 2/2001 | Cosford et al. | |
| 6,211,372 B1 | 4/2001 | Crooks et al. | |
| 6,297,375 B1 | 10/2001 | Boes et al. | |
| 6,369,229 B1 | 4/2002 | Head et al. | |
| 6,479,483 B2 | 11/2002 | Boes et al. | |
| 6,605,625 B2 | 8/2003 | Peukert et al. | |
| 6,794,377 B2 | 9/2004 | Peukert et al. | |
| 6,916,809 B2 | 7/2005 | Chen et al. | |
| 6,960,599 B2 | 11/2005 | Dorsch et al. | |
| 6,998,409 B2 | 2/2006 | Sundermann et al. | |
| 7,074,742 B2 | 7/2006 | Neubert et al. | |
| 7,098,241 B2 | 8/2006 | Grossmann et al. | |
| 7,211,595 B2 | 5/2007 | Claiborne et al. | |
| 7,314,931 B2 | 1/2008 | Cladingboel | |
| 7,432,280 B2 | 10/2008 | Beadle et al. | |
| 7,524,969 B2 | 4/2009 | Arrhenius et al. | |
| 7,566,718 B2 | 7/2009 | Wong et al. | |
| 7,619,096 B2 | 11/2009 | Beadle et al. | |
| 7,754,681 B2 | 7/2010 | Feng | |
| 7,776,862 B2 | 8/2010 | McGuinness et al. | |
| 7,781,426 B2 | 8/2010 | Ali et al. | |
| 7,781,437 B2 | 8/2010 | Kim et al. | |
| 7,799,789 B2 | 9/2010 | Anilkumar et al. | |
| 7,803,821 B2 | 9/2010 | Desbordes et al. | |
| 7,825,120 B2 | 11/2010 | Morgan et al. | |
| 7,863,454 B2 | 1/2011 | Hutchison et al. | |
| 8,003,642 B2 | 8/2011 | Kusuda et al. | |
| 8,044,209 B2 | 10/2011 | Charest et al. | |
| 8,110,595 B2 | 2/2012 | Morgan et al. | |
| 8,349,872 B2 | 1/2013 | Coleman et al. | |
| 8,461,183 B2 | 6/2013 | Masson et al. | |
| 8,598,167 B1 | 12/2013 | Kuntz et al. | |
| 8,598,209 B2 | 12/2013 | Burgey et al. | |
| 8,710,242 B2 | 4/2014 | Heil et al. | |
| 8,729,271 B2 | 5/2014 | Moriya et al. | |
| 8,742,123 B2 | 6/2014 | Stranix et al. | |
| 8,759,371 B2 | 6/2014 | Lucas | |
| 8,809,330 B2 | 8/2014 | Babaoglu et al. | |
| 8,906,942 B2 | 12/2014 | Chen et al. | |
| 8,912,331 B2 | 12/2014 | Muthuppalaniappan et al. | |
| 8,937,182 B2 | 1/2015 | Zeller et al. | |
| 9,090,562 B2 | 7/2015 | Kuntz et al. | |
| 9,096,545 B2 | 8/2015 | Gharat et al. | |
| 10,392,413 B2 * | 8/2019 | Lewis ................... | A61K 31/506 |
| 10,968,246 B2 * | 4/2021 | Lewis ................... | C07B 59/002 |
| 2002/0091265 A1 | 7/2002 | Bos et al. | |
| 2005/0164999 A1 | 7/2005 | Foor et al. | |
| 2006/0205790 A1 | 9/2006 | Coe et al. | |
| 2006/0229265 A1 | 10/2006 | Milburn et al. | |
| 2007/0078135 A1 | 4/2007 | Yuan et al. | |
| 2007/0232652 A1 | 10/2007 | Grundschober et al. | |
| 2008/0021024 A1 | 1/2008 | Sucholeiki et al. | |
| 2008/0207640 A1 | 8/2008 | Polvino | |
| 2009/0069320 A1 | 3/2009 | Reich et al. | |
| 2009/0149496 A1 | 6/2009 | Brendel et al. | |
| 2009/0192168 A1 | 7/2009 | Muci et al. | |
| 2010/0029609 A1 | 2/2010 | Berst et al. | |
| 2010/0099676 A1 | 4/2010 | Endoh et al. | |
| 2010/0256146 A1 | 10/2010 | Herold et al. | |
| 2010/0261743 A1 | 10/2010 | Londregan et al. | |
| 2011/0028509 A1 | 2/2011 | Crosignani et al. | |
| 2012/0035168 A1 | 2/2012 | Brandl et al. | |
| 2012/0077745 A1 | 3/2012 | Polvino | |
| 2013/0211095 A1 | 8/2013 | Parker et al. | |
| 2014/0100216 A1 | 4/2014 | Savchuk et al. | |
| 2014/0142083 A1 | 5/2014 | Kuntz et al. | |
| 2014/0142137 A1 | 5/2014 | Cohen et al. | |
| 2014/0155381 A1 | 6/2014 | Baloglu et al. | |
| 2014/0336377 A1 | 11/2014 | Yamagishi et al. | |
| 2014/0371240 A1 | 12/2014 | Maue et al. | |
| 2015/0011574 A1 | 1/2015 | Nishi et al. | |
| 2015/0099883 A1 | 4/2015 | Furukawa et al. | |
| 2015/0105429 A1 | 4/2015 | Fauber et al. | |
| 2015/0216175 A1 | 8/2015 | Heil et al. | |
| 2015/0232478 A1 | 8/2015 | Ishida et al. | |
| 2015/0284375 A1 | 10/2015 | Kobayashi et al. | |
| 2019/0233406 A1 | 8/2019 | Greshock et al. | |

FOREIGN PATENT DOCUMENTS

| | | |
|---|---|---|
| EP | 0132771 A2 | 2/1985 |
| JP | H08291168 A | 11/1996 |
| JP | 2002348310 A | 12/2002 |
| JP | 2006056881 A | 3/2006 |
| JP | 2007078889 A | 3/2007 |
| JP | 2007137810 A | 6/2007 |
| JP | 2007317714 A | 12/2007 |
| JP | 2012036125 A | 2/2012 |
| WO | 2003090869 A1 | 11/2003 |
| WO | 2004074252 A1 | 9/2004 |
| WO | 2005113499 A1 | 12/2005 |
| WO | 2008008852 A2 | 1/2008 |
| WO | 2009024342 A2 | 2/2009 |
| WO | 2011051535 A1 | 5/2011 |
| WO | 2011054436 A2 | 5/2011 |

(56) References Cited

FOREIGN PATENT DOCUMENTS

| | | |
|---|---|---|
| WO | WO 2011/089099 A1 | 7/2011 |
| WO | 2011112186 A1 | 9/2011 |
| WO | 2012079079 A1 | 6/2012 |
| WO | 2013096771 A1 | 6/2013 |
| WO | 2013167633 A1 | 11/2013 |
| WO | WO-2014100021 A1 * | 6/2014 ............ A61K 31/40 |
| WO | 2014141110 A2 | 9/2014 |
| WO | 2014152536 A2 | 9/2014 |
| WO | 2015013635 A2 | 1/2015 |
| WO | 2015051043 A1 | 4/2015 |
| WO | 2015055706 A2 | 4/2015 |
| WO | 2015104677 A1 | 7/2015 |
| WO | 2015115507 A1 | 8/2015 |
| WO | 2017103941 A1 | 6/2017 |
| WO | 2017105512 A1 | 6/2017 |
| WO | 2017106871 A1 | 6/2017 |

* cited by examiner

SUBSTITUTED 4-PHENYL PYRIDINE COMPOUNDS AS NON-SYSTEMIC TGR5 AGONISTS

RELATED APPLICATIONS

This application is a continuation-in-part of U.S. patent Application Ser. No. 16/456,661, filed Jun. 28, 2019, which is a continuation of U.S. patent Application Ser. No. 15/382,872, filed Dec. 19, 2016, which claims the benefit of and priority to U.S. Provisional Patent Application Ser. Nos. 62/269,804, filed Dec. 18, 2015; and 62/419,939, filed Nov. 9, 2016. Each of these is incorporated herein by reference in its entirety.

FIELD OF INVENTION

The present invention is directed to modulators of the TGR5 receptor useful in the treatment of TGR5 mediated diseases or disorders. Specifically, the invention is concerned with compounds and compositions thereof, which activate the TGR5 receptor, methods of treating diseases or disorders associated with TGR5, including chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis (UC), Crohn's disease (CD), disorders associated with parenteral nutrition especially during short bowel syndrome, and irritable bowel syndrome (IBS), and methods of synthesis of these compounds.

BACKGROUND OF THE INVENTION

Diabetes mellitus is an ever-increasing threat to human health. For example, in the United States current estimates maintain that about 16 million people suffer from diabetes mellitus. Type II diabetes accounts for approximately 90-95% of diabetes cases, killing about 193,000 U.S. residents each year. Type II diabetes is the seventh leading cause of all deaths. In Western societies, Type II diabetes currently affects 6% of the adult population with world-wide frequency expected to grow by 6% per annum. Although there are certain inheritable traits that may predispose particular individuals to developing Type II diabetes, the driving force behind the current increase in incidence of the disease is the increased sedentary life-style, diet, and obesity now prevalent in developed countries. About 80% of diabetics with Type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes can develop at any age, but most commonly becomes apparent during adulthood. However, the incidence of Type II diabetes in children is rising. In diabetics, glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Traditional therapies include: insulin secretagogues, such as sulphonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhance insulin action; and α-glucosidase inhibitors, which interfere with gut glucose production. There are, however, deficiencies associated with currently available treatments. For example sulphonylureas and insulin injections can be associated with hypoglycemic episodes and weight gain. Furthermore, patients often lose responsiveness to sulphonylureas over time. Metformin and α-glucosidase inhibitors often lead to gastrointestinal problems and PPARγ agonists tend to cause increased weight gain and edema.

More recently, new agents have been introduced to the market which prolong or mimic the effects of the naturally-secreted incretin hormones (Neumiller, *J Am Pharm Assoc.* 49(suppl 1):S16-S29, 2009). Incretins are a group of gastrointestinal hormones that are released from specialized intestinal cells when nutrients, especially glucose, are sensed in the gut. The two most important incretin hormones are glucose-dependent insulinotropic polypeptide (GIP) and GLP-1 (released from L-cells), which stimulate insulin secretion from the pancreas in a glucose-dependent manner and suppress glucagon secretion. However, GLP-1 itself is impractical as a clinical treatment for diabetes as it has a very short half-life in vivo. To address this, incretin-based agents currently available or in regulatory review for the treatment of T2DM are designed to achieve a prolonged incretin-action. For example, the dipeptidyl peptidase-4 inhibitors, such as sitagliptin, inhibit the normally rapid proteolytic breakdown of endogenous incretin hormones. There are also human-derived and synthetic incretin mimetics that are designed to be more stable and/or have a prolonged serum half-life compared to naturally secreted GLP-1, and include agents such as liraglutide and exenatide. In either approach, the goal is to provide a sustained incretin response and thus enhance glucose-dependent insulin secretion. It is the glucose-dependence of the insulin response that provides incretin therapies with low risk of hypoglycemia. In addition, GLP-1 can also delay gastric emptying and otherwise beneficially affect satiety and hence, weight loss (Neumiller 2009).

Inflammatory bowel disease (IBD) is a chronic, relapsing, inflammatory disorder of the gastrointestinal tract that causes segments of the gastrointestinal tract to become inflamed and ulcerated. IBD generally takes one of two forms, (CD) and (UC), and is generally thought to be a result of a combination of factors (environmental, genetic, microbiota alterations and immune dysfunction). These factors are likely all needed to some degree for clinical disease to be present. Ultimately, the dysregulation of the host immune system, which occurs in response to either environmental stimuli or intestinal bacteria, leaves the host at risk for chronic uncontrolled inflammation targeting the gut. The health of the intestine is compromised by reduced barrier function, which exacerbates the response to antigen load, creating a vicious circle of chronic inflammation and disease. The diversity of causal factors makes treating the disease very difficult and many IBD patients remain undertreated, resulting in a high proportion of surgical resections (especially in CD).

The worldwide incidence rate of UC varies greatly between 0.5-24.5/100,000 persons, while that of CD varies between 0.1-16/100,000 persons with prevalence rate of IBD reaching up to 396/100,000 persons (cdc.gov). In a 2012 review, the highest reported prevalence values for IBD were in Europe (UC, 505 per 100,000 persons; CD, 322 per 100,000 persons) and North America (UC, 249 per 100,000 persons; CD, 319 per 100,000 persons). Additionally, there was evidence of increasing incidence over time. IBD is one of the most important GI diseases in the US, requiring a lifetime of care for patients. Each year in the United States, IBD accounts for more than 700,000 physician visits, 100,000 hospitalizations, and 119,000 patients considered disabled (cdc.gov). Over the long term, up to 75% of patients with CD and 25% of those with UC will require surgery (Ref: http://www.cdc.gov/ibd/). IBD is more common in European Americans compared with African Americans, and the lowest rates of IBD have been reported in Hispanics and Asians. CD may affect as many as 700,000 Americans. Men and Women are equally likely to be affected, and while the disease can occur at any age, it is more prevalent among adolescents and young adults between the ages of 15 and 35.

Treatment of the IBD includes conservative measures as well as surgical approaches in those who are non-responders to medical treatment. The therapeutic goals are to improve patient quality of life, induce and maintain remission, prevent complications, restore nutritional deficits, and modify the disease course. The major therapeutic categories for this disease are anti-inflammatory drugs, immunosuppressant therapy, biologic agents, antibiotics, and drugs for symptomatic relief. Recent advances in understanding the pathogenesis of IBD have resulted in numerous new targeted therapies entering development. First line treatment is generally mesalamine and derivatives. It is relatively safe and efficacious with 30-50% of patients achieving long term relief. Second line therapy is steroid treatment, with 30% long term efficacy. After steroids, immune modulators are tried (Thiopurines, cyclosporine). Recently, TNF inhibitors have become more widely used in IBD. They demonstrate good mucosal healing and salvage but have a high rate of complications and do not maintain efficacy long term. Last line treatment in IBD is surgical removal of diseased tissue. This is highly invasive and decreases quality of life for these patients.

GLP-2 is of particular importance to GI health. The peripheral actions of GLP-2 are largely restricted to the intestinal mucosa where it acts as a trophic hormone. Most of its effects occur in the small and, to a lesser degree, large bowel. Chronic administration of GLP-2 to healthy rodents enhances intestinal weight through increased crypt cell proliferation and decreased villous apoptosis resulting in expansion of villous height and, less consistently, crypt depth. As stated above, the trophic effects of GLP-2 are more pronounced in the proximal small intestine, and all changes of intestinal morphology rapidly reverse after treatment cessation. GLP-2 treatment also increases the digestive and absorptive capacity of the gut as indicated by enhanced expression and activity of brush border enzymes and absorption of nutrients and enhances barrier function through decreased permeability. The positive effects of GLP-2 treatment on intestinal growth and/or function have been demonstrated in rodent models of intestinal damage involving resection, colitis (IBD), chemotherapy-induced diarrhea, necrotizing pancreatiti, food allergy, psychological stress, and thermal injury and in patients with short bowel syndrome. Additional effects of GLP-2 in intestine include stimulation of intestinal glucose transport; inhibition of gastrointestinal motility in rodent models [results conflicting in humans]; gastric emptying, and acid secretion (GLP-2 infusion in healthy humans reduces stimulated gastric acid secretion but has no effect on basal acid or volume secretion).

Intestinal L-cells, the source of GLP-1 and GLP-2 co-express TGR5 receptors. Activation of TGR5 with small molecule agonists or partial agonists therefore has the potential to be a treatment for chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS) and other disorders. For this reason, there remains a considerable need for non-systemic potent small molecule agonists of TGR5.

SUMMARY OF THE INVENTION

A first aspect of the invention relates to compounds of Formula (I'):

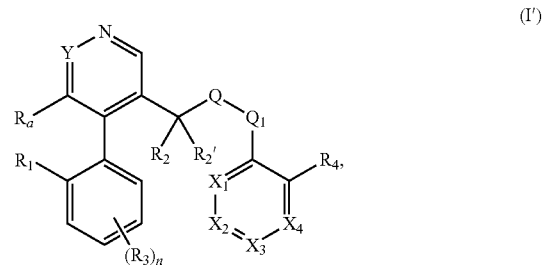

and pharmaceutically acceptable salts, hydrates, solvates, isotopes, prodrugs, stereoisomers, and tautomers thereof, wherein:

Q is C=(O), —CH$_2$—, —NR$_5$—, —SO$_2$—, or —O—; when Q is C=(O) then Q$_1$ is —NR$_5$—, when Q is —NR$_5$— or —O— then Q$_1$ is —CH$_2$—, when Q is —CH$_2$— then Q$_1$ is —O(CH$_2$)$_{0-1}$— or —NR$_5$—, or when Q is —SO$_2$— then Q$_1$ is —NR$_5$—, —CH$_2$—, or O(CH$_2$)$_{0-1}$;

X$_1$ is CR$_6$ or N;

X$_2$ is CR$_7$ or N;

X$_3$ is CR$_8$ or N;

X$_4$ is CR$_9$ or N;

Y is CR$_b$ or N;

R$_a$ and R$_b$ are each independently H, (C$_1$-C$_6$) alkyl, (C$_1$-C$_6$) alkoxy, (C$_1$-C$_6$) haloalkyl, (C$_1$-C$_6$) haloalkoxy, or halogen; or R$_1$ and R$_a$ together with the carbon atoms to which they are attached form a heterocycloalkyl;

R$_1$ is H, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —NH$_2$, —NH$(C_1-C_4)$ alkyl, and —N$((C_1-C_4)$ alkyl$)_2$; or $R_1$ and $R_a$ together with the carbon atoms to which they are attached form a heterocycloalkyl; or $R_1$ and $R_3$, when on adjacent atoms, together with the carbon atoms to which they are attached form a heterocycloalkyl optionally substituted with one or more substituents selected from $(C_1-C_6)$ alkyl, $(C_1-C_6)$ alkoxy, $(C_1-C_6)$ haloalkyl, $(C_1-C_6)$ haloalkoxy, and halogen;

$R_2$ and $R_{2'}$ are each independently H, $(C_1-C_6)$ alkyl, $(C_1-C_6)$ alkoxy, $(C_1-C_6)$ haloalkyl, or $(C_1-C_6)$ haloalkoxy; or $R_2$ and $R_{2'}$ together with the carbon atom to which they are attached form $(C_3-C_8)$ cycloalkyl or heterocycloalkyl;

each $R_3$ is independently, at each occurrence, $(C_1-C_6)$ alkyl, $(C_1-C_6)$ alkoxy, $(C_1-C_6)$ haloalkyl, $(C_1-C_6)$ haloalkoxy, halogen, —S(O)$_p$$(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —NH$_2$, —NH$(C_1-C_4)$ alkyl, and —N$((C_1-C_4)$ alkyl$)_2$; or $R_1$ and $R_3$ together with the carbon atoms to which they are attached form a heterocycloalkyl optionally substituted with one or more substituents selected from $(C_1-C_6)$ alkyl, $(C_1-C_6)$ alkoxy, $(C_1-C_6)$ haloalkyl, $(C_1-C_6)$ haloalkoxy, and halogen;

$R_4$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —NH$_2$, CN, —S(O)$_m$$(C_1-C_6)$ alkyl, —NH$(C_1-C_4)$ alkyl, or —N$((C_1-C_4)$ alkyl$)_2$;

$R_5$ is H, $(C_1-C_6)$ alkyl, —C(O)NR$_{10}$R$_{11}$, —C(O)$(C_1-C_6)$ alkyl, or —C(O)O$(C_1-C_6)$ alkyl;

each $R_6$ and $R_9$ is independently H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —NH$_2$, CN, —S(O)O$(C_1-C_6)$ alkyl, —NH$(C_1-C_4)$ alkyl, or —N$((C_1-C_4)$ alkyl$)_2$;

each $R_7$ and $R_8$ is independently H, $(C_1-C_8)$ alkenyl, $(C_1-C_8)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, $(C_3-C_8)$ cycloalkenyl, heterocycloalkyl, —OH, —NH$_2$, —S(O)$_q$ NH$_2$, —S(O)$_q$OH, CN, or $(C_1-C_{18})$ alkyl, wherein 0 to 7 methylene of the $(C_1-C_{18})$ alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;

$R_{10}$ and $R_{11}$ are each independently H or $(C_1-C_6)$ alkyl optionally substituted with one or more substituent independently selected from —NH$_2$ and OH;

$R_{12}$ is D, —OH, halogen, —NH$_2$, —NH$(C_1-C_6)$ alkyl, —N$((C_1-C_6)$ alkyl$)_2$, —C(O)OH, —OC(O)$(C_1-C_6)$ alkyl, $(C_3-C_8)$ cycloalkyl, heterocycloalkyl, $(C_6-C_{10})$ aryl, heteroaryl, or R$_{17}$, wherein the cycloalkyl, heterocycloalkyl, aryl, and heteroaryl are optionally substituted with one or more substituents selected from —OH, —NH$_2$, —NH$(C_1-C_6)$ alkyl, —N$((C_1-C_6)$ alkyl$)_2$, halogen, and R$_{10}$;

$R_{13}$ is H, —OH, $(C_3-C_8)$ cycloalkyl, heterocycloalkyl, $(C_6-C_{10})$ aryl, heteroaryl, or $(C_1-C_{12})$ alkyl, wherein 0 to 7 methylene of the $(C_1-C_{12})$ alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N, are not contiguous and wherein the alkyl is optionally substituted with one or more R$_{15}$, and wherein the cycloalkyl, heterocycloalkyl, aryl, and heteroaryl are optionally substituted with one or more substituents selected from —OH, —C(O)OH, —NH$_2$, —NH$(C_1-C_6)$ alkyl, and —N$((C_1-C_6)$ alkyl$)_2$;

$R_{14}$ is $(C_3-C_8)$ cycloalkyl, heterocycloalkyl, —O—$(C_3-C_8)$ cycloalkyl, —O-heterocycloalkyl, $(C_1-C_{12})$ alkyl or $(C_2-C_{12})$ alkenyl, wherein 0 to 7 methylene of the $(C_1-C_{12})$ alkyl and the $(C_2-C_{12})$ alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or when $R_{12}$ is cycloalkyl or heterocycloalkyl, two R$_{14}$ together with the atom to which they are attached form C=O; or when $R_{12}$ is cycloalkyl or heterocycloalkyl, two R$_{14}$ together with the atoms to which they are attached form a $(C_3-C_8)$ cycloalkyl or heterocycloalkyl optionally substituted with one or more R$_{13}$; or when $R_{12}$ is cycloalkyl or heterocycloalkyl, two R$_{14}$ together with the atom to which they are attached form a $(C_3-C_8)$ spirocycloalkyl or a spiroheterocycloalkyl optionally substituted with one or more R$_{13}$; or when $R_{12}$ is cycloalkyl or heterocycloalkyl, two R$_{14}$ together with the atom to which they are attached form a $(C_6-C_{10})$ aryl or heteroaryl optionally substituted with one or more R$_{13}$;

$R_{15}$ is —OH, —NH$_2$, —NH$(C_1-C_6)$ alkyl, —N$((C_1-C_6)$ alkyl$)_2$, $(C_3-C_8)$ cycloalkyl, heterocycloalkyl, $(C_6-C_{10})$ aryl or heteroaryl, wherein the $(C_3-C_8)$ cycloalkyl and heterocycloalkyl are optionally substituted with one or more substituents selected from $(C_1-C_6)$ hydroxyalkyl, $(C_1-C_6)$ aminoalkyl, —C(O)OH, —OH, —NH$_2$, —NH$(C_1-C_6)$ alkyl, —N$((C_1-C_6)$ alkyl$)_2$, and oxo;

$R_{16}$ is —OH, —C(O)OH, —NH$_2$, —NH$(C_1-C_6)$ alkyl, —N$((C_1-C_6)$ alkyl$)_2$, $(C_1-C_6)$ alkoxy, $(C_1-C_6)$ hydroxyalkyl, $(C_3-C_8)$ cycloalkyl, heterocycloalkyl, —O—$(C_3-C_8)$ cycloalkyl, —O-heterocycloalkyl, $(C_6-C_{10})$ aryl or heteroaryl, wherein the $(C_3-C_8)$ cycloalkyl and heterocycloalkyl are optionally substituted with one or more substituents selected from $(C_1-C_6)$ hydroxyalkyl, $(C_1-C_6)$ aminoalkyl, —C(O)OH, —OH, —NH$_2$, —NH$(C_1-C_6)$ alkyl, —N$((C_1-C_6)$ alkyl$)_2$, and oxo;

$R_{17}$ is $(C_1-C_{18})$ alkyl or $(C_2-C_{18})$ alkenyl, wherein 0 to 8 methylene of the $(C_1-C_{18})$ alkyl and the $(C_2-C_{18})$ alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more $R_{18}$;

$R_{18}$ is $R_{19}$, $(C_6-C_{10})$ aryl, or heteroaryl optionally substituted with one or more $R_{21}$;

$R_{19}$ is $(C_1-C_{18})$ alkyl wherein 0 to 8 methylene of the $(C_1-C_{18})$ alkyl is optionally replaced by a moiety selected from the group consisting of —O—, —$NR_{13}$—, —$S(O)_r$—, —C(O)—, or —C(NH)—, provided that a when any two methylene in the alkyl or alkenyl is replaced, then O and N are not contiguous and wherein the alkyl is optionally substituted with one or more $R_{20}$ $R_{20}$ is $(C_6-C_{10})$ aryl or heteroaryl optionally substituted with one or more $R_{21}$;

$R_{21}$ is H, $(C_1-C_6)$ alkyl, $(C_1-C_6)$ alkoxy, $(C_1-C_6)$ haloalkyl, $(C_1-C_6)$ haloalkoxy, or halogen; or two $R_{21}$ together when on adjacent atoms form a cycloalkyl or heterocycloalkyl optionally substituted with one or more $R_{22}$;

$R_{22}$ is —C(O)$NH_2$, —C(O)NH($C_1-C_6$) alkyl, —C(O)N(($C_1-C_6$) alkyl)$_2$, —C(O) ($C_3-C_7$) cycloalkyl, or —C(O)heterocycloalkyl, wherein the cycloalkyl and heterocycloalkyl are optionally substituted with one or more substituents independently selected from —OH and CN;

each m, o, p, q, and r is independently, at each occurrence, 0, 1, or 2; and n is 0, 1, or 2.

Another aspect of the invention relates to a method of treating or preventing a disease or disorder associated with modulation of TGR5. The method comprises administering to a patient in need of a treatment for diseases or disorders associated with modulation of TGR5 an effective amount of a compound of Formula (I'), or a pharmaceutically acceptable salt, hydrate, solvate, prodrug, stereoisomer, or tautomer thereof.

Another aspect of the invention relates to a method of treating a disease or disorder associated with activation of TGR5. The method comprises administering to a patient in need of a treatment for diseases or disorders associated with activation of TGR5 an effective amount of a compound of Formula (I'), or a pharmaceutically acceptable salt, hydrate, solvate, prodrug, stereoisomer, or tautomer thereof.

Another aspect of the invention relates to a method of treating chemotherapy-induced diarrhea. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method of treating Type II diabetes mellitus. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for treating or preventing hyperphosphatemia. The method comprises administering to a patient in need thereof, comprising, administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for treating or preventing a renal disease. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing serum creatinine levels. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for treating or preventing a proteinuria. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for delaying time to renal replacement therapy (RRT). The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing FGF23 levels. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing the hyperphosphatemic effect of active vitamin D. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for attenuating hyperparathyroidism. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing serum parathyroid hormone (PTH). The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for improving endothelial dysfunction. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing vascular calcification. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing urinary phosphorous. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for normalizing serum phosphorus levels. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing phosphate burden in an elderly patient. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for decreasing dietary phosphate uptake. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing renal hypertrophy. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing heart hypertrophy. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for treating and/or preventing a stomach and bowel-related disorder. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for treating and/or preventing a side effect of chemotherapy or radiation treatment. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof in the manufacture of a medicament for treating a disease associated with activating TGR5.

Another aspect of the invention relates to the use of a compound of Formula (I'), or a pharmaceutically acceptable salt, hydrate, solvate, prodrug, stereoisomer, or tautomer thereof in the treatment of a disease associated with activating TGR5.

Another aspect of the invention relates to a prodrug of a compound of Formula (I') having a Formula (II'):

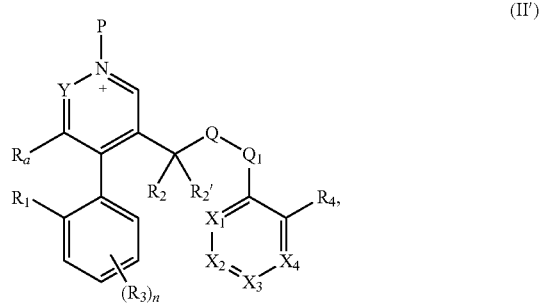

wherein:

P is —O, —CH$_2$OC(O)(C$_1$-C$_6$) alkyl, or —CH$_2$OC(O)NR$_s$ (C$_1$-C$_6$) alkyl, wherein the alkyl is optionally substituted with —OC(O)(C$_1$-C$_3$) alkyl; and R$_5$ is H or (C$_1$-C$_6$) alkyl; and wherein P is a cleavable group.

Another aspect of the invention relates to a prodrug of a compound of Formula (I') having a Formula (II):

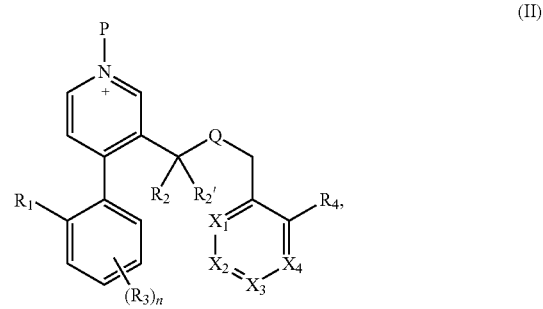

wherein:

P is —O, —CH$_2$OC(O)(C$_1$-C$_6$) alkyl, or —CH$_2$OC(O)NRS (C$_1$-C$_6$) alkyl, wherein the alkyl is optionally substituted with —OC(O)(C$_1$-C$_3$) alkyl; and R$_s$ is H or (C$_1$-C$_6$) alkyl; and wherein P is a cleavable group.

The present invention further provides methods of treating a disease or disorder associated with modulation of TGR5 including, but not limited to, chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS), comprising, administering to a patient suffering from at least one of said diseases or disorder a compound of Formula (I'), or a pharmaceutically acceptable salt, hydrate, solvate, prodrug, stereoisomer, or tautomer thereof.

The present invention provides agonists of TGR5 that are therapeutic agents in the treatment of diseases such as chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS) and other disease associated with the modulation of TGR5.

The present invention further provides compounds and compositions with an improved efficacy and safety profile relative to known TGR5 agonists. The present disclosure also provides agents with novel mechanisms of action toward the TGR5 receptor in the treatment of various types of diseases including chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS). Ultimately the present invention provides the medical community with a novel pharmacological strategy for the treatment of TGR5 mediated diseases and disorders.

DETAILED DESCRIPTION OF THE INVENTION

Figure 1:
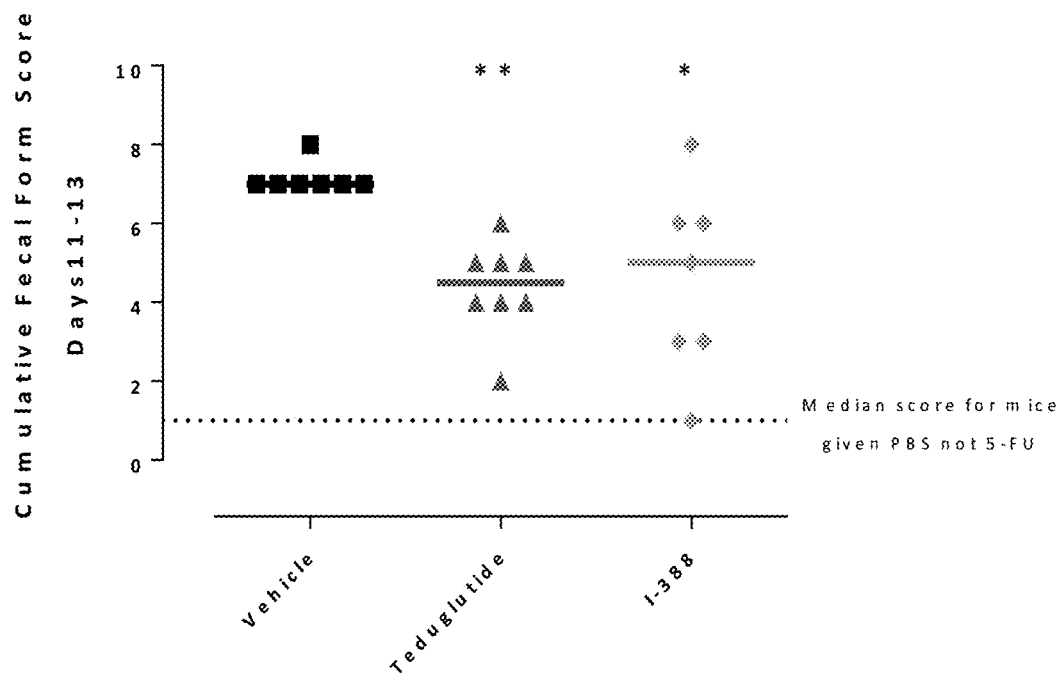
FIG. 1 shows the Fecal form score (FFS) in mice with 5-fluorouracil (5-FU)-induced diarrhea upon treatment with Compound I-388 at 30 mg/kg, teduglutide at 0.4 mg/kg, and vehicle.

The present invention relates to compounds and compositions that are capable of activating TGR5. The invention features methods of treating, preventing or ameliorating a disease or disorder in which TGR5 plays a role by administering to a patient in need thereof a therapeutically effective amount of a compound of Formula (I'), or a pharmaceutically acceptable salt, hydrate, solvate, prodrug, stereoisomer, or tautomer thereof. The methods of the present invention can be used in the treatment of a variety of TGR5 dependent diseases and disorders by activating the TGR5 receptor. Activation of TGR5 provides a novel approach to the treatment, prevention, or amelioration of diseases including, but not limited to, chemotherapy-induced diarrhea, diabetes, Type II diabetes, gestational diabetes, impaired fasting glucose, impaired glucose tolerance, insulin resistance, hyperglycemia, obesity, metabolic syndrome, ulcerative colitis, Crohn's disease, disorders associated with parenteral nutrition especially during short bowel syndrome, and irritable bowel syndrome (IBS).

In a first aspect of the invention, the compounds of Formula (I') are described:

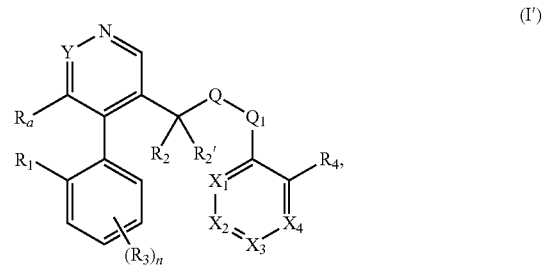

(I')

and pharmaceutically acceptable salts, hydrates, solvates, isotopes, prodrugs, stereoisomers, and tautomers thereof, wherein Q, $Q_1$, $R_a$, $R_1$, $R_2$, $R_{2'}$, $R_3$, $R_4$, $X_1$, $X_2$, $X_3$, $X_4$, Y, and n are as described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, $C_1$-$C_6$ alkoxy, ($C_1$-$C_6$) haloalkyl, $C_1$-$C_6$ haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

As used herein, the term "activation of TGR5" means that a compound or group of compounds acts as a TGR5 agonist or partial agonist.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "aminoalkyl" as used herein refers to an alkyl group, as defined herein, which is substituted one or more amino. Examples of aminoalkyl groups include, but are not limited to, aminomethyl, diaminomethyl, aminoethyl, 1,2-aminoethyl, etc.

"Cycloalkyl" means monocyclic or polycyclic saturated carbon rings (e.g., fused, bridged, or Spiro rings) containing 3-18 carbon atoms (e.g., $C_3$-$C_{10}$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" means monocyclic or polycyclic rings (e.g., fused, bridged, or Spiro rings) containing carbon and heteroatoms taken from oxygen, nitrogen, or sulfur and wherein there is not delocalized t electrons (aromaticity) shared among the ring carbon or heteroatoms. The heterocycloalkyl can be a 3-, 4-, 5-, 6-, 7-, 8-, 9-10-, 11-, or 12-membered ring. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In accordance with the present invention, 3- to 10-membered heterocyclyl refers to saturated or partially saturated non aromatic rings structures containing between 3 and 10 atoms in which there is at least one heteroatoms selected from the group N, O, or S.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "amino" as used herein means a substituent containing at least one nitrogen atom. Specifically, $NH_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or $NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I') may have one or more asymmetric carbon atom and may occur as racemates, racemic mixtures and as individual enantiomers or diastereomers.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the "IUPAC Naming Plugin" software program (ChemAxon) and/or ChemDraw software Struct=Name Pro 11.0 program (CambridgeSoft). For complex chemical names employed herein, a substituent group is named before the group to which it attaches. For example, cyclopropylethyl comprises an ethyl backbone with cyclopropyl substituent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methyl-glucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, N-oxides, and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The present invention relates to compounds or pharmaceutically acceptable salts, hydrates, solvates, prodrugs, stereoisomers, or tautomers thereof, capable of activating TGR5, which are useful for the treatment of diseases and disorders associated with modulation of a TGR5 receptor. The invention further relates to compounds, or pharmaceutically acceptable salts, hydrates, solvates, prodrugs, stereoisomers, or tautomers thereof, which are useful for activating TGR5.

In one embodiment, the compounds of Formula (I') have the structure of Formula (I) or (Ia'):

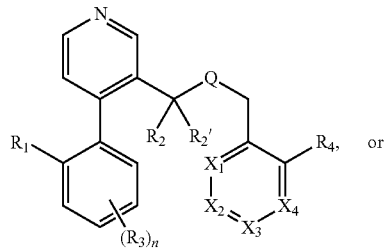

(I)

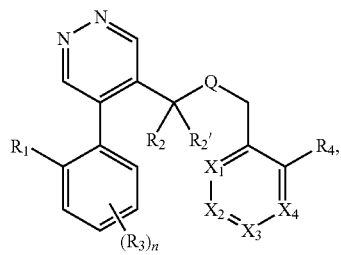

(Ia')

and pharmaceutically acceptable salts, hydrates, solvates, isotopes, prodrugs, stereoisomers, and tautomers thereof.

In one embodiment, the compounds of Formula (I') have the structure of Formula (Ib') or (Ic'):

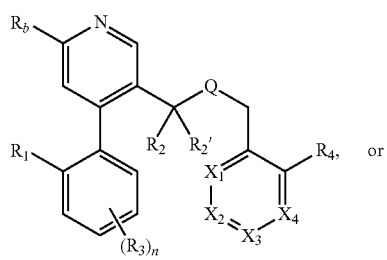

(I)

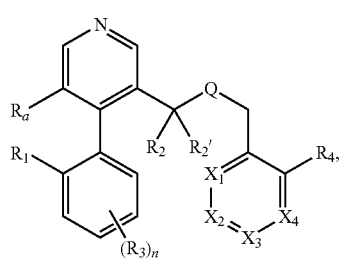

(Ia')

and pharmaceutically acceptable salts, hydrates, solvates, isotopes, prodrugs, stereoisomers, and tautomers thereof.

In another embodiment, the compounds of Formula (I') have the structure of Formula (Ia):

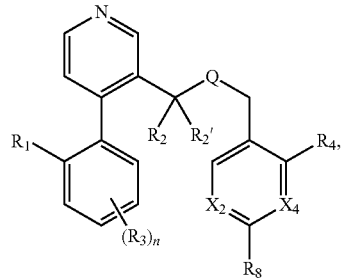

(Ia)

and pharmaceutically acceptable salts, hydrates, solvates, isotopes, prodrugs, stereoisomers, and tautomers thereof.

In another embodiment, the compounds of Formula (I') have the structure of Formula (Ib):

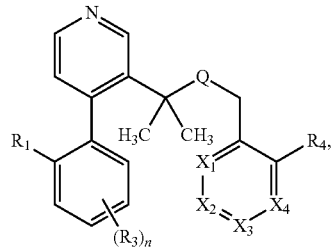

(Ib)

and pharmaceutically acceptable salts, hydrates, solvates, isotopes, prodrugs, stereoisomers, and tautomers thereof.

In one embodiment, the compounds of Formula (I') have the structure of Formula (Ic):

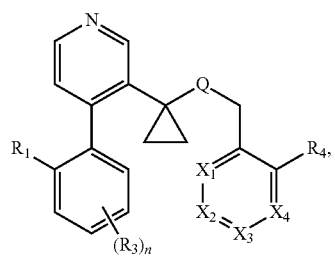

(Ic)

and pharmaceutically acceptable salts, hydrates, solvates, isotopes, prodrugs, stereoisomers, and tautomers thereof.

In another embodiment, the compounds of Formula (I') have the structure of Formula (Id), Formula (Ie), Formula (If), or Formula (Ig):

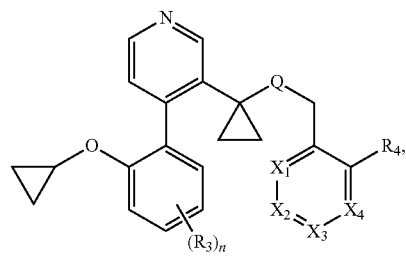

(Id)

(Ie)

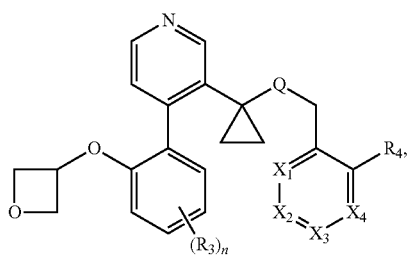

(If)

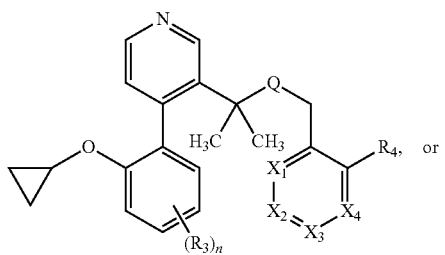

(Ig)

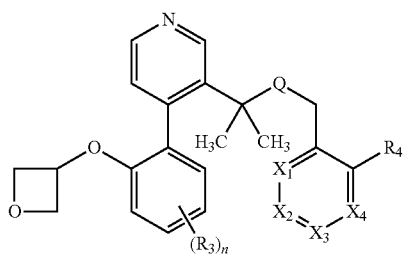

and pharmaceutically acceptable salts, hydrates, solvates, isotopes, prodrugs, stereoisomers, and tautomers thereof.

In another embodiment, the compounds of Formula (I') have the structure of Formula (Ih), Formula (Ij), Formula (Ik), Formula (Im):

(Ih)

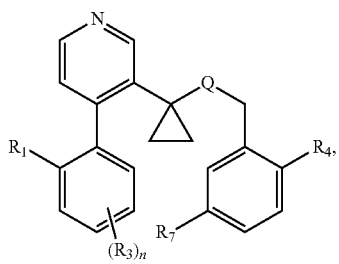

(Ij)

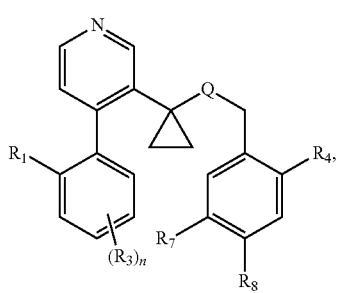

(Ik)

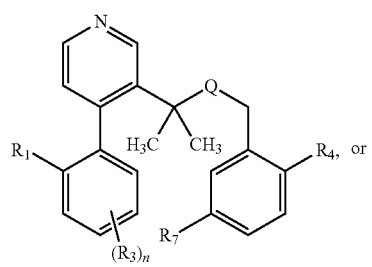

(Im)

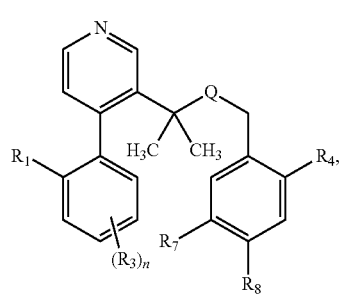

and pharmaceutically acceptable salts, hydrates, solvates, isotopes, prodrugs, stereoisomers, and tautomers thereof.

In another embodiment, the compounds of Formula (I') have the structure of Formula (Io), Formula (Ip), Formula (Iq), or Formula (Ir):

(Io)

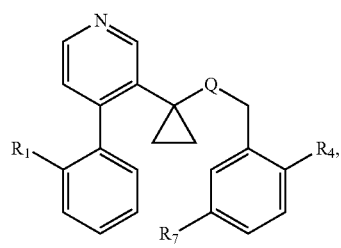

(Ip)

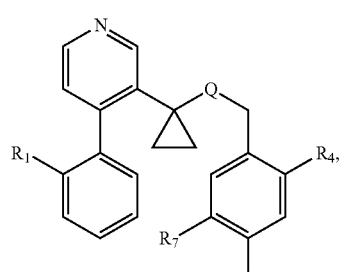

(Iq)

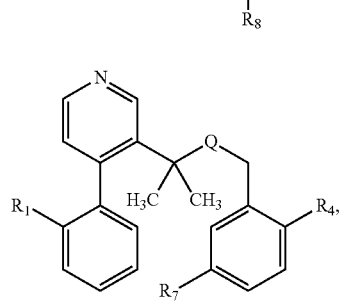

-continued

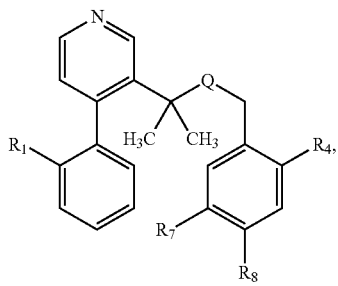
(Ir)

and pharmaceutically acceptable salts, hydrates, solvates, isotopes, prodrugs, stereoisomers, and tautomers thereof.

In another embodiment, the compounds of Formula (I') have the structure of Formula (Iu), Formula (Iv), Formula (Iw), or Formula (Ix):

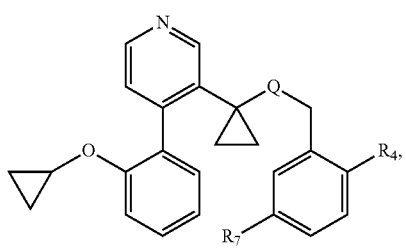
(Iu)

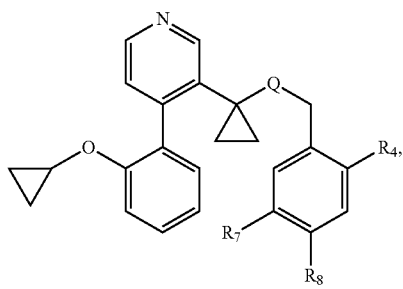
(Iv)

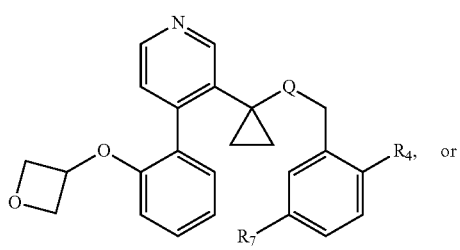
(Iw)

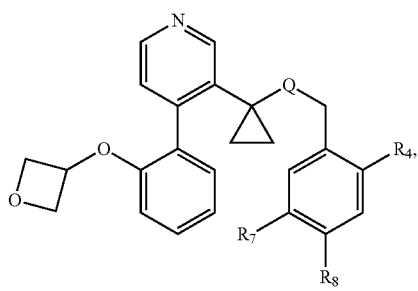
(Ix)

and pharmaceutically acceptable salts, hydrates, solvates, isotopes, prodrugs, stereoisomers, and tautomers thereof.

In another embodiment, the compounds of Formula (I') have the structure of Formula (Iy), Formula (Iz), Formula (Iaa), or Formula (Ibb):

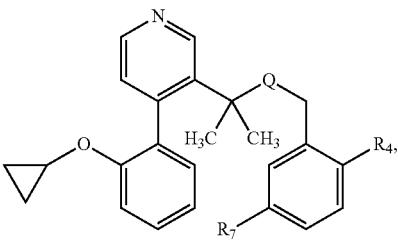
(Iy)

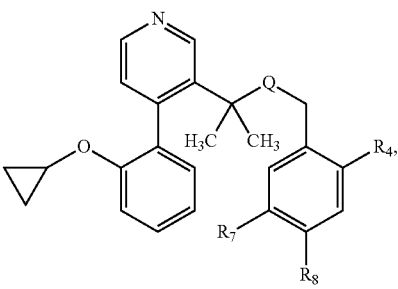
(Iz)

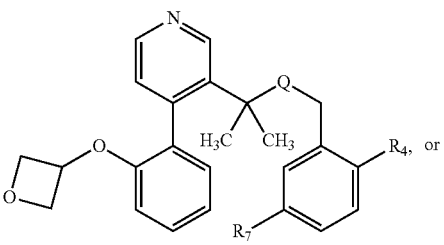
(Iaa)

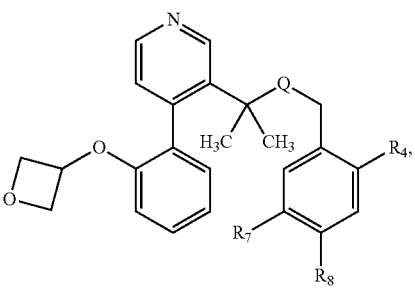
(Ibb)

and pharmaceutically acceptable salts, hydrates, solvates, isotopes, prodrugs, stereoisomers, and tautomers thereof.

In one embodiment, the compounds of Formula (I') have the structure of Formula (Icc):

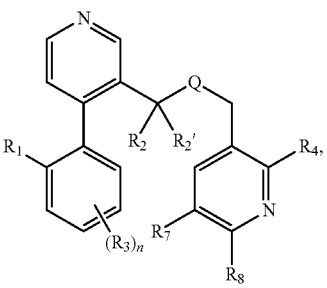
(Icc)

-continued

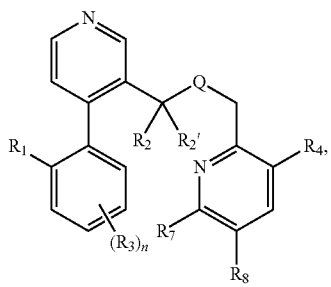
(Idd)

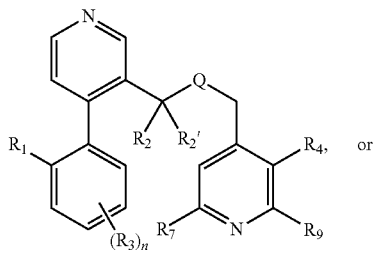
(Iee)

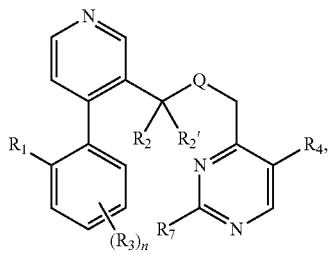
(Iff)

and pharmaceutically acceptable salts, hydrates, solvates, isotopes, prodrugs, stereoisomers, and tautomers thereof.

In one embodiment, the compound of Formula (I') is a prodrug having a Formula (II') or (II):

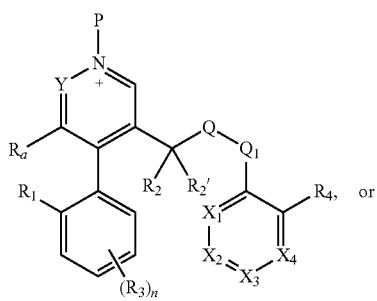
(II')

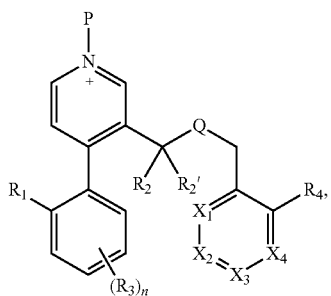
(II)

wherein:
P is —O, —CH$_2$OC(O)(C$_1$-C$_6$) alkyl, or —CH$_2$OC(O)NR$_s$ (C$_1$-C$_6$) alkyl, wherein the alkyl is optionally substituted with —OC(O)(C$_1$-C$_3$) alkyl; and
R$_s$ is H or (C$_1$-C$_6$) alkyl; and
wherein P is a cleavable group.
In one embodiment, P is —O,

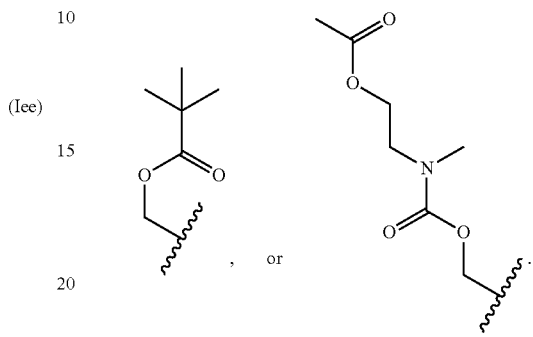

In some embodiment of the Formulae above,
Q is —NR$_5$— or —O—;
Q$_1$ is —CH$_2$—;
X$_1$ is CR$_6$ or N;
X$_2$ is CR$_7$ or N;
X$_3$ is CR$_8$ or N;
X$_4$ is CR$_9$ or N;
Y is CH;
R$_a$ is H;
R$_1$ is H, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;
R$_2$ is (C$_1$-C$_6$) alkyl, (C$_1$-C$_6$) alkoxy, (C$_1$-C$_6$) haloalkyl, or (C$_1$-C$_6$) haloalkoxy;
R$_{2'}$ is H, (C$_1$-C$_6$) alkyl, (C$_1$-C$_6$) alkoxy, (C$_1$-C$_6$) haloalkyl, or (C$_1$-C$_6$) haloalkoxy; or
R$_2$ and R$_{2'}$ together with the carbon atom to which they are attached form (C$_3$-C$_8$) cycloalkyl or heterocycloalkyl;
each R$_3$ is independently, at each occurrence, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;
R$_4$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_m$(C$_1$-C$_6$) alkyl, —NH(C$_1$-C$_4$) alkyl, or —N((C$_1$-C$_4$) alkyl)$_2$;
R$_5$ is H, (C$_1$-C$_6$) alkyl, —C(O)NR$_{10}$R$_{11}$, —C(O)(C$_1$-C$_6$) alkyl, or —C(O)O(C$_1$-C$_6$) alkyl;
each R$_6$ and R$_9$ is independently H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$)

cycloalkyl, heterocycloalkyl, —OH, —NH$_2$, CN, —S(O)$_o$(C$_1$-C$_6$) alkyl, —NH(C$_1$-C$_4$) alkyl, or —N((C$_1$-C$_4$) alkyl)$_2$;

each R$_7$ and R$_8$ is independently H, (C$_1$-C$_8$) alkenyl, (C$_1$-C$_8$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, (C$_3$-C$_8$) cycloalkenyl, heterocycloalkyl, —OH, —NH$_2$, —S(O)$_q$ NH$_2$, —S(O)$_q$OH, CN, or (C$_1$-C$_{18}$) alkyl, wherein 0 to 7 methylene of the (C$_1$-C$_{18}$) alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;

R$_{10}$ and R$_{11}$ are each independently H or (C$_1$-C$_6$) alkyl optionally substituted with one or more substituent independently selected from —NH$_2$ and OH;

R$_{12}$ is —OH, halogen, —NH$_2$, —NH(C$_1$-C$_6$) alkyl, —N((C$_1$-C$_6$) alkyl)$_2$, —C(O)OH, —OC(O)(C$_1$-C$_6$) alkyl, (C$_3$-C$_8$) cycloalkyl, heterocycloalkyl, (C$_6$-C$_{10}$) aryl, or heteroaryl, wherein the cycloalkyl, heterocycloalkyl, aryl, and heteroaryl are optionally substituted with one or more substituents selected from —OH, —NH$_2$, —NH(C$_1$-C$_6$) alkyl, —N((C$_1$-C$_6$) alkyl)$_2$, halogen, and R$_{10}$;

R$_{13}$ is H, (C$_3$-C$_8$) cycloalkyl, heterocycloalkyl, (C$_6$-C$_{10}$) aryl, heteroaryl, or (C$_1$-C$_{12}$) alkyl, wherein 0 to 7 methylene of the (C$_1$-C$_{12}$) alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N, are not contiguous and wherein the alkyl is optionally substituted with one or more R$_{15}$, and wherein the cycloalkyl, heterocycloalkyl, aryl, and heteroaryl are optionally substituted with one or more substituents selected from —OH, —C(O)OH, —NH$_2$, —NH(C$_1$-C$_6$) alkyl, and —N((C$_1$-C$_6$) alkyl)$_2$;

R$_{14}$ is (C$_3$-C$_8$) cycloalkyl, heterocycloalkyl, —O—(C$_3$-C$_8$) cycloalkyl, —O-heterocycloalkyl, (C$_1$-C$_{12}$) alkyl or (C$_2$-C$_{12}$) alkenyl, wherein 0 to 7 methylene of the (C$_1$-C$_{12}$) alkyl and the (C$_2$-C$_{12}$) alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or when R$_{12}$ is cycloalkyl or heterocycloalkyl, two R$_{14}$ together with the atom to which they are attached form C=(O); or when R$_{12}$ is cycloalkyl or heterocycloalkyl, two R$_{14}$ together with the atoms to which they are attached form a (C$_3$-C$_8$) cycloalkyl or heterocycloalkyl optionally substituted with one or more R$_{13}$; or when R$_{12}$ is cycloalkyl or heterocycloalkyl, two R$_{14}$ together with the atom to which they are attached form a (C$_3$-C$_8$) spirocycloalkyl or a spiroheterocycloalkyl optionally substituted with one or more R$_{13}$; or when R$_{12}$ is cycloalkyl or heterocycloalkyl, two R$_{14}$ together with the atom to which they are attached form a (C$_6$-C$_{10}$) aryl or heteroaryl optionally substituted with one or more OH or R$_{13}$;

R$_{15}$ is —OH, —NH$_2$, —NH(C$_1$-C$_6$) alkyl, —N((C$_1$-C$_6$) alkyl)$_2$, (C$_3$-C$_8$) cycloalkyl, heterocycloalkyl, (C$_6$-C$_{10}$) aryl or heteroaryl, wherein the (C$_3$-C$_8$) cycloalkyl and heterocycloalkyl are optionally substituted with one or more substituents selected from (C$_1$-C$_6$) hydroxyalkyl, (C$_1$-C$_6$) aminoalkyl, —C(O)OH, —OH, —NH$_2$, —NH (C$_1$-C$_6$) alkyl, —N((C$_1$-C$_6$) alkyl)$_2$, and oxo;

R$_{16}$ is —OH, —C(O)OH, —NH$_2$, —NH(C$_1$-C$_6$) alkyl, —N((C$_1$-C$_6$) alkyl)$_2$, (C$_1$-C$_6$) alkoxy, (C$_1$-C$_6$) hydroxyalkyl, (C$_3$-C$_8$) cycloalkyl, heterocycloalkyl, —O—(C$_3$-C$_8$) cycloalkyl, —O-heterocycloalkyl, (C$_6$-C$_{10}$) aryl or heteroaryl, wherein the (C$_3$-C$_8$) cycloalkyl and heterocycloalkyl are optionally substituted with one or more substituents selected from (C$_1$-C$_6$) hydroxyalkyl, (C$_1$-C$_6$) aminoalkyl, —C(O)OH, —OH, —NH$_2$, —NH(C$_1$-C$_6$) alkyl, —N((C$_1$-C$_6$) alkyl)$_2$, and oxo;

each m, o, p, q, and r is independently, at each occurrence, 0, 1, or 2; and n is 0, 1, or 2.

In some embodiments of the Formulae above:

Q is —NR$_5$— or —O—;

X$_1$ is CR$_6$ or N;

X$_2$ is CR$_7$ or N;

X$_3$ is CR$_8$ or N;

X$_4$ is CR$_9$ or N;

R$_1$ is H, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;

R$_2$ and R$_{2'}$ are each independently (C$_1$-C$_6$) alkyl, (C$_1$-C$_6$) alkoxy, (C$_1$-C$_6$) haloalkyl, or (C$_1$-C$_6$) haloalkoxy; or R$_2$ and R$_{2'}$ together with the carbon atom to which they are attached form (C$_3$-C$_8$) cycloalkyl or heterocycloalkyl;

each R$_3$ is independently, at each occurrence, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;

R$_4$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_m$(C$_1$-C$_6$) alkyl, —NH(C$_1$-C$_4$) alkyl, or —N((C$_1$-C$_4$) alkyl)$_2$;

R$_5$ is H, (C$_1$-C$_6$) alkyl, —C(O)NR$_{10}$R$_{11}$, —C(O)(C$_1$-C$_6$) alkyl, or —C(O)O(C$_1$-C$_6$) alkyl;

each R$_6$ and R$_9$ is independently H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_o$(C$_1$-C$_6$) alkyl, —NH(C$_1$-C$_4$) alkyl, or —N((C$_1$-C$_4$) alkyl)$_2$;

each R$_7$ and R$_8$ is independently H, (C$_1$-C$_8$) alkenyl, (C$_1$-C$_8$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, (C$_3$-C$_8$) cycloalkenyl, heterocycloalkyl, —OH, —NH$_2$, —S(O)$_q$ NH$_2$, —S(O)$_q$OH, CN, or (C$_1$-C$_{18}$) alkyl, wherein 0 to 7 methylene of the (C$_1$-C$_{18}$) alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;

R$_{10}$ and R$_{11}$ are each independently H or (C$_1$-C$_6$) alkyl optionally substituted with one or more substituent independently selected from —NH$_2$ and OH;

R$_{12}$ is —OH, —NH$_2$, —NH(C$_1$-C$_6$) alkyl, —N((C$_1$-C$_6$) alkyl)$_2$, —C(O)OH, (C$_3$-C$_8$) cycloalkyl, heterocycloalkyl, (C$_6$-C$_{10}$) aryl, or heteroaryl, wherein the cycloalkyl, heterocycloalkyl, aryl, and heteroaryl are optionally substituted with one or more substituents selected from —OH, —NH$_2$, —NH(C$_1$-C$_6$) alkyl, —N((C$_1$-C$_6$) alkyl)$_2$, and R$_{14}$;

R$_{13}$ is H, (C$_3$-C$_8$) cycloalkyl, heterocycloalkyl, (C$_6$-C$_{10}$) aryl, heteroaryl, or (C$_1$-C$_{12}$) alkyl, wherein 0 to 7 methylene of the (C$_1$-C$_{12}$) alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N, are not contiguous and wherein the alkyl is optionally substituted with one or more R$_{15}$, and wherein the cycloalkyl, heterocycloalkyl, aryl, and heteroaryl are optionally substituted with one or more substituents selected from —OH, —C(O)OH, —NH$_2$, —NH(C$_1$-C$_6$) alkyl, and —N((C$_1$-C$_6$) alkyl)$_2$;

R$_{14}$ is (C$_3$-C$_8$) cycloalkyl, heterocycloalkyl, —O—(C$_3$-C$_8$) cycloalkyl, —O-heterocycloalkyl, (C$_1$-C$_{12}$) alkyl or (C$_2$-C$_{12}$) alkenyl, wherein 0 to 7 methylene of the (C$_1$-C$_{12}$) alkyl and the (C$_2$-C$_{12}$) alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or when R$_{12}$ is cycloalkyl or heterocycloalkyl, two R$_{14}$ together with the atom to which they are attached form C=(O); or two R$_{14}$ together with the atoms to which they are attached form a (C$_3$-C$_8$) cycloalkyl or heterocycloalkyl optionally substituted with one or more R$_{13}$; or when R$_{12}$ is cycloalkyl or heterocycloalkyl, two R$_{14}$ together with the atom to which they are attached form a (C$_3$-C$_8$) spirocycloalkyl or a spiroheterocycloalkyl optionally substituted with one or more R$_{13}$;

R$_{15}$ is —OH, —NH$_2$, —NH(C$_1$-C$_6$) alkyl, —N((C$_1$-C$_6$) alkyl)$_2$, (C$_3$-C$_8$) cycloalkyl, heterocycloalkyl, (C$_6$-C$_{10}$) aryl or heteroaryl, wherein the (C$_3$-C$_8$) cycloalkyl and heterocycloalkyl are optionally substituted with one or more substituents selected from (C$_1$-C$_6$) hydroxyalkyl, (C$_1$-C$_6$) aminoalkyl, —C(O)OH, —OH, —NH$_2$, —NH(C$_1$-C$_6$) alkyl, —N((C$_1$-C$_6$) alkyl)$_2$, and oxo;

R$_{16}$ is —OH, —C(O)OH, —NH$_2$, —NH(C$_1$-C$_6$) alkyl, —N((C$_1$-C$_6$) alkyl)$_2$, (C$_1$-C$_6$) alkoxy, (C$_1$-C$_6$) hydroxyalkyl, (C$_3$-C$_8$) cycloalkyl, heterocycloalkyl, —O—(C$_3$-C$_8$) cycloalkyl, —O-heterocycloalkyl, (C$_6$-C$_{10}$) aryl or heteroaryl, wherein the (C$_3$-C$_8$) cycloalkyl and heterocycloalkyl are optionally substituted with one or more substituents selected from (C$_1$-C$_6$) hydroxyalkyl, (C$_1$-C$_6$) aminoalkyl, —C(O)OH, —OH, —NH$_2$, —NH(C$_1$-C$_6$) alkyl, —N((C$_1$-C$_6$) alkyl)$_2$, and oxo;

each m, o, p, q, and r is independently, at each occurrence, 0, 1, or 2; and n is 0, 1, or 2

In some embodiments of the Formulae above:

Q is —NR$_5$— or —O—;

X$_1$ is CR$_6$ or N;

X$_2$ is CR$_7$ or N;

X$_3$ is CR$_8$ or N;

X$_4$ is CR$_9$ or N;

R$_1$ is (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;

R$_2$ and R$_{2'}$ are each independently (C$_1$-C$_6$) alkyl, (C$_1$-C$_6$) alkoxy, (C$_1$-C$_6$) haloalkyl, or (C$_1$-C$_6$) haloalkoxy; or R$_2$ and R$_{2'}$ together with the carbon atom to which they are attached form (C$_3$-C$_8$) cycloalkyl or heterocycloalkyl;

each R$_3$ is independently, at each occurrence, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$;

R$_4$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_m$(C$_1$-C$_6$) alkyl, —NH(C$_1$-C$_4$) alkyl, or —N((C$_1$-C$_4$) alkyl)$_2$;

R$_5$ is H, (C$_1$-C$_6$) alkyl, —C(O)NR$_{10}$R$_{11}$, —C(O)(C$_1$-C$_6$) alkyl, or —C(O)O(C$_1$-C$_6$) alkyl;

each R$_6$ and R$_9$ is independently H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_o$(C$_1$-C$_6$) alkyl, —NH(C$_1$-C$_4$) alkyl, or —N((C$_1$-C$_4$) alkyl)$_2$;

each R$_7$ and R$_8$ is independently H, (C$_1$-C$_8$) alkenyl, (C$_1$-C$_8$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, (C$_3$-C$_8$) cycloalkenyl, heterocycloalkyl, —OH, —NH$_2$, CN, or (C$_1$-C$_{18}$) alkyl, wherein 0 to 7 methylene of the (C$_1$-C$_{18}$) alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;

R$_{10}$ and R$_{11}$ are each independently H or (C$_1$-C$_6$) alkyl optionally substituted with one or more substituent independently selected from —NH$_2$ and OH;

R$_{12}$ is —OH, —NH$_2$, —NH(C$_1$-C$_6$) alkyl, —N((C$_1$-C$_6$) alkyl)$_2$, —C(O)OH, (C$_3$-C$_8$) cycloalkyl, heterocycloalkyl, $(C_6$-$C_{10})$ aryl, or heteroaryl, wherein the cycloalkyl, heterocycloalkyl, aryl, and heteroaryl are optionally substituted with one or more substituents selected from —OH, —NH$_2$, —NH($C_1$-$C_6$) alkyl, —N(($C_1$-$C_6$) alkyl)$_2$, and R$_{10}$;

R$_{13}$ is H, ($C_3$-$C_8$) cycloalkyl, heterocycloalkyl, ($C_6$-$C_{10}$) aryl, heteroaryl, or (Ct-Cu) alkyl, wherein 0 to 7 methylene of the ($C_1$-$C_{12}$) alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N, are not contiguous and wherein the alkyl is optionally substituted with one or more R$_{15}$, and wherein the cycloalkyl, heterocycloalkyl, aryl, and heteroaryl are optionally substituted with one or more substituents selected from —OH, —C(O)OH, —NH$_2$, —NH($C_1$-$C_6$) alkyl, and —N(($C_1$-$C_6$) alkyl)$_2$;

R$_{14}$ is ($C_3$-$C_8$) cycloalkyl, heterocycloalkyl, —O—($C_3$-$C_8$) cycloalkyl, —O-heterocycloalkyl, ($C_1$-$C_{12}$) alkyl or ($C_2$-$C_{12}$) alkenyl, wherein 0 to 7 methylene of the ($C_1$-$C_{12}$) alkyl and the ($C_2$-$C_{12}$) alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or when R$_{12}$ is cycloalkyl or heterocycloalkyl, two R$_{14}$ together with the atom to which they are attached form C═(O); or two R$_{14}$ together with the atoms to which they are attached form a ($C_3$-$C_8$) cycloalkyl or heterocycloalkyl optionally substituted with one or more R$_{13}$; or when R$_{12}$ is cycloalkyl or heterocycloalkyl, two R$_{14}$ together with the atom to which they are attached form a ($C_3$-$C_8$) spirocycloalkyl or a spiroheterocycloalkyl optionally substituted with one or more R$_{13}$;

R$_{15}$ is —OH, —NH$_2$, —NH($C_1$-$C_6$) alkyl, —N(($C_1$-$C_6$) alkyl)$_2$, ($C_3$-$C_8$) cycloalkyl, heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —NH$_2$, —NH ($C_1$-$C_6$) alkyl, —N(($C_1$-$C_6$) alkyl)$_2$, and oxo;

R$_{16}$ is —OH, —C(O)OH, —NH$_2$, —NH($C_1$-$C_6$) alkyl, —N(($C_1$-$C_6$) alkyl)$_2$, ($C_1$-$C_6$) alkoxy, ($C_1$-$C_6$) hydroxyalkyl, ($C_3$-$C_8$) cycloalkyl, heterocycloalkyl, —O—($C_3$-$C_8$) cycloalkyl, —O-heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —NH$_2$, —NH($C_1$-$C_6$) alkyl, —N(($C_1$-$C_6$) alkyl)$_2$, and oxo;

each m, o, p, q, and r is independently, at each occurrence, 0, 1, or 2; and n is 0, 1, or 2.

In some embodiments of the Formulae above:

Q is —NR$_5$— or —O—;

R$_1$ is H, ($C_1$-$C_6$) alkyl, ($C_1$-$C_6$) alkoxy, ($C_1$-$C_6$) haloalkyl, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one or more substituents selected from ($C_1$-$C_4$) alkoxy or —OH;

R$_2$ and R$_{2'}$ are each independently ($C_1$-$C_4$) alkyl; or

R$_2$ and R$_{2'}$ together with the carbon atom to which they are attached form ($C_3$-$C_8$) cycloalkyl or heterocycloalkyl;

each R$_3$ is independently, at each occurrence, halogen; R$_4$ is H, ($C_1$-$C_6$) alkyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, heterocycloalkyl, —OH, —NH$_2$, CN, —S(O)$_m$($C_1$-$C_6$) alkyl, —NH($C_1$-$C_4$) alkyl, or —N(($C_1$-$C_4$) alkyl)$_2$;

R$_5$ is H, ($C_1$-$C_6$) alkyl, —C(O)NR$_{10}$R$_{11}$, —C(O)($C_1$-$C_6$) alkyl, or —C(O)O($C_1$-$C_6$) alkyl;

each R$_6$ and R$_9$ is independently H, ($C_1$-$C_6$) alkyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, heterocycloalkyl, —OH, —NH$_2$, CN, —S(O)$_o$($C_1$-$C_6$) alkyl, —NH($C_1$-$C_4$) alkyl, or —N(($C_1$-$C_4$) alkyl)$_2$;

each R$_7$ and R$_8$ is independently H, ($C_1$-$C_8$) alkenyl, ($C_1$-$C_8$) alkynyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, ($C_3$-$C_8$) cycloalkenyl, heterocycloalkyl, —OH, —NH$_2$, CN, or ($C_1$-$C_{18}$) alkyl, wherein 0 to 7 methylene of the ($C_1$-$C_{18}$) alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;

R$_{10}$ and R$_{11}$ are each independently H or ($C_1$-$C_6$) alkyl optionally substituted with one or more substituent independently selected from —NH$_2$ and OH;

R$_{12}$ is —OH, —NH$_2$, —NH($C_1$-$C_6$) alkyl, —N(($C_1$-$C_6$) alkyl)$_2$, —C(O)OH, ($C_3$-$C_8$) cycloalkyl, heterocycloalkyl, ($C_6$-$C_{10}$) aryl, or heteroaryl, wherein the cycloalkyl, heterocycloalkyl, aryl, and heteroaryl are optionally substituted with one or more substituents selected from —OH, —NH$_2$, —NH($C_1$-$C_6$) alkyl, —N(($C_1$-$C_6$) alkyl)$_2$, and R$_{14}$;

R$_{13}$ is H, ($C_3$-$C_8$) cycloalkyl, heterocycloalkyl, ($C_6$-$C_{10}$) aryl, heteroaryl, or ($C_1$-$C_{12}$) alkyl, wherein 0 to 7 methylene of the ($C_1$-$C_{12}$) alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N, are not contiguous and wherein the alkyl is optionally substituted with one or more R$_{15}$, and wherein the cycloalkyl, heterocycloalkyl, aryl, and heteroaryl are optionally substituted with one or more substituents selected from —OH, —C(O)OH, —NH$_2$, —NH($C_1$-$C_6$) alkyl, and —N(($C_1$-$C_6$) alkyl)$_2$;

R$_{14}$ is ($C_3$-$C_8$) cycloalkyl, heterocycloalkyl, —O—($C_3$-$C_8$) cycloalkyl, —O-heterocycloalkyl, ($C_1$-$C_{12}$) alkyl or ($C_2$-$C_{12}$) alkenyl, wherein 0 to 7 methylene of the ($C_1$-$C_{12}$) alkyl and the ($C_2$-$C_{12}$) alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or when $R_{12}$ is cycloalkyl or heterocycloalkyl, two $R_{14}$ together with the atom to which they are attached form C=(O); or two $R_{14}$ together with the atoms to which they are attached form a ($C_3$-$C_8$) cycloalkyl or heterocycloalkyl optionally substituted with one or more $R_{13}$; or when $R_{12}$ is cycloalkyl or heterocycloalkyl, two $R_{14}$ together with the atom to which they are attached form a ($C_3$-$C_8$) spirocycloalkyl or a spiroheterocycloalkyl optionally substituted with one or more $R_{13}$;

$R_{15}$ is —OH, —$NH_2$, —NH($C_1$-$C_6$) alkyl, —N(($C_1$-$C_6$) alkyl)$_2$, ($C_3$-$C_8$) cycloalkyl, heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —$NH_2$, —NH($C_1$-$C_6$) alkyl, —N(($C_1$-$C_6$) alkyl)$_2$, and oxo;

$R_{16}$ is —OH, —C(O)OH, —$NH_2$, —NH($C_1$-$C_6$) alkyl, —N(($C_1$-$C_6$) alkyl)$_2$, ($C_1$-$C_6$) alkoxy, ($C_1$-$C_6$) hydroxyalkyl, ($C_3$-$C_8$) cycloalkyl, heterocycloalkyl, —O—($C_3$-$C_8$) cycloalkyl, —O-heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —$NH_2$, —NH($C_1$-$C_6$) alkyl, —N(($C_1$-$C_6$) alkyl)$_2$, and oxo;

each m, o, p, q, and r is independently, at each occurrence, 0, 1, or 2; and n is 0 or 1.

In some embodiments of the Formulae above:

Q is —O—;

$R_1$ is H, ($C_1$-$C_6$) alkyl, ($C_1$-$C_6$) alkoxy, ($C_1$-$C_6$) haloalkyl, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one or more substituents selected from ($C_1$-$C_4$) alkoxy and —OH;

$R_2$ and $R_{2'}$ are each independently ($C_1$-$C_4$) alkyl; or $R_2$ and $R_{2'}$ together with the carbon atom to which they are attached form ($C_3$-$C_8$) cycloalkyl or heterocycloalkyl;

each $R_3$ is independently, at each occurrence, halogen;

$R_4$ is H, ($C_1$-$C_6$) alkyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, heterocycloalkyl, —OH, —$NH_2$, CN, —S(O)$_m$($C_1$-$C_6$) alkyl, —NH($C_1$-$C_4$) alkyl, or —N(($C_1$-$C_4$) alkyl)$_2$;

each $R_6$ and $R_9$ is independently H, ($C_1$-$C_6$) alkyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, heterocycloalkyl, —OH, —$NH_2$, CN, —S(O)$_o$($C_1$-$C_6$) alkyl, —NH($C_1$-$C_4$) alkyl, or —N(($C_1$-$C_4$) alkyl)$_2$;

each $R_7$ and $R_8$ is independently H, ($C_1$-$C_8$) alkenyl, ($C_1$-$C_8$) alkynyl, ($C_1$-$C_6$) alkoxy, ($C_1$-$C_6$) haloalkyl, ($C_1$-$C_6$) haloalkoxy, ($C_1$-$C_6$) hydroxyalkyl, ($C_1$-$C_6$) aminoalkyl, halogen, ($C_3$-$C_8$) cycloalkyl, ($C_3$-$C_8$) cycloalkenyl, heterocycloalkyl, —OH, —$NH_2$, CN, or ($C_1$-$C_{18}$) alkyl, wherein 0 to 7 methylene of the ($C_1$-$C_{18}$) alkyl is optionally replaced by a moiety selected from the group consisting of —O—, —$NR_{13}$—, —S(O)$_q$—, —C(O)—, —C($CH_2$)—, or —C(NH)—, provided that when any two methylene in the alkyl is replaced, then two —O—, two —S(O)$_q$—, or two —$NR_{13}$— and —O— and —$NR_{13}$— are not contiguous, wherein the alkyl is optionally substituted with one or more $R_{12}$, and wherein the cycloalkyl and cycloalkenyl are optionally substituted with one or more $R_{13}$;

$R_{10}$ and $R_{11}$ are each independently H or ($C_1$-$C_6$) alkyl optionally substituted with one or more substituent independently selected from —$NH_2$ and OH;

$R_{12}$ is —OH, —$NH_2$, —NH($C_1$-$C_6$) alkyl, —N(($C_1$-$C_6$) alkyl)$_2$, —C(O)OH, ($C_3$-$C_8$) cycloalkyl, heterocycloalkyl, ($C_6$-$C_{10}$) aryl, or heteroaryl, wherein the cycloalkyl, heterocycloalkyl, aryl, and heteroaryl are optionally substituted with one or more substituents selected from —OH, —$NH_2$, —NH($C_1$-$C_6$) alkyl, —N(($C_1$-$C_6$) alkyl)$_2$, and $R_{14}$;

$R_{13}$ is H, ($C_3$-$C_8$) cycloalkyl, heterocycloalkyl, ($C_6$-$C_{10}$) aryl, heteroaryl, or ($C_1$-$C_{12}$) alkyl, wherein 0 to 7 methylene of the ($C_1$-$C_{12}$) alkyl is optionally replaced by a moiety selected from the group consisting of —O—, —$NR_{13}$—, —S(O)$_r$—, —C(O)—, or —C(NH)—, provided that a when any two methylene in the alkyl is replaced, then O and N, are not contiguous and wherein the alkyl is optionally substituted with one or more $R_{15}$, and wherein the cycloalkyl, heterocycloalkyl, aryl, and heteroaryl are optionally substituted with one or more substituents selected from —OH, —C(O)OH, —$NH_2$, —NH($C_1$-$C_6$) alkyl, and —N(($C_1$-$C_6$) alkyl)$_2$;

$R_{14}$ is ($C_3$-$C_8$) cycloalkyl, heterocycloalkyl, —O—($C_3$-$C_8$) cycloalkyl, —O-heterocycloalkyl, ($C_1$-$C_{12}$) alkyl or ($C_2$-$C_{12}$) alkenyl, wherein 0 to 7 methylene of the ($C_1$-$C_{12}$) alkyl and the ($C_2$-$C_{12}$) alkenyl are optionally replaced by a moiety selected from the group consisting of —O—, —$NR_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more $R_{15}$, and the cycloalkyl and heterocycloalkyl are optionally substituted with one or more $R_{16}$; or when $R_{12}$, is cycloalkyl or heterocycloalkyl, two $R_{14}$ together with the atom to which they are attached form C=(O); or two $R_{10}$ together with the atoms to which they are attached form a ($C_3$-$C_8$) cycloalkyl or heterocycloalkyl optionally substituted with one or more $R_{13}$; or when $R_{12}$ is cycloalkyl or heterocycloalkyl, two $R_{10}$ together with the atom to which they are attached form a ($C_3$-$C_8$) spirocycloalkyl or a spiroheterocycloalkyl optionally substituted with one or more $R_{13}$;

$R_{15}$ is —OH, —$NH_2$, —NH($C_1$-$C_6$) alkyl, —N(($C_1$-$C_6$) alkyl)$_2$, ($C_3$-$C_8$) cycloalkyl, heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —$NH_2$, —NH($C_1$-$C_6$) alkyl, —N(($C_1$-$C_6$) alkyl)$_2$, and oxo;

$R_{16}$ is —OH, —C(O)OH, —$NH_2$, —NH($C_1$-$C_6$) alkyl, —N(($C_1$-$C_6$) alkyl)$_2$, ($C_1$-$C_6$) alkoxy, ($C_1$-$C_6$) hydroxyalkyl, ($C_3$-$C_8$) cycloalkyl, heterocycloalkyl, —O—($C_3$-$C_8$) cycloalkyl, —O-heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —$NH_2$, —NH($C_1$-$C_6$) alkyl, —N(($C_1$-$C_6$) alkyl)$_2$, and oxo;

each m, o, p, q, and r is independently, at each occurrence, 0, 1, or 2; and n is 0 or 1.

In some embodiments of the Formulae above, Q is —$NR_5$—. In another embodiment, Q is —O—. In yet another embodiment, —O—, —N(CH$_3$)—, —N(H)—, or —N(C(O)NH$_2$)—. In another embodiment, Q is —NH— or —O—.

In some embodiments of the Formulae above, X$_1$ is CR$_6$, X$_2$ is CR$_7$, X$_3$ is CR$_8$, and X$_4$ is CR$_9$. In another embodiment, X$_1$ is N, X$_2$ is CR$_7$, X$_3$ is CR$_8$, and X$_4$ is CR$_9$. In yet another embodiment, X$_1$ is CR$_6$, X$_2$ is N, X$_3$ is CR$_8$, and X$_4$ is CR$_9$. In another embodiment, X$_1$ is CR$_6$, X$_2$ is CR$_7$, X$_3$ is N, and X$_4$ is CR$_9$. In yet another embodiment, X$_1$ is CR$_6$, X$_2$ is CR$_7$, X$_3$ is CR$_8$, and X$_4$ is N. In another embodiment, X$_1$ is N, X$_2$ is CR$_7$, X$_3$ is N, and X$_4$ is CR$_9$. In yet another embodiment, X$_1$ is N, X$_2$ is CR$_7$, X$_3$ is CR$_8$, and X$_4$ is N. In another embodiment, X$_1$ is CR$_6$, X$_2$ is N, X$_3$ is CR$_8$, and X$_4$ is N.

In some embodiments of the Formulae above, R$_1$ is H, (C$_1$-C$_4$) alkyl, (C$_1$-C$_4$) alkoxy, (C$_1$-C$_4$) haloalkyl, (C$_1$-C$_4$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$. In another embodiment, R$_1$ is H, (C$_1$-C$_4$) alkyl, (C$_1$-C$_4$) alkoxy, (C$_1$-C$_4$) haloalkyl, (C$_1$-C$_4$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy and —OH. In yet another embodiment, R$_1$ is H, —CH$_3$, —CH$_2$CH$_3$, —CH(CH$_3$)$_2$, F, Cl, —OCH$_3$, —OCH$_2$CH$_3$, —OCH(CH$_3$)$_2$, —OCH$_2$CH(CH$_3$)$_3$, —OCF$_3$, —OCH$_2$CF$_3$, —CH$_2$OCH$_3$, —SCH$_3$, —SCH$_2$CH$_3$, or —SCH(CH$_3$)$_2$, wherein each is optionally substituted with —OH. In another embodiment, R$_1$ is cyclopropyl, cyclobutyl, cyclopentyl, cyclohexyl, —O-cyclopropyl, —O-cyclobutyl, —O— cyclopentyl, or —O-cyclohexyl, wherein each is optionally substituted with —OH. In yet another embodiment, R$_1$ is

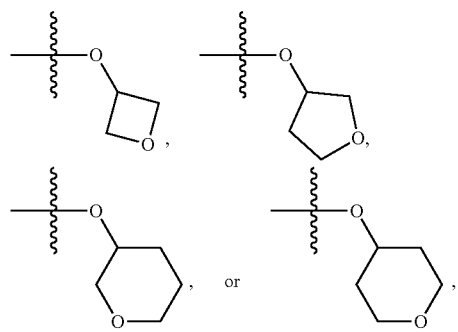

wherein each is optionally substituted with —OH.

In some embodiments of the Formulae above, R$_2$ is (C$_1$-C$_4$) alkyl, (C$_1$-C$_4$) alkoxy, (C$_1$-C$_4$) haloalkyl, or (C$_1$-C$_4$) haloalkoxy. In another embodiment, R$_2$ is (C$_1$-C$_2$) alkyl, (C$_1$-C$_2$) alkoxy, (C$_1$-C$_2$) haloalkyl, or (C$_1$-C$_2$) haloalkoxy. In yet another embodiment, R$_2$ is methyl, ethyl, methoxy, ethoxy, trifluoroalkyl, or trifluoroalkoxy. In another embodiment, R$_2$ is methyl or ethyl. In yet another embodiment, R$_2$ is methyl.

In some embodiments of the Formulae above, R$_{2'}$ is (C$_1$-C$_4$) alkyl, (C$_1$-C$_4$) alkoxy, (C$_1$-C$_4$) haloalkyl, or (C$_1$-C$_4$) haloalkoxy. In another embodiment, R$_{2'}$ is (C$_1$-C$_2$) alkyl, (C$_1$-C$_2$) alkoxy, (C$_1$-C$_2$) haloalkyl, or (C$_1$-C$_2$) haloalkoxy. In yet another embodiment, Rr is methyl, ethyl, methoxy, ethoxy, trifluoroalkyl, or trifluoroalkoxy. In another embodiment, R$_2$ is methyl or ethyl. In yet another embodiment, R$_{2'}$ is methyl.

In another embodiment, R$_2$ and R$_{2'}$ together with the carbon atom to which they are attached form (C$_3$-C$_8$) cycloalkyl or heterocycloalkyl ring. In yet another embodiment, R$_2$ and Rr together with the carbon atom to which they are attached form cyclopropyl, cyclobutyl, cyclopentyl, oxetanyl, or furanyl ring. In another embodiment, R$_2$ and R$_{2'}$ together with the carbon atom to which they are attached form cyclopropyl or oxetanyl ring.

In some embodiments of the Formulae above, R$_3$ is (C$_1$-C$_4$) alkyl, (C$_1$-C$_4$) alkoxy, (C$_1$-C$_4$) haloalkyl, (C$_1$-C$_4$) haloalkoxy, halogen, —S(O)$_p$(C$_1$-C$_4$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents selected from halogen, (C$_1$-C$_4$) alkoxy, —OH, —NH$_2$, —NH(C$_1$-C$_4$) alkyl, and —N((C$_1$-C$_4$) alkyl)$_2$. In another embodiment, R$_3$ is (C$_1$-C$_4$) alkyl, (C$_1$-C$_4$) alkoxy, (C$_1$-C$_4$) haloalkyl, or (C$_1$-C$_4$) haloalkoxy, halogen, wherein the alkyl and alkoxy are optionally substituted with one or more substituents selected from (C$_1$-C$_4$) alkoxy, —OH, —NH$_2$, —NH(C$_1$-C$_4$) alkyl, and —N((C$_1$-C$_4$) alkyl)$_2$. In yet another embodiment, R$_3$ is halogen or (C$_1$-C$_4$) alkyl optionally substituted with one or more substituents selected from (C$_1$-C$_4$) alkoxy, —OH, —NH$_2$, —NH(C$_1$-C$_4$) alkyl, and —N((C$_1$-C$_4$) alkyl)$_2$. In another embodiment, R$_3$ is halogen or (C$_1$-C$_4$) alkyl. In yet another embodiment, R$_3$ is halogen.

In some embodiments of the Formulae above, R$_4$ is H, (C$_1$-C$_3$) alkyl, (C$_1$-C$_3$) alkoxy, (C$_1$-C$_3$) haloalkyl, (C$_1$-C$_3$) haloalkoxy, (C$_1$-C$_3$) hydroxyalkyl, (C$_1$-C$_3$) aminoalkyl, halogen, (C$_3$-C$_8$) cycloalkyl, heterocycloalkyl, —OH, —NH$_2$, CN, —S(O)$_m$(C$_1$-C$_3$) alkyl, —NH(C$_1$-C$_3$) alkyl, or —N((C$_1$-C$_3$) alkyl)$_2$. In another embodiment, R$_4$ is H, (C$_1$-C$_3$) alkyl, (C$_1$-C$_3$) alkoxy, (C$_1$-C$_3$) haloalkyl, (C$_1$-C$_3$) haloalkoxy, (C$_1$-C$_3$) hydroxyalkyl, (C$_1$-C$_3$) aminoalkyl, halogen, —OH, —NH$_2$, CN, —S(O)$_o$(C$_1$-C$_3$) alkyl, —NH(C$_1$-C$_3$) alkyl, or —N((C$_1$-C$_3$) alkyl)$_2$. In yet another embodiment, R$_4$ is H, (C$_1$-C$_3$) alkyl, (C$_1$-C$_3$) haloalkyl, halogen, or —S(O)$_o$(C$_1$-C$_3$) alkyl. In another embodiment, R$_4$ is H, methyl, ethyl, n-propyl, iso-propyl, trifluoromethyl, F, Cl, or —S(O)$_2$CH$_3$.

In some embodiments of the Formulae above, R$_5$ is H, (C$_1$-C$_3$) alkyl, —C(O)NR$_{10}$R$_{11}$, —C(O)(C$_1$-C$_3$) alkyl, or —C(O)O(C$_1$-C$_3$) alkyl. In another embodiment, R$_5$ is H, (C$_1$-C$_3$) alkyl, or —C(O)NR$_{10}$R$_{11}$. In another embodiment, R$_5$ is H, methyl, ethyl, n-propyl, iso-propyl, or —C(O)NR$_{10}$R$_{11}$.

In some embodiments of the Formulae above, R$_6$ is H, (C$_1$-C$_3$) alkyl, (C$_1$-C$_3$) alkoxy, (C$_1$-C$_3$) haloalkyl, (C$_1$-C$_3$) haloalkoxy, (C$_1$-C$_3$) hydroxyalkyl, (C$_1$-C$_3$) aminoalkyl, halogen, (C$_3$-C$_8$) cycloalkyl, heterocycloalkyl, —OH, —NH$_2$, CN, —S(O)$_o$(C$_1$-C$_3$) alkyl, —NH(C$_1$-C$_3$) alkyl, or —N((C$_1$-C$_3$) alkyl)$_2$. In another embodiment, R$_6$ is H, (C$_1$-C$_3$) alkyl, (C$_1$-C$_3$) alkoxy, (C$_1$-C$_3$) haloalkyl, (C$_1$-C$_3$) haloalkoxy, (C$_1$-C$_3$) hydroxyalkyl, (C$_1$-C$_3$) aminoalkyl, halogen, —OH, —NH$_2$, CN, —S(O)$_o$(C$_1$-C$_3$) alkyl, —NH(C$_1$-C$_3$) alkyl, or —N((C$_1$-C$_3$) alkyl)$_2$. In yet another embodiment, R$_6$ is H, (C$_1$-C$_3$) alkyl, (C$_1$-C$_3$) haloalkyl, halogen, or —S(O)$_o$(C$_1$-C$_3$) alkyl. In another embodiment, R$_6$ is H, methyl, ethyl, n-propyl, iso-propyl, trifluoromethyl, F, Cl, or —S(O)$_2$CH$_3$. In yet another embodiment, R$_6$ is H.

In some embodiments of the Formulae above, R$_7$ is H, (C$_1$-C$_8$) alkenyl, (C$_1$-C$_8$) alkynyl, (C$_1$-C$_6$) alkoxy, (C$_1$-C$_6$)

haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, $(C_3-C_8)$ cycloalkenyl, heterocycloalkyl, —OH, —NH$_2$, CN, or $(C_1-C_{18})$ alkyl, wherein 0 to 7 methylene of the $(C_1-C_{18})$ alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one to eight R$_{12}$, and wherein the cycloalkyl and cycloalkenyl are optionally substituted with one to eight R$_{13}$.

In some embodiments of the Formulae above, R$_8$ is H, $(C_1-C_8)$ alkenyl, $(C_1-C_8)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, $(C_3-C_8)$ cycloalkenyl, heterocycloalkyl, —OH, —NH$_2$, CN, or $(C_1-C_{18})$ alkyl, wherein 0 to 7 methylene of the $(C_1-C_{18})$ alkyl is optionally replaced by a moiety selected from the group consisting of —O—, —NR$_{13}$—, —S(O)$_q$—, —C(O)—, —C(CH$_2$)—, or —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one to eight R$_{12}$, and wherein the cycloalkyl and cycloalkenyl are optionally substituted with one to eight R$_{13}$.

In some embodiments of the Formulae above, R$_9$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, $(C_1-C_3)$ aminoalkyl, halogen, $(C_3-C_8)$ cycloalkyl, heterocycloalkyl, —OH, —NH$_2$, CN, —S(O)$_o$($C_1-C_3$) alkyl, —NH($C_1-C_3$) alkyl, or —N(($C_1-C_3$) alkyl)$_2$. In another embodiment, R$_9$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, $(C_1-C_3)$ aminoalkyl, halogen, —OH, —NH$_2$, CN, —S(O)$_o$($C_1-C_3$) alkyl, —NH($C_1-C_3$) alkyl, or —N(($C_1-C_3$) alkyl)$_2$. In yet another embodiment, R$_9$ is H, $(C_1-C_3)$ alkyl, $(C_1-C_3)$ haloalkyl, halogen, or —S(O)$_o$($C_1-C_3$) alkyl. In another embodiment, R$_9$ is H, methyl, ethyl, n-propyl, iso-propyl, trifluoromethyl, F, Cl, or —S(O)$_2$CH$_3$. In yet another embodiment, R$_9$ is H or $C_1$.

In some embodiments of the Formulae above, R$_{10}$ is H or $(C_1-C_6)$ alkyl optionally substituted with one or more OH. In another embodiment, R$_{10}$ is H.

In some embodiments of the Formulae above, R$_{11}$ is H or $(C_1-C_6)$ alkyl optionally substituted with one or more OH. In another embodiment, R$_{11}$ is H.

In some embodiments of the Formulae above, R$_{12}$ is —OH, —NH$_2$, —NH($C_1-C_6$) alkyl, —N(($C_1-C_6$) alkyl)$_2$, —C(O)OH, $(C_3-C_8)$ cycloalkyl, heterocycloalkyl, $(C_6-C_{10})$ aryl, or heteroaryl, wherein the cycloalkyl, heterocycloalkyl, aryl, and heteroaryl are optionally substituted with one to six substituents selected from —OH, —NH$_2$, —NH($C_1-C_6$) alkyl, —N(($C_1-C_6$) alkyl)$_2$, and R$_{14}$.

In some embodiments of the Formulae above, R$_{13}$ is H, $(C_3-C_8)$ cycloalkyl, heterocycloalkyl, $(C_6-C_{10})$ aryl, heteroaryl, or $(C_1-C_{12})$ alkyl, wherein 0 to 7 methylene of the $(C_1-C_{12})$ alkyl is optionally replaced by a moiety selected from the group consisting of —O—, —NR$_{13}$—, —S(O)$_r$—, —C(O)—, or —C(NH)—, provided that a when any two methylene in the alkyl is replaced, then O and N are not contiguous and wherein the alkyl is optionally substituted with one to eight R$_{15}$, and wherein the cycloalkyl, heterocycloalkyl, aryl, and heteroaryl are optionally substituted with one to eight substituents selected from —OH, —C(O)OH, —NH$_2$, —NH($C_1-C_6$) alkyl, and —N(($C_1-C_6$) alkyl)$_2$.

In some embodiments of the Formulae above, R$_{10}$ is $(C_3-C_8)$ cycloalkyl, heterocycloalkyl, —O—$(C_3-C_8)$ cycloalkyl, —O-heterocycloalkyl, $(C_1-C_{12})$ alkyl or $(C_2-C_{12})$ alkenyl, wherein 0 to 7 methylene of the $(C_1-C_{12})$ alkyl and the $(C_2-C_{12})$ alkenyl are optionally replaced by a moiety selected from the group consisting of —O—, —NR$_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one to eight R$_{15}$, and the cycloalkyl and heterocycloalkyl are optionally substituted with one to eight R$_{16}$.

In some embodiments of the Formulae above, when R$_{12}$ is cycloalkyl or heterocycloalkyl, two R$_{14}$ together with the atom to which they are attached form C=(O). In another embodiment, two R$_{14}$ together with the atoms to which they are attached form a $(C_3-C_8)$ cycloalkyl or heterocycloalkyl optionally substituted with one or six R$_{13}$. In yet another embodiment, when R$_{12}$ is cycloalkyl or heterocycloalkyl, two R$_{14}$ together with the atom to which they are attached form a $(C_3-C_8)$ spirocycloalkyl or a spiroheterocycloalkyl optionally substituted with one or six R$_{13}$.

In some embodiments of the Formulae above, R$_{15}$ is —OH, —NH$_2$, —NH($C_1-C_6$) alkyl, —N(($C_1-C_6$) alkyl)$_2$, $(C_3-C_8)$ cycloalkyl, heterocycloalkyl, $(C_6-C_{10})$ aryl or heteroaryl, wherein the $(C_3-C_8)$ cycloalkyl and heterocycloalkyl are optionally substituted with one to eight substituents selected from $(C_1-C_6)$ hydroxyalkyl, $(C_1-C_6)$ aminoalkyl, —C(O)OH, —OH, —NH$_2$, —NH($C_1-C_6$) alkyl, —N(($C_1-C_6$) alkyl)$_2$, and oxo.

In some embodiments of the Formulae above, R$_{16}$ is —OH, —C(O)OH, —NH$_2$, —NH($C_1-C_6$) alkyl, —N(($C_1-C_6$) alkyl)$_2$, $(C_1-C_6)$ alkoxy, $(C_1-C_6)$ hydroxyalkyl, $(C_3-C_8)$ cycloalkyl, heterocycloalkyl, —O—$(C_3-C_8)$ cycloalkyl, —O-heterocycloalkyl, $(C_6-C_{10})$ aryl or heteroaryl, wherein the $(C_3-C_8)$ cycloalkyl and heterocycloalkyl are optionally substituted with one to eight substituents selected from $(C_1-C_6)$ hydroxyalkyl, $(C_1-C_6)$ aminoalkyl, —C(O)OH, —OH, —NH$_2$, —NH($C_1-C_6$) alkyl, —N(($C_1-C_6$) alkyl)$_2$, and oxo.

In some embodiments of the Formulae above, m is 0 or 1. In yet another embodiment, m is 1 or 2. In another embodiment, m is 0. In yet another embodiment, m is 1. In another embodiment, m is 2.

In some embodiments of the Formulae above, o is 0 or 1. In yet another embodiment, o is 1 or 2. In another embodiment, o is 0. In yet another embodiment, o is 1. In another embodiment, o is 2.

In some embodiments of the Formulae above, p is 0 or 1. In yet another embodiment, p is 1 or 2. In another embodiment, p is 0. In yet another embodiment, p is 1. In another embodiment, p is 2.

In some embodiments of the Formulae above, q is 0 or 1. In yet another embodiment, q is 1 or 2. In another embodiment, q is 0. In yet another embodiment, q is 1. In another embodiment, q is 2.

In some embodiments of the Formulae above, r is 0 or 1. In yet another embodiment, r is 1 or 2. In another embodiment, r is 0. In yet another embodiment, r is 1. In another embodiment, r is 2.

In some embodiments of the Formulae above, n is 0 or 1. In yet another embodiment, n is 1 or 2. In another embodiment, n is 0. In yet another embodiment, n is 1. In another embodiment, n is 2.

In some embodiments of the Formulae above, $X_1$ is $CR_6$ and $R_6$ is H or halogen.

In some embodiments of the Formulae above, $X_2$ is $CR_9$ and $R_9$ is H or halogen.

In some embodiments of the Formulae above, $X_2$ is N.

In some embodiments of the Formulae above, $X_3$ is $CR_7$.

In some embodiments of the Formulae above, $X_4$ is N.

In some embodiments of the Formulae above, $X_4$ is $CR_8$.

In some embodiments of the Formulae above, Q is —NH— or —O—.

In some embodiments of the Formulae above, Q is —NH— or —O— and $Q_1$ is —$CH_2$—.

In some embodiments of the Formulae above, Q is C=(O) and $Q_1$ is —$NR_5$—.

In some embodiments of the Formulae above, Q is $CH_2$— and $Q_1$ is —$O(CH_2)_{0-1}$— or —$NR_5$—.

In some embodiments of the Formulae above, Q is $CH_2$— and $Q_1$ is —$O(CH_2)_{0-1}$—. In another embodiment, Q is $CH_2$— and $Q_1$ is —$O(CH_2)$—. In another embodiment, Q is $CH_2$— and $Q_1$ is —$O(CH_2)$—.

In some embodiments of the Formulae above, Q is $CH_2$— and $Q_1$ is —$NR_5$—.

In some embodiments of the Formulae above, $R_2$ and $R_{2'}$ together with the carbon atom to which they are attached form ($C_3$-$C_8$) cycloalkyl or heterocycloalkyl.

In some embodiments of the Formulae above, $R_2$ is methyl.

In some embodiments of the Formulae above, $R_{2'}$ is methyl.

In some embodiments of the Formulae above, $R_3$ is halogen.

In some embodiments of the Formulae above, $X_1$ is $CR_6$ and $R_6$ is H or halogen.

In some embodiments of the Formulae above, $X_2$ is $CR_9$ and $R_9$ is H or halogen.

In some embodiments of the Formulae above, $X_2$ is N.

In some embodiments of the Formulae above, $X_3$ is $CR_7$.

In some embodiments of the Formulae above, $X_4$ is N.

In some embodiments of the Formulae above, $X_4$ is $CR_8$.

In some embodiments of the Formulae above, n is 1.

In some embodiments of the Formulae above, n is 0.

In some embodiments of the Formulae above, $R_2$ is H and $R_{2'}$ is H.

In some embodiments of the Formulae above, $R_2$ is H and $R_{2'}$ is ($C_1$-$C_6$) alkyl.

In some embodiments of the Formulae above, $R_2$ is H and $R_{2'}$ is methyl.

In some embodiments of the Formulae above, $R_2$ is ($C_1$-$C_6$) alkyl and $R_{2'}$ is H.

In some embodiments of the Formulae above, $R_2$ is methyl and $R_{2'}$ is H.

In some embodiments of the Formulae above, $R_2$ is ($C_1$-$C_6$) alkyl and Rr is ($C_1$-$C_6$) alkyl.

In some embodiments of the Formulae above, $R_2$ is ($C_1$-$C_6$) alkyl and Rr is ($C_1$-$C_3$) alkyl.

In some embodiments of the Formulae above, $R_2$ is methyl and $R_{2'}$ is methyl.

In some embodiments of the Formulae above, Y is $CR_b$. In another embodiment, Y is N. In another embodiment, Y is CH or N. In another embodiment, Y is CH. In another embodiment, Y is N.

In some embodiments of the Formulae above, $R_a$ is H, ($C_1$-$C_4$) alkyl, ($C_1$-$C_4$) alkoxy, ($C_1$-$C_4$) haloalkyl, ($C_1$-$C_4$) haloalkoxy, or halogen. In another embodiment, $R_a$ is H, ($C_1$-$C_4$) alkyl, or ($C_1$-$C_4$) alkoxy. In another embodiment, $R_a$ is H, ($C_1$-$C_3$) alkyl, or ($C_1$-$C_3$) alkoxy. In another embodiment, $R_a$ is ($C_1$-$C_3$) alkyl, or ($C_1$-$C_3$) alkoxy. In another embodiment, $R_a$ is ($C_1$-$C_3$) alkyl. In another embodiment, $R_a$ is H or ($C_1$-$C_3$) alkyl. In another embodiment, $R_a$ is H.

In some embodiments of the Formulae above, $R_b$ is H, ($C_1$-$C_4$) alkyl, ($C_1$-$C_4$) alkoxy, ($C_1$-$C_4$) haloalkyl, ($C_1$-$C_4$) haloalkoxy, or halogen. In another embodiment, $R_b$ is H, ($C_1$-$C_4$) alkyl, or ($C_1$-$C_4$) alkoxy. In another embodiment, $R_b$ is H, ($C_1$-$C_3$) alkyl, or ($C_1$-$C_3$) alkoxy. In another embodiment, $R_b$ is ($C_1$-$C_3$) alkyl, or ($C_1$-$C_3$) alkoxy. In another embodiment, $R_b$ is ($C_1$-$C_3$) alkoxy. In another embodiment, $R_b$ is H or ($C_1$-$C_3$) alkoxy. In another embodiment, $R_b$ is H.

In some embodiments of the Formulae above, $R_1$ and $R_a$ together with the carbon atoms to which they are attached form a heterocycloalkyl. In another embodiment, $R_1$ and $R_a$ together with the carbon atoms to which they are attached form a 5- to 7-membered heterocycloalkyl comprising 1 to 3 heteroatoms selected from N, O or S.

In some embodiments of the Formulae above, $R_1$ and $R_3$ together with the carbon atoms to which they are attached form a heterocycloalkyl optionally substituted with one or more substituents selected from ($C_1$-$C_6$) alkyl, ($C_1$-$C_6$) alkoxy, ($C_1$-$C_6$) haloalkyl, ($C_1$-$C_6$) haloalkoxy, and halogen. In another embodiment, $R_1$ and $R_3$, when on adjacent carbon atom, together with the carbon atoms to which they are attached form a heterocycloalkyl optionally substituted with one or more substituents selected from ($C_1$-$C_6$) alkyl, ($C_1$-$C_6$) alkoxy, ($C_1$-$C_6$) haloalkyl, ($C_1$-$C_6$) haloalkoxy, and halogen. In another embodiment, $R_1$ and $R_3$, when on adjacent carbon atom, together with the carbon atoms to which they are attached form a 5- to 7-membered heterocycloalkyl comprising 1 to 3 heteroatoms selected from N, O or S and optionally substituted with one or more substituents selected from ($C_1$-$C_6$) alkyl, ($C_1$-$C_6$) alkoxy, ($C_1$-$C_6$) haloalkyl, ($C_1$-$C_6$) haloalkoxy, and halogen. In another embodiment, $R_1$ and $R_3$, when on adjacent carbon atom, together with the carbon atoms to which they are attached form a 5- to 7-membered heterocycloalkyl comprising 1 to 3 heteroatoms selected from N, O or S and optionally substituted with halogen.

In some embodiments of the Formulae above, $R_{12}$ is D, —OH, halogen, —$NH_2$, —NH($C_1$-$C_6$) alkyl, —N(($C_1$-$C_6$) alkyl)$_2$, —C(O)OH, —OC(O)($C_1$-$C_6$) alkyl, ($C_3$-$C_8$) cycloalkyl, heterocycloalkyl, ($C_6$-$C_{10}$) aryl, heteroaryl, or $R_{17}$, wherein the cycloalkyl, heterocycloalkyl, aryl, and heteroaryl are optionally substituted with one or more substituents selected from —OH, —$NH_2$, —NH($C_1$-$C_6$) alkyl, —N(($C_1$-$C_6$) alkyl)$_2$, halogen, and $R_{14}$.

In some embodiments of the Formulae above, $R_{13}$ is H, —OH, ($C_3$-$C_8$) cycloalkyl, heterocycloalkyl, ($C_6$-$C_{10}$) aryl, heteroaryl, or ($C_1$-$C_{12}$) alkyl, wherein 0 to 7 methylene of the ($C_1$-$C_{12}$) alkyl is optionally replaced by a moiety selected from the group consisting of —O—, —$NR_{13}$—, —$S(O)_r$—, —C(O)—, or —C(NH)—, provided that a when any two methylene in the alkyl is replaced, then O and N, are not contiguous and wherein the alkyl is optionally substituted with one or more $R_{15}$, and wherein the cycloalkyl, heterocycloalkyl, aryl, and heteroaryl are optionally substituted with one or more substituents selected from —OH, —C(O)OH, —$NH_2$, —NH($C_1$-$C_6$) alkyl, and —N(($C_1$-$C_6$) alkyl)$_2$.

In some embodiments of the Formulae above, when $R_{12}$ is cycloalkyl or heterocycloalkyl, two $R_{14}$ together with the atom to which they are attached form a ($C_6$-$C_{10}$) aryl or heteroaryl optionally substituted with one or more $R_{13}$. In another embodiment, when $R_{12}$ is cycloalkyl or heterocycloalkyl, two $R_{14}$ together with the atom to which they are attached form a ($C_6$-$C_{10}$) aryl optionally substituted with one or more $R_{13}$. In another embodiment, when $R_{12}$ is cycloalkyl or heterocycloalkyl, two $R_{10}$ together with the atom to which they are attached form a 5- to 12-membered heteroaryl comprising 1 to 3 heteroatoms selected from N, O or S optionally substituted with one or more $R_{13}$. In another embodiment, when $R_{12}$ is cycloalkyl or heterocycloalkyl, two $R_{14}$ together with the atom to which they are attached form a 5- to 7-membered heteroaryl comprising 1 to 3 heteroatoms selected from N, O or S optionally substituted with one or more $R_{13}$. In another embodiment, when $R_{12}$ is cycloalkyl or heterocycloalkyl, two $R_{10}$ together with the atom to which they are attached form a 5- or 6-membered heteroaryl comprising 1 to 3 heteroatoms selected from N, O or S optionally substituted with one or more $R_{13}$.

In some embodiments of the Formulae above, $R_{17}$ is $(C_1-C_{18})$ alkyl or $(C_2-C_{18})$ alkenyl, wherein 0 to 8 methylene of the $(C_1-C_{18})$ alkyl and the $(C_2-C_{18})$ alkenyl are optionally replaced by a moiety selected from the group consisting of —O—, —$NR_{13}$—, —S(O)$_r$—, —C(O)—, or —C(NH)—, provided that a when any two methylene in the alkyl or alkenyl is replaced, then O and N are not contiguous and wherein the alkyl and alkenyl are optionally substituted with one or more $R_{18}$.

In some embodiments of the Formulae above, $R_{18}$ is $R_{19}$, $(C_6-C_{10})$ aryl, or heteroaryl optionally substituted with one or more $R_{21}$.

In some embodiments of the Formulae above, Rig is $(C_1-C_{18})$ alkyl wherein 0 to 8 methylene of the $(C_1-C_{18})$ alkyl is optionally replaced by a moiety selected from the group consisting of —O—, —$NR_{13}$—, —S(O)$_r$—, —C(O)—, or —C(NH)—, provided that a when any two methylene in the alkyl or alkenyl is replaced, then O and N are not contiguous and wherein the alkyl is optionally substituted with one or more $R_{20}$.

In some embodiments of the Formulae above, $R_{20}$ is $(C_6-C_{10})$ aryl or heteroaryl optionally substituted with one or more $R_{21}$.

In some embodiments of the Formulae above, $R_{21}$ is H, $(C_1-C_6)$ alkyl, $(C_1-C_6)$ alkoxy, $(C_1-C_6)$ haloalkyl, $(C_1-C_6)$ haloalkoxy, or halogen; or two $R_{21}$ together when on adjacent atoms form a cycloalkyl or heterocycloalkyl optionally substituted with one or more $R_{22}$. In another embodiment, $R_{21}$ is H, $(C_1-C_6)$ alkyl, $(C_1-C_6)$ alkoxy, $(C_1-C_6)$ haloalkyl, $(C_1-C_6)$ haloalkoxy, or halogen; or two $R_{21}$ together when on adjacent atoms form a $(C_5-C_8)$ cycloalkyl or 5- to 8-membered heterocycloalkyl comprising 1 to 3 heteroatoms selected from O, N, or S, wherein the cycloalkyl or heterocycloalkyl is optionally substituted with one or more $R_{22}$. In another embodiment, $R_{21}$ is H, $(C_1-C_6)$ alkyl, $(C_1-C_6)$ alkoxy, $(C_1-C_6)$ haloalkyl, $(C_1-C_6)$ haloalkoxy, or halogen. In another embodiment, two $R_{21}$ together when on adjacent atoms form a $(C_5-C_8)$ cycloalkyl or 5- to 8-membered heterocycloalkyl comprising 1 to 3 heteroatoms selected from O, N, or S, wherein the cycloalkyl or heterocycloalkyl is optionally substituted with one or more $R_{22}$. In another embodiment, two $R_{21}$ together when on adjacent atoms form a $(C_5-C_8)$ cycloalkyl optionally substituted with one or more $R_{22}$. In another embodiment, two $R_{21}$ together when on adjacent atoms form a 5- to 8-membered heterocycloalkyl comprising 1 to 3 heteroatoms selected from O, N, or S, optionally substituted with one or more $R_{22}$.

In some embodiments of the Formulae above, $R_{22}$ is —C(O)$NH_2$, —C(O)NH$(C_1-C_6)$ alkyl, —C(O)N$((C_1-C_6)$ alkyl)$_2$, —C(O) $(C_3-C_7)$ cycloalkyl, or —C(O)heterocycloalkyl, wherein the cycloalkyl and heterocycloalkyl are optionally substituted with one or more substituents independently selected from —OH and CN. In another embodiment, $R_{22}$ is —C(O)N$((C_1-C_6)$ alkyl)$_2$, —C(O) $(C_3-C_7)$ cycloalkyl, or —C(O)heterocycloalkyl, wherein the cycloalkyl and heterocycloalkyl are optionally substituted with one or more substituents independently selected from —OH and CN. In another embodiment, $R_{22}$ is —C(O)heterocycloalkyl optionally substituted with one or more substituents independently selected from —OH and CN.

In some embodiments of the Formulae above,

Q is —$NR_5$— or —O—;

$Q_1$ is —$CH_2$—;

$X_1$ is $CR_6$ or N;

$X_2$ is $CR_7$ or N;

$X_3$ is $CR_8$ or N;

$X_4$ is $CR_9$ or N;

Y is CH;

$R_a$ is H;

$R_1$ is H, $(C_1-C_6)$ alkyl, $(C_1-C_6)$ alkoxy, $(C_1-C_6)$ haloalkyl, $(C_1-C_6)$ haloalkoxy, halogen, —S(O)$_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —$NH_2$, —NH$(C_1-C_4)$ alkyl, and —N$((C_1-C_4)$ alkyl)$_2$;

$R_2$ and $R_{2'}$ are each independently $(C_1-C_6)$ alkyl, $(C_1-C_6)$ alkoxy, $(C_1-C_6)$ haloalkyl, or $(C_1-C_6)$ haloalkoxy; or $R_2$ and $R_{2'}$ together with the carbon atom to which they are attached form $(C_3-C_8)$ cycloalkyl or heterocycloalkyl;

each $R_3$ is independently, at each occurrence, $(C_1-C_6)$ alkyl, $(C_1-C_6)$ alkoxy, $(C_1-C_6)$ haloalkyl, $(C_1-C_6)$ haloalkoxy, halogen, —S(O)$_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —$NH_2$, —NH$(C_1-C_4)$ alkyl, and —N$((C_1-C_4)$ alkyl)$_2$;

$R_4$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —$NH_2$, CN, —S(O)$_m(C_1-C_6)$ alkyl, —NH$(C_1-C_4)$ alkyl, or —N$((C_1-C_4)$ alkyl)$_2$;

$R_5$ is H, $(C_1-C_6)$ alkyl, —C(O)$NR_{10}R_{11}$, —C(O)$(C_1-C_6)$ alkyl, or —C(O)O$(C_1-C_6)$ alkyl;

each $R_6$ and $R_9$ is independently H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —$NH_2$, CN, —S(O)$_o(C_1-C_6)$ alkyl, —NH$(C_1-C_4)$ alkyl, or —N$((C_1-C_4)$ alkyl)$_2$;

each $R_7$ and $R_8$ is independently H, $(C_1-C_8)$ alkenyl, $(C_1-C_8)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, $(C_3-C_8)$ cycloalkenyl, heterocycloalkyl, —OH, —$NH_2$, —S(O)$_q$ $NH_2$, —S(O)$_q$OH, CN, or $(C_1-C_{18})$ alkyl, wherein 0 to 7 methylene of the $(C_1-C_{18})$ alkyl is optionally replaced by a moiety selected from the group consisting of —O—, —$NR_{13}$—, —S(O)$_q$—, —C(O)—, —C(CH$_2$)—, or —C(NH)—, provided that when any two methylene in the alkyl is replaced, then two —O—, two —S(O)$_q$—, or two —$NR_{13}$— and —O— and —$NR_{13}$— are not contiguous, wherein the alkyl is optionally substituted with one or more $R_{12}$, and wherein the cycloalkyl and cycloalkenyl are optionally substituted with one or more $R_{13}$;

$R_{10}$ and $R_{11}$ are each independently H or $(C_1-C_6)$ alkyl optionally substituted with one or more substituent independently selected from —$NH_2$ and OH;

$R_{12}$ is —OH, —$NH_2$, —$NH(C_1-C_6)$ alkyl, —$N((C_1-C_6)$ alkyl$)_2$, —C(O)OH, $(C_3-C_8)$ cycloalkyl, heterocycloalkyl, $(C_6-C_{10})$ aryl, or heteroaryl, wherein the cycloalkyl, heterocycloalkyl, aryl, and heteroaryl are optionally substituted with one or more substituents selected from —OH, —$NH_2$, —$NH(C_1-C_6)$ alkyl, —$N((C_1-C_6)$ alkyl$)_2$, and $R_{10}$;

$R_{13}$ is H, $C_3-C_8)$ cycloalkyl, heterocycloalkyl, $(C_6-C_{10})$ aryl, heteroaryl, or $(C_1-C_{12})$ alkyl, wherein 0 to 7 methylene of the $(C_1-C_{12})$ alkyl is optionally replaced by a moiety selected from the group consisting of —O—, —$NR_{13}$—, —$S(O)_r$—, —C(O)—, or —C(NH)—, provided that a when any two methylene in the alkyl is replaced, then O and N, are not contiguous and wherein the alkyl is optionally substituted with one or more $R_{15}$, and wherein the cycloalkyl, heterocycloalkyl, aryl, and heteroaryl are optionally substituted with one or more substituents selected from —OH, —C(O)OH, —$NH_2$, —$NH(C_1-C_6)$ alkyl, and —$N((C_1-C_6)$ alkyl$)_2$;

$R_{14}$ is $(C_3-C_8)$ cycloalkyl, heterocycloalkyl, —O—$(C_3-C_8)$ cycloalkyl, —O-heterocycloalkyl, $(C_1-C_{12})$ alkyl or $(C_2-C_{12})$ alkenyl, wherein 0 to 7 methylene of the $(C_1-C_{12})$ alkyl and the $(C_2-C_{12})$ alkenyl are optionally replaced by a moiety selected from the group consisting of —O—, —$NR_{13}$—, —$S(O)_r$—, —C(O)—, or —C(NH)—, provided that a when any two methylene in the alkyl or alkenyl is replaced, then O and N are not contiguous and wherein the alkyl and alkenyl are optionally substituted with one or more $R_{15}$, and the cycloalkyl and heterocycloalkyl are optionally substituted with one or more $R_{16}$; or when $R_{12}$ is cycloalkyl or heterocycloalkyl, two $R_{14}$ together with the atom to which they are attached form C═(O); or when $R_{12}$ is cycloalkyl or heterocycloalkyl, two $R_{14}$ together with the atoms to which they are attached form a $(C_3-C_8)$ cycloalkyl or heterocycloalkyl optionally substituted with one or more $R_{13}$; or when $R_{12}$ is cycloalkyl or heterocycloalkyl, two $R_{10}$ together with the atom to which they are attached form a $(C_3-C_8)$ spirocycloalkyl or a spiroheterocycloalkyl optionally substituted with one or more $R_{13}$;

$R_{15}$ is —OH, —$NH_2$, —$NH(C_1-C_6)$ alkyl, —$N((C_1-C_6)$ alkyl$)_2$, $(C_3-C_8)$ cycloalkyl, heterocycloalkyl, $(C_6-C_{10})$ aryl or heteroaryl, wherein the $(C_3-C_8)$ cycloalkyl and heterocycloalkyl are optionally substituted with one or more substituents selected from $(C_1-C_6)$ hydroxyalkyl, $(C_1-C_6)$ aminoalkyl, —C(O)OH, —OH, —$NH_2$, —NH$(C_1-C_6)$ alkyl, —$N((C_1-C_6)$ alkyl$)_2$, and oxo;

$R_{16}$ is —OH, —C(O)OH, —$NH_2$, —$NH(C_1-C_6)$ alkyl, —$N((C_1-C_6)$ alkyl$)_2$, $(C_1-C_6)$ alkoxy, $(C_1-C_6)$ hydroxyalkyl, $(C_3-C_8)$ cycloalkyl, heterocycloalkyl, —O—$(C_3-C_8)$ cycloalkyl, —O-heterocycloalkyl, $(C_6-C_{10})$ aryl or heteroaryl, wherein the $(C_3-C_8)$ cycloalkyl and heterocycloalkyl are optionally substituted with one or more substituents selected from $(C_1-C_6)$ hydroxyalkyl, $(C_1-C_6)$ aminoalkyl, —C(O)OH, —OH, —$NH_2$, —NH$(C_1-C_6)$ alkyl, —$N((C_1-C_6)$ alkyl$)_2$, and oxo;

each m, o, p, q, and r is independently, at each occurrence, 0, 1, or 2; and n is 0, 1, or 2.

In some embodiments of the Formula (I'),

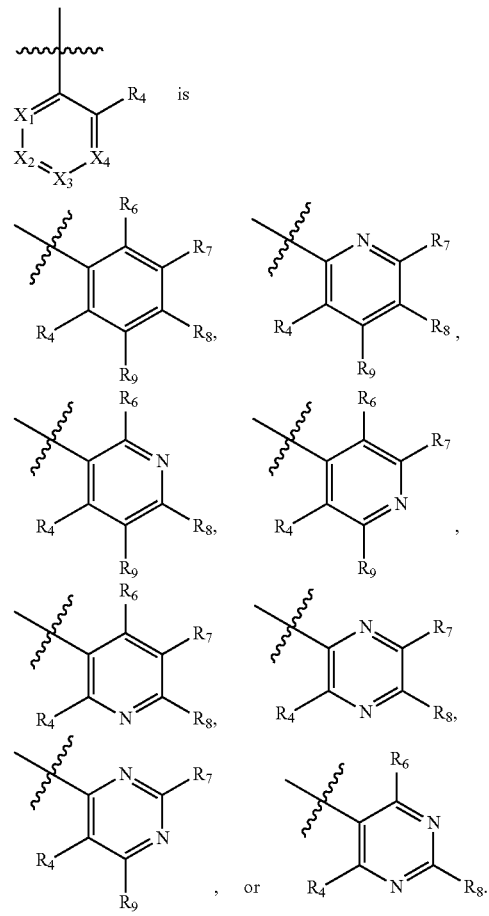

In some embodiments of the Formulae above, Q is O. In another embodiment, Q is O and $X_1$ is $CR_6$. In yet another embodiment, Q is O, $X_1$ is $CR_6$, and $X_2$ is $CR_7$. In another embodiment, Q is O, $X_1$ is $CR_6$, $X_2$ is $CR_7$, and $X_3$ is $CR_8$. In yet another embodiment, Q is O, $X_1$ is $CR_6$, $X_2$ is $CR_7$, $X_3$ is $CR_8$, and $X_4$ is $CR_9$. In another embodiment, Q is O, $X_1$ is $CR_6$, $X_2$ is $CR_7$, $X_3$ is $CR_8$, $X_4$ is $CR_9$ and $R_1$ is $(C_1-C_6)$ alkyl, $(C_1-C_6)$ alkoxy, $(C_1-C_6)$ haloalkoxy, halogen, —$S(O)_p$ $(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one to three —OH. In yet another embodiment, Q is O, $X_1$ is $CR_6$, $X_2$ is $CR_7$, $X_3$ is $CR_8$, $X_4$ is $CR_9$, $R_1$ is $(C_1-C_6)$ alkyl, $(C_1-C_6)$ alkoxy, $(C_1-C_6)$ haloalkoxy, halogen, —$S(O)_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one to three —OH, and $R_2$ and $R_{2'}$ are each independently $(C_1-C_6)$ alkyl. In another embodiment, Q is O, $X_1$ is $CR_6$, $X_2$ is $CR_7$, $X_3$ is $CR_8$, $X_4$ is $CR_9$, $R_1$ is $(C_1-C_6)$ alkyl, $(C_1-C_6)$ alkoxy, $(C_1-C_6)$ haloalkoxy, halogen, —$S(O)_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one to three —OH, $R_2$ and $R_{2'}$ are each independently $(C_1-C_6)$ alkyl, and $R_6$ is H.

In another embodiment, Q is O, $X_1$ is $CR_6$, $X_2$ is $CR_7$, $X_3$ is $CR_8$, $X_4$ is $CR_9$, $R_1$ is $(C_1-C_6)$ alkyl, $(C_1-C_6)$ alkoxy, $(C_1-C_6)$ haloalkoxy, halogen, —$S(O)_p(C_1-C_6)$ alkyl, $(C_3-C_8)$ cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ are each independently ($C_1$-$C_6$) alkyl, $R_6$ is H, and $R_9$ is H or halogen. In yet another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ are each independently ($C_1$-$C_6$) alkyl, $R_6$ is H, $R_9$ is H or halogen, and n is 0. In another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ are each independently ($C_1$-$C_6$) alkyl, $R_6$ is H, $R_9$ is H or halogen, n is 1 and $R_3$ is halogen.

In some embodiments of the Formulae above, Q is O. In another embodiment, Q is O and $X_1$ is $CR_6$. In yet another embodiment, Q is O, $X_1$ is $CR_6$, and $X_2$ is $CR_7$. In another embodiment, Q is O, $X_1$ is $CR_6$, $X_2$ is $CR_7$, and $X_3$ is $CR_8$. In yet another embodiment, Q is O, $X_1$ is $CR_6$, $X_2$ is $CR_7$, $X_3$ is $CR_8$, and $X_4$ is $CR_9$. In another embodiment, Q is O, $X_1$ is $CR_6$, $X_2$ is $CR_7$, $X_3$ is $CR_8$, $X_4$ is $CR_9$ and $R_1$ is ($C_1$-$C_6$) alkyl, ($C_1$-$C_6$) alkoxy, ($C_1$-$C_6$) haloalkoxy, halogen, —S(O)$_p$ ($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH. In yet another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, and $R_2$ and $R_{2'}$ together with the carbon atom to which they are attached form ($C_3$-$C_8$) cycloalkyl or heterocycloalkyl. In another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ together with the carbon atom to which they are attached form ($C_3$-$C_8$) cycloalkyl or heterocycloalkyl, and $R_6$ is H.

In another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ together with the carbon atom to which they are attached form ($C_3$-$C_8$) cycloalkyl or heterocycloalkyl, $R_6$ is H, and $R_9$ is H or halogen. In yet another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and Rr together with the carbon atom to which they are attached form ($C_3$-$C_8$) cycloalkyl or heterocycloalkyl, $R_6$ is H, $R_9$ is H or halogen, and n is 0. In another embodiment, Q is O, $X_1$ is $CR_6$, $X_2$ is $CR_7$, $X_3$ is $CR_8$, $X_4$ is $CR_9$, $R_1$ is ($C_1$-$C_6$) alkyl, ($C_1$-$C_6$) alkoxy, ($C_1$-$C_6$) haloalkoxy, halogen, —S(O)$_p$($C_1$-$C_6$) alkyl, ($C_3$-$C_8$) cycloalkyl, heterocycloalkyl, —O—($C_3$-$C_8$) cycloalkyl, or —O-heterocycloalkyl, wherein the alkyl, alkoxy, cycloalkyl, and heterocycloalkyl are optionally substituted with one to three —OH, $R_2$ and $R_{2'}$ together with the carbon atom to which they are attached form ($C_3$-$C_8$) cycloalkyl or heterocycloalkyl, $R_6$ is H, $R_9$ is H or halogen, n is 1 and $R_3$ is halogen.

In some embodiments of the Formulae above, Q is O. In another embodiment, Q is O and $X_1$ is $CR_6$. In yet another embodiment, Q is O, $X_1$ is $CR_6$, and $X_2$ is $CR_7$. In another embodiment, Q is O, $X_1$ is $CR_6$, $X_2$ is $CR_7$, and $X_3$ is $CR_8$. In yet another embodiment, Q is O, $X_1$ is $CR_6$, $X_2$ is $CR_7$, $X_3$ is $CR_8$, and $X_4$ is $CR_9$. In another embodiment, Q is O, $X_1$ is $CR_6$, $X_2$ is $CR_7$, $X_3$ is $CR_8$, $X_4$ is $CR_9$ and $R_1$ is —O—($C_3$-$C_8$) cycloalkyl or —O-heterocycloalkyl, wherein the cycloalkyl and heterocycloalkyl are optionally substituted with one to three —OH. In yet another embodiment, Q is O, $X_1$ is $CR_6$, $X_2$ is $CR_7$, $X_3$ is $CR_8$, $X_4$ is $CR_9$, $R_1$ is —O—($C_3$-$C_8$) cycloalkyl, or —O-heterocycloalkyl, wherein the cycloalkyl and heterocycloalkyl are optionally substituted with one to three —OH, and $R_2$ and $R_{2'}$ are each independently ($C_1$-$C_6$) alkyl. In another embodiment, Q is O, $X_1$ is $CR_6$, $X_2$ is $CR_7$, $X_3$ is $CR_8$, $X_4$ is $CR_9$, $R_1$ is —O—($C_3$-$C_8$) cycloalkyl, or —O-heterocycloalkyl, wherein the cycloalkyl and heterocycloalkyl are optionally substituted with one to three —OH, $R_2$ and $R_{2'}$ are each independently ($C_1$-$C_6$) alkyl, and $R_6$ is H.

In another embodiment, Q is O, $X_1$ is $CR_6$, $X_2$ is $CR_7$, $X_3$ is $CR_8$, $X_4$ is $CR_9$, $R_1$ is —O—($C_3$-$C_8$) cycloalkyl or —O-heterocycloalkyl, wherein the cycloalkyl and heterocycloalkyl are optionally substituted with one to three —OH, $R_2$ and $R_{2'}$ are each independently ($C_1$-$C_6$) alkyl, $R_6$ is H, and $R_9$ is H or halogen. In yet another embodiment, Q is O, $X_1$ is $CR_6$, $X_2$ is $CR_7$, $X_3$ is $CR_8$, $X_4$ is $CR_9$, $R_1$ is —O—($C_3$-$C_8$) cycloalkyl or —O-heterocycloalkyl, wherein the cycloalkyl and heterocycloalkyl are optionally substituted with one to three —OH, $R_2$ and $R_{2'}$ are each independently ($C_1$-$C_6$) alkyl, $R_6$ is H, $R_9$ is H or halogen, and n is 0. In another embodiment, Q is O, $X_1$ is $CR_6$, $X_2$ is $CR_7$, $X_3$ is $CR_8$, $X_4$ is $CR_9$, $R_1$ is —O—($C_3$-$C_8$) cycloalkyl or —O-heterocycloalkyl, wherein the cycloalkyl and heterocycloalkyl are optionally substituted with one to three —OH, $R_2$ and $R_{2'}$ are each independently ($C_1$-$C_6$) alkyl, $R_6$ is H, $R_9$ is H or halogen, n is 1 and $R_3$ is halogen.

In some embodiments of the Formulae above, Q is O. In another embodiment, Q is O and $X_1$ is $CR_6$. In yet another embodiment, Q is O, $X_1$ is $CR_6$, and $X_2$ is $CR_7$. In another embodiment, Q is O, $X_1$ is $CR_6$, $X_2$ is $CR_7$, and $X_3$ is $CR_8$. In yet another embodiment, Q is O, $X_1$ is $CR_6$, $X_2$ is $CR_7$, $X_3$ is $CR_8$, and $X_4$ is $CR_9$. In another embodiment, Q is O, $X_1$ is $CR_6$, $X_2$ is $CR_7$, $X_3$ is $CR_8$, $X_4$ is $CR_9$ and $R_1$ is —O—($C_3$-$C_8$) cycloalkyl or —O-heterocycloalkyl, wherein the cycloalkyl and heterocycloalkyl are optionally substituted with one to three —OH. In yet another embodiment, Q is O, $X_1$ is $CR_6$, $X_2$ is CRS, $X_3$ is $CR_8$, $X_4$ is $CR_9$, $R_1$ is —O—($C_3$-$C_8$) cycloalkyl or —O-heterocycloalkyl, wherein the cycloalkyl and heterocycloalkyl are optionally substituted with one to three —OH, and $R_2$ and $R_{2'}$ together with the carbon atom to which they are attached form ($C_3$-$C_8$) cycloalkyl or heterocycloalkyl. In another embodiment, Q is O, $X_1$ is $CR_6$, $X_2$ is CRS, $X_3$ is $CR_8$, $X_4$ is $CR_9$, $R_1$ is —O—($C_3$-$C_8$) cycloalkyl or —O-heterocycloalkyl, wherein the cycloalkyl and heterocycloalkyl are optionally substituted with one to three —OH, $R_2$ and $R_{2'}$ together with the carbon atom to which they are attached form $(C_3-C_8)$ cycloalkyl or heterocycloalkyl, and $R_6$ is H.

In another embodiment, Q is O, $X_1$ is $CR_6$, $X_2$ is $CR_7$, $X_3$ is $CR_8$, $X_4$ is $CR_9$, $R_1$ is —O—$(C_3-C_8)$ cycloalkyl, or —O-heterocycloalkyl, wherein the cycloalkyl and heterocycloalkyl are optionally substituted with one to three —OH, $R_2$ and $R_{2'}$ together with the carbon atom to which they are attached form $(C_3-C_8)$ cycloalkyl or heterocycloalkyl, $R_6$ is H, and $R_9$ is H or halogen.

In yet another embodiment, Q is O, $X_1$ is $CR_6$, $X_2$ is $CR_7$, $X_3$ is $CR_8$, $X_4$ is $CR_9$, $R_1$ is —O—$(C_3-C_8)$ cycloalkyl or —O-heterocycloalkyl, wherein the cycloalkyl and heterocycloalkyl are optionally substituted with one to three —OH, $R_2$ and $R_{2'}$ together with the carbon atom to which they are attached form $(C_3-C_8)$ cycloalkyl or heterocycloalkyl, $R_6$ is H, $R_9$ is H or halogen, and n is 0. In another embodiment, Q is O, $X_1$ is $CR_6$, $X_2$ is $CR_7$, $X_3$ is $CR_8$, $X_4$ is $CR_9$, $R_1$ is —O—$(C_3-C_8)$ cycloalkyl or —O-heterocycloalkyl, wherein the cycloalkyl and heterocycloalkyl are optionally substituted with one to three —OH, $R_2$ and $R_{2'}$ together with the carbon atom to which they are attached form $(C_3-C_8)$ cycloalkyl or heterocycloalkyl, $R_6$ is H, $R_9$ is H or halogen, n is 1 and $R_3$ is halogen.

In one embodiment of Formula (I') or Formula (I):

Q is —$NR_5$— or —O—;
$X_1$ is $CR_6$ or N;
$X_2$ is $CR_7$ or N;
$X_3$ is $CR_8$ or N;
$X_4$ is $CR_9$ or N;
$R_1$ is H, $(C_1-C_6)$ alkyl, $(C_1-C_6)$ alkoxy, $(C_1-C_6)$ haloalkyl, $(C_1-C_6)$ haloalkoxy, halogen, —$S(O)_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —$NH_2$, —$NH(C_1-C_4)$ alkyl, and —$N((C_1-C_4)$ alkyl)$_2$;
$R_2$ and $R_{2'}$, are each independently $(C_1-C_6)$ alkyl, $(C_1-C_6)$ alkoxy, $(C_1-C_6)$ haloalkyl, or $(C_1-C_6)$ haloalkoxy; or $R_2$ and $R_{2'}$ together with the carbon atom to which they are attached form $(C_3-C_8)$ cycloalkyl or heterocycloalkyl;
each $R_3$ is independently, at each occurrence, $(C_1-C_6)$ alkyl, $(C_1-C_6)$ alkoxy, $(C_1-C_6)$ haloalkyl, $(C_1-C_6)$ haloalkoxy, halogen, —$S(O)_p(C_1-C_6)$ alkyl, $(C_3-C_8)$ cycloalkyl, heterocycloalkyl, —O—$(C_3-C_8)$ cycloalkyl, or —O-heterocycloalkyl, wherein the alkyl, alkoxy, cycloalkyl, and heterocycloalkyl are optionally substituted with one or more substituents selected from halogen, $(C_1-C_4)$ alkoxy, —OH, —$NH_2$, —$NH(C_1-C_4)$ alkyl, and —$N((C_1-C_4)$ alkyl)$_2$;
$R_4$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —$NH_2$, CN, —$S(O)_m(C_1-C_6)$ alkyl, —$NH(C_1-C_4)$ alkyl, or —$N((C_1-C_4)$ alkyl)$_2$;
$R_5$ is H, $(C_1-C_6)$ alkyl, —$C(O)NR_{10}R_{11}$, —$C(O)(C_1-C_6)$ alkyl, or —$C(O)O(C_1-C_6)$ alkyl;
each $R_6$ and $R_9$ is independently H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, heterocycloalkyl, —OH, —$NH_2$, CN, —$S(O)_o(C_1-C_6)$ alkyl, —$NH(C_1-C_4)$ alkyl, or —$N((C_1-C_4)$ alkyl)$_2$;
each $R_7$ and $R_8$ is independently H, $(C_1-C_8)$ alkenyl, $(C_1-C_8)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_1-C_6)$ aminoalkyl, halogen, $(C_3-C_8)$ cycloalkyl, $(C_3-C_8)$ cycloalkenyl, heterocycloalkyl, —OH, —$NH_2$, —$S(O)_q NH_2$, —$S(O)_q OH$, CN, or $(C_1-C_{18})$ alkyl, wherein 0 to 7 methylene of the $(C_1-C_{18})$ alkyl is optionally replaced by a moiety selected from the group consisting of —O—, —$NR_{13}$—, —$S(O)_q$—, —C(O)—, —$C(CH_2)$—, or —C(NH)—, provided that when any two methylene in the alkyl is replaced, then two —O—, two —$S(O)_q$—, or two —$NR_{13}$— and —O— and —$NR_{13}$— are not contiguous, wherein the alkyl is optionally substituted with one or more $R_{12}$, and wherein the cycloalkyl and cycloalkenyl are optionally substituted with one or more $R_{13}$;
$R_{10}$ and $R_{11}$ are each independently H or $(C_1-C_6)$ alkyl optionally substituted with one or more substituent independently selected from —$NH_2$ and OH; $R_{12}$ is —OH, —$NH_2$, —$NH(C_1-C_6)$ alkyl, —$N((C_1-C_6)$ alkyl)$_2$, —C(O)OH, $(C_3-C_8)$ cycloalkyl, heterocycloalkyl, $(C_6-C_{10})$ aryl, or heteroaryl, wherein the cycloalkyl, heterocycloalkyl, aryl, and heteroaryl are optionally substituted with one or more substituents selected from —OH, —$NH_2$, —$NH(C_1-C_6)$ alkyl, —$N((C_1-C_6)$ alkyl)$_2$, and $R_{10}$;
$R_{13}$ is H, $(C_3-C_8)$ cycloalkyl, heterocycloalkyl, $(C_6-C_{10})$ aryl, heteroaryl, or $(C_1-C_{12})$ alkyl, wherein 0 to 7 methylene of the $(C_1-C_{12})$ alkyl is optionally replaced by a moiety selected from the group consisting of —O—, —$NR_{13}$—, —$S(O)_r$—, —C(O)—, or —C(NH)—, provided that a when any two methylene in the alkyl is replaced, then O and N, are not contiguous and wherein the alkyl is optionally substituted with one or more $R_{15}$, and wherein the cycloalkyl, heterocycloalkyl, aryl, and heteroaryl are optionally substituted with one or more substituents selected from —OH, —C(O)OH, —$NH_2$, —$NH(C_1-C_6)$ alkyl, and —$N((C_1-C_6)$ alkyl)$_2$;
$R_{14}$ is $(C_3-C_8)$ cycloalkyl, heterocycloalkyl, —O—$(C_3-C_8)$ cycloalkyl, —O-heterocycloalkyl, $(C_1-C_{12})$ alkyl or $(C_2-C_{12})$ alkenyl, wherein 0 to 7 methylene of the $(C_1-C_{12})$ alkyl and the $(C_2-C_{12})$ alkenyl are optionally replaced by a moiety selected from the group consisting of —O—, —$NR_{13}$—, —$S(O)_r$—, —C(O)—, or —C(NH)—, provided that a when any two methylene in the alkyl or alkenyl is replaced, then O and N are not contiguous and wherein the alkyl and alkenyl are optionally substituted with one or more $R_{15}$, and the cycloalkyl and heterocycloalkyl are optionally substituted with one or more $R_{16}$; or
when $R_{12}$ is cycloalkyl or heterocycloalkyl, two $R_{10}$ together with the atom to which they are attached form C=(O); or two $R_{14}$ together with the atoms to which they are attached form a $(C_3-C_8)$ cycloalkyl or heterocycloalkyl optionally substituted with one or more $R_{13}$; or when $R_{12}$ is cycloalkyl or heterocycloalkyl, two $R_{14}$ together with the atom to which they are attached form a $(C_3-C_8)$ spirocycloalkyl or a spiroheterocycloalkyl optionally substituted with one or more $R_{13}$; $R_{15}$ is —OH, —$NH_2$, —$NH(C_1-C_6)$ alkyl, —$N((C_1-C_6)$ alkyl)$_2$, $(C_3-C_8)$ cycloalkyl, heterocycloalkyl, $(C_6-C_{10})$ aryl or heteroaryl, wherein the $(C_3-C_8)$ cycloalkyl and heterocycloalkyl are optionally substituted with one or more substituents selected from $(C_1-C_6)$ hydroxyalkyl, $(C_1-C_6)$ aminoalkyl, —C(O)OH, —OH, —$NH_2$, —NH $(C_1-C_6)$ alkyl, —$N((C_1-C_6)$ alkyl)$_2$, and oxo;
$R_{16}$ is —OH, —C(O)OH, —$NH_2$, —$NH(C_1-C_6)$ alkyl, —$N((C_1-C_6)$ alkyl)$_2$, $(C_1-C_6)$ alkoxy, $(C_1-C_6)$ hydroxyalkyl, $(C_3-C_8)$ cycloalkyl, heterocycloalkyl, —O—$(C_3$-

$C_8$) cycloalkyl, —O-heterocycloalkyl, ($C_6$-$C_{10}$) aryl or heteroaryl, wherein the ($C_3$-$C_8$) cycloalkyl and heterocycloalkyl are optionally substituted with one or more substituents selected from ($C_1$-$C_6$) hydroxyalkyl, ($C_1$-$C_6$) aminoalkyl, —C(O)OH, —OH, —NH$_2$, —NH($C_1$-$C_6$) alkyl, —N(($C_1$-$C_6$) alkyl)$_2$, and oxo;

each m, o, p, q, and r is independently, at each occurrence, 0, 1, or 2; and n is 0, 1, or 2.

Non-limiting illustrative compounds of the invention include:

1-[4-(2-cyclopropoxyphenyl)pyridin-3-yl]-N-[(2,5-dichlorophenyl)methyl]cyclopropan-1-amine (I-1);
N-[(2,5-dichlorophenyl)methyl]-1-{4-[2-(propan-2-yloxy)phenyl]pyridin-3-yl}cyclopropan-1-amine (I-2);
1-[4-(2-cyclopropoxy-5-fluorophenyl)pyridin-3-yl]-N-[(2,5-dichlorophenyl)methyl]cyclopropan-1-amine (I-3);
N-[(2,5-dichlorophenyl)methyl]-1-[4-(2-methoxyphenyl)pyridin-3-yl]cyclopropan-1-amine (I-4);
1-[4-(2-cyclobutoxyphenyl)pyridin-3-yl]-N-[(2,5-dichlorophenyl)methyl]cyclopropan-1-amine (I-5);
N-[(2,5-dichlorophenyl)methyl]-1-[4-(2-methylphenyl)pyridin-3-yl]cyclopropan-1-amine (I-6);
N-[(2,5-dichlorophenyl)methyl]-1-{4-[2-(methylsulfanyl)phenyl]pyridin-3-yl}cyclopropan-1-amine (I-7);
N-[(2,5-dichlorophenyl)methyl]-1-{4-[2-(2,2,2-trifluoroethoxy)phenyl]pyridin-3-yl}cyclopropan-1-amine (I-8);
N-[(2,5-dichlorophenyl)methyl]-1-[4-(2-ethylphenyl)pyridin-3-yl]cyclopropan-1-amine (I-9);
1-[4-(2-cyclopropylphenyl)pyridin-3-yl]-N-[(2,5-dichlorophenyl)methyl]cyclopropan-1-amine (I-10);
N-[(2,5-dichlorophenyl)methyl]-1-{(4-[2-(trifluoromethoxy)phenyl]pyridin-3-yl}cyclopropan-1-amine (I-11);
N-[(2,5-dichlorophenyl)methyl]-1-{(4-[2-(methoxymethyl)phenyl]pyridin-3-yl}cyclopropan-1-amine (I-12);
1-(4-{2-[(tert-butoxy)methyl]phenyl}pyridin-3-yl)-N-[(2,5-dichlorophenyl)methyl]cyclopropan-1-amine (I-13);
N-[(2,5-dichlorophenyl)methyl]-1-(4-phenylpyridin-3-yl)cyclopropan-1-amine (I-14);
N-[(2,5-dichlorophenyl)methyl]-1-[4-(2-ethoxy-4,5-difluorophenyl)pyridin-3-yl]cyclopropan-1-amine (I-15);
1-[4-(2-chlorophenyl)pyridin-3-yl]-N-[(2,5-dichlorophenyl)methyl]cyclopropan-1-amine (I-16);
N-[(2,5-dichlorophenyl)methyl]-1-[4-(2-fluorophenyl)pyridin-3-yl]cyclopropan-1-amine (I-17);
1-[4-(2-cyclopropoxy-4-fluorophenyl)pyridin-3-yl]-N-[(2,5-dichlorophenyl)methyl]cyclopropan-1-amine (I-18);
N-[(2,5-dichlorophenyl)methyl]-1-{4-[2-(oxetan-3-yloxy)phenyl]pyridin-3-yl}cyclopropan-1-amine (I-19);
2-{2-[3-(1-{[(2,5-dichlorophenyl)methyl]amino}cyclopropyl)pyridin-4-yl]phenoxy}propan-1-ol (I-20);
N-[(2,5-dichlorophenyl)methyl]-1-{4-[2-(oxolan-3-yloxy)phenyl]pyridin-3-yl}cyclopropan-1-amine (I-21);
(3R,4R)-4-{2-[3-(1-{[(2,5-dichlorophenyl)methyl]amino}cyclopropyl)pyridin-4-yl]phenoxy}oxolan-3-ol (I-22);
N-{[2-chloro-5-(methylsulfanyl)phenyl]methyl}-1-[4-(2-cyclopropoxyphenyl)pyridin-3-yl]cyclopropan-1-amine (I-23);
1-[4-(2-cyclopropoxyphenyl)pyridin-3-yl]-N-[(2,5-dimethylphenyl)methyl]cyclopropan-1-amine (I-24);
1-[4-(2-cyclopropoxyphenyl)pyridin-3-yl]-N-{[3-methyl-6-(methylsulfanyl)pyridin-2-yl]methyl}cyclopropan-1-amine (I-25);
1-[4-(2-cyclopropoxyphenyl)pyridin-3-yl]-N-[(2,3-dichlorophenyl)methyl]cyclopropan-1-amine (I-26);
1-[4-(2-cyclopropoxyphenyl)pyridin-3-yl]-N-[(trimethylpyrazin-2-yl)methyl]cyclopropan-1-amine (I-27);
1-[4-(2-cyclopropoxyphenyl)pyridin-3-yl]-N-[(2,4-dichlorophenyl)methyl]cyclopropan-1-amine (I-28);
1-[4-(2-cyclopropoxyphenyl)pyridin-3-yl]-N-[(4-methoxy-2,5-dimethylphenyl)methyl]cyclopropan-1-amine (I-29);
N-{[5-chloro-2-(trifluoromethyl)phenyl]methyl}-1-[4-(2-cyclopropoxyphenyl)pyridin-3-yl]cyclopropan-1-amine (I-30);
N-[(2-chloro-5-cyclopropylphenyl)methyl]-1-[4-(2-cyclopropoxyphenyl)pyridin-3-yl]cyclopropan-1-amine (I-31);
N-{[2-chloro-5-(trifluoromethyl)phenyl]methyl}-1-[4-(2-cyclopropoxyphenyl)pyridin-3-yl]cyclopropan-1-amine (I-32);
N-[(2-chloro-5-methylphenyl)methyl]-1-[4-(2-cyclopropoxyphenyl)pyridin-3-yl]cyclopropan-1-amine (I-33);
N-[(5-chloro-2-methylpyridin-4-yl)methyl]-1-[4-(2-cyclopropoxyphenyl)pyridin-3-yl]cyclopropan-1-amine (I-34);
N-[(3-chloro-6-methylpyridin-2-yl)methyl]-1-[4-(2-cyclopropoxyphenyl)pyridin-3-yl]cyclopropan-1-amine (I-35);
N-[(3-chloro-5-fluoro-4-methoxy-2-methylphenyl)methyl]-1-[4-(2-cyclopropoxyphenyl)pyridin-3-yl]cyclopropan-1-amine (I-36);
1-[4-(2-cyclopropoxyphenyl)pyridin-3-yl]-N-{[2-methyl-5-(trifluoromethyl)phenyl]methyl}cyclopropan-1-amine (I-37);
1-[4-(2-cyclopropoxyphenyl)pyridin-3-yl]-N-{[4-methoxy-2-methyl-5-(propan-2-yl)phenyl]methyl}cyclopropan-1-amine (I-38);
1-[4-(2-cyclopropoxyphenyl)pyridin-3-yl]-N-{[3-methyl-5-(methylsulfanyl)pyridin-2-yl]methyl}cyclopropan-1-amine (I-39);
N-[(5-chloro-2-methylphenyl)methyl]-1-[4-(2-cyclopropoxyphenyl)pyridin-3-yl]cyclopropan-1-amine (I-40);
1-[4-(2-cyclopropoxyphenyl)pyridin-3-yl]-N-{[2-methyl-5-(methylsulfanyl)pyridin-4-yl]methyl}cyclopropan-1-amine (I-42);
N-[(5-chloro-2-methanesulfonylphenyl)methyl]-1-[4-(2-cyclopropoxyphenyl)pyridin-3-yl]cyclopropan-1-amine (I-43);
1-[4-(2-cyclopropoxyphenyl)pyridin-3-yl]-N-[(3,5-dichlorophenyl)methyl]cyclopropan-1-amine (I-44);
3-{1-[(2,5-dichlorophenyl)methoxy]cyclopropyl}-4-(2-methoxyphenyl)pyridine (I-45);
4-(2-cyclopropoxyphenyl)-3-{1-[(2,5-dichlorophenyl)methoxy]cyclopropyl}pyridine (I-46);
4-(2-cyclopropoxyphenyl)-3-{1-[(2,3-dichlorophenyl)methoxy]cyclopropyl}pyridine (I-47);
4-(2-cyclopropoxyphenyl)-3-{1-[(2,4-dichlorophenyl)methoxy]cyclopropyl}pyridine (I-48);
4-(2-cyclobutoxyphenyl)-3-{1-[(2,5-dichlorophenyl)methoxy]cyclopropyl}pyridine (I-49);
3-{1-[(2,5-dichlorophenyl)methoxy]cyclopropyl}-4-(2-fluorophenyl)pyridine (I-50);
3-(1-{[5-chloro-2-(trifluoromethyl)phenyl]methoxy}cyclopropyl)-4-(2-cyclopropoxyphenyl) pyridine (I-51);
3-(1-{[2-chloro-5-(trifluoromethyl)phenyl]methoxy}cyclopropyl)-4-(2-cyclopropoxyphenyl)pyridine (I-52);
3-{1-[(2-chloro-5-cyclopropylphenyl)methoxy]cyclopropyl}-4-(2-cyclopropoxyphenyl)pyridine (I-53);
3-{1-[(2-chloro-5-methylphenyl)methoxy]cyclopropyl}-4-(2-cyclopropoxyphenyl)pyridine (I-54);

3-{1-[(5-chloro-2-methylphenyl)methoxy]cyclopropyl}-4-(2-cyclopropoxyphenyl)pyridine (I-55);

4-(2-cyclopropoxyphenyl)-3-{1-[(3,5-dichlorophenyl)methoxy]cyclopropyl}pyridine (I-56);

1-{1-[4-(2-cyclopropoxyphenyl)pyridin-3-yl]cyclopropyl}-1-[(2,5-dichlorophenyl)methyl]urea (I-57);

1-[4-(2-cyclopropoxyphenyl)pyridin-3-yl]-N-[(2,5-dichlorophenyl)methyl]-N-methylcyclopropan-1-amine (I-58);

4-(2-cyclopropoxyphenyl)-3-{3-[(2,5-dichlorophenyl)methoxy]oxetan-3-yl}pyridine (I-59);

1-(5-{2,5-dichloro-4-[({1-[4-(2-cyclopropoxyphenyl)pyridin-3-yl]cyclopropyl}amino)methyl]phenyl}pentyl)-3-[(2S,3R,4R,5R)-2,3,4,5,6-pentahydroxyhexyl]urea (I-60);

5-{2,5-dichloro-4-[({1-[4-(2-cyclopropoxyphenyl)pyridin-3-yl]cyclopropyl}amino)methyl]phenyl}pentanoic acid (I-61);

5-{2,5-dichloro-4-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]pentanamide (I-62);

4-[(4-{2,5-dichloro-4-[({1-[4-(2-cyclopropoxyphenyl)pyridin-3-yl]cyclopropyl}amino)methyl]phenyl}butyl) [(2S,3R,4R,5R)-2,3,4,5,6-pentahydroxyhexyl]carbamoyl]butanoic acid (I-63);

1-{4-[4-chloro-3-({1-[4-(2-cyclopropoxyphenyl)pyridin-3-yl]cyclopropoxy}methyl)phenyl]butyl}-3-[(2S,3R,4R,5R)-2,3,4,5,6-pentahydroxyhexyl]urea (I-64);

1-{4-[5-chloro-4-({1-[4-(2-cyclopropoxyphenyl)pyridin-3-yl]cyclopropoxy}methyl)-2-methylphenyl]butyl}-3-[(2S,3R,4R,5R)-2,3,4,5,6-pentahydroxyhexyl]urea (I-65);

(2R,3R,4R,5S)-6-({4-[2,5-dichloro-4-({1-[4-(2-cyclopropoxyphenyl)pyridin-3-yl]cyclopropoxy}methyl)phenyl]butyl}amino)hexane-1,2,3,4,5-pentol (I-66);

N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]oxane-4-carboxamide (I-67);

N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]acetamide (I-68);

N-{4-[2,5-dichloro-4-({1-[4-(2-cyclopropoxyphenyl)pyridin-3-yl]cyclopropoxy}methyl)phenyl]butyl}-2-methyl-N-[(2S,3R,4R,5R)-2,3,4,5,6-pentahydroxyhexyl]propanamide (I-69);

3-(benzenesulfonyl)-N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]propanamide (I-70);

N-{4-[2,5-dichloro-4-({1-[4-(2-cyclopropoxyphenyl)pyridin-3-yl]cyclopropoxy}methyl)phenyl]butyl}-2-hydroxy-N-[(2S,3R,4R,5R)-2,3,4,5,6-pentahydroxyhexyl]acetamide (I-71);

N-{4-[2,5-dichloro-4-({1-[4-(2-cyclopropoxyphenyl)pyridin-3-yl]cyclopropoxy}methyl)phenyl]butyl}-2-methoxy-N-[(2S,3R,4R,5R)-2,3,4,5,6-pentahydroxyhexyl]acetamide (I-72);

N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]propanamide (I-73);

N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]butanamide (I-74);

N-{4-[2,5-dichloro-4-({1-[4-(2-cyclopropoxyphenyl)pyridin-3-yl]cyclopropoxy}methyl)phenyl]butyl}-3-methoxy-N-[(2S,3R,4R,5R)-2,3,4,5,6-pentahydroxyhexyl]propanamide (I-75);

1-{4-[2,5-dichloro-4-({1-[4-(2-cyclopropoxyphenyl)pyridin-3-yl]cyclopropoxy}methyl)phenyl]butyl}-3-(2-methoxyethyl)-1-[(2S,3R,4R,5R)-2,3,4,5,6-pentahydroxyhexyl]urea (I-76);

(5S)-3-{4-[2,5-dichloro-4-({1-[4-(2-cyclopropoxyphenyl)pyridin-3-yl]cyclopropoxy}methyl) phenyl]butyl}-5-[(1S,2R,3R)-1,2,3,4-tetrahydroxybutyl]-1,3-oxazolidin-2-one (I-77);

(2S)-4-{4-[2,5-dichloro-4-({1-[4-(2-cyclopropoxyphenyl)pyridin-3-yl]cyclopropoxy}methyl) phenyl]butyl}-2-[(1S,2R,3R)-1,2,3,4-tetrahydroxybutyl]-1,4-oxazepan-5-one (I-78);

1-{4-[2,5-dichloro-4-({1-[4-(2-cyclopropoxyphenyl)pyridin-3-yl]cyclopropoxy}methyl)phenyl]butyl}-3-methyl-1-[(2S,3R,4R,5R)-2,3,4,5,6-pentahydroxyhexyl]urea (I-79);

N-{4-[2,5-dichloro-4-({1-[4-(2-cyclopropoxyphenyl)pyridin-3-yl]cyclopropoxy}methyl)phenyl]butyl}-N-[(2S,3R,4R,5R)-2,3,4,5,6-pentahydroxyhexyl]formamide (I-80);

(2R,3S,4R,5R)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(4-hydroxybutyl)hexanamide (I-81);

(2S,3S,4R,5S)-N-(carbamoylmethyl)-N-{4-[2,5-dichloro-4-({1-[4-(2-cyclopropoxyphenyl) pyridin-3-yl]cyclopropoxy}methyl)phenyl]butyl}-2,3,4,5,6-pentahydroxyhexanamide (I-82);

(2R,3S,4R,5R)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(6-hydroxyhexyl)hexanamide (I-83);

(2R,3S,4R,5R)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(2-sulfamoylethyl)hexanamide (I-84);

(2S,3S,4R,5S)-N-(4-[2,5-dichloro-4-(1-[4-(2-cyclopropoxyphenyl)pyridin-3-yl]cyclopropoxy) methyl)phenyl]butyl }-2,3,4,5,6-pentahydroxy-N-[2-(2-hydroxyethoxy)ethyl]hexanamide (I-85);

1-{4-[2,5-dichloro-4-({1-[4-(2-cyclopropoxyphenyl)pyridin-3-yl]cyclopropoxy}methyl)phenyl]butyl}-1-[2-(2-hydroxyethoxy)ethyl]-3-[(2S,3R,4R,5R)-2,3,4,5,6-pentahydroxyhexyl]urea (I-86);

2-{5-[2,5-dichloro-4-({1-[4-(2-cyclopropoxyphenyl}pyridin-3-yl]cyclopropoxy}methyl)phenyl]-N-[(2S,3R,4R,5R)-2,3,4,5,6-pentahydroxyhexyl]pentanamido} acetic acid (I-87);

2-(4-{5-[2,5-dichloro-4-({1-[4-(2-cyclopropoxyphenyl)pyridin-3-yl]cyclopropoxy}methyl) phenyl]pentanoyl}piperazin-1-yl)acetic acid (I-88);

2-(4-{5-[2,5-dichloro-4-({1-[4-(2-cyclopropoxyphenyl)pyridin-3-yl]cyclopropoxy}methyl) phenyl]pentanoyl}piperazin-1-yl)-N-methyl-N-[(2S,3R,4R,5R)-2,3,4,5,6-pentahydroxyhexyl]acetamide (I-89);

5-[2,5-dichloro-4-({1-[4-(2-cyclopropoxyphenyl)pyridin-3-yl]cyclopropoxy}methyl)phenyl]-N-(2-{2-[2-(2-{5-[2,5-dichloro-4-({1-[4-(2-cyclopropoxyphenyl)pyridin-3-yl]cyclopropoxy}methyl)phenyl]pentanamido}ethoxy)ethoxy]ethoxy}ethyl)pentanamide (I-90);

2-[4-(2-{5-[2,5-dichloro-4-({1-[4-(2-cyclopropoxyphenyl)pyridin-3-yl]cyclopropoxy}methyl) phenyl]pentanamido}ethyl)piperazin-1-yl]acetic acid (I-91);

5-[2,5-dichloro-4-({1-[4-(2-cyclopropoxyphenyl)pyridin-3-yl]cyclopropoxy)methyl)phenyl]-1-{4-[(2S,3R,4S,5R)-2,3,4,5,6-pentahydroxyhexyl]piperazin-1-yl}pentan-1-one (I-92);

(2S,3S,4R,5R,6S)-6-({5-[2,5-dichloro-4-({1-[4-(2-cyclopropoxyphenyl)pyridin-3-yl]cyclopropoxy}methyl)phenyl]pentanamido}methyl)-3,4,5-trihydroxyoxane-2-carboxylic acid (I-93);

1-{4-[5-chloro-4-({1-[4-(2-cyclopropoxyphenyl)pyridin-3-yl]cyclopropoxy}methyl)-2-methylphenyl]butyl}-3-ethyl-3-[(2S,3R,4R,5R)-2,3,4,5,6-pentahydroxyhexyl]urea (I-94);

1-{4-[5-chloro-4-({1-[4-(2-cyclopropoxyphenyl)pyridin-3-yl]cyclopropoxy}methyl)-2-methylphenyl]butyl}-3-[(2S,3R,4S,5R)-1,3,4,5,6-pentahydroxyhexan-2-yl]urea (I-95);

1-{4-[5-chloro-4-({1-[4-(2-cyclopropoxyphenyl)pyridin-3-yl]cyclopropoxy}methyl)-2-methylphenyl]butyl}-1-ethyl-3-[(2S,3R,4R,5R)-2,3,4,5,6-pentahydroxyhexyl]urea (I-96);

1-{4-[5-chloro-4-({1-[4-(2-cyclopropoxyphenyl)pyridin-3-yl]cyclopropoxy}methyl)-2-methylphenyl]butyl}-1-(2-hydroxyethyl)-3-[(2S,3R,4R,5R)-2,3,4,5,6-pentahydroxyhexyl]urea (I-97);

2-(4-{5-[2,5-dichloro-4-({1-[4-(2-cyclopropoxyphenyl)pyridin-3-yl]cyclopropoxy}methyl) phenyl]pentanoyl}piperazin-1-yl)-N-[(2S,3R,4R,5R)-2,3,4,5,6-pentahydroxyhexyl]acetamide (I 98);

5-[2,5-dichloro-4-({1-[4-(2-cyclopropoxyphenyl)pyridin-3-yl]cyclopropoxy}methyl)phenyl]-N-{2-[4-({[(2S,3R,4R,5R)-2,3,4,5,6-pentahydroxyhexyl]carbamoyl}methyl)piperazin-1-yl]ethyl}pentanamide (I-99);

5-[2,5-dichloro-4-({1-[4-(2-cyclopropoxyphenyl)pyridin-3-yl]cyclopropoxy}methyl)phenyl]-N-{2-[4-({methyl[(2S,3R,4R,5R)-2,3,4,5,6-pentahydroxyhexyl]carbamoyl}methyl)piperazin-1-yl]ethyl}pentanamide (I-100);

5-[2,5-dichloro-4-({1-[4-(2-cyclopropoxyphenyl)pyridin-3-yl]cyclopropoxy}methyl)phenyl]-N-{3-[4-(3-{5-[2,5-dichloro-4-({1-[4-(2-cyclopropoxyphenyl)pyridin-3-yl]cyclopropoxy}methyl) phenyl]pentanamido}propyl)piperazin-1-yl]propyl}pentanamide (I-101);

4-(2-carboxyethyl)-4-{5-[2,5-dichloro-4-({1-[4-(2-cyclopropoxyphenyl)pyridin-3-yl]cyclopropoxy}methyl)phenyl]pentanamido}heptanedioic acid (I-102);

5-[2,5-dichloro-4-({1-[4-(2-cyclopropoxyphenyl)pyridin-3-yl]cyclopropoxy}methyl)phenyl]-1-{4-[(2S,3R,4R,5R)-2,3,5,6-tetrahydroxy-4-{[(2S,3R,4S,5R,6R)-3,4,5-trihydroxy-6-(hydroxymethyl)oxan-2-yl]oxy}hexyl] piperazin-1-yl}pentan-1-one (I-103);

5-[2,5-dichloro-4-({1-[4-(2-cyclopropoxyphenyl)pyridin-3-yl]cyclopropoxy}methyl)phenyl]-N-{[(3R,4R,5S,6R)-3,4,5-trihydroxy-6-(hydroxymethyl)oxan-2-yl]methyl}pentanamide (I-104);

5-[2,5-dichloro-4-({1-[4-(2-cyclopropoxyphenyl)pyridin-3-yl]cyclopropoxy}methyl)phenyl]-N-(2-hydroxyethyl)-N-[(2S,3R,4R,5R)-2,3,4,5,6-pentahydroxyhexyl]pentanamide (I-105);

(2R,3R,4S,5R)-2-[({4-[5-chloro-4-({1-[4-(2-cyclopropoxyphenyl)pyridin-3-yl]cyclopropoxy}methyl)-2-methylphenyl]butyl}carbamoyl)amino]-3,4,5,6-tetrahydroxyhexanoic acid (I-106);

1-{4-[5-chloro-4-({1-[4-(2-cyclopropoxyphenyl)pyridin-3-yl]cyclopropoxy}methyl)-2-methylphenyl]butyl}-3-(2-hydroxyethyl)-3-[(2S,3R,4R,5R)-2,3,4,5,6-pentahydroxyhexyl]urea (I-107);

5-[2,5-dichloro-4-({1-[4-(2-cyclopropoxyphenyl)pyridin-3-yl]cyclopropoxy}methyl)phenyl]-N-ethyl-N-[(2S,3R,4R,5R)-2,3,4,5,6-pentahydroxyhexyl]pentanamide (I-108);

3-{4-[5-chloro-4-({1-[4-(2-cyclopropoxyphenyl)pyridin-3-yl]cyclopropoxy}methyl)-2-methylphenyl]butyl}-1-{[(2S,3R,4R,5S,6R)-3,4,5-trihydroxy-6-(hydroxymethyl)oxan-2-yl]methyl}urea (I-109);

(2S,3S,4R,5R,6S)-6-{[({4-[5-chloro-4-({1-[4-(2-cyclopropoxyphenyl)pyridin-3-yl]cyclopropoxy}methyl)-2-methylphenyl]butyl}carbamoyl)amino]methyl}-3,4,5-trihydroxyoxane-2-carboxylic acid (I-110);

2-(2-{2-[({4-[5-chloro-4-({1-[4-(2-cyclopropoxyphenyl)pyridin-3-yl]cyclopropoxy}methyl)-2-methylphenyl]butyl}carbamoyl)amino]acetamido}acetamido)acetic acid (I-111);

(2S)-2-[(2S)-2-[(2S)-2-[({4-[5-chloro-4-({1-[4-(2-cyclopropoxyphenyl)pyridin-3-yl]cyclopropoxy}methyl)-2-methylphenyl]butyl}carbamoyl)amino]propanamido]propanamido]propanoic acid (I-112);

(2S)-5-carbamimidamido-2-[({4-[5-chloro-4-({1-[4-(2-cyclopropoxyphenyl)pyridin-3-yl]cyclopropoxy}methyl)-2-methylphenyl]butyl}carbamoyl)amino]pentanoic acid (I-113);

N-{4-[5-chloro-4-({1-[4-(2-cyclopropoxyphenyl)pyridin-3-yl]cyclopropoxy}methyl)-2-methylphenyl]butyl}-4-[(2S,3R,4S,5R)-2,3,4,5,6-pentahydroxyhexyl]piperazine-1-carboxamide (I-114);

1-{4-[5-chloro-4-({1-[4-(2-cyclopropoxyphenyl)pyridin-3-yl]cyclopropoxy}methyl)-2-methylphenyl]butyl}-1-methyl-3-[(2S,3R,4R,5R)-2,3,4,5,6-pentahydroxyhexyl]urea (I-115);

1-{4-[5-chloro-4-({1-[4-(2-cyclopropoxyphenyl)pyridin-3-yl]cyclopropoxy}methyl)-2-methylphenyl]butyl}-1-(2-methoxyethyl)-3-[(2S,3R,4R,5R)-2,3,4,5,6-pentahydroxyhexyl]urea (I-116);

1-{4-[5-chloro-4-({1-[4-(2-cyclopropoxyphenyl)pyridin-3-yl]cyclopropoxy}methyl)-2-methylphenyl]butyl}-1-[2-(2-hydroxyethoxy)ethyl]-3-[(2S,3R,4R,5R)-2,3,4,5,6-pentahydroxyhexyl]urea (I-117);

1-{4-[5-chloro-4-({1-[4-(2-cyclopropoxyphenyl)pyridin-3-yl]cyclopropoxy}methyl)-2-methylphenyl]butyl}-1-(5-hydroxypentyl)-3-[(2S,3R,4R,5R)-2,3,4,5,6-pentahydroxyhexyl]urea (I-118);

(2R)-6-amino-2-[({4-[5-chloro-4-({1-[4-(2-cyclopropoxyphenyl)pyridin-3-yl]cyclopropoxy}methyl)-2-methylphenyl]butyl}carbamoyl)amino]hexanoic acid (I-119);

N-benzyl-5-[2,5-dichloro-4-({1-[4-(2-cyclopropoxyphenyl)pyridin-3-yl]cyclopropoxy}methyl) phenyl]-N-[(2R,3S,4R,5R)-2,3,4,5,6-pentahydroxyhexyl]pentanamide (I-120);

5-[2,5-dichloro-4-({1-[4-(2-cyclopropoxyphenyl)pyridin-3-yl]cyclopropoxy}methyl)phenyl]-N-methyl-N-(2-{[(2R,3R,4S,5S,6R)-3,4,5-trihydroxy-6-(hydroxymethyl)oxan-2-yl]oxy}ethyl) pentanamide (I-121);

5-[2,5-dichloro-4-({1-[4-(2-cyclopropoxyphenyl)pyridin-3-yl]cyclopropoxy}methyl)phenyl]-N-(2,3-dihydroxypropyl)-N-[(2S,3R,4R,5R)-2,3,4,5,6-pentahydroxyhexyl]pentanamide (I-122);

5-[2,5-dichloro-4-({1-[4-(2-cyclopropoxyphenyl)pyridin-3-yl]cyclopropoxy}methyl)phenyl]-N-[(2R)-2-hydroxybutyl]-N-[(2S,3R,4R,5R)-2,3,4,5,6-pentahydroxyhexyl]pentanamide (I-123);

5-[2,5-dichloro-4-({1-[4-(2-cyclopropoxyphenyl)pyridin-3-yl]cyclopropoxy}methyl)phenyl]-N-[(2R)-2-hydroxy-3-methoxypropyl]-N-[(2S,3R,4R,5R)-2,3,4,5,6-pentahydroxyhexyl]pentanamide (I-124);

5-[2,5-dichloro-4-({1-[4-(2-cyclopropoxyphenyl)pyridin-3-yl]cyclopropoxy}methyl)phenyl]-N-[(2S)-2-hydroxy-3-methoxypropyl]-N-[(2S,3R,4R,5R)-2,3,4,5,6-pentahydroxyhexyl]pentanamide (I-125);

N-benzyl-5-[2,5-dichloro-4-({1-[4-(2-cyclopropoxyphenyl)pyridin-3-yl]cyclopropoxy}methyl) phenyl]-N-[(2S,3R,4R,5R)-2,3,4,5,6-pentahydroxyhexyl]pentanamide (I-126);

5-[2,5-dichloro-4-({1-[4-(2-cyclopropoxyphenyl)pyridin-3-yl]cyclopropoxy}methyl)phenyl]-N-(2-methoxyethyl)-N-[(2S,3R,4R,5R)-2,3,4,5,6-pentahydroxyhexyl]pentanamide (I-127);

5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]-N-(propan-2-yl)pentanamide (I-128);

5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]-N-propylpentanamide (I-129);

5-[2,5-dichloro-4-({1-[4-(2-cyclopropoxyphenyl)pyridin-3-yl]cyclopropoxy}methyl)phenyl]-N-(2-methanesulfonylethyl)-N-[(2S,3R,4R,5R)-2,3,4,5,6-pentahydroxyhexyl]pentanamide (I-130);

5-[2,5-dichloro-4-({1-[4-(2-cyclopropoxyphenyl)pyridin-3-yl]cyclopropoxy}methyl)phenyl]-N-(oxan-4-yl)-N-[(2S,3R,4R,5R)-2,3,4,5,6-pentahydroxyhexyl]pentanamide (I-131);

(2S,3S,4R,5S)-N-{4-[5-chloro-4-({1-[4-(2-cyclopropoxyphenyl)pyridin-3-yl]cyclopropoxy}methyl)-2-methylphenyl]butyl}-2,3,4,5,6-pentahydroxy-N-methylhexanamide (I-132);

5-{2,5-dichloro-4-[({1-[4-(2-methoxyphenyl)pyridin-3-yl]cyclopropyl}amino)methyl]phenyl}-N-[(2S,3R,4R,5R)-2,3,4,5,6-pentahydroxyhexyl]pentanamide (I-133);

5-{2,5-dichloro-4-[({1-[4-(2-methoxyphenyl)pyridin-3-yl]cyclopropyl}amino)methyl]phenyl}-N-methyl-N-[(2S,3R,4R,5R)-2,3,4,5,6-pentahydroxyhexyl]pentanamide (I-134);

5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]pentanamide (I-135);

5-[2,5-dichloro-4-({1-[4-(2-cyclopropoxyphenyl)pyridin-3-yl]cyclopropoxy}methyl)phenyl]-N-methyl-N-[(2S,3R,4R,5R)-2,3,4,5,6-pentahydroxyhexyl]pentanamide (I-136);

5-{2,5-dichloro-4-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]pentanamide (I-137);

1-(4-{2,5-dichloro-4-[({1-[4-(2-cyclopropoxyphenyl)pyridin-3-yl]cyclopropyl}amino)methyl]phenyl}butyl)-3-[(2S,3R,4R,5R)-2,3,4,5,6-pentahydroxyhexyl]urea (I-138);

5-[2,5-dichloro-4-({1-[4-(2-cyclopropoxyphenyl)pyridin-3-yl]cyclopropoxy}methyl)phenyl]-2-methyl-N-[(2S,3R,4R,5R)-2,3,4,5,6-pentahydroxyhexyl]pentanamide (I-139);

5-[2,5-dichloro-4-({1-[4-(2-cyclopropoxyphenyl)pyridin-3-yl]cyclopropoxy}methyl)phenyl]-N,2-dimethyl-N-[(2S,3R,4R,5R)-2,3,4,5,6-pentahydroxyhexyl]pentanamide (I-140);

1-{4-[2,5-dichloro-4-({1-[4-(2-cyclopropoxyphenyl)pyridin-3-yl]cyclopropoxy}methyl)phenyl]butyl}-3-[(2S,3R,4R,5R)-2,3,4,5,6-pentahydroxyhexyl]urea (I-141);

5-{5-chloro-4-[({1-[4-(2-cyclopropoxyphenyl)pyridin-3-yl]cyclopropyl}amino)methyl]-2-methylphenyl}-N-[(2S,3R,4R,5R)-2,3,4,5,6-pentahydroxyhexyl]pentanamide (I-142);

5-{5-chloro-4-[({1-[4-(2-cyclopropoxyphenyl)pyridin-3-yl]cyclopropyl}amino)methyl]-2-methylphenyl}-N-methyl-N-[(2S,3R,4R,5R)-2,3,4,5,6-pentahydroxyhexyl]pentanamide (I-143);

5-[2,5-dichloro-4-({1-[4-(2-cyclopropoxyphenyl)pyridin-3-yl]cyclopropoxy}methyl)phenyl]-2,2-dimethyl-N-[(2S,3R,4R,5R)-2,3,4,5,6-pentahydroxyhexyl]pentanamide (I-144);

5-[5-chloro-4-({1-[4-(2-cyclopropoxyphenyl)pyridin-3-yl]cyclopropoxy}methyl)-2-methylphenyl]-N-[(2S,3R,4R,5R)-2,3,4,5,6-pentahydroxyhexyl]pentanamide (I-145);

5-[5-chloro-4-({1-[4-(2-cyclopropoxyphenyl)pyridin-3-yl]cyclopropoxy}methyl)-2-methylphenyl]-N-methyl-N-[(2S,3R,4R,5R)-2,3,4,5,6-pentahydroxyhexyl]pentanamide (I-146);

1-(4-{4-[({1-[4-(2-cyclopropoxyphenyl)pyridin-3-yl]cyclopropyl}amino)methyl]-2,5-dimethylphenyl}butyl)-3-[(2S,3R,4R,5R)-2,3,4,5,6-pentahydroxyhexyl]urea (I-147);

5-{4-[({1-[4-(2-cyclopropoxyphenyl)pyridin-3-yl]cyclopropyl}amino)methyl]-2,5-dimethylphenyl}-N-[(2S,3R,4R,5R)-2,3,4,5,6-pentahydroxyhexyl]pentanamide (I-148);

5-{4-[({1-[4-(2-cyclopropoxyphenyl)pyridin-3-yl]cyclopropyl}amino)methyl]-2,5-dimethylphenyl}-N-methyl-N-[(2S,3R,4R,5R)-2,3,4,5,6-pentahydroxyhexyl]pentanamide (I-149);

1-{4-[4-({1-[4-(2-cyclopropoxyphenyl)pyridin-3-yl]cyclopropoxy}methyl)-2,5-dimethylphenyl]butyl}-3-[(2S,3R,4R,5R)-2,3,4,5,6-pentahydroxyhexyl]urea (I-150);

1-(4-{5-chloro-4-[({1-[4-(2-cyclopropoxyphenyl)pyridin-3-yl]cyclopropyl}amino)methyl]-2-methylphenyl}butyl)-3-[(2S,3R,4R,5R)-2,3,4,5,6-pentahydroxyhexyl]urea (I-151);

2-{2-[2,5-dichloro-4-({1-[4-(2-cyclopropoxyphenyl)pyridin-3-yl]cyclopropoxy}methyl)phenyl]ethoxy}-N-[(2S,3R,4R,5R)-2,3,4,5,6-pentahydroxyhexyl]propanamide (I-152);

(2R,3R,4S,5R)-2-(5-[2,5-dichloro-4-({1-[4-(2-cyclopropoxyphenyl)pyridin-3-yl]cyclopropoxy methyl)phenyl]pentanamido}-3,4,5,6-tetrahydroxyhexanoic acid (I-153);

5-[2,5-dichloro-4-({1-[4-(2-cyclopropoxyphenyl)pyridin-3-yl]cyclopropoxy}methyl)phenyl]-N-[(2R,3R,4R,5S,6R)-2,4,5-trihydroxy-6-(hydroxymethyl)oxan-3-yl]pentanamide (I-154);

2-{2-[2,5-dichloro-4-({1-[4-(2-cyclopropoxyphenyl)pyridin-3-yl]cyclopropoxy}methyl)phenyl]ethoxy}-N-methyl-N-[(2S,3R,4R,5R)-2,3,4,5,6-pentahydroxyhexyl]propanamide (I-155);

5-[2,5-dichloro-4-({1-[4-(2-cyclopropoxyphenyl)pyridin-3-yl]cyclopropoxy}methyl)phenyl]-N-[(2S,3R,4S,5R)-1,3,4,5,6-pentahydroxyhexan-2-yl]pentanamide (I-156);

5-[2,5-dichloro-4-({1-[4-(2-cyclopropoxyphenyl)pyridin-3-yl]cyclopropoxy}methyl)phenyl]pentanoic acid (I-157);

1-(1-{5-[2,5-dichloro-4-({1-[4-(2-cyclopropoxyphenyl)pyridin-3-yl]cyclopropoxy}methyl) phenyl]pentanoyl}piperidin-4-yl)-3-[(2S,3R,4R,5R)-2,3,4,5,6-pentahydroxyhexyl]urea (I-158);

1-(1-{5-[2,5-dichloro-4-({1-[4-(2-cyclopropoxyphenyl)pyridin-3-yl]cyclopropoxy}methyl) phenyl]

pentanoyl}piperidin-4-yl)-3-methyl-3-[(2S,3R,4R,5R)-2,3,4,5,6-pentahydroxyhexyl]urea (I-159);

5-[2,5-dichloro-4-({1-[4-(2-cyclopropoxyphenyl)pyridin-3-yl]cyclopropoxy}methyl)phenyl]-N-[(2S,3R,4S,5R)-3,4,5,6-tetrahydroxy-1-(morpholin-4-yl)hexan-2-yl]pentanamide (I-160);

5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]hexanamide (I-161);

5-[2,5-dichloro-4-({1-[4-(2-cyclopropoxyphenyl)pyridin-3-yl]cyclopropoxy}methyl)phenyl]-N-methyl-N-[(2S,3R,4R,5R)-2,3,4,5,6-pentahydroxyhexyl]hexanamide (I-162);

1-(5-{2,5-dichloro-4-[({1-[4-(2-cyclopropoxyphenyl)pyridin-3-yl]cyclopropyl}amino)methyl]phenyl}pentyl)-3-methyl-3-[(2S,3R,4R,5R)-2,3,4,5,6-pentahydroxyhexyl]urea (I-163);

2-{[(2S,3R,4S,5R)-2-{5-[2,5-dichloro-4-({1-[4-(2-cyclopropoxyphenyl)pyridin-3-yl]cyclopropoxy}methyl)phenyl]pentanamido}-3,4,5,6-tetrahydroxyhexyl](methyl)amino}acetic acid (I-164);

5-[2,5-dichloro-4-({1-[4-(2-cyclopropoxyphenyl)pyridin-3-yl]cyclopropoxy}methyl)phenyl]-N-[(2S,3R,4S,5R)-1-(dimethylamino)-3,4,5,6-tetrahydroxyhexan-2-yl]pentanamide (I-165);

4-[5-chloro-4-({1-[4-(2-cyclopropoxyphenyl)pyridin-3-yl]cyclopropoxy}methyl)-2-methylphenyl]butan-1-amine (I-166);

1-{4-[5-chloro-4-({1-[4-(2-cyclopropoxyphenyl)pyridin-3-yl]cyclopropoxy}methyl)-2-methylphenyl]butyl}-3-methyl-3-[(2S,3R,4R,5R)-2,3,4,5,6-pentahydroxyhexyl]urea (I-167);

5-[2,5-dichloro-4-({1-[4-(2-cyclopropoxyphenyl)pyridin-3-yl]cyclopropoxy}methyl)phenyl]-N,N-bis(2-{[(2S,3R,4R,5R)-2,3,4,5,6-pentahydroxyhexyl]carbamoyl}ethyl)pentanamide (I 168);

5-[2,5-dichloro-4-({1-[4-(2-cyclopropoxyphenyl)pyridin-3-yl]cyclopropoxy}methyl)phenyl]-N,N-bis(2-{methyl[(2S,3R,4R,5R)-2,3,4,5,6-pentahydroxyhexyl]carbamoyl}ethyl)pentanamide (I-169);

5-{2,5-dichloro-4-[({1-[4-(2-cyclopropoxyphenyl)pyridin-3-yl]cyclopropyl}amino)methyl]phenyl}-N,N-bis(2-{[(2S,3R,4R,5R)-2,3,4,5,6-pentahydroxyhexyl]carbamoyl}ethyl) pentanamide (I-170);

5-{2,5-dichloro-4-[({1-[4-(2-cyclopropoxyphenyl)pyridin-3-yl]cyclopropyl}amino)methyl]phenyl}-N,N-bis(2-{methyl[(2S,3R,4R,5R)-2,3,4,5,6-pentahydroxyhexyl]carbamoyl}ethyl) pentanamide (I-171);

(2S,3S,4R,5S)-N-{4-[5-chloro-4-({1-[4-(2-cyclopropoxyphenyl)pyridin-3-yl]cyclopropoxy)methyl)-2-methylphenyl]butyl}-2,3,4,5,6-pentahydroxyhexanamide (I-172);

(2S,3S,4R,5S)-6-[(1-{5-[2,5-dichloro-4-({1-[4-(2-cyclopropoxyphenyl)pyridin-3-yl]cyclopropoxy}methyl)phenyl]pentanoyl}piperidin-4-yl)amino]-2,3,4,5-tetrahydroxyhexanoic acid (I-173);

1-[4-(2,5-dichloro-4-([(1-{4-[2-(oxetan-3-yloxy)phenyl]pyridin-3-yl}cyclopropyl)amino]methyl)phenyl)butyl]-3-[(2S,3R,4R,5R)-2,3,4,5,6-pentahydroxyhexyl]urea (I-174);

1-[4-(2,5-dichloro-4-{[(1-{4-[2-(oxetan-3-yloxy)phenyl]pyridin-3-yl}cyclopropyl)amino]methyl}phenyl)butyl]-3-methyl-3-[(2S,3R,4R,5R)-2,3,4,5,6-pentahydroxyhexyl]urea (I-175);

(2S,3S,4R,5S)-N-{4-[5-chloro-4-({1-[4-(2-cyclopropoxyphenyl)pyridin-3-yl]cyclopropoxy) methyl)-2-methylphenyl]butyl}-2,3,4,5-tetrahydroxy-6-(morpholin-4-yl)hexanamide (I-176);

5-(2,5-dichloro-4-{[(1-(4-[2-(oxetan-3-yloxy)phenyl]pyridin-3-yl}cyclopropyl)amino]methyl) phenyl)-N-methyl-N-[(2S,3R,4R,5R)-2,3,4,5,6-pentahydroxyhexyl]pentanamide (I-177);

3-(5-{2,5-dichloro-4-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]pentanamido)propanoic acid (I-178);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5-tetrahydroxy-6-(morpholin-4-yl)hexanamide (I-179);

(2S,3S,4R,5S)-6-[(3-{5-[2,5-dichloro-4-({1-[4-(2-cyclopropoxyphenyl)pyridin-3-yl]cyclopropoxy}methyl)phenyl]-N-methylpentanamido}propyl)amino]-2,3,4,5-tetrahydroxyhexanoic acid (I-180);

N-{[(2R,3S,4S,5R,6R)-6-{[(1R,2R,3S,4R,6S)-4,6-diamino-3-{[(2S,3R,4S,5S,6R)-4-amino-3,5-dihydroxy-6-(hydroxymethyl)oxan-2-yl]oxy}-2-hydroxycyclohexyl]oxy}-3,4,5-trihydroxyoxan-2-yl]methyl}-5-[2,5-dichloro-4-({1-[4-(2-cyclopropoxyphenyl)pyridin-3-yl]cyclopropoxy}methyl)phenyl]pentanamide (I-181);

4-({4-[2,5-dichloro-4-({1-[4-(2-cyclopropoxyphenyl)pyridin-3-yl]cyclopropoxy}methyl)phenyl]butyl}[(2S,3R,4R,5R)-2,3,4,5,6-pentahydroxyhexyl]carbamoyl)butanoic acid (I-182);

3-{5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]pentanamido}propanoic acid (I-183);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5-pentahydroxy-N-methylhexanamide (I-184);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxyhexanamide (I-185);

2-[({4-[2,5-dichloro-4-({1-[4-(2-cyclopropoxyphenyl)pyridin-3-yl]cyclopropoxy}methyl) phenyl]butyl}[(2S,3R,4R,5R)-2,3,4,5,6-pentahydroxyhexyl]carbamoyl)methoxy]acetic acid (I-186);

3-({4-[2,5-dichloro-4-({1-[4-(2-cyclopropoxyphenyl)pyridin-3-yl]cyclopropoxy}methyl)phenyl]butyl}[(2S,3R,4R,5R)-2,3,4,5,6-pentahydroxyhexyl]carbamoyl)propanoic acid (I-187);

2-({2-[(carboxymethyl)[({4-[2,5-dichloro-4-({1-[4-(2-cyclopropoxyphenyl)pyridin-3-yl]cyclopropoxy}methyl)phenyl]butyl}(methyl)carbamoyl)methyl]amino]ethyl}[({4-[2,5-dichloro-4-({1-[4-(2-cyclopropoxyphenyl)pyridin-3-yl]cyclopropoxy}methyl)phenyl]butyl}(methyl) carbamoyl)methyl]amino)acetic acid (I-188);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5-tetrahydroxy-N-methyl-6-(morpholin-4-yl)hexanamide (I-189);

1-(4-{5-chloro-2-methyl-4-[(1-{4-[2-(oxetan-3-yloxy)phenyl]pyridin-3-yl}cyclopropoxy) methyl]phenyl}butyl)-3-[(2S,3R,4R,5R)-2,3,4,5,6-pentahydroxyhexyl]urea (I-190);

1-(4-{5-chloro-2-methyl-4-[(1-{4-[2-(oxetan-3-yloxy)phenyl]pyridin-3-yl}cyclopropoxy) methyl]phenyl}butyl)-3-methyl-3-[(2S,3R,4R,5R)-2,3,4,5,6-pentahydroxyhexyl]urea (I-191);

5-{2,5-dichloro-4-[(1-{4-[2-(oxetan-3-yloxy)phenyl]pyridin-3-yl}cyclopropoxy)methyl]phenyl}-N-methyl-N-[(2S,3R,4R,5R)-2,3,4,5,6-pentahydroxyhexyl]pentanamide (I-192);

1-(4-{2,5-dichloro-4-[(1-{4-[2-(oxetan-3-yloxy)phenyl]pyridin-3-yl}cyclopropoxy)methyl]phenyl}butyl)-3-[(2S,3R,4R,5R)-2,3,4,5,6-pentahydroxyhexyl]urea (I-193);

1-({4-[2,5-dichloro-4-({1-[4-(2-cyclopropoxyphenyl)pyridin-3-yl]cyclopropoxy}methyl)phenyl]butyl}sulfamoyl)-3-methyl-3-[(2S,3R,4R,5R)-2,3,4,5,6-pentahydroxyhexyl]urea (I-194);

2-{[({4-[2,5-dichloro-4-({1-[4-(2-cyclopropoxyphenyl)pyridin-3-yl]cyclopropoxy}methyl) phenyl]butyl}[(2S,3R,4R,5R)-2,3,4,5,6-pentahydroxyhexyl]carbamoyl)methyl](methyl)amino}acetic acid (I-195);

4-({4-[2,5-dichloro-4-({1-[4-(2-cyclopropoxyphenyl)pyridin-3-yl]cyclopropoxy}methyl)phenyl]butyl}[(2S,3R,4R,5R)-2,3,4,5,6-pentahydroxyhexyl]carbamoyl)-3,3-dimethylbutanoic acid (I-196);

2-[({4-[2,5-dichloro-4-({1-[4-(2-cyclopropoxyphenyl)pyridin-3-yl]cyclopropoxy}methyl) phenyl]butyl}[(2S,3R,4R,5R)-2,3,4,5,6-pentahydroxyhexyl]carbamoyl)amino]acetic acid (I-197);

3-[({4-[2,5-dichloro-4-({1-[4-(2-cyclopropoxyphenyl)pyridin-3-yl]cyclopropoxy}methyl) phenyl]butyl}[(2S,3R,4R,5R)-2,3,4,5,6-pentahydroxyhexyl]carbamoyl)amino]propanoic acid (I-198);

4-[({4-[2,5-dichloro-4-({1-[4-(2-cyclopropoxyphenyl)pyridin-3-yl]cyclopropoxy}methyl) phenyl]butyl}[(2S,3R,4R,5R)-2,3,4,5,6-pentahydroxyhexyl]carbamoyl)amino]butanoic acid (I-199);

2-({[(4-{2,5-dichloro-4-[({1-[4-(2-cyclopropoxyphenyl)pyridin-3-yl]cyclopropyl}amino)methyl]phenyl}butyl)[(2S,3R,4R,5R)-2,3,4,5,6-pentahydroxyhexyl]carbamoyl]methyl}(methyl)amino) acetic acid (I-200);

4-[(4-{2,5-dichloro-4-[({1-[4-(2-cyclopropoxyphenyl)pyridin-3-yl]cyclopropyl}amino)methyl]phenyl}butyl)[(2S,3R,4R,5R)-2,3,4,5,6-pentahydroxyhexyl]carbamoyl]-3,3-dimethylbutanoic acid (I-201);

N-{4-[2,5-dichloro-4-({1-[4-(2-cyclopropoxyphenyl)pyridin-3-yl]cyclopropoxy}methyl)phenyl]butyl}-2-methanesulfonyl-N-[(2S,3R,4R,5R)-2,3,4,5,6-pentahydroxyhexyl]acetamide (I-202);

N-{4-[2,5-dichloro-4-({1-[4-(2-cyclopropoxyphenyl)pyridin-3-yl]cyclopropoxy}methyl)phenyl]butyl}-2-(dimethylamino)-N-[(2S,3R,4R,5R)-2,3,4,5,6-pentahydroxyhexyl]acetamide (I-203);

1-{4-[2,5-dichloro-4-({1-[4-(2-cyclopropoxyphenyl)pyridin-3-yl]cyclopropoxy}methyl)phenyl]butyl}-1-methyl-3-[(2S,3R,4R,5R)-2,3,4,5,6-pentahydroxyhexyl]urea (I-204);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-propylhexanamide (I-205);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(2-methoxyethyl)hexanamide (I-206);

5-[2,5-dichloro-4-({1-[4-(2-cyclopropoxyphenyl)pyridin-3-yl]cyclopropoxy}methyl)phenyl]-N-[2-(dimethylamino)ethyl]-N-[(2S,3R,4R,5R)-2,3,4,5,6-pentahydroxyhexyl]pentanamide (I-207);

N-(carbamoylmethyl)-5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]pentanamide (I-208);

(2S,3S,4R,5S)-N-{4-[2,5-dichloro-4-({1-[4-(2-cyclopropoxyphenyl)pyridin-3-yl]cyclopropoxy}methyl)phenyl]butyl}-N-ethyl-2,3,4,5,6-pentahydroxyhexanamide (I-209);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(propan-2-yl)hexanamide (I-210);

(2S,3S,4R,5S)-N-(cyclopropylmethyl)-N-{4-[2,5-dichloro-4-({1-[4-(2-cyclopropoxyphenyl) pyridin-3-yl]cyclopropoxy}methyl)phenyl]butyl}-2,3,4,5,6-pentahydroxyhexanamide (I-211);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(3-methoxypropyl)hexanamide (I-212);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(2-hydroxyethyl)hexanamide (I-213);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-[(2R)-2-hydroxypropyl]hexanamide (I-214);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-[(2S)-2-hydroxypropyl]hexanamide (I-215);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(oxan-4-yl)hexanamide (I-216);

(2S,3S,4R,5S)-N-{4-[2,5-dichloro-4-({1-[4-(2-cyclopropoxyphenyl)pyridin-3-yl]cyclopropoxy}methyl)phenyl]butyl}-2,3,4,5,6-pentahydroxy-N-(3-hydroxypropyl)hexanamide (I-217);

5-[2,5-dichloro-4-({1-[4-(2-cyclopropoxyphenyl)pyridin-3-yl]cyclopropoxy}methyl)phenyl]-N-(3-hydroxypropyl)-N-[(2S,3R,4R,5R)-2,3,4,5,6-pentahydroxyhexyl]pentanamide (I-218);

5-[2,5-dichloro-4-({1-[4-(2-cyclopropoxyphenyl)pyridin-3-yl]cyclopropoxy}methyl)phenyl]-N-[(methylcarbamoyl)methyl]-N-[(2S,3R,4R,5R)-2,3,4,5,6-pentahydroxyhexyl]pentanamide (I-219);

5-[2,5-dichloro-4-({1-[4-(2-cyclopropoxyphenyl)pyridin-3-yl]cyclopropoxy}methyl)phenyl]-N-(3-methoxypropyl)-N-[(2S,3R,4R,5R)-2,3,4,5,6-pentahydroxyhexyl]pentanamide (I-220);

5-[2,5-dichloro-4-({1-[4-(2-cyclopropoxyphenyl)pyridin-3-yl]cyclopropoxy}methyl)phenyl]-N-[(dimethylcarbamoyl)methyl]-N-[(2S,3R,4R,5R)-2,3,4,5,6-pentahydroxyhexyl]pentanamide (I-221);

5-[2,5-dichloro-4-({1-[4-(2-cyclopropoxyphenyl)pyridin-3-yl]cyclopropoxy}methyl)phenyl]-N-[2-(dimethylcarbamoyl)ethyl]-N-[(2S,3R,4R,5R)-2,3,4,5,6-pentahydroxyhexyl]pentanamide (I-222);

N-(2-carbamoylethyl)-5-[2,5-dichloro-4-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]pentanamide (I-223);

(2S,3S,4R,5S)-N-{5-[2,5-dichloro-4-({1-[4-(2-cyclopropoxyphenyl)pyridin-3-yl]cyclopropoxy}methyl)phenyl]pentyl}-2,3,4,5,6-pentahydroxy-N-[2-(2-hydroxyethoxy)ethyl]hexanamide (I-224);

1-{5-[2,5-dichloro-4-({1-[4-(2-cyclopropoxyphenyl)pyridin-3-yl]cyclopropoxy}methyl)phenyl]pentyl}-3-[(2S,3R,4R,5R)-2,3,4,5,6-pentahydroxyhexyl]urea (I-225);

(2S,3S,4R,5S)-N-{5-[2,5-dichloro-4-({1-[4-(2-cyclopropoxyphenyl)pyridin-3-yl]cyclopropoxy}methyl)phenyl]pentyl}-2,3,4,5,6-pentahydroxy-N-(2-methanesulfonylethyl)hexanamide (I-226);

(2S,3S,4R,5S)-N-{5-[2,5-dichloro-4-({1-[4-(2-cyclopropoxyphenyl)pyridin-3-yl]cyclopropoxy}methyl)phenyl]pentyl}-N-[2-(ethanesulfonyl)ethyl]-2,3,4,5,6-pentahydroxyhexanamide (I-227);

(2S,3S,4R,5S)-N-{5-[2,5-dichloro-4-({1-[4-(2-cyclopropoxyphenyl)pyridin-3-yl]cyclopropoxy}methyl)phenyl]pentyl}-2,3,4,5,6-pentahydroxy-N-methylhexanamide (I-228);

5-[4-({1-[4-(2-cyclopropoxyphenyl)pyridin-3-yl]cyclopropoxy}methyl)-2,5-dimethylphenyl]-N-[(2S,3R,4R,5R)-2,3,4,5,6-pentahydroxyhexyl]pentanamide (I-229);

5-[4-({1-[4-(2-cyclopropoxyphenyl)pyridin-3-yl]cyclopropoxy}methyl)-2,5-dimethylphenyl]-N-methyl-N-[(2S,3R,4R,5R)-2,3,4,5,6-pentahydroxyhexyl]pentanamide (I-230);

5-[4-chloro-3-({1-[4-(2-cyclopropoxyphenyl)pyridin-3-yl]cyclopropoxy}methyl)phenyl]-N-[(2S,3R,4R,5R)-2,3,4,5,6-pentahydroxyhexyl]pentanamide (I-231);

5-[4-chloro-3-({1-[4-(2-cyclopropoxyphenyl)pyridin-3-yl]cyclopropoxy}methyl)phenyl]-N-methyl-N-[(2S,3R,4R,5R)-2,3,4,5,6-pentahydroxyhexyl]pentanamide (I-232);

5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]pentanamide (I-233);

5-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]pentanamide (I-234);

5-[3-({1-[4-(2-cyclopropoxyphenyl)pyridin-3-yl]cyclopropoxy}methyl)-4-methylphenyl]-N-[(2S,3R,4R,5R)-2,3,4,5,6-pentahydroxyhexyl]pentanamide (I-235);

5-[3-({1-[4-(2-cyclopropoxyphenyl)pyridin-3-yl]cyclopropoxy}methyl)-4-methylphenyl]-N-methyl-N-[(2S,3R,4R,5R)-2,3,4,5,6-pentahydroxyhexyl]pentanamide (I-236);

5-{3-[({1-[4-(2-cyclopropoxyphenyl)pyridin-3-yl]cyclopropyl}amino)methyl]-4-methylphenyl}-N-[(2S,3R,4R,5R)-2,3,4,5,6-pentahydroxyhexyl]pentanamide (I-237);

5-{3-[({1-[4-(2-cyclopropoxyphenyl)pyridin-3-yl]cyclopropyl}amino)methyl]-4-methylphenyl}-N-methyl-N-[(2S,3R,4R,5R)-2,3,4,5,6-pentahydroxyhexyl]pentanamide (I-238);

1-{4-[3-({1-[4-(2-cyclopropoxyphenyl)pyridin-3-yl]cyclopropoxy}methyl)-4-methylphenyl]butyl}-3-[(2S,3R,4R,5R)-2,3,4,5,6-pentahydroxyhexyl]urea (I-239);

1-(4-{3-[({1-[4-(2-cyclopropoxyphenyl)pyridin-3-yl]cyclopropyl}amino)methyl]-4-methylphenyl} butyl)-3-[(2S,3R,4R,5R)-2,3,4,5,6-pentahydroxyhexyl]urea (I-240);

1-(4-{4-chloro-3-[({1-[4-(2-cyclopropoxyphenyl)pyridin-3-yl]cyclopropyl}amino)methyl]phenyl}butyl)-3-[(2S,3R,4R,5R)-2,3,4,5,6-pentahydroxyhexyl]urea (I-241);

N-{[5-(6-aminohexan-2-yl)-2-chlorophenyl]methyl}-1-[4-(2-cyclopropoxyphenyl)pyridin-3-yl]cyclopropan-1-amine (I-242);

N-({5-[(2S)-6-aminohexan-2-yl]-2-chlorophenyl}methyl)-1-[4-(2-cyclopropoxyphenyl)pyridin-3-yl]cyclopropan-1-amine (I-243);

N-({5-[(2R)-6-aminohexan-2-yl]-2-chlorophenyl}methyl)-1-[4-(2-cyclopropoxyphenyl)pyridin-3-yl]cyclopropan-1-amine (I-244);

(5S)-5-[4-chloro-3-({1-[4-(2-cyclopropoxyphenyl)pyridin-3-yl]cyclopropoxy}methyl)phenyl]hexan-1-amine (I-245);

(5R)-5-[4-chloro-3-({1-[4-(2-cyclopropoxyphenyl)pyridin-3-yl]cyclopropoxy}methyl)phenyl]hexan-1-amine (I-246);

(5S)-5-{4-chloro-3-[({1-[4-(2-cyclopropoxyphenyl)pyridin-3-yl]cyclopropyl}amino)methyl]phenyl}hexanoic acid (I-247);

(5R)-5-{4-chloro-3-[({1-[4-(2-cyclopropoxyphenyl)pyridin-3-yl]cyclopropyl}amino)methyl]phenyl}hexanoic acid (I-248);

6-{4-chloro-3-[({1-[4-(2-cyclopropoxyphenyl)pyridin-3-yl]cyclopropyl}amino)methyl]phenyl}heptanoic acid (I-249);

N-({5-[(2S)-5-aminopentan-2-yl]-2-chlorophenyl}methyl)-1-[4-(2-cyclopropoxyphenyl)pyridin-3-yl]cyclopropan-1-amine (I-250);

N-({5-[(2R)-5-aminopentan-2-yl]-2-chlorophenyl}methyl)-1-[4-(2-cyclopropoxyphenyl)pyridin-3-yl]cyclopropan-1-amine (I-251);

N-{[5-(5-aminopentan-2-yl)-2-chlorophenyl]methyl}-1-[4-(2-cyclopropoxyphenyl)pyridin-3-yl]cyclopropan-1-amine (I-252);

(5S)-5-{3-[({1-[4-(2-cyclopropoxyphenyl)pyridin-3-yl]cyclopropyl}amino)methyl]-4-methylphenyl}hexanoic acid (I-253);

(5R)-5-{3-[({1-[4-(2-cyclopropoxyphenyl)pyridin-3-yl]cyclopropyl}amino)methyl]-4-methylphenyl}hexanoic acid (I-254);

1-[(5S)-5-{4-chloro-3-[({1-[4-(2-cyclopropoxyphenyl)pyridin-3-yl]cyclopropyl}amino)methyl]phenyl}hexyl]-3-[(2S,3R,4R,5R)-2,3,4,5,6-pentahydroxyhexyl]urea (I-255);

1-[(5R)-5-{4-chloro-3-[({1-[4-(2-cyclopropoxyphenyl)pyridin-3-yl]cyclopropyl}amino)methyl]phenyl}hexyl]-3-[(2S,3R,4R,5R)-2,3,4,5,6-pentahydroxyhexyl]urea (I-256);

5-{3-[({1-[4-(2-cyclopropoxyphenyl)pyridin-3-yl]cyclopropyl}amino)methyl]-4-methylphenyl}-N-[(2S,3R,4R,5R)-2,3,4,5,6-pentahydroxyhexyl]hexanamide (I-257);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-methylhexanamide (I-258);

N-benzyl-5-{3-[({1-[4-(2-cyclopropoxyphenyl)pyridin-3-yl]cyclopropyl}amino)methyl]-4-methylphenyl}-N-[(2S,3R,4R,5R)-2,3,4,5,6-pentahydroxyhexyl]hexanamide (I-259);

5-{2,5-dichloro-4-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-260);

5-{4-chloro-3-[({1-[4-(2-cyclopropoxyphenyl)pyridin-3-yl]cyclopropyl}amino)methyl]phenyl}-N-(5-hydroxypentyl)-N-[(2S,3R,4R,5R)-2,3,4,5,6-pentahydroxyhexyl]hexanamide (I-261);

5-{4-chloro-3-[({1-[4-(2-cyclopropoxyphenyl)pyridin-3-yl]cyclopropyl}amino)methyl]phenyl}-N-[2-(morpholine-4-sulfonyl)ethyl]-N-[(2S,3R,4R,5R)-2,3,4,5,6-pentahydroxyhexyl]hexanamide (I-262);

1-[(5S)-5-[4-chloro-3-({1-[4-(2-cyclopropoxyphenyl)pyridin-3-yl]cyclopropoxy}methyl) phenyl]hexyl]-3-[(2S,3R,4S,5R)-1,3,4,5,6-pentahydroxyhexan-2-yl]urea (I-263);

1-[(5R)-5-[4-chloro-3-({1-[4-(2-cyclopropoxyphenyl)pyridin-3-yl]cyclopropoxy}methyl)phenyl]hexyl]-3-[(2S,3R,4S,5R)-1,3,4,5,6-pentahydroxyhexan-2-yl]urea (I-264);

1-(4-{4-chloro-3-[({1-[4-(2-cyclopropoxyphenyl)pyridin-3-yl]cyclopropyl}amino)methyl]phenyl}pentyl)-3-[(2S,3R,4R,5R)-2,3,4,5,6-pentahydroxyhexyl]urea (I-265);

1-(5-{4-chloro-3-[({1-[4-(2-cyclopropoxyphenyl)pyridin-3-yl]cyclopropyl}amino)methyl]phenyl}hexyl)-3-[(2S,3R,4S,5R)-1,3,4,5,6-pentahydroxyhexan-2-yl]urea (I-266);

1-(5-{4-chloro-3-[({1-[4-(2-cyclopropoxyphenyl)pyridin-3-yl]cyclopropyl}amino)methyl]phenyl}hexyl)-3-[(2S,3R,4R,5R)-2,3,4,5,6-pentahydroxyhexyl]urea (I-267);

1-(6-{4-chloro-3-[({1-[4-(2-cyclopropoxyphenyl)pyridin-3-yl]cyclopropyl}amino)methyl]phenyl}heptyl)-3-[(2S,3R,4R,5R)-2,3,4,5,6-pentahydroxyhexyl]urea (I-268);

1-(5-{4-chloro-3-[({1-[4-(2-cyclopropoxyphenyl)pyridin-3-yl]cyclopropyl}amino)methyl]phenyl}hexyl)-1-methyl-3-[(2S,3R,4R,5R)-2,3,4,5,6-pentahydroxyhexyl]urea (I-269);

1-(5-{4-chloro-3-[({1-[4-(2-cyclopropoxyphenyl)pyridin-3-yl]cyclopropyl}amino)methyl]phenyl}hexyl)-1-[2-(2-hydroxyethoxy)ethyl]-3-[(2S,3R,4R,5R)-2,3,4,5,6-pentahydroxyhexyl]urea (I-270);

1-(4-{3-[({1-[4-(2-cyclopropoxyphenyl)pyridin-3-yl]cyclopropyl}amino)methyl]-4-methylphenyl}pentyl)-3-[(2S,3R,4R,5R)-2,3,4,5,6-pentahydroxyhexyl]urea (I-271);

1-(5-{3-[({1-[4-(2-cyclopropoxyphenyl)pyridin-3-yl]cyclopropyl}amino)methyl]-4-methylphenyl}hexyl)-3-[(2S,3R,4R,5R)-2,3,4,5,6-pentahydroxyhexyl]urea (I-272);

1-[(5R)-5-[4-chloro-3-({1-[4-(2-cyclopropoxyphenyl)pyridin-3-yl]cyclopropoxy}methyl) phenyl]hexyl]-3-[(2S,3R,4R,5R)-2,3,4,5,6-pentahydroxyhexyl]urea (I-273);

1-[(5S)-5-[4-chloro-3-({1-[4-(2-cyclopropoxyphenyl)pyridin-3-yl]cyclopropoxy}methyl) phenyl]hexyl]-3-[(2S,3R,4R,5R)-2,3,4,5,6-pentahydroxyhexyl]urea (I-274);

1-{5-[4-chloro-3-({1-[4-(2-cyclopropoxyphenyl)pyridin-3-yl]cyclopropoxy}methyl)phenyl]hexyl}-3-[(2S,3R,4R,5R)-2,3,4,5,6-pentahydroxyhexyl]urea (I-275);

1-{5-[3-({1-[4-(2-cyclopropoxyphenyl)pyridin-3-yl]cyclopropoxy}methyl)-4-methylphenyl]hexyl}-3-[(2S,3R,4R,5R)-2,3,4,5,6-pentahydroxyhexyl]urea (I-276);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-[2-(2-oxoimidazolidin-1-yl)ethyl]hexanamide (I-277);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxyhexanamide (I-278);

(2S,3S,4R,5S)-N-(5-{4-chloro-3-[({1-[4-(2-cyclopropoxyphenyl)pyridin-3-yl]cyclopropyl}amino)methyl]phenyl}hexyl)-2,3,4,5,6-pentahydroxyhexanamide (I-279);

(2S,3S,4R,5S)-N-(6-{4-chloro-3-[({1-[4-(2-cyclopropoxyphenyl)pyridin-3-yl]cyclopropyl}amino)methyl]phenyl}heptyl)-2,3,4,5,6-pentahydroxyhexanamide (I-280);

(2S,3S,4R,5S)-N-(5-{4-chloro-3-[({1-[4-(2-cyclopropoxyphenyl)pyridin-3-yl]cyclopropyl}amino)methyl]phenyl}hexyl)-2,3,4,5,6-pentahydroxy-N-methylhexanamide (I-281);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(2-methoxyethyl)hexanamide (I-282);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(4-hydroxybutyl)hexanamide (I-283);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(3-methoxypropyl)hexanamide (I-284);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(oxan-4-yl)hexanamide (I-285);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-[2-(2-hydroxyethoxy)ethyl]hexanamide (I-286);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(oxan-4-ylmethyl)hexanamide (I-287);

(2S,3S,4R,5S)-N-(5-{4-chloro-3-[({1-[4-(2-cyclopropoxyphenyl)pyridin-3-yl]cyclopropyl}amino)methyl]phenyl}hexyl)-2,3,4,5,6-pentahydroxy-N-[2-(2-hydroxyethoxy)ethyl]hexanamide (I-288);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(2-methanesulfonylethyl)hexanamide (I-289);

(2S,3S,4R,5S)-N-(4-{4-chloro-3-[({1-[4-(2-cyclopropoxyphenyl)pyridin-3-yl]cyclopropyl}amino)methyl]phenyl}pentyl)-N-(4-acetamidobutyl)-2,3,4,5,6-pentahydroxyhexanamide (I-290);

(2S,3S,4R,5S)-N-(5-{4-chloro-3-[({1-[4-(2-cyclopropoxyphenyl)pyridin-3-yl]cyclopropyl}amino)methyl]phenyl}hexyl)-2,3,4,5,6-pentahydroxy-N-(2-methanesulfonylethyl)hexanamide (I-291);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(3-methanesulfonylpropyl)hexanamide (I-292);

(2S,3S,4R,5S)-N-(4-{4-chloro-3-[({1-[4-(2-cyclopropoxyphenyl)pyridin-3-yl]cyclopropyl}amino)methyl]phenyl}pentyl)-N-[2-(ethanesulfonyl)ethyl]-2,3,4,5,6-pentahydroxyhexanamide (I-293);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-[3-(2-oxopyrrolidin-1-yl)propyl]hexanamide (I-294);

(2S,3S,4R,5S)-N-(4-{4-chloro-3-[({1-[4-(2-cyclopropoxyphenyl)pyridin-3-yl]cyclopropyl}amino)methyl]phenyl}pentyl)-N-(1,1-dioxo-1$\lambda^6$-thian-4-yl)-2,3,4,5,6-pentahydroxyhexanamide (I-295);

(2S,3S,4R,5S)-N-(5-{4-chloro-3-[({1-[4-(2-cyclopropoxyphenyl)pyridin-3-yl]cyclopropyl}amino)methyl]phenyl}hexyl)-N-[2-(ethanesulfonyl)ethyl]-2,3,4,5,6-pentahydroxyhexanamide (I-296);

(2S,3S,4R,5S)-N-(4-{4-chloro-3-[({1-[4-(2-cyclopropoxyphenyl)pyridin-3-yl]cyclopropyl}amino)methyl]phenyl}pentyl)-2,3,4,5,6-pentahydroxy-N-(4-methanesulfonamidobutyl) hexanamide (I-297);

(2S,3S,4R,5S)-N-(4-{4-chloro-3-[({1-[4-(2-cyclopropoxyphenyl)pyridin-3-yl]cyclopropyl}amino)methyl]phenyl}pentyl)-N-[2-(1,1-dioxo-1$\lambda^6$,4-thiomorpholin-4-yl)ethyl]-2,3,4,5,6-pentahydroxyhexanamide (I-298);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxyhexanamide (I-299);

(2S,3S,4R,5S)-N-(5-{3-[({1-[4-(2-cyclopropoxyphenyl)pyridin-3-yl]cyclopropyl}amino) methyl]-4-methylphenyl}hexyl)-2,3,4,5,6-pentahydroxyhexanamide (I-300);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxy-N-methylhexanamide (I-301);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxy-N-(2-methoxyethyl)hexanamide (I-302);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxy-N-(3-methoxypropyl)hexanamide (I-303);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxy-N-(oxan-4-yl)hexanamide (I-304);

(2S,3S,4R,5S)-N-(4-{3-[({1-[4-(2-cyclopropoxyphenyl)pyridin-3-yl]cyclopropyl}amino) methyl]-4-methylphenyl}pentyl)-2,3,4,5,6-pentahydroxy-N-(2-methanesulfonylethyl) hexanamide (I-305);

(2S,3S,4R,5S)-N-(4-{3-[({1-[4-(2-cyclopropoxyphenyl)pyridin-3-yl]cyclopropyl}amino) methyl]-4-methylphenyl}pentyl)-N-(1,1-dioxo-1$\lambda^6$-thian-4-yl)-2,3,4,5,6-pentahydroxyhexanamide (I-306);

(2S,3S,4R,5S)-N-(4-{3-[({1-[4-(2-cyclopropoxyphenyl)pyridin-3-yl]cyclopropyl}amino) methyl]-4-methylphenyl}pentyl)-N-[2-(ethanesulfonyl)ethyl]-2,3,4,5,6-pentahydroxyhexanamide (I-307);

(2S,3S,4R,5S)-N-{5-[4-chloro-3-({1-[4-(2-cyclopropoxyphenyl)pyridin-3-yl]cyclopropoxy}methyl)phenyl]hexyl}-2,3,4,5,6-pentahydroxyhexanamide (I-308);

(2S,3S,4R,5S)-N-(4-[4-chloro-3-({1-[4-(2-cyclopropoxyphenyl)pyridin-3-yl]cyclopropoxy) methyl)phenyl]pentyl}-2,3,4,5,6-pentahydroxy-N-(2-methanesulfonylethyl) hexanamide (I-309);

(2S,3S,4R,5S)-N-{4-[4-chloro-3-({1-[4-(2-cyclopropoxyphenyl)pyridin-3-yl]cyclopropoxy}methyl)phenyl]pentyl}-N-[2-(ethanesulfonyl)ethyl]-2,3,4,5,6-pentahydroxyhexanamide (I-310);

(2S,3S,4R,5S)-N-{4-[4-chloro-3-({1-[4-(2-cyclopropoxyphenyl)pyridin-3-yl]cyclopropoxy}methyl)phenyl]pentyl}-N-(1,1-dioxo-1$\lambda^6$-thian-4-yl)-2,3,4,5,6-pentahydroxyhexanamide (I-311);

(2S,3S,4R,5S)-N-{5-[3-({1-[4-(2-cyclopropoxyphenyl)pyridin-3-yl]cyclopropoxy}methyl)-4-methylphenyl]hexyl}-2,3,4,5,6-pentahydroxyhexanamide (I-312);

5-{4-chloro-3-[({1-[4-(2-cyclopropoxyphenyl)pyridin-3-yl]cyclopropyl}amino)methyl]phenyl}-N-[(2S,3R,4S,5R)-1,3,4,5,6-pentahydroxyhexan-2-yl]hexanamide (I-313);

(5S)-5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-314);

(5R)-5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-315);

5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-316);

6-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]heptanamide (I-317);

(2S,3S,4R,5S)-6-{[1-(5-{4-chloro-3-[({1-[4-(2-cyclopropoxyphenyl)pyridin-3-yl]cyclopropyl}amino)methyl]phenyl}hexanoyl)piperidin-4-yl]amino}-2,3,4,5-tetrahydroxyhexanoic acid (I-318);

4-(5-{4-chloro-3-[({1-[4-(2-cyclopropoxyphenyl)pyridin-3-yl]cyclopropyl}amino)methyl]phenyl}hexanoyl)-N-[(2S,3R,4R,5R)-2,3,4,5,6-pentahydroxyhexyl]piperazine-1-carboxamide (I-319);

1-[1-(5-{4-chloro-3-[({1-[4-(2-cyclopropoxyphenyl)pyridin-3-yl]cyclopropyl}amino)methyl]phenyl}hexanoyl)piperidin-4-yl]-3-[(2S,3R,4R,5R)-2,3,4,5,6-pentahydroxyhexyl]urea (I-320);

2-[4-(5-{4-chloro-3-[({1-[4-(2-cyclopropoxyphenyl)pyridin-3-yl]cyclopropyl}amino)methyl]phenyl}hexanoyl)piperazin-1-yl]-N-[(2S,3R,4R,5R)-2,3,4,5,6-pentahydroxyhexyl]acetamide (I-321);

4-[2-(5-{4-chloro-3-[({1-[4-(2-cyclopropoxyphenyl)pyridin-3-yl]cyclopropyl}amino)methyl]phenyl}hexanamido)ethyl]-N-[(2S,3R,4R,5R)-2,3,4,5,6-pentahydroxyhexyl]piperazine-1-carboxamide (I-322);

1-{2-[4-(5-{4-chloro-3-[({1-[4-(2-cyclopropoxyphenyl)pyridin-3-yl]cyclopropyl}amino)methyl]phenyl}hexanoyl)piperazin-1-yl]ethyl}-3-[(2S,3R,4R,5R)-2,3,4,5,6-pentahydroxyhexyl]urea (I-323);

5-{4-chloro-3-[({1-[4-(2-cyclopropoxyphenyl)pyridin-3-yl]cyclopropyl}amino)methyl]phenyl}-N-{2-[4-({[(2S,3R,4R,5R)-2,3,4,5,6-pentahydroxyhexyl]carbamoyl}methyl)piperazin-1-yl]ethyl}hexanamide (I-324);

(5S)-5-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]hexanamide (I-325);

(5R)-5-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]hexanamide (I-326);

5-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]hexanamide (I-327);

(6S)-6-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]heptanamide (I-328);

(6R)-6-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]heptanamide (I-329);

6-{4-chloro-3-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]heptanamide (I-330);

5-{4-chloro-3-[({1-[4-(2-cyclopropoxyphenyl)pyridin-3-yl]cyclopropyl}amino)methyl]phenyl}-N-(2-hydroxyethyl)-N-[(2R,3S,4S,5S)-2,3,4,5,6-pentahydroxyhexyl]hexanamide (I-331);

N-(carbamoylmethyl)-5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-332);

5-{4-chloro-3-[({1-[4-(2-cyclopropoxyphenyl)pyridin-3-yl]cyclopropyl}amino)methyl]phenyl}-N-(2-methoxyethyl)-N-[(2R,3S,4S,5S)-2,3,4,5,6-pentahydroxyhexyl]hexanamide (I-333);

5-{4-chloro-3-[({1-[4-(2-cyclopropoxyphenyl)pyridin-3-yl]cyclopropyl}amino)methyl]phenyl}-N-(3-hydroxypropyl)-N-[(2S,3R,4R,5R)-2,3,4,5,6-pentahydroxyhexyl]hexanamide (I-334);

N-(2-carbamoylethyl)-5-{4-chloro-3-[({1-[4-(2-cyclopropoxyphenyl)pyridin-3-yl]cyclopropyl}amino)methyl]phenyl}-N-[(2S,3R,4R,5R)-2,3,4,5,6-pentahydroxyhexyl]hexanamide (I-335);

5-{4-chloro-3-[({1-[4-(2-cyclopropoxyphenyl)pyridin-3-yl]cyclopropyl}amino)methyl]phenyl}-N-[(methylcarbamoyl)methyl]-N-[(2S,3R,4R,5R)-2,3,4,5,6-pentahydroxyhexyl]hexanamide (I-336);

5-{4-chloro-3-[({1-[4-(2-cyclopropoxyphenyl)pyridin-3-yl]cyclopropyl}amino)methyl]phenyl}-N-[$^2$-(dimethylamino)ethyl]-N-[(2S,3R,4R,5R)-2,3,4,5,6-pentahydroxyhexyl]hexanamide (I-337);

5-{4-chloro-3-[({11-[4-(2-cyclopropoxyphenyl)pyridin-3-yl]cyclopropyl}amino)methyl]phenyl}-N-(3-methoxypropyl)-N-[(2S,3R,4R,5R)-2,3,4,5,6-pentahydroxyhexyl]hexanamide (I-338);

5-{4-chloro-3-[({11-[4-(2-cyclopropoxyphenyl)pyridin-3-yl]cyclopropyl}amino)methyl]phenyl}-N-(oxan-4-yl)-N-[(2R,3S,4S,5S)-2,3,4,5,6-pentahydroxyhexyl]hexanamide (I-339);

5-{4-chloro-3-[({1-[4-(2-cyclopropoxyphenyl)pyridin-3-yl]cyclopropyl}amino)methyl]phenyl}-N-[(dimethylcarbamoyl)methyl]-N-[(2S,3R,4R,5R)-2,3,4,5,6-pentahydroxyhexyl]hexanamide (I-340);

5-{4-chloro-3-[({1-[4-(2-cyclopropoxyphenyl)pyridin-3-yl]cyclopropyl}amino)methyl]phenyl}-N-(3-hydroxy-2,2-dimethylpropyl)-N-[(2R,3S,4S,5S)-2,3,4,5,6-pentahydroxyhexyl]hexanamide (I-341);

5-{4-chloro-3-[({1-[4-(2-cyclopropoxyphenyl)pyridin-3-yl]cyclopropyl]amino)methyl]phenyl}-N-[2-(2-hydroxyethoxy)ethyl]-N-[(2S,3R,4R,5R)-2,3,4,5,6-pentahydroxyhexyl]hexanamide (I-342);

5-{4-chloro-3-[({1-[4-(2-cyclopropoxyphenyl)pyridin-3-yl]cyclopropyl}amino)methyl]phenyl}-N-[(2R,3S,4S,5S)-2,3,4,5,6-pentahydroxyhexyl]-N-[(1s,4s)-4-hydroxycyclohexyl]hexanamide (I-343);

5-{4-chloro-3-[({1-[4-(2-cyclopropoxyphenyl)pyridin-3-yl]cyclopropyl}amino)methyl]phenyl}-N-[2-(ethylcarbamoyl)ethyl]-N-[(2S,3R,4R,5R)-2,3,4,5,6-pentahydroxyhexyl]hexanamide (I-344);

5-{4-chloro-3-[({1-[4-(2-cyclopropoxyphenyl)pyridin-3-yl]cyclopropyl}amino)methyl]phenyl}-N-[2-(dimethylcarbamoyl)ethyl]-N-[(2S,3R,4R,5R)-2,3,4,5,6-pentahydroxyhexyl]hexanamide (I-345);

5-{4-chloro-3-[({1-[4-(2-cyclopropoxyphenyl)pyridin-3-yl]cyclopropyl}amino)methyl]phenyl}-N-(2-methanesulfonylethyl)-N-[(2R,3S,4S,5S)-2,3,4,5,6-pentahydroxyhexyl]hexanamide (I-346);

5-{4-chloro-3-[({1-[4-(2-cyclopropoxyphenyl)pyridin-3-yl]cyclopropyl}amino)methyl]phenyl}-N-(3-methanesulfonylpropyl)-N-[(2S,3R,4R,5R)-2,3,4,5,6-pentahydroxyhexyl]hexanamide (I-347);

5-{4-chloro-3-[({1-[4-(2-cyclopropoxyphenyl)pyridin-3-yl]cyclopropyl}amino)methyl]phenyl}-N-[2-(dimethylsulfamoyl)ethyl]-N-[(2S,3R,4R,5R)-2,3,4,5,6-pentahydroxyhexyl]hexanamide (I-348);

5-{3-[({1-[4-(2-cyclopropoxyphenyl)pyridin-3-yl]cyclopropyl}amino)methyl]-4-ethylphenyl}-N-[(2S,3R,4R,5R)-2,3,4,5,6-pentahydroxyhexyl]hexanamide (I-349);

(5S)-5-{3-[({1-[4-(2-cyclopropoxyphenyl)pyridin-3-yl]cyclopropyl}amino)methyl]-4-methylphenyl}-N-methyl-N-[(2S,3R,4R,5R)-2,3,4,5,6-pentahydroxyhexyl]hexanamide (I-350);

(5R)-5-{3-[({1-[4-(2-cyclopropoxyphenyl)pyridin-3-yl]cyclopropyl}amino)methyl]-4-methylphenyl}-N-methyl-N-[(2S,3R,4R,5R)-2,3,4,5,6-pentahydroxyhexyl]hexanamide (I-351);

5-{3-[({1-[4-(2-cyclopropoxyphenyl)pyridin-3-yl]cyclopropyl}amino)methyl]-4-methylphenyl}-N-methyl-N-[(2S,3R,4R,5R)-2,3,4,5,6-pentahydroxyhexyl]hexanamide (I-352);

5-{3-[({1-[4-(2-cyclopropoxyphenyl)pyridin-3-yl]cyclopropyl}amino)methyl]-4-methylphenyl}-N-[(2S,3R,4R,5R)-2,3,4,5,6-pentahydroxyhexyl]-N-(propan-2-yl)hexanamide (I-353);

5-{3-[({1-[4-(2-cyclopropoxyphenyl)pyridin-3-yl]cyclopropyl}amino)methyl]-4-methylphenyl}-N-[(2S,3R,4R,5R)-2,3,4,5,6-pentahydroxyhexyl]-N-propylhexanamide (I-354);

5-{3-[({1-[4-(2-cyclopropoxyphenyl)pyridin-3-yl]cyclopropyl}amino)methyl]-4-methylphenyl}-N-(2-hydroxyethyl)-N-[(2S,3R,4R,5R)-2,3,4,5,6-pentahydroxyhexyl]hexanamide (I-355);

N-(carbamoylmethyl)-5-{3-[({1-[4-(2-cyclopropoxyphenyl)pyridin-3-yl]cyclopropyl}amino) methyl]-4-methylphenyl}-N-[(2S,3R,4R,5R)-2,3,4,5,6-pentahydroxyhexyl]hexanamide (I-356);

5-{3-[({1-[4-(2-cyclopropoxyphenyl)pyridin-3-yl]cyclopropyl}amino)methyl]-4-methylphenyl}-N-(2-methoxyethyl)-N-[(2S,3R,4R,5R)-2,3,4,5,6-pentahydroxyhexyl]hexanamide (I-357);

5-{3-[({1-[4-(2-cyclopropoxyphenyl)pyridin-3-yl]cyclopropyl}amino)methyl]-4-methylphenyl}-N-(3-hydroxypropyl)-N-[(2S,3R,4R,5R)-2,3,4,5,6-pentahydroxyhexyl]hexanamide (I-358);

N-(2-carbamoylethyl)-5-{3-[({1-[4-(2-cyclopropoxyphenyl)pyridin-3-yl]cyclopropyl}amino) methyl]-4-methylphenyl}-N-[(2S,3R,4R,5R)-2,3,4,5,6-pentahydroxyhexyl]hexanamide (I-359);

5-{3-[({1-[4-(2-cyclopropoxyphenyl)pyridin-3-yl]cyclopropyl}amino)methyl]-4-methylphenyl}-N-[(methylcarbamoyl)methyl]-N-[(2S,3R,4R,5R)-2,3,4,5,6-pentahydroxyhexyl]hexanamide (I-360);

5-{3-[({1-[4-(2-cyclopropoxyphenyl)pyridin-3-yl]cyclopropyl}amino)methyl]-4-methylphenyl}-N-[2-(dimethylamino)ethyl]-N-[(2S,3R,4R,5R)-2,3,4,5,6-pentahydroxyhexyl]hexanamide (I-361);

5-{3-[({1-[4-(2-cyclopropoxyphenyl)pyridin-3-yl]cyclopropyl}amino)methyl]-4-methylphenyl}-N-(3-methoxypropyl)-N-[(2S,3R,4R,5R)-2,3,4,5,6-pentahydroxyhexyl]hexanamide (I-362);

5-{3-[({1-[4-(2-cyclopropoxyphenyl)pyridin-3-yl]cyclopropyl}amino)methyl]-4-methylphenyl}-N-(oxan-4-yl)-N-[(2S,3R,4R,5R)-2,3,4,5,6-pentahydroxyhexyl]hexanamide (I-363);

5-{3-[({1-[4-(2-cyclopropoxyphenyl)pyridin-3-yl]cyclopropyl}amino)methyl]-4-methylphenyl}-N-[(dimethylcarbamoyl)methyl]-N-[(2S,3R,4R,5R)-2,3,4,5,6-pentahydroxyhexyl]hexanamide (I-364);

5-{3-[({1-[4-(2-cyclopropoxyphenyl)pyridin-3-yl]cyclopropyl}amino)methyl]-4-methylphenyl}-N-[2-(ethylcarbamoyl)ethyl]-N-[(2S,3R,4R,5R)-2,3,4,5,6-pentahydroxyhexyl]hexanamide (I-365);

5-{3-[({1-[4-(2-cyclopropoxyphenyl)pyridin-3-yl]cyclopropyl}amino)methyl]-4-methylphenyl}-N-[2-(dimethylcarbamoyl)ethyl]-N-[(2S,3R,4R,5R)-2,3,4,5,6-pentahydroxyhexyl]hexanamide (I-366);

(5S)-5-{3-[({1-[4-(2-cyclopropoxyphenyl)pyridin-3-yl]cyclopropyl}amino)methyl]-4-methylphenyl}-N-(2-methanesulfonylethyl)-N-[(2S,3R,4R,5R)-2,3,4,5,6-pentahydroxyhexyl]hexanamide (I-367);

(5R)-5-{3-[({1-[4-(2-cyclopropoxyphenyl)pyridin-3-yl]cyclopropyl}amino)methyl]-4-methylphenyl}-N-(2-methanesulfonylethyl)-N-[(2S,3R,4R,5R)-2,3,4,5,6-pentahydroxyhexyl]hexanamide (I-368);

5-{3-[({1-[4-(2-cyclopropoxyphenyl)pyridin-3-yl]cyclopropyl}amino)methyl]-4-methylphenyl}-N-(2-methanesulfonylethyl)-N-[(2S,3R,4R,5R)-2,3,4,5,6-pentahydroxyhexyl]hexanamide (I-369);

5-{3-[({1-[4-(2-cyclopropoxyphenyl)pyridin-3-yl]cyclopropyl}amino)methyl]-4-methylphenyl}-N-(3-methanesulfonylpropyl)-N-[(2S,3R,4R,5R)-2,3,4,5,6-pentahydroxyhexyl]hexanamide (I-370);

2-[4-(5-{3-[({1-[4-(2-cyclopropoxyphenyl)pyridin-3-yl]cyclopropyl}amino)methyl]-4-methylphenyl}hexanoyl)piperazin-1-yl]-N-[(2S,3R,4R,5R)-2,3,4,5,6-pentahydroxyhexyl]acetamide (I-371);

4-[2-(5-{4-chloro-3-[(1-{1-[4-(2-cyclopropoxyphenyl)pyridin-3-yl]cyclopropyl}{[(2S,3R,4R,5R)-2,3,4,5,6-pentahydroxyhexyl]carbamoyl}amino)methyl]phenyl}hexanamido) ethyl]-N-[(2S,3R,4R,5R)-2,3,4,5,6-pentahydroxyhexyl]piperazine-1-carboxamide (I-372);

5-[4-chloro-3-({1-[4-(2-cyclopropoxyphenyl)pyridin-3-yl]cyclopropoxy}methyl)phenyl]-N-ethyl-N-[(2S,3R,4R,5R)-2,3,4,5,6-pentahydroxyhexyl]hexanamide (I-373);

5-[4-chloro-3-({1-[4-(2-cyclopropoxyphenyl)pyridin-3-yl]cyclopropoxy}methyl)phenyl]-N-(2-hydroxyethyl)-N-[(2S,3R,4R,5R)-2,3,4,5,6-pentahydroxyhexyl]hexanamide (I-374);

5-[3-({1-[4-(2-cyclopropoxyphenyl)pyridin-3-yl]cyclopropoxy}methyl)-4-methylphenyl]-N-ethyl-N-[(2S,3R,4R,5R)-2,3,4,5,6-pentahydroxyhexyl]hexanamide (I-375);

5-[3-({1-[4-(2-cyclopropoxyphenyl)pyridin-3-yl]cyclopropoxy}methyl)-4-methylphenyl]-N-(2-hydroxyethyl)-N-[(2S,3R,4R,5R)-2,3,4,5,6-pentahydroxyhexyl]hexanamide (I-376);

N-(4-{4-chloro-3-[({1-[4-(2-cyclopropoxyphenyl)pyridin-3-yl]cyclopropyl}amino)methyl]phenyl}pentyl)-N-[(2S,3R,4R,5R)-2,3,4,5,6-pentahydroxyhexyl]acetamide (I-377);

N-(5-{4-chloro-3-[({1-[4-(2-cyclopropoxyphenyl)pyridin-3-yl]cyclopropyl}amino)methyl]phenyl}hexyl)-N-[(2S,3R,4R,5R)-2,3,4,5,6-pentahydroxyhexyl]acetamide (I-378);

5-{2,5-dichloro-4-[({1-[4-(2-cyclopropoxyphenyl)pyridin-3-yl]cyclopropyl}amino)methyl]phenyl}-N-methyl-N-[(2S,3R,4R,5R)-2,3,4,5,6-pentahydroxyhexyl]hexanamide (I-379);

(2S,3S,4R,5S)-N-(4-{4-chloro-3-[({1-[4-(2-cyclopropoxyphenyl)pyridin-3-yl]cyclopropyl}amino)methyl]phenyl}-5-hydroxypentyl)-2,3,4,5,6-pentahydroxyhexanamide (I-380);

(2S,3S,4R,5S)-N-(4-{4-chloro-3-[({1-[4-(2-cyclopropoxyphenyl)pyridin-3-yl]cyclopropyl}amino)methyl]phenyl}pent-4-en-1-yl)-2,3,4,5,6-pentahydroxyhexanamide (I-381);

(2S,3S,4R,5S)-N-[3-(1-{4-chloro-3-[({1-[4-(2-cyclopropoxyphenyl)pyridin-3-yl]cyclopropyl}amino)methyl]phenyl}cyclopropyl)propyl]-2,3,4,5,6-pentahydroxyhexanamide (I-382);

1-(4-{4-chloro-3-[({1-[4-(2-cyclopropoxyphenyl)pyridin-3-yl]cyclopropyl}amino)methyl]phenyl}pent-4-en-1-yl)-3-[(2S,3R,4R,5R)-2,3,4,5,6-pentahydroxyhexyl]urea (I-383);

1-(4-{4-chloro-3-[({1-[4-(2-cyclopropoxyphenyl)pyridin-3-yl]cyclopropyl}amino)methyl]phenyl}-5-hydroxypentyl)-3-[(2S,3R,4R,5R)-2,3,4,5,6-pentahydroxyhexyl]urea (I-384);

1-[3-(1-{4-chloro-3-[({1-[4-(2-cyclopropoxyphenyl)pyridin-3-yl]cyclopropyl}amino)methyl]phenyl}cyclopropyl)propyl]-3-[(2S,3R,4R,5R)-2,3,4,5,6-pentahydroxyhexyl]urea (I-385);

(2S,3S,4R,5S)-N-(4-{3-[({1-[4-(2-cyclopropoxyphenyl)pyridin-3-yl]cyclopropyl}amino) methyl]-4-methylphenyl}-5-hydroxypentyl)-2,3,4,5,6-pentahydroxyhexanamide (I-386);

1-(4-{3-[({1-[4-(2-cyclopropoxyphenyl)pyridin-3-yl]cyclopropyl}amino)methyl]-4-methylphenyl}-5-hydroxypentyl)-3-[(2S,3R,4R,5R)-2,3,4,5,6-pentahydroxyhexyl]urea (I-387);

(2S,3S,4R,5S)-N-{4-[4-chloro-3-({1-[4-(2-cyclopropoxyphenyl)pyridin-3-yl]cyclopropoxy}methyl)benzenesulfonamido]butyl}-2,3,4,5,6-pentahydroxyhexanamide (I-388);

1-{4-[N-methyl4-chloro-3-({1-[4-(2-cyclopropoxyphenyl)pyridin-3-yl]cyclopropoxy}methyl) benzenesulfonamido]butyl}-3-[(2S,3R,4S,5R)-1,3,4,5,6-pentahydroxyhexan-2-yl]urea (I-389);

1-{4-[N-ethyl4-chloro-3-({1-[4-(2-cyclopropoxyphenyl)pyridin-3-yl]cyclopropoxy}methyl) benzenesulfonamido]butyl}-3-[(2S,3R,4R,5R)-2,3,4,5,6-pentahydroxyhexyl]urea (I-390);

3-[(2S,3R,4R,5R)-2,3,4,5,6-pentahydroxyhexyl]-1-{4-[N-(propan-2-yl)4-chloro-3-({1-[4-(2-cyclopropoxyphenyl)pyridin-3-yl]cyclopropoxy}methyl)benzenesulfonamido]butyl}urea (I-391);

1-(4-{N-methyl2,4-dichloro-5-[({1-[4-(2-cyclopropoxyphenyl)pyridin-3-yl]cyclopropyl}amino) methyl] benzenesulfonamido}butyl)-3-[(2S,3R,4R,5R)-2,3,4,5,6-pentahydroxyhexyl]urea (I-392);

4-chloro-3-({1-[4-(2-cyclopropoxyphenyl)pyridin-3-yl]cyclopropoxy}methyl)-N,N-dimethylbenzene-1-sulfonamide (I-393);

4-chloro-3-({1-[4-(2-cyclopropoxyphenyl)pyridin-3-yl]cyclopropoxy}methyl)-N-methylbenzene-1-sulfonamide (I-394);

3-(1-{[2-chloro-5-(pyrrolidine-1-sulfonyl)phenyl]methoxy}cyclopropyl)-4-(2-cyclopropoxyphenyl)pyridine (I-395);

3-(1-{[2-chloro-5-(piperidine-1-sulfonyl)phenyl]methoxy}cyclopropyl)-4-(2-cyclopropoxyphenyl)pyridine (I-396);

(2S,3R,4R,5R)-S-[4-chloro-3-({1-[4-(2-cyclopropoxyphenyl)pyridin-3-yl]cyclopropoxy}methyl) phenyl]-2,3,4,5,6-pentahydroxyhexane-1-sulfonamido (I-397);

(2S,3R,4R,5R)-S-[4-chloro-3-({1-[4-(2-cyclopropoxyphenyl)pyridin-3-yl]cyclopropoxy}methyl) phenyl]-2,3,4,5,6-pentahydroxy-N-methylhexane-1-sulfonamido (I-398);

N-[2-(2-aminoethoxy)ethyl]-4-chloro-3-({1-[4-(2-cyclopropoxyphenyl)pyridin-3-yl]cyclopropoxy}methyl)benzene-1-sulfonamide (I-399);

N-[2-(2-aminoethoxy)ethyl]-4-chloro-3-({1-[4-(2-cyclopropoxyphenyl)pyridin-3-yl]cyclopropoxy}methyl)-N-methylbenzene-1-sulfonamide (I-400);

1-{4-[4-chloro-3-({1-[4-(2-cyclopropoxyphenyl)pyridin-3-yl]cyclopropoxy}methyl) benzenesulfonamido]butyl}-3-[(2S,3R,4R,5R)-2,3,4,5,6-pentahydroxyhexyl]urea (I-401);

1-{4-[N-methyl4-chloro-3-({1-[4-(2-cyclopropoxyphenyl)pyridin-3-yl]cyclopropoxy}methyl) benzenesulfonamido]butyl}-3-[(2S,3R,4R,5R)-2,3,4,5,6-pentahydroxyhexyl]urea (I-402);

1-(2-{2-[4-chloro-3-({1-[4-(2-cyclopropoxyphenyl)pyridin-3-yl]cyclopropoxy}methyl) benzenesulfonamido]ethoxy}ethyl)-3-[(2S,3R,4R,5R)-2,3,4,5,6-pentahydroxyhexyl]urea (I-403);

1-(2-{2-[N-methyl4-chloro-3-({1-[4-(2-cyclopropoxyphenyl)pyridin-3-yl]cyclopropoxy}methyl) benzenesulfonamido]ethoxy}ethyl)-3-[(2S,3R,4R,5R)-2,3,4,5,6-pentahydroxyhexyl]urea (I-404);

1-{5-[N-methyl4-chloro-3-({1-[4-(2-cyclopropoxyphenyl)pyridin-3-yl]cyclopropoxy}methyl) benzenesulfonamido]pentyl}-3-[(2S,3R,4S,5R)-1,3,4,5,6-pentahydroxyhexan-2-yl]urea (I-405);

1-(2-{2-[N-methyl4-chloro-3-({1-[4-(2-cyclopropoxyphenyl)pyridin-3-yl]cyclopropoxy}methyl) benzenesulfonamido]ethoxy}ethyl)-3-[(2S,3R,4S,5R)-1,3,4,5,6-pentahydroxyhexan-2-yl]urea (I-406);

1-{4-[N-(2-methoxyethyl)4-chloro-3-({1-[4-(2-cyclopropoxyphenyl)pyridin-3-yl]cyclopropoxy}methyl)benzenesulfonamido]butyl}-3-[(2S,3R,4R,5R)-2,3,4,5,6-pentahydroxyhexyl]urea (I-407);

1-(2-{2-[4-chloro-3-({1-[4-(2-cyclopropoxyphenyl)pyridin-3-yl]cyclopropoxy}methyl) benzenesulfonamido]ethoxy}ethyl)-3-[(2S,3R,4S,5R)-1,3,4,5,6-pentahydroxyhexan-2-yl]urea (I-408);

1-{5-[4-chloro-3-({1-[4-(2-cyclopropoxyphenyl)pyridin-3-yl]cyclopropoxy}methyl) benzenesulfonamido]pentyl}-3-[(2S,3R,4S,5R)-1,3,4,5,6-pentahydroxyhexan-2-yl]urea (I-409);

1-{4-[4-chloro-3-({1-[4-(2-cyclopropoxyphenyl)pyridin-3-yl]cyclopropoxy}methyl) benzenesulfonamido]butyl}-3-[(2S,3R,4S,5R)-1,3,4,5,6-pentahydroxyhexan-2-yl]urea (I-410);

1-(2-{2-[N-ethyl4-chloro-3-({1-[4-(2-cyclopropoxyphenyl)pyridin-3-yl]cyclopropoxy}methyl) benzenesulfonamido]ethoxy}ethyl)-3-[(2S,3R,4R,5R)-2,3,4,5,6-pentahydroxyhexyl]urea (I-411);

1-{5-[N-(2-methoxyethyl)4-chloro-3-({1-[4-(2-cyclopropoxyphenyl)pyridin-3-yl]cyclopropoxy}methyl)benzenesulfonamido]pentyl}-3-[(2S,3R,4R,5R)-2,3,4,5,6-pentahydroxyhexyl]urea (I-412);

1-{5-[N-(2-methoxyethyl)4-chloro-3-({1-[4-(2-cyclopropoxyphenyl)pyridin-3-yl]cyclopropoxy}methyl)benzenesulfonamido]pentyl}-3-[(2S,3R,4S,5R)-1,3,4,5,6-pentahydroxyhexan-2-yl]urea (I-413);

1-{4-[N-(2-hydroxyethyl)4-chloro-3-({1-[4-(2-cyclopropoxyphenyl)pyridin-3-yl]cyclopropoxy}methyl)benzenesulfonamido]butyl}-3-[(2S,3R,4R,5R)-2,3,4,5,6-pentahydroxyhexyl]urea (I-414);

1-(2-{2-[N-ethyl4-chloro-3-({1-[4-(2-cyclopropoxyphenyl)pyridin-3-yl]cyclopropoxy}methyl) benzenesulfonamido]ethoxy}ethyl)-3-[(2S,3R,4S,5R)-1,3,4,5,6-pentahydroxyhexan-2-yl]urea (I-415);

1-{4-[N-(2-methoxyethyl)4-chloro-3-({1-[4-(2-cyclopropoxyphenyl)pyridin-3-yl]cyclopropoxy}methyl)benzenesulfonamido]butyl}-3-[(2S,3R,4S,5R)-1,3,4,5,6-pentahydroxyhexan-2-yl]urea (I-416);

1-(2-{1-[4-chloro-3-({1-[4-(2-cyclopropoxyphenyl)pyridin-3-yl]cyclopropoxy}methyl) benzenesulfonyl]piperidin-4-yl}ethyl)-3-[(2S,3R,4R,5R)-2,3,4,5,6-pentahydroxyhexyl]urea (I-417);

3-[(2S,3R,4R,5R)-2,3,4,5,6-pentahydroxyhexyl]-1-[(1r,4r)-4-[4-chloro-3-({1-[4-(2-cyclopropoxyphenyl)pyridin-3-yl]cyclopropoxy}methyl)benzenesulfonamido]cyclohexyl]urea (I-418);

3-[(2S,3R,4R,5R)-2,3,4,5,6-pentahydroxyhexyl]-1-[(1s,4s)-4-[4-chloro-3-({1-[4-(2-cyclopropoxyphenyl)pyridin-3-yl]cyclopropoxy}methyl)benzenesulfonamido]cyclohexyl]urea (I-419);

1-({1-[4-chloro-3-({1-[4-(2-cyclopropoxyphenyl)pyridin-3-yl]cyclopropoxy}methyl) benzenesulfonyl]pyrrolidin-3-yl}methyl)-3-[(2S,3R,4R,5R)-2,3,4,5,6-pentahydroxyhexyl]urea (I-420);

1-(2-{1-[4-chloro-3-({1-[4-(2-cyclopropoxyphenyl)pyridin-3-yl]cyclopropoxy}methyl) benzenesulfonyl]azetidin-3-yl}ethyl)-3-[(2S,3R,4R,5R)-2,3,4,5,6-pentahydroxyhexyl]urea (I-421);

1-(4-{2-[4-chloro-3-({1-[4-(2-cyclopropoxyphenyl)pyridin-3-yl]cyclopropoxy}methyl) benzenesulfonamido]ethyl}cyclohexyl)-3-[(2S,3R,4R,5R)-2,3,4,5,6-pentahydroxyhexyl]urea (I-422);

1-(3-{4-[4-chloro-3-({1-[4-(2-cyclopropoxyphenyl)pyridin-3-yl]cyclopropoxy}methyl) benzenesulfonyl]piperazin-1-yl}propyl)-3-[(2S,3R,4R,5R)-2,3,4,5,6-pentahydroxyhexyl]urea (1-423);

1-({1-[4-chloro-3-({1-[4-(2-cyclopropoxyphenyl)pyridin-3-yl]cyclopropoxy}methyl) benzenesulfonyl]piperidin-4-yl}methyl)-3-[(2S,3R,4R,5R)-2,3,4,5,6-pentahydroxyhexyl]urea (I-424);

1-(2-{4-[4-chloro-3-({1-[4-(2-cyclopropoxyphenyl)pyridin-3-yl]cyclopropoxy}methyl) benzenesulfonyl]piperazin-1-yl}ethyl)-3-[(2S,3R,4R,5R)-2,3,4,5,6-pentahydroxyhexyl]urea (I-425);

1-({1-[4-chloro-3-({1-[4-(2-cyclopropoxyphenyl)pyridin-3-yl]cyclopropoxy}methyl) benzenesulfonyl]piperidin-3-yl}methyl)-3-[(2S,3R,4R,5R)-2,3,4,5,6-pentahydroxyhexyl]urea (I-426);

1-{1-[4-chloro-3-({1-[4-(2-cyclopropoxyphenyl)pyridin-3-yl]cyclopropoxy}methyl) benzenesulfonyl]azetidin-3-yl}-3-[(2S,3R,4R,5R)-2,3,4,5,6-pentahydroxyhexyl]urea (I-427);

1-{7-[4-chloro-3-({1-[4-(2-cyclopropoxyphenyl)pyridin-3-yl]cyclopropoxy}methyl) benzenesulfonyl]-7-azaspiro[3.5]nonan-2-yl}-3-[(2S,3R,4R,5R)-2,3,4,5,6-pentahydroxyhexyl]urea (I-428);

1-{1-[4-chloro-3-({1-[4-(2-cyclopropoxyphenyl)pyridin-3-yl]cyclopropoxy}methyl) benzenesulfonyl]pyrrolidin-3-yl}-3-[(2S,3R,4R,5R)-2,3,4,5,6-pentahydroxyhexyl]urea (I-429);

1-{2-[4-chloro-3-({1-[4-(2-cyclopropoxyphenyl)pyridin-3-yl]cyclopropoxy}methyl) benzenesulfonyl]-2-azaspiro[3.3]heptan-6-yl}-3-[(2S,3R,4R,5R)-2,3,4,5,6-pentahydroxyhexyl]urea (I-430);

6-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]hexanamide (I-431);

7-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]heptanamide (I-432);

5-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]pentanamide (I-433);

3-[N-methyl4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]propanamide (I-434);

(1R,5S,6S)-3-[4-chloro-3-({1-[4-(2-cyclopropoxyphenyl)pyridin-3-yl]cyclopropoxy}methyl) benzenesulfonyl]-N-[(2S,3R,4R,5R)-2,3,4,5,6-pentahydroxyhexyl]-3-azabicyclo[3.1.0]hexane-6-carboxamide (I-435);

(1r,4r)-4-[4-chloro-3-({1-[4-(2-cyclopropoxyphenyl)pyridin-3-yl]cyclopropoxy}methyl) benzenesulfonamidomethyl]-N-[(2S,3R,4R,5R)-2,3,4,5,6-pentahydroxyhexyl]cyclohexane-1-carboxamide (I-436);

1-[4-chloro-3-({1-[4-(2-cyclopropoxyphenyl)pyridin-3-yl]cyclopropoxy}methyl) benzenesulfonyl]-N-[(2S,3R,5R)-2,3,4,5,6-pentahydroxyhexyl]piperidine-4-carboxamide (I-437);

2-{1-[4-chloro-3-({1-[4-(2-cyclopropoxyphenyl)pyridin-3-yl]cyclopropoxy}methyl) benzenesulfonyl]azetidin-3-yl}-N-[(2S,3R,4R,5R)-2,3,4,5,6-pentahydroxyhexyl]acetamide (I-438);

3-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]cyclopentane-1-carboxamide (I-439);

2-{4-[4-chloro-3-({1-[4-(2-cyclopropoxyphenyl)pyridin-3-yl]cyclopropoxy}methyl) benzenesulfonyl]piperazin-1-yl}-N-[(2S,3R,4R,5R)-2,3,4,5,6-pentahydroxyhexyl]acetamide (I-440);

2-{1-[4-chloro-3-({1-[4-(2-cyclopropoxyphenyl)pyridin-3-yl]cyclopropoxy}methyl) benzenesulfonyl]piperidin-4-yl}-N-[(2S,3R,4R,5R)-2,3,4,5,6-pentahydroxyhexyl]acetamide (I-441);

(1r,4r)-4-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]cyclohexane-1-carboxamide (I-442);

3-{4-[4-chloro-3-({1-[4-(2-cyclopropoxyphenyl)pyridin-3-yl]cyclopropoxy}methyl) benzenesulfonyl]piperazin-1-yl}-N-[(2S,3R,4R,5R)-2,3,4,5,6-pentahydroxyhexyl]propanamide (I-443);

2-({1-[4-chloro-3-({1-[4-(2-cyclopropoxyphenyl)pyridin-3-yl]cyclopropoxy}methyl) benzenesulfonyl]piperidin-4-yl}oxy)-N-[(2S,3R,4R,5R)-2,3,4,5,6-pentahydroxyhexyl]acetamide (I-444);

4-[4-chloro-3-({1-[4-(2-cyclopropoxyphenyl)pyridin-3-yl]cyclopropoxy}methyl) benzenesulfonamido]-N-[(2S,3R,4R,5R)-2,3,4,5,6-pentahydroxyhexyl]bicyclo[2.2.2]octane-1-carboxamide (I-445);

(2E)-3-{1-[4-chloro-3-({1-[4-(2-cyclopropoxyphenyl)pyridin-3-yl]cyclopropoxy}methyl) benzenesulfonyl]azetidin-3-yl}-N-[(2S,3R,4R,5R)-2,3,4,5,6-pentahydroxyhexyl]prop-2-enamide (I-446);

2-{1-[4-chloro-3-({1-[4-(2-cyclopropoxyphenyl)pyridin-3-yl]cyclopropoxy}methyl) benzenesulfonyl]azetidin-3-yl}-N-methyl-N-[(2S,3R,4R,5R)-2,3,4,5,6-pentahydroxyhexyl]acetamide (I-447);

3-{1-[4-chloro-3-({1-[4-(2-cyclopropoxyphenyl)pyridin-3-yl]cyclopropoxy}methyl) benzenesulfonyl]azetidin-3-yl}-N-[(2S,3R,4S,5R)-2,3,4,5,6-pentahydroxyhexyl]propanamide (I-448);

3-{1-[4-chloro-3-({1-[4-(2-cyclopropoxyphenyl)pyridin-3-yl]cyclopropoxy}methyl) benzenesulfonyl]piperidin-4-yl}-N-[(2S,3R,4R,5R)-2,3,4,5,6-pentahydroxyhexyl]propanamide (I-449);

(2E)-3-{1-[4-chloro-3-({1-[4-(2-cyclopropoxyphenyl)pyridin-3-yl]cyclopropoxy}methyl) benzenesulfonyl]pyrrolidin-3-yl}-N-[(2S,3R,4R,5R)-2,3,4,5,6-pentahydroxyhexyl]prop-2-enamide (I-450);

3-{1-[4-chloro-3-({-[4-(2-cyclopropoxyphenyl)pyridin-3-yl]cyclopropoxy}methyl) benzenesulfonyl]pyrrolidin-3-yl}-N-[(2S,3R,4R,5R)-2,3,4,5,6-pentahydroxyhexyl]propanamide (I-451);

(2E)-4-{1-[4-chloro-3-({1-[4-(2-cyclopropoxyphenyl)pyridin-3-yl]cyclopropoxy}methyl) benzenesulfonyl]azetidin-3-yl}-N-[(2S,3R,4R,5R)-2,3,4,5,6-pentahydroxyhexyl]but-2-enamide (I-452);

4-{1-[4-chloro-3-({1-[4-(2-cyclopropoxyphenyl)pyridin-3-yl]cyclopropoxy}methyl) benzenesulfonyl]azetidin-3-yl}-N-[(2S,3R,4R,5R)-2,3,4,5,6-pentahydroxyhexyl]butanamide (I-453);

2-({1-[4-chloro-3-({1-[4-(2-cyclopropoxyphenyl)pyridin-3-yl]cyclopropoxy}methyl) benzenesulfonyl]azetidin-3-yl}oxy)-N-[(2S,3R,4R,5R)-2,3,4,5,6-pentahydroxyhexyl]acetamide (I-454);

2-({1-[4-chloro-3-({1-[4-(2-cyclopropoxyphenyl)pyridin-3-yl]cyclopropoxy}methyl) benzenesulfonyl]pyrrolidin-3-yl}methoxy)-N-[(2S,3R,4R,5R)-2,3,4,5,6-pentahydroxyhexyl]acetamide (I-455);

2-({1-[4-chloro-3-({1-[4-(2-cyclopropoxyphenyl)pyridin-3-yl]cyclopropoxy}methyl) benzenesulfonyl]azetidin-3-yl}methoxy)-N-[(2S,3R,4R,5R)-2,3,4,5,6-pentahydroxyhexyl]acetamide (I-456);

(2S,3S,4R,5S)-N-{4-[4-chloro-3-({1-[4-(2-cyclopropoxyphenyl)pyridin-3-yl]cyclopropoxy}methyl)benzenesulfonamido]butyl}-2,3,4,5,6-pentahydroxy-N-(2-methanesulfonylethyl) hexanamide (I-457);

(2S,3S,4R,5S)-2,3,4,5,6-pentahydroxy-N-{4-[N-methyl4-chloro-3-({1-[4-(2-cyclopropoxyphenyl)pyridin-3-yl]cyclopropoxy}methyl)benzenesulfonamido]butyl}hexanamide (I-458);

(2S,3S,4R,5S)-2,3,4,5,6-pentahydroxy-N-(2-methanesulfonylethyl)-N-{4-[N-methyl4-chloro-3-({1-[4-(2-cyclopropoxyphenyl)pyridin-3-yl]cyclopropoxy}methyl)benzenesulfonamido]butyl}hexanamide (I-459);

(2S,3S,4R,5S)-N-{4-[4-chloro-3-({1-[4-(2-cyclopropoxyphenyl)pyridin-3-yl]cyclopropoxy}methyl)benzenesulfonamido]butyl}-2,3,4,5,6-pentahydroxy-N-methylhexanamide (I-460);

(2S,3S,4R,5S)-2,3,4,5,6-pentahydroxy-N-methyl-N-{4-[N-methyl4-chloro-3-({1-[4-(2-cyclopropoxyphenyl)pyridin-3-yl]cyclopropoxy}methyl)benzenesulfonamido]butyl}hexanamide (I-461);

(2S,3S,4R,5S)-N-(2-{1-[4-chloro-3-({1-[4-(2-cyclopropoxyphenyl)pyridin-3-yl]cyclopropoxy}methyl)benzenesulfonyl]piperidin-4-yl}ethyl)-2,3,4,5,6-pentahydroxyhexanamide (I-462);

N-(4-aminobutyl)-4-chloro-3-({1-[4-(2-cyclopropoxyphenyl)pyridin-3-yl]cyclopropoxy}methyl)-N-ethylbenzene-1-sulfonamide (I-463);

1-(4-{N-methyl4-chloro-3-[(1-{4-[2-(oxetan-3-yloxy)phenyl]pyridin-3-yl}cyclopropoxy)methyl]benzenesulfonamido}butyl)-3-[(2S,3R,4R,5R)-2,3,4,5,6-pentahydroxyhexyl]urea (I-464);

1-{4-[N-ethyl4-chloro-3-({1-[4-(2-cyclopropoxyphenyl)pyridin-3-yl]cyclopropoxy}methyl) benzenesulfonamido]butyl}-3-[(2S,3R,4S,5R)-1,3,4,5,6-pentahydroxyhexan-2-yl]urea (I-465);

1-{4-[N-methyl4-chloro-5-({1-[4-(2-cyclopropoxyphenyl) pyridin-3-yl]cyclopropoxy}methyl)-2-fluorobenzenesulfonamido]butyl}-3-[(2S,3R,4R,5R)-2,3,4,5,6-pentahydroxyhexyl]urea (I-466);

1-{4-[N-methyl2,4-dichloro-5-({1-[4-(2-cyclopropoxyphenyl)pyridin-3-yl]cyclopropoxy}methyl)benzenesulfonamido]butyl}-3-[(2S,3R,4R,5R)-2,3,4,5,6-pentahydroxyhexyl]urea (I-467);

1-(4-{N-methyl3-[({11-[4-(2-cyclopropoxyphenyl)pyridin-3-yl]cyclopropyl}amino)methyl]-4-(trifluoromethyl) benzenesulfonamido}butyl)-3-[(2S,3R,4R,5R)-2,3,4,5,6-pentahydroxyhexyl]urea (I-468);

1-{4-[N-methyl3-({1-[4-(2-cyclopropoxyphenyl)pyridin-3-yl]cyclopropoxy}methyl)-4-(trifluoromethyl)benzenesulfonamido]butyl}-3-[(2S,3R,4R,5R)-2,3,4,5,6-pentahydroxyhexyl]urea (I-469);

1-(4-{N-methyl3-[({1-[4-(2-cyclopropoxyphenyl)pyridin-3-yl]cyclopropyl}amino)methyl]-4-(trifluoromethyl) benzenesulfonamido}butyl)-3-[(2S,3R,4S,5R)-1,3,4,5,6-pentahydroxyhexan-2-yl]urea (I-470);

1-(4-{N-methyl4-chloro-3-[({1-[4-(2-cyclopropoxyphenyl) pyridin-3-yl]cyclopropyl}amino) methyl] benzenesulfonamido}butyl)-3-[(2S,3R,4R,5R)-2,3,4,5,6-pentahydroxyhexyl]urea (I-471);

1-(4-{N-methyl4-chloro-3-[({1-[4-(2-cyclopropoxyphenyl) pyridin-3-yl]cyclopropyl}amino) methyl] benzenesulfonamido}butyl)-3-[(2S,3R,4S,5R)-1,3,4,5,6-pentahydroxyhexan-2-yl]urea (I-472);

1-(4-{N-ethyl4-chloro-3-[({1-[4-(2-cyclopropoxyphenyl) pyridin-3-yl]cyclopropyl}amino) methyl] benzenesulfonamido}butyl)-3-[(2S,3R,4R,5R)-2,3,4,5,6-pentahydroxyhexyl]urea (I-473);

1-(4-{N-methyl4-chloro-5-[({1-[4-(2-cyclopropoxyphenyl) pyridin-3-yl]cyclopropyl}amino) methyl]-2-fluorobenzenesulfonamido}butyl)-3-[(2S,3R,4R,5R)-2,3,4,5,6-pentahydroxyhexyl]urea (I-474);

1-(4-{N-methyl4-chloro-5-[({1-[4-(2-cyclopropoxyphenyl) pyridin-3-yl]cyclopropyl}amino) methyl]-2-fluorobenzenesulfonamido}butyl)-3-[(2S,3R,4S,5R)-1,3,4,5,6-pentahydroxyhexan-2-yl]urea (I-475);

1-(4-{N-methyl2,4-dichloro-5-[({1-[4-(2-cyclopropoxyphenyl)pyridin-3-yl]cyclopropyl}amino) methyl] benzenesulfonamido}butyl)-3-[(2S,3R,4S,5R)-1,3,4,5,6-pentahydroxyhexan-2-yl]urea (I-476);

1-(4-{N-methyl3-[({1-[4-(2-cyclopropoxyphenyl)pyridin-3-yl]cyclopropyl}amino)methyl]-4-methylbenzenesulfonamido}butyl)-3-[(2S,3R,4R,5R)-2,3,4,5,6-pentahydroxyhexyl]urea (I-477);

1-(4-{N-methyl3-[({1-[4-(2-cyclopropoxyphenyl)pyridin-3-yl]cyclopropyl}amino)methyl]-4-methylbenzenesulfonamido}butyl)-3-[(2S,3R,4S,5R)-1,3,4,5,6-pentahydroxyhexan-2-yl]urea (I-478);

1-{4-[N-methyl3-({1-[4-(2-cyclopropoxyphenyl)pyridin-3-yl]cyclopropoxy}methyl)-4-methylbenzenesulfonamido]butyl}-3-[(2S,3R,4R,5R)-2,3,4,5,6-pentahydroxyhexyl]urea (I-479);

(2S)-5-[4-chloro-3-({1-[4-(2-cyclopropoxyphenyl)pyridin-3-yl]cyclopropoxy}methyl) benzenesulfonamido]-2-{[(2,3,4,5,6-pentahydroxyhexyl)carbamoyl]amino}pentanoic acid (I-480);

(2R)-2-amino-6-[4-chloro-3-({1-[4-(2-cyclopropoxyphenyl)pyridin-3-yl]cyclopropoxy}methyl) benzenesulfonamido]-N-ethylhexanamide (I-481);

(2R)-6-[4-chloro-3-({1-[4-(2-cyclopropoxyphenyl)pyridin-3-yl]cyclopropoxy}methyl) benzenesulfonamido]-N-ethyl-2-({[(2S,3R,4R,5R)-2,3,4,5,6-pentahydroxyhexyl] carbamoyl}amino)hexanamide (I-482);

(2S)-2-[4-chloro-3-({1-[4-(2-cyclopropoxyphenyl)pyridin-3-yl]cyclopropoxy}methyl) benzenesulfonamido]-6-({[(2S,3R,4R,5R)-2,3,4,5,6-pentahydroxyhexyl] carbamoyl}amino) hexanoic acid (I-483);

(2S)-2-amino-6-[4-chloro-3-({1-[4-(2-cyclopropoxyphenyl) pyridin-3-yl]cyclopropoxy}methyl) benzenesulfonamido]hexanoic acid (I-484);

(2S)-6-[4-chloro-3-({1-[4-(2-cyclopropoxyphenyl)pyridin-3-yl]cyclopropoxy}methyl) benzenesulfonamido]-2-({ [(2S,3R,4R,5R)-2,3,4,5,6-pentahydroxyhexyl] carbamoyl}amino) hexanoic acid (I-485);

(2S)-2-amino-6-[4-chloro-3-({1-[4-(2-cyclopropoxyphenyl) pyridin-3-yl]cyclopropoxy}methyl) benzenesulfonamido]-N-ethylhexanamide (I-486);

(2S)-6-[4-chloro-3-({1-[4-(2-cyclopropoxyphenyl)pyridin-3-yl]cyclopropoxy}methyl) benzenesulfonamido]-N-ethyl-2-({[(2S,3R,4R,5R)-2,3,4,5,6-pentahydroxyhexyl] carbamoyl}amino)hexanamide (I-487);

1-(5-{[4-chloro-3-({1-[4-(2-cyclopropoxyphenyl)pyridin-3-yl]cyclopropoxy}methyl)phenyl]sulfanyl}pentyl)-3-[(2S,3R,4R,5R)-2,3,4,5,6-pentahydroxyhexyl]urea (I-488);

(2S,3S,4R,5S)-N-(5-{[4-chloro-3-({1-[4-(2-cyclopropoxyphenyl)pyridin-3-yl]cyclopropoxy}methyl)phenyl] sulfanyl}pentyl)-2,3,4,5,6-pentahydroxy-N-[2-(2-hydroxyethoxy)ethyl]hexanamide (I-489);

1-[2-(2-{[4-chloro-3-({1-[4-(2-cyclopropoxyphenyl)pyridin-3-yl]cyclopropoxy}methyl)phenyl]sulfanyl}ethoxy)ethyl]-3-[(2S,3R,4R,5R)-2,3,4,5,6-pentahydroxyhexyl] urea (I-490);

1-(2-{2-[4-chloro-3-({1-[4-(2-cyclopropoxyphenyl)pyridin-3-yl]cyclopropoxy}methyl) benzenesulfinyl] ethoxy}ethyl)-3-[(2S,3R,4R,5R)-2,3,4,5,6-pentahydroxyhexyl]urea (I-491);

1-(2-{2-[4-chloro-3-({1-[4-(2-cyclopropoxyphenyl)pyridin-3-yl]cyclopropoxy}methyl) benzenesulfonyl] ethoxy}ethyl)-3-[(2S,3R,4R,5R)-2,3,4,5,6-pentahydroxyhexyl]urea (I-492);

1-{2-[2-({4-chloro-3-[(1-{4-[2-(oxetan-3-yloxy)phenyl] pyridin-3-yl}cyclopropoxy)methyl]phenyl}sulfanyl) ethoxy]ethyl}-3-[(2S,3R,4R,5R)-2,3,4,5,6-pentahydroxyhexyl]urea (I-493);

1-[5-({4-chloro-3-[({1-[4-(2-cyclopropoxyphenyl)pyridin-3-yl]cyclopropyl}amino)methyl]phenyl}sulfanyl)pentyl]-3-[(2S,3R,4R,5R)-2,3,4,5,6-pentahydroxyhexyl]urea (I-494);

5-({6-[({1-[4-(2-cyclopropoxyphenyl)pyridin-3-yl] cyclopropyl}amino)methyl]-5-methylpyridin-2-yl}sulfanyl)-N-methyl-N-[(2S,3R,4R,5R)-2,3,4,5,6-pentahydroxyhexyl]pentanamide (I-495);

1-[4-(2-cyclopropoxyphenyl)pyridin-3-yl]-N-{5-methyl-2-(methylsulfanyl)pyrimidin-4-yl]methyl}cyclopropan-1-amine (I-496);

4-{[3-({1-[4-(2-cyclopropoxyphenyl)pyridin-3-yl] cyclopropoxy}methyl)-4-ethylphenyl]sulfanyl}-N-[(2S,3R,4R,5R)-2,3,4,5,6-pentahydroxyhexyl]butanamide (I-497);

4-{[4-chloro-3-({1-[4-(2-cyclopropoxyphenyl)pyridin-3-yl] cyclopropoxy}methyl)phenyl]sulfanyl}-N-[(2S,3R,4R,5R)-2,3,4,5,6-pentahydroxyhexyl]butanamide (I-498);

N-[5-({4-chloro-3-[({1-[4-(2-cyclopropoxyphenyl)pyridin-3-yl]cyclopropyl}amino)methyl]phenyl}sulfanyl)pentyl]-N-[(2S,3R,4R,5R)-2,3,4,5,6-pentahydroxyhexyl]acetamide (I-499);

N-(3-{[4-chloro-3-({1-[4-(2-cyclopropoxyphenyl)pyridin-3-yl]cyclopropoxy}methyl)phenyl]sulfanyl}propyl)-N-[(2S,3R,4R,5R)-2,3,4,5,6-pentahydroxyhexyl]acetamide (I-500);

N-(4-{[4-chloro-3-({1-[4-(2-cyclopropoxyphenyl)pyridin-3-yl]cyclopropoxy}methyl)phenyl]sulfanyl}butyl)-N-[(2S,3R,4R,5R)-2,3,4,5,6-pentahydroxyhexyl]acetamide (I-501);

N-[3-({4-chloro-3-[({1-[4-(2-cyclopropoxyphenyl)pyridin-3-yl]cyclopropyl}amino)methyl]phenyl}sulfanyl)propyl]-N-[(2S,3R,4R,5R)-2,3,4,5,6-pentahydroxyhexyl]acetamide (I-502);

N-[4-({4-chloro-3-[({1-[4-(2-cyclopropoxyphenyl)pyridin-3-yl]cyclopropyl}amino)methyl]phenyl}sulfanyl)butyl]-N-[(2S,3R,4R,5R)-2,3,4,5,6-pentahydroxyhexyl]acetamide (I-503);

N-[2-({4-chloro-3-[({1-[4-(2-cyclopropoxyphenyl)pyridin-3-yl]cyclopropyl}amino)methyl]phenyl}sulfanyl)ethyl]-N-[(2S,3R,4R,5R)-2,3,4,5,6-pentahydroxyhexyl]acetamide (I-504);

N-(2-{[4-chloro-3-({1-[4-(2-cyclopropoxyphenyl)pyridin-3-yl]cyclopropoxy}methyl)phenyl]sulfanyl}ethyl)-N-[(2S,3R,4R,5R)-2,3,4,5,6-pentahydroxyhexyl]acetamide (I-505);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-methylhexanamide (I-506);

(2S,3S,4R,5S)-N-[5-({4-chloro-3-[({11-[4-(2-cyclopropoxyphenyl)pyridin-3-yl]cyclopropyl}amino)methyl]phenyl}sulfanyl)pentyl]-2,3,4,5,6-pentahydroxy-N-methylhexanamide (I-507);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-methylhexanamide (I-508);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxy-N-methylhexanamide (I-509);

(2S,3S,4R,5S)-N-(4-{[4-chloro-3-({11-[4-(2-cyclopropoxyphenyl)pyridin-3-yl]cyclopropoxy}methyl)phenyl]sulfanyl}butyl)-2,3,4,5,6-pentahydroxy-N-methylhexanamide (I-510);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-methylhexanamide (I-511);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-[2-(2-hydroxyethoxy)ethyl]hexanamide (I-512);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(4-hydroxybutyl)hexanamide (I-513);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(oxan-4-yl)hexanamide (I-514);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-[3-(2-oxopyrrolidin-1-yl)propyl]hexanamide (I-515);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(oxan-4-ylmethyl)hexanamide (I-516);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-[2-(2-oxoimidazolidin-1-yl)ethyl]hexanamide (I-517);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-[2-(2-hydroxyethoxy)ethyl]hexanamide (I-518);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(4-hydroxybutyl)hexanamide (I-519);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-[3-(2-oxopyrrolidin-1-yl)propyl]hexanamide (I-520);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-N-[2-(1,1-dioxo-1$\lambda^6$,4-thiomorpholin-4-yl)ethyl]-2,3,4,5,6-pentahydroxyhexanamide (I-521);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(oxan-4-ylmethyl)hexanamide (I-522);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(3-methanesulfonylpropyl)hexanamide (I-523);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-N-[2-(1,1-dioxo-1$\lambda^6$,4-thiomorpholin-4-yl)ethyl]-2,3,4,5,6-pentahydroxyhexanamide (I-524);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(3-methanesulfonylpropyl) hexanamide (I-525);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-[2-(2-hydroxyethoxy)ethyl]hexanamide (I-526);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(4-hydroxybutyl)hexanamide (I-527);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(oxan-4-yl)hexanamide (I-528);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-[3-(2-oxopyrrolidin-1-yl)propyl]hexanamide (I-529);

(2S,3S,4R,5S)-N-[3-({4-chloro-3-[({1-[4-(2-cyclopropoxyphenyl)cyclopropyl) amino)methyl]phenyl}sulfanyl)propyl]-N-[2-(1,1-dioxo-1$\lambda^6$,4-thiomorpholin-4-yl)ethyl]-2,3,4,5,6-pentahydroxyhexanamide (I-530);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-[2-(2-oxoimidazolidin-1-yl)ethyl]hexanamide (I-531);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(3-methanesulfonylpropyl) hexanamide (I-532);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-[2-(2-hydroxyethoxy)ethyl]hexanamide (I-533);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(4-hydroxybutyl)hexanamide (I-534);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(oxan-4-yl)hexanamide (I-535);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(oxan-4-ylmethyl)hexanamide (I-536);

(2S,3S,4R,5S)-N-(3-{[3-({1-[4-(2-cyclopropoxyphenyl)pyridin-3-yl]cyclopropoxy}methyl)-4-methylphenyl]sulfanyl}propyl)-2,3,4,5,6-pentahydroxy-N-(3-methanesulfonylpropyl) hexanamide (I-537);

(2S,3S,4R,5S)-N-(3-{[3-({1-[4-(2-cyclopropoxyphenyl)pyridin-3-yl]cyclopropoxy}methyl)-4-methylphenyl]sulfanyl}propyl)-2,3,4,5,6-pentahydroxy-N-[2-(2-hydroxyethoxy)ethyl]hexanamide (I-538);

(2S,3S,4R,5S)-N-(3-{[3-({1-[4-(2-cyclopropoxyphenyl)pyridin-3-yl]cyclopropoxy}methyl)-4-methylphenyl]sulfanyl}propyl)-2,3,4,5,6-pentahydroxy-N-(4-hydroxybutyl)hexanamide (I-539);

(2S,3S,4R,5S)-N-(3-{[3-({1-[4-(2-cyclopropoxyphenyl)pyridin-3-yl]cyclopropoxy}methyl)-4-methylphenyl]sulfanyl}propyl)-2,3,4,5,6-pentahydroxy-N-(oxan-4-yl)hexanamide (I-540);

(2S,3S,4R,5S)-N-(4-{[3-({1-[4-(2-cyclopropoxyphenyl)pyridin-3-yl]cyclopropoxy}methyl)-4-methylphenyl]sulfanyl}butyl)-2,3,4,5,6-pentahydroxy-N-(4-hydroxybutyl)hexanamide (I-541);

(2S,3S,4R,5S)-N-[2-({4-chloro-3-[({1-[4-(2-cyclopropoxyphenyl)pyridin-3-yl]cyclopropyl}amino)methyl]phenyl}sulfanyl)ethyl]-2,3,4,5,6-pentahydroxy-N-methylhexanamide (I-542);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-[2-(2-oxoimidazolidin-1-yl)ethyl]hexanamide (I-543);

(2S,3S,4R,5S)-N-[3-({3-[({1-[4-(2-cyclopropoxyphenyl)pyridin-3-yl]cyclopropyl}amino) methyl]-4-methylphenyl}sulfanyl)propyl]-2,3,4,5,6-pentahydroxy-N-(3-methanesulfonylpropyl) hexanamide (I-544);

(2S,3S,4R,5S)-N-[3-({3-[({1-[4-(2-cyclopropoxyphenyl)pyridin-3-yl]cyclopropyl}amino) methyl]-4-methylphenyl}sulfanyl)propyl]-2,3,4,5,6-pentahydroxy-N-[2-(2-hydroxyethoxy)ethyl]hexanamide (I-545);

(2S,3S,4R,5S)-N-[3-({3-[({1-[4-(2-cyclopropoxyphenyl)pyridin-3-yl]cyclopropyl}amino) methyl]-4-methylphenyl}sulfanyl)propyl]-2,3,4,5,6-pentahydroxy-N-(4-hydroxybutyl) hexanamide (I-546);

(2S,3S,4R,5S)-N-[3-({3-[({1-[4-(2-cyclopropoxyphenyl)pyridin-3-yl]cyclopropyl}amino) methyl]-4-methylphenyl}sulfanyl)propyl]-2,3,4,5,6-pentahydroxy-N-(oxan-4-yl)hexanamide (I-547);

(2S,3S,4R,5S)-N-[4-({3-[({1-[4-(2-cyclopropoxyphenyl)pyridin-3-yl]cyclopropyl}amino) methyl]-4-methylphenyl}sulfanyl)butyl]-2,3,4,5,6-pentahydroxy-N-(3-methanesulfonylpropyl) hexanamide (I-548);

(2S,3S,4R,5S)-N-[4-({3-[({1-[4-(2-cyclopropoxyphenyl)pyridin-3-yl]cyclopropyl}amino) methyl]-4-methylphenyl}sulfanyl)butyl]-2,3,4,5,6-pentahydroxy-N-[2-(2-hydroxyethoxy)ethyl]hexanamide (I-549);

(2S,3S,4R,5S)-N-[4-({3-[({1-[4-(2-cyclopropoxyphenyl)pyridin-3-yl]cyclopropyl}amino) methyl]-4-methylphenyl}sulfanyl)butyl]-2,3,4,5,6-pentahydroxy-N-(4-hydroxybutyl)hexanamide (I-550);

(2S,3S,4R,5S)-N-(4-{[3-({1-[4-(2-cyclopropoxyphenyl)pyridin-3-yl]cyclopropoxy}methyl)-4-methylphenyl]sulfanyl}butyl)-2,3,4,5,6-pentahydroxy-N-[2-(2-hydroxyethoxy)ethyl]hexanamide (I-551);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-N-(1,1-dioxo-1$\lambda^6$-thian-4-yl)-2,3,4,5,6-pentahydroxyhexanamide (I-552);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(oxan-4-ylmethyl)hexanamide (I-553);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-[3-(2-oxopyrrolidin-1-yl)propyl]hexanamide (I-554);

(2S,3S,4R,5S)-N-(2-{[4-chloro-3-({1-[4-(2-cyclopropoxyphenyl)pyridin-3-yl]cyclopropoxy}methyl)phenyl]sulfanyl}ethyl)-2,3,4,5,6-pentahydroxy-N-methylhexanamide (I-555);

(2S,3S,4R,5S)-N-(3-{[4-chloro-3-({-[4-(2-cyclopropoxyphenyl)pyridin-3-yl]cyclopropoxy}methyl)phenyl]sulfanyl}propyl)-N-(1,1-dioxo-1$\lambda^6$-thian-4-yl)-2,3,4,5,6-pentahydroxyhexanamide (I-556);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-N-[2-(1,1-dioxo-1$\lambda^6$,4-thiomorpholin-4-yl)ethyl]-2,3,4,5,6-pentahydroxyhexanamide (I-557);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(3-methanesulfonylpropyl) hexanamide (I-558);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(2-methanesulfonylethyl)hexanamide (I-559);

(2S,3S,4R,5S)-N-[4-({3-[({1-[4-(2-cyclopropoxyphenyl)pyridin-3-yl]cyclopropyl}amino) methyl]-4-methylphenyl}sulfanyl)butyl]-2,3,4,5,6-pentahydroxy-N-(oxan-4-yl)hexanamide (I-560);

(2S,3S,4R,5S)-N-(4-{[3-({1-[4-(2-cyclopropoxyphenyl)pyridin-3-yl]cyclopropoxy}methyl)-4-methylphenyl]sulfanyl}butyl)-2,3,4,5,6-pentahydroxy-N-(3-methanesulfonylpropyl)hexanamide (I-561);

(2S,3S,4R,5S)-N-(4-{[3-({1-[4-(2-cyclopropoxyphenyl)pyridin-3-yl]cyclopropoxy}methyl)-4-methylphenyl]sulfanyl}butyl)-2,3,4,5,6-pentahydroxy-N-(oxan-4-yl)hexanamide (I-562);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-N-(2-acetamidoethyl)-2,3,4,5,6-pentahydroxyhexanamide (I-563);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-N-(2-acetamidoethyl)-2,3,4,5,6-pentahydroxyhexanamide (I-564);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(oxan-4-yl)hexanamide (I-565);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-N-(3-acetamidopropyl)-2,3,4,5,6-pentahydroxyhexanamide (I-566);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-N-(4-acetamidobutyl)-2,3,4,5,6-pentahydroxyhexanamide (I-567);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-N-(4-acetamidobutyl)-2,3,4,5,6-pentahydroxyhexanamide (I-568);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-N-(1,1-dioxo-1λ⁶-thian-4-yl)-2,3,4,5,6-pentahydroxyhexanamide (I-569);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(4-methanesulfonamidobutyl) hexanamide (I-570);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(2-methanesulfonamidoethyl) hexanamide (I-571);

ethyl N-{2-[(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxyhexanamido]ethyl}carbamate (I-572);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-N-(3-acetamidopropyl)-2,3,4,5,6-pentahydroxyhexanamide (I-573);

ethyl N-{3-[(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxyhexanamido]propyl}carbamate (I-574);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(2-methanesulfonamidoethyl) hexanamide (I-575);

ethyl N-{2-[(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxyhexanamido]ethyl}carbamate (I-576);

(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxy-N-(3-methanesulfonamidopropyl) hexanamide (I-577);

ethyl N-{3-[(2S,3S,4R,5S)-N-(4-{[4-chloro-3-({1-[4-(2-cyclopropoxyphenyl)pyridin-3-yl]cyclopropoxy}methyl)phenyl]sulfanyl}butyl)-2,3,4,5,6-pentahydroxyhexanamido]propyl}carbamate (I-578);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-N-(4-acetamidobutyl)-2,3,4,5,6-pentahydroxyhexanamide (I-579);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(4-methanesulfonamidobutyl) hexanamide (I-580);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-N-(1,1-dioxo-1λ⁶-thian-4-yl)-2,3,4,5,6-pentahydroxyhexanamide (I-581);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(4-methanesulfonamidobutyl) hexanamide (I-582);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(2-methanesulfonylethyl) hexanamide (I-583);

(2S,3S,4R,5S)-N-[4-({4-chloro-3-[({-[4-(2-cyclopropoxyphenyl)pyridin-3-yl]cyclopropyl}amino)methyl]phenyl}sulfanyl)butyl]-2,3,4,5,6-pentahydroxy-N-(2-methanesulfonylethyl) hexanamide (I-584);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(2-methanesulfonamidoethyl) hexanamide (I-585);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-N-(2-acetamidoethyl)-2,3,4,5,6-pentahydroxyhexanamide (I-586);

ethyl N-{2-[(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxyhexanamido]ethyl}carbamate (I-587);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(3-methanesulfonamidopropyl) hexanamide (I-588);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-N-(3-acetamidopropyl)-2,3,4,5,6-pentahydroxyhexanamide (I-589);

ethyl N-{3-[(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxyhexanamido]propyl} carbamate (I-590);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-(3-methanesulfonamidopropyl) hexanamide (I-591);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(3-methanesulfonamidopropyl) hexanamide (I-592);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxy-N-(2-methanesulfonamidoethyl) hexanamide (I-593);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-N-(3-acetamidopropyl)-2,3,4,5,6-pentahydroxyhexanamide (I-594);

(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-N-(2-acetamidoethyl)-2,3,4,5,6-pentahydroxyhexanamide (I-595);

ethyl N-{3-[(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxyhexanamido]propyl}carbamate (I-596);

ethyl N-{2-[(2S,3S,4R,5S)-N-(3-{[4-chloro-3-({1-[4-(2-cyclopropoxyphenyl)pyridin-3-yl]cyclopropoxy}methyl)phenyl]sulfanyl}propyl)-2,3,4,5,6-pentahydroxyhexanamido]ethyl}carbamate (I-597);

(2S,3S,4R,5S)-N-[5-({4-chloro-3-[({1-[4-(2-cyclopropoxyphenyl)pyridin-3-yl]cyclopropyl}amino)methyl]phenyl}sulfanyl)pentyl]-2,3,4,5,6-pentahydroxy-N-[2-(2-hydroxyethoxy)ethyl]hexanamide (I-598);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-2,3,4,5,6-pentahydroxy-N-(4-methanesulfonamidobutyl) hexanamide (I-599);

(2S,3S,4R,5S)-N-[5-({4-chloro-3-[({1-[4-(2-cyclopropoxyphenyl)pyridin-3-yl]cyclopropyl}amino)methyl]phenyl}sulfanyl)pentyl]-2,3,4,5,6-pentahydroxy-N-(4-hydroxybutyl)hexanamide (I-600);

(2S,3S,4R,5S)-N-[5-({4-chloro-3-[({1-[4-(2-cyclopropoxyphenyl)pyridin-3-yl]cyclopropyl}amino)methyl]phenyl}sulfanyl)pentyl]-2,3,4,5,6-pentahydroxy-N-(5-hydroxypentyl)hexanamide (I-601);

(2S,3S,4R,5S)-N-[3-({4-chloro-3-[({1-[4-(2-cyclopropoxyphenyl)pyridin-3-yl]cyclopropyl}amino)methyl]phenyl}sulfanyl)propyl]-N-(4-acetamidobutyl)-2,3,4,5,6-pentahydroxyhexanamide (I-602);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxy-N-(2-methanesulfonylethyl)hexanamide (I-603);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-N-[2-(ethanesulfonyl)ethyl]-2,3,4,5,6-pentahydroxyhexanamide (I-604);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxy-N-(4-hydroxybutyl)hexanamide (I-605);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxy-N-(5-hydroxypentyl)hexanamide (I-606);

(2S,3S,4R,5S)-N-{5-[4-chloro-3-({1-[4-(2-cyclopropoxyphenyl)pyridin-3-yl]cyclopropoxy}methyl)benzenesulfinyl]pentyl}-2,3,4,5,6-pentahydroxyhexanamide (I-607);

(2S,3S,4R,5S)-N-{5-[4-chloro-3-({1-[4-(2-cyclopropoxyphenyl)pyridin-3-yl]cyclopropoxy}methyl)benzenesulfonyl]pentyl}-2,3,4,5,6-pentahydroxyhexanamide (I-608);

(2S,3S,4R,5S)-N-(carbamoylmethyl)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxyhexanamide (I-609);

(2S,3S,4R,5S)-N-(carbamoylmethyl)-N-[5-({4-chloro-3-[({1-[4-(2-cyclopropoxyphenyl)pyridin-3-yl]cyclopropyl}amino)methyl]phenyl}sulfanyl)pentyl]-2,3,4,5,6-pentahydroxyhexanamide (I-610);

(2S,3S,4R,5S)-N-(5-{[4-chloro-3-({1-[4-(2-cyclopropoxyphenyl)pyridin-3-yl]cyclopropoxy}methyl)phenyl]sulfanyl}pentyl)-2,3,4,5,6-pentahydroxyhexanamide (I-611);

2-({2-[(carboxymethyl)({[2-(2-{[4-chloro-3-({1-[4-(2-cyclopropoxyphenyl)pyridin-3-yl]cyclopropoxy}methyl)phenyl]sulfanyl}ethoxy)ethyl]carbamoyl}methyl)amino]ethyl}({[2-(2-{[4-chloro-3-({1-[4-(2-cyclopropoxyphenyl)pyridin-3-yl]cyclopropoxy}methyl)phenyl]sulfanyl} ethoxy)ethyl]carbamoyl}methyl)amino) acetic acid (I-612);

(2R,3R,4R,5S)-6-[(4-{[4-chloro-3-({1-[4-(2-cyclopropoxyphenyl)pyridin-3-yl]cyclopropoxy}methyl)phenyl]sulfanyl}butyl)(2-methanesulfonylethyl)amino]hexane-1,2,3,4,5-pentol (I-613);

(2R,3R,4R,5S)-6-[(3-{[3-({1-[4-(2-cyclopropoxyphenyl)pyridin-3-yl]cyclopropoxy}methyl)-4-methylphenyl]sulfanyl}propyl)(2-methanesulfonylethyl)amino]hexane-1,2,3,4,5-pentol (I-614);

(2R,3R,4R,5S)-6-[(4-{[3-({1-[4-(2-cyclopropoxyphenyl)pyridin-3-yl]cyclopropoxy}methyl)-4-methylphenyl]sulfanyl}butyl)(2-methanesulfonylethyl)amino]hexane-1,2,3,4,5-pentol (I-615);

3-(1-{[2-chloro-5-(methylsulfanyl)phenyl]methoxy}cyclopropyl)-4-(2-cyclopropoxyphenyl) pyridine (I-617);

[4-(2-cyclopropoxyphenyl)pyridin-3-yl]-N-{[5-methyl-2-(methylsulfanyl)pyridin-4-yl]methyl}cyclopropan-1-amine (I-619);

4-{[3-({1-[4-(2-cyclopropoxyphenyl)pyridin-3-yl]cyclopropoxy}methyl)-4-(propan-2-yl)phenyl]sulfanyl}-N-methyl-N-[(2S,3R,4R,5R)-2,3,4,5,6-pentahydroxyhexyl]butanamide (I-620);

1-(4-{[4-chloro-3-({1-[4-(2-cyclopropoxyphenyl)pyridin-3-yl]cyclopropoxy}methyl)phenyl]sulfanyl}butyl)-3-[(2S,3R,4R,5R)-2,3,4,5,6-pentahydroxyhexyl]urea (I-621);

1-[3-({4-chloro-3-[({1-[4-(2-cyclopropoxyphenyl)pyridin-3-yl]cyclopropyl}amino)methyl]phenyl}sulfanyl)propyl]-3-[(2S,3R,4R,5R)-2,3,4,5,6-pentahydroxyhexyl]urea (I-622);

1-[4-({4-chloro-3-[({1-[4-(2-cyclopropoxyphenyl)pyridin-3-yl]cyclopropyl}amino)methyl]phenyl}sulfanyl)butyl]-3-[(2S,3R,4R,5R)-2,3,4,5,6-pentahydroxyhexyl]urea I-623);

(2S,3S,4R,5S)-N-[4-({4-chloro-3-[({1-[4-(2-cyclopropoxyphenyl)pyridin-3-yl]cyclopropyl}amino)methyl]phenyl}sulfanyl)butyl]-2,3,4,5,6-pentahydroxy-N-[2-(2-oxoimidazolidin-1-yl) ethyl]hexanamide (I-624);

1-(3-{[4-chloro-3-({1-[4-(2-cyclopropoxyphenyl)pyridin-3-yl]cyclopropoxy}methyl)phenyl]sulfanyl}propyl)-3-[(2S,3R,4R,5R)-2,3,4,5,6-pentahydroxyhexyl]urea (I-625);

1-{2-[2-({4-chloro-3-[({1-[4-(2-cyclopropoxyphenyl)pyridin-3-yl]cyclopropyl}amino)methyl]phenyl}sulfanyl)ethoxy]ethyl}-3-[(2S,3R,4R,5R)-2,3,4,5,6-pentahydroxyhexyl]urea (I-626);

1-(4-{[(5-[4-chloro-3-({1-[4-(2-cyclopropoxyphenyl)pyridin-3-yl]cyclopropoxy}methyl) phenyl]sulfanyl}pentyl)carbamoyl]amino}butyl)-3-[(2S,3R,4R,5R)-2,3,4,5,6-pentahydroxyhexyl]urea (I-627);

1-(4-{[4-chloro-3-({1-[4-(2-cyclopropoxyphenyl)pyridin-3-yl]cyclopropoxy}methyl)phenyl]sulfanyl}butyl)-3-[(2S,3R,4S,5R)-1,3,4,5,6-pentahydroxyhexan-2-yl]urea (I-628);

1-(4-{[(4-{[4-chloro-3-({1-[4-(2-cyclopropoxyphenyl)pyridin-3-yl]cyclopropoxy}methyl) phenyl]sulfanyl}butyl)carbamoyl]amino}butyl)-3-[(2S,3R,4R,5R)-2,3,4,5,6-pentahydroxyhexyl]urea (I-629);

1-(5-{[4-chloro-3-({1-[4-(2-cyclopropoxyphenyl)pyridin-3-yl]cyclopropoxy}methyl)phenyl]sulfanyl}pentyl)-3-[(1r,4r)-4-({[(2S,3R,4R,5R)-2,3,4,5,6-pentahydroxyhexyl]carbamoyl}amino) cyclohexyl]urea (I-630);

2-(4-{[(5-{[4-chloro-3-({1-[4-(2-cyclopropoxyphenyl)pyridin-3-yl]cyclopropoxy}methyl) phenyl]sulfanyl}pentyl)carbamoyl]amino}piperidin-1-yl)-N-[(2S,3R,4R,5R)-2,3,4,5,6-pentahydroxyhexyl]acetamide (I-631);

1-(4-{[4-chloro-3-({1-[4-(2-cyclopropoxyphenyl)pyridin-3-yl]cyclopropoxy}methyl)phenyl]sulfanyl}butyl)-3-[(1r,4r)-4-({[(2S,3R,4R,5R)-2,3,4,5,6-pentahydroxyhexyl]carbamoyl}amino) cyclohexyl]urea (I-632);

2-(4-{[(4-{[4-chloro-3-({1-[4-(2-cyclopropoxyphenyl)pyridin-3-yl]cyclopropoxy}methyl) phenyl]sulfanyl}butyl)carbamoyl]amino}piperidin-1-yl)-N-[(2S,3R,4R,5R)-2,3,4,5,6-pentahydroxyhexyl]acetamide (I-633);

1-(5-{[4-chloro-3-({1-[4-(2-cyclopropoxyphenyl)pyridin-3-yl]cyclopropoxy}methyl)phenyl]sulfanyl}pentyl)-3-[(1s,4s)-4-({[(2S,3R,4R,5R)-2,3,4,5,6-pentahydroxyhexyl]carbamoyl}amino) cyclohexyl]urea (I-634);

1-(4-{[4-chloro-3-({1-[4-(2-cyclopropoxyphenyl)pyridin-3-yl]cyclopropoxy}methyl)phenyl]sulfanyl}butyl)-3-[(1s, 4s)-4-({[(2S,3R,4R,5R)-2,3,4,5,6-pentahydroxyhexyl]carbamoyl}amino) cyclohexyl]urea (I-635);

1-(5-{[4-chloro-3-({1-[4-(2-cyclopropoxyphenyl)pyridin-3-yl]cyclopropoxy}methyl)phenyl]sulfanyl}pentyl)-3-[(2S,3R,4S,5R)-1,3,4,5,6-pentahydroxyhexan-2-yl]urea (I-636);

1-[2-(2-{[4-chloro-3-({1-[4-(2-cyclopropoxyphenyl)pyridin-3-yl]cyclopropoxy}methyl)phenyl]sulfanyl}ethoxy)ethyl]-3-[(2S,3R,4S,5R)-1,3,4,5,6-pentahydroxyhexan-2-yl]urea (I-637);

3-[2-(2-{[4-chloro-3-({1-[4-(2-cyclopropoxyphenyl)pyridin-3-yl]cyclopropoxy}methyl)phenyl]sulfanyl}ethoxy)ethyl]-1-[4-({[2-(2-{[4-chloro-3-({1-[4-(2-cyclopropoxyphenyl)pyridin-3-yl]cyclopropoxy}methyl)phenyl]sulfanyl}ethoxy)ethyl]carbamoyl}amino)butyl]urea (I-638);

1-{5-[4-chloro-3-({1-[4-(2-cyclopropoxyphenyl)pyridin-3-yl]cyclopropoxy}methyl) benzenesulfinyl]pentyl}-3-[(2S,3R,4R,5R)-2,3,4,5,6-pentahydroxyhexyl]urea (I-639);

1-{5-[4-chloro-3-({1-[4-(2-cyclopropoxyphenyl)pyridin-3-yl]cyclopropoxy}methyl) benzenesulfonyl]pentyl}-3-[(2S,3R,4R,5R)-2,3,4,5,6-pentahydroxyhexyl]urea (I-640);

1-(2-{2-[4-chloro-3-({1-[4-(2-cyclopropoxyphenyl)pyridin-3-yl]cyclopropoxy}methyl) benzenesulfonyl]ethoxy}ethyl)-3-[(2S,3R,4S,5R)-1,3,4,5,6-pentahydroxyhexan-2-yl]urea (I-641);

1-{5-[4-chloro-3-({1-[4-(2-cyclopropoxyphenyl)pyridin-3-yl]cyclopropoxy}methyl) benzenesulfinyl]pentyl}-3-[(2S,3R,4S,5R)-1,3,4,5,6-pentahydroxyhexan-2-yl]urea (I-642);

1-{5-[4-chloro-3-({1-[4-(2-cyclopropoxyphenyl)pyridin-3-yl]cyclopropoxy}methyl) benzenesulfonyl]pentyl}-3-[(2S,3R,4S,5R)-1,3,4,5,6-pentahydroxyhexan-2-yl]urea (I-643);

1-(2-{2-[4-chloro-3-({1-[4-(2-cyclopropoxyphenyl)pyridin-3-yl]cyclopropoxy}methyl) benzenesulfinyl]ethoxy}ethyl)-3-[(2S,3R,4S,5R)-1,3,4,5,6-pentahydroxyhexan-2-yl]urea (I-644);

5-({6-[({1-[4-(2-cyclopropoxyphenyl)pyridin-3-yl]cyclopropyl}amino)methyl]-5-methylpyridin-2-yl}sulfanyl)-N-[(2S,3R,4R,5R)-2,3,4,5,6-pentahydroxyhexyl]pentanamide (I-645);

4-{4-chloro-3-[({1-[4-(2-cyclopropoxyphenyl)pyridin-3-yl]cyclopropyl}amino)methyl]benzenesulfonyl}-N-methyl-N-[(2S,3R,4R,5R)-2,3,4,5,6-pentahydroxyhexyl]butanamide (I-646);

4-{4-chloro-3-[({1-[4-(2-cyclopropoxyphenyl)pyridin-3-yl]cyclopropyl}amino)methyl]benzenesulfinyl}-N-methyl-N-[(2S,3R,4R,5R)-2,3,4,5,6-pentahydroxyhexyl]butanamide (I-647);

4-{[4-chloro-3-({1-[4-(2-cyclopropoxyphenyl)pyridin-3-yl]cyclopropoxy}methyl) phenyl]sulfanyl}-N-methyl-N-[(2S,3R,4R,5R)-2,3,4,5,6-pentahydroxyhexyl]butanamide (I-648);

4-({4-chloro-3-[({1-[4-(2-cyclopropoxyphenyl)pyridin-3-yl]cyclopropyl}amino)methyl]phenyl}sulfanyl)-N-[(2S,3R,4R,5R)-2,3,4,5,6-pentahydroxyhexyl]butanamide (I-649);

4-({4-chloro-3-[({1-[4-(2-cyclopropoxyphenyl)pyridin-3-yl]cyclopropyl}amino) methyl]phenyl}sulfanyl)-N-methyl-N-[(2S,3R,4R,5R)-2,3,4,5,6-pentahydroxyhexyl]butanamide (1-650);

4-{[3-({1-[4-(2-cyclopropoxyphenyl)pyridin-3-yl]cyclopropoxy}methyl)-4-methylphenyl]sulfanyl}-N-[(2S,3R,4R,5R)-2,3,4,5,6-pentahydroxyhexyl]butanamide (I-651);

4-{[3-({1-[4-(2-cyclopropoxyphenyl)pyridin-3-yl]cyclopropoxy}methyl)-4-methylphenyl]sulfanyl}-N-methyl-N-[(2S,3R,4R,5R)-2,3,4,5,6-pentahydroxyhexyl]butanamide (I-652);

4-({6-[({1-[4-(2-cyclopropoxyphenyl)pyridin-3-yl]cyclopropyl}amino)methyl]-5-methylpyridin-2-yl}sulfanyl)-N-[(2S,3R,4R,5R)-2,3,4,5,6-pentahydroxyhexyl]butanamide (I-653);

4-({6-[({1-[4-(2-cyclopropoxyphenyl)pyridin-3-yl]cyclopropyl}amino)methyl]-5-methylpyridin-2-yl}sulfanyl)-N-methyl-N-[(2S,3R,4R,5R)-2,3,4,5,6-pentahydroxyhexyl]butanamide (I-654);

4-({4-[({1-[4-(2-cyclopropoxyphenyl)pyridin-3-yl]cyclopropyl}amino)methyl]-5-methylpyrimidin-2-yl}sulfanyl)-N-[(2S,3R,4R,5R)-2,3,4,5,6-pentahydroxyhexyl]butanamide (I-655);

4-({4-[({1-[4-(2-cyclopropoxyphenyl)pyridin-3-yl]cyclopropyl}amino)methyl]-5-methylpyrimidin-2-yl}sulfanyl)-N-methyl-N-[(2S,3R,4R,5R)-2,3,4,5,6-pentahydroxyhexyl]butanamide (I-656);

5-{[6-({1-[4-(2-cyclopropoxyphenyl)pyridin-3-yl]cyclopropoxy}methyl)-5-methylpyridin-2-yl]sulfanyl}-N-[(2S,3R,4R,5R)-2,3,4,5,6-pentahydroxyhexyl]pentanamide (I-657);

5-{[6-({1-[4-(2-cyclopropoxyphenyl)pyridin-3-yl]cyclopropoxy}methyl)-5-methylpyridin-2-yl]sulfanyl}-N-methyl-N-[(2S,3R,4R,5R)-2,3,4,5,6-pentahydroxyhexyl]pentanamide (I-658);

4-{[4-chloro-3-({1-[4-(2-cyclopropoxyphenyl)pyridin-3-yl]cyclopropoxy}methyl)phenyl]sulfanyl}-N-ethyl-N-[(2S,3R,4R,5R)-2,3,4,5,6-pentahydroxyhexyl]butanamide (I-659);

4-{[4-chloro-3-({1-[4-(2-cyclopropoxyphenyl)pyridin-3-yl]cyclopropoxy}methyl)phenyl]sulfanyl}-N-(2-hydroxyethyl)-N-[(2S,3R,4R,5R)-2,3,4,5,6-pentahydroxyhexyl]butanamide (I-660);

4-{[4-chloro-3-({1-[4-(2-cyclopropoxyphenyl)pyridin-3-yl]cyclopropoxy}methyl)phenyl]sulfanyl}-N-(3-hydroxypropyl)-N-[(2S,3R,4R,5R)-2,3,4,5,6-pentahydroxyhexyl]butanamide (I-661);

4-{[4-chloro-3-({1-[4-(2-cyclopropoxyphenyl)pyridin-3-yl]cyclopropoxy}methyl)phenyl]sulfanyl}-N-[2-(dimethylamino)ethyl]-N-[(2S,3R,4R,5R)-2,3,4,5,6-pentahydroxyhexyl]butanamide (I-662);

N-(carbamoylmethyl)-4-{[4-chloro-3-({1-[4-(2-cyclopropoxyphenyl)pyridin-3-yl]cyclopropoxy} methyl)phenyl]sulfanyl}-N-[(2S,3R,4R,5R)-2,3,4,5,6-pentahydroxyhexyl]butanamide (I-663);

4-{[4-chloro-3-({1-[4-(2-cyclopropoxyphenyl)pyridin-3-yl]cyclopropoxy}methyl)phenyl]sulfanyl}-N-(2-methoxyethyl)-N-[(2S,3R,4R,5R)-2,3,4,5,6-pentahydroxyhexyl]butanamide (I-664);

4-{[4-chloro-3-({1-[4-(2-cyclopropoxyphenyl)pyridin-3-yl]cyclopropoxy}methyl)phenyl]sulfanyl}-N-(2-methanesulfonylethyl)-N-[(2S,3R,4R,5R)-2,3,4,5,6-pentahydroxyhexyl]butanamide (I-665);

4-{[4-chloro-3-({1-[4-(2-cyclopropoxyphenyl)pyridin-3-yl]cyclopropoxy}methyl)phenyl]sulfanyl}-N-[(2S,3R,4R,5R)-2,3,4,5,6-pentahydroxyhexyl]-N-propylbutanamide (I-666);

N-benzyl-4-{[4-chloro-3-({1-[4-(2-cyclopropoxyphenyl)pyridin-3-yl]cyclopropoxy}methyl) phenyl]sulfanyl}-N-[(2S,3R,4R,5R)-2,3,4,5,6-pentahydroxyhexyl]butanamide (I-667);

4-{[4-chloro-3-({1-[4-(2-cyclopropoxyphenyl)pyridin-3-yl]cyclopropoxy}methyl)phenyl]sulfanyl}-N-[(2S,3R,4R,5R)-2,3,4,5,6-pentahydroxyhexyl]-N-(propan-2-yl)butanamide (I-668);

4-{[4-chloro-3-({1-[4-(2-cyclopropoxyphenyl)pyridin-3-yl]cyclopropoxy}methyl)phenyl]sulfanyl}-N-(oxan-4-yl)-N-[(2S,3R,4R,5R)-2,3,4,5,6-pentahydroxyhexyl]butanamide (I-669);

4-{[4-chloro-3-({1-[4-(2-cyclopropoxyphenyl)pyridin-3-yl]cyclopropoxy}methyl)phenyl]sulfanyl}-N-[(methylcarbamoyl)methyl]-N-[(2S,3R,4R,5R)-2,3,4,5,6-pentahydroxyhexyl]butanamide (I-670);

4-{[4-chloro-3-({1-[4-(2-cyclopropoxyphenyl)pyridin-3-yl]cyclopropoxy}methyl)phenyl]sulfanyl}-N-[2-(dimethylcarbamoyl)ethyl]-N-[(2S,3R,4R,5R)-2,3,4,5,6-pentahydroxyhexyl]butanamide (I-671);

4-{[4-chloro-3-({1-[4-(2-cyclopropoxyphenyl)pyridin-3-yl]cyclopropoxy}methyl)phenyl]sulfanyl}-N-[2-(ethylcarbamoyl)ethyl]-N-[(2S,3R,4R,5R)-2,3,4,5,6-pentahydroxyhexyl]butanamide (I-672);

4-{[4-chloro-3-({1-[4-(2-cyclopropoxyphenyl)pyridin-3-yl]cyclopropoxy}methyl)phenyl]sulfanyl}-N-(3-methoxypropyl)-N-[(2S,3R,4R,5R)-2,3,4,5,6-pentahydroxyhexyl]butanamide (I-673);

4-{[4-chloro-3-({1-[4-(2-cyclopropoxyphenyl)pyridin-3-yl]cyclopropoxy}methyl)phenyl]sulfanyl}-N-[(dimethylcarbamoyl)methyl]-N-[(2S,3R,4R,5R)-2,3,4,5,6-pentahydroxyhexyl]butanamide (I-674);

N-(2-carbamoylethyl)-4-{[4-chloro-3-({1-[4-(2-cyclopropoxyphenyl)pyridin-3-yl]cyclopropoxy} methyl)phenyl]sulfanyl}-N-[(2S,3R,4R,5R)-2,3,4,5,6-pentahydroxyhexyl]butanamide (I-675);

3-({4-chloro-3-[({1-[4-(2-cyclopropoxyphenyl)pyridin-3-yl]cyclopropyl}amino)methyl]phenyl}sulfanyl)-N-methyl-N-[(2S,3R,4R,5R)-2,3,4,5,6-pentahydroxyhexyl]propanamide (I-676);

3-{[4-chloro-3-({1-[4-(2-cyclopropoxyphenyl)pyridin-3-yl]cyclopropoxy}methyl)phenyl]sulfanyl}-N-methyl-N-[(2S,3R,4R,5R)-2,3,4,5,6-pentahydroxyhexyl]propanamide (I-677);

5-({4-chloro-3-[({1-[4-(2-cyclopropoxyphenyl)pyridin-3-yl]cyclopropyl}amino)methyl]phenyl}sulfanyl)-N-methyl-N-[(2S,3R,4R,5R)-2,3,4,5,6-pentahydroxyhexyl]pentanamide (I-678);

2-[1-({[4-chloro-3-({1-[4-(2-cyclopropoxyphenyl)pyridin-3-yl]cyclopropoxy}methyl)phenyl]sulfanyl}methyl)cyclopropyl]-N-methyl-N-[(2S,3R,4R,5R)-2,3,4,5,6-pentahydroxyhexyl]acetamide (I-679);

4-[({4-chloro-3-[({1-[4-(2-cyclopropoxyphenyl)pyridin-3-yl]cyclopropyl}amino)methyl]phenyl}sulfanyl)methyl]-N-methyl-N-[(2S,3R,4R,5R)-2,3,4,5,6-pentahydroxyhexyl]benzamide (I-680);

2-{1-[({4-chloro-3-[({1-[4-(2-cyclopropoxyphenyl)pyridin-3-yl]cyclopropyl}amino)methyl]phenyl}sulfanyl)methyl]cyclopropyl}-N-methyl-N-[(2S,3R,4R,5R)-2,3,4,5,6-pentahydroxyhexyl]acetamide (I-681);

5-{[4-chloro-3-({1-[4-(2-cyclopropoxyphenyl)pyridin-3-yl]cyclopropoxy}methyl)phenyl]sulfanyl}-N-methyl-N-[(2S,3R,4R,5R)-2,3,4,5,6-pentahydroxyhexyl]pentanamide (I-682);

4-{[4-chloro-3-({1-[4-(2-cyclopropoxyphenyl)pyridin-3-yl]cyclopropoxy}methyl)phenyl]sulfanyl}-N-[2-(2-hydroxyethoxy)ethyl]-N-[(2S,3R,4R,5R)-2,3,4,5,6-pentahydroxyhexyl]butanamide (I-683);

4-f{[4-chloro-3-({1-[4-(2-cyclopropoxyphenyl)pyridin-3-yl]cyclopropoxy}methyl)phenyl]sulfanyl}-N-(5-hydroxypentyl)-N-[(2S,3R,4R,5R)-2,3,4,5,6-pentahydroxyhexyl]butanamide (I-684);

4-({[4-chloro-3-({1-[4-(2-cyclopropoxyphenyl)pyridin-3-yl]cyclopropoxy}methyl)phenyl]sulfanyl}methyl)-N-methyl-N-[(2S,3R,4R,5R)-2,3,4,5,6-pentahydroxyhexyl]benzamide (I-685);

4-{[4-chloro-3-({1-[4-(2-cyclopropoxyphenyl)pyridin-3-yl]cyclopropoxy}methyl)phenyl]sulfanyl}-N-[2-(morpholine-4-sulfonyl)ethyl]-N-[(2S,3R,4R,5R)-2,3,4,5,6-pentahydroxyhexyl]butanamide (I-686);

4-{[4-chloro-3-({1-[4-(2-cyclopropoxyphenyl)pyridin-3-yl]cyclopropoxy}methyl)phenyl]sulfanyl}-N-(3-hydroxy-2,2-dimethylpropyl)-N-[(2R,3S,4S,5S)-2,3,4,5,6-pentahydroxyhexyl]butanamide (I-687);

4-{[4-chloro-3-({1-[4-(2-cyclopropoxyphenyl)pyridin-3-yl]cyclopropoxy}methyl)phenyl]sulfanyl}-N-[(2R,3S,4S,5S)-2,3,4,5,6-pentahydroxyhexyl]-N-[(1s,4s)-4-hydroxycyclohexyl]butanamide (I-688);

4-{[4-chloro-3-({1-[4-(2-cyclopropoxyphenyl)pyridin-3-yl]cyclopropoxy}methyl)phenyl]sulfanyl}-N,2-dimethyl-N-[(2S,3R,4R,5R)-2,3,4,5,6-pentahydroxyhexyl]butanamide (I-689);

4-{[4-chloro-3-({1-[4-(2-cyclopropoxyphenyl)pyridin-3-yl]cyclopropoxy}methyl)phenyl]sulfanyl}-2-methyl-N-[(2S,3R,4R,5R)-2,3,4,5,6-pentahydroxyhexyl]butanamide (I-690);

4-{[3-({1-[4-(2-cyclopropoxyphenyl)pyridin-3-yl]cyclopropoxy}methyl)-4-ethylphenyl]sulfanyl}-N-methyl-N-[(2S,3R,4R,5R)-2,3,4,5,6-pentahydroxyhexyl]butanamide (I-691);

4-{[4-chloro-3-({1-[4-(2-cyclopropoxyphenyl)pyridin-3-yl]cyclopropoxy}methyl)phenyl]sulfanyl}-N-(4-hydroxybutyl)-N-[(2S,3R,4R,5R)-2,3,4,5,6-pentahydroxyhexyl]butanamide (I-692);

4-{[4-chloro-3-({1-[4-(2-cyclopropoxyphenyl)pyridin-3-yl]cyclopropoxy}methyl)phenyl]sulfanyl}-N-[2-(dimethylsulfamoyl)ethyl]-N-[(2S,3R,4R,5R)-2,3,4,5,6-pentahydroxyhexyl]butanamide (I-693);

4-{[4-chloro-3-({1-[4-(2-cyclopropoxyphenyl)pyridin-3-yl]cyclopropoxy}methyl)phenyl]sulfanyl}-N-[2-(methylsulfamoyl)ethyl]-N-[(2S,3R,4R,5R)-2,3,4,5,6-pentahydroxyhexyl]butanamide (I-694);

N-(5-{[4-chloro-3-({1-[4-(2-cyclopropoxyphenyl)pyridin-3-yl]cyclopropoxy}methyl)phenyl]sulfanyl}pentyl)-N-[(2S,3R,4R,5R)-2,3,4,5,6-pentahydroxyhexyl]acetamide (I-695);

1-(4-{N-ethyl4-chloro-3-[({1-[4-(2-cyclopropoxyphenyl)pyridin-3-yl]cyclopropyl}amino) methyl]benzenesulfonamido}butyl)-3-[(2S,3R,4S,5R)-1,3,4,5,6-pentahydroxyhexan-2-yl]urea (I-696);

3-{1-[(2-chloro-5-{methyl[4-({[(2S,3R,4S,5R)-1,3,4,5,6-pentahydroxyhexan-2-yl]carbamoyl}amino)butyl]sulfamoyl}phenyl)methoxy]cyclopropyl}-4-(2-cyclopropoxyphenyl)pyridin-1-ium-1-olate (I-697);

3-[1-({2-chloro-5-[(2S)-6-({[(2S,3R,4S,5R)-1,3,4,5,6-pentahydroxyhexan-2-yl]carbamoyl}amino)hexan-2-yl]phenyl}methoxy)cyclopropyl]-4-(2-cyclopropoxyphenyl)pyridin-1-ium-1-olate (I-698);

3-{1-[(2-chloro-5-{ethyl[4-({[(2S,3R,4R,5R)-2,3,4,5,6-pentahydroxyhexyl]carbamoyl}amino) butyl]sulfamoyl}phenyl)methoxy]cyclopropyl}-4-(2-cyclopropoxyphenyl)pyridin-1-ium-1-olate (I-699);

2,5-dichloro-4-[({1-[4-(2-cyclopropoxyphenyl)pyridin-3-yl]cyclopropyl}amino)methyl]phenol (I-700);

3-{1-[(2-chloro-5-{ethyl[4-({[(2S,3R,4R,5R)-2,3,4,5,6-pentahydroxyhexyl]carbamoyl}amino) butyl]sulfamoyl}phenyl)methoxy]cyclopropyl}-4-(2-cyclopropoxyphenyl)-1-{[(2,2-dimethylpropanoyl)oxy]methyl}pyridin-1-ium (I-701);

1-[({[2-(acetyloxy)ethyl](methyl)carbamoyl}oxy)methyl]-3-{1-[(2-chloro-5-{ethyl[4-({[(2S,3R,4R,5R)-2,3,4,5,6-pentahydroxyhexyl]carbamoyl}amino)butyl]sulfamoyl}phenyl) methoxy]cyclopropyl}-4-(2-cyclopropoxyphenyl)pyridin-1-ium (I-702)

3-(1-{[2-chloro-5-(ethylsulfamoyl)phenyl]methoxy}cyclopropyl)-4-(2-cyclopropoxyphenyl) pyridin-1-ium-1-olate (I-703);

3-(1-{[2-chloro-5-(methylsulfamoyl)phenyl]methoxy}cyclopropyl)-4-(2-cyclopropoxyphenyl) pyridin-1-ium-1-olate (I-704);

4-chloro-3-({1-[4-(2-cyclopropoxyphenyl)pyridin-3-yl]cyclopropoxy}methyl)-N,N-diethylbenzene-1-sulfonamide (I-705);

1,3-bis[(5S)-5-[4-chloro-3-({1-[4-(2-cyclopropoxyphenyl)pyridin-3-yl]cyclopropoxy}methyl) phenyl]hexyl]urea (I-706);

2-[4-chloro-3-({1-[4-(2-cyclopropoxyphenyl)pyridin-3-yl]cyclopropoxy}methyl) benzenesulfonamido]ethane-1-sulfonic acid (I-707);

3-{1-[(2-chloro-5-sulfamoylphenyl)methoxy]cyclopropyl}-4-(2-cyclopropoxyphenyl)pyridin-1-ium-1-olate (I-708);

4-chloro-3-({1-[4-(2-cyclopropoxyphenyl)pyridin-3-yl]cyclopropoxy}methyl)benzene-1-sulfonamide (I-709);

1-{2-[2-({4-chloro-3-[(1-{4-[2-(oxetan-3-yloxy)phenyl]pyridin-3-yl}cyclopropoxy)methyl]phenyl}sulfanyl) ethoxy]ethyl}-3-[(2S,3R,4S,5R)-1,3,4,5,6-pentahydroxyhexan-2-yl]urea (I-710);

4-chloro-3-({1-[4-(2-cyclopropoxyphenyl)pyridin-3-yl]cyclopropoxy}methyl)-N-methyl-N-(propan-2-yl)benzene-1-sulfonamide (I-711);

4-chloro-3-({1-[4-(2-cyclopropoxyphenyl)pyridin-3-yl]cyclopropoxy}methyl)-N-(propan-2-yl)benzene-1-sulfonamide (I-712);

4-chloro-3-({1-[4-(2-cyclopropoxyphenyl)pyridin-3-yl]cyclopropoxy}methyl)-N-methyl-N-propylbenzene-1-sulfonamide (I-713);

4-chloro-N-cyclopentyl-3-({1-[4-(2-cyclopropoxyphenyl)pyridin-3-yl]cyclopropoxy}methyl)-N-methylbenzene-1-sulfonamide (I-714);

4-[4-chloro-3-({1-[4-(2-cyclopropoxyphenyl)pyridin-3-yl]cyclopropoxy}methyl) benzenesulfonyl]-3,3-dimethylmorpholine (I-715);

3-{1-[(2-chloro-5-{[4-({[(2S,3R,4R,5R)-2,3,4,5,6-pentahydroxyhexyl]carbamoyl}amino)butyl](propan-2-yl)sulfamoyl}phenyl)methoxy]cyclopropyl}-4-(2-cyclopropoxyphenyl)pyridin-1-ium-1-olate (I-716);

3-[(2S,3R,4S,5R)-1,3,4,5,6-pentahydroxyhexan-2-yl]-1-{4-[N-(propan-2-yl)4-chloro-3-({1-[4-(2-cyclopropoxyphenyl)pyridin-3-yl]cyclopropoxy}methyl)benzenesulfonamido]butyl}urea (I-717);

(2S,3S,4R,5S)-2,3,4,5,6-pentahydroxy-N-{4-[N-(propan-2-yl)4-chloro-3-({1-[4-(2-cyclopropoxyphenyl)pyridin-3-yl]cyclopropoxy}methyl)benzenesulfonamido]butyl}hexanamide (I-718);

N-tert-butyl-4-chloro-3-({1-[4-(2-cyclopropoxyphenyl)pyridin-3-yl]cyclopropoxy}methyl) benzene-1-sulfonamide (I-719);

4-chloro-3-({1-[4-(2-cyclopropoxyphenyl)pyridin-3-yl]cyclopropoxy}methyl)-N-(oxan-4-yl)benzene-1-sulfonamide (I-720);

(2S)-S-[4-chloro-3-({1-[4-(2-cyclopropoxyphenyl)pyridin-3-yl]cyclopropoxy}methyl)phenyl]-1-hydroxypropane-2-sulfonamido (I-721);

(2R)-S-[4-chloro-3-({1-[4-(2-cyclopropoxyphenyl)pyridin-3-yl]cyclopropoxy}methyl)phenyl]-1-hydroxypropane-2-sulfonamido (I-722);

2-(4-(2-cyclopropoxyphenyl)pyridin-3-yl)-N-(2,5-dichlorobenzyl)propan-2-amine (I-723);

4-(4-chloro-3-((1-(4-(2-cyclopropoxyphenyl)pyridin-3-yl)cyclopropoxy)methyl)phenethyl)-N-((2S,3R,4R,5R)-2,3,4,5,6-pentahydroxyhexyl)benzamide (I-724);

4-chloro-3-((1-(4-(2-cyclopropoxyphenyl)pyridin-3-yl)cyclopropoxy)methyl)-N,N-dimethylbenzamide (I-725);

1-(5-(4-chloro-3-((1-(4-(2-cyclopropoxyphenyl)pyridin-3-yl)cyclopropoxy)methyl)phenoxy) pentyl)-3-((2S,3R,4R,5R)-2,3,4,5,6-pentahydroxyhexyl)urea (I-726);

3-((4-chloro-3-((1-(4-(2-cyclopropoxyphenyl)pyridin-3-yl)cyclopropoxy)methyl)benzyl)oxy)-N-((2S,3R,4R,5R)-2,3,4,5,6-pentahydroxyhexyl)benzamide (I-727);

4-chloro-5-((1-(4-(2-cyclopropoxyphenyl)pyridin-3-yl)cyclopropoxy)methyl)-2-fluoro-N-isopropyl-N-(4-(3-((2S,3R,4R,5R)-2,3,4,5,6-pentahydroxyhexyl)ureido)butyl) benzenesulfonamide (I-728);

N-((4-chloro-3-((1-(4-(2-cyclopropoxyphenyl)pyridin-3-yl)cyclopropoxy)methyl)phenyl)sulfonyl)acetamide (I-729);

4-chloro-5-((1-(4-(2-cyclopropoxyphenyl)pyridin-3-yl)cyclopropoxy)methyl)-2-methoxy-N,N-dimethylbenzenesulfonamide (I-730);

4-chloro-5-((1-(4-(2-cyclopropoxyphenyl)pyridin-3-yl)cyclopropoxy)methyl)-2-hydroxy-N,N-dimethylbenzenesulfonamide (I-731);

1-(4-((4-chloro-3-((1-(4-(2-cyclopropoxyphenyl)pyridin-3-yl)cyclopropoxy)methyl)phenyl)sulfonyl)-1,4-diazepan-1-yl)ethan-1-one (I-732);

6-((4-chloro-3-((1-(4-(2-cyclopropoxyphenyl)pyridin-3-yl)cyclopropoxy)methyl)phenyl)sulfonyl)-2-methoxy-5,6,7,8-tetrahydro-1,6-naphthyridine (I-733);

6-((4-chloro-3-((1-(4-(2-cyclopropoxyphenyl)pyridin-3-yl)cyclopropoxy)methyl)phenyl)sulfonyl)-5,6,7,8-tetrahydro-1,6-naphthyridin-2-ol (I-734);

4-chloro-3-((1-(4-(2-cyclopropoxyphenyl)pyridin-3-yl)cyclopropoxy)methyl)-N-methyl-N-(4-(3-((2S,3R,4S,5R)-1,3,4,5,6-pentahydroxyhexan-2-yl)ureido)butyl-1,1,2,2,3,3,4,4-d8)benzenesulfonamide (I-735);

(2R,3S,4R,5S)-5-(3-(4-((4-chloro-3-((1-(4-(2-cyclopropoxyphenyl)pyridin-3-yl)cyclopropoxy)methyl)-N-methylphenyl)sulfonamido)butyl)ureido)hexane-1,2,3,4,6-pentayl pentapropionate (I-738);

3-(1-((2,5-dichlorobenzyl)oxy)cyclopropyl)-4-(2-(methylthio)phenyl)pyridine (I-739);

4-(2-cyclopropoxyphenyl)-3-(2-((2,5-dichlorobenzyl)oxy) propan-2-yl)pyridine (I-740);

4-(2-cyclopropoxyphenyl)-3-(1-((2,5-dichlorobenzyl)oxy) cyclobutyl)pyridine (I-741);

4-(2-cyclopropoxyphenyl)-3-(1-((2,5-dichlorobenzyl)oxy) cyclopentyl)pyridine (I-742);

4-(2-cyclopropoxyphenyl)-3-(3-((2,5-dichlorobenzyl)oxy) tetrahydrofuran-3-yl)pyridine (I-743);

4-chloro-3-(((1-(4-(2-cyclopropoxyphenyl)pyridin-3-yl)cyclopropyl)amino)methyl)-N-isopropyl-N-(4-(3-((2S,3R,4S,5R)-1,3,4,5,6-pentahydroxyhexan-2-yl)ureido)butyl) benzenesulfonamide (I-744);

4-(2-cyclopropoxyphenyl)-3-(1-((2,5-dichlorobenzyl)oxy) ethyl)pyridine (I-745);

4-chloro-3-((1-(4-(2-cyclopropoxyphenyl)pyridin-3-yl)cyclobutoxy)methyl)-N-isopropyl-N-(4-(3-((2S,3R,4S,5R)-1,3,4,5,6-pentahydroxyhexan-2-yl)ureido)butyl)benzenesulfonamide (I-746);

4-chloro-3-((1-(4-(2-cyclopropoxyphenyl)pyridin-3-yl)cyclobutoxy)methyl)-N-isopropyl-N-(4-(3-((2S,3R,4R,5R)-2,3,4,5,6-pentahydroxyhexyl)ureido)butyl)benzenesulfonamide (I-747);

5-(4-chloro-3-((1-(4-(2-cyclopropoxyphenyl)pyridin-3-yl)cyclopropoxy)methyl)phenethyl)-N-((2S,3R,4R,5R)-2,3,4,5,6-pentahydroxyhexyl)picolinamide (I-748);

4-chloro-3-(((3-(4-(2-cyclopropoxyphenyl)pyridin-3-yl)tetrahydrofuran-3-yl)oxy)methyl)-N-isopropyl-N-(4-(3-((2S,3R,4S,5R)-1,3,4,5,6-pentahydroxyhexan-2-yl)ureido)butyl)benzenesulfonamide (I-749);

4-chloro-3-(((3-(4-(2-cyclopropoxyphenyl)pyridin-3-yl)tetrahydrofuran-3-yl)oxy)methyl)-N-isopropyl-N-(4-(3-((2S,3R,4R,5R)-2,3,4,5,6-pentahydroxyhexyl)ureido)butyl) benzenesulfonamide (I-750);

4-chloro-3-(((1-(4-(2-cyclopropoxyphenyl)pyridin-3-yl)cyclopropyl)amino)methyl)-N-isopropyl-N-(4-(3-((2S,3R,4R,5R)-2,3,4,5,6-pentahydroxyhexyl)ureido)butyl) benzenesulfonamide (I-751);

4-chloro-3-((1-(4-(2-cyclopropoxyphenyl)pyridin-3-yl)ethoxy)methyl)-N-isopropyl-N-(4-(3-((2S,3R,4S,5R)-1,3,4,5,6-pentahydroxyhexan-2-yl)ureido)butyl)benzenesulfonamide (I-752);

4-chloro-3-((1-(4-(2-cyclopropoxyphenyl)pyridin-3-yl)ethoxy)methyl)-N-isopropyl-N-(4-(3-((2S,3R,4R,5R)-2,3,4,5,6-pentahydroxyhexyl)ureido)butyl)benzenesulfonamide (I-753);

4-chloro-3-(((2-(4-(2-cyclopropoxyphenyl)pyridin-3-yl)propan-2-yl)amino)methyl)-N-isopropyl-N-(4-(3-((2S,3R,4S,5R)-1,3,4,5,6-pentahydroxyhexan-2-yl)ureido)butyl) benzenesulfonamide (I-754);

1-(4-(4-chloro-3-((1-(4-(2-cyclopropoxyphenyl)pyridin-3-yl)cyclopropoxy)methyl) phenoxy)butyl)-3-((2S,3R,4R,5R)-2,3,4,5,6-pentahydroxyhexyl)urea (I-755);

3-((4-chloro-3-((1-(4-(2-cyclopropoxyphenyl)pyridin-3-yl)cyclopropoxy)methyl)benzyl)oxy)-N-((2S,3R,4S,5R)-1,3,4,5,6-pentahydroxyhexan-2-yl)benzamide (I-756);

6-((4-chloro-3-((1-(4-(2-cyclopropoxyphenyl)pyridin-3-yl)cyclopropoxy)methyl)benzyl)oxy)-N-((2S,3R,4S,5R)-1,3,4,5,6-pentahydroxyhexan-2-yl)nicotinamide (I-757);

2-((4-chloro-3-((1-(4-(2-cyclopropoxyphenyl)pyridin-3-yl)cyclopropoxy)methyl)benzyl)thio)-1-methyl-N-((2S,3R,4R,5R)-2,3,4,5,6-pentahydroxyhexyl)-1H-imidazole-5-carboxamide (I-758);

2-((4-chloro-3-((1-(4-(2-cyclopropoxyphenyl)pyridin-3-yl)cyclopropoxy)methyl)benzyl)thio)-1-methyl-N-((2S,3R,4S,5R)-1,3,4,5,6-pentahydroxyhexan-2-yl)-1H-imidazole-5-carboxamide (I-759);

1-(5-(4-chloro-3-((1-(4-(2-cyclopropoxyphenyl)pyridin-3-yl)cyclopropoxy)methyl)phenoxy) pentyl)-3-((2S,3R,4S,5R)-1,3,4,5,6-pentahydroxyhexan-2-yl)urea (I-760);

4-chloro-3-((1-(4-(2-cyclopropoxyphenyl)pyridin-3-yl)cyclopropoxy)methyl)-N-isobutyl-N-(4-(3-((2S,3R,4S,5R)-1,3,4,5,6-pentahydroxyhexan-2-yl)ureido)butyl)benzenesulfonamide (I-761)

4-chloro-3-((1-(4-(2-cyclopropoxyphenyl)pyridin-3-yl)cyclopropoxy)methyl)-N-isobutyl-N-(4-(3-((2S,3R,4R,5R)-2,3,4,5,6-pentahydroxyhexyl)ureido)butyl)benzenesulfonamide (I-762);

4-chloro-5-((1-(4-(2-cyclopropoxyphenyl)pyridin-3-yl)cyclopropoxy)methyl)-2-fluoro-N-isopropyl-N-(4-(3-((2S,3R,4S,5R)-1,3,4,5,6-pentahydroxyhexan-2-yl)ureido)butyl) benzenesulfonamide (I-763);

4-chloro-5-((1-(4-(2-cyclopropoxyphenyl)pyridin-3-yl)cyclopropoxy)methyl)-2-fluoro-N-isopropyl-N-(4-(3-((2S,3R,4R,5R)-2,3,4,5,6-pentahydroxyhexyl)ureido)butyl) benzenesulfonamide (I-764);

4-(2-chloro-6-methoxyphenyl)-3-(1-((2,5-dichlorobenzyl)oxy)cyclopropyl)pyridine I-765);

N-(4-((4-chloro-3-((1-(4-(2-cyclopropoxyphenyl)pyridin-3-yl)cyclopropoxy)methyl)-N-methylphenyl)sulfonamido) butyl)acetamide (I-766);

4-(2-chlorophenyl)-3-(1-((2,5-dichlorobenzyl)oxy)cyclopropyl)pyridine (I-768);

1-((4-chloro-3-((1-(4-(2-cyclopropoxyphenyl)pyridin-3-yl)cyclopropoxy)methyl)phenyl) sulfonyl)-4-methyl-1,4-diazepane (I-769);

4-chloro-3-((1-(4-(2-cyclopropoxyphenyl)pyridin-3-yl)cyclopropoxy)methyl)-N-(thiazol-2-yl)benzenesulfonamide (I-770);

4-chloro-3-((1-(4-(2-cyclopropoxyphenyl)pyridin-3-yl)cyclopropoxy)methyl)-N-phenylbenzenesulfonamide (I-771);

4-chloro-3-((1-(4-(2-cyclopropoxyphenyl)pyridin-3-yl)cyclopropoxy)methyl)-N-(2,2,2-trifluoroethyl)benzenesulfonamide (I-772);

3-(1-((2,5-dichlorobenzyl)oxy)cyclopropyl)-4-(o-tolyl)pyridine (I-773);

3-(1-((2,5-dichlorobenzyl)oxy)cyclopropyl)-4-(2-methoxy-4-methylphenyl)pyridine I-774);

3-(1-((2-chloro-5-(N-(4-((2S,3S,4R,5S)-2,3,4,5,6-pentahydroxyhexanamido)butyl) sulfamoyl)benzyl)oxy)cyclopropyl)-4-(2-cyclopropoxyphenyl)pyridine 1-oxide (I-775);

4-chloro-3-((1-(4-(2-cyclopropoxyphenyl)pyridin-3-yl)cyclopropoxy)methyl)-N-methyl-N-(4-(3-((2S,3R,4R,5R)-1,3,4,5,6-pentahydroxyhexan-2-yl)ureido)butyl)benzenesulfonamide I-776);

(1S,4S)-2-((4-chloro-3-((1-(4-(2-cyclopropoxyphenyl)pyridin-3-yl)cyclopropoxy)methyl) phenyl)sulfonyl)-5-methyl-2,5-diazabicyclo[2.2.1]heptane (I-777);

4-(2-cyclopropoxyphenyl)-3-(1-((2,5-dichlorobenzyl)oxy)propyl)pyridine (I-779);

1-((1S,4S)-5-((4-chloro-3-((1-(4-(2-cyclopropoxyphenyl)pyridin-3-yl)cyclopropoxy)methyl)phenyl)sulfonyl)-2,5-diazabicyclo[2.2.1]heptan-2-yl)ethan-1-one (I-780);

4-chloro-N-(1-(((S)-3-((S)-2-cyanopyrrolidine-1-carbonyl)-1,2,3,4-tetrahydroisoquinolin-7-yl)oxy)-10,21-dioxo-3,6,14,17-tetraoxa-9,11,20,22-tetraazahexacosan-26-yl)-3-((1-(4-(2-cyclopropoxyphenyl)pyridin-3-yl) cyclopropoxy)methyl)-N-methylbenzenesulfonamide (I-781);

4-chloro-N-(1-(((S)-3-((S)-2-cyanopyrrolidine-1-carbonyl)-1,2,3,4-tetrahydroisoquinolin-7-yl)oxy)-10,21,28,39-tetraoxo-3,6,14,17,32,35-hexaoxa-9,11,20,22,27,29,38,40-octaazatetratetracontan-44-yl)-3-((1-(4-(2-cyclopropoxyphenyl)pyridin-3-yl)cyclopropoxy)methyl)-N-methylbenzenesulfonamide (I-782) 4-(2-cyclopropoxyphenyl)-3-(1-((2,5-dichlorobenzyl)oxy)cyclopropyl)pyridazine (I-783)

1-(4-(2-cyclopropoxyphenyl)pyridazin-3-yl)-N-(2,5-dichlorobenzyl)cyclopropan-1-amine (I-784);

4-chloro-3-((1-(4-(2-cyclopropoxyphenyl)-6-ethylpyridin-3-yl)cyclopropoxy)methyl)-N-methyl-N-(4-(3-((2S,3R,4R,5R)-2,3,4,5,6-pentahydroxyhexyl)ureido)butyl)benzenesulfonamide I-785);

4-chloro-3-((1-(4-(2-cyclopropoxyphenyl)-6-ethylpyridin-3-yl)cyclopropoxy)methyl)-N-methyl-N-(4-(3-methyl-3-((2S,3R,4R,5R)-2,3,4,5,6-pentahydroxyhexyl)ureido) butyl) benzenesulfonamide (I-786);

4-(2-cyclopropoxyphenyl)-5-(1-((2,5-dichlorobenzyl)oxy) cyclopropyl)-2-ethylpyridine (I-787);

1-(1-((2,5-dichlorobenzyl)oxy)cyclopropyl)-5H-chromeno [3,4-c]pyridine (I-788);

3-(1-((2,5-dichlorobenzyl)oxy)cyclopropyl)-5-ethoxy-4-phenylpyridine (1-789);

3-(1-((2,5-dichlorobenzyl)oxy)cyclopropyl)-5-methoxy-4-phenylpyridine (1-790);

1-(4-(2-cyclopropoxyphenyl)pyridin-3-yl)-N-(2,5-dichlorophenyl)cyclopropane-1-carboxamide (I-791);

4-(2-cyclopropoxyphenyl)-3-(1-((2,5-dichlorophenoxy) methyl)cyclopropyl)pyridine (1-792);

6-((4-chloro-3-((1-(4-(2-cyclopropoxyphenyl)pyridin-3-yl) cyclopropoxy)methyl)phenoxy) methyl)-N-((2S,3R,4R,5R)-2,3,4,5,6-pentahydroxyhexyl)nicotinamide (I-793);

4-(2-cyclopropoxyphenyl)-3-(1-(((2,5-dichlorobenzyl)oxy) methyl)cyclopropyl)pyridine (I-794);

4-(2-cyclopropoxyphenyl)-3-(((2,5-dichlorobenzyl)oxy) methyl)pyridine (1-795);

6-((4-chloro-3-((1-(4-(2-cyclopropoxyphenyl)pyridin-3-yl) cyclopropoxy)methyl)benzyl)oxy)-N-((2S,3R,4R,5R)-2,3,4,5,6-pentahydroxyhexyl)nicotinamide (I-796);

3-(1-((2,5-dichlorobenzyl)oxy)cyclopropyl)-4-(2-methoxy-6-methylphenyl)pyridine (I-797);

3-(1-((2,5-dichlorobenzyl)oxy)cyclopropyl)-4-(2-methoxy-3-methylphenyl)pyridine (1-798);

4-chloro-3-((1-(4-(2-cyclopropoxyphenyl)pyridin-3-yl)cyclopropoxy)methyl)-N-methyl-N-(4-(3-((2S,3R,4R,5R)-2,3,4,5,6-pentahydroxyhexyl)ureido)butyl)benzamide (I-799);

3-(1-((2,5-dichlorobenzyl)oxy)cyclopropyl)-4-(2-methoxy-5-(trifluoromethoxy)phenyl)pyridine (I-800);

3-(1-((2,5-dichlorobenzyl)oxy)cyclopropyl)-4-(2-methoxy-5-(trifluoromethyl)phenyl)pyridine (I-801)

4-(3-chloro-2-methoxyphenyl)-3-(1-((2,5-dichlorobenzyl) oxy)cyclopropyl)pyridine (1-802);

3-(1-((2,5-dichlorobenzyl)oxy)cyclopropyl)-4-phenylpyridine (I-803);

3-(1-((2,5-dichlorobenzyl)oxy)cyclopropyl)-4-(2-methoxy-5-methylphenyl)pyridine (I-804);

3-(1-((2,5-dichlorobenzyl)oxy)cyclopropyl)-4-(2,2-difluorobenzo[d][1,3]dioxol-4-yl)pyridine (I-805);

3-(1-((2,5-dichlorobenzyl)oxy)cyclopropyl)-4-(3-methoxyphenyl)pyridine (I-806);

4-(3-chlorophenyl)-3-(1-((2,5-dichlorobenzyl)oxy)cyclopropyl)pyridine (I-807);

3-(1-((2,5-dichlorobenzyl)oxy)cyclopropyl)-4-(4-methoxyphenyl)pyridine (I-808);

3-(1-((2,5-dichlorobenzyl)oxy)cyclopropyl)-4-(2-(methylsulfonyl)phenyl)pyridine (I-809); and 4-(4-chlorophenyl)-3-(1-((2,5-dichlorobenzyl)oxy)cyclopropyl)pyridine (I-810).

In another embodiment, compounds of the invention include:

3-(4-[N-methyl[4-chloro-3-([1-[4-(2-cyclopropoxyphenyl) pyridin-3-yl]cyclopropoxy]methyl)benzene]sulfonamido]butyl)-1-[2-(2-[2-[((4-[((2-[2-(2-[[(4-[N-methyl[4-chloro-3-([1-[4-(2-cyclopropoxyphenyl)pyridin-3-yl] cyclopropoxy]methyl) benzene]sulfonamido]butyl) carbamoyl]amino]ethoxy)ethoxy]ethyl]carbamoyl) amino]butyl]carbamoyl)amino]ethoxy]ethoxy)ethyl]urea (I-736);

3-(4-[N-methyl[4-chloro-3-([1-[4-(2-cyclopropoxyphenyl) pyridin-3-yl]cyclopropoxy]methyl)benzene]sulfonamido]butyl)-1-[2-(2-[2-[((2-[2-(2-[[(4-[N-methyl[4-chloro-3-([1-[4-(2-cyclopropoxyphenyl)pyridin-3-yl] cyclopropoxy]methyl)benzene]sulfonamido]butyl) carbamoyl]amino]ethoxy)ethoxy]ethyl]carbamoyl) amino]ethoxy]ethoxy)ethyl]urea (I-737);

N,N'-((carbonylbis(azanediyl))bis(butane-4,1-diyl))bis(4-chloro-3-((1-(4-(2-cyclopropoxyphenyl)pyridin-3-yl)cyclopropoxy)methyl)-N-methylbenzenesulfonamide)(I-767);

N,N'-(piperazine-1,4-diylbis(propane-3,1-diyl))bis(5-(2,5-dichloro-4-((1-(4-(2-cyclopropoxyphenyl)pyridin-3-yl) cyclopropoxy)methyl)phenyl)pentanamide) (I-811);

N,N'-(((oxybis(ethane-2,1-diyl))bis(oxy))bis(ethane-2,1-diyl))bis(5-(2,5-dichloro-4-((1-(4-(2-cyclopropoxyphenyl)pyridin-3-yl)cyclopropoxy)methyl)phenyl)pentanamide) (I-812);

2,2'-(1,18-bis(2,5-dichloro-4-((1-(4-(2-cyclopropoxyphenyl)pyridin-3-yl)cyclopropoxy)methyl)phenyl)-5,14-dimethyl-6,13-dioxo-5,8,11,14-tetraazaoctadecane-8,11-diyl)diacetic acid (I-813);

1,1'-(butane-1,4-diyl)bis(3-(2-(2-((4-chloro-3-((1-(4-(2-cyclopropoxyphenyl)pyridin-3-yl)cyclopropoxy)methyl) phenyl)thio)ethoxy)ethyl)urea) (I-814); and 6-(carboxymethyl)-14-((4-chloro-3-((1-(4-(2-cyclopropoxyphenyl)pyridin-3-yl)cyclopropoxy)methyl)phenyl)thio)-3-(2-((2-(2-((4-chloro-3-((1-(4-(2-cyclopropoxyphenyl)pyridin-3-yl)cyclopropoxy)methyl) phenyl)thio)ethoxy)ethyl)amino)-2-oxoethyl)-8-oxo-12-oxa-3,6,9-triazatetradecanoic acid (I-815).

In another embodiment of the invention, the compounds of Formula (I') are enantiomers. In some embodiments the compounds are the (S)-enantiomer. In other embodiments the compounds are the (R)-enantiomer. In yet other embodiments, the compounds of Formula (I') may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I') incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of TGR5. In one embodiment, the compounds of the present invention are agonists of TGR5.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method for Preparation of Compounds

The compounds of the present invention may be made by a variety of methods, including standard chemistry. Suitable synthetic routes are depicted in the Schemes given below.

The compounds of Formula (I') may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I').

Those skilled in the art will recognize if a stereocenter exists in the compounds of Formula (I'). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1 to 5 which comprise different sequences of assembling intermediates B-1 to B-20. Starting materials are either commercially available or made by known procedures in the reported literature or as illustrated.

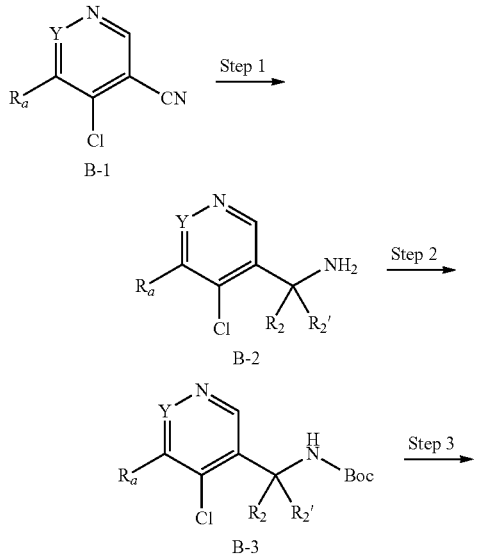

General Scheme 1

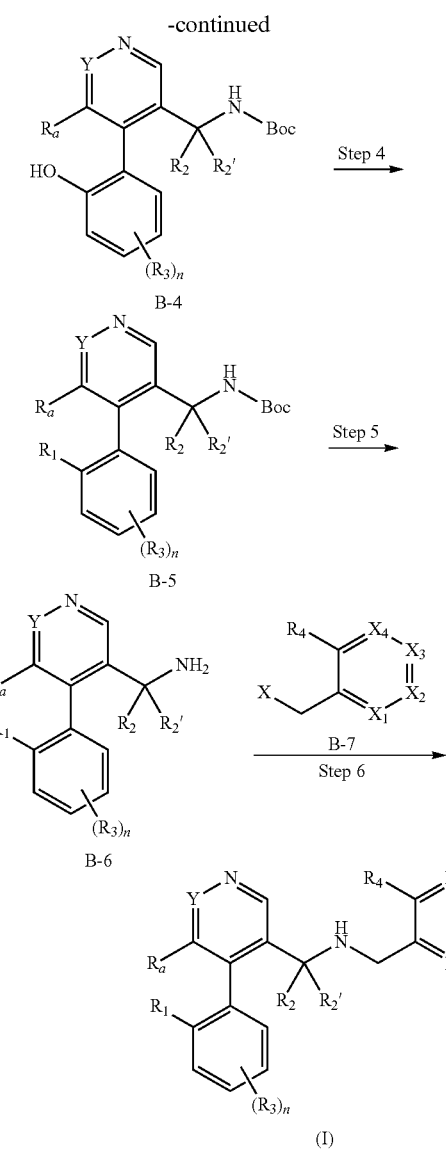

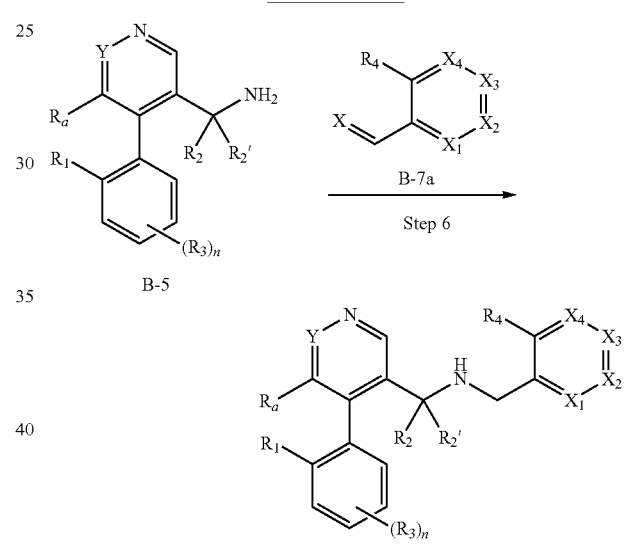

wherein $R_a$, $R_1$, $R_2$, $R_{2'}$, $R_3$, $R_4$, $X_1$-$X_4$, Y, and n are defined as in Formula (I').

The general way of preparing compounds of Formula (I') using intermediates B-1, B-2, B-3, B-4, B-4, B-5, B-6, and B-7 is outlined in General Scheme 1. Alkylation of nitrile B-1 using an alkyl lithium or Grignard reagent in a solvent, i.e., tetrahydrofuran (THF) or diethyl ether, and optionally in the presence of a Lewis acid i.e., cerium(III) chloride or titanium(IV) isopropoxide provides amine B-2. Alternatively, alkylation of nitrile B-1 using an alkyl zinc or Grignard reagent in a solvent, i.e., tetrahydrofuran (THF), diethyl ether or toluene, in the presence of boron trifluoride etherate and a Lewis acid i.e., titanium(IV) isopropoxide or bis(cyclopentadienyl) zirconium(IV)dichloride, provides amine B-2 wherein $R_2$ and $R_{2'}$ form a cyclopropane ring. Boc protection of the primary amine B-2 using known protection methods (i.e., treatment of B-2 with di-tert-butyl dicarbonate using a base, i.e., $NaHCO_3$, in a solvent, i.e., water and/or tetrahydrofuran (THF)) provides B-3. Arylation of B-3 with an aryl boronic acid or ester in the presence of a metal catalyst, i.e., palladium (II) acetate $(Pd(OAc)_2)$, tris(dibenzylideneacetone)dipalladium $(Pd_2(dba)_3)$ etc., and a base, i.e., potassium carbonate $(K_2CO_3)$, cesium carbonate $(Cs_2CO_3)$, in a solvent, i.e., dichloromethane, toluene, etc., provides B-4.

Alkylation of B-4 with an aryl halide, aryl sulfonate, or aryl sulfate in the presence of a base, i.e., $K_2CO_3$, $Cs_2CO_3$, KOH or NaH, in a solvent, i.e., acetonitrile or acetone, and optionally at an elevated temperature provides B-5. Alternatively, B-5 can be obtained by alkylation of B-4 with a phenol using a Mitsunobu reagent (i.e., diethyl azodicarboxylate (DEAD) or diisopropyl azodicarboxylate (DIAD)) and triphenyl phosphine in a solvent, i.e., tetrahydrofuran (THF), dichloromethane (DCM). Deprotection of B-4 in the presence of an acid, i.e., hydrochloric acid (HCl) and in a solvent, i.e., dioxane and/or tetrahydrofuran (THF) provides free amine B-6. Alkylation of B-6 with aryl halide or heteroaryl halide B-7 using a base, i.e., potassium carbonate $(K_2CO_3)$ or cesium carbonate $(Cs_2CO_3)$, in a solvent, i.e., N,N-dimethylformamide (DMF) or tetrahydrofuran (THF) provides the desired compound of Formula (I').

wherein $R_a$, $R_1$, $R_2$, $R_{2'}$, $R_3$, $R_4$, $X_1$-$X_4$, Y, and n are defined as in Formula (I').

Alternatively, compounds of Formula (I') can be obtained via reductive amination of amine B-6 using aldehyde B-7a in the presence of a reducing agent, i.e., sodium triacetoxyborohydride, sodium cyanoborohydride, or sodiumborohydride, in a solvent, i.e., tetrahydrofuran (THF).

General Scheme 3

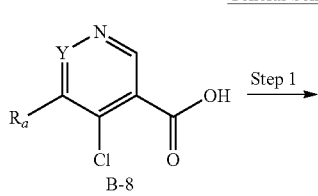

-continued

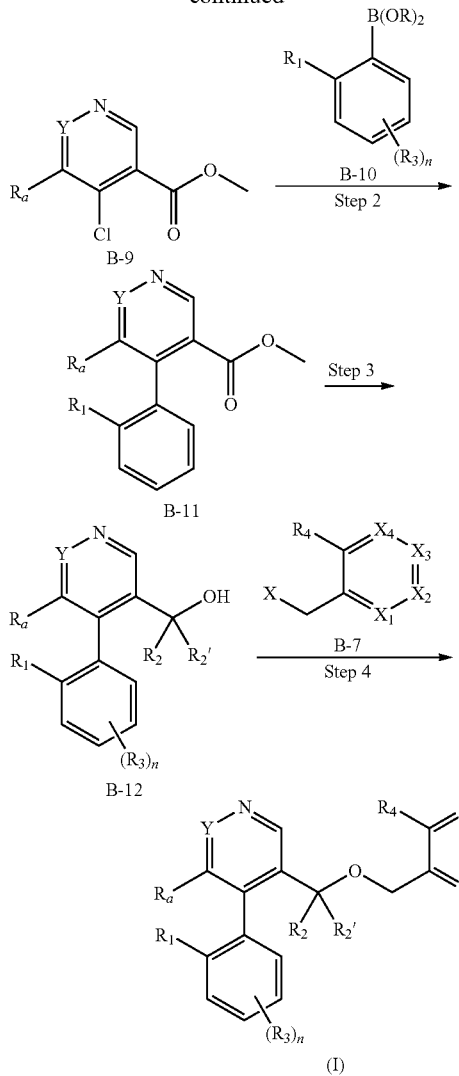

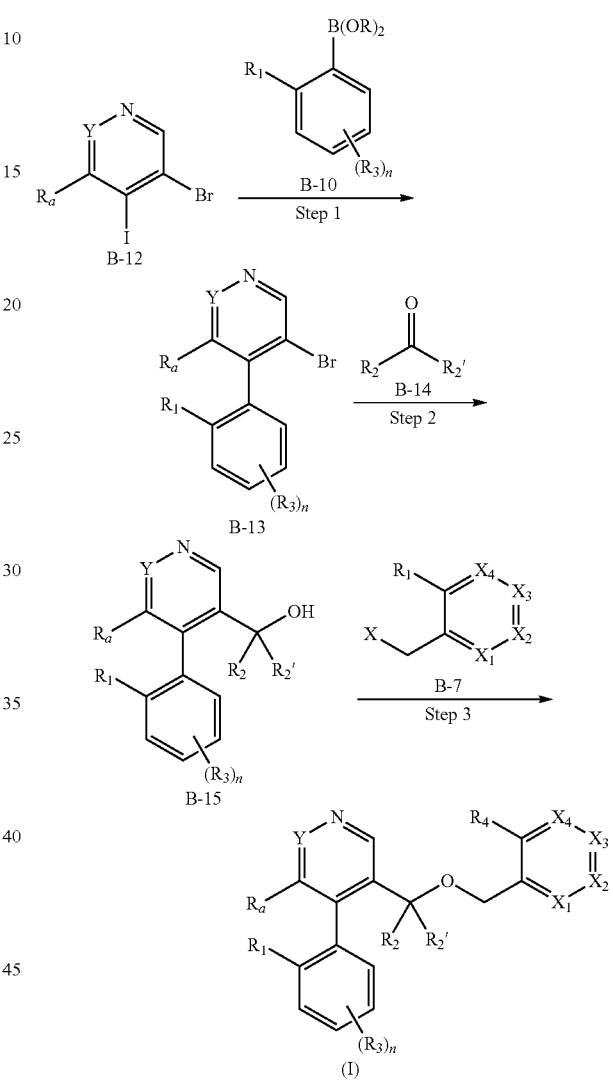

wherein $R_a$, $R_1$, $R_2$, $R_{2'}$, $R_3$, $R_4$, $X_1$-$X_4$, Y and n are defined as in Formula (I').

Alternatively, compounds of Formula (I') can be prepared using intermediates B-7, B-8, B-9, B-10, B-11, and B-12 as outlined in General Scheme 3. Esterification of B-8 using trimethylsilylmethyldiazene in a solvent, i.e., dichloromethane or methanol, yields B-9. Alternatively, B-9 can be obtained by treating B-8 with oxaloyl chloride in a solvent, i.e., methanol. Coupling of B-9 and aryl- or heteroarylboronic acid or aryl- or heteroarylboronate ester B-10 in the presence of a metal catalyst, i.e., palladium (II) acetate (Pd(OAc)$_2$), tris(dibenzylideneacetone)dipalladium (Pd$_2$(dba)$_3$) etc., and a base, i.e., potassium phosphate, in a solvent, i.e., 1,4-dioxane, THF, and/or water, provides B-11. Alkylation of ester B-11 using an alkyl lithium or Grignard reagent in a solvent, i.e., tetrahydrofuran (THF) or diethyl ether, and optionally in the presence of a Lewis acid i.e., cerium(III) chloride or titanium(IV) isopropoxide provides alcohol B-12. For compounds wherein $R_2$ and $R_{2'}$ form a cyclopropane ring, intermediate B-11 is treated with a Grignard reagent and bis(cyclopentadienyl)zirconium(IV) dichloride in a solvent, i.e., tetrahydrofuran (THF), diethyl ether, or toluene, to provide the desired product. Alkylation of B-12 with aryl halide or heteroaryl halide B-7 in the presence a strong base, i.e., sodium hydride (NaH), potassium bis(trimethylsilyl)amide (KHMDS), or potassium tert-butoxide and in a solvent, i.e., N,N-dimethylformamide (DMF), N-methyl-2-pyrrolidone (NMP), or tetrahydrofuran (THF), provides the desired compound of Formula (I').

wherein $R_a$, $R_1$, $R_2$, $R_{2'}$, $R_3$, $R_4$, $X_1$-$X_4$, Y and n are defined as in Formula (I').

The general way of preparing target molecules of Formula (I') using intermediates B-7, B-10, B-12, B-13, B-14, and B-15 is outlined in General Scheme 4. Coupling of B-12 and aryl- or heteroarylboronic acid or aryl- or heteroarylboronate ester B-10 in the presence of a metal catalyst, i.e., palladium (II) acetate (Pd(OAc)$_2$), tris(dibenzylideneacetone)dipalladium (Pd$_2$(dba)$_3$) etc., and a base, i.e., potassium phosphate, in a solvent, i.e., 1,4-dioxane, THF, and/or water, provides B-11. Treatment of B-11 with an alkyl lithium or alkyl magnesium halide (i.e., butyl lithium and iso-propyl magnesium bromide) followed by addition of ketone B-14 in a solvent, i.e., tetrahydrofuran (THF) or diethylether, provides alcohol B-15. Alkylation of B-15 with aryl halide or heteroaryl halide B-7 in the presence a strong base, i.e., sodium hydride (NaH), potassium bis(trimethylsilyl)amide (KHMDS), or potassium tert-butoxide, and in a solvent, i.e., N,N-dimethylformamide (DMF), N-methyl-2-pyrrolidone (NMP), or tetrahydrofuran (THF), provides the desired compound of Formula (I').

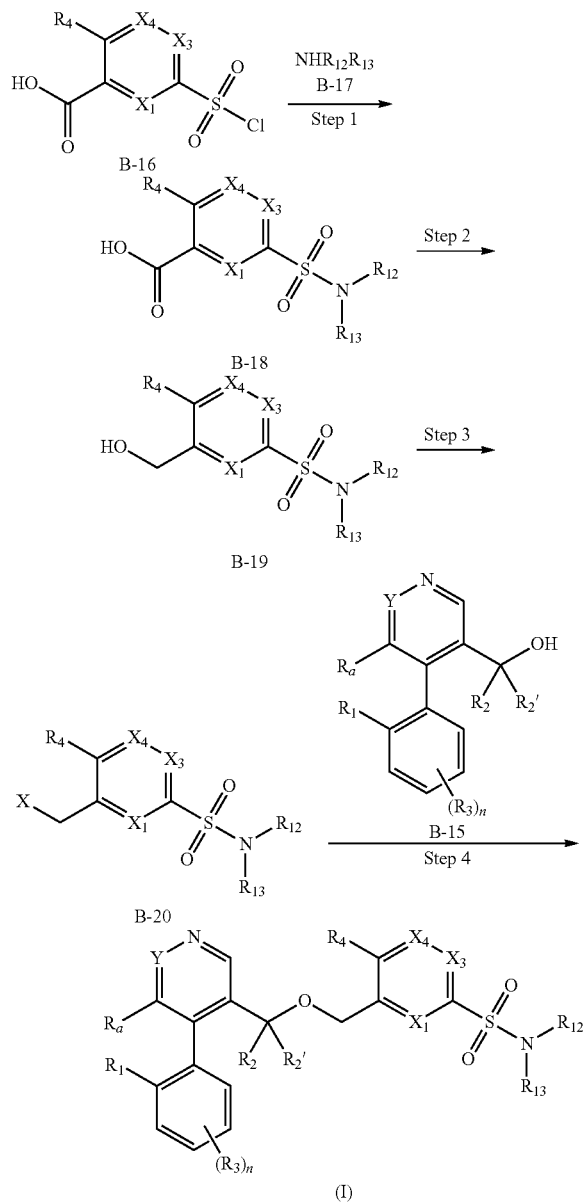

wherein $R_a$, $R_1$, $R_2$, $R_2'$, $R_3$, $R_4$, $X_1$-$X_4$, Y and n are defined as in Formula (I').

Alternatively, compounds of Formula (I') can be prepared using intermediates B-15, B-16, B-17, B-18, B-19, and B-20 as outlined in General Scheme 5. Treatment of sulfonylchloride B-13 with amine B-17 in the presence of a base, i.e., pyridine, triethylamine or $NaHCO_3$, and in a solvent, i.e., tetrahydrofuran (THF), dichloromethane (DCM), or water, provides sulfonylamide B-18. Reduction of carboxylic acid B-18 using isobuytylchloroformate in the presence of a base, i.e., N-methylmorpholine or trimethylamine, in a solvent, i.e., tetrahydrofuran (THF), followed by the addition of sodiumborohydride provides B-19. Halomethylene B-20 is obtained by reaction of B-19 with dibromotriphenylphosphorane in a solvent, i.e., acetonitrile. Alkylation of B-15 with aryl halide or heteroaryl halide B-20 in the presence a strong base, i.e., sodium hydride (NaH), potassium bis (trimethylsilyl)amide (KHMDS), KHMDS, or potassium tert-butoxide, and in a solvent, i.e., N,N-dimethylformamide (DMF), N-methyl-2-pyrrolidone (NMP), or tetrahydrofuran (THF), provides the desired compound of Formula (I').

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R_a$, $R_1$, $R_2$, $R_2'$, $R_3$, $R_4$, $X_1$-$X_4$, Y, and n are defined as in Formula (I') and other variables are as defined above, except where otherwise indicated. Furthermore, for synthetic purposes, the compounds of General Schemes 1 to 5 are mere representative with elected radicals to illustrate the general synthetic methodology of the compounds of Formula (I') as defined herein.

Methods of Using the Compounds

Another aspect of the invention relates to a method of treating or preventing a disease or disorder associated with modulation of TGR5. The method comprises administering to a patient in need of a treatment for diseases or disorders associated with modulation of TGR5 an effective amount the compositions and compounds of Formula (I'), or a pharmaceutically acceptable salt, hydrate, solvate, prodrug, stereoisomer, or tautomer thereof. In some embodiments, the disease or disorder associated with the modulation of TGR5 activity is selected from chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, anorexia nervosa, intestinal motility, bulimia nervosa and neurological disorders such as Alzheimer's disease, multiple sclerosis, schizophrenia and impaired cognition.

In another aspect, the present invention relates to a method of treating or preventing a disease or disorder associated with activation of TGR5. The method comprises administering to a patient in need of a treatment for diseases or disorders associated with activation of TGR5 an effective amount the compositions and compounds of Formula (I'), or a pharmaceutically acceptable salt, hydrate, solvate, prodrug, stereoisomer, or tautomer thereof. In some embodiments, the disease or disorder associated with the activation of TGR5 activity is selected from chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, intestinal motility, anorexia nervosa, bulimia nervosa and neurological disorders such as Alzheimer's disease, multiple sclerosis, schizophrenia and impaired cognition.

Another aspect of the invention relates to a method of treating or preventing chemotherapy-induced diarrhea in a patient in need thereof. The method comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof.

In another aspect, the present invention relates to a method of treating or preventing Type II diabetes mellitus. The method comprises administering to a patient in need of a treatment for Type II diabetes mellitus an effective amount of a compound of Formula (I'), or a pharmaceutically acceptable salt, hydrate, solvate, prodrug, stereoisomer, or tautomer thereof.

Another aspect of the invention relates to a method for treating or preventing hyperphosphatemia. The method comprises administering to a patient in need thereof an effective amount of a compound of Formula (I'), or a pharmaceutically acceptable salt, hydrate, solvate, prodrug, stereoisomer, or tautomer thereof. In one embodiment, the hyperphosphatemia is postprandial hyperphosphatemia.

In another aspect, the present invention relates to a method for treating or preventing a renal disease. The method comprises administering to a patient in need thereof an effective amount of a compound of Formula (I'), or a pharmaceutically acceptable salt, hydrate, solvate, prodrug, stereoisomer, or tautomer thereof. In one embodiment, the renal disease is chronic kidney disease (CKD) or end-stage renal disease (ESRD).

Another aspect of the invention relates to a method for reducing serum creatinine levels. The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for treating or preventing a proteinuria. The method comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof.

Another aspect of the invention relates to a method for delaying time to renal replacement therapy (RRT). The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for reducing FGF23 levels. The method comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof.

Another aspect of the invention relates to a method for reducing the hyperphosphatemic effect of active vitamin D. The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for attenuating hyperparathyroidism. The method comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof. In one embodiment, the hyperparathyroidism is secondary hyperparathyroidism.

Another aspect of the invention relates to a method for reducing serum parathyroid hormone (PTH). The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for improving endothelial dysfunction. The method comprises administering to a patient in need thereof an effective amount of a compound of Formula (I'), or a pharmaceutically acceptable salt, hydrate, solvate, prodrug, stereoisomer, or tautomer thereof. In one embodiment, the endothelial dysfunction is induced by postprandial serum phosphorus.

Another aspect of the invention relates to a method for reducing vascular calcification. The method comprises administering to a patient in need thereof an effective amount of a compound of Formula (I'), or a pharmaceutically acceptable salt, hydrate, solvate, prodrug, stereoisomer, or tautomer thereof. In one embodiment, the calcification is intima-localized vascular calcification.

In another aspect, the present invention relates to a method for reducing urinary phosphorous. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for normalizing serum phosphorus levels. The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for reducing phosphate burden in an elderly patient. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for decreasing dietary phosphate uptake. The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for reducing renal hypertrophy. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to a method for reducing heart hypertrophy.

The method comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to a method for treating and/or preventing a stomach and bowel-related disorder. The method comprises administering to a patient in need thereof an effective amount of a compound of Formula (I'), or a pharmaceutically acceptable salt, hydrate, solvate, prodrug, stereoisomer, or tautomer thereof. In one embodiment, the stomach and bowel-related disorder is ulcers, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemic sprue, enteritis, regional enteritis (Crohn's disease), ulcerative colitis, small intestine damage or short bowel syndrome. In another embodiment, the stomach and bowel-related disorder is radiation enteritis, infectious or post-infectious enteritis, bone marrow transplant induced enteritis, or small intestinal damage due to toxic, or other chemotherapeutic agents.

Another aspect of the invention relates to a method for treating and/or preventing a side effect of chemotherapy or radiation treatment. The method comprises administering to a patient in need thereof an effective amount of a compound of Formula (I'), or a pharmaceutically acceptable salt, hydrate, solvate, prodrug, stereoisomer, or tautomer thereof. In some embodiments, the side effect of chemotherapy is diarrhea, abdominal cramping, vomiting or structural and functional damage of the intestinal epithelium resulting from chemotherapy treatment. In one embodiment, the diarrhea is induced by an immune checkpoint inhibitor.

In another aspect, the present invention relates to the use of a compound of Formula (I'), or a pharmaceutically acceptable salt, hydrate, solvate, prodrug, stereoisomer, or tautomer thereof, in the treatment or prevention of a disease associated with activating TGR5. In some embodiments, the disease or disorder associated with the activation of TGR5 activity is selected from chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, intestinal motility, anorexia nervosa, bulimia nervosa and neurological disorders such as Alzheimer's disease, multiple sclerosis, schizophrenia and impaired cognition.

In some embodiments, the disease or disorder associated with the activation of TGR5 activity is selected from chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, anorexia nervosa, bulimia nervosa and neurological disorders such as Alzheimer's disease, multiple sclerosis, schizophrenia, impaired cognition, dismotility, Parkinson's gut (DIOS), Cystic Fibrosis gut, intestinal motility, and Gastroparesis.

In another embodiment, the disease or disorder associated with the activation of TGR5 activity is selected from intestinal motility, gastrointestinal motility disorder, irritable bowel syndrome, chronic constipation, chronic idiopathic constipation, chronic constipation occurring in cystic fibrosis, opioid-induced constipation, chronic intestinal pseudo-obstruction, colonic pseudo-obstruction, ulcerative colitis, inflammatory bowel disease, gastrointestinal tract disorder is associated with chronic kidney disease (stage 4 or 5), constipation induced by calcium supplement, constipation associated with the use of a therapeutic agent, constipation associated with a neuropathic disorder, post-surgical constipation (postoperative ileus), idiopathic constipation (functional constipation or slow transit constipation), constipation associated with neuropathic, metabolic or an endocrine disorder, constipation due the use of drugs selected from analgesics (e.g., opioids), antihypertensive, anticonvulsants, antidepressants, antispasmodics and antipsychotics, gastric ulcers, infectious diarrhea, leaky gut syndrome, cystic fibrosis gastrointestinal disease, microscopic colitis, necrotizing enterocolitis, atopy, food allergy, acute inflammation, chronic inflammation, obesity-induced metabolic diseases, kidney disease, chronic kidney disease, diabetic kidney disease, heart disease, heart failure, congestive heart failure, liver disease, cirrhosis, nonalcoholic steatohepatitis, nonalcoholic fatty liver disease, steatosis, primary sclerosing cholangitis, primary biliary cholangitis, portal hypertension, Type 1 diabetes, celiac disease, multiple sclerosis, ankylosing spondylitis, rheumatoid arthritis, lupus, alopecia areata, polymyalgia rheumatica, multiple sclerosis, fibromyalgia, chronic fatigue syndrome, Sjogren's syndrome, vitiligo, thyroiditis, vasculitis, Crohn's disease, ulcerative colitis, urticaria (hives), Raynaud's syndrome, schizophrenia, autism spectrum disorders, multiple sclerosis, hepatic encephalopathy, small intestitinal bacterial overgrowth, and chronic alcoholism.

Another aspect of the invention relates to a compound of Formula (I'), or a pharmaceutically acceptable salt, hydrate, solvate, prodrug, stereoisomer, or tautomer thereof, for use in the manufacture of a medicament for treating or preventing chemotherapy-induced diarrhea in a patient in need thereof. The compound is administered to a patient in need of a treatment for chemotherapy-induced diarrhea.

In another aspect, the present invention relates to the use of a compound of Formula (I'), or a pharmaceutically acceptable salt, hydrate, solvate, prodrug, stereoisomer, or tautomer thereof, in the treatment or prevention of Type II diabetes mellitus. The use comprises administering to a patient in need of a treatment for Type II diabetes mellitus an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, in the treatment or prevention of hyperphosphatemia. The use comprises administering to a patient in need thereof an effective amount of a compound of Formula (I'), or a pharmaceutically acceptable salt, hydrate, solvate, prodrug, stereoisomer, or tautomer thereof. In one embodiment, the hyperphosphatemia is postprandial hyperphosphatemia.

In another aspect, the present invention relates to the use of a compound of Formula (I'), or a pharmaceutically acceptable salt, hydrate, solvate, prodrug, stereoisomer, or tautomer thereof, in the treatment or prevention of a renal disease. The use comprises administering to a patient in need thereof an effective amount of a compound of Formula (I'), or a pharmaceutically acceptable salt, hydrate, solvate, prodrug, stereoisomer, or tautomer thereof.

In one embodiment, the renal disease is chronic kidney disease (CKD) or end-stage renal disease (ESRD).

Another aspect of the invention relates to the use of a compound of Formula (I'), or a pharmaceutically acceptable salt, hydrate, solvate, prodrug, stereoisomer, or tautomer thereof, in the reduction serum creatinine levels. The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the treatment or prevention of a proteinuria. The use comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, for delaying time to renal replacement therapy (RRT). The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the reduction of FGF23 levels. The use comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, in the reduction of the hyperphosphatemic effect of active vitamin D. The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the attenuation of hyperparathyroidism. The use comprises administering to a patient in need of a treatment for chemotherapy-induced diarrhea an effective amount of a compound of Formula (I'), or a pharmaceutically acceptable salt, hydrate, solvate, prodrug, stereoisomer, or tautomer thereof. In one embodiment, the hyperparathyroidism is secondary hyperparathyroidism.

Another aspect of the invention relates to the use of a compound of Formula (I'), or a pharmaceutically acceptable salt, hydrate, solvate, prodrug, stereoisomer, or tautomer thereof, in the reduction of serum parathyroid hormone (PTH). The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the improvement of endothelial dysfunction. The use comprises administering to a patient in need thereof an effective amount of a compound of Formula (I'), or a pharmaceutically acceptable salt, hydrate, solvate, prodrug, stereoisomer, or tautomer thereof. In one embodiment, the endothelial dysfunction is induced by postprandial serum phosphorus.

Another aspect of the invention relates to the use of a compound of Formula (I'), or a pharmaceutically acceptable salt, hydrate, solvate, prodrug, stereoisomer, or tautomer thereof, in the reduction of vascular calcification. The use comprises administering to a patient in need thereof an effective amount of a compound of Formula (I'), or a pharmaceutically acceptable salt, hydrate, solvate, prodrug, stereoisomer, or tautomer thereof. In one embodiment, the calcification is intima-localized vascular calcification.

In another aspect, the present invention relates to the use of a compound of Formula (I'), or a pharmaceutically acceptable salt, hydrate, solvate, prodrug, stereoisomer, or tautomer thereof, in the reduction of urinary phosphorous. The method comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, for normalizing serum phosphorus levels. The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the reduction of phosphate burden in an elderly patient. The use comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, for decreasing dietary phosphate uptake. The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the reduction of renal hypertrophy. The use comprises administering to a patient in need thereof an effective amount of a compound of Formula (I'), or a pharmaceutically acceptable salt, hydrate, solvate, prodrug, stereoisomer, or tautomer thereof.

Another aspect of the invention relates to the use of a compound of Formula (I'), or a pharmaceutically acceptable salt, hydrate, solvate, prodrug, stereoisomer, or tautomer thereof, in the reduction of heart hypertrophy. The use comprises administering to a patient in need thereof an effective amount of a compound of Formula (I'), or a pharmaceutically acceptable salt, hydrate, solvate, prodrug, stereoisomer, or tautomer thereof.

In another aspect, the present invention relates to the use of a compound of Formula (I'), or a pharmaceutically acceptable salt, hydrate, solvate, prodrug, stereoisomer, or tautomer thereof, in the treatment or prevention of a stomach and bowel-related disorder. The use comprises administering to a patient in need thereof an effective amount of a compound of Formula (I'), or a pharmaceutically acceptable salt, hydrate, solvate, prodrug, stereoisomer, or tautomer thereof. In one embodiment, the stomach and bowel-related disorder is ulcers, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemic sprue, enteritis, regional enteritis (Crohn's disease), ulcerative colitis, small intestine damage or short bowel syndrome. In another embodiment, the stomach and bowel-related disorder is radiation enteritis, infectious or post-infectious enteritis, bone marrow transplant induced enteritis, or small intestinal damage due to toxic, or other chemotherapeutic agents.

Another aspect of the invention relates to the use of a compound of Formula (I'), or a pharmaceutically acceptable salt, hydrate, solvate, prodrug, stereoisomer, or tautomer thereof, in the treatment or prevention of a side effect of chemotherapy or radiation treatment. The use comprises administering to a patient in need thereof an effective amount of a compound of Formula (I'), or a pharmaceutically acceptable salt, hydrate, solvate, prodrug, stereoisomer, or tautomer thereof. In some embodiments, the side effect of chemotherapy is diarrhea, abdominal cramping, vomiting or structural and functional damage of the intestinal epithelium resulting from chemotherapy treatment. In one embodiment, the diarrhea is induced by an immune checkpoint inhibitor.

Another aspect of the invention relates to a compound of Formula (I'), or a pharmaceutically acceptable salt, hydrate, solvate, prodrug, stereoisomer, or tautomer thereof, for use in the manufacture of a medicament for treating or preventing hyperphosphatemia. The compound of Formula (I'), or a pharmaceutically acceptable salt, hydrate, solvate, prodrug, stereoisomer, or tautomer thereof is administered in an effective amount to a patient in need thereof. In one embodiment, the hyperphosphatemia is postprandial hyperphosphatemia.

In another aspect, the present invention relates to a compound of Formula (I'), or a pharmaceutically acceptable salt, hydrate, solvate, prodrug, stereoisomer, or tautomer thereof, for use in the manufacture of a medicament for treating or preventing a renal disease. The compound of Formula (I'), or a pharmaceutically acceptable salt, hydrate, solvate, prodrug, stereoisomer, or tautomer thereof is administered in an effective amount to a patient in need thereof. In one embodiment, the renal disease is chronic kidney disease (CKD) or end-stage renal disease (ESRD).

Another aspect of the invention relates to a compound of Formula (I'), or a pharmaceutically acceptable salt, hydrate, solvate, prodrug, stereoisomer, or tautomer thereof, for use in the manufacture of a medicament for reducing serum creatinine levels. The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for treating or preventing a proteinuria. The compound of Formula (I'), or a pharmaceutically acceptable salt, hydrate, solvate, prodrug, stereoisomer, or tautomer thereof is administered in an effective amount to a patient in need of a treatment for chemotherapy-induced diarrhea.

Another aspect of the invention relates to a compound of Formula (I'), or a pharmaceutically acceptable salt, hydrate, solvate, prodrug, stereoisomer, or tautomer thereof, for use in the manufacture of a medicament for delaying time to renal replacement therapy (RRT). The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for reducing FGF23 levels. The compound of Formula (I'), or a pharmaceutically acceptable salt, hydrate, solvate, prodrug, stereoisomer, or tautomer thereof is administered in an effective amount to a patient in need thereof.

Another aspect of the invention relates to a compound of Formula (I'), or a pharmaceutically acceptable salt, hydrate, solvate, prodrug, stereoisomer, or tautomer thereof, for use in the manufacture of a medicament for reducing the hyperphosphatemic effect of active vitamin D. The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for attenuating hyperparathyroidism. The compound of Formula (I'), or a pharmaceutically acceptable salt, hydrate, solvate, prodrug, stereoisomer, or tautomer thereof is administered in an effective amount to a patient in need of a treatment for chemotherapy-induced diarrhea. In one embodiment, the hyperparathyroidism is secondary hyperparathyroidism.

Another aspect of the invention relates to a compound of Formula (I'), or a pharmaceutically acceptable salt, hydrate, solvate, prodrug, stereoisomer, or tautomer thereof, for use in the manufacture of a medicament for reducing serum parathyroid hormone (PTH). The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for improving endothelial dysfunction. The compound of Formula (I'), or a pharmaceutically acceptable salt, hydrate, solvate, prodrug, stereoisomer, or tautomer thereof is administered in an effective amount to a patient in need thereof. In one embodiment, the endothelial dysfunction is induced by postprandial serum phosphorus.

Another aspect of the invention relates to a compound of Formula (I'), or a pharmaceutically acceptable salt, hydrate, solvate, prodrug, stereoisomer, or tautomer thereof, for use in the manufacture of a medicament for reducing vascular calcification. The compound of Formula (I'), or a pharmaceutically acceptable salt, hydrate, solvate, prodrug, stereoisomer, or tautomer thereof is administered in an effective amount to a patient in need thereof. In one embodiment, the calcification is intima-localized vascular calcification.

In another aspect, the present invention relates to a compound of Formula (I'), or a pharmaceutically acceptable salt, hydrate, solvate, prodrug, stereoisomer, or tautomer thereof, for use in the manufacture of a medicament for reducing urinary phosphorous. The compound of Formula (I'), or a pharmaceutically acceptable salt, hydrate, solvate, prodrug, stereoisomer, or tautomer thereof is administered in an effective amount to a patient in need thereof.

Another aspect of the invention relates to a compound of Formula (I'), or a pharmaceutically acceptable salt, hydrate, solvate, prodrug, stereoisomer, or tautomer thereof, for use in the manufacture of a medicament for normalizing serum phosphorus levels. The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for reducing phosphate burden in an elderly patient. The compound of Formula (I'), or a pharmaceutically acceptable salt, hydrate, solvate, prodrug, stereoisomer, or tautomer thereof is administered in an effective amount to a patient in need thereof.

Another aspect of the invention relates to a compound of Formula (I'), or a pharmaceutically acceptable salt, hydrate, solvate, prodrug, stereoisomer, or tautomer thereof, for use in the manufacture of a medicament for decreasing dietary phosphate uptake. The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for reducing renal hypertrophy. The compound of Formula (I'), or a pharmaceutically acceptable salt, hydrate, solvate, prodrug, stereoisomer, or tautomer thereof is administered in an effective amount to a patient in need thereof.

Another aspect of the invention relates to a compound of Formula (I'), or a pharmaceutically acceptable salt, hydrate, solvate, prodrug, stereoisomer, or tautomer thereof, for use in the manufacture of a medicament for reducing heart hypertrophy. The compound of Formula (I'), or a pharmaceutically acceptable salt, hydrate, solvate, prodrug, stereoisomer, or tautomer thereof is administered in an effective amount to a patient in need thereof.

In another aspect, the present invention relates to a compound of Formula (I'), or a pharmaceutically acceptable salt, hydrate, solvate, prodrug, stereoisomer, or tautomer thereof, for use in the manufacture of a medicament for treating and/or preventing a stomach and bowel-related disorder. The compound of Formula (I'), or a pharmaceutically acceptable salt, hydrate, solvate, prodrug, stereoisomer, or tautomer thereof is administered in an effective amount to a patient in need thereof. In one embodiment, the stomach and bowel-related disorder is ulcers, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemic sprue, enteritis, regional enteritis (Crohn's disease), ulcerative colitis, small intestine damage or short bowel syndrome. In another embodiment, the stomach and bowel-related disorder is radiation enteritis, infectious or post-infectious enteritis, bone marrow transplant induced enteritis, or small intestinal damage due to toxic, or other chemotherapeutic agents.

Another aspect of the invention relates to a compound of Formula (I'), or a pharmaceutically acceptable salt, hydrate, solvate, prodrug, stereoisomer, or tautomer thereof, for use in the manufacture of a medicament for treating and/or preventing a side effect of chemotherapy or radiation treatment. The compound of Formula (I'), or a pharmaceutically acceptable salt, hydrate, solvate, prodrug, stereoisomer, or tautomer thereof is administered in an effective amount to a patient in need thereof. In some embodiments, the side effect of chemotherapy is diarrhea, abdominal cramping, vomiting or structural and functional damage of the intestinal epithelium resulting from chemotherapy treatment. In one embodiment, the diarrhea is induced by an immune checkpoint inhibitor.

Another aspect of the invention relates to a compound of Formula (I'), or a pharmaceutically acceptable salt, hydrate, solvate, prodrug, stereoisomer, or tautomer thereof, for use in the manufacture of a medicament for treating or preventing a disease associated with activating TGR5. In some embodiments, the disease or disorder associated with the activation of TGR5 activity is selected from chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, intestinal motility, anorexia nervosa, bulimia nervosa and neurological disorders such as Alzheimer's disease, multiple sclerosis, schizophrenia and impaired cognition.

Another aspect of the invention is directed to pharmaceutical compositions comprising a compound of Formula (I'), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, methods of treating a disease or disorder associated with modulation of TGR5 including, chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, anorexia nervosa, bulimia nervosa and neurological disorders such as Alzheimer's disease, multiple sclerosis, schizophrenia, intestinal motility, and impaired cognition comprise administering to a patient suffering from at least one of said diseases or disorder a compound of Formula (I'). In another embodiment, the disease or disorder associated with the modulation of TGR5 activity is intestinal motility.

One therapeutic use of the compounds or compositions of the present invention which activate TGR5 is to provide treatment to patients or subjects suffering from one or more diseases or disorders selected from, chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver, non-alcoholic fatty liver disease (NAFLD), liver fibrosis, non-alcoholic steatohepatitis (NASH), primary sclerosing cholangitis (PSC), liver cirrhosis, primary biliary cirrhosis (PBC), kidney fibrosis, anorexia nervosa, bulimia nervosa and neurological disorders such as Alzheimer's disease, multiple sclerosis, schizophrenia and impaired cognition.

The disclosed compounds of the invention can be administered in effective amounts to treat or prevent a disorder and/or prevent the development thereof in subjects.

Compounds of the invention can be administered in therapeutically effective amounts in a combinational therapy with one or more therapeutic agents (pharmaceutical combinations) or modalities, e.g., non-drug therapies. For example, synergistic effects can occur with other anti-diabetic, anti-diarrhea, anti-obesity, or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as an anti-diabetes agent (i.e., a DPP-IV inhibitor, insulin, etc.), an antidiarrheal agent, or an anti-obesity agent) and non-drug therapies (such as, but not limited to, surgery). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy or treatment modality. In general, a combination therapy envisions administration of two or more drugs during a single cycle or course of therapy.

In some embodiments, the disclosure provides a pharmaceutical composition comprising any of the foregoing compounds (i.e., a compound of Formula (I')), a pharmaceutically acceptable carrier or adjuvant, and at least one additional biologically active agent. In some embodiments, the pharmaceutical composition comprises one or more additional biologically active agents. In some embodiments, the at least one additional biologically active agent is selected from dipeptidyl peptidase 4 (DPP-4) inhibitors, biguanidines, sulfonylureas, α-glucosidates inhibitors, thiazolidinediones, incretin mimetics, CB 1 antagonists, VPAC2 agonists, glucokinase activators, glucagon receptor antagonists, PEPCK inhibitors, SGLT1 inhibitors, SGLT2 inhibitors, IL-1 receptor antagonists, SIRT1 activators, SPPARMs or 11βHSD1 inhibitors.

In other embodiments, the at least one additional biologically active agent prolongs the TGR5-mediated GLP-1 or GLP-2 signal. In other embodiments, the at least one additional biologically active agent is a DPP-4 inhibitor. In still other embodiments, the at least one additional biologically active agent is a DPP-4 inhibitor selected from sitagliptin, vildagliptin, saxagliptin, linagliptin, alogliptin, gemigliptin, omarigliptin or dutogliptin.

In other embodiments, the at least one additional biologically active agent is selected from metformin or other biguanidine, glyburide or other sulfonyl urea; acarbose or other α-glucosidase inhibitor; rosiglitazone or other thiazolidinedione and exenatide, liraglutide or other incretin mimetic; Mesalazine and its prodrugs Olsalazine, Sulfasalazine or Balsalazide; agents useful in the treatment of chemotherapy induced diarrhea including, but not limited to, Loperamide, tincture of opium, Lomotil, Octreotide, Elsiglutide, Teduglutide or other GLP-2 mimetics; corticosteroids including, but not limited to, Cortisone, Prednisone, Hydrocortisone, Methylprednisolone or Budesonide; immunosuppressants including, but not limited to, Mercaptopurine, Azathioprine, Methotrexate, Ciclosporin or Tacrolimus; JAK kinase inhibitors including, but not limited to, Tofacitinib or Filgotinib; biologic immunomodulators including, but not limited to, Infliximab, Adalimumab, Certolizumab or Natalizumab; FXR (Farnesoid X receptor) agonists including, but not limited to, obeticholic acid, INT-767, Px-104 or LJN-452; agents useful in the treatment of NASH (non-alcoholic steatohepatitis) including, but not limited to, Eicosapentaenoic acid ethyl ester, cenicriviroc mesylate, aramchol, emricasan or tipelukast; and agents used to treat hyperphosphatemia including, but not limited to, Sevelamer, Tenapanor, sucroferric oxyhydroxide, ferric citrate, Bixalomer, Lanthanum carbonate, Calcium acetate, Niacin, Fermagate or Colestilan.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, and PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I') and a pharmaceutically acceptable carrier. The pharmaceutical acceptable carrier may further include an excipient, diluent, or surfactant.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained with a Varian spectrometer at 400 MHz. Spectra are given in ppm (S) and coupling constants, J, are reported in Hertz. Tetramethylsilane (TMS) or the solvent peak was used as an internal standard. Purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

Abbreviations used in the following examples and elsewhere herein are:

AcOH acetic acid
Ac$_2$O acetic anhydride
aq. aqueous
[(A-taPhos)PdCl$_2$]$_2$ bis(di-tert-butyl(4-dimethylaminophenyl)phosphine) dichloropalladium(II)
BID twice a day
Boc$_2$O di-tert-butyl dicarbonate
CbzCl benzyl chloroformate
CDI 1,1'-carbonyldiimidazole
Cp$_2$ZrCl$_2$ bis(cyclopentadienyl)zirconium(IV)dichloride
Cs$_2$CO$_3$ Cesium carbonate
DCC N,N'-methanediylidenedicyclohexanamine
DCM dichloromethane
DEA diethanolamine Dess-Martin Periodinane 1,1,1-Tris(acetyloxy)-1,1-dihydro-1,2-benziodoxol-3-(1H)-one
DEAD diethyl azodicarboxylate
DIAD diisopropyl azodicarboxylate
DIBAL-H diisbutylaluminumhydride
DIEA N,N-diisopropylethylamine
DMA dimethylacetamide
DMAP 4-dimethylaminopyridine
DMF N,N-dimethylformamide
DMSO dimethylsulfoxide
dppf bis(diphenylphosphino)ferrocene
DSC bis(2,5-dioxopyrrolidin-1-yl) carbonate
EDC-HCl $N^1$-((ethylimino)methylene)-$N^2$,$N^2$-dimethylethane-1,2-diamine hydrochloride
equiv. equivalents
ESI electrospray ionization
EtI ethyliodide
Et$_2$O diethylether
EtOAc ethyl acetate
EtOH ethanol
h hours
HATU 1-[bis(dimethylamino)methylene]-1H-1,2,3-triazolo[4,5-b]pyridinium 3-oxid hexafluorophosphate
HCl hydrogen chloride
HOAt 3H-[1,2,3]triazolo[4,5-b]pyridin-3-ol
HPCD 2-hydroxypropyl-β-cyclodextrin
HPLC high performance liquid chromatography
IBCF Isobutyl chloroformate
i-PrOH isopropyl alcohol
i.p. intraperitoneal injection
KOAc potassium acetate
LCMS liquid chromatography-mass spectrometry
m-CPBA m-chloroperoxybenzoic acid
MeOH methanol
min minutes
MS mass spectrometry
MsCl methanesulfonyl chloride
NaBH(OAc)$_3$ sodium triacetoxyborohydride
NaCNBH$_3$ sodium cyanoborohydride
NaOMe sodium methoxide
NaOH sodium hydroxide
NBS N-bromosuccinimide
NCS N-chlorosuccinimide
Ni(dppp)Cl$_2$ [1,3-bis(diphenylphosphino)propane]dichloronickel(II)
NIS N-Iodosuccinimide
Pd(OAc)$_2$ palladium (II) acetate
Pd$_2$(dba)$_3$ tris(dibenzylideneacetone)dipalladium
Pd(dppf)Cl$_2$·CH$_2$Cl$_2$ [1,1'-bis(diphenylphosphino)ferrocene]dichloropalladium(II), complex with dichloromethane
Pd(PPh$_3$)$_4$ dichloropalladium bis(triphenylphosphine)
PPh$_3$ triphenylphosphine
QD once a day
R$_f$ retention factor
Sat. saturated
SQ subcutaneous
TBAF tetrabutylammonium fluoride
TBDPSCl tert-butylchlorodiphenylsilane
TEA triethylamine
TEMPO 2,2,6,6-tetramethylpiperidine N-oxide
THF tetrahydrofuran
TFA trifluoroacetic acid
Tf$_2$O triflic anhydride
TMSOTf trimethylsilyl trifluoromethanesulfonate
TLC thin layer chromatography
XPhos dicyclohexyl(2',4',6'-triisopropylbiphenyl-2-yl)phosphine
Xantphos 4,5-bis(diphenylphosphino)-9,9-dimethylxanthene Example 1: Intermediate A-1. 1-[4-(2-cyclopropoxyphenyl)pyridin-3-yl]cyclopropan-1-amine

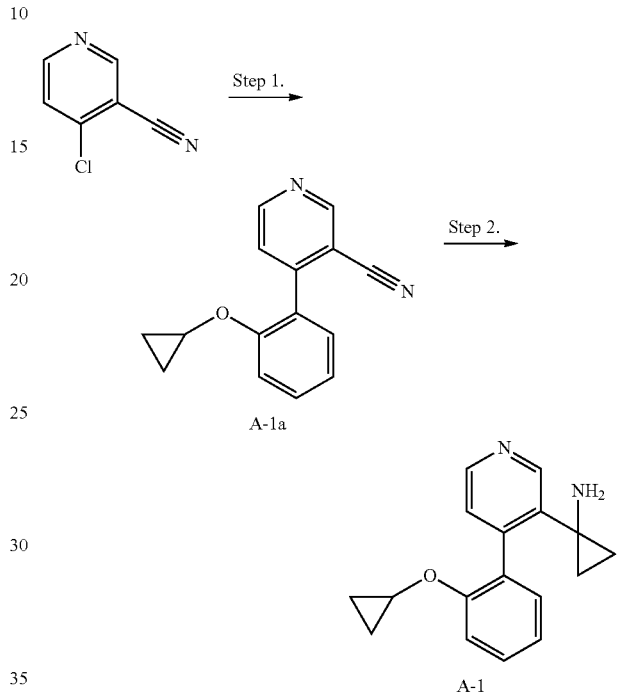

Step 1.
4-(2-cyclopropoxyphenyl)pyridine-3-carbonitrile (A-1a)

To a 100-mL round-bottom flask purged and maintained under an inert atmosphere of nitrogen, charged with 4-chloropyridine-3-carbonitrile (997.5 mg, 7.20 mmol, 1.00 equiv), toluene (50 mL), (2-cyclopropoxyphenyl)boronic acid (1.2 g, 6.74 mmol, 0.95 equiv), Pd(OAc)$_2$ (16.14 mg, 0.07 mmol, 0.01 equiv), K$_3$PO$_4$ (3.11 g, 14.65 mmol, 2.00 equiv) and butyldi-1-adamantylphosphine (358.5 mg, 0.144 mmol, 0.02 equiv). The resulting solution was stirred for 2 h at 100° C. in an oil bath. The resulting mixture was concentrated under vacuum. The residue was applied onto a silica gel column with ethyl acetate/petroleum ether (1:5). This resulted in 1.6 g (94%) of 4-(2-cyclopropoxyphenyl)pyridine-3-carbonitrile (A-1a) as light yellow oil.

Step 2. 1-[4-(2-cyclopropoxyphenyl)pyridin-3-yl]cyclopropan-1-amine (A-1)

To a 250-mL 3-necked round-bottom flask purged and maintained under an inert atmosphere of nitrogen, charged with 4-(2-cyclopropoxyphenyl)pyridine-3-carbonitrile (1.7 g, 7.20 mmol, 1.00 equiv) and ether (200 mL). This was followed by the addition of Ti(OiPr)$_4$ (3.4 mL, 1.66 equiv) at −78° C. To this was added 3M EtMgBr (7.86 mL, 3.32 equiv) at −78° C. To the mixture was added BF$_3$-Et$_2$O (3.4 mL, 3.03 equiv). The resulting solution was stirred for 5 min at −78° C. in a NZ/EtOH bath. The resulting solution was allowed to react, with stirring, for an additional 2 h at room temperature. The resulting solution was allowed to react, with stirring, for an additional 1 h at room temperature. The pH value of the solution was adjusted to 1-2 with 1M HCl. The resulting solution was extracted with 100 mL of ethyl acetate and the aqueous layers combined. Sodium hydroxide (1 mol/L) was employed to adjust the pH to 10. The resulting solution was extracted with 100 mL of ethyl acetate and the organic layers combined and concentrated under vacuum. The residue was applied onto a silica gel column with dichloromethane/methanol (10:1). This resulted in 580 mg (30%) of intermediate (A-1) as light yellow oil.

The general method above for the synthesis of Intermediate A1 in Example 1 can be used to prepare intermediates (Int.) A-2-A-18 in Table 1 below starting from 4-chloropyridine-3-carbonitrile and the appropriate boronate.

TABLE 1

| Int. No.: | Structure |
|---|---|
| A-1 | |
| A-2 | |
| A-3 | |
| A-4 | |
| A-5 | 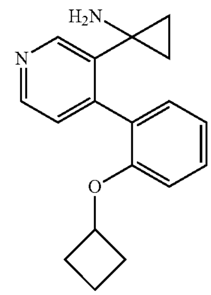 [SMILES: NC1(c2cnccc2-c2ccccc2OC2CCC2)CC1] |
| A-6 | 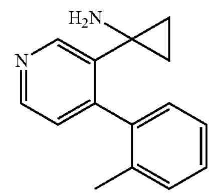 [SMILES: Cc1ccccc1-c1ccncc1C1(N)CC1] |
| A-7 | 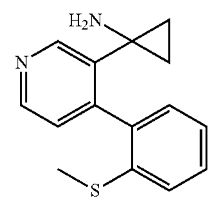 [SMILES: CSc1ccccc1-c1ccncc1C1(N)CC1] |
| A-8 | 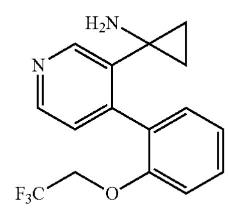 [SMILES: NC1(c2cnccc2-c2ccccc2OCC(F)(F)F)CC1] |
| A-9 | 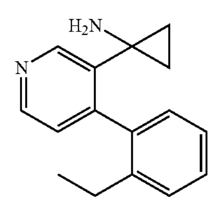 [SMILES: CCc1ccccc1-c1ccncc1C1(N)CC1] |
| A-10 | 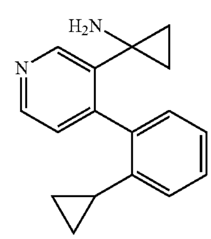 [SMILES: NC1(c2cnccc2-c2ccccc2C2CC2)CC1] |
| A-11 | 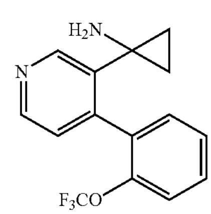 [SMILES: NC1(c2cnccc2-c2ccccc2OC(F)(F)F)CC1] |

TABLE 1-continued

| Int. No.: | Structure |
|---|---|
| A-12 | 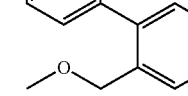 |
| A-13 | 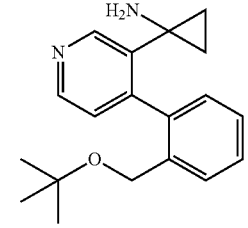 [SMILES: CC(C)(C)OCc1ccccc1-c1ccncc1C1(N)CC1] |
| A-14 | 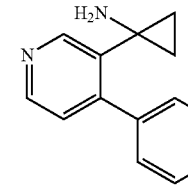 |
| A-15 | 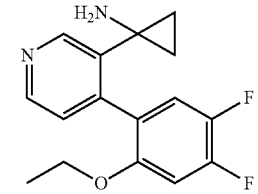 [SMILES: CCOc1cc(F)c(F)cc1-c1ccncc1C1(N)CC1] |
| A-16 | 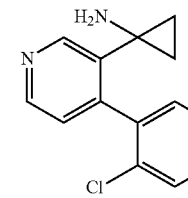 |
| A-17 | 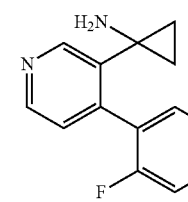 |
| A-18 | 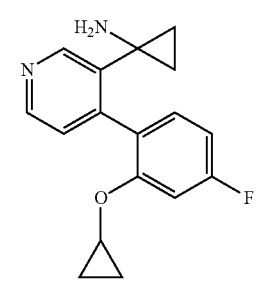 [SMILES: NC1(c2cnccc2-c2ccc(F)cc2OC2CC2)CC1] |

Example 2: Intermediate A-19 1-[4-[2-(oxetan-3-yloxy)phenyl]pyridin-3-yl]cyclopropan-1-amine

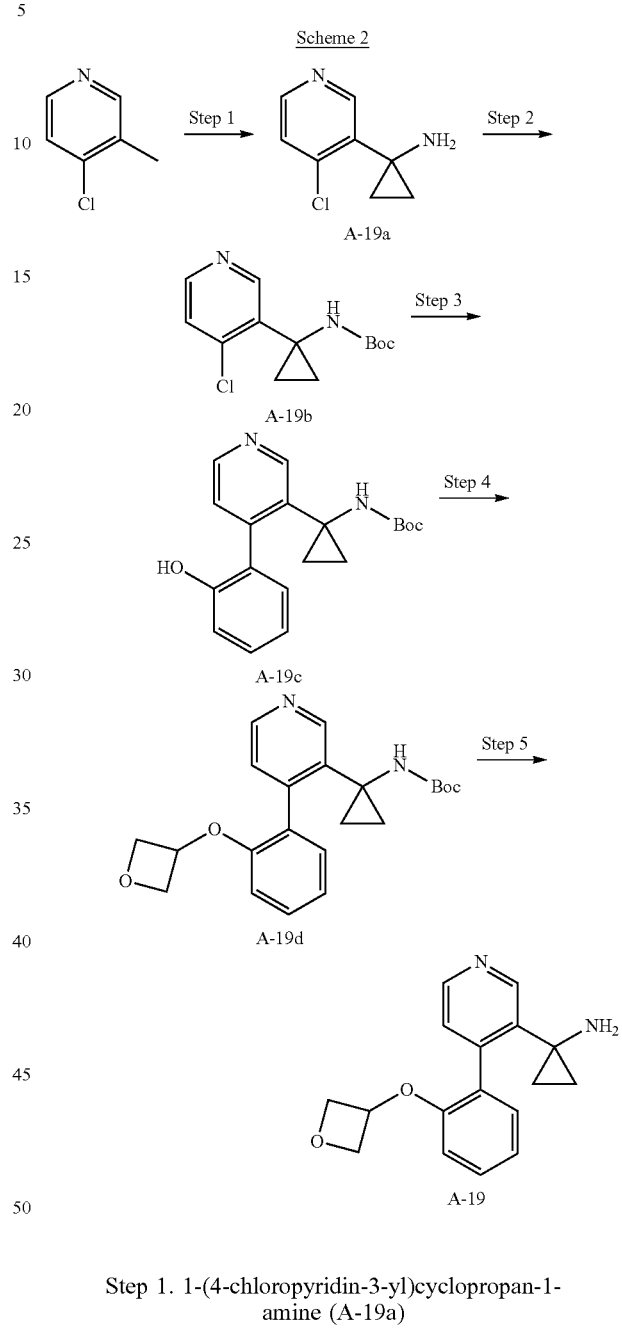

Step 1. 1-(4-chloropyridin-3-yl)cyclopropan-1-amine (A-19a)

To a 500-mL round-bottom flask purged and maintained under an inert atmosphere of nitrogen, charged with 4-chloropyridine-3-carbonitrile (5.75 g, 41.50 mmol, 1.00 equiv) and ether (150 mL). This was followed by the addition of Ti(OiPr)$_4$ (17.7 g, 1.50 equiv) dropwise with stirring at −78° C. in 30 min. To this was added EtMgBr (34.6 mL, 2.50 equiv, 3M in Et$_2$O) dropwise with stirring at −78° C. in 30 min and stirred for 2 h at room temperature. To the mixture was added BF$_3$·Et$_2$O (23.56 g, 4.00 equiv). The resulting solution was stirred for 2 h at room temperature. The reaction was then quenched by the addition of 1M hydrogen chloride. The pH value of the solution was adjusted to 10 with sodium hydroxide (4 mol/L). The resulting solution was extracted with 3×80 mL of ethyl acetate and the organic layers combined and dried over anhydrous sodium sulfate and concentrated under vacuum. The residue was applied onto a silica gel column with dichloromethane/methanol (0-10%). The collected fractions were combined and concentrated under vacuum. This resulted in 2 g (29%) of Intermediate A-19a as yellow oil.

Step 2. tert-butyl N-[1-(4-chloropyridin-3-yl)cyclopropyl]carbamate (A-19b)

To a 250-mL round-bottom flask, charged with 1-(4-chloropyridin-3-yl)cyclopropan-1-amine (1.9 g, 11.27 mmol, 1.00 equiv), tetrahydrofuran (30 mL), water (30 mL), sodium carbonate (4.78 g, 45.10 mmol, 4.00 equiv), Boc$_2$O (3.688 g, 16.90 mmol, 1.50 equiv). The resulting solution was stirred overnight at room temperature. The reaction was then quenched by the addition of 50 mL of water. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (0-30%). The collected fractions were combined and concentrated under vacuum. This resulted in 1.2 g (40%) of Intermediate A-19b as a light yellow solid.

Step 3. tert-butyl N-[1-[4-(2-hydroxyphenyl)pyridin-3-yl]cyclopropyl]carbamate (A-19c)

To a 8-mL round-bottom flask purged and maintained under an inert atmosphere of nitrogen, charged with tert-butyl N-[1-(4-chloropyridin-3-yl)cyclopropyl]carbamate (100 mg, 0.37 mmol, 1.00 equiv), (2-hydroxyphenyl)boronic acid (77 mg, 0.56 mmol, 1.50 equiv), K$_3$PO$_4$ (158 mg, 0.74 mmol, 2.00 equiv), Pd(OAc)$_2$ (4 mg, 0.02 mmol, 0.05 equiv), butyldi-1-adamantylphosphine (13 mg, 0.10 equiv) and toluene (1 mL). The resulting solution was stirred for 3 h at 100° C. The resulting mixture was concentrated under vacuum. The resulting solution was extracted with 3×30 mL of ethyl acetate and the organic layers combined and dried over anhydrous sodium sulfate and concentrated under vacuum. The residue was applied onto a silica gel column with dichloromethane/methanol (0-5%). The collected fractions were combined and concentrated under vacuum. This resulted in 30 mg (25%) of Intermediate A-19c as a light yellow solid.

Step 4. tert-butyl N-(1-[4-[2-(oxetan-3-yloxy)phenyl]pyridin-3-yl]cyclopropyl)carbamate (A-19d)

To a 25-mL round-bottom flask, charged with tert-butyl N-[1-[4-(2-hydroxyphenyl)pyridin-3-yl]cyclopropyl]carbamate (50 mg, 0.15 mmol, 1.00 equiv), 3-iodooxetane (34 mg, 0.18 mmol, 1.20 equiv), potassium carbonate (42 mg, 0.30 mmol, 2.00 equiv), N,N-dimethylformamide (10 mL). The resulting solution was stirred overnight at 90° C. in an oil bath. The reaction was then quenched by the addition of 10 mL of water. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (0-50%). The collected fractions were combined and concentrated under vacuum. This resulted in 50 mg (85%) of Intermediate A-19d as a light yellow oil.

Step 5. 1-[4-[2-(oxetan-3-yloxy)phenyl]pyridin-3-yl]cyclopropan-1-amine (A-19)

To a 25-mL round-bottom flask, charged with tert-butyl N-(1-[4-[2-(oxetan-3-yloxy)phenyl]pyridin-3-yl]cyclopropyl)carbamate (50 mg, 0.13 mmol, 1.00 equiv), dichloromethane (4 mL), trifluoroacetic acid (4 mL). The resulting solution was stirred for 1 h at room temperature. The resulting mixture was concentrated under vacuum. This resulted in 36 mg (crude) of Intermediate A-19 as a yellow oil.

The intermediates A-20, A-21, and A-22 shown in Table 2 below were prepared using the route shown above in Example 2 to make intermediate A-19. Alkylation of phenol intermediate A19c with the appropriate halide, epoxide or other electrophilic reagent and removal the Boc protecting group using the general synthetic method described herein above provides Intermediates A-20, A-21, and A-22. Substitution of the appropriate reagents and conditions in Step 4 of Example 2 is generally known to those skilled in the art.

TABLE 2

| Int. No.: | Structure |
|---|---|
| A-20 | [structure] |
| A-21 | [structure] |
| A-22 | [structure] |

Method A

Example 3: 1-[4-(2-cyclopropoxyphenyl)pyridin-3-yl]-N-[(2,5-dichlorophenyl)methyl]cyclopropan-1-amine (I-1)

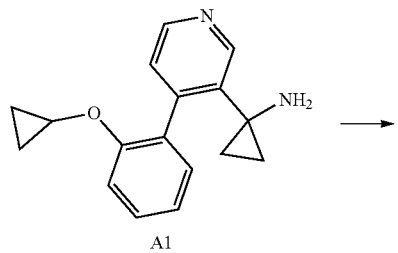

A1

→

I-1

To a 50-mL round-bottom flask purged and maintained under an inert atmosphere of nitrogen, charged with 1-[4-(2-cyclopropoxyphenyl)pyridin-3-yl]cyclopropan-1-amine (200 mg, 0.75 mmol, 1.00 equiv), dichloromethane (20 mL), 2,5-dichlorobenzaldehyde (183 mg, 1.05 mmol, 1.00 equiv) and NaBH(OAc)$_3$ (1.34 g, 6.32 mmol, 6.00 equiv). The resulting solution was stirred overnight at room temperature. The resulting mixture was concentrated under vacuum. The residue was applied onto a silica gel column with ethyl acetate/petroleum ether (1:5). This resulted in 100 mg (31%) of Compound I-1 as a light yellow solid. MS (ES, m/z): 425.05 [M+H]$^+$; $^1$H NMR (400 MHz, CDCl$_3$): δ ppm 8.63 (s, 1H), 8.54-8.52 (d, 1H), 7.43-7.34 (m, 2H), 7.26-7.20 (m, 2H), 7.14-7.03 (m, 4H), 3.67-3.59 (m, 3H), 2.12 (brs, 1H), 0.84 (s, 4H), 0.73-0.64 (m, 2H), 0.62-0.52 (m, 2H).

The compounds in Table 1, Compounds I-2 to I-40 and I-42 to I-44, were prepared using Method A described herein above in Example 1 and methods generally known to those skilled in the art from commercial or known starting materials and amine intermediates A2-A22 from charts 1 and 2 above.

TABLE 1

Compounds I-1 to I-40 and I-42 to I-44

| Cmpd No.: | Amine | Compound Structure | Obs Mass [M + H]$^+$ |
|---|---|---|---|
| I-1 | A-1 | 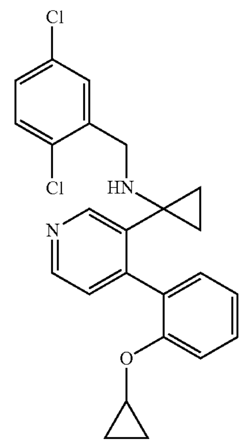 [SMILES: Clc1ccc(Cl)c(CNC2(c3cnccc3-c3ccccc3OC3CC3)CC2)c1] | 425 |
| I-2 | A-2 | 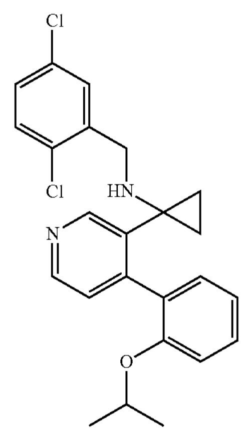 [SMILES: CC(C)Oc1ccccc1-c1ccncc1C1(NCc2cc(Cl)ccc2Cl)CC1] | 427 |
| I-3 | A-3 | 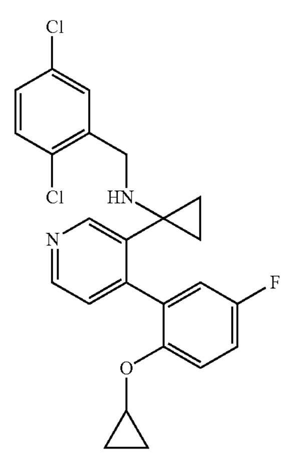 [SMILES: Fc1ccc(OC2CC2)c(-c2ccncc2C2(NCc3cc(Cl)ccc3Cl)CC2)c1] | 443 |

TABLE 1-continued
Compounds I-1 to I-40 and I-42 to I-44
| Cmpd No.: | Amine | Compound Structure | Obs Mass [M + H]+ |
|---|---|---|---|
| I-4 | A-4 | 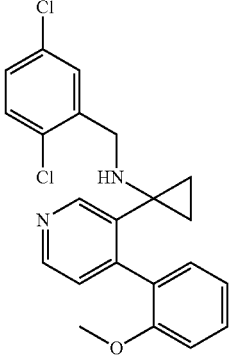 [SMILES: COc1ccccc1-c1ccncc1C1(NCc2cc(Cl)ccc2Cl)CC1] | 399 |
| I-5 | A-5 | 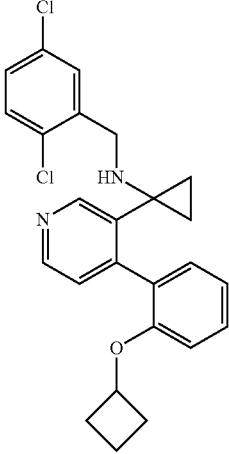 [SMILES: Clc1ccc(Cl)c(CNC2(c3cnccc3-c3ccccc3OC3CCC3)CC2)c1] | 339 |
| I-6 | A-6 | 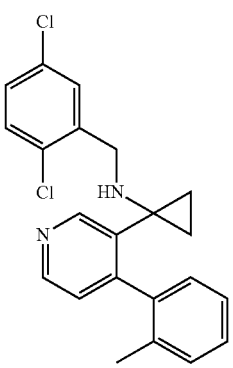 [SMILES: Cc1ccccc1-c1ccncc1C1(NCc2cc(Cl)ccc2Cl)CC1] | 383 |
| I-7 | A-7 | 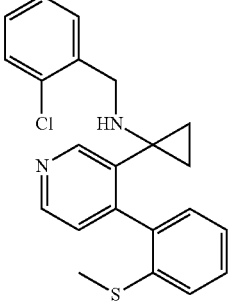 | 415 |
| I-8 | A-8 | 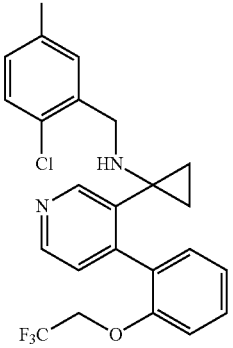 | 467 |
| I-9 | A-9 | 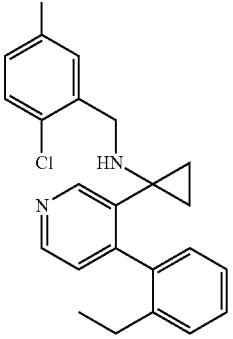 | 397 |
| I-10 | A-10 | 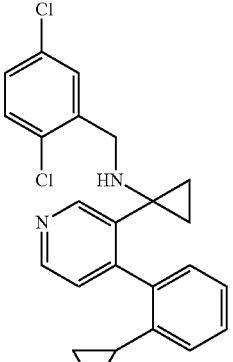 | 409 |

TABLE 1-continued
Compounds I-1 to I-40 and I-42 to I-44
| Cmpd No.: | Amine | Compound Structure | Obs Mass [M + H]+ |
|---|---|---|---|
| I-11 | A-11 | 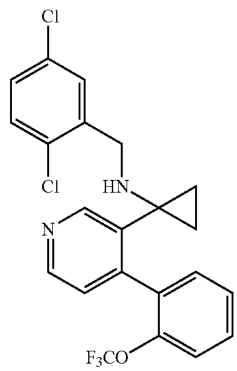 [SMILES: FC(F)(F)Oc1ccccc1-c1ccncc1C1(NCc2cc(Cl)ccc2Cl)CC1] | 453 |
| I-12 | A-12 | 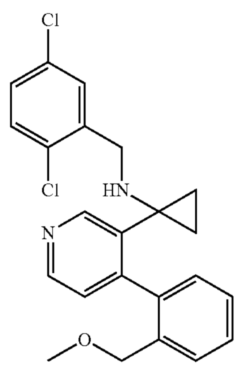 [SMILES: COCc1ccccc1-c1ccncc1C1(NCc2cc(Cl)ccc2Cl)CC1] | 412 |
| I-13 | A-13 | 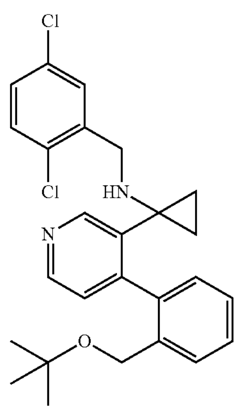 [SMILES: CC(C)(C)OCc1ccccc1-c1ccncc1C1(NCc2cc(Cl)ccc2Cl)CC1] | 455 |
| I-14 | A-14 | 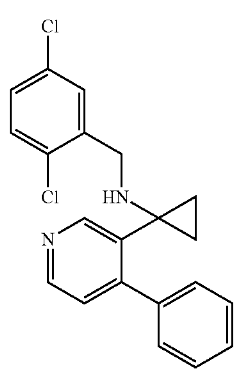 [SMILES: Clc1ccc(Cl)c(CNC2(c3cnccc3-c3ccccc3)CC2)c1] | 369 |
| I-15 | A-15 | | 449 |
| I-16 | A-16 | | 403 |
| I-17 | A-17 | | 387 |
| I-18 | A-18 | | 443 |
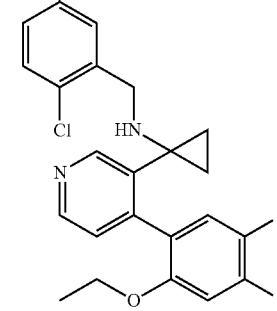
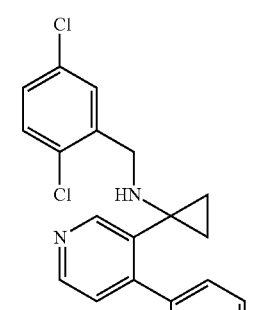
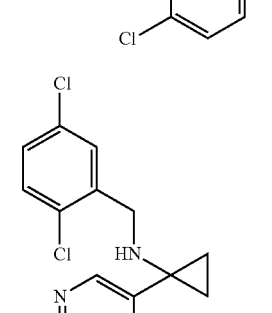
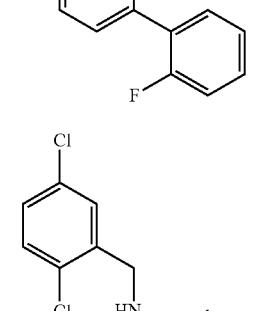

TABLE 1-continued

Compounds I-1 to I-40 and I-42 to I-44

| Cmpd No.: | Amine | Compound Structure | Obs Mass [M + H]+ |
|---|---|---|---|
| I-19 | A-19 | 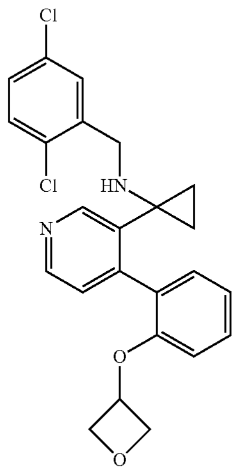 [SMILES: Clc1ccc(Cl)c(CNC2(c3cnccc3-c3ccccc3OC3COC3)CC2)c1] | 441 |
| I-20 | A-20 | 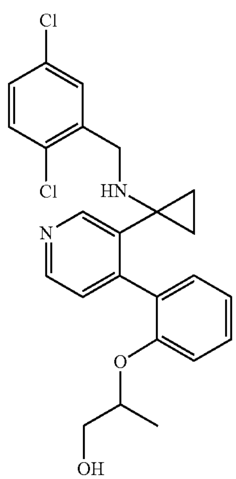 [SMILES: CC(CO)Oc1ccccc1-c1ccncc1C1(NCc2cc(Cl)ccc2Cl)CC1] | 443 |
| I-21 | A-21 | 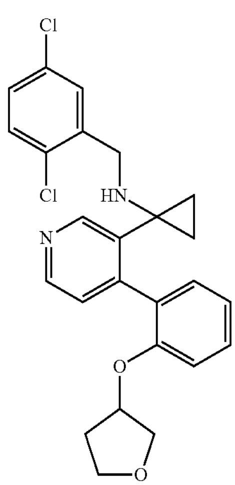 [SMILES: Clc1ccc(Cl)c(CNC2(c3cnccc3-c3ccccc3OC3CCOC3)CC2)c1] | 455 |
| I-22 | A-22 | | 471 |
| I-23 | A-1 | | 437 |
| I-24 | A-1 | | 385 |

TABLE 1-continued

Compounds I-1 to I-40 and I-42 to I-44

| Cmpd No.: | Amine | Compound Structure | Obs Mass [M + H]+ |
|---|---|---|---|
| I-25 | A-1 | 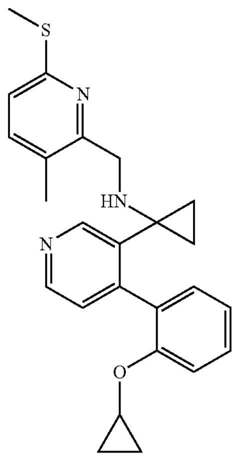 [SMILES: CSc1ccc(C)c(CNC2(c3cnccc3-c3ccccc3OC3CC3)CC2)n1] | 418 |
| I-26 | A-1 | 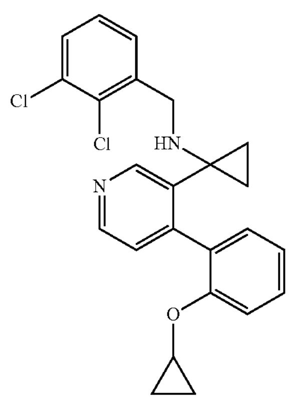 [SMILES: Clc1cccc(CNC2(c3cnccc3-c3ccccc3OC3CC3)CC2)c1Cl] | 425 |
| I-27 | A-1 | 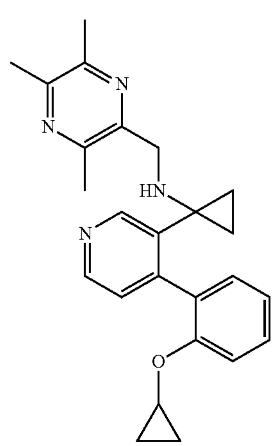 [SMILES: Cc1nc(C)c(CNC2(c3cnccc3-c3ccccc3OC3CC3)CC2)nc1C] | 401 |
| I-28 | A-1 | | 425 |
| I-29 | A-1 | | 415 |
| I-30 | A-1 | | 459 |

TABLE 1-continued

Compounds I-1 to I-40 and I-42 to I-44

| Cmpd No.: | Amine | Compound Structure | Obs Mass [M + H]+ |
|---|---|---|---|
| I-31 | A-1 | 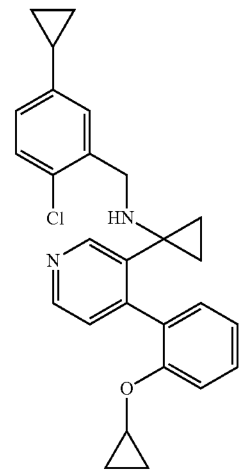 [SMILES: Clc1ccc(C2CC2)cc1CNC1(c2cnccc2-c2ccccc2OC2CC2)CC1] | 431 |
| I-32 | A-1 | 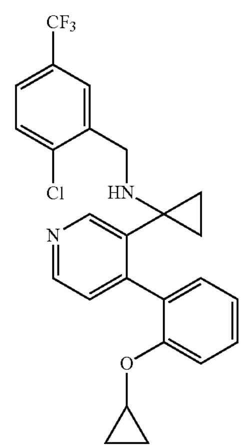 [SMILES: FC(F)(F)c1ccc(Cl)c(CNC2(c3cnccc3-c3ccccc3OC3CC3)CC2)c1] | 459 |
| I-33 | A-1 | 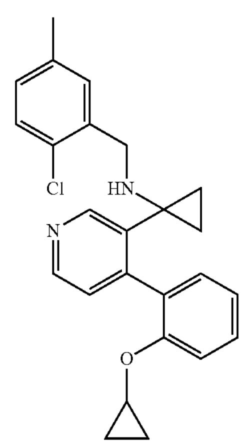 | 405 |
| I-34 | A-1 | 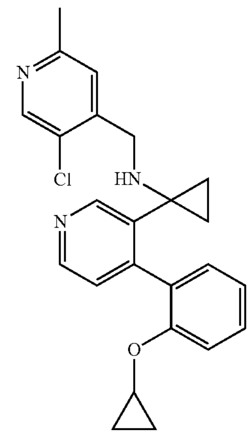 [SMILES: Cc1cc(CNC2(c3cnccc3-c3ccccc3OC3CC3)CC2)c(Cl)cn1] | 406 |
| I-35 | A-1 | 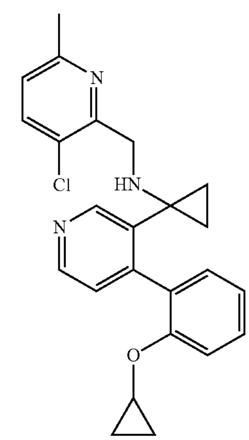 [SMILES: Cc1ccc(Cl)c(CNC2(c3cnccc3-c3ccccc3OC3CC3)CC2)n1] | 406 |
| I-36 | A-1 | 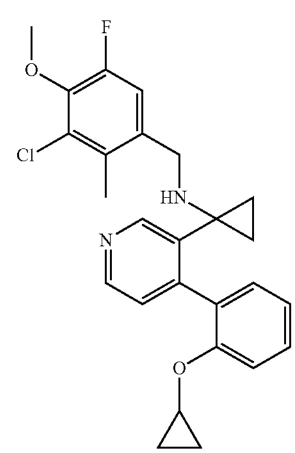 [SMILES: COc1c(F)cc(CNC2(c3cnccc3-c3ccccc3OC3CC3)CC2)c(C)c1Cl] | 453 |

TABLE 1-continued
Compounds I-1 to I-40 and I-42 to I-44
| Cmpd No.: | Amine | Compound Structure | Obs Mass [M + H]+ |
|---|---|---|---|
| I-37 | A-1 | 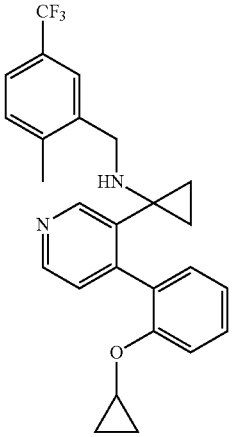 [SMILES: Cc1ccc(C(F)(F)F)cc1CNC1(c2cnccc2-c2ccccc2OC2CC2)CC1] | 439 |
| I-38 | A-1 | 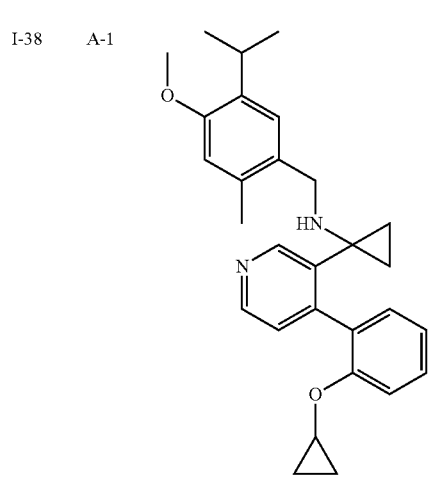 | 443 |
| I-39 | A-1 | 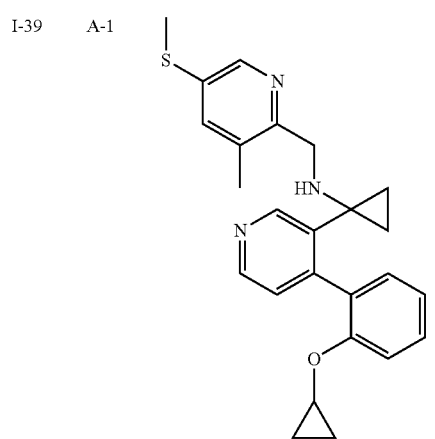 | 418 |
TABLE 1-continued
Compounds I-1 to I-40 and I-42 to I-44
| Cmpd No.: | Amine | Compound Structure | Obs Mass [M + H]+ |
|---|---|---|---|
| I-40 | A-1 | 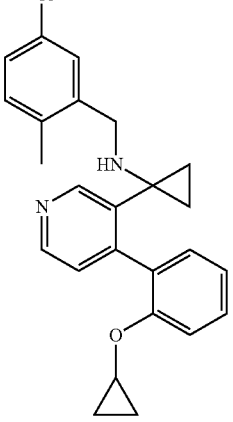 | 405 |
| I-42 | A-1 | 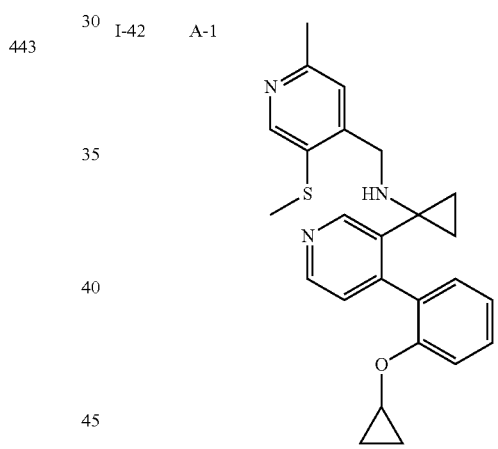 | 418 |
| I-43 | A-1 | 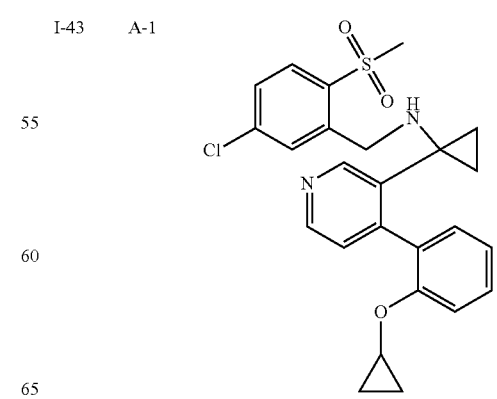 | 469 |

TABLE 1-continued

Compounds I-1 to I-40 and I-42 to I-44

| Cmpd No.: | Amine | Compound Structure | Obs Mass [M + H]+ |
|---|---|---|---|
| I-44 | A-1 | 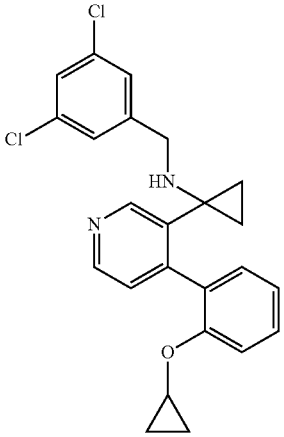 [SMILES: Clc1cc(Cl)cc(CNC2(c3cnccc3-c3ccccc3OC3CC3)CC2)c1] | 425 |

Example 4: 3-[1-[(2,5-dichlorophenyl)methoxy]cyclopropyl]-4-(2-methoxyphenyl)pyridine (I-45)

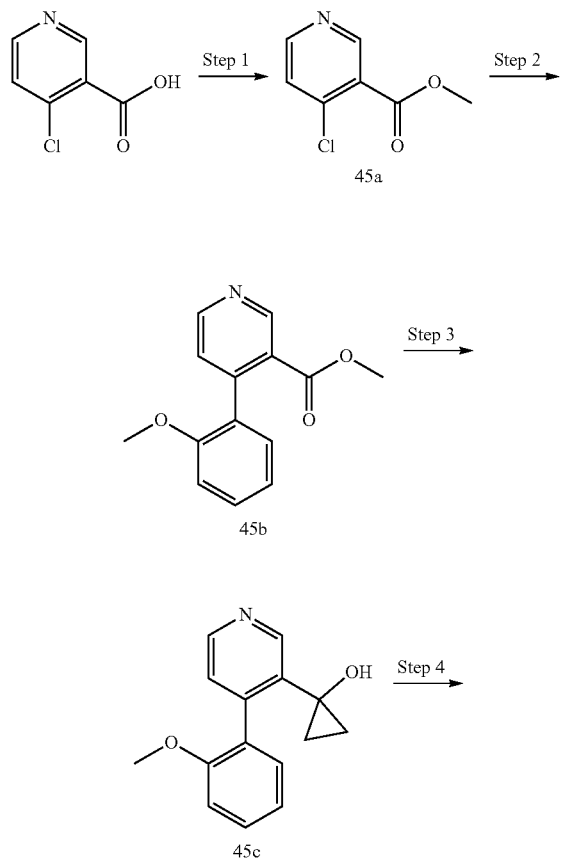

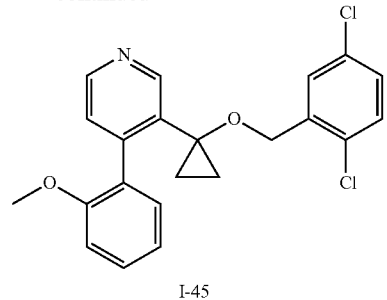

I-45

Step 1. Methyl 4-chloropyridine-3-carboxylate (Intermediate 45a)

A 100-mL 3-necked round-bottom flask was charged with 4-chloropyridine-3-carboxylic acid (1 g, 6.35 mmol, 1.00 equiv), dichloromethane (15 mL), methanol (6 mL). This was followed by the addition of 2.0 M TMS-diazomethane in Et$_2$O (4.76 mL, 1.50 equiv) dropwise with stirring at 0° C. The resulting solution was stirred for 1 h at 0° C. The resulting mixture was concentrated under vacuum. This resulted in 1.4 g of methyl 4-chloropyridine-3-carboxylate (Intermediate 45a) as white oil, which was used in the next experiment without further purification.

Step 2. Methyl 4-(2-methoxyphenyl)pyridine-3-carboxylate (Intermediate 45b)

A 100-mL round-bottom flask was charged with methyl 4-chloropyridine-3-carboxylate (900 mg, 5.25 mmol, 1.00 equiv), (2-methoxyphenyl)boronic acid (1.2 g, 7.90 mmol, 1.50 equiv), Pd(OAc)$_2$ (11.7 mg, 0.05 mmol, 0.01 equiv), K$_3$PO$_4$ (2.22 g, 10.46 mmol, 2.00 equiv), Butyl di-1-adamantylphosphine (37.5 mg, 0.02 equiv), toluene (50 mL). The resulting solution was stirred for 1.5 h at 100° C. The solids were filtered out. The resulting mixture was concentrated under vacuum. The residue was applied onto a silica gel column with ethyl acetate/petroleum ether (14.6:100). This resulted in 0.2 g (16%) of methyl 4-(2-methoxyphenyl)pyridine-3-carboxylate (Intermediate 45b) as a yellow oil.

Step 3. 1-[4-(2-methoxyphenyl)pyridin-3-yl]cyclopropan-1-ol (Intermediate 45c)

A 50-mL 3 neck round-bottom flask purged and maintained under an inert atmosphere of nitrogen was charged with a solution of Cp$_2$ZrCl$_2$ (1.20 g, 4.11 mmol, 2.00 equiv) in Toluene (10 mL). This was followed by the addition of bromo(ethyl)magnesium (2.74 mL, 4.00 equiv) dropwise with stirring at 0° C. The mixture was stirred for 1 h at 0 degree C. To this was added a solution of methyl 4-(2-methoxyphenyl)pyridine-3-carboxylate (500 mg, 2.06 mmol, 1.00 equiv) in Toluene (5 mL) dropwise with stirring at 0° C. The resulting solution was stirred for 3 h at 0° C. The reaction was then quenched by the addition of 10 mL of NH$_4$Cl (aq.). The resulting solution was extracted with 3×30 mL of dichloromethane and the organic layers combined and dried over sodium sulfate and concentrated under vacuum. The residue was applied onto a silica gel column with PE:EA (1:1). This resulted in 150 mg (30%) of 1-[4-(2-methoxyphenyl)pyridin-3-yl]cyclopropan-1-ol (Intermediate 45c) as light yellow oil.

Step 4.3-[1-[[(2,5-dichlorophenyl)methoxy]cyclopropyl]-4-(2-methoxyphenyl)pyridine (I-45)

A 50-mL round-bottom flask was charged with a solution of 1-[4-(2-methoxyphenyl)pyridin-3-yl]cyclopropan-1-ol (150 mg, 0.62 mmol, 1.00 equiv) in N,N-dimethylformamide (5 mL), 2-(bromomethyl)-1,4-dichlorobenzene (179 mg, 0.75 mmol, 1.20 equiv). This was followed by the addition of sodium hydride (37 mg, 1.54 mmol, 1.50 equiv) in several batches at 0° C. The resulting solution was stirred for 2 h at 0° C. The resulting solution was diluted with 10 mL of ethyl acetate. The reaction was then quenched by the addition of 10 mL of. The resulting solution was extracted with 3×30 mL of ethyl acetate and the organic layers combined and dried over anhydrous sodium sulfate and concentrated under vacuum. The residue was applied onto a silica gel column with ethyl acetate/petroleum ether (1:5). This resulted in 121.5 mg (49%) of I-45 as a light yellow solid. MS (ES, m/z): 400 [M+H]+; 1H-NMR (400 MHz, CD3OD) δ 8.63 (s, 1H), 8.49 (d, J=5.1 Hz, 1H), 7.38-7.44 (m, 1H), 7.19-7.30 (m, 4H), 6.97-7.02 (m, 3H), 4.35 (s, 2H), 3.51 (s, 3H), 1.03 (s, 4H).

Example 5: 1-Cyclopropoxy-2-iodobenzene
(Intermediate A-23)

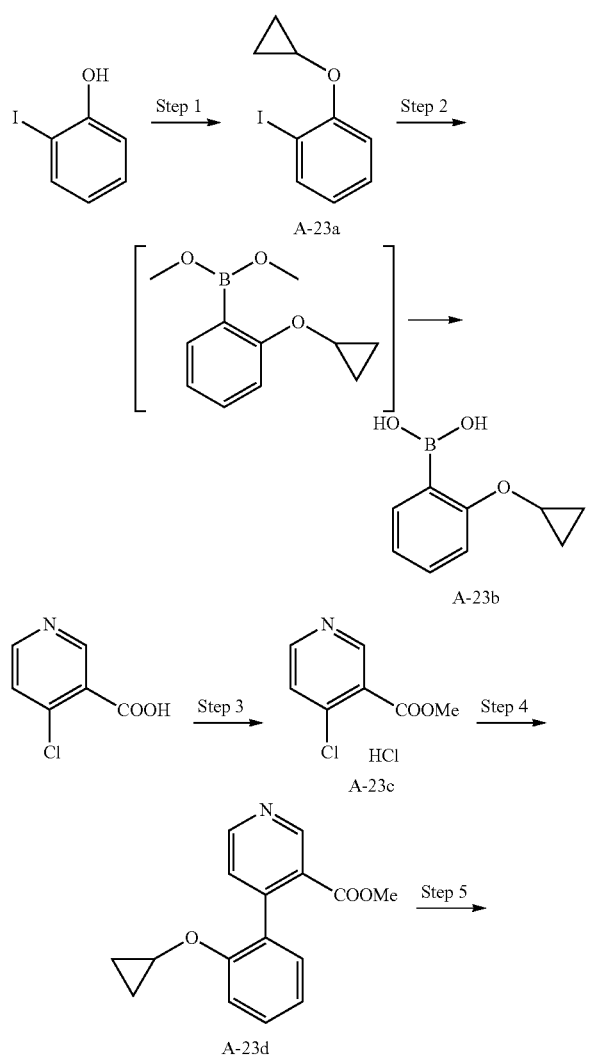

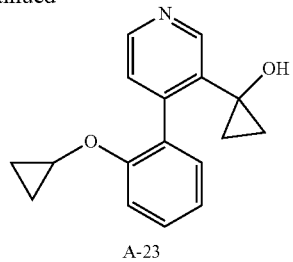

Step 1. 1-cyclopropoxy-2-iodobenzene
(Intermediate A-23a)

A 2000-mL round-bottom flask was charged with 2-iodophenol (50 g, 227.26 mmol, 1.00 equiv), DMA (750 mL), Cs2CO3 (185.1 g, 566.35 mmol, 2.49 equiv), bromocyclopropane (55 g, 454.64 mmol, 2.00 equiv). The resulting solution was stirred for 3 days at 120° C. The resulting solution was diluted with 2000 mL of H2O. The resulting solution was extracted with 3×500 mL of ethyl acetate and the organic layers combined and concentrated under vacuum. The residue was applied onto a silica gel column with ethyl acetate/petroleum ether. This resulted in 38 g (64%) of 1-cyclopropoxy-2-iodobenzene (A-23a) as off-white oil.

Step 2. (2-cyclopropoxyphenyl)boronic acid
(Intermediate A-23b)

A 1000-mL 3-necked round-bottom flask purged and maintained under an inert atmosphere of nitrogen was charged with 1-cyclopropoxy-2-iodobenzene (75 g, 288.38 mmol, 1.00 equiv), THF (600 mL). This was followed by the addition of butyllithium (138 mL) dropwise with stirring at −78° C. The above mixture was stirred for 1 h at −78° C. To this was added trimethyl borate (61.2 g, 588.95 mmol, 2.04 equiv) dropwise with stirring at −78° C. The above mixture was stirred for 1 h at −78° C. The resulting solution was stirred for 1 h at 15-25° C. The reaction was then quenched by the addition of 150 mL of MeOH. The resulting mixture was concentrated under vacuum. The crude product was washed with hexane. The solids were collected by filtration. This resulted in 55 g of dimethyl (2-cyclopropoxyphenyl) (A-23b) boronate as a white solid. A 1000-mL round-bottom flask was charged with dimethyl(2-cyclopropoxyphenyl) boronate (55 g, 266.9 mmol, 1.00 equiv), water (500 mL), Conc. HCl (30 mL). The resulting solution was stirred for 1 h at 15-25° C. The solids were collected by filtration and dried. This resulted in 41 g of (2-cyclopropoxyphenyl) boronic acid as a white solid. Then it was purified by recrystallization with hexane (150-200 ml) and resulted in 35 g (68%) product as a white solid.

Step 2. Methyl 4-chloronicotinate hydrochloride
(Intermediate A23c)

4-chloronicotinic acid (3.00 g, 19 mmol) was slurried in DCM (25 mL) and a solution of oxalyl chloride (4.1 mL, 6.1 g, 48 mmol) in DCM (25 mL) was added dropwise over 15 min. After the addition, DMF was added (7×100 μL aliquots over 1 hour). The slurry was stirred for 30 min after the last addition. The reaction mixture was cooled in ice and MeOH (15 mL) was added slowly. The resulting solution was stirred at 0° C. for 15 minutes and then at RT for an additional 30 minutes. Toluene (10 mL) was added and the solvents were removed at reduced pressure to give the crude product as a tan solid. The solid was triturated with 50% EtOAc/heptane (15 mL) and collected on a Buchner funnel. The solids were rinsed with 50% EtOAc/heptane (2×10 mL) and then dried under vacuum to give the HCl salt of the title compound (A-23c) as a tan powder (3.93 g, 99%).

Step 3. Methyl 4-(2-cyclopropoxyphenyl)pyridine-3-carboxylate (Intermediate A23d)

A 250-mL 3-necked round-bottom flask purged and maintained under an inert atmosphere of nitrogen was charged with (2-cyclopropoxyphenyl)boronic acid (940 mg, 5.28 mmol, 1.10 equiv), $K_3PO_4$ (4.08 g, 19.2 mmol, 4.00 equiv), methyl 4-chloropyridine-3-carboxylate hydrochloride (1.0 g, 4.81 mmol, 1.00 equiv), $Pd(OAc)_2$ (22 mg, 0.10 mmol, 0.02 equiv), XPhos (138 mg, 0.29 mmol, 0.06 equiv), tetrahydrofuran (14 mL), water (0.35 mL, 4.00 equiv). The resulting solution was stirred for 1 h at 75° C. in an oil bath. The reaction was monitored by LCMS. The resulting mixture was concentrated under vacuum. The resulting solution was diluted with 40 mL of sodium bicarbonate (sat.). The resulting solution was extracted with 3×50 mL of ethyl acetate and the organic layers combined. The resulting mixture was washed with 1×50 mL of brine. The mixture was dried over anhydrous sodium sulfate and concentrated under vacuum. The crude product (2.2 g) was purified by Flash-Preparative HPLC with the following conditions (CombiFlash-1): Column, silica gel; mobile phase, ethyl acetate/petroleum ether 0% increasing to 25.7% within 30 min; Detector, UV 254 nm. This resulted in 951 mg (73%) of methyl 4-(2-cyclopropoxyphenyl)pyridine-3-carboxylate (A-23d) as yellow oil.

Step 4. 1-[4-(2-cyclopropoxyphenyl)pyridin-3-yl]cyclopropan-1-ol (Intermediate A-23)

A 500-mL 3-necked round-bottom flask was charged with a solution of $Cp_2ZrCl_2$ (14.77 g, 50.64 mmol, 2.10 equiv) in freshly distilled toluene (400 mL). The flask was evacuated and flushed three times with $N_2$. This was followed by the addition of EtMgBr (3M in ether) (33.7 mL, 101.3 mmol, 4.2 equiv) dropwise with stirring at 0° C. in 20 min and stirred for 40 min. To this was added a solution of A-23d (6.5 g, 24.14 mmol, 1.00 equiv) in toluene (60 mL) dropwise with stirring at 0° C. in 20 min. The resulting solution was stirred overnight at room temperature. The reaction was then quenched by the addition of 50 mL of $NH_4Cl$ sat. The resulting mixture was concentrated under vacuum. The resulting solution was diluted with 300 mL of water. The resulting solution was extracted with 5×500 mL of ethyl acetate and the organic layers combined. The resulting mixture was washed with 2×500 mL of saturated brine. The mixture was dried over anhydrous sodium sulfate. The solids were filtered out. The resulting mixture was concentrated under vacuum. The residue was applied onto a silica gel column with ethyl acetate/petroleum ether (1:3 to 1:1). The crude product was re-crystallized from DCM/hexane in the ratio of 1:10. This resulted in 2.5 g (39%) of 1-[4-(2-cyclopropoxyphenyl)pyridin-3-yl]cyclopropan-1-ol (A-23) as a light yellow solid.

Example 6: 1-(4-(2-fluorophenyl)pyridin-3-yl)cyclopropan-1-ol (Intermediate A-24); 1-(4 (2-cyclobutoxyphenyl)pyridin-3-yl)cyclopropan-1-ol (Intermediate A-25); 1-(4-(2-(oxetan-3-yloxy)phenyl) pyridin-3-yl)cyclopropan-1-ol (Intermediate A-26)

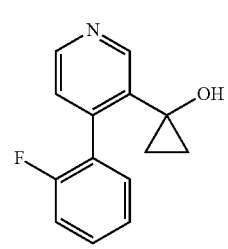

A-24

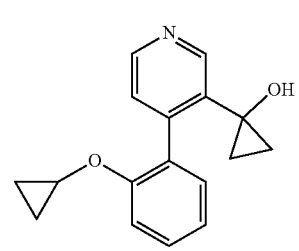

A-25

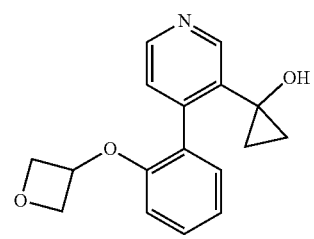

A-26

The intermediates A24-A26 were prepared from commercial or known starting materials according to the procedure used for the preparation of Intermediate 45c in Example 4.

The compounds in Table 2 below, Compounds I-46 to I-56, were prepared from commercial or known starting materials according to the procedure used for the preparation of Compound I-45 in Example 4 and methods generally known to those skilled in the art.

TABLE 2
Compounds 1-46 to 1-56
| Cmpd No.: | Compound Structure | Obs. Mass [M + H]+ |
|---|---|---|
| 1-46 | 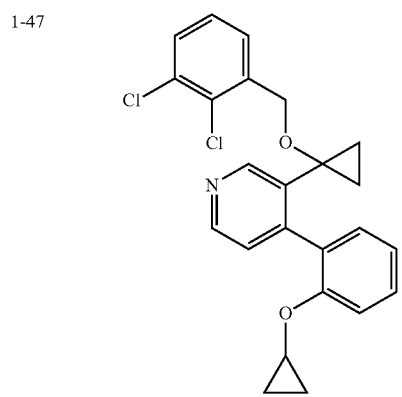 | 426 |
| 1-47 | 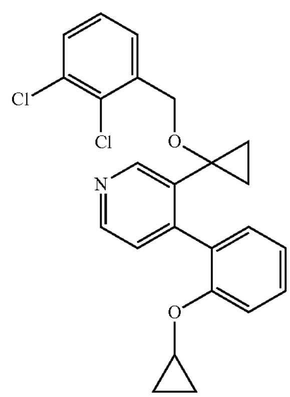 [SMILES: Clc1cccc(COC2(c3cnccc3-c3ccccc3OC3CC3)CC2)c1Cl] | 426 |
| 1-48 | 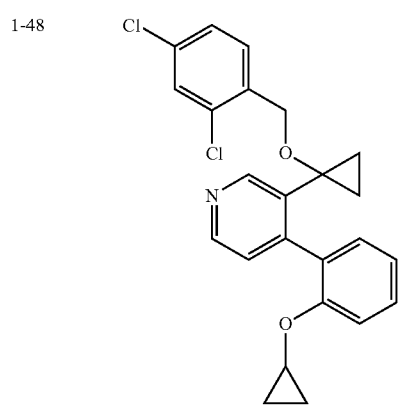 | 426 |
TABLE 2-continued
Compounds 1-46 to 1-56
| Cmpd No.: | Compound Structure | Obs. Mass [M + H]+ |
|---|---|---|
| 1-49 | 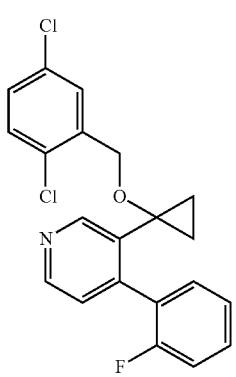 | 440 |
| 1-50 | 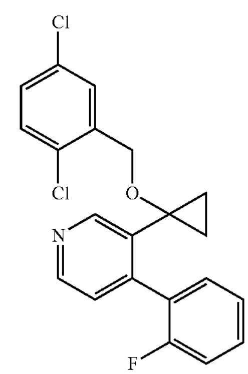 [SMILES: Fc1ccccc1-c1ccncc1C1(OCc2cc(Cl)ccc2Cl)CC1] | 388 |
| 1-51 | 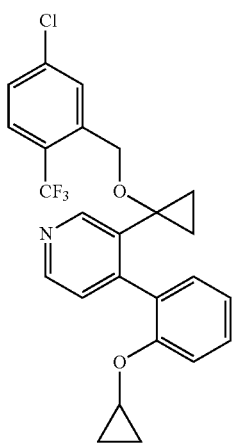 | 460 |

TABLE 2-continued

Compounds 1-46 to 1-56

| Cmpd No.: | Compound Structure | Obs. Mass [M + H]+ |
|---|---|---|
| 1-52 | 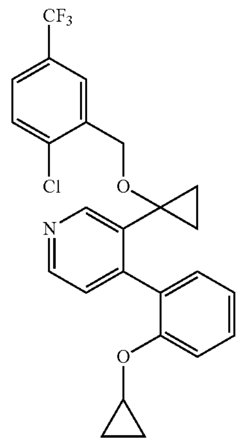 [SMILES: FC(F)(F)c1ccc(Cl)c(COC2(c3cnccc3-c3ccccc3OC3CC3)CC2)c1] | 460 |
| 1-53 | 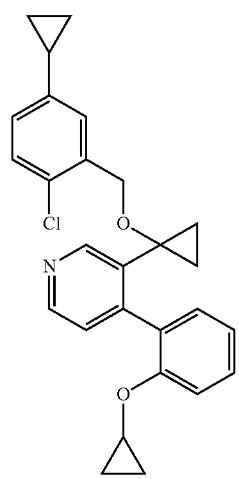 [SMILES: Clc1ccc(C2CC2)cc1COC1(c2cnccc2-c2ccccc2OC2CC2)CC1] | 432 |
| 1-54 | 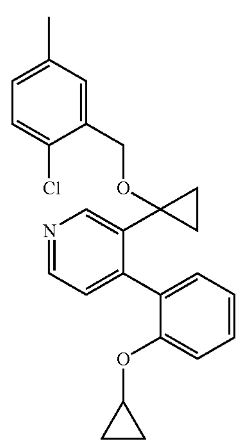 [SMILES: Cc1ccc(Cl)c(COC2(c3cnccc3-c3ccccc3OC3CC3)CC2)c1] | 406 |
| 1-55 | 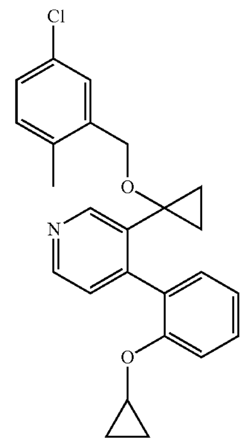 [SMILES: Cc1ccc(Cl)cc1COC1(c2cnccc2-c2ccccc2OC2CC2)CC1] | 406 |
| 1-56 | 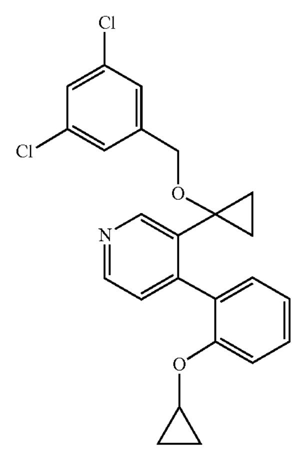 [SMILES: Clc1cc(Cl)cc(COC2(c3cnccc3-c3ccccc3OC3CC3)CC2)c1] | 426 |

Example 7: 1-[1-[4-(2-cyclopropoxyphenyl)pyridin-3-yl]cyclopropyl]-1-[(2,5-dichloro-phenyl)methyl] urea (I-57)

I-1

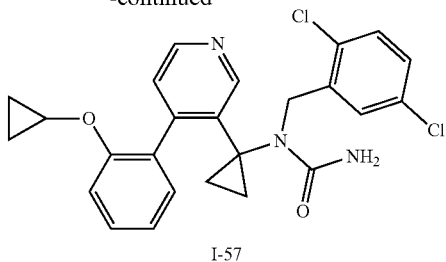

I-57

A 50-mL round-bottom flask charged with 1-[4-(2-cyclopropoxyphenyl) pyridin-3-yl]-N-[(2,5-dichlorophenyl)methyl]cyclopropan-1-amine (I-1, 50 mg, 0.12 mmol, 1.00 equiv), DCM (10 mL) and chlorosulfonyl isocyanate (50 mg, 0.35 mmol, 3.00 equiv). This was followed by the addition of water (10 mL) after 2 hr. The resulting solution was stirred for 3 h at room temperature. The resulting solution was extracted with 3×25 mL of dichloromethane and the organic layers combined and dried over anhydrous sodium sulfate and concentrated under vacuum. The crude product was purified by Preparative HPLC with the following conditions: Column, Atlantis Prep T3 OBD Column, 19×150 mm 5 μm 10 nm; mobile phase, water with 10 mmol $NH_4HCO_3$ and MeCN (20.0% MeCN up to 50.0% in 8 min); Detector, 254 nm. This resulted in 5.3 mg (10%) of I-57 as a white solid. MS (ES, m/z): 468 [M+H]$^+$; $^1$H-NMR (400 MHz, CD$_3$OD) δ 8.85 (s, 1H), 8.42 (d, J=4.9 Hz, 1H), 7.60-7.47 (m, 2H), 7.27 (d, J=8.5 Hz, 1H), 7.22-7.12 (m, 3H), 7.10 (d, J=5.0 Hz, 1H), 6.89 (d, J=2.4 Hz, 1H), 3.87-3.74 (m, 3H), 1.81-1.22 (m, 2H), 1.11 (s, 1H), 0.99 (s, 1H), 0.78-0.69 (m, 2H), 0.64 (s, 2H).

Example 8: 1-[4-(2-cyclopropoxyphenyl)pyridin-3-yl]-N-[(2,5-dichlorophenyl)methyl]-N-1-amine

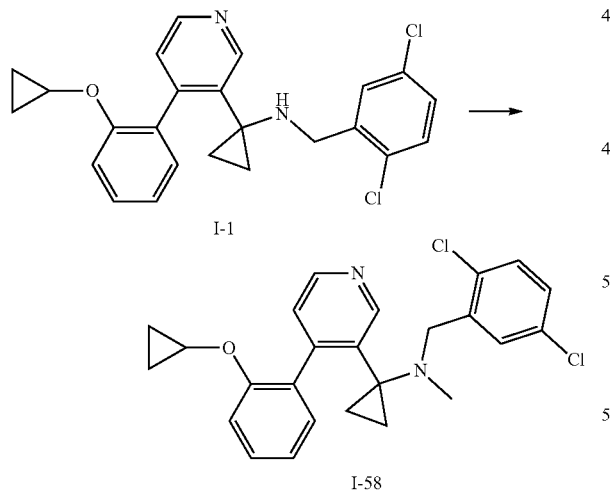

A 50-mL round-bottom flask was charged with 1-[4-(2-cyclopropoxyphenyl) pyridin-3-yl]-N-[(2,5-dichlorophenyl)methyl]cyclopropan-1-amine (100 mg, 0.24 mmol, 1.00 equiv), formalin (40%) (0.7 mL, 23.45 mmol, 10.00 equiv), methanol (20 mL) and AcOH (1 mg, 0.02 mmol, 0.10 equiv). This was followed by the addition of NaBH(OAc)$_3$ (300 mg, 1.42 mmol, 6.00 equiv), in portions at 0° C. The resulting solution was stirred for 3 h at room temperature. The reaction was then quenched by the addition of 5 mL of water. The resulting solution was extracted with 4×60 mL of ethyl acetate and the organic layers combined. The resulting mixture was washed with 3×30 mL of Brine. The mixture was dried over anhydrous sodium sulfate and concentrated under vacuum. The crude product was purified by Preparative HPLC with the following conditions: Column, Gemini-NX C18, 21.2×150 mm 5 μm; mobile phase, 10 mM aqueous $NH_4HCO_3$ and MeCN (40.0% MeCN up to 70.0% in 10 min); Detector, 254 nm. This resulted in 68.8 mg (67%) of Compound I-58 as a white solid. MS (ES, m/z): 439 [M+H]$^+$; $^1$H-NMR (400 MHz, CD$_3$OD) δ 8.66 (s, 1H), 8.42 (d, J=5.1 Hz, 1H), 7.48-7.38 (m, 2H), 7.36-7.25 (m, 2H), 7.26-7.17 (m, 2H), 7.13 (d, J=5.2 Hz, 1H), 7.07-7.03 (m, 1H), 3.77 (tt, J=6.0, 2.9 Hz, 1H), 3.51 (s, 2H), 1.98 (s, 3H), 1.04-0.94 (m, 4H), 0.81-0.71 (m, 2H), 0.55 (h, J=2.8 Hz, 2H).

Example 9: 4-(2-cyclopropoxyphenyl)-3-[3-[(2,5-dichlorophenyl)methoxy]oxetan-3-yl]pyridine (I-59)

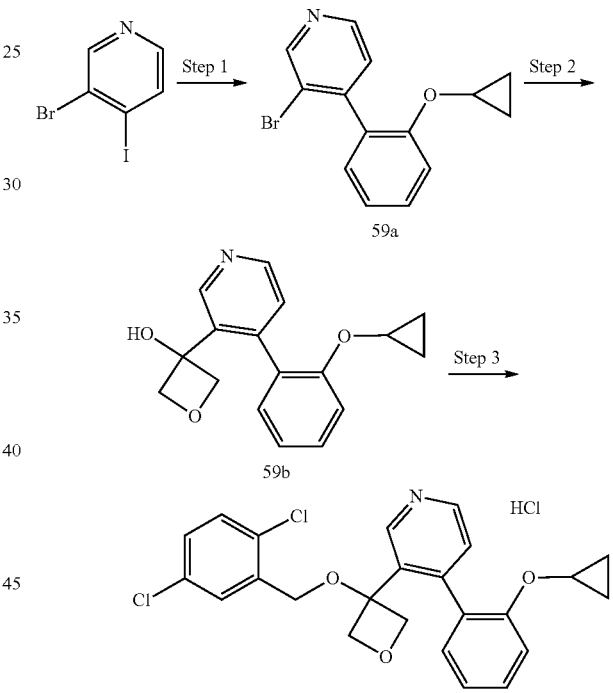

Step 1. 3-bromo-4-(2-cyclopropoxyphenyl)pyridine (Intermediate 59a)

A 100-mL round-bottom flask purged and maintained under an inert atmosphere of nitrogen, charged with 3-bromo-4-iodopyridine (568 mg, 2.00 mmol, 1.00 equiv), (2-cyclopropoxyphenyl)boronic acid (430 mg, 2.42 mmol, 2.00 equiv), sodium carbonate (640 mg, 6.04 mmol, 3.00 equiv), potassium hydroxide (112 mg, 2.00 mmol, 1.00 equiv). The above compounds were dissolved by tetrahydrofuran (40 mL), water (20 mL). This was followed by the addition of Pd(PPh$_3$)$_4$ (230 mg, 0.20 mmol, 0.10 equiv) in portions with stirring at room temperature. The resulting solution was heated to reflux for 20 hr. The resulting mixture was concentrated under vacuum. The resulting solution was extracted with 3×40 mL of ethyl acetate and the organic layers combined. The resulting mixture was washed with 2×100 mL of water and 1×100 mL of sodium chloride sat. The mixture was dried over anhydrous sodium sulfate. The residue was applied onto a silica gel column with ethyl acetate/petroleum ether (1:10). This resulted in 500 mg (86%) of 3-bromo-4-(2-cyclopropoxyphenyl)pyridine (59a) as a brown oil.

Step 2. 3-[4-(2-cyclopropoxyphenyl)pyridin-3-yl]oxetan-3-ol (Intermediate 59b)

A 50-mL round-bottom flask purged and maintained under an inert atmosphere of nitrogen, charged with 3-bromo-4-(2-cyclopropoxyphenyl)pyridine (59a, 290 mg, 1.00 mmol, 1.00 equiv), ether (30 mL). This was followed by the addition of n-BuLi (2.5 M in hexane) (0.8 mL, 2.00 equiv) dropwise with stirring at −78° C. The resulting solution was stirred for 15 min at −78° C. To this was added a solution of oxetan-3-one (144 mg, 2.00 mmol, 2.00 equiv) in tetrahydrofuran (1 mL) dropwise with stirring at −78° C. The resulting solution was allowed to react, with stirring, for an additional 1 h at −78° C. The resulting solution was allowed to react, with stirring, for an additional 14 h at room temperature. The reaction was then quenched by the addition of 20 mL of water. The resulting solution was extracted with 3×30 mL of ethyl acetate and the organic layers combined. The resulting mixture was washed with 1×50 mL of water and 1×50 mL of sodium chloride sat. The mixture was dried over anhydrous sodium sulfate. The residue was applied onto a silica gel column with ethyl acetate. This resulted in 160 mg (57%) of 3-[4-(2-cyclopropoxyphenyl)pyridin-3-yl]oxetan-3-ol (59b) as a colorless oil.

Step 3. 4-(2-cyclopropoxyphenyl)-3-[3-[(2,5-dichlorophenyl)methoxy]oxetan-3-yl]pyridine (I-59)

A 25-mL round-bottom flask was charged with 3-[4-(2-cyclopropoxyphenyl)pyridin-3-yl]oxetan-3-ol (100 mg, 0.35 mmol, 1.00 equiv), 2-(bromomethyl)-1,4-dichlorobenzene (169 mg, 0.70 mmol, 2.00 equiv), N,N-dimethylformamide (10 mL). Sodium hydride (60% in oil) (56 mg, 2.33 mmol, 4.00 equiv) was then added. The resulting solution was stirred for 1 h at room temperature. The reaction was then quenched by the addition of 15 mL of water. The resulting solution was extracted with 3×30 mL of ethyl acetate and the organic layers combined. The resulting mixture was washed with 1×50 mL of water and 1×50 mL of sodium chloride sat. The mixture was dried over anhydrous sodium sulfate. The residue was applied onto a silica gel column with ethyl acetate/hexane (1:1). The crude product was purified by Preparative HPLC with the following conditions: Column, Gemini-NX 5u C18 11 OA, AXIA Packed, 150×21.2 mm; mobile phase, water with 10 mmol NH₄HCO₃ and MeCN (66.0% MeCN up to 86.0% in 8 min); Detector, 254 nm. This resulted in 58 mg (37%) of 59 as a white solid. MS (ES, m/z): 442 [M+H]⁺; ¹H-NMR (400 MHz, DMSO-d₆) δ 0.30-0.55 (m, 2H), 0.60-0.80 (m, 2H), 3.68 (s, 1H), 4.15-4.50 (m, 3H), 4.60-4.80 (m, 2H), 5.00-5.20 (m, 1H), 7.93-7.00 (m, 1H), 7.10-7.21 (m, 1H), 7.35-7.70 (m, 6H), 8.70-8.90 (m, 1H), 8.93-9.12 (m, 1H).

Example 9: (1-(4-(3-aminopropyl)-2,5-dichlorobenzylamino)cyclopropyl)(4-cyclopropyl-3,4-dihydroquinoxalin-1(2H)-yl)methanone (Intermediate B1)

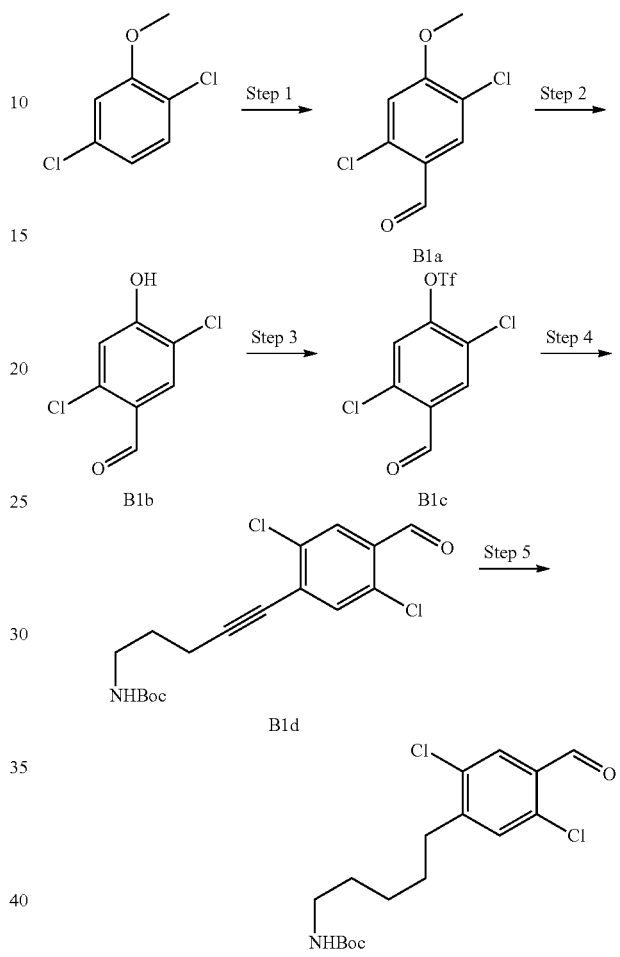

Step 1. 2,5-dichloro-4-methoxybenzaldehyde (Intermediate B1a)

A stirred 0° C. solution of 1,4-dichloro-2-methoxybenzene (25.0 g, 141.2 mmol, 1.00 equiv) and TiCl₄ (30.9 mL) in dichloromethane (300 mL) was added dichloro(methoxy)methane (16.2 g, 140.9 mmol, 1.00 equiv) dropwise. The resulting reaction mixture was stirred for 2 h at 60° C. then quenched by the addition of water/ice. The pH value of the solution was adjusted to 1.0 with concentrated HCl extracted with ethyl acetate (4×500 mL) and the combined organic layers washed with brine (2×500 mL), dried over anhydrous sodium sulfate and concentrated under reduced pressure to provide 31.0 g (crude) of B1a as a yellow solid.

Step 2. 2,5-dichloro-4-hydroxybenzaldehyde (Intermediate B1b)

A solution of 2,5-dichloro-4-methoxybenzaldehyde (14.0 g, 68.3 mmol, 1.00 equiv), LiCl (11.6 g, 274 mmol, 4.00 equiv) in DMF (150 mL) under an inert atmosphere of nitrogen was stirred overnight at 140° C. in an oil bath. The reaction mixture was then quenched by the addition of water/ice and the pH value of the solution was adjusted to 1-2 with concentrated HCl. The resulting solution was extracted with ethyl acetate (3×400 mL) and the combined organic layers were dried over anhydrous sodium sulfate and concentrated under reduced pressure. The resulting residue was purified using silica gel column chromatography with a ethyl acetate/petroleum ether (1:10-1:5) gradient to provide 10.0 g (77%) of B1b as a light yellow solid. (300 Hz, DMSO-$d_6$): δ 11.99 (s, 1H), 10.08 (s, 1H), 7.81 (s, 1H), 7.09 (s, 1H).

Step 3. 2,5-dichloro-4-formylphenyl trifluoromethanesulfonate (Intermediate B1c)

A stirred 0° C. solution of 2,5-dichloro-4-hydroxybenzaldehyde (3.0 g, 15.71 mmol, 1.00 equiv) and triethylamine (3.2 g, 31.62 mmol, 2.00 equiv) in dichloromethane (50 mL) was added a solution of trifluoromethanesulfonic anhydride (6.8 g, 24.10 mmol, 1.50 equiv) in dichloromethane (10 mL) dropwise. The resulting reaction mixture was stirred for 30 min at room temperature then washed with brine (2×30 mL). The organic layer was dried over anhydrous sodium sulfate and concentrated under reduced pressure. Purification by silica gel column chromatography with an eluent gradient of ethyl acetate/petroleum ether (1:50-1:10) provided 3.0 g (59%) of B1c as a white solid. $^1$H-NMR (300 Hz, DMSO-$d_6$): 10.22 (s, 1H), 8.14-8.15 (m, 2H).

Step 3. tert-butyl N-[5-(2,5-dichloro-4-formylphenyl)pent-4-yn-1-yl]carbamate (Intermediate B1d)

A 250-mL round-bottom flask purged and maintained under an inert atmosphere of nitrogen was charged with 2,5-dichloro-4-formylphenyl trifluoromethanesulfonate (1 g, 3.10 mmol, 1.00 equiv), tert-butyl N-(pent-4-yn-1-yl) carbamate (567 mg, 3.09 mmol, 1.00 equiv), N,N-dimethylformamide (80 mL), DIEA (1.2 g, 9.29 mmol, 3.00 equiv), CuI (88 mg, 0.46 mmol, 0.15 equiv), Pd(PPh$_3$)$_2$Cl$_2$ (326 mg, 0.46 mmol, 0.15 equiv). The resulting solution was stirred for 3 h at room temperature. The resulting mixture was washed with 3×80 mL of brine. The mixture was dried over anhydrous sodium sulfate and concentrated under vacuum. The residue was applied onto a silica gel column with ethyl acetate/petroleum ether (0-20%). The collected fractions were combined and concentrated under vacuum. This resulted in 800 mg (73%) of tert-butyl N-[5-(2,5-dichloro-4-formylphenyl)pent-4-yn-1-yl]carbamate (B1d) as a light yellow oil.

Step 4. tert-butyl N-[5-(2,5-dichloro-4-formylphenyl)pentyl]carbamate (Intermediate B1)

A 100-mL round-bottom flask purged and maintained with one atmosphere of H$_2$ was charged with tert-butyl N-[5-(2,5-dichloro-4-formylphenyl)pent-4-yn-1-yl]carbamate (800 mg, 2.25 mmol, 1.00 equiv), ethyl acetate (40 mL), Rh/C (1.2 g). The resulting solution was stirred overnight at room temperature. The solids were filtered out. The resulting mixture was concentrated under vacuum. The residue was applied onto a silica gel column with ethyl acetate/petroleum ether (0-20%). The collected fractions were combined and concentrated under vacuum. This resulted in 320 mg (40%) of tert-butyl N-[5-(2,5-dichloro-4-formylphenyl)pentyl]carbamate (B1) as a light yellow oil.

The intermediates B2 to B8 (Table 2a) were prepared from commercial or known starting materials according to the procedure used for the preparation of Intermediate B1 in Example 9 above.

TABLE 2a

Intermediates B2, B3, B4, B5, B5a, B6, B7 and B8

| Intermediate No | Compound Structure |
|---|---|
| B-2 | *structure: BocHN-(CH$_2$)$_4$-phenyl(2-Cl, 5-Cl)-CHO* |
| B-3 | *structure: BocHN-(CH$_2$)$_4$-phenyl(2-Me, 5-Me)-CHO* |
| B-4 | *structure: BocHN-(CH$_2$)$_4$-phenyl(2-Me, 5-Cl)-CHO* |
| B-5 | *structure: MeO-C(=O)-(CH$_2$)$_3$-phenyl(2-Cl, 5-Cl)-CHO* |
| B-5a | *structure: MeO-C(=O)-(CH$_2$)$_3$-phenyl(2-Me, 5-Me)-CHO* |
| B-6 | *structure: MeO-C(=O)-(CH$_2$)$_3$-phenyl(2-Me, 5-Cl)-CHO* |
| B-7 | *structure: TBS-O-(CH$_2$)$_4$-phenyl(2-Cl, 5-Cl)-CHO* |
| B-8 | *structure: TBDPS-O-(CH$_2$)$_4$-phenyl(2-Cl, 5-Cl)-CHO* |

Example 10: 5-(5-(tert-butyldiphenylsilyloxy)pentan-2-yl)-2-chlorobenzaldehyde (Intermediate B9)

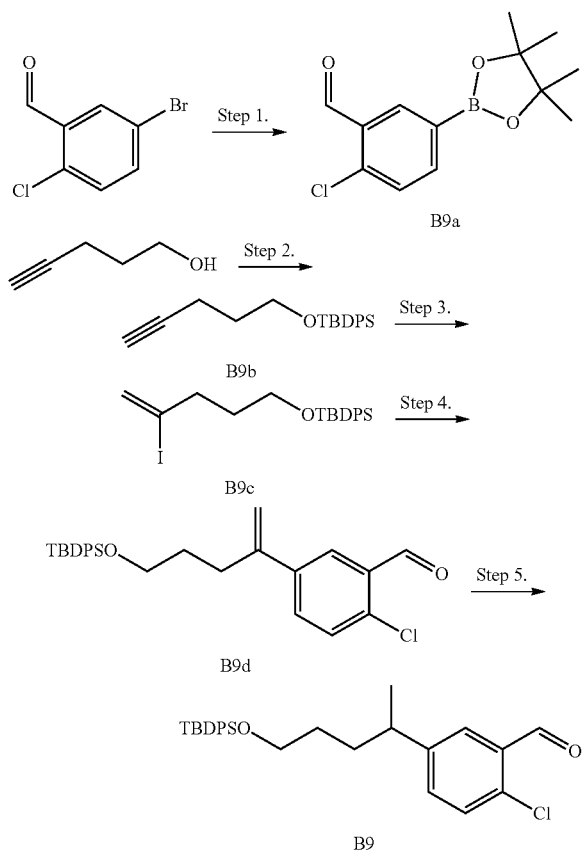

Step 1. 2-chloro-5-(tetramethyl-1,3,2-dioxaborolan-2-yl)benzaldehyde (Intermediate B9a)

A 250-mL round-bottom flask was charged with 5-bromo-2-chlorobenzaldehyde (5.0 g, 22.78 mmol, 1.00 equiv), 4,4,5,5-tetramethyl-2-(tetramethyl-1,3,2-dioxaborolan-2-yl)-1,3,2-dioxaborolane (6.41 g, 25.24 mmol, 1.10 equiv), dioxane (100 mL), KOAc (6.75 g, 68.78 mmol, 3.00 equiv) and Pd(dppf)Cl$_2$ (500 mg, 0.68 mmol, 0.03 equiv). The resulting solution was stirred overnight at 80° C. The reaction mixture was diluted with 300 mL of water. The resulting solution was extracted with 300 mL of ethyl acetate and the organic layers combined and dried over anhydrous sodium sulfate and concentrated under vacuum. The crude product (5.5 g) was purified by flash chromatography with the following conditions: Column, silica gel; mobile phase, ethyl acetate: petroleum ether=100:0 increasing to ethyl acetate: petroleum ether=95:5 within 30 min; Detector, UV 254 nm. This resulted in 3.6 g (59%) of 2-chloro-5-(tetramethyl-1,3,2-dioxaborolan-2-yl)benzaldehyde (B9a) as a white solid.

Step 2. tert-butyl(pent-4-yn-1-yloxy)diphenylsilane (Intermediate B9b)

A 1000-mL round-bottom flask purged and maintained under an inert atmosphere of nitrogen was charged with pent-4-yn-1-ol (15 g, 178.32 mmol, 1.00 equiv), imidazole (30.4 g, 2.50 equiv), dichloromethane (600 mL). This was followed by the addition of TBDPSCl (61.3 g, 1.25 equiv) dropwise with stirring at 0° C. The resulting solution was stirred for 1 h at room temperature. The reaction was then quenched by the addition of 200 mL of water. The resulting solution was extracted with 3×150 mL of dichloromethane and the organic layers combined. The resulting mixture was washed with 3×100 mL of brine. The mixture was dried over anhydrous sodium sulfate and concentrated under vacuum. The residue was applied onto a silica gel column with petroleum ether. This resulted in 58.7 g (crude) of B9b as a colorless oil.

Step 3. tert-butyl[(4-iodopent-4-en-1-yl)oxy]diphenylsilane (Intermediate B9c)

A 500-mL 3-necked round-bottom flask purged and maintained under an inert atmosphere of nitrogen was charged with a solution of Ni(dppp)Cl$_2$ (1.01 g, 0.03 equiv) in tetrahydrofuran (62 mL). This was followed by the addition of DIBAL-H (81 mL, 1.30 equiv, 1 mol/L in hexane) dropwise with stirring. To this was added tert-butyl(pent-4-yn-1-yloxy)diphenylsilane (B9b) (20 g, 62.01 mmol, 1.00 equiv) dropwise with stirring at 0° C. The mixture was stirred for 2 hr. To the mixture was added a solution of NIS (28 g, 124.46 mmol, 2.00 equiv) in tetrahydrofuran (186 mL) dropwise with stirring at 0° C. The resulting solution was stirred for 1 h at room temperature. The resulting solution was diluted with 250 mL of ether. The reaction was then quenched by the addition of 250 mL of saturated aqueous Rochelle's salt. After stirring for 15 min., the resulting mixture was filtered on the cotton. The resulting clear filtrate was extracted with 5×100 mL of ether and the organic layers combined. The resulting mixture was washed with 3×100 mL of brine. The mixture was dried over anhydrous sodium sulfate and concentrated under vacuum. The residue was applied onto a silica gel column with petroleum ether. This resulted in 23.8 g (77%) of B9c as a light yellow oil.

Step 4. 5-[5-[(tert-butyldiphenylsilyl)oxy]pent-1-en-2-yl]-2-chlorobenzaldehyde (Intermediate B9d)

A 100-mL round-bottom flask purged and maintained under an inert atmosphere of nitrogen was charged with tert-butyl[(4-iodopent-4-en-1-yl)oxy]diphenylsilane (B9c) (5.2 g, 11.54 mmol, 1.00 equiv), Pd(PPh$_3$)$_4$ (1.3 g, 1.12 mmol, 0.10 equiv), K$_3$PO$_4$ (4.9 g, 23.08 mmol, 2.00 equiv), 2-chloro-5-(tetramethyl-1,3,2-dioxaborolan-2-yl)benzaldehyde (B9a) (3.1 g, 11.63 mmol, 1.00 equiv), dioxane/H$_2$O (31/3.1 mL). The resulting solution was stirred for 4 h at 80° C. in an oil bath. The reaction mixture was cooled. The resulting solution was diluted with 100 mL of H$_2$O. The resulting solution was extracted with 4×80 mL of ethyl acetate and the organic layers combined. The resulting mixture was washed with 1×50 mL of brine. The mixture was dried over anhydrous sodium sulfate and concentrated under vacuum. The residue was applied onto a silica gel column with ethyl acetate/petroleum ether (5/100). This resulted in 3.7 g (64%) of B9d as a yellow oil.

Step 5. 5-[5-[(tert-butyldiphenylsilyl)oxy]pentan-2-yl]-2-chlorobenzaldehyde (Intermediate B9)

A 100-mL round-bottom flask purged and maintained with an atmosphere of hydrogen was charged with 5-[5-[(tert-butyldiphenylsilyl)oxy]pent-1-en-2-yl]-2-chlorobenzaldehyde (B9d, 600 mg, 1.30 mmol, 1.00 equiv), ethyl acetate (20 mL), Rh/C (600 mg). The resulting solution was stirred overnight at room temperature. The solids were filtered out. The resulting mixture was concentrated under vacuum. The residue was applied onto a silica gel column with ethyl acetate/petroleum ether (0:1-1:3). This resulted in 300 mg (50%) of B9 as a light yellow oil.

Example 11: Ethyl 5-(4-chloro-3-formylphenyl)hexanoate (Intermediate B10)

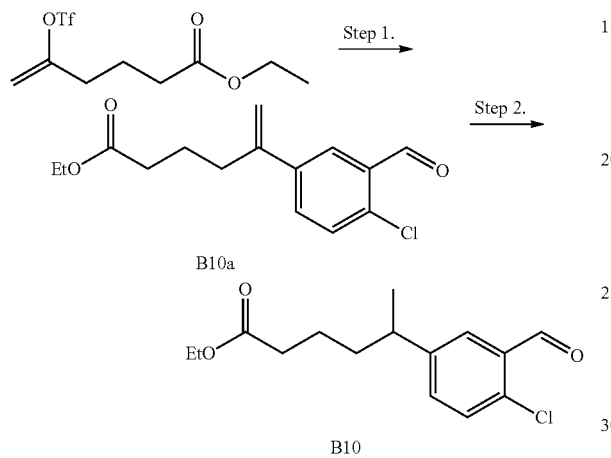

Step 1. Ethyl 5-(4-chloro-3-formylphenyl)hex-5-enoate (Intermediate B10a)

A 250-mL round-bottom flask was charged with 2-chloro-5-(tetramethyl-1,3,2-dioxaborolan-2-yl)benzaldehyde (3.5 g, 13.13 mmol, 1.10 equiv), ethyl 5-[(trifluoromethane)sulfonyloxy]hex-5-enoate (3.5 g, 12.06 mmol, 1.00 equiv), $K_3PO_4$ (7.7 g, 36.27 mmol, 3.00 equiv), Pd(pph3)$_4$ (1.4 g, 1.21 mmol, 0.10 equiv), dioxane (120 mL), water (20 mL). The resulting solution was stirred for 1 overnight at 80° C. in an oil bath. The reaction was then quenched by the addition of 300 mL of water. The resulting solution was extracted with 300 mL of ethyl acetate and the organic layers combined and dried over anhydrous sodium sulfate and concentrated under vacuum. The crude product (4.5 g) was purified by Flash chromatography with the following conditions (IntelFlash-1): Column, silica gel; mobile phase, ethyl acetate: petroleum ether=100:0 increasing to ethyl acetate: petroleum ether=95:5 within 30 min; Detector, UV 254 nm. This resulted in 2.2 g (65%) of ethyl 5-(4-chloro-3-formylphenyl)hex-5-enoate (B10a) as light red oil.

Step 2. Ethyl 5-(4-chloro-3-formylphenyl)hexanoate (Intermediate B10)

A 250-mL round-bottom flask was charged with ethyl 5-(4-chloro-3-formylphenyl)hex-5-enoate (B10a)(2.2 g, 7.84 mmol, 1.00 equiv), Rh/C (2.2 g, 21.36 mmol, 3.00 equiv), ethyl acetate (50 mL). The resulting solution was stirred for 5 h at 30° C. in an oil bath. The resulting solution was diluted with 100 mL of ethyl acetate. The solids were filtered out. The resulting mixture was concentrated under vacuum. The crude product (2.5 g) was purified by Flash chromatography with the following conditions (IntelFlash-1): Column, silica gel; mobile phase, ethyl acetate: petroleum ether=100:0 increasing to ethyl acetate: petroleum ether=95:5 within 30 min; Detector, UV 254 nm. This resulted in 2.1 g (95%) of ethyl 5-(4-chloro-3-formylphenyl)hexanoate (B10) as colorless oil.

Example 12: Methyl 5-(6-formyl-5-methylpyridin-2-yl)pentanoate (Intermediate B11)

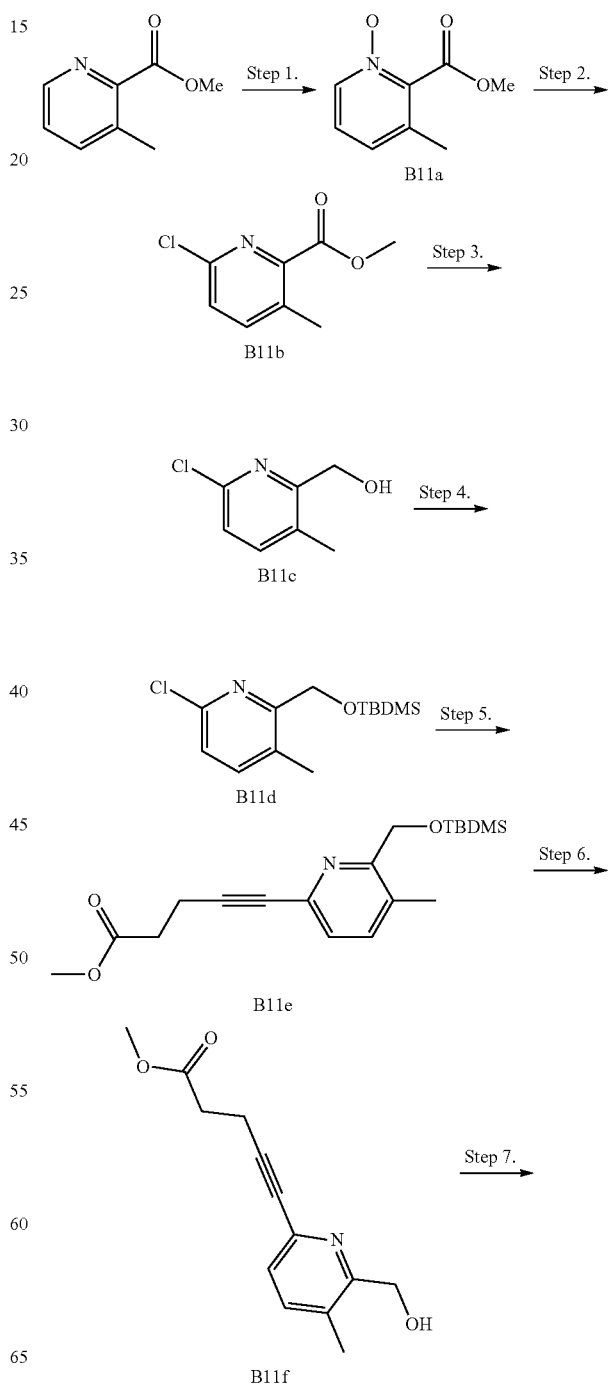

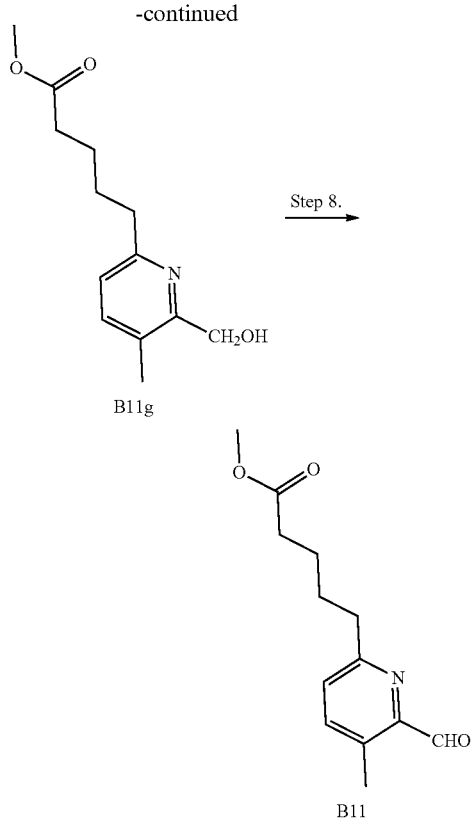

Step 3. (6-Chloro-3-methylpyridin-2-yl)methanol (Intermediate B11c)

A 250-mL 3-necked round-bottom flask (1 atm) purged and maintained under an inert atmosphere of nitrogen was charged with methyl 6-chloro-3-methylpyridine-2-carboxylate (1.86 g, 10.02 mmol, 1.00 equiv), THF (100 mL). This was followed by the addition of DIBAL-H (40 ml, 4.00 equiv) at −78° C. The resulting solution was stirred for 3 h at room temperature in an ethanol/liquid $N_2$ bath. The resulting solution was diluted with 100 mL of ethyl acetate. The reaction was then quenched by the addition of 60 mL of $C_4H_4KNaO_6$. diatomite. The mixture was dried over anhydrous sodium sulfate and concentrated under vacuum. The residue was applied onto a silica gel column with ethyl acetate/petroleum ether (0-50%). This resulted in 1.3 g (82%) of (6-chloro-3-methylpyridin-2-yl)methanol (B11c:) as colorless oil.

Step 4. 2-[[(tert-butyldimethylsilyl)oxy]methyl]-6-chloro-3-methylpyridine (Intermediate B11d)

To a 500-mL 3-necked round-bottom flask was charged with (6-chloro-3-methylpyridin-2-yl)methanol (6.4 g, 40.61 mmol, 1.00 equiv), dichloromethane (300 mL), imidazole (4.2 g), TBDMSCl (7.6 g). The resulting solution was stirred for 2 h at 0° C. in an ice/salt bath. The reaction was then quenched by the addition of 30 mL of water. The resulting solution was extracted with 3×50 mL of dichloromethane and the organic layers combined. The resulting mixture was washed with 2×50 mL of brine. The mixture was dried over anhydrous sodium sulfate and concentrated under vacuum. This resulted in 10.4 g (94%) of 2-[[(tert-butyldimethylsilyl)oxy]methyl]-6-chloro-3-methylpyridine (B11d) as a brown solid.

Step 5. Methyl 5-(6-[[(tert-butyldimethylsilyl)oxy]methyl]-5-methylpyridin-2-yl)pent-4-ynoate (Intermediate B11e)

A 100-mL 3-necked round-bottom flask purged and maintained under an inert atmosphere of nitrogen was charged with $Cs_2CO_3$ (6.9 g, 21.18 mmol, 1.92 equiv), (A-taPhos-PdCl_2)_2 (195 mg), 2-[[(tert-butyldimethylsilyl)oxy]methyl]-6-chloro-3-methylpyridine (3 g, 11.04 mmol, 1.00 equiv) in $CH_3CN$ (20 mL), methyl pent-4-ynoate (3.5 g, 31.21 mmol, 2.83 equiv) in $CH_3CN$ (20 mL). The resulting solution was stirred overnight at 95° C. in an oil bath. The resulting mixture was concentrated under vacuum. The residue was applied onto a silica gel column with ethyl acetate/petroleum ether (1/100-10/100). This resulted in 1.1 g (29%) of methyl 5-(6-[[(tert-butyldimethylsilyl)oxy]methyl]-5-methylpyridin-2-yl)pent-4-ynoate (B11e) as brown oil.

Step 6. Methyl 5-[6-(hydroxymethyl)-5-methylpyridin-2-yl]pent-4-ynoate (Intermediate B11f)

To a 100-mL round-bottom flask charged with methyl 5-(6-[[(tert-butyldimethylsilyl)oxy]methyl]-5-methylpyridin-2-yl)pent-4-ynoate (1.5 g, 4.32 mmol, 1.00 equiv) in tetrahydrofuran (10 mL) was added TBAF (6.5 mL, 1M) dropwise with stirring. The resulting solution was stirred for 1 h at room temperature. The resulting mixture was concentrated under vacuum. The residue was applied onto a silica gel column with ethyl acetate/petroleum ether (1/100-

Step 1. 2-(methoxycarbonyl)-3-methylpyridine 1-oxide (Intermediate B11a)

A 250-mL round-bottom flask (1 atm) purged and maintained under an inert atmosphere of nitrogen was charged with methyl 3-methylpyridine-2-carboxylate (8.0 g, 52.92 mmol, 1.00 equiv), dichloromethane (100 mL), m-CPBA (27.3 g, 158.72 mmol, 3.00 equiv). The resulting solution was stirred overnight at 25° C. in an oil bath. The resulting solution was diluted with 100 mL of DCM. The resulting mixture was washed with 1×100 mL of water and 1×100 mL of brine. The mixture was dried over anhydrous sodium sulfate and concentrated under vacuum. The residue was applied onto a silica gel column with dichloromethane/methanol (20:1). This resulted in 6.0 g (68%) of product (B11a) as colorless oil.

Step 2. methyl 6-chloro-3-methylpyridine-2-carboxylate (Intermediate B11b)

A 250-mL round-bottom flask (1 atm) purged and maintained under an inert atmosphere of nitrogen was charged with 2-(methoxycarbonyl)-3-methylpyridin-1-ium-1-olate (1.5 g, 8.97 mmol, 1.00 equiv), phosphoroyl trichloride (60 mL). The resulting solution was stirred overnight at 60° C. in an oil bath. The resulting solution was diluted with 200 mL of DCM. The resulting mixture was washed with 1×100 mL of brine. The mixture was dried over anhydrous sodium sulfate and concentrated under vacuum. The residue was applied onto a silica gel column with ethyl acetate/petroleum ether (0%-25%). This resulted in 318 mg (19%) of methyl 6-chloro-3-methylpyridine-2-carboxylate (B11b) as a white solid.

20/100). This resulted in 600 mg (60%) of methyl 5-[6-(hydroxymethyl)-5-methylpyridin-2-yl]pent-4-ynoate (B11f) as brown oil.

Step 7. Methyl 5-[6-(hydroxymethyl)-5-methylpyridin-2-yl]pentanoate (Intermediate B11g)

A 100-mL round-bottom flask charged with methyl 5-[6-(hydroxymethyl)-5-methylpyridin-2-yl]pent-4-ynoate (700 mg, 3.00 mmol, 1.00 equiv), ethyl acetate (10 mL) and Rh/C (0.7 g) was purged and maintained with an atmosphere of $H_2$. The resulting suspension was stirred for 2 h at 25° C. in an oil bath. The solids were filtered out. The resulting mixture was concentrated under vacuum. This resulted in 0.6 g (84%) of methyl 5-[6-(hydroxymethyl)-5-methylpyridin-2-yl]pentanoate (B11g) as brown oil.

Step 8. Methyl 5-(6-formyl-5-methylpyridin-2-yl)pentanoate (B11)

A 50-mL round-bottom flask was charged with a solution of methyl 5-[6-(hydroxymethyl)-5-methylpyridin-2-yl]pentanoate (202 mg, 0.85 mmol, 1.00 equiv) in dichloromethane (5 mL), $MnO_2$ (741.5 mg, 8.53 mmol, 10.02 equiv). The resulting solution was stirred overnight at 50° C. in an oil bath. The solids were filtered out. The resulting mixture was concentrated under vacuum. This resulted in 180 mg (90%) of methyl 5-(6-formyl-5-methylpyridin-2-yl)pentanoate (B11) as light brown oil.

Example 13: tert-butyl N-[4-[3-(bromomethyl)-4-chlorophenyl]butyl]carbamate (Intermediate $C_1$)

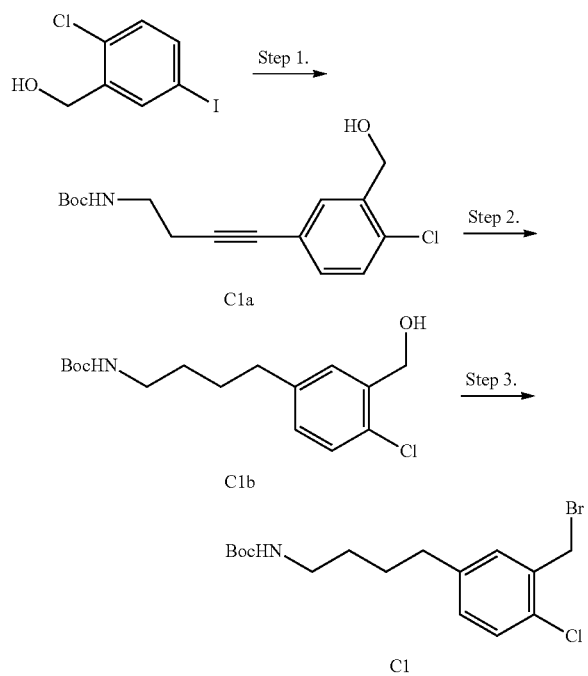

Step 1. tert-butyl N-[4-[4-chloro-3-(hydroxymethyl)phenyl]but-3-yn-1-yl]carbamate (Intermediate $C_1$a)

A 100-mL round-bottom flask purged and maintained under an inert atmosphere of nitrogen was charged with (2-chloro-5-iodophenyl)methanol (212 mg, 0.79 mmol, 1.00 equiv), tert-butyl N-(but-3-yn-1-yl)carbamate (160 mg, 0.95 mmol, 1.20 equiv), DIEA (0.39 mL, 3.00 equiv), CuI (15 mg, 0.08 mmol, 0.10 equiv), dichloropalladium bis(triphenylphosphine) (55.5 mg, 0.08 mmol, 0.10 equiv) and N,N-dimethylformamide (8 mL). The resulting solution was stirred overnight at room temperature. The resulting solution was diluted with 20 mL of water. The resulting solution was extracted with 4×20 mL of ethyl acetate and the organic layers combined. The resulting mixture was washed with 5×100 mL of brine. The mixture was dried over anhydrous sodium sulfate and concentrated under vacuum. The residue was applied onto a silica gel column with ethyl acetate/petroleum ether (1:3). This resulted in 220 mg (90%) of tert-butyl N-[4-[4-chloro-3-(hydroxymethyl)phenyl]but-3-yn-1-yl]carbamate ($C_1$a) as a yellow oil.

Step 2. tert-butyl N-[4-[4-chloro-3-(hydroxymethyl)phenyl]butyl]carbamate (Intermediate C1b)

A 100-mL round-bottom flask purged and maintained with one atmosphere of hydrogen was added tert-butyl N-[4-[4-chloro-3-(hydroxymethyl)phenyl]but-3-yn-1-yl]carbamate (350 mg, 1.13 mmol, 1.00 equiv), ethyl acetate (20 mL), Rh/C (350 mg). The resulting solution was stirred overnight at room temperature. The solids were filtered out. The resulting mixture was concentrated under vacuum. The residue was applied onto a silica gel column with ethyl acetate/petroleum ether (1:3). This resulted in 300 mg (85%) of tert-butyl N-[4-[4-chloro-3-(hydroxymethyl)phenyl]butyl]carbamate (C1b) as a light yellow oil.

Step 3. tert-butyl N-[4-[3-(bromomethyl)-4-chlorophenyl]butyl]carbamate (Intermediate C1)

A 100-mL round-bottom flask was charged with tert-butyl N-[4-[4-chloro-3-(hydroxymethyl)phenyl]butyl]carbamate (300 mg, 0.96 mmol, 1.00 equiv), dichloromethane (10 mL), THF (10 mL), NBS (255 mg, 4.33 mmol, 1.50 equiv). This was followed by the addition of triphenylphosphane (375 mg, 1.43 mmol, 1.50 equiv) in several batches at 0-5° C. The resulting solution was stirred for 2 h at room temperature. The resulting mixture was concentrated under vacuum. The residue was applied onto a silica gel column with ethyl acetate/petroleum ether (1:3). This resulted in 270 mg (75%) of tert-butyl N-[4-[3-(bromomethyl)-4-chlorophenyl]butyl]carbamate ($C_1$) as a yellow oil.

Example 14: tert-butyl N-[4-[4-(bromomethyl)-5-chloro-2-methylphenyl]butyl]carbamate (Intermediate $C_2$)

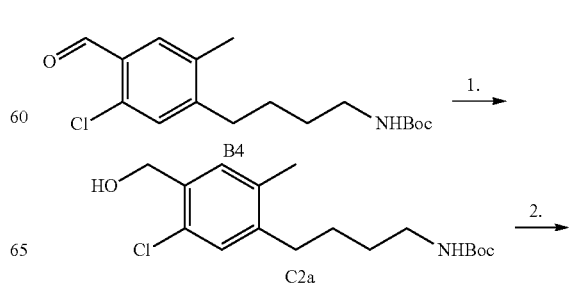

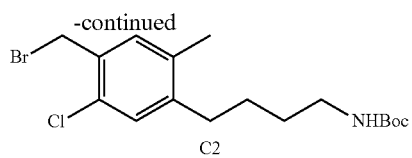

Step 1. tert-butyl N-[4-[5-chloro-4-(hydroxymethyl)-2-methylphenyl]butyl]carbamate (Intermediate C₂a)

A 50-mL round-bottom flask was charged with tert-butyl N-[4-(5-chloro-4-formyl-2-methylphenyl)butyl]carbamate (B4) (150 mg, 0.46 mmol, 1.00 equiv), methanol (15 mL) and NaBH₄ (34.83 mg, 0.92 mmol, 2.00 equiv). The resulting solution was stirred for 0.5 h at room temperature. The reaction mixture was cooled to 0° C. with a water/ice bath. The reaction was then quenched by the addition of 10 mL of water. The resulting solution was extracted with 3×20 mL of ethyl acetate and the organic layers combined. The resulting mixture was washed with 2×20 mL of brine. The mixture was dried over anhydrous sodium sulfate. The solids were filtered out, and the resulting mixture was concentrated under vacuum. This resulted in 180 mg (crude) of tert-butyl N-[4-[5-chloro-4-(hydroxymethyl)-2-methylphenyl]butyl]carbamate (C₂a) as a white oil.

Step 2. tert-butyl N-[4-[4-(bromomethyl)-5-chloro-2-methylphenyl]butyl]carbamate (Intermediate C₂)

A 100-mL round-bottom flask was charged with tert-butyl N-[4-[5-chloro-4-(hydroxymethyl)-2-methylphenyl]butyl]carbamate (180 mg, 0.55 mmol, 1.00 equiv) and tetrahydrofuran/DCM (10/10 mL). This was followed by the addition of NBS (156.7 mg, 0.88 mmol, 1.60 equiv) in several batches at 0° C. This was followed by the addition of Ph₃P (216.73 mg) in several batches at 0° C. The resulting solution was stirred for 20 min at room temperature. The resulting mixture was concentrated under vacuum. The residue was applied onto a silica gel column with ethyl acetate/petroleum ether (1:10). This resulted in 194 mg (90%) of tert-butyl N-[4-[4-(bromomethyl)-5-chloro-2-methylphenyl]butyl]carbamate (C2) as a white oil.

Intermediates C3 to C10 (Table 2b) were prepared from commercial or known starting materials according to according to the procedure used to synthesize Intermediate C1 in Example 14.

TABLE 2b

C-ring Bromides C3 to C10

| Int. No.: | Compound Structure |
|---|---|
| C3 | 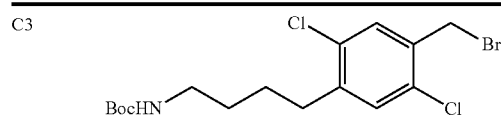 |
| | 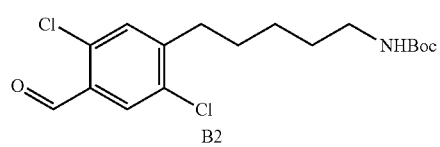 |
| C4 | 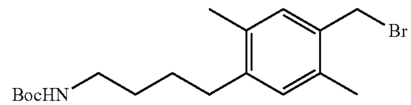 [SMILES: Cc1cc(CCCCNC(=O)OC(C)(C)C)c(C)cc1CBr] |
| C5 | 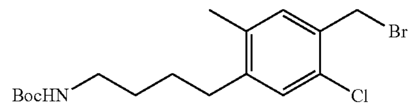 [SMILES: Cc1cc(CBr)c(Cl)cc1CCCCNC(=O)OC(C)(C)C] |
| C6 | 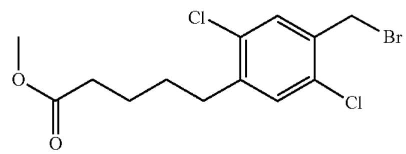 [SMILES: COC(=O)CCCCc1cc(Cl)c(CBr)cc1Cl] |
| C7 | 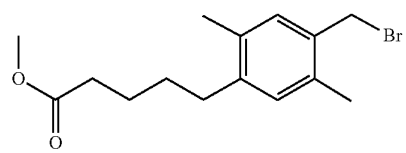 [SMILES: COC(=O)CCCCc1cc(C)c(CBr)cc1C] |
| C8 | 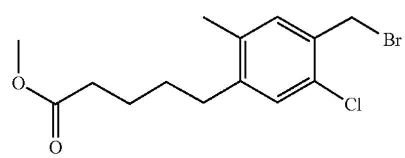 [SMILES: COC(=O)CCCCc1cc(Cl)c(CBr)cc1C] |
| C9 | 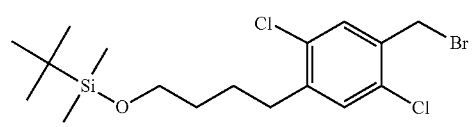 [SMILES: CC(C)(C)[Si](C)(C)OCCCCc1cc(Cl)c(CBr)cc1Cl] |
| C10 | 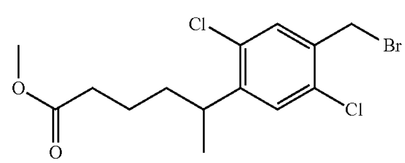 [SMILES: COC(=O)CCCC(C)c1cc(Cl)c(CBr)cc1Cl] |

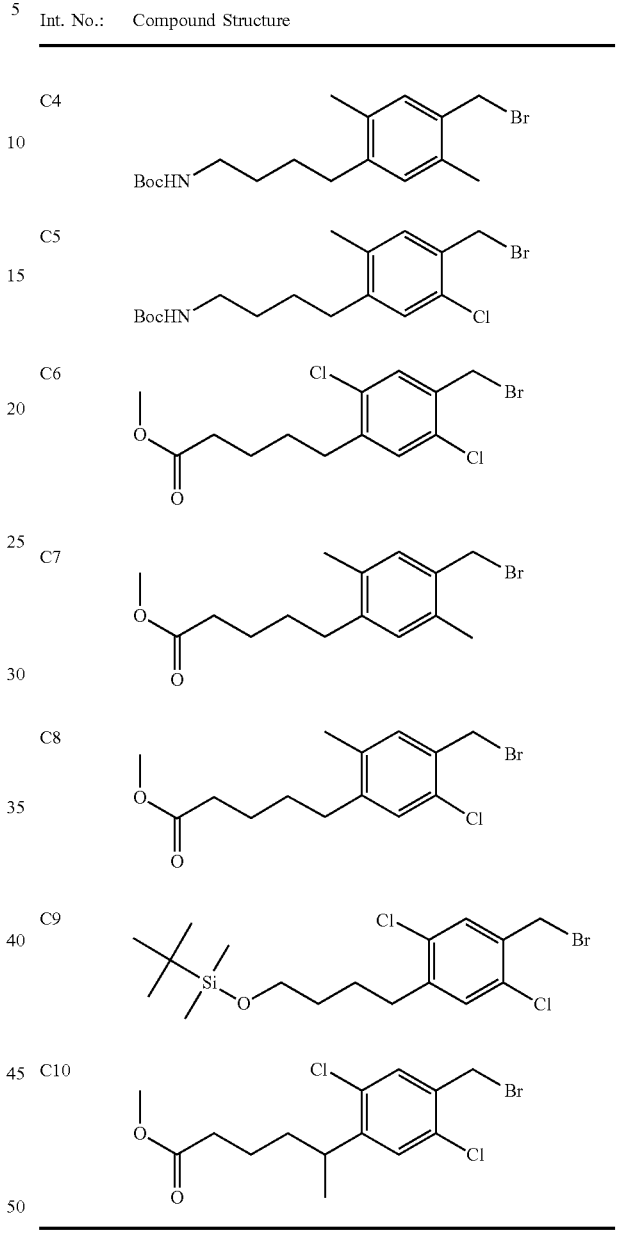

Example 15: 1-(5-[2,5-dichloro-4-[([1-[4-(2-cyclopropoxyphenyl)pyridin-3-yl]cyclopropyl]amino)methyl]phenyl]pentyl)-3-[(2S,3R,4R,5R)-2,3,4,5,6-pentahydroxyhexyl]urea hydrochloride (I-60)

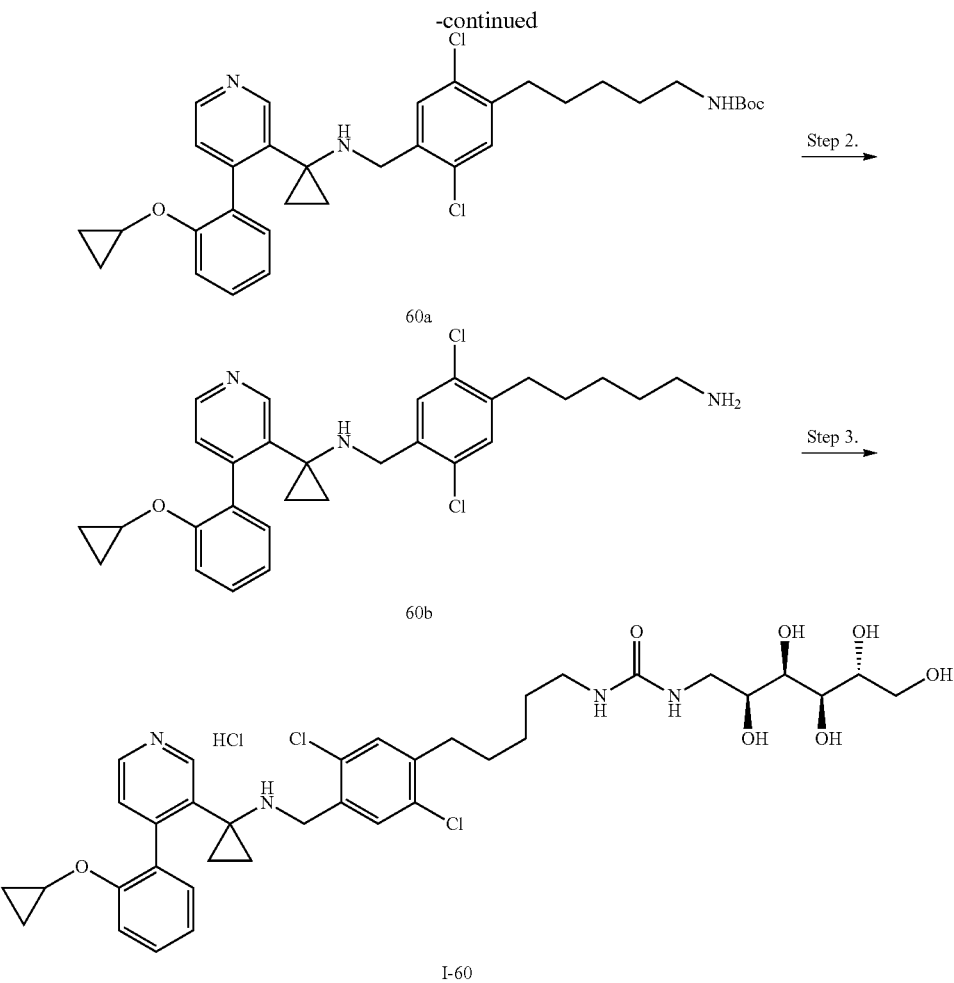

I-60

Step 1. tert-butyl N-(5-[2,5-dichloro-4-[([1-[4-(2-cyclopropoxyphenyl)pyridin-3-yl]cyclopropyl]amino)methyl]phenyl]pentyl)carbamate (Intermediate 60a)

A 50-mL round-bottom flask was charged with tert-butyl N-[5-(2,5-dichloro-4-formylphenyl)pentyl]carbamate (B2) (320 mg, 0.89 mmol, 1.00 equiv), 1-[4-(2-cyclopropoxyphenyl)pyridin-3-yl]cyclopropan-1-amine (A1) (236 mg, 0.89 mmol, 1.00 equiv), dichloromethane (10 mL), NaBH(OAc)$_3$ (1.13 g, 6.00 equiv). The resulting solution was stirred overnight at room temperature. The reaction was then quenched by the addition of 10 mL of water. The resulting solution was extracted with 3×20 mL of dichloromethane and the organic layers combined and dried over anhydrous sodium sulfate and concentrated under vacuum. The residue was applied onto a silica gel column with ethyl acetate/petroleum ether (0-20%). The collected fractions were combined and concentrated under vacuum. This resulted in 280 mg (52%) of tert-butyl N-(5-[2,5-dichloro-4-[([1-[4-(2-cyclopropoxyphenyl)pyridin-3-yl]cyclopropyl]amino)methyl]phenyl]pentyl)carbamate (60a) as a light yellow oil.

Step 2. N-[[4-(5-aminopentyl)-2,5-dichlorophenyl]methyl]-1-[4-(2-cyclopropoxyphenyl) pyridin-3-yl]cyclopropan-1-amine (Intermediate 60b)

A 100-mL round-bottom flask was charged with tert-butyl N-(5-[2,5-dichloro-4-[([1-[4-(2-cyclopropoxyphenyl)pyridin-3-yl]cyclopropyl]amino)methyl]phenyl]pentyl)carbamate (350 mg, 0.57 mmol, 1.00 equiv), dichloromethane (5 mL) and trifluoroacetic acid (5 mL). The resulting solution was stirred for 1 h at room temperature. The resulting mixture was concentrated under vacuum. The pH value of the solution was adjusted to 10 with sodium hydroxide (1 mol/L). The resulting solution was extracted with 3×20 mL of ethyl acetate and the organic layers combined and dried in an oven under reduced pressure and concentrated under vacuum. This resulted in 280 mg (96%) of N-[[4-(5-aminopentyl)-2,5-dichlorophenyl]methyl]-1-[4-(2-cyclopropoxyphenyl)pyridin-3-yl]cyclopropan-1-amine (60b) as a light yellow oil.

Step 3. 1-(5-[2,5-dichloro-4-[([1-[4-(2-cyclopropoxyphenyl)pyridin-3-yl]cyclopropyl]amino)methyl]phenyl]pentyl)-3-[(2S,3R,4R,5R)-2,3,4,5,6-pentahydroxyhexyl]urea hydrochloride (I-60)

A 100-mL round-bottom flask was charged with N-[[4-(5-aminopentyl)-2,5-dichlorophenyl]methyl]-1-[4-(2-cyclopropoxyphenyl)pyridin-3-yl]cyclopropan-1-amine (130 mg, 0.25 mmol, 1.00 equiv), N,N-dimethylformamide (10 mL), DIEA (39 mg, 0.30 mmol, 1.20 equiv), DSC (78 mg, 1.20 equiv), the resulting solution was stirred for 1.5 h at 25° C. Then (2R,3R,4R,5S)-6-aminohexane-1,2,3,4,5-pentol (138.4 mg, 0.76 mmol, 3.00 equiv) was added. The resulting solution was stirred overnight at 25° C. The resulting solution was diluted with 50 mL of ethyl acetate. The resulting mixture was washed with 3×50 mL of brine. The crude product was purified by Preparative HPLC with the following conditions: Column, Gemini-NX 5u C18 110A, AXIA Packed, 150×21.2 mm; mobile phase, water with 10 mM NH$_4$HCO$_3$ and MeCN (28.0% MeCN up to 54.0% in 8 min); Detector, 254 nm. Product was obtained and concentrated under vacuum. This resulted in 70.6 mg (37%) of 1-(5-[2,5-dichloro-4-[([1-[4-(2-cyclopropoxyphenyl)pyridin-3-yl]cyclopropyl]amino)methyl]phenyl]pentyl)-3-[(2S,3R,4R,5R)-2,3,4,5,6-pentahydroxyhexyl]urea hydrochloride (I-60) as a white solid. MS (ES, m/z): 717 [M+H]$^+$; $^1$H-NMR (400 MHz, CD$_3$OD) δ 0.51 (s, 2H), 0.71 (d, J=6.1 Hz, 2H), 1.26-1.67 (m, 10H), 2.70 (d, J=7.3 Hz, 2H), 3.08-3.15 (m, 3H), 3.35 (dd, J=14.0, 4.3 Hz, 1H), 3.53-3.80 (m, 6H), 3.80-3.92 (m, 1H), 4.26 (m, 2H), 7.17-7.50 (m, 3H), 7.59 (td, J=7.1, 6.3, 1.7 Hz, 3H), 7.87 (s, 1H), 8.86 (dd, J=23.4, 6.1 Hz, 1H), 9.33 (s, 1H).

Example 16: 5-[2,5-dichloro-4-[([1-[4-(2-cyclopropoxyphenyl)pyridin-3-yl]cyclopropyl]amino)methyl]phenyl]pentanoic acid (I-61)

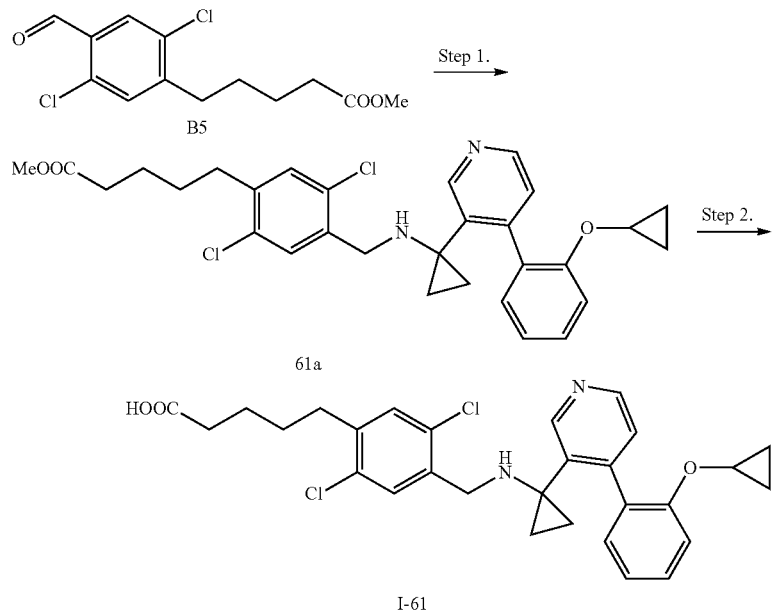

Step 1. Methyl 5-[2,5-dichloro-4-[([1-[4-(2-cyclopropoxyphenyl)pyridin-3-yl]cyclopropyl]amino)methyl]phenyl]pentanoate (Intermediate 61a)

A 50-mL round-bottom flask was charged with 1-[4-(2-cyclopropoxyphenyl)pyridin-3-yl]cyclopropan-1-amine (A-1) (350 mg, 1.31 mmol, 1.00 equiv), methyl 5-(2,5-dichloro-4-formylphenyl)pentanoate (B5) (416 mg, 1.44 mmol, 1.00 equiv). The above compound was dissolved by dichloromethane (25 mL). acetic acid (1 drop, cat.) was added. This was followed by the addition of NaBH(OAc)$_3$ (1.4 g, 6.61 mmol, 5.00 equiv), in portions at room temperature. The resulting solution was stirred for 16 h at room temperature. The reaction was then quenched by the addition of 20 mL of water. The resulting solution was extracted with 2× mL of ethyl acetate and the organic layers combined. The resulting mixture was washed with 1×100 mL of water and 1×100 mL of sodium chloride sat. The mixture was dried over anhydrous sodium sulfate. The residue was applied onto a silica gel column with ethyl acetate/petroleum ether (1:3). This resulted in 535 mg (76%) of methyl 5-[2,5-dichloro-4-[([1-[4-(2-cyclopropoxyphenyl) pyridin-3-yl]cyclopropyl]amino)methyl]phenyl]pentanoate (61a) as colorless oil.

Step 2. 5-[2,5-dichloro-4-[([1-[4-(2-cyclopropoxyphenyl)pyridin-3-yl]cyclopropyl]amino) methyl] phenyl]pentanoic acid (I-61)

A 50-mL round-bottom flask was charged with methyl 5-[2,5-dichloro-4-[([1-[4-(2-cyclopropoxyphenyl)pyridin-3-yl]cyclopropyl]amino)methyl]phenyl]pentanoate (61a, 535 mg, 0.99 mmol, 1.00 equiv), methanol (15 mL), water (15 mL). This was followed by the addition of LiOH·H$_2$O (168 mg, 4.00 mmol, 4.00 equiv), in portions at room temperature. The resulting solution was stirred for 2 h at 50° C. The resulting solution was diluted with 20 mL of water. The pH value of the solution was adjusted to 2-3 with hydrogen chloride con. The resulting solution was extracted with 3×50 mL of ethyl acetate and the organic layers combined. The resulting mixture was washed with 1×50 mL of water and 1×50 mL of sodium chloride sat. The mixture was dried over anhydrous sodium sulfate and concentrated under vacuum. This resulted in 500 mg (96%) of 5-[2,5-dichloro-4-[([1-[4-(2-cyclopropoxyphenyl)pyridin-3-yl]cyclopropyl]amino) methyl]phenyl]pentanoic acid (I-61) as a light yellow oil. MS (ES, m/z): 525 [M+H]$^+$ H-NMR (CD$_3$OD, 400 M, ppm): 8.56 (s, 1H), 8.46-8.44 (d, 1H), 7.48-7.46 (d, 2H), 7.27 (s, 1H), 7.20-7.16 (m, 3H), 7.12-7.06 (m, 1H), 3.68-3.65 (m, 3H), 2.71-2.68 (m, 2H), 2.32-2.29 (m, 2H), 1.63-1.29 (m, 4H), 0.89-0.81 (m, 4H), 0.68 (t, 2H), 0.50 (t, 2H).

Example 17: 5-[2,5-dichloro-4-[([1-[4-(2-cyclopropoxyphenyl)pyridin-3-yl]cyclopropyl]amino)methyl]phenyl]-N-[(2S,3R,4R,5R)-2,3,4,5,6-pentahydroxyhexyl]pentanamide (I-62)

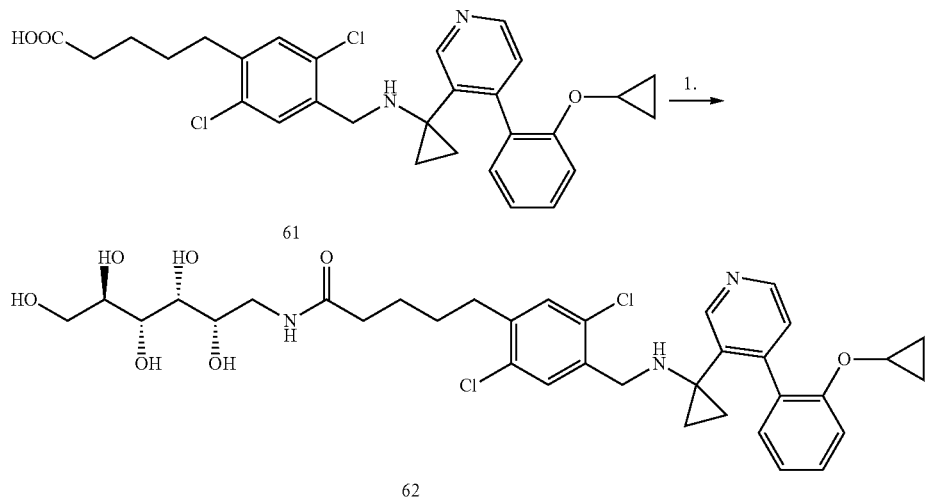

A 25-mL round-bottom flask was charged with 5-[2,5-dichloro-4-[([1-[4-(2-cyclopropoxyphenyl)pyridin-3-yl]cyclopropyl]amino)methyl]phenyl]pentanoic acid (61) (260 mg, 0.49 mmol, 1.00 equiv), N,N-dimethylformamide (10 mL), DIEA (161 mg, 2.50 equiv). The resulting solution was stirred for 10 min at room temperature. This was followed by the addition of HATU (475 mg, 1.25 mmol, 2.50 equiv), in portions at room temperature. To this was added D-glucamine (181 mg, 2.00 equiv). The resulting solution was stirred for 16 h at room temperature. The reaction was then quenched by the addition of 15 mL of water. The resulting solution was diluted with 30 mL of water. The resulting solution was extracted with 3×50 mL of ethyl acetate and the organic layers combined. The resulting mixture was washed with 1×100 mL of water and 1×100 mL of sat. sodium chloride. The mixture was dried over anhydrous sodium sulfate. The crude product was purified by Preparative HPLC with the following conditions: Column, XBridge C18 OBD Prep Column, 5 μm, 19 mm×250 mm; mobile phase, 10 mM aqueous $NH_4HCO_3$ and MeCN (38.0% MeCN up to 61.0% in 8 min); Detector, 254 nm. This resulted in 170 mg (50%) of 5-[2,5-dichloro-4-[([1-[4-(2-cyclopropoxyphenyl)pyridin-3-yl]cyclopropyl]amino)methyl]phenyl]-N-[(2S,3R,4R,5R)-2,3,4,5,6-pentahydroxyhexyl]pentanamide (I-62) as a yellow solid. MS (ES, m/z): 717 [M+H]$^+$; $^1$H-NMR (400 MHz, $CD_3OD$) δ 0.35-0.48 (m, 2H), 0.62-0.75 (m, 2H), 1.00-1.25 (m, 4H), 1.40-1.60 (m, 4H), 2.10 (s, 2H), 2.66 (s, 2H), 2.96-3.08 (m, 1H), 3.20-3.30 (m, 1H), 3.35-3.65 (m, 6H), 3.78-3.85 (m, 1H), 3.91 (s, 2H), 7.14 (t, J=7.2 Hz, 1H), 7.35-7.45 (m, 2H), 7.48-7.60 (m, 4H), 7.74 (t, J=5.2 Hz, 1H), 8.70 (d, J=4.8 Hz, 1H), 8.98 (s, 1H).

Example 18: 4-[(4-[2,5-dichloro-4-[([1-[4-(2-cyclopropoxyphenyl)pyridin-3-yl]cyclopropyl]amino)methyl]phenyl]butyl) [(2S,3R,4R,5R)-2,3,4,5,6-pentahydroxyhexyl]carbamoyl]butanoic acid (I-63)

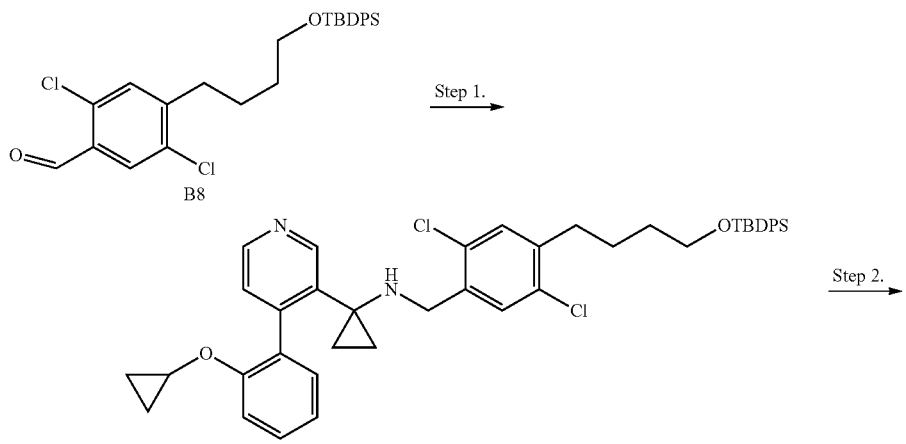

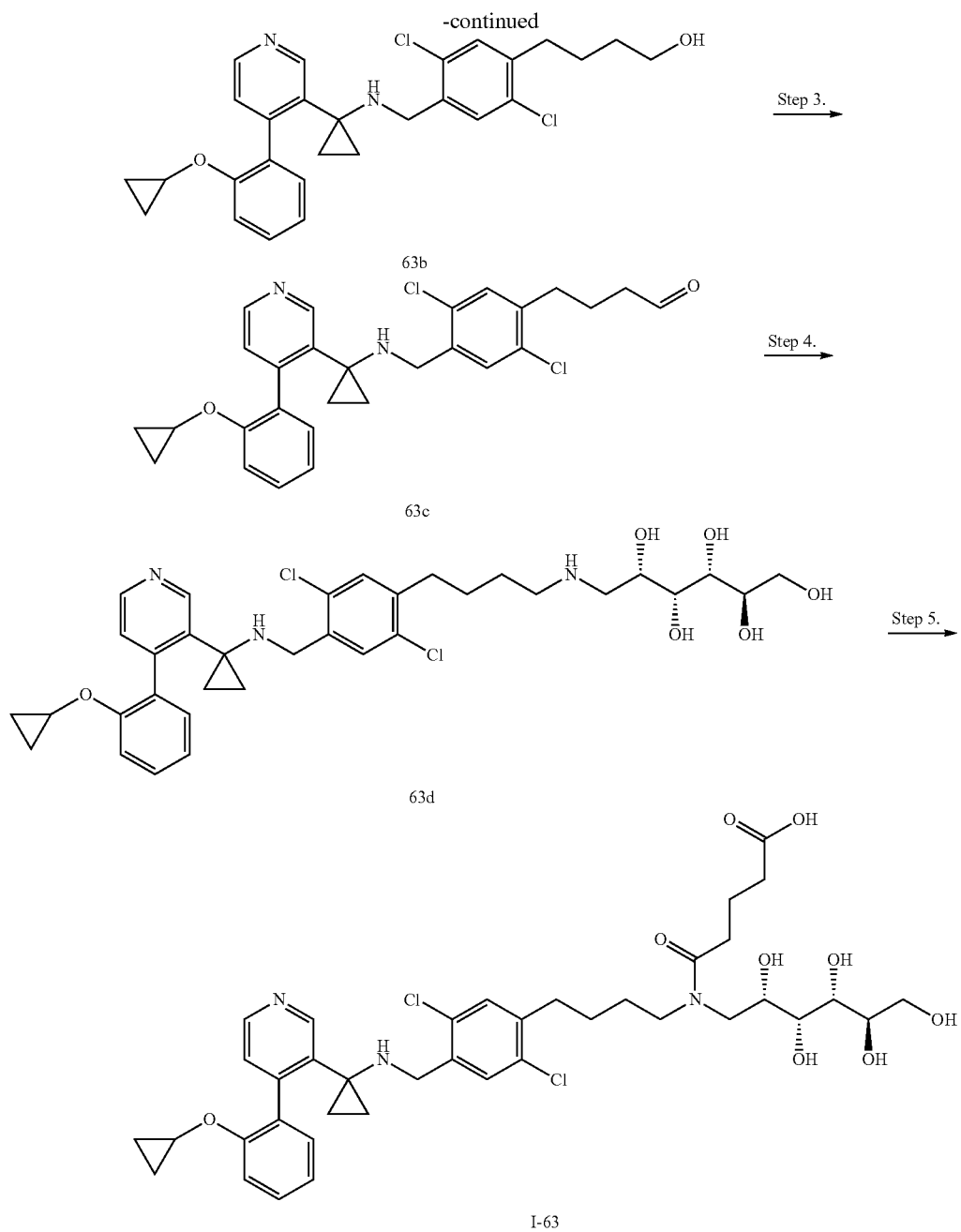

Step 1. N-[(4-[4-[(tert-butyldiphenylsilyl)oxy]butyl]-2,5-dichlorophenyl)methyl]-1-[4-(2-cyclopropoxyphenyl)pyridin-3-yl]cyclopropan-1-amine (Intermediate 63a)

A 500-mL round-bottom flask was charged with a solution of (NE)-N-[(4-[4-[(tert-butyldiphenylsilyl)oxy]butyl]-2,5-dichlorophenyl)methylidene]-1-[4-(2-cyclopropoxyphenyl)pyridin-3-yl]cyclopropan-1-amine (5.8 g, 7.90 mmol, 1.00 equiv) in dichloromethane (200 mL), NaBH(OAc)₃ (5.2 g, 24.54 mmol, 3.00 equiv). The resulting solution was stirred for 2 days at 30° C. in an oil bath. The resulting solution was diluted with 800 mL of ethyl acetate. The resulting mixture was washed with 3×150 mL of brine. The mixture was dried over anhydrous sodium sulfate and concentrated under vacuum. The residue was applied onto a silica gel column with ethyl acetate/petroleum ether (0:100-50:50). This resulted in 4.7 g (81%) of N-[(4-[4-[(tert-butyldiphenylsilyl)oxy]butyl]-2,5-dichlorophenyl)methyl]-1-[4-(2-cyclopropoxyphenyl)pyridin-3-yl]cyclopropan-1-amine (63a) as light yellow oil.

Step 2. 4-[2,5-dichloro-4-[([1-[4-(2-cyclopropoxyphenyl)pyridin-3-yl]cyclopropyl]amino)methyl]phenyl]butan-1-ol (Intermediate 63b)

A 250-mL round-bottom flask was charged with N-[(4-[4-[(tert-butyldiphenylsilyl)oxy]butyl]-2,5-dichlorophenyl)methyl]-1-[4-(2-cyclopropoxyphenyl)pyridin-3-yl]cyclopropan-1-amine (63a) (4.0 g, 5.44 mmol, 1.00 equiv), tetrahydrofuran (100 mL), TBAF (2.8 g, 10.71 mmol, 2.00 equiv). The resulting solution was stirred for 1.5 h at room temperature. The resulting solution was diluted with 500 mL of $H_2O$. The resulting solution was extracted with 3×150 mL of ethyl acetate and the organic layers combined and dried over anhydrous sodium sulfate and concentrated under vacuum. The residue was applied onto a silica gel column with ethyl acetate/petroleum ether (100:0-50:50). This resulted in 2.2 g (81%) of 4-[2,5-dichloro-4-[([1-[4-(2-cyclopropoxyphenyl)pyridin-3-yl]cyclopropyl]amino) methyl]phenyl]butan-1-ol (63b) as an off-white solid.

Step 3. 4-[2,5-dichloro-4-[([1-[4-(2-cyclopropoxyphenyl)pyridin-3-yl]cyclopropyl]amino)methyl]phenyl]butanal (Intermediate 63c)

A 250-mL 3-necked round-bottom flask purged and maintained under an inert atmosphere of nitrogen was charged with a solution of oxalyl chloride (486 mg, 3.83 mmol, 1.50 equiv) in dichloromethane (100 mL). This was followed by the addition of a solution of DMSO (684 mg, 8.75 mmol, 3.00 equiv) in dichloromethane (5 mL) dropwise with stirring at −78° C. in 30 min. The mixture was stirred for 30 min in −78° C. To this was added a solution of 4-[2,5-dichloro-4-[([1-[4-(2-cyclopropoxyphenyl)pyridin-3-yl]cyclopropyl] amino)methyl]phenyl]butan-1-ol (63b) (1.2 g, 2.41 mmol, 1.00 equiv) in dichloromethane (10 mL) dropwise with stirring at −78° C. in 5 min. The mixture was stirred for 5 min in −78° C. To the mixture was added a solution of TEA (1.2 g, 11.86 mmol, 5.00 equiv) in dichloromethane (5 mL) dropwise with stirring at −78° C. in 3 min. The mixture was stirred for 30 min in −78° C. The resulting solution was stirred for 2 h at room temperature. The reaction was then quenched by the addition of 600 mL of water. The resulting solution was extracted with 4×150 mL of dichloromethane and the organic layers combined and dried over anhydrous sodium sulfate and concentrated under vacuum. The residue was applied onto a silica gel column with ethyl acetate/ petroleum ether (1:1). This resulted in 600 mg (50%) of 4-[2,5-dichloro-4-[([1-[4-(2-cyclopropoxyphenyl) pyridin-3-yl]cyclopropyl]amino)methyl]phenyl]butanal (63c) as a light yellow oil.

Step 4. (2R,3R,4R,5S)-6-[(4-[2,5-dichloro-4-[([1-[4-(2-cyclopropoxyphenyl) pyridin-3-yl]cyclopropyl] amino)methyl]phenyl]butyl)amino]hexane-1,2,3,4,5-pentol (Intermediate 63d)

A 50-mL flask was charged with 4-[2,5-dichloro-4-[([1-[4-(2-cyclopropoxyphenyl) pyridin-3-yl]cyclopropyl] amino)methyl]phenyl]butanal (63c) (320 mg, 0.65 mmol, 1.00 equiv), methanol (6 mL), dichloromethane (2 mL). This was followed by the addition of (2R,3R,4R,5S)-6-aminohexane-1,2,3,4,5-pentol (234 mg, 1.29 mmol, 1.20 equiv). The mixture was stirred at rt for 30 mins. To this was added $NaBH(OAc)_3$ (274 mg, 1.29 mmol, 2.00 equiv). The resulting solution was stirred for 1 overnight at 30° C. in an oil bath. The resulting solution was diluted with 200 ml of ethyl acetate. The resulting mixture was washed with 2×50 mL of 0.5 M sodium hydroxide. The resulting mixture was washed with 2×50 mL of brine. The mixture was dried over sodium sulfate and concentrated under vacuum. This resulted in 400 mg (94%) of (2R,3R,4R,5S)-6-[(4-[2,5-dichloro-4-[([1-[4-(2-cyclopropoxyphenyl)pyridin-3-yl]cyclopropyl]amino) methyl]phenyl]butyl)amino]hexane-1,2,3,4,5-pentol (63d) as a light yellow crude solid.

Step 5. 4-[(4-[2,5-dichloro-4-[([1-[4-(2-cyclopropoxyphenyl)pyridin-3-yl]cyclopropyl]amino) methyl]phenyl]butyl)[(2S,3R,4R,5R)-2,3,4,5,6-pentahydroxyhexyl]carbamoyl]butanoic acid (I-63)

A 50-mL round-bottom flask was charged with (2R,3R, 4R,5S)-6-[(4-[2,5-dichloro-4-[([1-[4-(2-cyclopropoxyphenyl)pyridin-3-yl]cyclopropyl]amino)methyl]phenyl]butyl) amino]hexane-1,2,3,4,5-pentol (63d) (400 mg, 0.30 mmol, 1.00 equiv, 50%), DMSO (3 mL), oxane-2,6-dione (70 mg, 0.61 mmol, 1.00 equiv). The resulting solution was stirred for 2 h at 50° C. in an oil bath. The solids were filtered out. The crude product was purified by Preparative HPLC with the following conditions: Column, Gemini-NX 5µ C18 110A, AXIA Packed, 150×21.2 mm; mobile phase, 10 mM aqueous $NH_4HCO_3$ and MeCN (30.0% MeCN up to 80.0% in 10 min); Detector, UV 254 nm. This resulted in 30.9 mg (13%) of 4-[(4-[2,5-dichloro-4-[([1-[4-(2-cyclopropoxyphenyl)pyridin-3-yl]cyclopropyl]amino)methyl]phenyl]butyl) [(2S,3R,4R,5R)-2,3,4,5,6-pentahydroxyhexyl]carbamoyl] butanoic acid (I-63) as a white solid. MS (ES, m/z): 774 [M+H]$^+$; $^1$H-NMR (400 MHz, $CD_3OD$) δ 8.55 (1H, s), 8.46 (1H, s), 7.46-7.46 (2H, m), 7.23 (1H, s), 7.20-7.16 (3H, m), 7.11-7.09 (1H, m), 3.96 (1H, m), 3.76-3.46 (11H, m), 3.34-3.31 (1H, m), 2.89-2.83 (2H, m), 2.73-2.70 (4H, m), 2.32-2.30 (2H, m), 1.90-1.89 (2H, m), 1.65-1.57 (4H, m), 0.89-0.81 (4H, m), 0.67-0.65 (2H, d), 0.43 (2H, d).

Example 19: 1-(4-[4-chloro-3-[([1-[4-(2-cyclopropoxyphenyl)pyridin-3-yl]cyclopropyl]amino) methyl]phenyl]butyl)-3-[(2S,3R,4R,5R)-2,3,4,5,6-pentahydroxyhexyl]urea (I-64)

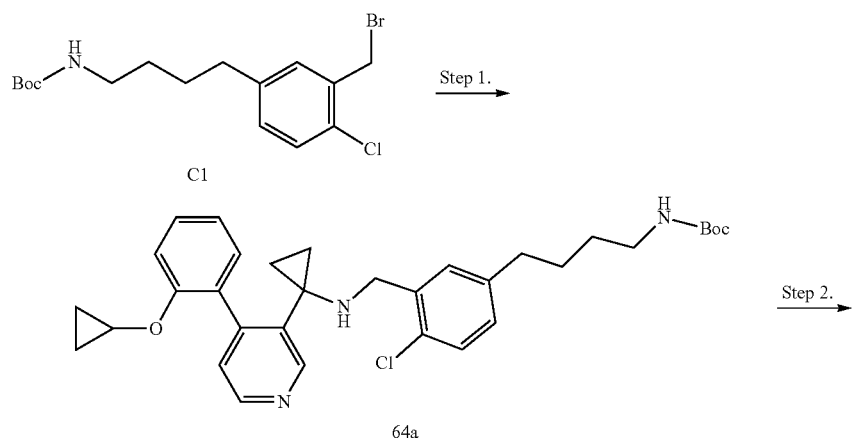

64a

-continued

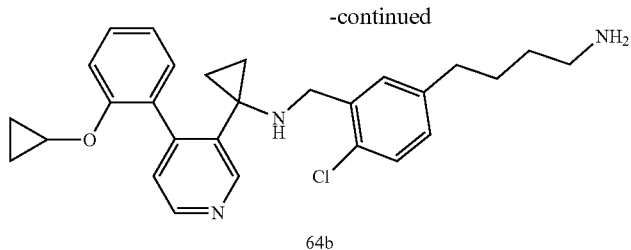

64b

Step 3.

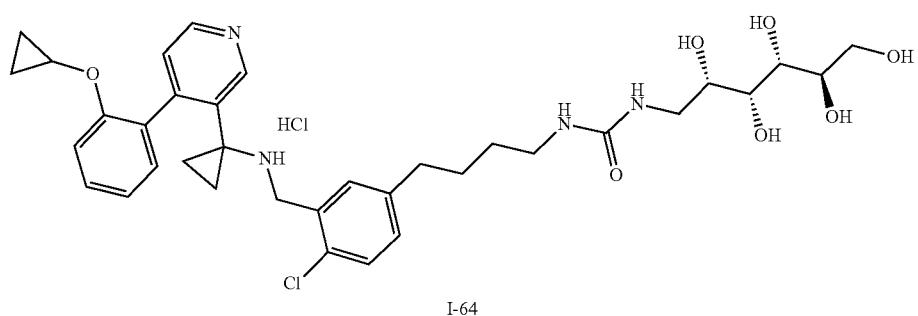

I-64

Step 1. N-(4-[4-chloro-3-[([1-[4-(2-cyclopropoxy-phenyl)pyridin-3-yl]cyclopropyl]amino) methyl]phenyl]butyl)carbamate (Intermediate 64a)

A 100-mL round-bottom flask was charged with 1-[4-(2-cyclopropoxyphenyl)pyridin-3-yl]cyclopropan-1-amine (101.1 mg, 0.38 mmol, 1.00 equiv), tert-butyl N-[4-[3-(bromomethyl)-4-chlorophenyl]butyl]carbamate (143 mg, 0.38 mmol, 1.00 equiv), DIEA (0.19 mL, 3.00 equiv), acetonitrile (10 mL). The resulting solution was stirred overnight at 50° C. in an oil bath. The resulting mixture was concentrated under vacuum. The resulting solution was extracted with 3×30 mL of ethyl acetate and the organic layers combined. The resulting mixture was washed with 3×80 mL of brine. The solid was dried in an oven under reduced pressure. The residue was applied onto a silica gel column with ethyl acetate/petroleum ether (1:3). This resulted in 180 mg (84%) of tert-butyl N-(4-[4-chloro-3-[([1-[4-(2-cyclopropoxyphenyl)pyridin-3-yl]cyclopropyl]amino)methyl]phenyl]butyl)carbamate (64a) as a yellow oil.

Step 2. N-[[5-(4-aminobutyl)-2-chlorophenyl]methyl]-1-[4-(2-cyclopropoxyphenyl)pyridin-3-yl]cyclopropan-1-amine (Intermediate 64b)

A 100-mL round-bottom flask was charged with tert-butyl N-(4-[4-chloro-3-[([1-[4-(2-cyclopropoxyphenyl)pyridin-3-yl]cyclopropyl]amino)methyl]phenyl]butyl)carbamate (300 mg, 0.53 mmol, 1.00 equiv), dichloromethane (10 mL), trifluoroacetic acid (10 mL). The resulting solution was stirred for 2 h at room temperature. The resulting mixture was concentrated under vacuum. The resulting solution was diluted with 30 mL of ethyl acetate. The pH value of the solution was adjusted to 8-9 with sodium hydroxide (1 mol/L). The resulting solution was extracted with 4×30 mL of ethyl acetate and the organic layers combined and dried over anhydrous sodium sulfate and concentrated under vacuum. This resulted in 235 mg (95%) of N-[[5-(4-aminobutyl)-2-chlorophenyl]methyl]-1-[4-(2-cyclopropoxy-phenyl)pyridin-3-yl]cyclopropan-1-amine (64b) as a light yellow oil.

Step 3. 1-(4-[4-chloro-3-[([1-[4-(2-cyclopropoxy-phenyl)pyridin-3-yl]cyclopropyl]amino) methyl]phenyl]butyl)-3-[(2S,3R,4R,5R)-2,3,4,5,6-pentahydroxyhexyl]urea (I-64)

A 50-mL round-bottom flask was charged with N-[[5-(4-aminobutyl)-2-chlorophenyl]methyl]-1-[4-(2-cyclopropoxyphenyl)pyridin-3-yl]cyclopropan-1-amine (235 mg, 0.51 mmol, 1.00 equiv), DSC (157 mg, 3.20 mmol, 0.20 equiv), N,N-dimethylformamide (10 mL), DIEA (0.1 mL, 1.20 equiv). This was followed by the addition of (2R,3R,4R,5S)-6-aminohexane-1,2,3,4,5-pentol (276 mg, 1.52 mmol, 3.00 equiv) after 2 hr. To this was added hydrogen chloride (1 mol/L) (0.15 mL). The resulting solution was stirred overnight at room temperature. The resulting solution was extracted with 5×50 mL of ethyl acetate and the organic layers combined and dried over anhydrous sodium sulfate and concentrated under vacuum. The crude product was purified by Preparative HPLC with the following conditions: Column, Gemini-NX 5μ C18 110A, AXIA Packed, 150× 21.2 mm; mobile phase, 10 mM aqueous $NH_4HCO_3$ and MeCN (28.0% MeCN up to 56.0% in 8 min); Detector, nm. After lyophilization, to the product in 50 ml of MeCN was added 10 drops of hydrogen chloride (1 mol/L). After lyophilization, this resulted in 123.1 mg (36%) of 1-(4-[4-chloro-3-[([1-[4-(2-cyclopropoxyphenyl)pyridin-3-yl]cyclopropyl]amino)methyl]phenyl]butyl)-3-[(2S,3R,4R,5R)-2,3,4,5,6-pentahydroxyhexyl]urea (I-64) as a white solid. MS (ES, m/z): 669 [M+H]$^+$; $^1$H-NMR (400 MHz, CD$_3$OD) δ 0.40-0.47 (m, 2H), 0.60-0.69 (m, 2H), 1.11 (s, 2H), 1.21 (s, 2H), 1.40-1.53 (m, 2H), 1.55-1.68 (m, 2H), 2.61 (t, J=7.5 Hz, 2H), 3.07-3.21 (m, 3H), 3.32-3.42 (m, 1H), 3.57-3.81 (m, 7H), 4.06 (s, 2H), 7.11-7.39 (m, 6H), 7.47-7.58 (m, 2H), 8.63-8.87 (m, 1H), 8.87 (s, 1H).

Example 20: 1-[4-[5-chloro-4-([1-[4-(2-cyclo-
propoxyphenyl)pyridin-3-yl]cyclopropoxy]methyl)-
2-methylphenyl]butyl]-3-[(2S,3R,4R,5R)-2,3,4,5,6-
pentahydroxyhexyl]urea (I-65)

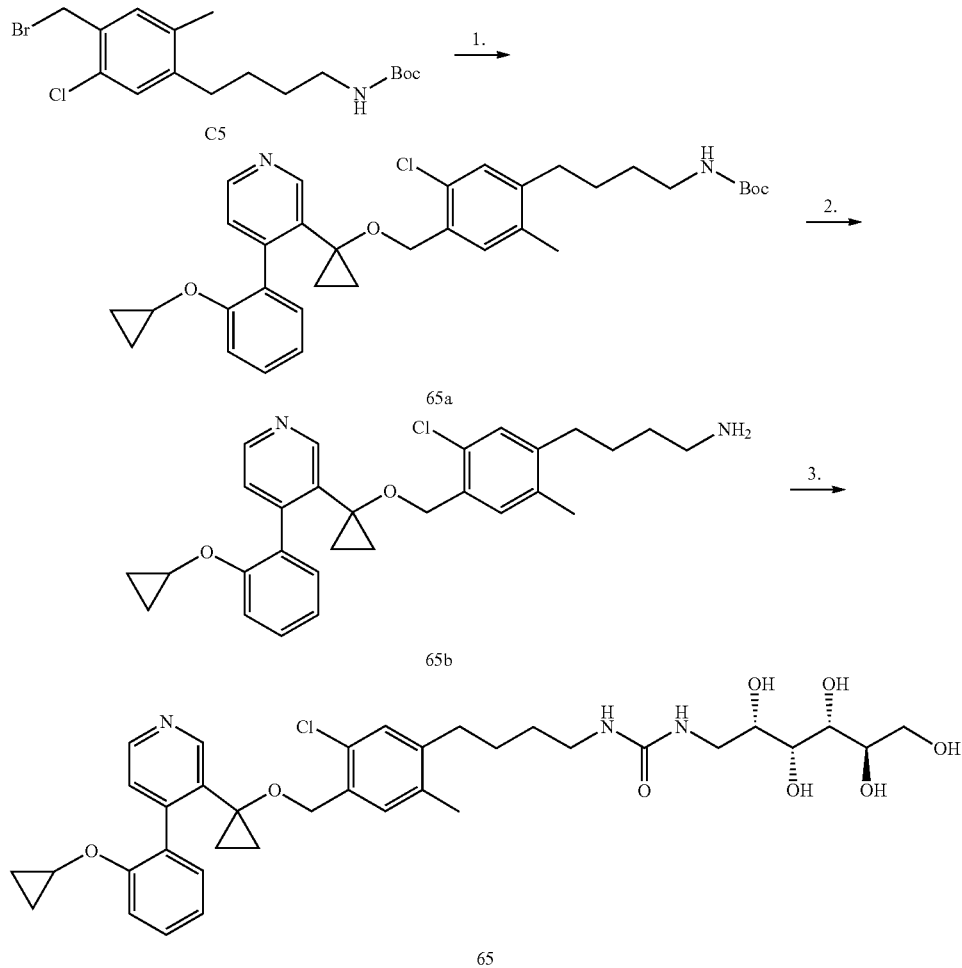

Step 1. tert-butyl N-[4-[5-chloro-4-([1-[4-(2-cyclo-propoxyphenyl)pyridin-3-yl]cyclopropoxy]methyl)-2-methylphenyl]butyl]carbamate (Intermediate 65a)

A 100-mL round-bottom flask was charged with tert-butyl N-[4-[4-(bromomethyl)-5-chloro-2-methylphenyl]butyl]carbamate (C5) (194 mg, 0.50 mmol, 1.00 equiv), 1-[4-(2-cyclopropoxyphenyl)pyridin-3-yl]cyclopropan-1-ol (A23) (140 mg, 0.52 mmol, 1.05 equiv), N,N-dimethylformamide (13 mL). This was followed by the addition of sodium hydride (40 mg, 1.67 mmol, 3.36 equiv) in several batches at 0° C. The resulting solution was stirred for 0.5 h at room temperature. The reaction mixture was cooled to 0° C. with a water/ice bath. The resulting solution was diluted with 20 mL of ethyl acetate. The reaction was then quenched by the addition of 10 mL of NH₄Cl. The resulting solution was extracted with 2×20 mL of ethyl acetate and the organic layers combined. The resulting mixture was washed with 2×20 mL of Brine. The mixture was dried over anhydrous sodium sulfate. The resulting mixture was concentrated under vacuum. This resulted in 143 mg (50%) of tert-butyl N-[4-[5-chloro-4-([1-[4-(2-cyclopropoxyphenyl)pyridin-3-yl]cyclopropoxy]methyl)-2-methylphenyl]butyl]carbamate (65a) as a white solid.

Step 2. 4-[5-chloro-4-([1-[4-(2-cyclopropoxyphenyl)pyridin-3-yl]cyclopropoxy]methyl)-2-methylphenyl]butan-1-amine (Intermediate 65b)

A 100-mL round-bottom flask was charged with tert-butyl N-[4-[5-chloro-4-([1-[4-(2-cyclopropoxyphenyl)pyridin-3-yl]cyclopropoxy]methyl)-2-methylphenyl]butyl]carbamate (65a) (143 mg, 0.25 mmol, 1.00 equiv), TFA/DCM (8/10 mL). The resulting solution was stirred for 1.0 h at room temperature. The resulting mixture was concentrated under vacuum. The resulting solution was diluted with 20 mL of ethyl acetate. The pH value of the solution was adjusted to 9 with sodium bicarbonate (100%). The resulting solution was extracted with 2×20 mL of ethyl acetate and the organic layers combined. The resulting mixture was washed with 1×20 mL of Brine. The mixture was dried over anhydrous sodium sulfate. The solids were filtered out. The resulting mixture was concentrated under vacuum. This resulted in 120 mg (crude) of 4-[5-chloro-4-([1-[4-(2-cyclopropoxyphenyl)pyridin-3-yl]cyclopropoxy]methyl)-2-methylphenyl]butan-1-amine (65b) as a yellow oil.

Step 3. 1-[4-[5-chloro-4-([1-[4-(2-cyclopropoxyphenyl)pyridin-3-yl]cyclopropoxy]methyl)-2-methylphenyl]butyl]-3-[(2S,3R,4R,5R)-2,3,4,5,6-pentahydroxyhexyl]urea (I-65)

A 100-mL round-bottom flask was charged with 4-[5-chloro-4-([1-[4-(2-cyclopropoxyphenyl)pyridin-3-yl]cyclopropoxy]methyl)-2-methylphenyl]butan-1-amine (65b) (120 mg, 0.25 mmol, 1.00 equiv), N,N-dimethylformamide (10 mL), DIEA (0.054 mL), DSC (84.48 mg), The resulting solution was stirred for 1.0 h at room temperature. Then (2S,3S,4S,5R)-6-aminohexane-1,2,3,4,5-pentol (136.8 mg, 0.76 mmol, 3.00 equiv) was added. The resulting solution was stirred for an additional 12 h at room temperature. The solids were filtered out. The resulting mixture was concentrated under vacuum. The crude product was purified by Preparative HPLC with the following conditions: Column, Gemini-NX 5μ C18 110A, AXIA Packed, 150×21.2 mm; mobile phase, 10 mM aqueous NH$_4$HCO$_3$ and MeCN (30.0% MeCN up to 54.0% in 10 min); Detector, 254 nm. This resulted in 50.2 mg (29%) of 1-[4-[5-chloro-4-([1-[4-(2-cyclopropoxyphenyl)pyridin-3-yl]cyclopropoxy]methyl)-2-methylphenyl]butyl]-3-[(2S,3R,4R,5R)-2,3,4,5,6-pentahydroxyhexyl]urea (I-65) as a white solid. MS (ES, m/z): 684 [M+H]$^+$; $^1$H-NMR (400 MHz, CD$_3$OD) δ 0.40 (s, 2H), 0.62 (d, J=6.2 Hz, 2H), 0.91 (s, 3H), 0.99 (s, 2H), 1.53 (q, J=7.1, 6.4 Hz, 4H), 2.21 (s, 3H), 2.57 (t, J=7.3 Hz, 2H), 3.15 (dt, J=12.5, 6.2 Hz, 3H), 3.38 (dd, J=13.9, 4.5 Hz, 1H), 3.49-3.81 (m, 7H), 4.33 (s, 2H), 6.83 (s, 1H), 6.99 (td, J=7.3, 1.4 Hz, 1H), 7.06 (s, 1H), 7.22 (d, J=5.0 Hz, 1H), 7.26-7.43 (m, 3H), 8.46 (d, J=5.1 Hz, 1H), 8.64 (d, J=0.7 Hz, 1H).

Example 21: (2R,3R,4R,5S)-6-(4-(2,5-dichloro-4-((1-(4-(2-cyclopropoxyphenyl)pyridin-3-yl)cyclopropoxy)methyl)phenyl)butylamino)hexane-1,2,3,4,5-pentaol (I-66)

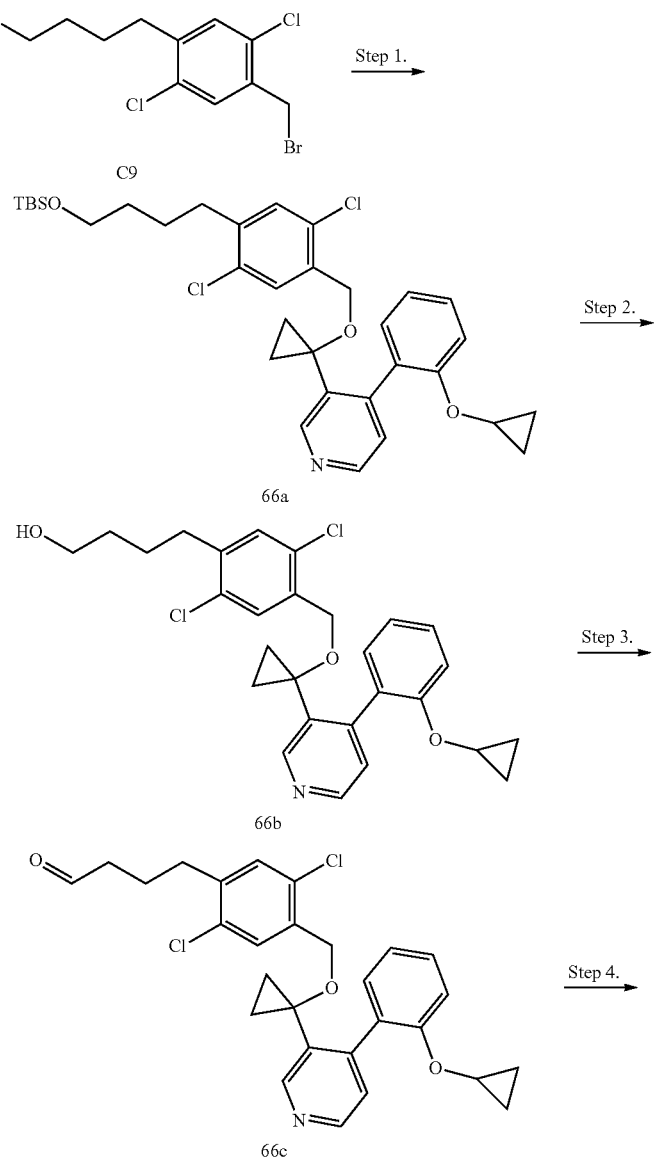

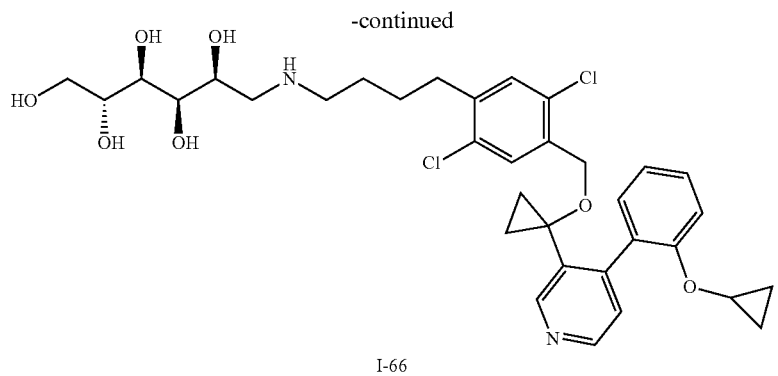

I-66

Step 1. 3-[1-[(4-[4-[(tert-butyldiphenylsilyl)oxy]butyl]-2,5-dichlorophenyl)methoxy]cyclopropyl]-4-(2-cyclopropoxyphenyl)pyridine (Intermediate 66a)

1-[4-(2-cyclopropoxyphenyl)pyridin-3-yl]cyclopropan-1-ol (C9) (3.4 g, 12.72 mmol, 1.00 equiv), [4-[4-(bromomethyl)-2,5-dichlorophenyl]butoxy](tert-butyl)diphenylsilane (7.6 g, 13.81 mmol, 1.09 equiv) were dissolved in N,N-dimethylformamide (100 mL). This was followed by the addition of sodium hydride (60% in oil) (1.5 g, 62.50 mmol, 3.00 equiv), in portions at 0° C. The resulting solution was stirred for 1 h at 0° C. The reaction was then quenched by the addition of 100 mL of water. The resulting solution was extracted with 3×100 mL of ethyl acetate and the organic layers combined. The resulting mixture was washed with 2×200 mL of water and 1×100 mL of sodium chloride sat. The mixture was dried over anhydrous sodium sulfate. The residue was applied onto a silica gel column with ethyl acetate/petroleum ether (1:20-1:10). This resulted in 6.3 g (67%) of 3-[1-[(4-[4-[(tert-butyldiphenylsilyl)oxy]butyl]-2,5-dichlorophenyl)methoxy]cyclopropyl]-4-(2-cyclopropoxyphenyl)pyridine (66a) as brown oil.

Step 2. 4-[2,5-dichloro-4-([1-[4-(2-cyclopropoxyphenyl)pyridin-3-yl]cyclopropoxy]methyl) phenyl]butan-1-ol (Intermediate 66b)

3-[1-[(4-[4-[(tert-butyldiphenylsilyl)oxy]butyl]-2,5-dichlorophenyl)methoxy]cyclopropyl]-4-(2-cyclopropoxyphenyl)pyridine (66a) (4.6 g, 6.24 mmol, 1.00 equiv) was dissolved in tetrahydrofuran (20 mL). This was followed by the addition of TBAF (1.0 M in tetrahydrofuran) (12.5 mL, 2.00 equiv) dropwise with stirring at room temperature. The resulting solution was stirred for 2 h at room temperature. The resulting mixture was concentrated under vacuum. The resulting solution was diluted with 300 mL of ethyl acetate. The resulting mixture was washed with 2×100 mL of water and 1×100 mL of sodium chloride sat. The mixture was dried over anhydrous sodium sulfate. The residue was applied onto a silica gel column with ethyl acetate/petroleum ether (1:4-1:1). This resulted in 2.8 g (90%) of 4-[2,5-dichloro-4-([1-[4-(2-cyclopropoxyphenyl)pyridin-3-yl]cyclopropoxy]methyl)phenyl]butan-1-ol (66b) as a light yellow semi-solid: MS (ES, m/z): 498.15 [M+H]$^+$; $^1$H NMR (CDCl$_3$, 300 MHz, ppm): S: 0.40-0.50 (m, 2H), 0.58-0.70 (m, 2H), 0.80-0.92 (m, 2H), 0.93-1.02 (m, 2H), 1.55-1.75 (m, 4H), 2.68 (t, J=7.2 Hz, 2H), 3.47-3.58 (m, 1H), 3.67 (t, J=6.0 Hz, 2H), 4.34 (s, 2H), 6.95-7.07 (m, 2H), 7.10-7.20 (m, 2H), 7.23-7.35 (m, 2H), 7.36-7.43 (m, 1H), 8.53 (d, J=4.8 Hz, 1H), 8.67 (s, 1H).

Step 3. 4-(2,5-dichloro-4-((1-(4-(2-cyclopropoxyphenyl)pyridin-3-yl)cyclopropoxy)methyl) phenyl) butanal (Intermediate 66c)

4-[2,5-dichloro-4-([1-[4-(2-cyclopropoxyphenyl)pyridin-3-yl]cyclopropoxy]methyl)phenyl]butan-1-ol (66b) (996 mg, 2.00 mmol) was dissolved in dry dichloromethane (20 mL) under a nitrogen atmosphere. Dess-Martin Periodinane (1.017 g, 2.40 mmol) was added and the reaction mixture was stirred at room temperature for 30 minutes at which point LCMS indicated complete conversion to the aldehyde. The crude mixture was diluted with dichloromethane and washed successively with 20 mL portions of 15% Na$_2$S$_2$O$_3$, saturated NaHCO$_3$, and brine. The resulting solution was dried over Na$_2$SO$_4$ and purified by flash chromatography (24 g SiO$_2$. DCM to 25% EtOAc in DCM over 15 minutes) to give 939 mg of intermediate 66c (95%) as a clear oil.

Step 4. (2R,3R,4R,5S)-6-(4-(2,5-dichloro-4-((1-(4-(2-cyclopropoxyphenyl)pyridin-3-yl) cyclopropoxy) methyl)phenyl)butylamino)hexane-1,2,3,4,5-pentaol (I-66)

4-(2,5-dichloro-4-((1-(4-(2-cyclopropoxyphenyl)pyridin-3-yl)cyclopropoxy)methyl) phenyl)butanal (66c) (939 mg, 1.90 mmol) was dissolved in dichloromethane/methanol (1:1, 20 mL). D-Glucamine (377 mg, 2.08 mmol) was added and the mixture stirred at room temperature for 15 minutes. NaBH(OAc)$_3$ (483 mg, 2.28 mmol) was added and the reaction mixture stirred at room temperature for a further 1 hour, at which point LCMS indicated complete conversion. The crude mixture was diluted with dichloromethane and washed successively with 30 mL portions of saturated NaHCO$_3$, water, and brine. The resulting solution was dried over Na$_2$SO$_4$ to give 1.18 g of I-66 (95%) as a free base. A portion of this material was purified by preparative HPLC (10 to 95% MeCN in H$_2$O with 0.1% TFA) to give I-66 (19.5 mg) as the TFA salt. MS (ES, m/z): 661.30 [M+H]$^+$; $^1$H-NMR (400 MHz, DMSO-d$_6$) δ 8.37 (s, 1H), 8.23 (d, J=4.4 Hz, 1H), 7.95 (s, 2H), 7.05 (s, 2H), 6.99 (d, J=8.4 Hz, 1H), 6.92 (d, J=5.9 Hz, 2H), 6.70-6.57 (m, 2H), 5.40 (d, J=1.0 Hz, 2H), 3.26 (dd, J=22.0, 15.2 Hz, 11H), 3.08 (dd, J=15.7, 10.8 Hz, 6H), 2.69 (s, 2H), 2.56 (s, 3H), 2.30 (s, 2H), 2.14 (s, 5H), 1.21 (s, 4H), 0.61 (d, J=10.8 Hz, 4H), 0.28 (d, J=10.8 Hz, 4H), 0.28 (d, J=5.9 Hz, 2H).

The following amino alcohols were prepared as the free base from 4-(2,5-dichloro-4-((1-(4-(2-cyclopropoxyphenyl)pyridin-3-yl)cyclopropoxy)methyl)phenyl)butanal using the same method as described in Example 21 substituting the described amine for D-Glucamine.

TABLE 3

Intermediates G1-G5

| Intermediate No. | Compound Structure | Amine Reagent | Observed Mass [M + H]+ |
|---|---|---|---|
| G1 | 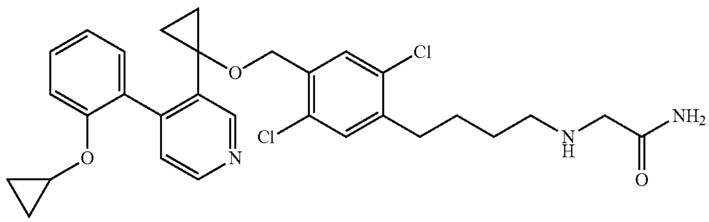 [SMILES: NC(=O)CNCCCCc1cc(Cl)c(COC2(c3cnccc3-c3ccccc3OC3CC3)CC2)cc1Cl] | 2-amino acetamide | 554.51 |
| G2 | 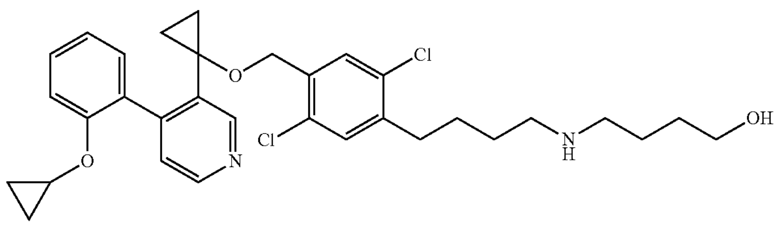 [SMILES: OCCCCNCCCCc1cc(Cl)c(COC2(c3cnccc3-c3ccccc3OC3CC3)CC2)cc1Cl] | 4-amino butan-1-ol | 569.56 |
| G3 | 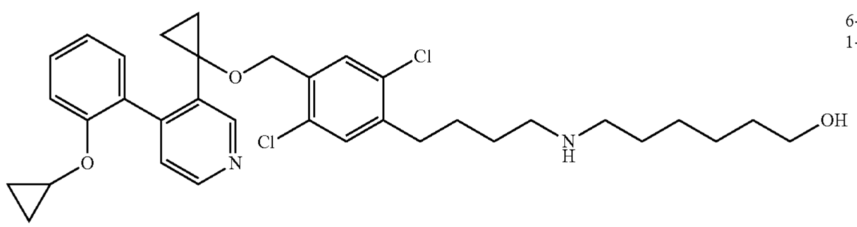 [SMILES: OCCCCCCNCCCCc1cc(Cl)c(COC2(c3cnccc3-c3ccccc3OC3CC3)CC2)cc1Cl] | 6-aminohexan-1-ol | 597.61 |
| G4 | 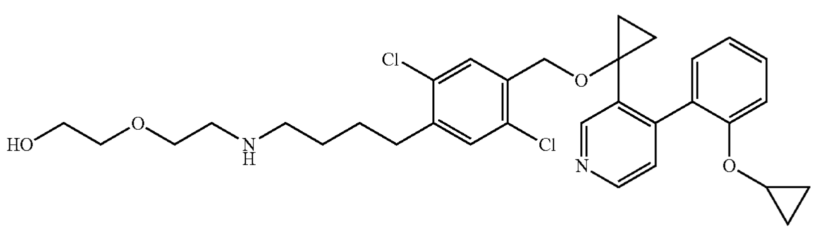 [SMILES: OCCOCCNCCCCc1cc(Cl)c(COC2(c3cnccc3-c3ccccc3OC3CC3)CC2)cc1Cl] | 2-(2-amino-ethoxy)-ethanol | 585.56 |
| G5 | 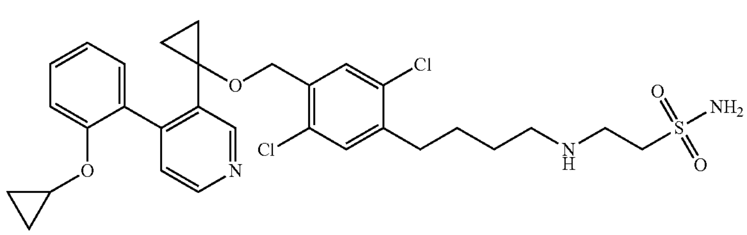 [SMILES: NS(=O)(=O)CCNCCCCc1cc(Cl)c(COC2(c3cnccc3-c3ccccc3OC3CC3)CC2)cc1Cl] | 2-aminoethane sulfonamide | 604.59 |

Example 22: N-(4-(2,5-dichloro-4-((1-(4-(2-cyclo-propoxyphenyl)pyridin-3-yl)cyclopropoxy) methyl)phenyl)butyl)-N-((2S,3R,4R,5R)-2,3,4,5,6-pentahydroxyhexyl)tetrahydro-2H-pyran-4-carboxamide
(I-67)

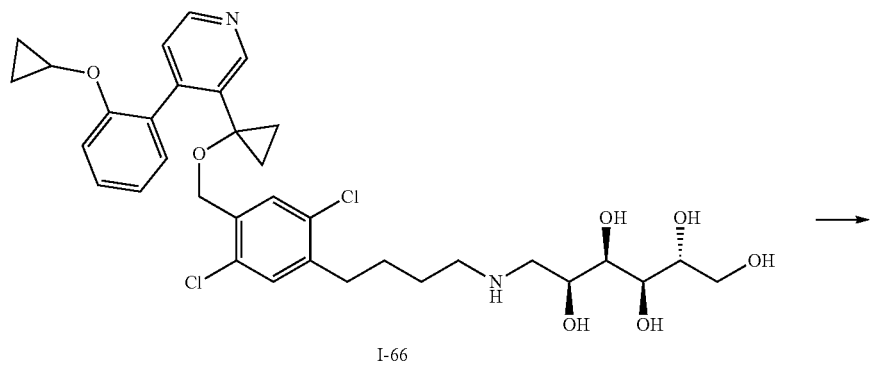

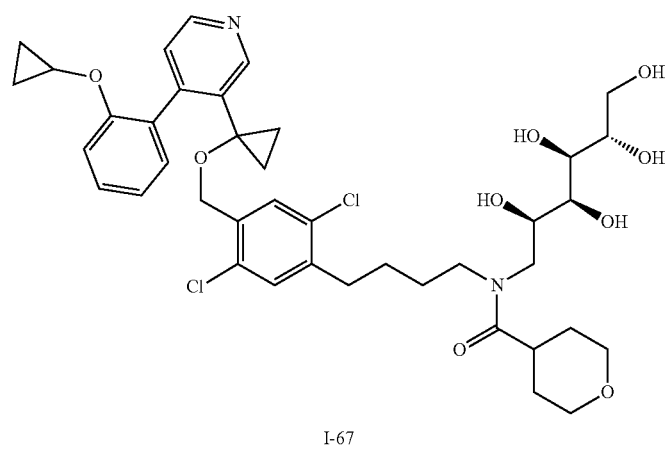

(2R,3R,4R,5S)-6-(4-(2,5-dichloro-4-((1-(4-(2-cyclopropoxyphenyl)pyridin-3-yl)cyclopropoxy)methyl)phenyl) butylamino)hexane-1,2,3,4,5-pentaol (I-66) (30 mg, 0.044 mmol) in N,N-dimethylformamide (0.25 mL) was added tetrahydro-2H-pyran-4-carboxylic acid (8.6 mg, 0.066 mmol), DIEA 8.5 mg, 0.066 mmol), and finally HATU (25.7 mg, 0.066 mmol). After stirring at room temperature for 17.5 hours, LCMS showed complete conversion to the product with some over-acylation. The crude mixture was diluted with MeCN (1 mL) and then H$_2$O (3 mL). TFA was added until the solution was acidic, and the resulting clear solution was purified by preparative HPLC (10 to 95% MeCN in H$_2$O over 30 minutes). The product fractions were collected and neutralized with Amberlyst A26 hydroxide resin until pH 6-7. The resulting mixture was filtered and lyophilized to provide 9.0 mg of Compound I-67 (25%) as a TFA salt. MS (ES, m/z): 773.4 [M+H]$^+$; $^1$H-NMR (400 MHz, DMSO-d$_6$) δ 8.75 (s, 1H), 8.62 (d, J=5.0 Hz, 1H), 7.44-7.31 (m, 4H), 7.29 (d, J=7.2 Hz, 1H), 7.04-6.95 (m, 1H), 6.93 (s, 1H), 4.24 (s, 3H), 3.87-3.76 (m, 4H), 3.76-3.68 (m, 5H), 3.22-3.10 (m, 2H), 3.04-2.91 (m, 2H), 2.71-2.58 (m, 3H), 1.65-1.49 (m, 3H), 1.49-1.36 (m, 4H), 1.01 (d, J=11.7 Hz, 4H), 0.63 (d, J=6.1 Hz, 2H), 0.32 (s, 2H).

The following compounds were prepared from I-66 according to the procedure described in Example 22 substituting the described acid for tetrahydro-2H-pyran-4-carboxylic acid:

TABLE 4

Compounds 1-68 to 1-74

| Cmpd No.: | Compound structure | Carboxylic acid reagent | Observed Mass [M + H]+ |
|---|---|---|---|
| I-68 | 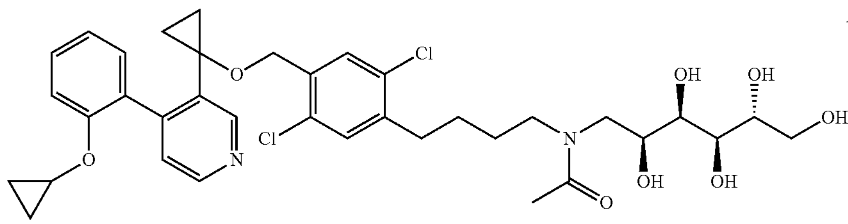 [SMILES: CC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | Acetic acid | 703 |
| I-69 | 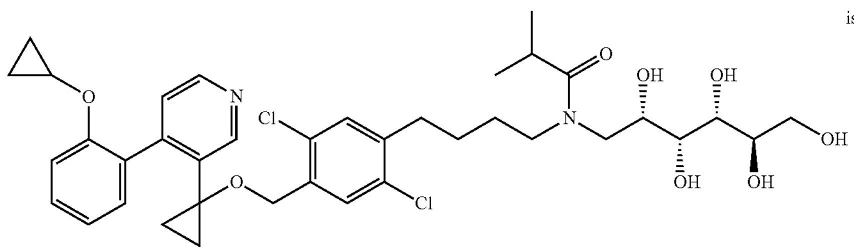 [SMILES: CC(C)C(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | isobutyric acid | 731 |
| I-70 | 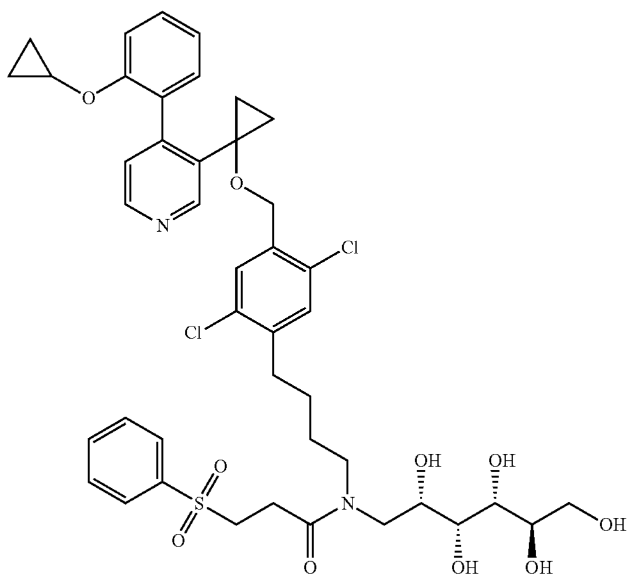 [SMILES: O=C(CCS(=O)(=O)c1ccccc1)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 3-(phenylsulfonyl) propanoic acid | 857 |
| I-71 | 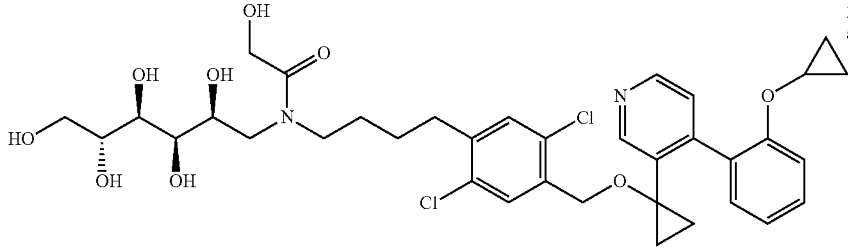 [SMILES: O=C(CO)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 2-hydroxyacetic acid | 719 |

TABLE 4-continued
Compounds 1-68 to 1-74
| Cmpd No.: | Compound structure | Carboxylic acid reagent | Observed Mass [M + H]+ |
|---|---|---|---|
| I-72 | 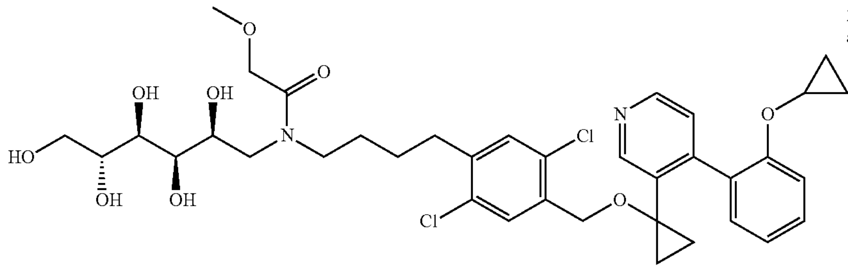 [SMILES: CCCC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 2-methoxyacetic acid | 733 |
| I-73 | 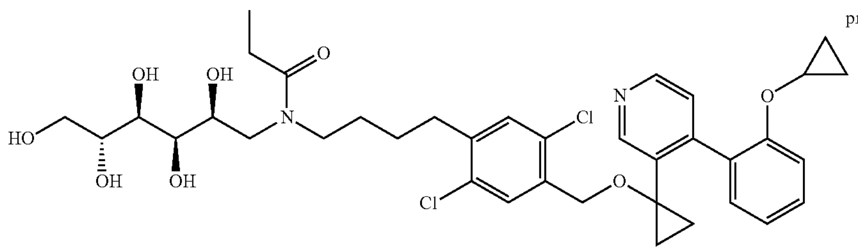 | propionic acid | 717 |
| I-74 | 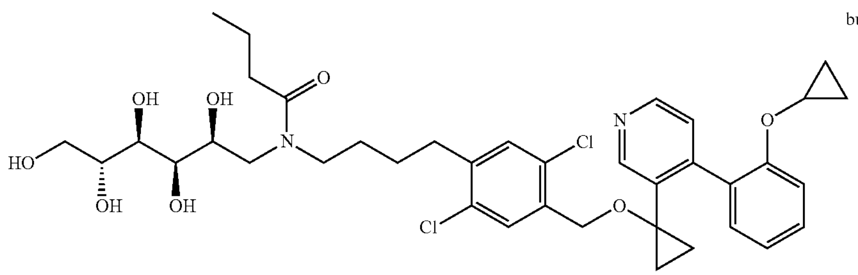 | butyric acid | 731 |
Example 23: N-(4-(2,5-dichloro-4-((1-(4-(2-cyclo-propoxyphenyl)pyridin-3-yl)cyclopropoxy) methyl) phenyl)butyl)-3-methoxy-N-((2S,3R,4R,5R)-2,3,4,5,6-pentahydroxyhexyl)propanamide (I-75)
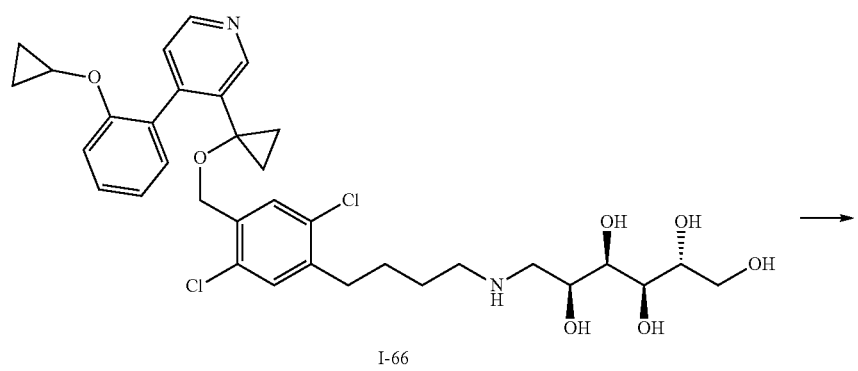
I-66

-continued

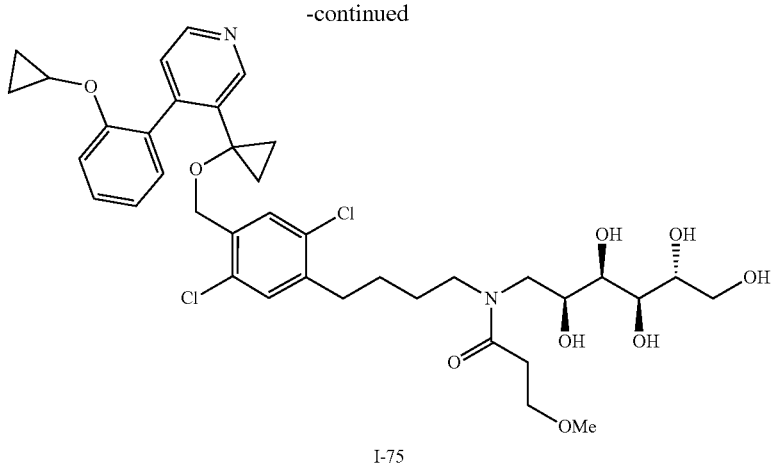

I-75

A solution of (2R,3R,4R,5S)-6-(4-(2,5-dichloro-4-((1-(4-(2-cyclopropoxyphenyl) pyridin-3-yl)cyclopropoxy)methyl)phenyl)butylamino)hexane-1,2,3,4,5-pentaol (66) (41 mg, 0.061 mmol) in DCM (0.5 mL) was added TEA (9.3 mg, 0.09 mmol) followed by 3-methoxypropanoyl chloride (7.5 mg, 0.061 mmol). After 5 hours, additional 3-methoxypropanoyl chloride (15 mg, 0.12 mmol) was added. After a further 16 hours, the starting material was consumed giving a mixture of over-acylated products. The reaction mixture was diluted with EtOAc (2 mL), washed with brine (2 mL) and dried over $Na_2SO_4$. The solvent was removed and the crude residue diluted with a mixture of THF/MeOH (1.2 mL, 1:1). 1N NaOH (0.3 mL) was added and the mixture stirred for 30 minutes at which point only the desired product was observed. The solvent was removed and the reaction mixture was diluted with MeCN (1 mL) and $H_2O$ (3 mL) and acidified with TFA. Purification by preparative HPLC (10-90% over 30 minutes) gave 14.5 mg of I-75 as a TFA salt. MS (ES, m/z): 747 [M+H]$^+$; $^1$H-NMR (400 MHz, DMSO-$d_6$) δ 8.76 (s, 1H), 8.63 (d, J=5.8 Hz, 1H), 7.45-7.26 (m, 6H), 7.00 (t, J=7.7 Hz, 1h), 6.94 (d, J=5.6 Hz, 1H), 4.24 (s, 3H), 3.19 (s, 5H), 2.69-2.60 (m, 6H), 1.57-1.49 (m, 2H), 1.45 (s, 3H), 1.01 (d, J=11.6 Hz, 4H), 0.63 (d, J=6.5 Hz, 2H), 0.33 (s, 2H).

The following compounds (Table 5) were prepared according to the procedure described in Example 23 from (2R,3R,4R,5S)-6-(4-(2,5-dichloro-4-((1-(4-(2-cyclopropoxy-phenyl)pyridin-3-yl)cyclopropoxy)methyl)phenyl)butylamino)hexane-1,2,3,4,5-pentaol (I-66) substituting the described reagent for 4-methoxybutanoyl chloride.

TABLE 5

Compounds 1-76 to 1-77

| Cmpd No.: | Compound Structure | Reagent | Observed Mass [M + H]$^+$ |
|---|---|---|---|
| 1-76 | 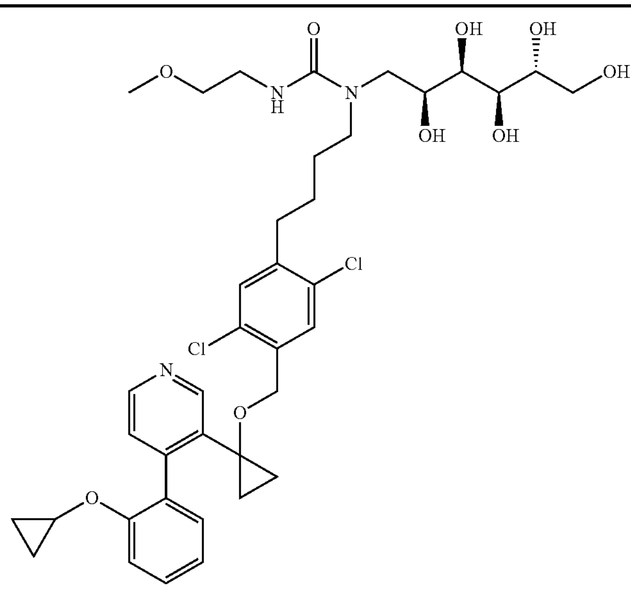 | 1-isocyanato-2-methoxyethane | 762.08 [M + H]$^+$ |

TABLE 5-continued

Compounds 1-76 to 1-77

| Cmpd No.: | Compound Structure | Reagent | Observed Mass [M + H]+ |
|---|---|---|---|
| 1-77 | 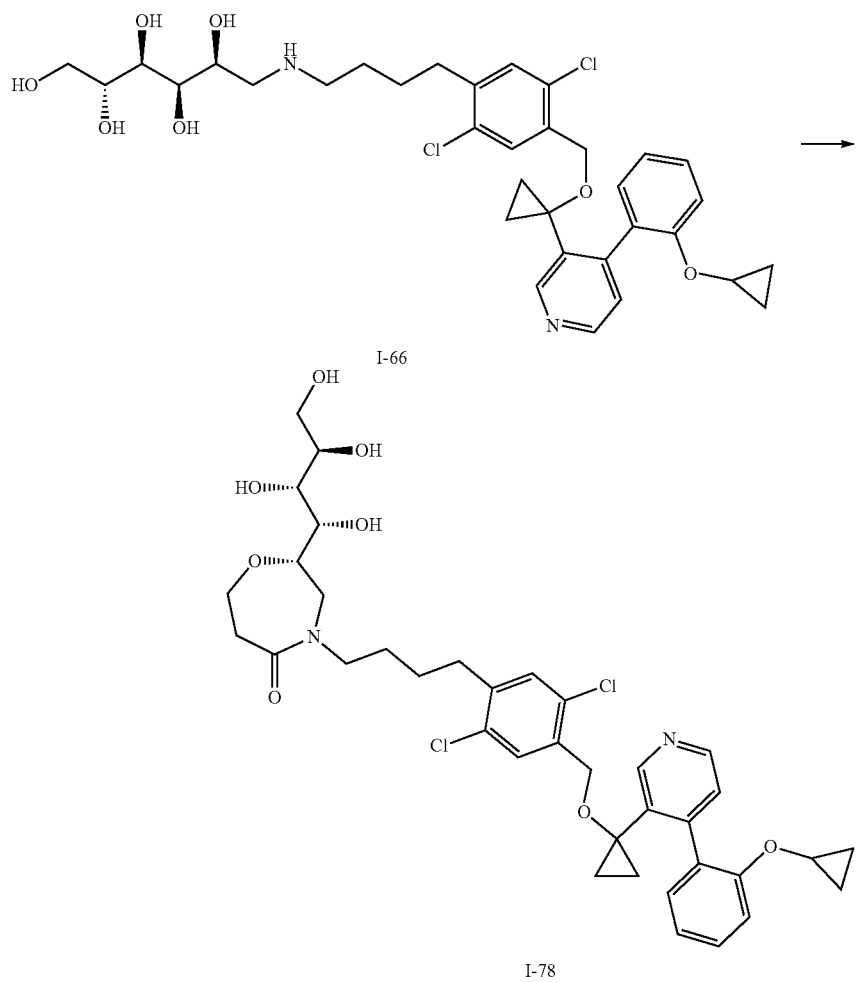 | Disuccinimidyl carbonate | 687.20 [M + H]+ |

Example 24: (S)-4-(4-(2,5-dichloro-4-((1-(4-(2-cyclopropoxyphenyl)pyridin-3-yl) cyclopropoxy) methyl)phenyl)butyl)-2-((1S,2R,3R)-1,2,3,4-tetrahydroxybutyl)-1,4-oxazepan-5-one (I-78)

solution of (2R,3R,4R, 5S)-6-(4-(2,5-dichloro-4-((1-(4-(2-cyclopropoxyphenyl)pyridin-3-yl) cyclopropoxy)methyl)phenyl)butylamino)hexane-1,2,3,4,5-pentaol (I-66) (30 mg, 0.044 mmol) in DMF (0.25 mL) was added DIEA (8.5 mg, 0.066 mmol) followed by 3-(phenylsulfonyl)propanoic acid (S)-4-(4-(2,5-dichloro-4-((1-(4-(2-cyclopropoxyphenyl) pyridin-3-yl)cyclopropoxy) methyl)phenyl)butyl)-2-((1S, 2R,3R)-1,2,3,4-tetrahydroxybutyl)-1,4-oxazepan-5-one: A (9.3 mg, 0.044 mmol) and finally HATU (25.7 mg, 0.066 mmol). After 3.5 hours a mixture of product and overacylation was observed. The reaction mixture was diluted with MeOH (0.5 mL) and NaOMe (50 μL, 25 wt % in MeOH) was added. After 30 minutes LCMS showed complete conversion to the cyclized product. The solvent was removed and the crude residue was diluted with MeCN (1 mL) and H₂O (3 mL), and acidified with TFA. Purification by preparative HPLC (10-90% over 30 minutes) gave 10.0 mg of Example I-78 as a TFA salt. MS (ES, m/z): 715.4 [M+H]⁺; ¹H-NMR (400 MHz, DMSO-d₆) δ 8.75 (s, 1H), 8.62 (d, J=5.5 Hz, 1H), 7.47-7.31 (m, 4H), 7.29 (d, J=7.2 Hz, 1H), 7.00 (t, J=8.1 Hz, 1H), 6.94 (s, 1H), 4.24 (s, 2H), 2.69-2.60 (m, 4H), 1.56-1.38 (m, 4H), 1.00 (d, J=11.0 Hz, 4H), 0.63 (d, J=5.0 Hz, 2H), 0.33 (s, 2H).

Example 25: 1-(4-(2,5-dichloro-4-((1-(4-(2-cyclopropoxyphenyl)pyridin-3-yl)cyclopropoxy) methyl) phenyl)butyl)-3-methyl-1-(2S,3R,4R,5R)-2,3,4,5,6-pentahydroxyhexyl)urea (I-79)

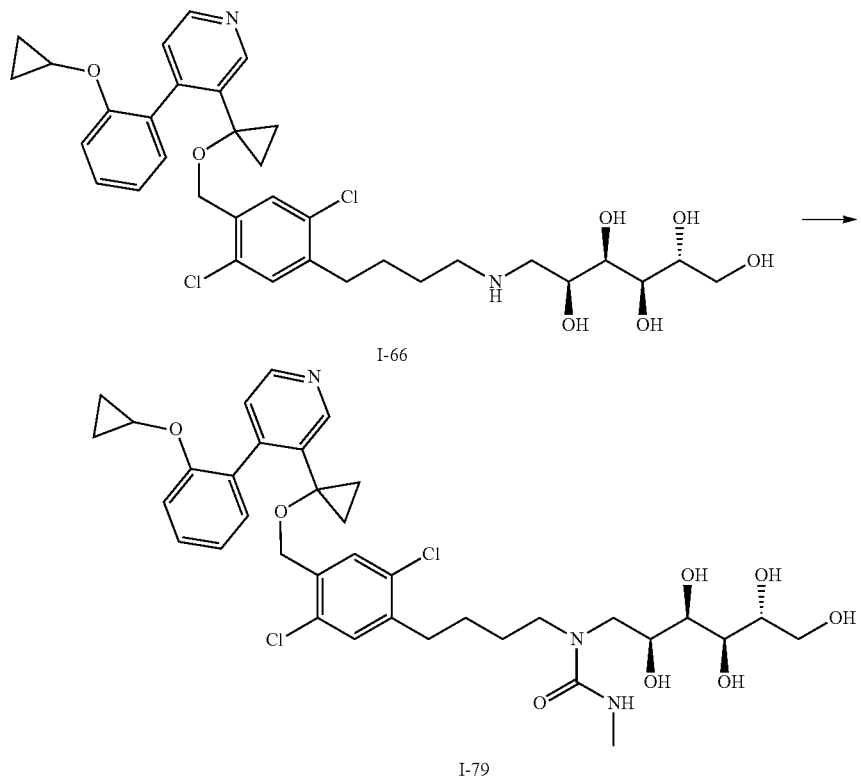

A suspension of (2R,3R,4R,5S)-6-(4-(2,5-dichloro-4-((1-(4-(2-cyclopropoxy-phenyl)pyridin-3-yl)cyclopropoxy) methyl)phenyl)butylamino)hexane-1,2,3,4,5-pentaol (I-66) (182 mg, 0.275 mmol) in dry DMF (1.0 mL) under a N₂ atmosphere was added TEA (42 mg, 0.415 mmol) and then 2,5-dioxopyrrolidin-1-yl methylcarbamate (47 mg, 0.275 mmol). After 18 hours LCMS indicated complete conversion to the product. The crude reaction mixture was diluted with MeCN (1 mL) and H₂O (3 mL) and acidified with TFA. Purification by preparative HPLC (10-95% over 30 minutes) gave 85 mg of Example 79 contaminated with 15% of the TFA ester byproduct. This mixture was dissolved in MeOH (1 mL) and NaOMe (20 μL, 25 wt % in MeOH) was added. After 2 hours, only product remained. Amberlite IR-120(H) resin (50 mg) was added and the mixture was stirred for 10 minutes. After filtration, the solvent was removed and lyophilization from MeCN/H₂O (1:1, 2.0 mL) gave 64 mg of Example I-79 as a TFA salt. MS (ES, m/z): 718.12 [M+H]⁺; ¹H-NMR (400 MHz, DMSO-d₆) δ 8.85 (s, 1h), 8.72 (d, J=5.6 Hz, 1H), 7.57 (d, J=5.3 Hz, 1H), 7.44 (d, J=8.7 Hz, 1H), 7.35 (dd, J=16.2, 7.0 Hz, 3H), 7.03 (t, J=7.3 Hz, 1H), 6.92 (s, 1H), 4.25 (s, 4H), 3.70 (s, 1H), 3.60 (d, J=14.9 Hz, 2H), 3.55 (s, 2H), 3.46 (s, 2H), 3.37 (dd, J=10.9, 5.2 Hz, 1H), 3.32-3.06 (m, 5H), 2.64 (s, 2H), 2.54 (s, 4H), 2.52-2.43 (m, 6H), 1.45 (s, 4H), 1.06 (d, J=14.7 Hz, 4H), 0.64 (d, J=5.9 Hz, 2H), 0.34 (s, 2H).

Example 26: N-(4-(2,5-dichloro-4-((1-(4-(2-cyclopropoxyphenyl)pyridin-3-yl)cyclopropoxy) methyl) phenyl)butyl)-N-((2S,3R,4R,5R)-2,3,4,5,6-pentahydroxyhexyl)formamide (I-80)

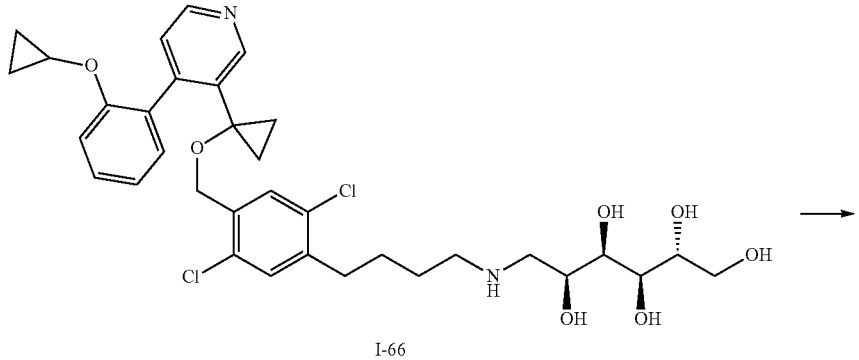

I-66

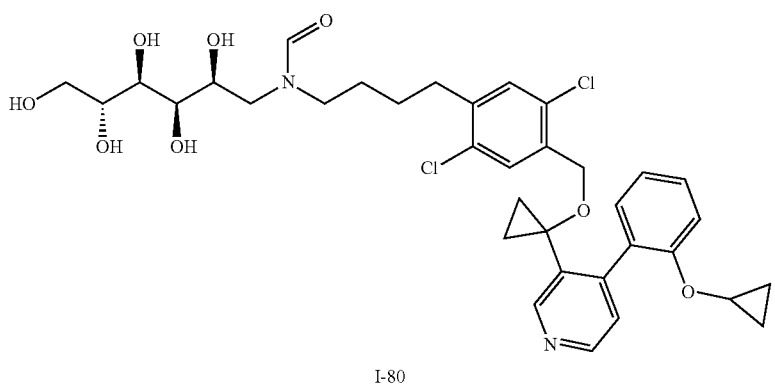

I-80

Formic acid (51.1 mg, 1.11 mmol) and acetic anhydride (75 mg, 0.74 mmol) were stirred at 0° C. for 10 minutes. A solution of (2R,3R,4R,5S)-6-(4-(2,5-dichloro-4-((1-(4-(2-cyclopropoxyphenyl)pyridin-3-yl)cyclopropoxy)methyl) phenyl)butylamino)hexane-1,2,3,4,5-pentaol (I-66, 49 mg, 0.074 mmol) in THF (0.2 mL) was added and the reaction mixture was allowed to warm to room temperature. After 2 hours, no starting material remained, and LCMS showed a mixture of acylated and formylated product. EtOAc (5 mL) was added, and the reaction mixture was washed with saturated NaHCO$_3$ (2×5 mL), water (2×5 mL) and dried over Na$_2$SO$_4$. The solvent was removed, and the crude residue diluted with MeOH (0.5 mL). NaOMe (20 μL, 25 wt % in MeOH) was added. After 15 minutes LCMS showed only the desired product. The solvent was removed, and the crude residue diluted with MeCN (1 mL), H$_2$O (3 mL), and acidified with TFA. This solution was purified by preparative HPLC (10-95% over 30 minutes). The product fractions were combined and neutralized with Amberlyst A26 hydroxide resin to pH 6-7. After filtration, lyophilization gave the desired compound (I-80, 10.5 mg) as a TFA salt. MS (ES, m/z): 689 [M+H]$^+$; $^1$H-NMR (400 MHz, DMSO-d$_6$) δ 8.64 (s, 1H), 8.50 (s, 1H), 8.04-8.00 (m, 1H), 7.91 (s, 1H), 7.36 (d, J=7.8 Hz, 2H), 7.31 (s, 1H), 7.23 (s, 1H), 7.13 (s, 1H), 6.95 (s, 2H), 4.56-4.9 (m, 3H), 4.21 (s, 2H), 3.55 (s, 9H), 2.99 (s, 2H), 2.98 (s, 3H), 2.62 (s, 5H), 1.45 (s, 5H), 0.93 (s, 4H), 0.59 (s, 2H), 0.30 (s, 2H).

Example 26: (2R,3S,4R,5R)-N-(4-(2,5-dichloro-4-((1-(4-(2-cyclopropoxyphenyl)pyridin-3-yl)cyclopropoxy)methyl)phenyl)butyl)-2,3,4,5,6-pentahydroxy-N-(4-hydroxybutyl)hexanamide (I-81)
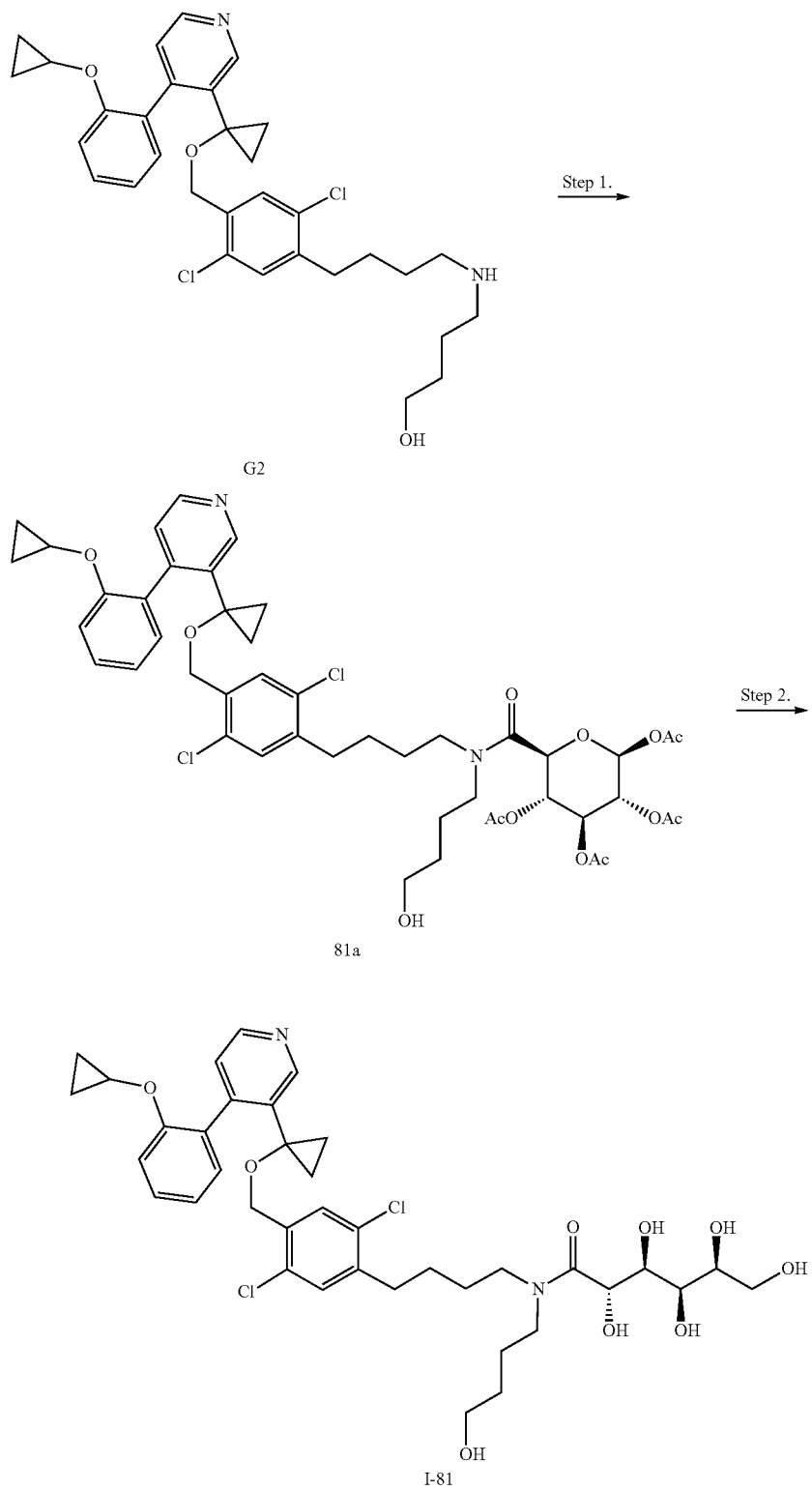

Step 1. (2S,3R,4S,5S,6S)-6-((4-(2,5-dichloro-4-((1-(4-(2-cyclopropoxyphenyl)pyridin-3-yl)cyclopropoxy)methyl)phenyl)butyl)(4-hydroxybutyl)carbamoyl)tetrahydro-2H-pyran-2,3,4,5-tetrayl tetraacetate (Intermediate 81a)

A solution of G2 (284 mg, 0.50 mmol) in DMF (5 mL) was added (2S,3S,4S,5R,6S)-3,4,5,6-tetraacetoxytetrahydro-2H-pyran-2-carboxylic acid (181 mg, 0.50 mmol) and DIEA 97 mg, 0.75 mmol). HATU (285 mg, 0.75 mmol) was added and the reaction mixture was stirred for 16 hours. The crude solution was diluted with EtOAc (10 mL), washed with saturated NaHCO$_3$ (5 mL) and brine (5 mL), and dried over Na$_2$SO$_4$. Purification by flash chromatography (12 g SiO$_2$, DCM to 5% MeOH in DCM over 15 minutes) provided 408 mg (89%) of intermediate 81a as an oil.

Step 2. (2S,3S,4R,5S)-N-(4-(2,5-dichloro-4-((1-(4-(2-cyclopropoxyphenyl)pyridin-3-yl) cyclopropoxy)methyl)phenyl)butyl)-2,3,4,5,6-pentahydroxy-N-(4-hydroxybutyl) hexanamide (I-81)

81a (408 mg, 0.44 mmol) was dissolved in MeOH (1 mL) and NaOMe solution (100 μL, 25 wt % in MeOH) was added. After 90 minutes, no starting material remained. NaBH$_4$ (92 mg, 2.5 mmol) was added. After a further 30 minutes, the reaction was complete and the solvent was removed. The crude residue was diluted with MeCN (9 mL) and water (9 mL) and acidified with TFA. After purification by preparative HPLC (10% to 60% MeCN in H$_2$O with 0.1% TFA over 30 minutes), the combined product fractions were neutralized (pH 6-7) with Amberlyst A26 hydroxide resin. Filtration followed by lyophilization provided 26 mg of Compound I-81 (7%) as a white solid. MS (ES, m/z): 747 [M+H]$^+$; $^1$H-NMR (400 MHz, DMSO-d$_6$) δ 8.70 (s, 1H), 8.55 (s, 1H), 7.38 (d, J=5.4 Hz, 2H), 7.33 (d, J=8.2 Hz, 1H), 7.30-7.20 (m, 3H), 7.11 (s, 1H), 6.98 (d, J=8.8 Hz, 2H), 4.30 (d, J=8.5 Hz, 1h), 4.24 (s, 3H), 2.65 (s, 3H), 1.49 (s, 7H), 1.38 (s, 2H), 0.96 (s, 2H), 0.33 (s, 2H).

The following examples n Table 6 were made according to the procedure used in Example 26 from the appropriate starting amine in Table 3.

TABLE 6

Compounds 1-82 to 1-85

| Cmpd. No.: | Compound Structure | Starting Amine | Observed Mass [M + H]$^+$ |
|---|---|---|---|
| 1-82 | 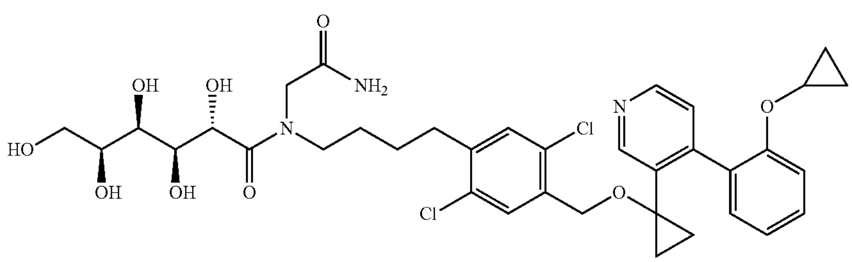 [SMILES: NC(=O)CN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | G1 | 732 [M + H]$^+$ |
| 1-83 | 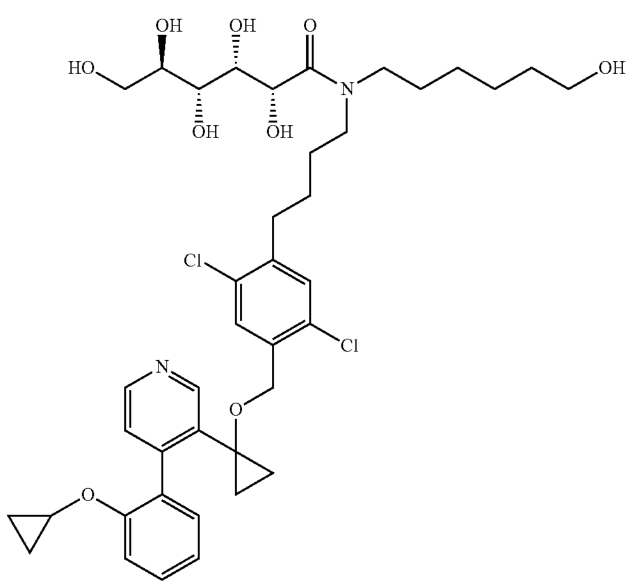 [SMILES: O=C([C@H](O)[C@@H](O)[C@H](O)[C@H](O)CO)N(CCCCCCO)CCCCc1cc(Cl)c(COC2(c3cnccc3-c3ccccc3OC3CC3)CC2)cc1Cl] | G3 | 775 [M + H]$^+$ |

TABLE 6-continued
Compounds 1-82 to 1-85
| Cmpd. No.: | Compound Structure | Starting Amine | Observed Mass [M + H]+ |
|---|---|---|---|
| 1-84 | 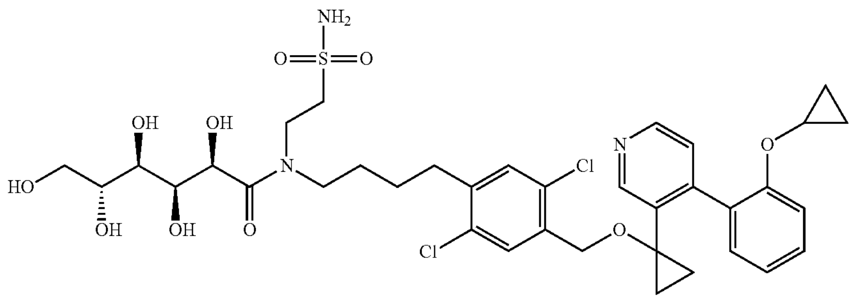 [SMILES: NS(=O)(=O)CCN(CCCCc1cc(Cl)c(COC2(c3cnccc3-c3ccccc3OC3CC3)CC2)cc1Cl)C(=O)[C@H](O)[C@@H](O)[C@H](O)[C@H](O)CO] | G5 | 782 [M + H]+ |
| 1-85 | 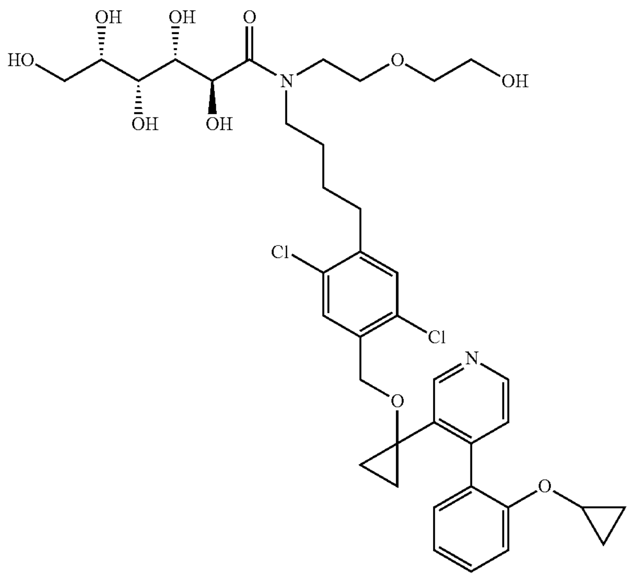 [SMILES: O=C([C@@H](O)[C@@H](O)[C@H](O)[C@@H](O)CO)N(CCCCc1cc(Cl)c(COC2(c3cnccc3-c3ccccc3OC3CC3)CC2)cc1Cl)CCOCCO] | G4 | 763 [M + H]+ |
Example 27: 1-(4-(2,5-dichloro-4-((1-(4-(2-cyclo-propoxyphenyl)pyridin-3-yl)cyclopropoxy) methyl) phenyl)butyl)-1-(2-(2-hydroxyethoxy)ethyl)-3-((2S, 3R,4R,5R)-2,3,4,5,6-pentahydroxyhexyl)urea (I-86)
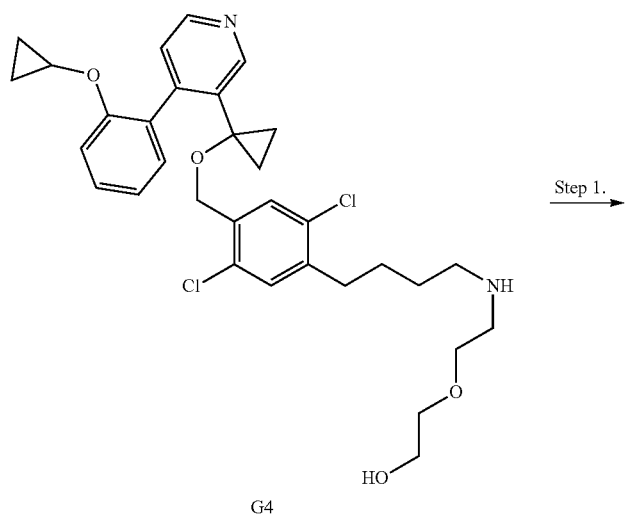

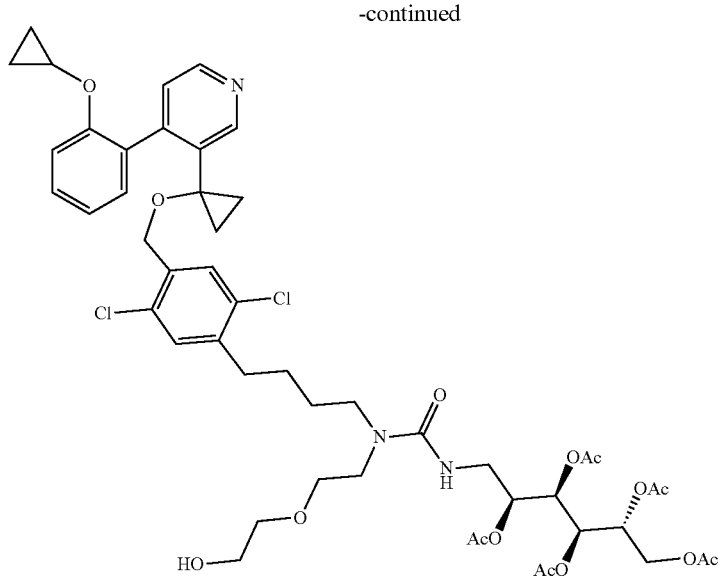

86a

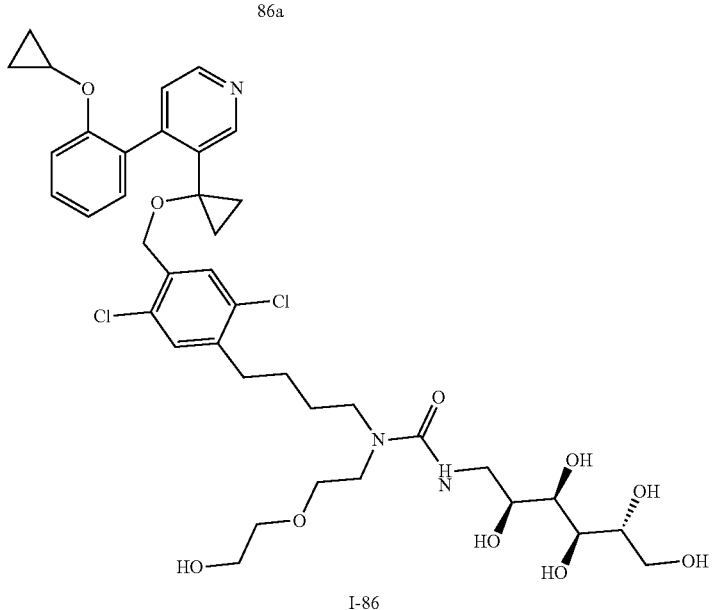

I-86

Step 1. (2R,3R,4R,5S)-6-(3-(4-(2,5-dichloro-4-((1-(4-(2-cyclopropoxyphenyl)pyridin-3-yl)cyclopropoxy)methyl)phenyl)butyl)-3-(2-(2-hydroxyethoxy)ethyl)ureido)hexane-1,2,3,4,5-pentayl pentaacetate (Intermediate 86a)

A solution of intermediate G4 (280 mg, 0.48 mmol) and TEA (63 mg, 0.624 mmol) in dichloromethane (4 mL) was added as solution of (2R,3R,4R,5S)-6-isocyanatohexane-1,2,3,4,5-pentayl pentaacetate (260 mg, 0.624 mmol) in dichloromethane (1 mL). After 24 hours, additional TEA (63 mg, 0.624 mmol) and ((2R,3R,4R,5S)-6-isocyanatohexane-1,2,3,4,5-pentayl pentaacetate (D10) (41 mg, 0.1 mmol) in DCM (0.2 mL) was added. After a further 5 minutes, the reaction was complete. The crude mixture was diluted with dichloromethane (15 mL), washed with saturated NaHCO₃ solution (15 mL), water (15 mL) and brine (15 mL), and dried over Na₂SO₄. The solvent was removed to give crude Intermediate 86a as an oil which was used without further purification.

Step 2. 1-(4-(2,5-dichloro-4-((1-(4-(2-cyclopropoxyphenyl)pyridin-3-yl)cyclopropoxy) methyl)phenyl)butyl)-1-(2-(2-hydroxyethoxy)ethyl)-3-((2S,3R,4R,5R)-2,3,4,5,6-pentahydroxyhexyl)urea (I-86)

Crude Intermediate 86a was diluted with MeOH (2 mL). NaOMe (50 µL, 25 wt % in MeOH) was added, and the reaction mixture was stirred for 1 hour. The solvent was removed, the crude residue was diluted with MeCN (4 mL) and water (4 mL), and the sample was acidified with TFA. After purification by preparative HPLC (30% to 95% MeCN in H₂O with 0.1% TFA over 18 minutes), the product fractions were combined and neutralized with Amberlyst A26 hydroxide resin. Filtration and lyophilization gave 38.6 mg of Example I-86 (9%) as a trifluoroacetate salt. MS (ES, m/z): 792 [M+H]⁺; ¹H-NMR (400 MHz, DMSO-d₆) δ 8.66 (s, 1H), 8.52 (d, J=4.9 Hz, 1H), 7.42-7.35 (m, 3H), 7.32 (d, J=8.2 Hz, 1H), 7.25 (d, J=6.0 Hz, 1H), 7.15 (d, J=4.9 Hz, 1H), 7.01-6.93 (m, 2H), 6.23 (s, 1H), 4.92 (d, J=4.1 Hz, 1H), 4.58 (t, J=5.4 Hz, 1H), 4.44 (d, J=5.6 Hz, 1H), 4.37 (d, J=5.5 Hz, 1H), 4.31 (d, J=6.0 Hz, 2H), 4.23 (s, 2H), 3.57 (d, J=5.6 Hz, 5H), 3.46 (dd, J=13.9, 5.3 Hz, 6H), 3.40 (t, J=5.1 Hz, 4H), 3.19 (s, 4H), 3.01 (d, J=11.6 Hz, 2H), 2.64 (s, 2H), 1.46 (s, 4H), 0.96 (s, 4H), 0.62 (d, J=5.9 Hz, 2H), 0.32 (s, 2H).

Example 28: 2-(5-(2,5-dichloro-4-((1-(4-(2-cyclopropoxyphenyl)pyridin-3-yl)cyclopropoxy) methyl)phenyl)-N-((2S,3R,4R,5R)-2,3,4,5,6-pentahydroxyhexyl)pentanamido)acetic acid (I-87)

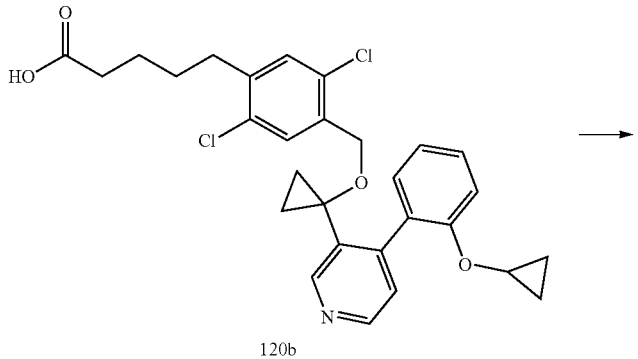

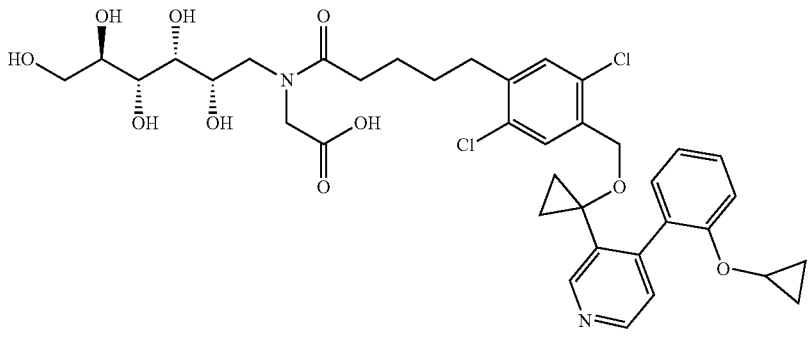

A mixture of 5-(2,5-dichloro-4-((1-(4-(2-cyclopropoxyphenyl)pyridin-3-yl)cyclopropoxy)methyl)phenyl)pentanoic acid, 120b (50 mg, 0.095 mmol, 1.0 equiv), in DMF (0.4 mL) were added HOAt (15.5 mg, 0.114 mmol, 1.2 equiv) and EDC-HCl (20 mg, 0.104 mmol, 1.1 equiv). The mixture was stirred at room temperature for 30 minutes. To the resulting mixture was added N,N-diisopropylethylamine (66.2 μL, 0.38 mmol, 4.0 equiv), followed by addition of (9H-fluoren-9-yl)methyl 2-(((2S,3R,4R,5R)-2,3,4,5,6-pentahydroxyhexyl)amino) acetate, D7 (75.7 mg, 0.142 mmol, 1.5 equiv). The resulting reaction mixture was stirred at room temperature over weekend and purified by Preparative HPLC to give 18.7 mg (23%) of the title compound I-87 TFA salt as a white solid. MS (ES, m/z): 747 [M+H]⁺; ¹H-NMR (400 MHz, CD₃OD) δ 8.88 (s, 1H), 8.72 (d, J=5.7 Hz, 1H), 7.82 (d, J=5.9 Hz, 1H), 7.51 (t, J=8.0 Hz, 1H), 7.43-7.34 (m, 2H), 7.27 (s, 1H), 7.09 (t, J=7.6 Hz, 1H), 6.89 (s, 1H), 4.38-4.27 (m, 3H), 4.13 (s, 1H), 4.00-3.90 (m, 1H), 3.81-3.74 (m, 2H), 3.73-3.58 (m, 5H), 3.58-3.43 (m, 2H), 2.76-2.67 (m, 2H), 2.66-2.48 (m, 1H), 1.72-1.55 (m, 4H), 1.23-1.13 (m, 4H), 0.68-0.59 (m, 2H), 0.44-0.29 (m, 2H).

Example 29: 2-(4-(5-(2,5-dichloro-4-((1-(4-(2-cyclopropoxyphenyl)pyridin-3-yl) cyclopropoxy)methyl)phenyl)pentanoyl)piperazin-1-yl)acetic acid (I-88)

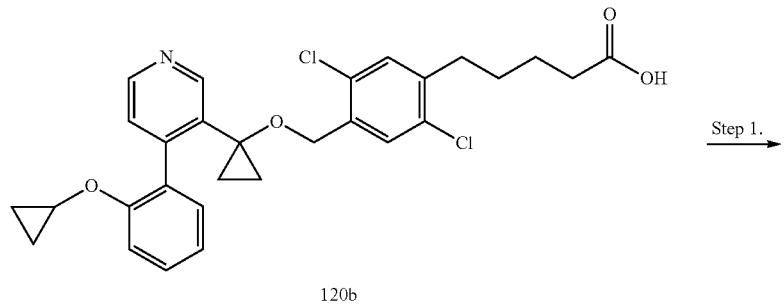

120b

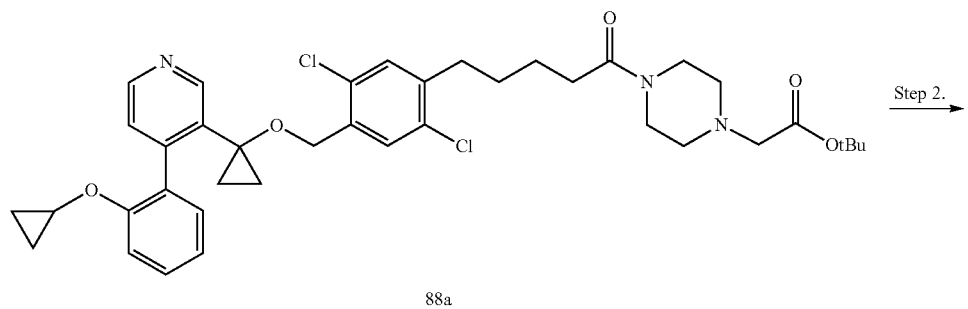

88a

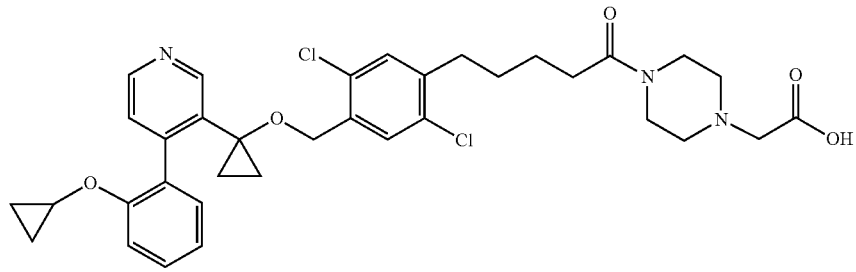

I-88

Step 1. t-Butyl 2-(4-(5-(2,5-dichloro-4-((1-(4-(2-cyclopropoxyphenyl)pyridin-3-yl) cyclopropoxy)methyl)phenyl)pentanoyl)piperazin-1-yl)acetate (Intermediate 88a)

A mixture of 5-(2,5-dichloro-4-((1-(4-(2-cyclopropoxyphenyl)pyridin-3-yl) cyclopropoxy)methyl)phenyl)pentanoic acid, 120b (80.6 mg, 0.153 mmol, 1.0 equiv) and t-butyl 2-(piperazin-1-yl) acetate dihydrochloride (50.2 mg, 0.184 mmol, 1.2 equiv) in DMF (0.8 mL) were added N,N-diisopropylethylamine (106.7 μL, 0.612 mmol, 4.0 equiv) and HATU (69.8 mg, 0.184 mmol, 1.2 equiv). The mixture was stirred at room temperature overnight. The resulting mixture was diluted with ethyl acetate, washed with $H_2O$ (2×) and brine (1×), dried, and concentrated. The residue was purified by column to give 98 mg (90%) of 88a as clear syrup.

Step 2. 2-(4-(5-(2,5-dichloro-4-((1-(4-(2-cyclopropoxyphenyl)pyridin-3-yl)cyclopropoxy) methyl) phenyl)pentanoyl)piperazin-1-yl)acetic acid (I-88)

To t-butyl 2-(4-(5-(2,5-dichloro-4-((1-(4-(2-cyclopropoxyphenyl)pyridin-3-yl)cyclopropoxy)methyl)phenyl) pentanoyl)piperazin-1-yl)acetate, 88a (122 mg, 0.172 mmol) was added 4.0 M HCl in dioxane (5 mL). The mixture was stirred at room temperature for 3 h and concentrated to give 138 mg of the crude title compound dihydrochloride salt as a yellow solid. The crude product (8 mg) was purified by Preparative HPLC to give 5.4 mg (62%) of the title compound I-88 TFA salt as a white solid. MS (ES, m/z): 652 $[M+H]^+$, $^1$H-NMR (400 MHz, $CD_3OD$) δ 8.90 (s, 1H), 8.73 (d, J=5.8 Hz, 1H), 7.81 (d, J=5.8 Hz, 1H), 7.50 (t, J=7.9 Hz, 1H), 7.43-7.36 (m, 2H), 7.26 (s, 1H), 7.08 (t, J=7.5 Hz, 1H), 6.90 (s, 1H), 4.34 (s, 2H), 4.09 (s, 2H), 3.94-3.79 (m, 4H), 3.59-3.50 (m, 1H), 3.46-3.33 (m, 4H), 2.77-2.66 (m, 2H), 2.52-2.43 (m, 2H), 1.70-1.56 (m, 4H), 1.23-1.13 (m, 4H), 0.69-0.59 (m, 2H), 0.43-0.34 (m, 2H).

Example 30: 2-(4-(5-(2,5-dichloro-4-((1-(4-(2-cyclopropoxyphenyl)pyridin-3-yl) cyclopropoxy)methyl)phenyl)pentanoyl)piperazin-1-yl)-N-methyl-N-((2S,3R,4R,5R)-2,3,4,5,6-pentahydroxyhexyl) acetamide (I-89)

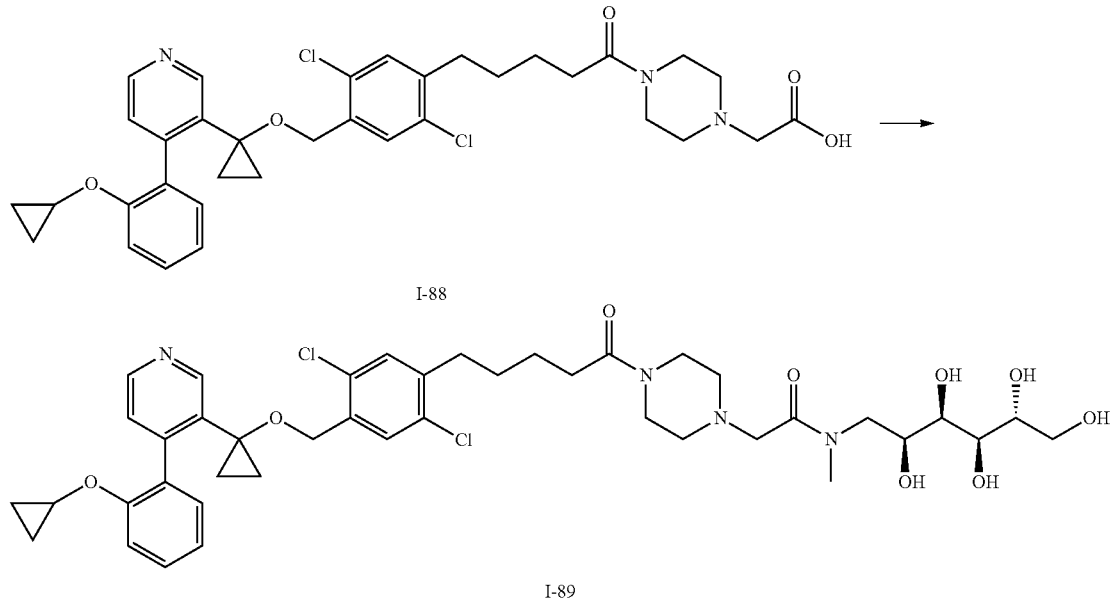

A mixture of 2-(4-(5-(2,5-dichloro-4-((1-(4-(2-cyclopropoxyphenyl)pyridin-3-yl)cyclopropoxy)methyl)phenyl)pentanoyl)piperazin-1-yl)acetic acid dihydrochloride salt, crude example I-89 (60.7 mg, 0.0837 mmol, 1.0 equiv) and N-methyl-D-glucamine (19.6 mg, 0.100 mmol, 1.2 equiv) in DMF (0.4 mL) were added N,N-diisopropylethylamine (58.3 μL, 0.335 mmol, 4.0 equiv) and HATU (38.2 mg, 0.100 mmol, 1.2 equiv). The mixture was stirred at room temperature for 2 h and purified by Preparative HPLC to give 61.4 mg (69%) of the title compound TFA salt I-89 as a white solid. MS (ES, m/z): 829 [M+H]$^+$; $^1$H-NMR (400 MHz, CD$_3$OD) δ 8.86 (s, 1H), 8.70 (d, J=5.7 Hz, 1H), 7.75 (d, J=5.7 Hz, 1H), 7.52-7.46 (m, if), 7.41-7.35 (m, 2H), 7.26 (s, 1H), 7.07 (td, J=7.5, 1.0 Hz, 1H), 6.91 (s, 1H), 4.48 (d, J=15.8 Hz, 1H), 4.33 (s, 2H), 4.29 (d, J=13.6 Hz, 1H), 4.02 (tt, J=7.9, 4.0 Hz, 1H), 3.95-3.82 (m, 2H), 3.81-3.75 (m, 2H), 3.73 (dd, J=4.0, 2.2 Hz, 1H), 3.72-3.51 (m, 7H), 3.46-3.33 (m, 4H), 3.09 (s, 1H), 3.03 (s, 2H), 2.77-2.65 (m, 2H), 2.53-2.42 (m, 2H), 1.73-1.57 (m, 4H), 1.21-1.11 (m, 4H), 0.68-0.56 (m, 2H), 0.45-0.33 (m, 2H).

Example 31: N,N'-(((oxybis(ethane-2,1-diyl))bis(oxy))bis(ethane-2,1-diyl))bis(5-(2,5-dichloro-4-((1-(4-(2-cyclopropoxyphenyl)pyridin-3-yl)cyclopropoxy)methyl)phenyl) pentanamide) (I-90)

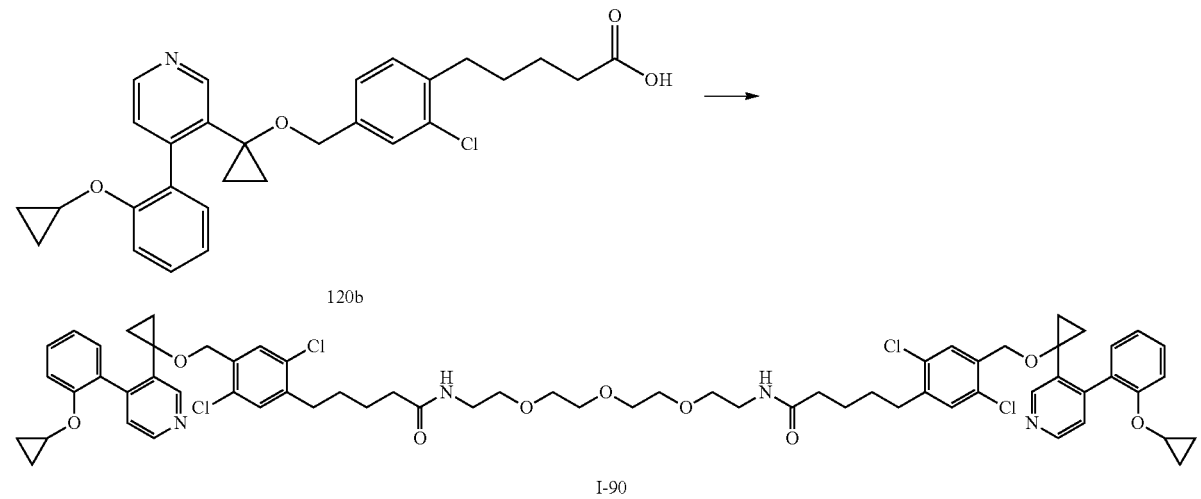

A mixture of 5-(2,5-dichloro-4-((1-(4-(2-cyclopropoxyphenyl)pyridin-3-yl)cyclopropoxy)methyl)phenyl)pentanoic acid, 120b (31.2 mg, 0.0593 mmol, 2.0 equiv), and 2,2'-((oxybis(ethane-2,1-diyl))bis(oxy))diethanamine (5.7 mg, 0.030 mmol, 1.0 equiv) in DMF (0.3 mL) were added N,N-diisopropylethylamine (31 μL, 0.178 mmol, 6.0 equiv) and HATU (24.7 mg, 0.0652 mmol, 2.2 equiv). The mixture was stirred at room temperature for 2 h and purified by Preparative HPLC to give 31.1 mg (36%) of the title compound I-90 TFA salt as a white solid. MS (ES, m/z): 1207 [M+H]$^+$; $^1$H-NMR (400 MHz, CD$_3$OD) δ 8.89 (s, 2H), 8.73 (d, J=5.8 Hz, 2H), 7.82 (d, J=5.9 Hz, 2H), 7.53-7.46 (m, 2H), 7.42-7.35 (m, 4H), 7.24 (s, 2H), 7.08 (td, J=7.5, 1.0 Hz, 2H), 6.89 (s, 2H), 4.33 (s, 4H), 3.61-3.54 (m, 10H), 3.53-3.49 (m, 4H), 3.34 (t, J=5.5 Hz, 4H), 2.68 (t, J=7.3 Hz, 4H), 2.22 (t, J=7.0 Hz, 4H), 1.69-1.52 (m, 8H), 1.21-1.14 (m, 8H), 0.69-0.60 (m, 4H), 0.42-0.33 (m, 4H).

Example 32: 2-(4-(2-(5-(2,5-dichloro-4-((1-(4-(2-cyclopropoxyphenyl)pyridin-3-yl)cyclopropoxy)methyl)phenyl)pentanamido)ethyl)piperazin-1-yl)acetic acid (I-91)

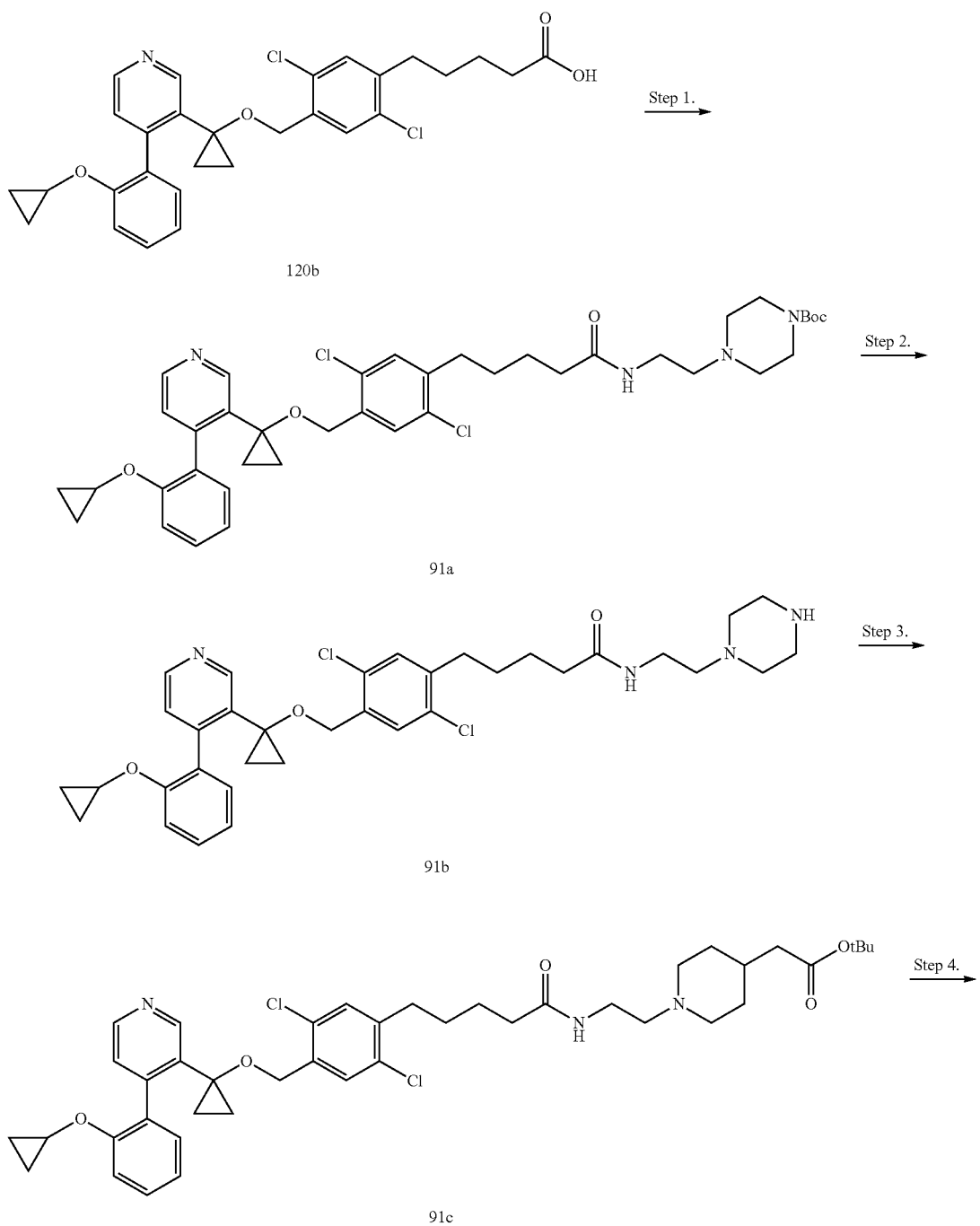

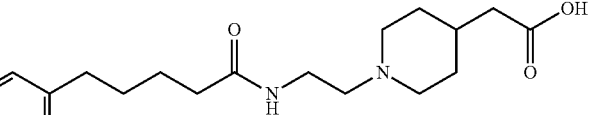

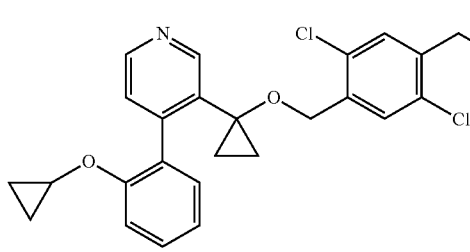

I-91

Step 1. t-butyl 4-(2-(5-(2,5-dichloro-4-((1-(4-(2-cyclopropoxyphenyl)pyridin-3-yl) cyclopropoxy) methyl)phenyl)pentanamido)ethyl)piperazine-1-carboxylate (Intermediate 91a)

A mixture of 5-(2,5-dichloro-4-((1-(4-(2-cyclopropoxyphenyl)pyridin-3-yl) cyclopropoxy)methyl)phenyl)pentanoic acid, 120b (101 mg, 0.192 mmol, 1.0 equiv), and t-butyl 4-(2-aminoethyl)piperazine-1-carboxylate (52.8 mg, 0.23 mmol, 1.2 equiv) in DMF (0.9 mL) were added N,N-diisopropylethylamine (100.3 μL, 0.576 mmol, 3.0 equiv) and HATU (87.5 mg, 0.23 mmol, 1.2 equiv). The mixture was stirred at room temperature for 2 h. The resulting mixture was diluted with ethyl acetate, washed with H₂O (2×) and brine (1×), dried, and concentrated. The residue was purified by column to give 135.5 mg (96%) of 91a as a white solid.

Step 2. 5-(2,5-dichloro-4-((1-(4-(2-cyclopropoxyphenyl)pyridin-3-yl)cyclopropoxy)methyl) phenyl)-N-(2-(piperazin-1-yl)ethyl)pentanamide (Intermediate 91b)

To t-butyl 4-(2-(5-(2,5-dichloro-4-((1-(4-(2-cyclopropoxyphenyl)pyridin-3-yl) cyclopropoxy)methyl)phenyl) pentanamido)ethyl)piperazine-1-carboxylate, 91a (135.5 mg, 0.184 mmol), was added 4.0 M HCl in dioxane (4 mL). The mixture was stirred at room temperature for 30 minutes and concentrated to give 160 mg of the crude title compound (91b) HCl salt as a yellow solid.

Step 3. Intermediate 91c: t-butyl 2-(4-(2-(5-(2,5-dichloro-4-((1-(4-(2-cyclopropoxyphenyl)pyridin-3-yl)cyclopropoxy)methyl)phenyl)pentanamido)ethyl) piperazin-1-yl)acetate (Intermediate 91c)

A mixture of 5-(2,5-dichloro-4-((1-(4-(2-cyclopropoxyphenyl)pyridin-3-yl) cyclopropoxy)methyl)phenyl)-N-(2-(piperazin-1-yl)ethyl)pentanamide, crude 91b (0.191 mmol, 1.0 equiv), in THF (1.0 mL) was added trimethylamine (133 μL, 0.955 mmol, 5 equiv), followed by dropwise addition of t-butyl 2-bromoacetate (29.6 μL, 0.201 mmol, 1.05 equiv). The mixture was stirred at room temperature for 2 h. The resulting mixture was diluted with ethyl acetate, washed with H₂O (2×) and brine (1×), dried, and concentrated. The residue was purified by column to give 130 mg (90%, 3 steps) of 91c.

Step 4. 2-(4-(2-(5-(2,5-dichloro-4-((1-(4-(2-cyclopropoxyphenyl)pyridin-3-yl)cyclopropoxy) methyl) phenyl)pentanamido)ethyl)piperazin-1-yl)acetic acid (I-91)

To t-butyl 2-(4-(2-(5-(2,5-dichloro-4-((1-(4-(2-cyclopropoxyphenyl)pyridin-3-yl) cyclopropoxy)methyl)phenyl) pentanamido)ethyl)piperazin-1-yl)acetate, 91c (130 mg, 0.173 mmol), was added 4.0 M HCl in dioxane (4 mL). The mixture was stirred at room temperature for 4 h and concentrated to give 146 mg of the crude title compound HCl salt as a yellow solid. The crude product (7 mg) was purified by Preparative HPLC to give 3.6 mg (47%) of the title compound (I-91) TFA salt as a white solid. MS (ES, m/z): 695 [M+H]⁺; ¹H-NMR (400 MHz, CD₃OD) δ 8.89 (s, 1H), 8.72 (d, J=5.7 Hz, 1H), 7.80 (d, J=5.8 Hz, 1H), 7.49 (t, J=7.9 Hz, 1H), 7.39 (dd, J=7.9, 6.5 Hz, 2H), 7.25 (s, 1H), 7.08 (t, J=7.5 Hz, 1H), 6.90 (s, 1H), 4.33 (s, 2H), 3.60-3.53 (m, 1H), 3.53-3.46 (m, 4H), 3.28-3.21 (m, 4H), 3.12 (t, J=5.6 Hz, 2H), 3.08-2.96 (m, 4H), 2.70 (t, J=6.9 Hz, 2H), 2.27 (t, J=6.7 Hz, 2H), 1.70-1.54 (m, 4H), 1.24-1.13 (m, 4H), 0.68-0.59 (m, 2H), 0.42-0.32 (m, 2H).

Example 33: 5-(2,5-dichloro-4-((1-(4-(2-cyclopropoxyphenyl)pyridin-3-yl)cyclopropoxy) methyl) phenyl)-1-(4-((2S,3R,4S,5R)-2,3,4,5,6-pentahydroxyhexyl)piperazin-1-yl)pentan-1-one (I-92)

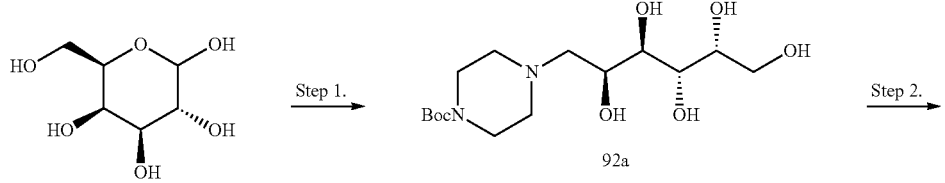

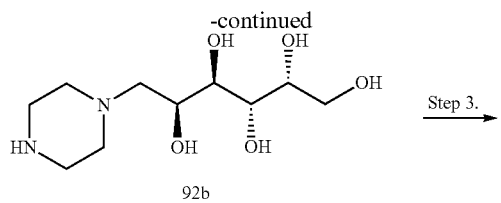

92b

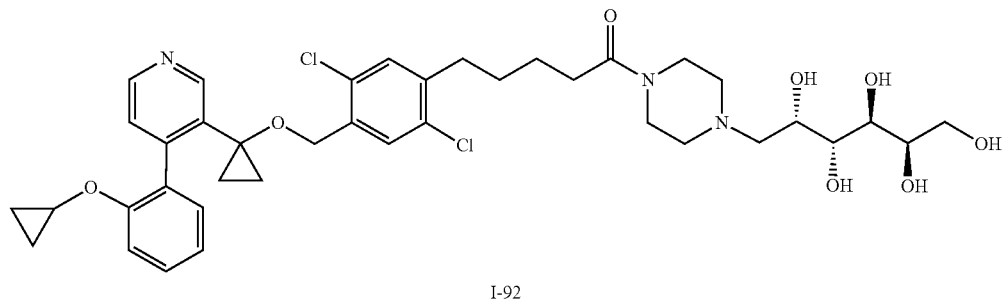

I-92

Step 1. tert-butyl 4-((2S,3R,4S,5R)-2,3,4,5,6-pentahydroxyhexyl)piperazine-1-carboxylate (Intermediate 92a)

A mixture of galactose (241.8 mg, 1.342 mmol, 1.25 equiv) and tert-butyl piperazine-1-carboxylate (200 mg, 1.074 mmol, 1.00 equiv) in MeOH (11 mL) was added HOAc (615 μL, 10.74 mmol, 10.00 equiv). The mixture was stirred at room temperature for 30 minutes and then NaCNBH$_3$ (202.4 mg, 3.22 mmol, 3.00 equiv) was added. The resulting mixture was stirred at room temperature overnight and concentrated. The residue was diluted with 10% MeOH in DCM, filtered, and concentrated to give 0.76 g of the crude 92a as a white solid.

Step 2. (2R,3S,4R,5S)-6-(piperazin-1-yl)hexane-1,2,3,4,5-pentaol (Intermediate 92b)

To crude t-butyl 4-((2S,3R,4S,5R)-2,3,4,5,6-pentahydroxyhexyl)piperazine-1-carboxylate, crude (92a, 0.76 g), was added 4.0 M HCl in dioxane (5 mL). The mixture was stirred at room temperature for 2 h and concentrated. The residue was triturated with ether to give 0.616 g of the crude 92b HCl salt as a white solid.

Step 3. 5-(2,5-dichloro-4-((1-(4-(2-cyclopropoxyphenyl)pyridin-3-yl)cyclopropoxy)methyl) phenyl)-1-(4-((2S,3R,4S,5R)-2,3,4,5,6-pentahydroxyhexyl)piperazin-1-yl)pentan-1-one (I 92)

A mixture of 5-(2,5-dichloro-4-((1-(4-(2-cyclopropoxyphenyl)pyridin-3-yl) cyclopropoxy)methyl)phenyl)pentanoic acid, 120b (30 mg, 0.057 mmol, 1.0 equiv), and (2R,3S,4R,5S)-6-(piperazin-1-yl)hexane-1,2,3,4,5-pentaol, crude 92b (40.5 mg, 0.125 mmol, 2.2 equiv), in DMF (0.3 mL) were added N,N-diisopropylethylamine (79.4 μL, 0.456 mmol, 8.0 equiv) and HATU (30.3 mg, 0.080 mmol, 1.4 equiv). The mixture was stirred at room temperature for 2 h and purified by preparative HPLC to give 25.2 mg (45%) of the title compound (I-92) TFA salt as a white solid. MS (ES, m/z): 758 [M+H]$^+$; $^1$H-NMR (400 MHz, CD$_3$OD) δ 8.86 (s, 1H), 8.70 (d, J=5.6 Hz, 1H), 7.75 (d, J=5.3 Hz, 1H), 7.49 (t, J=7.9 Hz, 1H), 7.42-7.35 (m, 2H), 7.27 (s, 1H), 7.08 (t, J=7.5 Hz, 1H), 6.91 (s, 1H), 4.38-4.30 (m, 4H), 3.90 (t, J=6.3 Hz, 1H), 3.69-3.63 (m, 5H), 3.57-3.50 (m, 4H), 3.49-3.41 (m, 3H), 3.28-3.22 (m, 2H), 2.76-2.68 (m, 2H), 2.52-2.44 (m, 2H), 1.69-1.59 (m, 4H), 1.19-1.11 (m, 4H), 0.68-0.58 (m, 2H), 0.42-0.34 (m, 2H).

Example 34: (2S,3S,4R,5R,6S)-6-((5-(2,5-dichloro-4-((1-(4-(2-cyclopropoxyphenyl)pyridin-3-yl)cyclopropoxy)methyl)phenyl)pentanamido)methyl)-3,4,5-trihydroxytetrahydro-2H-pyran-2-carboxylic acid (I-93)

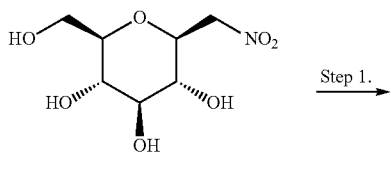

93a

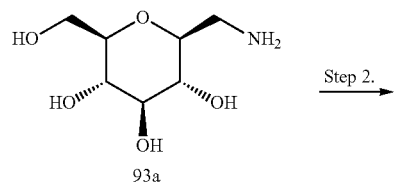

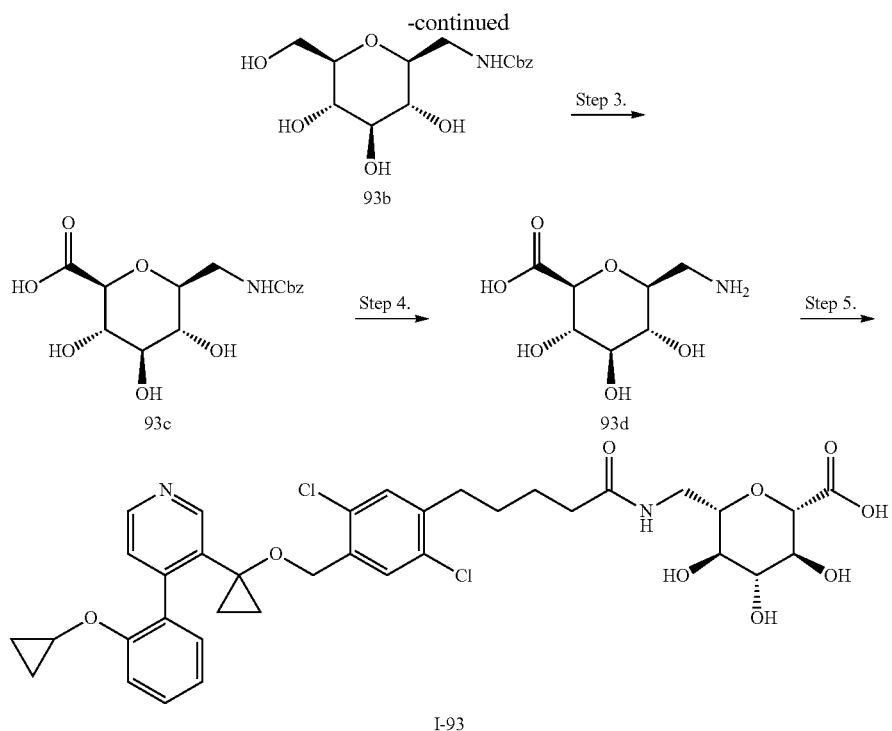

I-93

Step 1. (2S,3R,4R,5S,6R)-2-(aminomethyl)-6-(hydroxymethyl)tetrahydro-2H-pyran-3,4,5-triol (Intermediate 93a)

A mixture of (2R,3S,4R,5R,6S)-2-(hydroxymethyl)-6-(nitromethyl)tetrahydro-2H-pyran-3,4,5-triol (510 mg, 2.285 mmol) in MeOH (9.6 mL) and water (2.4 mL) was added 10% Pd on carbon (350 mg) and purged with hydrogen gas. The mixture was stirred under hydrogen at room temperature overnight, filtered, and concentrated to give 93a as a white solid.

Step 2. Benzyl (((2S,3R,4R,5S,6R)-3,4,5-trihydroxy-6-(hydroxymethyl)tetrahydro-2H-pyran-2-yl)methyl)carbamate (Intermediate 93b)

A mixture of (2S,3R,4R,5S,6R)-2-(aminomethyl)-6-(hydroxymethyl)tetrahydro-2H-pyran-3,4,5-triol, 93a (2.285 mmol, 1.0 equiv), in MeOH (9.6 mL) and water (2.4 mL) was added NaHCO$_3$ (1.07 g, 12.74 mmol, 5.6 equiv) and benzyl chloroformate (1.73 mL, 12.11 mmol, 5.3 equiv). The mixture was stirred at room temperature for 2 h and concentrated. The residue was diluted with water, washed with ether (2×), and lyophilized to give a white solid. The solid was taken up in 10% MeOH in DCM (30 mL), filtered, and concentrated to give 700 mg (94%, 2 steps) of 93b as a white solid.

Step 3. (2S,3S,4R,5R,6S)-6-((((benzyloxy)carbonyl)amino)methyl)-3,4,5-trihydroxy-tetrahydro-2H-pyran-2-carboxylic acid (Intermediate 93c)

A mixture of benzyl (((2S,3R,4R,5S,6R)-3,4,5-trihydroxy-6-(hydroxymethyl) tetrahydro-2H-pyran-2-yl)methyl)carbamate, 93b (503.4 mg, 1.539 mmol, 1.0 equiv), in THF (18 mL) and sat. aq. NaHCO$_3$ (18 mL) were added TEMPO (48.1 mg, 0.308, mmol, 0.2 equiv) and KBr (54.9 mg, 0.462 mmol, 0.3 equiv). The mixture was cooled to 0° C. and bleach (5.5 mL) was added dropwise. The mixture was stirred at room temperature for 2 h and cooled to 0° C. More tempo (25 mg, 0.16, mmol, 0.1 equiv) and bleach (3 mL) was added. The resulting mixture was stirred at room temperature for additional 1 h and extracted with ether (2×). The aqueous layer was acidified with 2M HCl to pH 1-2, extracted with ethyl acetate (5×). The combined organic layers were washed with brine (1×), dried, concentrated, and purified by preparative HPLC to give 241.6 mg (46%) of 93c.

Step 4. (2S,3S,4R,5R,6S)-6-(aminomethyl)-3,4,5-trihydroxytetrahydro-2H-pyran-2-carboxylic acid (Intermediate 93d)

A mixture of (2S,3S,4R,5R,6S)-6-((((benzyloxy)carbonyl)amino)methyl)-3,4,5-trihydroxytetrahydro-2H-pyran-2-carboxylic acid, 93c (167 mg, 0.49 mmol), in MeOH (10 mL) was added 10% Pd on carbon (35 mg) and purged with hydrogen. The mixture was stirred under hydrogen at room temperature for 3 h, filtered, washed with water (3×) and concentrated to give 102 mg (100%) of 93d as a white solid.

Step 5. (2S,3S,4R,5R,6S)-6-((5-(2,5-dichloro-4-((1-(4-(2-cyclopropoxyphenyl)pyridin-3-yl) cyclopropoxy)methyl)phenyl)pentanamido)methyl)-3,4,5-trihydroxytetrahydro-2H-pyran-2-carboxylic acid (I-93)

A mixture of 5-(2,5-dichloro-4-((1-(4-(2-cyclopropoxyphenyl)pyridin-3-yl) cyclopropoxy)methyl)phenyl)pentanoic acid, 120b (50 mg, 0.095 mmol, 1.0 equiv), in DCM (0.7 mL) were added N,N'-N,N'-disuccinimidyl carbonate (36.5 mg, 0.142 mmol, 1.5 equiv) and trimethylamine (26.5 µL, 0.190 mmol, 2.0 equiv). The mixture was stirred at room temperature for 1 h, concentrated, and purified by column to give the acid N-succinimidyl ester. To the mixture of N-succinimidyl ester (0.095 mmol, 1.0 equiv) in DCM (1.1 mL) were added (2S,3S,4R, 5R, 6S)-6-(aminomethyl)-3,4,5-trihydroxytetrahydro-2H-pyran-2-carboxylic acid, 93d (29.5 mg, 0.142 mmol, 1.49 equiv), and trimethylamine (76.1 µL, 0.546 mmol, 5.75 equiv). The mixture was stirred at room temperature overnight and purified by Preparative HPLC to give 42.7 mg (54%) of the title compound (I-93) TFA salt as a white solid. MS (ES, m/z): 715 [M+H]+. 1H-NMR (400 MHz, CD3OD) δ 8.88 (s, 1H), 8.72 (d, J=5.9 Hz, 1H), 7.81 (d, J=5.7 Hz, 1H), 7.51 (t, J=7.9 Hz, 1H), 7.43-7.36 (m, 2H), 7.26 (s, 1H), 7.09 (t, J=7.5 Hz, 1H), 6.90 (s, 1H), 4.34 (s, 2H), 3.76 (d, J=9.6 Hz, 1H), 3.64-3.52 (m, 2H), 3.49-3.33 (m, 4H), 3.14 (t, J=8.7 Hz, 1H), 2.71 (t, J=7.0 Hz, 2H), 2.26 (t, J=6.8 Hz, 2H), 1.70-1.54 (m, 4H), 1.24-1.12 (m, 4H), 0.70-0.60 (m, 2H), 0.41-0.34 (m, 2H).

Example 35: 3-(4-(5-chloro-4-((1-(4-(2-cyclopropoxyphenyl)pyridin-3-yl)cyclopropoxy) methyl)-2-methylphenyl)butyl)-1-ethyl-1-((2S,3R,4R,5R)-2,3,4,5,6-pentahydroxyhexyl)urea (I-94)

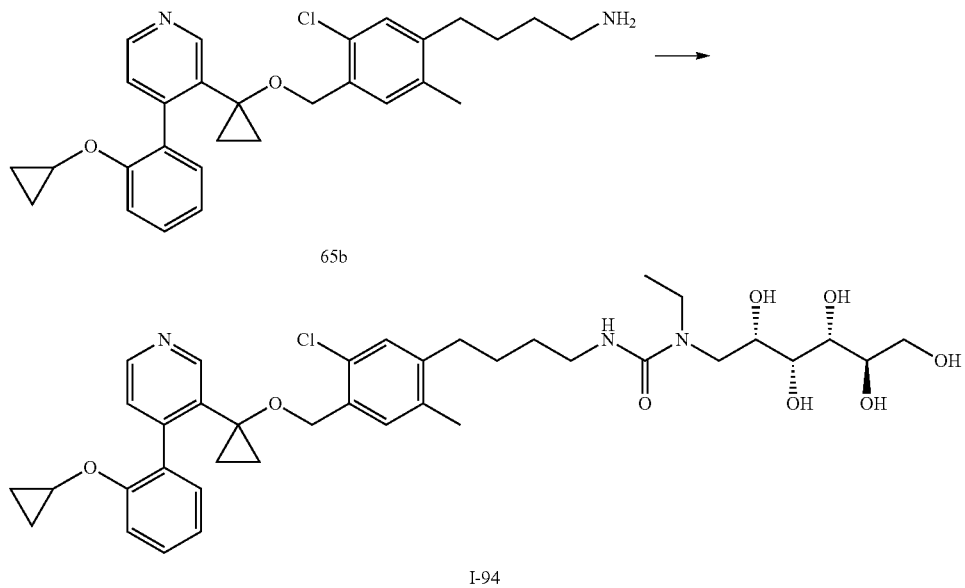

A mixture of 4-(5-chloro-4-((1-(4-(2-cyclopropoxyphenyl)pyridin-3-yl) cyclopropoxy)methyl)-2-methylphenyl)butan-1-amine, 65b (50 mg, 0.105 mmol, 1.0 equiv), in DMF (0.5 mL) was added N,N'-disuccinimidyl carbonate (32.2 mg, 0.126 mmol, 1.2 equiv). The mixture was stirred at room temperature for 1 h. Then (2R,3R,4R,5S)-6-(ethylamino)hexane-1,2,3,4,5-pentaol (43.9 mg, 0.210 mmol, 2.0 equiv) was added. The resulting mixture was stirred at 60° C. overnight and purified by Preparative HPLC to give 64.7 mg (75%) of the title compound (I-94) TFA salt as a white solid. MS (ES, m/z): 712 [M+H]+. 1H-NMR (400 MHz, CD3OD) δ 8.92 (s, 1H), 8.74 (d, J=5.8 Hz, 1H), 7.87 (d, J=5.9 Hz, 1H), 7.51 (t, J=7.8 Hz, 1H), 7.44 (dd, J=16.2, 8.0 Hz, 2H), 7.12-7.05 (m, 2H), 6.77 (s, 1H), 4.38 (s, 2H), 3.94-3.87 (m, 1H), 3.80-3.74 (m, 1H), 3.73-3.55 (m, 6H), 3.42 (dd, J=15.1, 4.5 Hz, 1H), 3.38-3.34 (m, 2H), 3.20-3.12 (m, 2H), 2.62-2.53 (m, 2H), 2.21 (s, 3H), 1.63-1.48 (m, 4H), 1.21-1.01 (m, 7H), 0.70-0.62 (m, 2H), 0.44-0.36 (m, 2H).

Example 36: 1-(4-(5-chloro-4-((1-(4-(2-cyclopropoxyphenyl)pyridin-3-yl)cyclopropoxy) methyl)-2-methylphenyl)butyl)-3-((2S,3R,4S,5R)-1,3,4,5,6-pentahydroxyhexan-2-yl)urea (I 95)

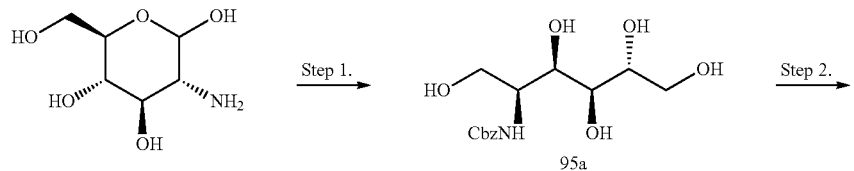

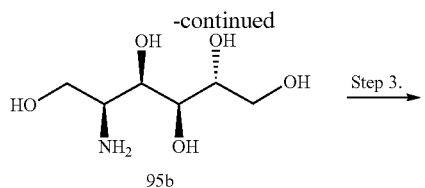

95b

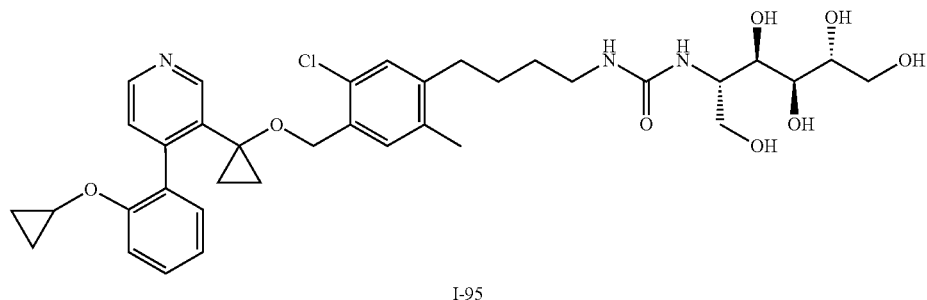

I-95

Step 1. Benzyl ((2S,3R,4S,5R)-1,3,4,5,6-pentahydroxyhexan-2-yl)carbamate (Intermediate 95a)

A mixture of glucosamine HCl salt (500 mg, 2.32 mmol, 1.0 equiv) in MeOH (10 mL) at 0° C. was added NaBH$_4$ (395 mg, 10.44 mmol, 4.5 equiv) portionwise. The mixture was stirred at 0-10° C. for 3 h. To the mixture was added water (2.5 mL) and NaHCO$_3$ (584.6 mg, 6.96 mmol, 3.0 equiv), followed by dropwise addition of benzyl chloroformate (1.66 mL, 11.63 mmol, 5.0 equiv). The mixture was stirred at room temperature overnight and concentrated. The residue was diluted with water and extracted with ether (2×). The aqueous layer was purified by preparative HPLC to give 258.3 mg (35%) of 95a as a white solid.

Step 2. (2R,3S,4R,5S)-5-aminohexane-1,2,3,4,6-pentaol (Intermediate 95b)

A mixture of benzyl ((2S,3R,4S,5R)-1,3,4,5,6-pentahydroxyhexan-2-yl)carbamate, 95a (258.3 mg, 0.82 mmol), in MeOH (10 mL) was added 10% Pd in carbon (40 mg) and purged with hydrogen. The mixture was stirred under hydrogen at room temperature for 1 h, filtered, washed with water (3×) and concentrated to give 150 mg (100%) of 95b as a brown sticky solid.

Step 3. 1-(4-(5-chloro-4-((1-(4-(2-cyclopropoxyphenyl)pyridin-3-yl)cyclopropoxy)methyl)-2-methylphenyl)butyl)-3-((2S,3R,4S,5R)-1,3,4,5,6-pentahydroxyhexan-2-yl)urea (I-95)

A mixture of 4-(5-chloro-4-((1-(4-(2-cyclopropoxyphenyl)pyridin-3-yl) cyclopropoxy)methyl)-2-methylphenyl) butan-1-amine, 65b (28.2 mg, 0.059 mmol, 1.0 equiv), in DMF (0.3 mL) was added N,N'-disuccinimidyl carbonate (16.7 mg, 0.065 mmol, 1.1 equiv). The mixture was stirred at room temperature for 1 h. (2R,3S,4R,5S)-5-aminohexane-1,2,3,4,6-pentaol, 95b (14 mg, 0.077 mmol, 1.3 equiv), was added. The mixture was stirred at 55° C. for 2 h. Then more 95b (6 mg, 0.033 mmol, 0.56 equiv) was added. The resulting mixture was stirred at 55° C. overnight and purified by Preparative HPLC to give 16.3 mg (35%) of the title compound (I-95) TFA salt as a white solid. MS (ES, m/z): 684 [M+H]$^+$. $^1$H-NMR (400 MHz, CD$_3$OD) δ 8.88 (s, 1H), 8.73-8.67 (m, 1H), 7.85-7.77 (m, 1H), 7.53-7.37 (m, 3H), 7.12-7.04 (m, 2H), 6.79 (s, 1H), 4.38 (s, 2H), 3.98-3.91 (m, 1H), 3.88-3.81 (m, 1H), 3.81-3.73 (m, 1H), 3.72-3.52 (m, 6H), 3.22-3.09 (m, 2H), 2.62-2.52 (m, 2H), 2.21 (s, 3H), 1.63-1.44 (m, 4H), 1.20-1.11 (m, 2H), 1.11-1.00 (m, 2H), 0.70-0.60 (m, 2H), 0.45-0.36 (m, 2H).

Example 37: 1-(4-(5-chloro-4-((1-(4-(2-cyclopropoxyphenyl)pyridin-3-yl)cyclopropoxy) methyl)-2-methylphenyl)butyl)-1-ethyl-3-((2S,3R,4R,5R)-2,3,4,5,6-pentahydroxyhexyl)urea (I-96)

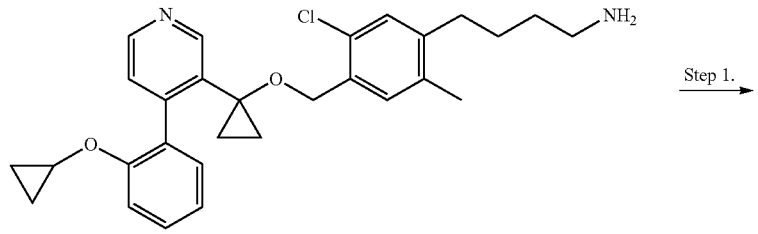

65b

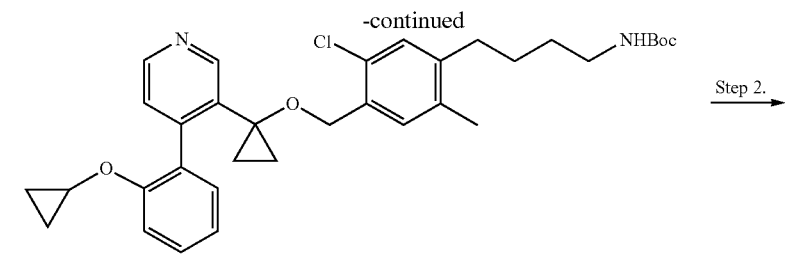

96a

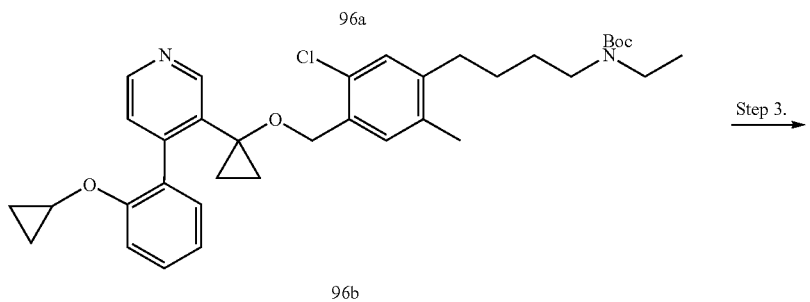

96b

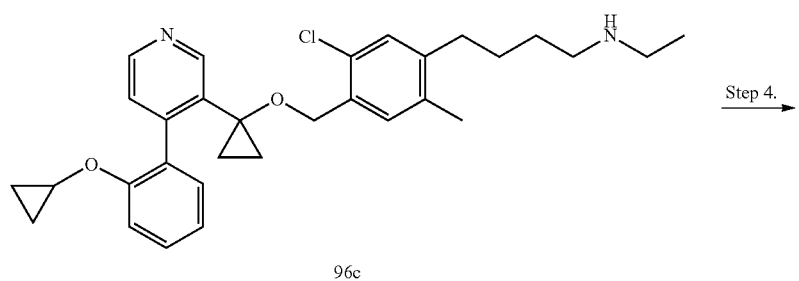

96c

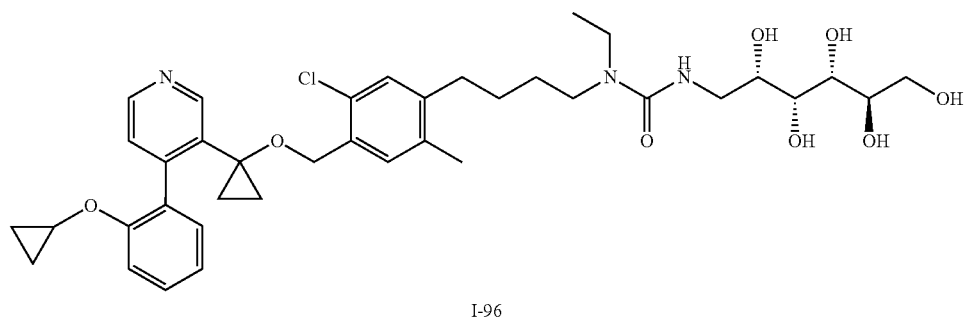

I-96

Step 1. t-butyl (4-(5-chloro-4-((1-(4-(2-cyclo-propoxyphenyl)pyridin-3-yl)cyclopropoxy) methyl)-2-methylphenyl)butyl)carbamate (Intermediate 96a)

A mixture of 4-(5-chloro-4-((1-(4-(2-cyclopropoxyphenyl)pyridin-3-yl) cyclopropoxy)methyl)-2-methylphenyl) butan-1-amine, 65b (200 mg, 0.419 mmol, 1.0 equiv), in DCM (0.5 mL) at 0° C. was added a solution of (Boc)$_2$O (100.7 mg, 0.461 mmol, 1.1 equiv) in DCM (0.5 mL) dropwise. The mixture was stirred at room temperature overnight and cooled to 0° C. More (Boc)$_2$O (50 mg, 0.229 mmol, 0.55 equiv) and TEA (70 µL, 0.50 mmol, 1.2 equiv) were added. The resulting mixture was stirred at room temperature for 1 h, concentrated, and purified by column to give 200 mg (83%) of 96a as clear syrup.

Step 2. t-butyl (4-(5-chloro-4-((1-(4-(2-cyclo-propoxyphenyl)pyridin-3-yl)cyclopropoxy) methyl)-2-methylphenyl)butyl)(ethyl)carbamate (Intermediate 96b)

A mixture of t-butyl (4-(5-chloro-4-((1-(4-(2-cyclopropoxyphenyl)pyridin-3-yl)cyclopropoxy)methyl)-2-methylphenyl)butyl)carbamate, 96b (108.4 mg, 0.188 mmol, 1.0 equiv), in THF (0.44 mL) at 0° C. was added NaH (60% in mineral oil, 22.5 mg, 0.563 mmol, 3.0 equiv). The mixture was stirred at room temperature for 30 minutes, cooled to 0° C., and then ethyl iodide (30.2 µL, 0.376 mmol, 2.0 equiv) was added. The mixture was stirred at room temperature overnight, quenched with water and extracted with ethyl acetate. The organic layer was washed with brine (1×), dried, concentrated, and purified by column to give 47.4 (42%) of 96b as a yellow solid.

Step 4. 4-(5-chloro-4-((1-(4-(2-cyclopropoxyphenyl)pyridin-3-yl)cyclopropoxy)methyl)-2-methylphenyl)-N-ethylbutan-1-amine (Intermediate 96c)

To t-butyl (4-(5-chloro-4-((1-(4-(2-cyclopropoxyphenyl)pyridin-3-yl)cyclopropoxy) methyl)-2-methylphenyl)butyl)(ethyl)carbamate, 96b (47.4 mg, 0.0783 mmol), was added 4.0 M HCl in dioxane (1 mL). The mixture was stirred at room temperature for 30 minutes and concentrated to give the crude 96c HCl salt as a solid.

Step 5. 1-(4-(5-chloro-4-((1-(4-(2-cyclopropoxyphenyl)pyridin-3-yl)cyclopropoxy)methyl)-2-methylphenyl)butyl)-1-ethyl-3-((2S,3R,4R,5R)-2,3,4,5,6-pentahydroxyhexyl)urea (I-96)

A mixture of 4-(5-chloro-4-((1-(4-(2-cyclopropoxyphenyl)pyridin-3-yl) cyclopropoxy)methyl)-2-methylphenyl)-N-ethylbutan-1-amine, crude 96c HCl salt (0.0783 mmol, 1.0 equiv), in DCM (0.5 mL) was added trimethylamine (32.8 µL, 0.235 mmol, 3.0 equiv), followed by dropwise addition of a solution of (2R,3R,4R,5S)-6-isocyanato-hexane-1,2,3,4,5-pentayl pentaacetate (D10) (35.9 mg, 0.0862 mmol, 1.1 equiv) in DCM (0.5 mL). The mixture was stirred at room temperature for 1 h and purified by column to give a urea. A mixture of the urea in MeOH (3 mL) was added (25 wt. % in MeOH, 60 µL). The mixture was stirred at room temperature for 5 minutes and purified by preparative HPLC. The HPLC fractions were combined, neutralized with Amberlyst® A26 hydroxide form to pH 6, and lyophilized to give 36.1 mg (65%) of the title compound I-96 as a white solid. MS (ES, m/z): 712 [M+H]$^+$. $^1$H-NMR (400 MHz, CD$_3$OD) δ 8.64 (d, J=0.7 Hz, 1H), 8.46 (d, J=5.1 Hz, 1H), 7.41-7.32 (m, 2H), 7.29 (dd, J=7.5, 1.5 Hz, 1H), 7.22 (dd, J=5.1, 0.6 Hz, 1H), 7.07 (s, 1H), 7.01-6.96 (m, 1H), 6.83 (s, 1H), 4.34 (s, 2H), 3.82-3.73 (m, 3H), 3.72-3.67 (m, 1H), 3.67-3.58 (m, 2H), 3.55 (tt, J=6.0, 3.0 Hz, 1H), 3.43 (dd, J=13.9, 5.1 Hz, 1H), 3.29-3.20 (m, 5H), 2.59 (t, J=7.4 Hz, 2H), 2.21 (s, 3H), 1.65-1.47 (m, 4H), 1.11 (t, J=7.1 Hz, 3H), 1.02-0.86 (m, 4H), 0.65-0.56 (m, 2H), 0.43-0.36 (m, 2H).

Example 38: 1-(4-(5-chloro-4-((1-(4-(2-cyclopropoxyphenyl)pyridin-3-yl)cyclopropoxy) methyl)-2-methylphenyl)butyl)-1-(2-hydroxyethyl)-3-((2S,3R,4R,5R)-2,3,4,5,6-pentahydroxyhexyl)urea (I-97)

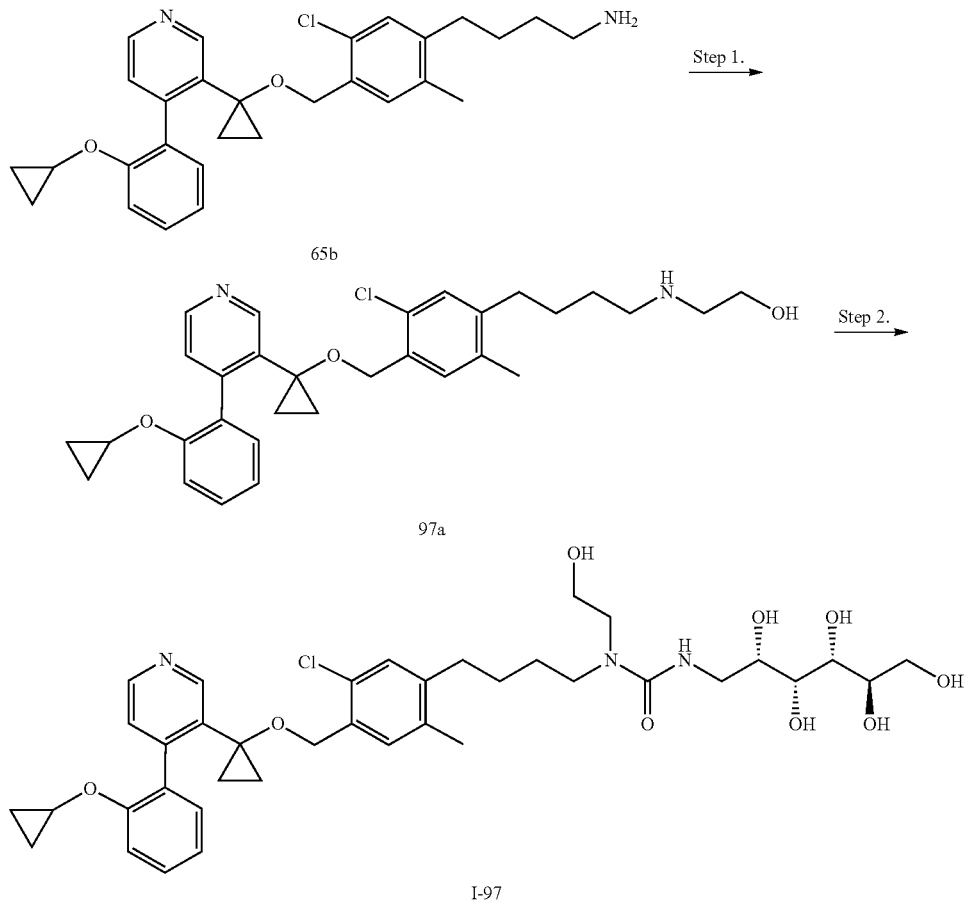

Step 1. 2-((4-(5-chloro-4-((1-(4-(2-cyclopropoxyphenyl)pyridin-3-yl)cyclopropoxy)methyl)-2-methylphenyl)butyl)amino)ethanol (Intermediate 97a)

A mixture of 4-(5-chloro-4-((1-(4-(2-cyclopropoxyphenyl)pyridin-3-yl) cyclopropoxy)methyl)-2-methylphenyl)butan-1-amine, 65b (50.3 mg, 0.105 mmol, 1.0 equiv), in acetonitrile (1.0 mL) were added 2-bromoethanol (8.2 µL, 0.116 mmol, 1.1 equiv) and trimethylamine (22 μL, 0.158 mmol, 1.5 equiv). The mixture was stirred at 60° C. for 4 h, diluted with ethyl acetate, washed with brine (1×), dried, and concentrated to give 47.9 mg (88%) of 97a as yellow syrup.

Step 2. 1-(4-(5-chloro-4-((1-(4-(2-cyclopropoxyphenyl)pyridin-3-yl)cyclopropoxy)methyl)-2-methylphenyl)butyl)-1-(2-hydroxyethyl)-3-((2S,3R,4R,5R)-2,3,4,5,6-pentahydroxyhexyl) urea (I-97)

I-97 was prepared according to the procedures described in Example 37. MS (ES, m/z): 728 [M+H]$^+$. $^1$H NMR (400 MHz, CD$_3$OD) δ 8.64 (s, 1H), 8.46 (d, J=4.7 Hz, 1H), 7.42-7.32 (m, 2H), 7.29 (d, J=7.5 Hz, 1H), 7.22 (d, J=4.9 Hz, 1H), 7.07 (s, 1H), 6.99 (t, J=7.3 Hz, 1H), 6.84 (s, 1H), 4.34 (s, 2H), 3.83-3.70 (m, 4H), 3.70-3.58 (m, 5H), 3.58-3.52 (m, 1H), 3.42 (dd, J=14.0, 4.8 Hz, 1H), 3.35 (t, J=5.3 Hz, 2H), 3.29-3.19 (m, 2H), 2.59 (t, J=7.4 Hz, 2H), 2.22 (s, 3H), 1.65-1.45 (m, 4H), 1.04-0.88 (m, 4H), 0.67-0.58 (m, 2H), 0.44-0.36 (m, 2H).

Compounds I-98 to I-119 in Table 7 were prepared from commercial or known starting materials according to the methods described in Examples 30 to 38 for Compounds I-88 to I-97 and methods generally known to those skilled in the art.

TABLE 7

Compounds 1-98 to 1-119

| Cmpd No.: | Synthetic Method | Compound Structure | [M + H]+ Obs |
|---|---|---|---|
| 1-98 | Example 30 | 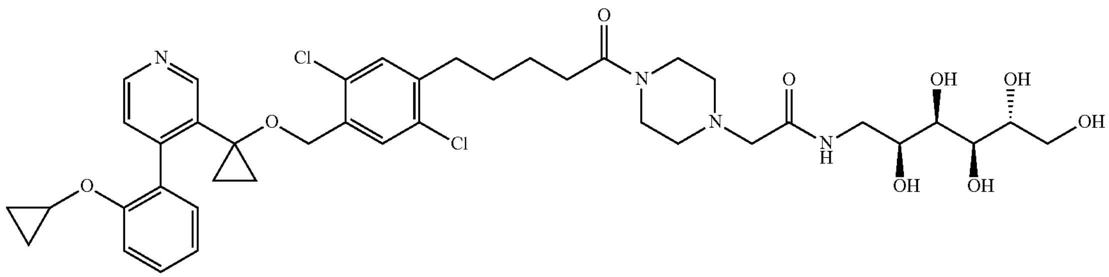 [SMILES: O=C(CN1CCN(C(=O)CCCCc2cc(Cl)c(COC3(c4cnccc4-c4ccccc4OC4CC4)CC3)cc2Cl)CC1)NC[C@H](O)[C@@H](O)[C@H](O)[C@H](O)CO] | 815 |
| 1-99 | Example 30 | 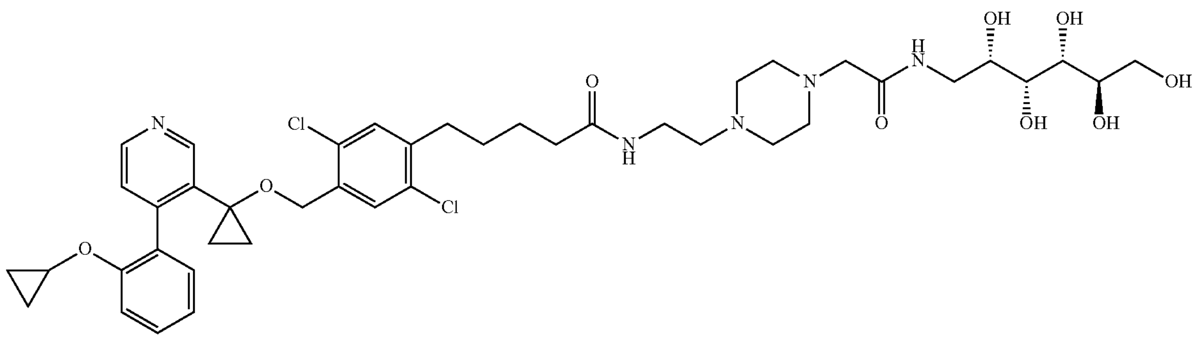 [SMILES: O=C(CCCCc1cc(Cl)c(COC2(c3cnccc3-c3ccccc3OC3CC3)CC2)cc1Cl)NCCN1CCN(CC(=O)NC[C@H](O)[C@@H](O)[C@H](O)[C@H](O)CO)CC1] | 858 |
| 1-100 | Example 30 | 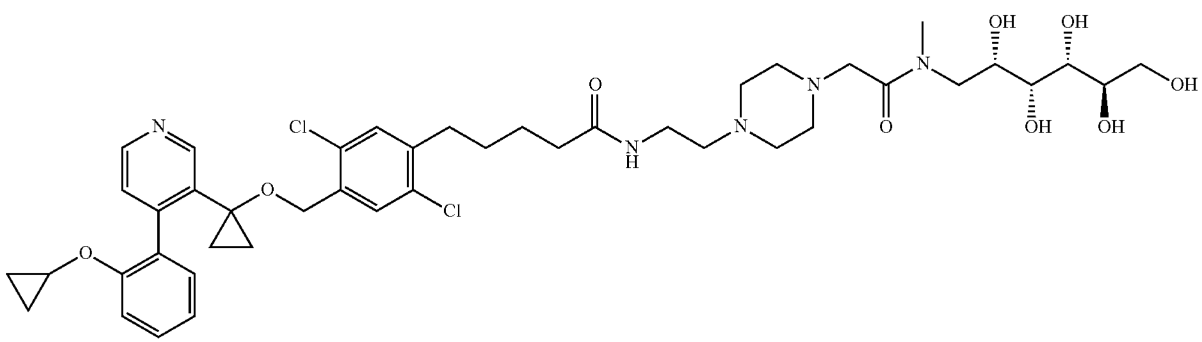 [SMILES: CN(C[C@H](O)[C@@H](O)[C@H](O)[C@H](O)CO)C(=O)CN1CCN(CCNC(=O)CCCCc2cc(Cl)c(COC3(c4cnccc4-c4ccccc4OC4CC4)CC3)cc2Cl)CC1] | 872 |

TABLE 7-continued

Compounds 1-98 to 1-119

| Cmpd No.: | Synthetic Method | Compound Structure | [M + H]+ Obs |
|---|---|---|---|
| 1-101 | Example 31 | 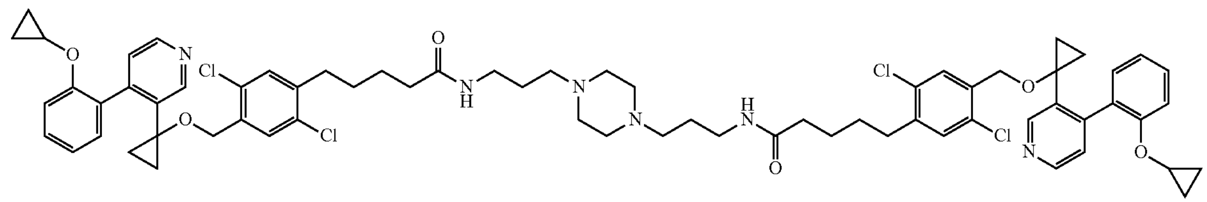 [SMILES: O=C(CCCCc1cc(Cl)c(COC2(c3cnccc3-c3ccccc3OC3CC3)CC2)cc1Cl)NCCCN1CCN(CCCNC(=O)CCCCc2cc(Cl)c(COC3(c4cnccc4-c4ccccc4OC4CC4)CC3)cc2Cl)CC1] | 1215 |
| 1-102 | Example 31 | 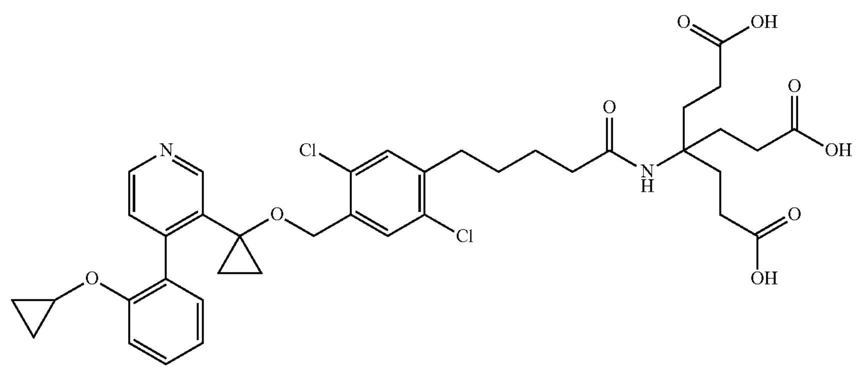 [SMILES: O=C(O)CCC(CCC(=O)O)(CCC(=O)O)NC(=O)CCCCc1cc(Cl)c(COC2(c3cnccc3-c3ccccc3OC3CC3)CC2)cc1Cl] | 755 |
| 1-103 | Example 33 | 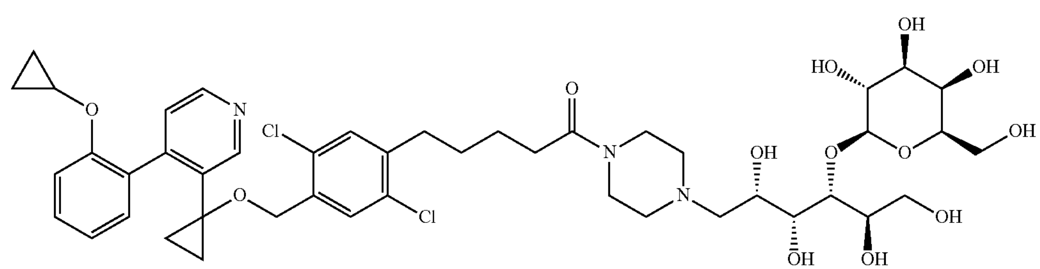 [SMILES: O=C(CCCCc1cc(Cl)c(COC2(c3cnccc3-c3ccccc3OC3CC3)CC2)cc1Cl)N1CCN(C[C@H](O)[C@@H](O)[C@H](O[C@@H]2O[C@H](CO)[C@H](O)[C@H](O)[C@H]2O)[C@H](O)CO)CC1] | 920 |

TABLE 7-continued

Compounds 1-98 to 1-119

| Cmpd No.: | Synthetic Method | Compound Structure | [M + H]+ Obs |
|---|---|---|---|
| 1-104 | Example 30 | 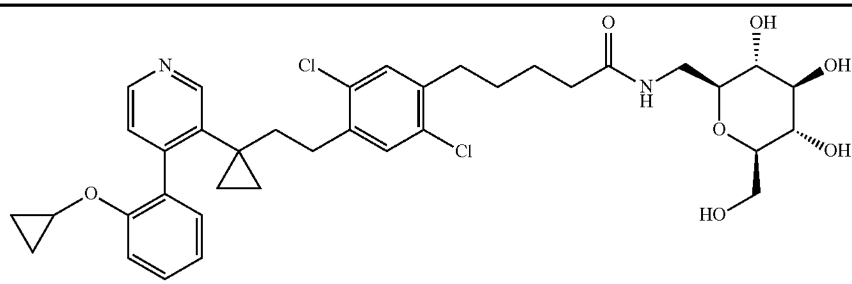 | 701 |
| 1-105 | Example 30 | 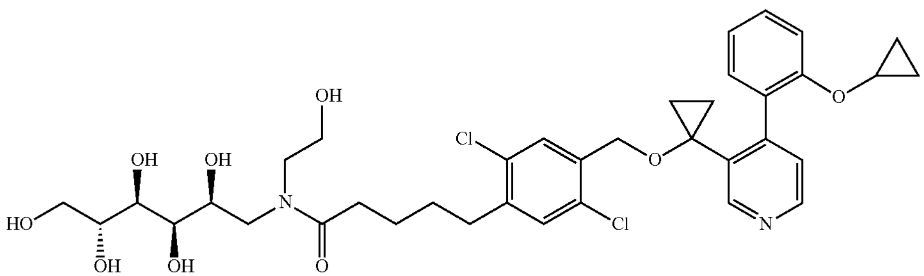 [SMILES: O=C(CCCCc1cc(Cl)c(COC2(c3cnccc3-c3ccccc3OC3CC3)CC2)cc1Cl)N(CCO)C[C@H](O)[C@@H](O)[C@H](O)[C@H](O)CO] | 733 |
| 1-106 | Example 35 | 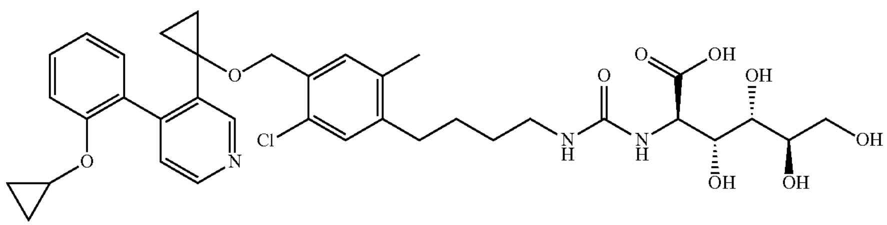 [SMILES: Cc1cc(COC2(c3cnccc3-c3ccccc3OC3CC3)CC2)c(Cl)cc1CCCCNC(=O)N[C@@H](C(=O)O)[C@@H](O)[C@H](O)[C@H](O)CO] | 698 |

TABLE 7-continued

Compounds 1-98 to 1-119

| Cmpd No.: | Synthetic Method | Compound Structure | [M + H]+ Obs |
|---|---|---|---|
| 1-107 | Example 35 | 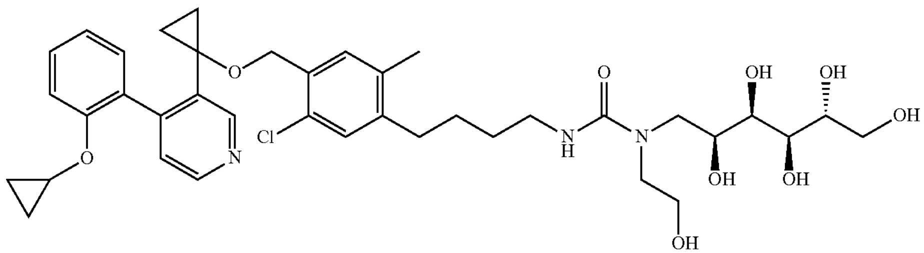 [SMILES: Cc1cc(COC2(c3cnccc3-c3ccccc3OC3CC3)CC2)c(Cl)cc1CCCCNC(=O)N(CCO)C[C@H](O)[C@@H](O)[C@H](O)[C@H](O)CO] | 728 |
| 1-108 | Example 30 | 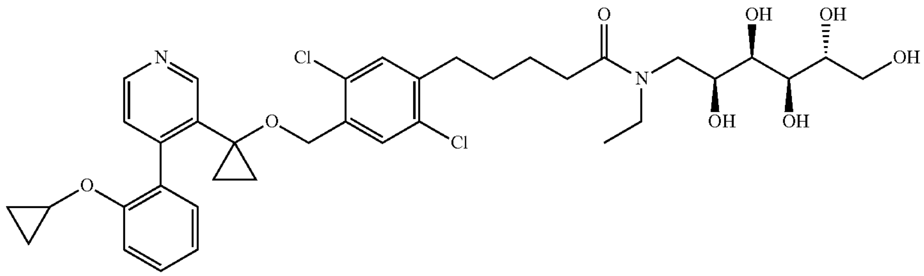 [SMILES: CCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 717 |
| 1-109 | Example 35 | 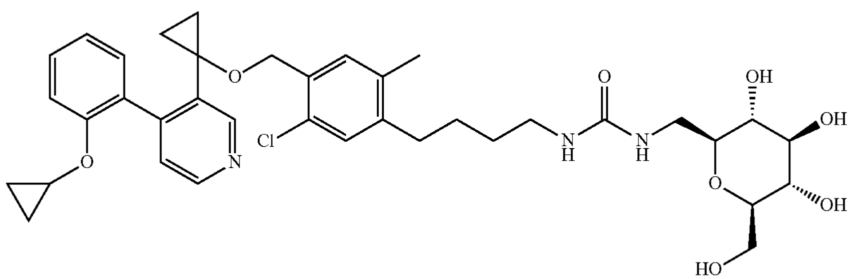 [SMILES: Cc1cc(COC2(c3cnccc3-c3ccccc3OC3CC3)CC2)c(Cl)cc1CCCCNC(=O)NC[C@@H]1O[C@H](CO)[C@@H](O)[C@H](O)[C@H]1O] | 696 |

TABLE 7-continued

Compounds 1-98 to 1-119

| Cmpd No.: | Synthetic Method | Compound Structure | [M + H]+ Obs |
|---|---|---|---|
| 1-110 | Example 35 | 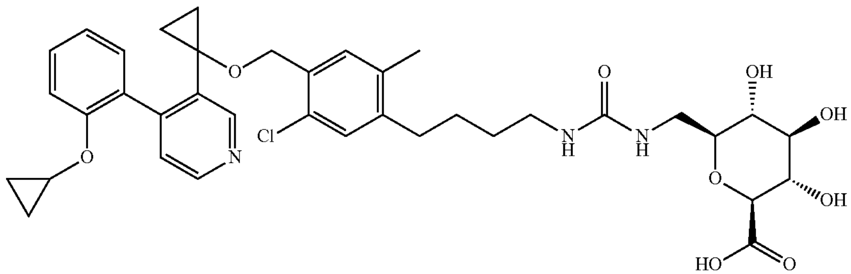 [SMILES: Cc1cc(COC2(c3cnccc3-c3ccccc3OC3CC3)CC2)c(Cl)cc1CCCCNC(=O)NC[C@@H]1O[C@H](C(=O)O)[C@@H](O)[C@H](O)[C@H]1O] | 710 |
| 1-111 | Example 35 | 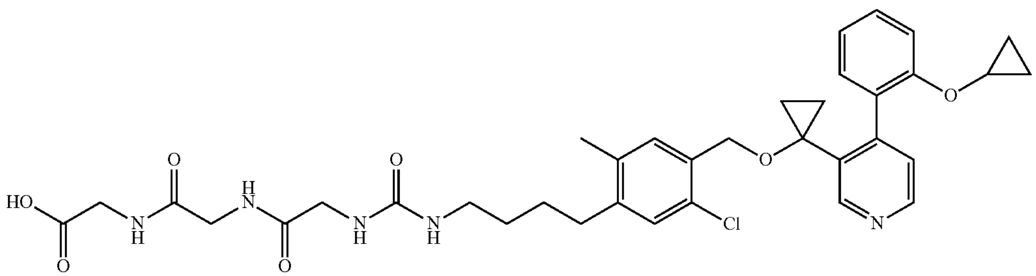 [SMILES: Cc1cc(COC2(c3cnccc3-c3ccccc3OC3CC3)CC2)c(Cl)cc1CCCCNC(=O)NCC(=O)NCC(=O)NCC(=O)O] | 692 |
| 1-112 | Example 35 | 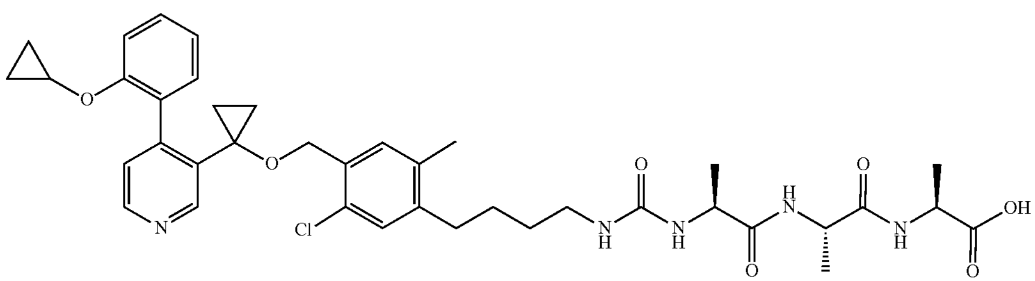 [SMILES: Cc1cc(COC2(c3cnccc3-c3ccccc3OC3CC3)CC2)c(Cl)cc1CCCCNC(=O)N[C@@H](C)C(=O)N[C@@H](C)C(=O)N[C@@H](C)C(=O)O] | 734 |

TABLE 7-continued
Compounds 1-98 to 1-119
| Cmpd No.: | Synthetic Method | Compound Structure | [M + H]+ Obs |
|---|---|---|---|
| 1-113 | Example 35 | 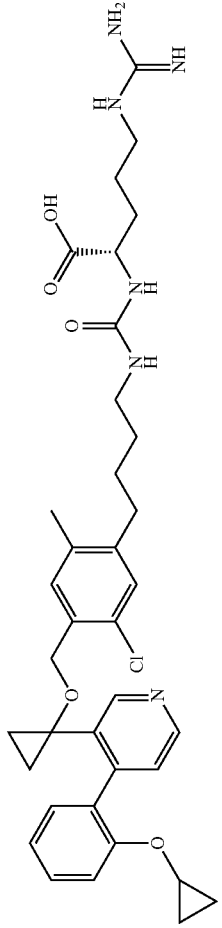 | 677 |
| 1-114 | Example 35 | 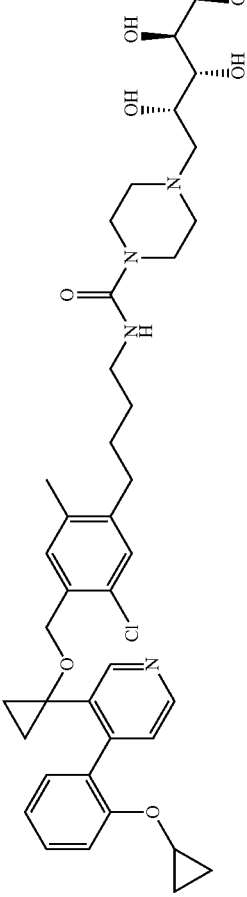 | 753 |
| 1-115 | Example 37 | 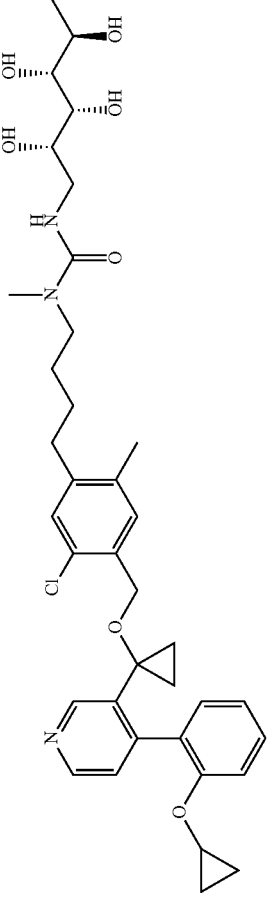 | 698 |

TABLE 7-continued

Compounds 1-98 to 1-119

| Cmpd No.: | Synthetic Method | Compound Structure | [M + H]+ Obs |
|---|---|---|---|
| 1-116 | Example 38 | 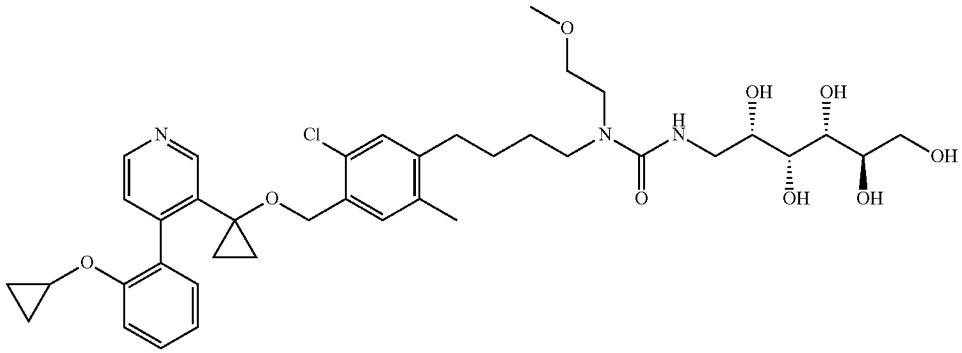 [SMILES: COCCN(CCCCc1cc(Cl)c(COC2(c3cnccc3-c3ccccc3OC3CC3)CC2)cc1C)C(=O)NC[C@H](O)[C@@H](O)[C@H](O)[C@H](O)CO] | 742 |
| 1-117 | Example 38 | 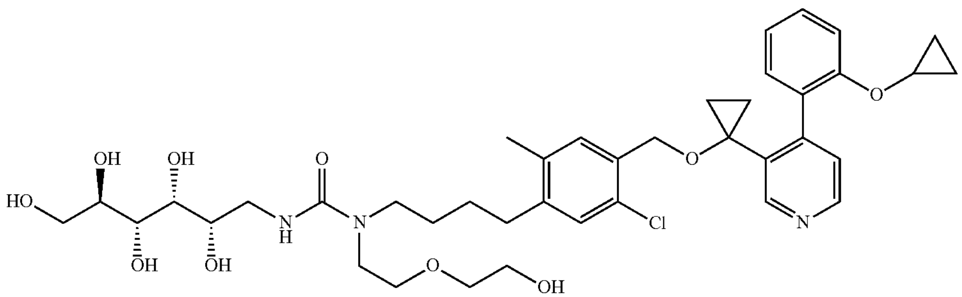 [SMILES: Cc1cc(COC2(c3cnccc3-c3ccccc3OC3CC3)CC2)c(Cl)cc1CCCCN(CCOCCO)C(=O)NC[C@H](O)[C@@H](O)[C@H](O)[C@H](O)CO] | 772 |
| 1-118 | Example 38 | 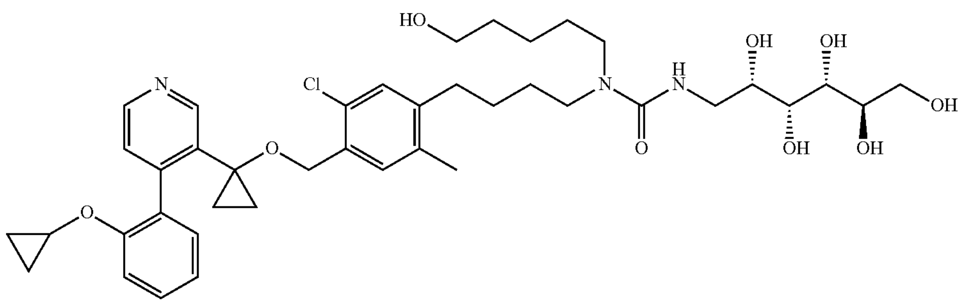 [SMILES: Cc1cc(COC2(c3cnccc3-c3ccccc3OC3CC3)CC2)c(Cl)cc1CCCCN(CCCCCO)C(=O)NC[C@H](O)[C@@H](O)[C@H](O)[C@H](O)CO] | 770 |

TABLE 7-continued

Compounds 1-98 to 1-119

| Cmpd No.: | Synthetic Method | Compound Structure | [M + H]+ Obs |
|---|---|---|---|
| 1-119 | Example 35 | (structure) | 649 |

Example 39: (2R,3R,4R,5S)-6-(benzylamino)hexane-1,2,3,4,5-pentaol (Intermediate D1)

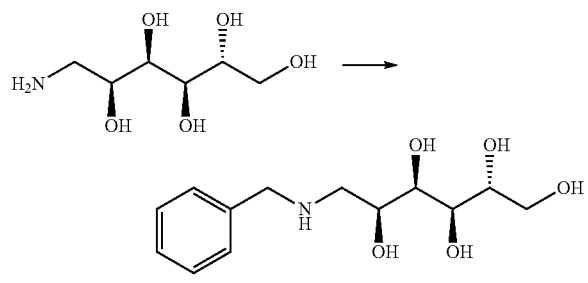

A solution of benzaldehyde (4.69 g, 44.15 mmol, 1.00 equiv) in MeOH (300 mL) was added d-glucamine (8.00 g, 44.15 mmol, 1.00 equiv), The mixture was stirred at 15° C. for 1 h, then warmed to 65° C. and stirred for 2 h. The mixture was cooled to 10° C., NaBH$_4$ (3.34 g, 88.30 mmol, 2.00 equiv) was added, the mixture was stirred at 10° C. for 30 min, then water (30 mL) was added and continued to stir for 30 min at 15° C. LCMS showed the desired compound was detected. The mixture was concentrated. The residue was dissolved in EtOH, Amberlite IR-120 resin (H+) (10 g) was added and stirred for 15 min. The mixture was filtered, the filtrate was collected. 4N HCl/1,4-dioxane solution was added drop wise to the filtrate at 20° C. until the pH=3. The precipitate was filtered and collected, then dried to give D1 (13.80 g, HCl salt) as a white solid. $^1$H NMR: (400 MHz, D$_2$O, ppm): 7.44 (m, 5H), 4.27 (s, 2H), 4.01 (m, 1H), 3.74-3.71 (m, 3H), 3.58-3.54 (m, 2H), 3.18-3.11 (m, 2H).

Example 40: (2R,3R,4R,5S)-6-(propylamino)hexane-1,2,3,4,5-pentaol (Intermediate D2)

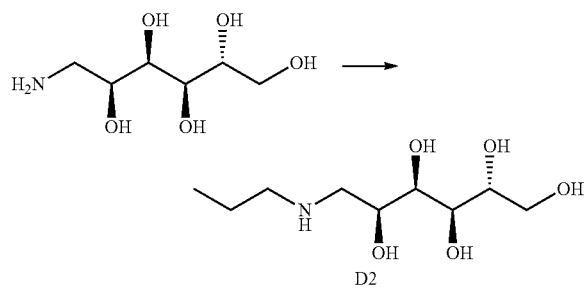

A solution of propanal (2.00 g, 34.50 mmol, 1.25 equiv) in MeOH (200 mL) was added d-glucamine (5.00 g, 27.60 mmol, 1.00 equiv), The mixture was stirred at 15° C. for 1 h, then warmed to 65° C. and stirred for 2 h. The mixture was concentrated under reduced pressure. The residue was dissolved in MeOH (200 mL), NaBH$_4$ (2.09 g, 55.20 mmol, 2.00 equiv) was added at 10° C. and stirred for 30 min. Then water (20 mL) was added and continued to stir for 30 min. The mixture was concentrated. The residue was dissolved in EtOH; Amberlite IR-120 resin (H+) (8 g) was added and stirred for 15 min. Then the mixture was filtered, the filtrate was collected. 4N HCl/1,4-dioxane solution was added dropwise to the filtrate at 20° C. until the pH=3. The precipitate was filtered out (2.3 g, most of the solid was inorganic salt). The filtrate was concentrated to about 80 mL, Then EtOAc (160 mL) was added dropwise, a white precipitate was formed. The second batch of precipitate was filtered and collected, then dried to give D2 (4.20 g, 16.17 mmol, 58.59% yield, HCl salt) as a white solid. MS: (ES, m/z): 224 [M+H]. $^1$H NMR: (400 MHz, D$_2$O, ppm): 4.03-4.02 (m, 1H), 3.74-3.66 (m, 5H), 3.15-2.96 (m, 4H), 1.67-1.61 (m, 2H), 0.91-0.87 (m, 3H).

Example 41: (2R,3R,4R,5S)-6-(2-methoxyethylamino)hexane-1,2,3,4,5-pentaol (Intermediate D3)

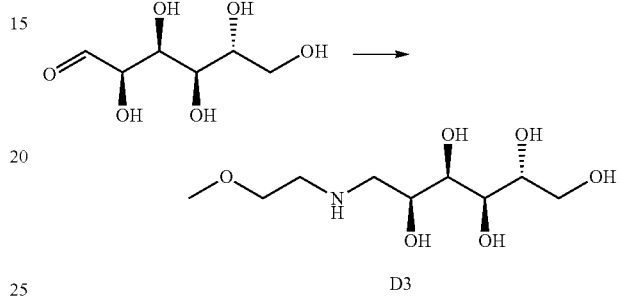

A solution of 2-methoxyethanamine (2.29 g, 30.53 mmol, 1.10 equiv) in MeOH (200.00 mL) was added glucose (5.00 g, 27.75 mmol, 1.00 equiv), The mixture was stirred at 15° C. for 1 h, then warmed to 65° C. and stirred for 2 h. NaBH$_4$ (2.10 g, 55.50 mmol, 2.00 equiv) was added at 10° C. and stirred for 30 min. Then water (20 mL) was added and continued to stir for 30 min. The mixture was concentrated. The residue was dissolved in EtOH, Amberlite IR-120 resin (H+) (8 g) was added, the mixture was stirred for 15 min. Then the mixture was filtered, the filtrate was collected. 4N HCl/1,4-dioxane solution was added dropwise to the filtrate at 20° C. until the pH=3. The precipitate was filtered out (about 2.2 g, most of the solid was inorganic salt). The filtrate was concentrated to about 80 mL, Then EtOAc (160 mL) was added dropwise, a white precipitate was formed. The second batch of precipitate was filtered and collected, then dried to give D3 (4.30 g, 15.59 mmol, 56.20% yield, HCl salt) as a white solid. MS: (ES, m/z): 240 [M+H]. $^1$H NMR: (400 MHz, D$_2$O, ppm): 4.02-4.01 (m, 1H), 3.73-3.72 (m, 2H), 3.69-3.62 (m, 3H), 3.55-3.55 (m, 2H), 3.30 (s, 3H), 3.22-3.22 (m, 3H), 3.07 (m, 1H).

Example 42: (2R,3R,4R,5S)-6-(2-(methylsulfonyl)ethylamino)hexane-1,2,3,4,5-pentaol (Intermediate D4)

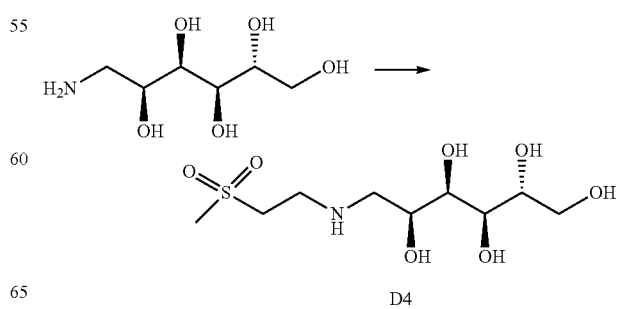

A mixture of d-glucamine (2.00 g, 11.04 mmol, 1.00 equiv) in MeOH (20 mL) was added 1-methylsulfonylethylene (1.17 g, 11.04 mmol, 1.00 equiv) dropwise at 15° C. The reaction mixture was degassed and purged with $N_2$ for 3 times, and then the mixture was stirred at 15° C. for 16 h under $N_2$ atmosphere. LC-MS showed the reaction was completely. The reaction mixture was concentrated to about 10 mL and filtered. The filter cake was washed with MeOH (5 mL). D4 (2.20 g, 7.66 mmol, 69.35% yield) was obtained as a white solid. $^1$H NMR: (400 MHz, $D_2O$, ppm): 3.70-3.64 (m, 4H), 3.53-3.51 (m, 2H), 3.38-3.34 (m, 2H), 3.05-3.02 (m, 5H), 3.67-2.60 (m, 2H)

Example 43: (2R,3R,4R,5S)-6-(isopropylamino)hexane-1,2,3,4,5-pentaol (Intermediate D5)

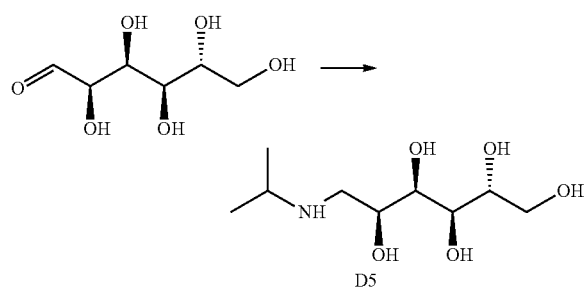

A solution of glucose (5.00 g, 27.75 mmol, 1.00 equiv) in MeOH (100 mL) was added propan-2-amine (16.40 g, 277.50 mmol, 10.00 equiv). The mixture was stirred at 15° C. for 1 h. Then the mixture was warmed to 60° C. and stirred at 60° C. for 2 h. LC-MS showed that the starting material was converted to the intermediate. The solvent and excess propan-2-amine was removed under reduced pressure. The residue was dissolved in MeOH (100 mL), to the mixture was added $NaBH_4$ (1.57 g, 41.63 mmol, 1.50 equiv) and the mixture was stirred at 15° C. for 30 min. To the mixture was added $H_2O$ (6 mL) to quenched the reaction. The solvent was removed under reduced pressure and the residue was dissolved in ethanol (60 mL). To the solution was added Amberlite IR-120 resin (H+) (12 g) and the mixture was stirred for 30 min. Then the mixture was filtered and the filtrate was adjusted to pH=4 with a solution of HCl (4 mol/L) dioxane. The mixture was filtered and the solid was collected. The solid was dissolved in $H_2O$ (10 mL) and the solution was added A column which was stuffed with Amberlite IR-120 resin (H+). The column was washed with $H_2O$ and 15% $NH_3$ solution. The solution was concentrated under reduced pressure. D5 (700.00 mg, 3.07 mmol, 11.06% yield, and 97.9% purity) was obtained as a light yellow solid. MS: (ES, m/z): 224.1 [M+H]. $^1$H NMR: (400 MHz, $D_2O$, ppm): 3.84-3.70 (m, 4H), 3.62-3.59 (m, 2H), 2.80-2.72 (m, 2H), 2.60-2.58 (m, 1H), 1.10 (d, J=5.6 Hz, 6H).

Example 44: (2R,3R,4R,5S)-6-(tetrahydro-2H-pyran-4-ylamino)hexane-1,2,3,4,5-pentaol (Intermediate D6)

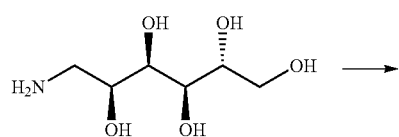

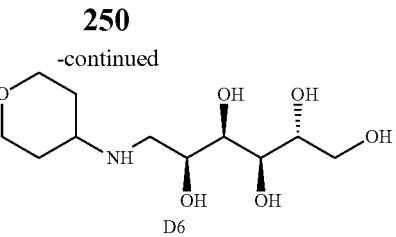

Intermediate D6 (2R,3R,4R,5S)-6-((tetrahydro-2H-pyran-4-yl)amino)hexane-1,2,3,4,5-pentaol: A mixture of D-glucamine (5.00 g, 27.60 mmol, 1.00 equiv) and tetrahydropyran-4-one (4.14 g, 41.39 mmol, 1.50 equiv) in MeOH (15.00 mL) was stirred at 20° C. for 1 h. Then the mixture was heated to 70° C. and stirred for 18 h. LCMS showed imine was formed. The mixture was cooled down to 20° C. and $NaBH_4$ (3.13 g, 82.79 mmol, 3.00 equiv) was added. The mixture was stirred continuously for another 2 h. LCMS showed desired product was formed. To the reaction mixture was added 5 g of H+ ion-exchange resin and stirred for 30 min. The mixture was filtered. The filtrate was concentrated to give a white solid. The solid was dissolved in 20 mL of water and loaded on H+ ion-exchange resin column and eluted by water to removed excess salt. Desired product was eluted by 25% ammonium hydroxide. The eluent containing product was concentrated under reduced pressure and lyophilized to give D6 (1.58 g, 5.96 mmol, 21.58% yield, 100% purity) as a gum. $^1$H NMR (400 MHz, $CD_3OD$, ppm): 3.96-3.95 (m, 3H), 3.81-3.76 (m, 2H), 3.65-3.63 (m, 3H), 3.43 (m, 2H), 2.99-2.94 (m. 3H), 1.94-1.92 (m, 2H), 1.56-1.49 (m, 2H).

Example 44: (9H-fluoren-9-yl)methyl 2-((tert-butoxycarbonyl)amino)acetate (Intermediate D7)

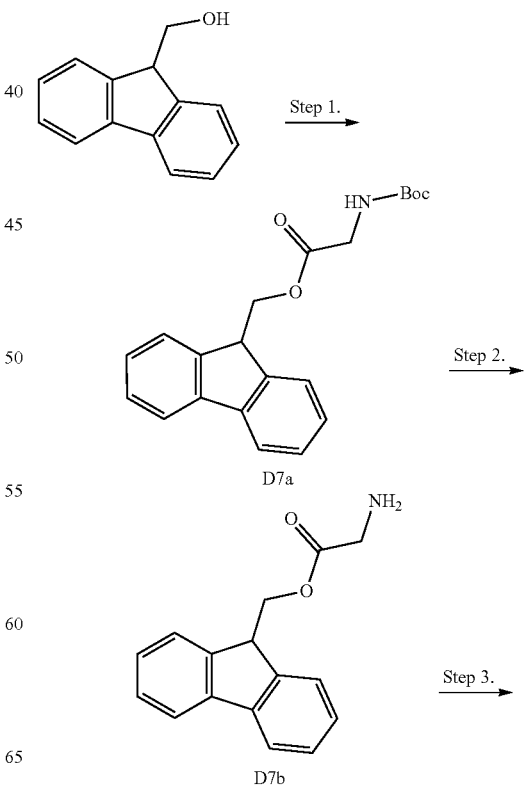

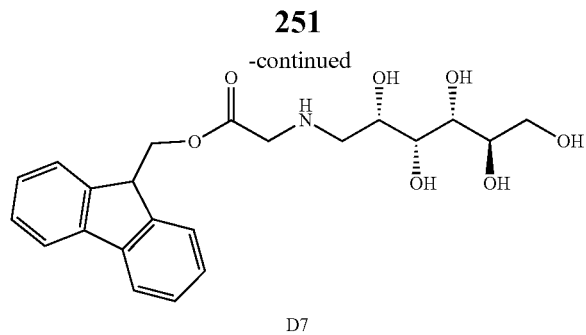

D7

Step 1. (9H-fluoren-9-yl)methyl 2-((tert-butoxycarbonyl)amino)acetate (Intermediate D7a)

A 1000-mL round-bottom flask was charged with a solution of 2-[[(tert-butoxy)carbonyl]amino]acetic acid (30 g, 171.25 mmol, 1.00 equiv) in N,N-dimethylformamide (500 mL), 9H-fluoren-9-ylmethanol (39 g, 198.73 mmol, 1.20 equiv), DCC (42 g, 203.56 mmol, 1.20 equiv), 4-dimethylaminopyridine (1 g, 8.19 mmol, 0.05 equiv). The resulting solution was stirred overnight at room temperature. The solids were filtered out. The resulting mixture was concentrated under vacuum. This resulted in 40 g (crude) of D7a as colorless oil.

Step 2. (9H-fluoren-9-yl)methyl 2-aminoacetate (Intermediate D7b)

A 1000-mL round-bottom flask was charged with a solution of 9H-fluoren-9-ylmethyl 2-[[(tert-butoxy)carbonyl]amino]acetate, D7a (40 g, 113.18 mmol, 1.00 equiv), in 1,4-dioxane (200 mL), hydrogen chloride (6 mol/L) (200 mL). The resulting solution was stirred overnight at room temperature. The resulting mixture was concentrated under vacuum. The resulting solution was diluted with 200 mL of ether. The solids were collected by filtration. This resulted in 40 g (crude) of D7b as a white solid.

Step 3. (9H-fluoren-9-yl)methyl 2-(((2S,3R,4R,5R)-2,3,4,5,6-pentahydroxyhexyl)amino) acetate (Intermediate D7)

A 500-mL round-bottom flask was charged with a solution of 9H-fluoren-9-ylmethyl 2-aminoacetate hydrochloride, D7b (20 g, 69.02 mmol, 1.00 equiv), in DMF/PBS (140/60 mL), (3R,4S,5S,6R)-6-(hydroxymethyl)oxane-2,3,4,5-tetrol (15 g, 83.26 mmol, 1.20 equiv), NaCNBH₃ (3.4 g, 54.11 mmol, 0.80 equiv). The resulting solution was stirred overnight at 30° C. in an oil bath. The solids were filtered out. The resulting mixture was concentrated under vacuum. The crude product (10 g) was purified by Preparative HPLC with the following conditions (SHIMADZU): Column, Sunfire C18 50*150; mobile phase, water with 0.05% TFA and CH₃CN (5% CH₃CN up to 36% in 13 min); Detector, 254 nm. 6 g product was obtained. This resulted in 5.97 g (21%) of D7 as a white solid. MS (ES, m/z): 418 [M+H]⁺. ¹H-NMR (300 MHz, CD₃OD, ppm): 7.82 (d, J=7.5 Hz, 2H), 7.65 (d, J=7.5 Hz, 2H), 7.40 (m, 4H), 4.67 (d, J=6.3 Hz, 2H), 4.33 (m, 1H), 4.10 (m, 1H), 3.99 (s, 2H), 3.79 (m, 4H), 3.22 (m, 2H).

Example 45: (2R,3R,4R,5S)-6-(5-hydroxypentylamino)hexane-1,2,3,4,5-pentaol (Intermediate D8)

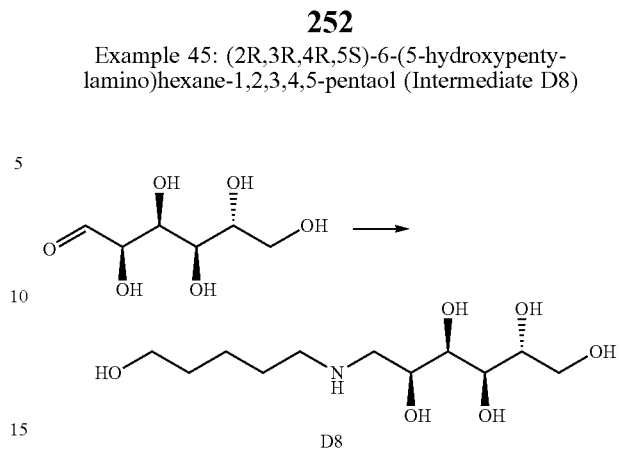

A mixture of D-glucose monohydrate (3.0 g, 15.14 mmol, 1.0 equiv) in MeOH (100 mL) was added 5-aminopentan-1-ol (1.81 mL, 16.64 mmol, 1.1 equiv). The mixture was stirred at room temperature for 1 h, warmed to 60° C., and stirred for 2 h. The mixture was cooled to 10° C. and NaBH₄ (1.145 g, 30.28 mmol, 2.0 equiv) was added portionwise. The mixture was stirred at room temperature for 2 h and water (10 mL) was added. The mixture was attired at room temperature for 30 minutes and concentrated. The residue was taken up in ethanol and amberlite resin (H+) (6 g) was added. The resulting mixture was stirred at room temperature for 30 minutes and filtered. The filtrate was acidified with a 4.0 M HCl solution in dioxane to pH 3. The white precipitate was removed by filtration. To the filtrate was added ethyl acetate dropwise to form a white precipitate. The precipitate was triturated with ether to give 3.5 g (76%) of D8 HCl salt as a white solid.

Example 46: (2R,3R,4R,5S)-6-(2-(morpholinosulfonyl)ethylamino)hexane-1,2,3,4,5-pentaol (Intermediate D9)

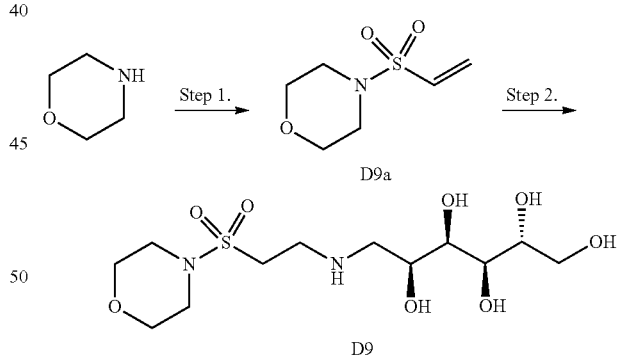

Step 1. 4-(vinylsulfonyl)morpholino (Intermediate D9a)

A mixture of morpholine (96.9 mg, 1.112 mmol, 1.0 equiv) in DCM (8.0 mL) at 0° C. was added trimethylamine (620 µL, 4.45 mmol, 4.0 equiv), followed by slow addition of a solution of 2-chloroethanesulfonyl chloride (116.2 µL, 1.112 mmol, 1.0 equiv) in DCM (2.0 mL). The mixture was stirred at 0° C. for 1 h, warmed to room temperature, and stirred for additional 2 h. The resulting mixture was washed with water (1×), dried, concentrated, and purified by column to give 120 mg (61%) of D9a as clear oil.

Step 2. (2R,3R,4R,5S)-6-((2-(morpholinosulfonyl)ethyl)amino)hexane-1,2,3,4,5-pentaol (Intermediate D9)

A mixture of D-glucamine (102.9 mg, 0.568 mmol, 1.0 equiv) in MeOH (1.0 mL) was added a mixture of 4-(vinylsulfonyl)morpholine (D9a) (100.6 mg, 0.568 mmol, 4.0 equiv) in MeOH (0.5 mL). The mixture was stirred at room temperature overnight. The white precipitate was collected by filtration to provide 162 mg (80%) of D9 as a white solid.

Example 47: ((2R,3R,4R,5S)-6-isocyanatohexane-1,2,3,4,5-pentayl pentaacetate (Intermediate D10)

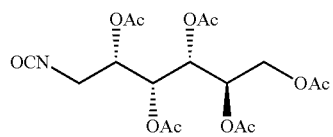

D10

Intermediate D10 was according to the method of Martín Ávalos, Reyes Babiano, Pedro Cintas, Michael B. Hursthouse, José L. Jiménez, Mark E. Light, Juan C. Palacios, and Esther M. S. Pérez *Eur. J. Org. Chem.* 2006, 657-671.

Example 48: (2R,3S,4R,5S)-5-isocyanatohexane-1,2,3,4,6-pentayl pentaacetate (Intermediate D11)

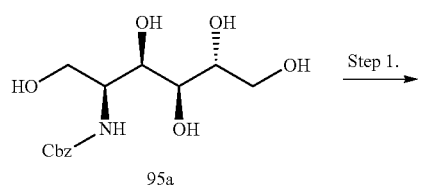

95a

↓ Step 1.

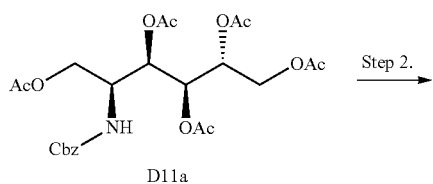

D11a

↓ Step 2.

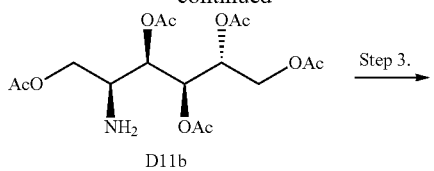

D11b

↓ Step 3.

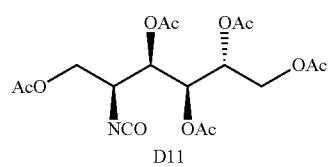

D11

Step 1. (2R,3S,4R,5S)-5-(((benzyloxy)carbonyl)amino)hexane-1,2,3,4,6-pentayl pentaacetate (Intermediate D11a)

A mixture benzyl ((2S,3R,4S,5R)-1,3,4,5,6-pentahydroxyhexan-2-yl)carbamate, (557 mg, 1.774 mmol, 1.0 equiv), in pyridine (5.4 mL) at 0° C. was added acetic anhydride (7.71 mL) dropwise. The mixture was slowed warmed to room temperature and stirred at room temperature overnight. The mixture was poured into ice water and extracted with DCM (2×). The combined organic layers were washed with 1N HCl (1×), sat. NaHCO₃ (1×), and brine (1×), dried, concentrated and purified by column to give 0.76 g (82%) of D11a as a clear syrup.

Step 2. (2R,3S,4R,5S)-5-aminohexane-1,2,3,4,6-pentayl pentaacetate (Intermediate Dub)

A mixture of (2R,3S,4R,5S)-5-(((benzyloxy)carbonyl)amino)hexane-1,2,3,4,6-pentayl pentaacetate (760 mg, 1.448 mmol, 1.0 equiv.) in MeOH (10 mL) was added 4.0 M HCl in dioxane (0.54 mL, 2.16 mmol, 1.5 equiv.) and 10% palladium on carbon (152 mg). The mixture was stirred at room temperature under hydrogen for 1 h, filtered, and concentrated to give 581 mg (94%) of D11b HCl salt as a white solid.

Step 3. (2R,3S,4R,5S)-5-isocyanatohexane-1,2,3,4,6-pentayl pentaacetate (Intermediate D11)

A mixture of triphosgene (239.5 mg, 0.807 mmol, 1.0 equiv.) in DCM (7.6 mL) were added saturated aqueous NaHCO₃ (5.1 mL) and (2R,3S,4R,5S)-5-aminohexane-1,2,3,4,6-pentayl pentaacetate (345 mg, 0.807 mmol, 1.0 equiv.). The mixture was stirred at 0° C. for 45 minutes and extracted with DCM. The organic layer was washed with brine (1×), dried, and concentrated to give 257.3 mg (62%) of the crude D11 as a clear syrup.

Example 49: N-benzyl-5-(2,5-dichloro-4-((1-(4-(2-cyclopropoxyphenyl)pyridin-3-yl) cyclopropoxy) methyl)phenyl)-N-((2R,3S,4R,5R)-2,3,4,5,6-pentahydroxyhexyl)pentanamide (I-120)

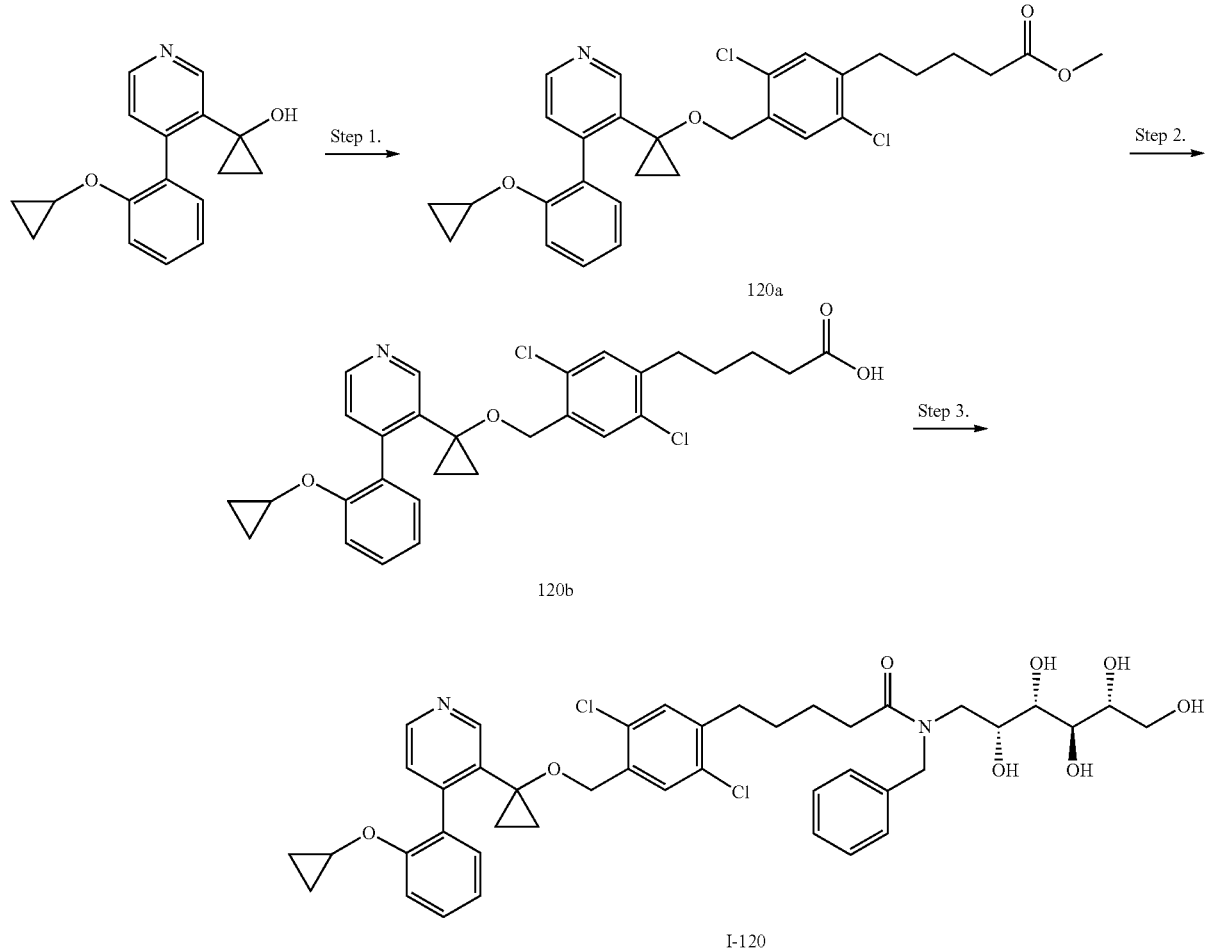

Step 1: Methyl 5-(2,5-dichloro-4-((1-(4-(2-cyclopropoxyphenyl)pyridin-3-yl)cyclopropoxy) methyl) phenyl)pentanoate (Intermediate 120a)

A 250-mL round-bottom flask was charged with 1-[4-(2-cyclopropoxyphenyl)pyridin-3-yl]cyclopropan-1-ol, A23 (1.5 g, 5.61 mmol, 1.00 equiv), methyl 5-[4-(bromomethyl)-2,5-dichlorophenyl]pentanoate, C6 (2.2 g, 6.21 mmol, 1.10 equiv), N,N-dimethylformamide (100 mL). This was followed by the addition of sodium hydride (60% in oil) (900 mg, 37.50 mmol, 4.00 equiv), in portions at room temperature. The resulting solution was stirred for 1 h at 0° C. The reaction was then quenched by the addition of 20 mL of water. The resulting solution was diluted with 100 mL of water. The resulting solution was extracted with 3×100 mL of ethyl acetate and the organic layers combined. The resulting mixture was washed with 2×150 mL of water and 1×100 mL of sodium chloride sat. The mixture was dried over anhydrous sodium sulfate and concentrated under vacuum. This resulted in 2.0 g (66%) of 120a as brown oil.

Step 2. 5-(2,5-dichloro-4-((1-(4-(2-cyclopropoxyphenyl)pyridin-3-yl)cyclopropoxy)methyl) phenyl) pentanoic acid (Intermediate 120b)

A 100-mL round-bottom flask was charged with methyl 5-[2,5-dichloro-4-([1-[4-(2-cyclopropoxyphenyl)pyridin-3-yl]cyclopropoxy]methyl)phenyl]pentanoate, 120a (1.02 g, 1.89 mmol, 1.00 equiv), methanol (15 mL), water (20 mL). This was followed by the addition of LiOH·H$_2$O (400 mg, 9.52 mmol, 5.00 equiv), in portions at room temperature. The resulting solution was stirred for 2 h at 50° C. The resulting mixture was concentrated under vacuum. The resulting solution was diluted with 20 mL of water. The resulting mixture was washed with 1×40 mL of ethyl acetate. The pH value of the solution was adjusted to 3-4 with hydrogen chloride cons. The resulting solution was extracted with 3×50 mL of dichloromethane and the organic layers combined. The resulting mixture was washed with 1×50 mL of water and 1×50 mL of sodium chloride sat. The mixture was dried over anhydrous sodium sulfate. This resulted in 0.6 g (60%) of 120b as colorless oil. MS: (ES, m/z): 526 [M+H]$^+$.

Step 3. N-benzyl-5-(2,5-dichloro-4-((1-(4-(2-cyclo-propoxyphenyl)pyridin-3-yl)cyclopropoxy) methyl) phenyl)-N-((2R,3S,4R,5R)-2,3,4,5,6-pentahydroxy-hexyl)pentanamide (I-120)

D1 (12 mg, 0.0456 mmol, 1.2 equiv) was added to a solution of 120b (20 mg, 0.038 mmol, 1.00 equiv), HATU (17 mg, 0.0456 mmol, 1.20 equiv), and DIEA (15 mg, 0.114 mmol, 3.00 equiv) in DMF (0.2 mL). The resulting solution was stirred for 1 h at room temperature. The crude product was purified by preparative HPLC with a CH$_3$CN/H$_2$O gradient containing 0.1% TFA (40% CH$_3$CN to 80% CH$_3$CN over 18 min) to obtain 8 mg (27%) of the title compound (I-120) trifluoroacetate salt as a white solid. MS (ES, m/z): 779 [M+H]$^+$; $^1$H-NMR (400 MHz, DMSO-d$_6$, ppm): δ 8.82 (s, 1H), 8.69 (d, J=5.5 Hz, 1H), 7.54 (d, J=4.9 Hz, 1H), 7.47-7.41 (m, 1H), 7.37-7.32 (m, 3H), 7.29 (dd, J=13.0, 4.7 Hz, 2H), 7.22 (d, J=7.3 Hz, 1H), 7.15 (d, J=6.9 Hz, 2H), 7.02 (t, J=7.5 Hz, 1H), 6.91 (d, J=7.1 Hz, 1H), 4.68 (d, J=15.1 Hz, 1H), 4.43 (d, J=15.4 Hz, 1H), 4.24 (s, 2H), 3.81 (s, 1H), 3.64-3.50 (m, 3H), 3.37-3.20 (m, 2H), 2.65 (s, 1H), 1.50 (d, J=30.5 Hz, 4H), 1.05 (d, J=13.0 Hz, 4H), 0.62 (d, J=6.1 Hz, 2H), 0.33 (s, 2H).

Example 50: 5-(2,5-dichloro-4-((1-(4-(2-cyclo-propoxyphenyl)pyridin-3-yl)cyclopropoxy) methyl) phenyl)-N-methyl-N-(2-(((2R,3R,4S,5S,6R)-3,4,5-trihydroxy-6-(hydroxymethyl) tetrahydro-2H-pyran-2-yl)oxy)ethyl)pentanamide (I-121)

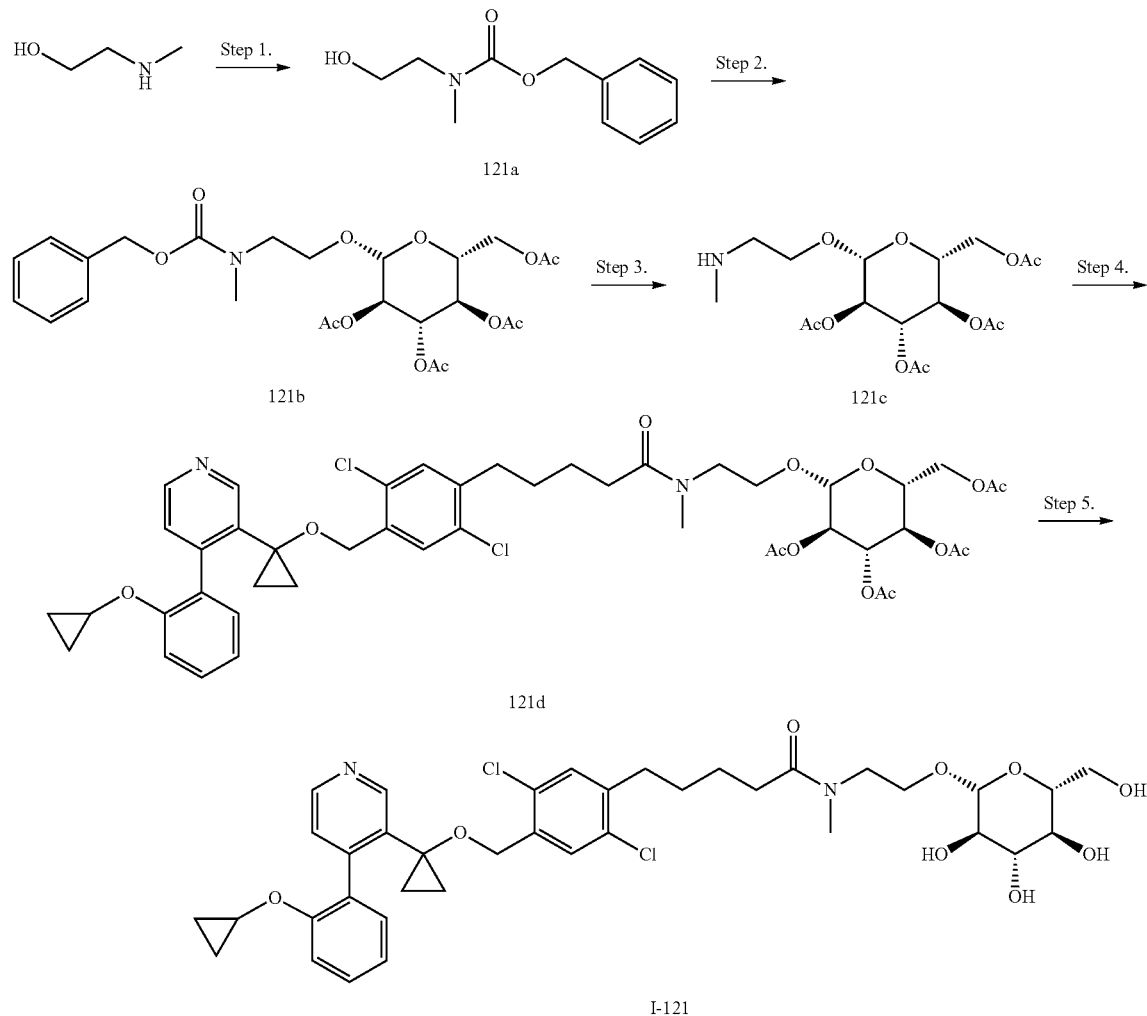

Step 1. Benzyl (2-hydroxyethyl)(methyl)carbamate (Intermediate 121a)

A solution of 2-methylamine ethanol (3.98 g, 53 mmol, 2.12 equiv) in DCM (35 mL) was cooled to 0° C. Benzyl chloroformate (4.26 g, 25 mmol, 1.00 equiv) was then added dropwise and the reaction mixture was stirred for 1 h at 0° C. and then warmed to room temperature. The solution was concentrated under vacuum and extracted with ethyl acetate (150 mL). The organic extract was washed with 1N HCl (50 mL), water (50 mL), NaHCO$_3$ (50 mL), and brine (50 mL). The mixture was dried over anhydrous sodium sulfate and concentrated under vacuum to yield 4.37 g (84%) of 121a.

Step 2. (2R,3R,4S,5R,6R)-2-(acetoxymethyl)-6-(2-(((benzyloxy)carbonyl)(methyl)amino) ethoxy)tetrahydro-2H-pyran-3,4,5-triyl triacetate (Intermediate 121b)

Anhydrous $Na_2SO_4$ (500 mg, 3.52 mmol, 2.89 equiv) was added A mixture tetra-O-acetyl glucopyranosyl bromide (500 mg, 1.22 mmol, 1.00 equiv) and benzyl (2-hydroxyethyl)(methyl)carbamate (347 mg, 1.66 mmol, 1.40 equiv) in dichloromethane (3 mL). The resulting mixture was stirred for 30 min at room temperature. $Ag_2CO_3$ (480 mg, 1.75 mmol, 1.40 equiv) was then added to the mixture. The resulting reaction was purged with $N_2$, wrapped in foil, and stirred for 18 h at room temperature. The reaction progress was monitored by LCMS and TLC (1:1 EtOAc/hexane). Additional tetra-O-acetyl glucopyranosyl bromide (340 mg, 0.827 mg, 0.678 equiv) and $Ag_2CO_3$ (340 mg, 1.23 mmol, 1.01 equiv) were added to the mixture and was stirred for an additional 16 h at room temperature. The reaction mixture was then filtered through celite and washed with 5×10 mL dichloromethane. The crude product was purified using flash chromatography, eluting on $SiO_2$ (50 g) with a 40% to 60% EtOAc/hexane gradient to yield 975 mg of 121b.

Step 3. (2R,3R,4S,5R,6R)-2-(acetoxymethyl)-6-(2-(methylamino)ethoxy)tetrahydro-2H-pyran-3,4,5-triyl triacetate (Intermediate 121c)

A mixture of 121b (975 mg, 1.81 mmol) and 10% Pd/C (10 wt % C) (120 mg, 1.13 mmol, 0.624 equiv) in methanol (15 mL) was stirred under $H_2$ for 90 min at room temperature. The reaction progress was monitored by LCMS. The resulting reaction mixture was filtered through celite and concentrated under vacuum and was used without further purification.

Step 4. (2R,3R,4S,5R,6R)-2-(acetoxymethyl)-6-(2-(5-(2,5-dichloro-4-((1-(4-(2-cyclopropoxy-phenyl)pyridin-3-yl)cyclopropoxy)methyl)phenyl)-N-methylpentanamido)ethoxy)tetrahydro-2H-pyran-3,4,5-triyl triacetate (Intermediate 121d)

121c (23 mg, 0.0570 mmol, 1.20 equiv) was added to a solution of 5-(2,5-dichloro-4-((1-(4-(2-cyclopropoxyphenyl)pyridine-3-yl)cyclopropoxy)methyl)phenyl)pentanoic acid, 120b (25 mg, 0.0475 mmol, 1.00 equiv), HATU (30 mg, 0.079 mmol, 1.7 equiv), and DIEA (18 mg, 0.142 mmol, 3 equiv) in DMF (0.3 mL). The resulting solution was stirred for 2 h at room temperature and the reaction progress was monitored by LCMS. The crude product was purified by preparative HPLC with a $CH_3CN/H_2O$ gradient containing 0.1% TFA (10% $CH_3CN$ to 80% $CH_3CN$ over 18 min) and was used directly.

Step 4. 5-(2,5-dichloro-4-((1-(4-(2-cyclopropoxy-phenyl)pyridin-3-yl)cyclopropoxy)methyl) phenyl)-N-methyl-N-(2-((((2R,3R,4S,5S,6R)-3,4,5-trihydroxy-6-(hydroxymethyl)tetrahydro-2H-pyran-2-yl)oxy)ethyl)pentanamide (I-121)

Sodium methoxide (25 wt % in MeOH) (0.20 mL) was added to solution of 121d in methanol (0.5 mL). The resulting mixture was stirred for 1 h at room temperature and the reaction progress was monitored by LCMS. The mixture was concentrated under vacuum and the crude product was purified by preparative HPLC with a $CH_3CN/H_2O$ gradient containing 0.1% TFA (10% $CH_3CN$ to 80% $CH_3CN$ over 18 min) to provide 3 mg (8.6%) of the title compound (I-121) trifluoroacetate salt as a white solid. MS (ES, m/z): 745 $[M+H]^+$. $^1$H-NMR (400 MHz, DMSO-$d_6$, ppm): δ 8.79 (s, 1H), 8.66 (d, J=5.5 Hz, 1H), 7.53-7.49 (m, 1H), 7.43 (t, J=7.6 Hz, 1H), 7.36-7.28 (m, 3H), 7.01 (t, J=7.4 Hz, 1H), 6.90 (s, 1H), 4.23 (s, 2H), 2.98 (s, 3H), 2.88 (s, 3H), 2.78 (d, J=8.5 Hz, 3H), 2.72 (s, 2H), 2.67 (t, J=7.3 Hz, 5H), 2.63 (s, 4H), 2.39-2.24 (m, 4H), 1.90 (d, J=0.8 Hz, 4H), 1.50 (s, 4H), 1.03 (d, J=14.2 Hz, 4H), 0.62 (d, J=5.8 Hz, 2H), 0.32 (s, 2H).

Example 51: 5-(2,5-dichloro-4-((1-(4-(2-cyclopropoxyphenyl)pyridin-3-yl)cyclopropoxy) methyl) phenyl)-N-(2,3-dihydroxypropyl)-N-((2S,3R,4R,5R)-2,3,4,5,6-pentahydroxyhexyl) pentanamide (I-122)

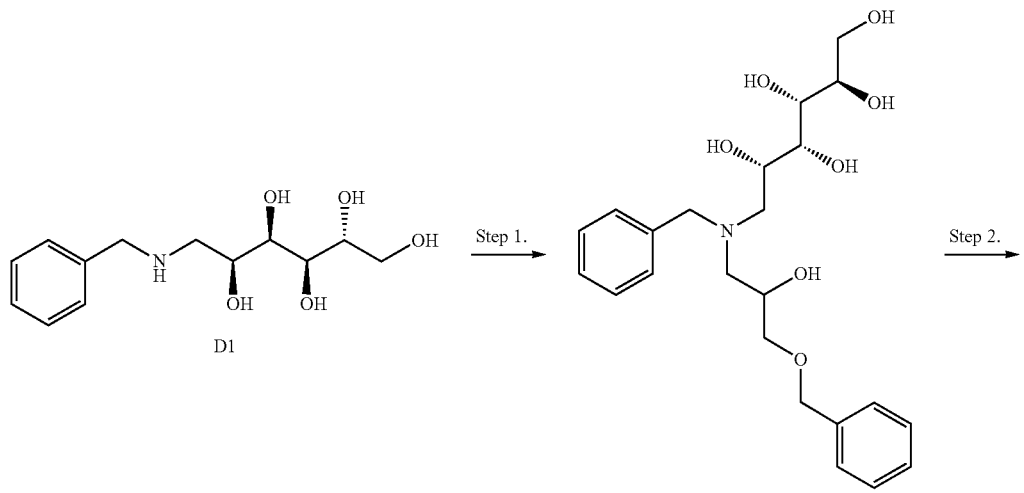

D1

122a

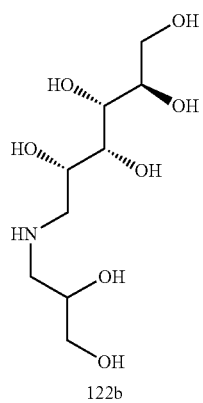

122b

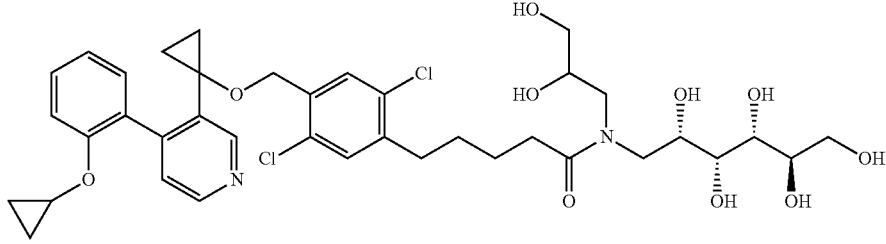

I-122

Step 1. (2R,3R,4R,5S)-6-(benzyl(3-(benzyloxy)-2-hydroxypropyl)amino)hexane-1,2,3,4,5-pentaol (Intermediate 121a)

K$_2$CO$_3$ (48 mg, 0.351 mmol, 0.950 equiv) was added to a solution of D1 (100 mg, 0.369 mmol, 1.00 equiv) and benzyl glycidyl ether (58 mg, 0.351 mmol, 0.950 equiv) in water (2 mL). The resulting mixture was stirred for 17 h at 60° C. The resulting mixture became an emulsion with the crude product in the oil layer. The solution was decanted and the oil was purified by preparative HPLC with a CH$_3$CN/H$_2$O gradient containing 0.1% TFA (10% CH$_3$CN to 50% CH$_3$CN over 18 min) to provide 74 mg of 122a (30%) as a white solid.

Step 2. (2R,3R,4R,5S)-6-((2,3-dihydroxypropyl)amino)hexane-1,2,3,4,5-pentaol (Intermediate 122b)

Pd/C (10 wt % C) (50 mg, 0.470 mmol, 2.80 equiv) and concentrated HCl (0.20 mL) were added A solution of 122a (72 mg, 0.165 mmol, 1.00 equiv) in ethanol (2 mL). The resulting mixture was purged with H$_2$ and was allowed to stir for 90 min at room temperature. The resulting solution was diluted with methanol (20 mL), washed with 2×20 mL water, dried over anhydrous sodium sulfate and concentrated under reduced pressure to provide 42 mg of 122b which was used without further purification.

Step 3. 5-(2,5-dichloro-4-((1-(4-(2-cyclopropoxyphenyl)pyridin-3-yl)cyclopropoxy)methyl) phenyl)-N-(2,3-dihydoxypropyl)-N-((2S,3R,4R,5R)-2,3,4,5,6-pentahydroxyhexyl) pentanamide (I-122)

HATU (63 mg, 0.165 mmol, 1.90 equiv) was added to a solution of 5-(2,5-dichloro-4-((1-(4-(2-cyclopropoxyphenyl)pyridine-3-yl)cyclopropoxy)methyl)phenyl)pentanoic acid, 120b (46 mg, 0.0867 mmol, 1.00 equiv), 122b (42 mg, 0.165 mmol, 1.90 equiv), and DIEA (64 mg, 0.494 mmol, 3.00 equiv) in DMF (2 mL). The resulting solution was stirred for 16 h at room temperature. The crude product was purified by preparative HPLC with a CH$_3$CN/H$_2$O gradient containing 0.1% TFA (10% CH$_3$CN to 80% CH$_3$CN over 18 min) to provide 41 mg (62%) of the title compound trifluoroacetate salt I-122 as a light yellow solid. MS (ES, m/z): 763 [M+H]$^+$; $^1$H-NMR (400 MHz, DMSO-d$_6$) δ 8.84 (s, 1H), 8.71 (d, J=5.6 Hz, 1H), 7.60 (d, J=5.5 Hz, 1H), 7.45 (t, 1H), 7.33 (dt, J=9.1, 3.9 Hz, 3H), 7.02 (t, J=7.4 Hz, 1H), 6.90 (s, 1H), 4.24 (s, 4H), 3.25 (d, 4H), 2.62 (s, 3H), 1.49 (s, 4H), 1.12-1.00 (m, 5H), 0.63 (d, J=6.1 Hz, 2H), 0.33 (s, 2H).

The compounds in Table 8 Compounds I-123 to I-124 were prepared from commercial or known starting materials according to the method described in Example 50 and methods generally known to those skilled in the art.

TABLE 8

Compounds I-123 to I-125

| Cmpd No.: | Synthetic Method | Structure | Obs. [M + H] |
|---|---|---|---|
| I-123 | Example 50 | 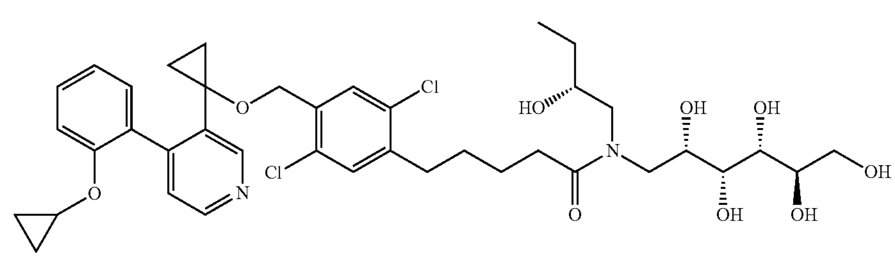 [SMILES: CC[C@@H](O)CN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 761 |

TABLE 8-continued

Compounds I-123 to I-125

| Cmpd No.: | Synthetic Method | Structure | Obs. [M + H] |
|---|---|---|---|
| I-124 | Example 50 | 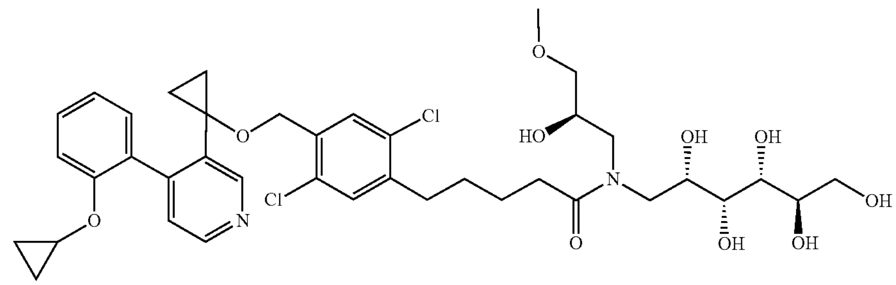 [SMILES: COC[C@H](O)CN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 777 |
| I-125 | Example 50 | 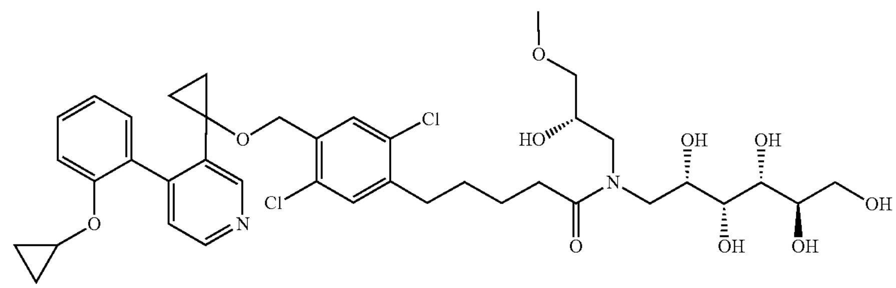 [SMILES: COC[C@@H](O)CN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 777 |

Example 52: N-benzyl-5-(2,5-dichloro-4((1-(4-(2-cyclopropoxyphenyl)pyridin-3-yl) cyclopropoxy)methyl)phenyl)-N-((2S,3R,4R,5R)-2,3,4,5,6-pentahydroxyhexyl)pentanamide (I-126)

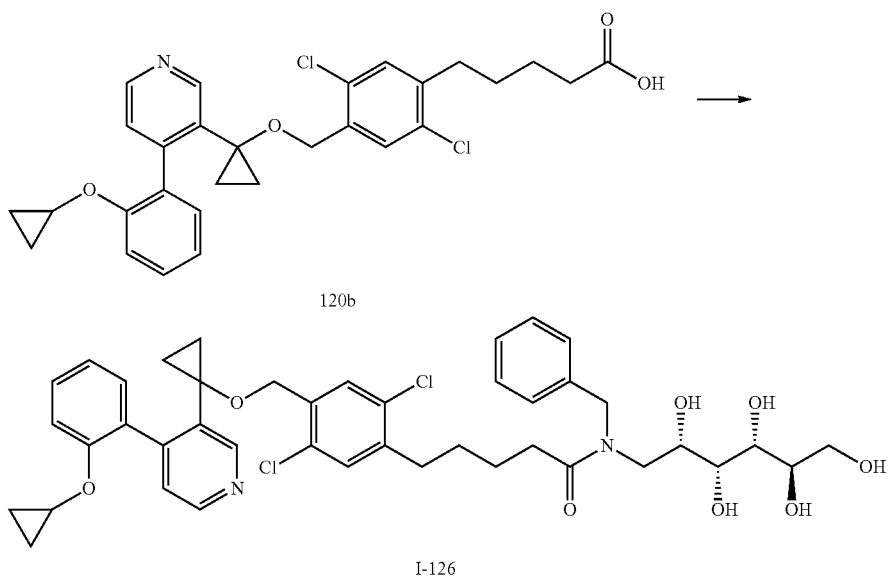

D1 (53 mg, 0.171 mmol, 2.00 equiv) was added to solution of 5-(2,5-dichloro-4-((1-(4-(2-cyclopropoxyphenyl)pyridine-3-yl)cyclopropoxy)methyl)phenyl)pentanoic acid, 120b (45 mg, 0.0856 mmol, 1.00 equiv), HATU (65 mg, 0.171 mmol, 2.00 equiv), and DIEA (33 mg, 0.257 mmol, 3.00 equiv) in DMF (1 mL). The resulting solution was allowed to stir for 1 h at room temperature. The crude product was purified by preparative HPLC with a $CH_3CN/H_2O$ gradient containing 0.1% TFA (10% $CH_3CN$ to 80% $CH_3CN$ over 18 min). The fractions containing the desired product were then neutralized with Amberlyst A26 hydroxide resin and filtered to provide 15 mg (22%) of the title compound I-126 as a white solid. MS (ES, m/s): 779 [M+H]$^+$; $^1$H-NMR (400 MHz, DMSO-d$_6$) δ 8.77 (s, 1H), 8.64 (d, J=5.3 Hz, 1H), 7.45-7.38 (m, 2H), 7.37-7.26 (m, 5H), 7.23 (d, J=7.4 Hz, 1H), 7.16 (d, J=7.0 Hz, 2H), 7.01 (t, J=7.4 Hz, 1H), 6.94 (d, J=7.3 Hz, 1H), 4.69 (d, J=15.4 Hz, 2H), 4.44 (d, J=15.0 Hz, 1H), 4.25 (s, 2H), 3.82 (s, 1H), 3.57 (t, J=9.7 Hz, 3H), 3.51-3.25 (m, 5H), 2.66 (s, 2H), 1.51 (d, J=30.1 Hz, 4H), 1.01 (d, J=9.5 Hz, 4H), 0.62 (d, J=6.0 Hz, 2H), 0.34 (s, 2H).

Compounds I-127 to I-131 were prepared from intermediate 120b and commercial or known starting materials according to the methods specified in Table 9 and methods generally known to those skilled in the art.

TABLE 9

Compounds I-127 to I-131.

| Cmpd. No.: | Amine | Synthetic Method | Compound Structure | [M + H]+ Obs. |
|---|---|---|---|---|
| I-127 | D3 | Example 52 | 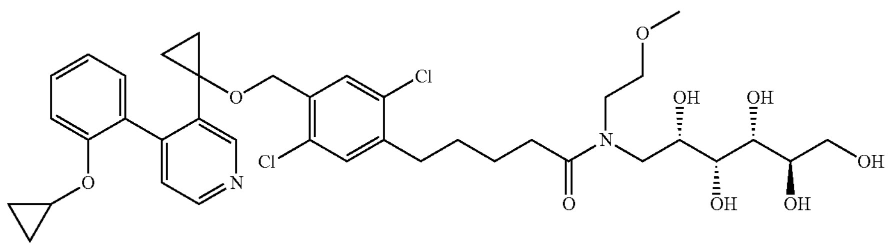 | 747 |
| I-128 | D5 | Example 52 | 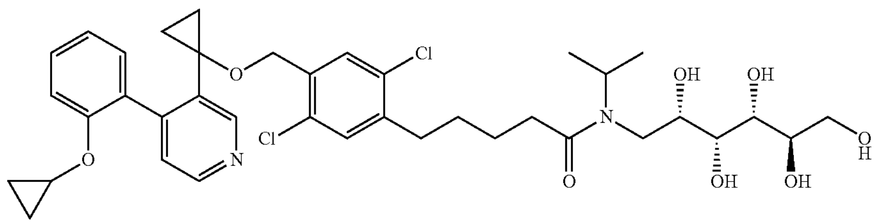 [SMILES: CC(C)N(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 731 |
| I-129 | D2 | Example 52 | 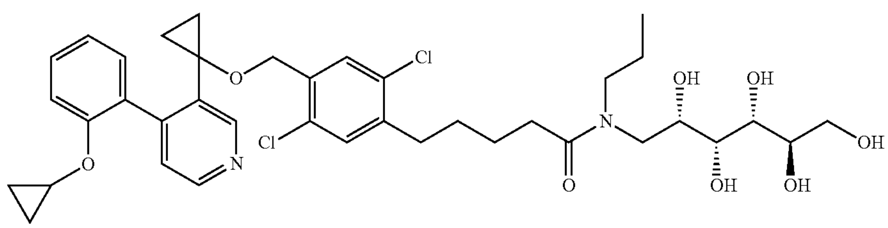 [SMILES: CCCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 731 |
| I-130 | D4 | Example 52 | 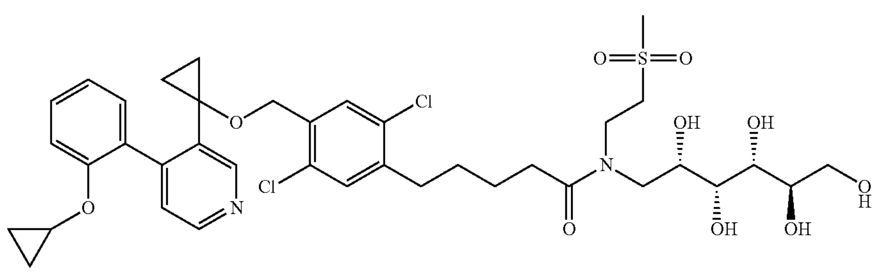 [SMILES: CS(=O)(=O)CCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 795 |
| I-131 | D6 | Example 52 | 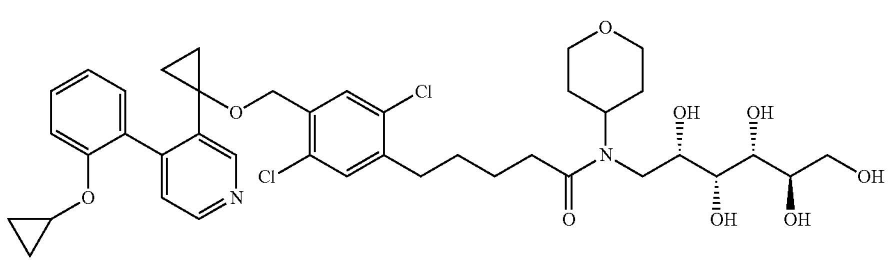 [SMILES: O=C(CCCCc1cc(Cl)c(COC2(c3cnccc3-c3ccccc3OC3CC3)CC2)cc1Cl)N(C[C@H](O)[C@@H](O)[C@H](O)[C@H](O)CO)C1CCOCC1] | 773 |

Compounds I-132 to I-241 in Table 10 were prepared from commercial, known starting materials or the appropriate intermediates disclosed herein according to methods from the examples specified in Table 10 and methods generally known to those skilled in the art.

TABLE 10

Compounds I-132 to I-241

| Cmpd. No.: | Synthetic Method | Compound Structure | Obs. [M + H]+ |
|---|---|---|---|
| I-132 | Example 26 | 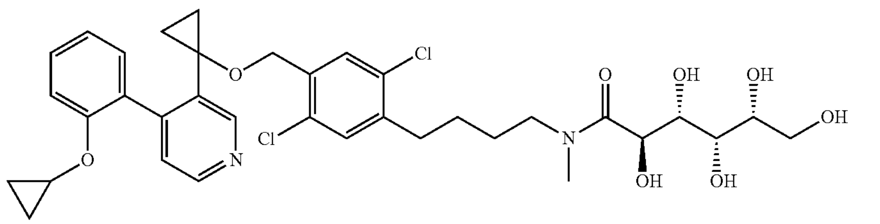 [SMILES: CN(CCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 669.26 |
| I-133 | Example 17 | 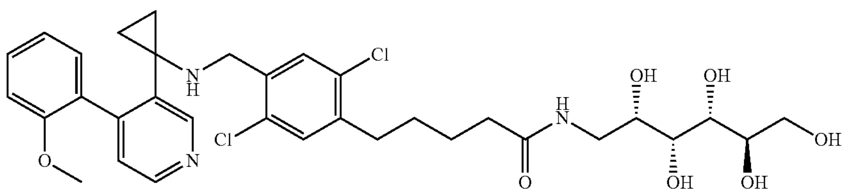 [SMILES: COc1ccccc1-c1ccncc1C1(NCc2cc(Cl)c(CCCCC(=O)NC[C@H](O)[C@@H](O)[C@H](O)[C@H](O)CO)cc2Cl)CC1] | 662.15 |
| I-134 | Example 17 | 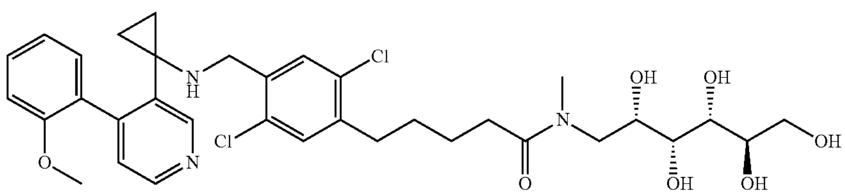 [SMILES: COc1ccccc1-c1ccncc1C1(NCc2cc(Cl)c(CCCCC(=O)N(C)C[C@H](O)[C@@H](O)[C@H](O)[C@H](O)CO)cc2Cl)CC1] | 676.15 |
| I-135 | Example 49 | 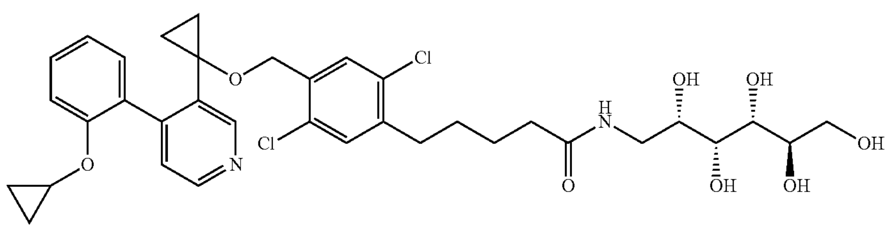 [SMILES: O=C(CCCCc1cc(Cl)c(COC2(c3cnccc3-c3ccccc3OC3CC3)CC2)cc1Cl)NC[C@H](O)[C@@H](O)[C@H](O)[C@H](O)CO] | 689.25 |
| I-136 | Example 49 | 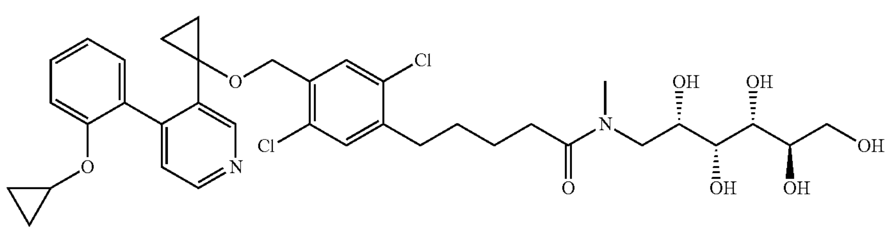 [SMILES: CN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 703.25 |
| I-137 | Example 17 | 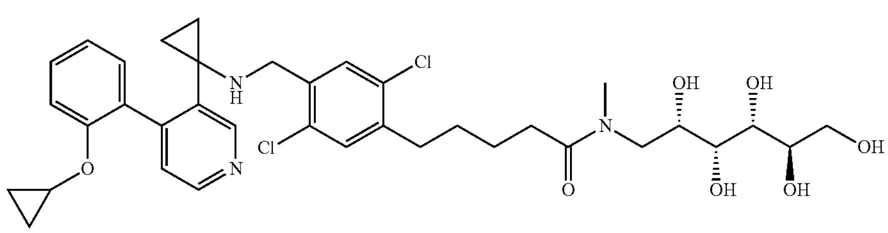 [SMILES: CN(C[C@H](O)[C@@H](O)[C@H](O)[C@H](O)CO)C(=O)CCCCc1cc(Cl)c(CNC2(c3cnccc3-c3ccccc3OC3CC3)CC2)cc1Cl] | 702.2 |

TABLE 10-continued
Compounds I-132 to I-241
| Cmpd. No.: | Synthetic Method | Compound Structure | Obs. [M + H]+ |
|---|---|---|---|
| I-138 | Example 15 | 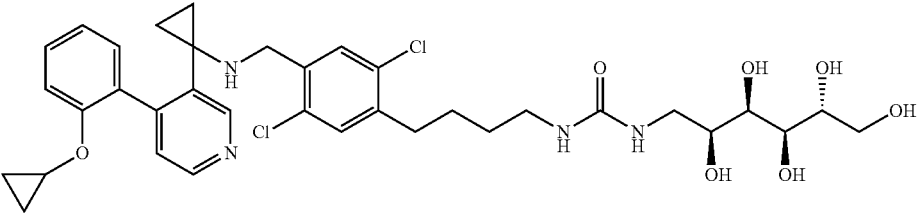 [SMILES: O=C(NCCCCc1cc(Cl)c(CNC2(c3cnccc3-c3ccccc3OC3CC3)CC2)cc1Cl)NC[C@H](O)[C@@H](O)[C@H](O)[C@H](O)CO] | 703.2 |
| I-139 | Example 49 | 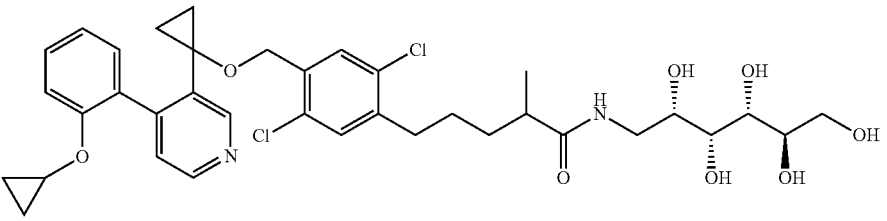 | 703.2 |
| I-140 | Example 49 | 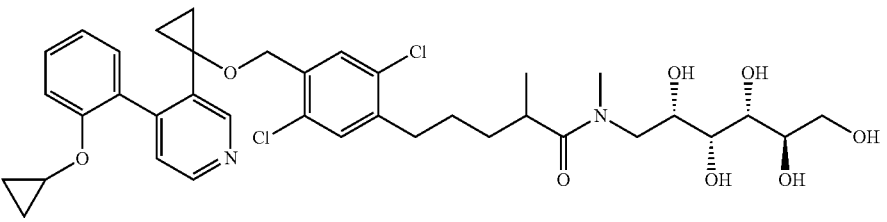 [SMILES: CC(CCCc1cc(Cl)c(COC2(c3cnccc3-c3ccccc3OC3CC3)CC2)cc1Cl)C(=O)N(C)C[C@H](O)[C@@H](O)[C@H](O)[C@H](O)CO] | 717.2 |
| I-141 | Example 20 | 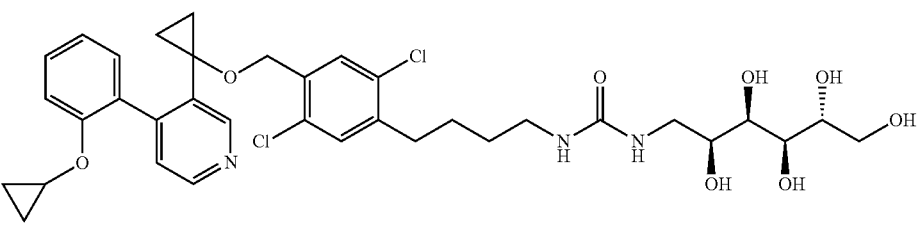 [SMILES: O=C(NCCCCc1cc(Cl)c(COC2(c3cnccc3-c3ccccc3OC3CC3)CC2)cc1Cl)NC[C@H](O)[C@@H](O)[C@H](O)[C@H](O)CO] | 704.3 |
| I-142 | Example 17 | 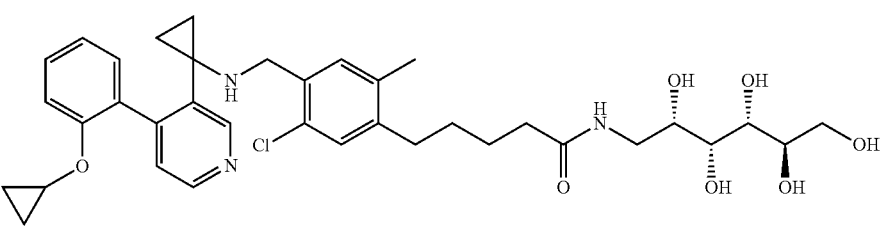 [SMILES: Cc1cc(CNC2(c3cnccc3-c3ccccc3OC3CC3)CC2)c(Cl)cc1CCCCC(=O)NC[C@H](O)[C@@H](O)[C@H](O)[C@H](O)CO] | 668.30 |
| I-143 | Example 17 | 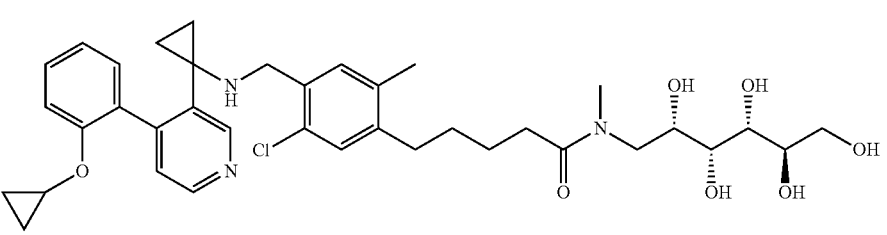 | 682.35 |

TABLE 10-continued

Compounds I-132 to I-241

| Cmpd. No.: | Synthetic Method | Compound Structure | Obs. [M + H]+ |
|---|---|---|---|
| I-144 | Example 49 | 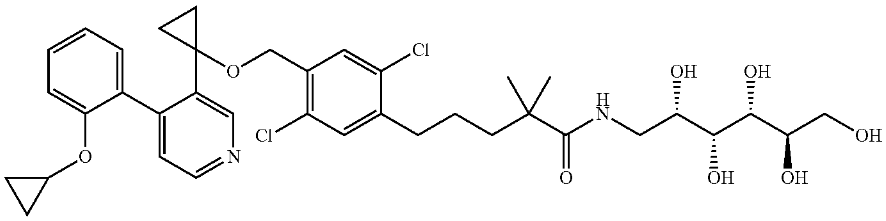 [SMILES: CC(C)(CCCc1cc(Cl)c(COC2(c3cnccc3-c3ccccc3OC3CC3)CC2)cc1Cl)C(=O)NC[C@H](O)[C@@H](O)[C@H](O)[C@H](O)CO] | 717.30 |
| I-145 | Example 49 | 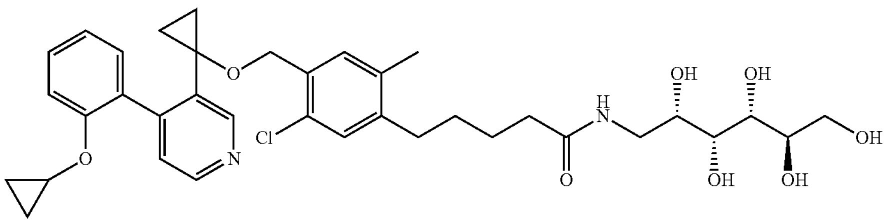 [SMILES: Cc1cc(COC2(c3cnccc3-c3ccccc3OC3CC3)CC2)c(Cl)cc1CCCCC(=O)NC[C@H](O)[C@@H](O)[C@H](O)[C@H](O)CO] | 669.30 |
| I-146 | Example 49 | 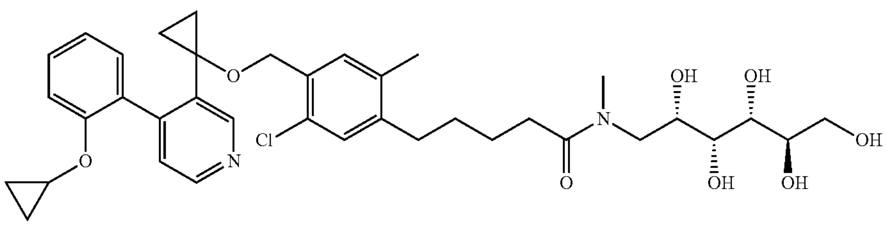 | 683.3 |
| I-147 | Example 15 | 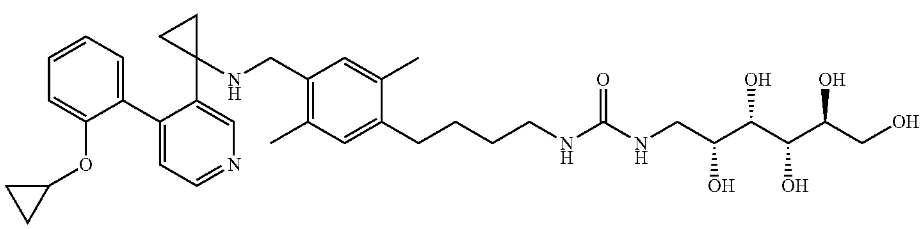 [SMILES: Cc1cc(CNC2(c3cnccc3-c3ccccc3OC3CC3)CC2)c(C)cc1CCCCNC(=O)NC[C@@H](O)[C@H](O)[C@@H](O)[C@@H](O)CO] | 663.40 |
| I-148 | Example 17 | 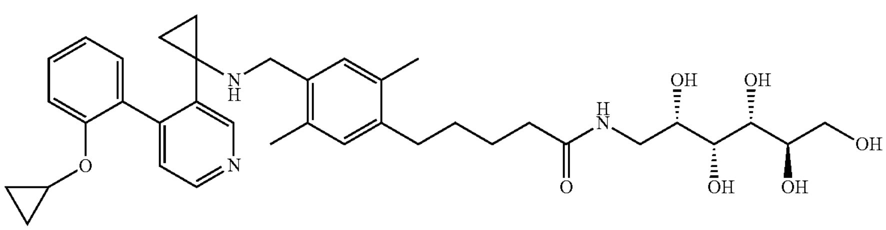 [SMILES: Cc1cc(CNC2(c3cnccc3-c3ccccc3OC3CC3)CC2)c(C)cc1CCCCC(=O)NC[C@H](O)[C@@H](O)[C@H](O)[C@H](O)CO] | 648.35 |
| I-149 | Example 17 | 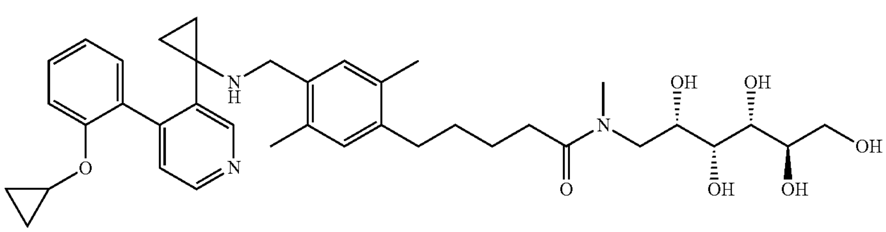 [SMILES: Cc1cc(CNC2(c3cnccc3-c3ccccc3OC3CC3)CC2)c(C)cc1CCCCC(=O)N(C)C[C@H](O)[C@@H](O)[C@H](O)[C@H](O)CO] | 662.40 |

TABLE 10-continued

Compounds I-132 to I-241

| Cmpd. No.: | Synthetic Method | Compound Structure | Obs. [M + H]+ |
|---|---|---|---|
| I-150 | Example 20 | 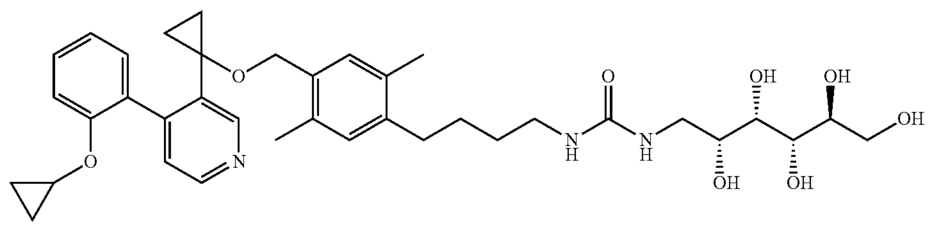 [SMILES: Cc1cc(COC2(c3cnccc3-c3ccccc3OC3CC3)CC2)c(C)cc1CCCCNC(=O)NC[C@@H](O)[C@H](O)[C@@H](O)[C@@H](O)CO] | 664.2 |
| I-151 | Example 15 | 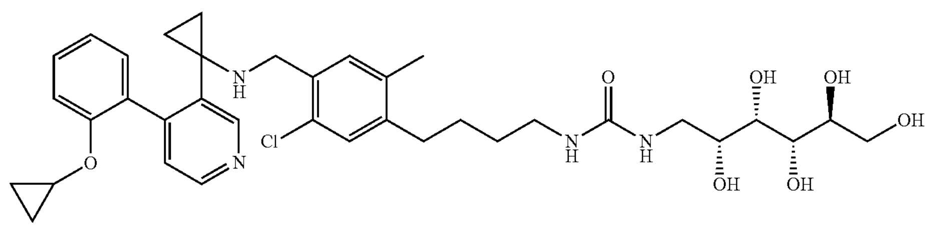 [SMILES: Cc1cc(CNC2(c3cnccc3-c3ccccc3OC3CC3)CC2)c(Cl)cc1CCCCNC(=O)NC[C@@H](O)[C@H](O)[C@@H](O)[C@@H](O)CO] | 683.30 |
| I-152 | Example 49 | 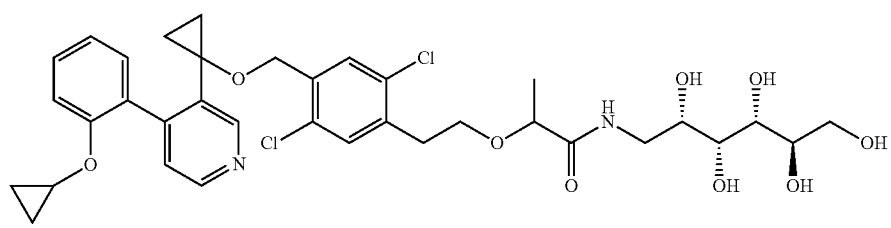 | 705.1 |
| I-153 | Example 49 | 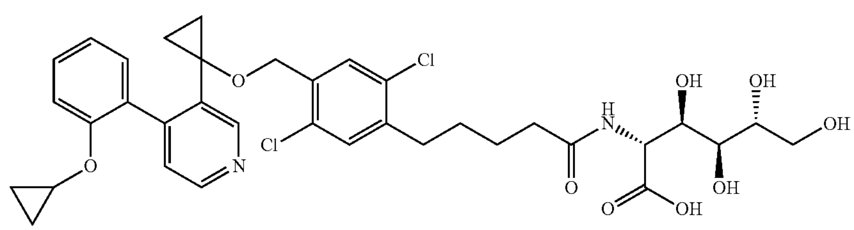 [SMILES: O=C(CCCCc1cc(Cl)c(COC2(c3cnccc3-c3ccccc3OC3CC3)CC2)cc1Cl)N[C@@H](C(=O)O)[C@@H](O)[C@H](O)[C@H](O)CO] | 703.61 |
| I-154 | Example 49 | 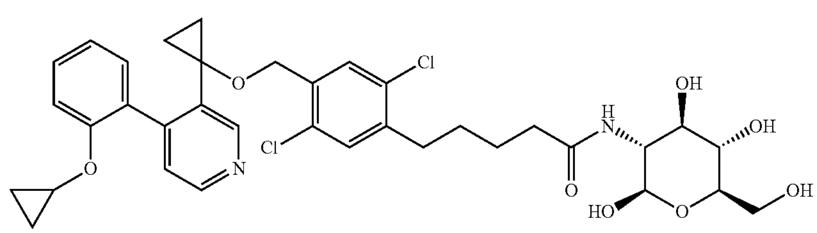 [SMILES: O=C(CCCCc1cc(Cl)c(COC2(c3cnccc3-c3ccccc3OC3CC3)CC2)cc1Cl)N[C@@H]1[C@@H](O)[C@H](O)[C@@H](CO)O[C@H]1O] | 687.2 |
| I-155 | Example 49 | 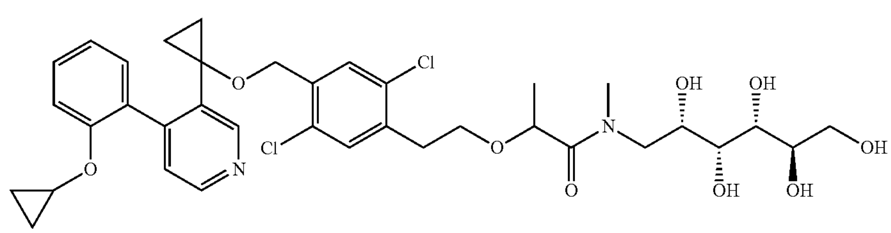 [SMILES: CC(OCCc1cc(Cl)c(COC2(c3cnccc3-c3ccccc3OC3CC3)CC2)cc1Cl)C(=O)N(C)C[C@H](O)[C@@H](O)[C@H](O)[C@H](O)CO] | 719.1 |

TABLE 10-continued
Compounds I-132 to I-241
| Cmpd. No.: | Synthetic Method | Compound Structure | Obs. [M + H]+ |
|---|---|---|---|
| I-156 | Example 49 | 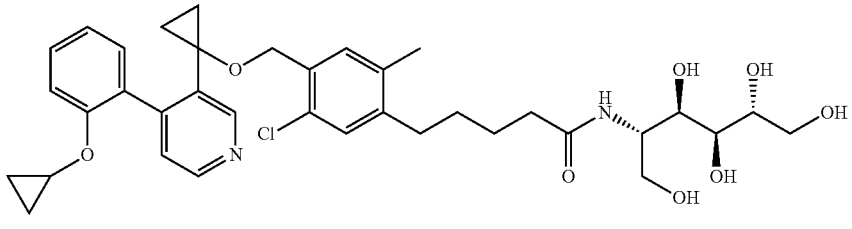 [SMILES: Cc1cc(COC2(c3cnccc3-c3ccccc3OC3CC3)CC2)c(Cl)cc1CCCCC(=O)N[C@@H](CO)[C@@H](O)[C@H](O)[C@H](O)CO] | 689.15 |
| I-157 | Example 49 | 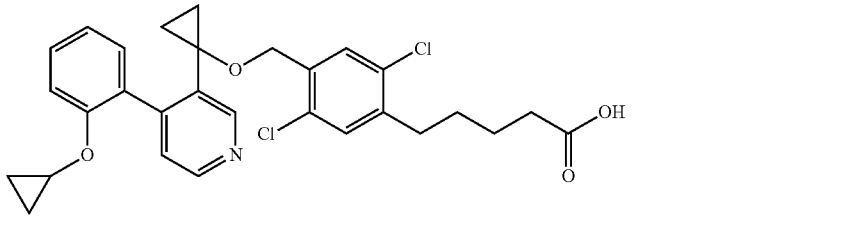 [SMILES: O=C(O)CCCCc1cc(Cl)c(COC2(c3cnccc3-c3ccccc3OC3CC3)CC2)cc1Cl] | 526.2 |
| I-158 | Example 33 | 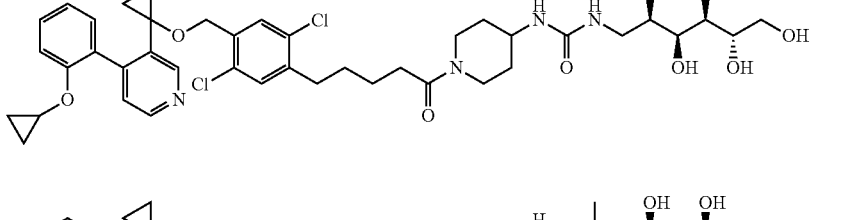 | 815.2 |
| I-159 | Example 33 | 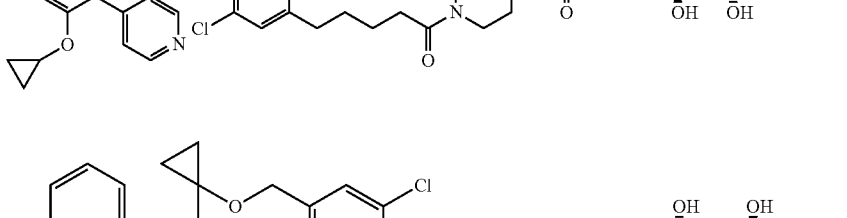 | 829.2 |
| I-160 | Example 49 | 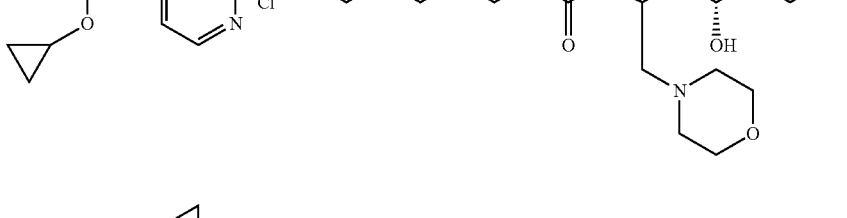 | 758.30 |
| I-161 | Example 49 | 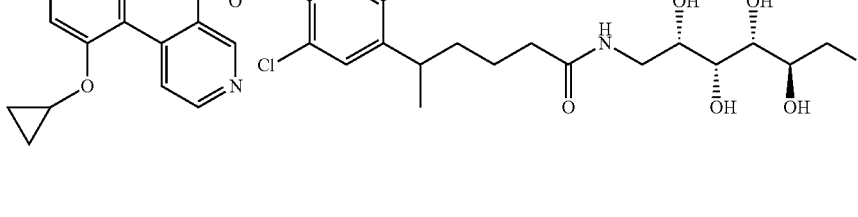 | 703.30 |

TABLE 10-continued

Compounds I-132 to I-241

| Cmpd. No.: | Synthetic Method | Compound Structure | Obs. [M + H]+ |
|---|---|---|---|
| I-162 | Example 49 | 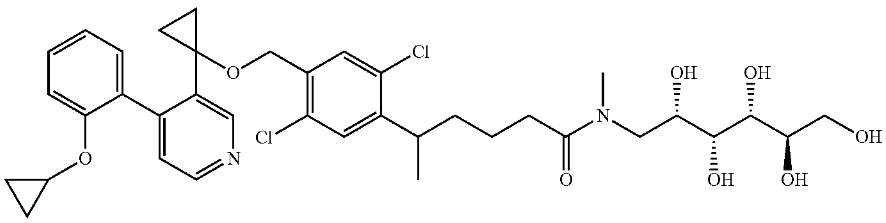 [SMILES: CC(CCCC(=O)N(C)C[C@H](O)[C@@H](O)[C@H](O)[C@H](O)CO)c1cc(Cl)c(COC2(c3cnccc3-c3ccccc3OC3CC3)CC2)cc1Cl] | 717.10 |
| I-163 | Example 15 | 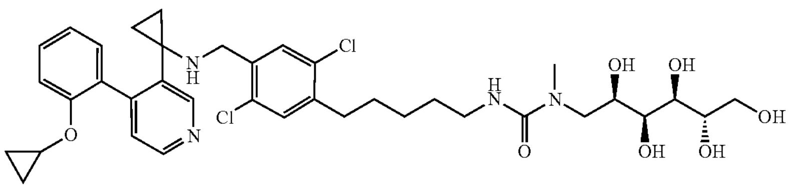 [SMILES: CN(C[C@@H](O)[C@H](O)[C@@H](O)[C@@H](O)CO)C(=O)NCCCCCc1cc(Cl)c(CNC2(c3cnccc3-c3ccccc3OC3CC3)CC2)cc1Cl] | 731.1 |
| I-164 | Example 49 | 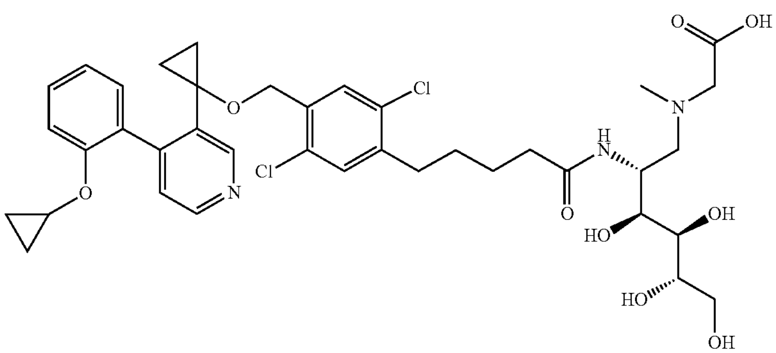 [SMILES: CN(CC(=O)O)C[C@@H](NC(=O)CCCCc1cc(Cl)c(COC2(c3cnccc3-c3ccccc3OC3CC3)CC2)cc1Cl)[C@H](O)[C@@H](O)[C@@H](O)CO] | 760.05 |
| I-165 | Example 49 | 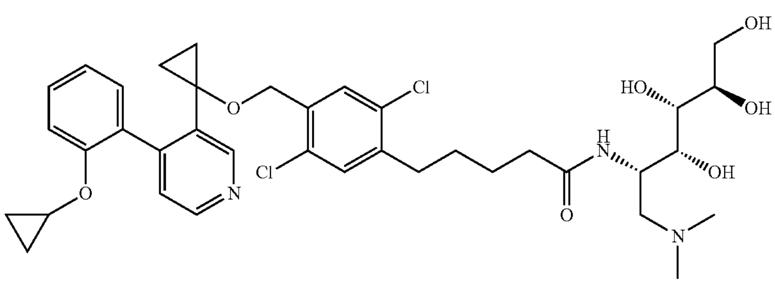 [SMILES: CN(C)C[C@H](NC(=O)CCCCc1cc(Cl)c(COC2(c3cnccc3-c3ccccc3OC3CC3)CC2)cc1Cl)[C@@H](O)[C@H](O)[C@H](O)CO] | 716.10 |
| I-166 | Example 20 | 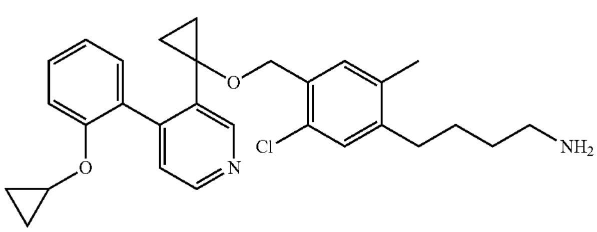 [SMILES: Cc1cc(COC2(c3cnccc3-c3ccccc3OC3CC3)CC2)c(Cl)cc1CCCCN] | 477.15 |
| I-167 | Example 20 | 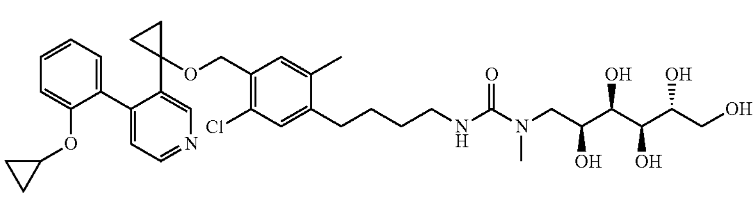 [SMILES: Cc1cc(COC2(c3cnccc3-c3ccccc3OC3CC3)CC2)c(Cl)cc1CCCCNC(=O)N(C)C[C@H](O)[C@@H](O)[C@H](O)[C@H](O)CO] | 698.25 |

TABLE 10-continued
Compounds I-132 to I-241
| Cmpd. No.: | Synthetic Method | Compound Structure | Obs. [M + H]+ |
|---|---|---|---|
| I-168 | Example 30 | 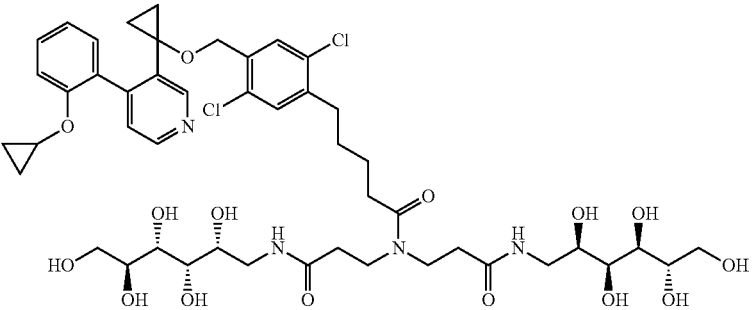 [SMILES: O=C(CCN(CCC(=O)NC[C@@H](O)[C@H](O)[C@@H](O)[C@@H](O)CO)C(=O)CCCCc1cc(Cl)c(COC2(c3cnccc3-c3ccccc3OC3CC3)CC2)cc1Cl)NC[C@@H](O)[C@H](O)[C@@H](O)[C@@H](O)CO] | 499.35 [M + 2H]+2/2 |
| I-169 | Example 30 | 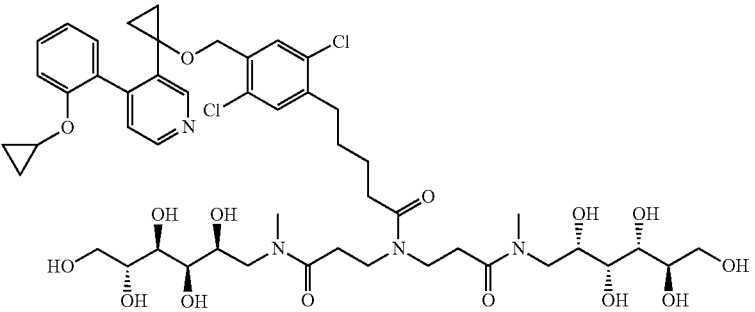 [SMILES: CN(C[C@H](O)[C@@H](O)[C@H](O)[C@H](O)CO)C(=O)CCN(CCC(=O)N(C)C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 513.25 [M + 2H]+2/2 |
| I-170 | Example 30 | 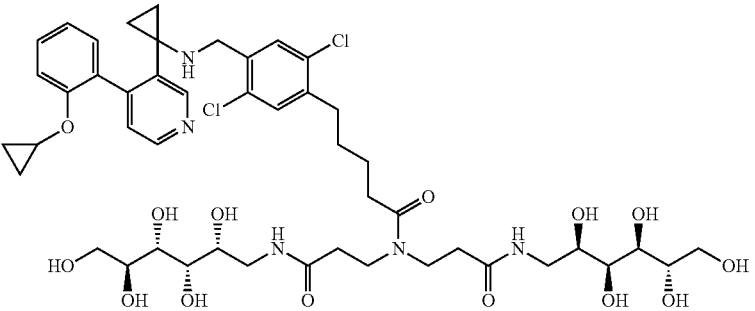 | 497.85 [M + 2H]+2/2 |
| I-171 | Example 30 | 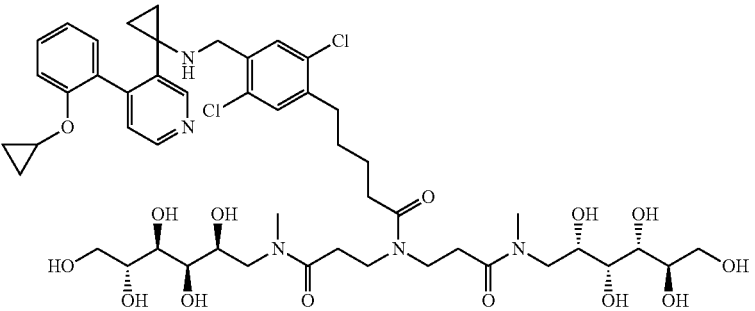 [SMILES: CN(C[C@H](O)[C@@H](O)[C@H](O)[C@H](O)CO)C(=O)CCN(CCC(=O)N(C)C[C@H](O)[C@@H](O)[C@H](O)[C@H](O)CO)C(=O)CCCCc1cc(Cl)c(CNC2(c3cnccc3-c3ccccc3OC3CC3)CC2)cc1Cl] | 512 |
| I-172 | Example 26 | 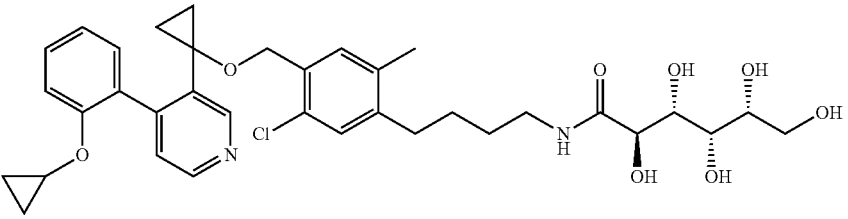 [SMILES: Cc1cc(COC2(c3cnccc3-c3ccccc3OC3CC3)CC2)c(Cl)cc1CCCCNC(=O)[C@H](O)[C@H](O)[C@@H](O)[C@H](O)CO] | 655.2 |

TABLE 10-continued

Compounds I-132 to I-241

| Cmpd. No.: | Synthetic Method | Compound Structure | Obs. [M + H]+ |
|---|---|---|---|
| I-173 | Example 33 | 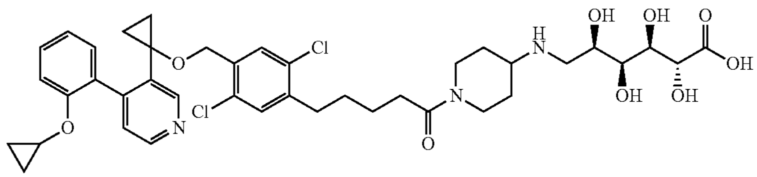 [SMILES: O=C(O)[C@H](O)[C@H](O)[C@@H](O)[C@H](O)CNC1CCN(C(=O)CCCCc2cc(Cl)c(COC3(c4cnccc4-c4ccccc4OC4CC4)CC3)cc2Cl)CC1] | 786.10 |
| I-174 | Example 15 | 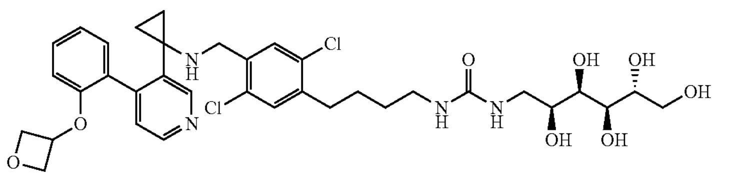 [SMILES: O=C(NCCCCc1cc(Cl)c(CNC2(c3cnccc3-c3ccccc3OC3COC3)CC2)cc1Cl)NC[C@H](O)[C@@H](O)[C@H](O)[C@H](O)CO] | 719.0 |
| I-175 | Example 15 | 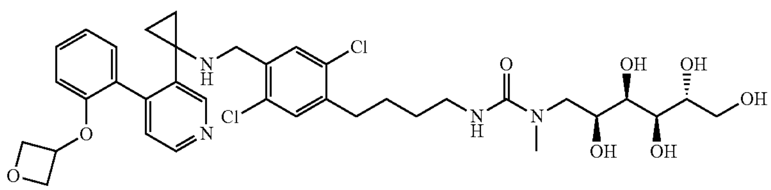 [SMILES: CN(C[C@H](O)[C@@H](O)[C@H](O)[C@H](O)CO)C(=O)NCCCCc1cc(Cl)c(CNC2(c3cnccc3-c3ccccc3OC3COC3)CC2)cc1Cl] | 733.1 |
| I-176 | Example 26 | 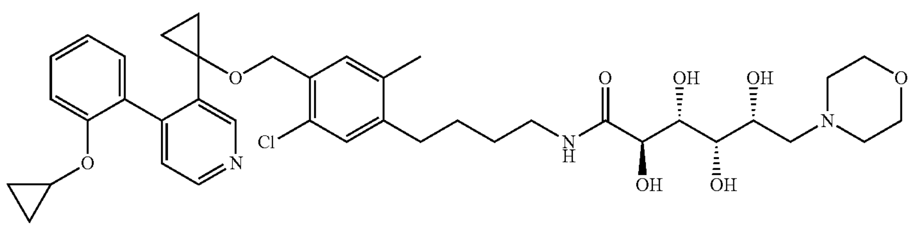 [SMILES: Cc1cc(COC2(c3cnccc3-c3ccccc3OC3CC3)CC2)c(Cl)cc1CCCCNC(=O)[C@H](O)[C@H](O)[C@@H](O)[C@H](O)CN1CCOCC1] | 724.10 |
| I-177 | Example 17 | 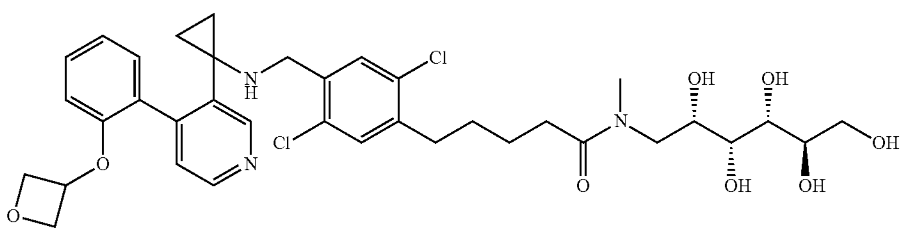 [SMILES: CN(C[C@H](O)[C@@H](O)[C@H](O)[C@H](O)CO)C(=O)CCCCc1cc(Cl)c(CNC2(c3cnccc3-c3ccccc3OC3COC3)CC2)cc1Cl] | 718.6 |
| I-178 | Example 17 | 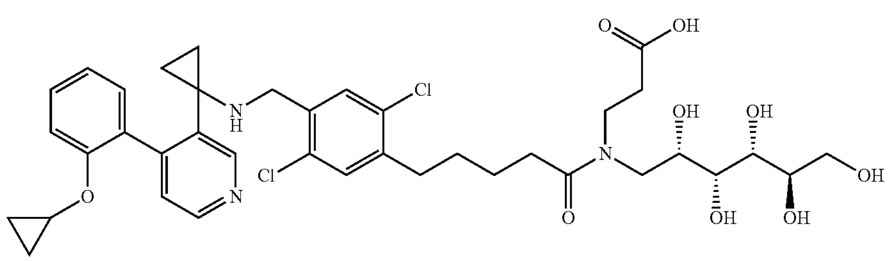 | 760.0 |
| I-179 | Example 26 | 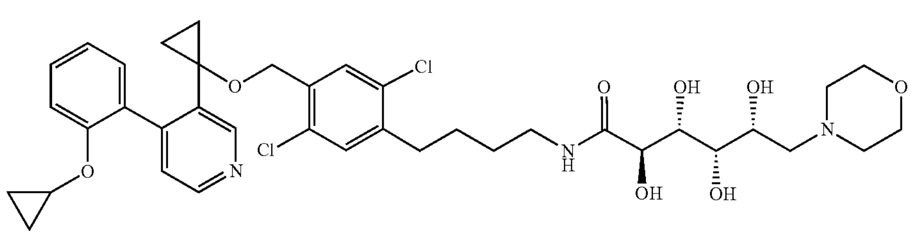 [SMILES: O=C(NCCCCc1cc(Cl)c(COC2(c3cnccc3-c3ccccc3OC3CC3)CC2)cc1Cl)[C@H](O)[C@H](O)[C@@H](O)[C@H](O)CN1CCOCC1] | 744.3 |

TABLE 10-continued
Compounds I-132 to I-241
| Cmpd. No.: | Synthetic Method | Compound Structure | Obs. [M + H]+ |
|---|---|---|---|
| I-180 | Example 33 | 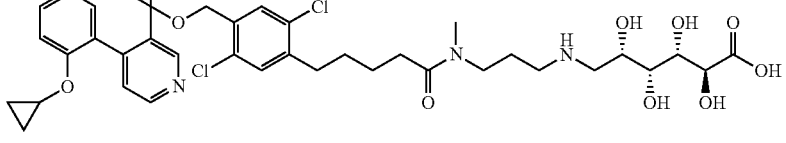 | 774.10 |
| I-181 | Example 49 | 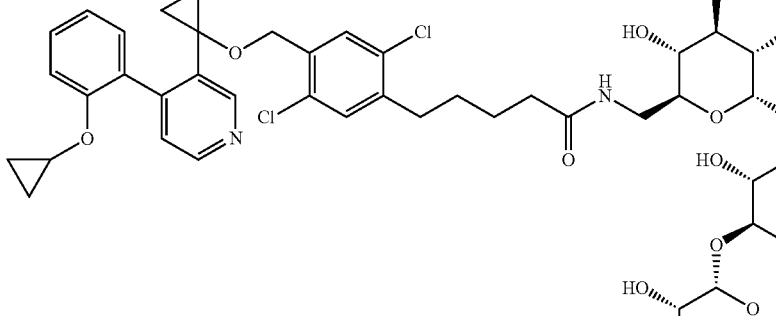 | 497.30 [M + 2H]+2/2 |
| I-182 | Example 22 | 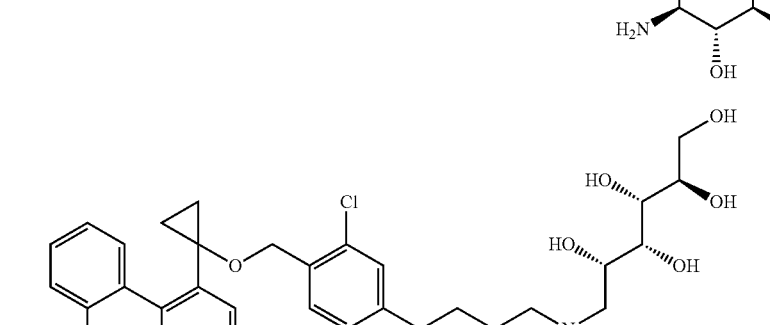 | 775.05 |
| I-183 | Example 49 | 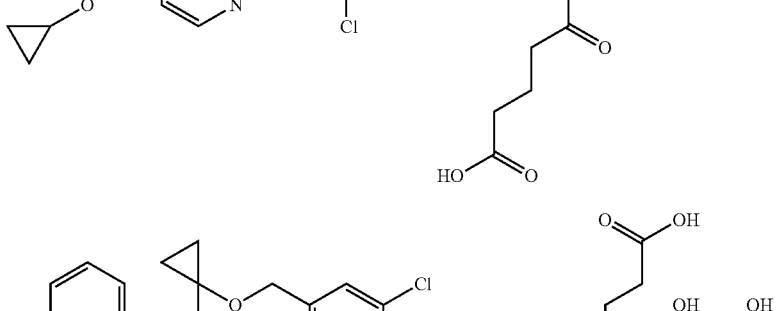 | 761.19 |
| I-184 | Example 26 | 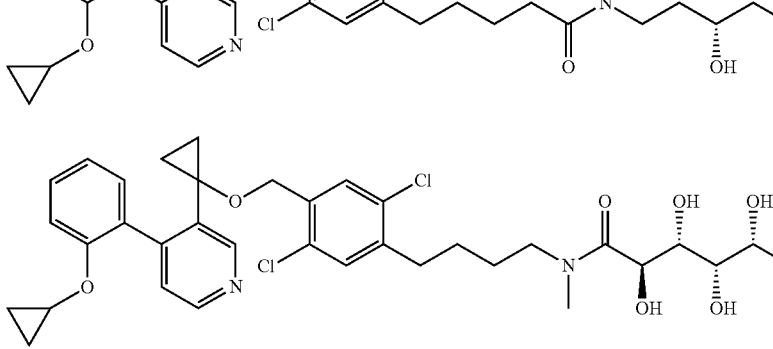 | 689.0 |

TABLE 10-continued

Compounds I-132 to I-241

| Cmpd. No.: | Synthetic Method | Compound Structure | Obs. [M + H]+ |
|---|---|---|---|
| I-185 | Example 26 | 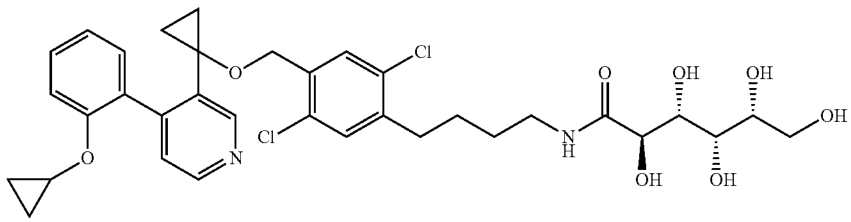 [SMILES: O=C(NCCCCc1cc(Cl)c(COC2(c3cnccc3-c3ccccc3OC3CC3)CC2)cc1Cl)[C@H](O)[C@H](O)[C@@H](O)[C@H](O)CO] | 675.1 |
| I-186 | Example 22 | 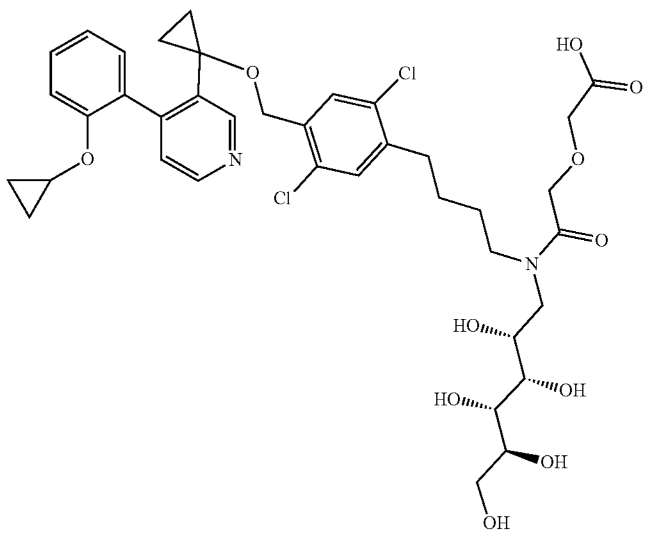 [SMILES: O=C(O)COCC(=O)N(CCCCc1cc(Cl)c(COC2(c3cnccc3-c3ccccc3OC3CC3)CC2)cc1Cl)C[C@@H](O)[C@H](O)[C@@H](O)[C@@H](O)CO] | 777.1 |
| I-187 | Example 22 | 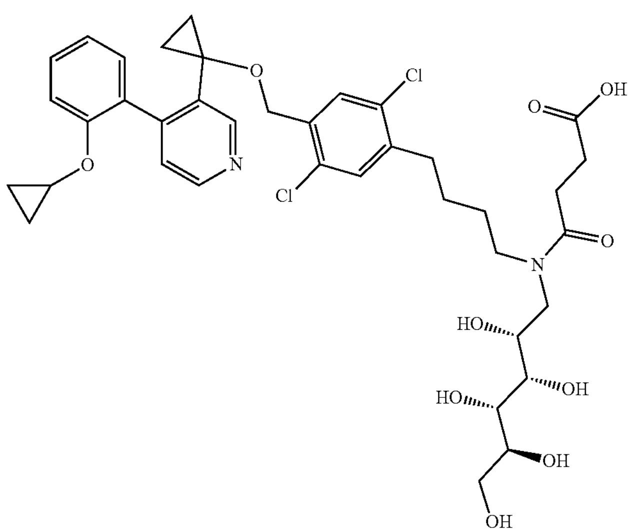 [SMILES: O=C(O)CCC(=O)N(CCCCc1cc(Cl)c(COC2(c3cnccc3-c3ccccc3OC3CC3)CC2)cc1Cl)C[C@@H](O)[C@H](O)[C@@H](O)[C@@H](O)CO] | 761.1 |

TABLE 10-continued

Compounds I-132 to I-241

| Cmpd. No.: | Synthetic Method | Compound Structure | Obs. [M + H]+ |
|---|---|---|---|
| I-188 | Example 63 | 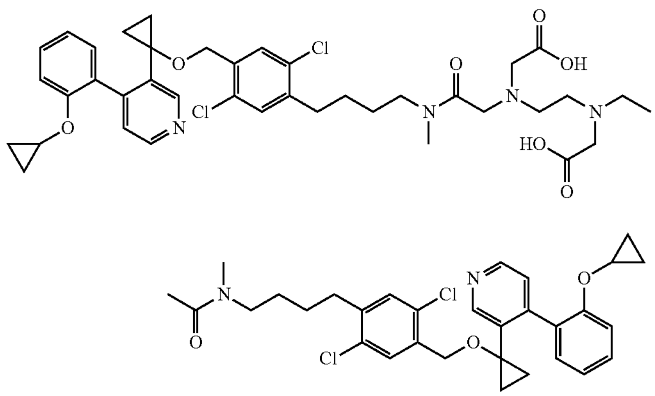 | 1278.9 |
| I-189 | Example 26 | 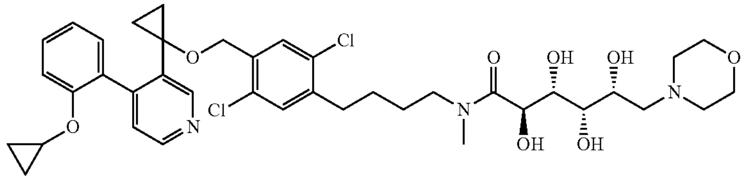 [SMILES: CN(CCCCc1cc(Cl)c(COC2(c3cnccc3-c3ccccc3OC3CC3)CC2)cc1Cl)C(=O)[C@H](O)[C@H](O)[C@@H](O)[C@H](O)CN1CCOCC1] | 758.1 |
| I-190 | Example 20 | 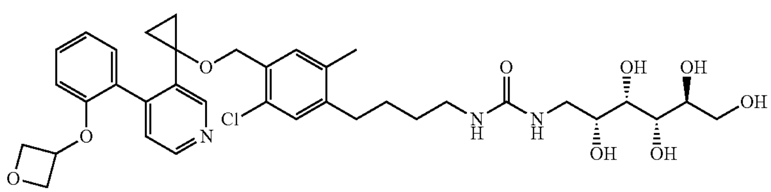 [SMILES: Cc1cc(COC2(c3cnccc3-c3ccccc3OC3COC3)CC2)c(Cl)cc1CCCCNC(=O)NC[C@@H](O)[C@H](O)[C@@H](O)[C@@H](O)CO] | 700.0 |
| I-191 | Example 20 | 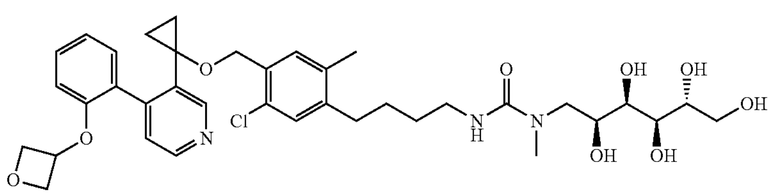 [SMILES: Cc1cc(COC2(c3cnccc3-c3ccccc3OC3COC3)CC2)c(Cl)cc1CCCCNC(=O)N(C)C[C@H](O)[C@@H](O)[C@H](O)[C@H](O)CO] | 714.4 |
| I-192 | Example 49 | 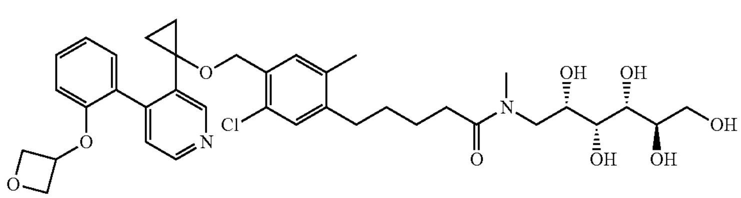 [SMILES: Cc1cc(COC2(c3cnccc3-c3ccccc3OC3COC3)CC2)c(Cl)cc1CCCCC(=O)N(C)C[C@H](O)[C@@H](O)[C@H](O)[C@H](O)CO] | 719.35 |
| I-193 | Example 20 | 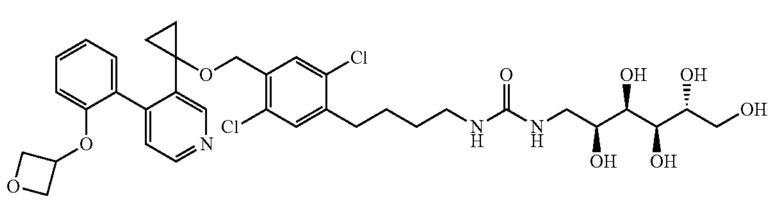 [SMILES: O=C(NCCCCc1cc(Cl)c(COC2(c3cnccc3-c3ccccc3OC3COC3)CC2)cc1Cl)NC[C@H](O)[C@@H](O)[C@H](O)[C@H](O)CO] | 720.0 |
| I-194 | Example 20 | 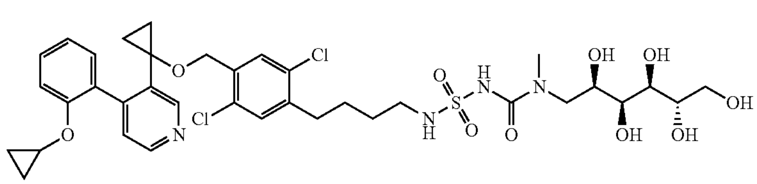 [SMILES: CN(C[C@@H](O)[C@H](O)[C@@H](O)[C@@H](O)CO)C(=O)NS(=O)(=O)NCCCCc1cc(Cl)c(COC2(c3cnccc3-c3ccccc3OC3CC3)CC2)cc1Cl] | 797.0 |

| Cmpd. No.: | Synthetic Method | Compound Structure | Obs. [M + H]+ |
|---|---|---|---|
| I-195 | Example 22 | 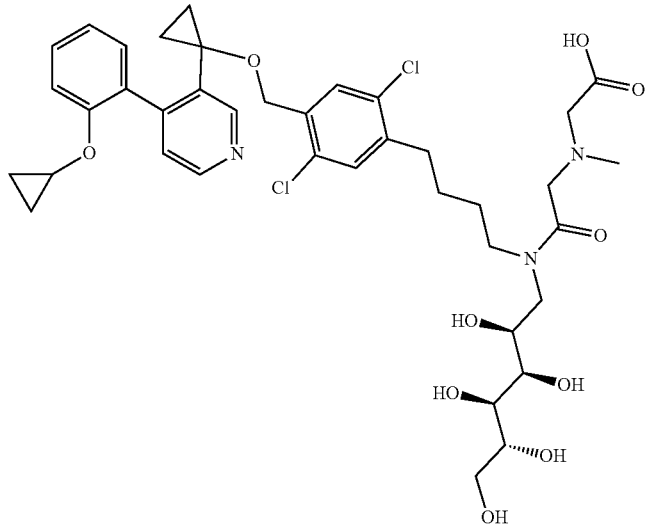 [SMILES: CN(CC(=O)O)CC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 790.06 |
| I-196 | Example 22 | 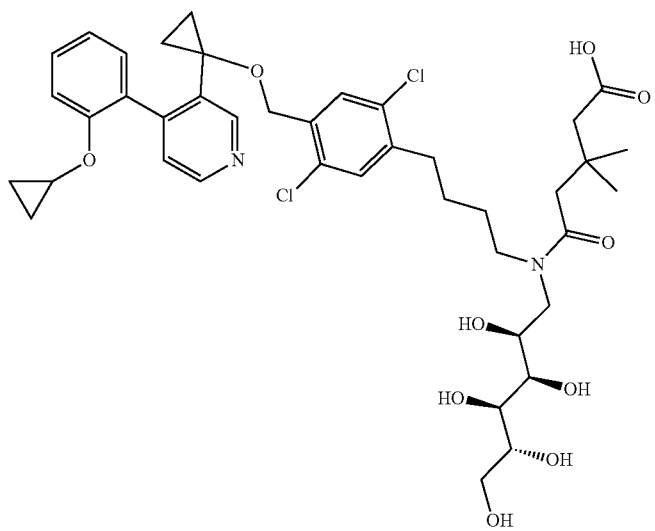 [SMILES: CC(C)(CC(=O)O)CC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 803.10 |

TABLE 10-continued

Compounds I-132 to I-241

| Cmpd. No.: | Synthetic Method | Compound Structure | Obs. [M + H]+ |
|---|---|---|---|
| I-197 | Example 25 | 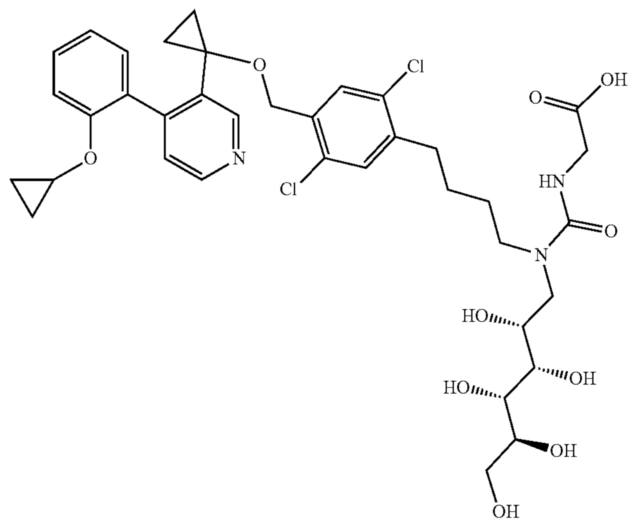 [SMILES: O=C(O)CNC(=O)N(CCCCc1cc(Cl)c(COC2(c3cnccc3-c3ccccc3OC3CC3)CC2)cc1Cl)C[C@@H](O)[C@H](O)[C@@H](O)[C@@H](O)CO] | 762.05 |
| I-198 | Example 25 | 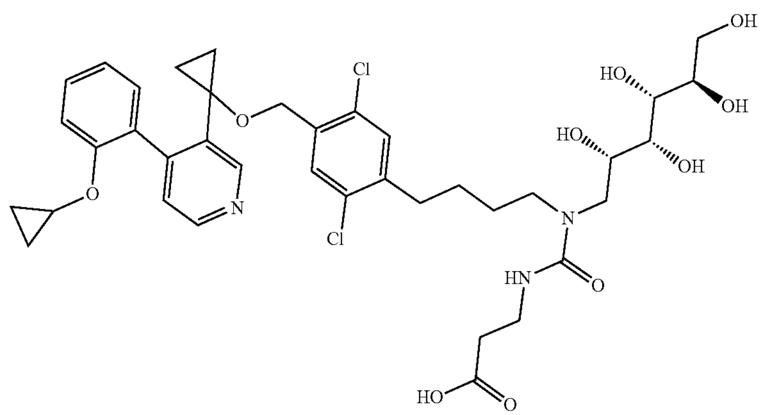 [SMILES: O=C(O)CCNC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 776.05 |
| I-199 | Example 25 | 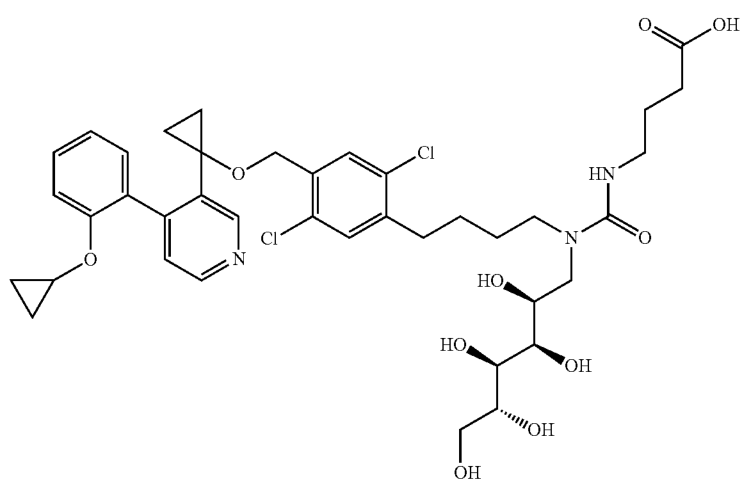 [SMILES: O=C(O)CCCNC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 790.05 |

TABLE 10-continued
Compounds I-132 to I-241
| Cmpd. No.: | Synthetic Method | Compound Structure | Obs. [M + H]+ |
|---|---|---|---|
| I-200 | Example 63 | 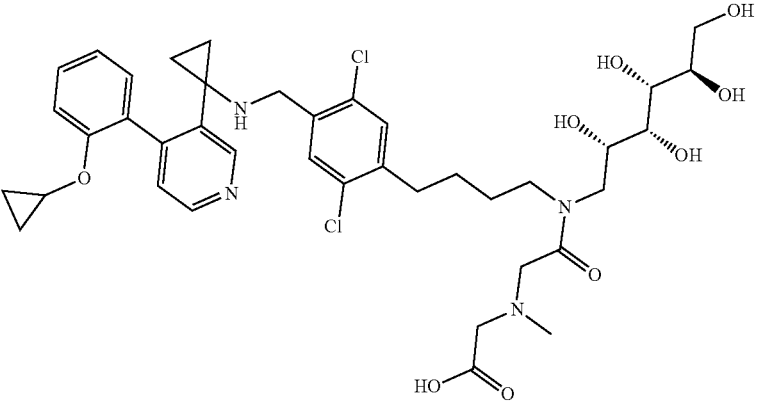 [SMILES: CN(CC(=O)O)CC(=O)N(CCCCc1cc(Cl)c(CNC2(c3cnccc3-c3ccccc3OC3CC3)CC2)cc1Cl)C[C@H](O)[C@@H](O)[C@H](O)[C@H](O)CO] | 395.20 [M + 2H]+2/2 |
| I-201 | Example 63 | 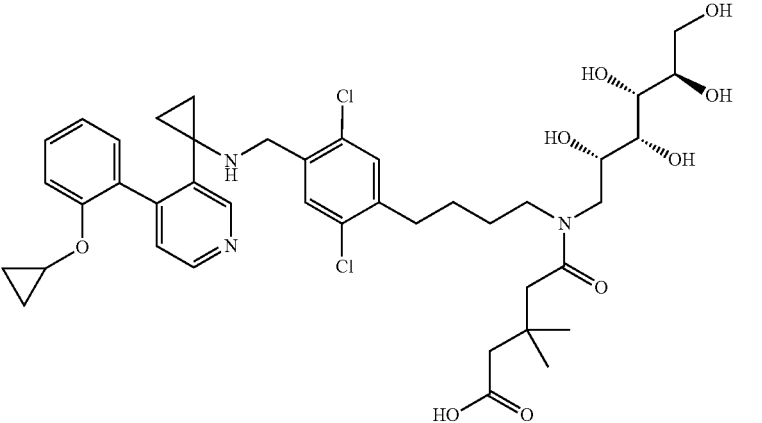 [SMILES: CC(C)(CC(=O)O)CC(=O)N(CCCCc1cc(Cl)c(CNC2(c3cnccc3-c3ccccc3OC3CC3)CC2)cc1Cl)C[C@H](O)[C@@H](O)[C@H](O)[C@H](O)CO] | 802.5 |
| I-202 | Example 22 | 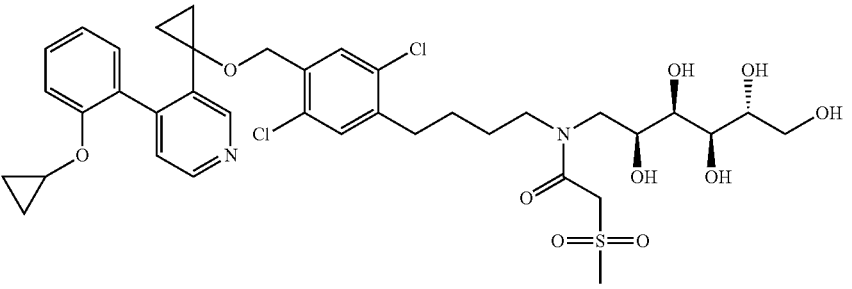 [SMILES: CS(=O)(=O)CC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 781.25 |
| I-203 | Example 25 | 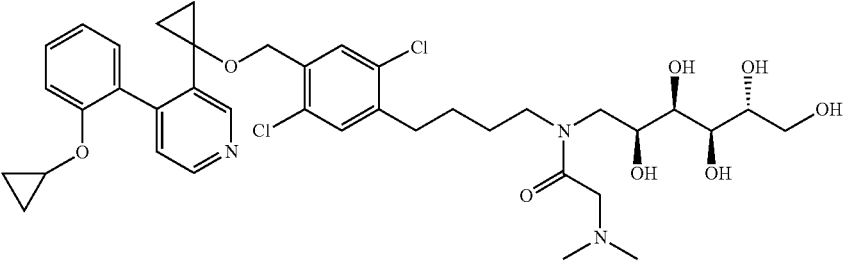 [SMILES: CN(C)CC(=O)N(CCCCc1cc(Cl)c(COC2(c3cnccc3-c3ccccc3OC3CC3)CC2)cc1Cl)C[C@H](O)[C@@H](O)[C@H](O)[C@H](O)CO] | 746.05 |

TABLE 10-continued

Compounds I-132 to I-241

| Cmpd. No.: | Synthetic Method | Compound Structure | Obs. [M + H]+ |
|---|---|---|---|
| I-204 | Example 20 | 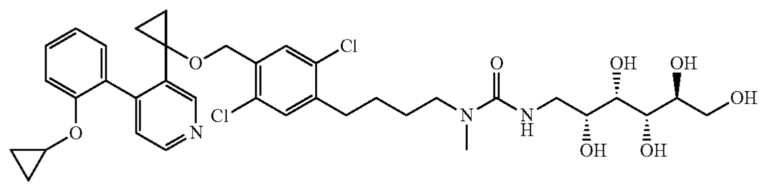 [SMILES: CN(CCCCc1cc(Cl)c(COC2(c3cnccc3-c3ccccc3OC3CC3)CC2)cc1Cl)C(=O)NC[C@@H](O)[C@H](O)[C@@H](O)[C@@H](O)CO] | 718.0 |
| I-205 | Example 26 | 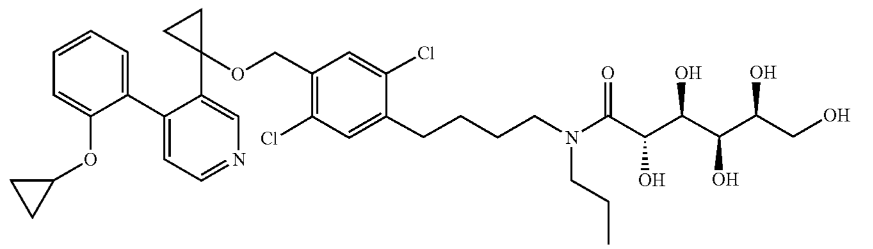 [SMILES: CCCN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | 717.2 |
| I-206 | Example 26 | 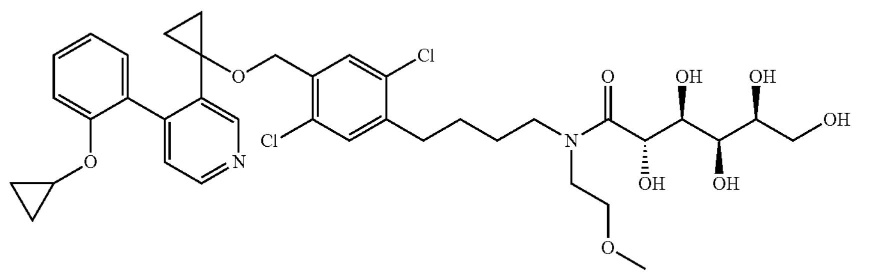 [SMILES: COCCN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | 733.2 |
| I-207 | Example 49 | 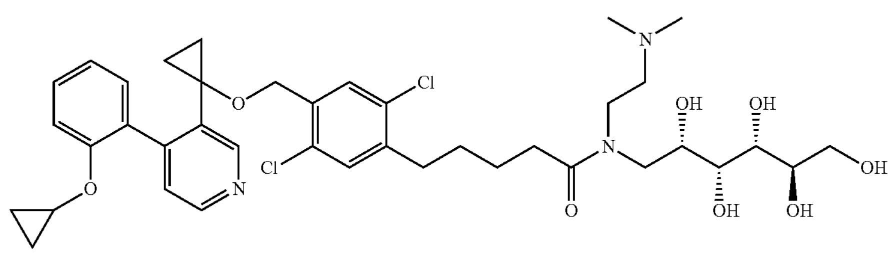 | 760.0 |
| I-208 | Example 49 | 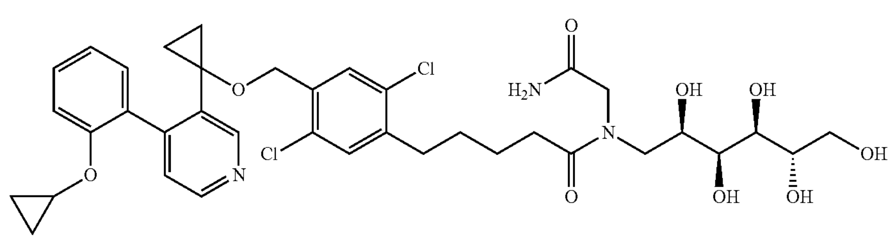 [SMILES: NC(=O)CN(C[C@@H](O)[C@H](O)[C@@H](O)[C@@H](O)CO)C(=O)CCCCc1cc(Cl)c(COC2(c3cnccc3-c3ccccc3OC3CC3)CC2)cc1Cl] | 746.00 |
| I-209 | Example 26 | 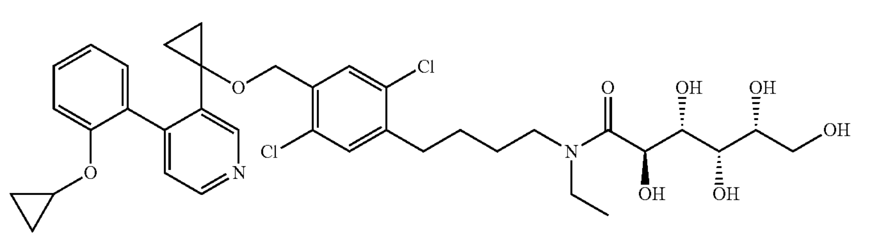 [SMILES: CCN(CCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 703.2 |

TABLE 10-continued

Compounds I-132 to I-241

| Cmpd. No.: | Synthetic Method | Compound Structure | Obs. [M + H]+ |
|---|---|---|---|
| I-210 | Example 26 | 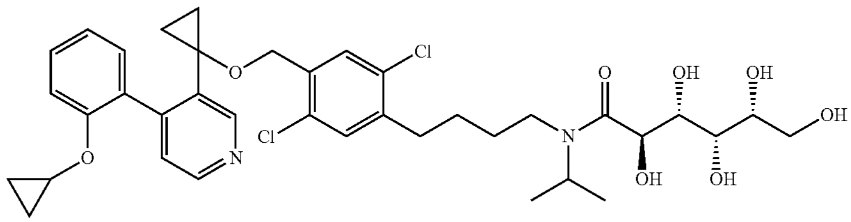 [SMILES: CC(C)N(CCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 717.2 |
| I-211 | Example 26 | 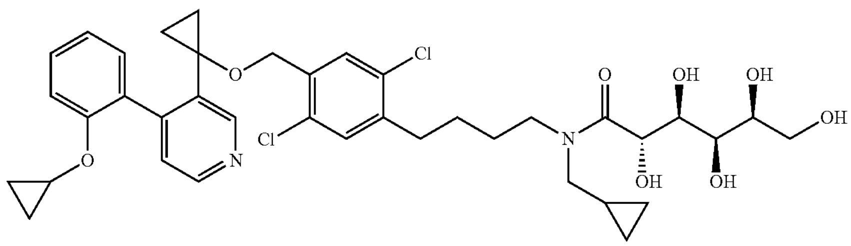 [SMILES: O=C([C@@H](O)[C@@H](O)[C@H](O)[C@@H](O)CO)N(CCCCc1cc(Cl)c(COC2(c3cnccc3-c3ccccc3OC3CC3)CC2)cc1Cl)CC1CC1] | 729.2 |
| I-212 | Example 26 | 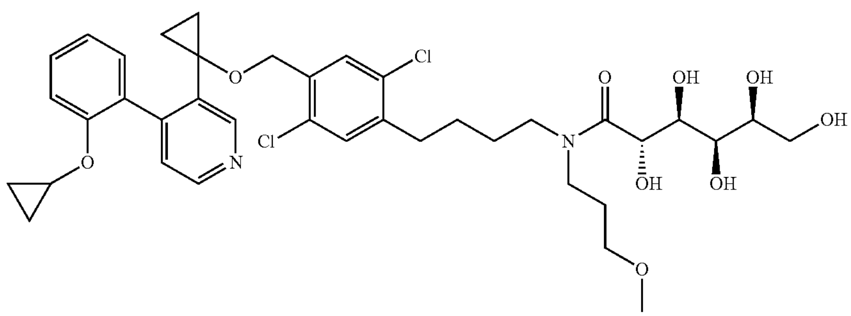 [SMILES: COCCCN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | 747.25 |
| I-213 | Example 26 | 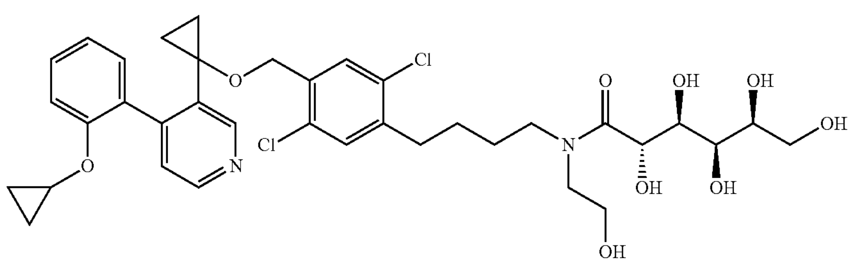 [SMILES: O=C([C@@H](O)[C@@H](O)[C@H](O)[C@@H](O)CO)N(CCO)CCCCc1cc(Cl)c(COC2(c3cnccc3-c3ccccc3OC3CC3)CC2)cc1Cl] | 719.2 |
| I-214 | Example 26 | 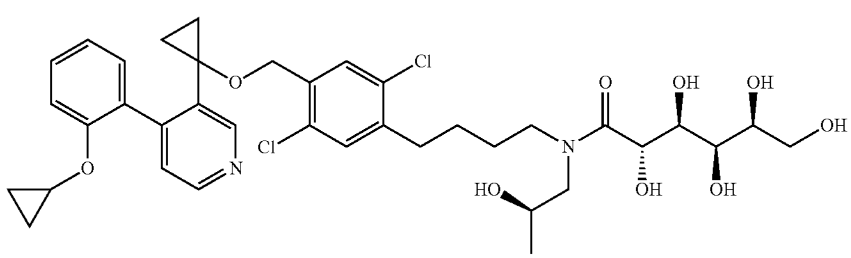 [SMILES: C[C@@H](O)CN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | 733.2 |

TABLE 10-continued

Compounds I-132 to I-241

| Cmpd. No.: | Synthetic Method | Compound Structure | Obs. [M + H]+ |
|---|---|---|---|
| I-215 | Example 26 | 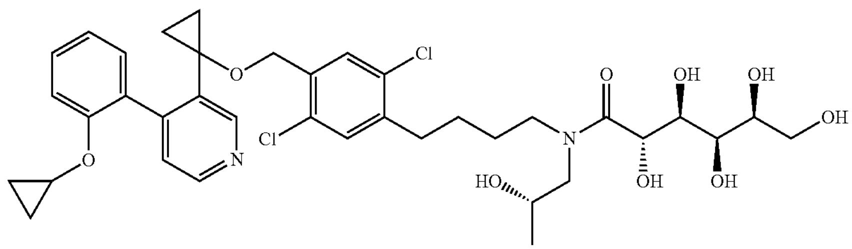 [SMILES: C[C@H](O)CN(CCCCc1cc(Cl)c(COC2(c3cnccc3-c3ccccc3OC3CC3)CC2)cc1Cl)C(=O)[C@@H](O)[C@@H](O)[C@H](O)[C@@H](O)CO] | 733.2 |
| I-216 | Example 26 | 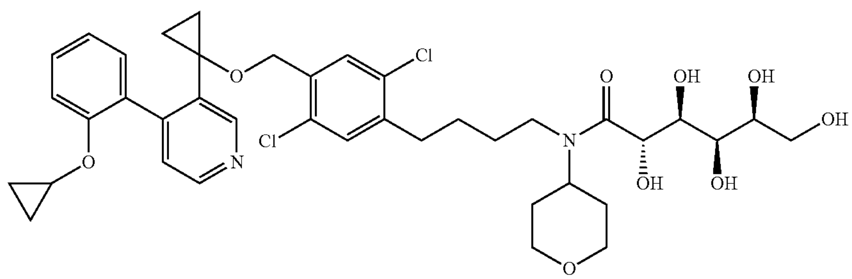 [SMILES: O=C([C@@H](O)[C@@H](O)[C@H](O)[C@@H](O)CO)N(CCCCc1cc(Cl)c(COC2(c3cnccc3-c3ccccc3OC3CC3)CC2)cc1Cl)C1CCOCC1] | 759.2 |
| I-217 | Example 26 | 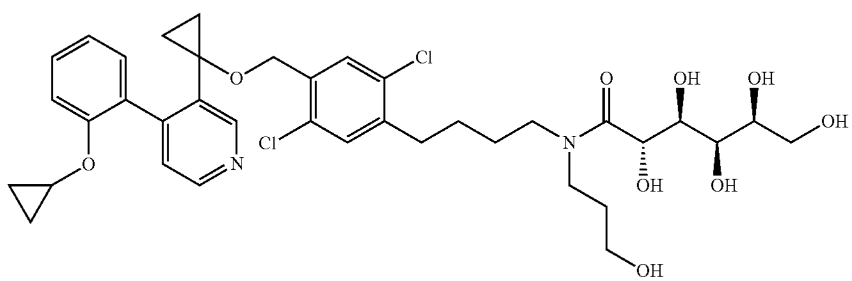 [SMILES: O=C([C@@H](O)[C@@H](O)[C@H](O)[C@@H](O)CO)N(CCCO)CCCCc1cc(Cl)c(COC2(c3cnccc3-c3ccccc3OC3CC3)CC2)cc1Cl] | 703.2 |
| I-218 | Example 49 | 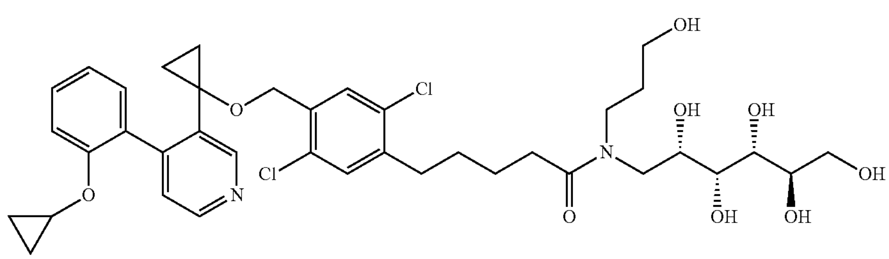 [SMILES: O=C(CCCCc1cc(Cl)c(COC2(c3cnccc3-c3ccccc3OC3CC3)CC2)cc1Cl)N(CCCO)C[C@H](O)[C@@H](O)[C@H](O)[C@H](O)CO] | 747.35 |
| I-219 | Example 49 | 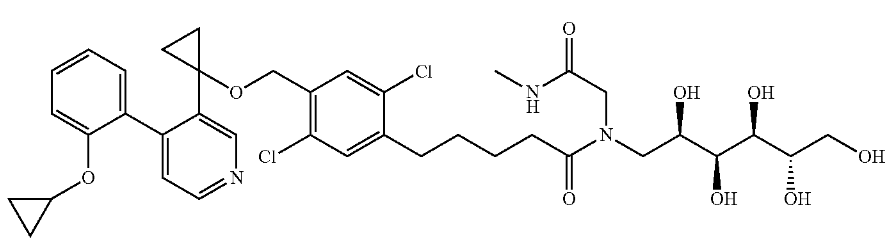 [SMILES: CNC(=O)CN(C[C@@H](O)[C@H](O)[C@@H](O)[C@@H](O)CO)C(=O)CCCCc1cc(Cl)c(COC2(c3cnccc3-c3ccccc3OC3CC3)CC2)cc1Cl] | 760.30 |

TABLE 10-continued

Compounds I-132 to I-241

| Cmpd. No.: | Synthetic Method | Compound Structure | Obs. [M + H]+ |
|---|---|---|---|
| I-220 | Example 49 | 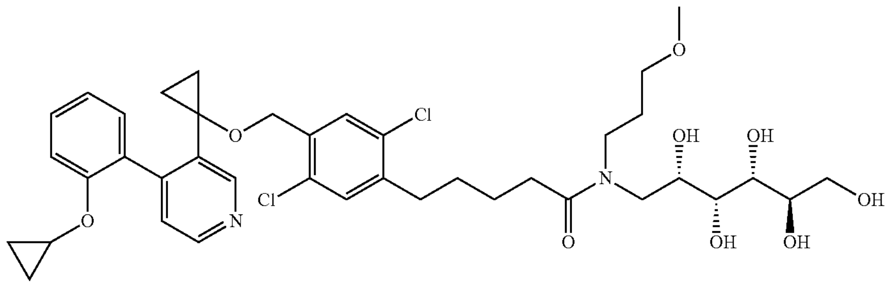 [SMILES: COCCCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 763.05 |
| I-221 | Example 49 | 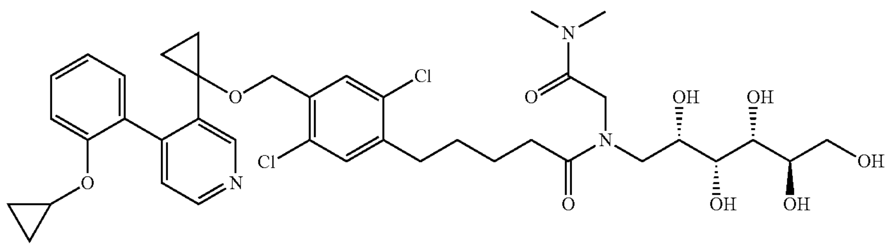 [SMILES: CN(C)C(=O)CN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 774.15 |
| I-222 | Example 49 | 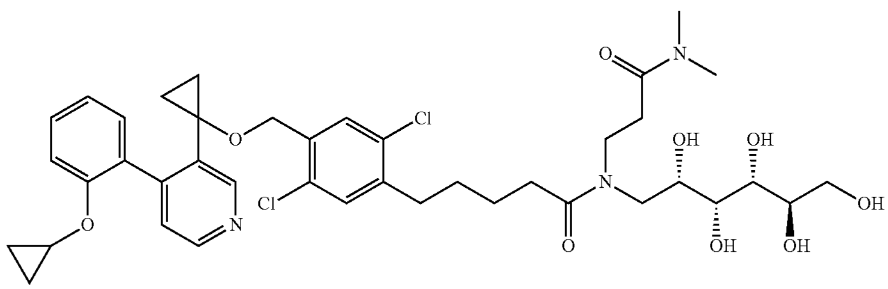 [SMILES: CN(C)C(=O)CCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 788.1 |
| I-223 | Example 49 | 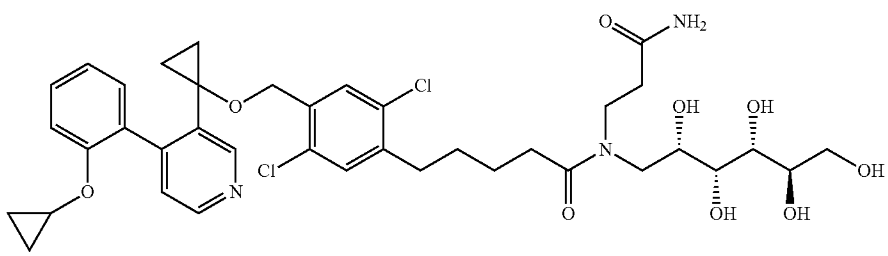 [SMILES: NC(=O)CCN(C[C@H](O)[C@@H](O)[C@H](O)[C@H](O)CO)C(=O)CCCCc1cc(Cl)c(COC2(c3cnccc3-c3ccccc3OC3CC3)CC2)cc1Cl] | 760.25 |
| I-224 | Example 26 | 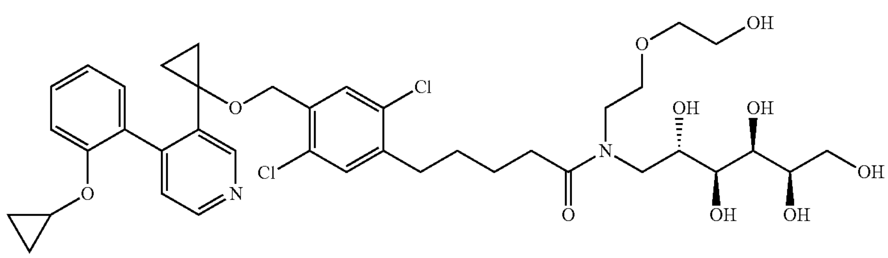 [SMILES: O=C(CCCCc1cc(Cl)c(COC2(c3cnccc3-c3ccccc3OC3CC3)CC2)cc1Cl)N(CCOCCO)C[C@H](O)[C@H](O)[C@@H](O)[C@H](O)CO] | 777.35 |
| I-225 | Example 20 | 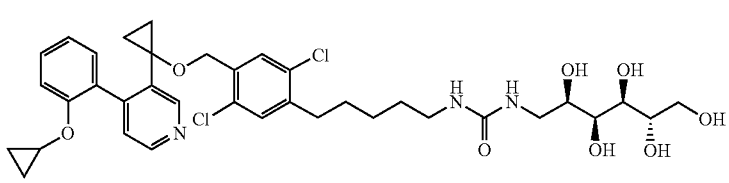 [SMILES: O=C(NCCCCCc1cc(Cl)c(COC2(c3cnccc3-c3ccccc3OC3CC3)CC2)cc1Cl)NC[C@@H](O)[C@H](O)[C@@H](O)[C@@H](O)CO] | 718.2 |

TABLE 10-continued

Compounds I-132 to I-241

| Cmpd. No.: | Synthetic Method | Compound Structure | Obs. [M + H]+ |
|---|---|---|---|
| I-226 | Example 26 | 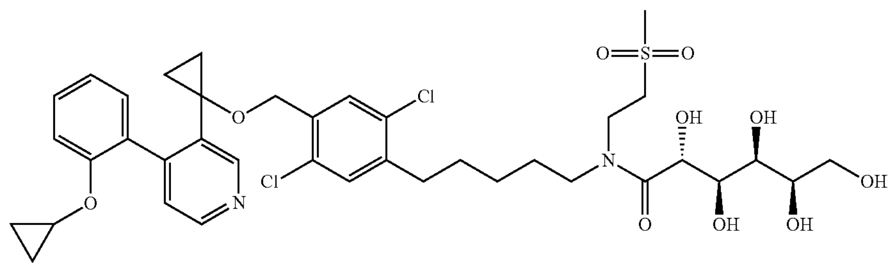 [SMILES: CS(=O)(=O)CCN(CCCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 795.30 |
| I-227 | Example 26 | 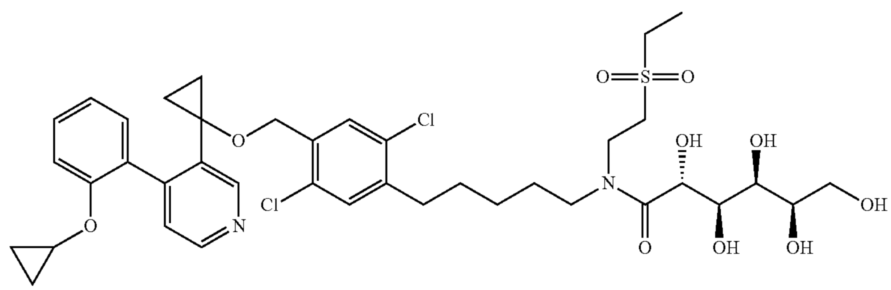 [SMILES: CCS(=O)(=O)CCN(CCCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 809.25 |
| I-228 | Example 26 | 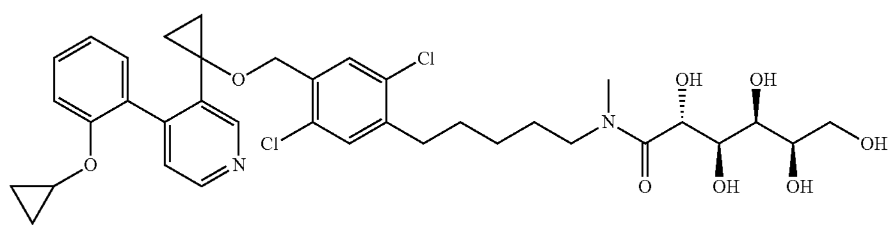 [SMILES: CN(CCCCCc1cc(Cl)c(COC2(c3cnccc3-c3ccccc3OC3CC3)CC2)cc1Cl)C(=O)[C@H](O)[C@H](O)[C@@H](O)[C@H](O)CO] | 703.30 |
| I-229 | Example 49 | 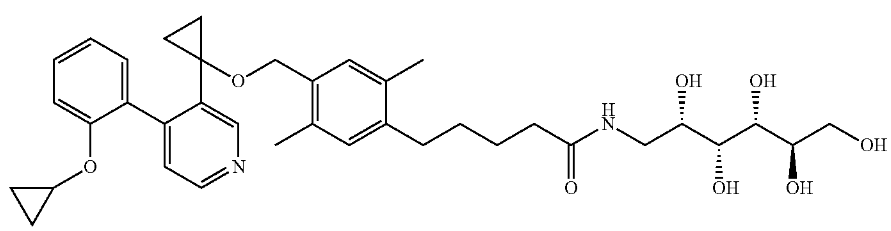 | 649.35 |
| I-230 | Example 49 | 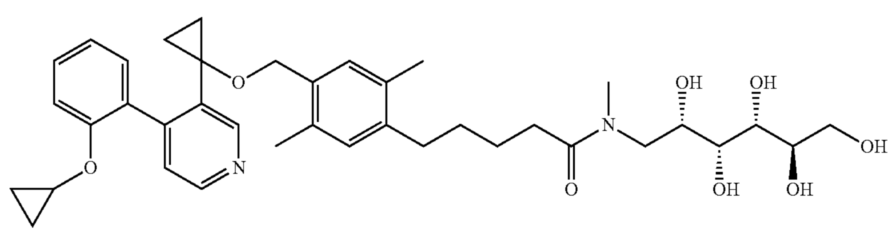 [SMILES: Cc1cc(COC2(c3cnccc3-c3ccccc3OC3CC3)CC2)c(C)cc1CCCCC(=O)N(C)C[C@H](O)[C@@H](O)[C@H](O)[C@H](O)CO] | 663.40 |
| I-231 | Example 49 | 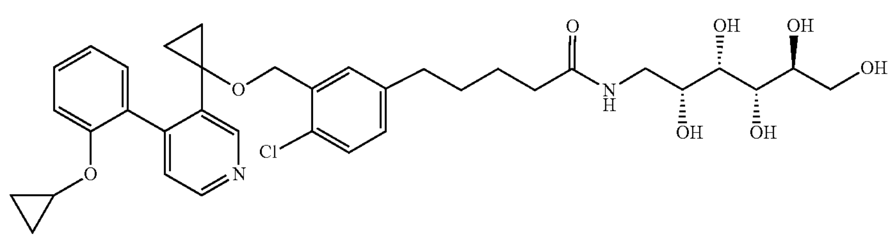 [SMILES: O=C(CCCCc1ccc(Cl)c(COC2(c3cnccc3-c3ccccc3OC3CC3)CC2)c1)NC[C@@H](O)[C@H](O)[C@@H](O)[C@@H](O)CO] | 655.2 |

TABLE 10-continued

Compounds I-132 to I-241

| Cmpd. No.: | Synthetic Method | Compound Structure | Obs. [M + H]+ |
|---|---|---|---|
| I-232 | Example 49 | 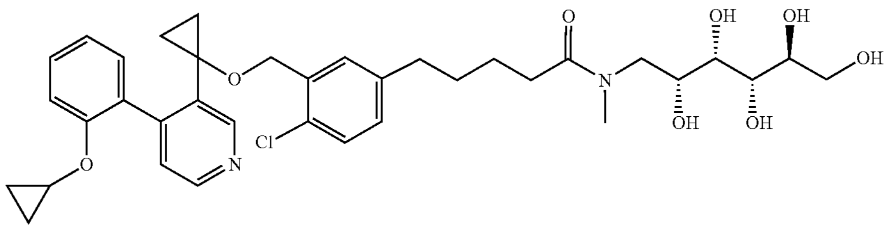 [SMILES: CN(C[C@@H](O)[C@H](O)[C@@H](O)[C@@H](O)CO)C(=O)CCCCc1ccc(Cl)c(COC2(c3cnccc3-c3ccccc3OC3CC3)CC2)c1] | 669.2 |
| I-233 | Example 19 | 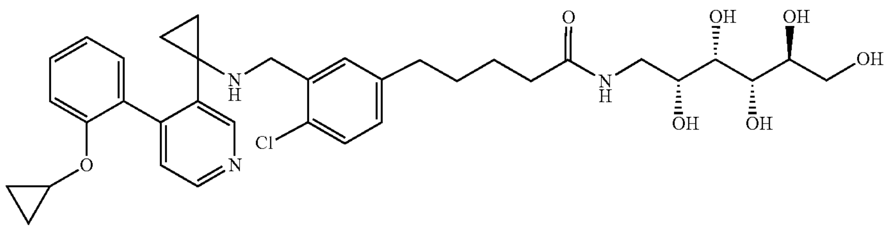 [SMILES: O=C(CCCCc1ccc(Cl)c(CNC2(c3cnccc3-c3ccccc3OC3CC3)CC2)c1)NC[C@@H](O)[C@H](O)[C@@H](O)[C@@H](O)CO] | 654.2 |
| I-234 | Example 19 | 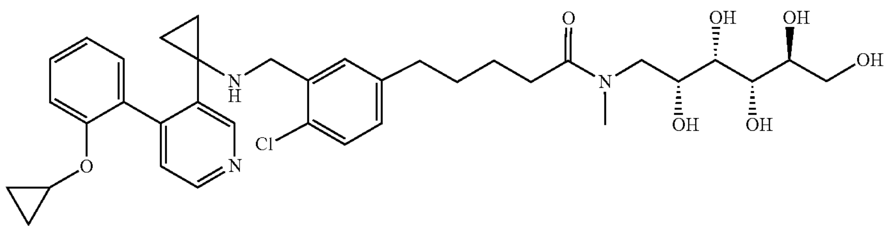 [SMILES: CN(C[C@@H](O)[C@H](O)[C@@H](O)[C@@H](O)CO)C(=O)CCCCc1ccc(Cl)c(CNC2(c3cnccc3-c3ccccc3OC3CC3)CC2)c1] | 668.3 |
| I-235 | Example 49 | 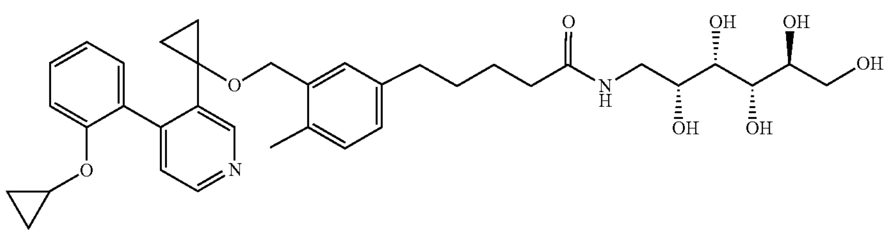 [SMILES: Cc1ccc(CCCCC(=O)NC[C@@H](O)[C@H](O)[C@@H](O)[C@@H](O)CO)cc1COC1(c2cnccc2-c2ccccc2OC2CC2)CC1] | 635.4 |
| I-236 | Example 49 | 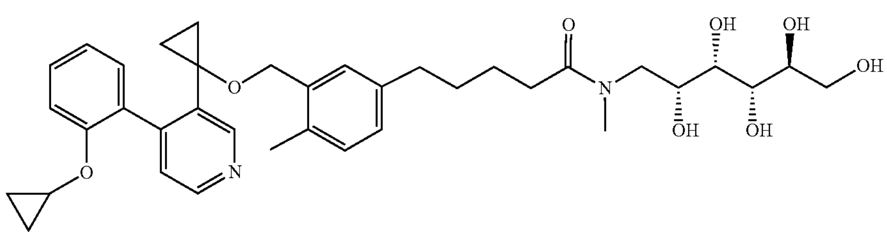 [SMILES: Cc1ccc(CCCCC(=O)N(C)C[C@@H](O)[C@H](O)[C@@H](O)[C@@H](O)CO)cc1COC1(c2cnccc2-c2ccccc2OC2CC2)CC1] | 649 |
| I-237 | Example 17 | 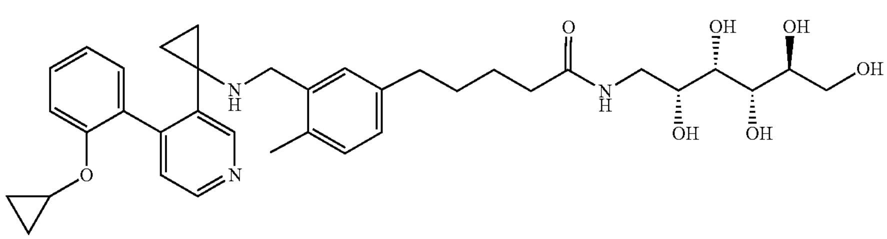 [SMILES: Cc1ccc(CCCCC(=O)NC[C@@H](O)[C@H](O)[C@@H](O)[C@@H](O)CO)cc1CNC1(c2cnccc2-c2ccccc2OC2CC2)CC1] | 634.4 |

TABLE 10-continued
Compounds I-132 to I-241
| Cmpd. No.: | Synthetic Method | Compound Structure | Obs. [M + H]+ |
|---|---|---|---|
| I-238 | Example 17 | 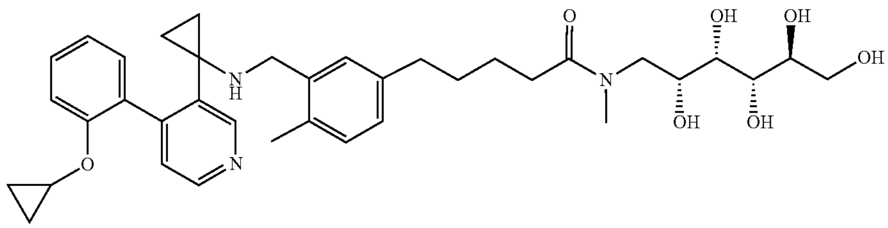 [SMILES: Cc1ccc(CCCCC(=O)N(C)C[C@@H](O)[C@H](O)[C@@H](O)[C@@H](O)CO)cc1CNC1(c2cnccc2-c2ccccc2OC2CC2)CC1] | 648.40 |
| I-239 | Example 20 | 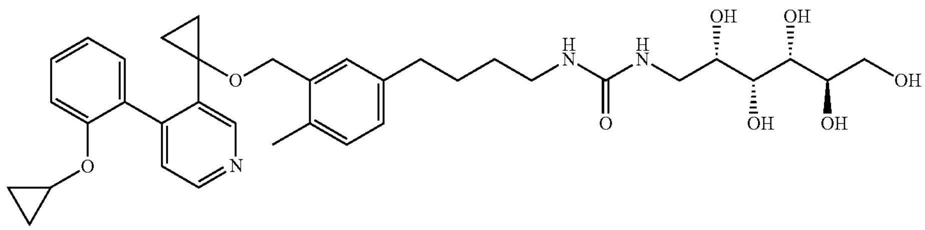 [SMILES: Cc1ccc(CCCCNC(=O)NC[C@H](O)[C@@H](O)[C@H](O)[C@H](O)CO)cc1COC1(c2cnccc2-c2ccccc2OC2CC2)CC1] | 650.35 |
| I-240 | Example 15 | 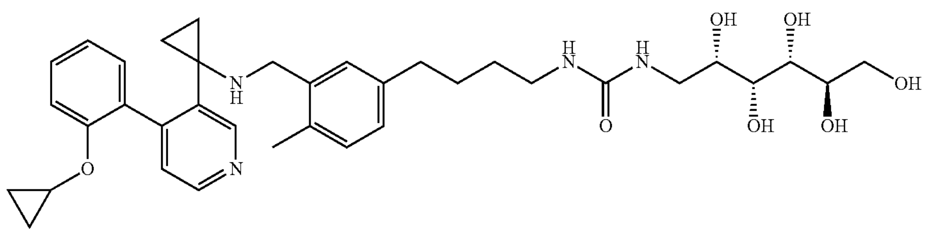 [SMILES: Cc1ccc(CCCCNC(=O)NC[C@H](O)[C@@H](O)[C@H](O)[C@H](O)CO)cc1CNC1(c2cnccc2-c2ccccc2OC2CC2)CC1] | 649.25 |
| I-241 | Example 15 | 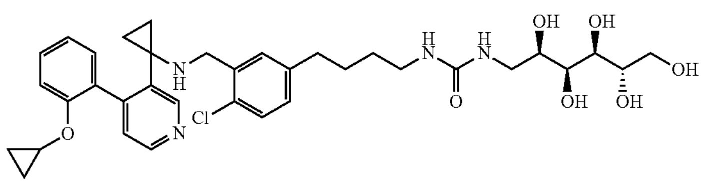 [SMILES: O=C(NCCCCc1ccc(Cl)c(CNC2(c3cnccc3-c3ccccc3OC3CC3)CC2)c1)NC[C@@H](O)[C@H](O)[C@@H](O)[C@@H](O)CO] | 669.1 |
Example 53: 2-(5-[4-chloro-3-[([1-[4-(2-cyclopropoxyphenyl)pyridin-3-yl]cyclopropyl]amino)methyl]phenyl]hexyl)-2,3-dihydro-1H-isoindole-1,3-dione
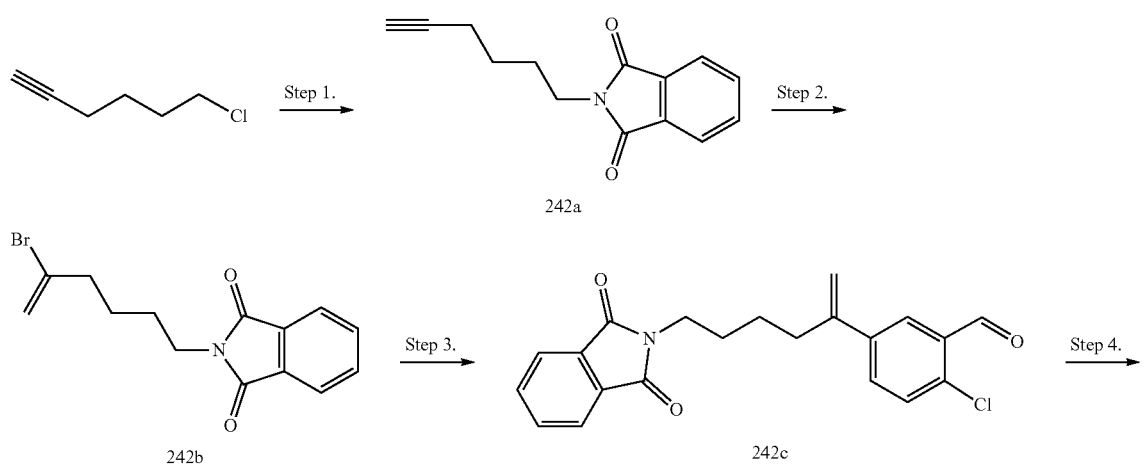

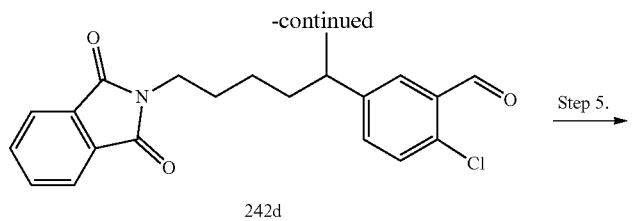

242d

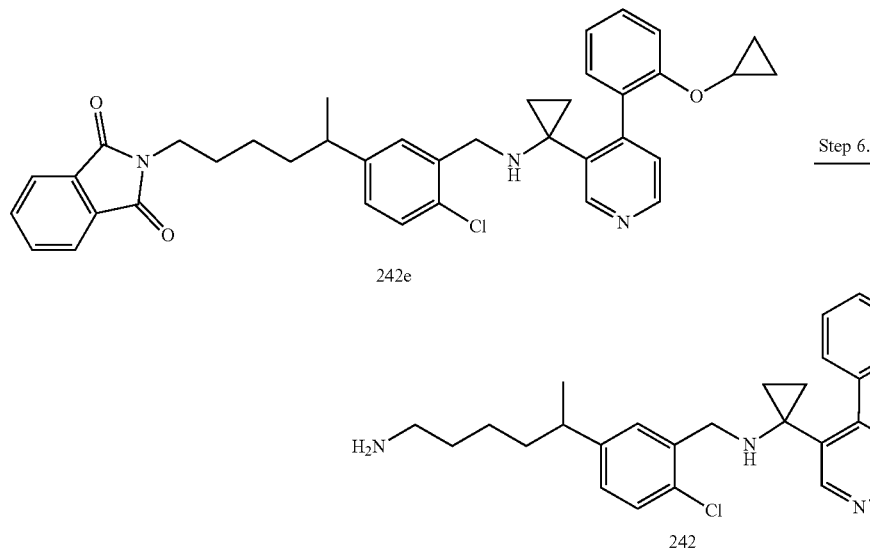

242e

242

Step 1. 2-(hex-5-yn-1-yl)-2,3-dihydro-1H-isoindole-1,3-dione (Intermediate 242a)

A solution of 6-chlorohex-1-yne (5 g, 42.89 mmol, 1.00 equiv) and 2-potassio-2,3-dihydro-1H-isoindole-1,3-dione (10.3 g, 55.61 mmol, 1.30 equiv) in N,N-dimethylformamide (60 mL) was stirred overnight at 80° C. in an oil bath. The reaction mixture was cooled to 15-25° C. The resulting solution was diluted with 500 mL of $H_2O$. The solids were collected by filtration and dried in an oven under reduced pressure to produce 9.2 g (94%) of 2-(hex-5-yn-1-yl)-2,3-dihydro-1H-isoindole-1,3-dione (242a) as an off-white solid.

Step 2. 2-(5-bromohex-5-en-1-yl)-2,3-dihydro-1H-isoindole-1,3-dione (Intermediate 242b)

A stirred −78° C. solution of 2-(hex-5-yn-1-yl)-2,3-dihydro-1H-isoindole-1,3-dione (17.9 g, 78.76 mmol, 1.00 equiv) in dichloromethane (80 mL) was added $BBr_3$ (19.6 g, 1.00 equiv) dropwise. The mixture was stirred for 1 h at room temperature. The reaction was then quenched by the addition of 20 mL of water. The resulting solution was extracted with 2×200 mL of dichloromethane and the organic layers combined and dried over sodium sulfate and concentrated under vacuum. To this was added hexanes (300 mL), acetic acid (18 mL). The resulting solution was stirred overnight at 80° C. in an oil bath. The pH value of the solution was adjusted to 7 with sodium bicarbonate. The resulting solution was extracted with 3×200 mL of dichloromethane and the organic layers combined and dried over sodium sulfate and concentrated under vacuum. This resulted in 22.4 g (92%) of 2-(5-bromohex-5-en-1-yl)-2,3-dihydro-1H-isoindole-1,3-dione (242b) as light yellow oil.

Step 3. 2-chloro-5-[6-(1,3-dioxo-2,3-dihydro-1H-isoindol-2-yl)hex-1-en-2-yl]benzaldehyde (Intermediate 242c)

A 500-mL round-bottom flask purged and maintained under an inert atmosphere of nitrogen was charged with 2-chloro-5-(tetramethyl-1,3,2-dioxaborolan-2-yl)benzaldehyde (8.1 g, 30.39 mmol, 1.10 equiv), 2-(5-bromohex-5-en-1-yl)-2,3-dihydro-1H-isoindole-1,3-dione (8.5 g, 27.58 mmol, 1.00 equiv), $Pd(PPh_3)_4$ (1.60 g, 1.38 mmol, 0.05 equiv), $K_3PO_4$ (11.7 g, 55.12 mmol, 2.00 equiv), dioxane (300 mL) and water (30 mL) was stirred overnight at 80° C. in an oil bath. The reaction was then quenched by the addition of 500 mL of $H_2O$. The resulting solution was extracted with 3×200 mL of ethyl acetate and the organic layers combined and dried over anhydrous sodium sulfate and concentrated under vacuum. The residue was applied onto a silica gel column with ethyl acetate/petroleum ether (5:95). This resulted in 5.5 g (54%) of 2-chloro-5-[6-(1,3-dioxo-2,3-dihydro-1H-isoindol-2-yl)hex-1-en-2-yl]benzaldehyde (242c) as an off-white solid.

Step 4. 2-chloro-5-[6-(1,3-dioxo-2,3-dihydro-1H-isoindol-2-yl)hexan-2-yl]benzaldehyde (Intermediate 242d)

To hydrogen was introduced into a stirred solution of 2-chloro-5-[6-(1,3-dioxo-2,3-dihydro-1H-isoindol-2-yl)hex-1-en-2-yl]benzaldehyde (5.5 g, 14.95 mmol, 1.00 equiv) in ethyl acetate (100 mL) and Rh/C (5.5 g). The resulting suspension was stirred overnight at room temperature. Solids were filtered out and the resulting mixture was concentrated under vacuum. The crude product (5.5 g) was purified by Flash chromatography with the following conditions: Column, silica gel; mobile phase, $CH_3CN:H_2O=0:100$ increasing to CH₃CN:H₂O=30:70 within 20 min; Detector, UV 254 nm. 3.5 g product was obtained. This resulted in 3.5 g (63%) of 2-chloro-5-[6-(1,3-dioxo-2,3-dihydro-1H-isoindol-2-yl)hexan-2-yl]benzaldehyde (242d) as pale-yellow oil.

Step 5. 2-(5-[4-chloro-3-[([1-[4-(2-cyclopropoxy-phenyl)pyridin-3-yl]cyclopropyl]amino) methyl]phenyl]hexyl)-2,3-dihydro-1H-isoindole-1,3-dione (Intermediate 242e)

A 500-mL round-bottom flask purged and maintained under an inert atmosphere of nitrogen was charged with a solution of 1-[4-(2-cyclopropoxyphenyl)pyridin-3-yl]cyclopropan-1-amine (4.5 g, 16.90 mmol, 1.00 equiv), 2-chloro-5-[6-(1,3-dioxo-2,3-dihydro-1H-isoindol-2-yl)hexan-2-yl]benzaldehyde (3.23 g, 8.73 mmol, 1.00 equiv) in dichloromethane (300 mL) and TFA (0.5 mL) was added NaBH(OAc)₃ (15.5 g, 73.13 mmol, 6.00 equiv), The resulting solution was stirred overnight at 30° C. The reaction mixture was then quenched by the addition of 500 mL of H₂O. The resulting solution was extracted with 3×200 mL of dichloromethane and the organic layers combined and dried over sodium sulfate and concentrated under vacuum. The residue was applied onto a silica gel column with ethyl acetate/petroleum ether (30:70). This resulted in 5.5 g (52%) of 2-(5-[4-chloro-3-[([1-[4-(2-cyclopropoxyphenyl)pyridin-3-yl]cyclopropyl]amino)methyl]phenyl]hexyl)-2,3-dihydro-1H-isoindole-1,3-dione as a pale-yellow solid.

Step 6. N-[[5-(6-aminohexan-2-yl)-2-chlorophenyl]methyl]-1-[4-(2-cyclopropoxyphenyl) pyridin-3-yl]cyclopropan-1-amine (I-242)

To a 250-mL round-bottom flask, was added 2-(5-[4-chloro-3-[([1-[4-(2-cyclopropoxyphenyl)pyridin-3-yl]cyclopropyl]amino)methyl]phenyl]hexyl)-2,3-dihydro-1H-isoindole-1,3-dione (200 mg, 0.32 mmol, 1.00 equiv), methanol (5 mL), tetrahydrofuran (5 mL) and hydrazine hydrate (0.2 mL, 10.00 equiv). The resulting solution was stirred for 3 h at 60° C. in an oil bath. The solids were filtered out. The crude product was purified by Prep-HPLC with the following conditions: Column, XBridge C18 OBD Prep Column, 5 μm, 19 mm×250 mm; mobile phase, Waters (0.05% TFA) and ACN (25% ACN-up to 50% in 10 min); Detector, UV 254 nm. 84.4 mg product was obtained. This resulted in 84.4 mg (53%) of N-[[5-(6-aminohexan-2-yl)-2-chlorophenyl]methyl]-1-[4-(2-cyclopropoxyphenyl)pyridin-3-yl]cyclopropan-1-amine (I-242) as a pale-yellow solid: (ES, m/z): [M+1]: 490; (CD₃OD, ppm): δ 9.53 (d, J=12.8 Hz, 1H), 8.99 (d, J=5.8 Hz, 1H), 8.03-7.92 (m, 1H), 7.75-7.59 (m, 3H), 7.45 (dd, J=8.0, 2.9 Hz, 2H), 7.42-7.24 (m, 2H), 4.44-4.36 (m, 2H), 3.97-3.85 (m, 1H), 2.84 (dt, J=27.5, 7.4 Hz, 3H), 1.66 (q, J=7.8, 7.3 Hz, 6H), 1.44-1.16 (m, 7H), 0.71 (t, J=5.9 Hz, 2H), 0.54 (d, J=3.3 Hz, 2H).

The absolute configuration of the separated enantiomers of the compounds in the examples described herein were not determined. As such, the configuration of the resolved materials were arbitrarily assigned as R or S in each case.

Examples 54: (S)-N-(5-(6-aminohexan-2-yl)-2-chlorobenzyl)-1-(4-(2-cyclopropoxyphenyl) pyridin-3-yl)cyclopropanamine (I-243) and (R)-N-(5-(6-aminohexan-2-yl)-2-chlorobenzyl)-1-(4-(2-cyclopropoxyphenyl)pyridin-3-yl)cyclopropanamine (I-244)

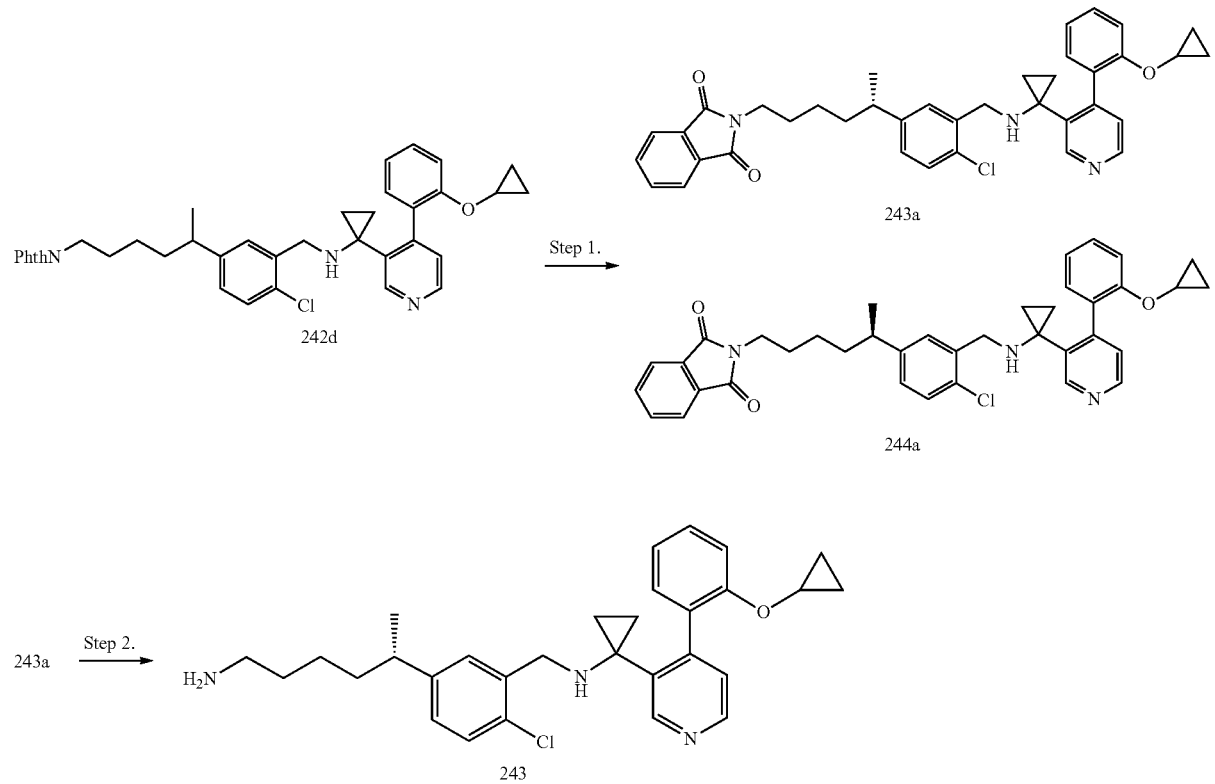

-continued

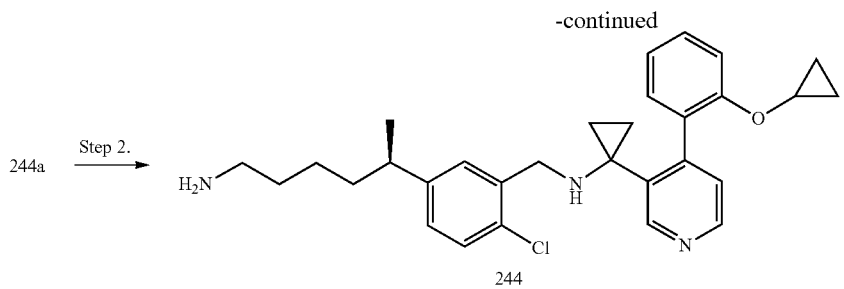

Step 1. 2-[(5S)-5-[4-chloro-3-[([1-[4-(2-cyclopropoxyphenyl)pyridin-3-yl]cyclopropyl]amino) methyl]phenyl]hexyl]-2,3-dihydro-1H-isoindole-1,3-dione (Intermediate 243a) and 2-[(5R)-5-[4-chloro-3-[([1-[4-(2-cyclopropoxyphenyl)pyridin-3-yl] cyclopropyl]amino)methyl]phenyl]hexyl]-2,3-dihydro-1H-isoindole-1,3-dione (Intermediate 244b)

2-(5-[4-chloro-3-[([1-[4-(2-cyclopropoxyphenyl)pyridin-3-yl]cyclopropyl]amino) methyl]phenyl]hexyl]-2,3-dihydro-1H-isoindole-1,3-dione intermediate 242e (5 g, 8.06 mmol, 1.00 equiv) was separated by chiral HPLC and resulted in 2.1 g (42%) of 243a as an off-white solid.

Step 2. (S)-N-(5-(6-aminohexan-2-yl)-2-chlorobenzyl)-1-(4-(2-cyclopropoxyphenyl)pyridin-3-yl)cyclopropanamine (I-243)

To a 250-mL round-bottom flask, was placed Intermediate 243a (2.1 g, 3.39 mmol, 1.00 equiv), methanol/H$_2$O (20/20 mL) and hydrazine hydrate (1.69 g, 33.80 mmol, 10.00 equiv). The resulting solution was stirred for 3 h at 60° C. in an oil bath. The reaction was then quenched by the addition of 500 mL of H$_2$O. The resulting solution was extracted with 3×30 mL of ethyl acetate and the organic layers combined and dried in an oven under reduced pressure. and concentrated under vacuum. This resulted in 518.6 mg (31%) of N-([5-[(2S)-6-aminohexan-2-yl]-2-chlorophenyl]methyl)-1-[4-(2-cyclopropoxyphenyl)pyridin-3-yl]cyclopropan-1-amine (I-243) as light yellow oil.

(R)-N-(5-(6-aminohexan-2-yl)-2-chlorobenzyl)-1-(4-(2-cyclopropoxyphenyl)pyridin-3-yl)cyclopropanamine (I-244)

(R)-N-(5-(6-aminohexan-2-yl)-2-chlorobenzyl)-1-(4-(2-cyclopropoxyphenyl)pyridin-3-yl)cyclopropanamine was prepared from 244b as described above for I-243.

Example 55: (5R)-5-[4-chloro-3-([1-[4-(2-cyclopropoxyphenyl)pyridin-3-yl]cyclopropoxy]methyl) phenyl]hexan-1-amine (I-245) and (5S)-5-[4-chloro-3-([1-[4-(2-cyclopropoxyphenyl)pyridin-3-yl] cyclopropoxy]methyl)phenyl]hexan-1-amine (I-246)

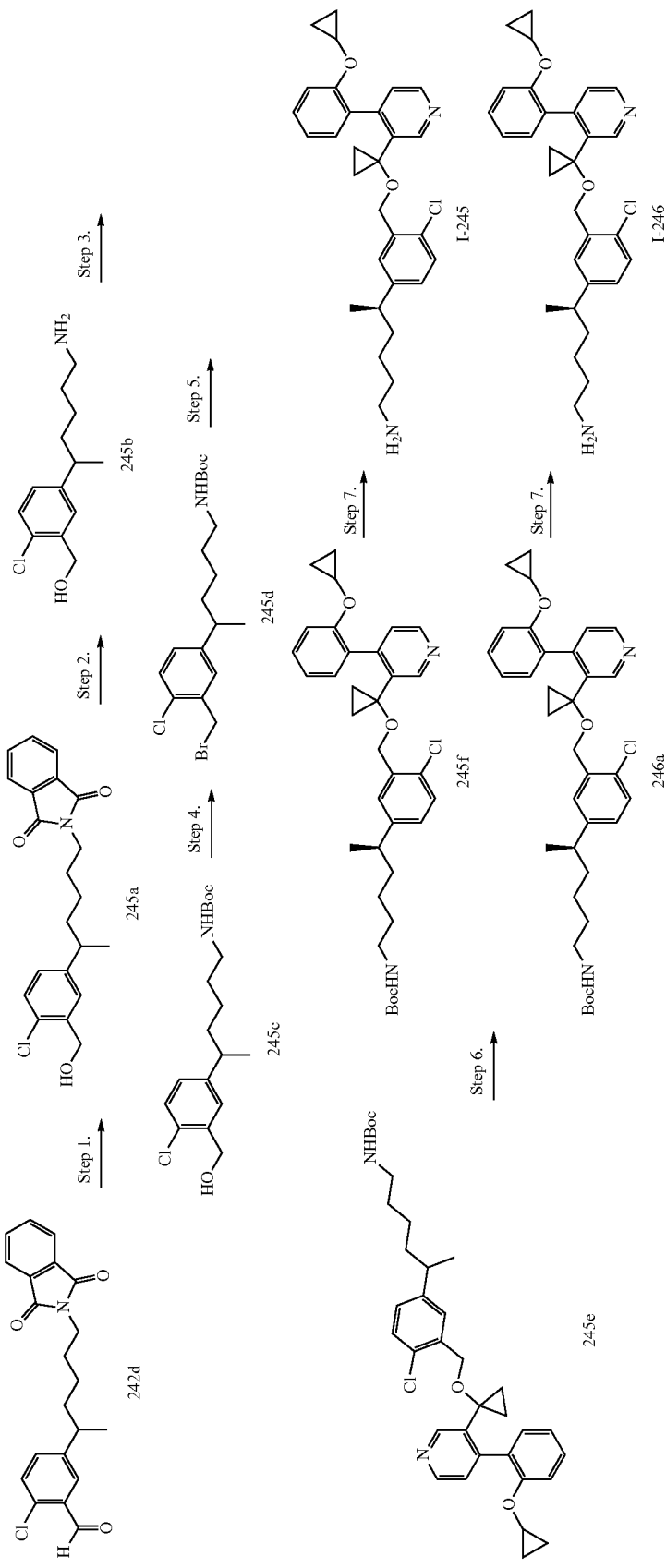

Step 1. 2-[5-[4-chloro-3-(hydroxymethyl)phenyl]hexyl]-2,3-dihydro-1H-isoindole-1,3-dione (Intermediate 245a)

To a 250-mL round-bottom flask purged and maintained under an inert atmosphere of nitrogen, was placed a solution of 2-chloro-5-[6-(1,3-dioxo-2,3-dihydro-1H-isoindol-2-yl)hexan-2-yl]benzaldehyde (560 mg, 1.51 mmol, 1.00 equiv) in tetrahydrofuran (10 mL). To the reaction mixture was added LiAlH(OtBu)$_3$ (390 mg, 1.00 equiv) in several batches at 0° C. The resulting solution was stirred for 0.5 h at room temperature. The reaction was then quenched by the addition of 50 mL of NH$_4$Cl (aq). The resulting solution was extracted with 3×30 mL of ethyl acetate and the organic layers combined and dried over sodium sulfate and concentrated under vacuum. This resulted in 0.56 g (99%) of 2-[5-[4-chloro-3-(hydroxymethyl)phenyl]hexyl]-2,3-dihydro-1H-isoindole-1,3-dione (245a) as light yellow oil.

Step 2. [5-(6-aminohexan-2-yl)-2-chlorophenyl]ethanol (Intermediate 245b)

To a solution of 2-[5-[4-chloro-3-(hydroxymethyl)phenyl]hexyl]-2,3-dihydro-1H-isoindole-1,3-dione (1.0 g, 2.69 mmol, 1.00 equiv) in methanol (15 mL) and tetrahydrofuran (15 mL) was added hydrazine hydrate (1.63 mL, 10.00 equiv). The resulting solution was stirred for 2.5 h at 60° C. in an oil bath. The resulting mixture was concentrated under vacuum. The resulting solution was diluted with 100 mL of DCM and the solids were filtered out. The mixture was dried over anhydrous sodium sulfate and concentrated under vacuum. This resulted in 700 mg (crude) of [5-(6-aminohexan-2-yl)-2-chlorophenyl]ethanol (245b) as crude yellow oil.

Step 3. tert-butyl N-[5-[4-chloro-3-(hydroxymethyl)phenyl]hexyl]carbamate (Intermediate 245c)

To a 500-mL round-bottom flask containing a stirred solution of [5-(6-aminohexan-2-yl)-2-chlorophenyl]methanol (21.1 g, 87.28 mmol, 1.00 equiv), sodium carbonate (37.1 g, 350.03 mmol, 4.00 equiv), tetrahydrofuran (100 mL) and water (100 mL) was added a solution of di-tert-butyl dicarbonate (19.1 g, 87.52 mmol, 1.00 equiv) in tetrahydrofuran (50 mL) dropwise with stirring at 0° C. The resulting solution was stirred for 12 h at room temperature. The solids were filtered out. The resulting solution was diluted with 200 mL of ethyl acetate. The resulting mixture was washed with 3×100 mL of water and 2×100 mL of brine. The mixture was dried over anhydrous sodium sulfate and concentrated under vacuum. The residue was applied onto a silica gel column with ethyl acetate/petroleum ether (1:6). This resulted in 28.2 g (95%) of tert-butyl N-[5-[4-chloro-3-(hydroxymethyl)phenyl]hexyl]carbamate (245c) as yellow oil.

Step 4. tert-butyl N-[5-[3-(bromomethyl)-4-chlorophenyl]hexyl]carbamate (Intermediate 245d)

To a 100-mL round-bottom flask purged and maintained under an inert atmosphere of nitrogen was added tert-butyl N-[5-[4-chloro-3-(hydroxymethyl)phenyl]hexyl]carbamate (780 mg, 2.28 mmol, 1.00 equiv), dichloromethane (10 mL) and tetrahydrofuran (10 mL). To the reaction mixture was added NBS (651 mg, 3.66 mmol, 1.60 equiv), in portions at 0° C. over 30 min. To the resulting solution was added PPh$_3$ (899 mg, 3.43 mmol, 1.50 equiv), in portions at 0° C. The resulting solution was stirred for 1.5 h at 0° C. in a water/ice bath. The resulting mixture was concentrated under vacuum. The residue was applied onto a silica gel column with ethyl acetate/petroleum ether (1:13). This resulted in 615 mg (67%) of tert-butyl N-[5-[3-(bromomethyl)-4-chlorophenyl]hexyl]carbamate (245d) as yellow oil.

Step 5. N-[5-[4-chloro-3-([1-[4-(2-cyclopropoxyphenyl)pyridin-3-yl]cyclopropoxy]methyl) phenyl]hexyl]carbamate (Intermediate 245e)

To a 25-mL round-bottom flask purged and maintained under an inert atmosphere of nitrogen, was added tert-butyl N-[5-[3-(bromomethyl)-4-chlorophenyl]hexyl]carbamate (50 mg, 0.12 mmol, 1.00 equiv), 1-[4-(2-cyclopropoxyphenyl)pyridin-3-yl]cyclopropan-1-ol (33 mg, 0.12 mmol, 1.00 equiv), N,N-dimethylformamide (2.5 ml). This was followed by the addition of sodium hydride (10 mg, 0.42 mmol, 2.00 equiv), in portions. The resulting solution was stirred for 40 min at 0° C. in a water/ice bath. The reaction was then quenched by the addition of 20 mL of NH$_4$Cl. The resulting solution was extracted with 3×5 mL of ethyl acetate and the organic layers combined and dried over anhydrous sodium sulfate and concentrated under vacuum. The residue was applied onto a silica gel column with ethyl acetate/petroleum ether (1:1). This resulted in 34 mg (47%) of tert-butyl N-[5-[4-chloro-3-([1-[4-(2-cyclopropoxyphenyl)pyridin-3-yl]cyclopropoxy]methyl)phenyl]hexyl]carbamate (245e) as yellow oil.

Step 6. tert-butyl (R)-(5-(4-chloro-3-((1-(4-(2-cyclopropoxyphenyl)pyridin-3-yl) cyclopropoxy)methyl) phenyl)hexyl)carbamate (Intermediate 245f) and tert-butyl (S)-(5-(4-chloro-3-((1-(4-(2-cyclopropoxyphenyl)pyridin-3-yl)cyclopropoxy)methyl)phenyl) hexyl) carbamate (Intermediate 246a)

50 g of 245e was separated by chiral HPLC with the following conditions: Column, Chiralpak IB 4.6*250 nm; 5 μm HPLC Chiral-A(IB)001IB00CE-LA026; mobile phase, Hex (0.1% DEA):EtOH=70:30; Detector, 254 nm. This resulted in 18 g (72%, 1$^{st}$ peak, ee>96%) intermediate 245f as a light yellow semi-solid and 15 g (60%, 2$^{nd}$ peak, ee>97%) of intermediate 246a as a light yellow semi-solid.

Step 7. N-[(5R)-5-[4-chloro-3-([1-[4-(2-cyclopropoxyphenyl)pyridin-3-yl]cyclopropoxy]methyl) phenyl]hexyl]carbamate (I-245) and N-[(5S)-5-[4-chloro-3-([1-[4-(2-cyclopropoxyphenyl)pyridin-3-yl] cyclopropoxy]methyl)phenyl]hexyl]carbamate (I-246)

I-245: To a stirred solution of tert-butyl N-[(5R)-5-[4-chloro-3-([1-[4-(2-cyclopropoxyphenyl)pyridin-3-yl]cyclopropoxy]methyl)phenyl]hexyl]carbamate (800 mg, 1.35 mmol, 1.00 equiv) in 1,4-dioxane (20 mL) was added hydrogen chloride (10 mL). The resulting solution was stirred for 2 h at room temperature. The resulting solution was diluted with 100 mL of ethyl acetate. The pH value of the solution was adjusted to 8 with sodium bicarbonate (aq.) (2 mol/L). The resulting solution was extracted with 3×100 mL of ethyl acetate and the organic layers combined. The resulting mixture was washed with 2×50 mL of brine. The resulting mixture was concentrated under vacuum. This resulted in 508.7 mg (77%) of (5R)-5-[4-chloro-3-([1-[4-(2-cyclopropoxyphenyl)pyridin-3-yl]cyclopropoxy]methyl)phenyl]hexan-1-amine (I-245) as a light yellow semi-solid:

(ES, m/z): [M+1]=491.30; (CDCl$_3$, ppm): δ 8.74 (s, 1H), 8.53 (d, J=5.0 Hz, 1H), 7.41-7.24 (m, 3H), 7.22-7.10 (m, 2H), 7.03-6.92 (m, 3H), 4.44 (s, 2H), 3.71 (s, 1H), 3.61-3.46 (m, 1H), 2.79 (t, J=7.4 Hz, 2H), 2.60 (q, J=7.1 Hz, 1H), 1.53 (q, J=7.7 Hz, 2H), 1.36-1.14 (m, 7H), 0.98 (d, J=5.7 Hz, 2H), 0.83-0.75 (m, 2H), 0.69-0.47 (m, 4H).

I-246: To a stirred solution of tert-butyl N-[(5S)-5-[4-chloro-3-([1-[4-(2-cyclopropoxyphenyl)pyridin-3-yl]cyclopropoxy]methyl)phenyl]hexyl]carbamate (500 mg, 0.85 mmol, 1.00 equiv in 1,4-dioxane (20 mL) was added hydrogen chloride (10 mL). The resulting solution was stirred for 2 h at room temperature. The resulting solution was diluted with 100 mL of ethyl acetate. The pH value of the solution was adjusted to 9 with sodium bicarbonate (aq) (2 mol/L). The resulting solution was extracted with 2×100 mL of ethyl acetate and the organic layers combined. The resulting mixture was washed with 2×50 mL of brine. The mixture was dried over anhydrous sodium sulfate and concentrated under vacuum. This resulted in 322.1 mg (78%) of (5S)-5-[4-chloro-3-([1-[4-(2-cyclopropoxyphenyl)pyridin-3-yl]cyclopropoxy]methyl) phenyl]hexan-1-amine as a light yellow solid: (ES, m/z): [M+1]=491.20; 1H-NMR (CDCl$_3$, ppm): δ 8.76 (s, 1H), 8.55 (d, J=5.0 Hz, 1H), 7.44-7.28 (m, 3H), 7.28-7.13 (m, 2H), 7.05-6.94 (m, 3H), 4.46 (s, 2H), 3.63-3.49 (m, 1H), 2.86 (t, J=7.4 Hz, 2H), 2.62 (p, J=7.1 Hz, 1H), 1.74-1.52 (m, 4H), 1.39-1.16 (m, 5H), 1.01 (s, 2H), 0.85-0.77 (m, 2H), 0.72-0.49 (m, 4H).

Examples 56: (R)-5-[4-chloro-3-[([1-[4-(2-cyclopropoxyphenyl)pyridin-3-yl]cyclopropyl]amino) methyl]phenyl]hexanoic acid (I-247) and (S)-5-[4-chloro-3-[([1-[4-(2-cyclopropoxyphenyl)pyridin-3-yl]cyclopropyl]amino)methyl]phenyl]hexanoic acid (I-248)

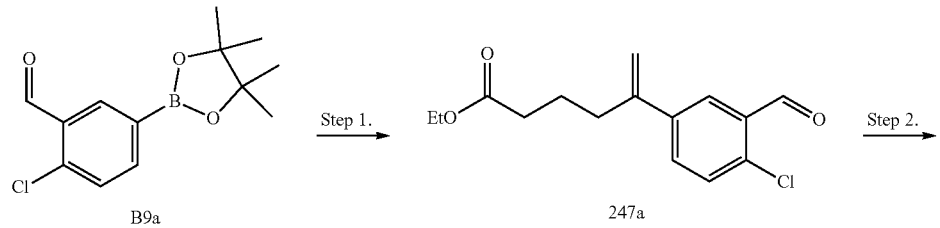

B9a  247a

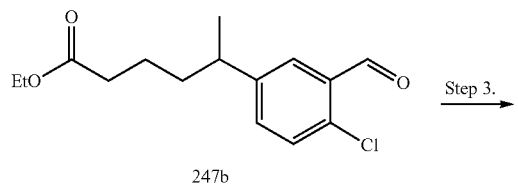

247b

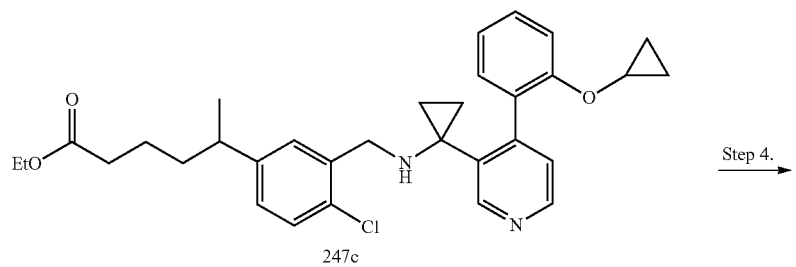

247c

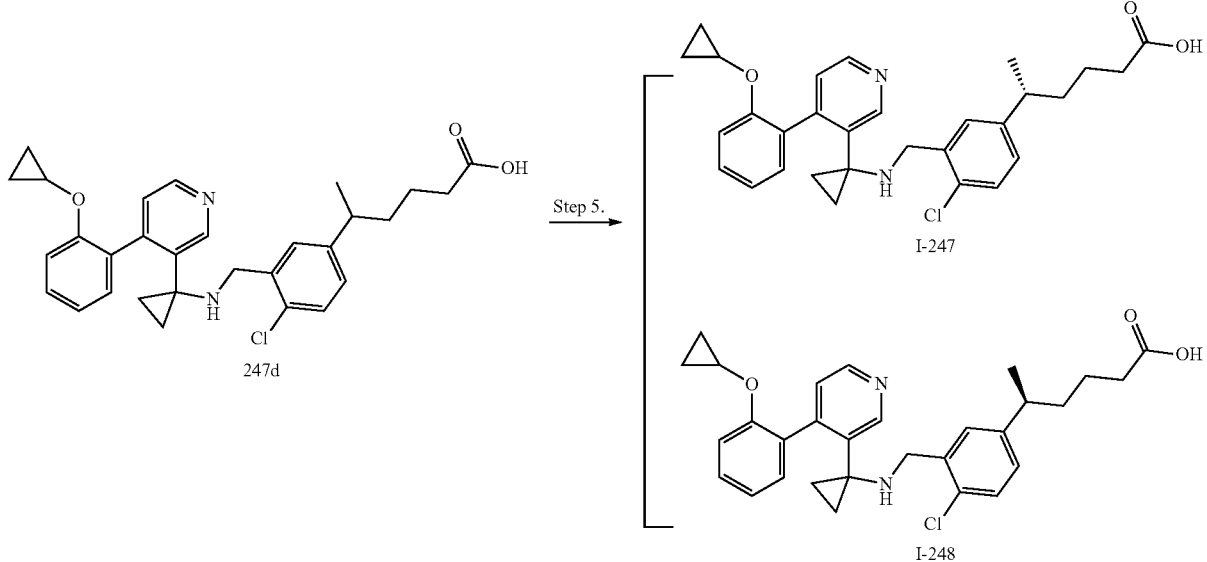

Step 1. ethyl 5-(4-chloro-3-formylphenyl)hex-5-enoate (Intermediate 247a)

2-chloro-5-(tetramethyl-1,3,2-dioxaborolan-2-yl)benzaldehyde (B9a, 3.5 g, 13.13 mmol, 1.10 equiv), ethyl 5-[(trifluoromethane)sulfonyloxy]hex-5-enoate (3.5 g, 12.06 mmol, 1.00 equiv), $K_3PO_4$ (7.7 g, 36.27 mmol, 3.00 equiv), $Pd(PPh_3)_4$ (1.4 g, 1.21 mmol, 0.10 equiv) were dissolved in dioxane (120 mL) and water (20 mL). The resulting solution was stirred for 1 overnight at 80° C. in an oil bath. The reaction was then quenched by the addition of 300 mL of water. The resulting solution was extracted with 300 mL of ethyl acetate and the organic layers combined and dried over anhydrous sodium sulfate and concentrated under vacuum. The crude product (4.5 g) was purified by Flash chromatography with the following conditions (IntelFlash-1): Column, silica gel; mobile phase, petroleum ether:ethyl acetate=100:0 increasing to petroleum ether:ethyl acetate=95:5 within 30 min; Detector, UV 254 nm. This resulted in 2.2 g (65%) of ethyl 5-(4-chloro-3-formylphenyl) hex-5-enoate (247a) as light red oil.

Step 2. ethyl 5-(4-chloro-3-formylphenyl)hexanoate (Intermediate 247b)

To 250-mL round-bottom flask, was placed ethyl 5-(4-chloro-3-formylphenyl)hex-5-enoate (247a, 2.2 g, 7.84 mmol, 1.00 equiv), Rh (2.2 g, 21.36 mmol, 3.00 equiv), ethyl acetate (50 mL) the vessel was purged with $N_2$ followed by $H_2$ and maintained under $H_2$ atmosphere at ambient pressure. The resulting solution was stirred for 5 h at 30° C. in an oil bath. The resulting solution was diluted with 100 mL of EtOAc. The solids were filtered out. The resulting mixture was concentrated under vacuum. The crude product (2.5 g) was purified by flash chromatography with the following conditions (IntelFlash-1): Column, silica gel; mobile phase, petroleum ether:ethyl acetate=100:0 increasing to petroleum ether:ethyl acetate=95:5 within 30 min; Detector, UV 254 nm. This resulted in 2.1 g (95%) of ethyl 5-(4-chloro-3-formylphenyl)hexanoate (247b) as colorless oil.

Step 3. ethyl 5-[4-chloro-3-[([1-[4-(2-cyclopropoxyphenyl)pyridin-3-yl]cyclopropyl]amino)methyl]phenyl]hexanoate (Intermediate 247c)

To a 25-mL round-bottom flask was added ethyl 5-(4-chloro-3-formylphenyl)hexanoate (247b, 382 mg, 1.35 mmol, 1.20 equiv), 1-[4-(2-cyclopropoxyphenyl)pyridin-3-yl]cyclopropan-1-amine (A-1, 300 mg, 1.13 mmol, 1.00 equiv), sodium triacetoxyborohydride (957 mg, 4.52 mmol, 4.00 equiv), AcOH (0.05 mL), dichloromethane (15 mL). The resulting solution was stirred for 1 overnight at room temperature. The resulting solution was diluted with 1000 mL of DCM. The resulting mixture was washed with 2×50 mL of $H_2O$. The mixture was dried over anhydrous sodium sulfate and concentrated under vacuum. The crude product (500 mg) was purified by Flash chromatography with the following conditions (IntelFlash-1): Column, silica gel; mobile phase, petroleum ether:ethyl acetate=100:0 increasing to petroleum ether:ethyl acetate=85:15 within 30 min; Detector, UV 254 nm. This resulted in 450 mg (75%) of ethyl 5-[4-chloro-3-[([1-[4-(2-cyclopropoxyphenyl)pyridin-3-yl]cyclopropyl]amino)methyl]phenyl]hexanoate (247c) as colorless oil.

Step 4. 5-[4-chloro-3-[([1-[4-(2-cyclopropoxyphenyl)pyridin-3-yl]cyclopropyl]amino) methyl]phenyl] hexanoic acid (Intermediate 247d)

To a 25-mL round-bottom flask, was added ethyl 5-[4-chloro-3-[([1-[4-(2-cyclopropoxyphenyl)pyridin-3-yl]cyclopropyl]amino)methyl]phenyl]hexanoate (450 mg, 0.84 mmol, 1.00 equiv), LiOH (122 mg, 5.09 mmol, 6.00 equiv), methanol (6 mL), water (0.5 mL). The resulting solution was stirred for 1 overnight at room temperature. The pH value of the solution was adjusted to 6.0 with hydrogen chloride (1 mol/L). The resulting solution was extracted with 2×50 mL of ethyl acetate and the organic layers combined and dried in an oven under reduced pressure. and concentrated under vacuum. This resulted in 420 mg (99%) of 5-[4-chloro-3-[([1-[4-(2-cyclopropoxyphenyl)pyridin-3-yl]cyclopropyl]amino)methyl]phenyl]hexanoic acid (247d) as colorless oil.

Step 5. (5R)-5-[4-chloro-3-[([1-[4-(2-cyclopropoxy-phenyl)pyridin-3-yl]cyclopropyl]amino) methyl]phenyl]hexanoic acid (I-247) and (5S)-5-[4-chloro-3-[([1-[4-(2-cyclopropoxyphenyl) pyridin-3-yl]cyclopropyl]amino)methyl]phenyl]hexanoic acid (I-248)

The racemic product (1 g) was purified by chiral HPLC with the following conditions: Column, Chiralpak IB 4.6× 250 mm, 5 μm HPLC Chiral-A(IB)001IB00CE-LA026; mobile phase, Hex (0.1% DEA): EtOH=80:20; Detector, 254 nm. 338.2 mg product was obtained. This resulted in 338.2 mg (34%) of (5R)-5-[4-chloro-3-[([1-[4-(2-cyclopropoxyphenyl)pyridin-3-yl]cyclopropyl]amino)methyl]phenyl]hexanoic acid as light yellow solid and 225.4 mg (23%) of (5S)-5-[4-chloro-3-[([1-[4-(2-cyclopropoxyphenyl)pyridin-3-yl]cyclopropyl]amino)methyl]phenyl]hexanoic acid as a light yellow solid.

I-247 Retention time 19.4 minutes; MS (ES, m/z): 505.2 [M+H]$^+$; $^1$H-NMR (Methanol-d$_4$, ppm): 8.72 (s, 1H), 8.54 (d, J=4.9 Hz, 1H), 7.54-7.43 (m, 2H), 7.32-7.19 (m, 3H), 7.18-7.08 (m, 3H), 3.88 (s, 2H), 3.67 (tt, J=6.0, 2.9 Hz, 1H), 2.67 (h, J=6.9 Hz, 1H), 2.33-2.17 (m, 2H), 1.65-1.31 (m, 5H), 1.20 (d, J=6.9 Hz, 3H), 1.10 (s, 2H), 1.01 (s, 2H), 0.62 (d, J=6.1 Hz, 2H), 0.41 (d, J=3.2 Hz, 2H).

I-248 Retention time 24.26 minutes MS (ES, m/z): 505.15 [M+H]$^+$; $^1$H-NMR (Methanol-d$_4$, ppm): 8.60 (s, 1H), 8.46 (d, J=5.6 Hz, 1H), 7.50-7.39 (m, 2H), 7.27-7.13 (m, 3H), 7.16-7.00 (m, 3H), 3.70 (s, 2H), 3.62 (tt, J=6.0, 2.9 Hz, 1H), 2.65 (h, J=7.0 Hz, 1H), 2.32-2.15 (m, 2H), 1.64-1.33 (m, 4H), 1.19 (d, J=6.9 Hz, 3H), 0.92 (s, 2H), 0.85 (s, 2H), 0.67-0.56 (m, 2H), 0.43-0.37 (m, 2H).

Compounds I-249 or I-254 (Table 11) were prepared from commercial, known starting materials or the appropriate intermediates disclosed herein using according to the examples specified in Table 11 and methods generally known to those skilled in the art.

TABLE 11

Compounds I-249 to I-254

| Cmpd No.: | Synthetic Method | Compound Structure | Obs. Mass [M + H]$^+$ |
|---|---|---|---|
| I-249 | Example 56 | 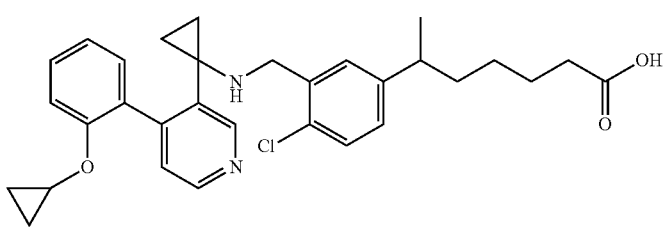 [SMILES: CC(CCCCC(=O)O)c1ccc(Cl)c(CNC2(c3cnccc3-c3ccccc3OC3CC3)CC2)c1] | 519.25 |
| I-250 | Example 54 | 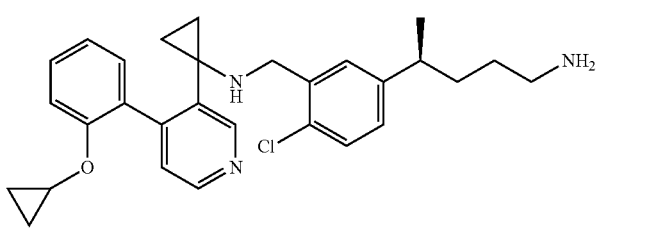 [SMILES: C[C@@H](CCCN)c1ccc(Cl)c(CNC2(c3cnccc3-c3ccccc3OC3CC3)CC2)c1] | 476.30 |
| I-251 | Example 54 | 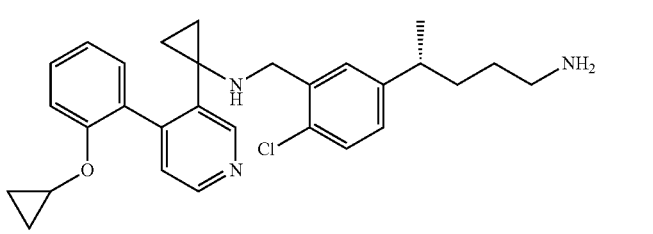 [SMILES: C[C@H](CCCN)c1ccc(Cl)c(CNC2(c3cnccc3-c3ccccc3OC3CC3)CC2)c1] | 476.20 |
| I-252 | Example 54 | 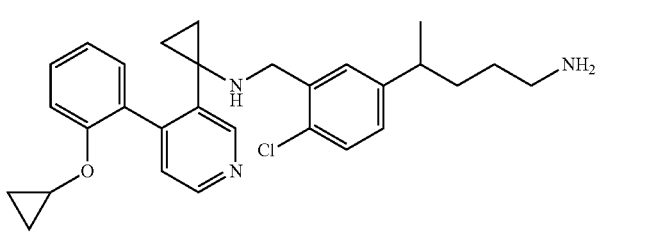 [SMILES: CC(CCCN)c1ccc(Cl)c(CNC2(c3cnccc3-c3ccccc3OC3CC3)CC2)c1] | 476.25 |

TABLE 11-continued

Compounds I-249 to I-254

| Cmpd No.: | Synthetic Method | Compound Structure | Obs. Mass [M + H]+ |
|---|---|---|---|
| I-253 | Example 55 | 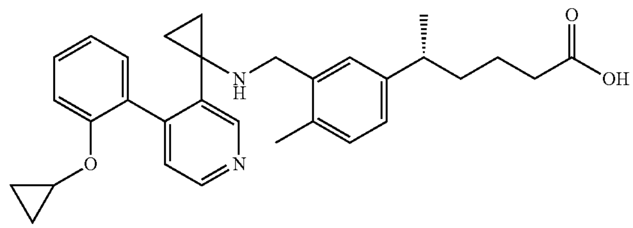 [SMILES: Cc1ccc([C@H](C)CCCC(=O)O)cc1CNC1(c2cnccc2-c2ccccc2OC2CC2)CC1] | 485.35 |
| I-254 | Example 55 | 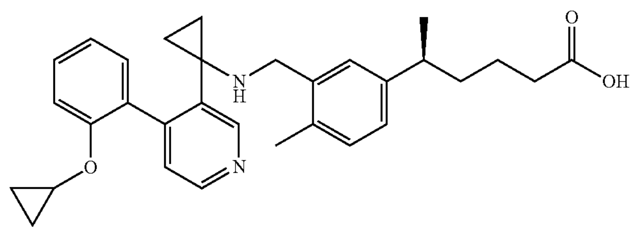 [SMILES: Cc1ccc([C@@H](C)CCCC(=O)O)cc1CNC1(c2cnccc2-c2ccccc2OC2CC2)CC1] | 485.35 |

Example 57: 1-[(5S)-5-[4-chloro-3-[([1-[4-(2-cyclopropoxyphenyl)pyridin-3-yl]cyclopropyl]amino)methyl]phenyl]hexyl]-3-[(2S,3R,4R,5R)-2,3,4,5,6-pentahydroxyhexyl]urea (I-255)

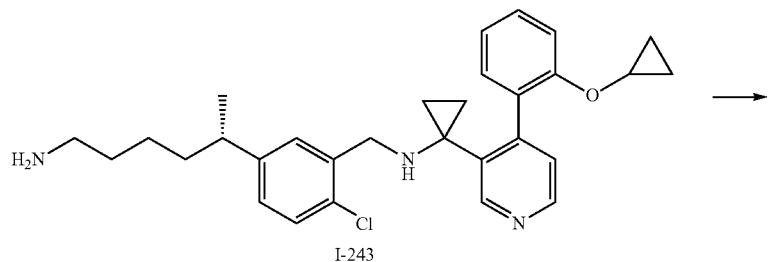

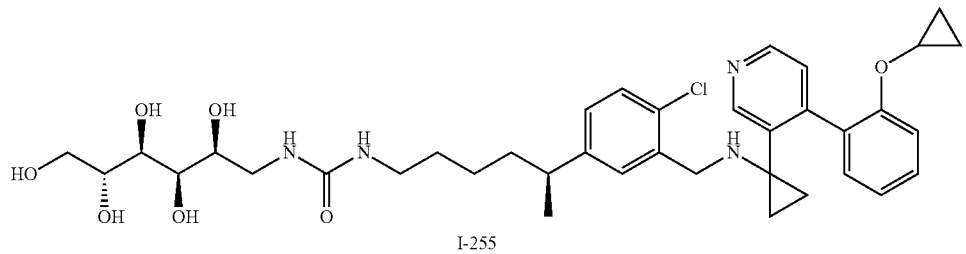

A 100-mL round-bottom flask was charged with a solution of DSC (259 mg, 1.01 mmol, 1.20 equiv) in N,N-dimethylformamide (5 mL), DIEA (159 mg, 1.23 mmol, 1.50 equiv). This was followed by the addition of a solution of N-([5-[(2S)-6-aminohexan-2-yl]-2-chlorophenyl]methyl)-1-[4-(2-cyclopropoxyphenyl)pyridin-3-yl]cyclopropan-1-amine (400 mg, 0.82 mmol, 1.00 equiv) in N,N-dimethylformamide (2 mL) dropwise with stirring at 0° C. The mixture was stirred for 1 h at room temperature. To the resulting was added (2R,3R,4R,5S)-6-aminohexane-1,2,3,4,5-pentol (192 mg, 1.06 mmol, 1.30 equiv). The resulting solution was stirred overnight at room temperature. The solids were filtered out. The crude product was purified by Preparative HPLC with the following conditions: Column, XBridge Shield RP18 OBD Column; 5 μm 19×150 mm; mobile phase, 10 mM NH$_4$HCO$_3$ in water and MeCN (35% to 48% in 6 min); Detector, UV 220 nm. This resulted in 109 mg (19%) of the title compound (I-255) as an off-white solid. MS (ES, m/z): 697 [M+H]+; $^1$H-NMR (CD$_3$OD, ppm): 8.59 (s, 1H), 8.46 (d, J=5.1 Hz, 1H), 7.45-7.47 (m, 2H), 7.10-7.24 (m, 3H), 7.02-7.09 (m, 3H), 3.61-3.80 (m, 9H), 3.36 (s, 1H), 3.02-3.35 (m, 3H), 2.64 (d, J=7.2 Hz, 1H), 1.18-1.57 (m, 9H), 0.65-0.91 (m, 6H), 0.42-0.63 (m, 2H).

Example 58: 1-[(5R)-5-[4-chloro-3-[([1-[4-(2-cyclo-propoxyphenyl)pyridin-3-yl]cyclopropyl]amino)methyl]phenyl]hexyl]-3-[(2S,3R,4R,5R)-2,3,4,5,6-pentahydroxyhexyl]urea (I-256)

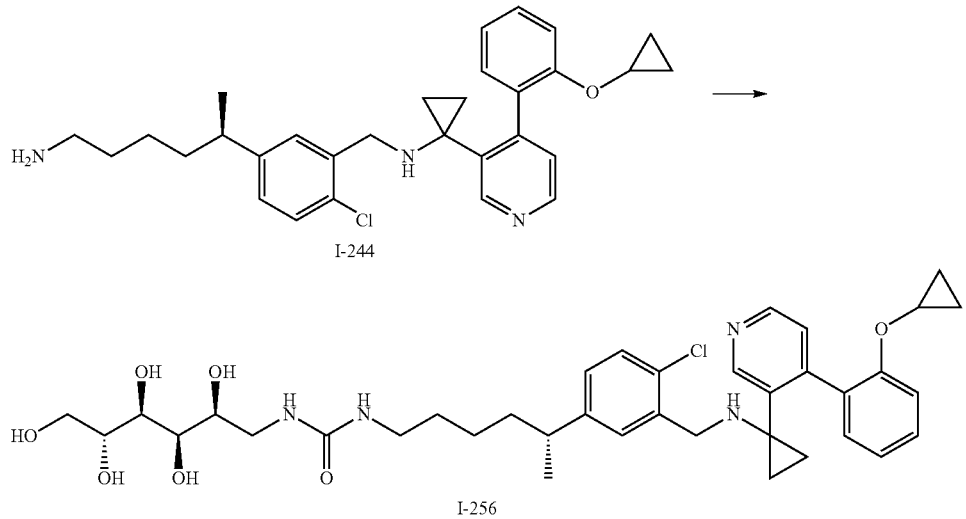

A 50-mL round-bottom flask was charged with a solution of DSC (251 mg, 0.98 mmol, 1.20 equiv) in N,N-dimethylformamide (5 mL), DIEA (159 mg, 1.23 mmol, 1.50 equiv). This was followed by the addition of a solution of N-([5-[(2R)-6-aminohexan-2-yl]-2-chlorophenyl]methyl)-1-[4-(2-cyclopropoxyphenyl)pyridin-3-yl]cyclopropan-1-amine (244) (400 mg, 0.82 mmol, 1.00 equiv) in N,N-dimethylformamide (2 mL) dropwise with stirring at 0° C. The mixture was stirred for 1 h at room temperature. To this was added (2R,3R,4R,5S)-6-aminohexane-1,2,3,4,5-pentol (192 mg, 1.06 mmol, 1.30 equiv). The resulting solution was stirred overnight at room temperature. The solids were filtered out. The crude product was purified by preparative HPLC with the following conditions: Column: XBridge Shield RP18 OBD Column, 5 μm, 19×150 mm; mobile phase: 10 mM NH$_4$HCO$_3$ in water and MeCN (35.0% MeCN up to 48.0% in 6 min); Detector, UV 220 nm. This resulted in 237.8 mg (42%) of the title compound (I-256) as an off-white solid. MS (ES, m/z): 697 [M+H]$^+$; $^1$H-NMR (CD$_3$OD, ppm): 8.59 (s, 1H), 8.47 (d, J=5.0 Hz, 1H), 7.53-7.40 (m, 2H), 7.28-6.98 (m, 6H), 3.84-3.56 (m, 8H), 3.44-3.32 (m, 1H), 3.22-2.99 (m, 3H), 2.64 (q, J=7.2 Hz, 1H), 1.63-1.36 (m, 4H), 1.35-1.06 (m, 5H), 0.91 (s, 2H), 0.83 (s, 2H), 0.71-0.57 (m, 2H), 0.46-0.38 (m, 2H).

Example 59: 5-[3-[([1-[4-(2-cyclopropoxyphenyl)pyridin-3-yl]cyclopropyl]amino)methyl]-4-methylphenyl]-N-[(2S,3R,4R,5R)-2,3,4,5,6-pentahydroxyhexyl]hexanamide dihydrochloride (I-257)

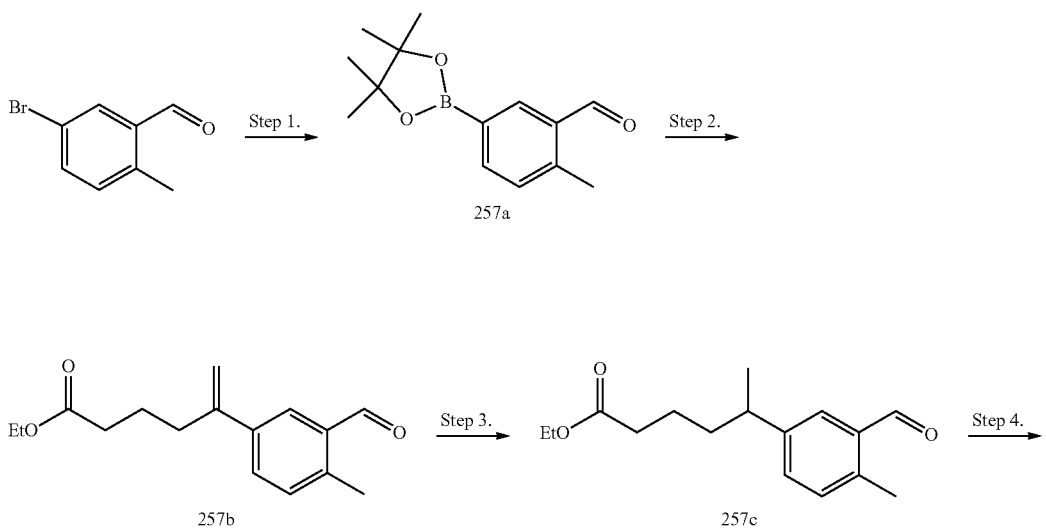

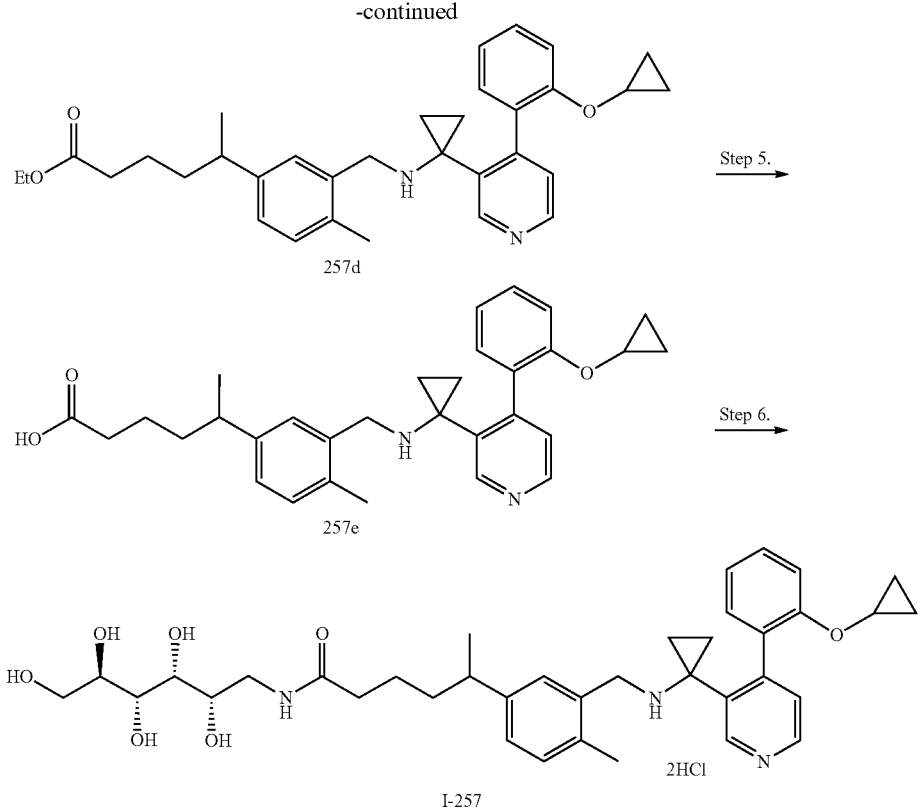

Step 1. 2-methyl-5-(tetramethyl-1,3,2-dioxaborolan-2-yl)benzaldehyde (Intermediate 257a)

A 250-mL round-bottom flask purged and maintained under an inert atmosphere of nitrogen was charged with a solution of 5-bromo-2-methylbenzaldehyde (3 g, 15.07 mmol, 1.00 equiv) in 1,4-dioxane (70 mL), 4,4,5,5-tetramethyl-2-(tetramethyl-1,3,2-dioxaborolan-2-yl)-1,3,2-dioxaborolane (4.23 g, 16.66 mmol, 1.10 equiv), KOAc (4.45 g, 45.34 mmol, 3.00 equiv), Pd(dppf)Cl$_2$ (333 mg, 0.46 mmol, 0.03 equiv). The resulting solution was stirred for 2 h at 100° C. in an oil bath. The resulting mixture was concentrated under vacuum. The residue was applied onto a silica gel column with ethyl acetate/petroleum ether (0:100-10:90). This resulted in 3.3 g (89%) of 257a as a light yellow solid.

Step 2. ethyl 5-(3-formyl-4-methylphenyl)hex-5-enoate (Intermediate 257b)

A 100-mL round-bottom flask purged and maintained under an inert atmosphere of nitrogen was charged with a solution of 2-methyl-5-(tetramethyl-1,3,2-dioxaborolan-2-yl) benzaldehyde (257a, 1 g, 4.06 mmol, 1.20 equiv) in 1,4-dioxane:H$_2$O (10:1), ethyl 5-[(trifluoromethane)sulfonyloxy]hex-5-enoate (1 g, 3.45 mmol, 1.00 equiv), Pd(PPh$_3$)$_4$ (400 mg, 0.35 mmol, 0.10 equiv), K$_3$PO$_4$ (2.2 g, 10.36 mmol, 3.00 equiv). The resulting solution was stirred overnight at 80° C. in an oil bath. The resulting mixture was concentrated under vacuum. The residue was applied onto a silica gel column with ethyl acetate/petroleum ether (0:100-10:90). This resulted in 770 mg (86%) of 257b as a colorless oil.

Step 3. ethyl 5-(3-formyl-4-methylphenyl)hexanoate (Intermediate 257c)

A 100-mL round-bottom flask was charged with ethyl 5-(3-formyl-4-methylphenyl)hex-5-enoate (257b, 770 mg, 2.96 mmol, 1.00 equiv), ethyl acetate (15 mL), Rh/C (770 mg, 1.00 equiv). To the above hydrogen was introduced in. The resulting solution was stirred for 6 h at 25° C. in an oil bath. The solids were filtered out. The resulting mixture was concentrated under vacuum. The residue was applied onto a silica gel column with ethyl acetate/petroleum ether (0:100-20:80). This resulted in 200 mg (26%) of 257c as a colorless oil.

Step 4. ethyl 5-[3-[([1-[4-(2-cyclopropoxyphenyl)pyridin-3-yl]cyclopropyl]amino)methyl]-4-methylphenyl]hexanoate (Intermediate 257d)

A 50-mL round-bottom flask was charged with a solution of ethyl 5-(3-formyl-4-methylphenyl)hexanoate (257c, 200 mg, 0.76 mmol, 1.00 equiv) in dichloromethane (6 mL), 1-[4-(2-cyclopropoxyphenyl)pyridin-3-yl]cyclopropan-1-amine (250 mg, 0.94 mmol, 1.20 equiv). This was followed by the addition of NaBH(OAc)$_3$ (970 mg, 4.58 mmol, 6.00 equiv) at 0° C. Four drops of AcOH were added. The resulting solution was stirred overnight at room temperature. The resulting solution was diluted with 25 mL of H$_2$O. The resulting solution was extracted with 3×50 mL of dichloromethane and the organic layers combined and dried in an oven under reduced pressure and concentrated under vacuum. The residue was applied onto a silica gel column with ethyl acetate/petroleum ether (1:3). This resulted in 200 mg (51%) of 257d as a light yellow oil.

Step 5. 5-[3-[([1-[4-(2-cyclopropoxyphenyl)pyridin-3-yl]cyclopropyl]amino)methyl]-4-methylphenyl]hexanoic acid (Intermediate 257e)

A 25-mL round-bottom flask was charged with a solution of ethyl 5-[3-[([1-[4-(2-cyclopropoxyphenyl)pyridin-3-yl]cyclopropyl]amino)methyl]-4-methylphenyl]hexanoate (257d, 200 mg, 0.39 mmol, 1.00 equiv) in ethanol/H$_2$O (10 mL: 1 mL), LiOH (93.8 mg, 3.92 mmol, 10.00 equiv). The resulting solution was stirred overnight at room temperature. The pH value of the solution was adjusted to 3 with 1M HCl solution. The resulting solution was extracted with 3×50 mL of ethyl acetate and the organic layers combined and dried in an oven under reduced pressure and concentrated under vacuum. This resulted in 160 mg (85%) of 257e as a colorless oil.

Step 6. 5-[3-[([1-[4-(2-cyclopropoxyphenyl)pyridin-3-yl]cyclopropyl]amino)methyl]-4-methylphenyl]-N-[(2S,3R,4R,5R)-2,3,4,5,6-pentahydroxyhexyl]hexanamide dihydrochloride (I-257)

A 25-mL round-bottom flask was charged with a solution of 5-[3-[([1-[4-(2-cyclopropoxyphenyl)pyridin-3-yl]cyclopropyl]amino)methyl]-4-methylphenyl]hexanoic acid (80 mg, 0.17 mmol, 1.00 equiv) in N,N-dimethylformamide (3 mL), HATU (130 mg, 0.34 mmol, 2.00 equiv), D-glucosamine (60 mg, 2.00 equiv), DIEA (0.11 mL, 4.00 equiv). The resulting solution was stirred for 4 h at room temperature. The solids were filtered out. The crude product was purified by Preparative HPLC with the following conditions: Column, Gemini-NX 5u C18 110A, AXIA Packed, 150× 21.2 mm; mobile phase, water with 10 mM NH$_4$HCO$_3$ and MeCN (30.0% MeCN up to 54.0% in 9 min); Detector, 254 and 220 nm. This resulted in 81.4 mg (68%) of the title compound as a light yellow solid. MS (ES, m/z): 648.3 [M+H]$^+$; $^1$H-NMR (CD$_3$OD, ppm): 9.38 (1H, s), 8.88 (1H, d), 7.88 (1H, d), 7.57 (2H, m), 7.31 (1H, d), 7.19 (2H, m), 7.00 (2H, m), 4.12 (2H, s), 3.81 (1H, m), 3.59 (6H, m), 3.36 (1H, m), 3.15 (1H, m), 2.53 (1H, m), 2.09 (5H, m), 1.50 (4H, m), 1.34 (4H, m), 1.12 (3H, d), 0.62 (2H, m), 0.42 (2H, m).

Example 60: (2S,3S,4R,5S)-N-(4-[4-chloro-3-[([1-[4-(2-cyclopropoxyphenyl)pyridin-3-yl]cyclopropyl]amino)methyl]phenyl]pentyl)-2,3,4,5,6-pentahydroxy-N-methylhexanamide (I-258)

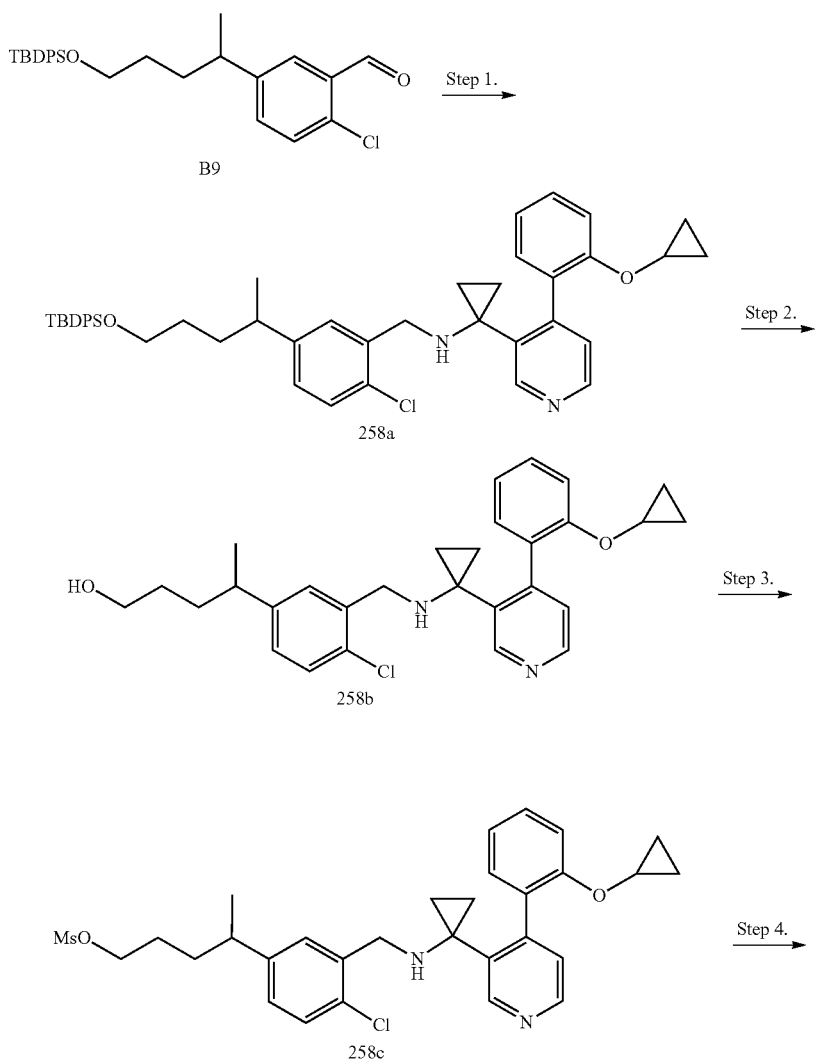

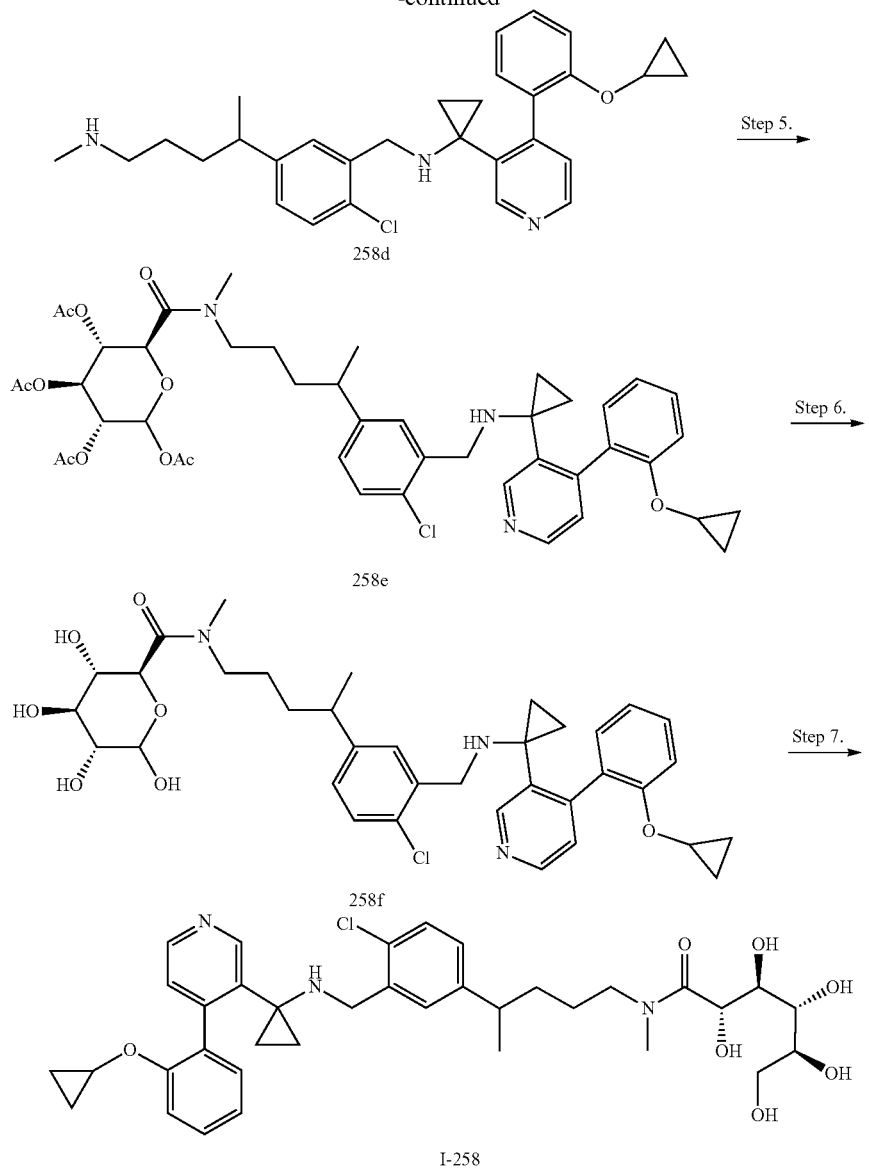

Step 1. N-[(5-[5-[(tert-butyldiphenylsilyl)oxy]pentan-2-yl]-2-chlorophenyl)methyl]-1-[4-(2-cyclopropoxyphenyl)pyridin-3-yl]cyclopropan-1-amine (Intermediate 258a)

A 100-mL round-bottom flask was charged with 5-[5-[(tert-butyldiphenylsilyl)oxy]pentan-2-yl]-2-chlorobenzaldehyde (B9) (300 mg, 0.65 mmol, 1.00 equiv), 1-[4-(2-cyclopropoxyphenyl)pyridin-3-yl]cyclopropan-1-amine (173 mg, 0.65 mmol, 1.00 equiv), dichloromethane (10 mL), NaBH(OAc)$_3$ (689 mg, 5.00 equiv) and AcOH (0.1 mL). The resulting solution was stirred overnight at room temperature. The reaction was then quenched by the addition of 5 mL of water. The resulting solution was extracted with 3×20 mL of dichloromethane and the organic layers combined. The resulting mixture was washed with 3×50 mL of brine. The mixture was dried over anhydrous sodium sulfate and concentrated under vacuum. The residue was applied onto a silica gel column with ethyl acetate/petroleum ether (1:3). This resulted in 389 mg (84%) of 258a as a yellow oil.

Step 2. 4-[4-chloro-3-[([1-[4-(2-cyclopropoxyphenyl)pyridin-3-yl]cyclopropyl]amino) methyl]phenyl] pentan-1-ol (Intermediate 258b)

A 100-mL round-bottom flask was charged with N-[(5-[5-[(tert-butyldiphenylsilyl)oxy]pentan-2-yl]-2-chlorophenyl)methyl]-1-[4-(2-cyclopropoxyphenyl) pyridin-3-yl]cyclopropan-1-amine (258a) (2 g, 2.80 mmol, 1.00 equiv), tetrahydrofuran (20 mL), TBAF/THF (4.2 mL, 1.50 equiv). The resulting solution was stirred for 4 h at room temperature. The resulting solution was extracted with 200 mL of ethyl acetate/diethyl ether (1:1) and the organic layers combined. The resulting mixture was washed with 3×200 mL of water. The mixture was dried over anhydrous sodium sulfate and concentrated under vacuum. The residue was applied onto a silica gel column with ethyl acetate/petroleum ether (0:1-1:1). This resulted in 1.3 g (97%) of 258b as a colorless oil.

Step 3. 4-[4-chloro-3-[([1-[4-(2-cyclopropoxyphenyl)pyridin-3-yl]cyclopropyl]amino) methyl]phenyl] pentyl methanesulfonate (Intermediate 258c)

A 100-mL round-bottom flask was charged with 4-[4-chloro-3-[([1-[4-(2-cyclopropoxyphenyl)pyridin-3-yl]cyclopropyl]amino)methyl]phenyl]pentan-1-ol (258b) (300 mg, 0.63 mmol, 1.00 equiv), dichloromethane (15 mL), TEA (0.2 mL, 2.00 equiv), MsCl (0.074 mL, 1.50 equiv). The resulting solution was stirred for 1 h at room temperature. The resulting mixture was concentrated under vacuum. The residue was applied onto a silica gel column with ethyl acetate/petroleum ether (1:1). This resulted in 290 mg (83%) of 258c as a light yellow solid.

Step 4. N-([2-chloro-5-[5-(methylamino)pentan-2-yl]phenyl]methyl)-1-[4-(2-cyclopropoxyphenyl)pyridin-3-yl]cyclopropan-1-amine (Intermediate 258d)

A 2.5-mL sealed tube was charged with 4-[4-chloro-3-[([1-[4-(2-cyclopropoxyphenyl)pyridin-3-yl]cyclopropyl]amino)methyl]phenyl]pentyl methanesulfonate (258c) (290 mg, 0.52 mmol, 1.00 equiv), $CH_3NH_2$/THF (2 mL). The resulting solution was stirred overnight at 60° C. in an oil bath. The resulting mixture was concentrated under vacuum. This resulted in 250 mg (98%) of 258d as a light yellow solid.

Step 5. (3R,4S,5S,6S)-3,4,5-tris(acetyloxy)-6-[(4-[4-chloro-3-[([1-[4-(2-cyclopropoxyphenyl)pyridin-3-yl]cyclopropyl]amino)methyl]phenyl]pentyl)(methyl) carbamoyl]oxan-2-yl acetate (Intermediate 258e)

A 100-mL round-bottom flask was charged with N-([2-chloro-5-[5-(methylamino)pentan-2-yl]phenyl]methyl)-1-[4-(2-cyclopropoxyphenyl)pyridin-3-yl]cyclopropan-1-amine (258d) (250 mg, 0.51 mmol, 1.00 equiv), (2S,3S,4S,5R)-3,4,5,6-tetraacetoxytetrahydro-2H-pyran-2-carboxylic acid (185 mg, 0.51 mmol, 1.00 equiv), HATU (291 mg, 1.21 mmol, 1.50 equiv), N,N-dimethylformamide (10 mL), DIEA (0.25 mL, 3.00 equiv). The resulting solution was stirred for 2 h at room temperature. The resulting solution was extracted with 4×20 mL of ethyl acetate and the organic layers combined. The resulting mixture was washed with 3×60 mL of brine. The mixture was dried over anhydrous sodium sulfate and concentrated under vacuum. The residue was applied onto a silica gel column with dichloromethane/methanol (1:1). This resulted in 230 mg (54%) of 258e as a light yellow solid.

Step 6. (2S,3S,4S,5R)-N-[4-[4-chloro-3-([1-[4-(2-cyclopropoxyphenyl)pyridin-3-yl]cyclopropoxy]methyl)phenyl]pentyl]-3,4,5,6-tetrahydroxy-N-methyloxane-2-carboxamide (Intermediate 258f)

A 100-mL round-bottom flask was charged with (2S,3S,4S,5R)-4,5,6-tris(acetyloxy)-2-([4-[4-chloro-3-([1-[4-(2-cyclopropoxyphenyl)pyridin-3-yl]cyclopropoxy]methyl)phenyl]pentyl](methyl)carbamoyl) oxan-3-yl acetate (258e) (230 mg, 0.28 mmol, 1.00 equiv), methanol (10 mL), methoxysodium (18 mg, 0.33 mmol, 0.60 equiv). The resulting solution was stirred overnight at room temperature. The reaction was then quenched by the addition of 0.02 mL of water. The resulting mixture was concentrated under vacuum. This resulted in 170 mg (93%) of 258f as a light yellow solid.

Step 7. (2S,3S,4R,5S)-N-(4-[4-chloro-3-[([1-[4-(2-cyclopropoxyphenyl)pyridin-3-yl]cyclopropyl]amino)methyl]phenyl]pentyl)-2,3,4,5,6-pentahydroxy-N-methylhexanamide (I 258)

A 25-mL round-bottom flask was charged with (2S,3S,4S,5R)-N-(4-[4-chloro-3-[([1-[4-(2-cyclopropoxyphenyl)pyridin-3-yl]cyclopropyl]amino)methyl]phenyl]pentyl)-3,4,5,6-tetrahydroxy-N-methyloxane-2-carboxamide (258f) (170 mg, 0.26 mmol, 1.00 equiv), methanol (3 mL), sodium borohydride (21 mg, 0.57 mmol, 2.00 equiv). The resulting solution was stirred for 1h at room temperature. The reaction was then quenched by the addition of 2 mL of water. The crude product was purified by Preparative HPLC with the following conditions: Column: Gemini-NX, 5μ C18 110A, AXIA Packed 150×21.2 mm; mobile phase, water with 10 mmol $NH_4HCO_3$ and MeCN (27.0% MeCN up to 55.0% in 6 min); Detector, UV 220 nm. This resulted in 57.1 mg (33%) of the title compound I-258 as a white solid. MS (ES, m/z): 668.35 [M+H]$^+$; $^1$H NMR (400 MHz, $CD_3OD$) δ 8.58 (d, J=1.1 Hz, 1H) 8.46 (d, J=5.0 Hz, 1H), 7.42-7.48 (m, 2H), 7.14-7.28 (m, 3H), 7.05 (d, J=18.2 Hz, 3H), 4.60 (s, 1H), 3.84-4.61 (m, 1H), 3.55-4.46 (m, 8H), 3.27 (s, 2H), 3.04 (s, 1H), 2.86 (d, J=6.2 Hz, 1H), 2.67 (s, 1H), 1.56 (m, 4H), 1.16-1.24 (m, 3H), 0.89 (s, 2H), 0.82 (s, 2H), 0.63 (s, 2H), 0.41 (s, 2H).

Example 61: N-benzyl-5-(3-(((1-(4-(2-cyclopropoxyphenyl)pyridin-3-yl)cyclopropyl) amino) methyl)-4-methylphenyl)-N-((2S,3R,4R,5R)-2,3,4,5,6-pentahydroxyhexyl) hexanamide (I-259)

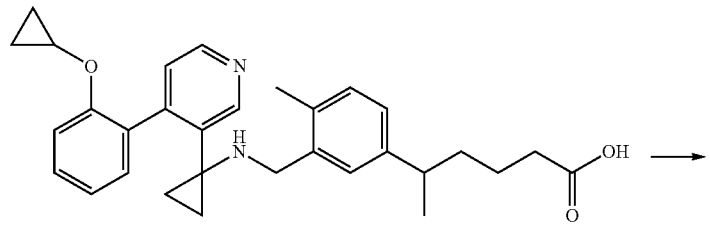

257e

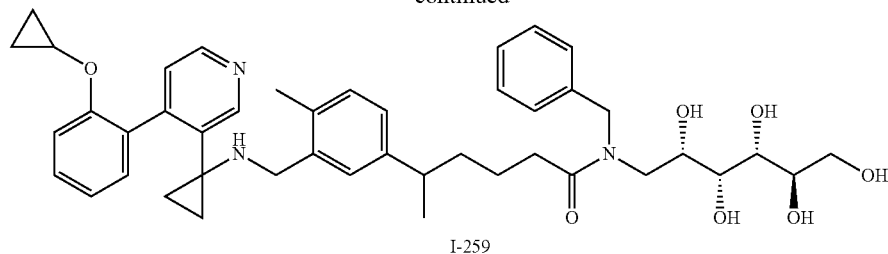

I-259

Intermediate D1 (50 mg, 0.186 mmol, 2.00 equiv) was added to a solution of Intermediate 257e (45 mg, 0.0928 mmol, 1.00 equiv), HATU (71 mg, 0.186 mmol, 2.00 equiv), and DIEA (36 mg, 0.278 mmol, 3.00 equiv) in DMF (1 mL). The resulting solution was allowed to stir for 1 h at room temperature. The crude product was purified by preparative HPLC with a $CH_3CN/H_2O$ gradient containing 0.1% TFA (10% $CH_3CN$ to 80% $CH_3CN$ over 18 min). The fractions containing the desired product were then neutralized with Amberlyst A26 hydroxide resin and filtered to provide 29 mg (43%) of the title compound (I-259) as an off-white solid. MS (ES, m/s): 738.3 $[M+H]^+$; $^1$H-NMR (400 MHz, DMSO-$d_6$) δ 8.59 (s, 1H), 8.48 (d, J=4.9 Hz, 1H), 7.40 (d, J=3.8 Hz, 2H), 7.26 (d, J=5.9 Hz, 3H), 7.12 (dd, J=15.4, 5.9 Hz, 4H), 6.95 (d, J=15.7 Hz, 2H), 6.80 (s, 1H), 4.96 (s, 1H), 4.64 (s, 2H), 4.52-4.23 (m, 6H), 2.08 (d, J=4.8 Hz, 4H), 1.09 (dd, J=24.0, 6.8 Hz, 3H), 0.79 (s, 2H), 0.63 (s, 4H), 0.37 (s, 2H).

Example 62: 5-[2,5-dichloro-4-[([1-[4-(2-cyclopropoxyphenyl)pyridin-3-yl]cyclopropyl]amino)methyl]phenyl]-N-[2S,3R,4R,5R)-2,3,4,5,6-pentahydroxyhexyl]hexanamide (I-260)

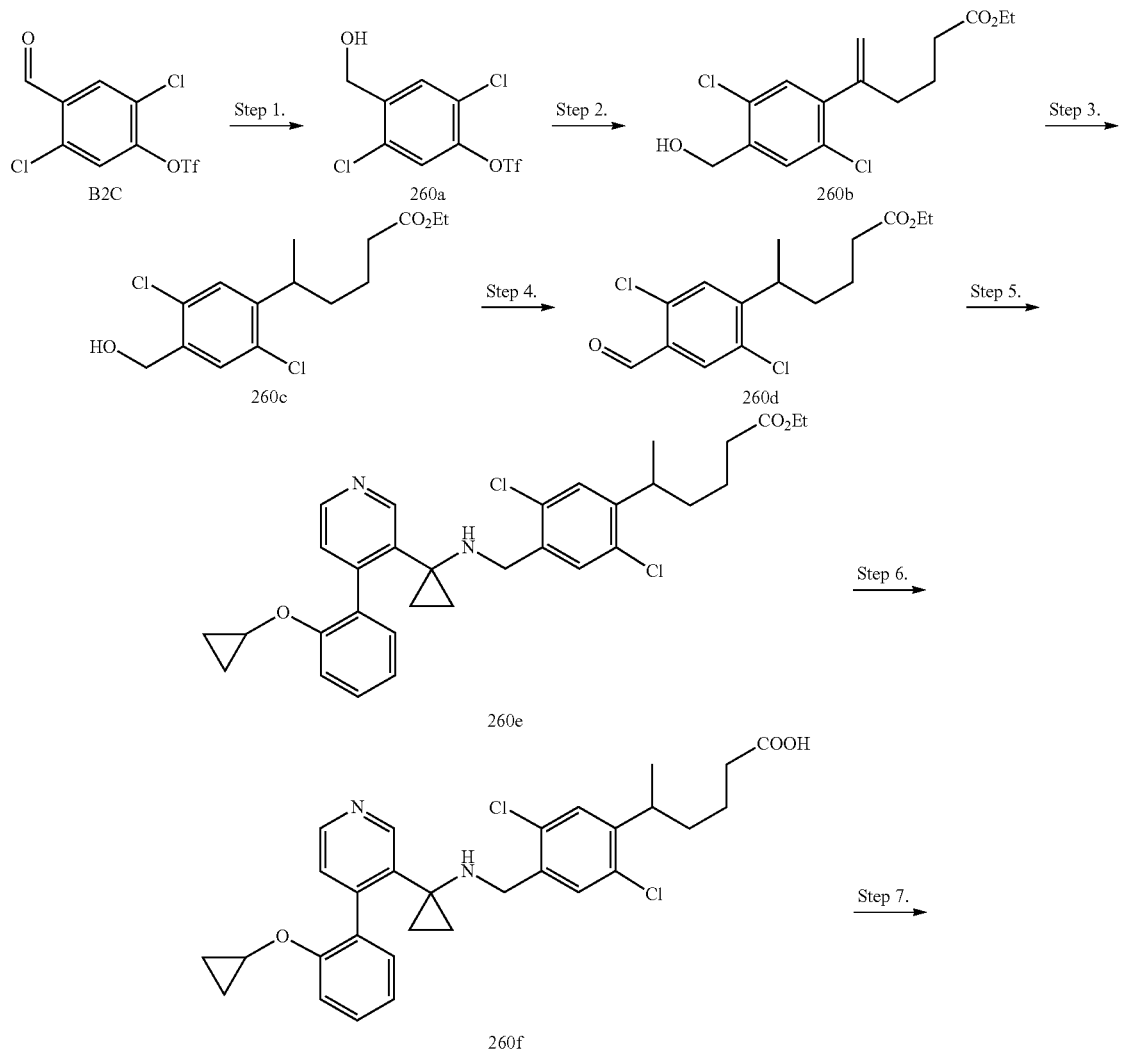

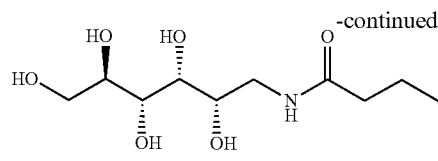
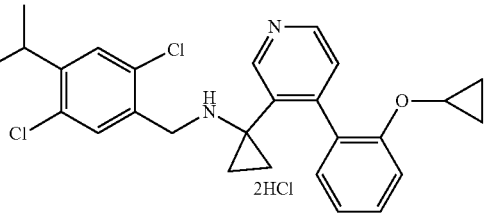

I-260

Step 1. 2,5-dichloro-4-(hydroxymethyl)phenyl trifluoromethanesulfonate (Intermediate 260a)

A 250-mL round-bottom flask was charged with a solution of 2,5-dichloro-4-formylphenyl trifluoromethanesulfonate (B2c) (4 g, 12.38 mmol, 1.00 equiv) in methanol (50 mL). This was followed by the addition of NaBH$_4$ (940 mg, 24.85 mmol, 2.00 equiv) in several batches at 0° C. The resulting solution was stirred for 30 min at 0° C. The reaction was then quenched by the addition of 50 mL of water. The resulting solution was extracted with 3×30 mL of ethyl acetate and the organic layers combined and dried over anhydrous sodium sulfate and concentrated under vacuum. This resulted in 4 g (99%) of 260a as a pale-yellow oil.

Step 2. ethyl 5-[2,5-dichloro-4-(hydroxymethyl)phenyl]hex-5-enoate (Intermediate 260b)

A 500-mL round-bottom flask was charged with a solution of ethyl 5-(tetramethyl 1,3,2-dioxaborolan-2-yl)hex-5-enoate (2.46 g, 9.17 mmol, 1.10 equiv) in DME/H$_2$O (200/10 mL), 2,5-dichloro-4-(hydroxymethyl)phenyl trifluoromethanesulfonate (260a, 2.7 g, 8.31 mmol, 1.00 equiv), Pd(PPh$_3$)$_4$ (960 mg, 0.83 mmol, 0.10 equiv), sodium carbonate (2.65 g, 25.00 mmol, 3.00 equiv). The resulting solution was stirred overnight at 90° C. in an oil bath. The reaction was then quenched by the addition of 50 mL of H$_2$O. The resulting solution was extracted with 3×30 mL of ethyl acetate and the organic layers combined and dried over sodium sulfate and concentrated under vacuum. The residue was applied onto a silica gel column with PE:EtOAc (95:5). This resulted in 900 mg (34%) of 260b as a colorless oil.

Step 3. ethyl 5-[2,5-dichloro-4-(hydroxymethyl)phenyl]hexanoate (Intermediate 260c)

A 250-mL round-bottom flask was charged with a solution of ethyl 5-[2,5-dichloro-4-(hydroxymethyl)phenyl]hex-5-enoate (260b, 900 mg, 2.84 mmol, 1.00 equiv) in ethyl acetate (20 mL), Rh/C (900 mg). The resulting solution was stirred overnight at room temperature. The solids were filtered out. The resulting mixture was concentrated under vacuum. The residue was applied onto a silica gel column with PE:E (95:5). This resulted in 300 mg (33%) of 260c as a pale-yellow oil.

Step 4. ethyl 5-(2,5-dichloro-4-formylphenyl)hexanoate (Intermediate 260d)

A 50-mL round-bottom flask was charged with a solution of ethyl 5-[2,5-dichloro-4-(hydroxymethyl)phenyl]hexanoate (260c, 300 mg, 0.94 mmol, 1.00 equiv) in dichloromethane (10 mL), MnO$_2$ (650 mg, 7.48 mmol, 8.00 equiv). The resulting solution was stirred for 5 h at 40° C. in an oil bath. The solids were filtered out. The mixture was dried over anhydrous sodium sulfate and concentrated under vacuum. The residue was applied onto a silica gel column with ethyl acetate/petroleum ether (0:100-20:80). This resulted in 110 mg (37%) of 260d as a light yellow oil.

Step 5. ethyl 5-[2,5-dichloro-4-[([1-[4-(2-cyclopropoxyphenyl)pyridin-3-yl]cyclopropyl]amino)methyl]phenyl]hexanoate (Intermediate 260e)

A 25-mL round-bottom flask was charged with ethyl 5-(2,5-dichloro-4-formylphenyl)hexanoate (260d, 110 mg, 0.35 mmol, 1.00 equiv), dichloromethane (5 mL), 1-[4-(2-cyclopropoxyphenyl)pyridin-3-yl]cyclopropan-1-amine (150 mg, 0.56 mmol, 1.50 equiv). This was followed by the addition of NaBH(OAc)$_3$ (440 mg, 2.08 mmol, 6.00 equiv) dropwise with stirring at 0° C. To this was added cat. AcOH (0.06 mL, 0.05 equiv). The resulting solution was stirred overnight at room temperature. The resulting solution was diluted with 120 mL of H$_2$O. The resulting solution was extracted with 3×120 mL of dichloromethane and the organic layers combined and dried over anhydrous sodium sulfate and concentrated under vacuum. The residue was applied onto a silica gel column with ethyl acetate/petroleum ether (1:3). This resulted in 170 mg (86%) of 260e as a light yellow oil.

Step 6. 5-[2,5-dichloro-4-[([1-[4-(2-cyclopropoxyphenyl)pyridin-3-yl]cyclopropyl]amino) methyl]phenyl]hexanoic acid (Intermediate 260f)

A 25-mL round-bottom flask was charged with ethyl 5-[2,5-dichloro-4-[([1-[4-(2-cyclopropoxyphenyl)pyridin-3-yl]cyclopropyl]amino)methyl]phenyl]hexanoate (260e, 170 mg, 0.30 mmol, 1.00 equiv), ethanol/H$_2$O (4/0.4 mL), LiOH (72 mg, 3.01 mmol, 10.00 equiv). The resulting solution was stirred for 1 h at 50° C. in an oil bath. The pH value of the solution was adjusted to 3 with hydrogen chloride (1 mol/L). The resulting solution was extracted with 3×50 mL of ethyl acetate and the organic layers combined and dried over anhydrous sodium sulfate and concentrated under vacuum. This resulted in 120 mg (74%) of 260f as a light yellow oil.

Step 7. 5-[2,5-dichloro-4-[([1-[4-(2-cyclopropoxyphenyl)pyridin-3-yl]cyclopropyl]amino) methyl]phenyl]-N-[(2S,3R,4R,5R)-2,3,4,5,6-pentahydroxyhexyl]hexanamide (I-260)

A 25-mL round-bottom flask was charged with a solution of 5-[2,5-dichloro-4-[([1-[4-(2-cyclopropoxyphenyl)pyridin-3-yl]cyclopropyl]amino)methyl]phenyl]hexanoic acid (260f, 80 mg, 0.15 mmol, 1.00 equiv) in N,N-dimethylformamide (5 mL), (2R,3R,4R,5S)-6-aminohexane-1,2,3,4,5- pentol (54 mg, 0.30 mmol, 2.00 equiv), HATU (113 mg, 0.30 mmol, 2.00 equiv), DIEA (77 mg, 0.60 mmol, 4.00 equiv). The resulting solution was stirred overnight at room temperature. The solids were filtered out. The crude product was purified by Preparative HPLC with the following conditions: Column, Gemini-NX 5μ C18 110A, AXIA Packed, 150× 21.2 mm; mobile phase, 10 mM aqueous NH$_4$HCO$_3$ and MeCN (38.0% MeCN up to 52.0% in 10 min); Detector, 254 nm. This resulted in 60.1 mg (52%) of the title compound (I-260) as an off-white solid. MS (ES, m/z): 702 [M+H]$^+$; $^1$H-NMR (CD$_3$OD, ppm): 9.45 (s, 1H), 8.99 (d, J=6.0 Hz, 1H), 7.98 (d, J=6.0 Hz, 1H), 7.64-7.71 (m, 3H), 7.27-7.50 (m, 3H), 4.38 (s, 2H), 3.95 (s, 1H), 3.29-3.78 (m, 9H), 2.20 (t, J=7.6 Hz, 2H), 1.21-1.65 (m, 11H), 0.77 (s, 2H), 0.58 (s, 2H).

Example 63: 5-(4-chloro-3-(((1-(4-(2-cyclopropoxyphenyl)pyridin-3-yl)cyclopropyl) amino)methyl) phenyl)-N-(5-hydroxypentyl)-N-((2S,3R,4R,5R)-2,3,4,5,6-pentahydroxyhexyl)hexanamide (I-261)

Step 1. ethyl 5-[4-chloro-3-[([1-[4-(2-cyclopropoxyphenyl)pyridin-3-yl]cyclopropyl]amino) methyl] phenyl]hexanoate (Intermediate 261a)

A 25-mL round-bottom flask was charged with ethyl 5-(4-chloro-3-formylphenyl)hexanoate (B10) (382 mg, 1.35 mmol, 1.20 equiv), 1-[4-(2-cyclopropoxyphenyl)pyridin-3-yl]cyclopropan-1-amine (A1) (300 mg, 1.13 mmol, 1.00 equiv), NaBH(OAc)$_3$ (957 mg, 4.52 mmol, 4.00 equiv), AcOH (0.05 mL), dichloromethane (15 mL). The resulting solution was stirred for 1 overnight at room temperature. The resulting solution was diluted with 1000 mL of DCM. The resulting mixture was washed with 2×50 mL of H$_2$O. The mixture was dried over anhydrous sodium sulfate and concentrated under vacuum. The crude product (500 mg) was purified by flash chromatography with the following conditions (IntelFlash-1): Column, silica gel; mobile phase, ethyl acetate:petroleum ether=100:0 increasing to ethyl acetate:petroleum ether=85:15 within 30 min; Detector, UV 254 nm. This resulted in 450 mg (75%) of ethyl 5-[4-chloro-

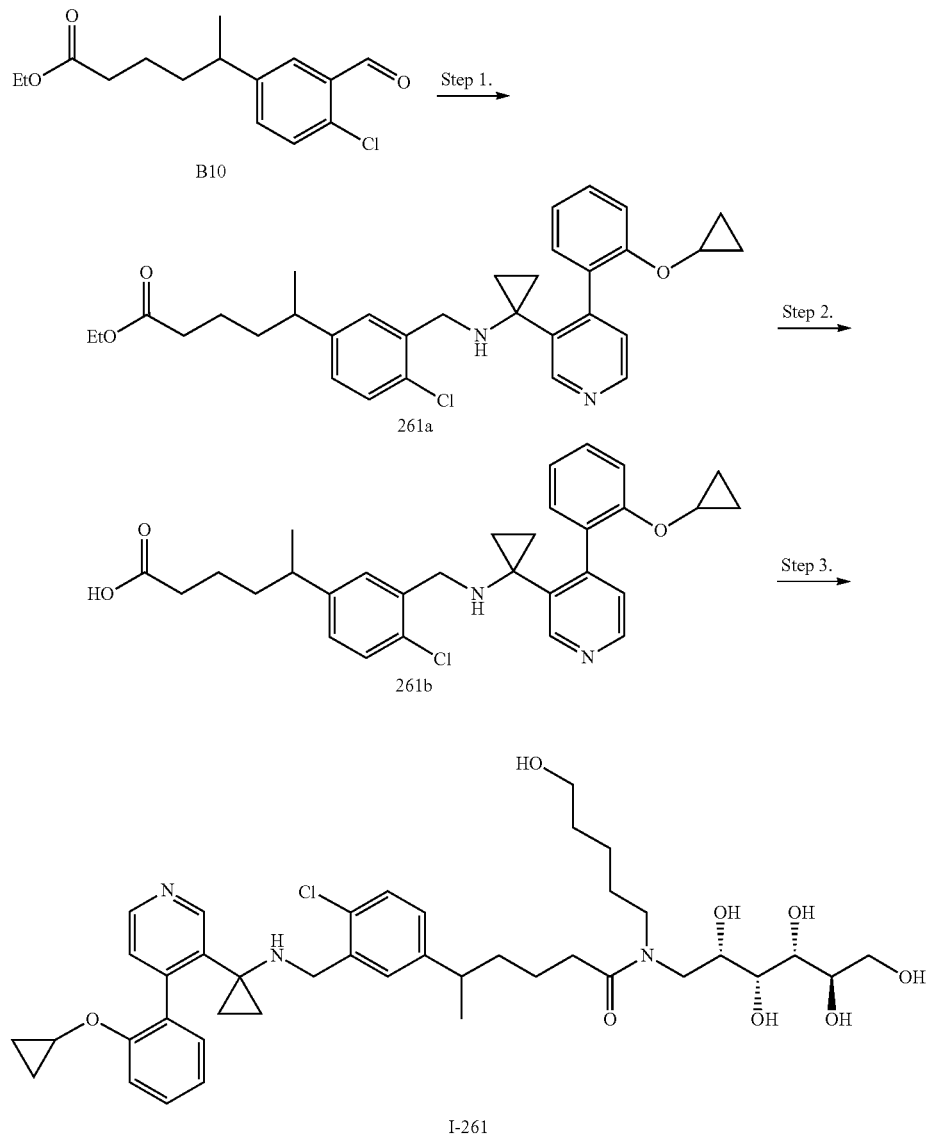

3-[([1-[4-(2-cyclopropoxyphenyl)pyridin-3-yl]cyclopropyl]amino)methyl]phenyl]hexanoate (261a) as colorless oil.

Step 2. 5-[4-chloro-3-[([1-[4-(2-cyclopropoxyphenyl)pyridin-3-yl]cyclopropyl]amino) methyl]phenyl] hexanoic acid (Intermediate 261b)

A 25-mL round-bottom flask was charged with ethyl 5-[4-chloro-3-[([1-[4-(2-cyclopropoxyphenyl)pyridin-3-yl.]cyclopropyl]amino)methyl]phenyl]hexanoate (261a) (450 mg, 0.84 mmol, 1.00 equiv), LiOH (122 mg, 5.09 mmol, 6.00 equiv), methanol (6 mL) and water (0.5 mL). The resulting solution was stirred overnight at room temperature. The pH value of the solution was adjusted to 6.0 with hydrogen chloride (1 mol/L). The resulting solution was extracted with 2×50 mL of ethyl acetate and the organic layers combined and dried at reduced pressure. This resulted in 420 mg (99%) of 5-[4-chloro-3-[([1-[4-(2-cyclopropoxyphenyl)pyridin-3-yl]cyclopropyl]amino)methyl]phenyl]hexanoic acid (261b) as colorless oil.

Step 3. 5-(4-chloro-3-(((1-(4-(2-cyclopropoxyphenyl)pyridin-3-yl)cyclopropyl)amino) methyl)phenyl)-N-(5-hydroxypentyl)-N-((2S,3R,4R,5R)-2,3,4,5,6-pentahydroxyhexyl) hexanamide (I-261)

A mixture of 5-(4-chloro-3-(((1-(4-(2-cyclopropoxyphenyl)pyridin-3-yl)cyclopropyl) amino)methyl)phenyl) hexanoic acid (261b) (27.1 mg, 0.0537 mmol, 1.0 equiv), and (2R,3R,4R,5S)-6-((5-hydroxypentyl)amino)hexane-1,2,3,4,5-pentaol (D8) (21.2 mg, 0.0698 mmol, 1.3 equiv), in DMF (0.3 mL) were added N,N-diisopropylethylamine (37.4 µL, 0.215 mmol, 4.0 equiv) and HATU (26.5 mg, 0.0698 mmol, 1.3 equiv). The mixture was stirred at room temperature for 1 h and purified by Preparative HPLC. The HPLC fractions were combined, neutralized with Amberlyst® A26 hydroxide form to pH 6, and lyophilized to give 22.2 mg (55%) of the title compound as a white solid. MS (ES, m/z): 754.3 [M+H]⁺. ¹H-NMR (400 MHz, CD₃OD) δ 8.66 (s, 1H), 8.51 (d, J=5.1 Hz, 1H), 7.49-7.44 (m, 2H), 7.27 (d, J=8.0 Hz, 1-1), 7.24-7.19 (m, 2H), 7.13-7.05 (m, 3H), 3.98-3.89 (m, 1H), 3.84-3.76 (m, 3H), 3.76-3.59 (m, 6H), 3.59-3.47 (m, 4H), 3.44-3.34 (m, 2H), 2.73-2.63 (m, 1H), 2.52-2.30 (m, 1H), 1.65-1.49 (m, 7H), 1.48-1.25 (m, 3H), 1.20 (dd, J=6.8, 3.4 Hz, 3H), 1.02-0.87 (m, 4H), 0.68-0.57 (m, 2H), 0.48-0.37 (m, 2H).

Example 64: 5-(4-chloro-3-(((1-(4-(2-cyclopropoxyphenyl)pyridin-3-yl)cyclopropyl)amino) methyl)phenyl)-N-(2-(morpholinosulfonyl)ethyl)-N-((2S,3R,4R,5R)-2,3,4,5,6-pentahydroxyhexyl)hexanamide (I-262)

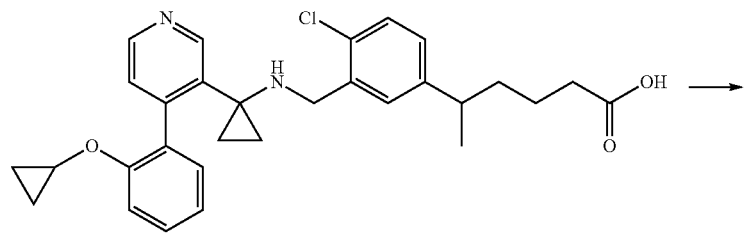

261b

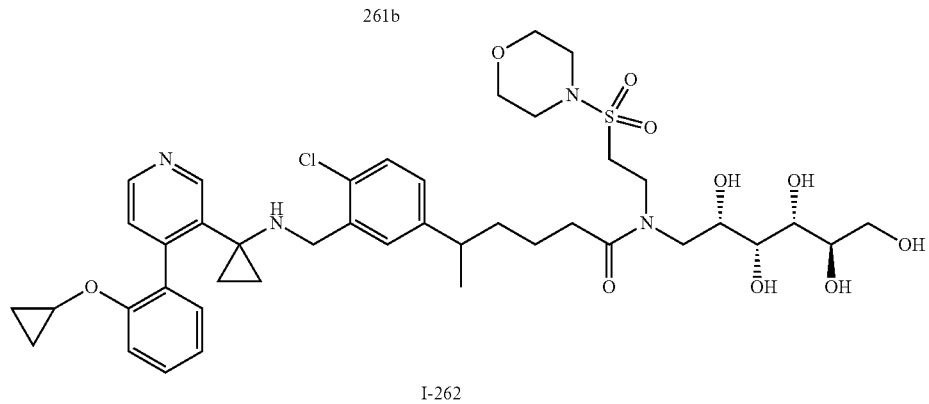

I-262

A mixture of 5-(4-chloro-3-(((1-(4-(2-cyclopropoxyphenyl)pyridin-3-yl)cyclopropyl)amino)methyl)phenyl) hexanoic acid (261b) (25.3 mg, 0.0501 mmol, 1.0 equiv), and (2R,3R,4R,5S)-6-((2-(morpholinosulfonyl)ethyl)amino)hexane-1,2,3,4,5-pentaol (D9) (23.3 mg, 0.0651 mmol, 1.3 equiv), in DMF (0.3 mL) were added N,N-diisopropylethylamine (35.7 µL, 0.205 mmol, 4.1 equiv) and HATU (24.7 mg, 0.065 mmol, 1.3 equiv). The mixture was stirred at room temperature for 1 h and purified by Preparative HPLC. The HPLC fractions were combined, neutralized with Amberlyst® A26 hydroxide form to pH 6, and lyophilized to give 31.3 mg (74%) of the title compound (I-262) as a white solid. MS (ES, m/z): 845.3 [M+H]⁺. ¹H-NMR (400 MHz, CD₃OD) δ 8.75 (s, 1H), 8.57 (d, J=5.2 Hz, 1H), 7.51-7.47 (m, 2H), 7.32-7.27 (m, 2H), 7.24 (d, J=7.5 Hz, 1H), 7.21-7.10 (m, 3H), 4.00-3.82 (m, 4H), 3.81-3.60 (m, 12H), 3.53 (d, J=6.0 Hz, 1H), 3.41-3.34 (m, 2H), 3.27-3.17 (m, 5H), 2.77-2.62 (m, 1H), 2.52-2.31 (m, 1H), 1.67-1.56 (m, 2H), 1.56-1.35 (m, 2H), 1.20 (d, J=6.8 Hz, 3H), 1.10-0.96 (m, 4H), 0.69-0.59 (m, 2H), 0.46-0.38 (m, 2H).

Example 65: 1-(4-(5-chloro-4-((1-(4-(2-cyclo-propoxyphenyl)pyridin-3-yl)cyclopropoxy) methyl)-2-methylphenyl)butyl)-1-ethyl-3-((2S,3R,4R,5R)-2,3,4,5,6-pentahydroxyhexyl)urea I-263

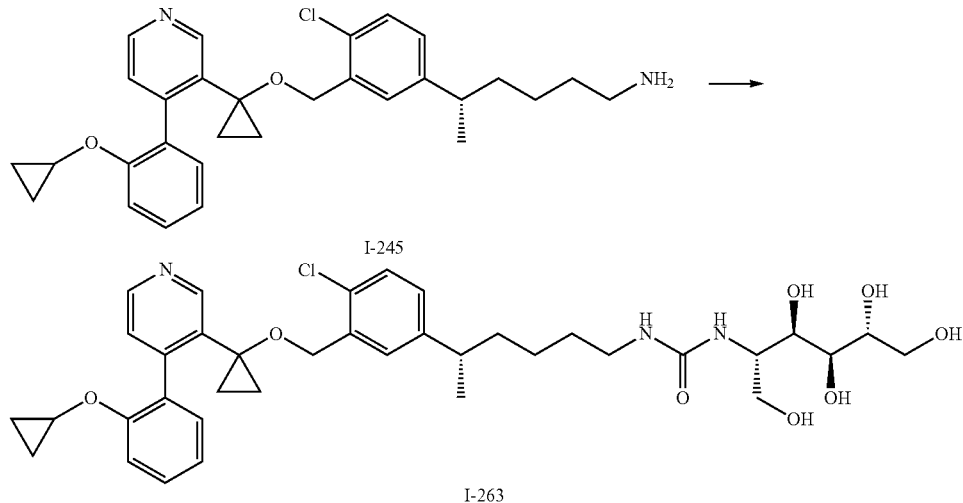

A mixture of (S)-5-(4-chloro-3-((1-(4-(2-cyclopropoxyphenyl)pyridin-3-yl)cyclopropoxy)methyl)phenyl)hexan-1-amine (I-245) (262.8 mg, 0.535 mmol, 1.0 equiv), in DCM (3 mL) was added trimethylamine (224 µL, 1.610 mmol, 3.0 equiv), followed by dropwise addition of a solution of (2R,3S,4R,5S)-5-isocyanatohexane-1,2,3,4,6-pentayl pentaacetate (257.3 mg, 0.617 mmol, 1.15 equiv) in DCM (3 mL). The mixture was stirred at room temperature for 1 h and diluted with ethyl acetate. The mixture was washed with water (1×) and brine (1×), dried, and concentrated to give a white solid. A mixture of the white solid in MeOH (10 mL) was added (25 wt. % in MeOH, 200 µL). The mixture was stirred at room temperature for 30 minutes, concentrated and purified by preparative HPLC (40-70% acetonitrile in 0.010M $NH_4HCO_3$ water solution) to give 258 mg (69%) of the title compound I-263 as a white solid. MS (ES, m/z): 699.45 [M+H]$^+$. $^1$H-NMR (400 MHz, CD$_3$OD) δ 8.67 (s, 1H), 8.49 (d, J=5.1 Hz, 1H), 7.44-7.29 (m, 3H), 7.28-7.20 (m, 2H), 7.07 (dd, J=8.2, 2.2 Hz, 1H), 7.01 (td, J=7.3, 1.4 Hz, 1H), 6.96 (d, J=2.2 Hz, 1H), 4.42 (s, 2H), 3.97 (dd, J=4.9, 2.9 Hz, 1H), 3.85 (q, J=4.7 Hz, 1H), 3.78 (dd, J=10.8, 3.3 Hz, 1H), 3.74-3.52 (m, 6H), 3.07 (dq, J=13.2, 6.4 Hz, 2H), 2.71-2.53 (m, 1H), 1.61-1.51 (m, 2H), 1.51-1.34 (m, 2H), 1.34-1.24 (m, 1H), 1.20 (d, J=6.9 Hz, 4H), 1.02 (t, J=6.0 Hz, 2H), 0.97-0.88 (m, 2H), 0.62 (d, J=6.0 Hz, 2H), 0.46-0.33 (m, 2H).

Example 66: 1-[(5R)-5-[4-chloro-3-([1-[4-(2-cyclopropoxyphenyl)pyridin-3-yl]cyclopropoxy]methyl)phenyl]hexyl]-3-[(2S,3R,4S,5R)-1,3,4,5,6-pentahydroxyhexan-2-yl]urea (I-264)

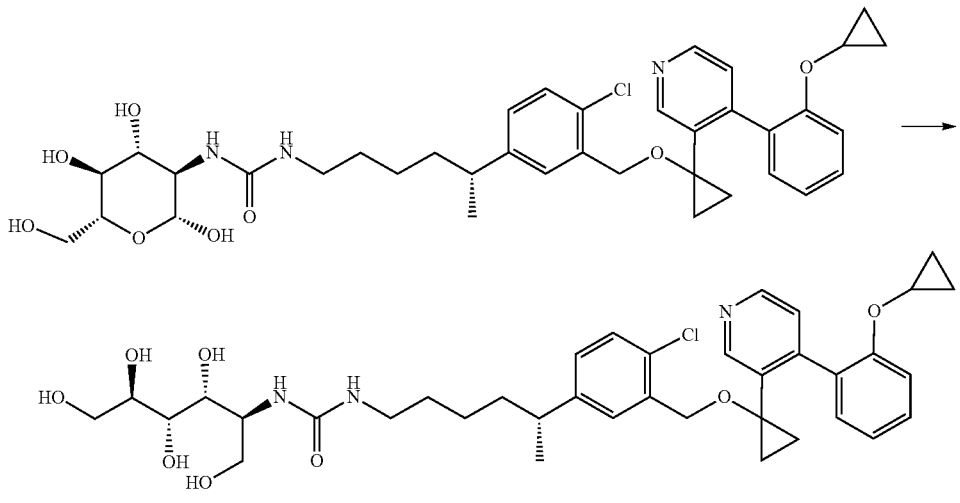

A 8-mL vial purged and maintained under an inert atmosphere of nitrogen was charged with 1-[(5R)-5-[4-chloro-3-([1-[4-(2-cyclopropoxyphenyl)pyridin-3-yl]cyclopropoxy]methyl) phenyl]hexyl]-3-[(2R,3R,4R,5S,6R)-2,4,5-trihydroxy-6-(hydroxymethyl)oxan-3-yl]urea (226 mg, 0.32 mmol, 1.00 equiv), methanol (1 mL) and NaBH$_4$ (25 mg, 0.68 mmol, 2.00 equiv). The resulting solution was stirred for 1 h at room temperature. The resulting mixture was concentrated under vacuum. The crude product was purified by Preparative HPLC with the following conditions: XBridge Shield RP18 OBD Column; 5 μm 19×150 mm; mobile phase:water (10 mM NH$_4$HCO$_3$) and MeCN (34.0% MeCN up to 54.0% in 6 min); Detector, UV 220 nm. This resulted in 75.2 mg (33%) of the title compound I-264 as a white solid. MS (ES, m/z): 698.34 [M+H]$^+$; $^1$H NMR (300 MHz, Methanol-d$_4$) δ 8.66 (s, 1H), 8.48 (d, J=5.1 Hz, 1H), 7.17-7.46 (m, 5H), 6.91-7.11 (m, 3H), 4.59 (s, 1H), 4.41 (s, 2H), 3.96 (dd, J=4.9, 2.8 Hz, 1H), 3.49-3.90 (m, 9H), 3.06 (td, J=7.0, 2.4 Hz, 2H), 2.62 (q, J=7.0 Hz, 1H), 1.50 (dq, J=33.5, 7.4, 6.9 Hz, 4H), 1.19 (d, J=6.9 Hz, 4H), 0.87-1.07 (m, 4H), 0.55-0.68 (m, 2H), 0.40 (d, J=3.8 Hz, 2H).

Compounds I-265 to I-379 (Table 12) were prepared from commercial, known starting materials or the appropriate intermediates disclosed herein using methods from the examples specified in Table 12 and methods generally known to those skilled in the art.

TABLE 12

Compounds I-265 to I-385.

| Cmpd. No: | Synthesis Method | Compound Structure | Obs Mass |
|---|---|---|---|
| I-265 | Example 15 | 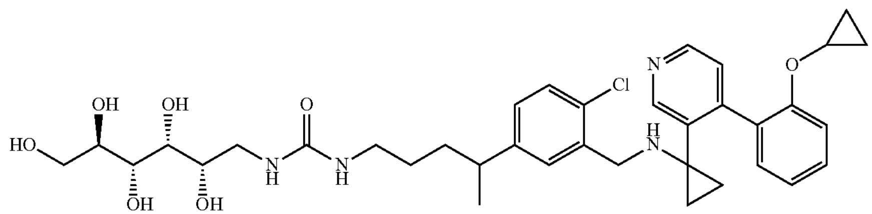 [SMILES: CC(CCCNC(=O)NC[C@H](O)[C@@H](O)[C@H](O)[C@H](O)CO)c1ccc(Cl)c(CNC2(c3cnccc3-c3ccccc3OC3CC3)CC2)c1] | 683.30 |
| I-266 | Example 15 | 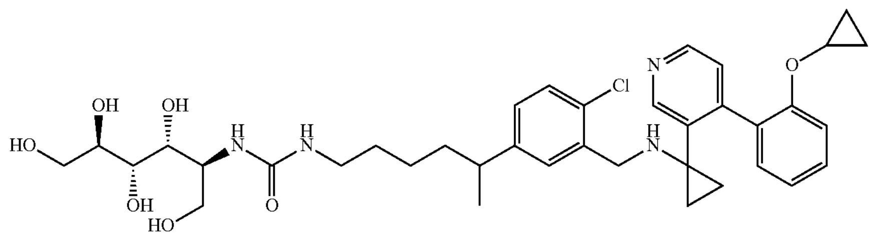 [SMILES: CC(CCCCNC(=O)N[C@@H](CO)[C@@H](O)[C@H](O)[C@H](O)CO)c1ccc(Cl)c(CNC2(c3cnccc3-c3ccccc3OC3CC3)CC2)c1] | 697.35 |
| I-267 | Example 15 | 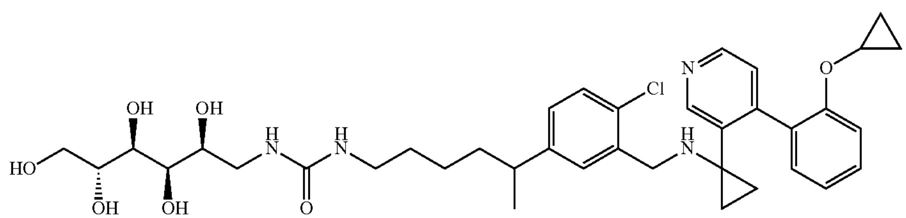 [SMILES: CC(CCCCNC(=O)NC[C@H](O)[C@@H](O)[C@H](O)[C@H](O)CO)c1ccc(Cl)c(CNC2(c3cnccc3-c3ccccc3OC3CC3)CC2)c1] | 697.30 |
| I-268 | Example 15 | 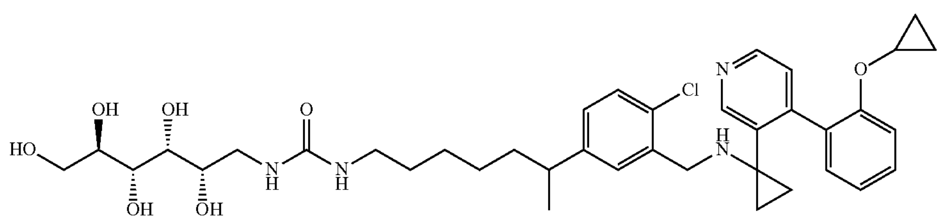 [SMILES: CC(CCCCCNC(=O)NC[C@H](O)[C@@H](O)[C@H](O)[C@H](O)CO)c1ccc(Cl)c(CNC2(c3cnccc3-c3ccccc3OC3CC3)CC2)c1] | 711.35 |

TABLE 12-continued
Compounds I-265 to I-385.
| Cmpd. No. | Synthesis Method | Compound Structure | Obs Mass |
|---|---|---|---|
| I-269 | Example 37 | 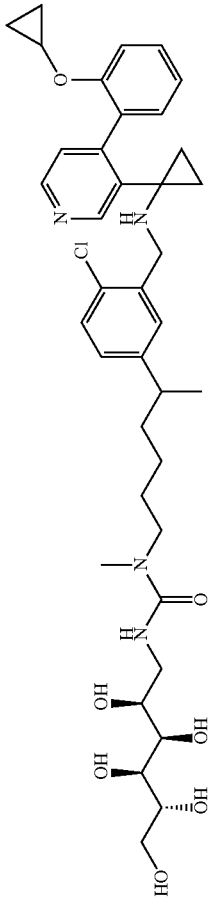 | 711.3 |
| I-270 | Example 27 | 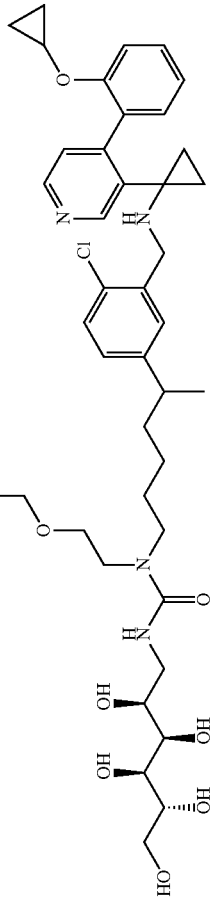 | 785.4 |
| I-271 | Example 15 | 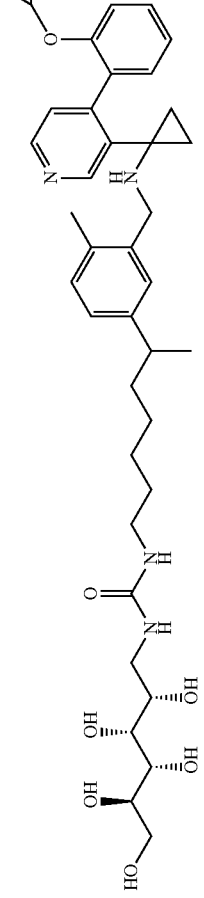 | 663.4 |
| I-272 | Example 15 | 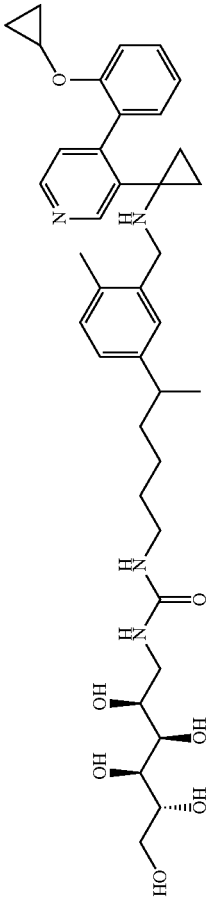 | 677.30 |

TABLE 12-continued
Compounds I-265 to I-385.
| Cmpd. No: | Synthesis Method | Compound Structure | Obs Mass |
|---|---|---|---|
| I-273 | Example 65 | 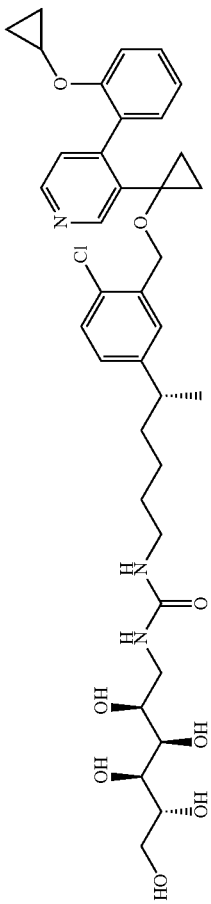 | 698.30 |
| I-274 | Example 65 | 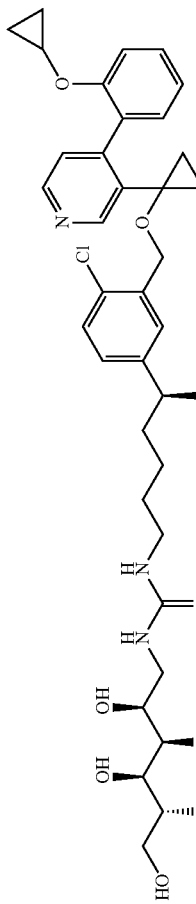 | 698.35 |
| I-275 | Example 20 | 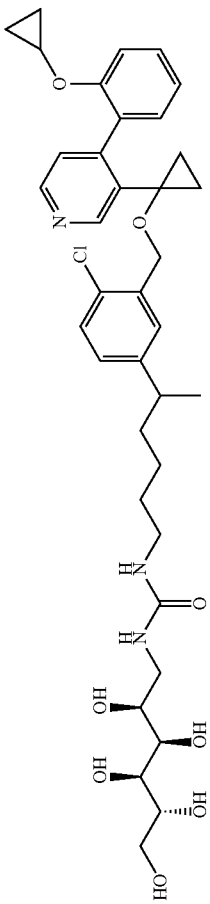 | 698.50 |
| I-276 | Example 20 | 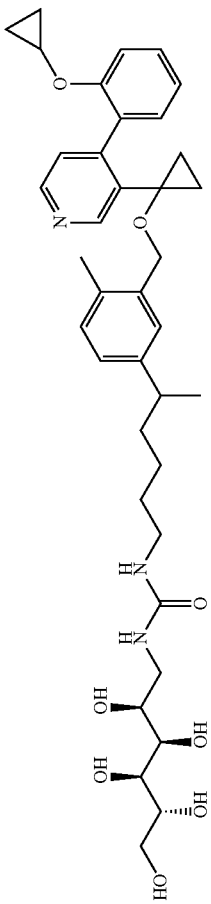 | 678.35 |

TABLE 12-continued

Compounds I-265 to I-385.

| Cmpd. No: | Synthesis Method | Compound Structure | Obs Mass |
|---|---|---|---|
| I-277 | Example 60 | 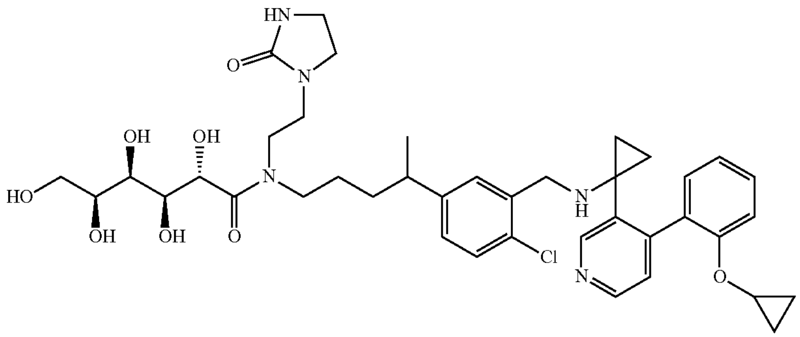 [SMILES: CC(CCCN(CCN1CCNC1=O)C(=O)[C@@H](O)[C@@H](O)[C@H](O)[C@@H](O)CO)c1ccc(Cl)c(CNC2(c3cnccc3-c3ccccc3OC3CC3)CC2)c1] | 766.5 |
| I-278 | Example 60 | 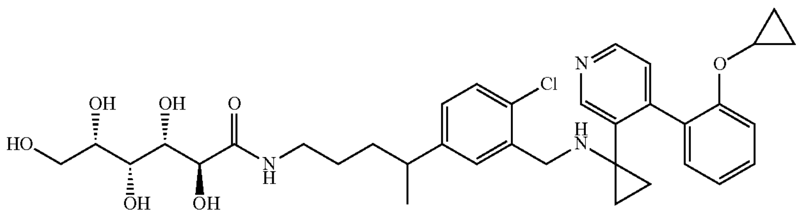 [SMILES: CC(CCCNC(=O)[C@@H](O)[C@@H](O)[C@H](O)[C@@H](O)CO)c1ccc(Cl)c(CNC2(c3cnccc3-c3ccccc3OC3CC3)CC2)c1] | 654.25 |
| I-279 | Example 60 | 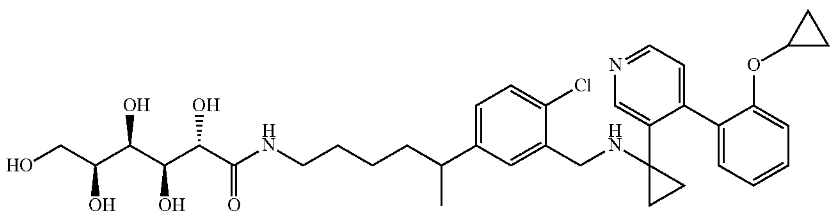 [SMILES: CC(CCCCNC(=O)[C@@H](O)[C@@H](O)[C@H](O)[C@@H](O)CO)c1ccc(Cl)c(CNC2(c3cnccc3-c3ccccc3OC3CC3)CC2)c1] | 668.35 |
| I-280 | Example 60 | 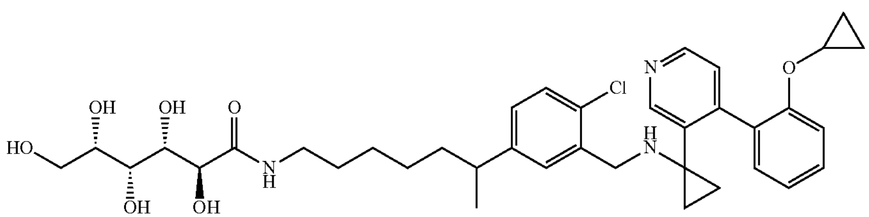 [SMILES: CC(CCCCCNC(=O)[C@@H](O)[C@@H](O)[C@H](O)[C@@H](O)CO)c1ccc(Cl)c(CNC2(c3cnccc3-c3ccccc3OC3CC3)CC2)c1] | 682.3 |

TABLE 12-continued
Compounds I-265 to I-385.
| Cmpd. No: | Synthesis Method | Compound Structure | Obs Mass |
|---|---|---|---|
| I-281 | Example 60 | 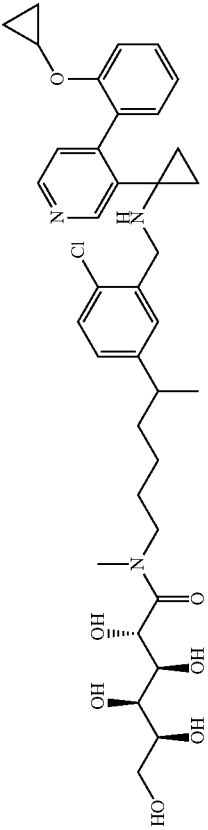 | 682.2 |
| I-282 | Example 60 | 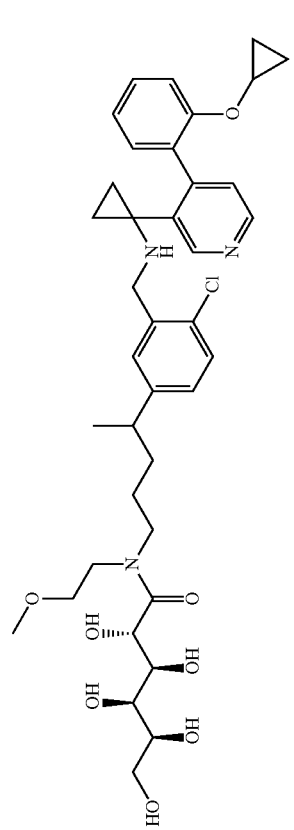 | 712.3 |
| I-283 | Example 60 | 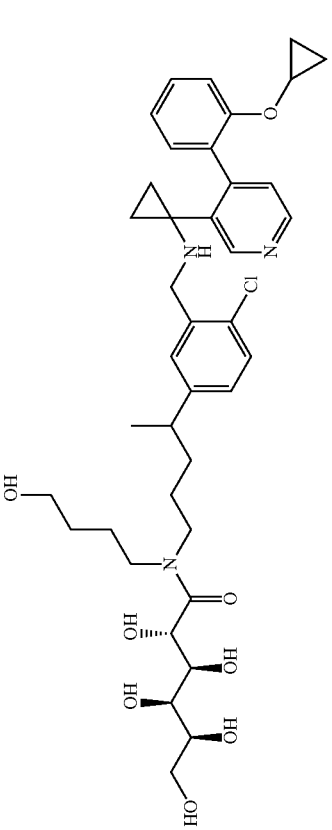 | 726.3 |

TABLE 12-continued
Compounds I-265 to I-385.
| Cmpd. No: | Synthesis Method | Compound Structure | Obs Mass |
|---|---|---|---|
| I-284 | Example 60 | 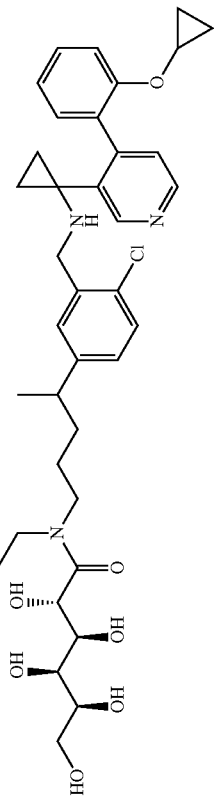 | 726.35 |
| I-285 | Example 60 | 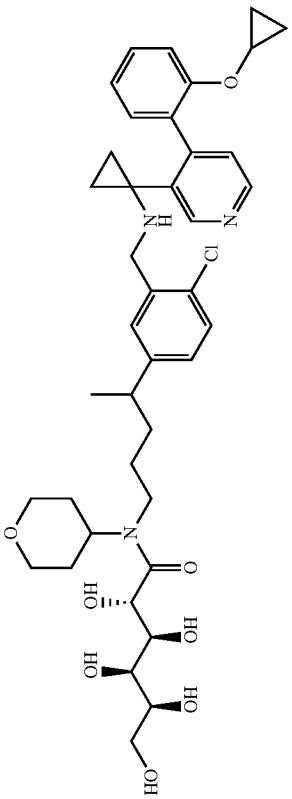 | 738.35 |
| I-286 | Example 60 | 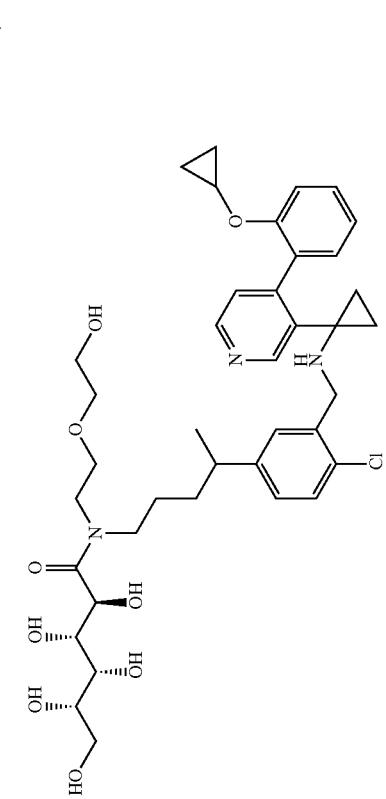 | 742.3 |

TABLE 12-continued
Compounds I-265 to I-385.
| Cmpd. No. | Synthesis Method | Compound Structure | Obs Mass |
|---|---|---|---|
| I-287 | Example 60 | 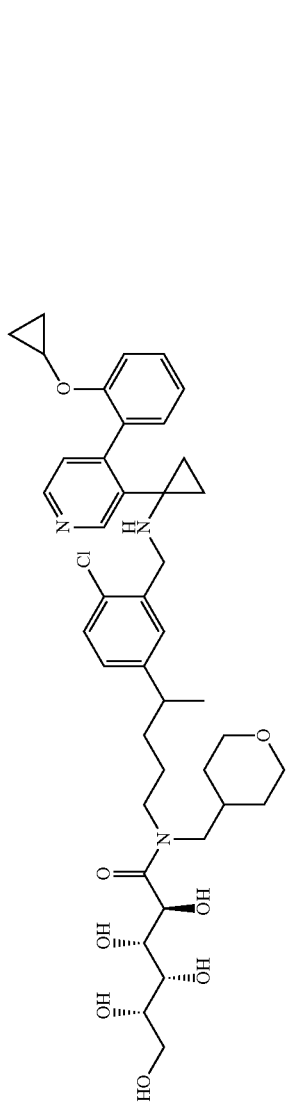 | 752.5 |
| I-288 | Example 60 | 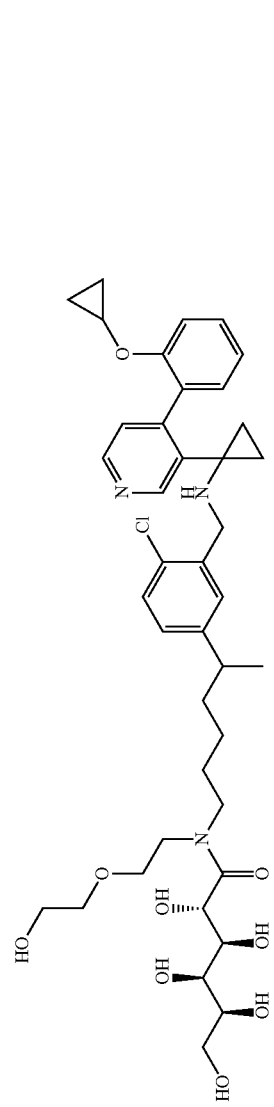 | 756.35 |
| I-289 | Example 60 | 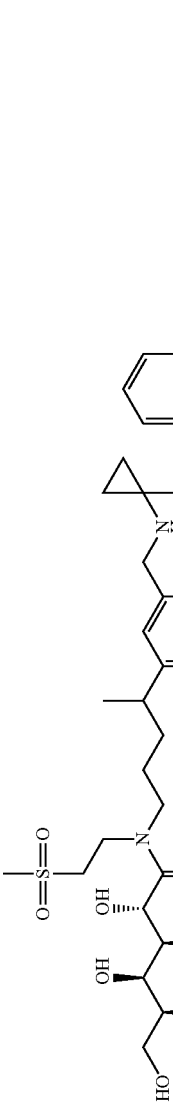 | 760.30 |

TABLE 12-continued

Compounds I-265 to I-385.

| Cmpd. No. | Synthesis Method | Compound Structure | Obs Mass |
|---|---|---|---|
| I-290 | Example 60 | 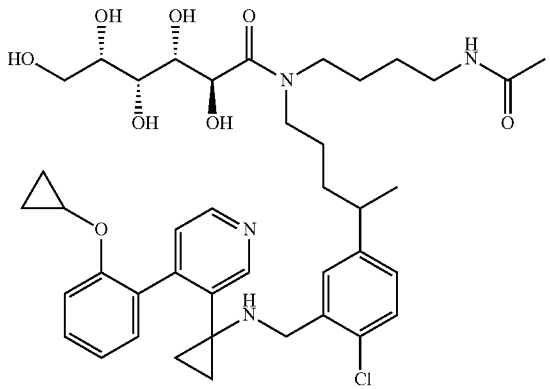 [SMILES: CC(=O)NCCCCN(CCCC(C)c1ccc(Cl)c(CNC2(c3cnccc3-c3ccccc3OC3CC3)CC2)c1)C(=O)[C@@H](O)[C@@H](O)[C@H](O)[C@@H](O)CO] | 767.35 |
| I-291 | Example 60 | 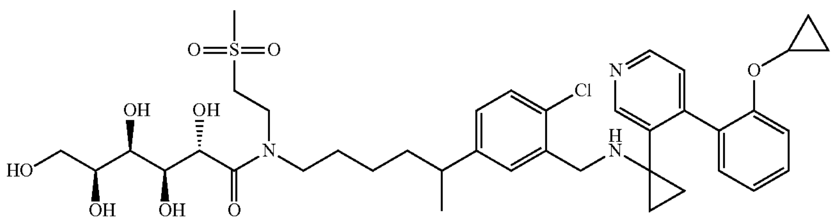 [SMILES: CC(CCCCN(CCS(C)(=O)=O)C(=O)[C@@H](O)[C@@H](O)[C@H](O)[C@@H](O)CO)c1ccc(Cl)c(CNC2(c3cnccc3-c3ccccc3OC3CC3)CC2)c1] | 774.15 |
| I-292 | Example 60 | 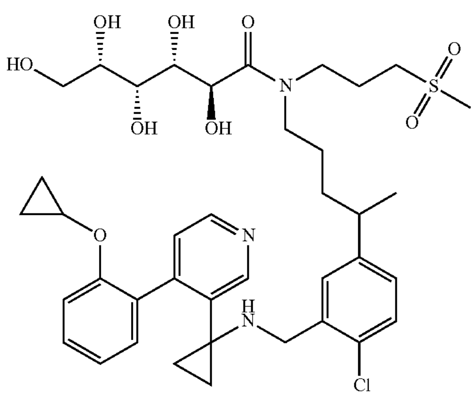 [SMILES: CC(CCCN(CCCS(C)(=O)=O)C(=O)[C@@H](O)[C@@H](O)[C@H](O)[C@@H](O)CO)c1ccc(Cl)c(CNC2(c3cnccc3-c3ccccc3OC3CC3)CC2)c1] | 774.30 |

TABLE 12-continued

Compounds I-265 to I-385.

| Cmpd. No: | Synthesis Method | Compound Structure | Obs Mass |
|---|---|---|---|
| I-293 | Example 60 | 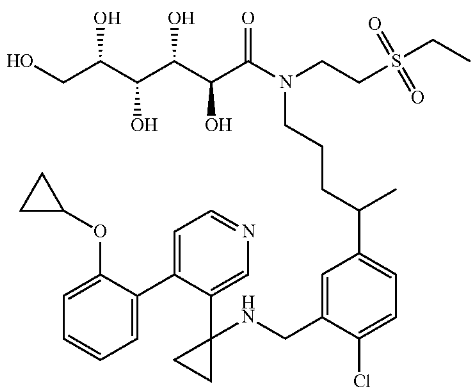 [SMILES: CCS(=O)(=O)CCN(CCCC(C)c1ccc(Cl)c(CNC2(c3cnccc3-c3ccccc3OC3CC3)CC2)c1)C(=O)[C@@H](O)[C@@H](O)[C@H](O)[C@@H](O)CO] | 774.30 |
| I-294 | Example 60 | 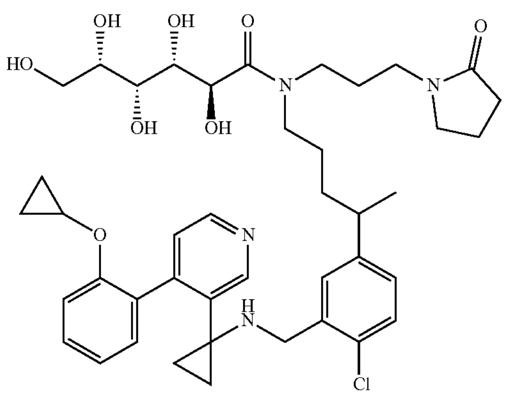 [SMILES: CC(CCCN(CCCN1CCCC1=O)C(=O)[C@@H](O)[C@@H](O)[C@H](O)[C@@H](O)CO)c1ccc(Cl)c(CNC2(c3cnccc3-c3ccccc3OC3CC3)CC2)c1] | 779.2 |

TABLE 12-continued
Compounds I-265 to I-385.
| Cmpd. No. | Synthesis Method | Compound Structure | Obs Mass |
|---|---|---|---|
| I-295 | Example 60 | 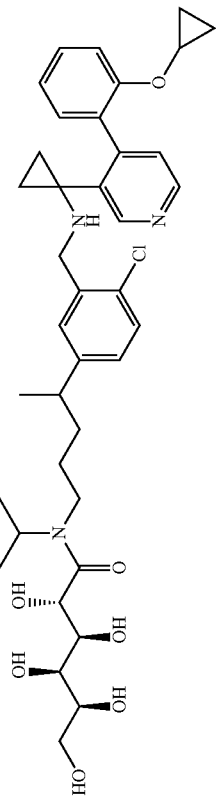 | 786.25 |
| I-296 | Example 60 | 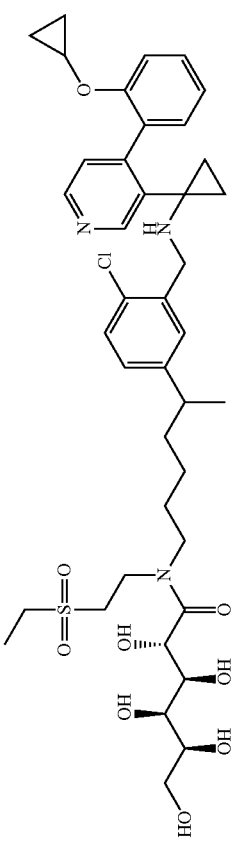 | 788.15 |
| I-297 | Example 60 | 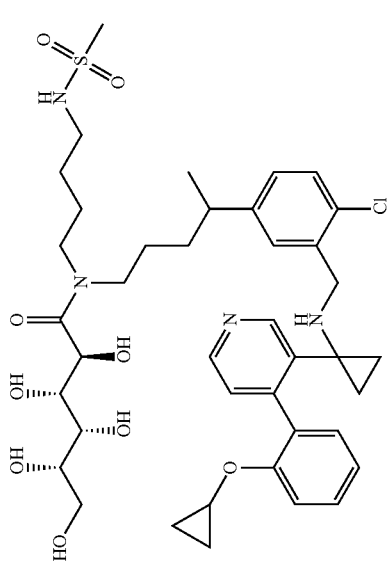 | 803.2 |

TABLE 12-continued

Compounds I-265 to I-385.

| Cmpd. No: | Synthesis Method | Compound Structure | Obs Mass |
|---|---|---|---|
| I-298 | Example 60 | 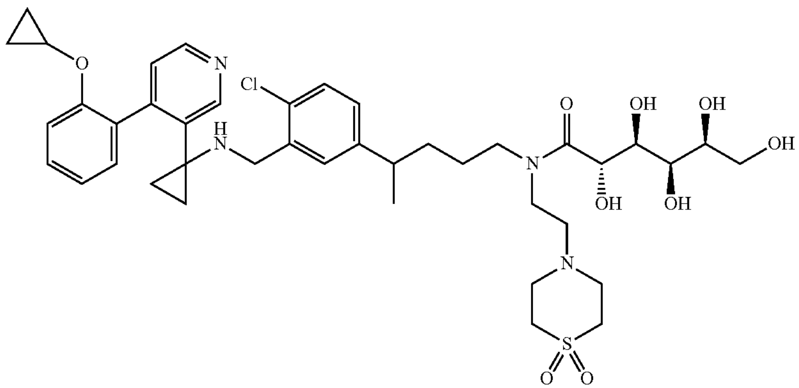 [SMILES: CC(CCCN(CCN1CCS(=O)(=O)CC1)C(=O)[C@@H](O)[C@@H](O)[C@H](O)[C@@H](O)CO)c1ccc(Cl)c(CNC2(c3cnccc3-c3ccccc3OC3CC3)CC2)c1] | 815.40 |
| I-299 | Example 60 | 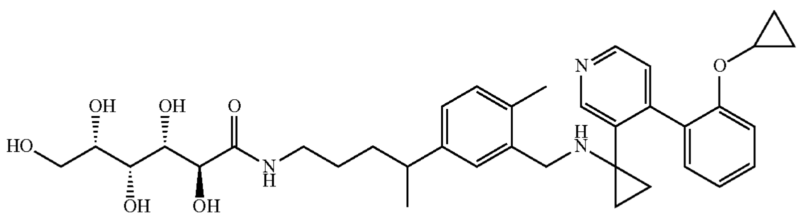 | 634.45 |
| I-300 | Example 60 | 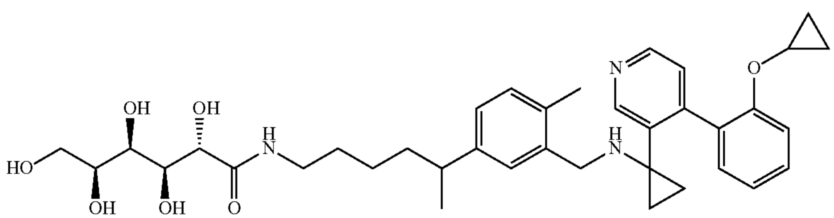 | 648.35 |

TABLE 12-continued

Compounds I-265 to I-385.

| Cmpd. No. | Synthesis Method | Compound Structure | Obs Mass |
|---|---|---|---|
| I-301 | Example 60 | 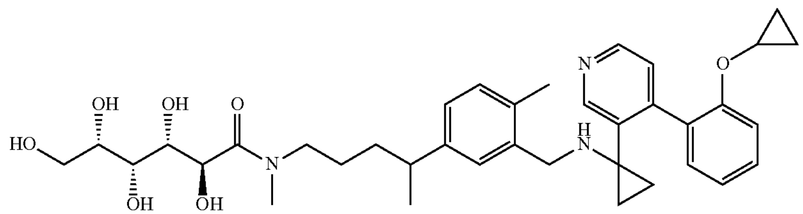 [SMILES: Cc1ccc(C(C)CCCN(C)C(=O)[C@@H](O)[C@@H](O)[C@H](O)[C@@H](O)CO)cc1CNC1(c2cnccc2-c2ccccc2OC2CC2)CC1] | 648.3 |
| I-302 | Example 60 | 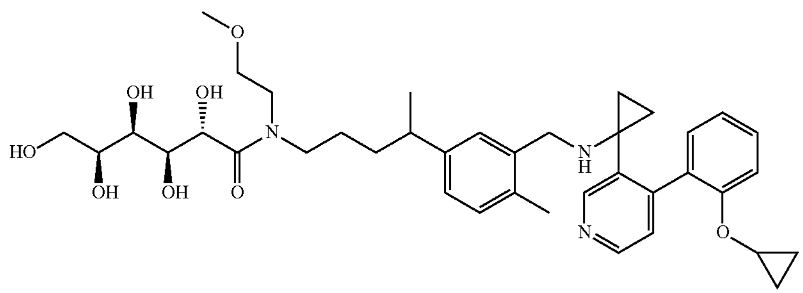 [SMILES: COCCN(CCCC(C)c1ccc(C)c(CNC2(c3cnccc3-c3ccccc3OC3CC3)CC2)c1)C(=O)[C@@H](O)[C@@H](O)[C@H](O)[C@@H](O)CO] | 692.4 |
| I-303 | Example 60 | 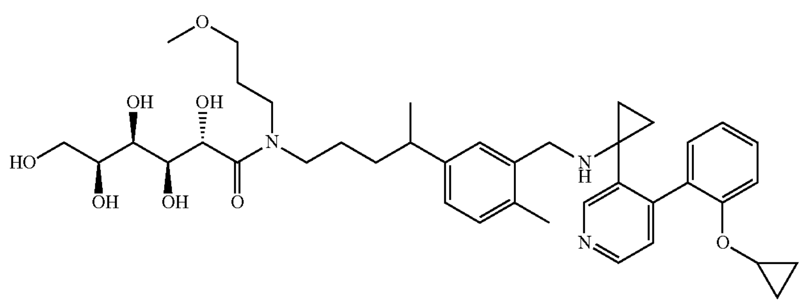 [SMILES: COCCCN(CCCC(C)c1ccc(C)c(CNC2(c3cnccc3-c3ccccc3OC3CC3)CC2)c1)C(=O)[C@@H](O)[C@@H](O)[C@H](O)[C@@H](O)CO] | 706.4 |

TABLE 12-continued
Compounds I-265 to I-385.
| Cmpd. No: | Synthesis Method | Compound Structure | Obs Mass |
|---|---|---|---|
| I-304 | Example 60 | 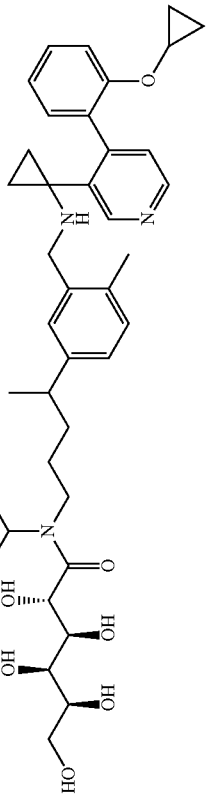 | 718.4 |
| I-305 | Example 60 | 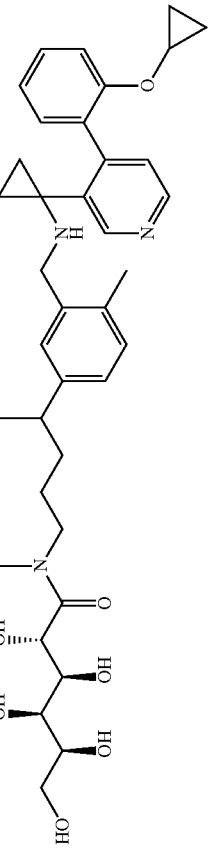 | 740.45 |
| I-306 | Example 60 | 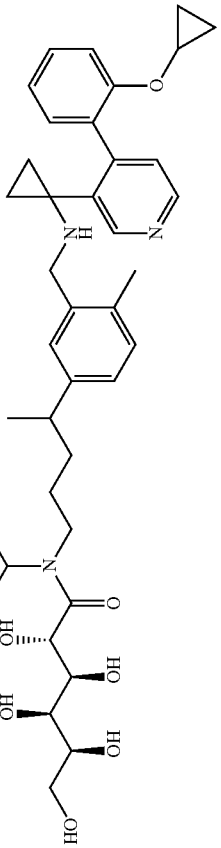 | 766.35 |

TABLE 12-continued

Compounds I-265 to I-385.

| Cmpd. No. | Synthesis Method | Compound Structure | Obs Mass |
|---|---|---|---|
| I-307 | Example 60 | 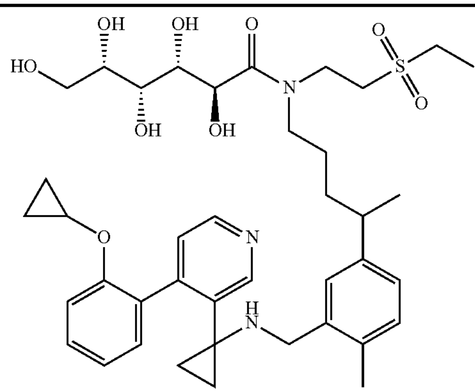 | 754.4 |
| I-308 | Example 26 | 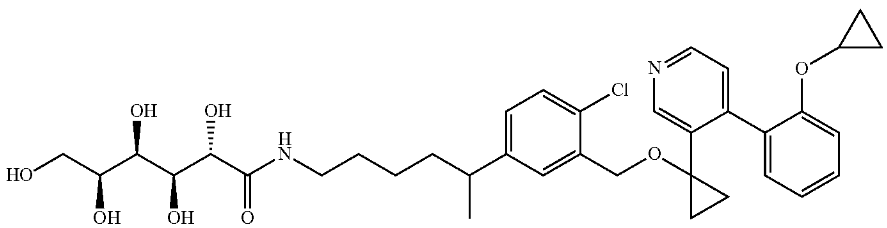 [SMILES: CC(CCCCNC(=O)[C@@H](O)[C@@H](O)[C@H](O)[C@@H](O)CO)c1ccc(Cl)c(COC2(c3cnccc3-c3ccccc3OC3CC3)CC2)c1] | 669.15 |
| I-309 | Example 26 | 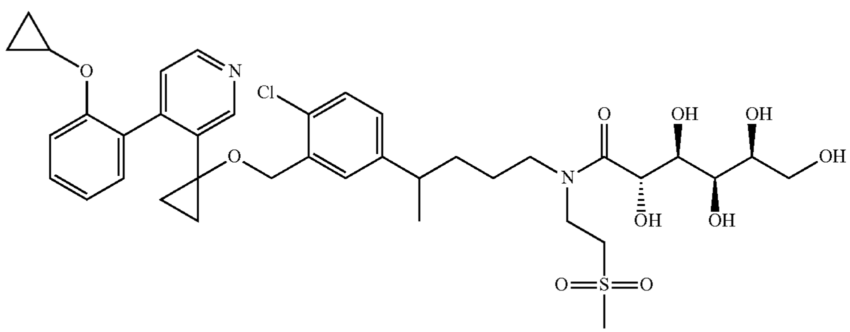 [SMILES: CC(CCCN(CCS(C)(=O)=O)C(=O)[C@@H](O)[C@@H](O)[C@H](O)[C@@H](O)CO)c1ccc(Cl)c(COC2(c3cnccc3-c3ccccc3OC3CC3)CC2)c1] | 761.3 |

TABLE 12-continued

Compounds I-265 to I-385.

| Cmpd. No: | Synthesis Method | Compound Structure | Obs Mass |
|---|---|---|---|
| I-310 | Example 26 | 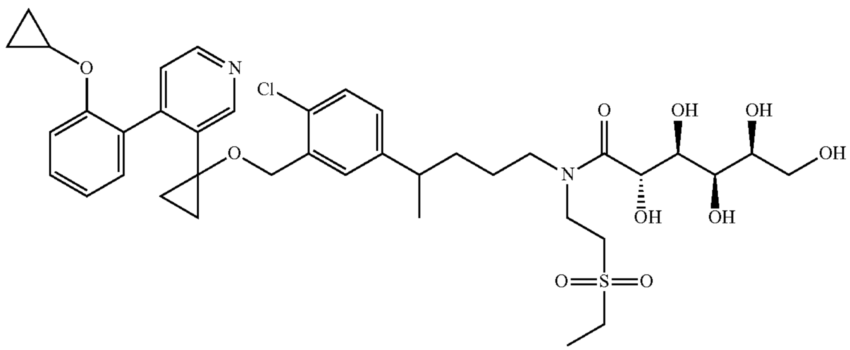 [SMILES: CCS(=O)(=O)CCN(CCCC(C)c1ccc(Cl)c(COC2(c3cnccc3-c3ccccc3OC3CC3)CC2)c1)C(=O)[C@@H](O)[C@@H](O)[C@H](O)[C@@H](O)CO] | 775.15 |
| I-311 | Example 26 | 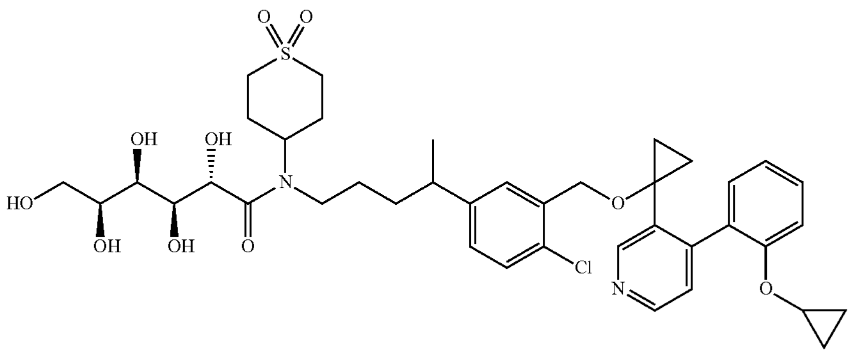 | 787.20 |
| I-312 | Example 26 | 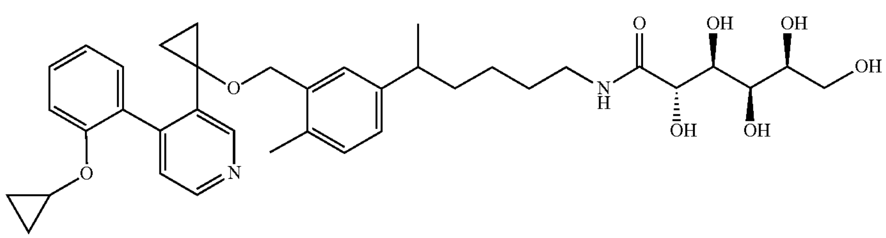 [SMILES: Cc1ccc(C(C)CCCCNC(=O)[C@@H](O)[C@@H](O)[C@H](O)[C@@H](O)CO)cc1COC1(c2cnccc2-c2ccccc2OC2CC2)CC1] | 649.30 |

TABLE 12-continued

Compounds I-265 to I-385.

| Cmpd. No. | Synthesis Method | Compound Structure | Obs Mass |
|---|---|---|---|
| I-313 | Example 63 | 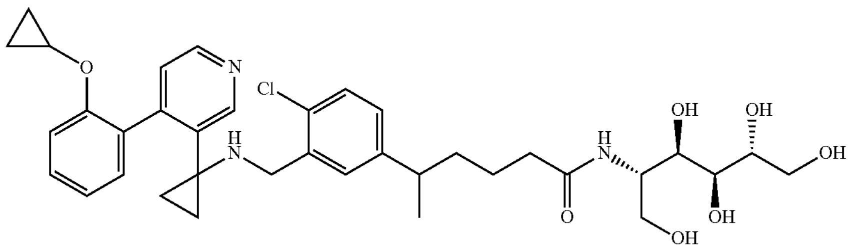 [SMILES: CC(CCCC(=O)N[C@@H](CO)[C@@H](O)[C@H](O)[C@H](O)CO)c1ccc(Cl)c(CNC2(c3cnccc3-c3ccccc3OC3CC3)CC2)c1] | 668.38 |
| I-314 | Example 59 | 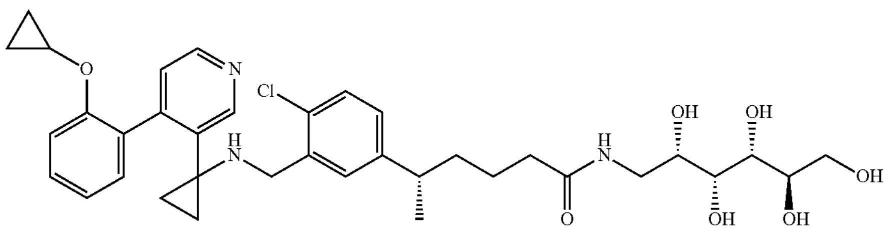 [SMILES: C[C@@H](CCCC(=O)NC[C@H](O)[C@@H](O)[C@H](O)[C@H](O)CO)c1ccc(Cl)c(CNC2(c3cnccc3-c3ccccc3OC3CC3)CC2)c1] | 668.35 |
| I-315 | Example 59 | 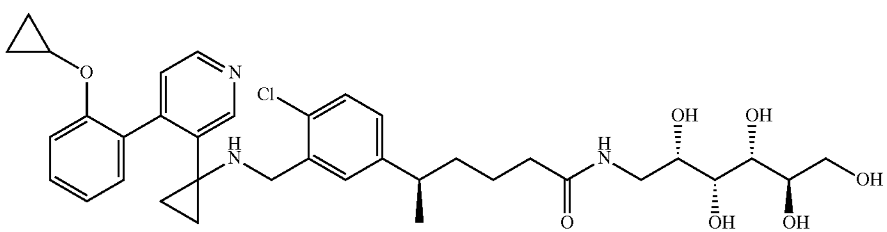 [SMILES: C[C@H](CCCC(=O)NC[C@H](O)[C@@H](O)[C@H](O)[C@H](O)CO)c1ccc(Cl)c(CNC2(c3cnccc3-c3ccccc3OC3CC3)CC2)c1] | 668.40 |
| I-316 | Example 59 | 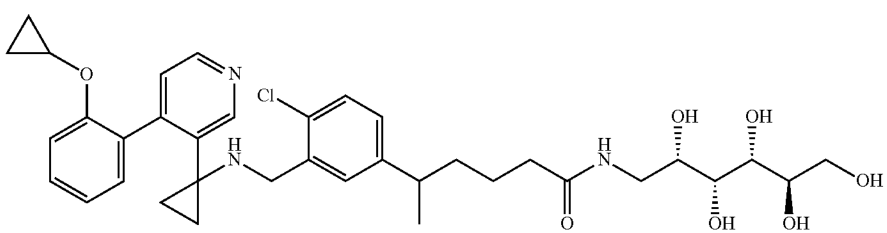 [SMILES: CC(CCCC(=O)NC[C@H](O)[C@@H](O)[C@H](O)[C@H](O)CO)c1ccc(Cl)c(CNC2(c3cnccc3-c3ccccc3OC3CC3)CC2)c1] | 668.20 |

TABLE 12-continued

Compounds I-265 to I-385.

| Cmpd. No. | Synthesis Method | Compound Structure | Obs Mass |
|---|---|---|---|
| I-317 | Example 59 | 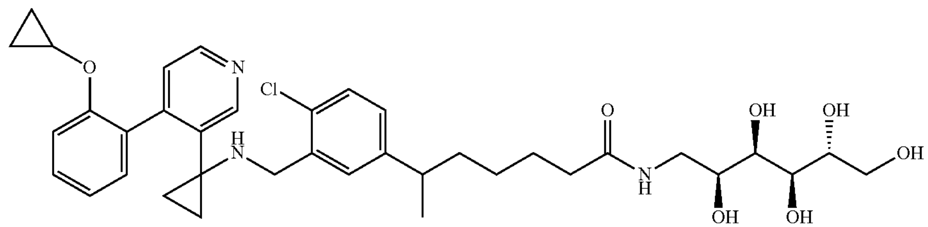 [SMILES: CC(CCCCC(=O)NC[C@H](O)[C@@H](O)[C@H](O)[C@H](O)CO)c1ccc(Cl)c(CNC2(c3cnccc3-c3ccccc3OC3CC3)CC2)c1] | 682.4 |
| I-318 | Example 33 | 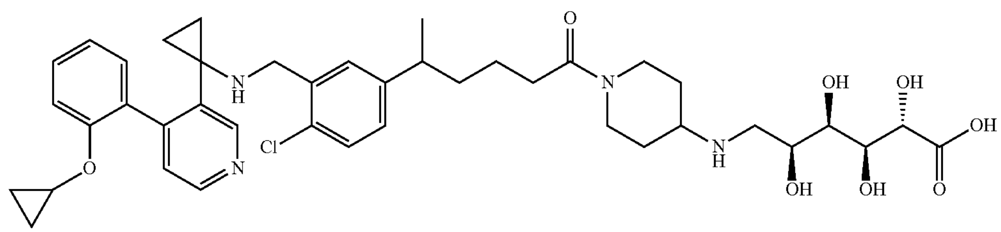 [SMILES: CC(CCCC(=O)N1CCC(NC[C@H](O)[C@@H](O)[C@H](O)[C@H](O)C(=O)O)CC1)c1ccc(Cl)c(CNC2(c3cnccc3-c3ccccc3OC3CC3)CC2)c1] | 765.3 |
| I-319 | Example 63 | 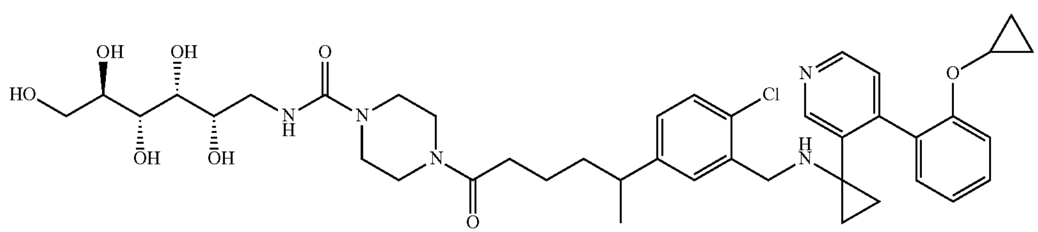 [SMILES: CC(CCCC(=O)N1CCN(C(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 780.39 |
| I-320 | Example 63 | 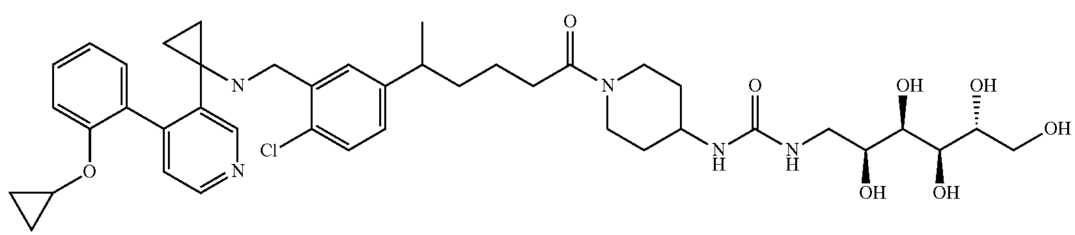 [SMILES: CC(CCCC(=O)N1CCC(NC(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 794.37 |

TABLE 12-continued

Compounds I-265 to I-385.

| Cmpd. No. | Synthesis Method | Compound Structure | Obs Mass |
|---|---|---|---|
| I-321 | Example 30 | 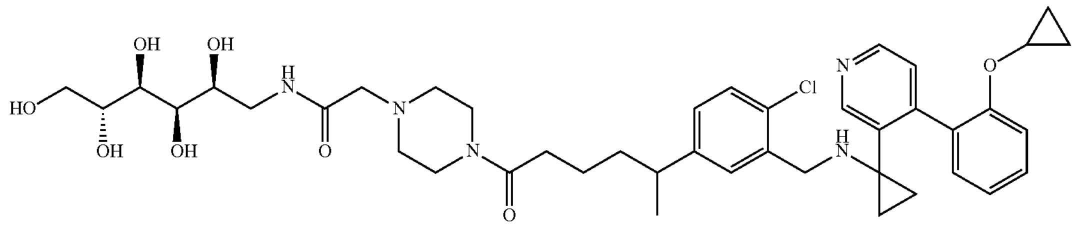 [SMILES: CC(CCCC(=O)N1CCN(CC(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 794.37 |
| I-322 | Example 63 | 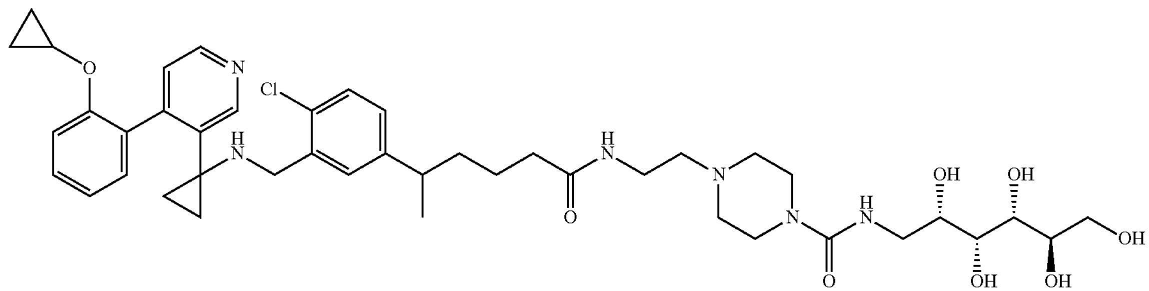 [SMILES: CC(CCCC(=O)NCCN1CCN(C(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 823.25 |
| I-323 | Example 63 | 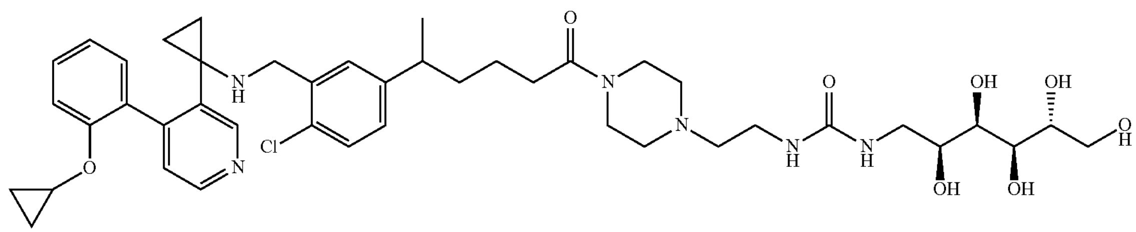 [SMILES: CC(CCCC(=O)N1CCN(CCNC(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 823.25 |

TABLE 12-continued

Compounds I-265 to I-385.

| Cmpd. No. | Synthesis Method | Compound Structure | Obs Mass |
|---|---|---|---|
| I-324 | Example 30 | 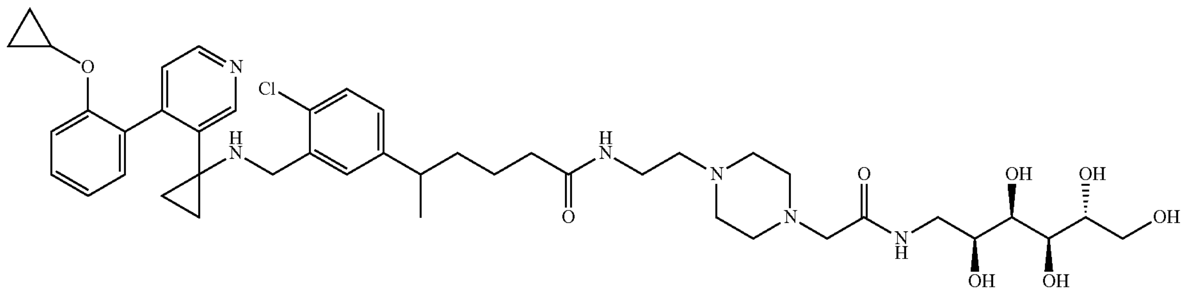 [SMILES: CC(CCCC(=O)NCCN1CCN(CC(=O)NC[C@H](O)[C@@H](O)[C@H](O)[C@H](O)CO)CC1)c1ccc(Cl)c(CNC2(c3cnccc3-c3ccccc3OC3CC3)CC2)c1] | 837.35 |
| I-325 | Example 63 | 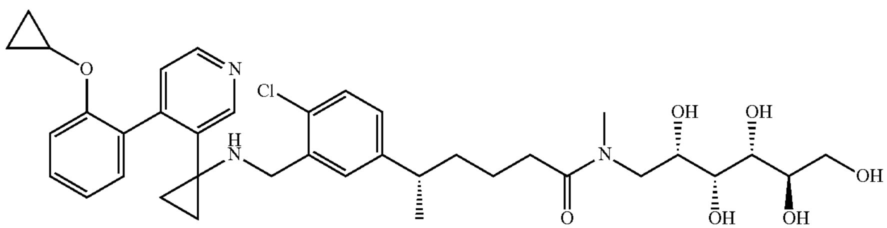 | 682.40 |
| I-326 | Example 63 | 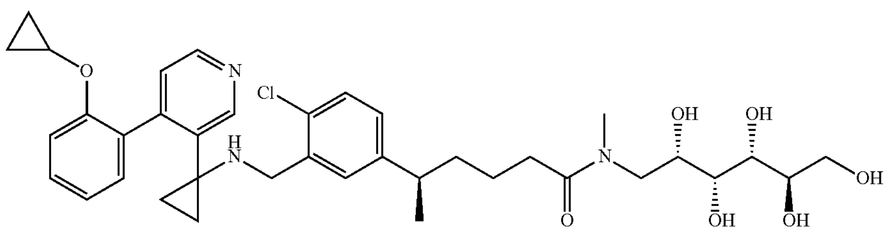 [SMILES: C[C@H](CCCC(=O)N(C)C[C@H](O)[C@@H](O)[C@H](O)[C@H](O)CO)c1ccc(Cl)c(CNC2(c3cnccc3-c3ccccc3OC3CC3)CC2)c1] | 682.4 |
| I-327 | Example 63 | 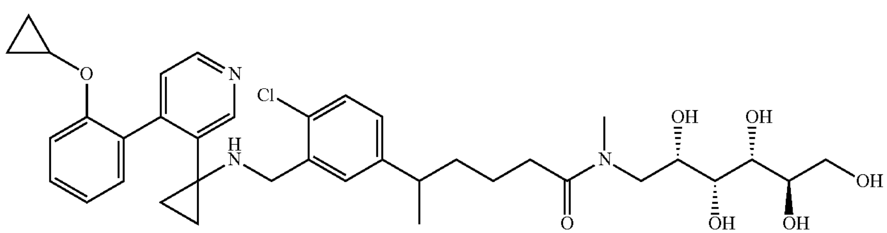 | 682.3 |

TABLE 12-continued
Compounds I-265 to I-385.
| Cmpd. No: | Synthesis Method | Compound Structure | Obs Mass |
|---|---|---|---|
| I-328 | Example 63 | 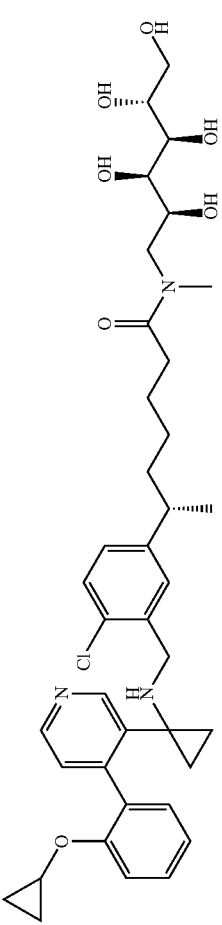 | 696.35 |
| I-329 | Example 63 | 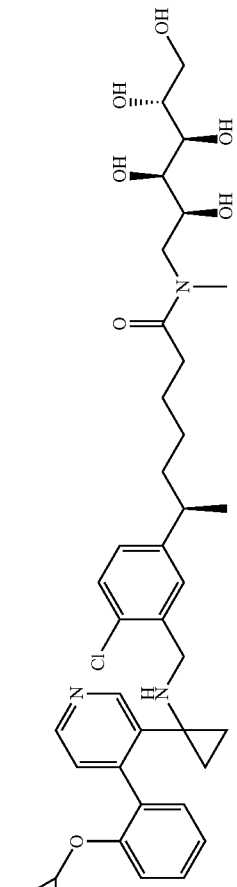 | 696.30 |
| I-330 | Example 63 | 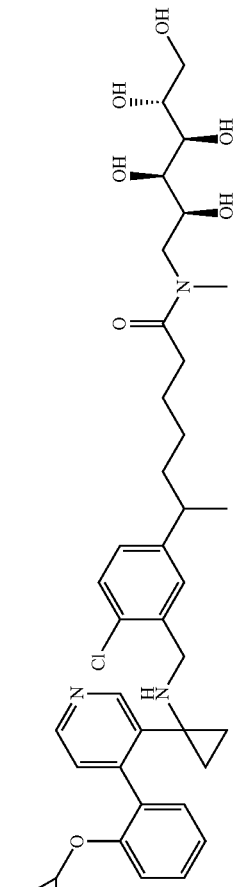 | 696.45 |
| I-331 | Example 63 | 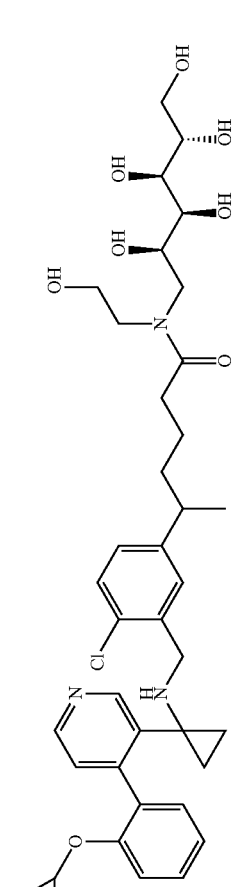 | 712.28 |

TABLE 12-continued
Compounds I-265 to I-385.
| Cmpd. No: | Synthesis Method | Compound Structure | Obs Mass |
|---|---|---|---|
| I-332 | Example 63 | 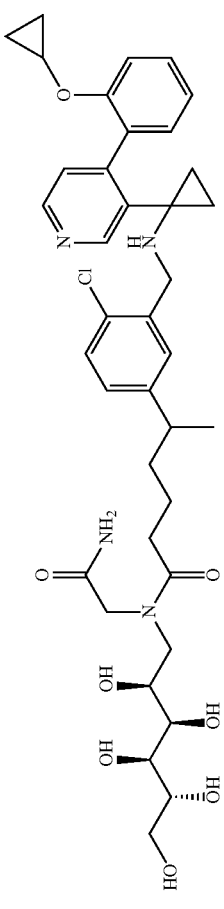 | 725.35 |
| I-333 | Example 63 | 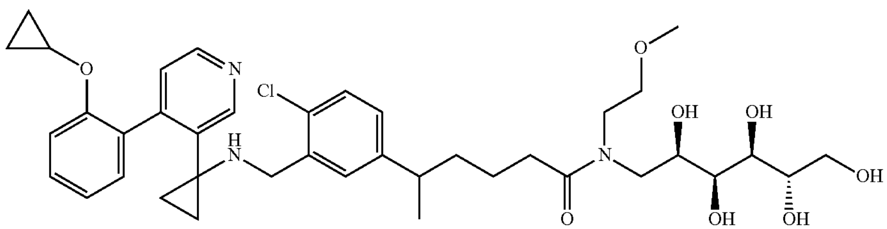 [SMILES: COCCN(C[C@@H](O)[C@H](O)[C@@H](O)[C@@H](O)CO)C(=O)CCCC(C)c1ccc(Cl)c(CNC2(c3cnccc3-c3ccccc3OC3CC3)CC2)c1] | 726.26 |
| I-334 | Example 63 | 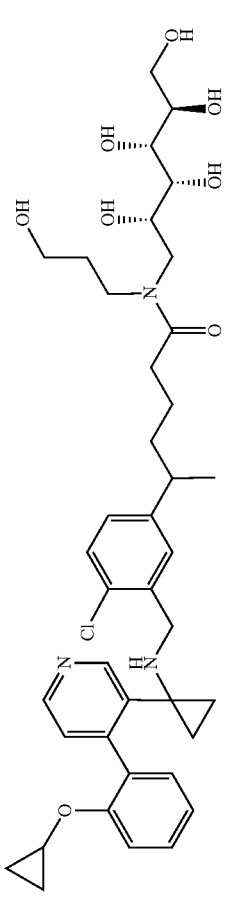 | 726.35 |
| I-335 | Example 63 | 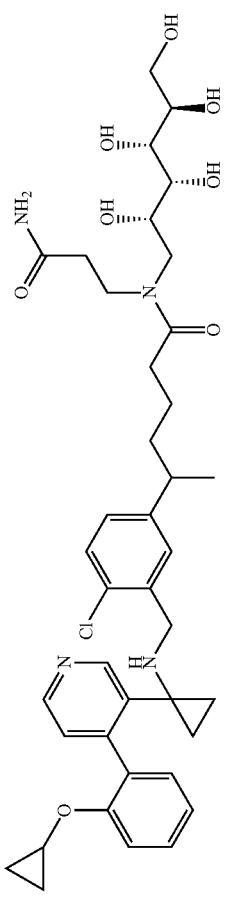 | 739.25 |

TABLE 12-continued
Compounds I-265 to I-385.
| Cmpd. No. | Synthesis Method | Compound Structure | Obs Mass |
|---|---|---|---|
| I-336 | Example 63 | 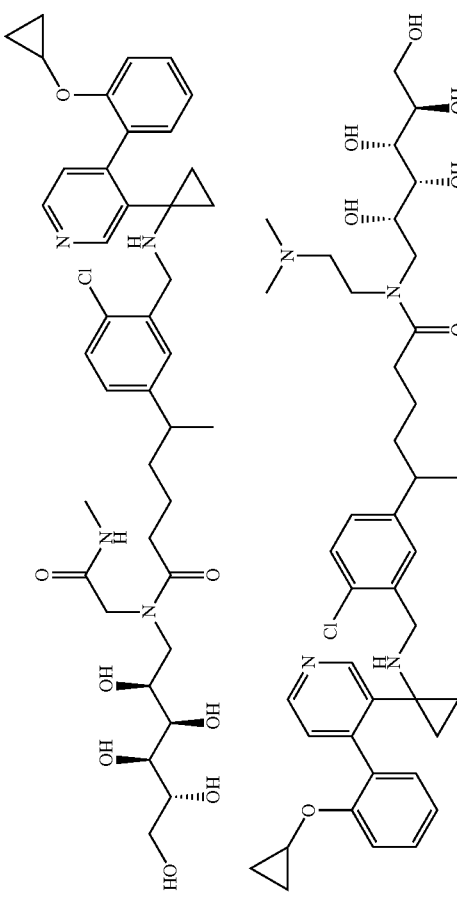 | 739.35 |
| I-337 | Example 63 | 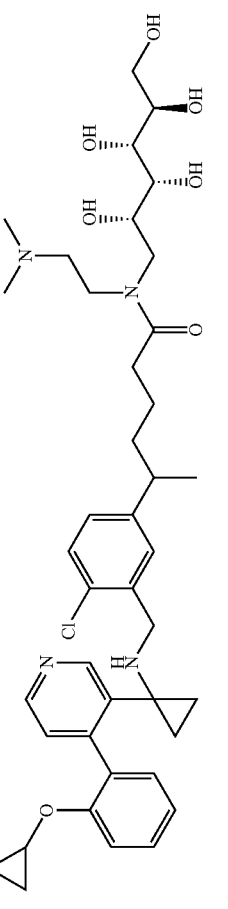 | 739.25 |
| I-338 | Example 63 | 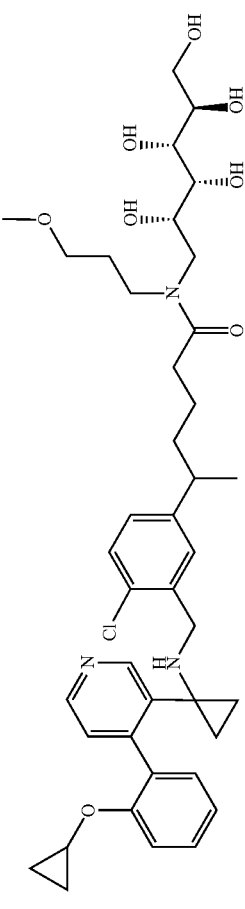 | 740.25 |
| I-339 | Example 63 | 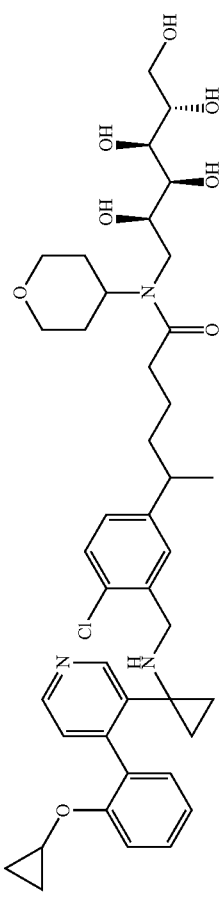 | 753.40 |

TABLE 12-continued

Compounds I-265 to I-385.

| Cmpd. No: | Synthesis Method | Compound Structure | Obs Mass |
|---|---|---|---|
| I-340 | Example 63 | 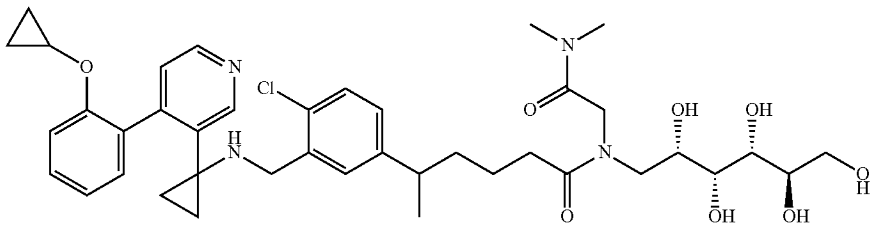 [SMILES: CC(CCCC(=O)N(CC(=O)N(C)C)C[C@H](O)[C@@H](O)[C@H](O)[C@H](O)CO)c1ccc(Cl)c(CNC2(c3cnccc3-c3ccccc3OC3CC3)CC2)c1] | 753.35 |
| I-341 | Example 63 | 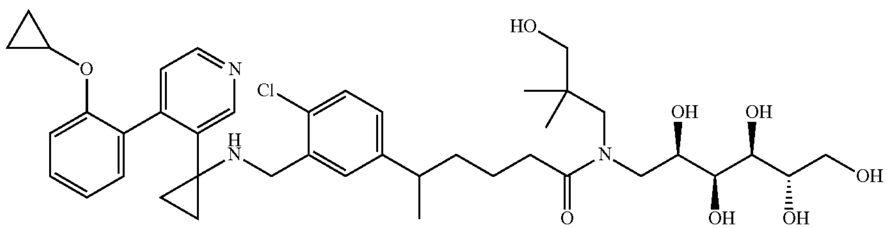 [SMILES: CC(CCCC(=O)N(C[C@@H](O)[C@H](O)[C@@H](O)[C@@H](O)CO)CC(C)(C)CO)c1ccc(Cl)c(CNC2(c3cnccc3-c3ccccc3OC3CC3)CC2)c1] | 754.22 |
| I-342 | Example 63 | 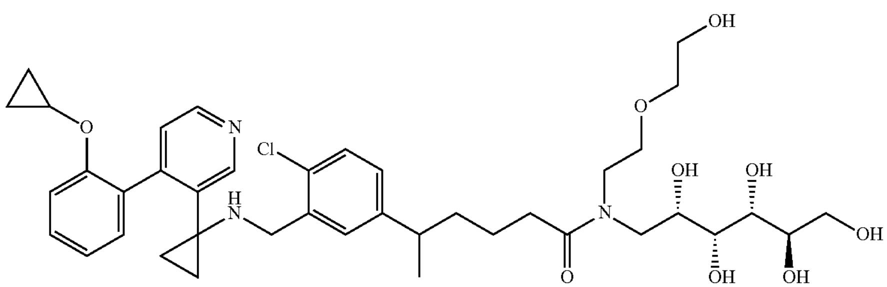 [SMILES: CC(CCCC(=O)N(CCOCCO)C[C@H](O)[C@@H](O)[C@H](O)[C@H](O)CO)c1ccc(Cl)c(CNC2(c3cnccc3-c3ccccc3OC3CC3)CC2)c1] | 756.4 |

TABLE 12-continued
Compounds I-265 to I-385.
| Cmpd. No. | Synthesis Method | Compound Structure | Obs Mass |
|---|---|---|---|
| I-343 | Example 63 | 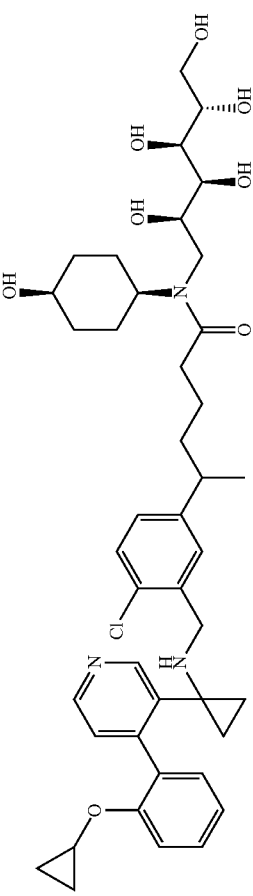 | 766.21 |
| I-344 | Example 63 | 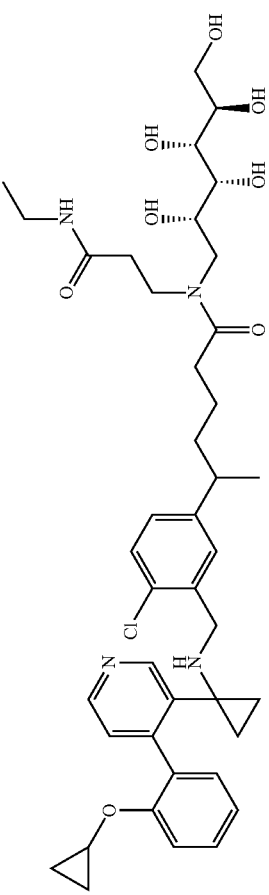 | 767.40 |
| I-345 | Example 63 | 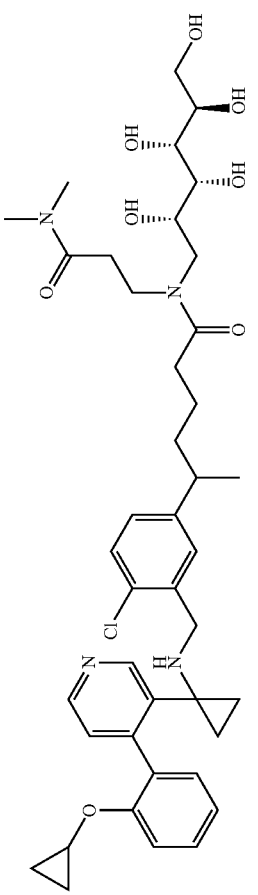 | 767.30 |

TABLE 12-continued

Compounds I-265 to I-385.

| Cmpd. No: | Synthesis Method | Compound Structure | Obs Mass |
|---|---|---|---|
| I-346 | Example 63 | 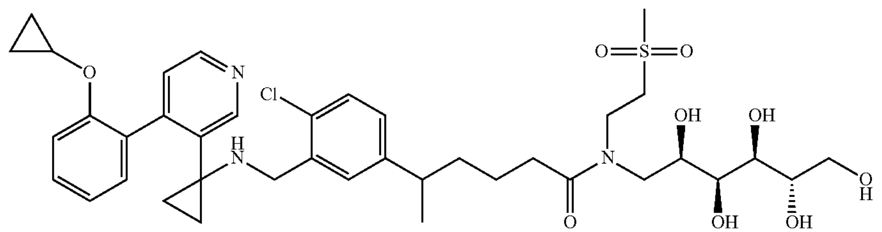 [SMILES: CC(CCCC(=O)N(CCS(C)(=O)=O)C[C@@H](O)[C@H](O)[C@@H](O)[C@@H](O)CO)c1ccc(Cl)c(CNC2(c3cnccc3-c3ccccc3OC3CC3)CC2)c1] | 774.28 |
| I-347 | Example 63 | 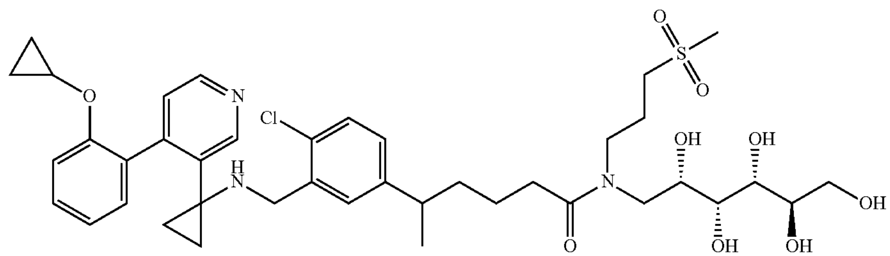 [SMILES: CC(CCCC(=O)N(CCCS(C)(=O)=O)C[C@H](O)[C@@H](O)[C@H](O)[C@H](O)CO)c1ccc(Cl)c(CNC2(c3cnccc3-c3ccccc3OC3CC3)CC2)c1] | 788.40 |
| I-348 | Example 63 | 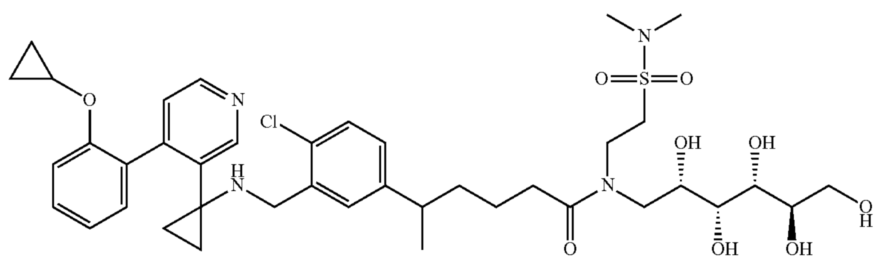 [SMILES: CC(CCCC(=O)N(CCS(=O)(=O)N(C)C)C[C@H](O)[C@@H](O)[C@H](O)[C@H](O)CO)c1ccc(Cl)c(CNC2(c3cnccc3-c3ccccc3OC3CC3)CC2)c1] | 803.3 |

TABLE 12-continued
Compounds I-265 to I-385.
| Cmpd. No. | Synthesis Method | Compound Structure | Obs Mass |
|---|---|---|---|
| I-349 | Example 59 | 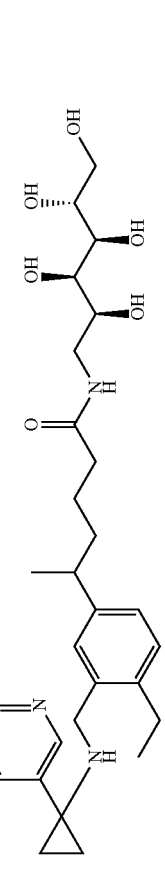 | 662.35 |
| I-350 | Example 59 | 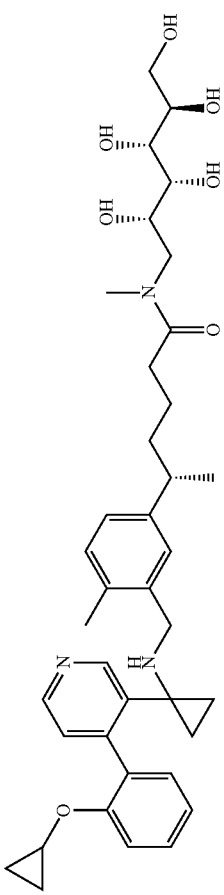 | 662.40 |
| I-351 | Example 59 | 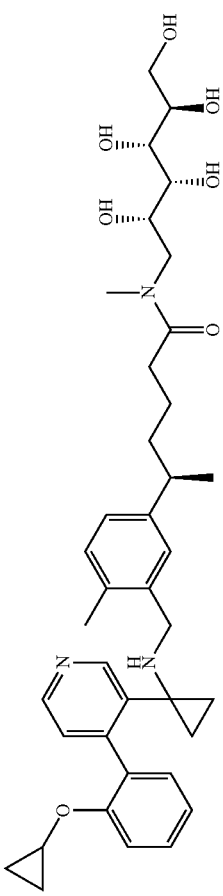 | 662.40 |

TABLE 12-continued
Compounds I-265 to I-385.
| Cmpd. No. | Synthesis Method | Compound Structure | Obs Mass |
|---|---|---|---|
| I-352 | Example 59 | 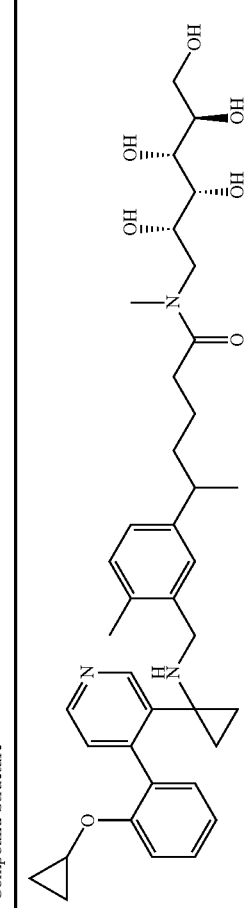 | 662.45 |
| I-353 | Example 59 | 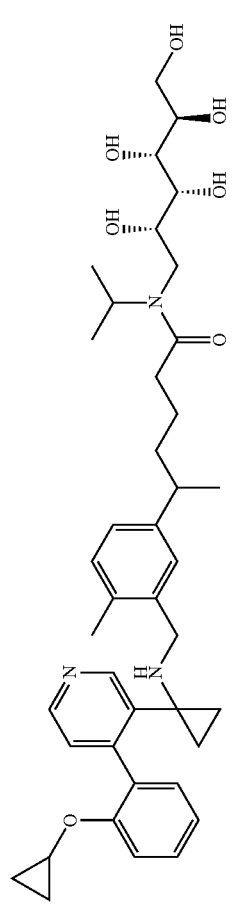 | 690.3 |
| I-354 | Example 59 | 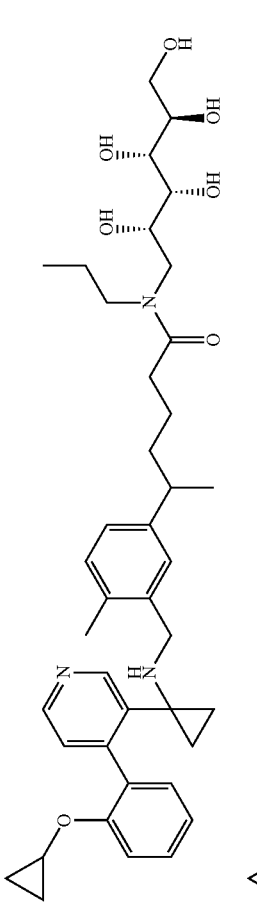 | 690.3 |
| I-355 | Example 59 | 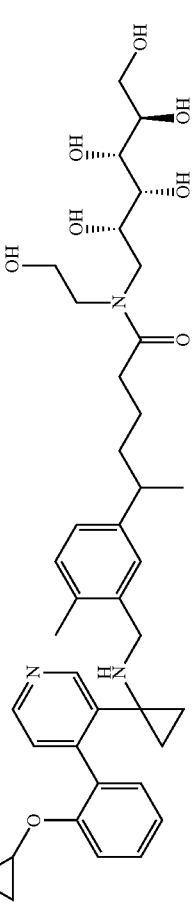 | 692.5 |

TABLE 12-continued
Compounds I-265 to I-385.
| Cmpd. No: | Synthesis Method | Compound Structure | Obs Mass |
|---|---|---|---|
| I-356 | Example 59 | 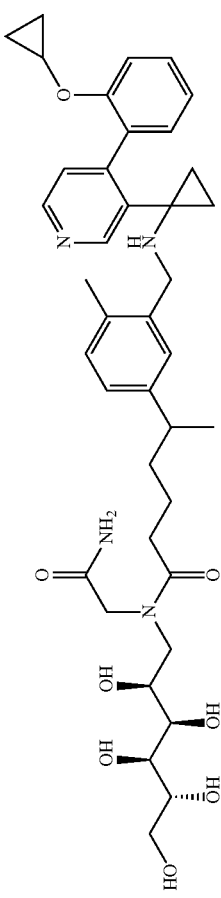 | 705.50 |
| I-357 | Example 59 | 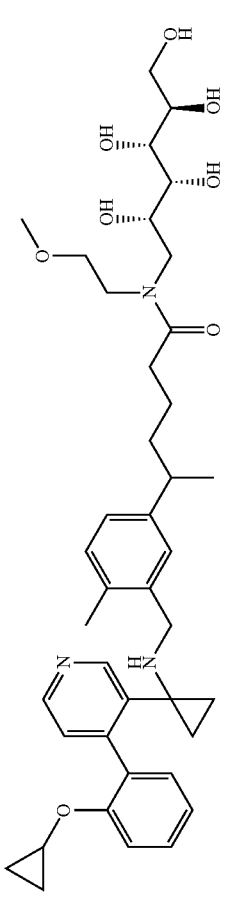 | 706.3 |
| I-358 | Example 59 | 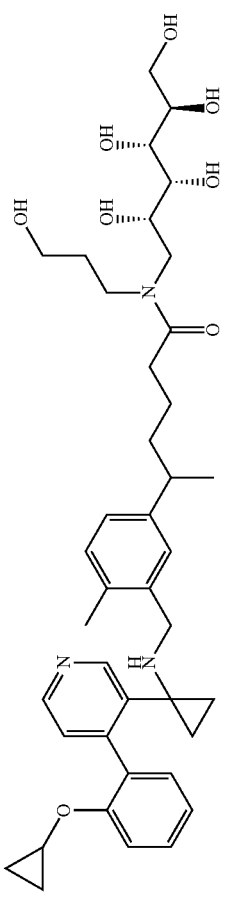 | 706.40 |
| I-359 | Example 59 | 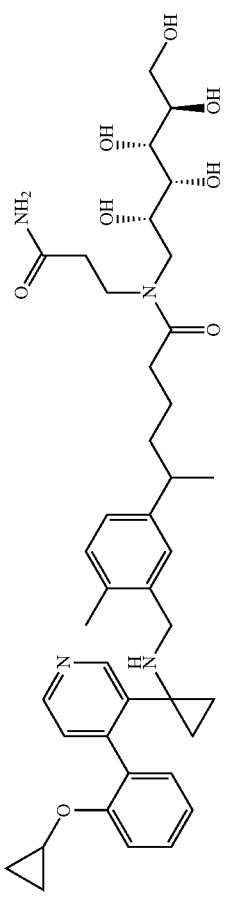 | 719.35 |

TABLE 12-continued

Compounds I-265 to I-385.

| Cmpd. No: | Synthesis Method | Compound Structure | Obs Mass |
|---|---|---|---|
| I-360 | Example 59 | 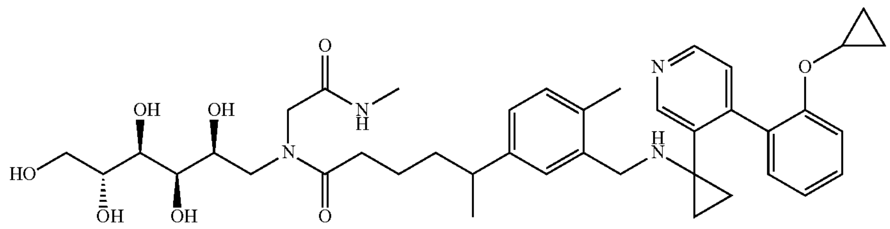 [SMILES: CNC(=O)CN(C[C@H](O)[C@@H](O)[C@H](O)[C@H](O)CO)C(=O)CCCC(C)c1ccc(C)c(CNC2(c3cnccc3-c3ccccc3OC3CC3)CC2)c1] | 719.20 |
| I-361 | Example 59 | 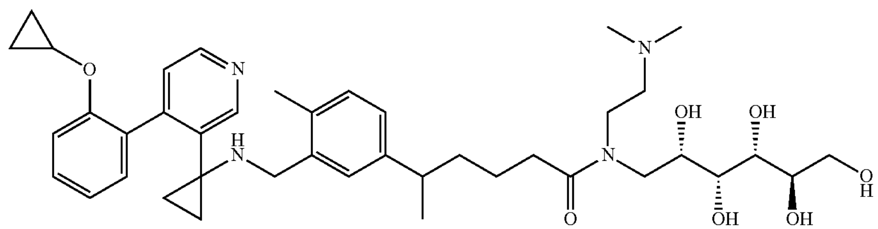 [SMILES: Cc1ccc(C(C)CCCC(=O)N(CCN(C)C)C[C@H](O)[C@@H](O)[C@H](O)[C@H](O)CO)cc1CNC1(c2cnccc2-c2ccccc2OC2CC2)CC1] | 719.40 |
| I-362 | Example 59 | 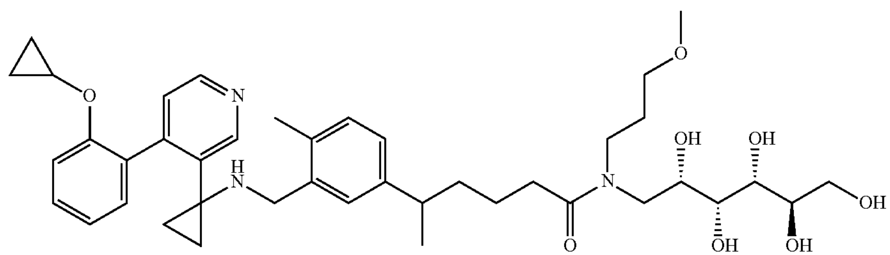 [SMILES: COCCCN(C[C@H](O)[C@@H](O)[C@H](O)[C@H](O)CO)C(=O)CCCC(C)c1ccc(C)c(CNC2(c3cnccc3-c3ccccc3OC3CC3)CC2)c1] | 720.40 |
| I-363 | Example 59 | 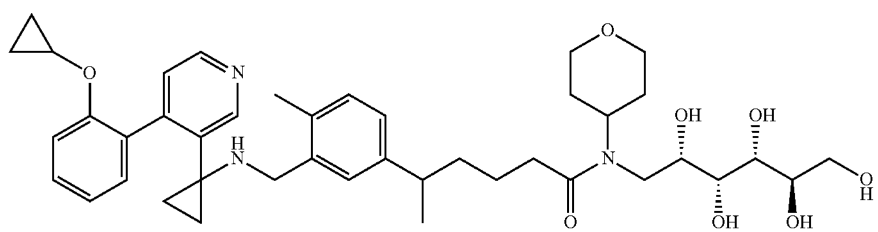 [SMILES: Cc1ccc(C(C)CCCC(=O)N(C[C@H](O)[C@@H](O)[C@H](O)[C@H](O)CO)C2CCOCC2)cc1CNC1(c2cnccc2-c2ccccc2OC2CC2)CC1] | 732.4 |

TABLE 12-continued

Compounds I-265 to I-385.

| Cmpd. No: | Synthesis Method | Compound Structure | Obs Mass |
|---|---|---|---|
| I-364 | Example 59 | 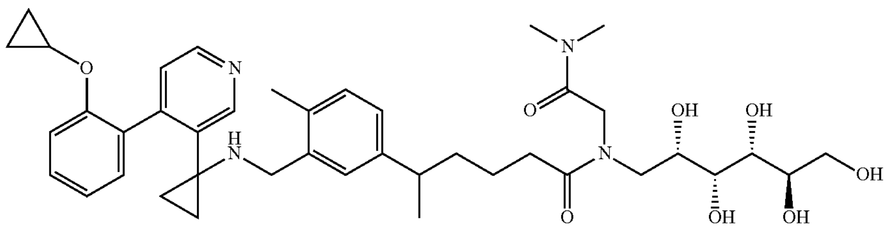 [SMILES: Cc1ccc(C(C)CCCC(=O)N(CC(=O)N(C)C)C[C@H](O)[C@@H](O)[C@H](O)[C@H](O)CO)cc1CNC1(c2cnccc2-c2ccccc2OC2CC2)CC1] | 733.35 |
| I-365 | Example 59 | 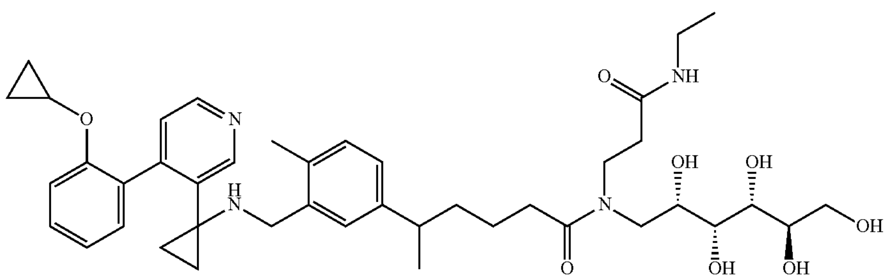 [SMILES: CCNC(=O)CCN(C[C@H](O)[C@@H](O)[C@H](O)[C@H](O)CO)C(=O)CCCC(C)c1ccc(C)c(CNC2(c3cnccc3-c3ccccc3OC3CC3)CC2)c1] | 747.40 |
| I-366 | Example 59 | 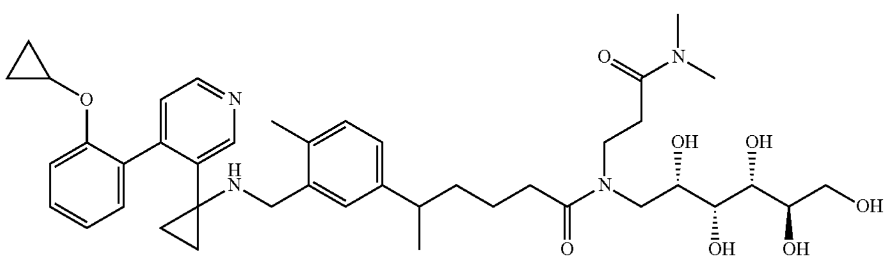 [SMILES: Cc1ccc(C(C)CCCC(=O)N(CCC(=O)N(C)C)C[C@H](O)[C@@H](O)[C@H](O)[C@H](O)CO)cc1CNC1(c2cnccc2-c2ccccc2OC2CC2)CC1] | 747.35 |
| I-367 | Example 59 | 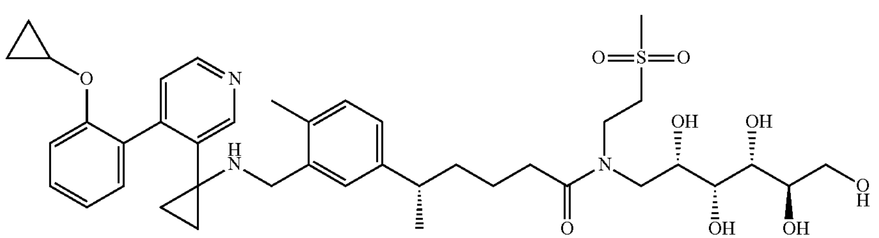 [SMILES: Cc1ccc(C(C)CCCC(=O)N(CCS(C)(=O)=O)C[C@H](O)[C@@H](O)[C@H](O)[C@H](O)CO)cc1CNC1(c2cnccc2-c2ccccc2OC2CC2)CC1] | 754.22 |

TABLE 12-continued
Compounds I-265 to I-385.
| Cmpd. No: | Synthesis Method | Compound Structure | Obs Mass |
|---|---|---|---|
| I-368 | Example 59 | 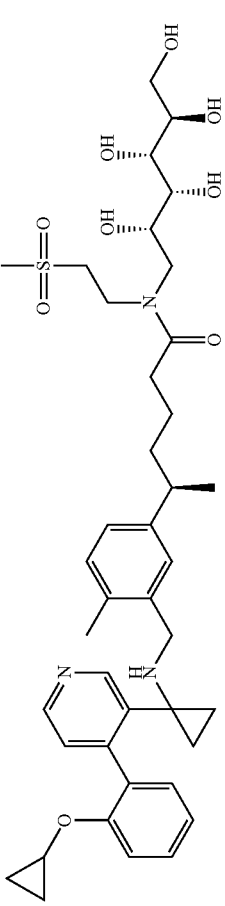 | 754.30 |
| I-369 | Example 59 | 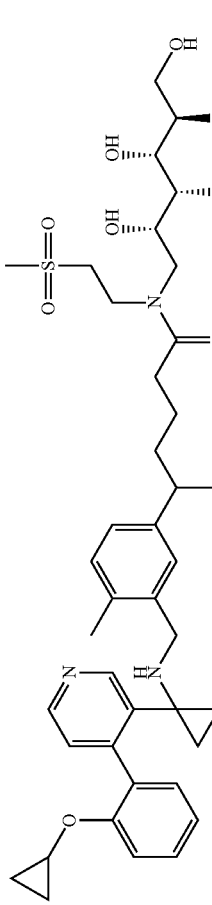 | 754.2 |
| I-370 | Example 59 | 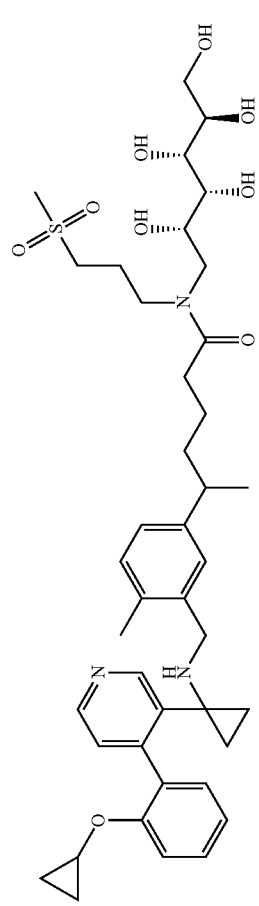 | 768.40 |
| I-371 | Example 30 | 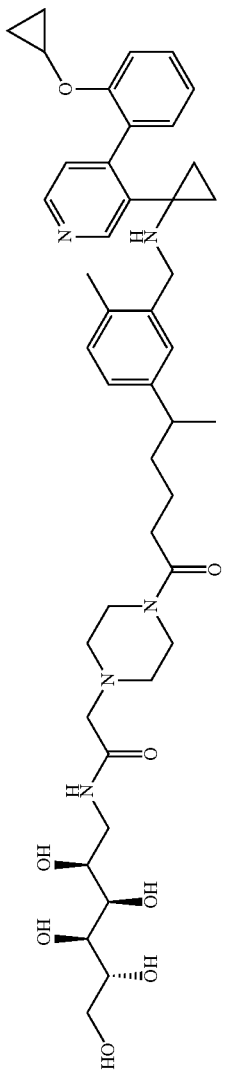 | 774.29 |

TABLE 12-continued
Compounds I-265 to I-385.
| Cmpd. No. | Synthesis Method | Compound Structure | Obs Mass |
|---|---|---|---|
| I-372 | Example 30 | 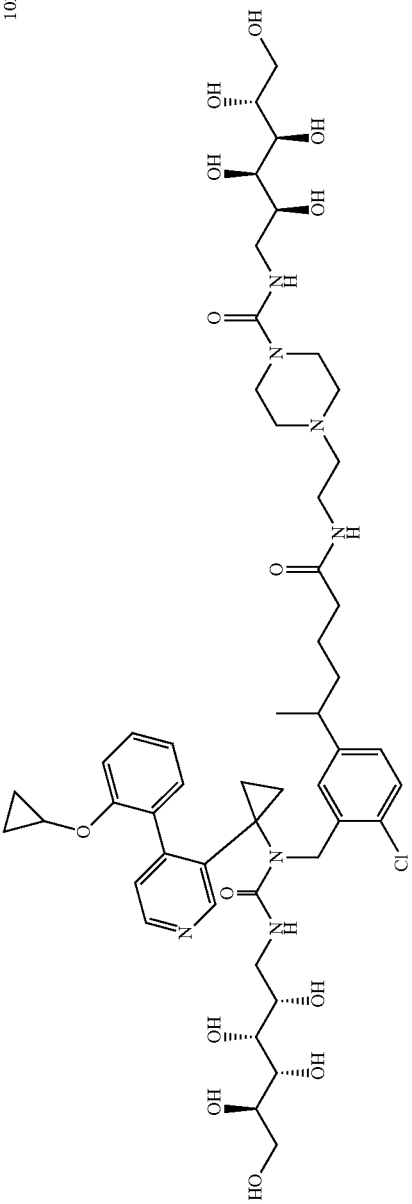 | 1030.37 |
| I-373 | Example 49 | 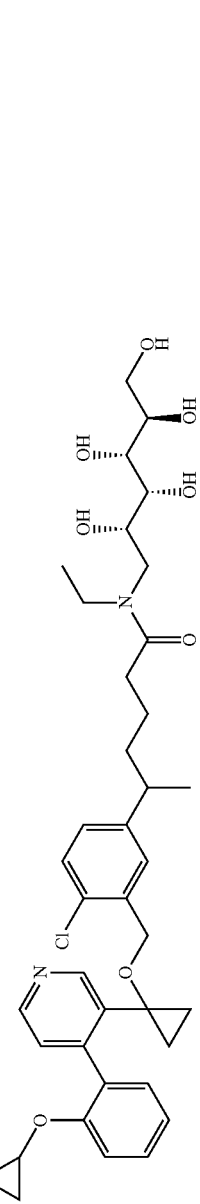 | 697.10 |
| I-374 | Example 49 | 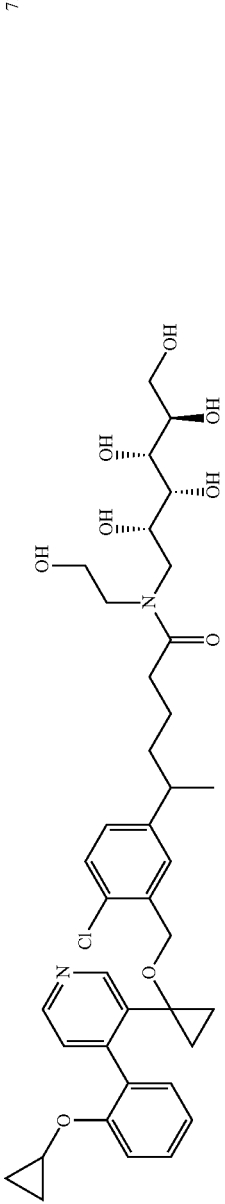 | 713.45 |

TABLE 12-continued
Compounds I-265 to I-385.
| Cmpd. No: | Synthesis Method | Compound Structure | Obs Mass |
|---|---|---|---|
| I-375 | Example 49 | 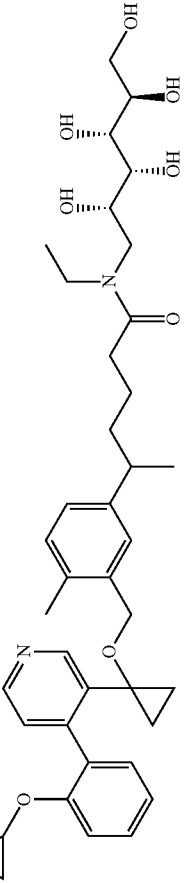 | 677.35 |
| I-376 | Example 49 | 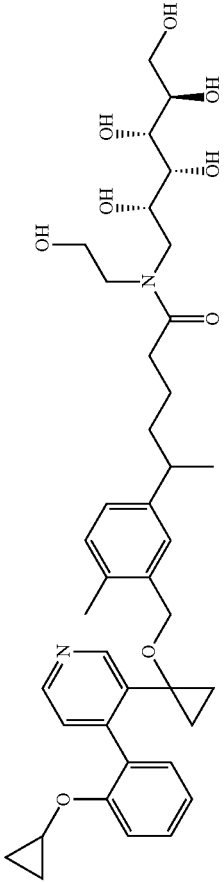 | 693.45 |
| I-377 | Example 22 | 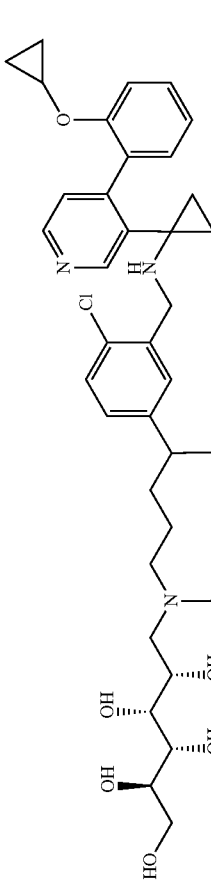 | 682.3 |
| I-378 | Example 22 | 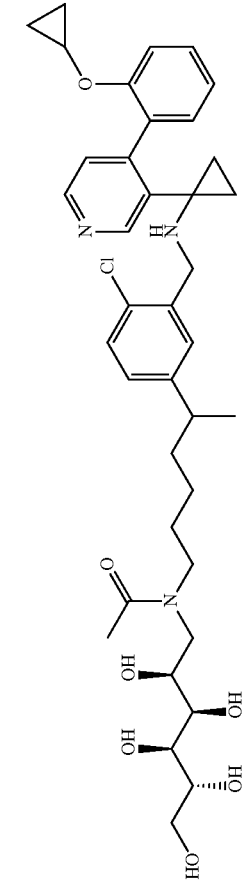 | 696.38 |

TABLE 12-continued
Compounds I-265 to I-385.
| Cmpd. No: | Synthesis Method | Compound Structure | Obs Mass |
|---|---|---|---|
| I-379 | Example 62 | 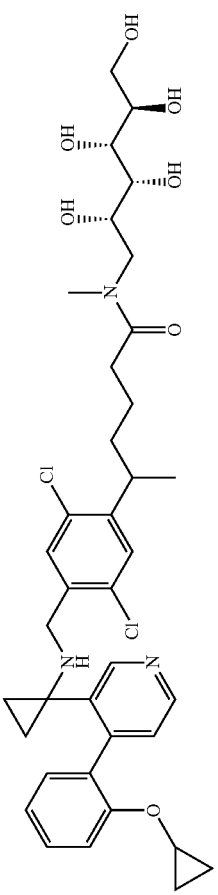 | 716.20 |

Example 67: (2S,3S,4R,5S)-N-(4-[4-chloro-3-[([1-[4-(2-cyclopropoxyphenyl)pyridin-3-yl]cyclopropyl]amino)methyl]phenyl]-5-hydroxypentyl)-2,3,4,5,6-pentahydroxyhexanamide (I-380)
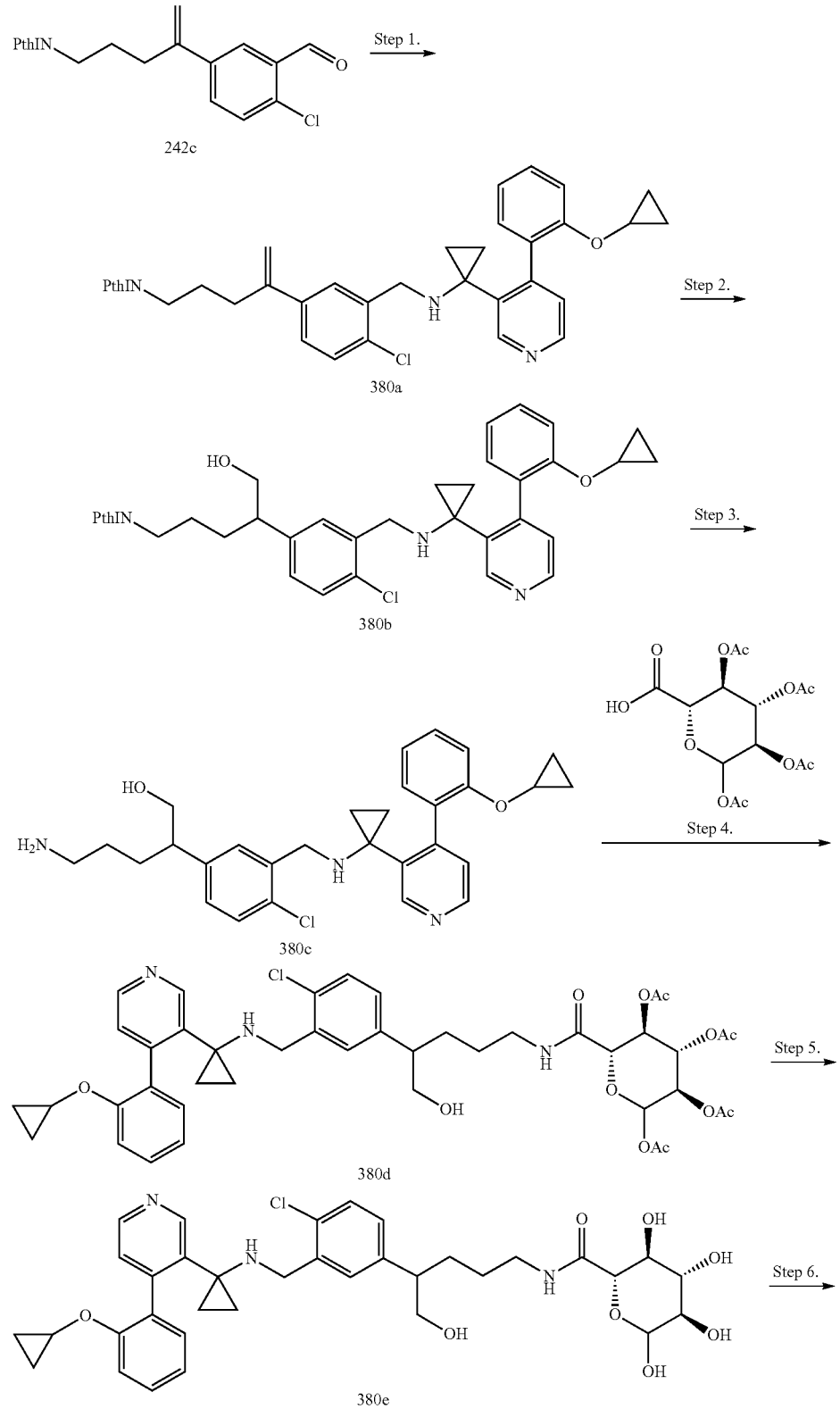

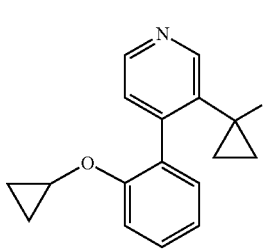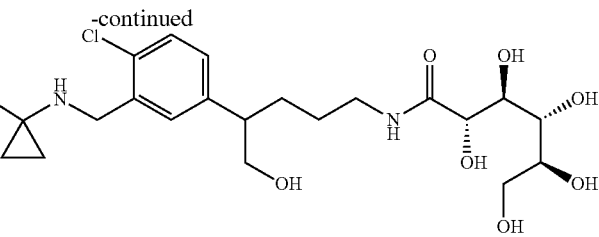

I-380

Step 1. 2-(4-[4-chloro-3-[([1-[4-(2-cyclopropoxy-phenyl)pyridin-3-yl]cyclopropyl]amino) methyl] phenyl]pent-4-en-1-yl)-2,3-dihydro-1H-isoindole-1, 3-dione (Intermediate 380a)

A 100-mL round-bottom flask was charged with 2-chloro-5-[5-(1,3-dioxo-2,3-dihydro-1H-isoindol-2-yl)pent-1-en-2-yl]benzaldehyde (242c, 1.7 g, 4.80 mmol, 1.00 equiv), 1-[4-(2-cyclopropoxyphenyl)pyridin-3-yl]cyclopropan-1-amine (1.41 g, 5.29 mmol, 1.10 equiv), dichloromethane (20 mL), NaBH(OAc)$_3$ (4.07 g, 19.20 mmol, 4.00 equiv). The resulting solution was stirred overnight at 25° C. in an oil bath. The reaction was then quenched by the addition of 100 mL of water. The resulting solution was extracted with 3×150 mL of ethyl acetate and the organic layers combined. The resulting mixture was washed with 3×150 mL of brine. The mixture was dried over anhydrous sodium sulfate. The solids were filtered out. The resulting mixture was concentrated under vacuum. The residue was applied onto a silica gel column with ethyl acetate/petroleum ether (0%-37%). The collected fractions were combined and concentrated under vacuum. This resulted in 2.8 g (96%) of 2-(4-[4-chloro-3-[([1-[4-(2-cyclopropoxyphenyl)pyridin-3-yl]cyclopropyl]amino)methyl]phenyl]pent-4-en-1-yl)-2,3-dihydro-1H-isoindole-1,3-dione (380a) as a colorless solid.

Step 2. 2-(4-[4-chloro-3-[([1-[4-(2-cyclopropoxy-phenyl)pyridin-3-yl]cyclopropyl]amino) methyl] phenyl]-5-hydroxypentyl)-2,3-dihydro-1H-isoindole-1,3-dione (Intermediate 380b)

A 100-mL 3-necked round-bottom flask purged and maintained under an inert atmosphere of nitrogen was charged with 2-(4-[4-chloro-3-[([1-[4-(2-cyclopropoxyphenyl) pyridin-3-yl]cyclopropyl]amino)methyl]phenyl]pent-4-en-1-yl)-2,3-dihydro-1H-isoindole-1,3-dione (380a, 600 mg, 0.99 mmol, 1.00 equiv), tetrahydrofuran (30 mL). This was followed by the addition of BH$_3$·Me$_2$S in tetrahydrofuran (2M) (2.48 mL, 5.00 equiv) dropwise with stirring at 0° C. in 3 min. The resulting solution was stirred overnight at room temperature. The solution was concentrated under vacuum. Tetrahydrofuran (30 mL) was added. To this was added the mixture of sodium hydroxide (2M) (3 mL) and H$_2$O$_2$ (33%) (1.5 mL) dropwise with stirring at 0° C. in 3 min. The resulting solution was stirred for 1 hour at room temperature. The reaction was then quenched by the addition of 60 mL of sat. aq. Na$_2$S$_2$O$_3$. The resulting solution was extracted with 3×100 mL of ethyl acetate and the organic layers combined. The resulting mixture was washed with 3×150 mL of brine. The mixture was dried over anhydrous sodium sulfate. The solids were filtered out. The resulting mixture was concentrated under vacuum. The residue was applied onto a silica gel column with ethyl acetate/petroleum ether (0%-37%). The collected fractions were combined and concentrated under vacuum. This resulted in 200 mg (32%) of 2-(4-[4-chloro-3-[([1-[4-(2-cyclopropoxyphenyl)pyridin-3-yl]cyclopropyl]amino)methyl]phenyl]-5-hydroxypentyl)-2,3-dihydro-1H-isoindole-1,3-dione (380b) as a white solid.

Step 3. 5-amino-2-[4-chloro-3-[([1-[4-(2-cyclo-propoxyphenyl)pyridin-3-yl]cyclopropyl]amino) methyl]phenyl]pentan-1-ol (Intermediate 380c)

A 100-mL round-bottom flask was charged with 2-(4-[4-chloro-3-[([1-[4-(2-cyclopropoxyphenyl)pyridin-3-yl]cyclopropyl]amino)methyl]phenyl]-5-hydroxypentyl)-2,3-dihydro-1H-isoindole-1,3-dione (380b, 200 mg, 0.32 mmol, 1.00 equiv), ethanol (30 mL), Hydrazine monohydrate (80 mg, 1.60 mmol, 5.00 equiv). The resulting solution was stirred for 2 days at room temperature. The solids were filtered out. The resulting mixture was concentrated under vacuum. The residue was applied onto a silica gel column with methanol/DCM (0.1% NH$_3$/H$_2$O) (0%-10%). The collected fractions were combined and concentrated under vacuum. This resulted in 160 mg (crude) of 5-amino-2-[4-chloro-3-[([1-[4-(2-cyclopropoxyphenyl) pyridin-3-yl]cyclopropyl]amino)methyl]phenyl]pentan-1-ol (380c) as light yellow oil.

Step 4. (3R,4S,5S,6S)-3,4,5-tris(acetyloxy)-6-[(4-[4-chloro-3-[([1-[4-(2-cyclopropoxyphenyl) pyridin-3-yl]cyclopropyl]amino)methyl]phenyl]-5-hydroxy-pentyl)carbamoyl]oxan-2-yl acetate (Intermediate 380d)

A 50-mL round-bottom flask was charged with 5-amino-2-[4-chloro-3-[([1-[4-(2-cyclopropoxyphenyl)pyridin-3-yl] cyclopropyl]amino)methyl]phenyl]pentan-1-ol (380c, 130 mg, 0.26 mmol, 1.00 equiv), (2S,3S,4S,5R)-3,4,5,6-tetrakis (acetyloxy)oxane-2-carboxylic acid (115 mg, 0.32 mmol, 1.20 equiv), HATU (120 mg, 0.32 mmol, 1.20 equiv), DIEA (51 mg, 0.39 mmol, 1.50 equiv), N,N-dimethylformamide (10 mL). The resulting solution was stirred overnight at room temperature. The reaction was then quenched by the addition of 40 mL of water. The resulting solution was extracted with 3×100 mL of ethyl acetate and the organic layers combined. The resulting mixture was washed with 3×150 mL of brine. The mixture was dried over anhydrous sodium sulfate. The solids were filtered out. The resulting mixture was concentrated under vacuum. The residue was applied onto a silica gel column with dichloromethane/methanol (0%-10%). The collected fractions were combined and concentrated under vacuum. This resulted in 170 mg (77%) of (3R,4S,5S,6S)-3,4,5-tris(acetyloxy)-6-[(4-[4-chloro-3-[([1-[4-(2-cyclopropoxyphenyl)pyridin-3-yl]cyclopropyl]amino)methyl]phenyl]-5-hydroxypentyl)carbamoyl]oxan-2-yl acetate (380d) as a light brown solid.

Step 5. (2S,3S,4S,5R)-N-(4-[4-chloro-3-[([1-[4-(2-cyclopropoxyphenyl)pyridin-3-yl]cyclopropyl]amino)methyl]phenyl]-5-hydroxypentyl)-3,4,5,6-tetrahydroxyoxane-2-carboxamide (Intermediate 380e)

A 50-mL round-bottom flask was charged with (3R,4S,5S,6S)-2,3,5-tris(acetyloxy)-6-[(4-[4-chloro-3-[([1-[4-(2-cyclopropoxyphenyl)pyridin-3-yl]cyclopropyl]amino)methyl]phenyl]-5-hydroxypentyl) carbamoyl]oxan-4-yl acetate (380d, 170 mg, 0.20 mmol, 1.00 equiv), methanol (10 mL), MeONa (11 mg, 0.20 mmol, 1.00 equiv). The resulting solution was stirred overnight at room temperature. The resulting mixture was concentrated under vacuum. This resulted in 70 mg (52%) of (2S,3S,4S,5R)-N-(4-[4-chloro-3-[([1-[4-(2-cyclopropoxyphenyl) pyridin-3-yl]cyclopropyl]amino)methyl]phenyl]-5-hydroxypentyl)-3,4,5,6-tetrahydroxyoxane-2-carboxamide (380e) as a light yellow solid.

Step 6. (2S,3S,4R,5S)-N-(4-[4-chloro-3-[([1-[4-(2-cyclopropoxyphenyl)pyridin-3-yl]cyclopropyl]amino)methyl]phenyl]-5-hydroxypentyl)-2,3,4,5,6-pentahydroxyhexanamide (I-380)

A 25-mL round-bottom flask was charged with (2S,3S,4S,5R)-N-(4-[4-chloro-3-[([1-[4-(2-cyclopropoxyphenyl)pyridin-3-yl]cyclopropyl]amino)methyl]phenyl]-5-hydroxypentyl)-3,4,5,6-tetrahydroxyoxane-2-carboxamide (380e, 70 mg, 0.10 mmol, 1.00 equiv), methanol (5 mL), NaBH$_4$ (8 mg, 0.21 mmol, 2.00 equiv). The resulting solution was stirred for 30 min at room temperature. The solids were filtered out. The crude product was purified by preparative HPLC with the following conditions: Column, XBridge Shield RP18 OBD Column; 5 μm 19×150 mm; mobile phase, 10 mM aqueous NH$_4$HCO$_3$ and MeCN (24.0% MeCN up to 42.0% in 6 min); Detector, UV 220 nm. This resulted in 38 mg (54%) of (2S,3S,4R,5S)-N-(4-[4-chloro-3-[([1-[4-(2-cyclopropoxyphenyl)pyridin-3-yl]cyclopropyl]amino)methyl]phenyl]-5-hydroxypentyl)-2,3,4,5,6-pentahydroxyhexanamide (I-380) as a white solid: MS (ES, m/z): 670.20 [M+H]$^+$; $^1$H NMR (Methanol-d$_4$, 400 MHz, ppm) δ 0.41-0.47 (m, 2H), 0.66 (d, J=6.5 Hz, 2H), 0.88 (d, J=32.3 Hz, 4H), 1.40 (dt, J=22.4, 11.1 Hz, 2H), 1.54 (s, 1H), 1.79-1.89 (m, 1H), 2.70 (dd, J=10.4, 5.2 Hz, 1H), 3.21 (t, J=7.0 Hz, 2H), 3.56-3.74 (m, 7H), 3.74-3.89 (m, 3H), 4.13 (d, J=5.9 Hz, 1H), 7.05-7.15 (m, 3H), 7.17-7.31 (m, 3H), 7.48 (d, J=3.6 Hz, 2H), 8.48 (d, J=5.0 Hz, 1H), 8.61 (s, 1H).

Example 68: (2S,3S,4R,5S)-N-(4-[4-chloro-3-[([1-[4-(2-cyclopropoxyphenyl)pyridin-3-yl]cyclopropyl]amino)methyl]phenyl]pent-4-en-1-yl]-2,3,4,5,6-pentahydroxyhexanamide (I-381)

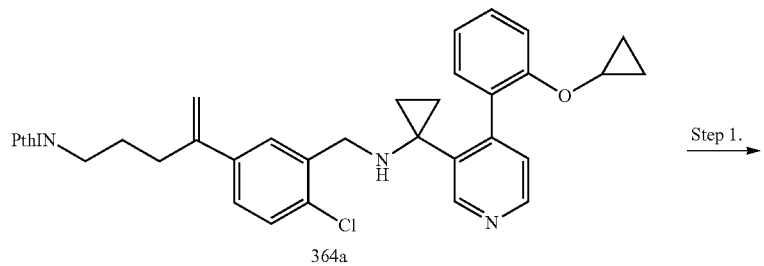

364a

Step 1.

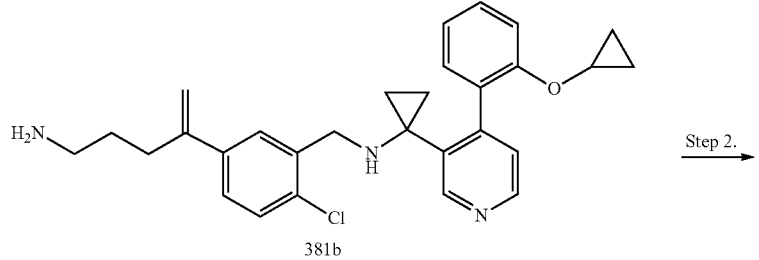

381b

Step 2.

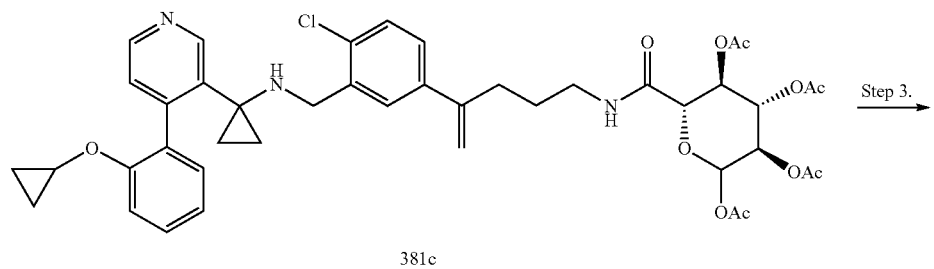

381c

Step 3.

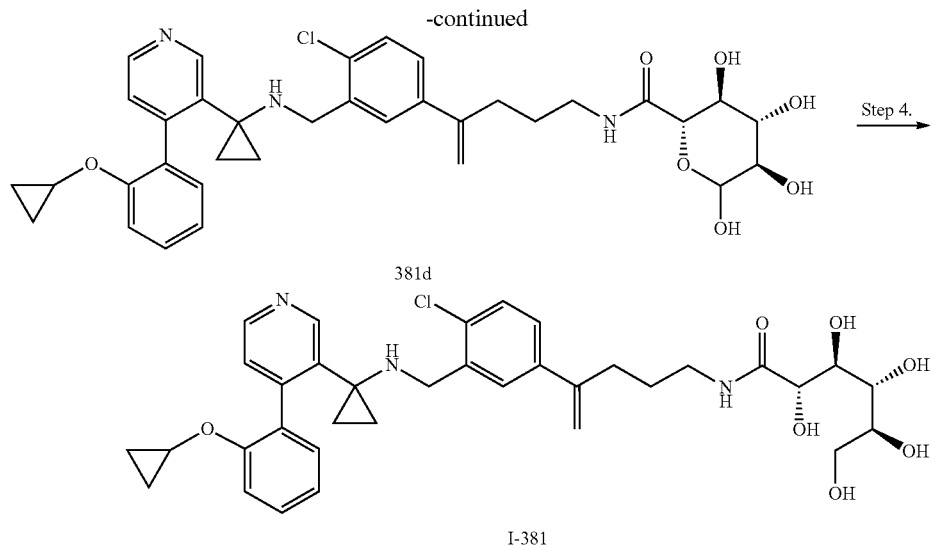

Step 1. N-[[5-(5-aminopent-1-en-2-yl)-2-chlorophenyl]methyl]-1-[4-(2-cyclopropoxyphenyl) pyridin-3-yl]cyclopropan-1-amine (Intermediate 381b)

A 100-mL round-bottom flask was charged with 2-(4-[4-chloro-3-[([1-[4-(2-cyclopropoxyphenyl)pyridin-3-yl]cyclopropyl]amino)methyl]phenyl]pent-4-en-1-yl)-2,3-dihydro-1H-isoindole-1,3-dione (364a, 500 mg, 0.83 mmol, 1.00 equiv), ethanol (30 mL) was added NH$_2$NH$_2$·H$_2$O (124 mg, 2.48 mmol, 3.00 equiv). The resulting solution was stirred for 2 days at room temperature. The solids were filtered out. The resulting mixture was concentrated under vacuum. The residue was applied onto a silica gel column with methanol/DCM (0.1% NH$_3$/H$_2$O) (0%-10%). The collected fractions were combined and concentrated under vacuum. This resulted in 330 mg (84%) of N-[[5-(5-aminopent-1-en-2-yl)-2-chlorophenyl]methyl]-1-[4-(2-cyclopropoxyphenyl)pyridin-3-yl]cyclopropan-1-amine (381b) as light yellow oil.

Step 2. (3R,4S,5S,6S)-2,3,5-tris(acetyloxy)-6-[(4-[4-chloro-3-[([1-[4-(2-cyclopropoxyphenyl) pyridin-3-yl]cyclopropyl]amino)methyl]phenyl]pent-4-en-1-yl) carbamoyl]oxan-4-yl acetate (Intermediate 381c)

A 50-mL round-bottom flask was charged with N-[[5-(5-aminopent-1-en-2-yl)-2-chlorophenyl]methyl]-1-[4-(2-cyclopropoxyphenyl)pyridin-3-yl]cyclopropan-1-amine (381b, 220 mg, 0.46 mmol, 1.00 equiv), (2S,3S,4S,5R)-3,4,5,6-tetrakis(acetyloxy)oxane-2-carboxylic acid (202 mg, 0.56 mmol, 1.20 equiv), HATU (212 mg, 0.56 mmol, 1.20 equiv), DIEA (90 mg, 0.70 mmol, 1.50 equiv), N,N-dimethylformamide (10 mL). The resulting solution was stirred overnight at room temperature. The reaction was then quenched by the addition of 50 mL of water. The resulting solution was extracted with 3×100 mL of ethyl acetate and the organic layers combined. The resulting mixture was washed with 3×150 mL of brine. The mixture was dried over anhydrous sodium sulfate. The solids were filtered out. The resulting mixture was concentrated under vacuum. The residue was applied onto a silica gel column with dichloromethane/methanol (0%-10%). The collected fractions were combined and concentrated under vacuum. This resulted in 320 mg (84%) of (3R,4S,5S,6S)-2,3,5-tris(acetyloxy)-6-[(4-[4-chloro-3-[([1-[4-(2-cyclopropoxyphenyl) pyridin-3-yl]cyclopropyl]amino)methyl]phenyl]pent-4-en-1-yl)carbamoyl]oxan-4-yl acetate (381c) as a light brown solid.

Step 3. (2S,3S,4S,5R)-N-(4-[4-chloro-3-[([1-[4-(2-cyclopropoxyphenyl)pyridin-3-yl]cyclopropyl] amino)methyl]phenyl]pent-4-en-1-yl)-3,4,5,6-tetrahydroxyoxane-2-carboxamide Intermediate (381d)

A 25-mL round-bottom flask was charged with (3R,4S,5S,6S)-3,4,5-tris(acetyloxy)-6-[(4-[4-chloro-3-[([1-[4-(2-cyclopropoxyphenyl)pyridin-3-yl]cyclopropyl]amino) methyl]phenyl]pent-4-en-1-yl)carbamoyl]oxan-2-yl acetate (281c, 320 mg, 0.39 mmol, 1.00 equiv), methanol (5 mL), MeONa (21 mg, 0.39 mmol, 1.00 equiv). The resulting solution was stirred for 1 h at 40° C. in an oil bath. The resulting mixture was concentrated under vacuum. This resulted in 254 mg (100%) of (2S,3S,4S,5R)-N-(4-[4-chloro-3-[([1-[4-(2-cyclopropoxyphenyl)pyridin-3-yl]cyclopropyl]amino)methyl]phenyl]pent-4-en-1-yl)-3,4,5,6-tetrahydroxyoxane-2-carboxamide (381d) as a light yellow solid.

Step 4. (2S,3S,4R,5S)-N-(4-[4-chloro-3-[([1-[4-(2-cyclopropoxyphenyl)pyridin-3-yl]cyclopropyl] amino)methyl]phenyl]pent-4-en-1-yl)-2,3,4,5,6-pentahydroxyhexanamide (I 381)

A 25-mL round-bottom flask was charged with (2S,3S,4S,5R)-N-(4-[4-chloro-3-[([1-[4-(2-cyclopropoxyphenyl)pyridin-3-yl]cyclopropyl]amino)methyl]phenyl]pent-4-en-1-yl)-3,4,5,6-tetrahydroxyoxane-2-carboxamide (381d, 254 mg, 0.39 mmol, 1.00 equiv), methanol (5 mL), NaBH$_4$ (30 mg, 0.79 mmol, 2.00 equiv). The resulting solution was stirred for 30 min at room temperature. The solids were filtered out. The crude product was purified by Preparative HPLC with the following conditions: Column, Gemini-NX, 5μ C18 110A, AXIA Packed 150×21.2 mm; mobile phase, 10 mM aqueous NH$_4$HCO$_3$ and MeCN (34.0% MeCN up to 54.0% in 6 min); Detector, UV 220 nm. This resulted in 88.2 mg (35%) of (2S,3S,4R,5S)-N-(4-[4-chloro-3-[([1-[4-(2-cyclopropoxyphenyl)pyridin-3-yl]cyclopropyl]amino)methyl]phenyl]pent-4-en-1-yl)-2,3,4,5,6-pentahydroxyhexanamide (I-381) as a white solid: MS (ES, m/z): 652.20 [M+H]⁺; ¹H NMR (Methanol-d₄, 300 MHz, ppm) δ 0.42 (s, 2H), 0.58-0.69 (m, 2H), 0.88 (d, J=19.0 Hz, 4H), 1.65 (p, J=7.2 Hz, 2H), 2.54 (t, J=7.7 Hz, 2H), 3.26 (t, J=7.1 Hz, 2H), 3.55-3.70 (m, 3H), 3.73 (s, 2H), 3.83 (tdd, J=11.6, 5.9, 3.4 Hz, 3H), 4.13 (t, J=5.5 Hz, 1H), 5.14 (d, J=1.7 Hz, 1H), 5.25 (d, J=1.4 Hz, 1H), 7.02-7.22 (m, 3H), 7.22-7.32 (m, 3H), 7.41-7.54 (m, 2H), 8.47 (d, J=5.0 Hz, 1H), 8.60 (s, 1H).

Example 69: (2S,3S,4R,5S)-N-[3-(1-[4-chloro-3-[([1-[4-(2-cyclopropoxyphenyl)pyridin-3-yl]cyclopropyl]amino)methyl]phenyl]cyclopropyl)propyl]-2,3,4,5,6-pentahydroxyhexanamide (I-382)

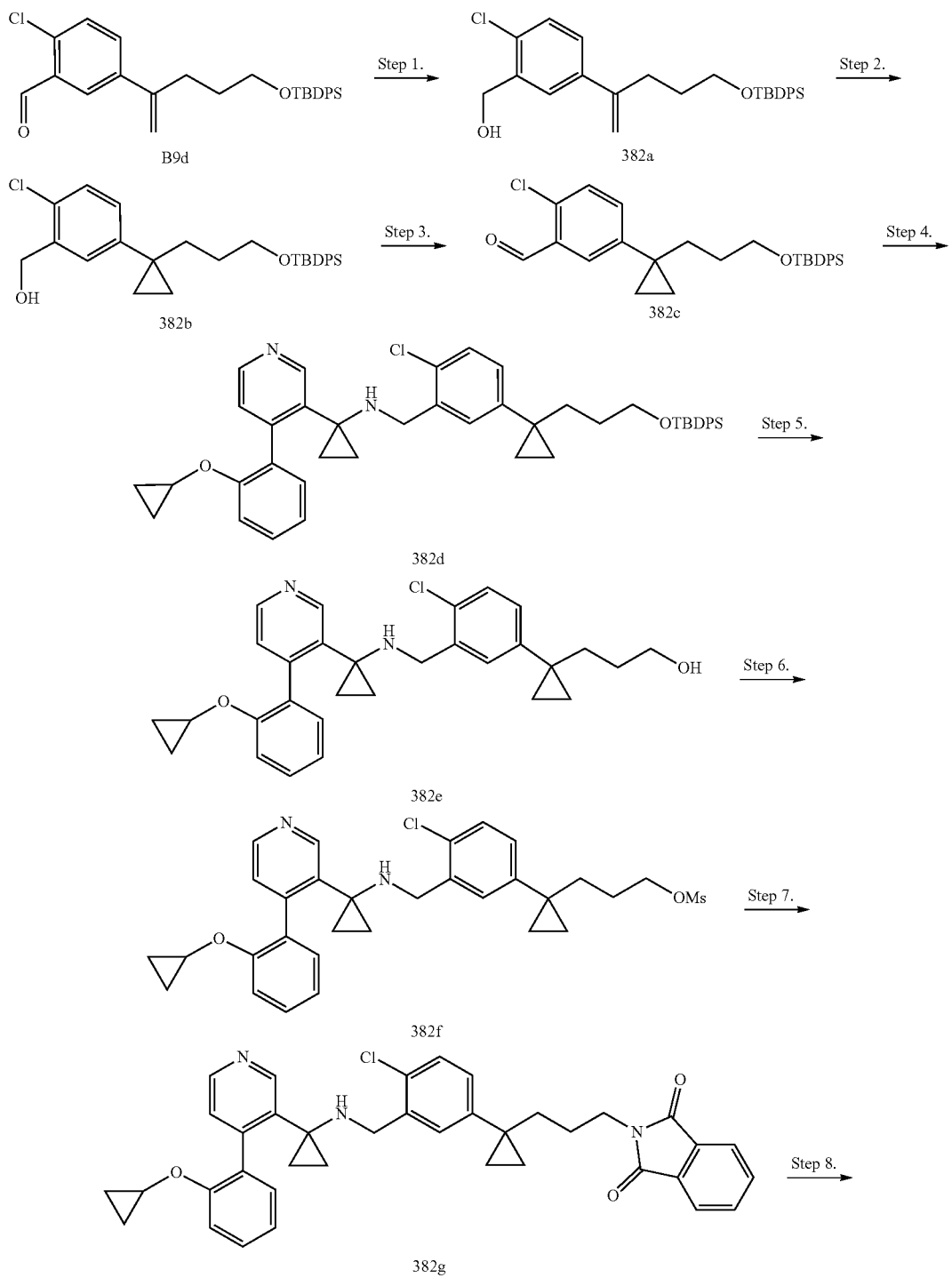

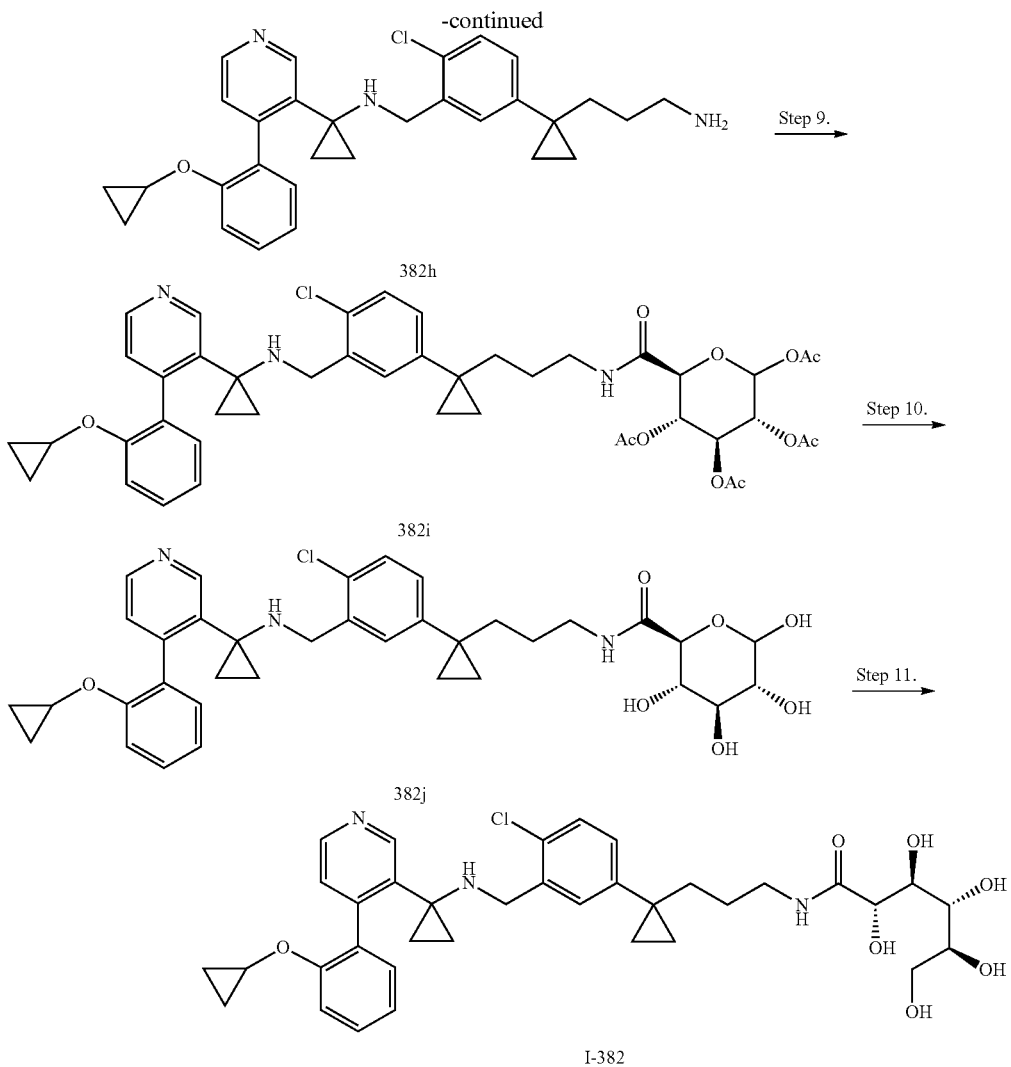

Step 1. (5-[5-[(tert-butyldiphenylsilyl)oxy]pent-1-en-2-yl]-2-chlorophenyl)methanol (Intermediate 382a)

A 100-mL round-bottom flask charged with 5-[5-[(tert-butyldiphenylsilyl)oxy]pent-1-en-2-yl]-2-chlorobenzaldehyde (1.7 g, 3.67 mmol, 1.00 equiv) and methanol (10 mL) was added NaBH$_4$ (279 mg, 7.38 mmol, 2.00 equiv), in portions. The resulting solution was stirred for 1 h at room temperature. The reaction was then quenched by the addition of 100 of NH$_4$Cl. The resulting solution was extracted with 3×30 mL of ethyl acetate and the organic layers combined and dried over anhydrous sodium sulfate and concentrated under vacuum. This resulted in 760 mg (45%) of (5-[5-[(tert-butyldiphenylsilyl)oxy]pent-1-en-2-yl]-2-chlorophenyl)methanol (382a) as yellow oil.

Step 2. [5-(1-[3-[(tert-butyldiphenylsilyl)oxy]propyl]cyclopropyl)-2-chlorophenyl]methanol (Intermediate 382b)

A 100-mL 3-necked round-bottom flask purged and maintained under an inert atmosphere of nitrogen charged with (5-[5-[(tert-butyldiphenylsilyl)oxy]pent-1-en-2-yl]-2-chlorophenyl)methanol (382a, 760 mg, 1.63 mmol, 1.00 equiv), diiodomethane (0.8 mL, 6.00 equiv) and DCE (10 mL) was added Et$_2$Zn (6.5 mL, 6.00 equiv, 1.5 M in hexane) dropwise with stirring at 0° C. The resulting solution was stirred for 12 h at room temperature. The reaction was then quenched by the addition of 100 mL of NH$_4$Cl. The resulting solution was extracted with 3×30 mL of dichloromethane and the organic layers combined and dried over anhydrous sodium sulfate. The residue was applied onto a silica gel column with ethyl acetate/petroleum ether (1:15). This resulted in 550 mg (70%) of [5-(1-[3-[(tert-butyldiphenylsilyl)oxy]propyl]cyclopropyl)-2-chlorophenyl]methanol (382b) as yellow oil.

Step 3. 5-(1-[3-[(tert-butyldiphenylsilyl)oxy]propyl]cyclopropyl)-2-chlorobenzaldehyde (Intermediate 382c)

To [5-(1-[3-[(tert-butyldiphenylsilyl)oxy]propyl]cyclopropyl)-2-chlorophenyl]methanol (382b, 550 mg, 1.15 mmol, 1.00 equiv) in chloroform (20 mL) was added MnO$_2$ (2.99 g, 34.39 mmol, 30.00 equiv). The resulting solution was stirred for 12 h at 60° C. in an oil bath. The solids were filtered out. The resulting mixture was concentrated under vacuum. The crude product (1.3 g) was purified by flash chromatography with the following conditions: Column, silica gel; mobile phase, ethyl acetate/petroleum ether=0% increasing to ethyl acetate/petroleum ether=10% within 30 min; Detector, UV 254 nm to furnish 450 mg (82%) of 5-(1-[3-[(tert-butyldiphenylsilyl)oxy]propyl]cyclopropyl)-2-chlorobenzaldehyde (382c) as yellow oil.

Step 4. N-[[5-(1-[3-[(tert-butyldiphenylsilyl)oxy] propyl]cyclopropyl)-2-chlorophenyl]methyl]-1-[4-(2-cyclopropoxyphenyl)pyridin-3-yl]cyclopropan-1-amine (Intermediate 382d)

To a solution of 5-(1-[3-[(tert-butyldiphenylsilyl)oxy]propyl]cyclopropyl)-2-chlorobenzaldehyde (382c, 450 mg, 0.94 mmol, 1.00 equiv), 1-[4-(2-cyclopropoxyphenyl)pyridin-3-yl]cyclopropan-1-amine (349 mg, 1.31 mmol, 1.00 equiv) in AcOH (0.5 mL) and dichloromethane (10 mL) stirred under an inert atmosphere of nitrogen was added NaHB(OAc)$_3$ (1.20 g, 5.66 mmol, 6.00 equiv), in portions over 1 hr. The resulting solution was stirred for 12 h at room temperature. The resulting mixture was concentrated under vacuum. The resulting solution was diluted with 100 mL of ethyl acetate. The resulting mixture was washed with 1×50 mL of sodium bicarbonate and 1×50 mL of brine. The mixture was dried over anhydrous sodium sulfate and concentrated under vacuum. The crude product (1.05 g) was purified by flash chromatography with the following conditions: Column, silica gel; mobile phase; ethyl acetate/petroleum ether=0% increasing to ethyl acetate/petroleum ether=30% within 50 min; Detector, UV 254 nm. 650 mg product was obtained. This resulted in 650 mg (95%) of N-[[5-(1-[3-[(tert-butyldiphenylsilyl)oxy]propyl]cyclopropyl)-2-chlorophenyl]methyl]-1-[4-(2-cyclopropoxyphenyl)pyridin-3-yl]cyclopropan-1-amine (382d) as yellow oil.

Step 5. 3-(1-[4-chloro-3-[([1-[4-(2-cyclopropoxyphenyl)pyridin-3-yl]cyclopropyl]amino) methyl]phenyl] cyclopropyl)propan-1-ol (Intermediate 382e)

A 50-mL round-bottom flask purged and maintained under an inert atmosphere of nitrogen, was placed N-[[5-(1-[3-[(tert-butyldiphenylsilyl)oxy]propyl]cyclopropyl)-2-chlorophenyl]methyl]-1-[4-(2-cyclopropoxyphenyl)pyridin-3-yl]cyclopropan-1-amine (382d, 650 mg, 0.89 mmol, 1.00 equiv) in THF (10 mL). TBAF (1.34 mL, 1.50 equiv) was added dropwise with stirring at room temperature. The resulting solution was stirred for 1 h at room temperature. The resulting mixture was concentrated under vacuum. The residue was applied onto a silica gel column with ethyl acetate/petroleum ether (1:1). This resulted in 403 mg (92%) of 3-(1-[4-chloro-3-[([1-[4-(2-cyclopropoxyphenyl)pyridin-3-yl]cyclopropyl]amino)methyl]phenyl]cyclopropyl)propan-1-ol (382e) as yellow oil.

Step 6. (3-(1-[4-chloro-3-[([1-[4-(2-cyclopropoxyphenyl)pyridin-3-yl]cyclopropyl]amino) methyl] phenyl]cyclopropyl) propyl methanesulfonate (Intermediate 382f)

A 100-mL round-bottom flask purged and maintained under an inert atmosphere of nitrogen, was placed 3-(1-[4-chloro-3-[([1-[4-(2-cyclopropoxyphenyl)pyridin-3-yl]cyclopropyl]amino)methyl]phenyl]cyclopropyl)propan-1-ol (382e, 403 mg, 0.82 mmol, 1.00 equiv), TEA (0.23 mL, 2.00 equiv), dichloromethane (10 mL). MsCl (0.097 mL, 1.50 equiv) was added dropwise with stirring at 0° C. The resulting solution was stirred for 30 min at room temperature. The resulting solution was diluted with 100 mL of DCM. The resulting mixture was washed with 2×50 mL of brine. The mixture was dried over anhydrous sodium sulfate and concentrated under vacuum. This resulted in 492 mg (crude) of 3-(1-[4-chloro-3-[([1-[4-(2-cyclopropoxyphenyl) pyridin-3-yl]cyclopropyl]amino)methyl]phenyl]cyclopropyl) propyl methanesulfonate (382f) as yellow crude oil.

Step 7. 2-[3-(1-[4-chloro-3-[([1-[4-(2-cyclopropoxyphenyl)pyridin-3-yl]cyclopropyl]amino) methyl] phenyl]cyclopropyl)propyl]-2,3-dihydro-1H-isoindole-1,3-dione (Intermediate 382g)

3-(1-[4-chloro-3-[([1-[4-(2-cyclopropoxyphenyl)pyridin-3-yl]cyclopropyl]amino) methyl]phenyl]cyclopropyl)propyl methanesulfonate (382f, 468 mg, 0.83 mmol, 1.00 equiv), 2-potassio-2,3-dihydro-1H-isoindole-1,3-dione (306 mg, 1.65 mmol, 1.50 equiv) dissolved in DMF (10 mL). The resulting solution was stirred for 2.5 h at 80° C. in an oil bath. The resulting solution was diluted with 100 mL of ethyl acetate. The resulting mixture was washed with 3×50 mL of Brine. The resulting mixture was concentrated under vacuum. The residue was applied onto a silica gel column with ethyl acetate/petroleum ether (1:1). This resulted in 450 mg (88%) of 2-[3-(1-[4-chloro-3-[([1-[4-(2-cyclopropoxyphenyl)pyridin-3-yl]cyclopropyl]amino)methyl]phenyl]cyclopropyl)propyl]-2,3-dihydro-1H-isoindole-1,3-dione (382g) as yellow oil.

Step 8. N-([5-[1-(3-aminopropyl)cyclopropyl]-2-chlorophenyl]methyl)-1-[4-(2-cyclopropoxyphenyl) pyridin-3-yl]cyclopropan-1-amine (Intermediate 382h)

2-[3-(1-[4-chloro-3-[([1-[4-(2-cyclopropoxyphenyl)pyridin-3-yl]cyclopropyl]amino) methyl]phenyl]cyclopropyl) propyl]-2,3-dihydro-1H-isoindole-1,3-dione (382g, 450 mg, 0.73 mmol, 1.00 equiv), tetrahydrofuran (5 mL), methanol (5 mL) and NH$_2$NH$_2$·H$_2$O (365 mg, 7.30 mmol, 10.00 equiv) was stirred for 12 h at 60° C. in an oil bath. The resulting mixture was concentrated under vacuum. The resulting solution was diluted with 100 mL of DCM. The resulting mixture was washed with 3×50 mL of Brine. The mixture was dried over anhydrous sodium sulfate and concentrated under vacuum. This resulted in 330 mg (93%) of N-([5-[1-(3-aminopropyl)cyclopropyl]-2-chlorophenyl] methyl)-1-[4-(2-cyclopropoxyphenyl)pyridin-3-yl]cyclopropan-1-amine (382h) as a yellow solid.

Step 9. (2S,3S,4S,5R)-4,5,6-tris(acetyloxy)-2-[[3-(1-[4-chloro-3-[([1-[4-(2-cyclopropoxyphenyl)pyridin-3-yl]cyclopropyl]amino)methyl]phenyl]cyclopropyl) propyl] carbamoyl]oxan-3-yl acetate (Intermediate 382i)

N-([5-[1-(3-aminopropyl)cyclopropyl]-2-chlorophenyl] methyl)-1-[4-(2-cyclopropoxyphenyl)pyridin-3-yl]cyclopropan-1-amine (382h, 210 mg, 0.43 mmol, 1.00 equiv), (2S,3S,4S,5R)-3,4,5,6-tetrakis(acetyloxy)oxane-2-carboxylic acid (156 mg, 0.43 mmol, 1.00 equiv), DIEA (0.28 mL, 4.00 equiv), HATU (245 mg, 0.64 mmol, 1.50 equiv) in dichloromethane (10 mL) was stirred for 3.5 h at room temperature. The resulting solution was diluted with 100 mL of DCM. The resulting mixture was washed with 3×50 mL of Brine. The solid was dried in an oven under reduced pressure. The residue was applied onto a silica gel column with ethyl acetate/petroleum ether (1:1). This resulted in 160 mg (45%) of (2S,3S,4S,5R)-4,5,6-tris(acetyloxy)-2-[[3-(1-[4-chloro-3-[([1-[4-(2-cyclopropoxyphenyl)pyridin-3-yl]cyclopropyl]amino)methyl]phenyl] cyclopropyl)propyl]carbamoyl]oxan-3-yl acetate (382i) as yellow oil.

Step 10. (2S,3S,4S,5R)-N-[3-(1-[4-chloro-3-[([1-[4-(2-cyclopropoxyphenyl)pyridin-3-yl]cyclopropyl]amino)methyl]phenyl]cyclopropyl)propyl]-3,4,5,6-tetrahydroxyoxane-2-carboxamide (Intermediate 382j)

A 50-mL round-bottom flask purged and maintained under an inert atmosphere of nitrogen charged with (2S,3S,4S,5R)-4,5,6-tris(acetyloxy)-2-[[3-(1-[4-chloro-3-[([1-[4-(2-cyclopropoxyphenyl)pyridin-3-yl]cyclopropyl]amino)methyl]phenyl]cyclopropyl)propyl]carbamoyl]oxan-3-yl acetate (382i, 160 mg, 0.19 mmol, 1.00 equiv) in methanol (5 mL) was added sodium methoxide (0.39 mL, 2.00 equiv) dropwise with stirring. The resulting solution was stirred for 30 min at room temperature. This resulted in 132 mg (crude) of (2S,3S,4S,5R)-N-[3-(1-[4-chloro-3-[([1-[4-(2-cyclopropoxyphenyl)pyridin-3-yl]cyclopropyl]amino)methyl]phenyl]cyclopropyl)propyl]-3,4,5,6-tetrahydroxyoxane-2-carboxamide (382j) as yellow oil.

Step 11. (2S,3S,4R,5S)-N-[3-(1-[4-chloro-3-[([1-[4-(2-cyclopropoxyphenyl)pyridin-3-yl] cyclopropyl]amino)methyl]phenyl]cyclopropyl)propyl]-2,3,4,5,6-pentahydroxyhexanamide (I 382)

To (2S,3S,4S,5R)-N-[3-(1-[4-chloro-3-[([1-[4-(2-cyclopropoxyphenyl)pyridin-3-yl]cyclopropyl]amino)methyl]phenyl]cyclopropyl)propyl]-3,4,5,6-tetrahydroxyoxane-2-carboxamide (382j, 128 mg, 0.19 mmol, 1.00 equiv) in methanol (5 mL) was added NaBH$_4$ (15 mg, 0.40 mmol, 2.00 equiv), in portions. The resulting solution was stirred for 40 min at room temperature. The resulting mixture was concentrated under vacuum. The crude product was purified by Prep-HPLC with the following conditions: Column, XBridge C18 OBD Prep Column; 5 μm, 19 mm×250 mm; mobile phase 10 mM aq. NH$_4$HCO$_3$) and MeCN (40.0% MeCN up to 60.0% in 10 min); Detector UV 254 nm. This resulted in 60.2 mg (47%) of (2S,3S,4R,5S)-N-[3-(1-[4-chloro-3-[([1-[4-(2-cyclopropoxyphenyl)pyridin-3-yl]cyclopropyl] amino)methyl]phenyl]cyclopropyl)propyl]-2,3,4,5,6-pentahydroxyhexanamide (I-382) as a white solid: MS (ES, m/z):[M+1]$^+$666.40; $^1$H NMR (400 MHz, Methanol-d$_4$) δ 8.57 (s, 1H), 8.46 (d, J=5.0 Hz, 1H), 7.52-7.42 (m, 2H), 7.26-7.05 (m, 6H), 4.59 (s, 1H), 4.09 (t, J=6.0 Hz, 1H), 3.79 (dddd, J=15.0, 10.7, 7.5, 3.4 Hz, 2H), 3.73-3.54 (m, 5H), 3.16 (tt, J=6.9, 3.6 Hz, 2H), 1.62-1.53 (m, 2H), 1.44 (p, J=7.1 Hz, 2H), 0.94-0.80 (m, 4H), 0.67 (dd, J=27.5, 6.6 Hz, 6H), 0.43-0.37 (m, 2H).

Compounds I-383 to I-387 in Table 13 below were prepared from commercial, known starting materials or the appropriate intermediates disclosed herein using methods from the examples specified in Table 13 and methods generally known to those skilled in the art.

TABLE 13

Compounds I-383 to I-387

| Cmpd. No.: | Synthetic Method | Compound Structure | Obs. Mass |
|---|---|---|---|
| I-383 | Example 68 | 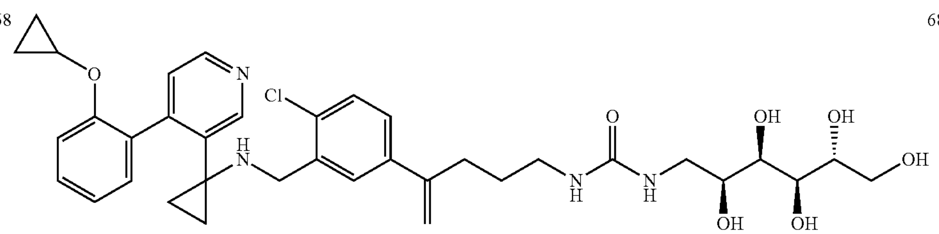 | 681.25 |
| I-384 | Example 67 | 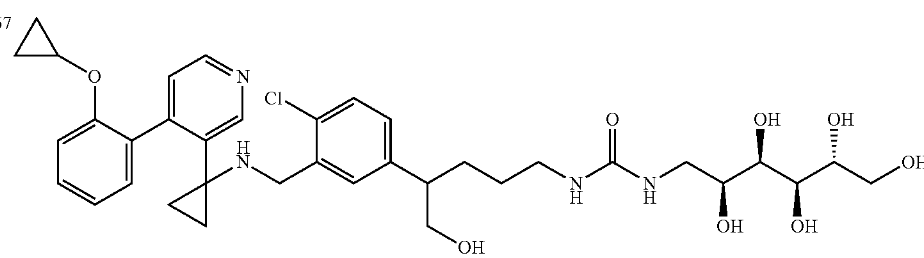 | 350.5 [M + 2H]$^2$ |
| I-385 | Example 69 | 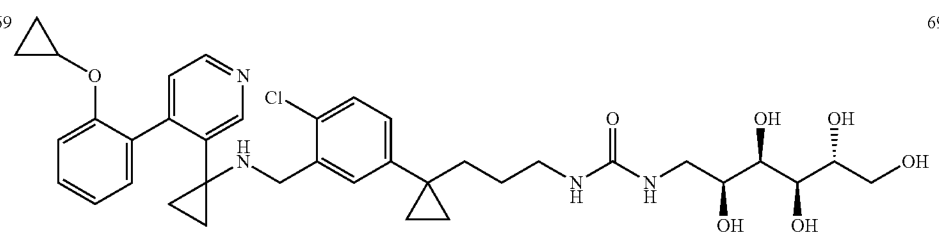 | 695.45 |

TABLE 13-continued
Compounds I-383 to I-387
| Cmpd. No.: | Synthetic Method | Compound Structure | Obs. Mass |
|---|---|---|---|
| I-386 | Example 67 | 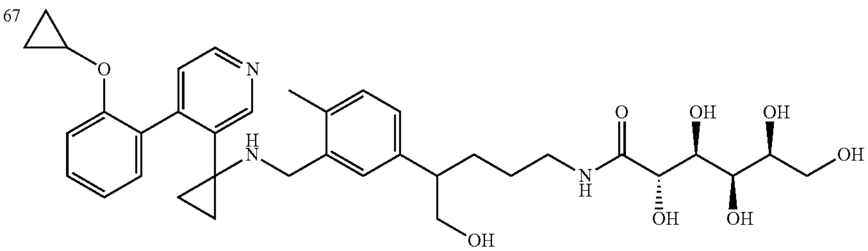 | 650.3 |
| I-387 | Example 67 | 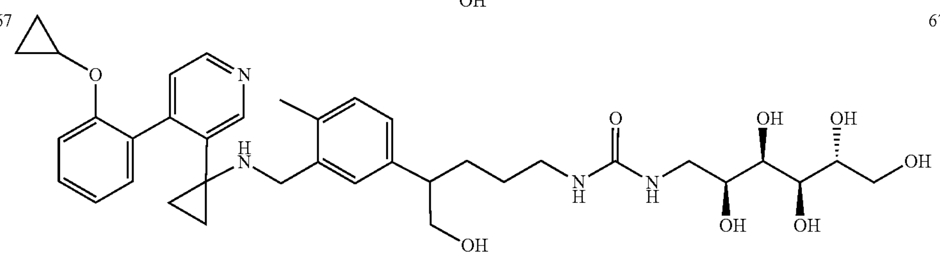 | 679.35 |
Example 70: (2S,3S,4R,5S)-N-(4-[[4-chloro-3-([1-[4-(2-cyclopropoxyphenyl)pyridin-3-yl]cyclopropoxy]methyl)benzene]sulfonamido]butyl)-2,3,4,5,6-pentahydroxyhexanamide (I 388)
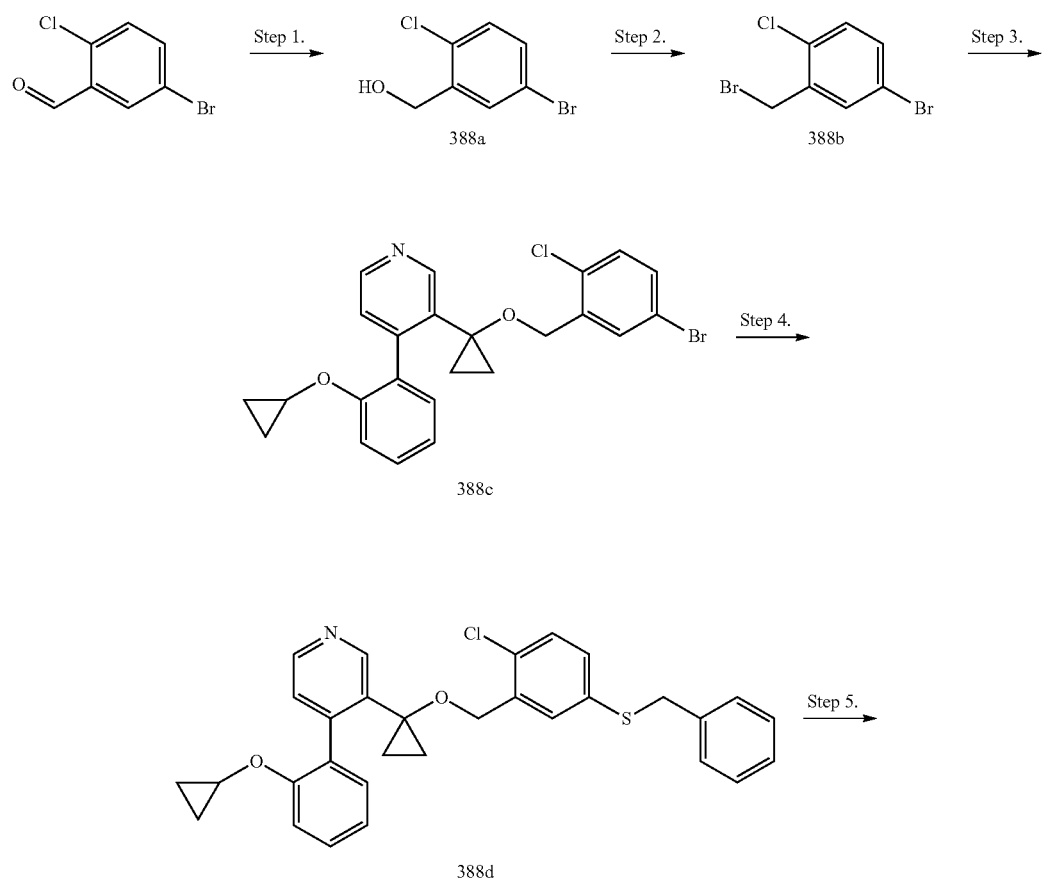

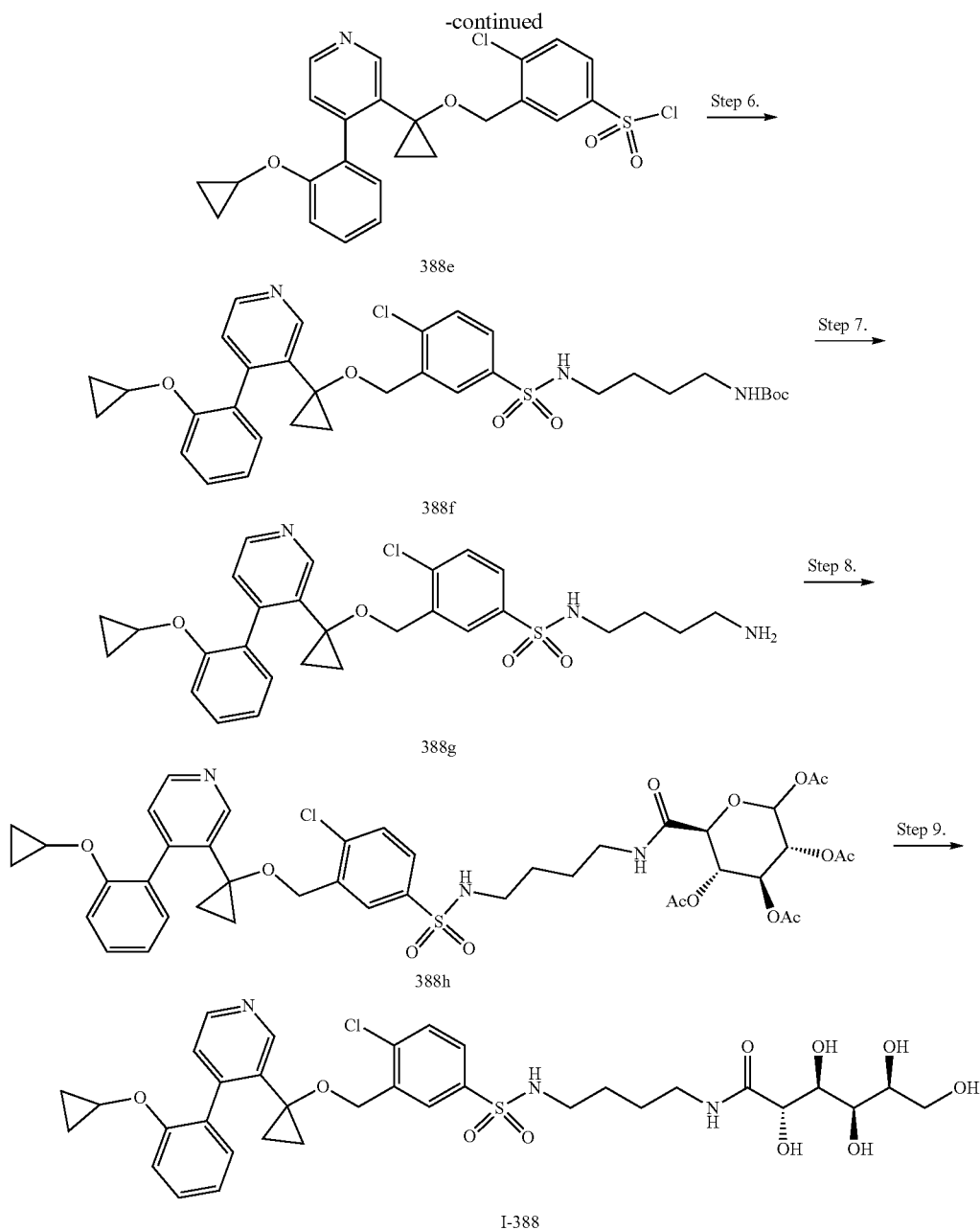

Step 1. (5-bromo-2-chlorophenyl)methanol (Intermediate 388a)

A 250-mL round-bottom flask was charged with 5-bromo-2-chlorobenzaldehyde (8.0 g, 36.45 mmol, 1.00 equiv), methanol (150 mL). This was followed by the addition of NaBH$_4$ (14.0 g, 370.08 mmol, 10.00 equiv). The resulting solution was stirred for 30 min at 0° C. in a water/ice bath. The resulting solution was diluted with 200 mL of H$_2$O. The resulting solution was extracted with 3×200 mL of ethyl acetate and the organic layers combined and dried over anhydrous sodium sulfate and concentrated under vacuum. This resulted in 7.7 g (95%) of (5-bromo-2-chlorophenyl)methanol (388a) as colorless oil.

Step 2. 4-bromo-2-(bromomethyl)-1-chlorobenzene (Intermediate 388b)

A 250-mL round-bottom flask was charged with (5-bromo-2-chlorophenyl)methanol (388a, 5.0 g, 22.58 mmol, 1.00 equiv), dichloromethane (75 mL), tetrahydrofuran (75 mL), NBS (6.03 g, 33.88 mmol, 1.50 equiv), PPh$_3$ (8.93 g, 34.05 mmol, 1.50 equiv). The resulting solution was stirred for 30 min at 0° C. in a water/ice bath. The resulting mixture was concentrated under vacuum. The crude product was purified by flash chromatography with the following conditions (IntelFlash-1): Column, silica gel; mobile phase, ethyl acetate:petroleum ether=100:0 increasing to ethyl acetate:petroleum ether=100:0 within 15 min; Detector, UV 254 nm. 6.8 g product was obtained. This resulted in 6.8 g (crude) of 4-bromo-2-(bromomethyl)-1-chlorobenzene (388b) as a white solid.

Step 3. 3-[1-[(5-bromo-2-chlorophenyl)methoxy]cyclopropyl]-4-(2-cyclopropoxyphenyl) pyridine (Intermediate 388c)

A 250-mL round-bottom flask was charged with 4-bromo-2-(bromomethyl)-1-chlorobenzene (388b, 6.3 g, 22.15 mmol, 1.00 equiv), N,N-dimethylformamide (150 mL), 1-[4-(2-cyclopropoxyphenyl)pyridin-3-yl]cyclopropan-1-ol (6.0 g, 22.44 mmol, 1.00 equiv), sodium hydride (1.1 g, 45.83 mmol, 2.00 equiv). The resulting solution was stirred for 2 h at 0° C. in an ice/salt bath. The resulting solution was diluted with 200 mL of H$_2$O. The resulting solution was extracted with 3×100 mL of ethyl acetate and the organic layers combined and dried over anhydrous sodium sulfate and concentrated under vacuum. This resulted in 5.5 g (53%) of 3-[1-[(5-bromo-2-chlorophenyl)methoxy]cyclopropyl]-4-(2-cyclopropoxyphenyl)pyridine (388c) as light yellow oil.

Step 4. 3-(1-[[5-(benzylsulfanyl)-2-chlorophenyl]methoxy]cyclopropyl)-4-(2-cyclopropoxyphenyl)pyridine (Intermediate 388d)

A 250-mL round-bottom flask was charged with 3-[1-[(5-bromo-2-chlorophenyl)methoxy]cyclopropyl]-4-(2-cyclopropoxyphenyl)pyridine (388c, 2.0 g, 4.25 mmol, 1.00 equiv), phenylmethanethiol (800 mg, 6.44 mmol, 1.20 equiv), DIEA (2 mL, 2.00 equiv), Xantphos (290 mg, 0.50 mmol, 0.10 equiv), Pd(dba)$_3$ (195 mg, 0.05 equiv), dioxane (50 mL). The resulting solution was stirred for 1 overnight at 100° C. in an oil bath. The resulting solution was diluted with 200 mL of H$_2$O. The resulting solution was extracted with 3×200 mL of ethyl acetate and the organic layers combined and dried over anhydrous sodium sulfate and concentrated under vacuum. The crude product (1.8 g) was purified by Flash chromatography with the following conditions (IntelFlash-1): Column, silica gel; mobile phase, ethyl acetate:petroleum ether=100:0 increasing to ethyl acetate:petroleum ether=70:30 within 30 min; Detector, UV 254 nm. 1.6 g product was obtained. This resulted in 1.6 g (73%) of 3-(1-[[5-(benzylsulfanyl)-2-chlorophenyl]methoxy]cyclopropyl)-4-(2-cyclopropoxyphenyl)pyridine (388d) as brown oil.

Step 5. 4-chloro-3-([1-[4-(2-cyclopropoxyphenyl)pyridin-3-yl]cyclopropoxy]methyl) benzene-1-sulfonyl chloride (Intermediate 388e)

A 100-mL round-bottom flask was charged with 3-(1-[[5-(benzylsulfanyl)-2-chlorophenyl]methoxy]cyclopropyl)-4-(2-cyclopropoxyphenyl)pyridine (388d, 400 mg, 0.78 mmol, 1.00 equiv), water (5 mL). This was followed by the addition of AcOH (14 mL). The solution cooled to 0° C. To this was added NCS (321 mg, 2.40 mmol, 3.10 equiv). The resulting solution was stirred overnight at room temperature. The resulting solution was extracted with 100 mL of dichloromethane and the organic layers combined. The resulting mixture was washed with 2×10 mL of brine. The solid was dried in an oven under reduced pressure. This resulted in 350 mg (92%) of 4-chloro-3-([1-[4-(2-cyclopropoxyphenyl)pyridin-3-yl]cyclopropoxy]methyl) benzene-1-sulfonyl chloride (388e) as light yellow crude oil.

Step 6. tert-butyl N-(4-[[4-chloro-3-([1-[4-(2-cyclopropoxyphenyl)pyridin-3-yl] cyclopropoxy]methyl)benzene] sulfonamido]butyl)carbamate (Intermediate 388f)

A 25-mL round-bottom flask was charged with tert-butyl N-(4-aminobutyl)carbamate (154 mg, 0.82 mmol, 2.00 equiv), DIEA (105 mg, 0.81 mmol, 2.00 equiv), dichloromethane (5 mL). This was followed by the addition of 4-chloro-3-([1-[4-(2-cyclopropoxyphenyl)pyridin-3-yl]cyclopropoxy]methyl)benzene-1-sulfonyl chloride (388e, 200 mg, 0.41 mmol, 1.00 equiv) dropwise with stirring at 0° C. The resulting solution was stirred for 5 min at 0° C. in a water/ice bath. The crude product (10 mL) was purified by Flash chromatography with the following conditions (IntelFlash-1): Column, silica gel; mobile phase, ethyl acetate:petroleum ether=100:0 increasing to ethyl acetate:petroleum ether=50:50 within 25 min; Detector, UV 254 nm. This resulted in 0.125 g (48%) of tert-butyl N-(4-[[4-chloro-3-([1-[4-(2-cyclopropoxyphenyl) pyridin-3-yl]cyclopropoxy]methyl)benzene] sulfonamido]butyl)carbamate (388f) as light yellow oil.

Step 7. N-(4-aminobutyl)-4-chloro-3-([1-[4-(2-cyclopropoxyphenyl)pyridin-3-yl] cyclopropoxy]methyl)benzene-1-sulfonamide (Intermediate 388g)

A 50-mL 3-necked round-bottom flask was charged with tert-butyl N-(4-[[4-chloro-3-([1-[4-(2-cyclopropoxyphenyl)pyridin-3-yl]cyclopropoxy]methyl)benzene]sulfonamido]butyl) carbamate (388f, 510 mg, 0.79 mmol, 1.00 equiv), dichloromethane (10 mL), lutidine (0.425 g, 5.00 equiv), TMSOTf (0.706 g, 5.00 equiv). The resulting solution was stirred for 5 min at 0° C. in an ice/salt bath. The resulting solution was allowed to react, with stirring, for an additional 90 min at room temperature. The reaction was then quenched by the addition of 20 mL of NH$_4$Cl (aq). The resulting solution was extracted with 200 mL of ethyl acetate and the organic layers combined and dried over anhydrous sodium sulfate and concentrated under vacuum. The residue was applied onto a silica gel column with dichloromethane/methanol (15:1). This resulted in 0.25 g (58%) of N-(4-aminobutyl)-4-chloro-3-([1-[4-(2-cyclopropoxyphenyl) pyridin-3-yl]cyclopropoxy]methyl)benzene-1-sulfonamide (388g) as yellow oil.

Step 8. (2S,3S,4S,5R)-4,5,6-tris(acetyloxy)-2-[(4-[[4-chloro-3-([1-[4-(2-cyclopropoxyphenyl) pyridin-3-yl]cyclopropoxy]methyl)benzene]sulfonamido]butyl)carbamoyl]oxan-3-yl acetate (Intermediate 388h)

A 25-mL round-bottom flask was charged with N-(4-aminobutyl)-4-chloro-3-([1-[4-(2-cyclopropoxyphenyl) pyridin-3-yl]cyclopropoxy]methyl)benzene-1-sulfonamide (388g, 220 mg, 0.41 mmol, 1.00 equiv), (2S,3S,4S,5R)-3,4,5,6-tetrakis(acetyloxy)oxane-2-carboxylic acid (442 mg, 1.22 mmol, 3.00 equiv), N,N-dimethylformamide (12 mL), HATU (232 mg, 0.61 mmol, 1.50 equiv), DIEA (105 mg, 0.81 mmol, 2.00 equiv). The resulting solution was stirred overnight at room temperature. The resulting solution was diluted with 200 mL of ethyl acetate. The resulting solution was extracted with 3×100 mL of brine and the organic layers combined and dried over anhydrous sodium sulfate and concentrated under vacuum. The residue was applied onto a silica gel column with dichloromethane/methanol (20:1). This resulted in 200 mg (56%) of (2S,3S,4S,5R)-4,5,6-tris (acetyloxy)-2-[(4-[[4-chloro-3-([1-[4-(2-cyclopropoxyphenyl) pyridin-3-yl]cyclopropoxy]methyl)benzene]sulfonamido]butyl)carbamoyl]oxan-3-yl acetate (388h) as light yellow oil.

Step 9. (2S,3S,4R,5S)-N-(4-[[4-chloro-3-([1-[4-(2-cyclopropoxyphenyl)pyridin-3-yl] cyclopropoxy] methyl)benzene]sulfonamido]butyl)-2,3,4,5,6-pentahydroxyhexanamide (I 388)

A 250-mL round-bottom flask was charged with (2S,3S, 4S,5R)-4,5,6-tris(acetyloxy)-2-[(4-[[4-chloro-3-([1-[4-(2-cyclopropoxyphenyl)pyridin-3-yl]cyclopropoxy]methyl) benzene]sulfonamido]butyl)carbamoyl]oxan-3-yl acetate (388h, 200 mg, 0.23 mmol, 1.00 equiv), methanol (20 mL), sodium methylate (35 mg, 0.65 mmol, 2.50 equiv), NaBH$_4$ (20 mg, 0.53 mmol, 2.50 equiv), methanol (5 mL). The resulting solution was stirred for 1 h at room temperature. The resulting solution was diluted with 2 mL of H$_2$O. The solids were filtered out. The crude product was purified by Preparative HPLC with the following conditions: Column, XBridge Shield RP18 OBD Column; 5 μm 19×150 mm; mobile phase, 10 mM aqueous NH$_4$HCO$_3$ and MeCN (30.0% CAN up to 50.0% in 6 min); Detector, UV 220 nm. This resulted in 108.5 mg (67%) of (2S,3S,4R,5S)-N-(4-[[4-chloro-3-([1-[4-(2-cyclopropoxyphenyl)pyridin-3-yl]cyclopropoxy]methyl)benzene]sulfonamido]butyl)-2,3,4,5,6-pentahydroxyhexanamide (I-388) as a white solid: MS (ES, m/z): 720; $^1$H-NMR (CDCl$_3$, ppm): 8.58 (1H, m), 8.45 (1H, m), 7.69 (2H, m), 7.65 (1H, m), 7.35 (2H, m), 7.22 (2H, m), 7.02 (1H, m), 4.47 (2H, m), 4.11 (1H, m), 3.83 (3H, m), 3.55 (3H, m), 3.19 (2H, m), 2.81 (2H, m), 1.51 (4H, m), 1.01 (4H, m), 0.59 (2H, m), 0.39 (2H, s)

Example 71: 1-(4-[N-methyl[4-chloro-3-([1-[4-(2-cyclopropoxyphenyl)pyridin-3-yl]cyclopropoxy] methyl)benzene]sulfonamido]butyl)-3-[(2S,3R,4S, 5R)-1,3,4,5,6-pentahydroxyhexan-2-yl]urea (I-389)

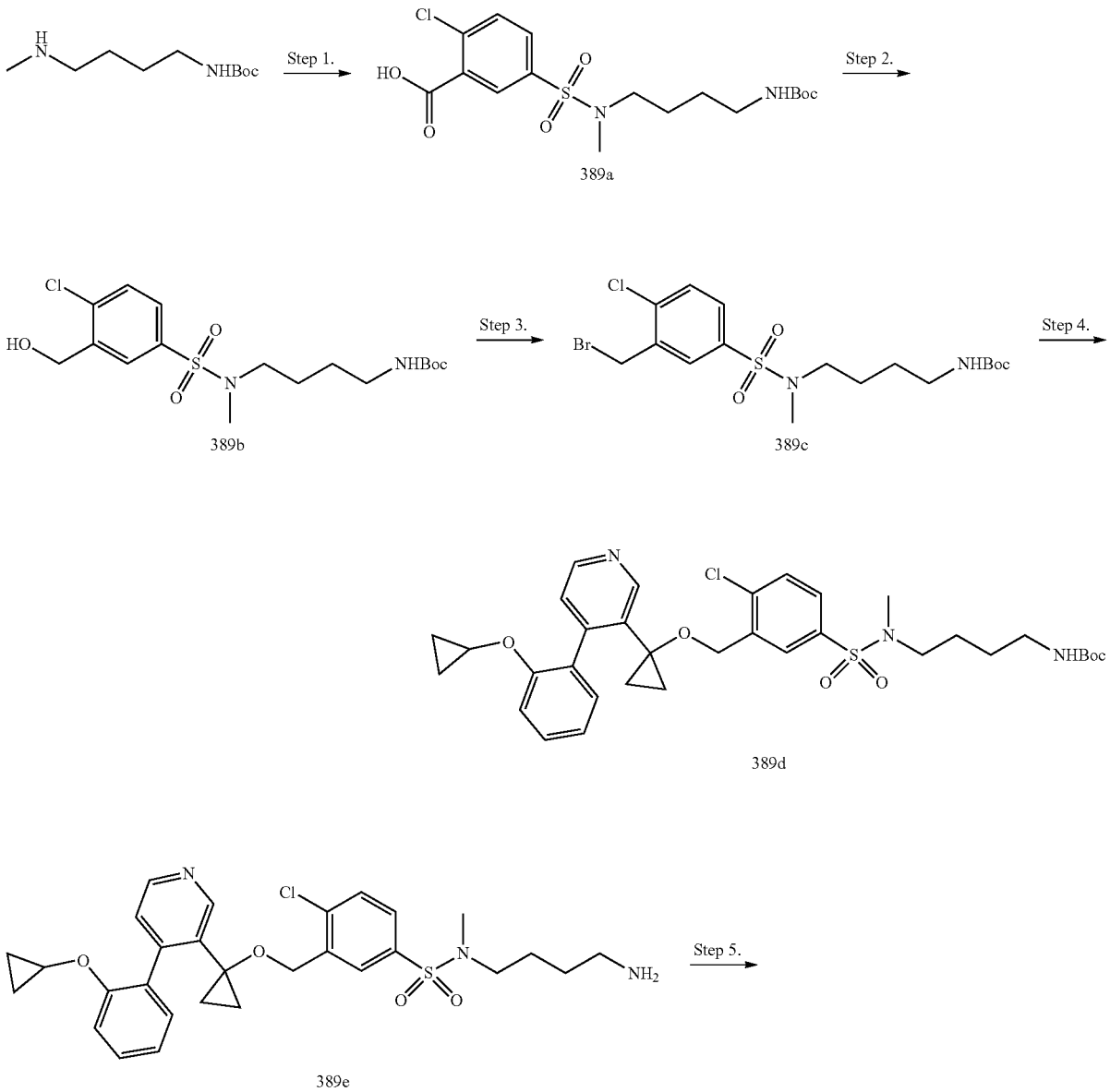

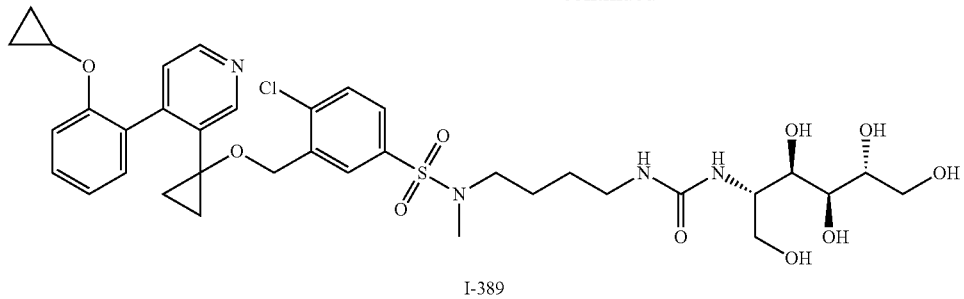

I-389

Step 1. 5-[(4-[[(tert-butoxy)carbonyl]amino]butyl)(methyl)sulfamoyl]-2-chlorobenzoic acid (Intermediate 389a)

A 100-mL round-bottom flask purged and maintained under an inert atmosphere of nitrogen was charged with 2-chloro-5-(chlorosulfonyl)benzoic acid (500 mg, 1.96 mmol, 1.50 equiv), dichloromethane (15 mL), tert-butyl N-[4-(methylamino)butyl]carbamate (266.3 mg, 1.32 mmol, 1.00 equiv), TEA (0.37 mL). The resulting solution was stirred for 3 h at room temperature. The resulting solution was extracted with 3×50 mL of dichloromethane and the organic layers combined and concentrated under vacuum. This resulted in 420 mg (76%) of 5-[(4-[[(tert-butoxy)carbonyl]amino]butyl)(methyl)sulfamoyl]-2-chlorobenzoic acid (389a) as yellow oil.

Step 2. tert-butyl N-(4-[N-methyl[4-chloro-3-(hydroxymethyl)benzene]sulfonamido]butyl) carbamate (Intermediate 389b)

A 500-mL round-bottom flask was charged with 5-[(4-[[(tert-butoxy)carbonyl]amino]butyl)(methyl) sulfamoyl]-2-chlorobenzoic acid (19 g, 45.14 mmol, 1.00 equiv), chloro(2-methylpropoxy)methanone (389a, 9.25 g, 67.73 mmol, 1.50 equiv), tetrahydrofuran (150 mL), triethylamine (6.85 g, 67.69 mmol, 1.50 equiv).The resulting solution was stirred for 0.5 h at 0° C., and then stirred for 1 h at room temperature. The reaction was then dropwise into NaBH₄ (6.8 g, 179.75 mmol, 4.00 equiv) in ethanol (150 mL), with stirring for 0.5 h at 0° C., and then stirred for 1 h at room temperature. The resulting solution was stirred for 3 h at room temperature. The reaction was then quenched by the addition of 100 mL of water. The resulting solution was extracted with 3×100 mL of dichloromethane and the organic layers combined and dried over anhydrous sodium sulfate and concentrated under vacuum. The residue was applied onto a silica gel column with ethyl acetate/petroleum ether (0-30%). The collected fractions were combined and concentrated under vacuum. This resulted in 12 g (65%) of tert-butyl N-(4-[N-methyl[4-chloro-3-(hydroxymethyl)benzene]sulfonamido]butyl)carbamate (389b) as yellow oil.

Step 3. tert-butyl N-(4-[N-methyl[3-(bromomethyl)-4-chlorobenzene]sulfonamido]butyl) carbamate (Intermediate 389c)

A 1000-mL round-bottom flask was charged with tert-butyl N-(4-[N-methyl[4-chloro-3-(hydroxymethyl)benzene]sulfonamido]butyl)carbamate (389b, 24 g, 58.98 mmol, 1.00 equiv), DCM/THF (200/200 mL). This was followed by the addition of NBS (17.1 g, 96.08 mmol, 1.63 equiv) in several batches at 0° C. in 5 min. To this was added PPh₃ (23.6 g, 89.98 mmol, 1.53 equiv) in several batches at 0° C. in 5 min. The resulting solution was stirred for 1 h at 0° C. in a water/ice bath. The resulting mixture was concentrated under vacuum. The residue was applied onto a silica gel column with ethyl acetate/petroleum ether (0-25%). This resulted in 17 g (61%) of tert-butyl N-(4-[N-methyl[3-(bromomethyl)-4-chlorobenzene]sulfonamido]butyl) carbamate (389c) as a white solid.

Step 4. tert-butyl N-(4-[N-methyl[4-chloro-3-([1-[4-(2-cyclopropoxyphenyl)pyridin-3-yl]cyclopropoxy]methyl)benzene]sulfonamido]butyl)carbamate (Intermediate 389d)

A 500-mL 3-necked round-bottom flask was charged with tert-butyl N-(4-[N-methyl[3-(bromomethyl)-4-chlorobenzene]sulfonamido]butyl)carbamate (389c, 5.9 g, 12.56 mmol, 1.10 equiv), N,N-dimethylformamide (360 mL), 1-[4-(2-cyclopropoxyphenyl)pyridin-3-yl]cyclopropan-1-ol (3.06 g, 11.45 mmol, 1.00 equiv). This was followed by the addition of sodium hydride (917 mg, 38.21 mmol, 3.34 equiv) in several batches at 0° C. in 5 min. The resulting solution was stirred for 20 min at 0° C. The resulting solution was diluted with 50 mL of ethyl acetate. The reaction was then quenched by the addition of 50 mL of NH₄Cl. The residue was dissolved in 50 mL of H₂O. The resulting solution was extracted with 3×200 mL of ethyl acetate and the organic layers combined. The resulting mixture was washed with 3×300 mL of Brine. The mixture was dried over anhydrous sodium sulfate. The solids were filtered out. The resulting mixture was concentrated under vacuum. The residue was applied onto a silica gel column with ethyl acetate/petroleum ether (1:1). This resulted in 4.0 g (53%) of tert-butyl N-(4-[N-methyl[4-chloro-3-([1-[4-(2-cyclopropoxyphenyl)pyridin-3-yl]cyclopropoxy]methyl)benzene]sulfonamido]butyl)carbamate (389d) as light yellow oil.

Step 5. N-(4-aminobutyl)-4-chloro-3-([1-[4-(2-cyclopropoxyphenyl)pyridin-3-yl]cyclopropoxy]methyl)-N-methylbenzene-1-sulfonamide (Intermediate 389e)

A 1000-mL round-bottom flask was charged with tert-butyl N-(4-[N-methyl[4-chloro-3-([1-[4-(2-cyclopropoxyphenyl)pyridin-3-yl]cyclopropoxy]methyl)benzene]sulfonamido]butyl)carbamate (389d, 17 g, 25.91 mmol, 1.00 equiv), TFA/DCM (42.5/425 mL). The resulting solution was stirred for 1 h at room temperature. The pH value of the solution was adjusted to 9.0-10.0 with sodium bicarbonate (100%). The resulting solution was extracted with 7×500 mL of dichloromethane and the organic layers combined and dried over anhydrous sodium sulfate. The solids were filtered out. The resulting mixture was concentrated under vacuum. The residue was applied onto a silica gel column with H₂O:acetonitrile (0-100%). This resulted in 10.4 g (72%) of N-(4-aminobutyl)-4-chloro-3-([1-[4-(2-cyclopropoxyphenyl)pyridin-3-yl]cyclopropoxy]methyl)-N-methylbenzene-1-sulfonamide (389e) as light yellow oil.

Step 6. 1-(4-[N-methyl[4-chloro-3-([1-[4-(2-cyclopropoxyphenyl)pyridin-3-yl]cyclopropoxy]methyl)benzene]sulfonamido]butyl)-3-[(2S,3R,4S,5R)-1,3,4,5,6-pentahydroxyhexan-2-yl]urea (I-389)

A 100-mL round-bottom flask was charged with N-(4-aminobutyl)-4-chloro-3-([1-[4-(2-cyclopropoxyphenyl)pyridin-3-yl]cyclopropoxy]methyl)-N-methylbenzene-1-sulfonamide (389e, 2 g, 3.60 mmol, 1.00 equiv) was dissolved in N,N-dimethylformamide (36 mL, 1 mol/L) and DSC (1.02 g, 3.96 mmol, 1.1 equiv) was added. The resulting solution was stirred for 1 h at room temperature (monitored by LC/MS). The (2R,3S,4R,5S)-5-aminohexane-1,2,3,4,6-pentol (1.63 g, 9.00 mmol, 2.50 equiv) was added. The resulting solution was allowed to react, with stirring, for an additional 30 min at 60° C. (monitored by LC/MS). The resulting mixture was concentrated to remove the solvent under vacuum. The reaction mixture was cooled to room temperature with a water bath. The reaction was then quenched by the addition of 44 mL of 10% Na₂CO₃. The resulting solution was diluted with 50 mL of H₂O. The resulting solution was extracted with 10×55 mL of ethyl acetate (we found ~4.5% acetylation byproduct formed). The organic layers combined and dried over anhydrous sodium sulfate. The solids were filtered out.

The resulting mixture was concentrated under vacuum. Then residue was dissolved in 60% MeCN/water (10 mL) and purified by combi-flash with C18 column using MeCN-water-6.5 mmol/L NH₄HCO₃ (pH adjusted to 10 with aqueous NH₄OH), the products were obtained in ~33% MeCN/water. Removed solvent and this resulted in 1.8 g (66%) of 1-(4-[N-methyl[4-chloro-3-([1-[4-(2-cyclo propoxyphenyl)pyridin-3-yl]cyclopropoxy]methyl)benzene]sulfonamido]butyl)-3-[(2S,3R,4S,5R)-1,3,4,5,6-pentahydroxyhexan-2-yl]urea (I-389) as a white solid: MS (ES, m/z): [M+1]: 763; ¹NMR (400 MHz, Methanol-d₄) δ 0.34-0.43 (m, 2H), 0.56-0.66 (m, 2H), 0.95-1.06 (m, 4H), 1.44-1.63 (m, 4H), 2.67 (s, 3H), 2.96 (t, J=6.6 Hz, 2H), 3.14 (t, J=6.6 Hz, 2H), 3.52-3.73 (m, 6H), 3.73-3.90 (m, 2H), 3.96 (dd, J=4.9, 2.8 Hz, 1H), 4.47 (s, 2H), 7.02 (td, J=7.2, 1.5 Hz, 1H), 7.19-7.29 (m, 2H), 7.31-7.43 (m, 2H), 7.55 (d, J=8.4 Hz, 2H), 7.64 (dd, J=8.2, 2.3 Hz, 1H), 8.49 (d, J=5.0 Hz, 1H), 8.66 (d, J=0.7 Hz, 1H).

Example 72: 1-(4-[N-ethyl[4-chloro-3-([1-[4-(2-cyclopropoxyphenyl)pyridin-3-yl]cyclopropoxy]methyl)benzene]sulfonamido]butyl)-3-[(2S,3R,4R,5R)-2,3,4,5,6-pentahydroxyhexyl] (I-390)

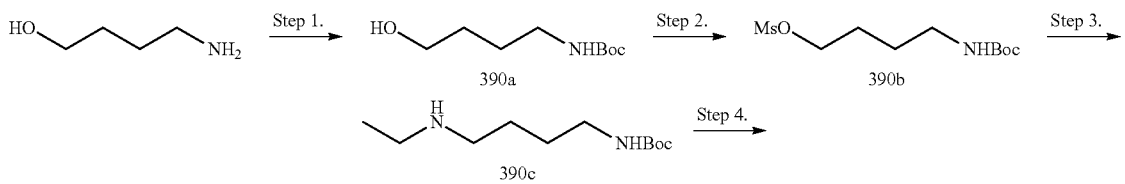

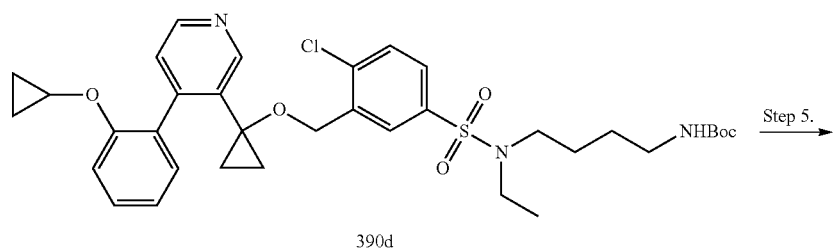

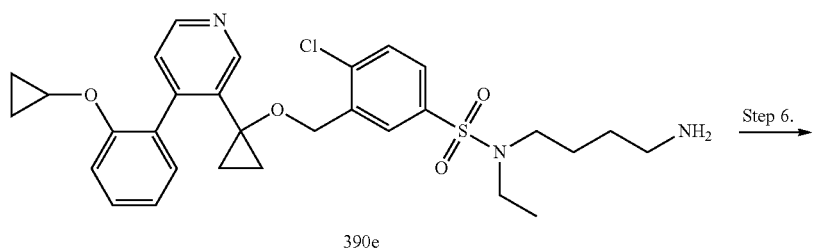

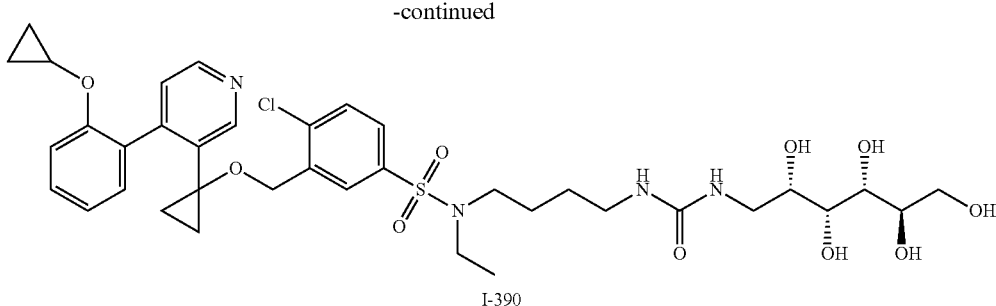

I-390

Step 1. tert-butyl N-(4-hydroxybutyl)carbamate (Intermediate 390a)

A 250-mL 3-necked round-bottom flask purged and maintained under an inert atmosphere of nitrogen was charged with 4-aminobutan-1-ol (9.8 g, 109.94 mmol, 1.00 equiv). This was followed by the addition of dichloromethane (200 mL). The mixture was stirred for 10 min at 0° C. To this was added Boc$_2$O (36 g, 164.95 mmol, 1.50 equiv), sodium carbonate (47 g, 443.40 mmol, 4.00 equiv). The resulting solution was stirred for 2 h at room temperature. The resulting mixture was concentrated under vacuum. The residue was applied onto a silica gel column with ethyl acetate/petroleum ether (1/2). The collected fractions were combined and concentrated under vacuum. This resulted in 20 g (96%) of tert-butyl N-(4-hydroxybutyl) carbamate (390a) as a yellow solid.

Step 2. tert-butyl N-[4-(methanesulfonyloxy)butyl]carbamate (Intermediate 390b)

A 250-mL 3-necked round-bottom flask purged and maintained under an inert atmosphere of nitrogen was charged with tert-butyl N-(4-hydroxybutyl)carbamate (390a, 10 g, 52.84 mmol, 1.00 equiv), dichloromethane (100 mL). This was followed by the addition of DIEA (28 g, 216.65 mmol, 4.00 equiv). The mixture was stirred for 10 mins at 0° C. To this was added MsCl (12 g, 105.26 mmol, 2.00 equiv). The resulting solution was stirred for 1 h at room temperature. The resulting solution was extracted with 3×50 mL of dichloromethane and the organic layers combined. The resulting mixture was washed with 1×50 mL of sodium chloride. The mixture was dried over anhydrous sodium sulfate and concentrated under vacuum. The residue was applied onto a silica gel column with ethyl acetate/petroleum ether (0-30%). The collected fractions were combined and concentrated under vacuum. This resulted in 10 g (71%) of tert-butyl N-[4-(methanesulfonyloxy)butyl]carbamate (390b) as light yellow crude oil.

Step 3. tert-butyl N-[4-[(2-methoxyethyl)amino]butyl]carbamate (Intermediate 390c)

A 50-mL round-bottom flask was charged with tert-butyl N-[4-(methanesulfonyloxy)butyl]carbamate (390b, 5 g, 18.70 mmol, 1.00 equiv), tetrahydrofuran (40 mL), 2-methoxyethan-1-amine (14 g, 186.39 mmol, 10.00 equiv). The resulting solution was stirred for 24 h at room temperature. The resulting solution was extracted with 2×300 mL of ethyl acetate and the organic layers combined. The resulting mixture was washed with 2×100 mL of brine. The mixture was dried over anhydrous sodium sulfate and concentrated under vacuum. The residue was applied onto a silica gel column with dichloromethane/methanol (10:1). This resulted in 2.0 g (43%) of tert-butyl N-[4-[(2-methoxyethyl)amino]butyl]carbamate (390c) as light yellow oil.

Step 4. tert-butyl N-(4-[N-ethyl[4-chloro-3-([1-[4-(2-cyclopropoxyphenyl)pyridin-3-yl]cyclopropoxy]methyl)benzene]sulfonamido]butyl)carbamate (Intermediate 390d)

A 250-mL round-bottom flask was charged with tert-butyl N-[4-(ethylamino)butyl]carbamate (390c, 406 mg, 1.88 mmol, 2.00 equiv), dichloromethane (5 mL). This was followed by the addition of DIEA (242 mg, 1.87 mmol, 2.00 equiv). The temperature was cooled to 0° C. To this was added a solution of 4-chloro-3-([1-[4-(2-cyclopropoxyphenyl)pyridin-3-yl]cyclopropoxy]methyl)benzene-1-sulfonyl chloride (460 mg, 0.94 mmol, 1.00 equiv) in dichloromethane (3 mL). The resulting solution was stirred for 5 min at room temperature. The resulting solution was extracted with 200 mL of dichloromethane and the organic layers combined. The resulting mixture was washed with 2×50 mL of brine. The mixture was dried over anhydrous sodium sulfate and concentrated under vacuum. The residue was applied onto a silica gel column with ethyl acetate/petroleum ether (0-60%). This resulted in 315 mg (50%) of tert-butyl N-(4-[N-ethyl[4-chloro-3-([1-[4-(2-cyclopropoxyphenyl)pyridin-3-yl]cyclopropoxy]methyl)benzene]sulfonamido]butyl)carbamate (390d) as light yellow oil.

Step 5. N-(4-aminobutyl)-4-chloro-3-([1-[4-(2-cyclopropoxyphenyl)pyridin-3-yl]cyclopropoxy]methyl)-N-ethylbenzene-1-sulfonamide (Intermediate 390e)

A 100-mL round-bottom flask was charged with tert-butyl N-(4-[N-ethyl[4-chloro-3-([1-[4-(2-cyclopropoxyphenyl)pyridin-3-yl]cyclopropoxy]methyl)benzene]sulfonamido]butyl) carbamate (390d, 315 mg, 0.47 mmol, 1.00 equiv), dioxane (10 mL), hydrogen chloride (5 mL). The resulting solution was stirred for 1 h at room temperature. The resulting solution was diluted with 100 mL of ethyl acetate. The pH value of the solution was adjusted to 10 with sodium bicarbonate. The resulting solution was extracted with 2×200 of ethyl acetate and the organic layers combined. The resulting mixture was washed with 2×50 mL of brine. The solid was dried in an oven under reduced pressure. This resulted in 250 mg (93%) of N-(4-aminobutyl)-4-chloro-3-([1-[4-(2-cyclopropoxyphenyl)pyridin-3-yl]cyclopropoxy]methyl)-N-ethylbenzene-1-sulfonamide (390e) as light yellow oil.

Step 6. 1-(4-[N-ethyl[4-chloro-3-([1-[4-(2-cyclo-propoxyphenyl)pyridin-3-yl]cyclopropoxy]methyl)benzene]sulfonamido]butyl)-3-[(2S,3R,4R,5R)-2,3,4,5,6-pentahydroxyhexyl]urea (I 390)

A 25-mL round-bottom flask was charged with DSC (136 mg, 1.20 equiv), N,N-dimethylformamide (5 mL), DIEA (85 mg, 0.66 mmol, 2.00 equiv). This was followed by the addition of N-(4-aminobutyl)-4-chloro-3-([1-[4-(2-cyclopropoxyphenyl)pyridin-3-yl]cyclopropoxy]methyl)-N-ethylbenzene-1-sulfonamide (390e, 250 mg, 0.44 mmol, 1.00 equiv). The mixture was stirred for 30 min. To this was added (2R,3R,4R,5S)-6-aminohexane-1,2,3,4,5-pentol (158 mg, 0.87 mmol, 1.50 equiv). The resulting solution was stirred overnight at room temperature. The solids were filtered out. The crude product (200 mg) was purified by preparative HPLC with the following conditions: Column, XBridge Shield RP18 OBD Column; 5 μm 19×150 mm; mobile phase, 10 mM aqueous NH$_4$HCO$_3$ and MeCN (34.0% MeCN up to 47.0% in 6 min); Detector, UV 220 nm. This resulted in 107.5 mg (32%) of 1-(4-[N-ethyl[4-chloro-3-([1-[4-(2-cyclopropoxyphenyl)pyridin-3-yl]cyclopropoxy]methyl)benzene]sulfonamido]butyl)-3-[(2S,3R,4R,5R)-2,3,4,5,6-pentahydroxyhexyl]urea as a white solid: MS (ES, m/z): [M+1]: 777; $^1$H-NMR (CD$_3$OD, ppm): 8.57 (d, J=0.7 Hz, 1H), 8.46 (d, J=5.0 Hz, 1H), 7.50-7.40 (m, 2H), 7.26-7.14 (m, 3H), 7.14-6.99 (m, 3H), 3.71-3.59 (m, 3H), 2.65 (dt, J=14.3, 7.2 Hz, 3H), 1.64-1.42 (m, 4H), 1.34-1.11 (m, 5H), 0.90 (s, 2H), 0.81 (s, 2H), 0.62 (t, J=6.3 Hz, 2H), 0.45-0.39 (m, 2H).

Example 73: 1-[4-(N-methyl[2,4-dichloro-5-[([1-[4-(2-cyclopropoxyphenyl)pyridin-3-yl]cyclopropyl]amino)methyl]benzene]sulfonamido)butyl]-3-[(2S,3R,4R,5R)-2,3,4,5,6-pentahydroxyhexyl]urea (I-391)

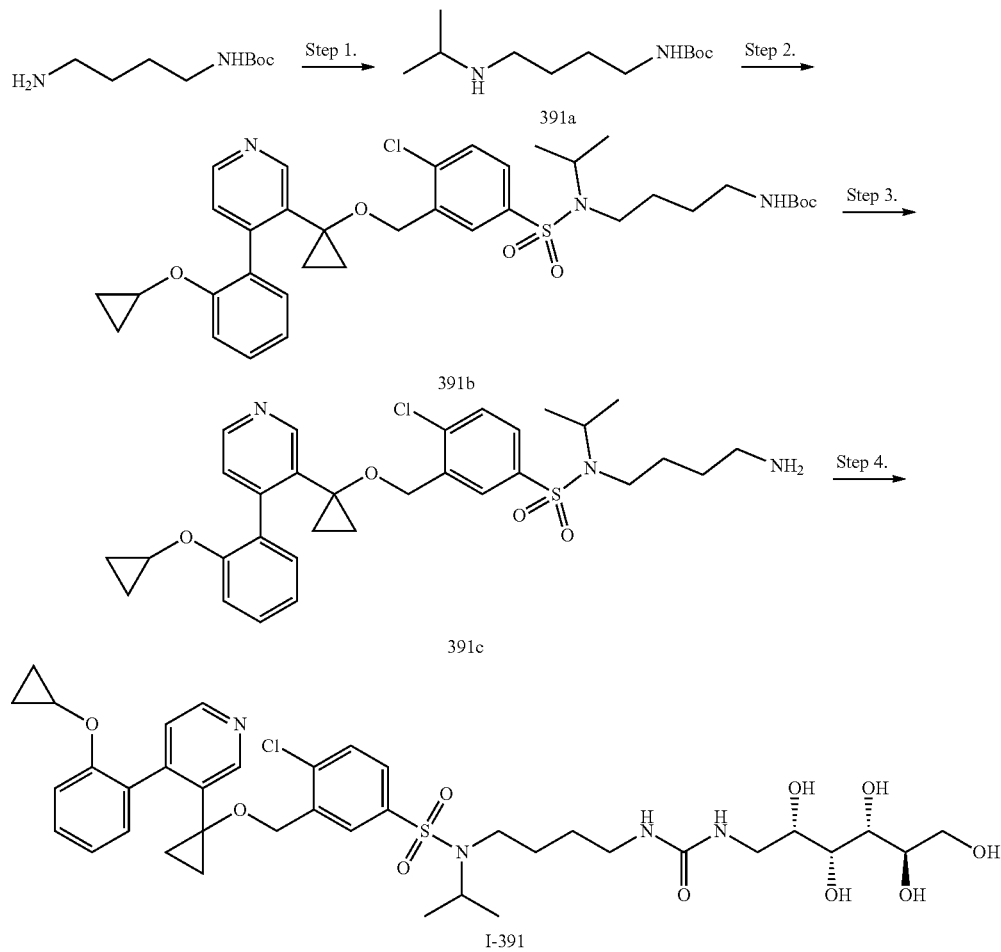

Step 1. tert-butyl N-[4-[(propan-2-yl)amino]butyl]carbamate (Intermediate 391a)

A 100-mL round-bottom flask was charged with tert-butyl N-(4-aminobutyl)carbamate (600 mg, 3.19 mmol, 1.00 equiv), dichloromethane (15 mL), propan-2-one (0.47 mL, 2.00 equiv). The resulting solution was stirred for 1 h at room temperature. To this was added NaBH(OAc)$_3$ (3.3 g, 15.57 mmol, 5.00 equiv). The resulting solution was stirred overnight at room temperature. The reaction was then quenched by the addition of 10 mL of water. The resulting solution was diluted with 15 mL of DCM. The pH value of the solution was adjusted to 9 with Na$_2$HCO$_3$ (100%). The resulting solution was extracted with 3×15 mL of dichloromethane and the organic layers combined and dried over anhydrous sodium sulfate. The solids were filtered out. The resulting mixture was concentrated under vacuum. This resulted in 630 mg (86%) of tert-butyl N-[4-[(propan-2-yl)amino]butyl]carbamate (391b) as yellow oil.

Step 2. tert-butyl N-[4-[N-(propan-2-yl)[4-chloro-3-([1-[4-(2-cyclopropoxyphenyl)pyridin-3-yl]cyclopropoxy]methyl)benzene]sulfonamido]butyl]carbamate (Intermediate 391b)

A 100-mL 3-necked round-bottom flask was charged with tert-butyl N-[4-[(propan-2-yl)amino]butyl]carbamate (391a, 188 mg, 0.82 mmol, 2.00 equiv), dichloromethane (10 mL), DIEA (0.08 mL, 1.20 equiv). This was followed by the addition of a solution of 4-chloro-3-([1-[4-(2-cyclopropoxyphenyl)pyridin-3-yl]cyclopropoxy]methyl)benzene-1-sulfonyl chloride (200 mg, 0.41 mmol, 1.00 equiv) in dichloromethane (3 mL) dropwise with stirring at 0° C. in 10 min. The resulting solution was stirred overnight at room temperature. The resulting mixture was concentrated under vacuum. The residue was applied onto a silica gel column with ethyl acetate/petroleum ether (1:1). This resulted in 116 mg (42%) of tert-butyl N-[4-[N-(propan-2-yl) [4-chloro-3-([1-[4-(2-cyclopropoxyphenyl)pyridin-3-yl]cyclopropoxy]methyl)benzene] sulfonamido]butyl]carbamate (391b) as light yellow oil.

Step 3. N-(4-aminobutyl)-4-chloro-3-([1-[4-(2-cyclopropoxyphenyl)pyridin-3-yl]cyclopropoxy]methyl)-N-(propan-2-yl)benzene-1-sulfonamide (Intermediate 391c)

A 50-mL round-bottom flask was charged with tert-butyl N-[4-[N-(propan-2-yl)[4-chloro-3-([1-[4-(2-cyclopropoxyphenyl)pyridin-3-yl]cyclopropoxy]methyl)benzene]sulfonamido]butyl]carbamate (391b, 116 mg, 0.17 mmol, 1.00 equiv), dichloromethane (2.5 Gil mL), trifluoroacetic acid (0.5 mL). The resulting solution was stirred for 30 min at room temperature. The pH value of the solution was adjusted to 9 with sodium bicarbonate (100%). The resulting solution was extracted with 2×10 mL of ethyl acetate and the organic layers combined and dried over anhydrous sodium sulfate and concentrated under vacuum. This resulted in 84 mg (85%) of N-(4-aminobutyl)-4-chloro-3-([1-[4-(2-cyclopropoxyphenyl)pyridin-3-yl]cyclopropoxy]methyl)-N-(propan-2-yl)benzene-1-sulfonamide (391c) as light yellow oil.

Step 4.3-[(2S,3R,4R,5R)-2,3,4,5,6-pentahydroxyhexyl]-1-[4-[N-(propan-2-yl)[4-chloro-3-([1-[4-(2-cyclopropoxyphenyl)pyridin-3-yl]cyclopropoxy]methyl)benzene]sulfonamido]butyl]urea (I-391)

A 50-mL round-bottom flask was charged with N-(4-aminobutyl)-4-chloro-3-([1-[4-(2-cyclopropoxyphenyl)pyridin-3-yl]cyclopropoxy]methyl)-N-(propan-2-yl)benzene-1-sulfonamide (391c, 84 mg, 0.14 mmol, 1.00 equiv), N,N-dimethylformamide (4 mL), DSC (44 mg, 1.20 equiv), DIEA (55.7 mg, 0.43 mmol, 3.00 equiv). The resulting solution was stirred for 1.5 h at room temperature. To this was added (2R,3R,4R,5S)-6-aminohexane-1,2,3,4,5-pentol (39 mg, 0.22 mmol, 1.50 equiv). The resulting solution was stirred overnight at room temperature. The solids were filtered out. The crude product was purified by Preparative HPLC with the following conditions: Column, XBridge C18 OBD Prep Column, 5 μm, 19 mm×250 mm; mobile phase, 10 mM aqueous $NH_4HCO_3$ and MeCN (30.0% MeCN up to 60.0% in 12 min); Detector, UV 254 nm. This resulted in 30.4 mg (27%) of 3-[(2S,3R,4R,5R)-2,3,4,5,6-pentahydroxyhexyl]-1-[4-[N-(propan-2-yl) [4-chloro-3-([1-[4-(2-cyclopropoxyphenyl)pyridin-3-yl]cyclopropoxy]methyl)benzene]sulfonamido]butyl]urea (I-391) as a white solid: (ES, m/z): [M+1]:791; $^1$H NMR (400 MHz, Methanol-$d_4$) δ 8.66 (s, 1H), 8.49 (d, J=5.0 Hz, 1H), 7.68 (dd, J=8.4, 2.3 Hz, 1H), 7.60 (d, J=2.2 Hz, 1H), 7.52 (d, J=8.3 Hz, 1H), 7.45-7.32 (m, 2H), 7.29-7.20 (m, 2H), 7.03 (td, J=7.3, 1.5 Hz, 1H), 4.46 (s, 2H), 3.97 (q, J=6.7 Hz, 1H), 3.81-3.51 (m, 7H), 3.40 (dd, J=13.9, 4.6 Hz, 1H), 3.22-3.05 (m, 4H), 1.68-1.59 (m, 2H), 1.48 (q, J=7.4 Hz, 2H), 1.01 (dd, J=15.4, 6.9 Hz, 11H), 0.59 (t, J=6.4 Hz, 2H), 0.39 (s, 2H).

Example 74: 1-[4-(N-methyl[2,4-dichloro-5-[([1-[4-(2-cyclopropoxyphenyl)pyridin-3-yl]cyclopropyl]amino)methyl]benzene]sulfonamido)butyl]-3-[(2S,3R,4R,5R)-2,3,4,5,6-pentahydroxyhexyl]urea (I-392)

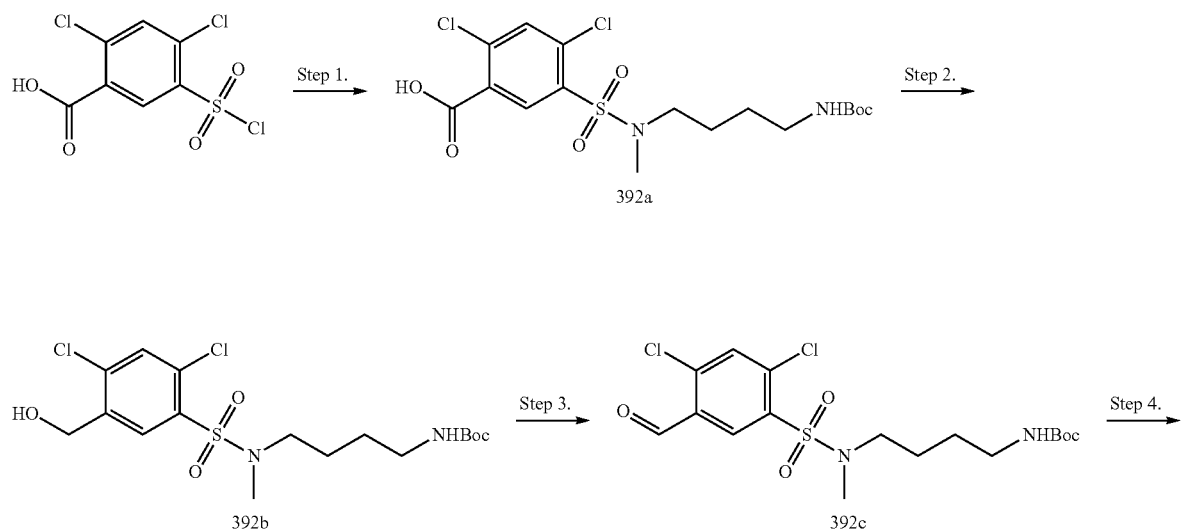

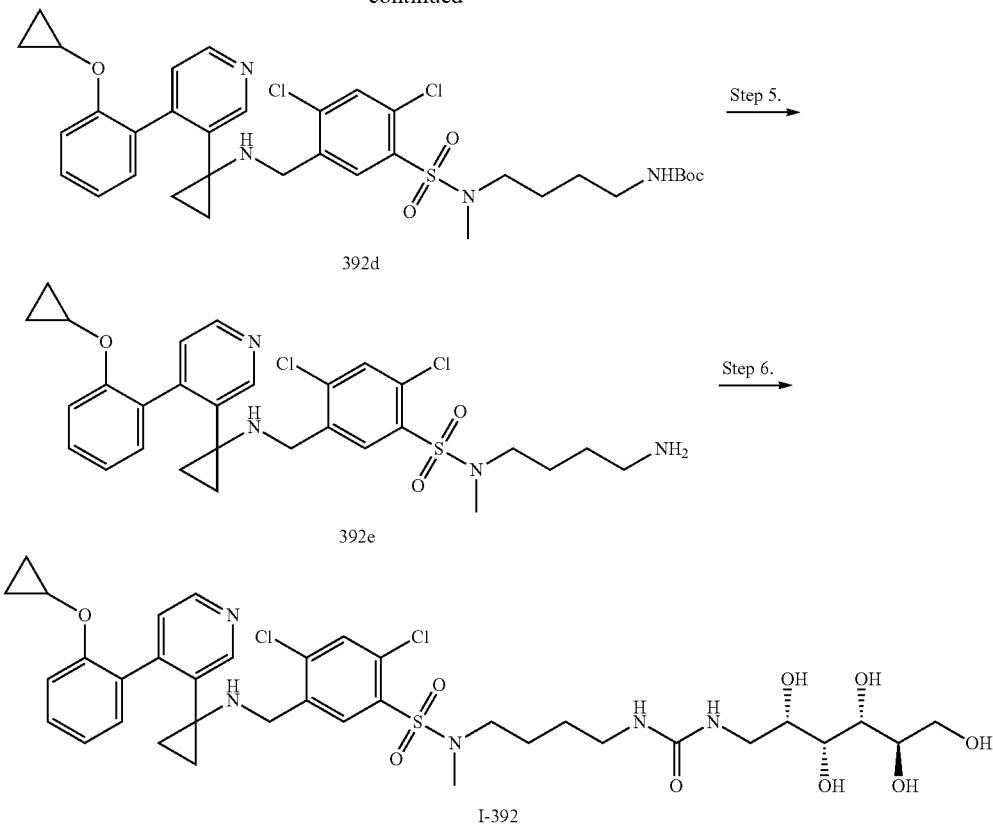

Step 1. 5-[(4-[[(tert-butoxy)carbonyl]amino]butyl)(methyl)sulfamoyl]-2,4-dichlorobenzoic acid (Intermediate 392a)

A 50-mL round-bottom flask was charged with 2,4-dichloro-5-(chlorosulfonyl)benzoic acid (700 mg, 2.42 mmol, 1.00 equiv), dichloromethane (20 mL), tert-butyl N-[4-(methylamino)butyl]carbamate (327.7 mg, 1.62 mmol, 0.67 equiv), TEA (0.32 mL). The resulting solution was stirred for 5 h at room temperature. The resulting solution was diluted with 50 mL of DCM. The reaction was then quenched by the addition of 50 mL of water. The resulting solution was extracted with 2×50 mL of dichloromethane and the organic layers combined. The resulting mixture was washed with 2×50 mL of Brine. The mixture was dried over anhydrous sodium sulfate. The solids were filtered out. The resulting mixture was concentrated under vacuum. The residue was applied onto a silica gel column with dichloromethane/methanol (10:1). This resulted in 700 mg (64%) of 5-[(4-[[(tert-butoxy)carbonyl]amino]butyl)(methyl)sulfamoyl]-2,4-dichlorobenzoic acid (392a) as a white solid.

Step 2. tert-butyl N-(4-[N-methyl[2,4-dichloro-5-(hydroxymethyl)benzene]sulfonamido]butyl)carbamate (Intermediate 392b)

A 50-mL round-bottom flask purged and maintained under an inert atmosphere of nitrogen was charged with 5-[(4-[[(tert-butoxy)carbonyl]amino]butyl)(methyl)sulfamoyl]-2,4-dichlorobenzoic acid (392a, 630 mg, 1.38 mmol, 1.00 equiv), oxolane (10 mL). This was followed by the addition of B2H6/THF (1M, 4.15 mL, 3.00 equiv) dropwise with stirring at 0° C. The resulting solution was stirred for 2.0 h at 40° C. in an oil bath. The reaction was then quenched by the addition of 10 mL of methanol. The resulting mixture was concentrated under vacuum. The residue was applied onto a silica gel column with ethyl acetate/petroleum ether (1:2). This resulted in 360 mg (59%) of tert-butyl N-(4-[N-methyl[2,4-dichloro-5-(hydroxymethyl)benzene]sulfonamido]butyl)carbamate (392b) as yellow oil.

Step 3. tert-butyl N-[4-[N-methyl(2,4-dichloro-5-formylbenzene)sulfonamido]butyl]carbamate (Intermediate 392c)

A 50-mL round-bottom flask was charged with tert-butyl N-(4-[N-methyl[2,4-dichloro-5-(hydroxymethyl)benzene]sulfonamido]butyl)carbamate (392b, 270 mg, 0.61 mmol, 1.00 equiv), chloroform (10 mL), MnO2 (798 mg, 9.18 mmol, 15.00 equiv). The resulting solution was stirred overnight at 60° C. The solids were filtered out. The resulting mixture was concentrated under vacuum. This resulted in 250 mg (93%) of tert-butyl N-[4-[N-methyl(2,4-dichloro-5-formylbenzene)sulfonamido]butyl]carbamate (392c) as light yellow oil Step 4. tert-butyl N-[4-(N-methyl[2,4-dichloro-5-[([1-[4-(2-cyclopropoxyphenyl)pyridin-3-yl]cyclopropyl]amino)methyl]benzene]sulfonamido)butyl]carbamate (Intermediate 392d)

A 50-mL round-bottom flask was charged with tert-butyl N-[4-[N-methyl(2,4-dichloro-5-formylbenzene)sulfonamido]butyl]carbamate (392c, 250 mg, 0.57 mmol, 1.00 equiv), 1-[4-(2-cyclopropoxyphenyl)pyridin-3-yl]cyclopropan-1-amine (151 mg, 0.57 mmol, 1.00 equiv), dichloromethane (10 mL), NaBH(OAc)3 (724 mg, 6.00 equiv).

The resulting solution was stirred overnight at room temperature. The reaction was then quenched by the addition of 10 mL of water. The resulting solution was extracted with 3×20 mL of dichloromethane and the organic layers combined and dried over anhydrous sodium sulfate and concentrated under vacuum. The residue was applied onto a silica gel column with ethyl acetate/petroleum ether (1:1). The collected fractions were combined and concentrated under vacuum. This resulted in 320 mg (82%) of tert-butyl N-[4-(N-methyl[2,4-dichloro-5-[([1-[4-(2-cyclopropoxyphenyl)pyridin-3-yl]cyclopropyl]amino)methyl]benzene]sulfonamido)butyl]carbamate (392d) as light yellow oil.

Step 5. N-(4-aminobutyl)-2,4-dichloro-5-[([1-[4-(2-cyclopropoxyphenyl)pyridin-3-yl] cyclopropyl] amino)methyl]-N-methylbenzene-1-sulfonamide (Intermediate 392e)

A 25-mL round-bottom flask was charged with tert-butyl N-[4-(N-methyl[2,4-dichloro-5-[([1-[4-(2-cyclopropoxyphenyl)pyridin-3-yl]cyclopropyl]amino)methyl]benzene] sulfonamido)butyl]carbamate (320 mg, 0.46 mmol, 1.00 equiv), dichloromethane (3 mL), trifluoroacetic acid (2 mL). The resulting solution was stirred for 0.5 h at room temperature. The pH value of the solution was adjusted to 9 with sodium bicarbonate. The residue was applied onto a silica gel column with dichloromethane/methanol (30:1). The collected fractions were combined and concentrated under vacuum. This resulted in 240 mg (88%) of N-(4-aminobutyl)-2,4-dichloro-5-[([1-[4-(2-cyclopropoxyphenyl)pyridin-3-yl]cyclopropyl]amino)methyl]-N-methylbenzene-1-sulfonamide (392e) as light yellow oil.

Step 6. 1-[4-(N-methyl[2,4-dichloro-5-[([1-[4-(2-cyclopropoxyphenyl)pyridin-3-yl]cyclopropyl] amino)methyl]benzene]sulfonamido)butyl]-3-[(2S,3R,4R,5R)-2,3,4,5,6-pentahydroxyhexyl]urea (I-392)

A 8-mL vial purged and maintained under an inert atmosphere of nitrogen was charged with N-(4-aminobutyl)-2,4-dichloro-5-[([1-[4-(2-cyclopropoxyphenyl)pyridin-3-yl]cyclopropyl]amino)methyl]-N-methylbenzene-1-sulfonamide (100 mg, 0.17 mmol, 1.00 equiv), DSC (52.2 mg, 0.20 mmol, 1.20 equiv), N,N-dimethylformamide (3 mL). This was followed by the addition of DIEA (26.68 mg, 0.22 mmol, 1.30 equiv). The mixture was stirring for 1.5 h at rt. To this was added (2R,3R,4R,5S)-6-aminohexane-1,2,3,4,5-pentol (30.81 mg, 0.17 mmol, 1.00 equiv). The resulting solution was stirred overnight at room temperature. The crude product was purified by Preparative HPLC with the following conditions: Column, XBridge C18 OBD Prep Column, 5 μm, 19 mm×250 mm; mobile phase, 10 mM aqueous NH$_4$HCO$_3$ and MeCN (35.0% MeCN up to 50.0% in 10 min); Detector, UV 254 nm. This resulted in 28.6 mg (21%) of 1-[4-(N-methyl[2,4-dichloro-5-[([1-[4-(2-cyclopropoxyphenyl)pyridin-3-yl]cyclopropyl]amino)methyl]benzene]sulfonamido)butyl]-3-[(2S,3R,4R,5R)-2,3,4,5,6-pentahydroxyhexyl]urea (I-392) as a white solid: MS (ES, m/z): [M+1]: 796; $^1$H NMR (400 MHz, Methanol-d$_4$) δ 0.39-0.45 (m, 2H), 0.66 (d, J=6.5 Hz, 2H), 0.81 (s, 2H), 0.90 (s, 2H), 1.46 (p, J=7.0 Hz, 2H), 1.59 (p, J=7.1 Hz, 2H), 2.82 (s, 3H), 3.06-3.26 (m, 5H), 3.39 (dd, J=13.9, 4.5 Hz, 1H), 3.57-3.81 (m, 9H), 4.58 (s, 1H), 7.06-7.20 (m, 2H), 7.21-7.29 (m, 1H), 7.43-7.51 (m, 2H), 7.65 (s, 1H), 7.92 (s, 1H), 8.46 (d, J=5.0 Hz, 1H), 8.56 (s, 1H).

Example 75: 4-chloro-3-([1-[4-(2-cyclopropoxyphenyl)pyridin-3-yl]cyclopropoxy]methyl)-N,N-dimethylbenzene-1-sulfonamide (I-393)

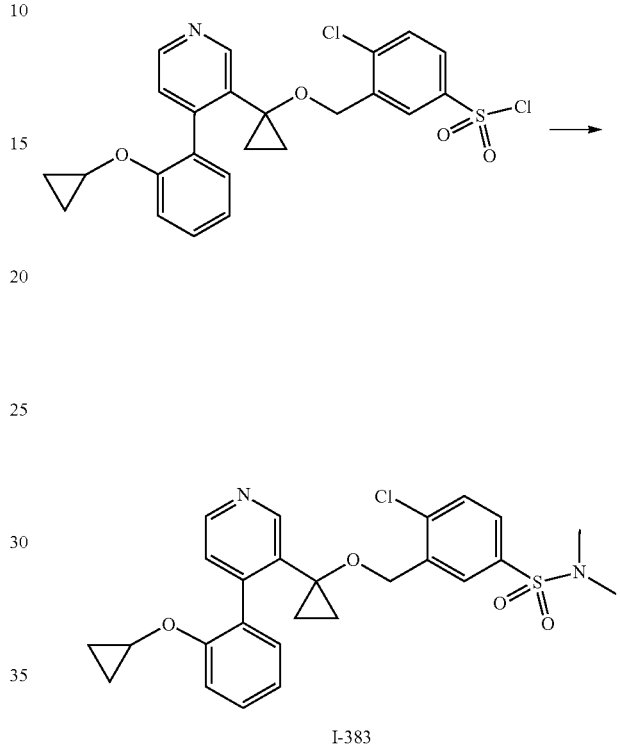

I-383

A 50-mL round-bottom flask was charged with dimethylamine/ethanol (0 mg). The solution cooled to 0° C. This was followed by the addition of 4-chloro-3-([1-[4-(2-cyclopropoxyphenyl)pyridin-3-yl]cyclopropoxy]methyl)benzene-1-sulfonyl chloride (200 mg, 0.41 mmol, 1.00 equiv) dropwise with stirring at 0° C. The resulting solution was stirred for 10 min at room temperature. The resulting solution was extracted with 100 mL of ethyl acetate and the organic layers combined. The resulting mixture was washed with 2×20 mL of brine. The mixture was dried over anhydrous sodium sulfate and concentrated under vacuum. The crude product was purified by preparative HPLC with the following conditions: Column; mobile phase, 10 mM aqueous NH$_4$HCO$_3$ and MeCN (52.0% MeCN up to 73.0% in 8 min); Detector, UV 220 nm. The desired product, 4-chloro-3-([1-[4-(2-cyclopropoxyphenyl)pyridin-3-yl] cyclopropoxy]methyl)-N,N-dimethylbenzene-1-sulfonamide, (I-393, 9.0 mg, 39%) was isolated as a white solid. MS (ES, m/z): [M+1]=499.20; $^1$H-NMR (CD$_3$OD, ppm): δ 8.66 (d, J=0.7 Hz, 1H), 8.49 (d, J=5.1 Hz, 1H), 7.67-7.53 (m, 3H), 7.42-7.30 (m, 2H), 7.30-7.19 (m, 2H), 7.01 (ddd, J=7.5, 6.6, 1.9 Hz, 1H), 4.48 (s, 2H), 3.57 (tt, J=6.0, 2.9 Hz, 1H), 2.64 (s, 6H), 1.06-0.93 (m, 4H), 0.66-0.56 (m, 2H), 0.43-0.35 (m, 2H).

Compounds I-394 to I-479 (Table 14) were prepared from commercial, known starting materials or the appropriate intermediates disclosed herein using methods from the examples specified in Table 14 and methods generally known to those skilled in the art.

TABLE 14
Compounds I-394 to I-479
| Cmpd no.: | Synthetic Method | Compound Structure | Obs Mass [M + H]² |
|---|---|---|---|
| I-394 | Example 75 | 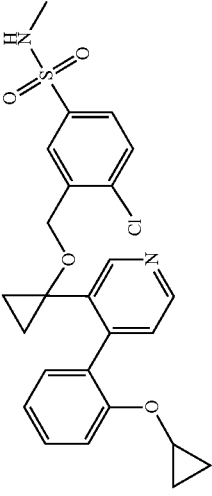 | 485.20 |
| I-395 | Example 75 | 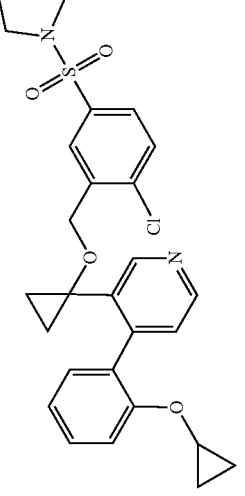 | 525.15 |
| I-396 | Example 75 | 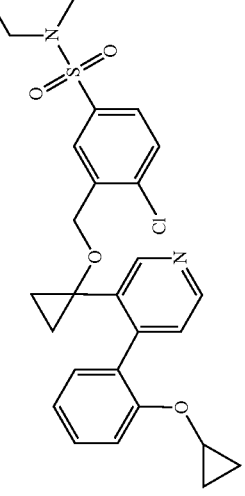 | 539.25 |

TABLE 14-continued

Compounds I-394 to I-479

| Cmpd no.: | Synthetic Method | Compound Structure | Obs Mass [M + H]$^2$ |
|---|---|---|---|
| I-397 | Example 75 | 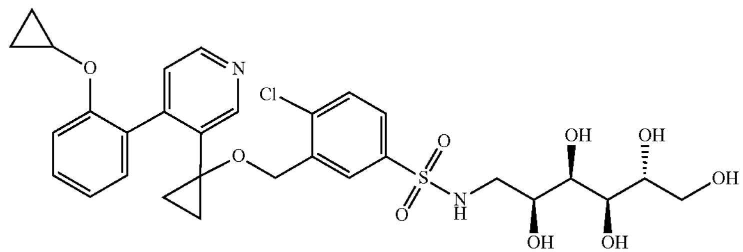 [SMILES: O=S(=O)(NC[C@H](O)[C@@H](O)[C@H](O)[C@H](O)CO)c1ccc(Cl)c(COC2(c3cnccc3-c3ccccc3OC3CC3)CC2)c1] | 635.25 |
| I-398 | Example 75 | 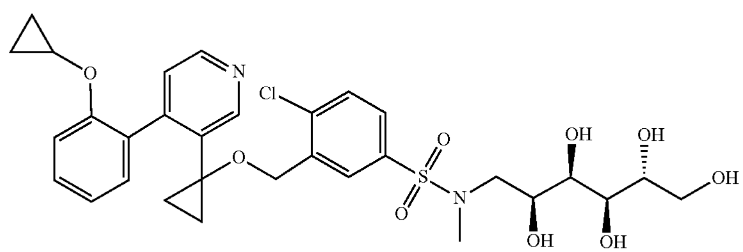 [SMILES: CN(C[C@H](O)[C@@H](O)[C@H](O)[C@H](O)CO)S(=O)(=O)c1ccc(Cl)c(COC2(c3cnccc3-c3ccccc3OC3CC3)CC2)c1] | 649.25 |
| I-399 | Example 75 | 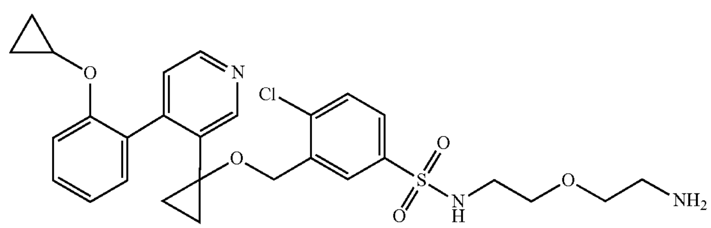 [SMILES: NCCOCCNS(=O)(=O)c1ccc(Cl)c(COC2(c3cnccc3-c3ccccc3OC3CC3)CC2)c1] | 558.25 |
| I-400 | Example 75 | 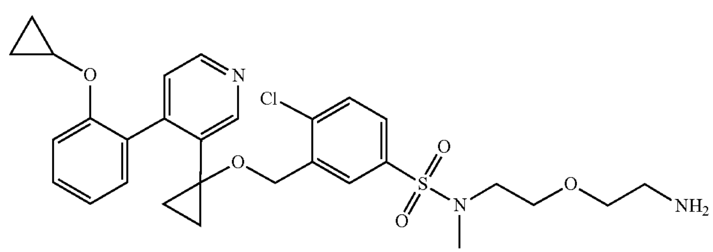 [SMILES: CN(CCOCCN)S(=O)(=O)c1ccc(Cl)c(COC2(c3cnccc3-c3ccccc3OC3CC3)CC2)c1] | 594.25 [M + Na] |

TABLE 14-continued

Compounds I-394 to I-479

| Cmpd no.: | Synthetic Method | Compound Structure | Obs Mass [M + H]$^2$ |
|---|---|---|---|
| I-401 | Example 72 | 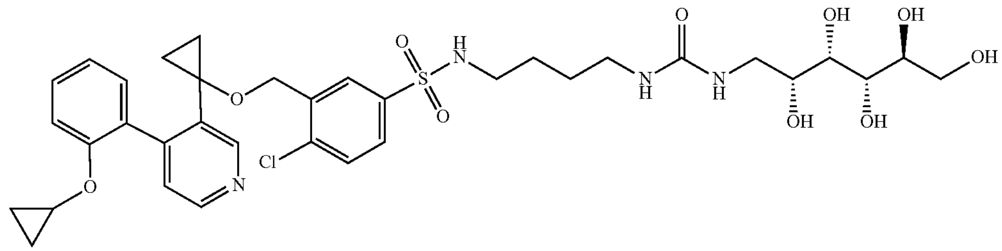 [SMILES: O=C(NCCCCNS(=O)(=O)c1ccc(Cl)c(COC2(c3cnccc3-c3ccccc3OC3CC3)CC2)c1)NC[C@@H](O)[C@H](O)[C@@H](O)[C@@H](O)CO] | 749.45 |
| I-402 | Example 71 | 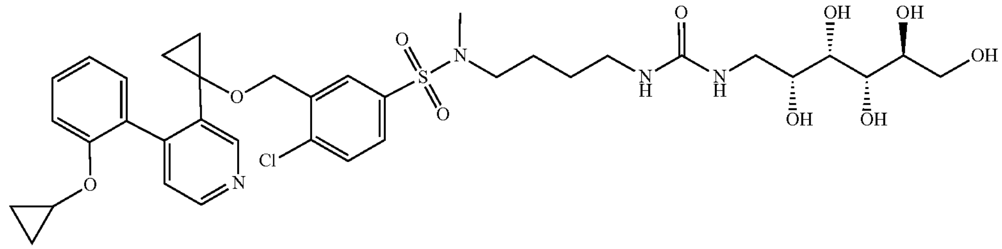 [SMILES: CN(CCCCNC(=O)NC[C@@H](O)[C@H](O)[C@@H](O)[C@@H](O)CO)S(=O)(=O)c1ccc(Cl)c(COC2(c3cnccc3-c3ccccc3OC3CC3)CC2)c1] | 763.35 |
| I-403 | Example 72 | 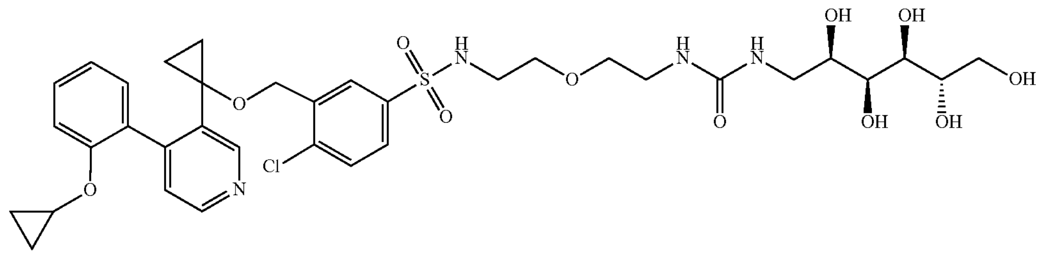 [SMILES: O=C(NCCOCCNS(=O)(=O)c1ccc(Cl)c(COC2(c3cnccc3-c3ccccc3OC3CC3)CC2)c1)NC[C@@H](O)[C@H](O)[C@@H](O)[C@@H](O)CO] | 765.40 |
| I-404 | Example 72 | 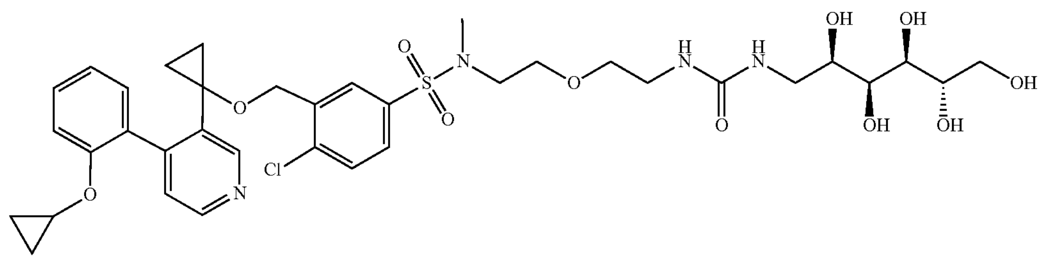 [SMILES: CN(CCOCCNC(=O)NC[C@@H](O)[C@H](O)[C@@H](O)[C@@H](O)CO)S(=O)(=O)c1ccc(Cl)c(COC2(c3cnccc3-c3ccccc3OC3CC3)CC2)c1] | 779.40 |

TABLE 14-continued

Compounds I-394 to I-479

| Cmpd no.: | Synthetic Method | Compound Structure | Obs Mass [M + H]² |
|---|---|---|---|
| I-405 | Example 72 | 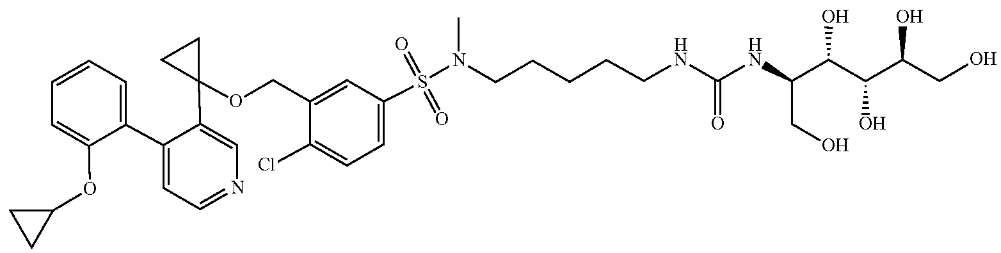 [SMILES: CN(CCCCCNC(=O)N[C@H](CO)[C@H](O)[C@@H](O)[C@@H](O)CO)S(=O)(=O)c1ccc(Cl)c(COC2(c3cnccc3-c3ccccc3OC3CC3)CC2)c1] | 777.35 |
| I-406 | Example 72 | 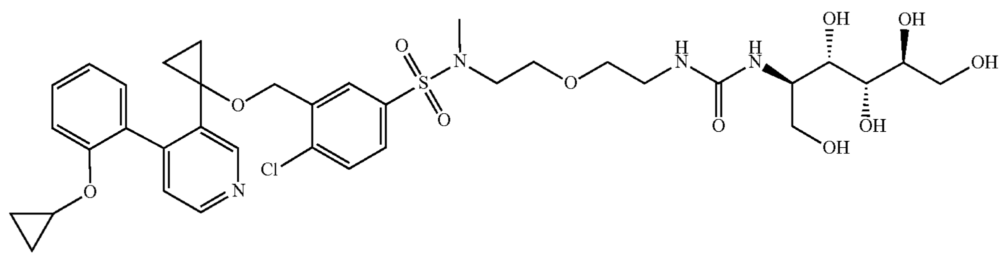 [SMILES: CN(CCOCCNC(=O)N[C@H](CO)[C@H](O)[C@@H](O)[C@@H](O)CO)S(=O)(=O)c1ccc(Cl)c(COC2(c3cnccc3-c3ccccc3OC3CC3)CC2)c1] | 779.35 |
| I-407 | Example 72 | 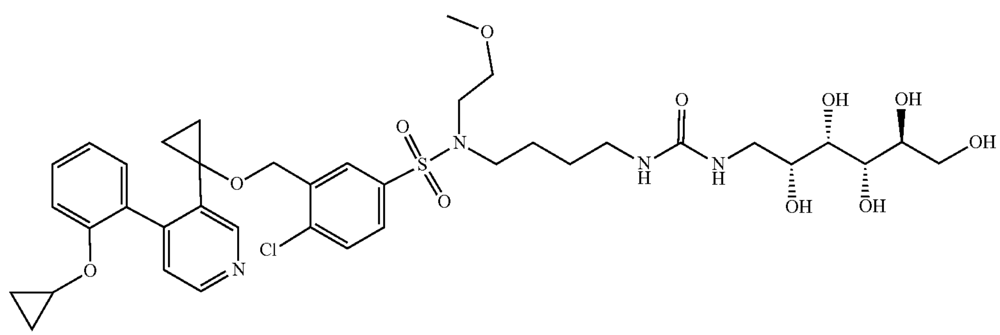 [SMILES: COCCN(CCCCNC(=O)NC[C@@H](O)[C@H](O)[C@@H](O)[C@@H](O)CO)S(=O)(=O)c1ccc(Cl)c(COC2(c3cnccc3-c3ccccc3OC3CC3)CC2)c1] | 807.30 |

TABLE 14-continued

Compounds I-394 to I-479

| Cmpd no.: | Synthetic Method | Compound Structure | Obs Mass [M + H]² |
|---|---|---|---|
| I-408 | Example 72 | 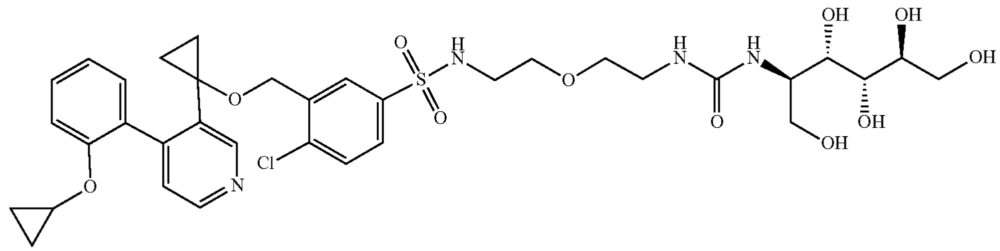 [SMILES: O=C(NCCOCCNS(=O)(=O)c1ccc(Cl)c(COC2(c3cnccc3-c3ccccc3OC3CC3)CC2)c1)N[C@H](CO)[C@H](O)[C@@H](O)[C@@H](O)CO] | 765.25 |
| I-409 | Example 72 | 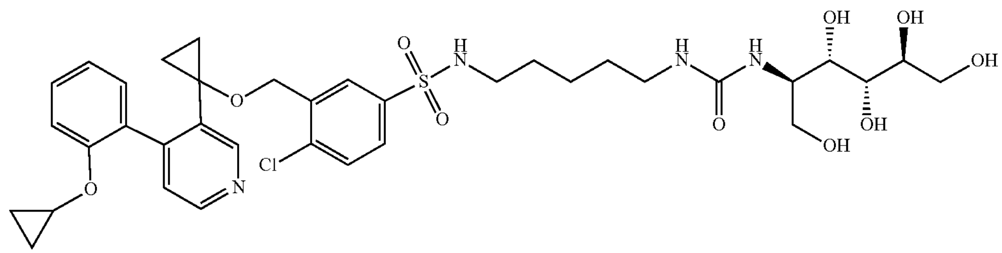 [SMILES: O=C(NCCCCCNS(=O)(=O)c1ccc(Cl)c(COC2(c3cnccc3-c3ccccc3OC3CC3)CC2)c1)N[C@H](CO)[C@H](O)[C@@H](O)[C@@H](O)CO] | 763.25 |
| I-410 | Example 72 | 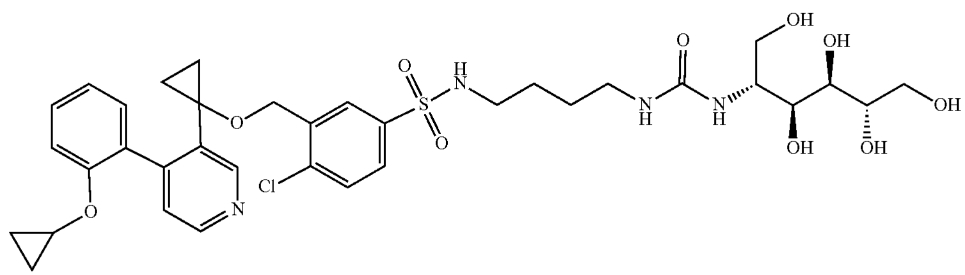 [SMILES: O=C(NCCCCNS(=O)(=O)c1ccc(Cl)c(COC2(c3cnccc3-c3ccccc3OC3CC3)CC2)c1)N[C@H](CO)[C@H](O)[C@@H](O)[C@@H](O)CO] | 749.30 |

TABLE 14-continued

Compounds I-394 to I-479

| Cmpd no.: | Synthetic Method | Compound Structure | Obs Mass [M + H]$^2$ |
|---|---|---|---|
| I-411 | Example 72 | 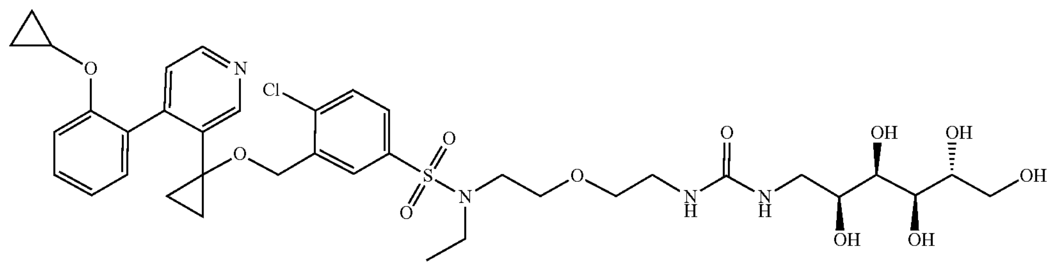 [SMILES: CCN(CCOCCNC(=O)NC[C@H](O)[C@@H](O)[C@H](O)[C@H](O)CO)S(=O)(=O)c1ccc(Cl)c(COC2(c3cnccc3-c3ccccc3OC3CC3)CC2)c1] | 793.50 |
| I-412 | Example 72 | 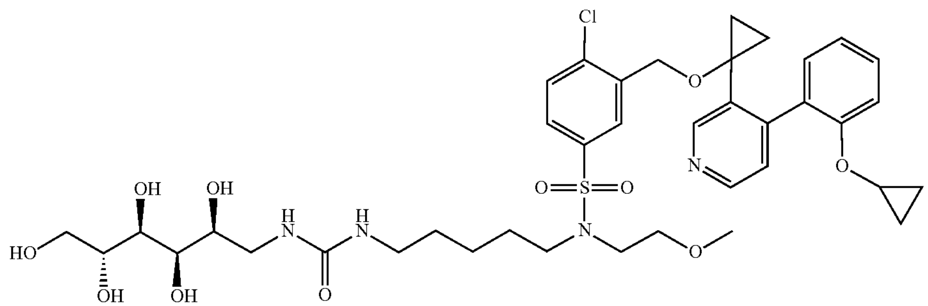 [SMILES: COCCN(CCCCCNC(=O)NC[C@H](O)[C@@H](O)[C@H](O)[C@H](O)CO)S(=O)(=O)c1ccc(Cl)c(COC2(c3cnccc3-c3ccccc3OC3CC3)CC2)c1] | 821.60 |
| I-413 | Example 72 | 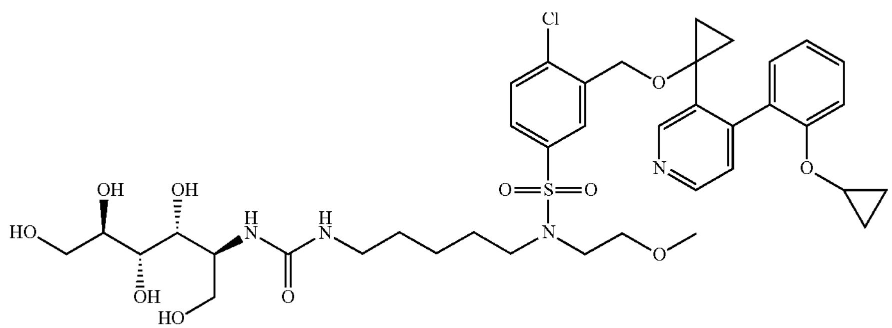 [SMILES: COCCN(CCCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CC2)c1] | 821.25 |

TABLE 14-continued

Compounds I-394 to I-479

| Cmpd no.: | Synthetic Method | Compound Structure | Obs Mass [M + H]² |
|---|---|---|---|
| I-414 | Example 72 | 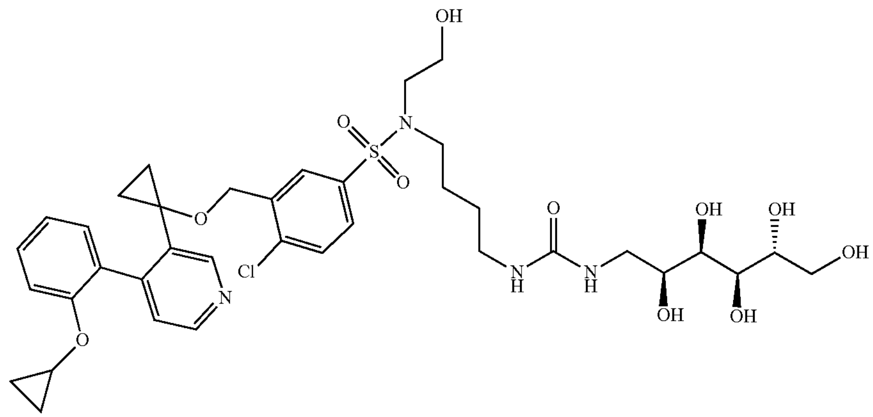 [SMILES: O=C(NCCCCN(CCO)S(=O)(=O)c1ccc(Cl)c(COC2(c3cnccc3-c3ccccc3OC3CC3)CC2)c1)NC[C@H](O)[C@@H](O)[C@H](O)[C@H](O)CO] | 793.2 |
| I-415 | Example 72 | 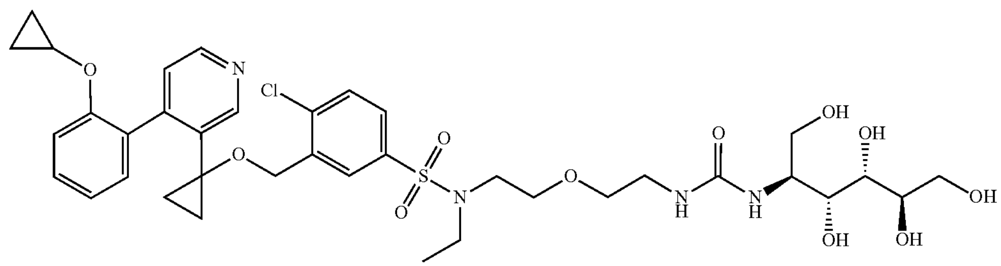 [SMILES: CCN(CCOCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CC2)c1] | 793.40 |
| I-416 | Example 72 | 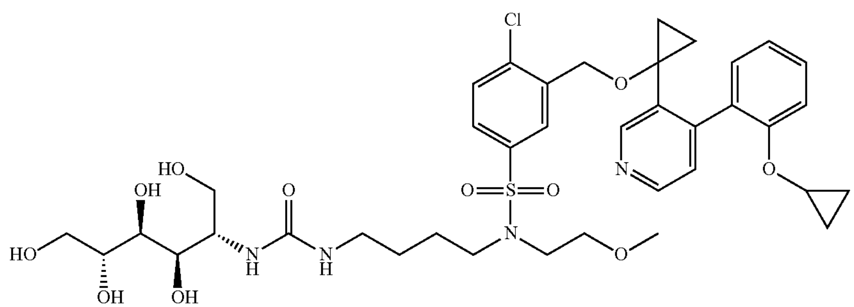 [SMILES: COCCN(CCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CC2)c1] | |

TABLE 14-continued
Compounds I-394 to I-479
| Cmpd no.: | Synthetic Method | Compound Structure | Obs Mass [M + H]² |
|---|---|---|---|
| I-417 | Example 72 | 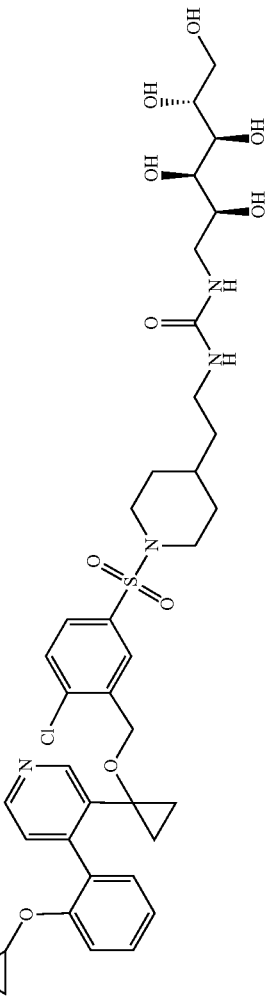 | 789.45 |
| I-418 | Example 72 | 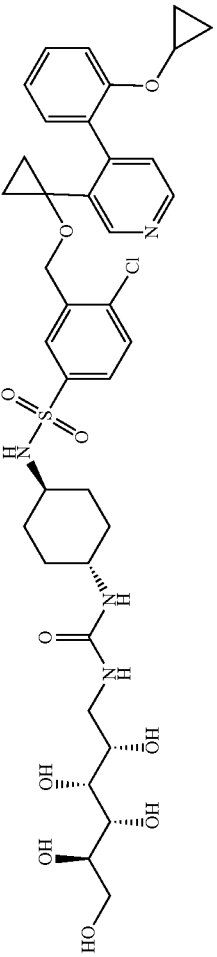 | 775.35 |
| I-419 | Example 72 | 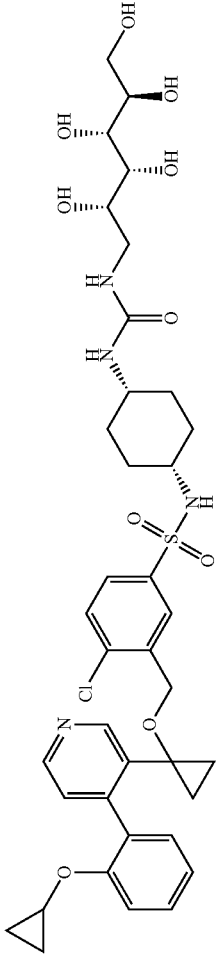 | 388.15 [M/2 + H] |

TABLE 14-continued

Compounds I-394 to I-479

| Cmpd no.: | Synthetic Method | Compound Structure | Obs Mass [M + H]$^2$ |
|---|---|---|---|
| I-420 | Example 72 | 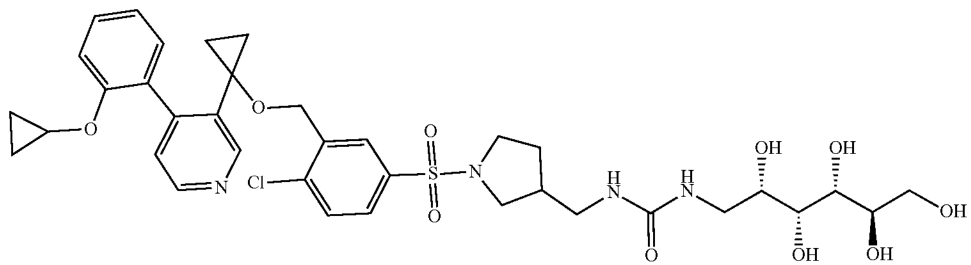 [SMILES: O=C(NCC1CCN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 761.3 |
| I-421 | Example 72 | 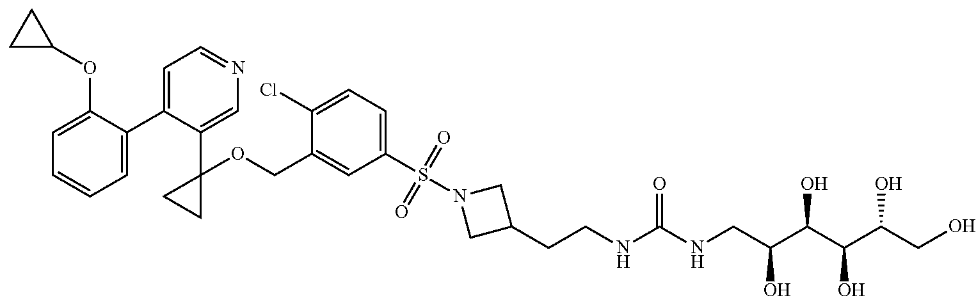 [SMILES: O=C(NCCC1CN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 761.3 |
| I-422 | Example 72 | 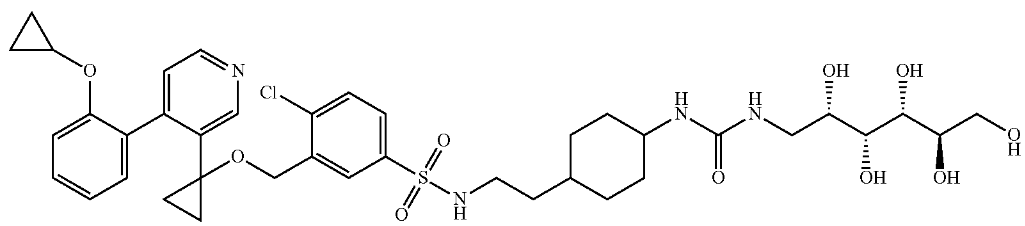 [SMILES: O=C(NC[C@H](O)[C@@H](O)[C@H](O)[C@H](O)CO)NC1CCC(CCNS(=O)(=O)c2ccc(Cl)c(COC3(c4cnccc4-c4ccccc4OC4CC4)CC3)c2)CC1] | 803.3 |

TABLE 14-continued

Compounds I-394 to I-479

| Cmpd no.: | Synthetic Method | Compound Structure | Obs Mass [M + H]$^2$ |
|---|---|---|---|
| I-423 | Example 72 | 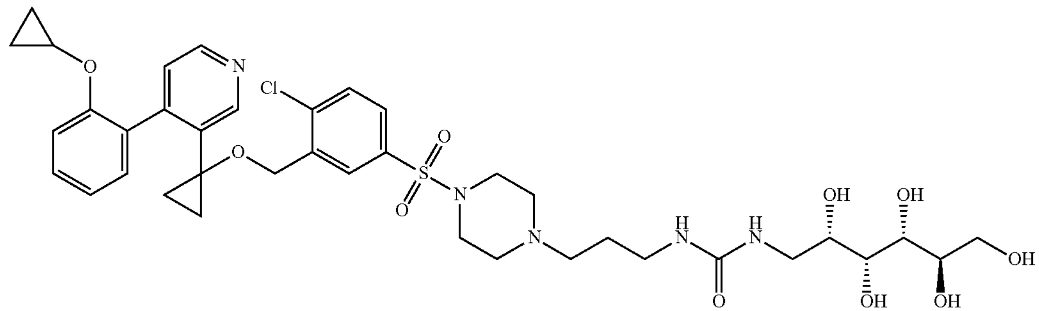 [SMILES: O=C(NCCCN1CCN(S(=O)(=O)c2ccc(Cl)c(COC3(c4cnccc4-c4ccccc4OC4CC4)CC3)c2)CC1)NC[C@H](O)[C@@H](O)[C@H](O)[C@H](O)CO] | 804.50 |
| I-424 | Example 72 | 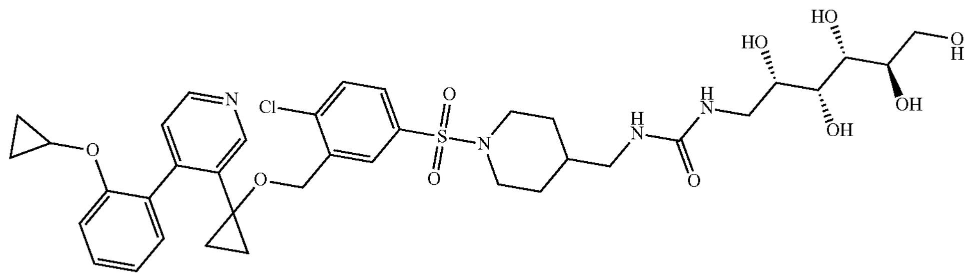 [SMILES: O=C(NCC1CCN(S(=O)(=O)c2ccc(Cl)c(COC3(c4cnccc4-c4ccccc4OC4CC4)CC3)c2)CC1)NC[C@H](O)[C@@H](O)[C@H](O)[C@H](O)CO] | 775.50 |
| I-425 | Example 72 | 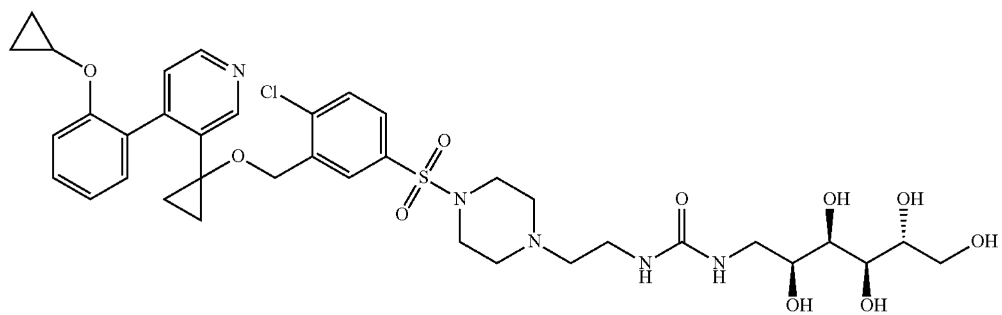 [SMILES: O=C(NCCN1CCN(S(=O)(=O)c2ccc(Cl)c(COC3(c4cnccc4-c4ccccc4OC4CC4)CC3)c2)CC1)NC[C@H](O)[C@@H](O)[C@H](O)[C@H](O)CO] | 790.25 |

TABLE 14-continued

Compounds I-394 to I-479

| Cmpd no.: | Synthetic Method | Compound Structure | Obs Mass [M + H]$^2$ |
|---|---|---|---|
| I-426 | Example 72 | 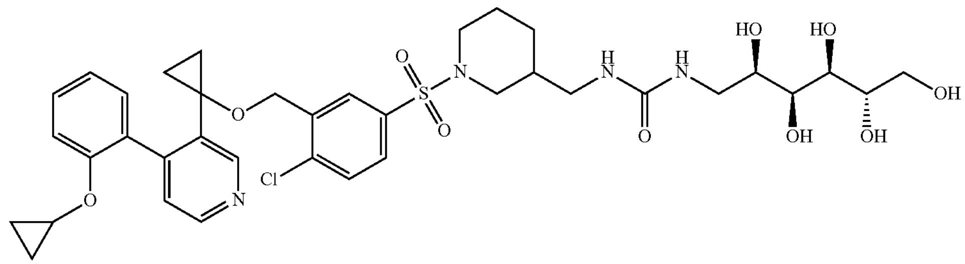 [SMILES: O=C(NCC1CCCN(S(=O)(=O)c2ccc(Cl)c(COC3(c4cnccc4-c4ccccc4OC4CC4)CC3)c2)C1)NC[C@@H](O)[C@H](O)[C@@H](O)[C@@H](O)CO] | 775.45 |
| I-427 | Example 72 | 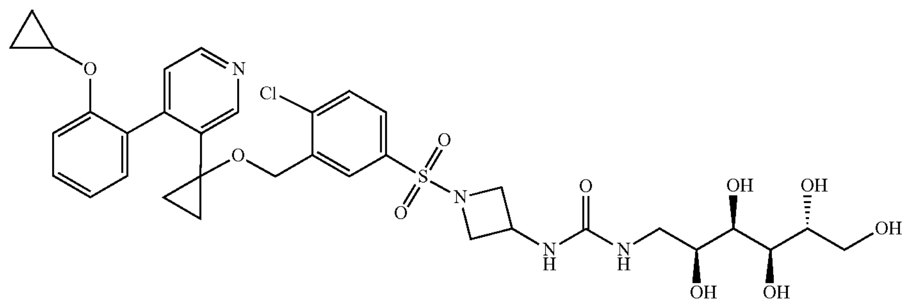 [SMILES: CC1CC1Oc1ccccc1-c1ccncc1C1(OCc2cc(S(=O)(=O)N3CC(NC(=O)NC[C@H](O)[C@@H](O)[C@H](O)[C@H](O)CO)C3)ccc2Cl)CC1] | 733.30 |
| I-428 | Example 72 | 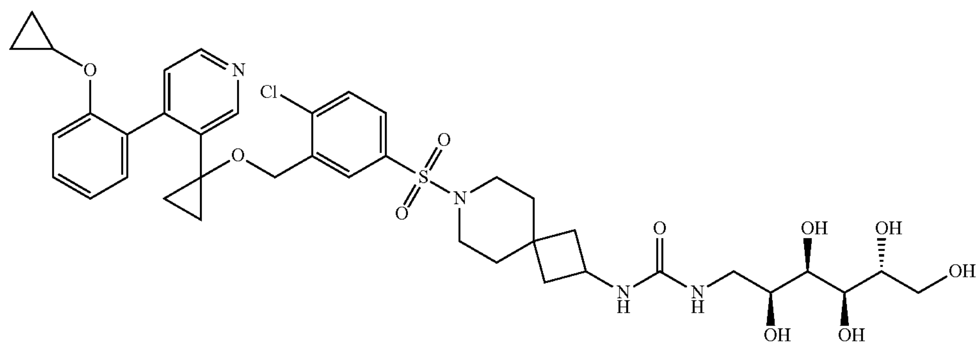 [SMILES: O=C(NC[C@H](O)[C@@H](O)[C@H](O)[C@H](O)CO)NC1CC2(CCN(S(=O)(=O)c3ccc(Cl)c(COC4(c5cnccc5-c5ccccc5OC5CC5)CC4)c3)CC2)C1] | 801.30 |

TABLE 14-continued

Compounds I-394 to I-479

| Cmpd no.: | Synthetic Method | Compound Structure | Obs Mass [M + H]$^2$ |
|---|---|---|---|
| I-429 | Example 72 | 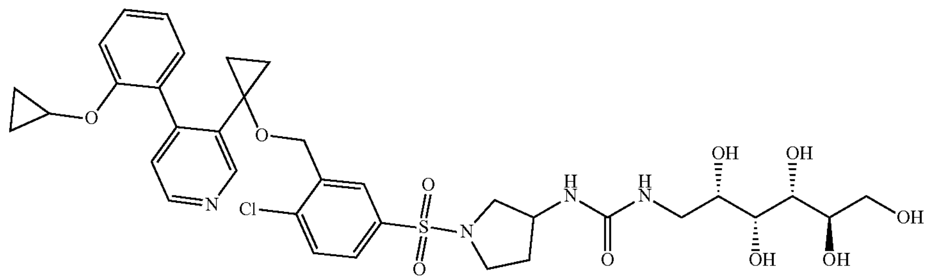 [SMILES: O=C(NC[C@H](O)[C@@H](O)[C@H](O)[C@H](O)CO)NC1CCN(S(=O)(=O)c2ccc(Cl)c(COC3(c4cnccc4-c4ccccc4OC4CC4)CC3)c2)C1] | 747.45 |
| I-430 | Example 72 | 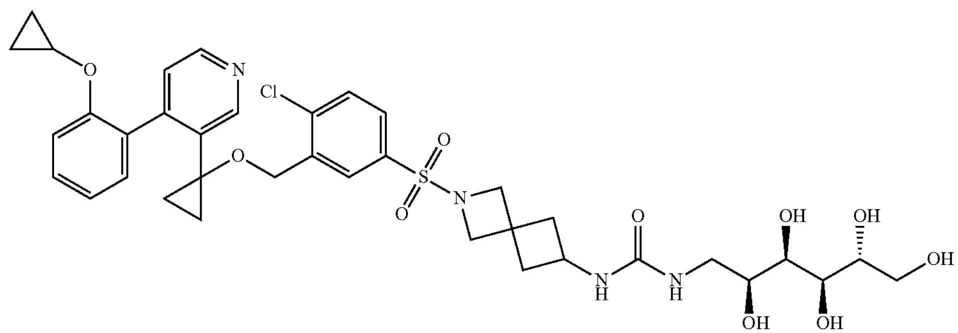 [SMILES: O=C(NC[C@H](O)[C@@H](O)[C@H](O)[C@H](O)CO)NC1CC2(C1)CN(S(=O)(=O)c1ccc(Cl)c(COC3(c4cnccc4-c4ccccc4OC4CC4)CC3)c1)C2] | 773.40 |
| I-431 | Example 70 | 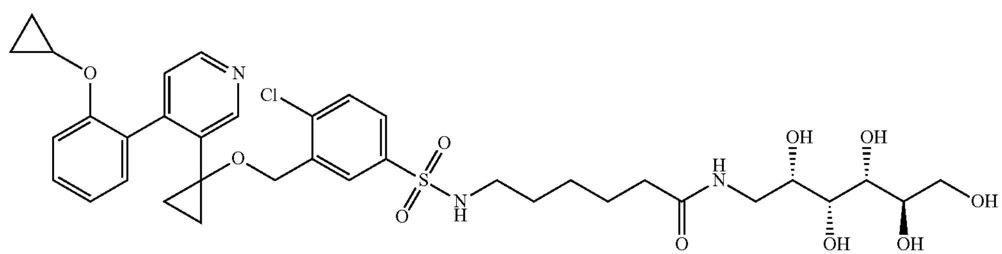 [SMILES: O=C(CCCCCNS(=O)(=O)c1ccc(Cl)c(COC2(c3cnccc3-c3ccccc3OC3CC3)CC2)c1)NC[C@H](O)[C@@H](O)[C@H](O)[C@H](O)CO] | |

TABLE 14-continued

Compounds I-394 to I-479

| Cmpd no.: | Synthetic Method | Compound Structure | Obs Mass [M + H]² |
|---|---|---|---|
| I-432 | Example 70 | 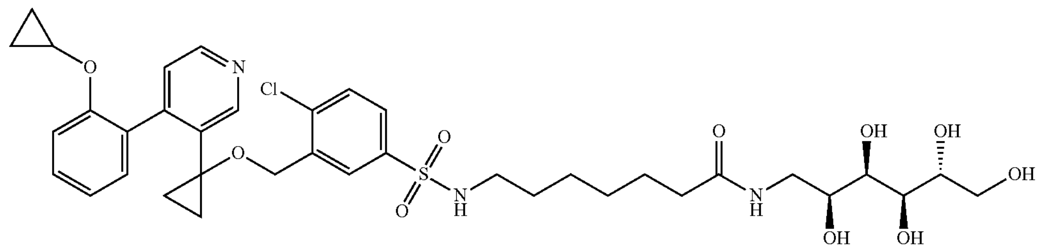 [SMILES: O=C(CCCCCCNS(=O)(=O)c1ccc(Cl)c(COC2(c3cnccc3-c3ccccc3OC3CC3)CC2)c1)NC[C@H](O)[C@@H](O)[C@H](O)[C@H](O)CO] | 762.4 |
| I-433 | Example 70 | 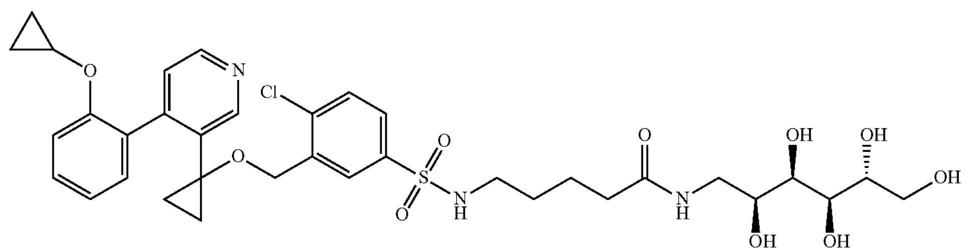 [SMILES: O=C(CCCCNS(=O)(=O)c1ccc(Cl)c(COC2(c3cnccc3-c3ccccc3OC3CC3)CC2)c1)NC[C@H](O)[C@@H](O)[C@H](O)[C@H](O)CO] | 734.4 |
| I-434 | Example 70 | 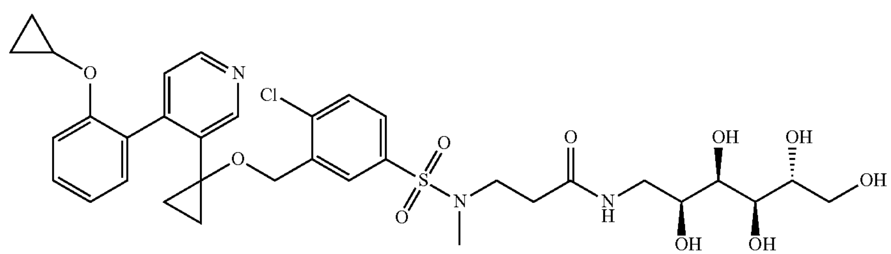 [SMILES: CN(CCC(=O)NC[C@H](O)[C@@H](O)[C@H](O)[C@H](O)CO)S(=O)(=O)c1ccc(Cl)c(COC2(c3cnccc3-c3ccccc3OC3CC3)CC2)c1] | 720.45 |

TABLE 14-continued

Compounds I-394 to I-479

| Cmpd no.: | Synthetic Method | Compound Structure | Obs Mass [M + H]$^2$ |
|---|---|---|---|
| I-435 | Example 70 | 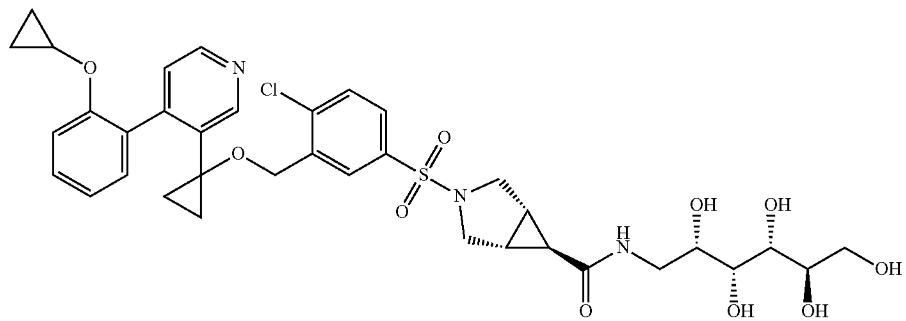 [SMILES: O=C(NC[C@H](O)[C@@H](O)[C@H](O)[C@H](O)CO)[C@H]1[C@@H]2CN(S(=O)(=O)c3ccc(Cl)c(COC4(c5cnccc5-c5ccccc5OC5CC5)CC4)c3)C[C@@H]21] | 744.3 |
| I-436 | Example 70 | 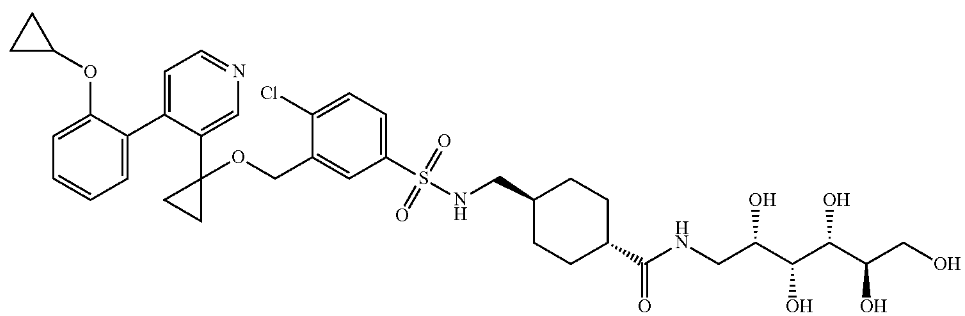 [SMILES: O=C(NC[C@H](O)[C@@H](O)[C@H](O)[C@H](O)CO)[C@H]1CC[C@H](CNS(=O)(=O)c2ccc(Cl)c(COC3(c4cnccc4-c4ccccc4OC4CC4)CC3)c2)CC1] | 774.45 |
| I-437 | Example 70 | 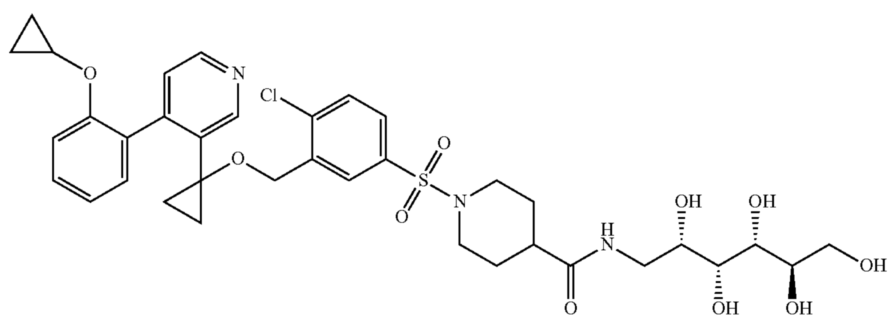 [SMILES: O=C(NC[C@H](O)[C@@H](O)[C@H](O)[C@H](O)CO)C1CCN(S(=O)(=O)c2ccc(Cl)c(COC3(c4cnccc4-c4ccccc4OC4CC4)CC3)c2)CC1] | 746.40 |

TABLE 14-continued

Compounds I-394 to I-479

| Cmpd no.: | Synthetic Method | Compound Structure | Obs Mass [M + H]$^2$ |
|---|---|---|---|
| I-438 | Example 70 | 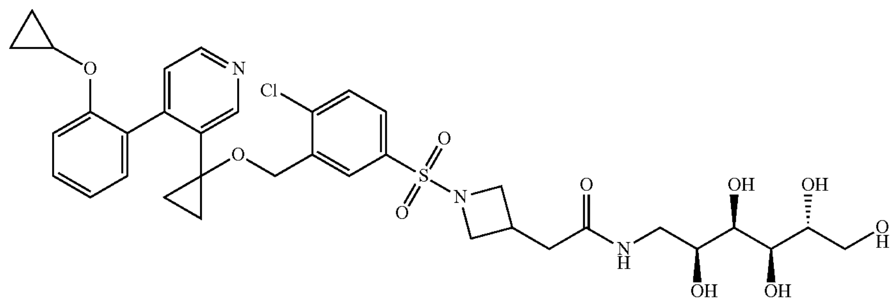 [SMILES: O=C(CC1CN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 732.20 |
| I-439 | Example 70 | 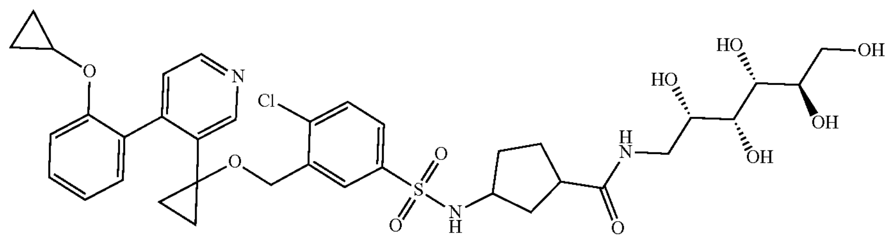 [SMILES: O=C(NC[C@H](O)[C@@H](O)[C@H](O)[C@H](O)CO)C1CCC(NS(=O)(=O)c2ccc(Cl)c(COC3(c4cnccc4-c4ccccc4OC4CC4)CC3)c2)C1] | 746.45 |
| I-440 | Example 70 | 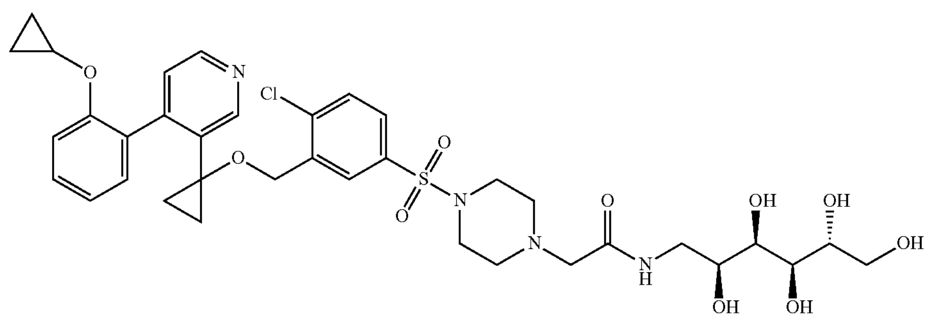 [SMILES: O=C(CN1CCN(S(=O)(=O)c2ccc(Cl)c(COC3(c4cnccc4-c4ccccc4OC4CC4)CC3)c2)CC1)NC[C@H](O)[C@@H](O)[C@H](O)[C@H](O)CO] | 761.40 |

TABLE 14-continued
Compounds I-394 to I-479
| Cmpd no.: | Synthetic Method | Compound Structure | Obs Mass [M + H]² |
|---|---|---|---|
| I-441 | Example 70 | 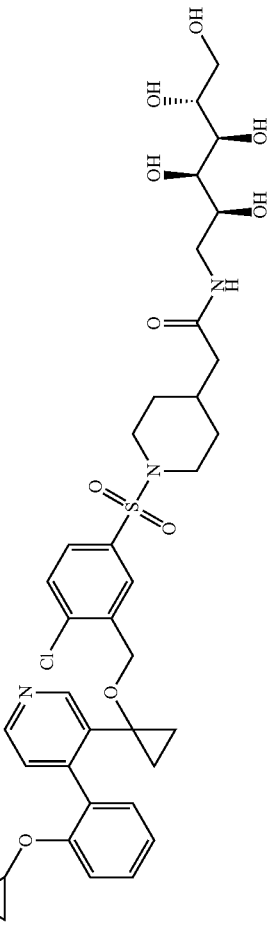 | 760.45 |
| I-442 | Example 70 | 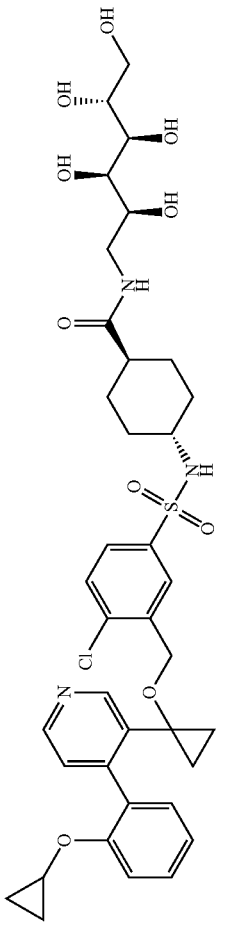 | 760.50 |
| I-443 | Example 70 | 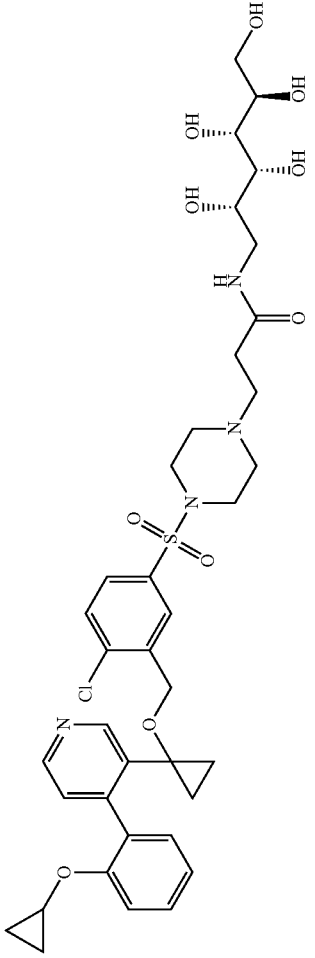 | 775.40 |

TABLE 14-continued

Compounds I-394 to I-479

| Cmpd no.: | Synthetic Method | Compound Structure | Obs Mass [M + H]² |
|---|---|---|---|
| I-444 | Example 70 | 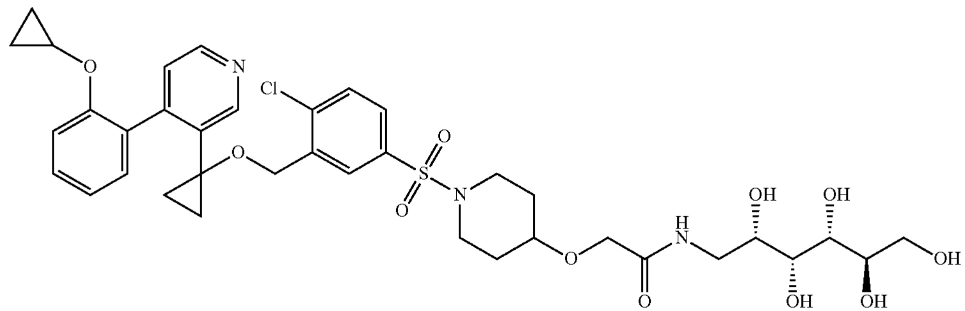 | 776.35 |
| I-445 | Example 70 | 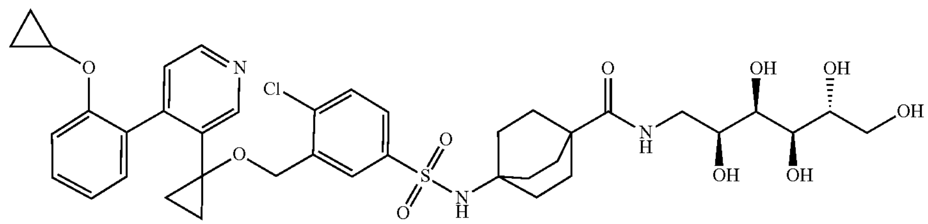 [SMILES: O=C(NC[C@H](O)[C@@H](O)[C@H](O)[C@H](O)CO)C12CCC(NS(=O)(=O)c3ccc(Cl)c(COC4(c5cnccc5-c5ccccc5OC5CC5)CC4)c3)(CC1)CC2] | 786.25 |
| I-446 | Example 70 | 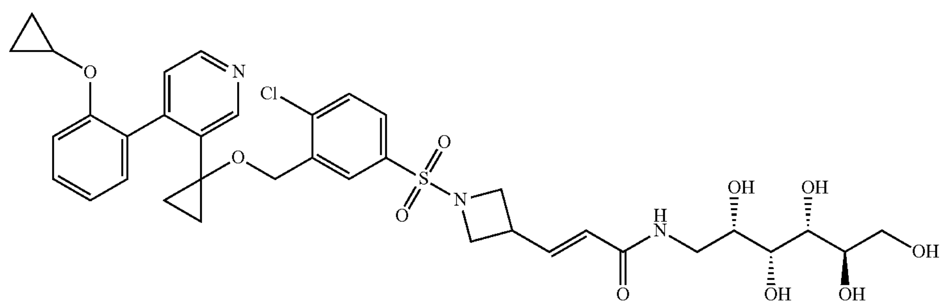 [SMILES: O=C(/C=C/C1CN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 744.4 |

TABLE 14-continued
Compounds I-394 to I-479
| Cmpd no.: | Synthetic Method | Compound Structure | Obs Mass [M + H]² |
|---|---|---|---|
| I-447 | Example 70 | 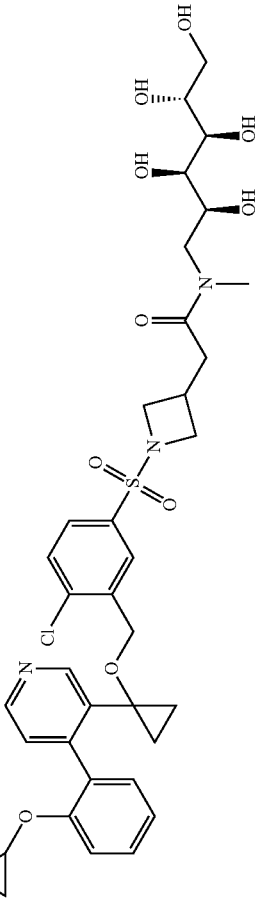 | 746.4 |
| I-448 | Example 70 | 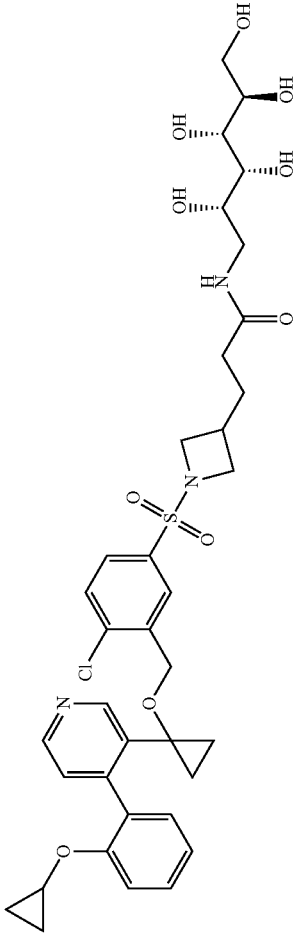 | 803.3 |
| I-449 | Example 70 | 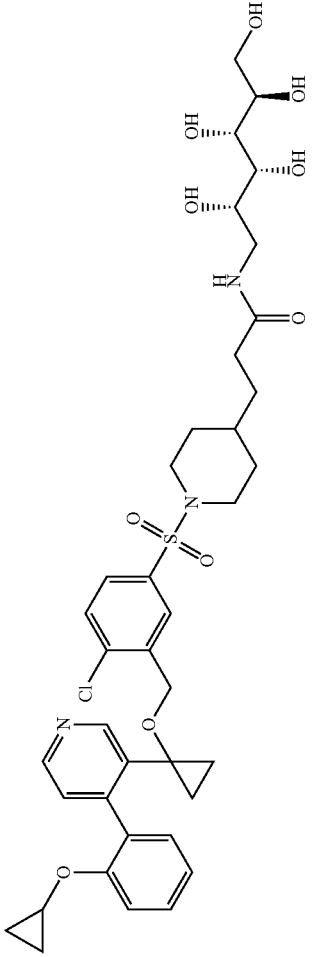 | 774.4 |

TABLE 14-continued

Compounds I-394 to I-479

| Cmpd no.: | Synthetic Method | Compound Structure | Obs Mass [M + H]$^2$ |
|---|---|---|---|
| I-450 | Example 70 | 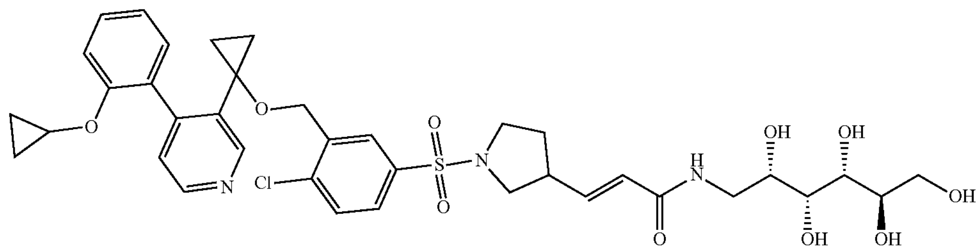 [SMILES: O=C(/C=C/C1CCN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 758.3 |
| I-451 | Example 70 | 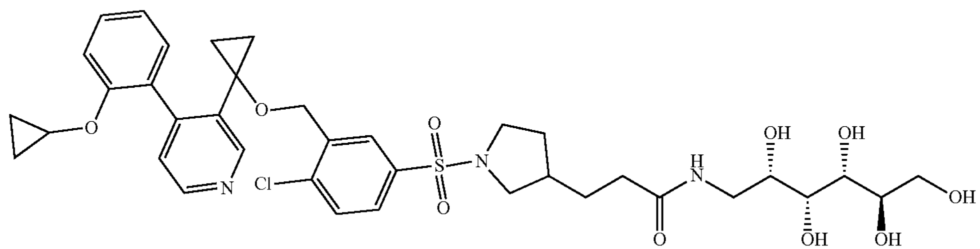 [SMILES: O=C(CCC1CCN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 760.4 |
| I-452 | Example 70 | 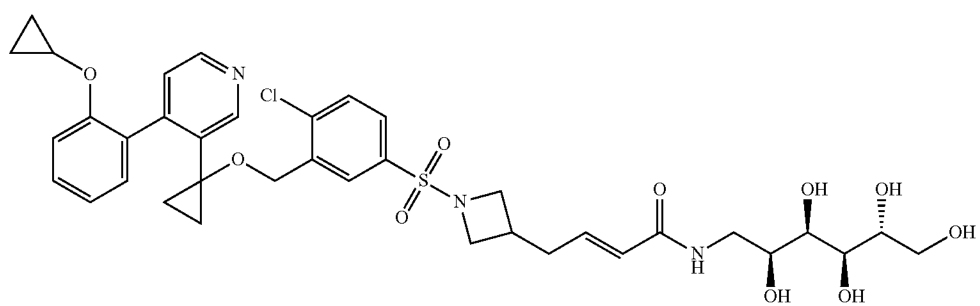 [SMILES: O=C(/C=C/CC1CN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 758.3 |

TABLE 14-continued
Compounds I-394 to I-479
| Cmpd no.: | Synthetic Method | Compound Structure | Obs Mass [M + H]² |
|---|---|---|---|
| I-453 | Example 70 | 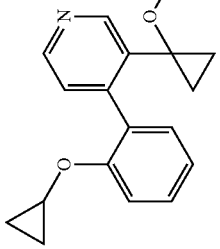 | 760.4 |
| I-454 | Example 70 | 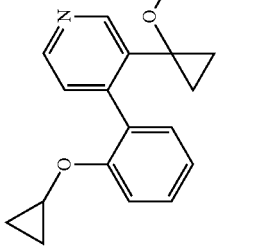 | 748.4 |
| I-455 | Example 70 | 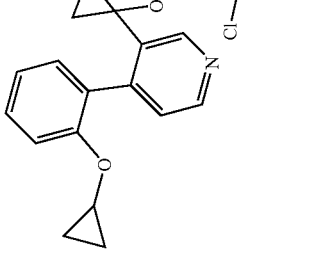 | 776.3 |

TABLE 14-continued

Compounds I-394 to I-479

| Cmpd no.: | Synthetic Method | Compound Structure | Obs Mass [M + H]² |
|---|---|---|---|
| I-456 | Example 70 | 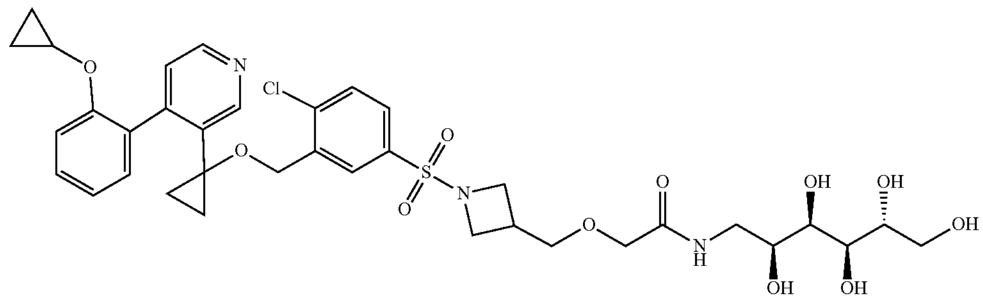 [SMILES: O=C(COCC1CN(S(=O)(=O)c2ccc(Cl)c(COC3(c4cnccc4-c4ccccc4OC4CC4)CC3)c2)C1)NC[C@H](O)[C@@H](O)[C@H](O)[C@H](O)CO] | 762.4 |
| I-457 | Example 70 | 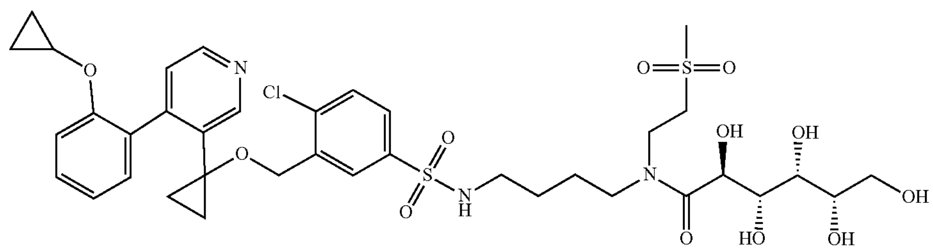 [SMILES: CS(=O)(=O)CCN(CCCCNS(=O)(=O)c1ccc(Cl)c(COC2(c3cnccc3-c3ccccc3OC3CC3)CC2)c1)C(=O)[C@@H](O)[C@@H](O)[C@H](O)[C@@H](O)CO] | |
| I-458 | Example 70 | 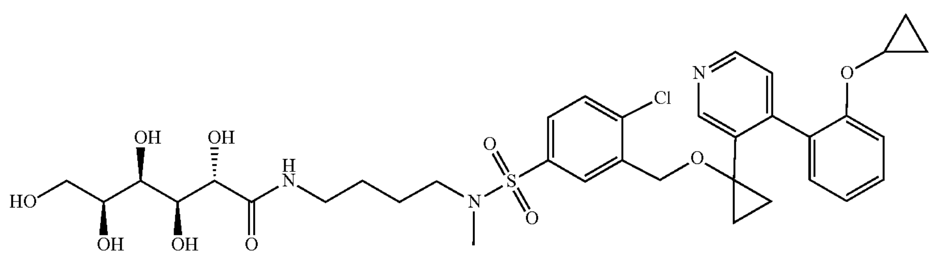 [SMILES: CN(CCCCNC(=O)[C@@H](O)[C@@H](O)[C@H](O)[C@@H](O)CO)S(=O)(=O)c1ccc(Cl)c(COC2(c3cnccc3-c3ccccc3OC3CC3)CC2)c1] | 734.40 |

TABLE 14-continued

Compounds I-394 to I-479

| Cmpd no.: | Synthetic Method | Compound Structure | Obs Mass [M + H]$^2$ |
|---|---|---|---|
| I-459 | Example 70 | 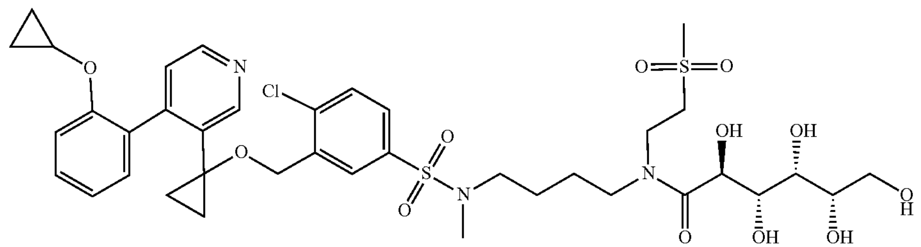 [SMILES: CN(CCCCN(CCS(C)(=O)=O)C(=O)[C@@H](O)[C@@H](O)[C@H](O)[C@@H](O)CO)S(=O)(=O)c1ccc(Cl)c(COC2(c3cnccc3-c3ccccc3OC3CC3)CC2)c1] | 840.40 |
| I-460 | Example 70 | 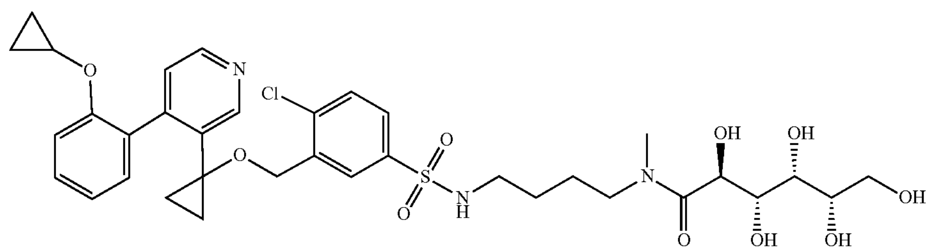 [SMILES: CN(CCCCNS(=O)(=O)c1ccc(Cl)c(COC2(c3cnccc3-c3ccccc3OC3CC3)CC2)c1)C(=O)[C@@H](O)[C@@H](O)[C@H](O)[C@@H](O)CO] | 734.35 |
| I-461 | Example 70 | 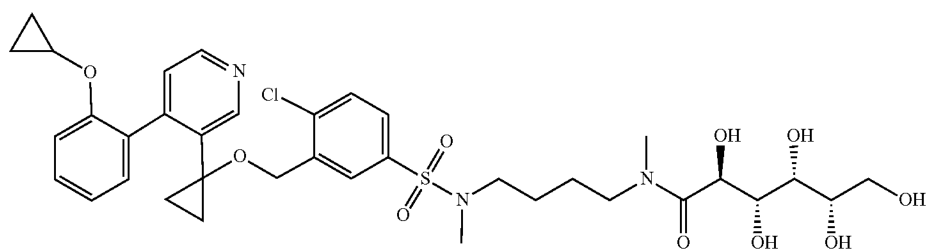 [SMILES: CN(CCCCN(C)S(=O)(=O)c1ccc(Cl)c(COC2(c3cnccc3-c3ccccc3OC3CC3)CC2)c1)C(=O)[C@@H](O)[C@@H](O)[C@H](O)[C@@H](O)CO] | 748.35 |

TABLE 14-continued
Compounds I-394 to I-479
| Cmpd no.: | Synthetic Method | Compound Structure | Obs Mass [M + H]² |
|---|---|---|---|
| I-462 | Example 70 | 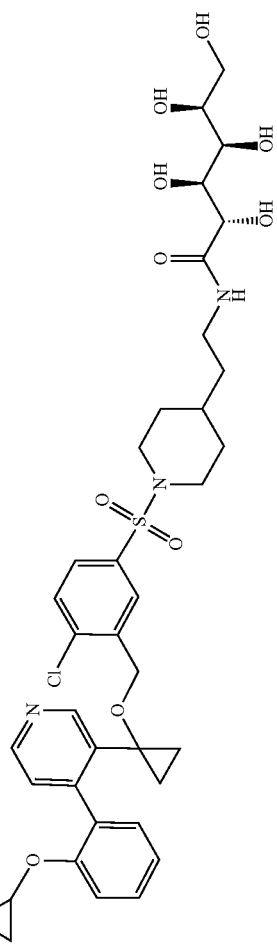 | 760.35 |
| I-463 | Example 72 | 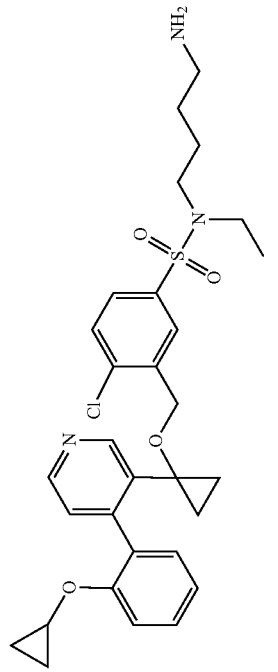 | 570.30 |
| I-464 | Example 71 | 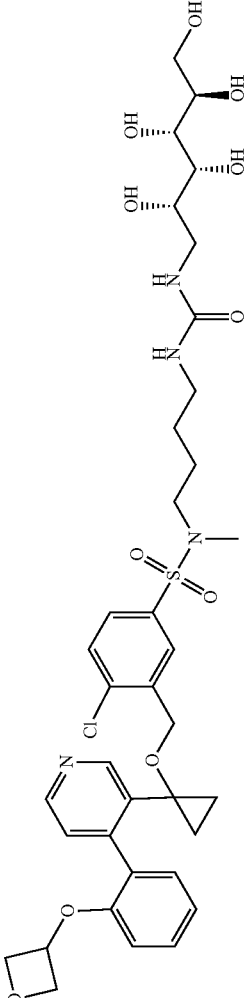 | 779.3 |

TABLE 14-continued

Compounds I-394 to I-479

| Cmpd no.: | Synthetic Method | Compound Structure | Obs Mass [M + H]² |
|---|---|---|---|
| I-465 | Example 72 | 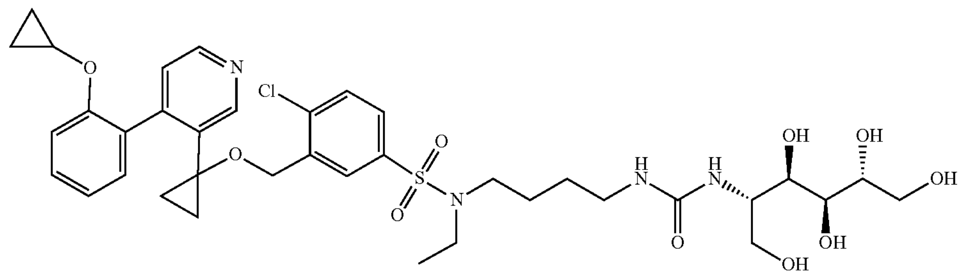 [SMILES: CCN(CCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CC2)c1] | 777.3 |
| I-466 | Example 74 | 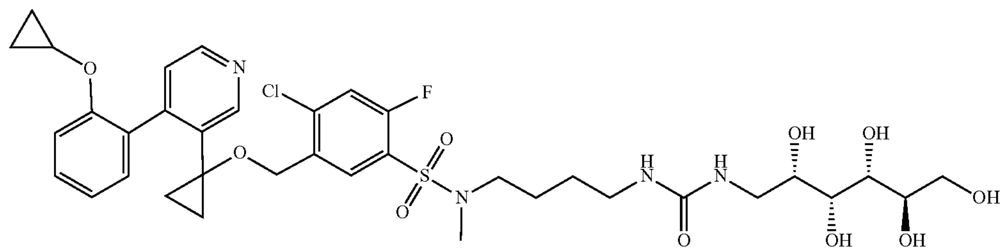 [SMILES: CN(CCCCNC(=O)NC[C@H](O)[C@@H](O)[C@H](O)[C@H](O)CO)S(=O)(=O)c1cc(COC2(c3cnccc3-c3ccccc3OC3CC3)CC2)c(Cl)cc1F] | |
| I-467 | Example 74 | 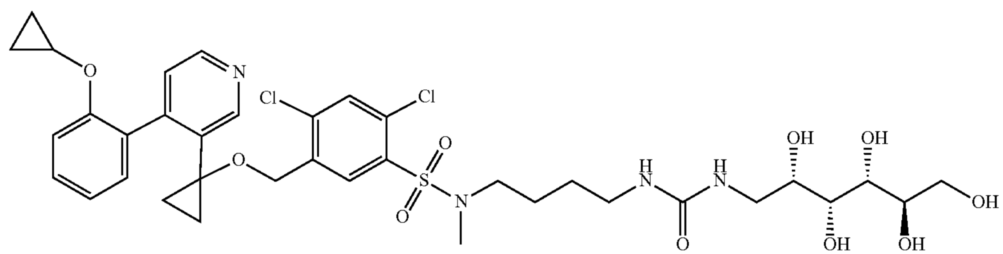 [SMILES: CN(CCCCNC(=O)NC[C@H](O)[C@@H](O)[C@H](O)[C@H](O)CO)S(=O)(=O)c1cc(COC2(c3cnccc3-c3ccccc3OC3CC3)CC2)c(Cl)cc1Cl] | 797.20 |

TABLE 14-continued

Compounds I-394 to I-479

| Cmpd no.: | Synthetic Method | Compound Structure | Obs Mass [M + H]$^2$ |
|---|---|---|---|
| I-468 | Example 96 | 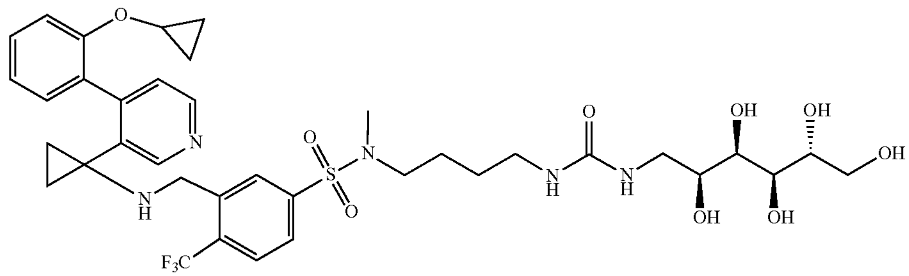 [SMILES: CN(CCCCNC(=O)NC[C@H](O)[C@@H](O)[C@H](O)[C@H](O)CO)S(=O)(=O)c1ccc(C(F)(F)F)c(CNC2(c3cnccc3-c3ccccc3OC3CC3)CC2)c1] | 797.0 |
| I-469 | Example 74 | 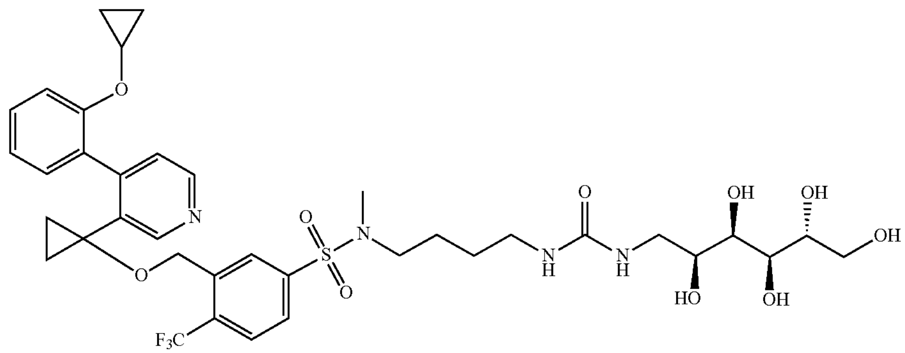 [SMILES: CN(CCCCNC(=O)NC[C@H](O)[C@@H](O)[C@H](O)[C@H](O)CO)S(=O)(=O)c1ccc(C(F)(F)F)c(COC2(c3cnccc3-c3ccccc3OC3CC3)CC2)c1] | 797.30 |
| I-470 | Example 96 | 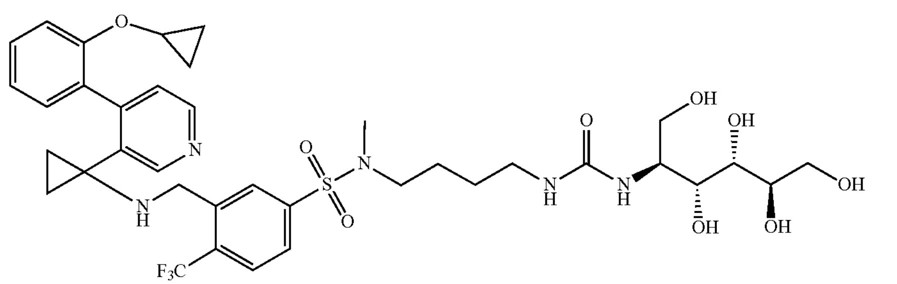 [SMILES: CN(CCCCNC(=O)N[C@@H](CO)[C@@H](O)[C@H](O)[C@H](O)CO)S(=O)(=O)c1ccc(C(F)(F)F)c(CNC2(c3cnccc3-c3ccccc3OC3CC3)CC2)c1] | 796.3 |

TABLE 14-continued

Compounds I-394 to I-479

| Cmpd no.: | Synthetic Method | Compound Structure | Obs Mass [M + H]² |
|---|---|---|---|
| I-471 | Example 96 | 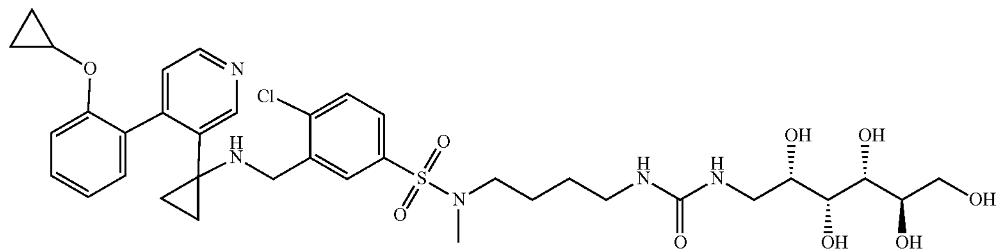 [SMILES: CN(CCCCNC(=O)NC[C@H](O)[C@@H](O)[C@H](O)[C@H](O)CO)S(=O)(=O)c1ccc(Cl)c(CNC2(c3cnccc3-c3ccccc3OC3CC3)CC2)c1] | 762.0 |
| I-472 | Example 96 | 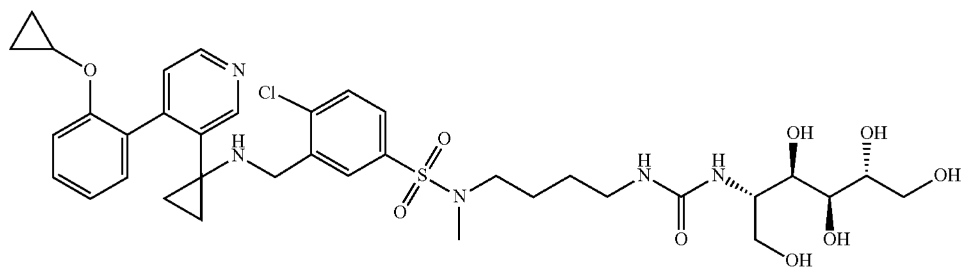 [SMILES: CN(CCCCNC(=O)N[C@@H](CO)[C@@H](O)[C@H](O)[C@H](O)CO)S(=O)(=O)c1ccc(Cl)c(CNC2(c3cnccc3-c3ccccc3OC3CC3)CC2)c1] | 762.3 |
| I-473 | Example 74 | 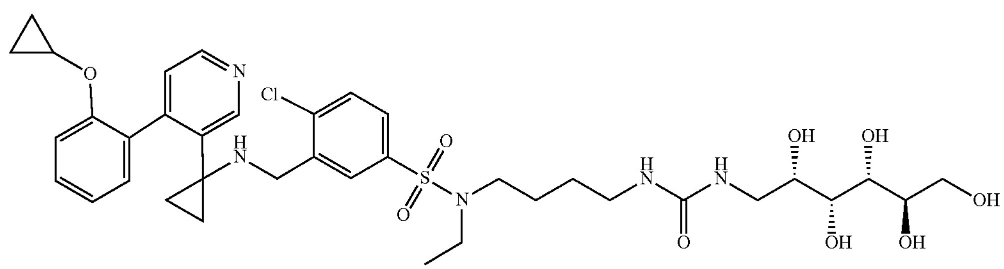 [SMILES: CCN(CCCCNC(=O)NC[C@H](O)[C@@H](O)[C@H](O)[C@H](O)CO)S(=O)(=O)c1ccc(Cl)c(CNC2(c3cnccc3-c3ccccc3OC3CC3)CC2)c1] | |

TABLE 14-continued

Compounds I-394 to I-479

| Cmpd no.: | Synthetic Method | Compound Structure | Obs Mass [M + H]² |
|---|---|---|---|
| I-474 | Example 96 | 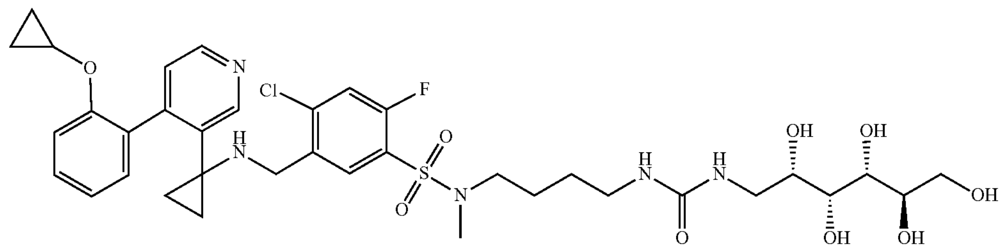 [SMILES: CN(CCCCNC(=O)NC[C@H](O)[C@@H](O)[C@H](O)[C@H](O)CO)S(=O)(=O)c1cc(CNC2(c3cnccc3-c3ccccc3OC3CC3)CC2)c(Cl)cc1F] | |
| I-475 | Example 96 | 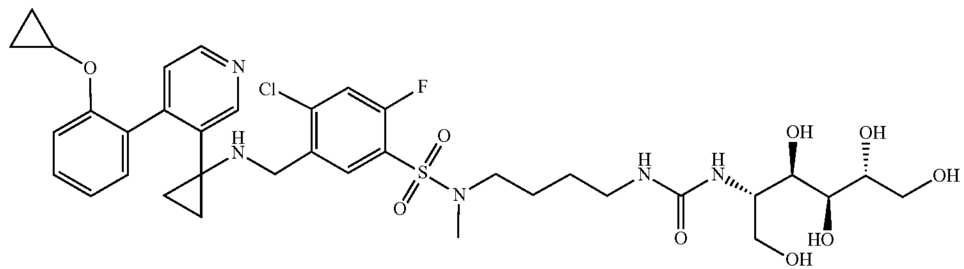 [SMILES: CN(CCCCNC(=O)N[C@@H](CO)[C@@H](O)[C@H](O)[C@H](O)CO)S(=O)(=O)c1cc(CNC2(c3cnccc3-c3ccccc3OC3CC3)CC2)c(Cl)cc1F] | |
| I-476 | Example 96 | 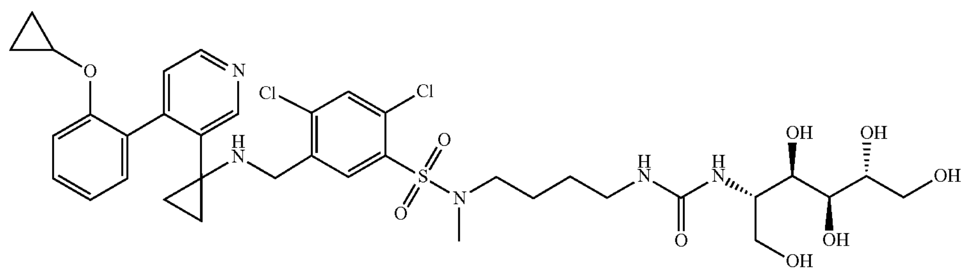 [SMILES: CN(CCCCNC(=O)N[C@@H](CO)[C@@H](O)[C@H](O)[C@H](O)CO)S(=O)(=O)c1cc(CNC2(c3cnccc3-c3ccccc3OC3CC3)CC2)c(Cl)cc1Cl] | |

TABLE 14-continued

Compounds I-394 to I-479

| Cmpd no.: | Synthetic Method | Compound Structure | Obs Mass [M + H]$^2$ |
|---|---|---|---|
| I-477 | Example 96 | 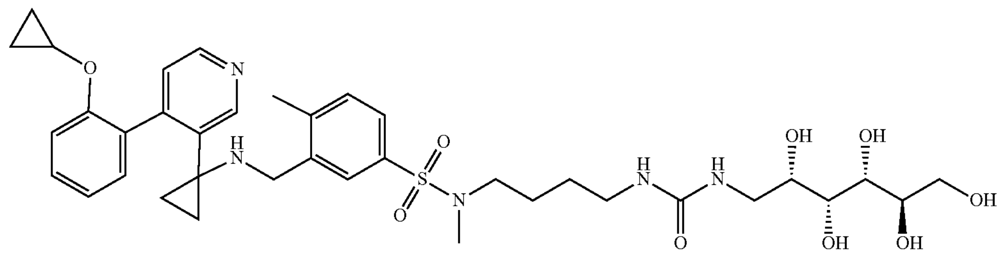 [SMILES: Cc1ccc(S(=O)(=O)N(C)CCCCNC(=O)NC[C@H](O)[C@@H](O)[C@H](O)[C@H](O)CO)cc1CNC1(c2cnccc2-c2ccccc2OC2CC2)CC1] | 742.35 |
| I-478 | Example 96 | 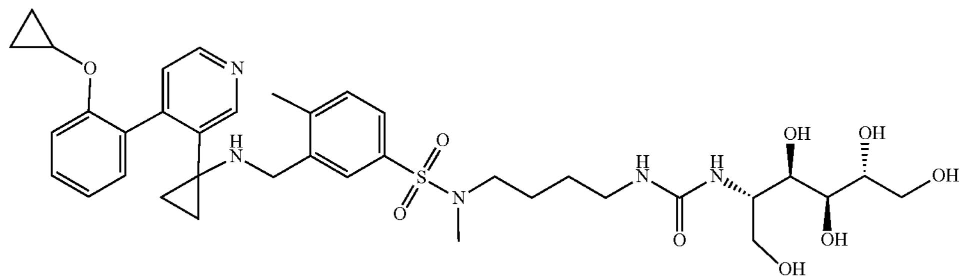 [SMILES: Cc1ccc(S(=O)(=O)N(C)CCCCNC(=O)N[C@@H](CO)[C@@H](O)[C@H](O)[C@H](O)CO)cc1CNC1(c2cnccc2-c2ccccc2OC2CC2)CC1] | 742.35 |
| I-479 | Example 74 | 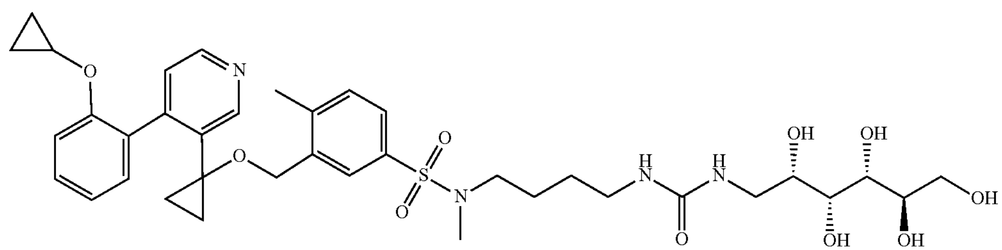 [SMILES: Cc1ccc(S(=O)(=O)N(C)CCCCNC(=O)NC[C@H](O)[C@@H](O)[C@H](O)[C@H](O)CO)cc1COC1(c2cnccc2-c2ccccc2OC2CC2)CC1] | 743.3 |

TABLE 14-continued

Compounds I-394 to I-479

| Cmpd no.: | Synthetic Method | Compound Structure | Obs Mass [M + H]² |
|---|---|---|---|
| I-480 | Example 78 | 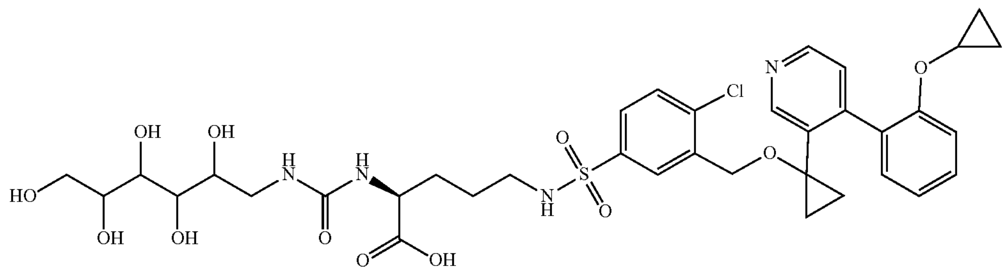 [SMILES: O=C(NCC(O)C(O)C(O)C(O)CO)N[C@@H](CCCNS(=O)(=O)c1ccc(Cl)c(COC2(c3cnccc3-c3ccccc3OC3CC3)CC2)c1)C(=O)O] | 793.19 |
| I-481 | Example 79 | 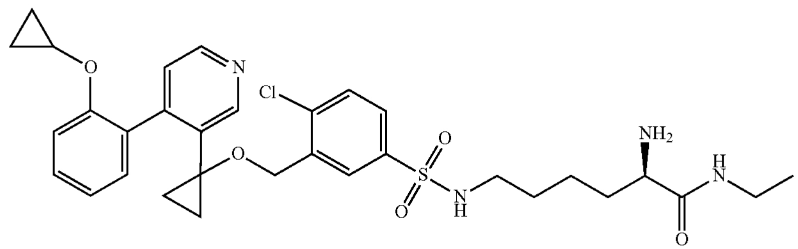 [SMILES: CCNC(=O)[C@H](N)CCCCNS(=O)(=O)c1ccc(Cl)c(COC2(c3cnccc3-c3ccccc3OC3CC3)CC2)c1] | 627.19 [M + H]⁺ |
| I-482 | Example 80 | 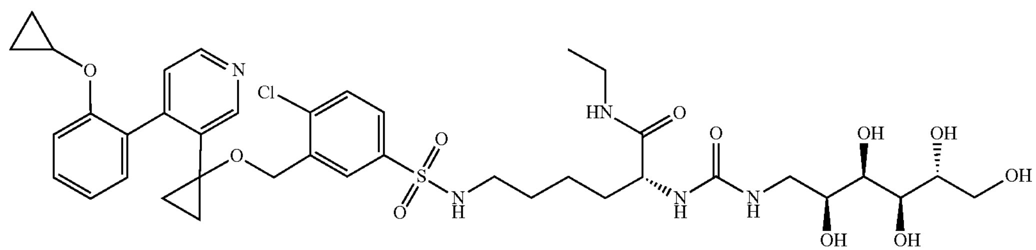 [SMILES: CCNC(=O)[C@@H](CCCCNS(=O)(=O)c1ccc(Cl)c(COC2(c3cnccc3-c3ccccc3OC3CC3)CC2)c1)NC(=O)NC[C@H](O)[C@@H](O)[C@H](O)[C@H](O)CO] | 834.26 |

Example 76: (2S)-2-[4-chloro-3-({1-[4-(2-cyclopropoxyphenyl)pyridin-3-yl]cyclopropoxy}methyl)benzenesulfonamido]-6-({[(2S,3R,4R,5R)-2,3,4,5,6-pentahydroxyhexyl]carbamoyl}amino)hexanoic acid (I-483)
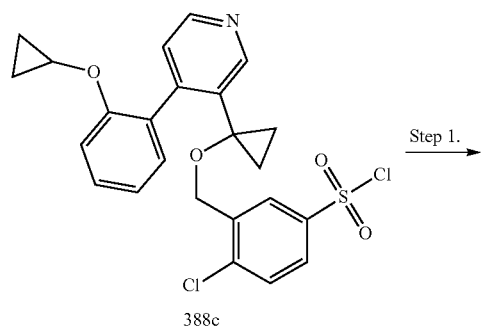
388c
Step 1.
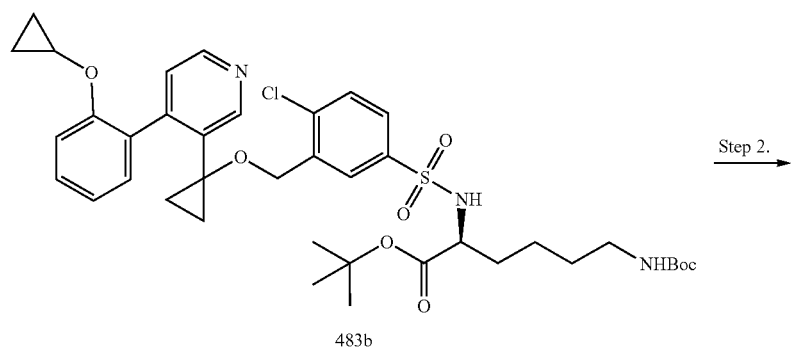
483b
Step 2.
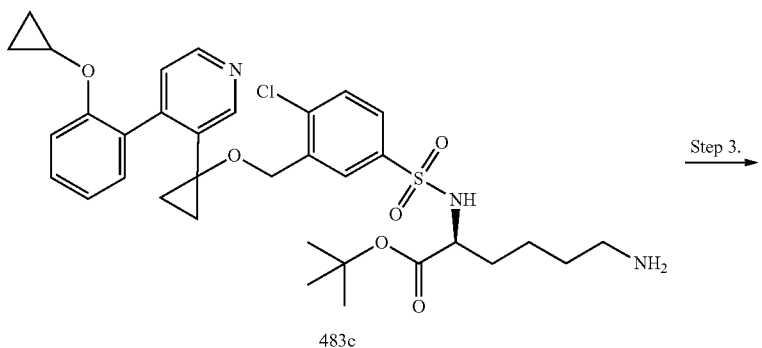
483c
Step 3.

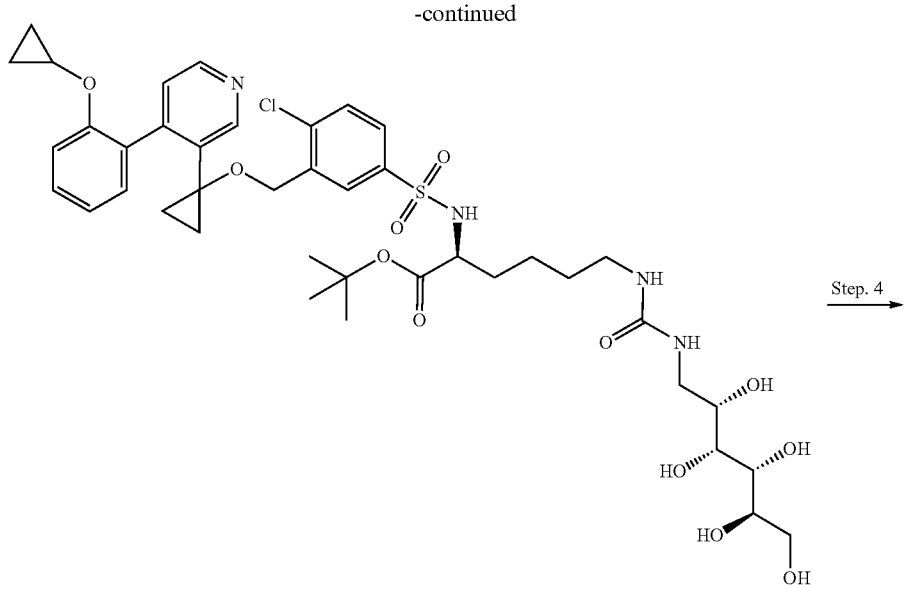

483d

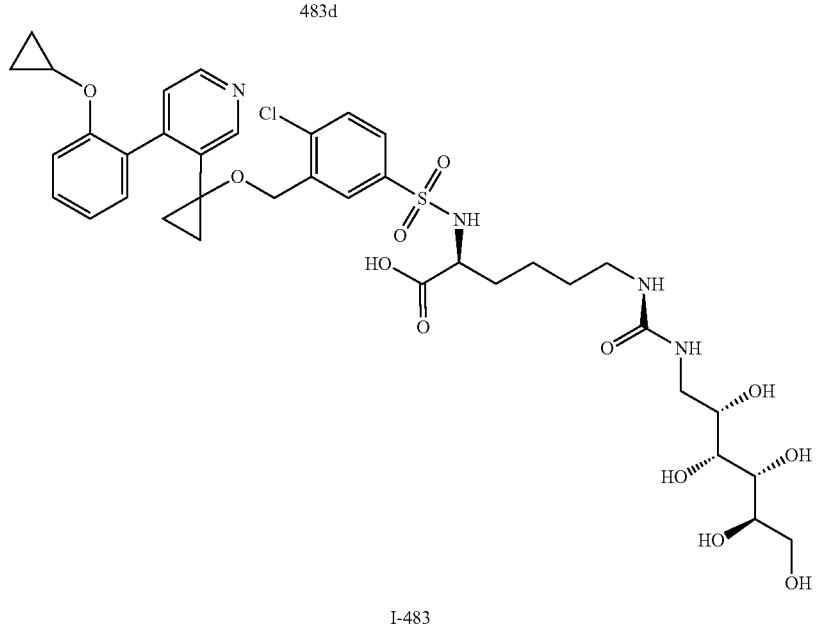

I-483

Step 1. (S)-tert-butyl 6-(tert-butoxycarbonylamino)-2-(3-chloro-4-((1-(4-(2-cyclopropoxyphenyl)pyridine-3-yl)cyclopropoxy)methyl)phenylsulfonamido) hexanoate (Intermediate 483b)

A solution of 388e (56 mg, 0.11 mmol, 1.0 equiv) in acetonitrile (0.5 mL) at 0° C. was added AcOH (33 mg, 0.55 mmol, 5.0 equiv), $H_2O$ (12 mg, 0.66 mmol, 6.0 equiv) and finally NCS (44 mg, 0.32 mmol, 3.0 equiv). After 30 minutes the reaction mixture was warmed to room temperature. After a further 2 hours the reaction was complete by LCMS. The solvent was removed and the product azeotroped twice from toluene. The residue was diluted with DCM (1 mL) and (S)-tert-butyl 2-amino-6-(tert-butoxycarbonylamino) hexanoate HCl (23.4 mg, 0.061 mmol, 1.1 equiv) and TEA (24.6 mg, 0.24 mmol, 4.4 equiv) were added. After 20 minutes the reaction was complete. The crude reaction mixture was applied directly to silica gel (4.0 g) and purification by flash chromatography (100% DCM to 100% EtOAc over 10 minutes) gave 29.3 mg (64%) of 483b.

Step 2. (S)-tert-butyl 6-amino-2-(3-chloro-4-((1-(4-(2-cyclopropoxyphenyl)pyridine-3-yl) cyclopropoxy)methyl)phenylsulfonamido)hexanoate (Intermediate 483c)

A solution of 483b (30 mg, 0.039 mmol, 1.0 equiv) in DCM (1 mL) was added TFA (0.25 mL) at 0° C. After 30 minutes the reaction was complete and quenched with $Na_2CO_3$ (5 mL). The product was extracted with DCM (3×10 mL) and dried over $Na_2SO_4$ to give 16.1 mg (65%) of crude 483c which was used without further purification.

Step 3. (S)-tert-butyl 2-(3-chloro-4-((1-(4-(2-cyclo-propoxyphenyl)pyridine-3-yl) cyclopropoxy)methyl) phenylsulfonamido)-6-(3-((2S,3R,4R,5R)-2,3,4,5,6-pentahydroxyhexyl)ureido)hexanoate (Intermediate 483d)

A solution of 483c (16 mg, 0.025 mmol, 1.0 equiv) in DMF (0.25 mL) was added DSC (7.0 mg, 0.028 mmol, 1.1 equiv). After 30 minutes LCMS indicated complete conversion to the carbamate intermediate. D-Glucamine (9.0 mg, 0.05 mmol, 2.0 equiv) was added and the reaction mixture was heated to 60° C. After 30 minutes, LCMS indicated that the reaction was complete and the crude mixture was cooled, diluted with EtOAc (10 mL) and washed successively with NaHCO$_3$ (10 mL) and water (10 mL). The combined aqueous phases were extracted with DCM (3×10 mL) and the organic layers were combined and dried over Na$_2$SO$_4$. Purification by flash chromatography (4 g SiO$_2$, 0% to 20% MeOH in DCM over 10 minutes) gave 9.7 mg (45%) of 483d.

Step 4. (2S)-2-[4-chloro-3-({1-[4-(2-cyclopropoxy-phenyl)pyridin-3-yl]cyclopropoxy}methyl) benzene-sulfonamido]-6-({[(2S,3R,4R,5R)-2,3,4,5,6-pentahy-droxyhexyl]carbamoyl}amino) hexanoic acid (I-483)

483d (9.7 mg, 0.011 mmol, 1.0 equiv) was dissolved in DCM (1.0 mL) and TFA (0.25 mL) was added. After 45 minutes the reaction was complete and the solvent was removed. The crude residue was diluted with MeCN (0.5 mL) and water (1.5 mL) and purified by preparative HPLC (10% to 55% MeCN in H$_2$O with 0.1% TFA over 18 minutes) to give 2.3 mg (25%) of (2S)-2-[4-chloro-3-({1-[4-(2-cyclopropoxyphenyl)pyridin-3-yl] cyclopropoxy}methyl) benzenesulfonamido]-6-({[(2S,3R, 4R,5R)-2,3,4,5,6-pentahydroxyhexyl]carbamoyl}amino) hexanoic acid (I-483) as a TFA salt. MS (ES, m/z): 807.20 [M+H]$^+$; $^1$H-NMR (400 MHz, DMSO-d$_6$) δ 8.79 (s, 1H), 8.60 (d, J=5.2 Hz, 1H), 8.23 (d, J=8.9 Hz, 1H), 7.66 (dd, J=8.4, 2.0 Hz, 1H), 7.59 (d, J=8.4 Hz, 2H), 7.44-7.25 (m, 5H), 7.02 (t, J=7.6 Hz, 1H), 4.39 (s, 2H), 3.70-3.60 (m, 5H), 3.23-3.08 (m, 6H), 3.06-2.95 (m, 3H), 2.96-2.81 (M, 5H), 1.23 (s, 4H), 0.93 (d, J=18.8 Hz, 4H), 0.64 (d, J=7.4 Hz, 2H), 0.39 (s, 2H).

Example 77: (S)-2-amino-6-(3-chloro-4-((1-(4-(2-cyclopropoxyphenyl)pyridine-3-yl) cyclopropoxy) methyl)phenylsulfonamido)hexanoic acid (I-484)

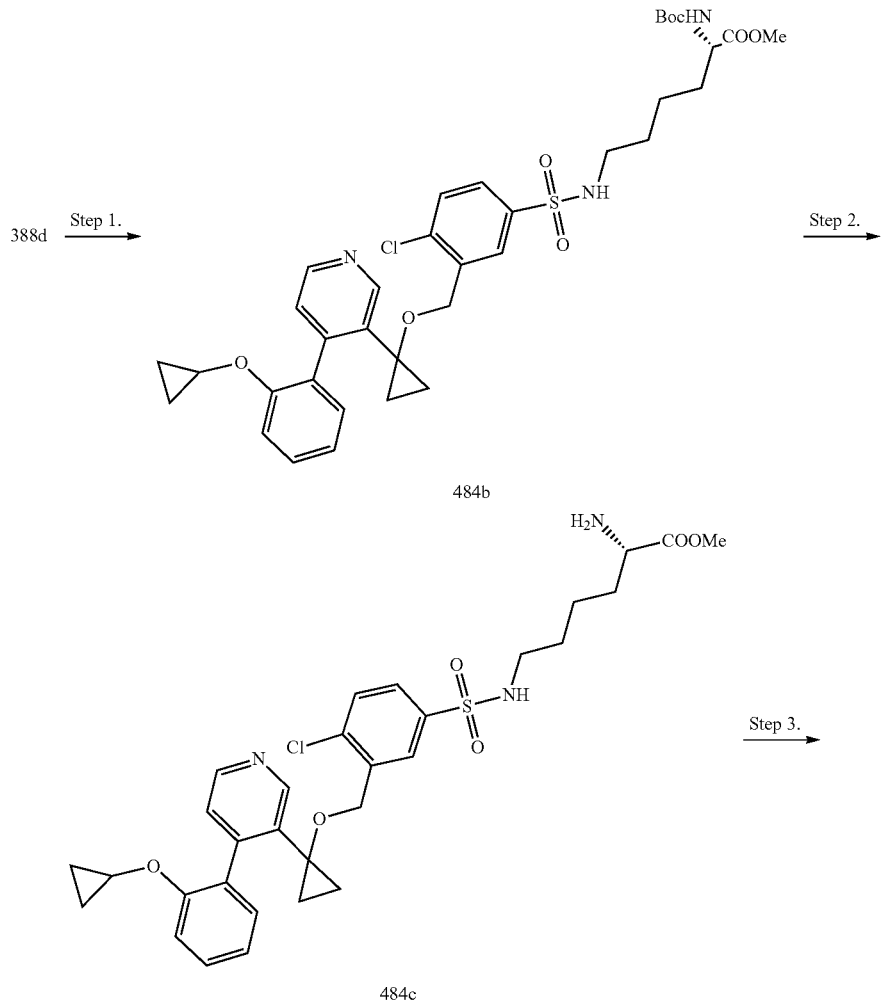

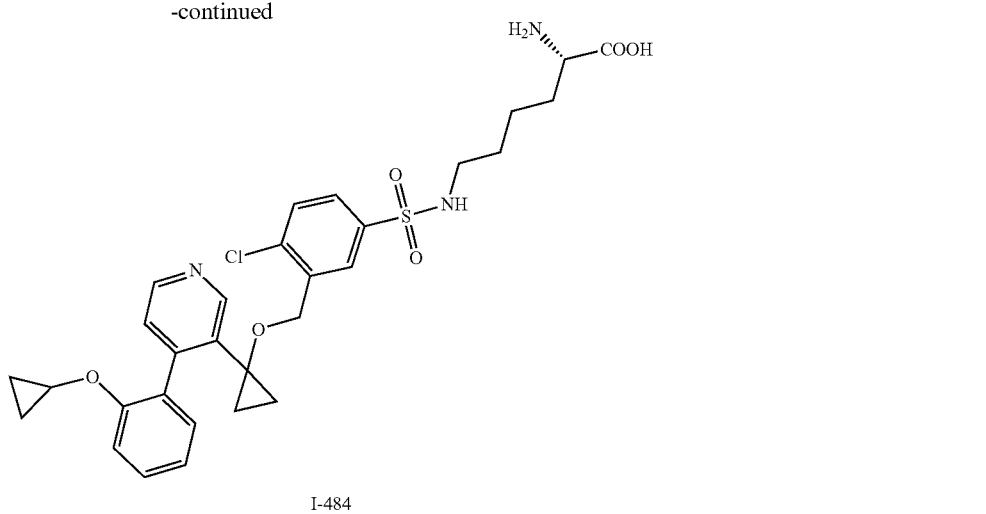

I-484

Step 1. (S)-methyl 2-(tert-butoxycarbonylamino)-6-(3-chloro-4-((1-(4-(2-cyclopropoxyphenyl)pyridine-3-yl)cyclopropoxy)methyl)phenylsulfonamido)hexanoate (Intermediate 484b)

A solution of 388d (338 mg, 0.66 mmol, 1.0 equiv) in MeCN (3.3 mL) was added AcOH (198 mg, 3.3 mmol, 5.0 equiv) and $H_2O$ (71.2 mg, 3.96 mmol, 6.0 equiv). The reaction mixture was cooled to 0° C. and NCS (246 mg, 1.98 mmol, 3.0 equiv) was added in 3 portions. The reaction was stirred at 0° C. for 30 minutes and then at room temperature for a further 45 minutes at which point LCMS indicated the reaction was complete. The crude mixture was diluted with DCM (30 mL) and washed with brine (2×30 mL). The combined aqueous layers were extracted with additional DCM (30 mL) and the combined organic layers were dried over $Na_2SO_4$ and the solvent was removed. The crude sulfonyl chloride was diluted with DCM (1.5 mL) and was added dropwise A solution of (S)-methyl 6-amino-2-(tert-butoxycarbonylamino)hexanoate HCl (172 mg, 0.66 mmol, 1.0 equiv) and TEA (101 mg, 1.0 mmol, 1.5 equiv) in DCM (1.5 mL) at 0° C. After 45 minutes the reaction was complete. The crude reaction mixture was applied directly to silica gel (4.0 g) and purification by flash chromatography (0% to 10% MeOH in DCM over 10 minutes) gave 314.9 mg (67%) of 484b as a yellow oil.

Step 2. (S)-methyl 2-amino-6-(3-chloro-4-((1-(4-(2-cyclopropoxyphenyl)yridine-3-yl) cyclopropoxy)methyl)phenylsulfonamido)hexanoate (Intermediate 484c)

A solution of 484b (315 mg, 0.442 mmol, 1.0 equiv) in dioxane (2 mL) was added HCl solution (4M in dioxane, 0.44 mL, 1.76 mmol, 4.0 equiv). After 40 minutes additional HCl solution (4M in dioxane, 0.44 mL, 1.76 mmol, 4.0 equiv) was added. After a further 3 hours, the reaction was complete and the solvent removed. The crude residue was diluted with DCM (30 mL) and neutralized with saturated $NaHCO_3$ solution. The mixture was extracted with DCM (4×30 mL) and dried over $Na_2SO_4$. Removing the solvent gave 281.8 mg (100%) of 484c.

Step 3. (S)-2-amino-6-(3-chloro-4-((1-(4-(2-cyclopropoxyphenyl)pyridine-3-yl)cyclopropoxy) methyl)phenylsulfonamido)hexanoic acid (I-484)

A solution of 484c (50 mg, 0.082 mmol, 1.0 equiv) in MeOH (0.3 mL) and THE (0.2 mL) was added LiOH (2M in water, 0.163 mL, 0.326 mmol, 4.0 equiv). After 90 minutes additional LiOH (2M in water, 0.163 mL, 0.326 mmol, 4.0 equiv) was added. The reaction was complete after an additional 20 minutes. The crude mixture was diluted with MeCN (1.0 mL) and $H_2O$ (3.0 mL) and acidified with TFA. Additional MeCN (0.5 mL) was added and the mixture was filtered. Purification by preparative HPLC (30% to 95% MeCN in water with 0.1% TFA over 18 minutes) gave 11.5 mg (24%) of I-484 as a TFA salt. MS (ES, m/z): 600.20 $[M+H]^+$; $^1$H-NMR (400 MHz, $CD_3OD$) δ 8.85 (s, 1H), 8.65 (d, J=5.8 Hz, 1H), 7.68 (d, J=5.8 Hz, 1H), 7.61 (dd, J=8.3, 2.3 Hz, 1H), 7.50 (d, J=2.3 Hz, 1H), 7.46 (d, J=8.4 Hz, 1H), 7.42-7.34 (m, 1H), 7.34-7.11 (m, 3H), 7.00 (td, J=7.4, 1.0 Hz, 1H), 4.41 (s, 2H), 4.26 (s, 1H), 3.85 (t, J=6.3 Hz, 1H), 3.51 (tt, J=6.0, 2.9 Hz, 1H), 2.74 (t, 6.3 Hz, 2H), 1.90 (s, 1H), 1.89-1.72 (m, 2H), 1.54-1.30 (m, 4H), 1.19-0.95 (m, 4H), 0.65-0.51 (m, 2H), 0.43-0.27 (m, 2H).

Example 78: (S)-6-(3-chloro-4-((1-(4-(2-cyclopropoxyphenyl)pyridine-3-yl)cyclopropoxy) methyl) phenylsulfonamido)-2-(3-((2S,3R,4R,5R)-2,3,4,5,6-pentahydroxyhexyl)ureido) hexanoic acid (I-485)

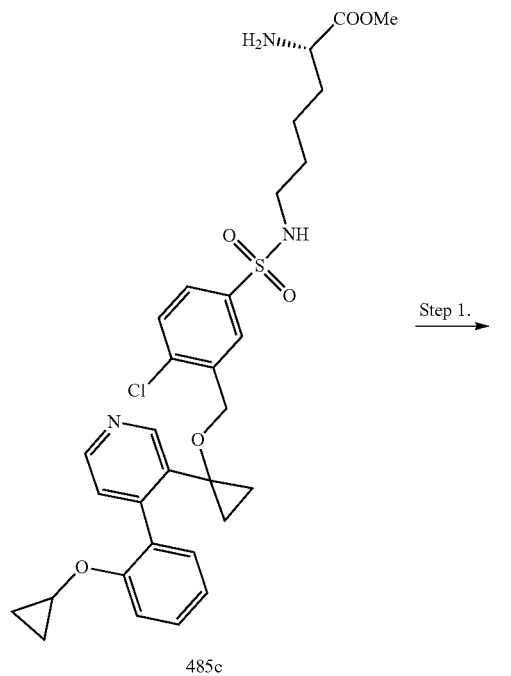

485c

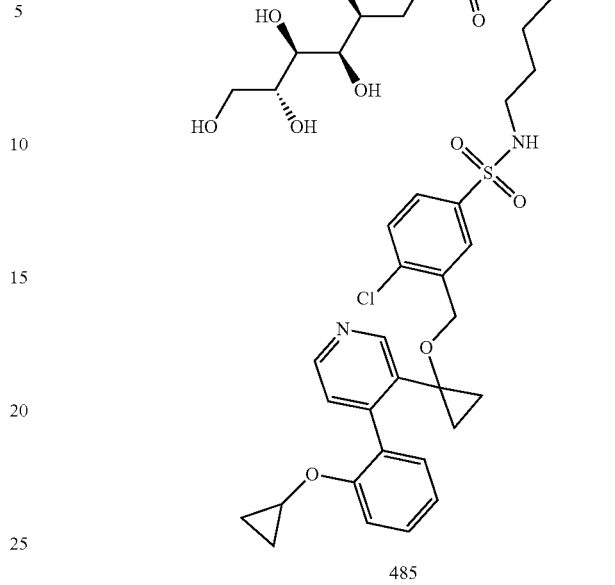

485

Step 1. (S)-methyl 6-(3-chloro-4-((1-(4-(2-cyclopropoxyphenyl)pyridine-3-yl)cyclopropoxy) methyl) phenylsulfonamido)-2-(3-((2S,3R,4R,5R)-2,3,4,5,6-pentahydroxyhexyl)ureido) hexanoate (Intermediate 485b)

A solution of 22c (231 mg, 0.377 mmol, 1.0 equiv) in DMF (1.0 mL) was added DSC (106 mg, 0.414 mmol, 1.1 equiv). After 30 minutes D-Glucamine (136 mg, 0.754 mmol, 2.0 equiv) was added and the reaction mixture was heated to 60° C. After an additional 1 hour, the reaction was complete and the crude mixture was cooled. Saturated NaHCO$_3$ solution (50 mL) was added and the mixture was washed with a 10% IPA in DCM mixture (4×50 mL). The combined organic layers were dried over Na$_2$SO$_4$ and concentrated to give crude 485b in quantitative yield.

Step 2. (S)-6-(3-chloro-4-((1-(4-(2-cyclopropoxyphenyl)pyridine-3-yl)cyclopropoxy) methyl) phenylsulfonamido)-2-(3-((2S,3R,4R,5R)-2,3,4,5,6-pentahydroxyhexyl)ureido)hexanoic acid (I-485)

485b (336 mg, 0.377 mmol, 1.0 equiv) was dissolved in MeOH (3.0 mL) and THF (2.0 mL). LiOH (2N in water, 0.38 mL, 0.76 mmol, 2.0 equiv) was added. After 45 minutes the reaction was complete and the solvent was removed. The crude residue was diluted with MeCN (1.8 mL) and H$_2$O (4.2 mL), filtered, and purified by preparative HPLC (10% to 70% MeCN in 0.01N NH$_4$HCO$_3$ solution over 20 minutes) to give 61 mg (20%) of I-485 as a free base. MS (ES, m/z): 807.22 [M+H]$^+$; $^1$H-NMR (400 MHz, DMSO-d$_6$) δ 8.71 (s, 1H), 8.53 (d, J=4.9 Hz, 1H), 7.70-7.55 (m, 3H), 7.42-7.28 (m, 2H), 7.24 (d, J=7.4 Hz1, 1H), 7.16 (d, J=4.9 Hz, 1H), 6.98 (t, J=7.4 Hz, 1H), 6.21 (s, 1H), 6.15 (s, 1H), 4.84 (s, 1H), 4.39 (s, 4H), 4.30 (s, 1H), 3.85 (s, 1H), 3.68-3.59 (m, 1H), 3.59-3.41 (m, 4H), 3.41-3.34 (m, 3H), 3.13-2.77 (m, 4H), 2.66 (t, J=6.8 Hz, 2H), 1.62-1.48 (m, 1H), 1.48-1.38 (m, 1H), 1.34 (s, 2H), 1.24 (s, 2H), 0.91 (d, J=13.9 Hz, 4H), 0.60 (d, J=6.2 Hz, 2H), 0.34 (s, 2H).

Example 79: (S)-2-amino-6-(3-chloro-4-((1-(4-(2-cyclopropoxyphenyl)pyridin-3-yl)cyclopropoxy)methyl)phenylsulfonamido)-N-ethylhexanamide (I-486)

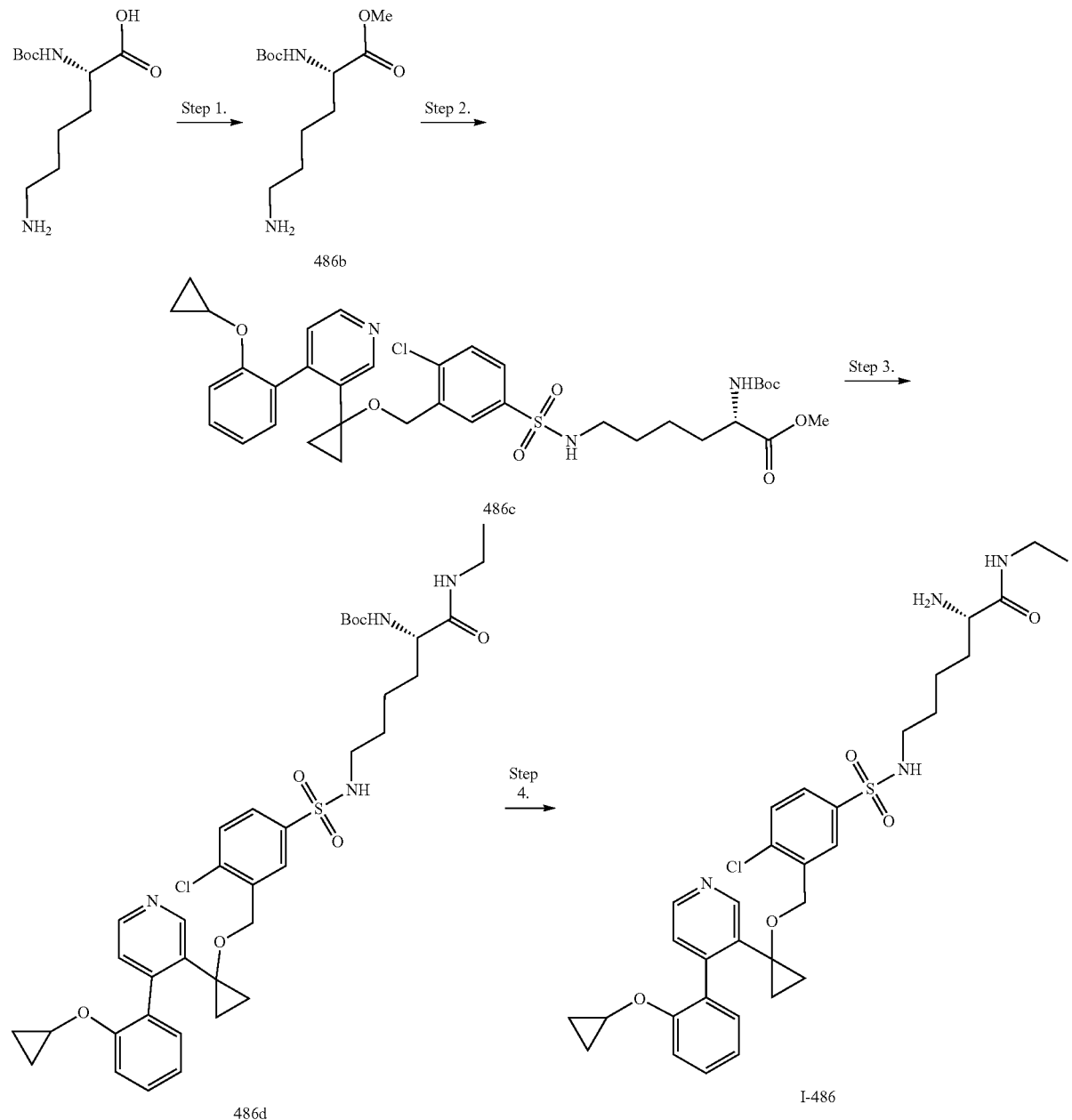

Step 1. (S)-methyl 6-amino-2-(tert-butoxycarbonylamino)hexanoate (Intermediate 486b)

(S)-methyl 6-amino-2-(tert-butoxycarbonylamino)hexanoate: A solution of (S)-6-amino-2-(tert-butoxycarbonylamino)hexanoic acid (167 mg, 0.66 mmol, 1.0 equiv) in DCM (2.6 mL) and MeOH (0.6 mL) was cooled to 0° C. under a nitrogen atmosphere. TMS-diazomethane (2M in ether, 0.5 mL, 1.0 mmol, 1.5 equiv) was added drop wise. After 45 minutes the reaction mixture was concentrated to give crude 486b, which was used without further purification.

Step 2. (S)-methyl 2-(tert-butoxycarbonylamino)-6-(3-chloro-4-((1-(4-(2-cyclopropoxyphenyl)pyridin-3-yl)cyclopropoxy)methyl)phenylsulfonamido)hexanoate (Intermediate 486c)

3-(1-(4-(benzylthio)-2-chlorobenzyloxy)cyclopropyl)-4-(2-cyclopropoxyphenyl) pyridine (338 mg, 0.66 mmol, 1.0 equiv) was dissolved in MeCN (3.3 mL) with AcOH (198 mg, 3.3 mmol, 5.0 equiv) and H₂O (71 mg, 3.96 mmol, 6.0 equiv). The mixture was cooled to 0° C. and NCS (246 mg, 1.98 mmol, 3.0 equiv) was added in 3 portions over 10 minutes. After 45 minutes the reaction mixture was warmed to room temperature. After an additional 45 minutes the reaction was complete. The crude mixture was diluted with DCM (40 mL) and washed with brine (2×30 mL). The combined aqueous layers were extracted with additional DCM (30 mL) and the combined organic layers were dried over Na₂SO₄ and the solvent was removed to give the crude sulfonyl chloride. Freshly prepared 486b (170 mg, 0.66 mmol, 1.0 equiv) was dissolved in DCM (2 mL) with TEA (100 mg, 0.99 mmol, 1.5 equiv). A solution of the sulfonyl chloride in DCM (2 mL) was added drop wise. After 5 minutes the reaction was complete and the crude mixture was purified directly by flash chromatography (12 g SiO₂, 0% to 10% MeOH in DCM over 15 minutes) to give 333 mg (71%) of 486c.

Step 3. (S)-tert-butyl 6-(3-chloro-4-((1-(4-(2-cyclopropoxyphenyl)pyridin-3-yl)cyclopropoxy) methyl) phenylsulfonamido)-1-(ethylamino)-1-oxohexan-2-ylcarbamate (Intermediate 486d)

486c (300 mg, 0.42 mmol, 1.0 equiv) was dissolved in THF (1.5 mL) and MeOH (1.5 mL). LiOH (2M in water, 0.42 mL, 0.84 mmol, 2.0 equiv) was added and the reaction mixture was stirred at room temperature for 30 minutes. The solvent was removed and the crude residue was diluted with EtOAc (20 mL) and washed successively with 1N HCl (10 mL), water (15 mL), saturated Na₂CO₃ (15 mL) and brine (10 mL). The organic layer was dried over Na₂SO₄ and concentrated to give the crude acid in quantitative yield, which was dissolved in DMF (3.0 mL). Ethyl amine (2M in THF, 0.21 mL, 0.42 mmol, 1.0 equiv), TEA (63 mg, 0.63 mmol, 1.5 equiv) and finally HATU (175 mg, 0.46 mmol, 1.1 equiv) were added. After 15 minutes the reaction was complete and EtOAc (15 mL) was added. The crude mixture was washed successively with water (2×15 mL) and brine (10 mL) and dried over Na₂SO₄. Purification by flash chromatography (24 g SiO₂, 0% to 5% MeOH in DCM over 20 minutes) gave 302 mg (97%) of 486d.

Step 4. (S)-2-amino-6-(3-chloro-4-((1-(4-(2-cyclopropoxyphenyl)pyridin-3-yl)cyclopropoxy) methyl) phenylsulfonamido)-N-ethylhexanamide (I-486)

TFA (0.2 mL) was added to solution of 486d (60 mg, 0.082 mmol, 1.0 equiv) in DCM (0.2 mL). After 30 minutes the solvent was removed and the crude residue was diluted with MeCN (1.5 mL) and water (1.5 mL). Purification by preparative HPLC (10% to 55% MeCN in water with 0.1% TFA over 18 minutes) gave 5.1 mg (10%) of I-486 as a TFA salt. MS (ES, m/z): 627.19 [M+H]⁺; ¹H-NMR (400 MHz, CD₃OD) δ 8.89 (s, 1H), 8.69 (d, J=5.6 Hz, 1H), 8.34 (s, 1H), 7.71-7.64 (m, 2H), 7.59 (s, 1H), 7.53 (d, J=8.3 Hz, 1H), 7.47-7.41 (m, 1H), 7.38 (d, J=8.4 Hz, 1H), 7.33 (d, J=7.6 Hz, 1H), 7.06 (t, J=7.4 Hz, 1H), 4.49 (s, 2H), 3.75 (t, J=6.4 Hz, 1H), 3.62-3.55 (m, 1H), 2.81 (t, J=6.6 Hz, 2H), 1.88-1.74 (m, 2H), 1.59-1.37 (m, 4H), 1.22-1.04 (m, 7H), 0.63 (d, J=5.9 Hz, 2H), 0.41 (s, 2H).

Example 80: (S)-6-(3-chloro-4-((1-(4-(2-cyclopropoxyphenyl)pyridin-3-yl)cyclopropoxy) methyl) phenylsulfonamido)-N-ethyl-2-(3-((2S,3R,4R,5R)-2,3,4,5,6-pentahydroxyhexyl)ureido)hexanamide (I-487)

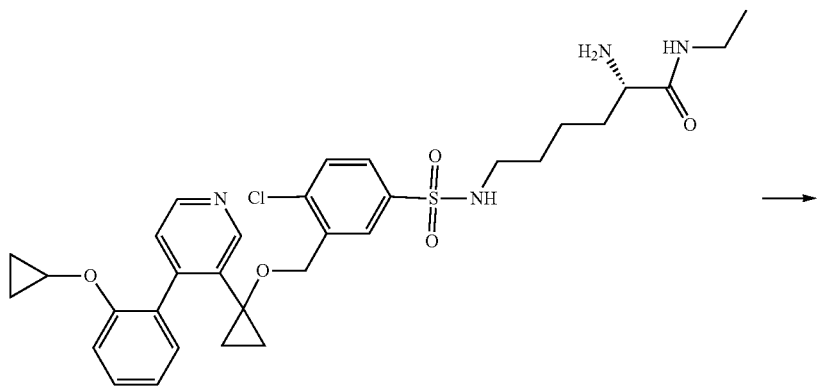

I-486

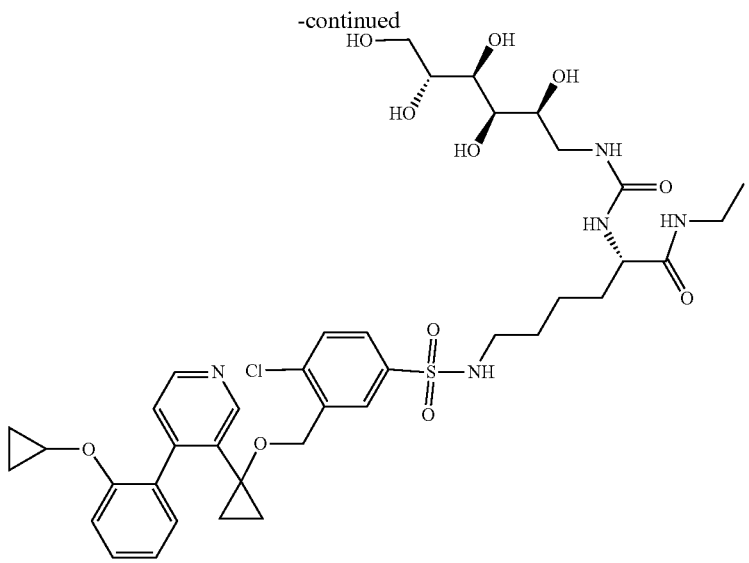

I-487

A solution of I-486 (140 mg, 0.22 mol, 1.0 equiv) in DMF (1.0 mL) was added DSC (57 mg, 0.22 mmol, 1.0 equiv). After 5 minutes, D-Glucamine (60 mg, 0.33 mmol, 1.5 equiv) was added and the reaction mixture was heated to 60° C. After an additional 90 minutes the reaction was complete and cooled to room temperature. MeCN (2.0 mL), TFA, and water (8.0 mL) was added and the mixture was filtered. Purification by preparative HPLC (10% to 55% MeCN in water with 0.1% TFA over 18 minutes) gave 88 mg (48%) of I-487 as a TFA salt. MS (ES, m/z): 834.25 [M+H]$^+$; $^1$H-NMR (400 MHz, CD$_3$OD) δ 8.95 (s, 1H), 8.74 (d, J=5.8 Hz, 1H), 7.81 (d, J=5.9 Hz, 1H), 7.69 (dd, J=8.3, 2.2 Hz, 1H), 7.59 (d, J=1.8 Hz, 1H), 7.54 (d, J=8.4 Hz, 1H), 7.52-7.44 (m, 1H), 7.40 (d, J=8.3 Hz, 1H), 7.36 (dd, J=7.6, 1.6 Hz, 1H), 7.30-7.19 (m, 1H), 7.08 (t, J=7.4 Hz, 1H), 4.50 (s, 2H), 4.07 (dd, J=8.6, 5.5 Hz, 1H), 3.81-3.73 (m, 3H), 3.73-3.65 (m, 1H), 3.65-3.56 (m, 3H), 3.37 (dd, J=14.2, 4.3 Hz, 1H), 3.27-3.14 (m, 3H), 2.79 (t, J=6.8 Hz, 2H), 1.76-1.59 (m, 1H), 1.59-1.42 (m, 3H), 1.42-1.31 (m, 2H), 1.29 (d, J=0.6 Hz, 3H), 1.18 (s, 2H), 1.10 (t, J=7.1 Hz, 5H), 0.72-0.60 (m, 2H), 0.50-0.36 (m, 2H).

Example 81: Ethyl 5-[(6-formyl-5-methylpyridin-2-yl)sulfanyl]pentanoate (Intermediate E1)

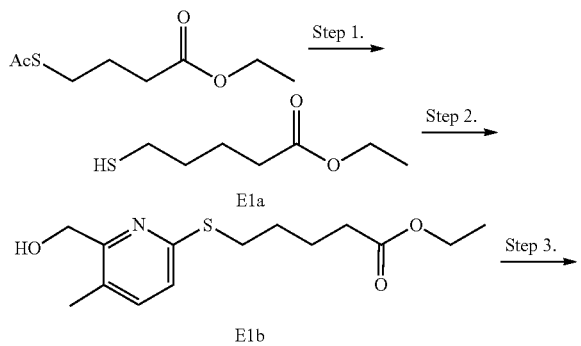

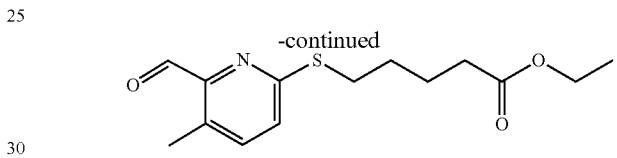

E1

Step 1. Ethyl 5-mercaptopentanoate (Intermediate E1a)

A 100-mL round-bottom flask (1 atm) purged and maintained under an inert atmosphere of nitrogen was charged with ethyl 5-(acetylsulfanyl)pentanoate (4 g, 19.58 mmol, 1.00 equiv), ethanol (50 mL) and potassium carbonate (4.06 g, 29.38 mmol, 1.50 equiv). The resulting solution was stirred for 3-4 h at 40° C. in an oil bath. The resulting solution was diluted with 100 mL of ethyl acetate. The resulting mixture was washed with 1×55 mL of water and 1×55 mL of brine. The mixture was dried over anhydrous sodium sulfate and concentrated under vacuum. This resulted in 3 g (94%) of ethyl 5-sulfanylpentanoate (E1a) as a yellow oil.

Step 2. Ethyl 5-(6-(hydroxymethyl)-5-methylpyridin-2-ylthio)pentanoate (Intermediate E1b)

To a 100-mL round-bottom flask (1 atm) purged and maintained under an inert atmosphere of nitrogen was charged with (6-chloro-3-methylpyridin-2-yl)methanol (1 g, 6.35 mmol, 1.00 equiv), ethyl 5-sulfanylpentanoate (E1a, 1.55 g, 9.55 mmol, 1.50 equiv), dioxane (20 mL), DIEA (1.64 g, 12.69 mmol, 2.00 equiv), xant-Phos (0.37 g, 0.10 equiv) and Pd$_2$(dba)$_3$ (580 mg, 0.63 mmol, 0.10 equiv). The resulting solution was stirred overnight at 110° C. in an oil bath. The resulting solution was diluted with 80 mL of ethyl acetate. The resulting mixture was washed with 1×50 ml of water and 1×50 mL of brine. The mixture was dried over anhydrous sodium sulfate and concentrated under vacuum. The residue was applied onto a silica gel column with ethyl acetate/petroleum ether (0%-50%). This resulted in 1.03 g (57%) of ethyl 5-[[6-(hydroxymethyl)-5-methylpyridin-2-yl]sulfanyl]pentanoate (E1b) as a yellow oil.

Step 3. Ethyl 5-(6-formyl-5-methylpyridin-2-ylthio)pentanoate (Intermediate E1)

A 50-mL round-bottom flask (1 atm) was charged with a solution of ethyl 5-[[6-(hydroxymethyl)-5-methylpyridin-2-yl]sulfanyl]pentanoate (E1b, 400 mg, 1.41 mmol, 1.00 equiv) in DCM (20 mL), MnO$_2$ (1.23 g, 14.15 mmol, 10.00 equiv). The resulting solution was stirred for 4-5 h at room temperature. The solids were collected by filtration. The resulting mixture was concentrated under vacuum. The residue was applied onto a silica gel column with ethyl acetate/petroleum ether (3.5:1). This resulted in 100 mg (25%) of ethyl 5-[(6-formyl-5-methylpyridin-2-yl)sulfanyl]pentanoate (E1) as a colorless oil.

Example 82: Ethyl 4-[(4-chloro-3-formylbenzene)sulfinyl]butanoate (Intermediate E2)

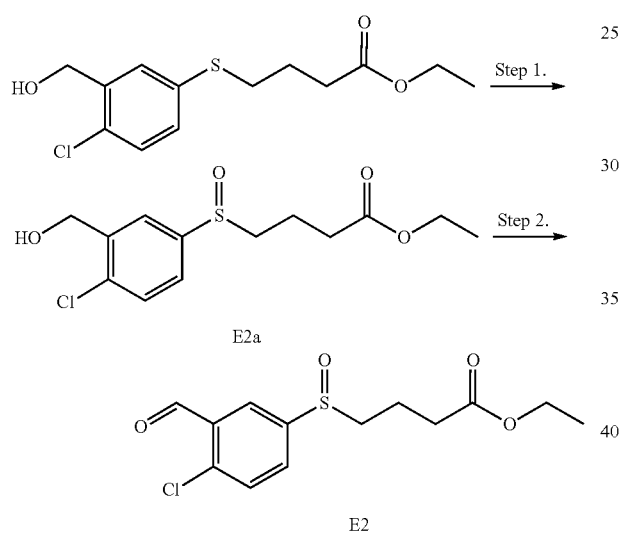

Step 1. Ethyl 4-[[4-chloro-3-(hydroxymethyl)benzene]sulfinyl]butanoate (Intermediate E2a)

A 50-mL round-bottom flask was charged with ethyl 4-[[4-chloro-3-(hydroxymethyl)phenyl]sulfanyl]butanoate (300 mg, 1.04 mmol, 1.00 equiv), dichloromethane (10 mL). This was followed by the addition of m-CPBA (164.58 mg, 1.04 mmol, 1.00 equiv) in several batches at 0° C. in 1 min. The resulting solution was stirred for 1 h at room temperature. The resulting solution was diluted with 10 mL of dichloromethane. The reaction was then quenched by the addition of 10 mL of water. The resulting solution was extracted with 3×20 ml of dichloromethane and the organic layers combined. The resulting mixture was washed with 2×20 mL of brine. The mixture was dried over anhydrous sodium sulfate. The solids were filtered out. The resulting mixture was concentrated under vacuum. The residue was applied onto a silica gel column with ethyl acetate/petroleum ether (2:1). This resulted in 283 mg (89%) of ethyl 4-[[4-chloro-3-(hydroxymethyl)benzene]sulfanyl]butanoate (E2a) as light brown oil.

Step 2. Ethyl 4-[(4-chloro-3-formylbenzene)sulfinyl]butanoate (Intermediate E2)

A 50-mL round-bottom flask was charged with ethyl 4-[[4-chloro-3-(hydroxymethyl)benzene]sulfinyl]butanoate (E2a, 283 mg, 0.93 mmol, 1.00 equiv), chloroform (15 mL), MnO$_2$ (809.34 mg, 9.31 mmol, 10.03 equiv). The resulting solution was stirred for 2 h at 60° C. in an oil bath. The reaction mixture was cooled to rt with a water bath. The solids were filtered out. The resulting mixture was concentrated under vacuum. This resulted in 286 mg (crude) of ethyl 4-[(4-chloro-3-formylbenzene)sulfinyl]butanoate (E2) as a light yellow oil.

Example 83: 5-Methyl-2-(methylsulfanyl)pyrimidine-4-carbaldehyde (Intermediate E3)

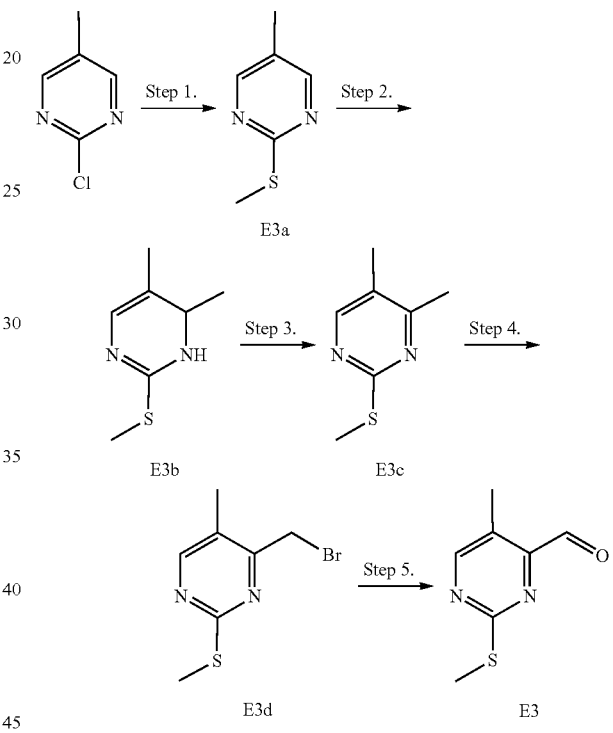

Step 1. 5-methyl-2-(methylsulfanyl)pyrimidine (Intermediate E3a)

A 250-mL round-bottom flask was charged with a solution of 2-chloro-5-methylpyrimidine (3 g, 23.34 mmol, 1.00 equiv) in DMF (50 mL) and MeSNa (16.4 g, 234.3 mmol, 10.00 equiv). The resulting solution was stirred overnight at room temperature. The reaction was then quenched by the addition of 200 mL of H$_2$O. The resulting solution was extracted with 3×50 mL of ethyl acetate and the organic layers combined and dried over sodium sulfate and concentrated under vacuum. The residue was applied onto a silica gel column with PE:EA (92:8). This resulted in 2.8 g (86%) of 5-methyl-2-(methylsulfanyl)pyrimidine (E3a) as a pale-yellow oil.

Step 2. 5,6-dimethyl-2-(methylsulfanyl)-1,6-dihydropyrimidine (Intermediate E3b)

A 100-mL 3-neck round-bottom flask purged and maintained under an inert atmosphere of nitrogen was charged with a solution of 5-methyl-2-(methylsulfanyl)pyrimidine (E3a, 2.8 g, 19.97 mmol, 1.00 equiv) in ether (60 mL). This was followed by the addition of CH₃Li (1.6M) (13.8 mL, 1.10 equiv) dropwise with stirring at 0° C. The resulting solution was stirred for 60 min at room temperature. The reaction was then quenched by the addition of 50 mL of NH₄Cl (aq). The resulting solution was extracted with 3×50 mL of ethyl acetate and the organic layers combined and dried over sodium sulfate and concentrated under vacuum. The residue was applied onto a silica gel column with DCM:MeOH (10:1). This resulted in 2.6 g (83%) of 5,6-dimethyl-2-(methylsulfanyl)-1,6-dihydropyrimidine (E3b) as a light yellow oil.

Step 3. 4,5-dimethyl-2-(methylsulfanyl)pyrimidine (Intermediate E3c)

A 250-mL round-bottom flask was charged with a solution of 5,6-dimethyl-2-(methylsulfanyl)-1,6-dihydropyrimidine (E3b, 2.6 g, 16.64 mmol, 1.00 equiv) in THF (30 mL) and water (390 mg, 21.67 mmol, 1.30 equiv). This was followed by the addition of a solution of DDQ (4.16 g, 18.33 mmol, 1.10 equiv) in THF (30 mL) dropwise with stirring. The mixture was stirred for 30 min at room temperature. To this was added hexane (20 mL) dropwise with stirring at 0° C. To the mixture was added NaOH (3M) (14 mL, 2.50 equiv) dropwise with stirring at 0° C. The resulting solution was stirred for 5 min at 0° C. The mixture was dried over sodium sulfate. The solids were filtered out. The resulting mixture was concentrated under vacuum. The residue was applied onto a silica gel column with PE:EA (95:5). This resulted in 2 g (78%) of 4,5-dimethyl-2-(methylsulfanyl)pyrimidine (E3c) as a light yellow oil.

Step 4. 4-(bromomethyl)-5-methyl-2-(methylsulfanyl)pyrimidine (Intermediate E3d)

A 250-mL round-bottom flask was charged with a solution of 4,5-dimethyl-2-(methylsulfanyl)pyrimidine (E3c, 3.3 g, 21.40 mmol, 1.00 equiv) in acetic acid (50 mL), Br₂ (3.77 g, 23.59 mmol, 1.10 equiv). The resulting solution was stirred for 5 h at 80° C. The pH value of the solution was adjusted to 7-8 with sodium bicarbonate(aq) (10%). The resulting solution was extracted with 3×50 mL of ethyl acetate and the organic layers combined. The mixture was dried over sodium sulfate. The residue was applied onto a silica gel column with PE:EA (99:1). This resulted in 3 g (60%) of 4-(bromomethyl)-5-methyl-2-(methylsulfanyl)pyrimidine (E3d) as an off-white solid.

Step 5. 5-methyl-2-(methylsulfanyl)pyrimidine-4-carbaldehyde (Intermediate E3)

A 250-mL round-bottom flask was charged with 4-(bromomethyl)-5-methyl-2-(methylsulfanyl)pyrimidine (E3d, 3 g, 12.87 mmol, 1.00 equiv), DMSO (30 mL). The resulting solution was stirred overnight at room temperature. The reaction was then quenched by the addition of 200 mL of H₂O. The resulting solution was extracted with 3×50 mL of ethyl acetate and the organic layers combined and dried over sodium sulfate and concentrated under vacuum. The residue was applied onto a silica gel column with PE:EA (95:5). This resulted in 1.5 g (69%) of 5-methyl-2-(methylsulfanyl) pyrimidine-4-carbaldehyde (E3) as a light yellow solid.

Example 84: 4-[[3-(Bromomethyl)-4-ethylphenyl]sulfanyl]butanoate (Intermediate E4)

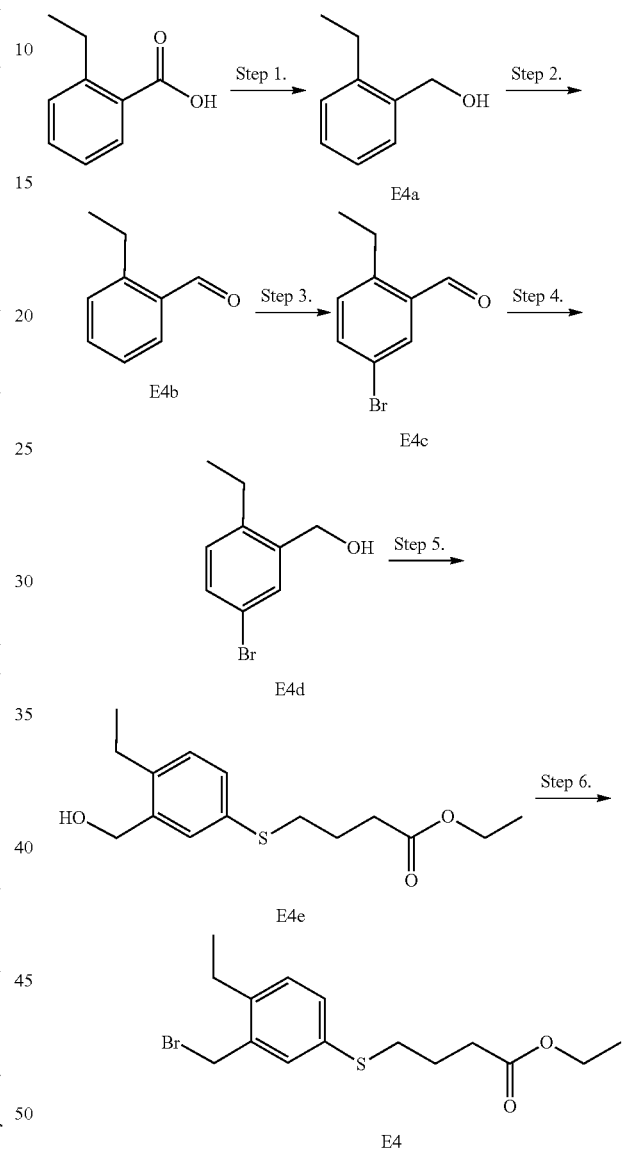

Step 1. (2-ethylphenyl)methanol (Intermediate E4a)

A 500-mL 3-necked round-bottom flask purged and maintained under an inert atmosphere of nitrogen was charged with 2-ethylbenzoic acid (10.0 g, 66.59 mmol, 1.00 equiv) and THF (100 mL). This was followed by the addition of BH₃-THF (200 mL, 3.00 equiv) dropwise with stirring at 0° C. The resulting solution was stirred for 10 min at room temperature. The reaction was then quenched by the addition of 50 mL of methanol. The resulting mixture was concentrated under vacuum. The resulting solution was diluted with 100 mL of ethyl acetate. The resulting mixture was washed with 3×50 mL of Brine. The mixture was dried over anhydrous sodium sulfate and concentrated under vacuum. This resulted in 8.3 g (92%) of (2-ethylphenyl)methanol (E4a) as a yellow oil.

Step 2. 2-ethylbenzaldehyde (Intermediate E4b)

A 250-mL round-bottom flask was charged with (2-ethylphenyl)methanol (9.1 g, 66.82 mmol, 1.00 equiv), MnO$_2$ (E4a, 58.3 g, 10.00 equiv) and chloroform (100 mL). The resulting solution was stirred for 12 h at 60° C. in an oil bath. The solids were filtered out. The resulting mixture was concentrated under vacuum. The residue was applied onto a silica gel column with ethyl acetate/petroleum ether (1:10). This resulted in 6.5 g (73%) of 2-ethylbenzaldehyde (E4b) as a yellow oil.

Step 3. 5-bromo-2-ethylbenzaldehyde (Intermediate E4c)

A 250-mL round-bottom flask purged and maintained under an inert atmosphere of nitrogen was charged with 2-ethylbenzaldehyde (E4b, 6.5 g, 48.44 mmol, 1.00 equiv) and DCM (30 mL). This was followed by the addition of AlCl$_3$ (11.0 g, 1.70 equiv), in portions at 0° C. To this was added a solution of Br$_2$ (7.76 g, 48.56 mmol, 1.00 equiv) in dichloromethane (30 mL) dropwise with stirring at 0° C. The resulting solution was stirred for 2 h at 0° C. in a water/ice bath. The resulting solution was allowed to react, with stirring, for an additional 12 h at room temperature. The reaction was then quenched by the addition of 100 mL of water/ice. The resulting solution was extracted with 3×30 mL of dichloromethane and the organic layers combined. The resulting mixture was washed with 2×50 mL of hydrogen chloride (2M) and 1×50 mL of sodium bicarbonate (sat.). The resulting mixture was washed with 1×50 mL of Brine. The mixture was dried over anhydrous sodium sulfate and concentrated under vacuum. This resulted in 8.2 g (79%) of 5-bromo-2-ethylbenzaldehyde (E4c) as a yellow crude oil.

Step 4. (5-bromo-2-ethylphenyl)methanol (Intermediate E4d)

A 250-mL round-bottom flask purged and maintained under an inert atmosphere of nitrogen was charged with 5-bromo-2-ethylbenzaldehyde (E4c, 3.0 g, 14.08 mmol, 1.00 equiv), methanol (25 mL), tetrahydrofuran (2 mL). This was followed by the addition of borane sodium (1.6 g, 43.45 mmol, 3.00 equiv), in portions at 0° C. The resulting solution was stirred for 2 h at room temperature. The reaction was then quenched by the addition of 50 mL of NH$_4$Cl. The resulting solution was diluted with 50 mL of water. The resulting solution was extracted with 3×mL of ethyl acetate and the organic layers combined and concentrated under vacuum. This resulted in 2.9 g (96%) of (5-bromo-2-ethylphenyl)methanol (E4d) as a yellow crude oil.

Step 5. Ethyl 4-[[4-ethyl-3-(hydroxymethyl)phenyl]sulfanyl]butanoate (Intermediate E4e)

A 250-mL round-bottom flask purged and maintained under an inert atmosphere of nitrogen was charged with (5-bromo-2-ethylphenyl)methanol (E4d, 2.9 g, 13.48 mmol, 1.00 equiv), ethyl 4-sulfanylbutanoate (800 mg, 5.40 mmol, 1.00 equiv), Pd$_2$(dba)$_3$·CHCl$_3$ (280 mg, 0.05 equiv), Xantphos (313 mg, 0.54 mmol, 0.10 equiv), DIEA (1.81 mL, 2.00 equiv), dioxane (100 mL). The resulting solution was stirred for 12 h at 100° C. in an oil bath. The resulting mixture was concentrated under vacuum. The resulting solution was diluted with 100 mL of ethyl acetate. The resulting mixture was washed with 3×50 mL of water and 1×50 mL of Brine. The mixture was dried over anhydrous sodium sulfate and concentrated under vacuum. The residue was applied onto a silica gel column with ethyl acetate/petroleum ether (1:4). This resulted in 320 mg (8%) of ethyl 4-[[4-ethyl-3-(hydroxymethyl)phenyl]sulfanyl]butanoate (E4e) as a yellow oil.

Step 6. Ethyl 4-[[3-(bromomethyl)-4-ethylphenyl]sulfanyl]butanoate (Intermediate E4)

A 100-mL round-bottom flask purged and maintained under an inert atmosphere of nitrogen was charged with ethyl 4-[[4-ethyl-3-(hydroxymethyl)phenyl]sulfanyl]butanoate (100 mg, 0.35 mmol, 1.00 equiv), dichloromethane (5 mL), tetrahydrofuran (5 mL). This was followed by the addition of 1-bromopyrrolidine-2,5-dione (101 mg, 0.57 mmol, 1.60 equiv), in portions at 0° C. To this was added PPh$_3$ (139 mg, 0.53 mmol, 1.50 equiv), in portions at 0° C. The resulting solution was stirred for 30 min at 0° C. in a water/ice bath. The resulting mixture was concentrated under vacuum. The residue was applied onto a silica gel column with ethyl acetate/petroleum ether (1:5). This resulted in 100 mg (82%) of ethyl 4-[[3-(bromomethyl)-4-ethylphenyl]sulfanyl]butanoate (E4) as a yellow oil.

Example 85: Methyl 4-[[3-(bromomethyl)-4-chlorophenyl]sulfanyl]butanoate (Intermediate E5)

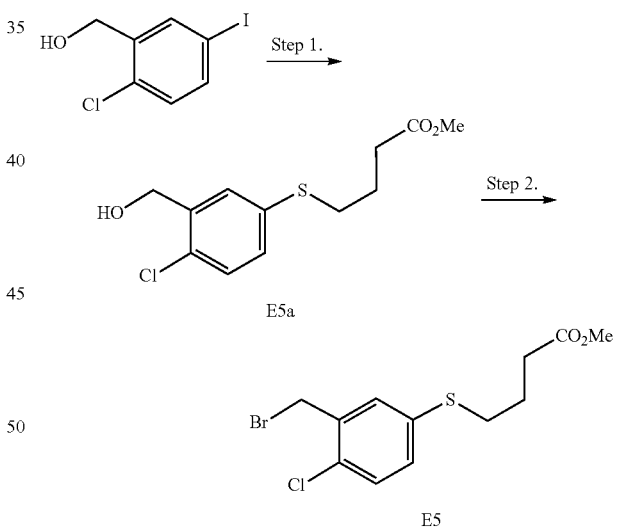

Step 1. methyl 4-[[4-chloro-3-(hydroxymethyl)phenyl]sulfanyl]butanoate (Intermediate E5a)

A 250-mL round-bottom flask was charged with methyl 4-sulfanylbutanoate (900 mg, 6.71 mmol, 1.00 equiv), (2-chloro-5-iodophenyl)methanol (2.4 g, 8.94 mmol, 1.20 equiv), DIEA (1.93 g, 14.93 mmol, 2.00 equiv), Pd$_2$(dba)$_3$ (340 mg, 0.37 mmol, 0.05 equiv), xantphos (440 mg, 0.76 mmol, 0.10 equiv) and dioxane (100 mL). The resulting solution was stirred for 1 overnight at 100° C. in an oil bath. The resulting solution was diluted with 500 mL of ethyl acetate. The resulting mixture was washed with 300 mL of water followed by 2×300 mL of brine. The organic layer was dried over anhydrous sodium sulfate and concentrated under vacuum. The crude product (2.0 g) was purified by Flash chromatography with the following conditions (IntelFlash-1): Column, silica gel; mobile phase, ethyl acetate:petroleum ether=100:0 increasing to ethyl acetate:petroleum ether=85:15 within 30 min; Detector, UV 254 nm. 1.7 g product was obtained. This resulted in 1.7 g (92%) of methyl 4-[[4-chloro-3-(hydroxymethyl)phenyl]sulfanyl]butanoate (E5a) as brown oil.

Step 2. 4-[[3-(bromomethyl)-4-chlorophenyl]sulfanyl]butanoate (Intermediate E5)

A 25-mL round-bottom flask was charged with methyl 4-[[4-chloro-3-(hydroxymethyl)phenyl] sulfanyl]butanoate (E5a, 100 mg, 0.36 mmol, 1.00 equiv), dichloromethane (5 mL), NBS (97 mg, 0.55 mmol, 1.50 equiv), PPh₃ (145 mg, 0.55 mmol, 1.50 equiv). The resulting solution was stirred for 10 min at 0° C. in an ice/salt bath. The resulting mixture was concentrated under vacuum. The crude product was purified by Flash chromatography with the following conditions (IntelFlash-1): Column, silica gel; mobile phase, ethyl acetate:petroleum ether=100:0 increasing to ethyl acetate:petroleum ether=95:5 within 20 min; Detector, UV 254 nm. 100 mg product was obtained. This resulted in 100 mg (81%) of methyl 4-[[3-(bromomethyl)-4-chlorophenyl]sulfanyl]butanoate (E5) as a colorless oil.

Example 85a: 1-(5-[[4-Chloro-3-([1-[4-(2-cyclopropoxyphenyl)pyridin-3-yl]cyclopropoxy]methyl)phenyl]sulfanyl]pentyl)-3-[(2S,3R,4R,5R)-2,3,4,5,6-pentahydroxyhexyl]urea (I-488)

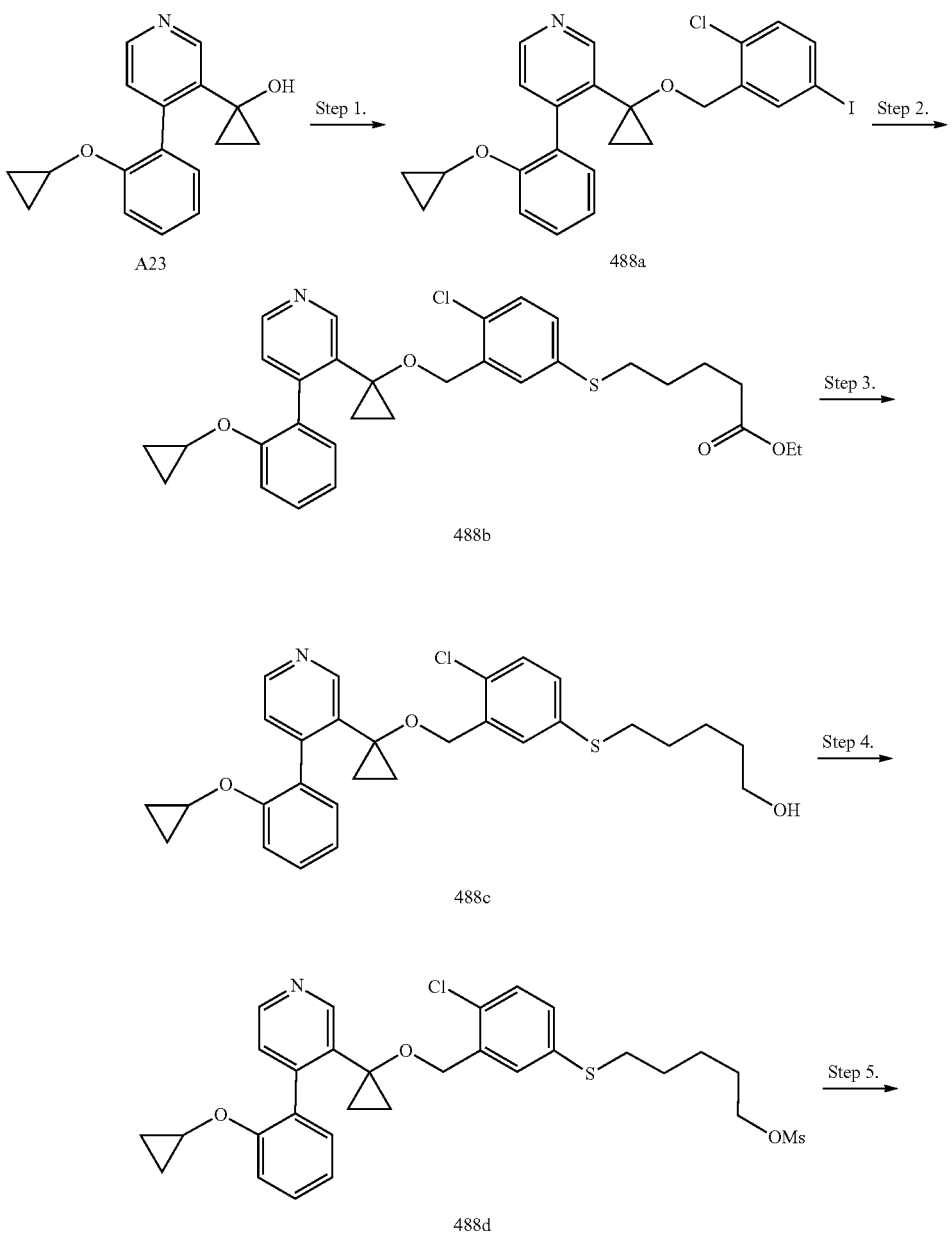

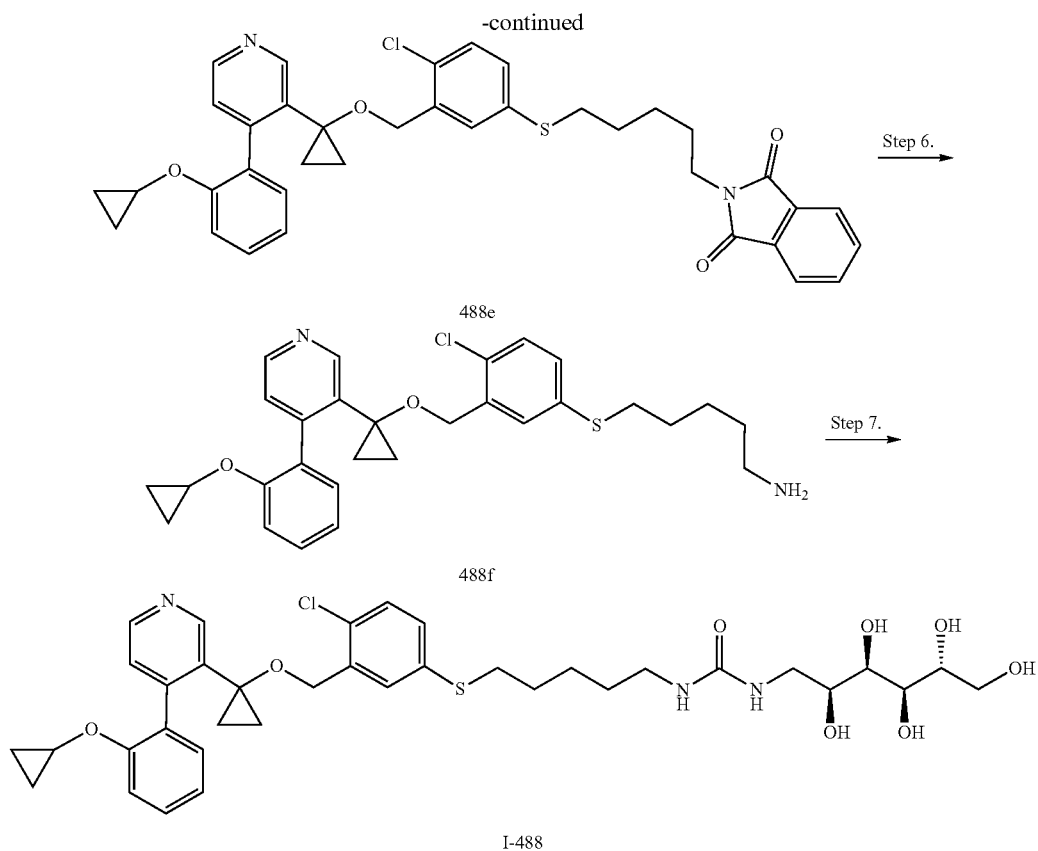

Step 1. 3-[1-[(2-chloro-5-iodophenyl)methoxy]cyclopropyl]-4-(2-cyclopropoxyphenyl) pyridine (Intermediate 488a)

A 250-mL round-bottom flask was charged with 1-[4-(2-cyclopropoxyphenyl)pyridin-3-yl]cyclopropan-1-ol (A23) (3.65 g, 13.65 mmol, 1.00 equiv), 2-(bromomethyl)-1-chloro-4-iodobenzene (5.43 g, 16.39 mmol, 1.20 equiv) and DMF (150 mL). This was followed by the addition of sodium hydride (60% in oil) (1.09 g, 45.42 mmol, 2.00 equiv), in portions at 0° C. The resulting solution was stirred for 30 min at 0° C. The resulting solution was allowed to react, with stirring, for an additional 1 h at room temperature. The reaction was then quenched by the addition of 100 mL of water. The resulting solution was extracted with 3×100 mL of ethyl acetate and the organic layers combined. The resulting mixture was washed with 2×200 mL of water and 1×200 mL of sodium chloride sat. The mixture was dried over anhydrous sodium sulfate. The residue was applied onto a silica gel column with ethyl acetate/petroleum ether (1:7-1:4). This resulted in 3.75 g (53%) of 3-[1-[(2-chloro-5-iodophenyl)methoxy]cyclopropyl]-4-(2-cyclopropoxyphenyl)pyridine (488a) as a brown oil.

Step 2. ethyl 5-[[4-chloro-3-([1-[4-(2-cyclopropoxyphenyl)pyridin-3-yl]cyclopropoxy]methyl)phenyl] (Intermediate 488b)

A 100-mL round-bottom flask purged and maintained under an inert atmosphere of nitrogen was charged with 3-[1-[(2-chloro-5-iodophenyl)methoxy]cyclopropyl]-4-(2-cyclopropoxyphenyl)pyridine (488a, 1.0 g, 1.93 mmol, 1.10 equiv), ethyl 5-sulfanylpentanoate (285 mg, 1.76 mmol, 1.00 equiv), 1,4-dioxane (32 mL), DIEA (455 mg, 3.52 mmol, 2.00 equiv), $Pd_2(dba)_3CHCl_3$ (91 mg, 0.05 equiv) and Xantphos (102 mg, 0.18 mmol, 0.10 equiv). The resulting solution was stirred overnight at 100° C. in an oil bath. The resulting mixture was concentrated under vacuum. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (0-20%). The collected fractions were combined and concentrated under vacuum. This resulted in 800 mg (82%) of ethyl 5-[[4-chloro-3-([1-[4-(2-cyclopropoxyphenyl)pyridin-3-yl]cyclopropoxy]methyl) phenyl] sulfanyl]pentanoate (488b) as a light yellow oil.

Step 3. 5-[[4-chloro-3-([1-[4-(2-cyclopropoxyphenyl)pyridin-3-yl]cyclopropoxy]methyl) phenyl]sulfanyl]pentan-1-ol (Intermediate 488c)

A 250-mL round-bottom flask was charged with ethyl 5-[[4-chloro-3-([1-[4-(2-cyclopropoxyphenyl)pyridin-3-yl]cyclopropoxy]methyl)phenyl]sulfanyl]pentanoate (488b, 4.8 g, 8.70 mmol, 1.00 equiv), tetrahydrofuran (100 mL), $LiAlH_4$ (500 mg, 13.0 mmol, 1.50 equiv). The resulting solution was stirred for 2 h at 0° C. The reaction was then quenched by the addition of 0.5 mL of water, 0.5 mL of 2M NaOH and 1.5 mL of water. The resulting mixture was diluted by 100 mL of EtOAc and stirred for 30 mins, solids were removed by filtration. The resulting mixture was concentrated under vacuum. The residue was applied onto a silica gel column with ethyl acetate/petroleum ether (0-30%). The collected fractions were combined and concentrated under vacuum. This resulted in 3.77 g (86%) (488c) of 5-[[4-chloro-3-([1-[4-(2-cyclopropoxyphenyl)pyridin-3-yl]cyclopropoxy]methyl)phenyl]sulfanyl]pentan-1-ol as a light yellow oil.

Step 4. 5-[[4-chloro-3-([1-[4-(2-cyclopropoxyphenyl)pyridin-3-yl]cyclopropoxy]methyl) phenyl]sulfanyl]pentyl methanesulfonate (Intermediate 488d)

A 50-mL round-bottom flask was charged with 5-[[4-chloro-3-([1-[4-(2-cyclopropoxyphenyl)pyridin-3-yl]cyclopropoxy]methyl)phenyl]sulfanyl]pentan-1-ol (488c, 300 mg, 0.59 mmol, 1.00 equiv), dichloromethane (20 mL), TEA (119 mg, 1.18 mmol, 2.00 equiv) and MsCl (101 mg, 1.50 equiv). The resulting solution was stirred for 0.5 h at room temperature. The resulting mixture was concentrated under vacuum. The residue was applied onto a silica gel column with ethyl acetate/petroleum ether (0-70%). The collected fractions were combined and concentrated under vacuum. This resulted in 280 mg (81%) of 5-[[4-chloro-3-([1-[4-(2-cyclopropoxyphenyl)pyridin-3-yl]cyclopropoxy]methyl) phenyl]sulfanyl]pentyl methanesulfonate (488d) as a light yellow oil.

Step 5. 2-(5-[[4-chloro-3-([1-[4-(2-cyclopropoxyphenyl)pyridin-3-yl]cyclopropoxy]methyl) phenyl]sulfanyl]pentyl)-2,3-dihydro-1H-isoindole-1,3-dione (Intermediate 488e)

A 50-mL round-bottom flask charged with 5-[[4-chloro-3-([1-[4-(2-cyclopropoxyphenyl)pyridin-3-yl]cyclopropoxy]methyl)phenyl]sulfanyl]pentyl methanesulfonate (488d, 290 mg, 0.49 mmol, 1.00 equiv), DMF (15 mL) and 1H,2H,4H-benzo[d]1-aza-2-potassacyclohexane-1,4-dione (182.8 mg, 0.98 mmol, 1.99 equiv). The resulting solution was stirred for 1.5 h at 80° C. in an oil bath. The reaction mixture was cooled to room temperature with a water bath. The resulting solution was diluted with 50 mL of ethyl acetate. The residue was dissolved in 30 mL of H$_2$O. The resulting solution was extracted with 2×30 mL of ethyl acetate and the organic layers combined. The resulting mixture was washed with 3×20 mL of brine. The mixture was dried over anhydrous sodium sulfate. The solids were filtered out. The resulting mixture was concentrated under vacuum. The residue was applied onto a silica gel column with ethyl acetate/petroleum ether (1:1). This resulted in 238 mg (76%) of 2-(5-[[4-chloro-3-([1-[4-(2-cyclopropoxyphenyl)pyridin-3-yl]cyclopropoxy]methyl)phenyl]sulfanyl]pentyl)-2,3-dihydro-1H-isoindole-1,3-dione (488e) as a brown oil.

Step 6. 3-[1-([5-[(5-aminopentyl)sulfanyl]-2-chlorophenyl]methoxy)cyclopropyl]-4-(2-cyclopropoxyphenyl)pyridine (Intermediate 488f)

A 50-mL round-bottom flask charged with 2-(5-[[4-chloro-3-([1-[4-(2-cyclopropoxyphenyl)pyridin-3-yl]cyclopropoxy]methyl)phenyl]sulfanyl]pentyl)-2,3-dihydro-1H-isoindole-1,3-dione (488e, 238 mg, 0.37 mmol, 1.00 equiv), ethanol (15 mL) and NH$_2$NH$_2$·H$_2$O (93.34 mg). The resulting solution was stirred for 1 day at room temperature. The solids were filtered out. The resulting mixture was concentrated under vacuum. The residue was applied onto a silica gel column with dichloromethane/methanol (10:1). This resulted in 100 mg (53%) of 3-[1-([5-[(5-aminopentyl)sulfanyl]-2-chlorophenyl]methoxy)cyclopropyl]-4-(2-cyclopropoxyphenyl)pyridine (488f) as a brown oil.

Step 7. 1-(5-[[4-chloro-3-([1-[4-(2-cyclopropoxyphenyl)pyridin-3-yl]cyclopropoxy]methyl) phenyl]sulfanyl]pentyl)-3-[(2S,3R,4R,5R)-2,3,4,5,6-pentahydroxyhexyl]urea (I-488)

A 25-mL round-bottom flask was charged with 3-[1-([5-[(5-aminopentyl)sulfanyl]-2-chlorophenyl]methoxy)cyclopropyl]-4-(2-cyclopropoxyphenyl)pyridine (488f, 100 mg, 0.20 mmol, 1.00 equiv), (2R,3R,4R,5S)-6-aminohexane-1,2,3,4,5-pentol (107 mg, 0.59 mmol, 3.00 equiv), DIEA (33 mg, 0.26 mmol, 1.30 equiv), DSC (66 mg, 1.30 equiv), N,N-dimethylformamide (4 mL). The resulting solution was stirred overnight at room temperature. The solids were filtered out. The crude product was purified by Preparative HPLC with the following conditions: Column, XBridge Shield RP18 OBD Column; 5 μm 19×150 mm; mobile phase, water with 10 mM NH$_4$HCO$_3$ and MeCN (35.0% MeCN up to 65.0% in 8 min); Detector, UV 254 nm. This resulted in 61.6 mg (44%) of 1-(5-[[4-chloro-3-([1-[4-(2-cyclopropoxyphenyl)pyridin-3-yl]cyclopropoxy]methyl) phenyl] sulfanyl]pentyl)-3-[(2S,3R,4R,5R)-2,3,4,5,6-pentahydroxyhexyl]urea (I-488) as a white solid. MS (ES, m/z): 716 [M+H]$^+$; $^1$H-NMR (300 MHz, CD$_3$OD) δ 0.34 (s, 2H), 0.50-0.61 (m, 2H), 0.96 (d, J=5.0 Hz, 4H), 1.43 (dd, J=6.7, 3.3 Hz, 4H), 1.58 (t, J=7.0 Hz, 2H), 2.84 (t, J=7.2 Hz, 2H), 3.11 (dt, J=22.5, 6.4 Hz, 3H), 3.29-3.51 (m, 2H), 3.52-3.80 (m, 6H), 4.32 (s, 2H), 6.92-7.03 (m, 2H), 7.06-7.43 (m, 6H), 8.44 (d, J=5.1 Hz, 1H), 8.60 (s, 1H).

Example 86: (2S,3S,4R,5S)-N-(5-[[4-chloro-3-([1-[4-(2-cyclopropoxyphenyl)pyridin-3-yl]cyclopropoxy]methyl)phenyl]sulfanyl]pentyl)-2,3,4,5,6-pentahydroxy-N-[2-(2-hydroxyethoxy)ethyl] hexanamide (I-489)

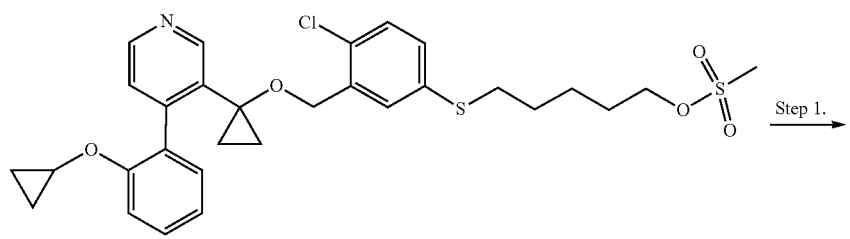

488d

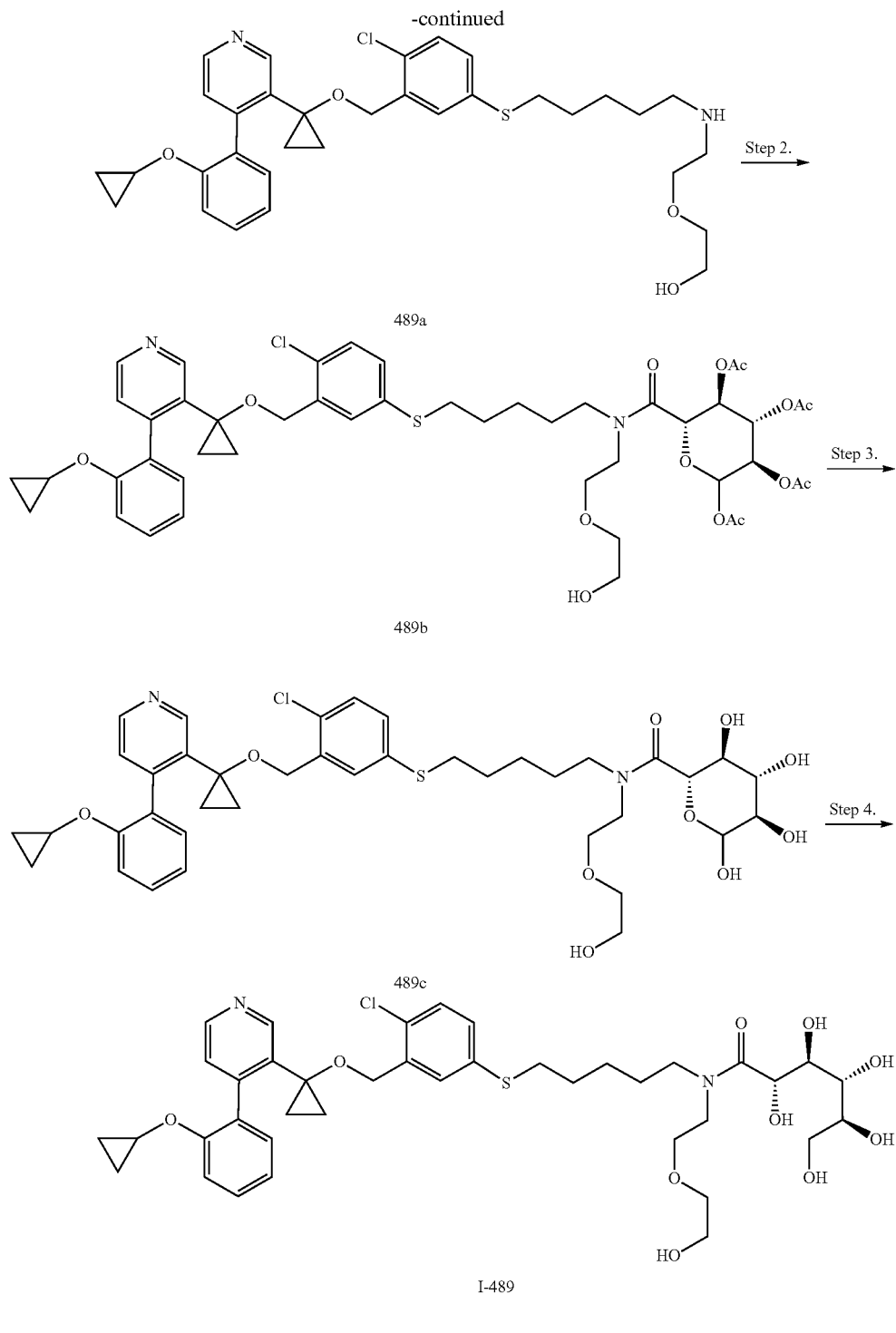

Step 1. 2-[2-[(5-[[4-chloro-3-([1-[4-(2-cyclo-propoxyphenyl)pyridin-3-yl]cyclopropoxy]methyl)phenyl]sulfanyl]pentyl)amino]ethoxy]ethan-1-ol (Intermediate 489a)

A 50-mL round-bottom flask was charged with 5-[[4-chloro-3-([1-[4-(2-cyclopropoxyphenyl)pyridin-3-yl]cyclopropoxy]methyl)phenyl]sulfanyl]pentyl methanesulfonate (488d, 280 mg, 0.48 mmol, 1.00 equiv), 2-(2-aminoethoxy)ethan-1-ol (266 mg, 2.53 mmol, 5.00 equiv) and THF (5 mL). The resulting solution was stirred overnight at 50° C. in an oil bath. The resulting solution was extracted with 3×30 mL of ethyl acetate and the organic layers combined. The resulting mixture was washed with 3×100 mL of brine. The mixture was dried over anhydrous sodium sulfate and concentrated under vacuum. The residue was applied onto a silica gel column with DCM/MeOH (10:1). This resulted in 240 mg (84%) of 2-[2-[(5-[[4-chloro-3-([1-[4-(2-cyclopropoxyphenyl)pyridin-3-yl]cyclopropoxy]methyl)phenyl]sulfanyl] pentyl)amino]ethoxy]ethan-1-ol (489a) as a light yellow oil.

Step 2. (3R,4S,5S,6S)-3,4,5-tris(acetyloxy)-6-[(5-[[4-chloro-3-([1-[4-(2-cyclopropoxyphenyl) pyridin-3-yl]cyclopropoxy]methyl)phenyl]sulfanyl]pentyl)[2-(2-hydroxyethoxy)ethyl]carbamoyl]oxan-2-yl acetate (Intermediate 489b)

A 50-mL round-bottom flask was charged with 2-[2-[(5-[[4-chloro-3-([1-[4-(2-cyclopropoxyphenyl)pyridin-3-yl]cyclopropoxy]methyl)phenyl]sulfanyl]pentyl)amino]ethoxy] ethan-1-ol (489a, 240 mg, 0.40 mmol, 1.00 equiv), (2S,3S,4S,5R)-3,4,5,6-tetrakis(acetyloxy)oxane-2-carboxylic acid (160 mg, 0.44 mmol, 1.10 equiv), HATU (183 mg, 0.48 mmol, 1.20 equiv), DIEA (78 mg, 0.60 mmol, 1.50 equiv) and DMF (10 mL). The resulting solution was stirred overnight at room temperature. The reaction was then quenched by the addition of 50 mL of water. The resulting solution was extracted with 3×100 mL of ethyl acetate and the organic layers combined. The resulting mixture was washed with 3×150 mL of brine. The mixture was dried over anhydrous sodium sulfate. The solids were filtered out. The resulting mixture was concentrated under vacuum. The residue was applied onto a silica gel column with DCM/MeOH (0%-10%). The collected fractions were combined and concentrated under vacuum. This resulted in 380 mg (100%) of (3R,4S,5S,6S)-3,4,5-tris(acetyloxy)-6-[(5-[[4-chloro-3-([1-[4-(2-cyclopropoxyphenyl)pyridin-3-yl]cyclopropoxy]methyl)phenyl] sulfanyl]pentyl)[2-(2-hydroxyethoxy)ethyl]carbamoyl]oxan-2-yl acetate (489b) as a light brown solid.

Step 3. (2S,3S,4S,5R)-N-(5-[[4-chloro-3-([1-[4-(2-cyclopropoxyphenyl) pyridin-3-yl]cyclopropoxy] methyl)phenyl]sulfanyl]pentyl)-3,4,5,6-tetrahydroxy-N-[2-(2-hydroxyethoxy) ethyl]oxane-2-carboxamide (Intermediate 489c)

A 25-mL round-bottom flask was charged with (3R,4S,5S,6S)-3,4,5-tris(acetyloxy)-6-[(5-[[4-chloro-3-([1-[4-(2-cyclopropoxyphenyl)pyridin-3-yl]cyclopropoxy] methyl)phenyl]sulfanyl]pentyl)[2-(2-hydroxyethoxy)ethyl] carbamoyl]oxan-2-yl acetate (489b, 380 mg, 0.40 mmol, 1.00 equiv), methanol (5 mL) and MeONa (22 mg, 0.41 mmol, 1.00 equiv). The resulting solution was stirred overnight at room temperature. The resulting mixture was concentrated under vacuum. This resulted in 200 mg (64%) of (2S,3S,4S,5R)-N-(5-[[4-chloro-3-([1-[4-(2-cyclopropoxyphenyl)pyridin-3-yl]cyclopropoxy]methyl)phenyl]sulfanyl]pentyl)-3,4,5,6-tetrahydroxy-N-[2-(2-hydroxyethoxy)ethyl]oxane-2-carboxamide (489c) as a light yellow solid.

Step 4. (2S,3S,4R,5S)-N-(5-[[4-chloro-3-([1-[4-(2-cyclopropoxyphenyl)pyridin-3-yl] cyclopropoxy]methyl)phenyl]sulfanyl]pentyl)-2,3,4,5,6-pentahydroxy-N-[2-(2-hydroxyethoxy)ethyl]hexanamide (I-489)

A 25-mL round-bottom flask was charged with (2S,3S,4S,5R)-N-(5-[[4-chloro-3-([1-[4-(2-cyclopropoxyphenyl)pyridin-3-yl]cyclopropoxy]methyl)phenyl] sulfanyl]pentyl)-3,4,5,6-tetrahydroxy-N-[2-(2-hydroxyethoxy)ethyl]oxane-2-carboxamide (489c, 200 mg, 0.26 mmol, 1.00 equiv), methanol (10 mL), $NaBH_4$ (20 mg, 0.53 mmol, 2.00 equiv). The resulting solution was stirred for 30 min at room temperature. The solids were filtered out. The resulting mixture was concentrated under vacuum. The resulting solution was diluted with 5 mL of methanol. The crude product was purified by Preparative HPLC with the following conditions (2 #-Analyse HPLC-SHIMADZU(HPLC-10)): Column, Gemini-NX 5μ C18 110A, AXIA Packed, 150×21.2 mm; mobile phase, 10 mM aqueous $NH_4HCO_3$ and MeCN (36.0% MeCN—up to 56.0% in 6 min); Detector, UV 220 nm. 150 mL product was obtained and concentrated under vacuum. This resulted in 96.9 mg (48%) of (2S,3S,4R,5S)-N-(5-[[4-chloro-3-([1-[4-(2-cyclopropoxyphenyl)pyridin-3-yl]cyclopropoxy]methyl)phenyl] sulfanyl]pentyl)-2,3,4,5,6-pentahydroxy-N-[2-(2-hydroxyethoxy) ethyl]hexanamide (I-489) as a white solid. MS (ES, m/z): 775.1 $[M+H]^+$; $^1$H-NMR (300 MHz, $CD_3OD$) δ 0.39 (s, 2H), 0.55-0.66 (m, 2H), 0.96-1.05 (m, 4H), 1.47 (s, 2H), 1.64 (dt, J=18.5, 8.7 Hz, 4H), 2.91 (q, J=6.7 Hz, 2H), 3.38-3.99 (m, 16H), 4.37 (s, 2H), 6.97-7.08 (m, 2H), 7.13-7.31 (m, 4H), 7.32-7.47 (m, 2H), 8.49 (d, J=5.1 Hz, 1H), 8.64 (s, 1H).

Example 87: 1-[2-(2-[[4-Chloro-3-([1-[4-(2-cyclopropoxyphenyl)pyridin-3-yl] cyclopropoxy]methyl)phenyl]sulfanyl]ethoxy)ethyl]-3-[(2S,3R,4R,5R)-2,3,4,5,6-pentahydroxyhexyl]urea (I-490)

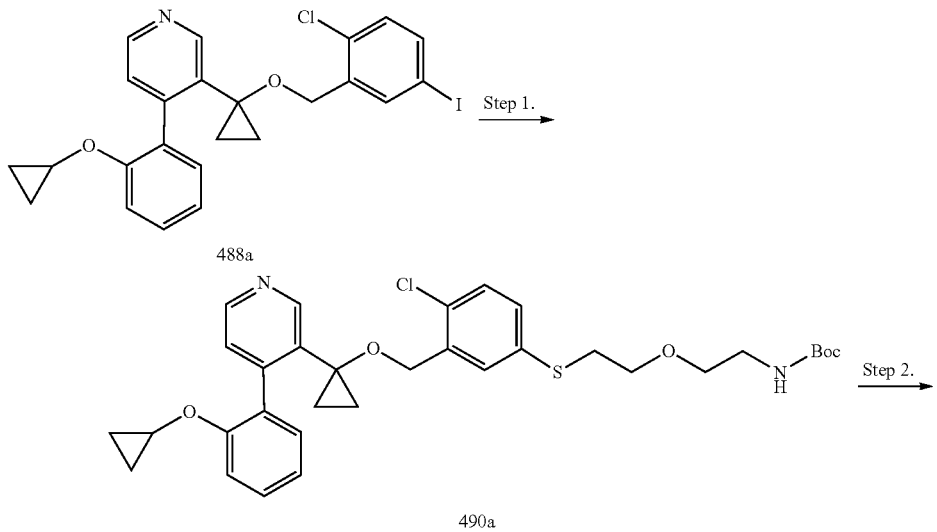

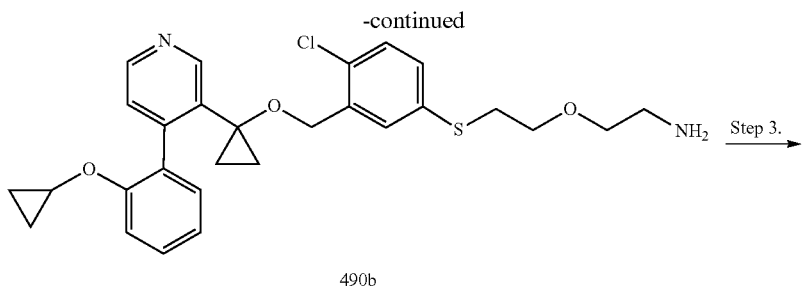

490b

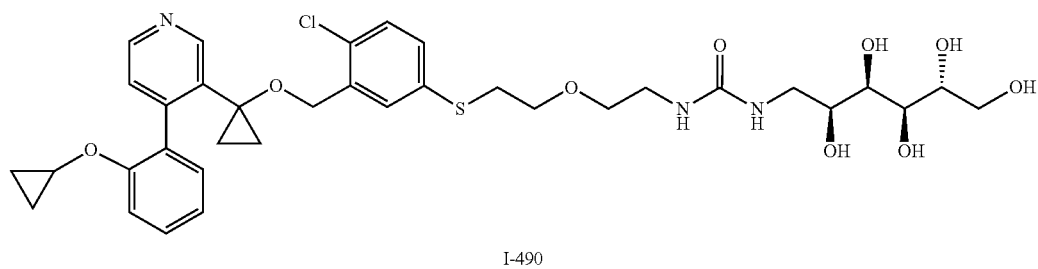

I-490

Step 1. tert-butyl N-[2-(2-[[4-chloro-3-([1-[4-(2-cyclopropoxyphenyl)pyridin-3-yl]cyclopropoxy]methyl)phenyl]sulfanyl]ethoxy)ethyl]carbamate (Intermediate 490a)

A 50-mL round-bottom flask was charged with 3-[1-[(2-chloro-5-iodophenyl)methoxy]cyclopropyl]-4-(2-cyclopropoxyphenyl)pyridine (488a, 250 mg, 0.48 mmol, 1.00 equiv), tert-butyl N-[2-(2-sulfanylethoxy)ethyl]carbamate (97.29 mg, 0.44 mmol, 0.91 equiv), dioxane (8.05 mL), DIEA (0.15 mL), Xantphos (25.46 mg, 0.04 mmol, 0.09 equiv) and Pd$_2$(dba)$_3$CHCl$_3$ (22.75 mg, 0.02 mmol, 0.05 equiv). The resulting solution was stirred overnight at 100° C. in an oil bath. The resulting mixture was concentrated under vacuum. The residue was dissolved in 200 mL of ethyl acetate. The resulting mixture was washed with 3×50 mL of H$_2$O. The resulting mixture was washed with 2×50 mL of brine. The mixture was dried over anhydrous sodium sulfate. The solids were filtered out. The residue was applied onto a silica gel column with ethyl acetate/petroleum ether (1:1). This resulted in 230 mg (78%) of tert-butyl N-[2-(2-[[4-chloro-3-([1-[4-(2-cyclopropoxyphenyl)pyridin-3-yl]cyclopropoxy]methyl) phenyl]sulfanyl]ethoxy)ethyl]carbamate (490a) as a brown oil.

Step 2. 2-(2-[[4-chloro-3-([1-[4-(2-cyclopropoxyphenyl)pyridin-3-yl]cyclopropoxy]methyl)phenyl] sulfanyl]ethoxy)ethan-1-amine (Intermediate 490b)

A 50-mL round-bottom flask was charged with tert-butyl N-[2-(2-[[4-chloro-3-([1-[4-(2-cyclopropoxyphenyl)pyridin-3-yl]cyclopropoxy]methyl)phenyl]sulfanyl]ethoxy) ethyl]carbamate (490a, 230 mg, 0.38 mmol, 1.00 equiv), TFA/DCM (10/10 mL). The resulting solution was stirred for 1 h at room temperature. The resulting mixture was concentrated under vacuum. The residue was dissolved in 200 mL of ethyl acetate. The pH value of the solution was adjusted to 9.0 with sodium bicarbonate (100%). The resulting solution was extracted with 2×30 mL of ethyl acetate and the organic layers combined. The resulting mixture was washed with 2×50 mL of brine. The mixture was dried over anhydrous sodium sulfate. The solids were filtered out. This resulted in 216 mg (crude) of 2-(2-[[4-chloro-3-([1-[4-(2-cyclopropoxyphenyl) pyridin-3-yl]cyclopropoxy]methyl) phenyl] sulfanyl]ethoxy)ethan-1-amine (490b) as a brown solid.

Step 3. 1-[2-(2-[[4-chloro-3-([1-[4-(2-cyclopropoxyphenyl)pyridin-3-yl]cyclopropoxy]methyl)phenyl] sulfanyl]ethoxy)ethyl]-3-[(2S,3R,4R,5R)-2,3,4,5,6-pentahydroxyhexyl]urea (I-490)

A 50-mL round-bottom flask was charged with 2-(2-[[4-chloro-3-([1-[4-(2-cyclopropoxyphenyl)pyridin-3-yl]cyclopropoxy]methyl)phenyl]sulfanyl]ethoxy)ethan-1-amine (490b, 216 mg, 0.42 mmol, 1.00 equiv), N,N-dimethylformamide (5 mL), DIEA (0.091 mL), DSC (140.7 mg), (2R,3R,4R,5S)-6-aminohexane-1,2,3,4,5-pentol (153.3 mg, 0.85 mmol, 2.00 equiv). The resulting solution was stirred for 1.5 h at room temperature. The resulting solution was allowed to react, with stirring, for an additional 1 overnight at room temperature. The resulting solution was diluted with 50 mL of ethyl acetate. The solids were filtered out. The resulting mixture was concentrated under vacuum. The crude product was purified by Preparative HPLC with the following conditions: Column, XBridge Shield RP18 OBD Column; 5 μm 19×150 mm; mobile phase, 10 mM aqueous NH$_4$HCO$_3$ and MeCN (30.0% MeCN up to 54.0% in 8 min); Detector, UV 254 nm. Product was obtained. This resulted in 127 mg (42%) of 1-[2-(2-[[4-chloro-3-([1-[4-(2-cyclopropoxyphenyl)pyridin-3-yl]cyclopropoxy]methyl)phenyl] sulfanyl] ethoxy)ethyl]-3-[(2S,3R,4R,5R)-2,3,4,5,6-pentahydroxyhexyl]urea (I-490) as a white solid. MS (ES, m/z): 718 [M+H]$^+$; $^1$H-NMR (400 MHz, CD$_3$OD) δ 0.38 (s, 2H), 0.55-0.65 (m, 2H), 0.99 (d, J=9.0 Hz, 4H), 3.06 (t, J=6.7 Hz, 2H), 3.17 (dd, J=13.9, 6.9 Hz, 1H), 3.26 (t, J=5.4 Hz, 2H), 3.34-3.55 (m, 4H), 3.56-3.81 (m, 8H), 4.36 (s, 2H), 6.96-7.07 (m, 2H), 7.17-7.29 (m, 4H), 7.30-7.44 (m, 2H), 8.47 (d, J=5.0 Hz, 1H), 8.63 (s, 1H).

Example 88: 1-[2-(2-[[4-chloro-3-([1-[4-(2-cyclo-propoxyphenyl)pyridin-3-yl]cyclopropoxy]methyl) benzene]sulfinyl]ethoxy)ethyl]-3-[(2S,3R,4R,5R)-2, 3,4,5,6-pentahydroxyhexyl]urea

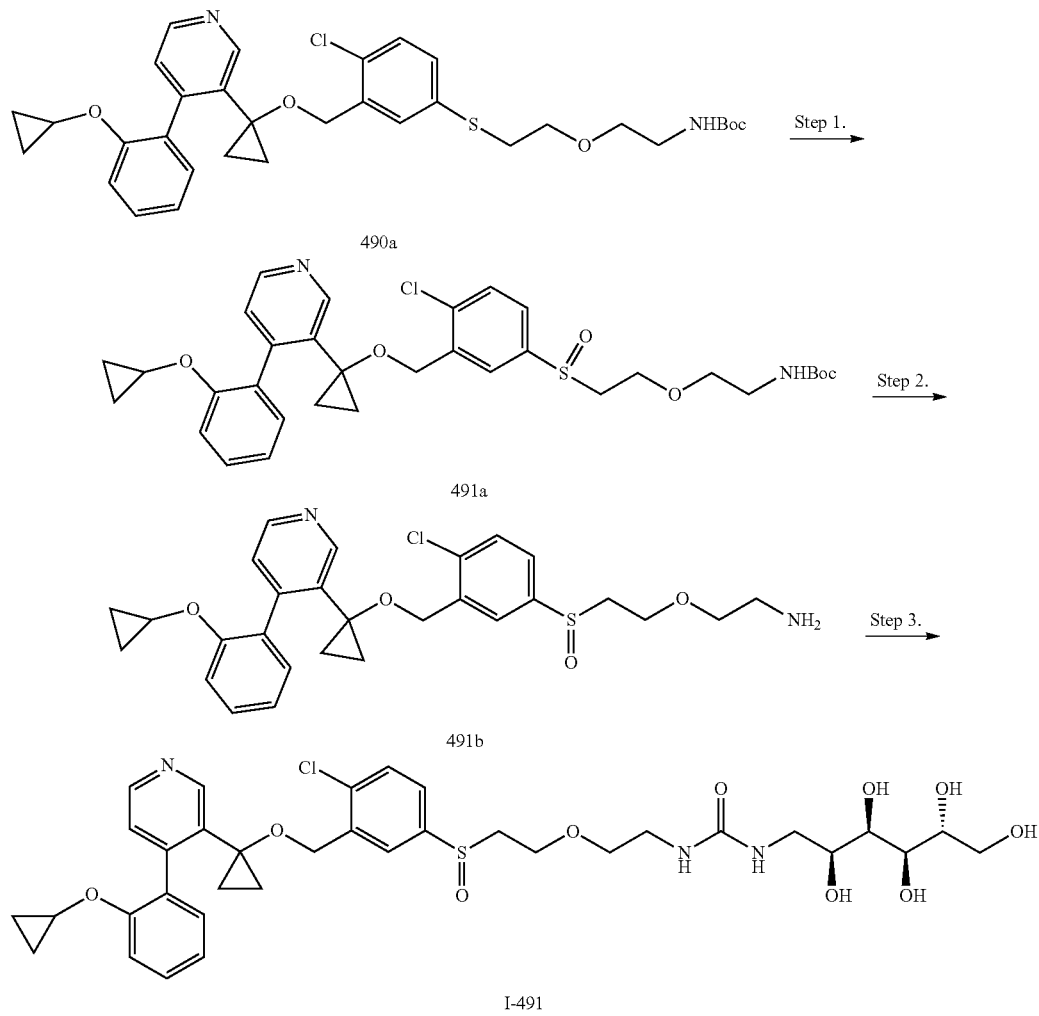

Step 1. tert-butyl N-[2-(2-[[4-chloro-3-([1-[4-(2-cyclopropoxyphenyl)pyridin-3-yl] cyclopropoxy] methyl)benzene] sulfinyl]ethoxy)ethyl]carbamate (Intermediate 491a)

A 25-mL round-bottom flask was charged with a solution of tert-butyl N-[2-(2-[[4-chloro-3-([1-[4-(2-cyclopropoxyphenyl)pyridin-3-yl]cyclopropoxy]methyl)phenyl]sulfanyl] ethoxy)ethyl]carbamate (200 mg, 0.33 mmol, 1.00 equiv) in DCM (8 mL). The solution was stirred for 5 min at 0° C. This was followed by the addition of mCPBA (51 mg, 0.32 mmol, 1.00 equiv) in several batches at 0° C. The resulting solution was stirred for 2-3 h at 0° C. in an ice/salt bath. The resulting solution was diluted with 30 mL of H₂O. The resulting solution was extracted with 2×20 mL of ethyl acetate and the organic layers combined. The resulting mixture was washed with 1×50 mL of brine. The mixture was dried over anhydrous sodium sulfate and concentrated under vacuum. This resulted in 200 mg (97%) of tert-butyl N-[2-(2-[[4-chloro-3-([1-[4-(2-cyclopropoxyphenyl)pyridin-3-yl]cyclopropoxy]methyl)benzene]sulfinyl]ethoxy) ethyl]carbamate (491a) as a light yellow oil.

Step 2. 2-(2-[[4-chloro-3-([1-[4-(2-cyclopropoxyphenyl)pyridin-3-yl]cyclopropoxy]methyl) benzene] sulfinyl]ethoxy)ethan-1-amine (Intermediate 491b)

A 25-mL round-bottom flask was charged with tert-butyl N-[2-(2-[[4-chloro-3-([1-[4-(2-cyclopropoxyphenyl)pyridin-3-yl]cyclopropoxy]methyl)benzene]sulfinyl]ethoxy) ethyl] carbamate (200 mg, 0.32 mmol, 1.00 equiv). The solution was stirred for 5 min at 0° C. This was followed by the addition of hydrogen chloride/dioxane (3/6 mL) dropwise with stirring at 0° C. The resulting solution was stirred for 0.5-1 h at room temperature in a water/ice bath. The resulting solution was diluted with 30 mL of H₂O. The pH value of the solution was adjusted to 8 with sodium carbonate (1 mol/L). The resulting solution was extracted with 2×20 mL of ethyl acetate and the organic layers combined. The resulting mixture was washed with 1×30 mL of brine.

The mixture was dried over anhydrous sodium sulfate and concentrated under vacuum. This resulted in 150 mg (89%) of 2-(2-[[4-chloro-3-([1-[4-(2-cyclopropoxyphenyl)pyridin-3-yl]cyclopropoxy]methyl)benzene]sulfinyl]ethoxy)ethan-1-amine (491b) as a light yellow oil.

Step 3. 1-[2-(2-[[4-chloro-3-([1-[4-(2-cyclopropoxyphenyl)pyridin-3-yl]cyclopropoxy]methyl)benzene]sulfinyl]ethoxy)ethyl]-3-[(2S,3R,4R,5R)-2,3,4,5,6-pentahydroxyhexyl]urea (I-491)

A 100-mL round-bottom flask was charged with 2-(2-[[4-chloro-3-([1-[4-(2-cyclopropoxyphenyl)pyridin-3-yl]cyclopropoxy]methyl)benzene]sulfinyl]ethoxy)ethan-1-amine (227 mg, 0.43 mmol, 1.00 equiv), DSC (133 mg, 0.52 mmol, 1.20 equiv). This was followed by the addition of a solution of DIEA (0.11 mL, 1.50 equiv) in N,N-dimethylformamide (20 mL). The solution was stirred for 1 h at room temperature. To this was added (2R,3R,4R,5S)-6-aminohexane-1,2,3,4,5-pentol (102 mg, 0.56 mmol, 1.30 equiv). The resulting solution was stirred overnight at room temperature. The solids were filtered out. The crude product was purified by Preparative HPLC with the following conditions: Column, XBridge Shield RP18 OBD Column; 5 μm 19×150 mm; mobile phase, 10 mM aqueous NH₄HCO₃ and MeCN (25.0% MeCN up to 50.0% in 10 min); Detector, UV 220 nm. This resulted in 65.8 mg (21%) of 1-[2-(2-[[4-chloro-3-([1-[4-(2-cyclopropoxyphenyl)pyridin-3-yl]cyclopropoxy]methyl)benzene] sulfinyl] ethoxy)ethyl]-3-[(2S,3R,4R,5R)-2,3,4,5,6-pentahydroxyhexyl]urea (I-491) as a white solid. MS (ES, m/z): 734.4 [M+H]⁺; ¹H-NMR (400 MHz, CD₃OD) δ 8.65 (s, 1H), 8.48 (d, J=5.1 Hz, 1H), 7.56 (t, J=1.3 Hz, 2H), 7.43-7.20 (m, 5H), 7.01 (td, J=7.4, 1.2 Hz, 1H), 4.46 (s, 2H), 3.90-3.82 (m, 1H), 3.82-3.56 (m, 7H), 3.56-3.47 (m, 3H), 3.45-3.35 (m, 1H), 3.29 (d, J=5.1 Hz, 2H), 3.14-3.00 (m, 3H), 1.02 (dd, J=11.1, 6.9 Hz, 4H), 0.60 (dd, J=6.1, 1.9 Hz, 2H), 0.36 (p, J=3.0 Hz, 2H).

Example 89: 1-[2-(2-[[4-Chloro-3-([1-[4-(2-cyclopropoxyphenyl)pyridin-3-yl]cyclopropoxy]methyl)benzene]sulfonyl]ethoxy)ethyl]-3-[(2S,3R,4R,5R)-2,3,4,5,6-pentahydroxyhexyl]urea (I-492)

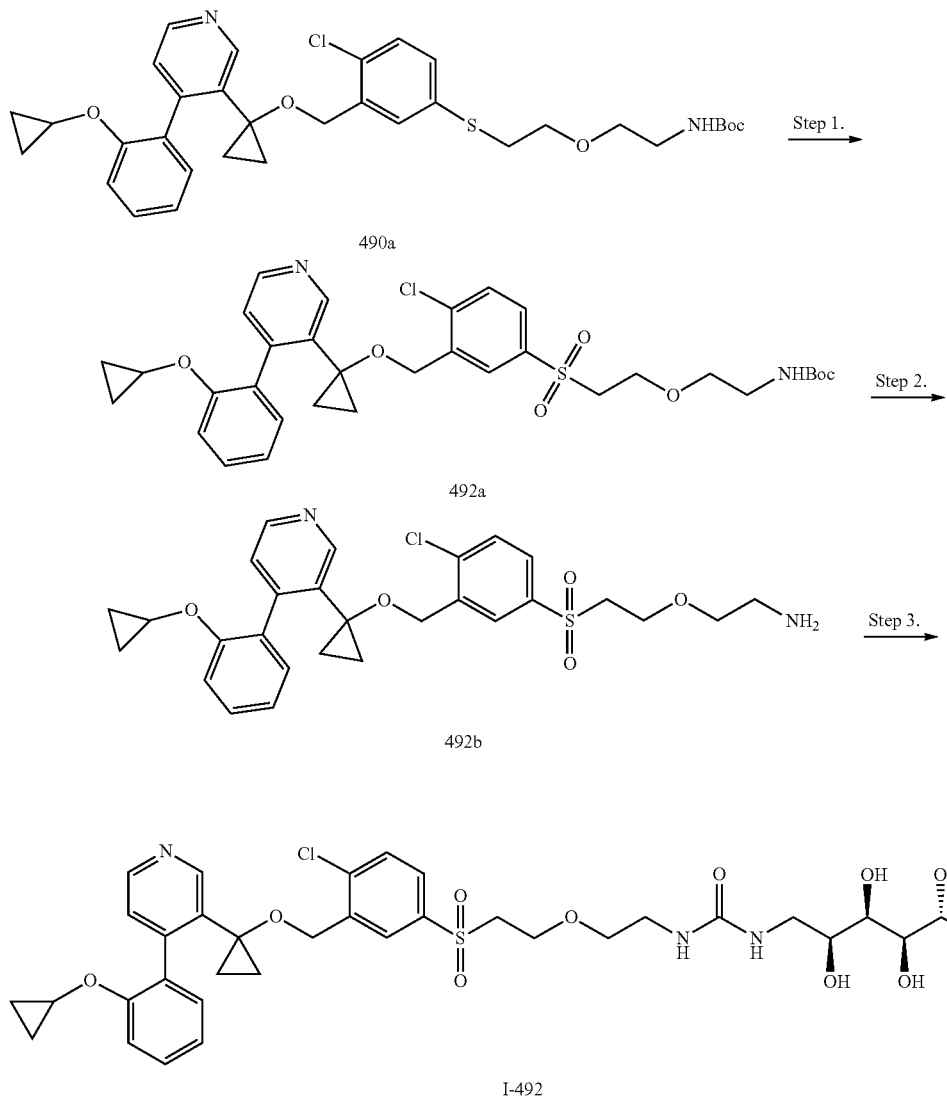

Step 1. tert-butyl N-[2-(2-[[4-chloro-3-([1-[4-(2-cyclopropoxyphenyl)pyridin-3-yl] cyclopropoxy]methyl)benzene]sulfonyl]ethoxy)ethyl]carbamate (Intermediate 492a)

A 25-mL round-bottom flask was charged with a solution of tert-butyl N-[2-(2-[[4-chloro-3-([1-[4-(2-cyclopropoxyphenyl)pyridin-3-yl]cyclopropoxy]methyl)phenyl]sulfanyl]ethoxy)ethyl]carbamate (400 mg, 0.65 mmol, 1.00 equiv) in THF (10 mL). The solution was stirred for 5 min at 0° C. This was followed by the addition of a solution of $RuCl_3$ (4 mg, 0.02 mmol, 0.03 equiv) in water (2 mL) dropwise with stirring at 0° C. To this was added a solution of $NaIO_4$ (702 mg, 3.28 mmol, 5.00 equiv) in water (8 mL) dropwise with stirring at 0° C. The resulting solution was stirred for 1-2 h at room temperature in a water/ice bath. The resulting solution was diluted with 80 mL of $H_2O$. The resulting solution was extracted with 2×40 mL of ethyl acetate and the organic layers combined. The resulting mixture was washed with 1×50 mL of brine. The mixture was dried over anhydrous sodium sulfate and concentrated under vacuum. This resulted in 400 mg (95%) of tert-butyl N-[2-(2-[[4-chloro-3-([1-[4-(2-cyclopropoxyphenyl)pyridin-3-yl]cyclopropoxy]methyl)benzene]sulfonyl]ethoxy)ethyl] carbamate (492a) as a yellow oil.

Step 2. 2-(2-[[4-chloro-3-([1-[4-(2-cyclopropoxyphenyl)pyridin-3-yl]cyclopropoxy]methyl) benzene]sulfonyl]ethoxy)ethan-1-amine (Intermediate 492b)

A 25-mL round-bottom flask was charged with tert-butyl N-[2-(2-[[4-chloro-3-([1-[4-(2-cyclopropoxyphenyl)pyridin-3-yl]cyclopropoxy]methyl)benzene]sulfonyl]ethoxy)ethyl] carbamate (400 mg, 0.62 mmol, 1.00 equiv). The solution was stirred for 5 min at 0° C. This was followed by the addition of hydrogen chloride/dioxane (4.5/9 mL) dropwise with stirring at 0° C. The resulting solution was stirred for 0.5-1 h at room temperature in a water/ice bath. The resulting solution was diluted with 50 mL of $H_2O$. The pH value of the solution was adjusted to 8 with sodium carbonate (1 mol/L). The resulting solution was extracted with 2×50 mL of ethyl acetate and the organic layers combined. The resulting mixture was washed with 1×80 mL of brine. The mixture was dried over anhydrous sodium sulfate and concentrated under vacuum. This resulted in 330 mg (98%) of 2-(2-[[4-chloro-3-([1-[4-(2-cyclopropoxyphenyl)pyridin-3-yl]cyclopropoxy]methyl)benzene]sulfonyl]ethoxy)ethan-1-amine (492b) as a yellow oil.

Step 3. 1-[2-(2-[[4-chloro-3-([1-[4-(2-cyclopropoxyphenyl)pyridin-3-yl]cyclopropoxy]methyl)benzene] sulfonyl]ethoxy)ethyl]-3-[(2S,3R,4R,5R)-2,3,4,5,6-pentahydroxyhexyl]urea (I-492)

A 25-mL round-bottom flask was charged with 2-(2-[[4-chloro-3-([1-[4-(2-cyclopropoxyphenyl)pyridin-3-yl]cyclopropoxy]methyl)benzene]sulfonyl]ethoxy)ethan-1-amine (330 mg, 0.61 mmol, 1.00 equiv) and DSC (187 mg, 0.73 mmol, 1.20 equiv). This was followed by the addition of a solution of DIEA (0.15 mL, 1.50 equiv) in DMF (8 mL). The solution was stirred for 1h at room temperature. To this was added (2R,3R,4R,5S)-6-aminohexane-1,2,3,4,5-pentol (143 mg, 0.79 mmol, 1.30 equiv). The resulting solution was stirred overnight at room temperature. The solids were filtered out. The crude product was purified by Preparative HPLC with the following conditions: Column, XBridge Shield RP18 OBD Column; 5 μm 19×150 mm; mobile phase, 10 mM aqueous $NH_4HCO_3$ and MeCN (30.0% MeCN up to 41.0% in 8 min); Detector, UV 220 nm. This resulted in 121.2 mg (27%) of 1-[2-(2-[[4-chloro-3-([1-[4-(2-cyclopropoxyphenyl)pyridin-3-yl]cyclopropoxy]methyl)benzene]sulfonyl]ethoxy)ethyl]-3-[(2S,3R,4R,5R)-2,3,4,5,6-pentahydroxyhexyl]urea (I-492) as a white solid. MS (ES, m/z): 750.3 [M+H]$^+$; $^1$H-NMR (400 MHz, $CD_3OD$) δ 8.66 (d, J=0.7 Hz, 1H), 8.48 (d, J=5.1 Hz, 1H), 7.78 (dd, J=8.4, 2.4 Hz, 1H), 7.69 (d, J=2.3 Hz, 1H), 7.59 (d, J=8.3 Hz, 1H), 7.43-7.31 (m, 2H), 7.29-7.19 (m, 2H), 7.03 (td, J=7.3, 1.5 Hz, 1H), 4.48 (s, 2H), 3.82-3.51 (m, 9H), 3.47 (t, J=5.7 Hz, 2H), 3.41-3.30 (m, 2H), 3.20-3.04 (m, 3H), 1.08-0.94 (m, 4H), 0.66-0.56 (m, 2H), 0.44-0.35 (m, 2H).

Example 90: 1-(2-(2-(4-Chloro-3-((1-(4-(2-(oxetan-3-yloxy)phenyl)pyridin-3-yl) cyclopropoxy)methyl)phenylthio)ethoxy)ethyl)-3-((2S,3R,4R,5R)-2,3,4,5,6-pentahydroxyhexyl)urea (I-493)

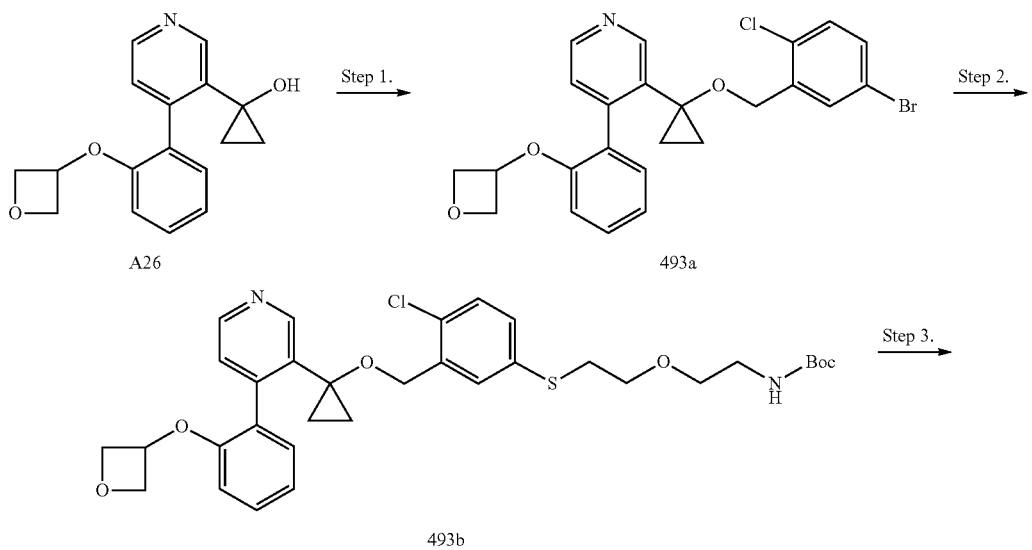

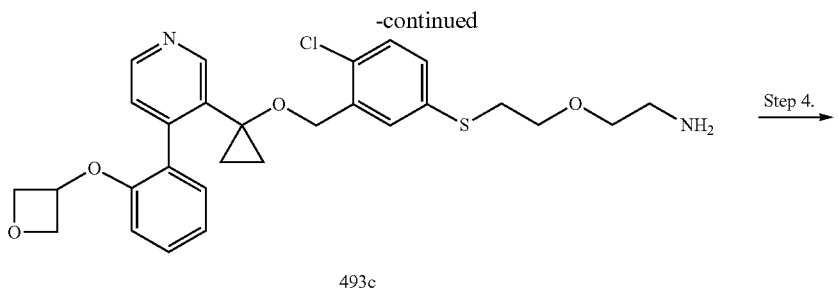

493c

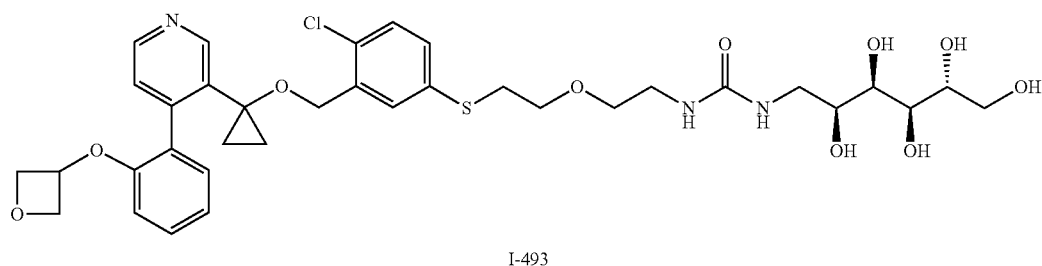

I-493

Step 1. 3-(1-(5-bromo-2-chlorobenzyloxy)cyclopropyl)-4-(2-(oxetan-3-yloxy)phenyl)pyridine (Intermediate 493a)

Sodium hydride (60% in oil, 116 mg, 2.8 mmol) was added to a solution of 1-(4-(2-(oxetan-3-yloxy)phenyl)pyridin-3-yl)cyclopropanol (A26) (398 mg, 1.40 mmol) and 4-bromo-2-(bromomethyl)-1-chlorobenzene (480 mg, 1.69 mmol) in DMF (8.0 mL) at 0° C. After 20 minutes, the reaction was quenched by the addition of 50% saturated $NaHCO_3$ (40 mL). The product was extracted into EtOAc (3×30 mL). The combined organic layers were washed with water (2×25 mL), and brine (25 mL), dried ($Na_2SO_4$) and concentrated. The crude product was combined with another run (0.35 mmol scale) and purified by flash chromatography (40 g $SiO_2$, eluting with 0-40% EtOAc/DCM) to give the title compound (564 mg, 66%).

Step 2. tert-butyl 2-(2-(4-chloro-3-((1-(4-(2-(oxetan-3-yloxy)phenyl)pyridin-3-yl) cyclopropoxy) ethyl) phenylthio)ethoxy)ethylcarbamate (Intermediate 493b)

3-(1-(5-bromo-2-chlorobenzyloxy)cyclopropyl)-4-(2-(oxetan-3-yloxy)phenyl) pyridine (564 mg, 1.16 mmol) and tert-butyl 2-(2-mercaptoethoxy)ethylcarbamate (310 mg, 1.40 mmol) were dissolved in dioxane (15 mL). The flask was evacuated and then purged with nitrogen. This was repeated 4×. Xantphos (60 mg, 0.10 mmol), $Pd_2(dba)_3$ (53 mg, 0.058 mmol) and DIEA (0.40 mL, 2.32 mmol) were added, and the evacuation/nitrogen purge cycle was repeated 5×. The reaction was heated at 100° C. for 3 hours, at which time it was cooled, concentrated and purified by flash chromatography on silica gel (50-80% EtOAc/hexane) to give the title compound (493b) (660 mg, 90%).

Step 3. 2-(2-(4-chloro-3-((1-(4-(2-(oxetan-3-yloxy)phenyl)pyridin-3-yl)cyclopropoxy)methyl) phenylthio)ethoxy)ethanamine (Intermediate 493c)

Trifluoroacetic acid (0.5 mL) was added to a solution of tert-butyl 2-(2-(4-chloro-3-((1-(4-(2-(oxetan-3-yloxy)phenyl)pyridin-3-yl)cyclopropoxy)methyl)phenylthio)ethoxy)ethylcarbamate (494b, 43 mg, 0.068 mmol) in DCM (0.5 mL). After 45 minutes, the solvent was removed at reduced pressure. 10% $Na_2CO_3$ (5 mL) was added and the product was extracted with DCM (4×10 mL). The combined organic layers were washed with water (5 mL) and brine (5 mL) and then dried ($Na_2SO_4$) and concentrated to give the crude amine (493c).

Step 4. 1-(2-(2-(4-chloro-3-((1-(4-(2-(oxetan-3-yloxy)phenyl)pyridin-3-yl)cyclopropoxy) methyl) phenylthio)ethoxy)ethyl)-3-((2S,3R,4R,5R)-2,3,4,5, 6-pentahydroxyhexyl)urea (I-493)

A solution of 2-(2-(4-chloro-3-((1-(4-(2-(oxetan-3-yloxy) phenyl)pyridin-3-yl) cyclopropoxy)methyl)phenylthio) ethoxy)ethanamine (493c) in DMF (0.7 mL) was treated with disuccinimidyl carbonate (19 mg, 0.075 mmol) and stirred at RT. After 30 minutes, the amine was consumed. D-glucamine (24.5 mg, 0.136 mmol) was added, and the reaction was heated at 60° C. After heating for 30 minutes, the reaction was complete by LC/MS. The cooled reaction mixture was diluted with 1:1 MeCN/water and purified by reverse phase HPLC (MeCN/0.01M $NH_4HCO_3$) to give the title compound (I-493) (33 mg). MS (ES, m/z): 734.2 (M+H)+. $^1$H NMR (400 MHz, $CD_3OD$) δ 8.65 (s, 1H), 8.53 (d, J=5.1 Hz, 1H), 7.37-7.31 (m, 3H), 7.23 (s, 2H), 7.04 (t, J=7.7 Hz, 1H), 6.97 (s, 1H), 6.55 (d, J=8.2 Hz, 1H), 4.92 (m, 1H), 4.74 (t, J=6.9 Hz, 2H), 4.36 (s, 2H), 4.32 (t, J=5.3 Hz, 2H), 3.78-3.67 (m, 4H), 3.63-3.59 (m, 4H), 3.47 (t, J=5.4 Hz, 2H), 3.38 (dd, J=13.7 Hz, J=4.3 Hz, 1H), 3.27 (t, J=5.3 Hz, 2H), 3.17 (dd, J=13.9 Hz, J=6.7 Hz, 1H), 3.07 (t, J=6.6 Hz), 1.05 (s, 4H).

Example 91: 1-[5-([4-Chloro-3-[([1-[4-(2-cyclopropoxyphenyl)pyridin-3-yl]cyclopropyl]amino)methyl]phenyl]sulfanyl)pentyl]-3-[(2S,3R,4R,5R)-2,3,4,5,6-pentahydroxyhexyl]urea (I-494)
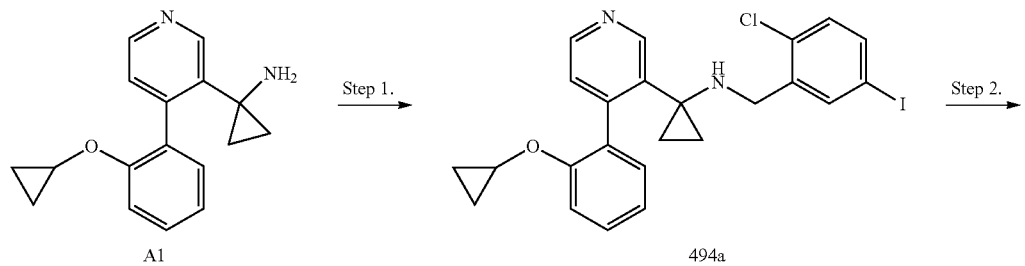
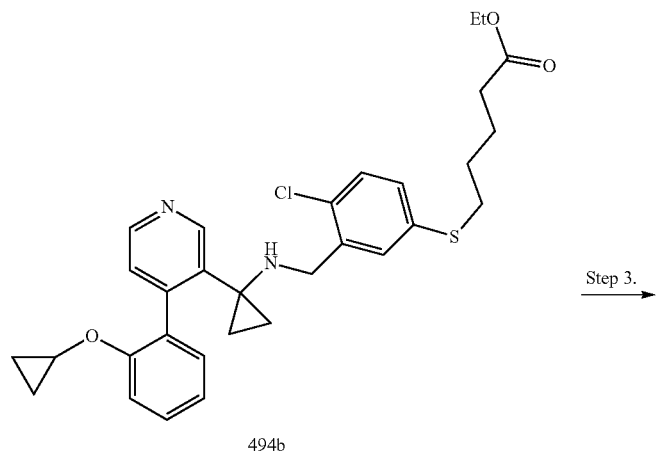
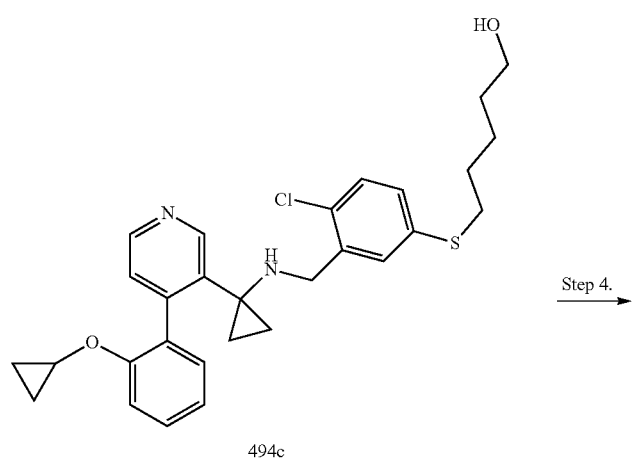

-continued
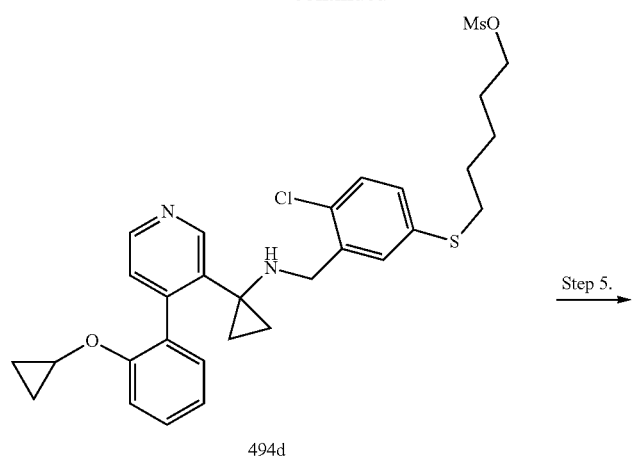
494d
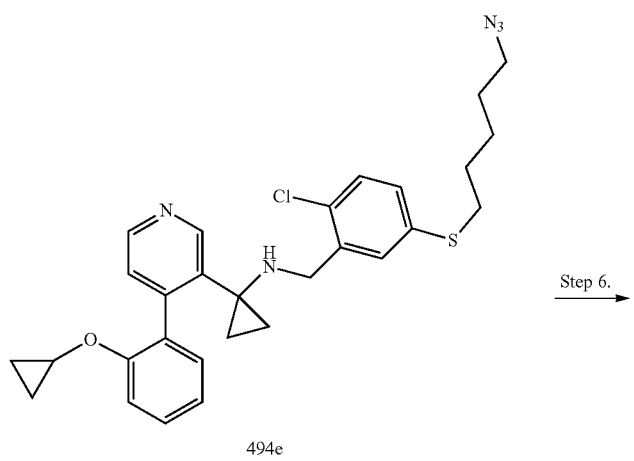
494e
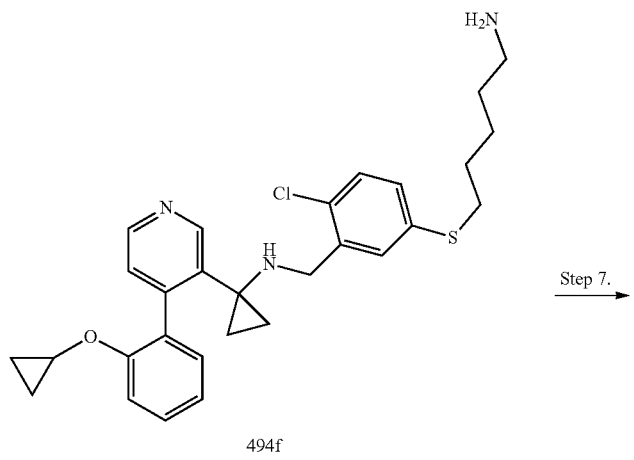
494f
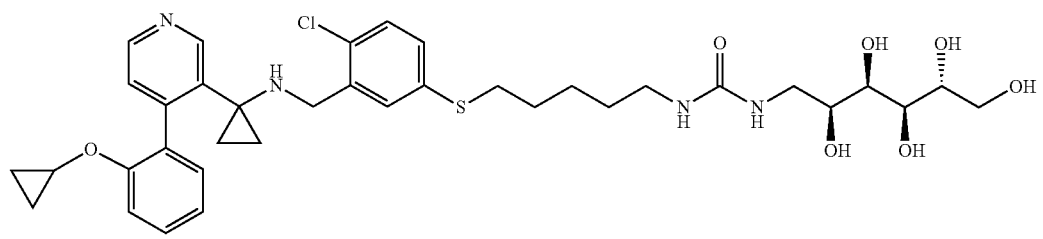
I-494

Step 1. N-[(2-chloro-5-iodophenyl)methyl]-1-[4-(2-cyclopropoxyphenyl)pyridin-3-yl] cyclopropan-1-amine (Intermediate 494a)

A 100-mL round-bottom flask was charged with a solution of 2-chloro-5-iodobenzaldehyde (500 mg, 1.88 mmol, 1.10 equiv) in DCM (50 mL). This was followed by the addition of 1-[4-(2-cyclopropoxyphenyl)pyridin-3-yl]cyclopropan-1-amine (500 mg, 1.88 mmol, 1.00 equiv). The mixture was stirred for 1 h at rt. To this was added NaBH(OAc)$_3$ (1.5 g, 7.08 mmol, 4.00 equiv) at 0° C. and AcOH (0.05 mL, 0.01 equiv). The resulting solution was stirred for 1 overnight at room temperature. The reaction was then quenched by the addition of 500 mL of water. The resulting solution was extracted with 3×100 mL of ethyl acetate and the organic layers combined. The residue was applied onto a silica gel column with ethyl acetate/petroleum ether (1:3). This resulted in 600 mg (62%) of N-[(2-chloro-5-iodophenyl)methyl]-1-[4-(2-cyclopropoxyphenyl)pyridin-3-yl]cyclopropan-1-amine (494a) as an off-white solid.

Step 2. ethyl 5-([4-chloro-3-[([1-[4-(2-cyclopropoxyphenyl)pyridin-3-yl]cyclopropyl]amino)methyl]phenyl]sulfanyl)pentanoate (Intermediate 494b)

A 50-mL round-bottom flask was charged with N-[(5-bromo-2-chlorophenyl)methyl]-1-[4-(2-cyclopropoxyphenyl)pyridin-3-yl]cyclopropan-1-amine (800 mg, 1.70 mmol, 1.20 equiv), ethyl 5-sulfanylpentanoate (230 mg, 1.42 mmol, 1.00 equiv), dioxane (15 mL), Xantphos (96 mg, 0.17 mmol, 0.10 equiv), Pd(dba)$_3$ (65 mg, 0.05 equiv) and DIEA (366 mg, 2.83 mmol, 2.00 equiv). The resulting solution was stirred overnight at 110° C. in an oil bath. The resulting solution was diluted with 100 mL of ethyl acetate. The resulting mixture was washed with 2×100 mL of brine. The mixture was dried over anhydrous sodium sulfate and concentrated under vacuum. The crude product (1 g) was purified by Flash chromatography with the following conditions (IntelFlash-1): Column, silica gel; mobile phase, petroleum ether:ethyl acetate=100:0 increasing to petroleum ether:ethyl acetate=50:50 within 30 min; Detector, UV 254 nm. 880 mg product was obtained. This resulted in 880 mg (crude) of ethyl 5-([4-chloro-3-[([1-[4-(2-cyclopropoxyphenyl)pyridin-3-yl]cyclopropyl]amino)methyl]phenyl]sulfanyl) pentanoate (494b) as a colorless oil.

Step 3. 5-([4-chloro-3-[([1-[4-(2-cyclopropoxyphenyl)pyridin-3-yl]cyclopropyl]amino) methyl] phenyl]sulfanyl)pentan-1-ol (Intermediate 494c)

A 50-mL round-bottom flask was charged with ethyl 5-([4-chloro-3-[([1-[4-(2-cyclopropoxyphenyl) pyridin-3-yl]cyclopropyl]amino)methyl]phenyl]sulfanyl)pentanoate (880 mg, 1.60 mmol, 1.00 equiv), THF (20 mL) and LiAlH$_4$ (150 mg, 3.95 mmol, 2.50 equiv). The resulting solution was stirred for 30 min at room temperature. The resulting solution was diluted with 50 mL of ethyl acetate. The resulting mixture was washed with 2×50 mL of brine. The mixture was dried over anhydrous sodium sulfate and concentrated under vacuum. The crude product (800 mg) was purified by Flash chromatography with the following conditions (IntelFlash-1): Column, silica gel; mobile phase, petroleum ether:ethyl acetate=100:0 increasing to petroleum ether:ethyl acetate=50:50 within 30 min; Detector, UV 254 nm. 750 mg product was obtained. This resulted in 750 mg (92%) of 5-([4-chloro-3-[([1-[4-(2-cyclopropoxyphenyl)pyridin-3-yl]cyclopropyl]amino)methyl]phenyl]sulfanyl)pentan-1-ol (494c) as a colorless oil.

Step 4. 5-([4-chloro-3-[([1-[4-(2-cyclopropoxyphenyl)pyridin-3-yl]cyclopropyl]amino) methyl]phenyl]sulfanyl)pentyl methanesulfonate (Intermediate 494d)

A 50-mL round-bottom flask was charged with 5-([4-chloro-3-[([1-[4-(2-cyclopropoxyphenyl)pyridin-3-yl]cyclopropyl]amino)methyl]phenyl]sulfanyl)pentan-1-ol (750 mg, 1.47 mmol, 1.00 equiv), DCM (20 mL), MsCl (420 mg, 3.68 mmol, 2.50 equiv) and DIEA (880 mg, 6.81 mmol, 5.00 equiv). The resulting solution was stirred for 1 h at room temperature. The resulting solution was diluted with 50 mL of H$_2$O. The resulting solution was extracted with 2×50 mL of ethyl acetate and the organic layers combined and dried over anhydrous sodium sulfate and concentrated under vacuum. The crude product (700 mg) was purified by Flash chromatography with the following conditions (IntelFlash-1): Column, silica gel; mobile phase, ethyl acetate:petroleum ether=100:0 increasing to ethyl acetate:petroleum ether=50:50 within 30 min; Detector, UV 254 nm. 600 mg product was obtained. This resulted in 600 mg (69%) of 5-([4-chloro-3-[([1-[4-(2-cyclopropoxyphenyl)pyridin-3-yl]cyclopropyl]amino)methyl]phenyl]sulfanyl)pentyl methanesulfonate (494d) as colorless oil.

Step 5. N-([5-[(5-azidopentyl)sulfanyl]-2-chlorophenyl]methyl)-1-[4-(2-cyclopropoxyphenyl) pyridin-3-yl]cyclopropan-1-amine (Intermediate 494e)

A 100-mL round-bottom flask was charged with 5-([4-chloro-3-[([1-[4-(2-cyclopropoxyphenyl)pyridin-3-yl]cyclopropyl]amino)methyl]phenyl]sulfanyl)pentyl methanesulfonate (600 mg, 1.02 mmol, 1.00 equiv), DMSO (10 mL) and NaN$_3$ (167 mg, 2.57 mmol, 2.50 equiv). The resulting solution was stirred for 1 overnight at 50° C. in an oil bath. The resulting solution was diluted with 50 mL of ethyl acetate. The resulting mixture was washed with 3×30 mL of brine. The mixture was dried over anhydrous sodium sulfate and concentrated under vacuum. This resulted in 500 mg (92%) of N-([5-[(5-azidopentyl)sulfanyl]-2-chlorophenyl]methyl)-1-[4-(2-cyclopropoxyphenyl)pyridin-3-yl]cyclopropan-1-amine (494e) as a colorless oil.

Step 6. N-([5-[(5-aminopentyl)sulfanyl]-2-chlorophenyl]methyl)-1-[4-(2-cyclopropoxy-phenyl)pyridin-3-yl]cyclopropan-1-amine (Intermediate 494f)

A 250-mL round-bottom flask was charged with N-([5-[(5-azidopentyl)sulfanyl]-2-chlorophenyl]methyl)-1-[4-(2-cyclopropoxyphenyl)pyridin-3-yl]cyclopropan-1-amine (500 mg, 0.94 mmol, 1.00 equiv), EtOH (20 mL) and Rh/C (400 mg). The resulting mixture was stirred overnight under 1 atm of H$_2$ at room temperature. The resulting mixture was diluted with 50 mL of methanol and the solids were filtered out. The resulting solution was concentrated under vacuum. This resulted in 400 mg (84%) of N-([5-[(5-aminopentyl)sulfanyl]-2-chlorophenyl]methyl)-1-[4-(2-cyclopropoxyphenyl)pyridin-3-yl]cyclopropan-1-amine (494f) as a colorless oil.

Step 7. 1-[5-([4-chloro-3-[([1-[4-(2-cyclopropoxyphenyl)pyridin-3-yl]cyclopropyl]amino) methyl]phenyl]sulfanyl)pentyl]-3-[(2S,3R,4R,5R)-2,3,4,5,6-pentahydroxyhexyl]urea (I-494)

A 25-mL round-bottom flask was charged with DSC (121 mg, 0.47 mmol, 1.20 equiv), DIEA (77 mg, 0.60 mmol, 1.50 equiv), N,N-dimethylformamide (5 mL), N-([5-[(5-aminopentyl)sulfanyl]-2-chlorophenyl]methyl)-1-[4-(2-cyclopropoxyphenyl)pyridin-3-yl]cyclopropan-1-amine (200 mg, 0.39 mmol, 1.00 equiv), (2R,3R,4R,5S)-6-aminohexane-1,2,3,4,5-pentol (214 mg, 1.18 mmol, 3.00 equiv). The resulting solution was stirred overnight at room temperature. The solids were filtered out. The crude product was purified by Preparative HPLC with the following conditions: Column, XBridge Shield RP18 OBD Column, 5 μm, 19×150 mm; mobile phase, water with 10 mM NH$_4$HCO$_3$ and MeCN (37.0% MeCN up to 45.0% in 8 min); Detector, UV 220 nm. This resulted in 61.9 mg (22%) of 1-[5-([4-chloro-3-[([1-[4-(2-cyclopropoxyphenyl)pyridin-3-yl]cyclopropyl]amino) methyl]phenyl]sulfanyl)pentyl]-3-[(2S,3R,4R,5R)-2,3,4,5,6-pentahydroxyhexyl]urea (I-494) as a light yellow oil. MS (ES, m/z): 715 [M+H]$^+$; $^1$H-NMR (400 MHz, CDCl$_3$) δ 8.46 (1H, m), 8.45 (1H, m), 7.46 (2H, m), 7.22 (5H, m), 7.15 (1H, m), 3.63 (9H, m), 3.31 (1H, m), 3.11 (111, m), 3.09 (2H, m), 2.88 (2H, m), 1.61 (2H, m), 1.46 (4H, m), 0.90 (4H, m), 0.64 (2H, s), 0.43 (211, s).

Example 92: 5-([6-[([1-[4-(2-Cyclopropoxyphenyl)pyridin-3-yl]cyclopropyl]amino) methyl]-5-methylpyridin-2-yl]sulfanyl)-N-methyl-N-[(2S,3R,4R,5R)-2,3,4,5,6-pentahydroxyhexyl]pentanamide (I-495)

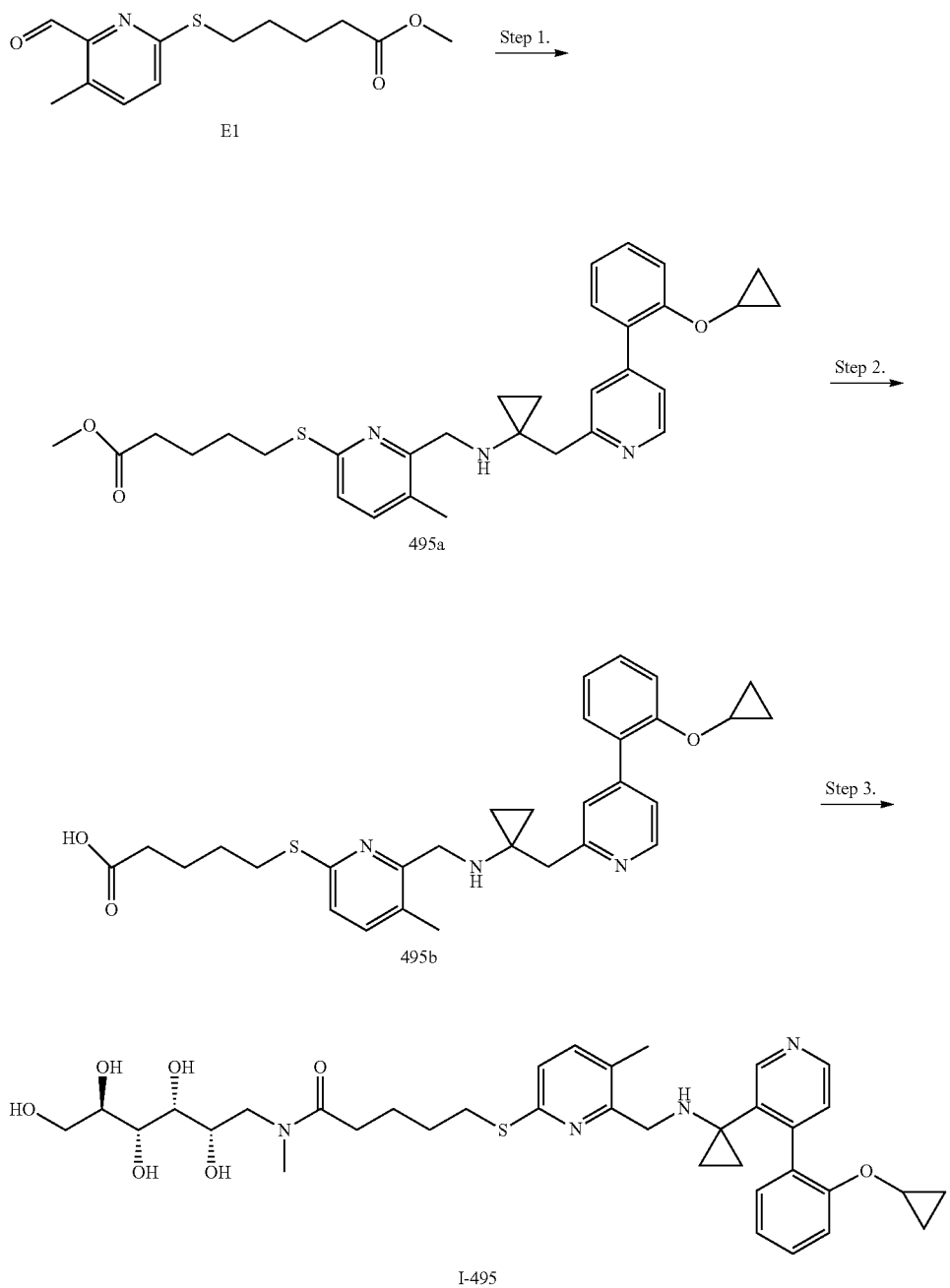

Step 1. Ethyl 5-([6-[([1-[4-(2-cyclopropoxyphenyl)pyridin-3-yl]cyclopropyl]amino)methyl]-5-methylpyridin-2-yl]sulfanyl)pentanoate (Intermediate 495a)

A 100-mL round-bottom flask charged with ethyl 5-[(6-formyl-5-methylpyridin-2-yl)sulfanyl]pentanoate (120 mg, 0.43 mmol, 1.00 equiv). This was followed by the addition of a solution of 1-[4-(2-cyclopropoxyphenyl)pyridin-3-yl]cyclopropan-1-amine (170.4 mg, 0.64 mmol, 1.50 equiv) in DCM (5.0 mL) and NaBH(OAc)$_3$ (543.2 mg, 2.56 mmol, 6.00 equiv) in several batches at 0° C. The resulting solution was stirred for 4-5 h at room temperature in a water/ice bath. The resulting solution was diluted with 20 mL of DCM. The reaction was then quenched by the addition of 30 mL of water. The resulting solution was extracted with 20 mL of dichloromethane and the organic layers combined. The resulting mixture was washed with 2×30 mL of water and 2×30 mL of brine. The mixture was dried over anhydrous sodium sulfate and concentrated under vacuum. The residue was applied onto a silica gel column with ethyl acetate/petroleum ether (2.5:1). This resulted in 107 mg (47%) of ethyl 5-([6-[([1-[4-(2-cyclopropoxyphenyl)pyridin-3-yl]cyclopropyl]amino)methyl]-5-methylpyridin-2-yl]sulfanyl)pentanoate (495a) as a colorless oil.

Step 2. 5-([6-[([1-[4-(2-cyclopropoxyphenyl)pyridin-3-yl]cyclopropyl]amino)methyl]-5-methylpyridin-2-yl]sulfanyl)pentanoic acid (Intermediate 495b)

A 500-mL round-bottom flask (1 atm) was charged with a solution of ethyl 5-([6-[([1-[4-(2-cyclopropoxyphenyl)pyridin-3-yl]cyclopropyl]amino)methyl]-5-methylpyridin-2-yl]sulfanyl)pentanoate (167 mg, 0.31 mmol, 1.00 equiv) in EtOH (6 mL). This was followed by the addition of water (0.5 mL) dropwise with stirring. To this was added LiOH (45.2 mg, 1.89 mmol, 6.00 equiv). The resulting solution was stirred for 1 h at 50° C. in an oil bath. The pH value of the solution was adjusted to 7 with hydrogen chloride (1 mol/L). The resulting solution was extracted with 2×30 mL of ethyl acetate and the organic layers combined. The resulting mixture was washed with 2×20 mL of water and 2×20 mL of brine. The mixture was dried over anhydrous sodium sulfate and concentrated under vacuum. This resulted in 150 mg (95%) of 5-([6-[([1-[4-(2-cyclopropoxyphenyl)pyridin-3-yl]cyclopropyl]amino)methyl]-5-methylpyridin-2-yl]sulfanyl)pentanoic acid (495b) as a colorless oil.

Step 3. 5-([6-[([1-[4-(2-cyclopropoxyphenyl)pyridin-3-yl]cyclopropyl]amino) methyl]-5-methylpyridin-2-yl]sulfanyl)-N-methyl-N-[(2S,3R,4R,5R)-2,3,4,5,6-pentahydroxyhexyl]pentanamide (I-495)

A 25-mL round-bottom flask purged and maintained under an inert atmosphere of nitrogen was charged with 5-([6-[([1-[4-(2-cyclopropoxyphenyl)pyridin-3-yl]cyclopropyl]amino) methyl]-5-methylpyridin-2-yl]sulfanyl)pentanoic acid (75 mg, 0.15 mmol, 1.00 equiv), (2R,3R,4R,5S)-6-(methylamino)hexane-1,2,3,4,5-pentol (54.5 mg, 0.28 mmol, 2.00 equiv) in DMF (6 mL), HATU (113.1 mg, 0.30 mmol, 2.00 equiv) and DIEA (100 mg, 0.77 mmol, 4.00 equiv). The resulting solution was stirred overnight at room temperature. The solids were filtered out. The crude product was purified by Preparative HPLC with the following conditions: Column, Gemini-NX 5μ C18 110A, AXIA Packed, 150×21.2 mm; mobile phase, water with 10 mM NH$_4$HCO$_3$ and MeCN (25% MeCN up to 55% in 8 min); Detector, UV 254 nm. This resulted in 52.9 mg (52%) of 5-([6-[([1-[4-(2-cyclopropoxyphenyl)pyridin-3-yl]cyclopropyl]amino) methyl]-5-methylpyridin-2-yl]sulfanyl)-N-methyl-N-[(2S,3R,4R,5R)-2,3,4,5,6-pentahydroxyhexyl]pentanamide (I-495) as an off-white solid. MS (ES, m/z): 681.2 [M+H]$^+$; $^1$H-NMR (400 MHz, CD$_3$OD) δ 8.66 (s, 1H), 8.50 (d, J=4.9 Hz, 1H), 7.48-7.33 (m, 2H), 7.21 (dd, J=7.5, 1.4 Hz, 2H), 7.13-7.03 (m, 2H), 6.94 (d, J=7.9 Hz, 1H), 3.93 (d, J=3.5 Hz, 1H), 3.80-3.59 (m, 8H), 3.54 (dd, J=6.2, 3.2 Hz, 1H), 3.42 (d, J=7.6 Hz, 1H), 3.05 (s, 5H), 2.32 (d, J=7.0 Hz, 2H), 2.16 (s, 3H), 0.89 (s, 3H), 0.59 (s, 2H), 0.45 (s, 2H).

Example 93: 1-[4-(2-Cyclopropoxyphenyl)pyridin-3-yl]-N-[[5-methyl-2-(methylsulfanyl) pyrimidin-4-yl]methyl]cyclopropan-1-amine (I-496)

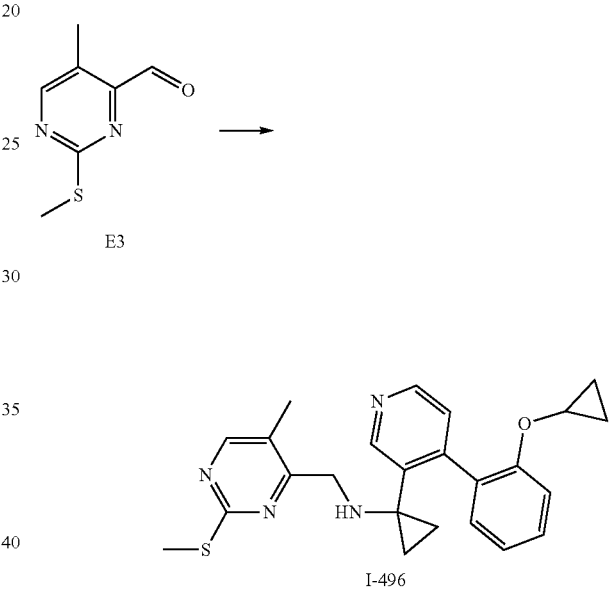

A 50-mL round-bottom flask was charged with a solution of 1-[4-(2-cyclopropoxyphenyl)pyridin-3-yl]cyclopropan-1-amine (70 mg, 0.26 mmol, 1.00 equiv) in dichloromethane (5 mL), 5-methyl-2-(methylsulfanyl)pyrimidine-4-carbaldehyde (53 mg, 0.32 mmol, 1.20 equiv), NaBH(OAc)$_3$ (167 mg, 0.79 mmol, 6.00 equiv). The resulting solution was stirred overnight at 25° C. The reaction was then quenched by the addition of 50 mL of H$_2$O. The resulting solution was extracted with 3×30 mL of dichloromethane and the organic layers combined and dried over sodium sulfate and concentrated under vacuum. The crude product was purified by following conditions: Column: XBridge Prep C18 OBD Column, 5 μm, 19×150 mm; Mobile Phase A: water with 10 mM NH$_4$HCO$_3$, Mobile Phase B: MeCN; Flow rate: 20 mL/min; Gradient: 35% B to 65% B in 8 min; 254 nm. This resulted in 46.7 mg (42%) of 1-[4-(2-cyclopropoxyphenyl)pyridin-3-yl]-N-[[5-methyl-2-(methylsulfanyl)pyrimidin-4-yl]methyl]cyclopropan-1-amine (I-496) as an off-white solid. MS (ES, m/z): 419 [M+H]$^+$; $^1$H-NMR (400 MHz, CD$_3$OD) δ 8.57 (s, 1H), 8.42 (d, J=4.8 Hz, 1H), 8.22 (s, 1H), 7.44-7.51 (m, 2H), 7.28 (dd, J=7.6 Hz, 1H), 7.12-7.16 (m, 2H), 3.69 (s, 2H), 3.52-3.56 (m, 1H), 2.45 (s, 3H), 2.12 (s, 3H), 0.98 (s, 3H), 0.82 (s, 2H), 0.58 (d, J=4.2 Hz, 2H), 0.35-0.36 (m, 2H).

Example 94: 4-[[3-([1-[4-(2-Cyclopropoxyphenyl)
pyridin-3-yl]cyclopropoxy]methyl)-4-ethylphenyl]
sulfanyl]-N-[(2S,3R,4R,5R)-2,3,4,5,6-pentahydroxy-
hexyl]butanamide (I-497)

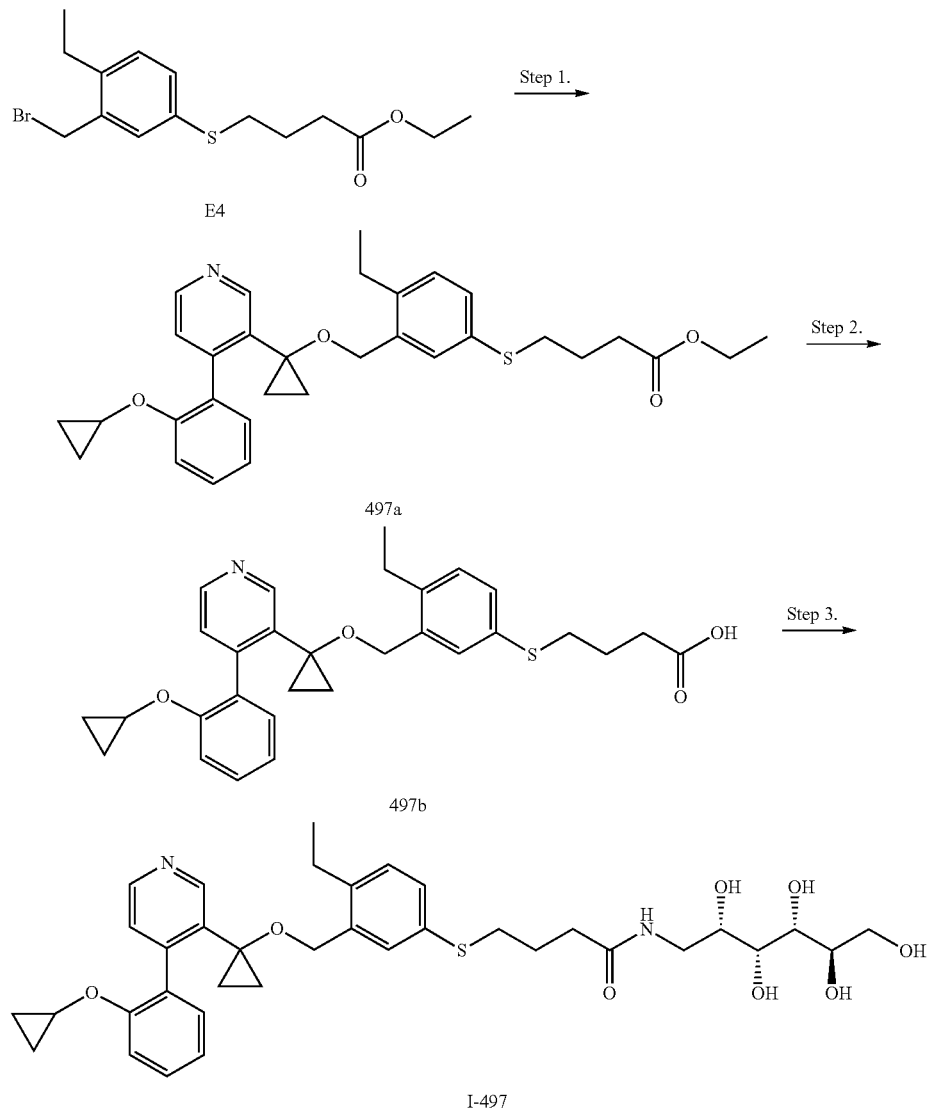

layers combined. The resulting mixture was washed with 1×50 mL of Brine. The mixture was dried over anhydrous sodium sulfate and concentrated under vacuum. The residue was applied onto a silica gel column with ethyl acetate/petroleum ether (1:1). This resulted in 340 mg (74%) of ethyl 4-[[3-([1-[4-(2-cyclopropoxyphenyl)pyridin-3-yl]cyclopropoxy]methyl)-4-ethylphenyl]sulfanyl]butanoate (497a) as a yellow oil.

Step 1. ethyl 4-[[3-([1-[4-(2-cyclopropoxyphenyl)
pyridin-3-yl]cyclopropoxy]methyl)-4-ethylphenyl]
sulfanyl]butanoate (Intermediate 497a)

A 100-mL round-bottom flask purged and maintained under an inert atmosphere of nitrogen was charged with ethyl 4-[[3-(bromomethyl)-4-ethylphenyl]sulfanyl]butanoate (300 mg, 0.87 mmol, 1.00 equiv), 1-[4-(2-cyclopropoxyphenyl)pyridin-3-yl]cyclopropan-1-ol (232 mg, 0.87 mmol, 1.00 equiv) and DMF (16 g, 218.91 mmol, 251.96 equiv). This was followed by the addition of sodium hydride (70 mg, 0.02 mmol, 2.00 equiv, 0.6%), in portions at 0° C. The resulting solution was stirred for 30 min at 0° C. in a water/ice bath. The reaction was then quenched by the addition of 100 mL of NH₄Cl. The resulting solution was extracted with 3×50 mL of ethyl acetate and the organic Step 2. 4-[[3-([1-[4-(2-cyclopropoxyphenyl)pyridin-
3-yl]cyclopropoxy]methyl)-4-ethylphenyl] sulfanyl]
butanoic acid (Intermediate 497b)

A 50-mL round-bottom flask was charged with ethyl 4-[[3-([1-[4-(2-cyclopropoxyphenyl)pyridin-3-yl]cyclopropoxy]methyl)-4-ethylphenyl]sulfanyl]butanoate (340 mg, 0.64 mmol, 1.00 equiv), LiOH·H₂O (81 mg, 1.93 mmol, 3.00 equiv), MeOH (10 mL) and water (2 mL). The resulting solution was stirred for 2.5 h at 60° C. in an oil bath. The resulting mixture was concentrated under vacuum. The resulting solution was diluted with 20 mL of water. The pH value of the solution was adjusted to 3 with hydrogen chloride (12 mol/L). The resulting solution was extracted with 3×10 mL of ethyl acetate and the organic layers combined and dried over anhydrous sodium sulfate and concentrated under vacuum. This resulted in 310 mg (96%) of 4-[[3-([1-[4-(2-cyclopropoxyphenyl)pyridin-3-yl]cyclopropoxy]methyl)-4-ethylphenyl]sulfanyl]butanoic acid (497b) as a yellow crude solid.

Step 3. 4-[[3-([1-[4-(2-cyclopropoxyphenyl)pyridin-3-yl]cyclopropoxy]methyl)-4-ethylphenyl]sulfanyl]-N-[(2S,3R,4R,5R)-2,3,4,5,6-pentahydroxyhexyl]butanamide (I-497)

A 100-mL round-bottom flask was charged with 4-[[3-([1-[4-(2-cyclopropoxyphenyl)pyridin-3-yl]cyclopropoxy] methyl)-4-ethylphenyl]sulfanyl]butanoic acid (150 mg, 0.30 mmol, 1.00 equiv), (2R,3R,4R,5S)-6-aminohexane-1,2,3,4,5-pentol (70 mg, 0.39 mmol, 1.20 equiv), DIEA (0.2 mL, 4.00 equiv), N,N-dimethylformamide (5 mL), HATU (170 mg, 0.45 mmol, 1.50 equiv). The resulting solution was stirred for 2 h at room temperature. The resulting mixture was concentrated under vacuum. The crude product was purified by Preparative HPLC with the following conditions: Column, XBridge Shield RP18 OBD Column, 5 μm, 19×150 mm; mobile phase, water with 10 mM NH$_4$HCO$_3$ and MeCN (29.0% MeCN up to 59.0% in 8 min); Detector, 254 and 220 nm. This resulted in 57.3 mg (29%) of 4-[[3-([1-[4-(2-cyclopropoxyphenyl)pyridin-3-yl]cyclopropoxy] methyl)-4-ethylphenyl]sulfanyl]-N-[(2S,3R,4R,5R)-2,3,4,5,6-pentahydroxyhexyl]butanamide (I-497) as a white sold.

MS (ES, m/z): 667 [M+H]$^+$; $^1$H-NMR (300 MHz, CD$_3$OD) δ 8.68 (s, 1H), 8.48 (d, J=5.1 Hz, 1H), 7.43-7.31 (m, 2H), 7.30-7.13 (m, 3H), 7.11-6.93 (m, 3H), 4.88 (s, 1H), 4.36 (s, 2H), 3.85-3.52 (m, 7H), 3.45 (dd, J=13.7, 4.6 Hz, 1H), 3.23 (dd, J=13.8, 7.4 Hz, 1H), 2.88 (t, J=7.2 Hz, 2H), 2.52-2.28 (m, 4H), 1.87 (p, J=7.4 Hz, 2H), 1.14-0.87 (m, 7H), 0.64 (t, J=6.6 Hz, 2H), 0.50-0.38 (m, 2H).

Example 95: 4-[[4-Chloro-3-([1-[4-(2-cyclopropoxyphenyl)pyridin-3-yl]cyclopropoxy]methyl) phenyl]sulfanyl]-N-[(2S,3R,4R,5R)-2,3,4,5,6-pentahydroxyhexyl]butanamide (I-498)

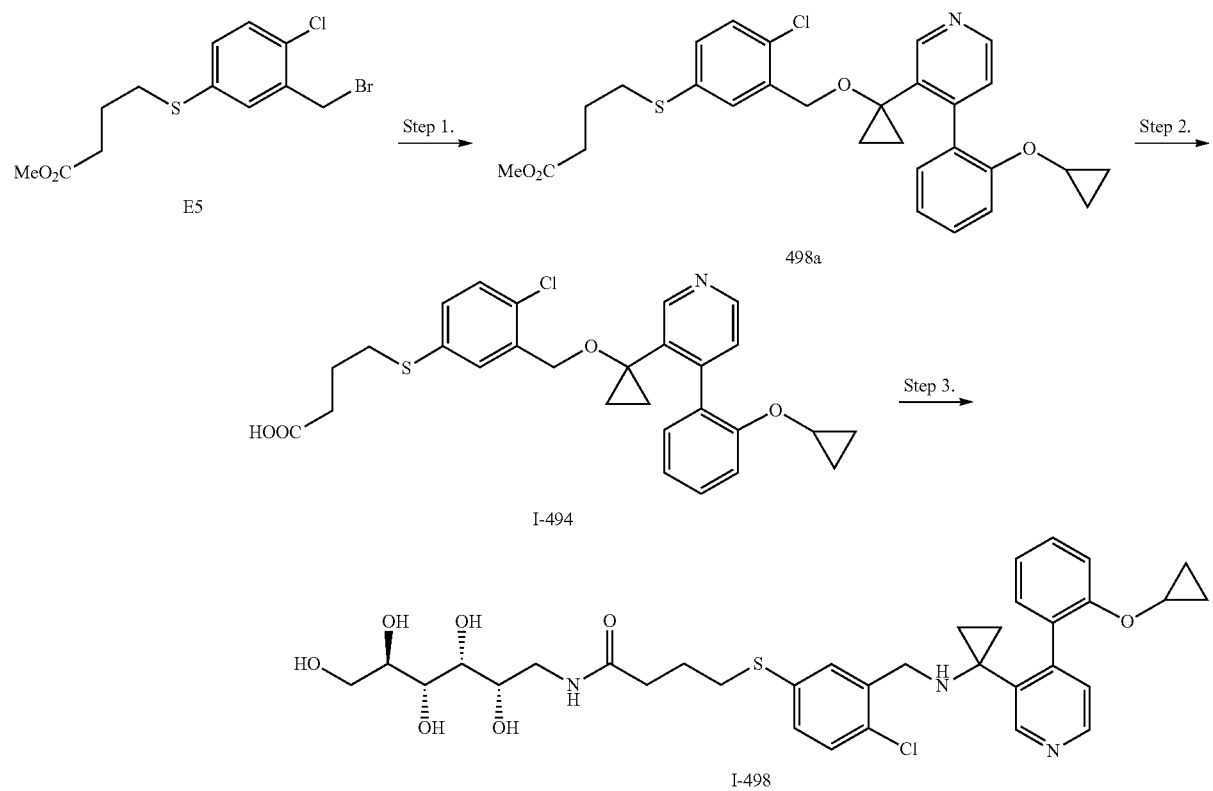

Step 1. Methyl 4-[[4-chloro-3-([1-[4-(2-cyclopropoxyphenyl)pyridin-3-yl]cyclopropoxy]methyl) phenyl]sulfanyl]butanoate (Intermediate 498a)

A 50-mL round-bottom flask was charged with 1-[4-(2-cyclopropoxyphenyl)pyridin-3-yl]cyclopropan-1-ol (220 mg, 0.82 mmol, 1.00 equiv), methyl 4-[[3-(bromomethyl)-4-chlorophenyl]sulfanyl]butanoate (320 mg, 0.95 mmol, 1.00 equiv), DMF (12 mL) and sodium hydride (70 mg, 2.92 mmol, 2.00 equiv). The resulting solution was stirred for 2 h at 0° C. in an ice/salt bath. The resulting solution was diluted with 100 mL of ethyl acetate. The resulting mixture was washed with 1×50 mL of water and 2×50 mL of brine. The solid was dried in an oven under reduced pressure. The crude product was purified by Flash chromatography with the following conditions (IntelFlash-1): Column, silica gel; mobile phase, ethyl acetate:petroleum ether=100:0 increasing to ethyl acetate:petroleum ether=85:15 within 30 min; Detector, UV 254 nm. 160 mg product was obtained. This resulted in 160 mg (37%) of methyl 4-[[4-chloro-3-([1-[4-(2-cyclopropoxyphenyl)pyridin-3-yl]cyclopropoxy]methyl) phenyl]sulfanyl]butanoate (498a) as a light yellow oil.

Step 2. 4-[[4-chloro-3-([1-[4-(2-cyclopropoxyphenyl)pyridin-3-yl]cyclopropoxy]methyl) phenyl]sulfanyl]butanoic acid (Intermediate 498b)

A 25-mL round-bottom flask was charged with methyl 4-[[4-chloro-3-([1-[4-(2-cyclopropoxyphenyl)pyridin-3-yl]cyclopropoxy]methyl)phenyl]sulfanyl]butanoate (230 mg, 0.44 mmol, 1.00 equiv), methanol (5 mL), water (1 mL), LiOH (65 mg, 2.71 mmol, 6.00 equiv). The resulting solution was stirred for 1 h at 60° C. in an oil bath. The pH value of the solution was adjusted to 1.0 with hydrogen chloride (1 mol/L). The resulting solution was extracted with 3×50 mL of ethyl acetate and the organic layers combined and dried over anhydrous sodium sulfate and concentrated under vacuum. This resulted in 220 mg (98%) of 4-[[4-chloro-3-([1-[4-(2-cyclopropoxyphenyl)pyridin-3-yl]cyclopropoxy] methyl) phenyl]sulfanyl]butanoic acid (498b) as a light yellow oil.

Step 3. 4-[[4-chloro-3-([1-[4-(2-cyclopropoxyphenyl)pyridin-3-yl]cyclopropoxy]methyl) phenyl]sulfanyl]-N-[(2S,3R,4R,5R)-2,3,4,5,6-pentahydroxyhexyl]butanamide (I-498)

A 25-mL round-bottom flask was charged with 4-[[4-chloro-3-([1-[4-(2-cyclopropoxyphenyl)pyridin-3-yl]cyclopropoxy]methyl)phenyl]sulfanyl]butanoic acid (110 mg, 0.22 mmol, 1.00 equiv), (2R,3R,4R,5S)-6-aminohexane-1,2,3,4,5-pentol (130 mg, 0.72 mmol, 2.00 equiv), HATU (180 mg, 0.47 mmol, 2.00 equiv), DIEA (150 mg, 1.16 mmol, 4.00 equiv) and DMF (3 mL). The resulting solution was stirred overnight at room temperature. The solids were filtered out. The crude product was purified by Preparative HPLC with the following conditions: Column, XBridge BEH C18 OBD Prep Column, 5 μm, 19 mm 250 mm; mobile phase, water with 0.05% TFA and MeCN (25.0% MeCN up to 49.0% in 8 min); Detector, 254 nm. This resulted in 81.7 mg (56%) of 4-[[4-chloro-3-([1-[4-(2-cyclopropoxyphenyl) pyridin-3-yl]cyclopropoxy]methyl)phenyl]sulfanyl]-N-[(2S,3R,4R,5R)-2,3,4,5,6-pentahydroxyhexyl]butanamide (I-498) as a white solid. MS (ES, m/z): 673 [M+H]$^+$; $^1$H-NMR (300 MHz, CD$_3$OD) δ 0.39 (2H,$), 0.64 (2H, d), 1.19 (4H, m), 1.91 (2H, m), 2.37 (2H, m), 2.93 (2H, m), 3.22 (1H, m), 3.42 (1H, m), 3.71 (8H, m), 4.38 (2H, s), 6.95 (1H, m), 7.09 (1H, m), 7.21 (2H, m), 7.40 (2H, m), 7.51 (2H, m), 7.81 (1H, m), 8.72 (1H, m), 8.73 (1H, m).

Compounds I-499 to I-695 in Table 15 were prepared from commercial, known starting materials or the appropriate intermediates disclosed herein according to the methods for examples specified in Table 15 and methods generally known to those skilled in the art.

TABLE 15

Compounds I-499 to I-695

| Cmpd No.: | Synthetic Method | Compound Structure | Obs. mass [M + H]+ |
|---|---|---|---|
| I-499 | Example 86 | 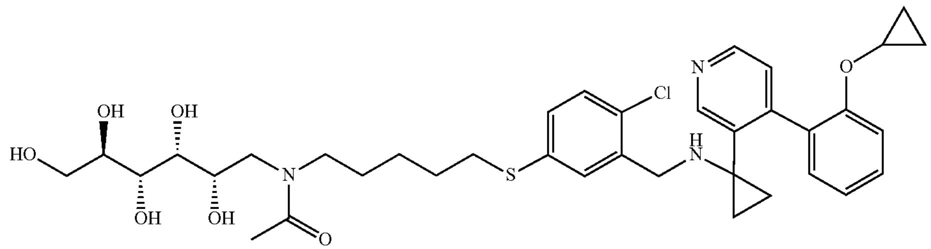 [SMILES: CC(=O)N(CCCCCSc1ccc(Cl)c(CNC2(c3cnccc3-c3ccccc3OC3CC3)CC2)c1)C[C@H](O)[C@@H](O)[C@H](O)[C@H](O)CO] | 714.3 |
| I-500 | Example 86 | 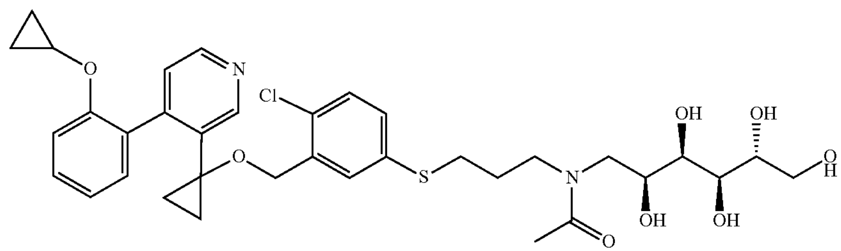 [SMILES: CC(=O)N(CCCSc1ccc(Cl)c(COC2(c3cnccc3-c3ccccc3OC3CC3)CC2)c1)C[C@H](O)[C@@H](O)[C@H](O)[C@H](O)CO] | 687.3 |
| I-501 | Example 86 | 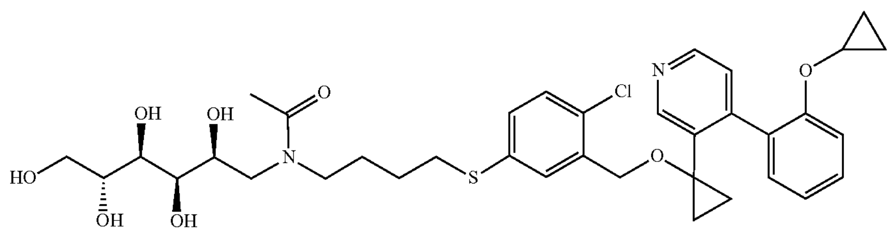 [SMILES: CC(=O)N(CCCCSc1ccc(Cl)c(COC2(c3cnccc3-c3ccccc3OC3CC3)CC2)c1)C[C@H](O)[C@@H](O)[C@H](O)[C@H](O)CO] | 701 |

TABLE 15-continued

Compounds I-499 to I-695

| Cmpd No.: | Synthetic Method | Compound Structure | Obs. mass [M + H]⁺ |
|---|---|---|---|
| I-502 | Example 86 | 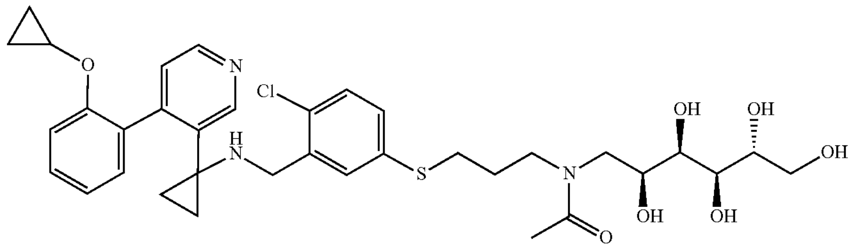 [SMILES: CC(=O)N(CCCSc1ccc(Cl)c(CNC2(c3cnccc3-c3ccccc3OC3CC3)CC2)c1)C[C@H](O)[C@@H](O)[C@H](O)[C@H](O)CO] | 686.3 |
| I-503 | Example 86 | 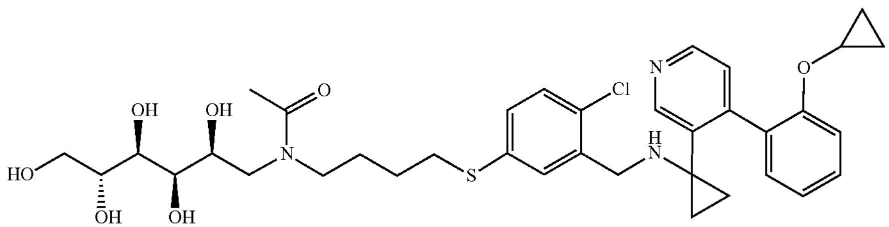 [SMILES: CC(=O)N(CCCCSc1ccc(Cl)c(CNC2(c3cnccc3-c3ccccc3OC3CC3)CC2)c1)C[C@H](O)[C@@H](O)[C@H](O)[C@H](O)CO] | 700.3 |
| I-504 | Example 86 | 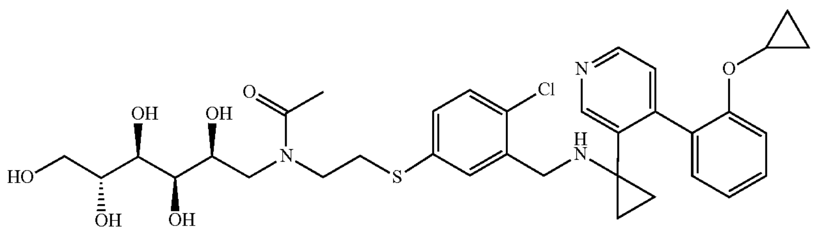 [SMILES: CC(=O)N(CCSc1ccc(Cl)c(CNC2(c3cnccc3-c3ccccc3OC3CC3)CC2)c1)C[C@H](O)[C@@H](O)[C@H](O)[C@H](O)CO] | 672 |
| I-505 | Example 86 | 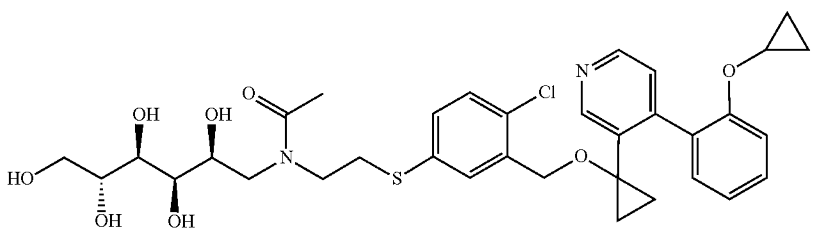 [SMILES: CC(=O)N(CCSc1ccc(Cl)c(COC2(c3cnccc3-c3ccccc3OC3CC3)CC2)c1)C[C@H](O)[C@@H](O)[C@H](O)[C@H](O)CO] | 673.3 |

TABLE 15-continued

Compounds I-499 to I-695

| Cmpd No.: | Synthetic Method | Compound Structure | Obs. mass [M + H]+ |
|---|---|---|---|
| I-506 | Example 86 | 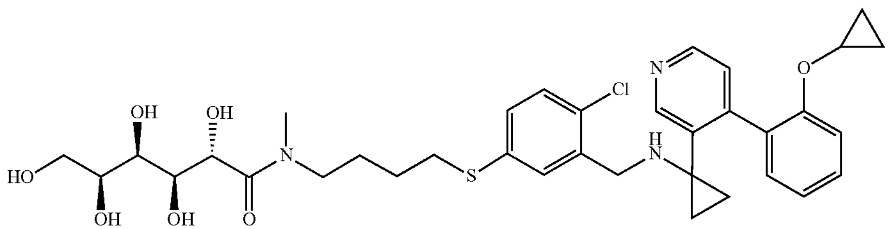 [SMILES: CN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 686.2 |
| I-507 | Example 86 | 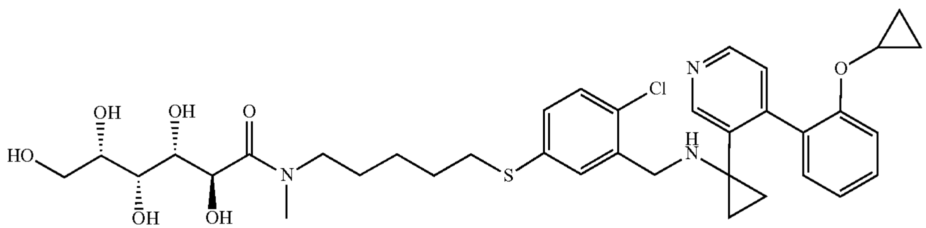 | 700.2 |
| I-508 | Example 86 | 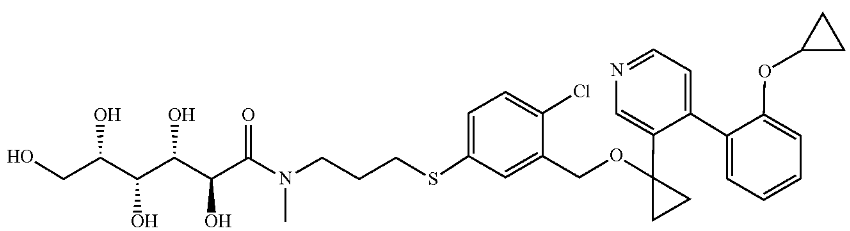 [SMILES: CN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 673.2 |
| I-509 | Example 86 | 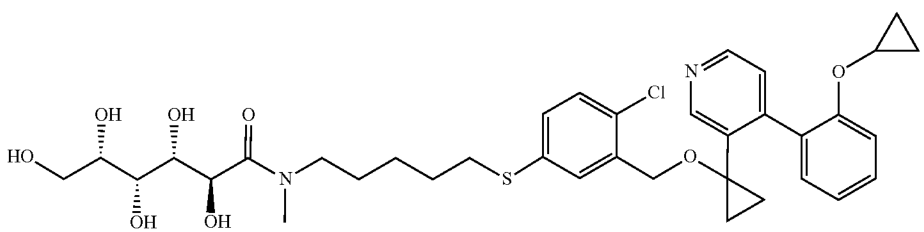 [SMILES: CN(CCCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 701.3 |

TABLE 15-continued

Compounds I-499 to I-695

| Cmpd No.: | Synthetic Method | Compound Structure | Obs. mass [M + H]+ |
|---|---|---|---|
| I-510 | Example 86 | 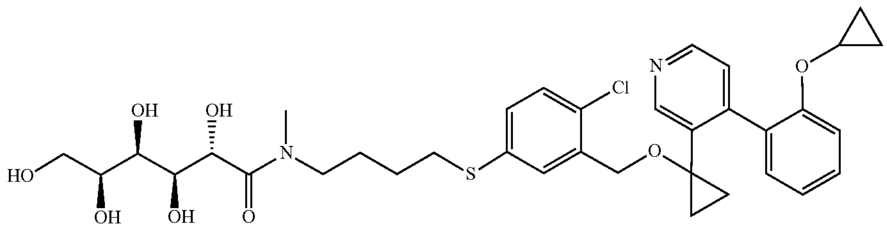 [SMILES: CN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 687 |
| I-511 | Example 86 | 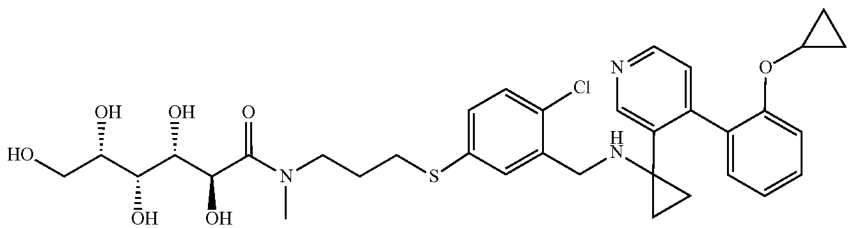 [SMILES: CN(CCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 672.2 |
| I-512 | Example 86 | 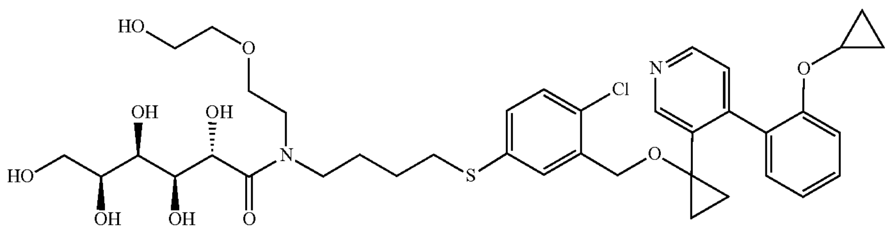 [SMILES: O=C([C@@H](O)[C@@H](O)[C@H](O)[C@@H](O)CO)N(CCCCSc1ccc(Cl)c(COC2(c3cnccc3-c3ccccc3OC3CC3)CC2)c1)CCOCCO] | 671 |
| I-513 | Example 86 | 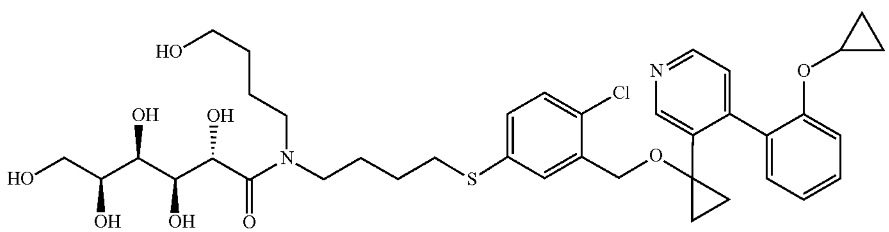 [SMILES: O=C([C@@H](O)[C@@H](O)[C@H](O)[C@@H](O)CO)N(CCCCO)CCCCSc1ccc(Cl)c(COC2(c3cnccc3-c3ccccc3OC3CC3)CC2)c1] | 745 |

TABLE 15-continued

Compounds I-499 to I-695

| Cmpd No.: | Synthetic Method | Compound Structure | Obs. mass [M + H]+ |
|---|---|---|---|
| I-514 | Example 86 | 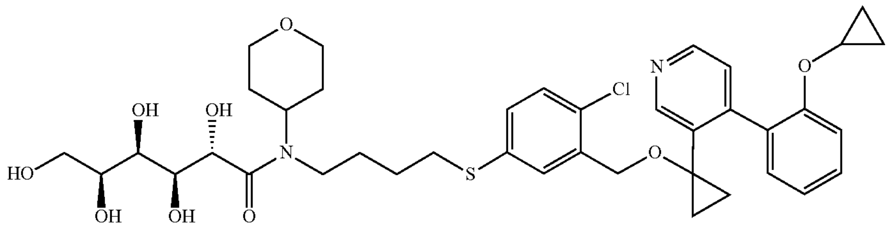 [SMILES: O=C([C@@H](O)[C@@H](O)[C@H](O)[C@@H](O)CO)N(CCCCSc1ccc(Cl)c(COC2(c3cnccc3-c3ccccc3OC3CC3)CC2)c1)C1CCOCC1] | 757 |
| I-515 | Example 86 | 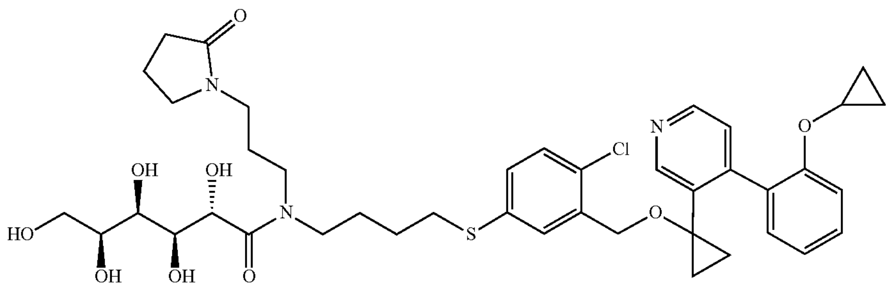 [SMILES: O=C1CCCN1CCCN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 798 |
| I-516 | Example 86 | 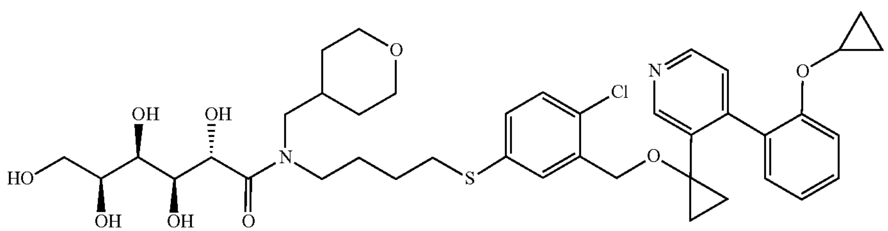 [SMILES: O=C([C@@H](O)[C@@H](O)[C@H](O)[C@@H](O)CO)N(CCCCSc1ccc(Cl)c(COC2(c3cnccc3-c3ccccc3OC3CC3)CC2)c1)CC1CCOCC1] | 771 |
| I-517 | Example 86 | 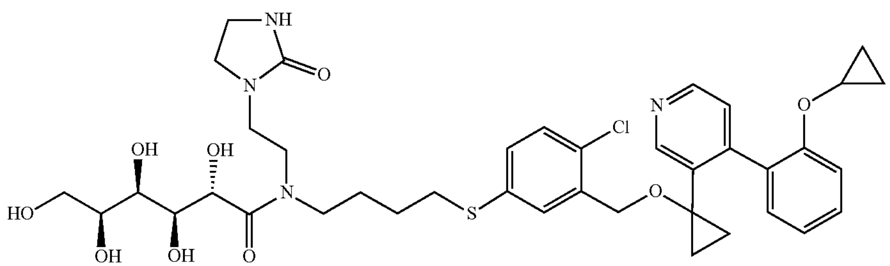 | 785 |

TABLE 15-continued
Compounds I-499 to I-695
| Cmpd No.: | Synthetic Method | Compound Structure | Obs. mass [M + H]+ |
|---|---|---|---|
| I-518 | Example 86 | 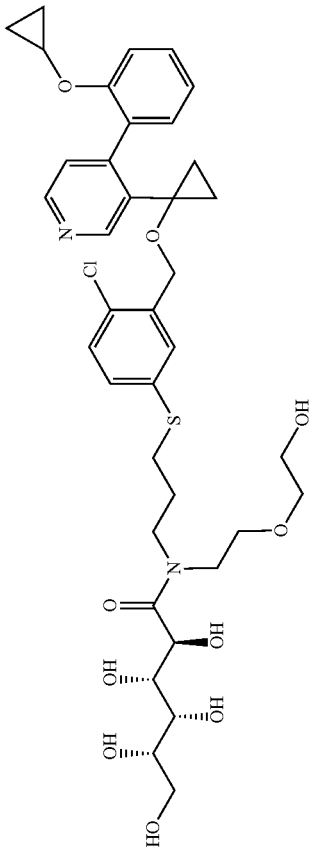 | 747.1 |
| I-519 | Example 86 | 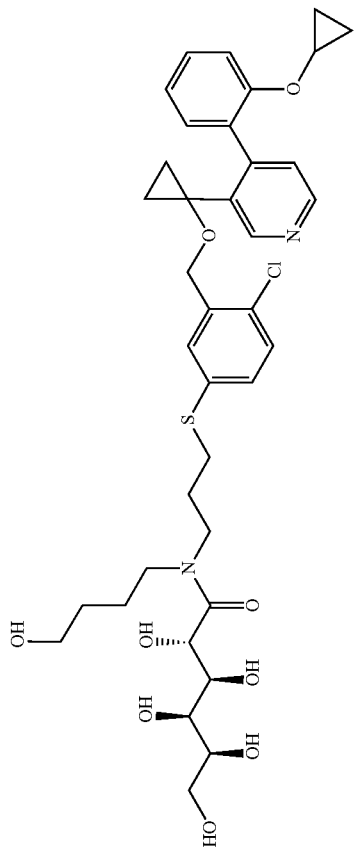 | 731 |

TABLE 15-continued
Compounds I-499 to I-695
| Cmpd No.: | Synthetic Method | Compound Structure | Obs. mass [M + H]+ |
|---|---|---|---|
| I-520 | Example 86 | 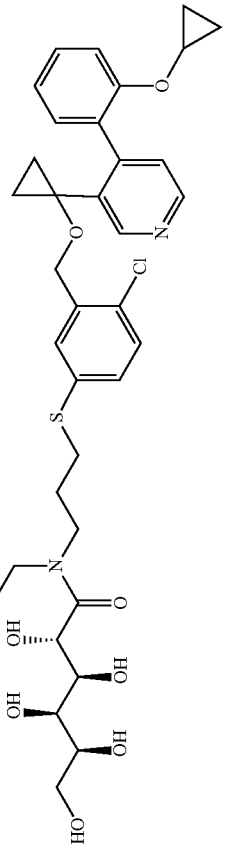 | 784.2 |
| I-521 | Example 86 | 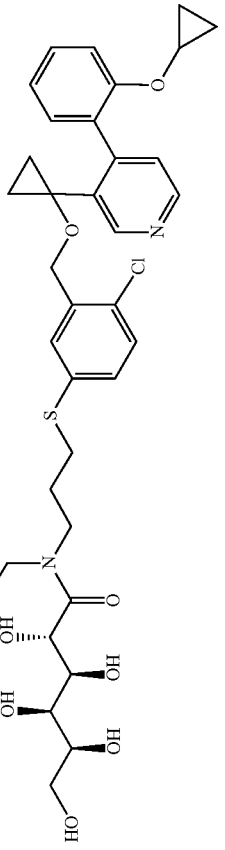 | 820.2 |

TABLE 15-continued

Compounds I-499 to I-695

| Cmpd No.: | Synthetic Method | Compound Structure | Obs. mass [M + H]+ |
|---|---|---|---|
| I-522 | Example 86 | 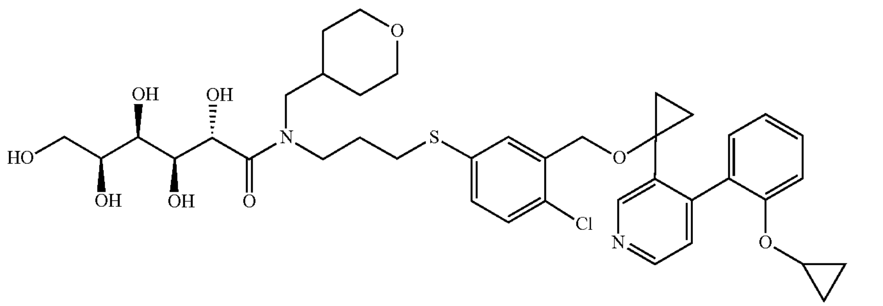 [SMILES: O=C([C@@H](O)[C@@H](O)[C@H](O)[C@@H](O)CO)N(CCCSc1ccc(Cl)c(COC2(c3cnccc3-c3ccccc3OC3CC3)CC2)c1)CC1CCOCC1] | 757 |
| I-523 | Example 86 | 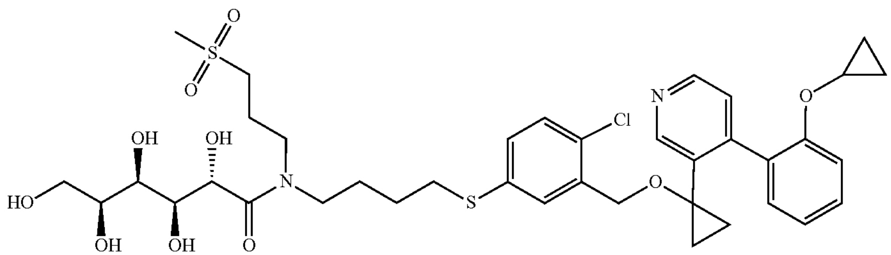 [SMILES: CS(=O)(=O)CCCN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 793 |
| I-524 | Example 86 | 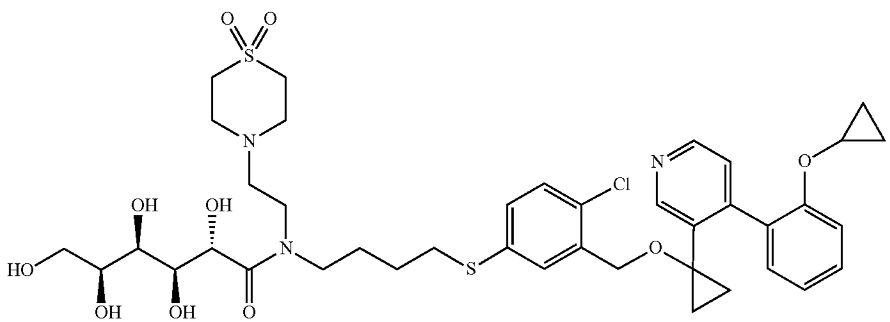 [SMILES: O=C([C@@H](O)[C@@H](O)[C@H](O)[C@@H](O)CO)N(CCCCSc1ccc(Cl)c(COC2(c3cnccc3-c3ccccc3OC3CC3)CC2)c1)CCN1CCS(=O)(=O)CC1] | 834 |

TABLE 15-continued
Compounds I-499 to I-695
| Cmpd No.: | Synthetic Method | Compound Structure | Obs. mass [M + H]+ |
|---|---|---|---|
| I-525 | Example 86 | 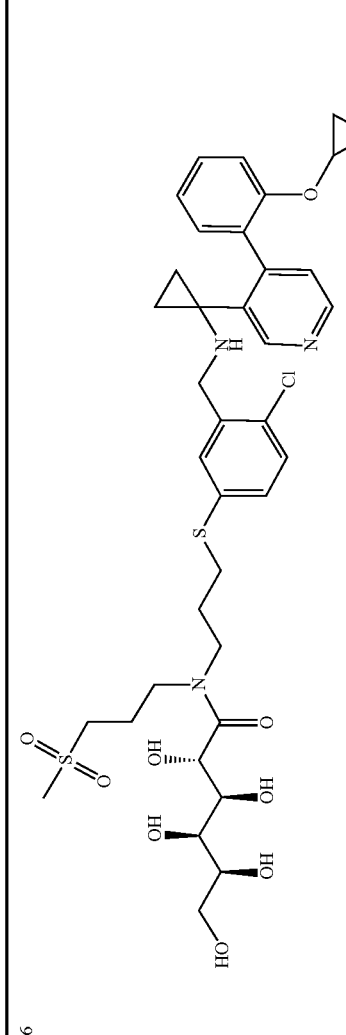 | 778.4 |
| I-526 | Example 86 | 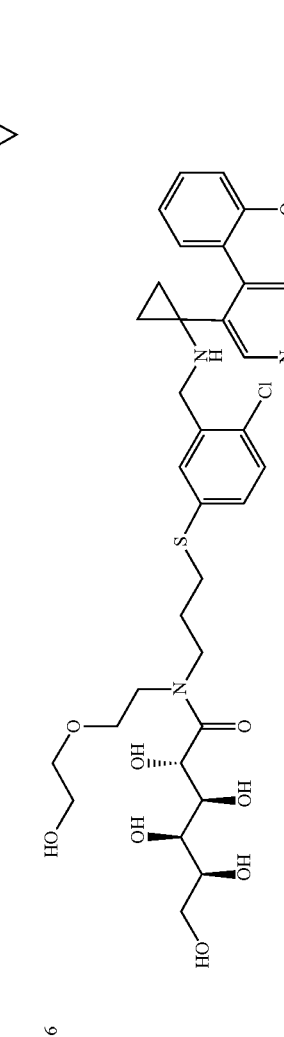 | 746.4 |

TABLE 15-continued
Compounds I-499 to I-695
| Cmpd No.: | Synthetic Method | Compound Structure | Obs. mass [M + H]+ |
|---|---|---|---|
| I-527 | Example 86 | 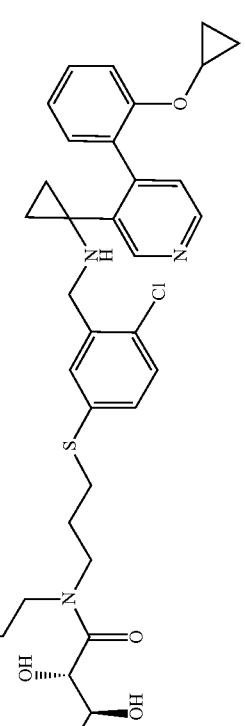 | 730.4 |
| I-528 | Example 86 | 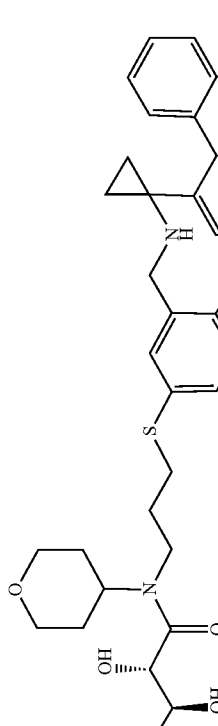 | 742.4 |

TABLE 15-continued

Compounds I-499 to I-695

| Cmpd No.: | Synthetic Method | Compound Structure | Obs. mass [M + H]+ |
|---|---|---|---|
| I-529 | Example 86 | 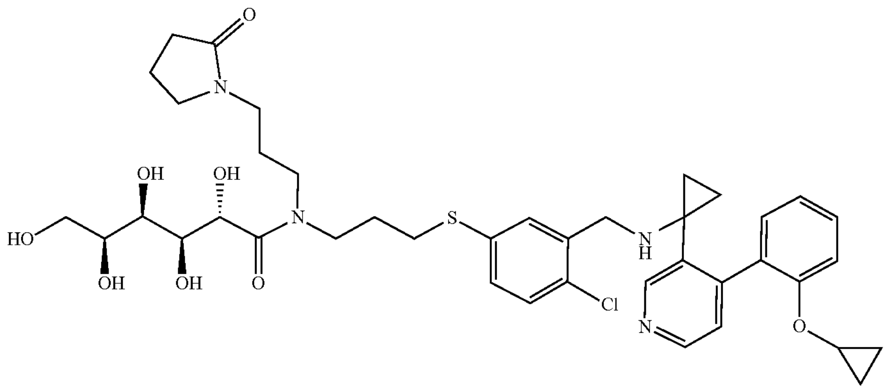 | 783.2 |
| I-530 | Example 86 | 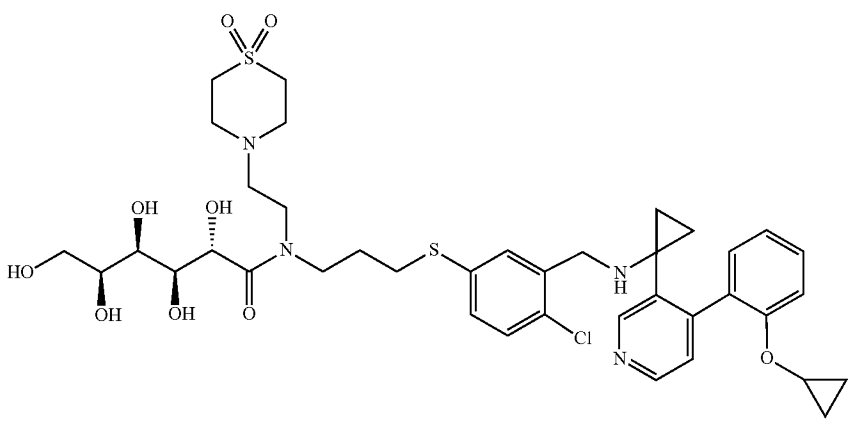 [SMILES: O=C([C@@H](O)[C@@H](O)[C@H](O)[C@@H](O)CO)N(CCCSc1ccc(Cl)c(CNC2(c3cnccc3-c3ccccc3OC3CC3)CC2)c1)CCN1CCS(=O)(=O)CC1] | 819.2 |

TABLE 15-continued

Compounds I-499 to I-695

| Cmpd No.: | Synthetic Method | Compound Structure | Obs. mass [M + H]+ |
|---|---|---|---|
| I-531 | Example 86 | 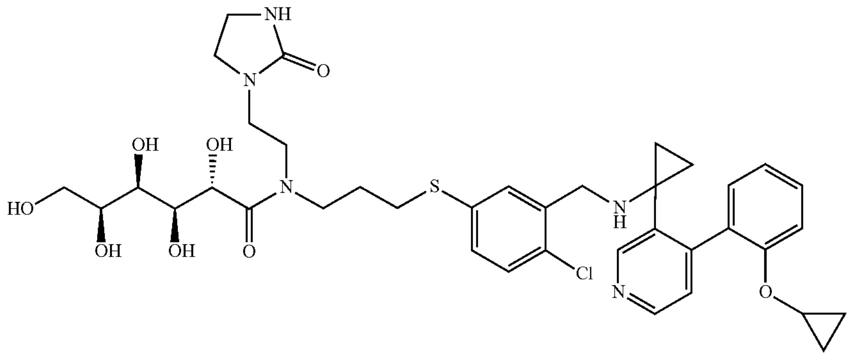 [SMILES: O=C1NCCN1CCN(CCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 770.4 |
| I-532 | Example 86 | 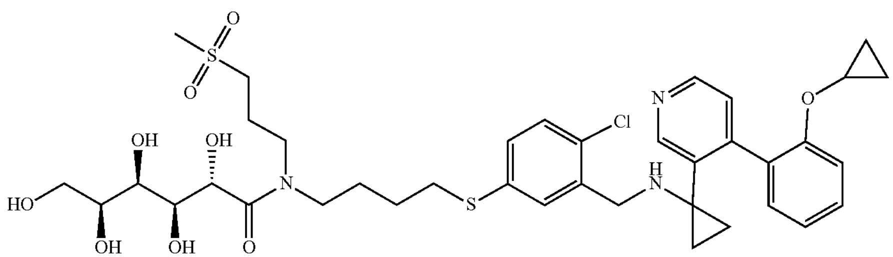 [SMILES: CS(=O)(=O)CCCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 792 |
| I-533 | Example 86 | 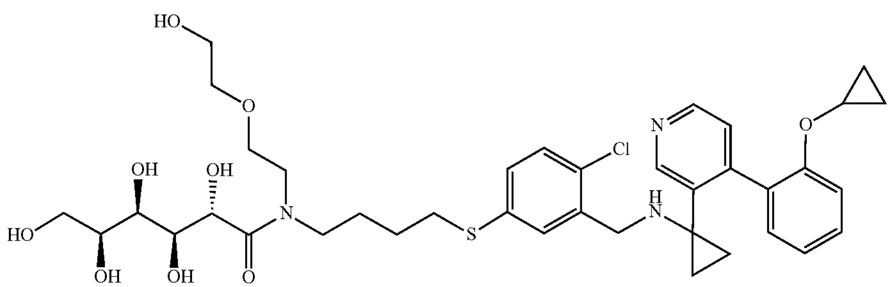 [SMILES: O=C([C@@H](O)[C@@H](O)[C@H](O)[C@@H](O)CO)N(CCCCSc1ccc(Cl)c(CNC2(c3cnccc3-c3ccccc3OC3CC3)CC2)c1)CCOCCO] | 760 |

TABLE 15-continued
Compounds I-499 to I-695
| Cmpd No.: | Synthetic Method | Compound Structure | Obs. mass [M + H]+ |
|---|---|---|---|
| I-534 | Example 86 | 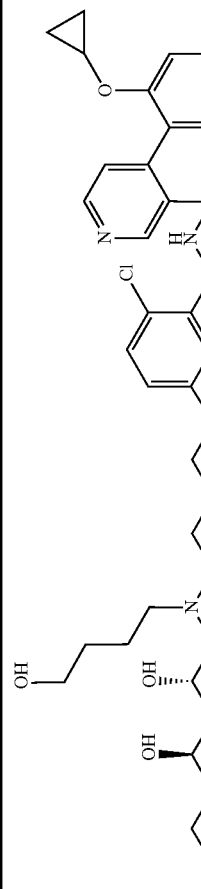 | 744 |
| I-535 | Example 86 | 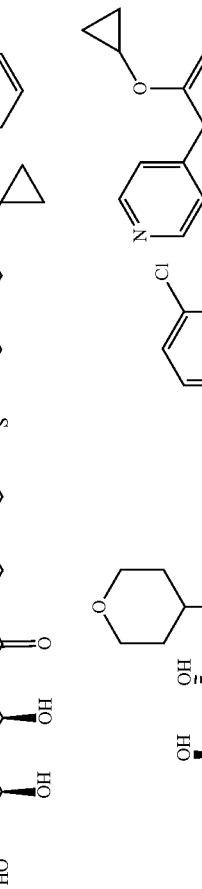 | 756 |
| I-536 | Example 86 | 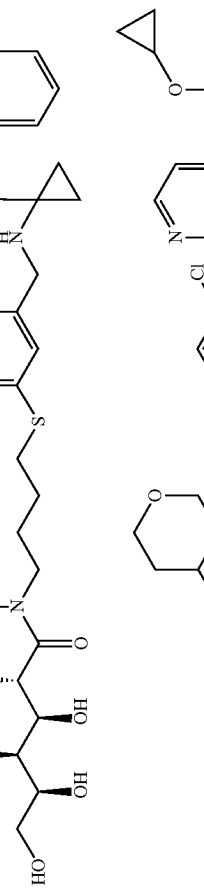 | 770 |

TABLE 15-continued

Compounds I-499 to I-695

| Cmpd No.: | Synthetic Method | Compound Structure | Obs. mass [M + H]+ |
|---|---|---|---|
| I-537 | Example 86 | 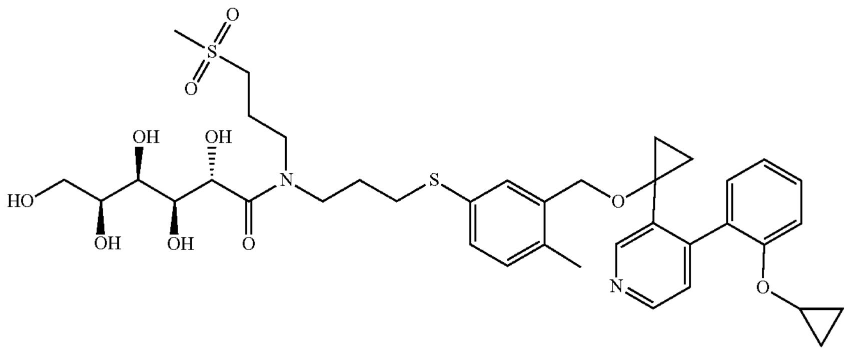 [SMILES: Cc1ccc(SCCCN(CCCS(C)(=O)=O)C(=O)[C@@H](O)[C@@H](O)[C@H](O)[C@@H](O)CO)cc1COC1(c2cnccc2-c2ccccc2OC2CC2)CC1] | 759.4 |
| I-538 | Example 86 | 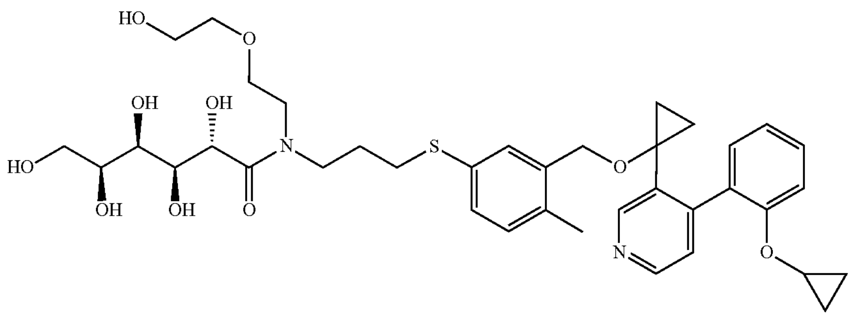 [SMILES: Cc1ccc(SCCCN(CCOCCO)C(=O)[C@@H](O)[C@@H](O)[C@H](O)[C@@H](O)CO)cc1COC1(c2cnccc2-c2ccccc2OC2CC2)CC1] | 727.3 |
| I-539 | Example 86 | 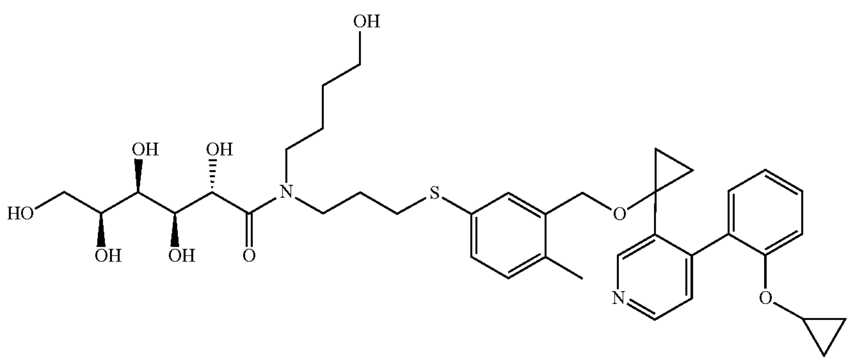 [SMILES: Cc1ccc(SCCCN(CCCCO)C(=O)[C@@H](O)[C@@H](O)[C@H](O)[C@@H](O)CO)cc1COC1(c2cnccc2-c2ccccc2OC2CC2)CC1] | 711.4 |

TABLE 15-continued

Compounds I-499 to I-695

| Cmpd No.: | Synthetic Method | Compound Structure | Obs. mass [M + H]+ |
|---|---|---|---|
| I-540 | Example 86 | 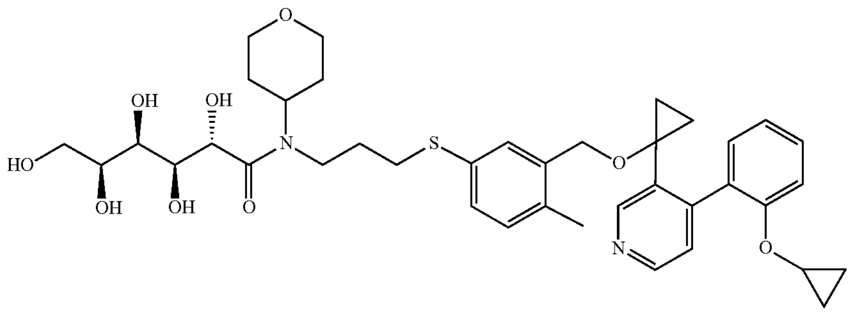 [SMILES: Cc1ccc(SCCCN(C(=O)[C@@H](O)[C@@H](O)[C@H](O)[C@@H](O)CO)C2CCOCC2)cc1COC1(c2cnccc2-c2ccccc2OC2CC2)CC1] | 723.4 |
| I-541 | Example 86 | 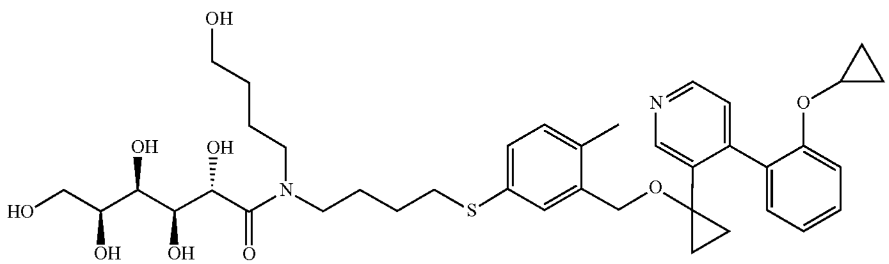 [SMILES: Cc1ccc(SCCCCN(CCCCO)C(=O)[C@@H](O)[C@@H](O)[C@H](O)[C@@H](O)CO)cc1COC1(c2cnccc2-c2ccccc2OC2CC2)CC1] | 725.4 |
| I-542 | Example 86 | 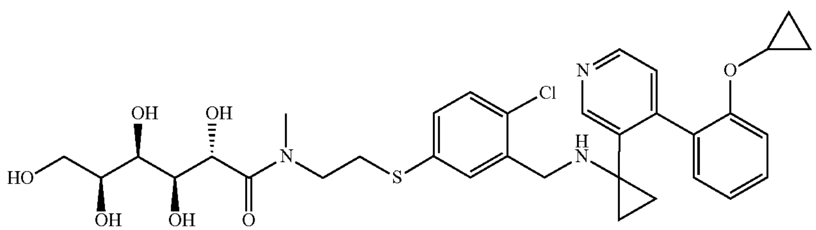 [SMILES: CN(CCSc1ccc(Cl)c(CNC2(c3cnccc3-c3ccccc3OC3CC3)CC2)c1)C(=O)[C@@H](O)[C@@H](O)[C@H](O)[C@@H](O)CO] | 658 |

TABLE 15-continued

Compounds I-499 to I-695

| Cmpd No.: | Synthetic Method | Compound Structure | Obs. mass [M + H]+ |
|---|---|---|---|
| I-543 | Example 86 | 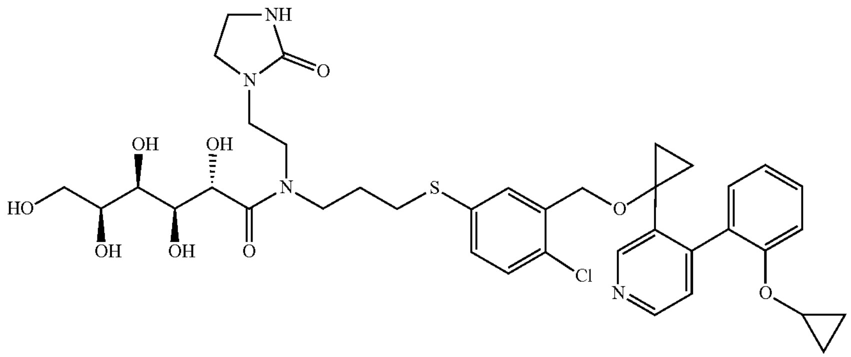 [SMILES: O=C1NCCN1CCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 771.2 |
| I-544 | Example 86 | 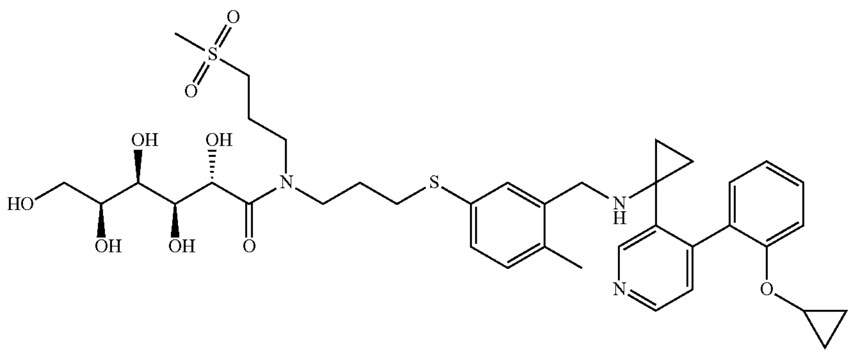 [SMILES: Cc1ccc(SCCCN(CCCS(C)(=O)=O)C(=O)[C@@H](O)[C@@H](O)[C@H](O)[C@@H](O)CO)cc1CNC1(c2cnccc2-c2ccccc2OC2CC2)CC1] | 758.4 |
| I-545 | Example 86 | 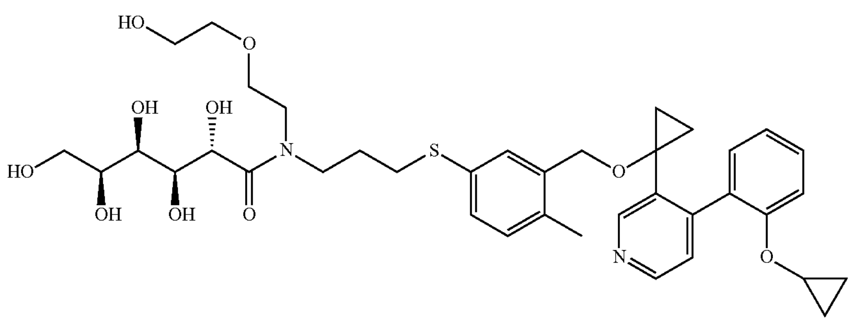 [SMILES: Cc1ccc(SCCCN(CCOCCO)C(=O)[C@@H](O)[C@@H](O)[C@H](O)[C@@H](O)CO)cc1COC1(c2cnccc2-c2ccccc2OC2CC2)CC1] | 726.4 |

TABLE 15-continued
Compounds I-499 to I-695
| Cmpd No.: | Synthetic Method | Compound Structure | Obs. mass [M + H]+ |
|---|---|---|---|
| I-546 | Example 86 | 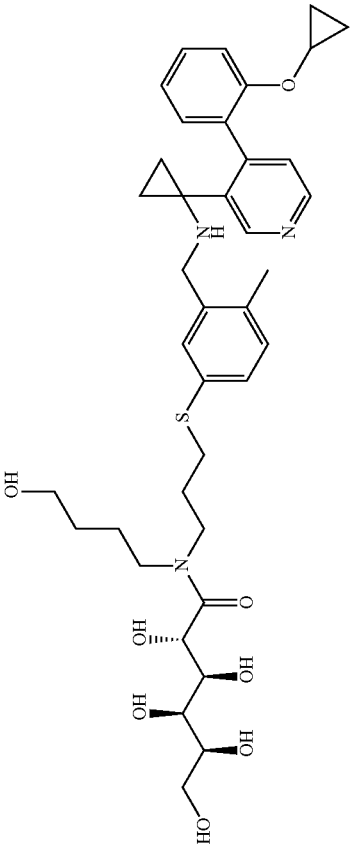 | 710.4 |
| I-547 | Example 86 | 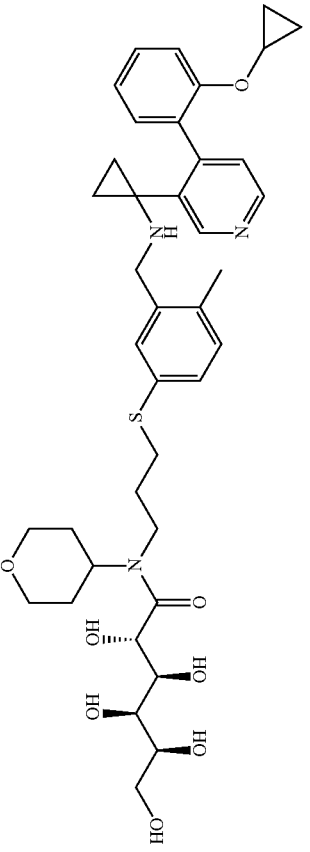 | 722.4 |
| I-548 | Example 86 | 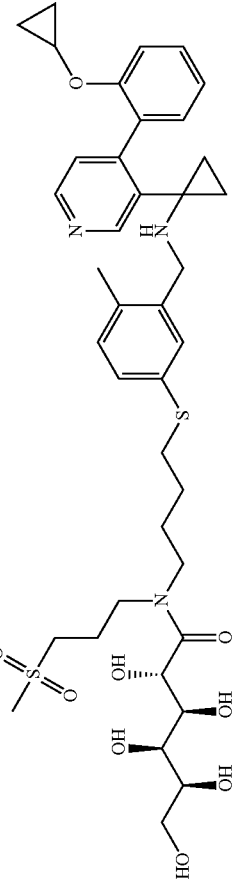 | 772.5 |

TABLE 15-continued

Compounds I-499 to I-695

| Cmpd No.: | Synthetic Method | Compound Structure | Obs. mass [M + H]+ |
|---|---|---|---|
| I-549 | Example 86 | 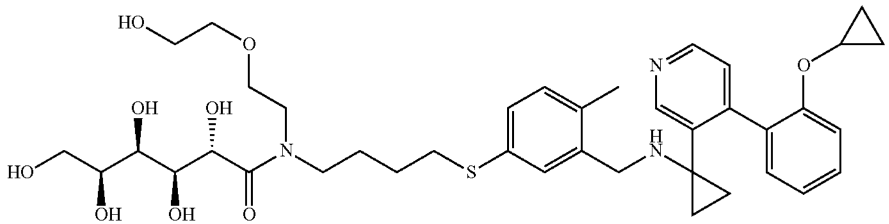 [SMILES: Cc1ccc(SCCCCN(CCOCCO)C(=O)[C@@H](O)[C@@H](O)[C@H](O)[C@@H](O)CO)cc1CNC1(c2cnccc2-c2ccccc2OC2CC2)CC1] | 740.5 |
| I-550 | Example 86 | 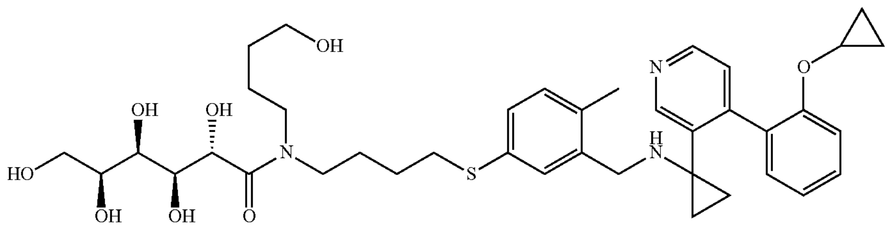 [SMILES: Cc1ccc(SCCCCN(CCCCO)C(=O)[C@@H](O)[C@@H](O)[C@H](O)[C@@H](O)CO)cc1CNC1(c2cnccc2-c2ccccc2OC2CC2)CC1] | 724.5 |
| I-551 | Example 86 | 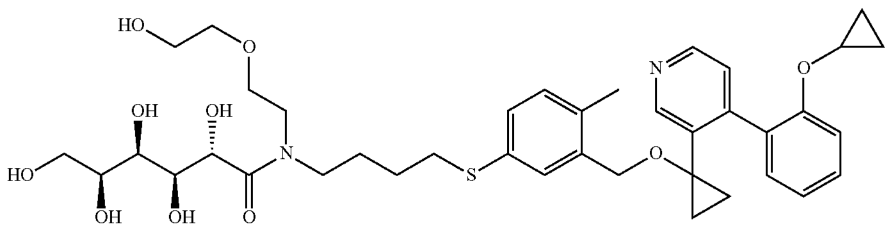 [SMILES: Cc1ccc(SCCCCN(CCOCCO)C(=O)[C@@H](O)[C@@H](O)[C@H](O)[C@@H](O)CO)cc1COC1(c2cnccc2-c2ccccc2OC2CC2)CC1] | 741.6 |

TABLE 15-continued

Compounds I-499 to I-695

| Cmpd No.: | Synthetic Method | Compound Structure | Obs. mass [M + H]+ |
|---|---|---|---|
| I-552 | Example 86 | 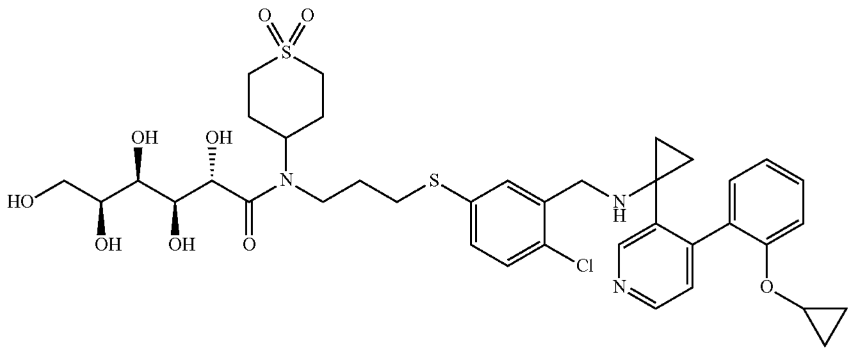 | 790.3 |
| I-553 | Example 86 | 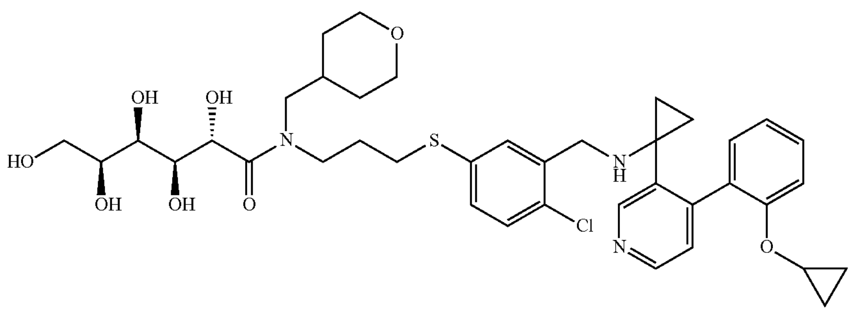 [SMILES: O=C([C@@H](O)[C@@H](O)[C@H](O)[C@@H](O)CO)N(CCCSc1ccc(Cl)c(CNC2(c3cnccc3-c3ccccc3OC3CC3)CC2)c1)CC1CCOCC1] | 756 |
| I-554 | Example 86 | 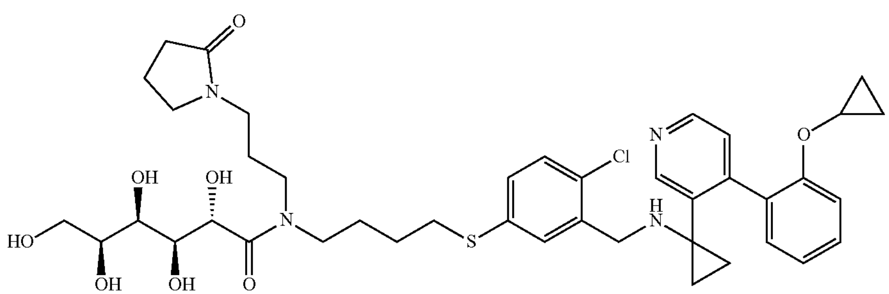 [SMILES: O=C1CCCN1CCCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 797 |

TABLE 15-continued

Compounds I-499 to I-695

| Cmpd No.: | Synthetic Method | Compound Structure | Obs. mass [M + H]⁺ |
| --- | --- | --- | --- |
| I-555 | Example 86 | 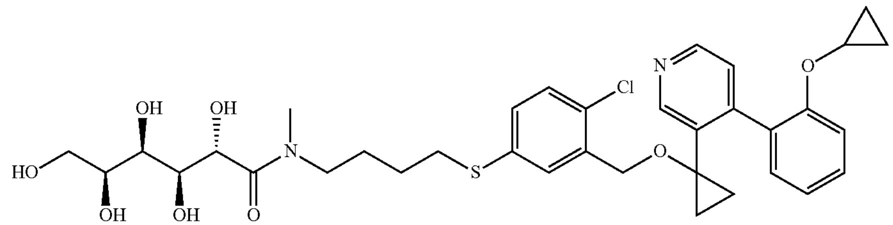 [SMILES: CN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 659.2 |
| I-556 | Example 86 | 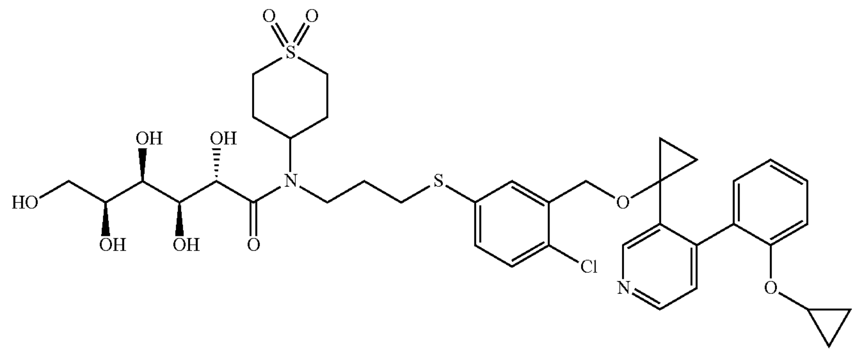 [SMILES: O=C([C@@H](O)[C@@H](O)[C@H](O)[C@@H](O)CO)N(CCCSc1ccc(Cl)c(COC2(c3cnccc3-c3ccccc3OC3CC3)CC2)c1)C1CCS(=O)(=O)CC1] | 791.2 |
| I-557 | Example 86 | 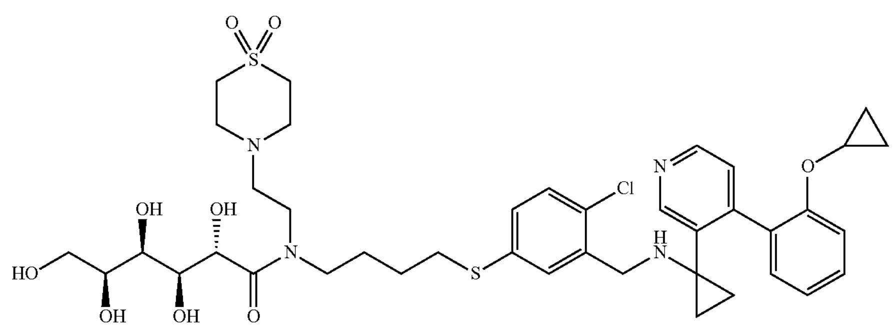 [SMILES: O=C([C@@H](O)[C@@H](O)[C@H](O)[C@@H](O)CO)N(CCCCSc1ccc(Cl)c(CNC2(c3cnccc3-c3ccccc3OC3CC3)CC2)c1)CCN1CCS(=O)(=O)CC1] | 833 |

TABLE 15-continued
Compounds I-499 to I-695
| Cmpd No.: | Synthetic Method | Compound Structure | Obs. mass [M + H]+ |
|---|---|---|---|
| I-558 | Example 86 | 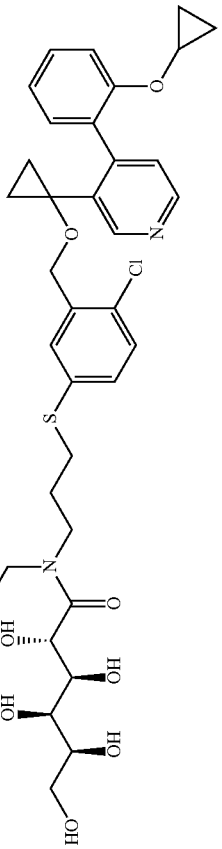 | 779.2 |
| I-559 | Example 86 | 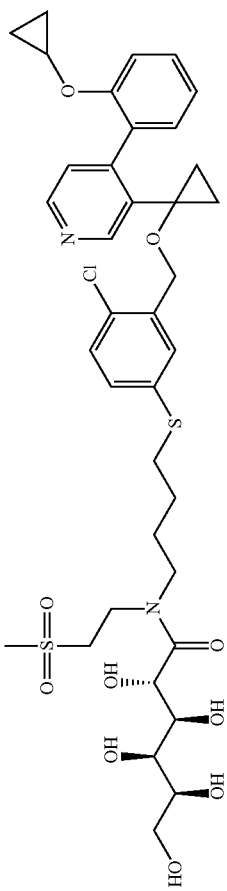 | 779 |
| I-560 | Example 86 | 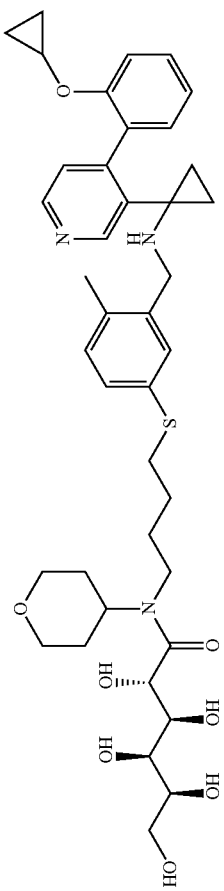 | 736 |

TABLE 15-continued

Compounds I-499 to I-695

| Cmpd No.: | Synthetic Method | Compound Structure | Obs. mass [M + H]+ |
|---|---|---|---|
| I-561 | Example 86 | 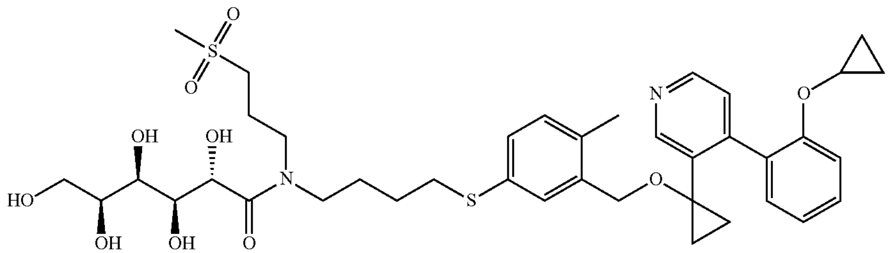 | 773.3 |
| I-562 | Example 86 | 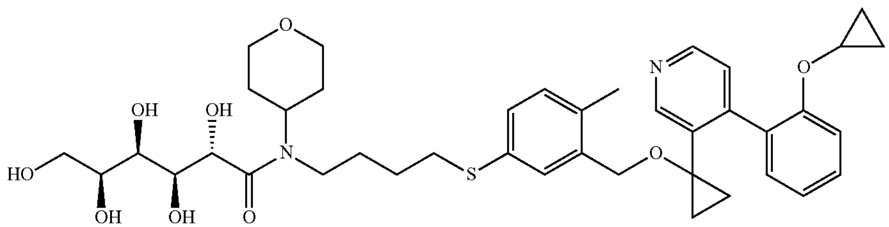 [SMILES: Cc1ccc(SCCCCN(C(=O)[C@@H](O)[C@@H](O)[C@H](O)[C@@H](O)CO)C2CCOCC2)cc1COC1(c2cnccc2-c2ccccc2OC2CC2)CC1] | 737.3 |
| I-563 | Example 86 | 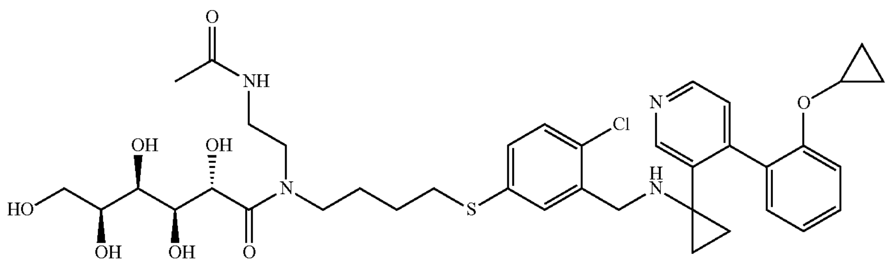 [SMILES: CC(=O)NCCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 757 |
| I-564 | Example 86 | 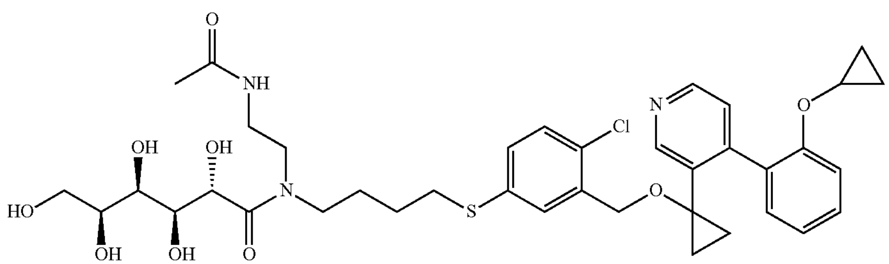 [SMILES: CC(=O)NCCN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 758 |

TABLE 15-continued

Compounds I-499 to I-695

| Cmpd No.: | Synthetic Method | Compound Structure | Obs. mass [M + H]+ |
|---|---|---|---|
| I-565 | Example 86 | 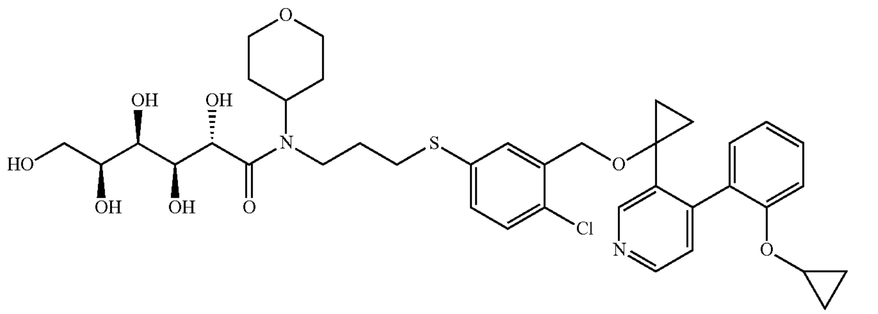 [SMILES: O=C([C@@H](O)[C@@H](O)[C@H](O)[C@@H](O)CO)N(CCCSc1ccc(Cl)c(COC2(c3cnccc3-c3ccccc3OC3CC3)CC2)c1)C1CCOCC1] | 743.3 |
| I-566 | Example 86 | 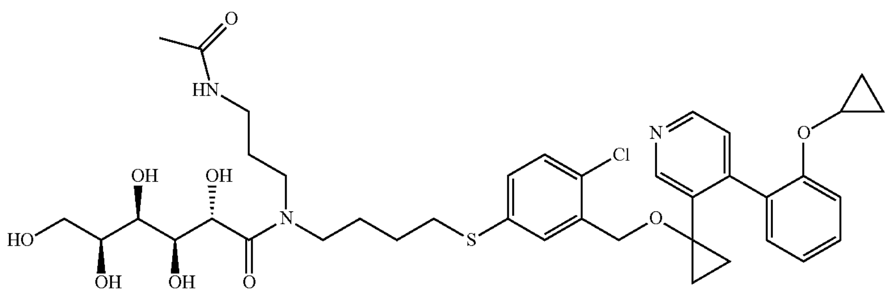 [SMILES: CC(=O)NCCCN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 772.3 |
| I-567 | Example 86 | 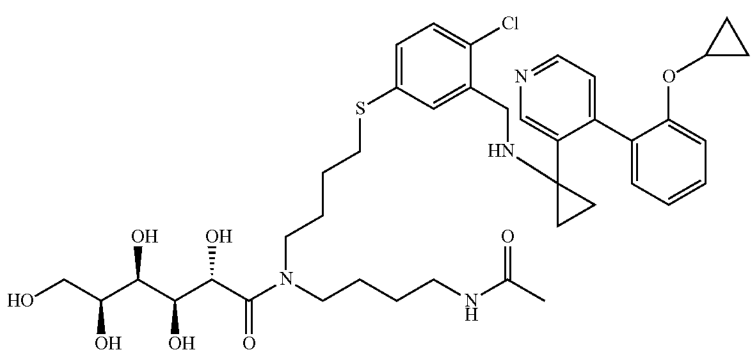 [SMILES: CC(=O)NCCCCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 785 |

TABLE 15-continued
Compounds I-499 to I-695
| Cmpd No. | Synthetic Method | Compound Structure | Obs. mass [M + H]+ |
|---|---|---|---|
| I-568 | Example 86 | 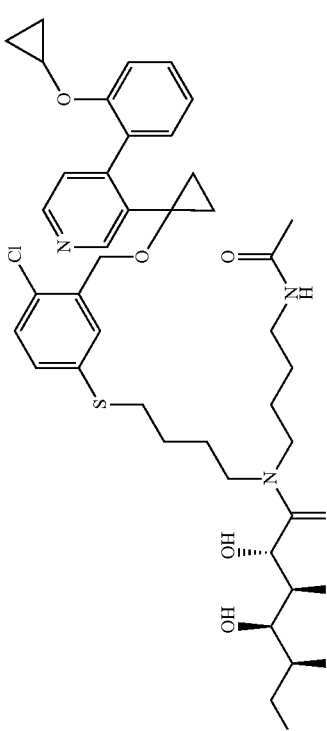 | 786 |
| I-569 | Example 86 | 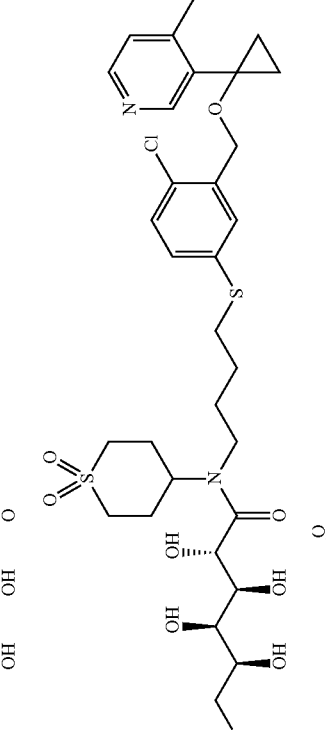 | 805 |
| I-570 | Example 86 | 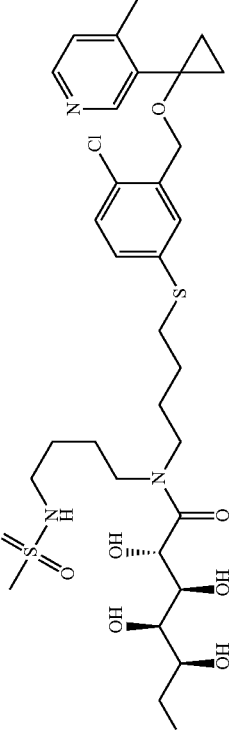 | 822 |

TABLE 15-continued
Compounds I-499 to I-695
| Cmpd No.: | Synthetic Method | Compound Structure | Obs. mass [M + H]+ |
|---|---|---|---|
| I-571 | Example 86 | 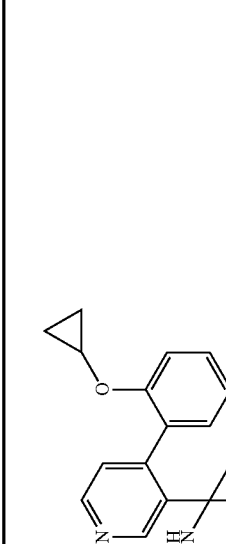 | 793 |
| I-572 | Example 86 | 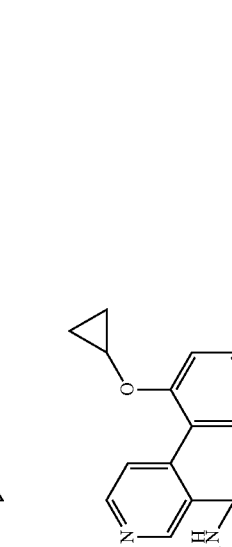 | 787 |

TABLE 15-continued

Compounds I-499 to I-695

| Cmpd No.: | Synthetic Method | Compound Structure | Obs. mass [M + H]+ |
|---|---|---|---|
| I-573 | Example 86 | (structure) | 771 |

TABLE 15-continued

Compounds I-499 to I-695

| Cmpd No.: | Synthetic Method | Compound Structure | Obs. mass [M + H]+ |
|---|---|---|---|
| I-574 | Example 86 | 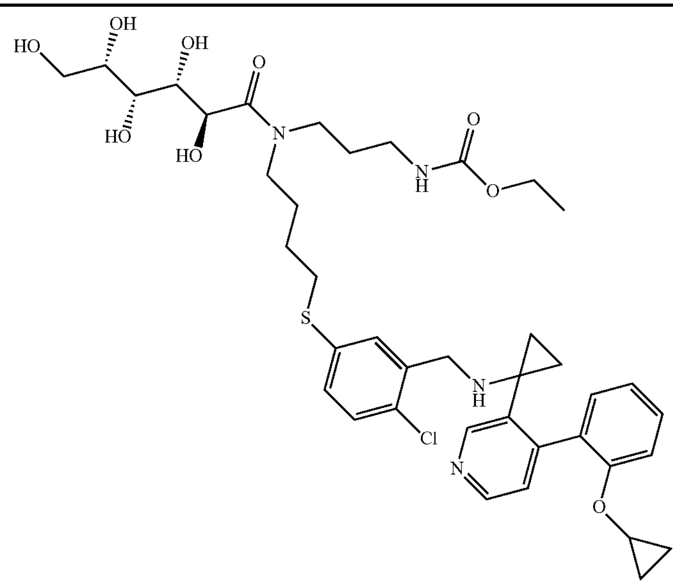 | 801 |

TABLE 15-continued

Compounds I-499 to I-695

| Cmpd No.: | Synthetic Method | Compound Structure | Obs. mass [M + H]⁺ |
|---|---|---|---|
| I-575 | Example 86 | (structure) | 794 |

TABLE 15-continued

Compounds I-499 to I-695

| Cmpd No.: | Synthetic Method | Compound Structure | Obs. mass [M + H]+ |
|---|---|---|---|
| I-576 | Example 86 | 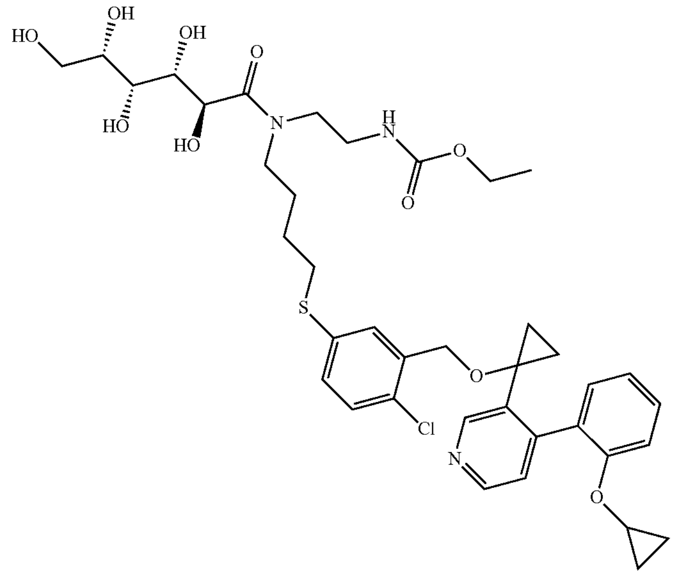 | 788 |
| I-577 | Example 86 | 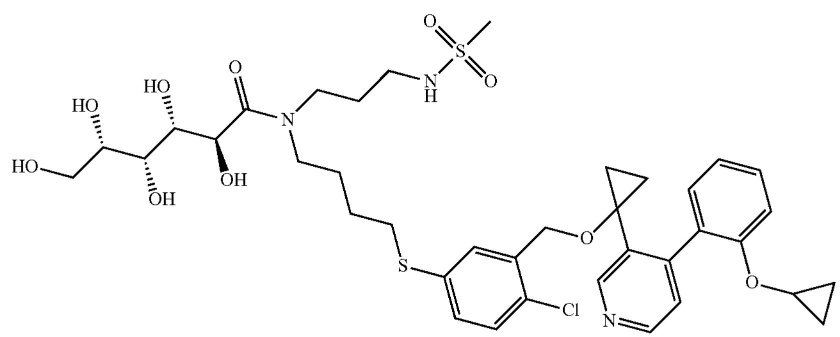 [SMILES: CS(=O)(=O)NCCCN(CCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 808 |

TABLE 15-continued
Compounds I-499 to I-695
| Cmpd No.: | Synthetic Method | Compound Structure | Obs. mass [M + H]+ |
|---|---|---|---|
| I-578 | Example 86 | 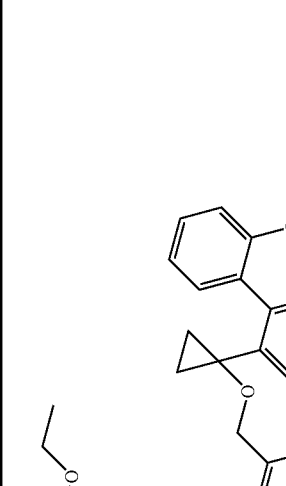 | 802 |
| I-579 | Example 86 | 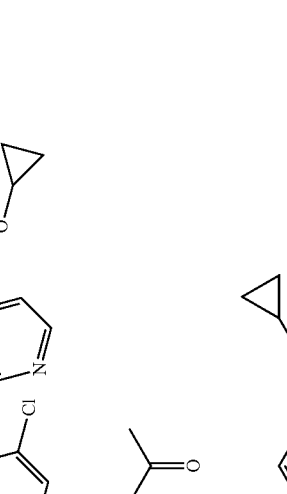 | 772.2 |

TABLE 15-continued
Compounds I-499 to I-695
| Cmpd No.: | Synthetic Method | Compound Structure | Obs. mass [M + H]+ |
|---|---|---|---|
| I-580 | Example 86 | 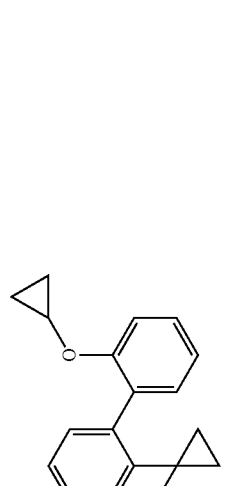 | 808.2 |
| I-581 | Example 86 | 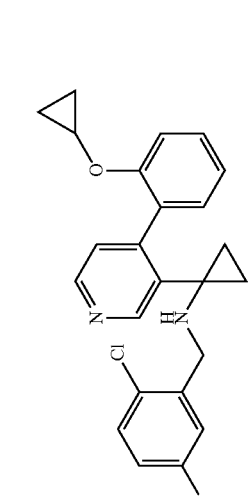 | 804 |
| I-582 | Example 86 | 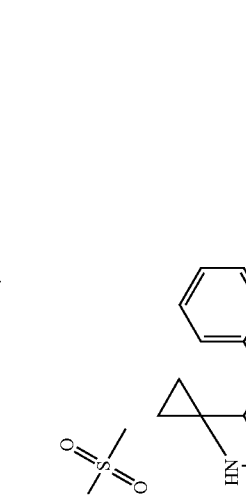 | 821 |

TABLE 15-continued

Compounds I-499 to I-695

| Cmpd No.: | Synthetic Method | Compound Structure | Obs. mass [M + H]+ |
|---|---|---|---|
| I-583 | Example 86 | 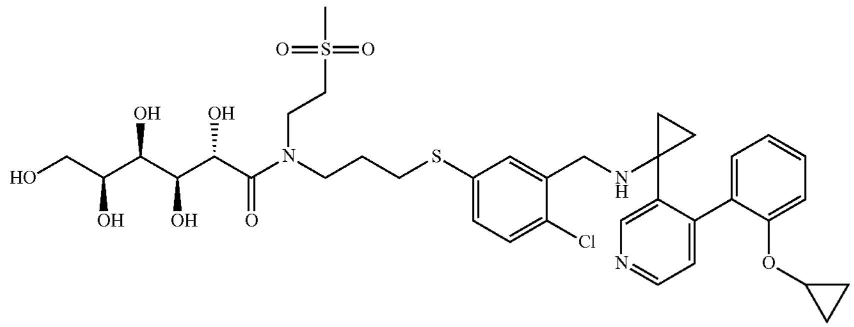 [SMILES: CS(=O)(=O)CCN(CCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 764.2 |
| I-584 | Example 86 | 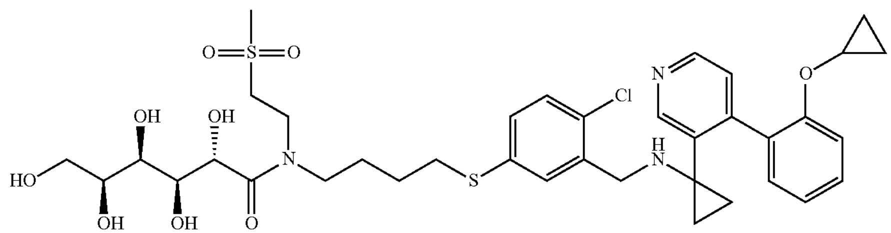 [SMILES: CS(=O)(=O)CCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 778.2 |
| I-585 | Example 86 | 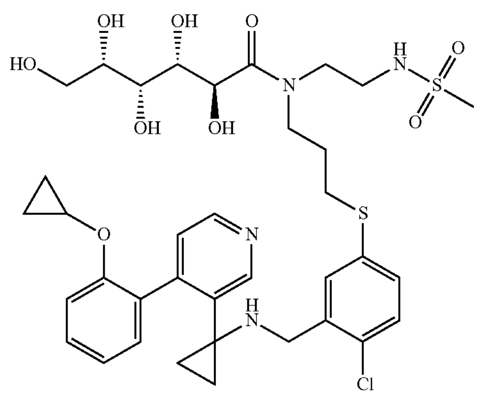 [SMILES: CS(=O)(=O)NCCN(CCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 779.2 |

TABLE 15-continued
Compounds I-499 to I-695
| Cmpd No.: | Synthetic Method | Compound Structure | Obs. mass [M + H]+ |
|---|---|---|---|
| I-586 | Example 86 | 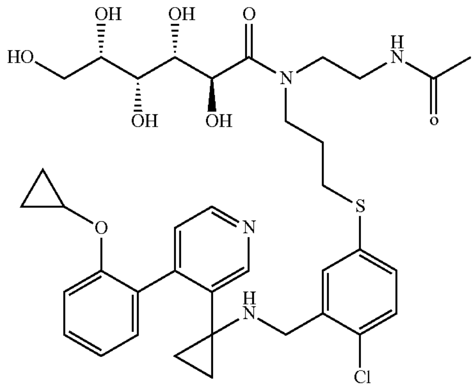 | 743.2 |
| I-587 | Example 86 | 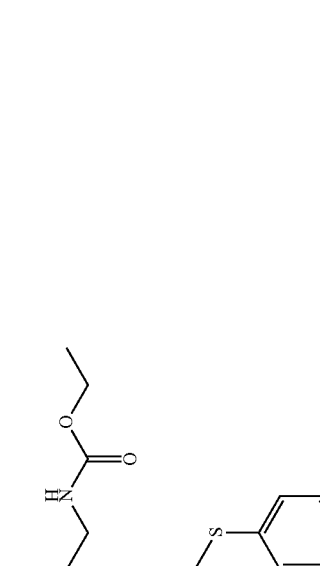 | 773.2 |

TABLE 15-continued
Compounds I-499 to I-695
| Cmpd No.: | Synthetic Method | Compound Structure | Obs. mass [M + H]+ |
|---|---|---|---|
| I-588 | Example 86 | 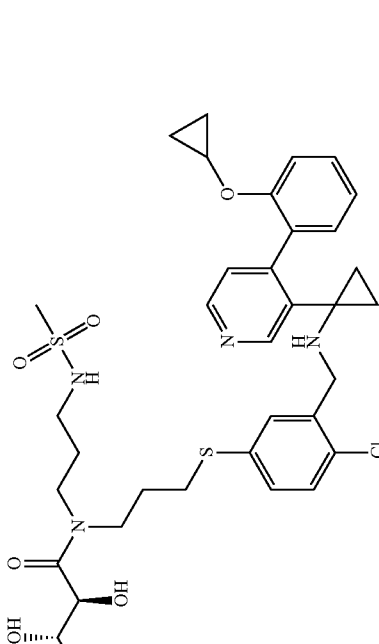 | 793 |
| I-589 | Example 86 | 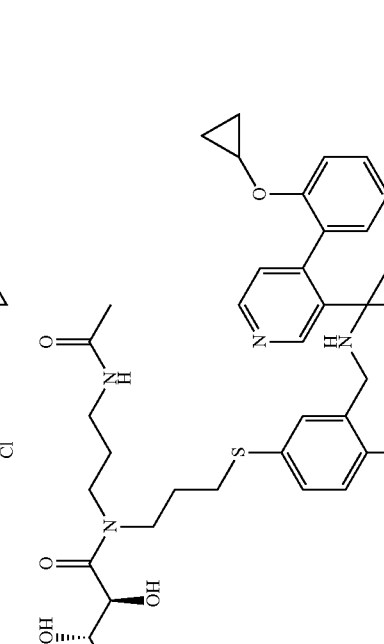 | 757 |

TABLE 15-continued

Compounds I-499 to I-695

| Cmpd No.: | Synthetic Method | Compound Structure | Obs. mass [M + H]+ |
|---|---|---|---|
| I-590 | Example 86 | 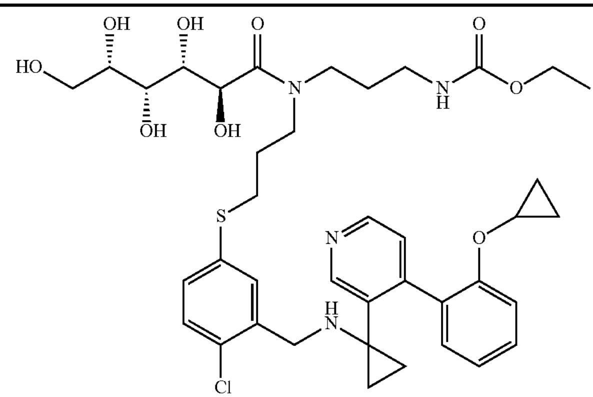 | 787 |
| I-591 | Example 86 | 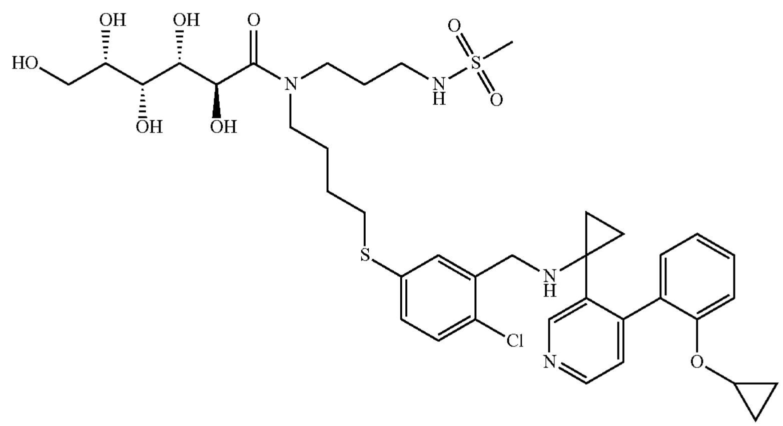 [SMILES: CS(=O)(=O)NCCCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 807 |

TABLE 15-continued

Compounds I-499 to I-695

| Cmpd No.: | Synthetic Method | Compound Structure | Obs. mass [M + H]+ |
|---|---|---|---|
| I-592 | Example 86 | 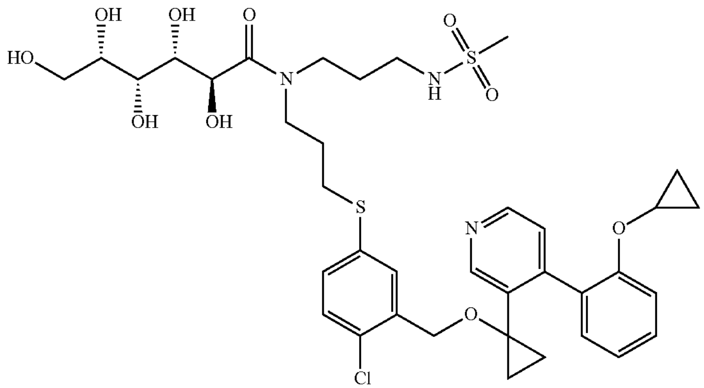 [SMILES: CS(=O)(=O)NCCCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 794.2 |
| I-593 | Example 86 | 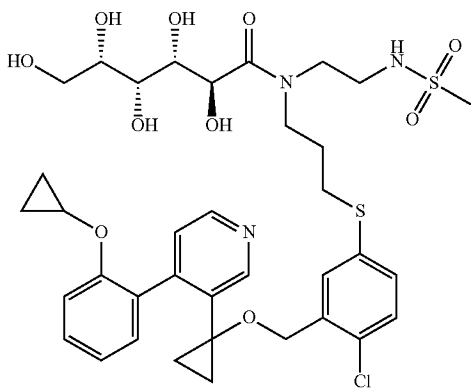 [SMILES: CS(=O)(=O)NCCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 780.2 |

TABLE 15-continued

Compounds I-499 to I-695

| Cmpd No.: | Synthetic Method | Compound Structure | Obs. mass [M + H]⁺ |
|---|---|---|---|
| I-594 | Example 86 | 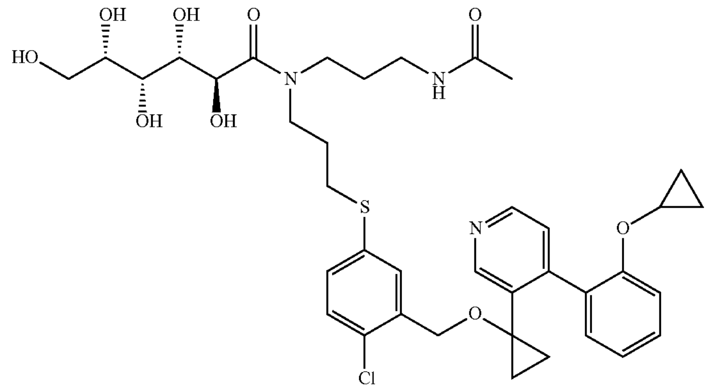 | 758.4 |
| I-595 | Example 86 | 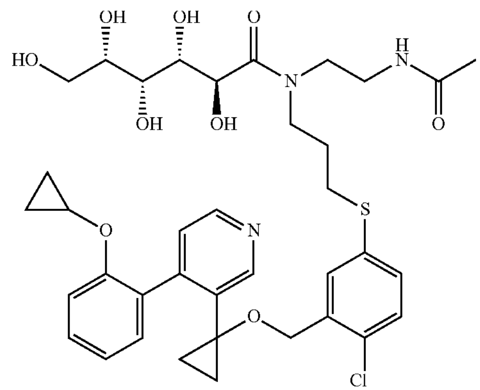 [SMILES: CC(=O)NCCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 744.1 |

TABLE 15-continued

Compounds I-499 to I-695

| Cmpd No.: | Synthetic Method | Compound Structure | Obs. mass [M + H]+ |
|---|---|---|---|
| I-596 | Example 86 | 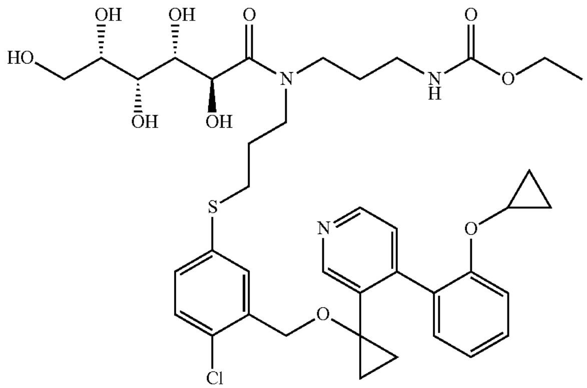 [SMILES: CCOC(=O)NCCCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 788.2 |
| I-597 | Example 86 | 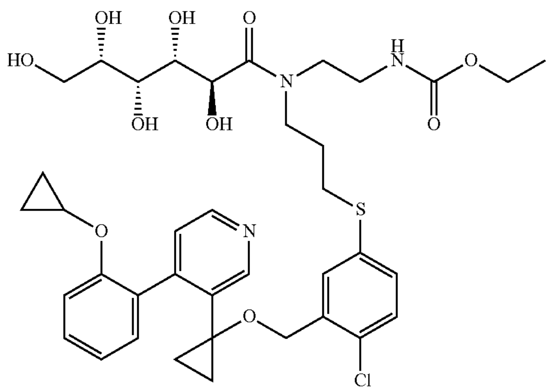 [SMILES: CCOC(=O)NCCN(CCCSc1ccc(Cl)c(COC2(c3cnccc3-c3ccccc3OC3CC3)CC2)c1)C(=O)[C@@H](O)[C@@H](O)[C@H](O)[C@@H](O)CO] | 774.1 |

TABLE 15-continued
Compounds I-499 to I-695
| Cmpd No.: | Synthetic Method | Compound Structure | Obs. mass [M + H]+ |
|---|---|---|---|
| I-598 | Example 86 | 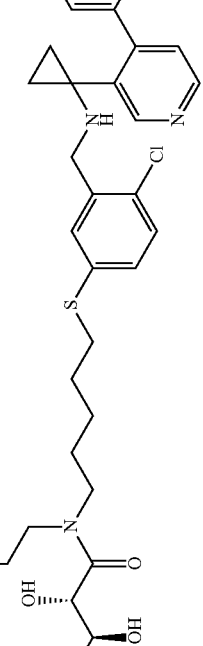 | 774.5 |
| I-599 | Example 86 | 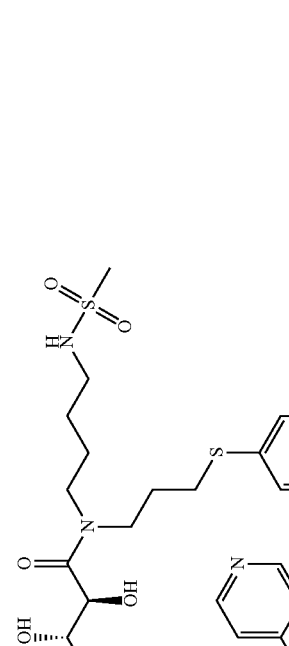 | 807 |

TABLE 15-continued

Compounds I-499 to I-695

| Cmpd No.: | Synthetic Method | Compound Structure | Obs. mass [M + H]+ |
|---|---|---|---|
| I-600 | Example 86 | 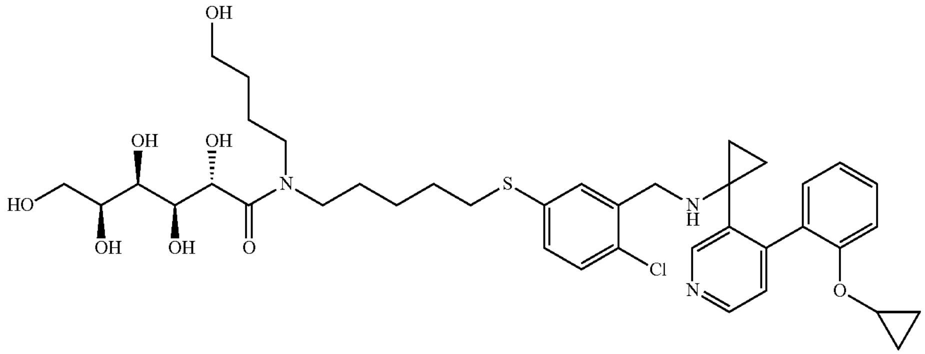 | 758 |
| I-601 | Example 86 | 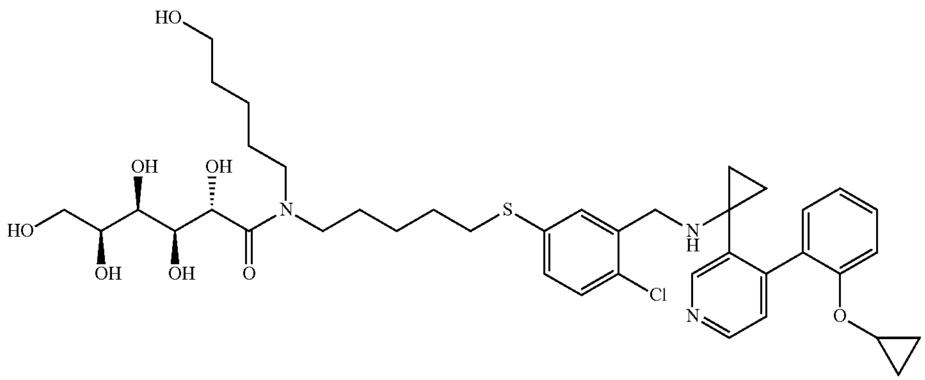 [SMILES: O=C([C@@H](O)[C@@H](O)[C@H](O)[C@@H](O)CO)N(CCCCCSc1ccc(Cl)c(CNC2(c3cnccc3-c3ccccc3OC3CC3)CC2)c1)CCOCCO] | 772 |

TABLE 15-continued

Compounds I-499 to I-695

| Cmpd No.: | Synthetic Method | Compound Structure | Obs. mass [M + H]+ |
|---|---|---|---|
| I-602 | Example 86 | 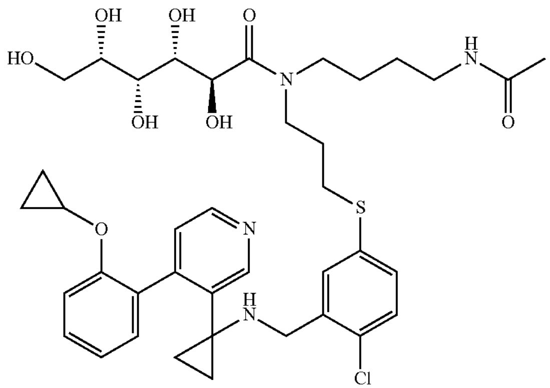 [SMILES: CC(=O)NCCCCN(CCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 771 |
| I-603 | Example 86 | 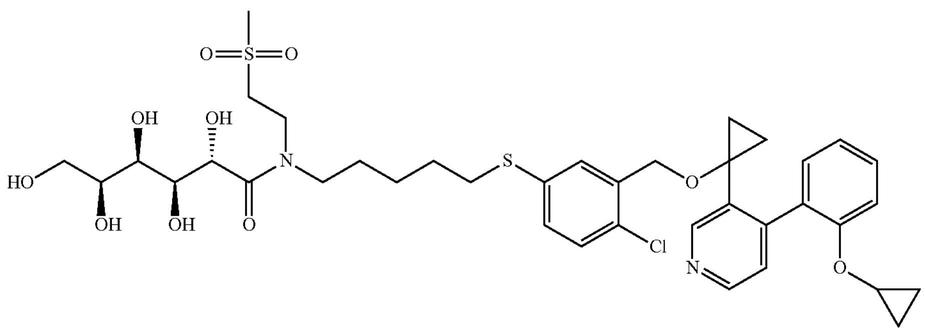 [SMILES: CS(=O)(=O)CCN(CCCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 793.3 |

TABLE 15-continued
Compounds I-499 to I-695
| Cmpd No.: | Synthetic Method | Compound Structure | Obs. mass [M + H]+ |
|---|---|---|---|
| I-604 | Example 86 | 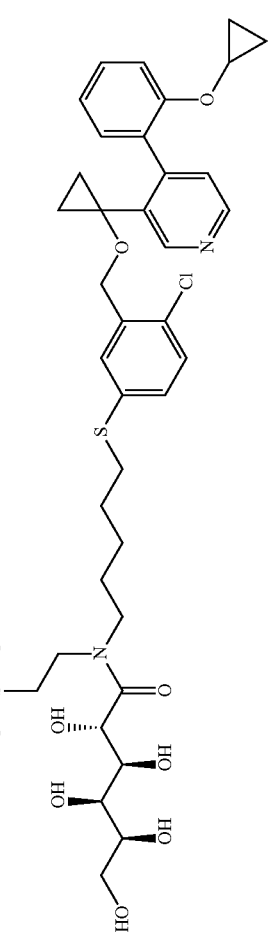 | 807.4 |
| I-605 | Example 86 | 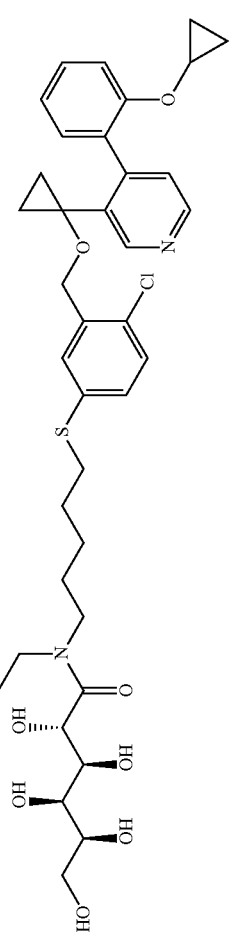 | 759.2 |
| I-606 | Example 86 | 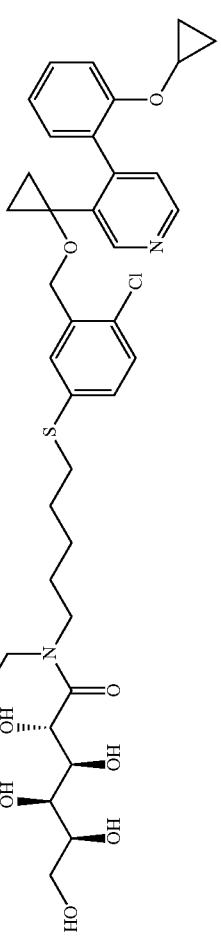 | 773.2 |

TABLE 15-continued

Compounds I-499 to I-695

| Cmpd No.: | Synthetic Method | Compound Structure | Obs. mass [M + H]+ |
|---|---|---|---|
| I-607 | Example 88 | 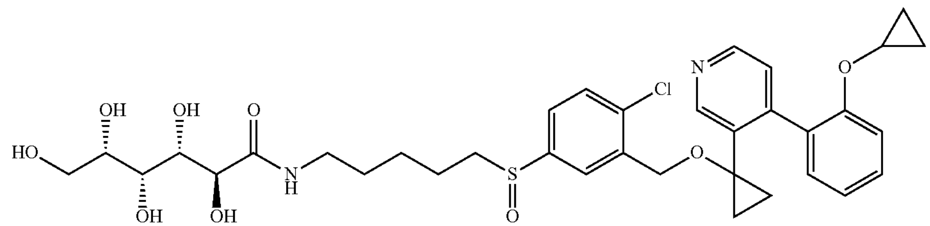 [SMILES: O=C(NCCCCCS(=O)c1ccc(Cl)c(COC2(c3cnccc3-c3ccccc3OC3CC3)CC2)c1)[C@@H](O)[C@@H](O)[C@H](O)[C@@H](O)CO] | 703 |
| I-608 | Example 89 | 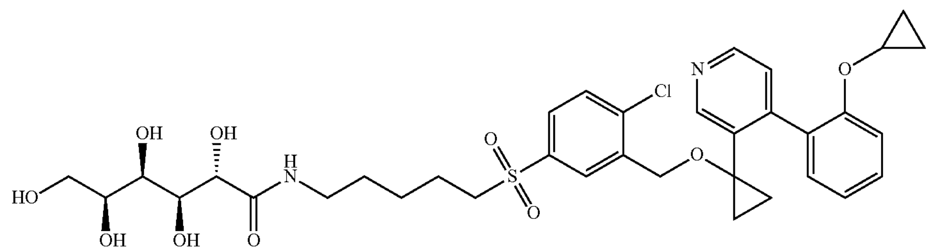 [SMILES: O=C(NCCCCCS(=O)(=O)c1ccc(Cl)c(COC2(c3cnccc3-c3ccccc3OC3CC3)CC2)c1)[C@@H](O)[C@@H](O)[C@H](O)[C@@H](O)CO] | 719 |
| I-609 | Example 86 | 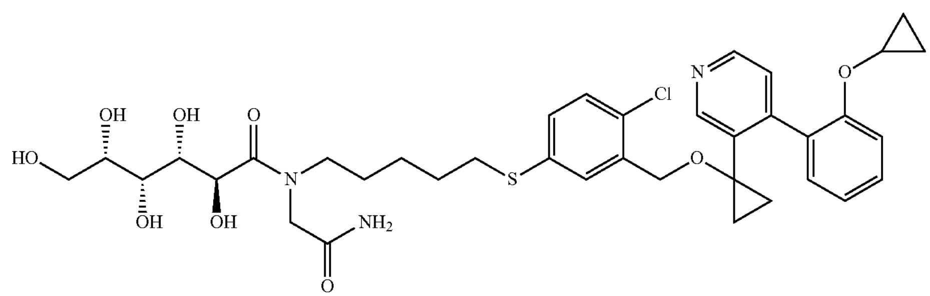 [SMILES: NC(=O)CN(CCCCCSc1ccc(Cl)c(COC2(c3cnccc3-c3ccccc3OC3CC3)CC2)c1)C(=O)[C@@H](O)[C@@H](O)[C@H](O)[C@@H](O)CO] | 744.2 |

TABLE 15-continued

Compounds I-499 to I-695

| Cmpd No.: | Synthetic Method | Compound Structure | Obs. mass [M + H]+ |
|---|---|---|---|
| I-610 | Example 86 | 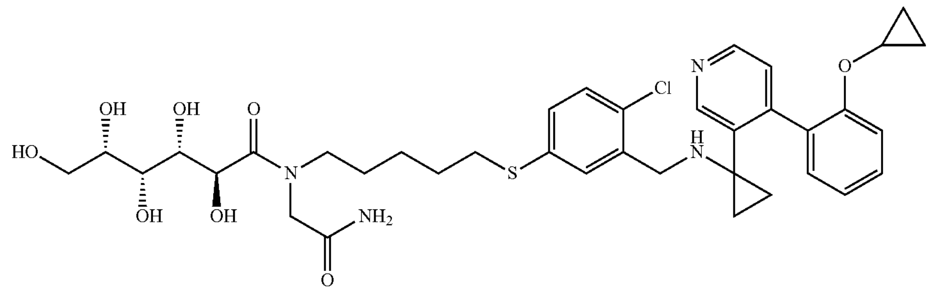 [SMILES: NC(=O)CN(CCCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 743 |
| I-611 | Example 86 | 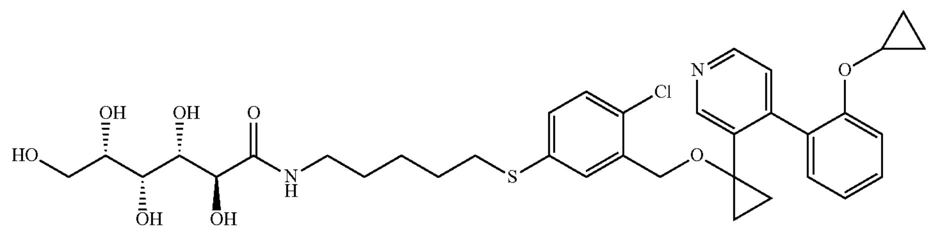 [SMILES: O=C(NCCCCCSc1ccc(Cl)c(COC2(c3cnccc3-c3ccccc3OC3CC3)CC2)c1)[C@@H](O)[C@@H](O)[C@H](O)[C@@H](O)CO] | 687.3 |
| I-612 | Example 86 | 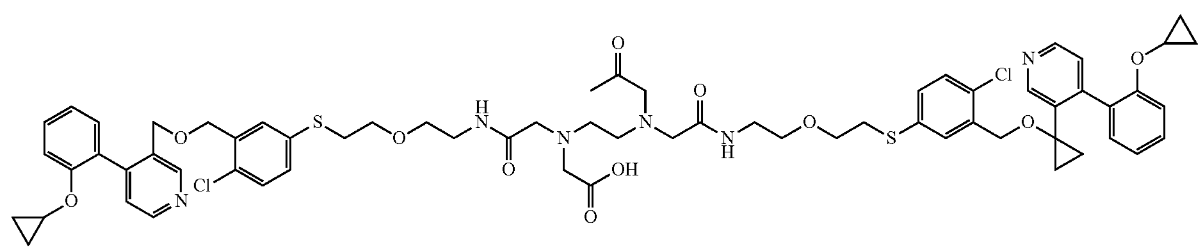 [SMILES: CC(=O)CN(CCN(CC(=O)O)CC(=O)NCCOCCSc1ccc(Cl)c(COCc2cnccc2-c2ccccc2OC2CC2)c1)CC(=O)NCCOCCSc1ccc(Cl)c(COC2(c3cnccc3-c3ccccc3OC3CC3)CC2)c1] | 1277 |
| I-613 | Example 86 | 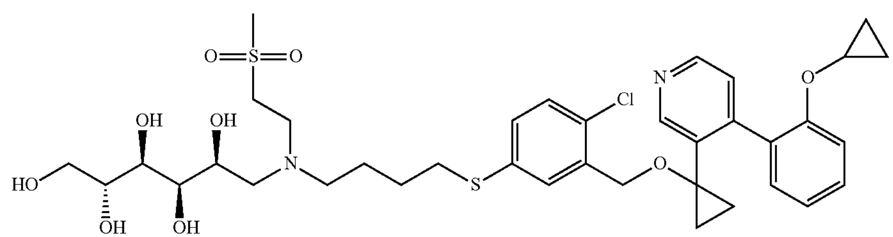 [SMILES: CS(=O)(=O)CCN(CCCCSc1ccc(Cl)c(COC2(c3cnccc3-c3ccccc3OC3CC3)CC2)c1)C[C@H](O)[C@@H](O)[C@H](O)[C@H](O)CO] | 765 |

TABLE 15-continued

Compounds I-499 to I-695

| Cmpd No.: | Synthetic Method | Compound Structure | Obs. mass [M + H]+ |
|---|---|---|---|
| I-614 | Example 86 | 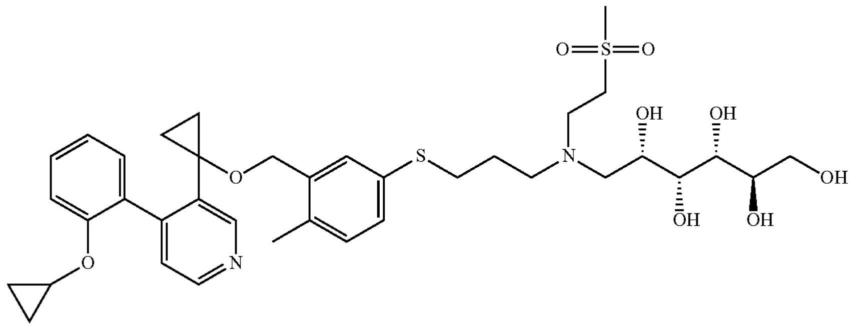 [SMILES: Cc1ccc(SCCCN(CCS(C)(=O)=O)C[C@H](O)[C@@H](O)[C@H](O)[C@H](O)CO)cc1COC1(c2cnccc2-c2ccccc2OC2CC2)CC1] | 731.3 |
| I-615 | Example 86 | 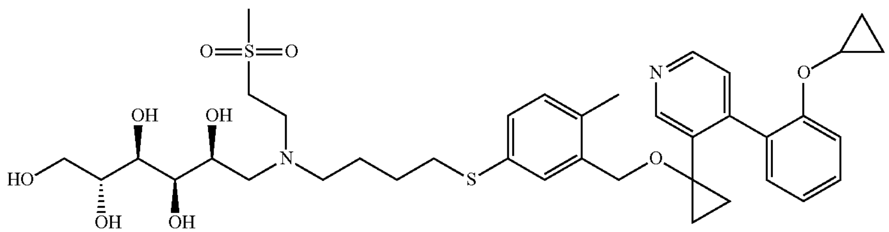 [SMILES: Cc1ccc(SCCCCN(CCS(C)(=O)=O)C[C@H](O)[C@@H](O)[C@H](O)[C@H](O)CO)cc1COC1(c2cnccc2-c2ccccc2OC2CC2)CC1] | 373 [M + 2H]+2/2 |
| I-617 | Example 92 | 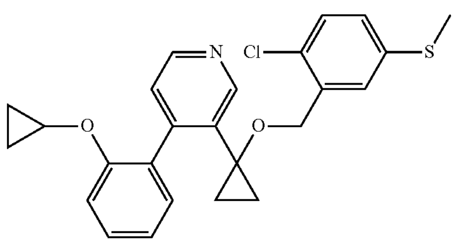 [SMILES: CSc1ccc(Cl)c(COC2(c3cnccc3-c3ccccc3OC3CC3)CC2)c1] | 438 |

TABLE 15-continued

Compounds I-499 to I-695

| Cmpd No.: | Synthetic Method | Compound Structure | Obs. mass [M + H]+ |
|---|---|---|---|
| I-619 | Example 93 | 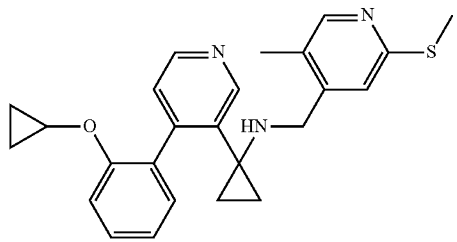 [SMILES: CSc1cc(CNC2(c3cnccc3-c3ccccc3OC3CC3)CC2)c(C)cn1] | 418.2 |
| I-620 | Example 94 | 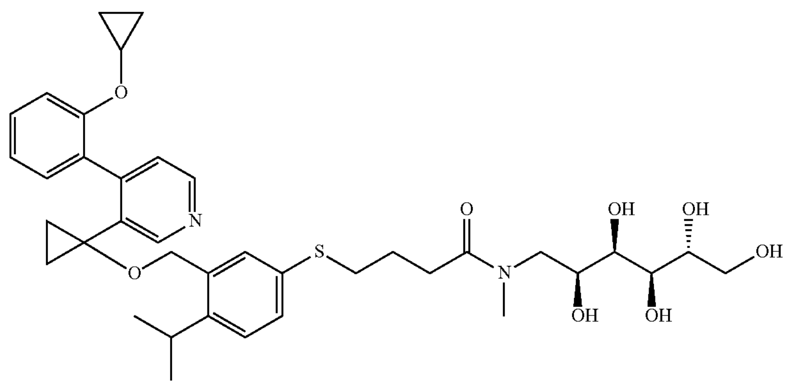 [SMILES: CC(C)c1ccc(SCCCC(=O)N(C)C[C@H](O)[C@@H](O)[C@H](O)[C@H](O)CO)cc1COC1(c2cnccc2-c2ccccc2OC2CC2)CC1] | 695 |
| I-621 | Example 85 | 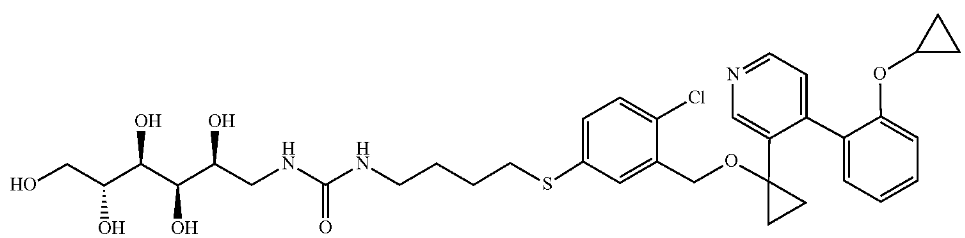 [SMILES: O=C(NCCCCSc1ccc(Cl)c(COC2(c3cnccc3-c3ccccc3OC3CC3)CC2)c1)NC[C@H](O)[C@@H](O)[C@H](O)[C@H](O)CO] | 702 |

TABLE 15-continued

Compounds I-499 to I-695

| Cmpd No.: | Synthetic Method | Compound Structure | Obs. mass [M + H]+ |
|---|---|---|---|
| I-622 | Example 91 | 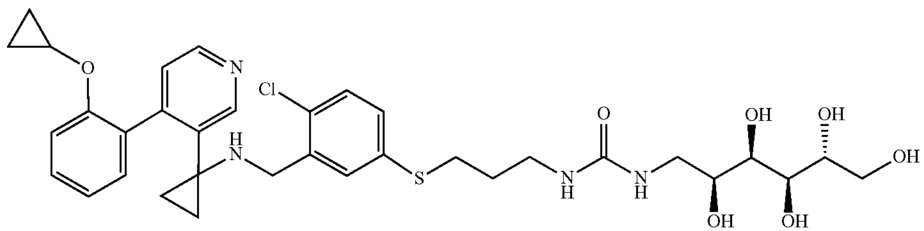 [SMILES: O=C(NCCCSc1ccc(Cl)c(CNC2(c3cnccc3-c3ccccc3OC3CC3)CC2)c1)NC[C@H](O)[C@@H](O)[C@H](O)[C@H](O)CO] | 687.2 |
| I-623 | Example 91 | 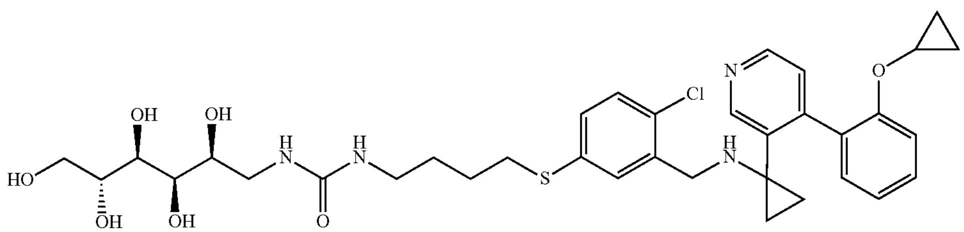 [SMILES: O=C(NCCCCSc1ccc(Cl)c(CNC2(c3cnccc3-c3ccccc3OC3CC3)CC2)c1)NC[C@H](O)[C@@H](O)[C@H](O)[C@H](O)CO] | 701.2 |
| I-624 | Example 86 | 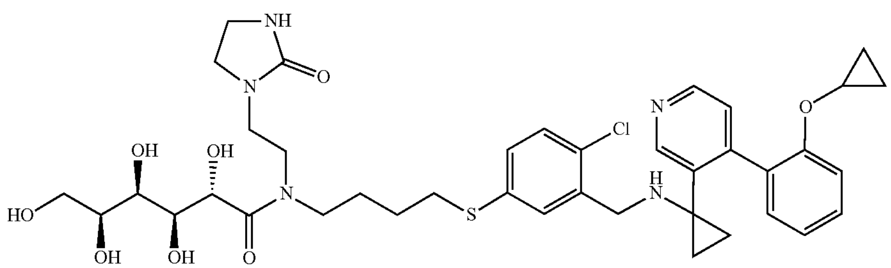 [SMILES: O=C1NCCN1CCN(CCCCSc1ccc(Cl)c(CNC2(c3cnccc3-c3ccccc3OC3CC3)CC2)c1)C(=O)[C@@H](O)[C@@H](O)[C@H](O)[C@@H](O)CO] | 784 |
| I-625 | Example 85 | 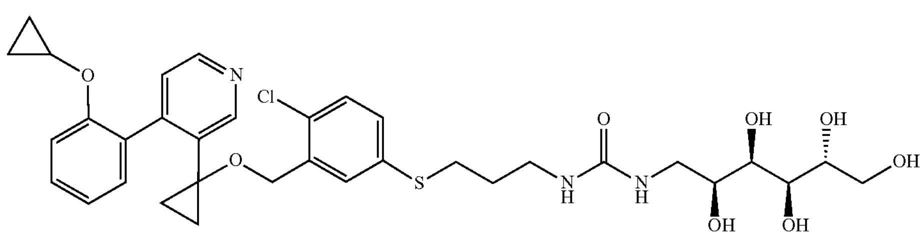 [SMILES: O=C(NCCCSc1ccc(Cl)c(COC2(c3cnccc3-c3ccccc3OC3CC3)CC2)c1)NC[C@H](O)[C@@H](O)[C@H](O)[C@H](O)CO] | 688.4 |

TABLE 15-continued

Compounds I-499 to I-695

| Cmpd No.: | Synthetic Method | Compound Structure | Obs. mass [M + H]+ |
|---|---|---|---|
| I-626 | Example 91 | 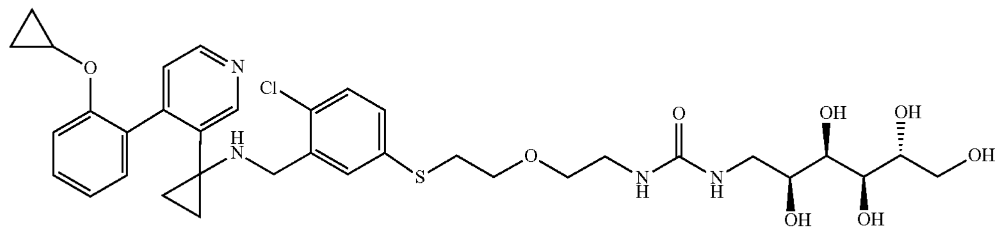 [SMILES: O=C(NCCOCCSc1ccc(Cl)c(CNC2(c3cnccc3-c3ccccc3OC3CC3)CC2)c1)NC[C@H](O)[C@@H](O)[C@H](O)[C@H](O)CO] | 717.4 |
| I-627 | Example 85 | 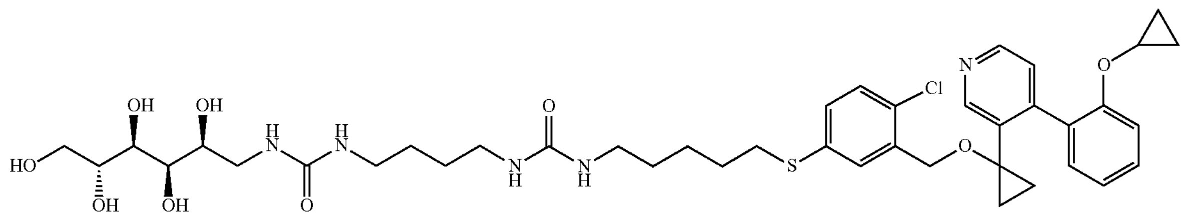 [SMILES: O=C(NCCCCCSc1ccc(Cl)c(COC2(c3cnccc3-c3ccccc3OC3CC3)CC2)c1)NCCCCNC(=O)NC[C@H](O)[C@@H](O)[C@H](O)[C@H](O)CO] | 830.4 |
| I-628 | Example 85 | 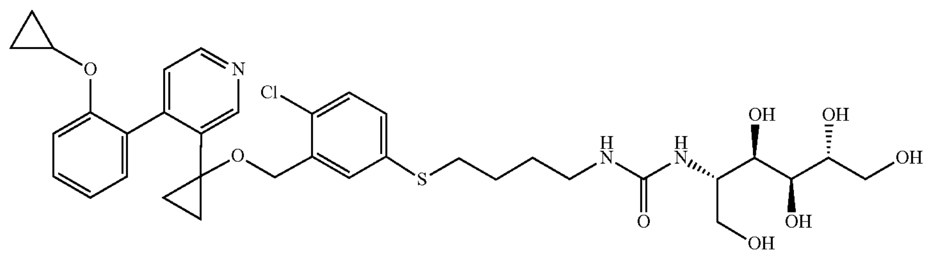 [SMILES: O=C(NCCCCSc1ccc(Cl)c(COC2(c3cnccc3-c3ccccc3OC3CC3)CC2)c1)N[C@@H](CO)[C@@H](O)[C@H](O)[C@H](O)CO] | 702 |
| I-629 | Example 85 | 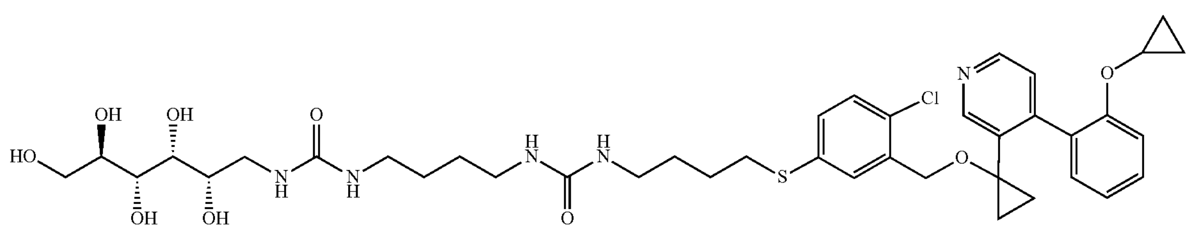 [SMILES: O=C(NCCCCNC(=O)NC[C@H](O)[C@@H](O)[C@H](O)[C@H](O)CO)NCCCCSc1ccc(Cl)c(COC2(c3cnccc3-c3ccccc3OC3CC3)CC2)c1] | 816.2 |

TABLE 15-continued

Compounds I-499 to I-695

| Cmpd No.: | Synthetic Method | Compound Structure | Obs. mass [M + H]+ |
|---|---|---|---|
| I-630 | Example 85 | 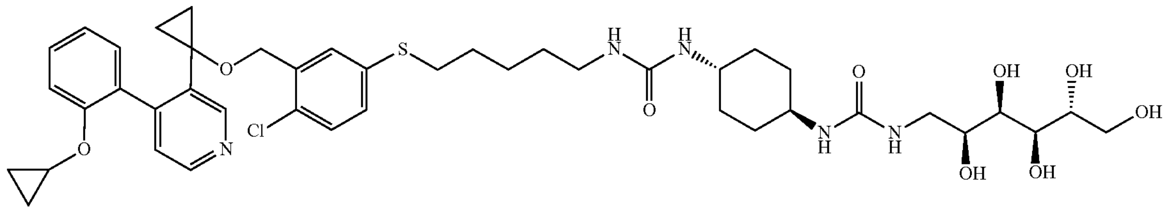 [SMILES: O=C(NCCCCCSc1ccc(Cl)c(COC2(c3cnccc3-c3ccccc3OC3CC3)CC2)c1)N[C@H]1CC[C@H](NC(=O)NC[C@H](O)[C@@H](O)[C@H](O)[C@H](O)CO)CC1] | 856.3 |
| I-631 | Example 85 | 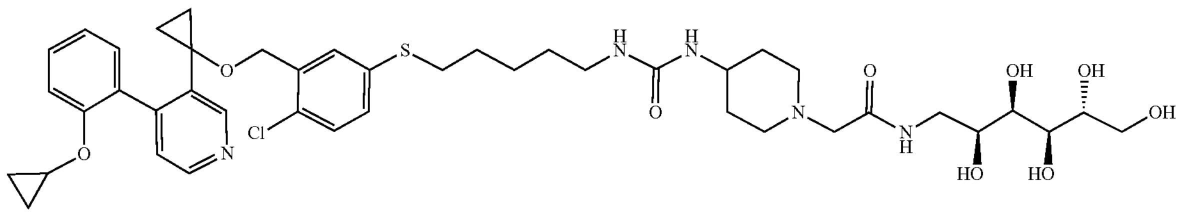 [SMILES: O=C(CN1CCC(NC(=O)NCCCCCSc2ccc(Cl)c(COC3(c4cnccc4-c4ccccc4OC4CC4)CC3)c2)CC1)NC[C@H](O)[C@@H](O)[C@H](O)[C@H](O)CO] | 856.4 |
| I-632 | Example 85 | 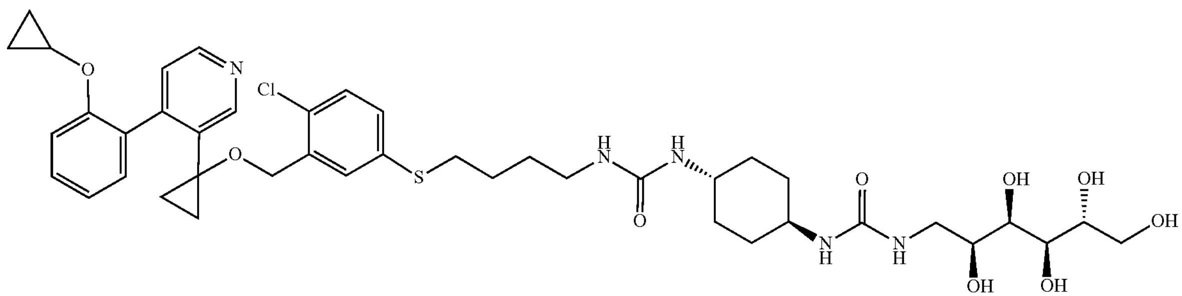 [SMILES: O=C(NCCCCSc1ccc(Cl)c(COC2(c3cnccc3-c3ccccc3OC3CC3)CC2)c1)N[C@H]1CC[C@H](NC(=O)NC[C@H](O)[C@@H](O)[C@H](O)[C@H](O)CO)CC1] | 842.4 |

TABLE 15-continued

Compounds I-499 to I-695

| Cmpd No.: | Synthetic Method | Compound Structure | Obs. mass [M + H]+ |
|---|---|---|---|
| I-633 | Example 85 | 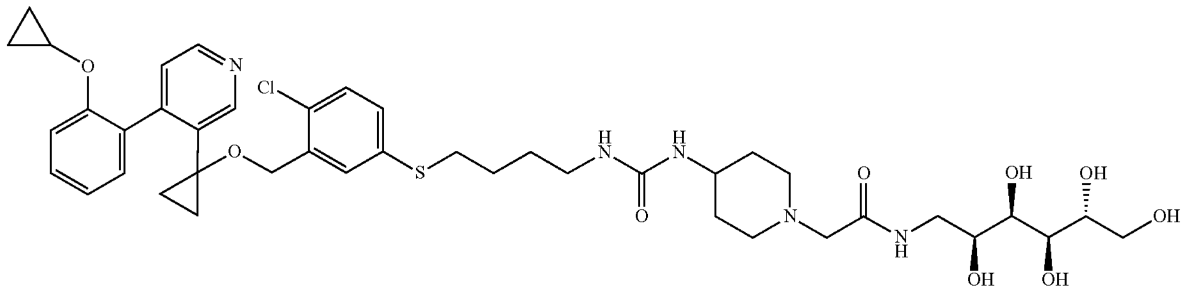 [SMILES: O=C(CN1CCC(NC(=O)NCCCCSc2ccc(Cl)c(COC3(c4cnccc4-c4ccccc4OC4CC4)CC3)c2)CC1)NC[C@H](O)[C@@H](O)[C@H](O)[C@H](O)CO] | 842.4 |
| I-634 | Example 85 | 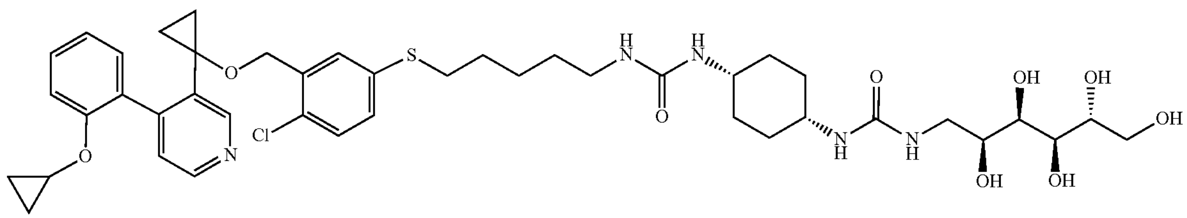 [SMILES: O=C(NCCCCCSc1ccc(Cl)c(COC2(c3cnccc3-c3ccccc3OC3CC3)CC2)c1)N[C@H]1CC[C@@H](NC(=O)NC[C@H](O)[C@@H](O)[C@H](O)[C@H](O)CO)CC1] | 856.4 |
| I-635 | Example 85 | 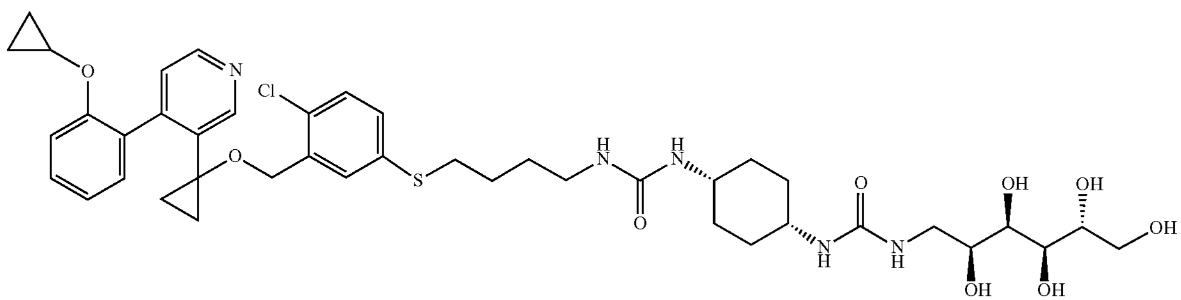 [SMILES: O=C(NCCCCSc1ccc(Cl)c(COC2(c3cnccc3-c3ccccc3OC3CC3)CC2)c1)N[C@H]1CC[C@@H](NC(=O)NC[C@H](O)[C@@H](O)[C@H](O)[C@H](O)CO)CC1] | 842.4 |

TABLE 15-continued

Compounds I-499 to I-695

| Cmpd No.: | Synthetic Method | Compound Structure | Obs. mass [M + H]+ |
|---|---|---|---|
| I-636 | Example 85 | 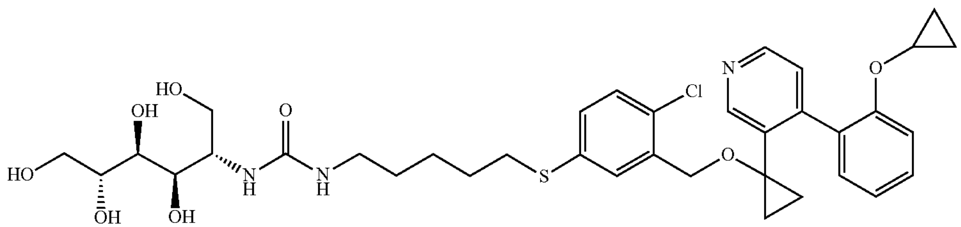 [SMILES: O=C(NCCCCCSc1ccc(Cl)c(COC2(c3cnccc3-c3ccccc3OC3CC3)CC2)c1)N[C@@H](CO)[C@@H](O)[C@H](O)[C@H](O)CO] | 716.3 |
| I-637 | Example 85 | 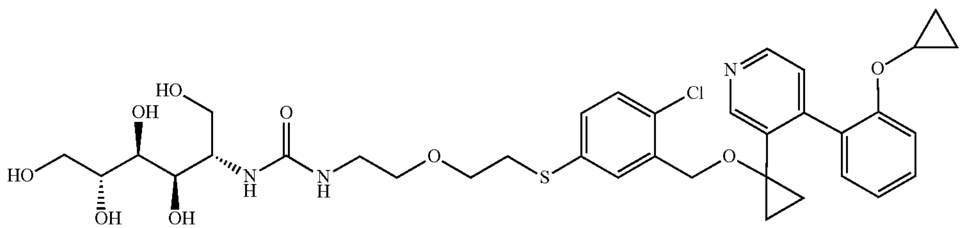 [SMILES: O=C(NCCOCCSc1ccc(Cl)c(COC2(c3cnccc3-c3ccccc3OC3CC3)CC2)c1)N[C@@H](CO)[C@@H](O)[C@H](O)[C@H](O)CO] | 718.4 |
| I-638 | Example 85 | 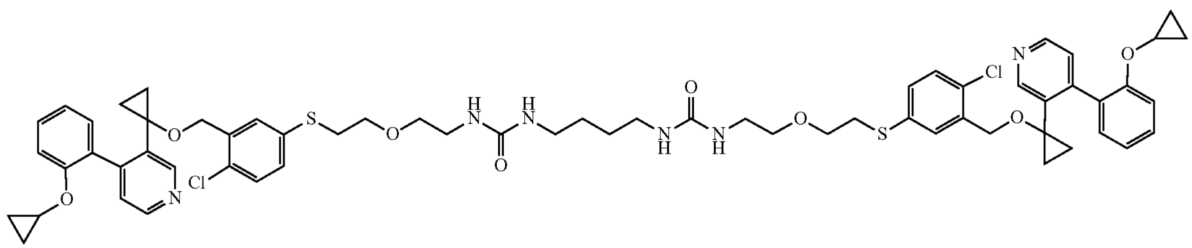 [SMILES: O=C(NCCCCNC(=O)NCCOCCSc1ccc(Cl)c(COC2(c3cnccc3-c3ccccc3OC3CC3)CC2)c1)NCCOCCSc1ccc(Cl)c(COC2(c3cnccc3-c3ccccc3OC3CC3)CC2)c1] | 1161 |
| I-639 | Example 88 | 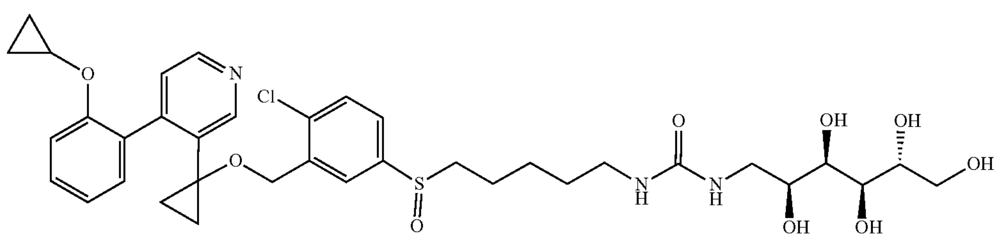 [SMILES: O=C(NCCCCCS(=O)c1ccc(Cl)c(COC2(c3cnccc3-c3ccccc3OC3CC3)CC2)c1)NC[C@H](O)[C@@H](O)[C@H](O)[C@H](O)CO] | 732.4 |

TABLE 15-continued

Compounds I-499 to I-695

| Cmpd No.: | Synthetic Method | Compound Structure | Obs. mass [M + H]+ |
|---|---|---|---|
| I-640 | Example 89 | 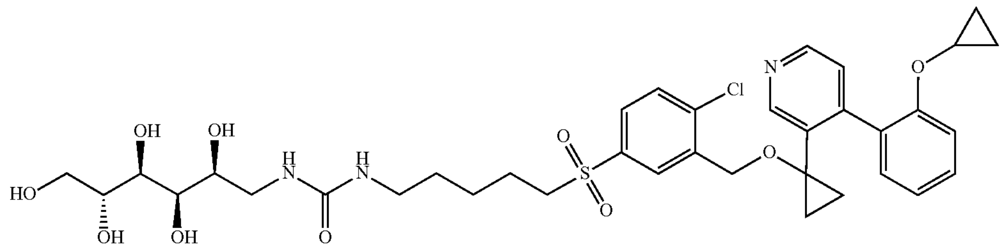 [SMILES: O=C(NCCCCCS(=O)(=O)c1ccc(Cl)c(COC2(c3cnccc3-c3ccccc3OC3CC3)CC2)c1)NC[C@H](O)[C@@H](O)[C@H](O)[C@H](O)CO] | 748.4 |
| I-641 | Example 89 | 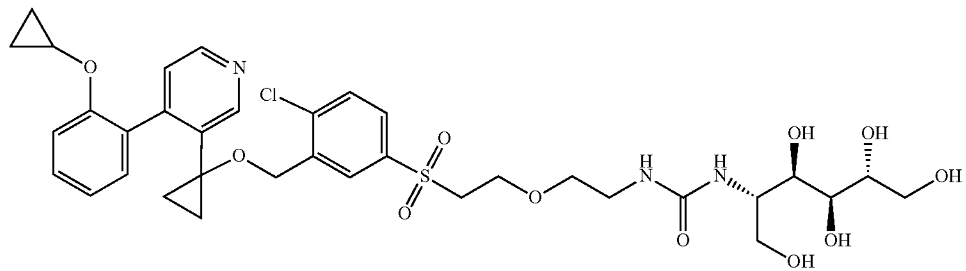 [SMILES: O=C(NCCOCCS(=O)(=O)c1ccc(Cl)c(COC2(c3cnccc3-c3ccccc3OC3CC3)CC2)c1)N[C@@H](CO)[C@@H](O)[C@H](O)[C@H](O)CO] | 750.4 |
| I-642 | Example 88 | 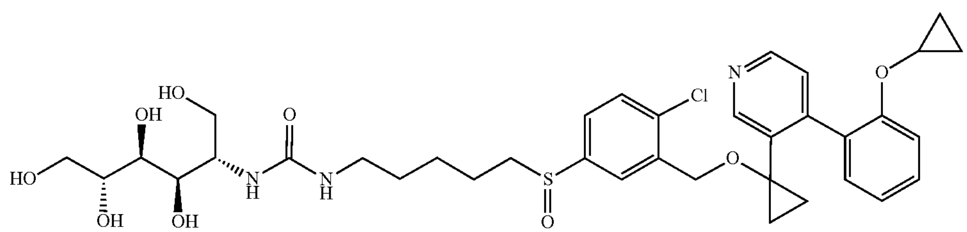 | 732.2 |

TABLE 15-continued

Compounds I-499 to I-695

| Cmpd No.: | Synthetic Method | Compound Structure | Obs. mass [M + H]+ |
|---|---|---|---|
| I-643 | Example 89 | 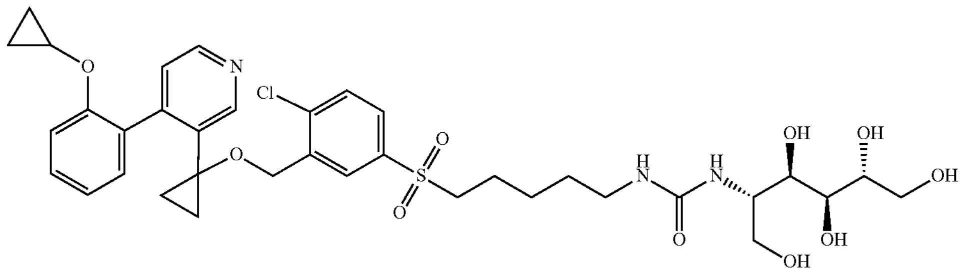 [SMILES: O=C(NCCCCCS(=O)(=O)c1ccc(Cl)c(COC2(c3cnccc3-c3ccccc3OC3CC3)CC2)c1)N[C@@H](CO)[C@@H](O)[C@H](O)[C@H](O)CO] | 748.2 |
| I-644 | Example 88 | 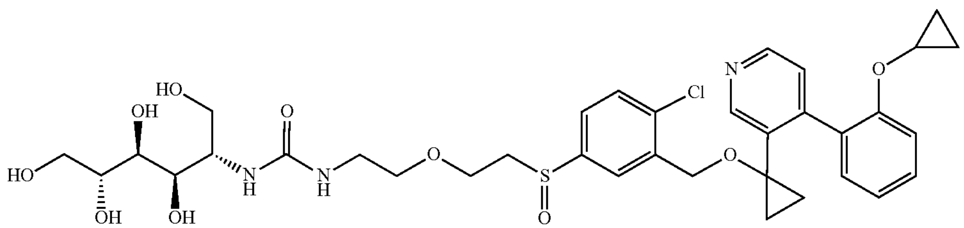 [SMILES: O=C(NCCOCCS(=O)c1ccc(Cl)c(COC2(c3cnccc3-c3ccccc3OC3CC3)CC2)c1)N[C@@H](CO)[C@@H](O)[C@H](O)[C@H](O)CO] | 734.4 |
| I-645 | Example 92 | 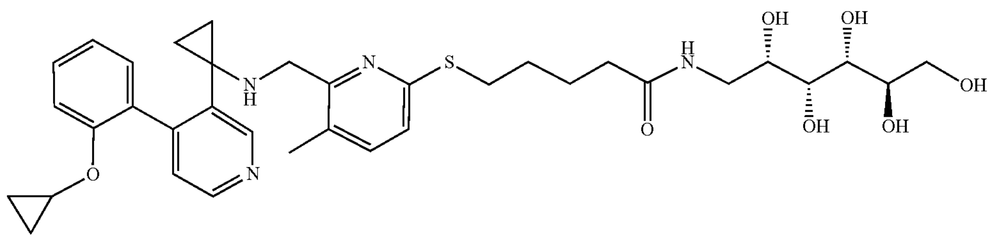 [SMILES: Cc1ccc(SCCCCC(=O)NC[C@H](O)[C@@H](O)[C@H](O)[C@H](O)CO)nc1CNC1(c2cnccc2-c2ccccc2OC2CC2)CC1] | 667.2 |
| I-646 | Example 89 | 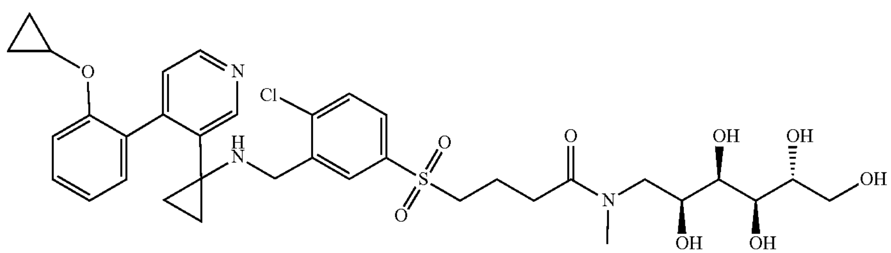 [SMILES: CN(C[C@H](O)[C@@H](O)[C@H](O)[C@H](O)CO)C(=O)CCCS(=O)(=O)c1ccc(Cl)c(CNC2(c3cnccc3-c3ccccc3OC3CC3)CC2)c1] | 718 |

TABLE 15-continued

Compounds I-499 to I-695

| Cmpd No.: | Synthetic Method | Compound Structure | Obs. mass [M + H]+ |
|---|---|---|---|
| I-647 | Example 88 | 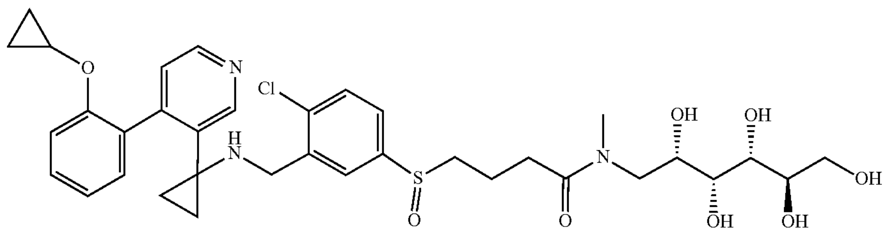 [SMILES: CN(C[C@H](O)[C@@H](O)[C@H](O)[C@H](O)CO)C(=O)CCCS(=O)c1ccc(Cl)c(CNC2(c3cnccc3-c3ccccc3OC3CC3)CC2)c1] | 702 |
| I-648 | Example 95 | 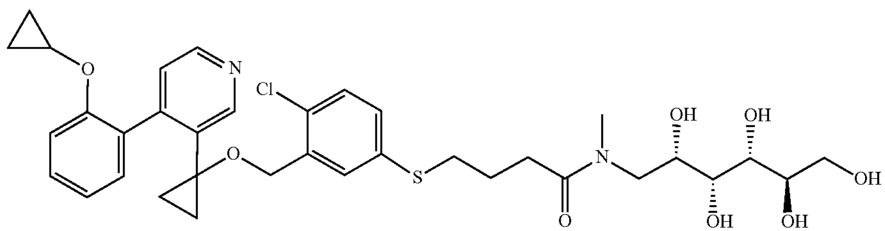 [SMILES: CN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 687.2 |
| I-649 | Example 95 | 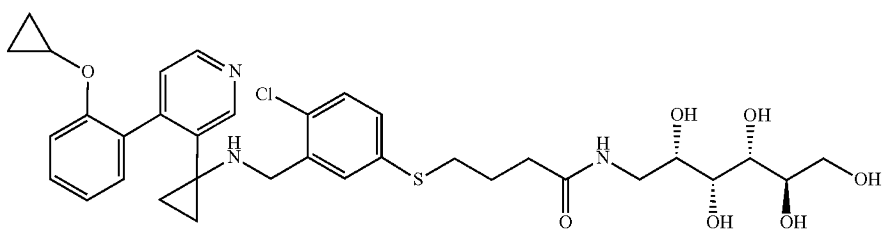 [SMILES: O=C(CCCSc1ccc(Cl)c(CNC2(c3cnccc3-c3ccccc3OC3CC3)CC2)c1)NC[C@H](O)[C@@H](O)[C@H](O)[C@H](O)CO] | 672.2 |
| I-650 | Example 95 | 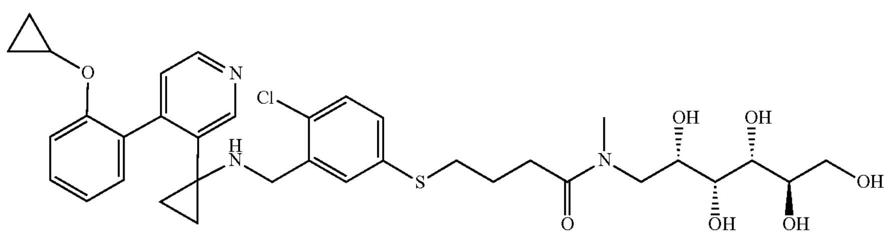 [SMILES: CN(C[C@H](O)[C@@H](O)[C@H](O)[C@H](O)CO)C(=O)CCCSc1ccc(Cl)c(CNC2(c3cnccc3-c3ccccc3OC3CC3)CC2)c1] | 686.3 |

TABLE 15-continued

Compounds I-499 to I-695

| Cmpd No.: | Synthetic Method | Compound Structure | Obs. mass [M + H]+ |
|---|---|---|---|
| I-651 | Example 95 | 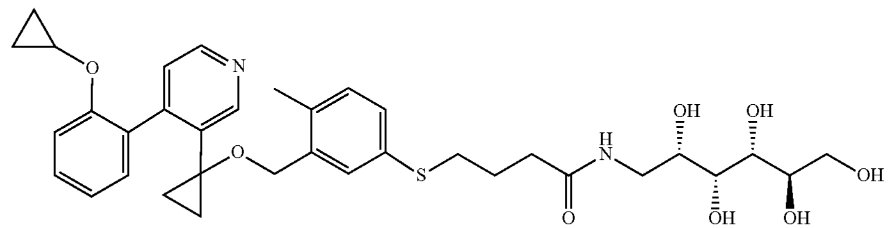 [SMILES: Cc1ccc(SCCCC(=O)NC[C@H](O)[C@@H](O)[C@H](O)[C@H](O)CO)cc1COC1(c2cnccc2-c2ccccc2OC2CC2)CC1] | 653.2 |
| I-652 | Example 95 | 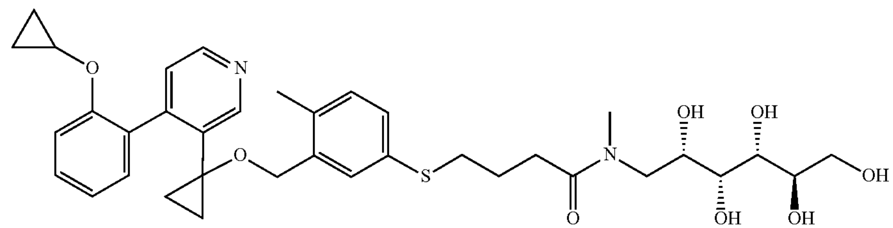 [SMILES: Cc1ccc(SCCCC(=O)N(C)C[C@H](O)[C@@H](O)[C@H](O)[C@H](O)CO)cc1COC1(c2cnccc2-c2ccccc2OC2CC2)CC1] | 667.2 |
| I-653 | Example 92 | 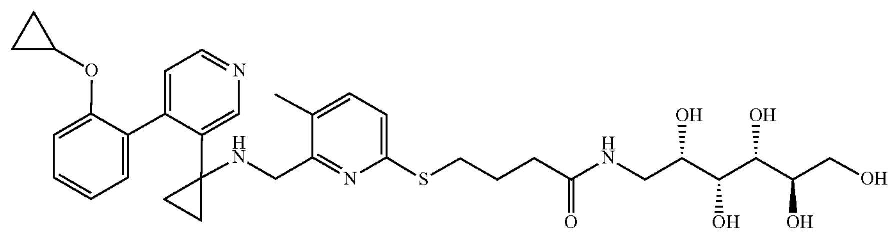 [SMILES: Cc1ccc(SCCCC(=O)NC[C@H](O)[C@@H](O)[C@H](O)[C@H](O)CO)nc1CNC1(c2cnccc2-c2ccccc2OC2CC2)CC1] | 653.2 |
| I-654 | Example 92 | 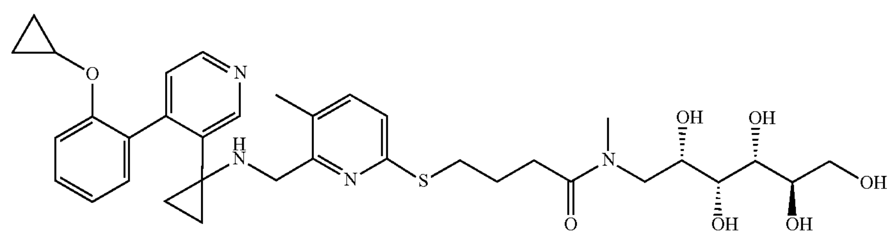 [SMILES: Cc1ccc(SCCCC(=O)N(C)C[C@H](O)[C@@H](O)[C@H](O)[C@H](O)CO)nc1CNC1(c2cnccc2-c2ccccc2OC2CC2)CC1] | 667.4 |

TABLE 15-continued

Compounds I-499 to I-695

| Cmpd No. | Synthetic Method | Compound Structure | Obs. mass [M + H]+ |
|---|---|---|---|
| I-655 | Example 92 | | 654.2 |
| I-656 | Example 92 | 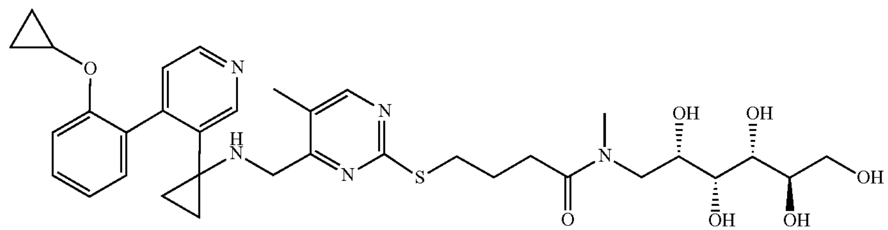 [SMILES: Cc1cnc(SCCCC(=O)N(C)C[C@H](O)[C@@H](O)[C@H](O)[C@H](O)CO)nc1CNC1(c2cnccc2-c2ccccc2OC2CC2)CC1] | 668.2 |
| I-657 | Example 92 | 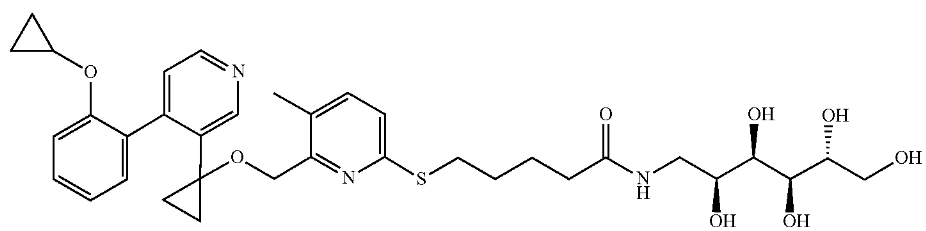 [SMILES: Cc1ccc(SCCCCC(=O)NC[C@H](O)[C@@H](O)[C@H](O)[C@H](O)CO)nc1COC1(c2cnccc2-c2ccccc2OC2CC2)CC1] | 668.3 |
| I-658 | Example 92 | 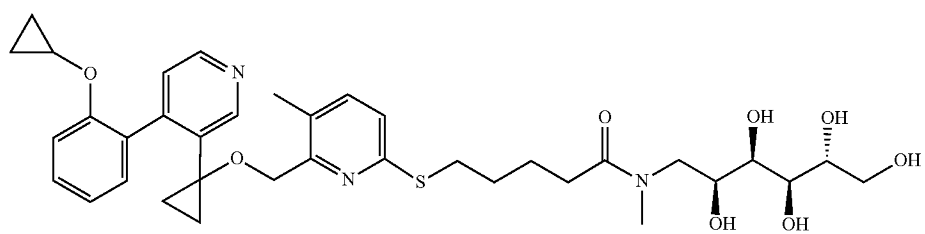 [SMILES: Cc1ccc(SCCCCC(=O)N(C)C[C@H](O)[C@@H](O)[C@H](O)[C@H](O)CO)nc1COC1(c2cnccc2-c2ccccc2OC2CC2)CC1] | 682.2 |

TABLE 15-continued

Compounds I-499 to I-695

| Cmpd No.: | Synthetic Method | Compound Structure | Obs. mass [M + H]+ |
|---|---|---|---|
| I-659 | Example 95 | 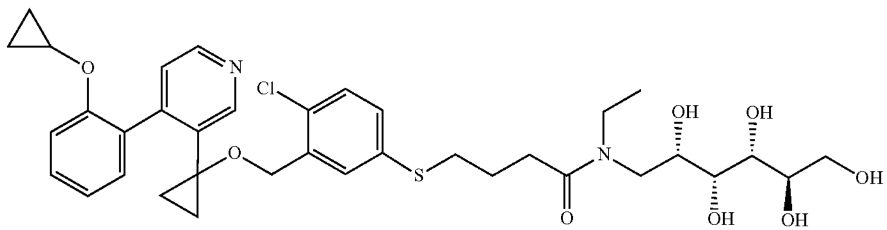 [SMILES: CCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 701.3 |
| I-660 | Example 95 | 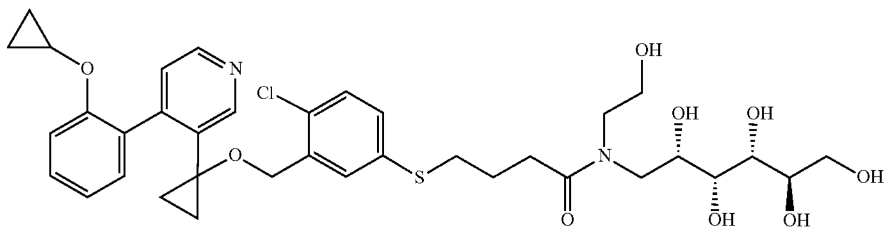 [SMILES: O=C(CCCSc1ccc(Cl)c(COC2(c3cnccc3-c3ccccc3OC3CC3)CC2)c1)N(CCO)C[C@H](O)[C@@H](O)[C@H](O)[C@H](O)CO] | 717.2 |
| I-661 | Example 95 | 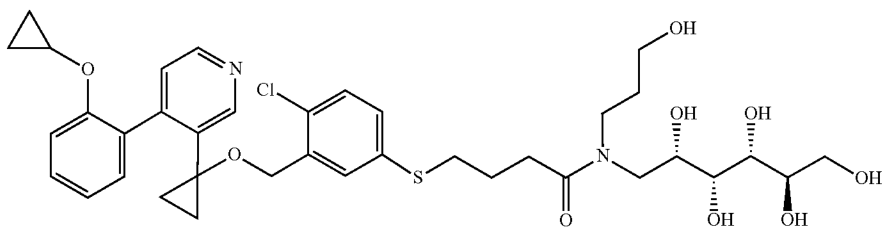 [SMILES: O=C(CCCSc1ccc(Cl)c(COC2(c3cnccc3-c3ccccc3OC3CC3)CC2)c1)N(CCCO)C[C@H](O)[C@@H](O)[C@H](O)[C@H](O)CO] | 731.5 |
| I-662 | Example 95 | 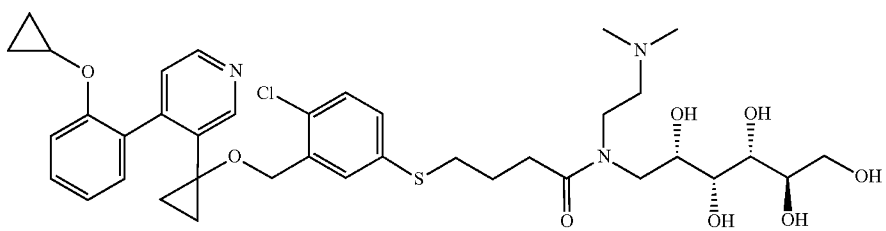 [SMILES: CN(C)CCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 744.5 |

TABLE 15-continued

Compounds I-499 to I-695

| Cmpd No.: | Synthetic Method | Compound Structure | Obs. mass [M + H]+ |
|---|---|---|---|
| I-663 | Example 95 | 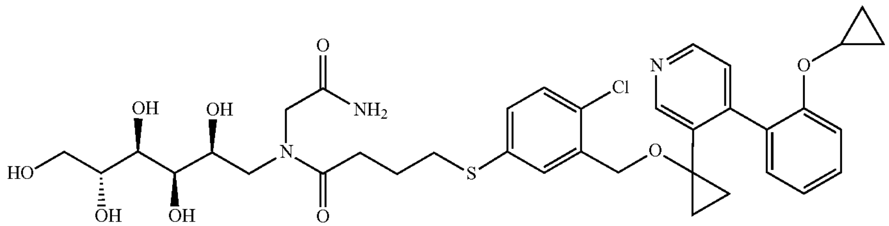 [SMILES: NC(=O)CN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 730.5 |
| I-664 | Example 95 | 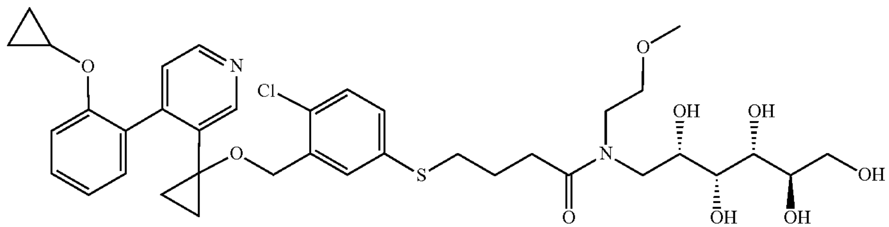 | 731.3 |
| I-665 | Example 95 | 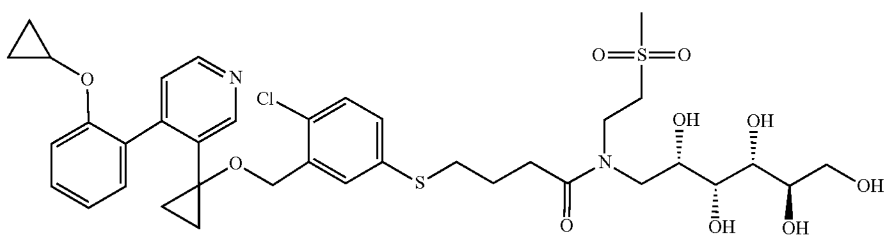 [SMILES: CS(=O)(=O)CCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 779.2 |
| I-666 | Example 95 | 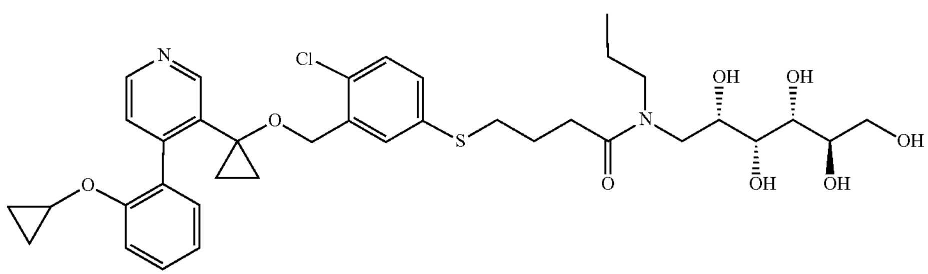 [SMILES: CCCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 715.3 |

TABLE 15-continued

Compounds I-499 to I-695

| Cmpd No.: | Synthetic Method | Compound Structure | Obs. mass [M + H]+ |
|---|---|---|---|
| I-667 | Example 95 | 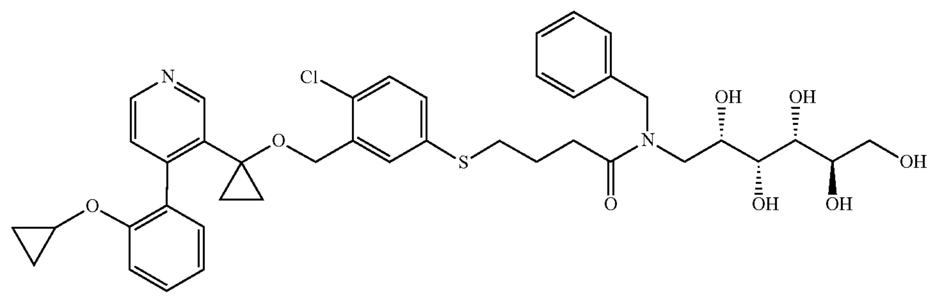 [SMILES: O=C(CCCSc1ccc(Cl)c(COC2(c3cnccc3-c3ccccc3OC3CC3)CC2)c1)N(Cc1ccccc1)C[C@H](O)[C@@H](O)[C@H](O)[C@H](O)CO] | 763.2 |
| I-668 | Example 95 | 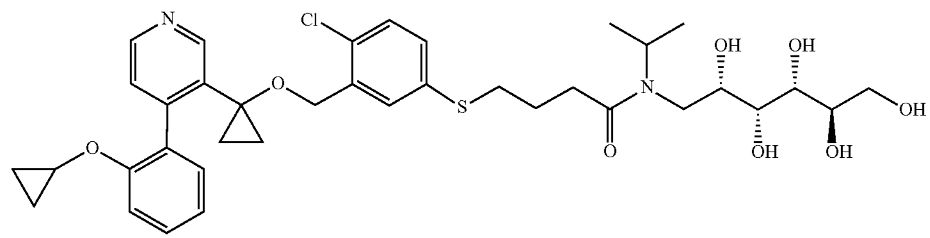 [SMILES: CC(C)N(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 715.2 |
| I-669 | Example 95 | 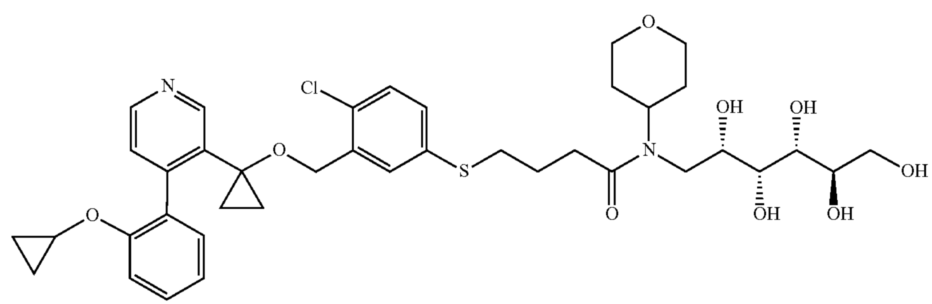 [SMILES: O=C(CCCSc1ccc(Cl)c(COC2(c3cnccc3-c3ccccc3OC3CC3)CC2)c1)N(C[C@H](O)[C@@H](O)[C@H](O)[C@H](O)CO)C1CCOCC1] | 757.3 |

TABLE 15-continued
Compounds I-499 to I-695
| Cmpd No.: | Synthetic Method | Compound Structure | Obs. mass [M + H]+ |
|---|---|---|---|
| I-670 | Example 95 | 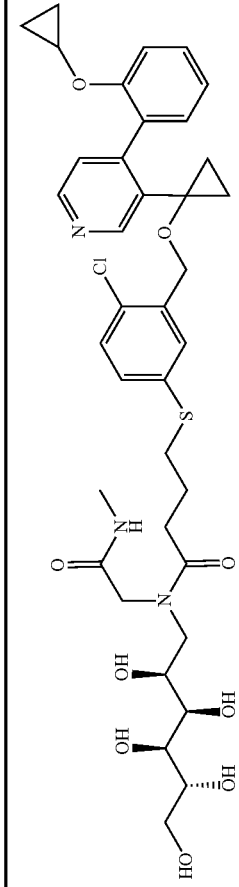 | 744.2 |
| I-671 | Example 95 | 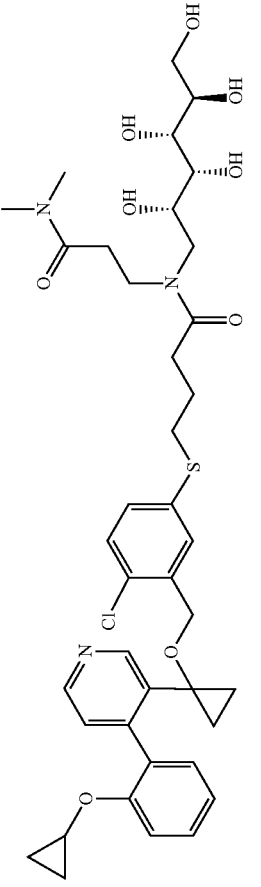 | 772.2 |
| I-672 | Example 95 | 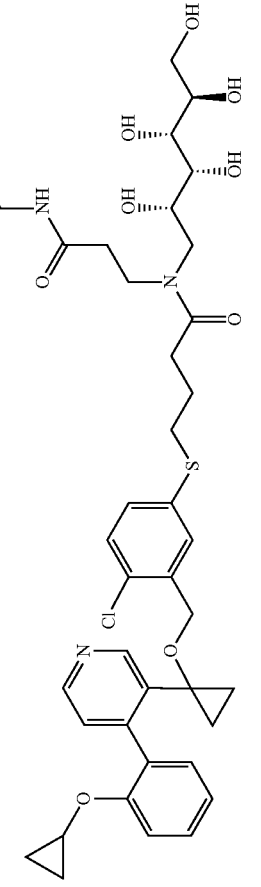 | 772.6 |

TABLE 15-continued

Compounds I-499 to I-695

| Cmpd No.: | Synthetic Method | Compound Structure | Obs. mass [M + H]+ |
|---|---|---|---|
| I-673 | Example 95 | 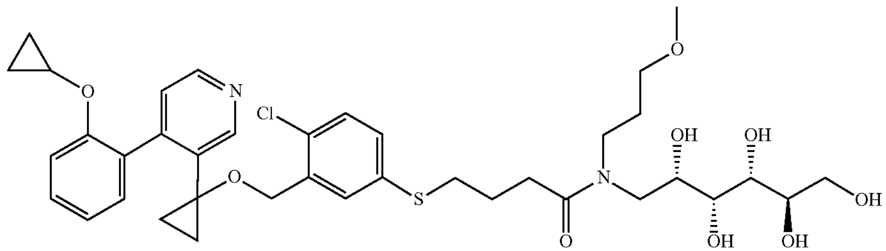 [SMILES: COCCCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 745.2 |
| I-674 | Example 95 | 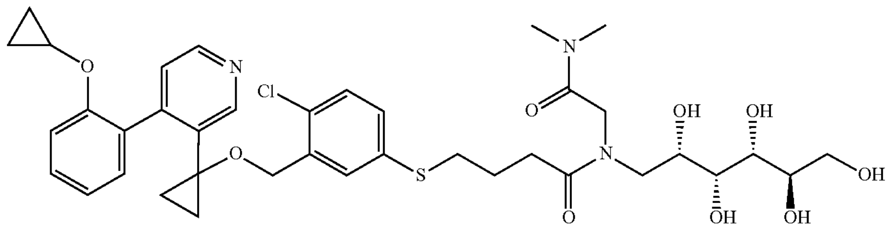 [SMILES: CN(C)C(=O)CN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 758.2 |
| I-675 | Example 95 | 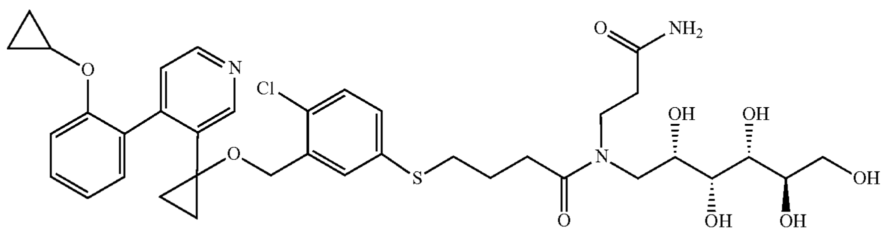 [SMILES: NC(=O)CCN(C[C@H](O)[C@@H](O)[C@H](O)[C@H](O)CO)C(=O)CCCSc1ccc(Cl)c(COC2(c3cnccc3-c3ccccc3OC3CC3)CC2)c1] | 744.4 |
| I-676 | Example 95 | 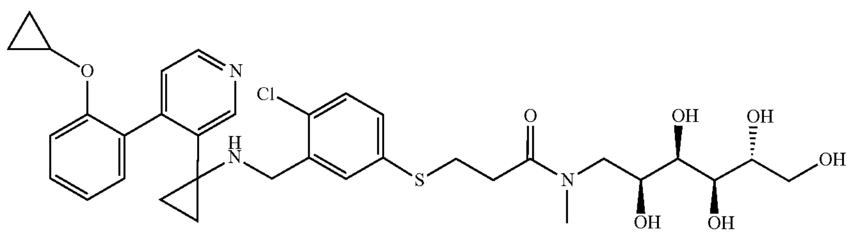 [SMILES: CN(C[C@H](O)[C@@H](O)[C@H](O)[C@H](O)CO)C(=O)CCSc1ccc(Cl)c(CNC2(c3cnccc3-c3ccccc3OC3CC3)CC2)c1] | 672.2 |

TABLE 15-continued
Compounds I-499 to I-695
| Cmpd No.: | Synthetic Method | Compound Structure | Obs. mass [M + H]+ |
|---|---|---|---|
| I-677 | Example 95 | 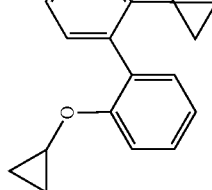 | 673.2 |
| I-678 | Example 95 | 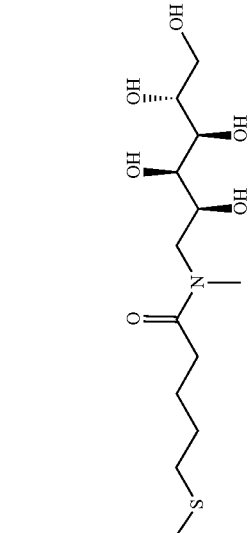 | 700.3 |
| I-679 | Example 95 | 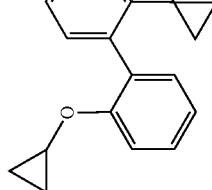 | 713.3 |
| I-680 | Example 95 | 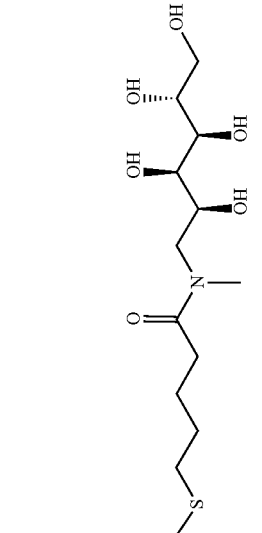 | 734.2 |

TABLE 15-continued

Compounds I-499 to I-695

| Cmpd No.: | Synthetic Method | Compound Structure | Obs. mass [M + H]+ |
|---|---|---|---|
| I-681 | Example 95 | 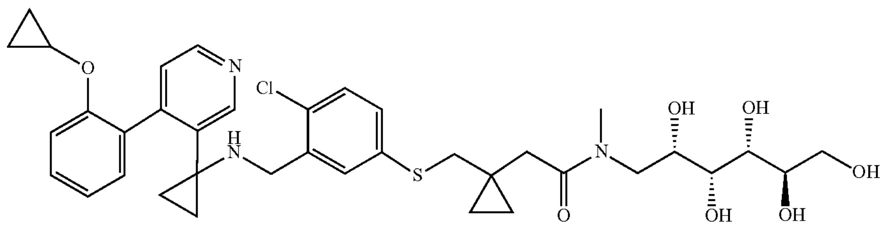 [SMILES: CN(C[C@H](O)[C@@H](O)[C@H](O)[C@H](O)CO)C(=O)CC1(CSc2ccc(Cl)c(CNC3(c4cnccc4-c4ccccc4OC4CC4)CC3)c2)CC1] | 712.2 |
| I-682 | Example 95 | 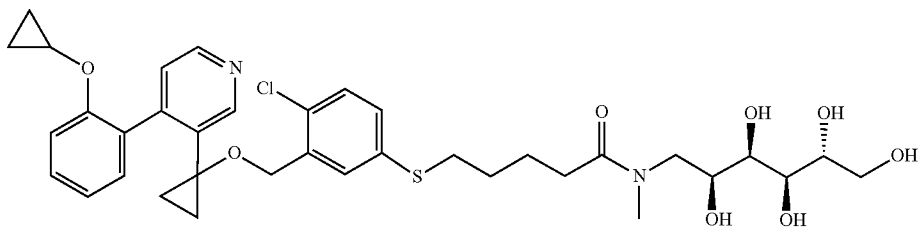 [SMILES: CN(C[C@H](O)[C@@H](O)[C@H](O)[C@H](O)CO)C(=O)CCCCSc1ccc(Cl)c(COC2(c3cnccc3-c3ccccc3OC3CC3)CC2)c1] | 701.4 |
| I-683 | Example 95 | 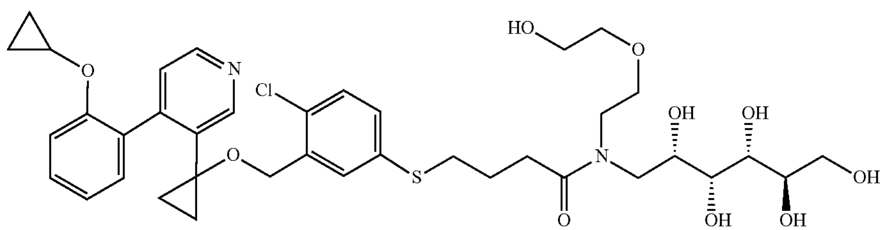 [SMILES: O=C(CCCSc1ccc(Cl)c(COC2(c3cnccc3-c3ccccc3OC3CC3)CC2)c1)N(CCOCCO)C[C@H](O)[C@@H](O)[C@H](O)[C@H](O)CO] | 761.1 |
| I-684 | Example 95 | 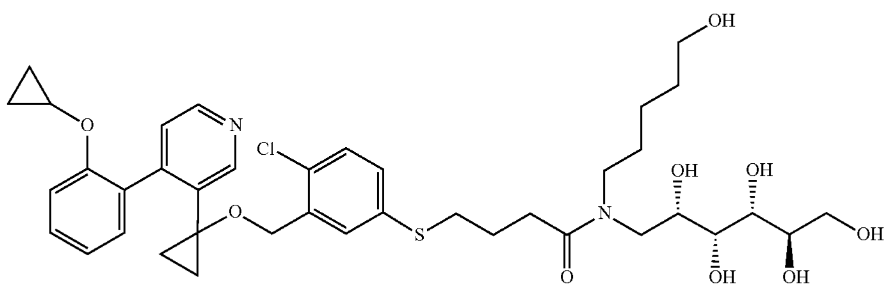 [SMILES: O=C(CCCSc1ccc(Cl)c(COC2(c3cnccc3-c3ccccc3OC3CC3)CC2)c1)N(CCCCCO)C[C@H](O)[C@@H](O)[C@H](O)[C@H](O)CO] | 759.3 |

TABLE 15-continued

Compounds I-499 to I-695

| Cmpd No.: | Synthetic Method | Compound Structure | Obs. mass [M + H]+ |
|---|---|---|---|
| I-685 | Example 95 | 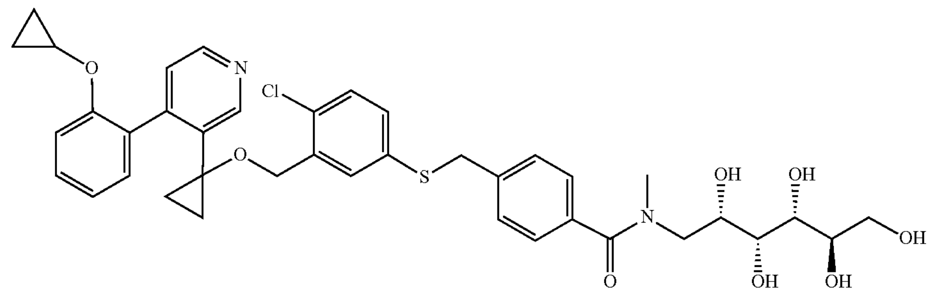 [SMILES: CN(C[C@H](O)[C@@H](O)[C@H](O)[C@H](O)CO)C(=O)c1ccc(CSc2ccc(Cl)c(COC3(c4cnccc4-c4ccccc4OC4CC4)CC3)c2)cc1] | 735.2 |
| I-686 | Example 95 | 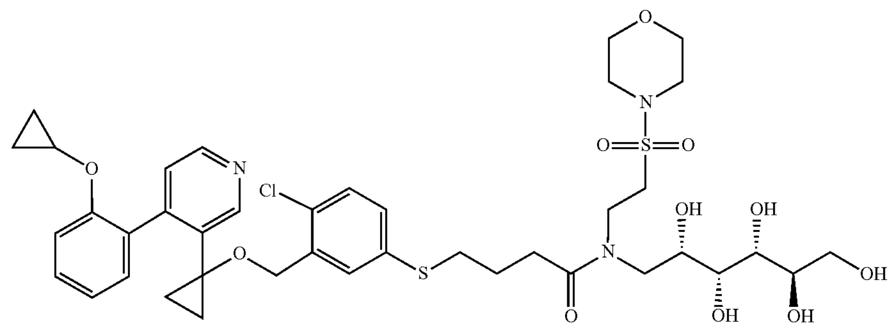 [SMILES: O=C(CCCSc1ccc(Cl)c(COC2(c3cnccc3-c3ccccc3OC3CC3)CC2)c1)N(CCS(=O)(=O)N1CCOCC1)C[C@H](O)[C@@H](O)[C@H](O)[C@H](O)CO] | 850.2 |
| I-687 | Example 95 | 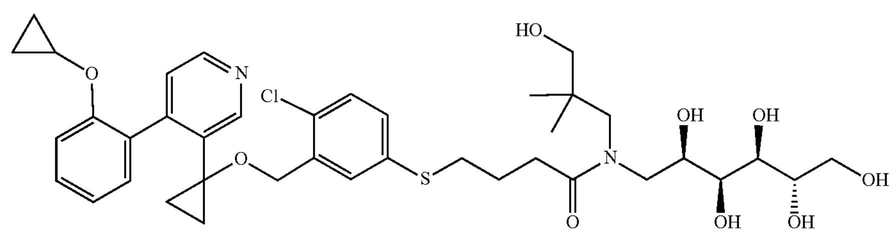 [SMILES: CC(C)(CO)CN(C[C@@H](O)[C@H](O)[C@@H](O)[C@@H](O)CO)C(=O)CCCSc1ccc(Cl)c(COC2(c3cnccc3-c3ccccc3OC3CC3)CC2)c1] | 759.2 |

TABLE 15-continued

Compounds I-499 to I-695

| Cmpd No.: | Synthetic Method | Compound Structure | Obs. mass [M + H]+ |
|---|---|---|---|
| I-688 | Example 95 | 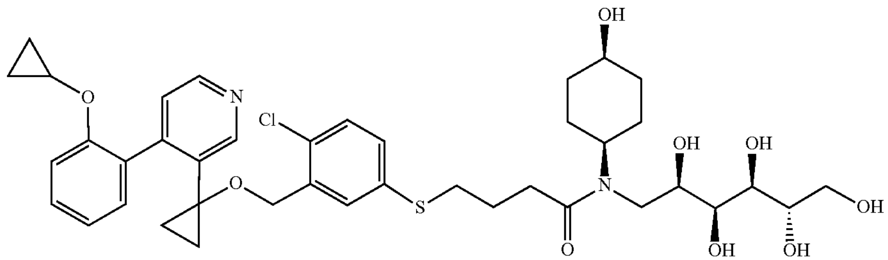 [SMILES: O=C(CCCSc1ccc(Cl)c(COC2(c3cnccc3-c3ccccc3OC3CC3)CC2)c1)N(C[C@@H](O)[C@H](O)[C@@H](O)[C@@H](O)CO)[C@H]1CC[C@@H](O)CC1] | 771.2 |
| I-689 | Example 95 | 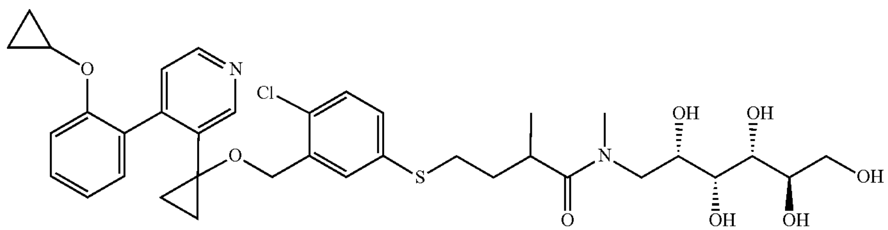 | 701.2 |
| I-690 | Example 95 | 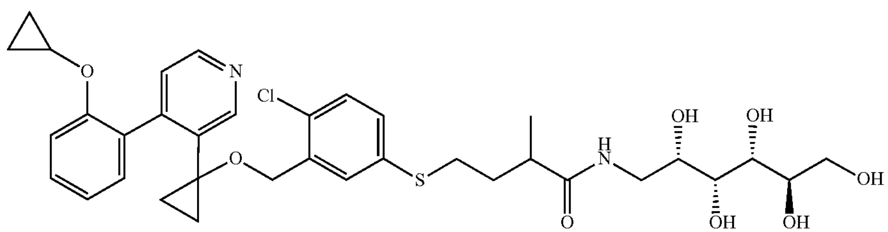 [SMILES: CC(CCSc1ccc(Cl)c(COC2(c3cnccc3-c3ccccc3OC3CC3)CC2)c1)C(=O)NC[C@H](O)[C@@H](O)[C@H](O)[C@H](O)CO] | 687.2 |
| I-691 | Example 95 | 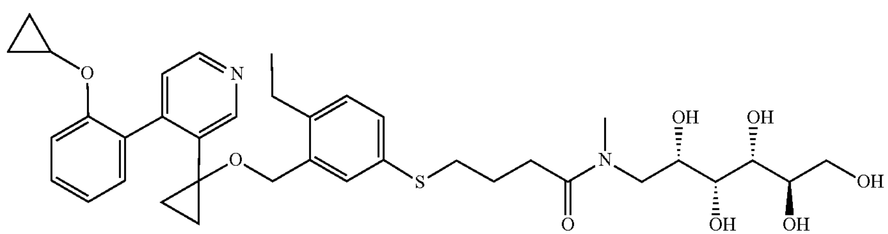 [SMILES: CCc1ccc(SCCCC(=O)N(C)C[C@H](O)[C@@H](O)[C@H](O)[C@H](O)CO)cc1COC1(c2cnccc2-c2ccccc2OC2CC2)CC1] | 681.4 |

TABLE 15-continued
Compounds I-499 to I-695
| Cmpd No.: | Synthetic Method | Compound Structure | Obs. mass [M + H]⁺ |
|---|---|---|---|
| I-692 | Example 95 | 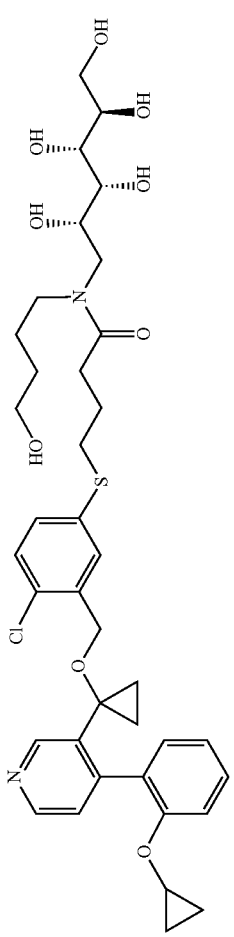 | 745.2 |
| I-693 | Example 95 | 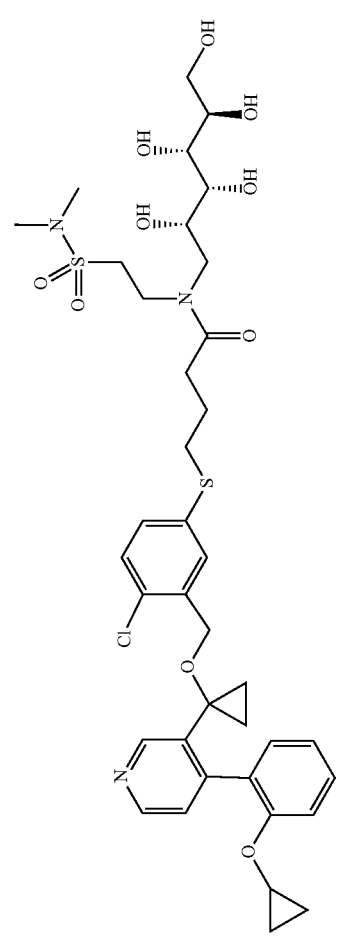 | 808.2 |
| I-694 | Example 95 | 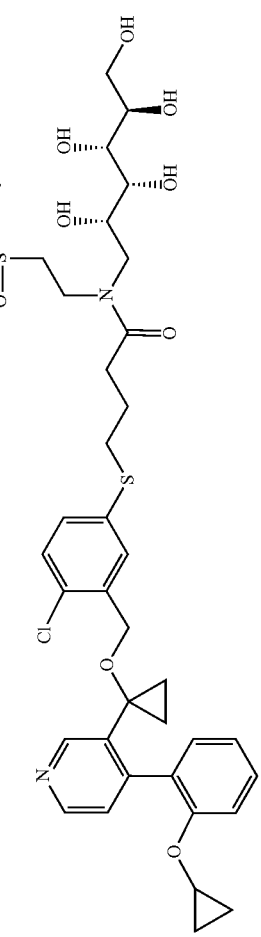 | 794.1 |

TABLE 15-continued
Compounds I-499 to I-695
| Cmpd No.: | Synthetic Method | Compound Structure | Obs. mass [M + H]+ |
|---|---|---|---|
| I-695 | Example 86 | 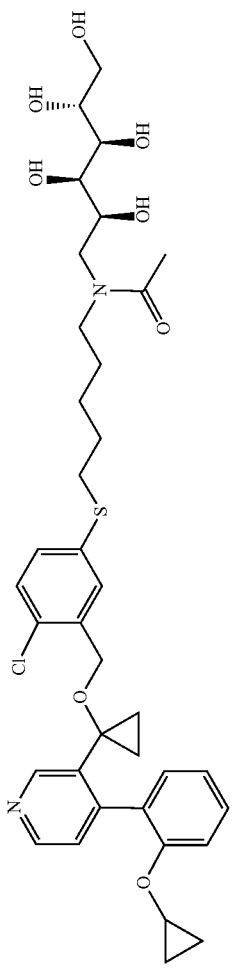 | 715.4 |

Example 96: 1-[4-(N-ethyl[4-chloro-3-[([1-[4-(2-cyclopropoxyphenyl)pyridin-3-yl]cyclopropyl]amino)methyl]benzene]sulfonamido)butyl]-3-[(2S,3R,4S,5R)-1,3,4,5,6-pentahydroxyhexan-2-yl]urea (I-696)

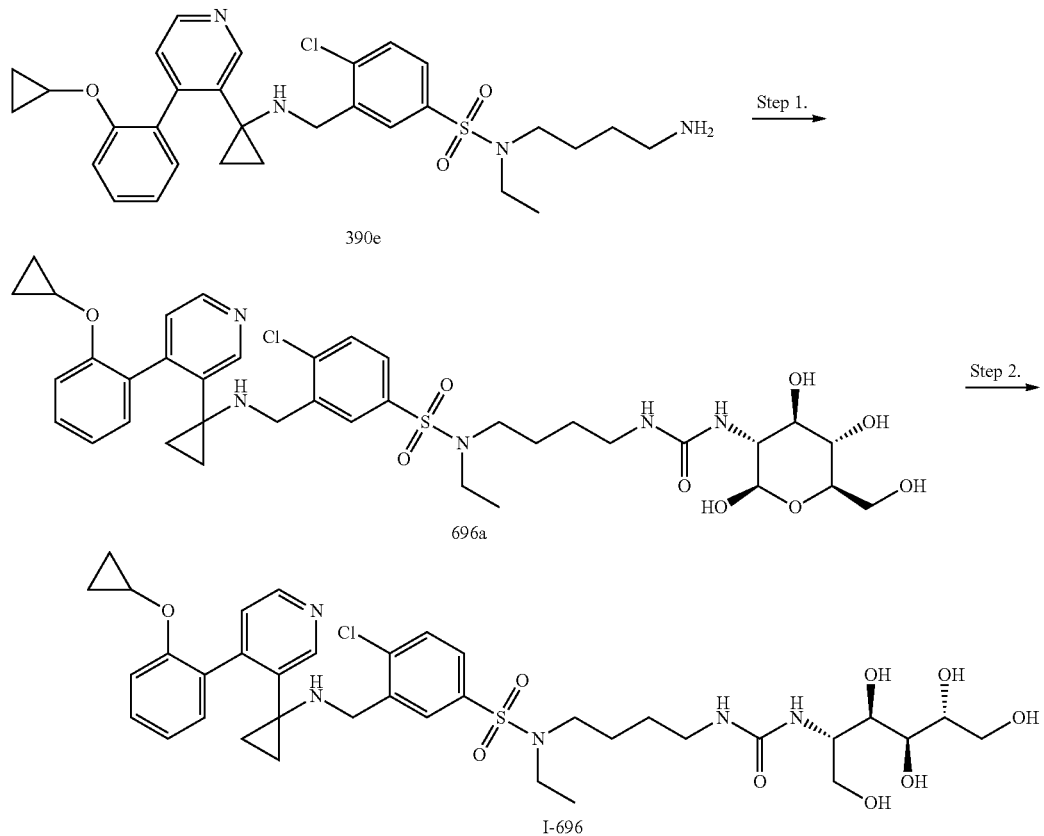

Step 1. 3-[4-(N-ethyl[4-chloro-3-[([1-[4-(2-cyclopropoxyphenyl)pyridin-3-yl]cyclopropyl]amino)methyl]benzene]sulfonamido)butyl]-1-[(2R,3R,4R,5S,6R)-2,4,5-trihydroxy-6-(hydroxymethyl)oxan-3-yl]urea (Intermediate 696a)

A 100-mL round-bottom flask was charged with N-(4-aminobutyl)-4-chloro-3-[([1-[4-(2-cyclopropoxyphenyl)pyridin-3-yl]cyclopropyl]amino)methyl]-N-ethylbenzene-1-sulfonamide (140 mg, 0.25 mmol, 1.00 equiv), N,N-dimethylformamide (4 mL), DSC (76 mg, 1.20 equiv), DIEA (148 mg, 1.15 mmol, 5.00 equiv). The resulting solution was stirred for 1.5 h at room temperature. To this was added (2R,3R,4R,5S,6R)-3-amino-6-(hydroxymethyl)oxane-2,4,5-triol hydrochloride (159 mg, 0.74 mmol, 3.00 equiv), The resulting solution was stirred overnight at room temperature. The reaction was then quenched by the addition of 10 mL of water. The resulting solution was extracted with 6×10 mL of ethyl acetate and the organic layers combined and dried over anhydrous sodium sulfate and concentrated under vacuum. This resulted in 150 mg (79%) of 3-[4-(N-ethyl[4-chloro-3-[([1-[4-(2-cyclopropoxyphenyl)pyridin-3-yl]cyclopropyl]amino)methyl]benzene]sulfonamido)butyl]-1-[(2R,3R,4R,5S,6R)-2,4,5-trihydroxy-6-(hydroxymethyl)oxan-3-yl]urea (696a) as light yellow oil.

Step 2. 1-[4-(N-ethyl[4-chloro-3-[([1-[4-(2-cyclopropoxyphenyl)pyridin-3-yl]cyclopropyl]amino)methyl]benzene]sulfonamido)butyl]-3-[(2S,3R,4S,5R)-1,3,4,5,6-pentahydroxyhexan-2-yl]urea (I-696b)

A 50-mL round-bottom flask was charged with 3-[4-(N-ethyl[4-chloro-3-[([1-[4-(2-cyclopropoxyphenyl)pyridin-3-yl]cyclopropyl]amino)methyl]benzene] sulfonamido)butyl]-1-[(2R,3R,4R,5S,6R)-2,4,5-trihydroxy-6-(hydroxymethyl)oxan-3-yl]urea (190 mg, 0.25 mmol, 1.00 equiv), methanol (5 mL), NaBH$_4$ (18 mg, 0.48 mmol, 2.00 equiv). The resulting solution was stirred for 1 h at room temperature. The reaction was then quenched by the addition of 0.5 mL of water. The solids were filtered out. The crude product was purified by Preparative HPLC with the following conditions: Column, Gemini-NX C18 AXAI Packed, 21.2×150 mm 5 µm; mobile phase, 10 mM aqueous NH$_4$HCO$_3$ and MeCN (36.0% MeCN up to 40.0% in 12 min); Detector, UV 220 nm. This resulted in 25.7 mg (13%) of 1-[4-(N-ethyl[4-chloro-3-[([1-[4-(2-cyclopropoxyphenyl)pyridin-3-yl]cyclopropyl]amino)methyl]benzene]sulfonamido)butyl]-3-[(2S,3R,4S,5R)-1,3,4,5,6-pentahydroxyhexan-2-yl]urea (I-696b) as a white solid: (ES, m/z):[M+1]= 776. $^1$H NMR (400 MHz, Methanol-d$_4$) δ 0.40 (s, 2H), 0.64 (s, 2H), 0.82 (s, 2H), 0.92 (s, 2H), 1.08 (t, J=7.1 Hz, 3H), 1.48 (d, J=7.9 Hz, 2H), 1.57 (d, J=7.7 Hz, 2H), 3.08-3.23 (m, 7H), 3.48 (p, J=1.6 Hz, 1H), 3.53-3.72 (m, 6H), 3.72-3.80 (m, 3H), 3.80-3.90 (m, 1H), 3.96 (dd, J=4.9, 2.8 Hz, 1H), 7.11 (ddd, J=8.0, 5.2, 3.2 Hz, 1H), 7.15-7.20 (m, 1H), 7.22-7.27 (m, 1H), 7.43-7.48 (m, 2H), 7.54 (d, J=8.3 Hz, 1H), 7.65 (dd, J=8.3, 2.4 Hz, 1H), 7.69 (d, J=2.3 Hz, 1H), 8.46 (d, J=5.1 Hz, 1H), 8.58 (d, J=0.7 Hz, 1H).

Example 97: 3-[1-[(2-chloro-5-[methyl[4-([[(3R,4S,5R)-1,3,4,5,6-pentahydroxyhexan-2-yl]carbamoyl]amino)butyl]sulfamoyl]phenyl)methoxy]cyclopropyl]-4-(2-cyclopropoxy-phenyl)pyridin-1-ium-1-olate (I-697)

(0.05% NH$_3$/H$_2$O) and MeCN (25.0% MeCN up to 36.0% in 10 min); Detector, UV 254 nm. This resulted in 48.5 mg (43%) of 3-[1-[(2-chloro-5-[methyl[4-([[(3R,4S,5R)-1,3,4;5,6-pentahydroxyhexan-2-yl] carbamoyl]amino)butyl]sulfamoyl]phenyl)methoxy]cyclopropyl]-4-(2-cyclopropoxyphenyl) pyridin-1-ium-1-olate (I-697) as a white solid: (ES, m/z): [M+1]:779; $^1$H NMR (400 MHz, Methanol-d$_4$) δ 0.41 (dt, J=5.5, 2.6 Hz, 2H), 0.63 (t, J=6.2 Hz, 2H), 1.01-1.12 (m, 4H), 1.48-1.61 (m, 4H), 2.67 (s, 3H), 2.97 (t, J=6.6 Hz, 2H), 3.14 (t, J=6.5 Hz, 2H), 3.52-3.72 (m, 6H), 3.72-3.89 (m, 2H), 3.96 (dd, J=4.9, 2.8 Hz, 1H), 4.50 (s, 2H), 7.03 (td,

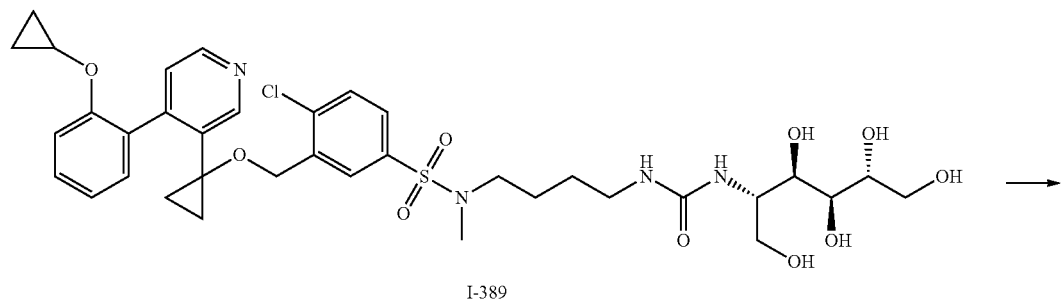

I-389

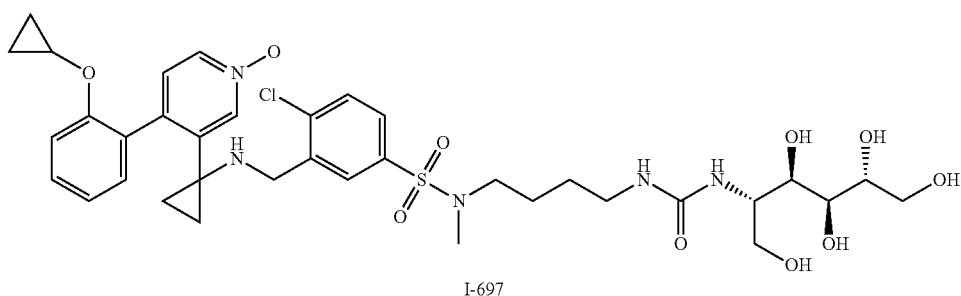

I-697

A 100-mL round-bottom flask purged and maintained under an inert atmosphere of nitrogen was charged with 1-(4-[N-methyl[4-chloro-3-([1-[4-(2-cyclopropoxyphenyl)pyridin-3-yl]cyclopropoxy]methyl) benzene]sulfonamido]butyl)-3-[(3R,4S,5R)-1,3,4,5,6-pentahydroxy-hexan-2-yl] urea I-389 (110 mg, 0.14 mmol, 1.00 equiv), dichloromethane (10 mL), m-CPBA (29.9 mg, 1.20 equiv). The resulting solution was stirred for 1 h at room temperature. The crude product was purified by Preparative HPLC with the following conditions: Column, XBridge Shield RP18 OBD Column; 5 μm 19×150 mm; mobile phase, water J=7.4, 1.3 Hz, 1H), 7.28-7.45 (m, 4H), 7.49-7.60 (m, 2H), 7.65 (dd, J=8.3, 2.3 Hz, 1H), 8.30 (dd, J=6.6, 2.0 Hz, 1H), 8.47 (d, J=2.0 Hz, 1H).

Example 98: 4-[3-[1-([2-chloro-5-[(2S)-6-([[(2S,3R,4S,5R)-1,3,4,5,6-pentahydroxyhexan-2-yl]carbamoyl]amino)hexan-2-yl]phenyl]methoxy)cyclopropyl]-1-oxidopyridin-1-ium-4-yl]-3-cyclopropoxybenzen-1-ide (I-698)

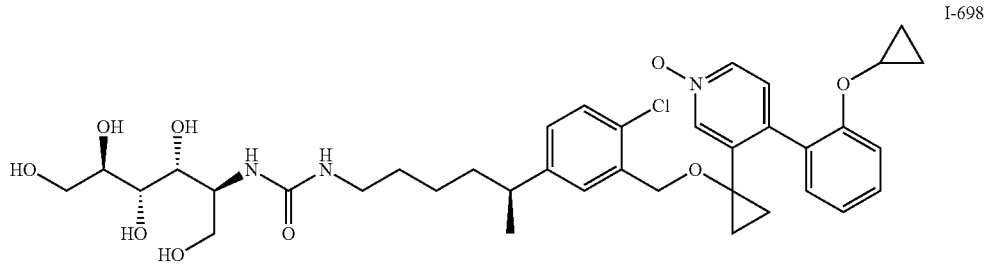

I-698

709

Compound I-698 was prepared from 1-[(5S)-5-[4-chloro-3-([1-[4-(2-cyclopropoxyphenyl)pyridin-3-yl]cyclopropoxy]methyl)phenyl]hexyl]-3-[(2S,3R,4S,5R)-1,3,4,5,6-pentahydroxyhexan-2-yl]urea according to the procedure used in I-697 68.3 mg (36%) to provide the desired compound as a white solid. MS (ES, m/z): [M+1]:714; $^1$H NMR (400 MHz, Methanol-$d_4$) δ 0.40 (s, 2H), 0.63 (dd, J=6.3, 1.8 Hz, 2H), 0.98 (s, 2H), 1.05 (d, J=4.8 Hz, 2H), 1.15-1.31 (m, 4H), 1.44 (s, 2H), 1.54 (d, J=7.8 Hz, 2H), 2.56-2.65 (m, 1H), 3.05 (q, J=6.5 Hz, 2H), 3.51-3.72 (m, 6H), 3.79 (ddd, J=25.3, 10.5, 4.2 Hz, 2H), 3.95 (dd, J=4.9, 2.9 Hz, 1H), 4.42 (s, 2H), 4.59 (s, 1H), 6.90 (d, J=2.1 Hz, 1H), 6.97-7.10 (m, 2H), 7.22 (d, J=8.2 Hz, 1H), 7.30-7.45 (m, 4H), 8.29 (dd, J=6.6, 2.0 Hz, 1H), 8.45 (d, J=2.0 Hz, 1H).

Example 99: 3-[1-[(2-chloro-5-[ethyl[4-([[(2S,3R,4R,5R)-2,3,4,5,6-pentahydroxyhexyl] carbamoyl] amino)butyl]sulfamoyl]phenyl)methoxy]cyclopropyl]-4-(2-cyclopropoxyphenyl) pyridin-1-ium-1-olate (I-699)

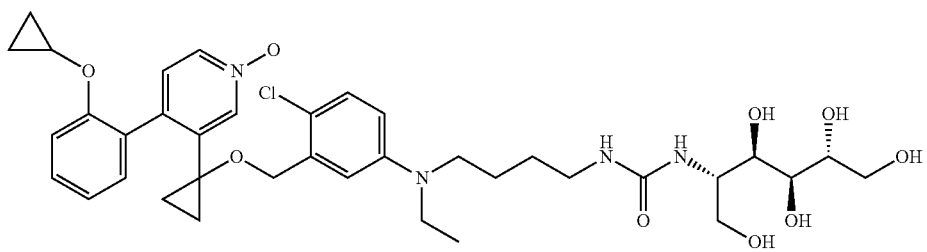

Compound I-699 was prepared from 1-(4-[N-ethyl[4-chloro-3-([1-[4-(2-cyclopropoxyphenyl)pyridin-3-yl]cyclopropoxy]methyl)benzene]sulfonamido]butyl)-3-[(2S,3R,4R,5R)-2,3,4,5,6-pentahydroxyhexyl]urea according to the procedure used in I-697 to provide 59.8 mg (59%) of 3-[1-[(2-chloro-5-[ethyl[4-([[(2S,3R,4R,5R)-2,3,4,5,6-pentahydroxyhexyl]carbamoyl]amino)butyl]sulfamoyl]phenyl)methoxy]cyclopropyl]-4-(2-cyclopropoxyphenyl)pyridin-1-ium-1-olate (I-699) as a white solid: MS (ES, m/z): [M+1]: 793; $^1$H NMR (400 MHz, Methanol-$d_4$) δ 0.41 (s, 2H), 0.58-0.68 (m, 2H), 1.01-1.12 (m, 7H), 1.51 (dq, J=33.3, 7.8 Hz, 4H), 3.06-3.22 (m, 7H), 3.27 (s, 1H), 3.39 (dd, J=13.9, 4.5 Hz, 1H), 3.53-3.81 (m, 6H), 4.49 (s, 2H), 6.99-7.08 (m, 1H), 7.28-7.46 (m, 4H), 7.54 (dd, J=5.3, 3.1 Hz, 2H), 7.68 (dd, J=8.4, 2.3 Hz, 1H), 8.31 (dd, J=6.6, 2.0 Hz, 1H), 8.47 (d, J=2.0 Hz, 1H).

710

Example 100: 2,5-dichloro-4-[([1-[4-(2-cyclopropoxyphenyl)pyridin-3-yl]cyclopropyl]amino) methyl]phenol (I-700)

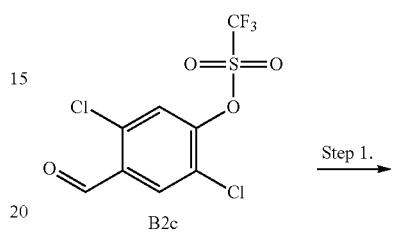

-continued

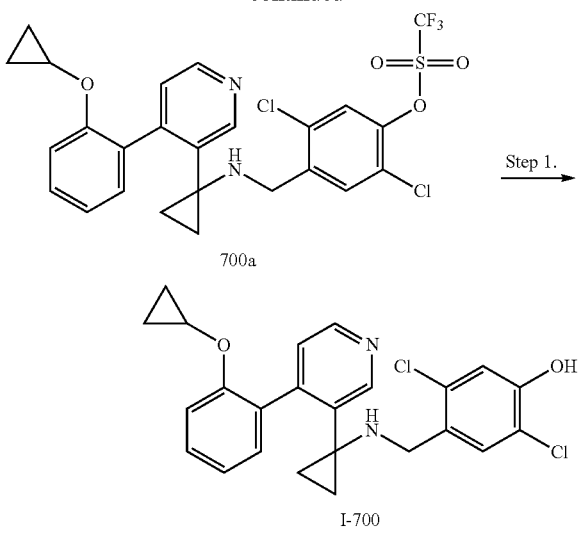

Step 1. 2,5-dichloro-4-[([1-[4-(2-cyclopropoxyphenyl)pyridin-3-yl]cyclopropyl]amino) methyl]phenyl trifluoromethanesulfonate (Intermediate 700a)

A 100-mL round-bottom flask purged and maintained under an inert atmosphere of nitrogen was charged with 2,5-dichloro-3-formylphenyl trifluoromethanesulfonate (B2c400 mg, 1.24 mmol, 1.00 equiv), dichloromethane (30 mL), 1-[2-(2-cyclopropoxyphenyl)phenyl] cyclopropan-1-amine (329.76 mg, 1.24 mmol, 1.00 equiv). This was followed by the addition of acetic acid (0.1 mL). The mixture was stirred for 1 h at rt. To this was added NaBH(OAc)$_3$ (1.31 g, 6.18 mmol, 5.00 equiv). The resulting solution was stirred overnight at room temperature. The resulting solution was extracted with 3×50 mL of ethyl acetate and the organic layers combined. This resulted in 709.95 mg (crude) of 2,5-dichloro-4-[([1-[4-(2-cyclopropoxyphenyl)pyridin-3-yl]cyclopropyl]amino)methyl] phenyl trifluoromethanesulfonate as yellow oil.

Step 2. 2,5-dichloro-4-[([1-[4-(2-cyclopropoxyphenyl)pyridin-3-yl]cyclopropyl]amino) methyl] phenol (I-700)

A 100-mL round-bottom flask purged and maintained under an inert atmosphere of nitrogen was charged with 2,5-dichloro-4-[([1-[4-(2-cyclopropoxyphenyl)pyridin-3-yl]cyclopropyl]amino)methyl]phenyl trifluoromethanesulfonate (709.95 mg, 1.24 mmol, 1.00 equiv), toluene (20 mL), Cs$_2$CO$_3$ (1.21 g, 3.70 mmol, 3.00 equiv). The resulting solution was stirred overnight at 80° C. in an oil bath. The resulting solution was extracted with 3×50 mL of ethyl acetate and the organic layers combined. The crude product was purified by Preparative HPLC with the following conditions: Column, SunFire Prep C18 OBD Column, 19×150 mm 5 μm 10 nm; mobile phase, 10 mM aqueous NH$_4$HCO$_3$ and MeCN (55.0% MeCN up to 65.0% in 10 min); Detector, UV 254 nm. This resulted in 200.6 mg (37%) of 2,5-dichloro-4-[([1-[4-(2-cyclopropoxyphenyl)pyridin-3-yl]cyclopropyl]amino)methyl] phenol (I-700) as a white solid: MS (ES, m/z): [M+1]:441; $^1$H NMR (400 MHz, DMSO-d$_6$) δ0.32-0.41 (m, 2H), 0.64 (td, J=5.6, 2.1 Hz, 4H), 0.76 (d, J=2.3 Hz, 2H), 1.86 (t, J=7.5 Hz, 1H), 3.45 (d, J=7.4 Hz, 2H), 3.71 (tt, J=6.0, 2.9 Hz, 1H), 6.91 (s, 1H), 6.98-7.10 (m, 2H), 7.14 (s, 1H), 7.21-7.28 (m, 1H), 7.37-7.47 (m, 2H), 8.45 (d, J=4.9 Hz, 1H), 8.56 (s, 1H), 10.48 (s, 1H).

Example 101: 3-(1-(2-chloro-5-(N-ethyl-N-(4-(3-((2S,3R,4R,5R)-2,3,4,5,6-penta-hydroxyhexyl) ureido)butyl)sulfamoyl)benzyloxy)cyclopropyl)-4-(2-cyclopropoxyphenyl)-1-(pivaloyloxymethyl) pyridinium chloride (I-701)

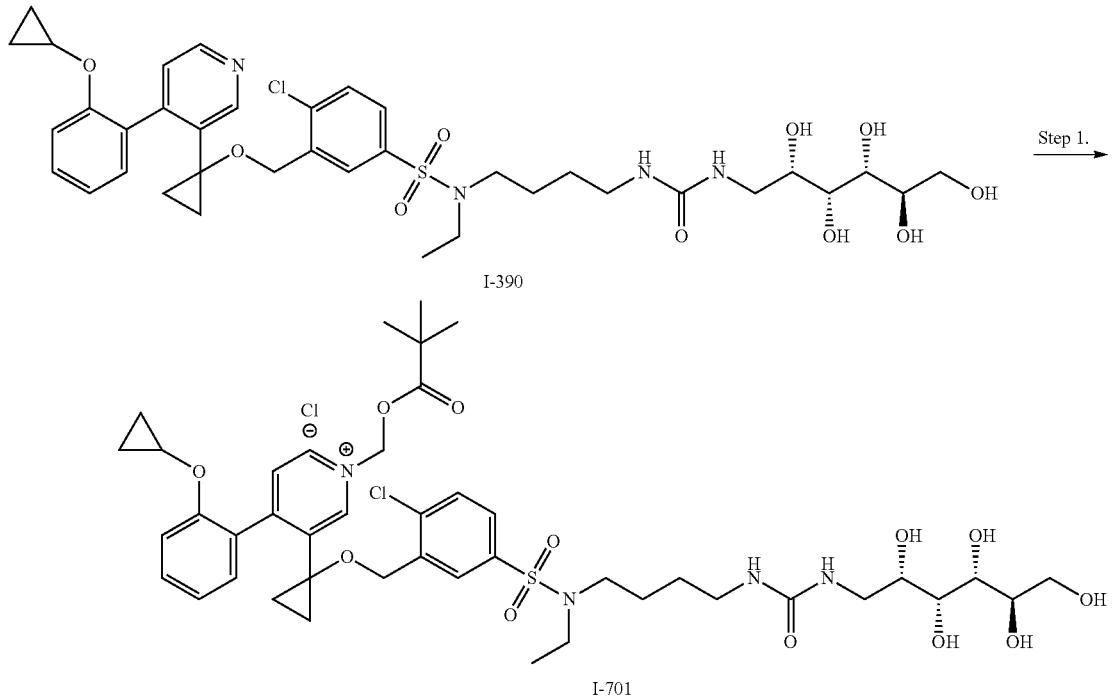

Step 1. 3-(1-(2-chloro-5-(N-ethyl-N-(4-(3-((2S,3R,4R,5R)-2,3,4,5,6-pentahydroxyhexyl) ureido)butyl) sulfamoyl)benzyloxy)cyclopropyl)-4-(2-cyclopropoxyphenyl)-1-(pivaloyloxymethyl)pyridinium chloride In a 50-mL round-bottom flask was slurried 4-chloro-3-((1-(4-(2-cyclopropoxyphenyl)pyridin-3-yl)cyclopropoxy) methyl)-N-ethyl-N-(4-(3-((2S,3R,4R,5R)-2,3,4,5,6-pentahydroxyhexyl)ureido)butyl) (I-390) (100 mg, 0.13 mmol, 1.0 equiv) and NaI (19 mg, 0.129 mmol, 1.0 equiv) in MeCN (0.5 mL). Chloromethyl pivalate (21.3 mg, 0.142 mmol, 1.1 equiv) was added and the reaction mixture was heated to 60° C. at which point a yellow solution was formed and the reaction vessel was covered in foil. After 5 hours, the LCMS indicated complete conversion. The reaction mixture was cooled, and diluted with IPA:MeCN (3:1, 25 mL). Dowex 1×2 Cl⁻ resin (1.7 g, washed with MeOH) was added and TLC indicated complete conversion to the chloride salt. The mixture was filtered and purified by flash chromatography (12 g SiO$_2$, DCM to 20% MeOH in DCM). Lyophilization gave 60 mg (50%) of the title compound as a white solid. MS (ES, m/z): 891.13 [M−Cl]⁺; ¹H-NMR (D$_2$O, ppm): δ 8.89 (s, 1H), 8.69 (d, J=6.4 Hz, 1H), 7.68 (d, J=6.3 Hz, 1H), 7.44-7.37 (m, 1H), 7.29 (d, J=8.4 Hz, 1H), 7.20 (d, J=7.3 Hz, 1H), 7.12 (dd, J=13.0, 8.1 Hz, 2H), 7.04 (s, 1H), 6.80 (s, 1H), 6.14 (s, 2H), 4.16 (s, 2H), 3.50 (d, J=2.8 Hz, 1H), 3.47 (s, 1H), 3.45-3.40 (m, 2H), 3.37-3.28 (m, 3H), 3.03 (d, J=4.5 Hz, 1H), 2.84 (dt, J=21.2, 7.2 Hz, 5H), 2.73 (t, J=6.8 Hz, 2H), 1.19 (s, 2H), 1.07 (s, 2H), 0.98 (d, J=20.5 Hz, 4H), 0.89 (s, 9H), 0.73 (t, J=7.1 Hz, 3H), 0.36 (d, J=7.4 Hz, 2H), 0.10 (s, 1H).

Example 102: 1-(((2-acetoxyethyl)(methyl)carbamoyloxy)methyl)-3-(1-(2-chloro-5-(N-ethyl-N-(4-(3-((2S,3R,4R,5R)-2,3,4,5,6-pentahydroxyhexyl)ureido)butyl)sulfamoyl)benzyloxy) cyclopropyl)-4-(2-cyclopropoxyphenyl)pyridinium chloride (I-702)

Step 2. 1-(((2-acetoxyethyl)(methyl)carbamoyloxy)methyl)-3-(1-(2-chloro-5-(N-ethyl-N-(4-(3-((2S,3R,4R,5R)-2,3,4,5,6-pentahydroxyhexyl)ureido)butyl) sulfamoyl) benzyloxy)cyclopropyl)-4-(2-cyclopropoxyphenyl)pyridinium chloride (I-702)

A slurry of 4-chloro-3-((1-(4-(2-cyclopropoxyphenyl)pyridin-3-yl)cyclopropoxy) methyl)-N-ethyl-N-(4-(3-((2S,3R,4R,5R)-2,3,4,5,6-pentahydroxyhexyl)ureido)butyl) benzenesulfonamide I-390 (100 mg, 0.129 mmol, 1.0 eq), NaI (19 mg, 0.129 mmol, 1.0 eq) in MeCN (0.5 mL) was added 2-(((chloromethoxy)carbonyl)(methyl)amino)ethyl acetate (30 mg, 0.142 mmol, 1.1 eq) in MeCN (0.5 mL). The reaction mixture was heated to 60° C. and wrapped in foil. After 2 hours additional 2-(((chloromethoxy)carbonyl)(methyl)amino)ethyl acetate (10 mg, 0.048 mmol, 0.37 eq) was added. After a further 3 hours the reaction was complete. The reaction mixture was cooled and diluted with brine (10 mL). The resulting solution was dried over Na$_2$SO$_4$ and purified by flash chromatography (24 g SiO$_2$, DCM to 100% EtOAc, ELSD detector) to yield 910 mg (quantitative) of Intermediate 702a as a clear oil.

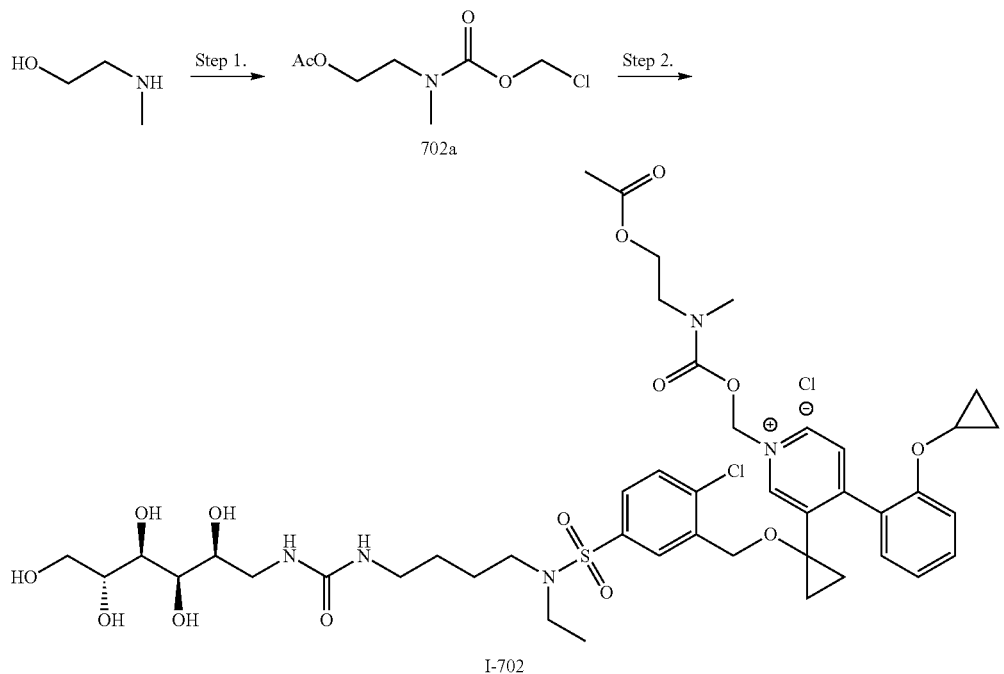

Step 1. 2-(((chloromethoxy)carbonyl)(methyl)amino)ethyl acetate (Intermediate 702a)

A solution of 2-(methylamino)ethanol (292 mg, 3.9 mmol, 1.0 equiv) and DIEA (505 mg, 3.9 mmol, 1.0 eq) in DCM (25 mL) was cooled to 0° C. under an atmosphere of N$_2$. Chloromethyl chloroformate (521 mg, 4.0 mmol, 1.05 eq) was added dropwise and the reaction was kept at 0° C. for 1 hour, at which point TLC indicated no starting material remained. DIEA (645 mg, 5.0 mmol, 1.3 equiv) and then Ac$_2$O (400 mg, 3.9 mmol, 1.0 eq) were added at 0° C. followed by DMAP (5 mg, catalytic). The ice bath was removed. After 50 minutes the reaction was complete and the reaction mixture was quenched with HCl (0.25M, 20 mL) and then washed successively with water (10 mL) and IPA:MeCN (3:1, 25 mL). Dowex 1×2 Cl⁻ resin (1.45 g, washed in MeOH) was added and TLC indicated complete conversion to the chloride salt. The resulting mixture was filtered and purified by flash chromatography (12 g SiO$_2$, DCM to 20% MeOH in DCM). Lyophilization gave 63 mg (51%) of the title compound I-702 as a white solid. MS (ES, m/z): 950.14 [M−Cl]⁺; ¹H-NMR D$_2$O, ppm): δ 9.23 (d, J=7.7 Hz, 1H), 9.08-8.96 (m, 1H), 8.02 (d, J=6.2 Hz, 1H), 7.72 (d, J=8.4 Hz, 1H), 7.62 (d, J=8.5 Hz, 1H), 7.52 (dd, J=12.1, 6.3 Hz, 2H), 7.39 (s, 2H), 7.12 (t, J=7.4 Hz, 1H), 6.45 (d, J=13.9 Hz, 2H), 5.14 (d, J=5.9 Hz, 1H), 4.52 (d, J=5.5 Hz, 2H), 4.25 (dt, J=16.3, 5.2 Hz, 2H), 3.93-3.75 (m, 5H), 3.75-3.59 (m, 5H), 3.59-3.44 (m, 1H), 3.38 (dd, J=4.4 Hz, 1H), 3.29-3.11 (m, 6H), 3.11-2.98 (m, 4H), 2.94 (d, J=7.8 Hz, 2H), 2.78 (s, 1H), 2.19-1.99 (m, 1H), 1.97 (s, 1H), 1.90 (s, 1H), 1.53 (s, 2H), 1.42 (d, J=7.9 Hz, 2H), 1.30 (d, J=23.5 Hz, 4H), 1.06 (t, J=7.1 Hz, 3H), 0.73 (s, 2H), 0.49 (s, 1H).

Example 103: 5-[6-[([1-[4-(2-cyclopropoxyphenyl) pyridin-3-yl]cyclopropyl]amino)methyl]-5-methylpyridin-2-yl]-N-[(2S,3R,4R,5R)-2,3,4,5,6-pentahydroxyhexyl]pentanamide trihydrochloride (I-703)

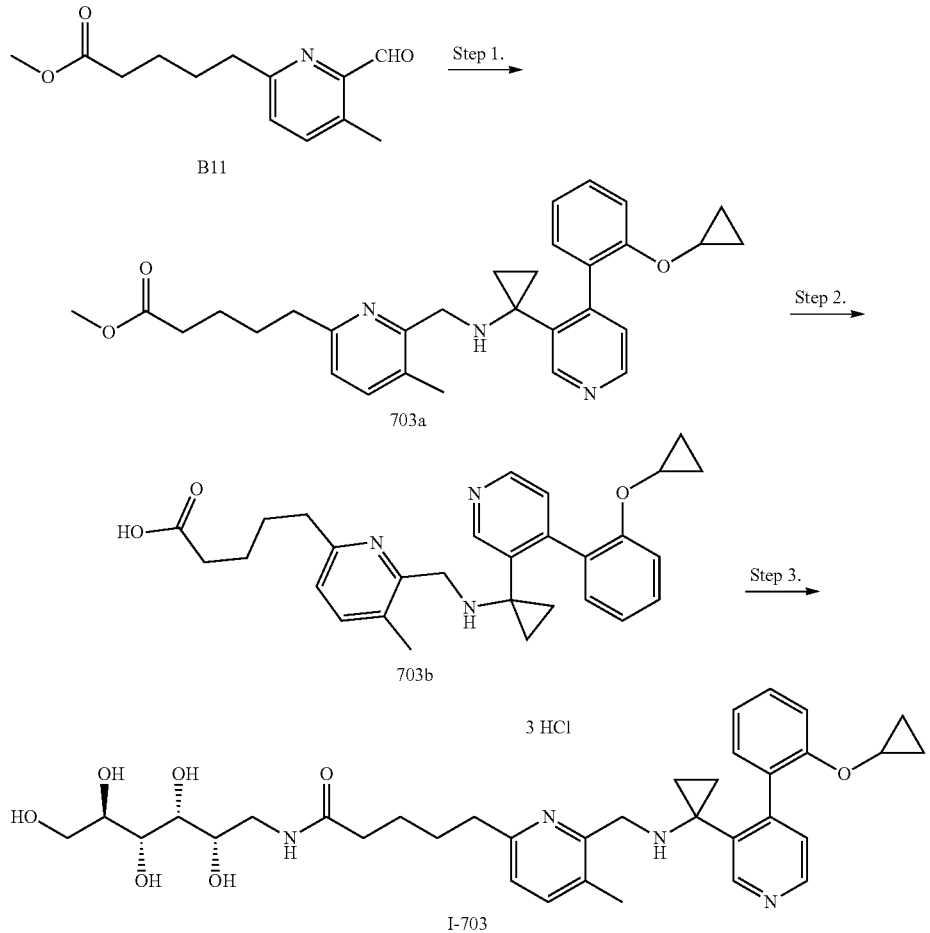

Step 1. 5-[6-[([1-[4-(2-cyclopropoxyphenyl)pyridin-3-yl]cyclopropyl]amino)methyl]-5-methylpyridin-2-yl]pentanoate (Intermediate 703a)

To a solution of methyl 5-(6-formyl-5-methylpyridin-2-yl)pentanoate (B11) (160 mg, 0.68 mmol, 1.00 equiv), intermediate A1 (182 mg, 0.68 mmol, 1.00 equiv) in dichloromethane (10 mL) and AcOH (0.01 mL) was added NaBH(OAc)₃ (721 mg). The resulting solution was stirred overnight at 25° C. in an oil bath. The reaction mixture was then quenched by the addition of 5 mL of water. The resulting solution was extracted with 3×10 mL of dichloromethane and the organic layers combined and dried over anhydrous sodium sulfate and concentrated under vacuum. The residue was applied onto a silica gel column with ethyl acetate/petroleum ether (1/100-20/100). This resulted in 200 mg (60%) of methyl 5-[6-[([1-[4-(2-cyclopropoxyphenyl)pyridin-3-yl]cyclopropyl]amino)methyl]-5-methylpyridin-2-yl]pentanoate (703a) as a light brown solid.

Step 2. 5-[6-[([1-[4-(2-cyclopropoxyphenyl)pyridin-3-yl]cyclopropyl]amino)methyl]-5-methylpyridin-2-yl]pentanoic acid (Intermediate 703b)

To a solution of methyl 5-[6-[([1-[4-(2-cyclopropoxyphenyl)pyridin-3-yl]cyclopropyl]amino)methyl]-5-methylpyridin-2-yl]pentanoate (200 mg, 0.41 mmol, 1.00 equiv) in methanol (5 mL) was added LiOH·H₂O (52 mg, 1.24 mmol, 3.01 equiv), in water (1 mL). The resulting solution was stirred for 1 h at 60° C. in an oil bath. The pH value of the solution was adjusted to 7 with HCl (2 mol/L). The resulting solution was extracted with 3×10 mL of ethyl acetate and the organic layers combined and dried over anhydrous sodium sulfate and concentrated under vacuum. This resulted in 150 mg (77%) of 5-[6-[([1-[4-(2-cyclopropoxyphenyl)pyridin-3-yl]cyclopropyl]amino)methyl]-5-methylpyridin-2-yl]pentanoic acid (703b) as a light brown solid.

Step 3. 5-[6-[([1-[4-(2-cyclopropoxyphenyl)pyridin-3-yl]cyclopropyl]amino) methyl]-5-methylpyridin-2-yl]-N-[(2S,3R,4R,5R)-2,3,4,5,6-pentahydroxyhexyl] pentanamide trihydrochloride (I-703)

To a solution of 5-[6-[([1-[4-(2-cyclopropoxyphenyl)pyridin-3-yl]cyclopropyl]amino) methyl]-5-methylpyridin-2-yl] pentanoic acid (150 mg, 0.32 mmol, 1.00 equiv), (2R,3R,4R,5S)-6-aminohexane-1,2,3,4,5-pentol (86.5 mg, 0.48 mmol, 1.50 equiv), in N,N-dimethylformamide (5 mL) and DIEA (123 mg, 0.95 mmol, 2.99 equiv) was added HATU (362.5 mg, 0.95 mmol, 3.00 equiv). The resulting solution was stirred overnight at 25° C. in an oil bath. The resulting solution was diluted with 5 mL of H$_2$O. The resulting solution was extracted with 4×10 mL of ethyl acetate and the organic layers combined and dried over anhydrous sodium sulfate and concentrated under vacuum. The solids were filtered out. The crude product was purified by Preparative HPLC with the following conditions: Column, XBridge Shield RP18 OBD Column, 5 μm, 19*150 mm; mobile phase, Water with 10 mmol NH$_4$HCO$_3$ and ACN (hold 37.0% ACN in 10 min); Detector, UV 254 nm. After lyophilization, the product was dissolved in 2 ml of ACN/20 ml of H$_2$O, 10 drops of HCl (1M) was added. After lyophilization, this resulted in 57.6 mg (24%) of 5-[6-[([1-[4-(2-cyclopropoxyphenyl)pyridin-3-yl]cyclopropyl]amino)methyl]-5-methylpyridin-2-yl]-N-[(2S,3R,4R,5R)-2,3,4,5,6-pentahydroxyhexyl]pentanamide trihydrochloride (I-703) as a white solid: (ES, nm/z): [M+1]:743. $^1$H-NMR: (400 MHz, MeOD, ppm): δ 9.16 (s, 1H), 8.87-8.87 (d, 1H), 8.86-7.23 (m, 7H), 4.91 (s, 2H), 3.87-3.03 (m, 10H), 2.43 (s, 3H), 2.35-2.33 (t, 2H), 2.06 (s, 3H), 1.79-1.70 (m, 4H), 1.68-1.14 (m, 4H), 0.78-0.58 (m, 4H).

Compounds I-704 to I-709 (Table 16) were prepared from commercial, known starting materials or the appropriate intermediates disclosed herein using methods from the examples specified in Table 16 and methods generally known to those skilled in the art.

TABLE 16

Compounds I-703 to I-709

| Cmpd No.: | Synthetic Method | Compound Structure | Obs. Mass |
|---|---|---|---|
| I-704 | Example 103 | 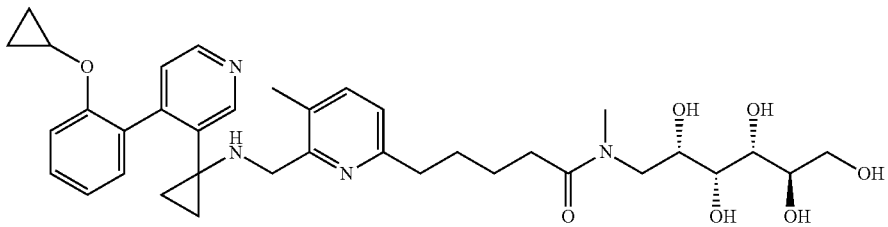 [SMILES: Cc1ccc(CCCCC(=O)N(C)C[C@H](O)[C@@H](O)[C@H](O)[C@H](O)CO)nc1CNC1(c2cnccc2-c2ccccc2OC2CC2)CC1] | 649.5 |
| I-705 | Example 19 | 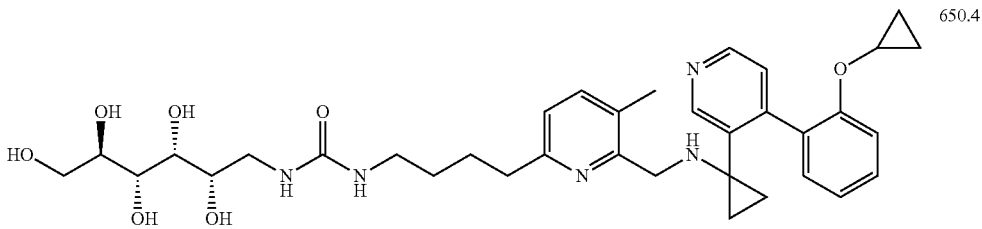 | 650.4 |
| I-706 | Example 19 | 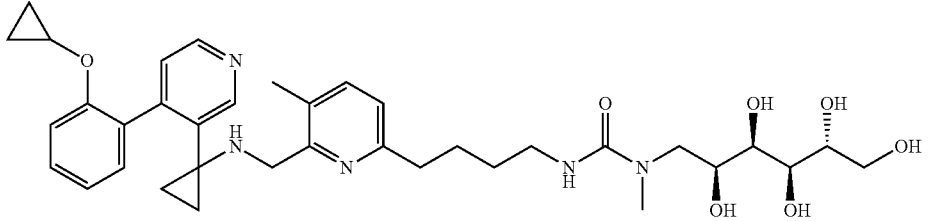 [SMILES: Cc1ccc(CCCCNC(=O)N(C)C[C@H](O)[C@@H](O)[C@H](O)[C@H](O)CO)nc1CNC1(c2cnccc2-c2ccccc2OC2CC2)CC1] | 664.4 |
| I-707 | Example 19 | 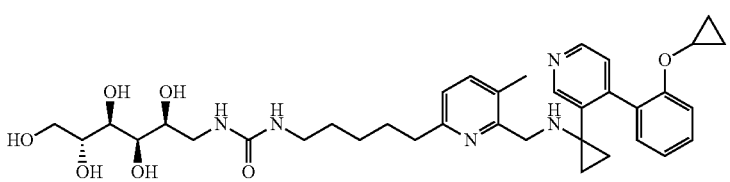 [SMILES: Cc1ccc(CCCCCNC(=O)NC[C@H](O)[C@@H](O)[C@H](O)[C@H](O)CO)nc1CNC1(c2cnccc2-c2ccccc2OC2CC2)CC1] | 332.8 [M + 2H]$^{+2}$/2 |

TABLE 16-continued

Compounds I-703 to I-709

| Cmpd No.: | Synthetic Method | Compound Structure | Obs. Mass |
|---|---|---|---|
| I-708 | Example 49 | 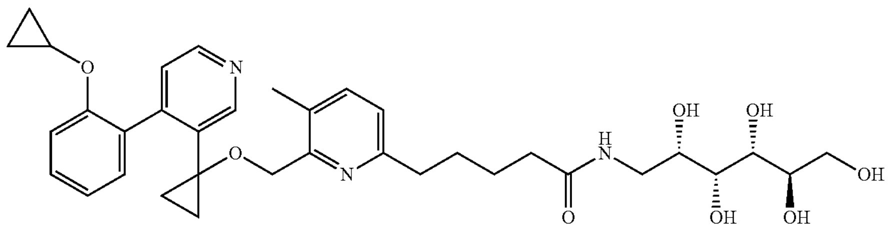 | 318.6 [M + 2H]+2/2 |
| I-709 | Example 49 | 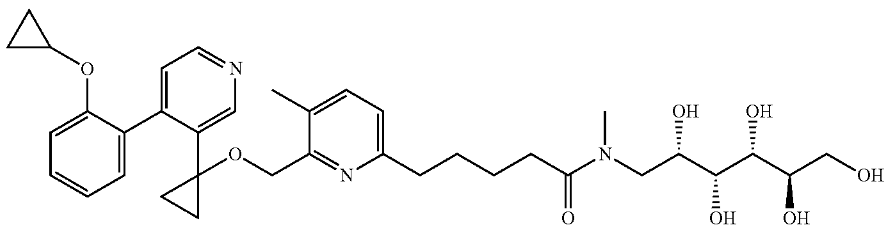 [SMILES: Cc1ccc(CCCCC(=O)N(C)C[C@H](O)[C@@H](O)[C@H](O)[C@H](O)CO)nc1COC1(c2cnccc2-c2ccccc2OC2CC2)CC1] | 325.7 [M + 2H]+2/2 |

Example 104: 2-(4-(2-Cyclopropoxyphenyl)pyridin-3-yl)-N-(2,5-dichlorobenzyl)propan-2-amine (I-723)

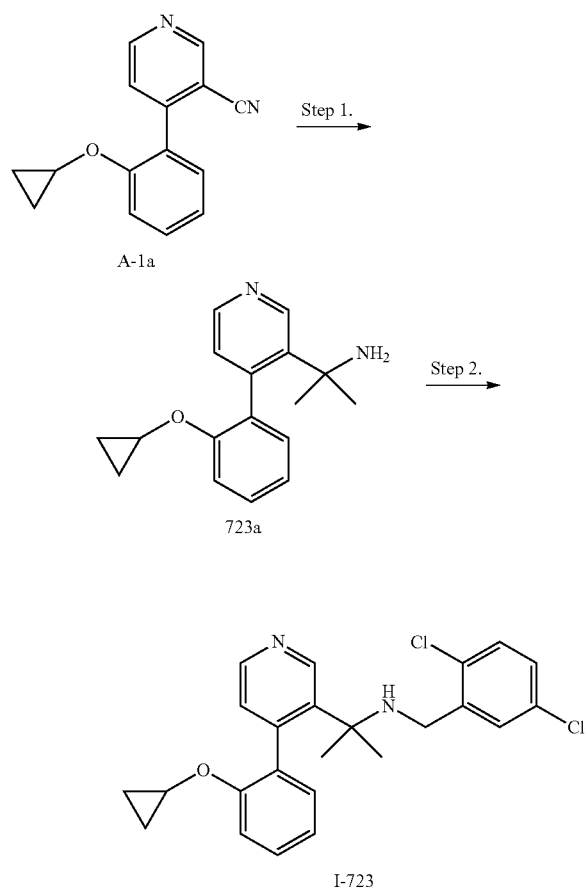

Step 1. 2-(4-(2-cyclopropoxyphenyl)pyridin-3-yl)propan-2-amine (Intermediate 723a)

A mixture of cerium trichloride (417.8 mg, 1.695 mmol, 4.0 equiv) in THF (3 mL) was stirred at room temperature for 2 h and cooled to −78° C. To the mixture was added a solution of methyllithium (1.6 M in ether, 1.06 mL, 1.70 mmol, 4.0 equiv) dropwise. The reaction mixture was stirred at −78° C. for 30 minutes. A solution of 4-(2-cyclopropoxyphenyl)nicotinonitrile (A-1a, 100 mg, 0.424 mmol, 1.0 equiv) in THF (0.5 mL) was added dropwise. The mixture was warmed to room temperature and stirred at room temperature overnight. The reaction was quenched with a few drops of saturated aqueous ammonium chloride, followed by addition of 28% ammonium hydroxide solution (~1 mL). The resulting mixture was filtered and the filtrate was extracted with ethyl acetate. The organic extract was washed with brine, dried over $Na_2SO_4$, then concentrated to dryness. The residue was purified by flash column chromatography on silica mobile phase of 0-20% MeOH/DCM to give 10 mg (9%) of 723a as yellow syrup.

Step 2. 2-(4-(2-Cyclopropoxyphenyl)pyridin-3-yl)-N-(2,5-dichlorobenzyl)propan-2-amine (I-723)

To a mixture of 2-(4-(2-cyclopropoxyphenyl)pyridin-3-yl)propan-2-amine (723a, 10 mg, 0.037 mmol, 1.0 equiv) in dichloroethane (0.5 mL) was added 2,5-dichlorobenzylaldehyde (6.5 mg, 0.037 mmol, 1.0 equiv). The mixture was stirred at room temperature for 30 minutes. $NaBH(OAc)_3$ (15.8 mg, 0.075 mmol, 2.0 equiv) and acetic acid (2.1 µL, 0.037 mmol, 1.0 equiv) were added. The resulting mixture was stirred at room temperature for 3 h and more NaBH(OAc)$_3$ (15.8 mg, 0.089 mmol, 2.4 equiv) was added. The mixture was stirred at room temperature overnight, quenched with saturated sodium bicarbonate, and extracted with ethyl acetate. The organic layer was washed with brine, dried, concentrated, and purified by preparative HPLC to give 9.9 mg (49%) of the I-723 TFA salt as a yellow solid. MS (ES, m/z): 427.03 [M+H]+; $^1$H NMR (400 MHz, CD₃OD): δ 9.03 (s, 1H), 8.63 (d, J=5.1 Hz, 1H), 7.62-7.43 (m, 5H), 7.28 (d, J=5.2 Hz, 1H), 7.22 (dd, J=7.5, 1.7 Hz, 1H), 7.14 (td, J=7.3, 1.3 Hz, 1H), 4.12 (s, 2H), 3.82 (tt, J=6.0, 2.9 Hz, 1H), 1.69 (s, 3H), 1.59 (s, 3H), 0.81-0.61 (m, 2H), 0.59-0.38 (m, 2H).

Example 105: 4-(4-Chloro-3-((1-(4-(2-cyclopropoxyphenyl)pyridin-3-yl)cyclopropoxy) methyl) phenethyl)-N-((2S,3R,4R,5R)-2,3,4,5,6-pentahydroxyhexyl)benzamide (I-724)

Step 1. Methyl 4-((4-chloro-3-((1-(4-(2-cyclopropoxyphenyl)pyridin-3-yl)cyclopropoxy) methyl) phenyl)ethynyl)benzoate (Intermediate 724a)

To a mixture of 3-(1-((2-chloro-5-iodobenzyl)oxy)cyclopropyl)-4-(2-cyclopropoxyphenyl)pyridine (Intermediate 488a, 119.9 mg, 0.232 mmol, 1.0 equiv) in DMF (270 μL) was added methyl 4-ethynylbenzoate (44.5 mg, 0.278 mmol, 1.2 equiv), triethylamine (390 μL), Pd(PPh₃)₂Cl₂ (8.2 mg, 0.012 mmol, 0.05 equiv), and CuI (4.4 mg, 0.023 mmol, 0.1 equiv). The mixture was purged with N₂ and stirred under N₂

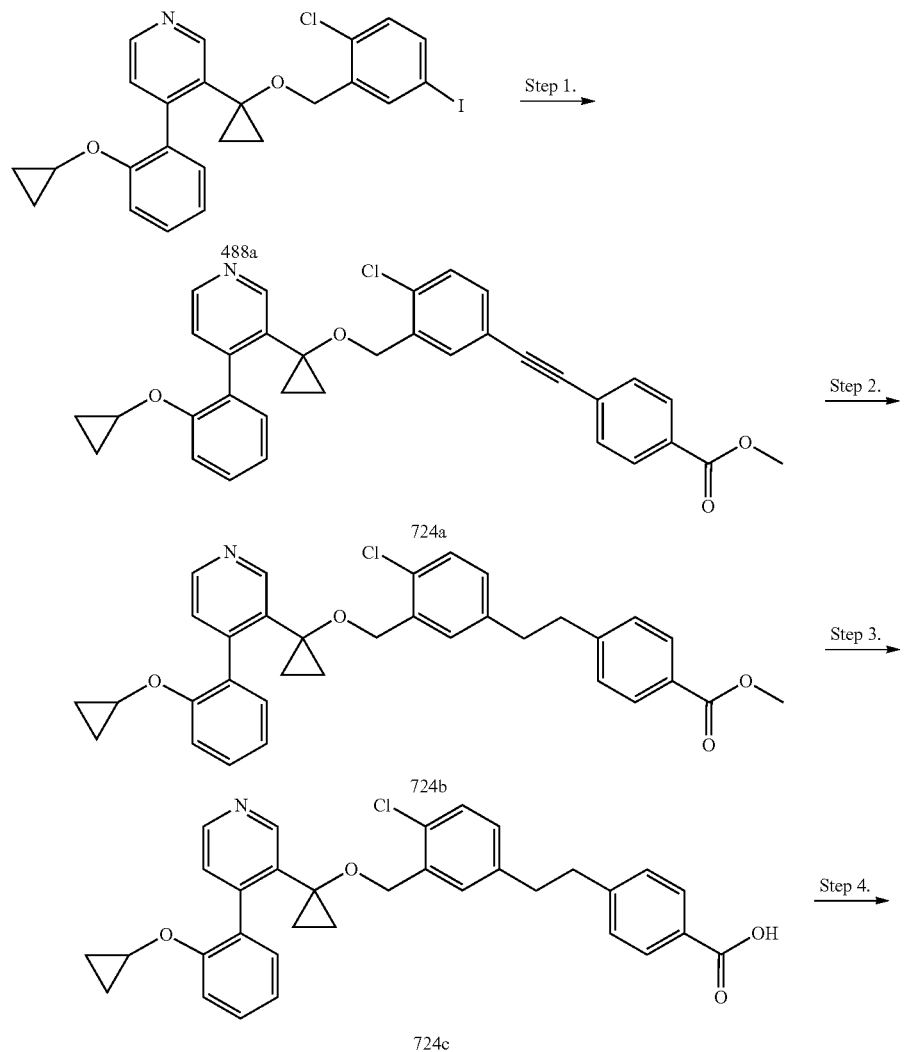

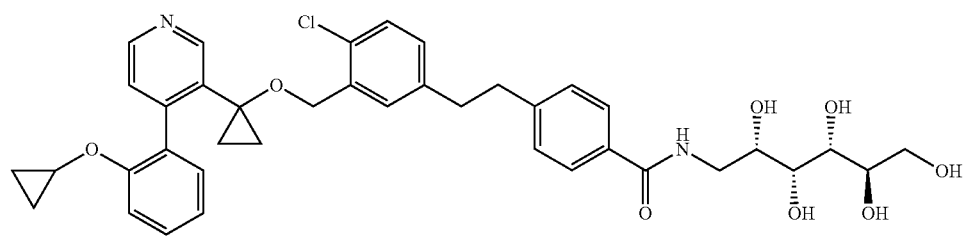

I-724 at 50° C. overnight, diluted with ethyl acetate, washed with water (2×) brine, dried over Na₂SO₄, filtered, concentrated, and the residue was purified by flash column chromatography on silica with ethyl acetate/hexanes to give 98.1 mg (77%) of 724a as a yellow solid.

Step 2. Methyl 4-(4-chloro-3-((1-(4-(2-cyclopropoxyphenyl)pyridin-3-yl)cyclopropoxy) methyl) phenethyl)benzoate (Intermediate 724b)

To a mixture of methyl 4-((4-chloro-3-((1-(4-(2-cyclopropoxyphenyl)pyridin-3-yl)cyclopropoxy)methyl)phenyl)ethynyl)benzoate (724a, 94.2 mg, 0.171 mmol) in ethyl acetate (3 mL) was added 5 wt. % Rh on alumina (95 mg). The mixture was stirred under hydrogen for 3 h and more 5 wt. % Rh on alumina (100 mg) was added. The resulting mixture was stirred under hydrogen overnight and filtered. The filtrate was concentrated to give 91.6 mg (97%) of 724b as yellow syrup.

Step 3. 4-(4-Chloro-3-((1-(4-(2-cyclopropoxyphenyl)pyridin-3-yl)cyclopropoxy) methyl) phenethyl) benzoic acid (Intermediate 724c)

To a solution of methyl 4-(4-chloro-3-((1-(4-(2-cyclopropoxyphenyl)pyridin-3-yl)cyclopropoxy)methyl)phenethyl)benzoate (724b, 91.6 mg, 0.166 mmol, 1 equiv) in THF (0.8 mL) and water (0.4 mL) was added lithium hydroxide monohydrate (10.4 mg, 0.248 mmol, 1.5 equiv). The mixture was stirred at room temperature overnight and an aqueous solution of NaOH (5 M, 50 μL, 1.5 equiv) was added. The resulting mixture was stirred overnight and additional NaOH solution (5 M, 50 μL, 1.5 equiv) was added. The mixture was stirred at room temperature for 5 h, acidified with 10% citric acid solution, and extracted with ethyl acetate (2×) and DCM (5×). The combined organic layers were dried and concentrated to give 74 mg (82%) of 724c as a white solid.

Step 4. 4-(4-Chloro-3-((1-(4-(2-cyclopropoxyphenyl)pyridin-3-yl)cyclopropoxy) methyl)phenethyl)-N-((2S,3R,4R,5R)-2,3,4,5,6-pentahydroxyhexyl) benzamide (I-724)

To a mixture of 4-(4-chloro-3-((1-(4-(2-cyclopropoxyphenyl)pyridin-3-yl)cyclopropoxy)methyl)phenethyl)benzoic acid, (724c, 23.4 mg, 0.043 mmol, 1.0 equiv) and D-glucamine (9.4 mg, 0.052 mmol, 1.2 equiv) in DMF (0.2 mL) were added N,N-diisopropylethylamine (38 μL, 0.22 mmol, 5.0 equiv) and HATU (19.8 mg, 0.521 mmol, 1.2 equiv). The mixture was stirred at room temperature for 1 h and purified by preparative HPLC to give I-724 (21.4 mg, 70%) as a white solid. MS (ES, m/z): 703.3 [M+H]⁺, ¹H-NMR (400 MHz, CD₃OD) δ 8.63 (s, 1H), 8.47 (d, J=5.1 Hz, 1H), 7.74 (d, J=7.6 Hz, 2H), 7.40-7.30 (m, 2H), 7.27 (d, J=7.5 Hz, 1H), 7.25-7.19 (m, 3H), 7.15 (d, J=8.2 Hz, 1H), 7.01-6.94 (m, 2H), 6.88 (s, 1H), 4.35 (s, 2H), 4.01-3.92 (m, 1H), 3.84-3.76 (m, 2H), 3.75-3.60 (m, 4H), 3.56-3.41 (m, 2H), 2.97-2.79 (m, 4H), 1.00-0.87 (m, 4H), 0.63-0.55 (m, 2H), 0.42-0.33 (m, 2H).

Example 106: 4-Chloro-3-((1-(4-(2-cyclopropoxyphenyl)pyridin-3-yl)cyclopropoxy)methyl)-N,N-dimethylbenzamide (I-725)

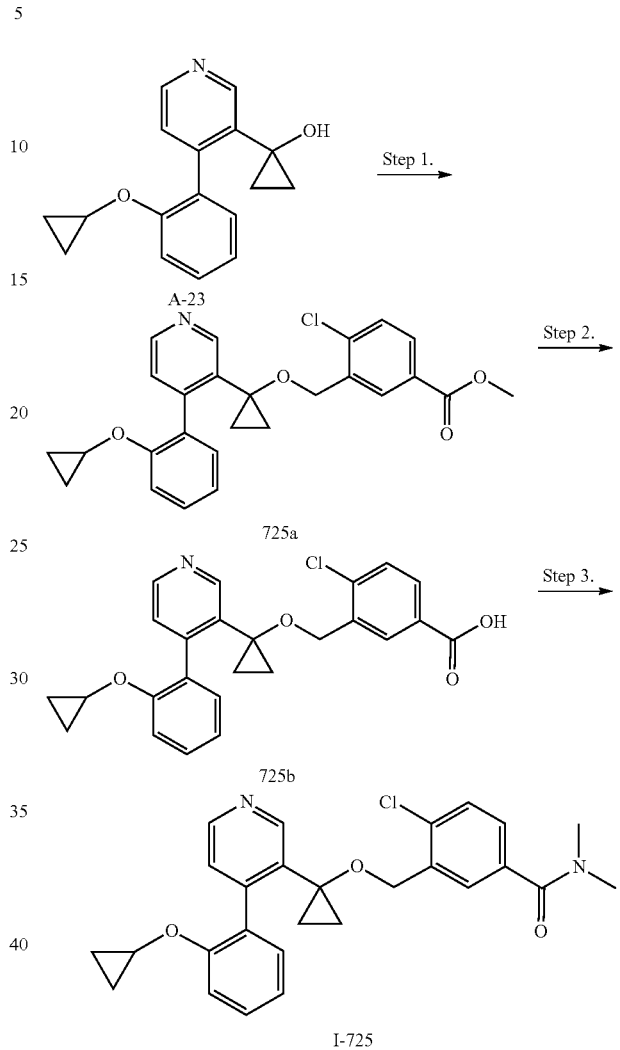

Step 1. Methyl 4-chloro-3-((1-(4-(2-cyclopropoxyphenyl)pyridin-3-yl)cyclopropoxy)methyl)benzoate (Intermediate 725a)

To a mixture of 1-(4-(2-cyclopropoxyphenyl)pyridin-3-yl)cyclopropanol (A-23, 93.5 mg, 0.35 mmol, 1.0 equiv) and methyl 3-(bromomethyl)-4-chlorobenzoate (110.6 mg, 0.42 mmol, 1.2 equiv) in DMF (1.4 mL) at 0° C. was added NaH (60% in mineral oil, 19.6 mg, 0.49 mmol, 1.4 equiv). The mixture was stirred at 0° C. for 1 h. The resulting mixture was quenched with 10% citric acid and extracted with ethyl acetate. The organic layer was washed with water (2×) and brine (1×), dried, and concentrated. The residue was dissolved in DCM (3 mL)/MeOH (1 mL) and cooled to 0° C. (Trimethylsilyl)diazomethane solution (2M in ether, 0.4 mL, 0.8 mmol, 2.3 equiv) was added. The mixture was stirred at 0° C. for 30 minutes, concentrated, and purified by flash column chromatography on silica eluting with ethyl acetate/hexanes to give 130.8 mg (83%) of 725a as orange syrup.

Step 2. 4-chloro-3-((1-(4-(2-cyclopropoxyphenyl)pyridin-3-yl)cyclopropoxy)methyl)benzoic acid (Intermediate 725b)

To a solution of methyl 4-chloro-3-((1-(4-(2-cyclopropoxyphenyl)pyridin-3-yl)cyclopropoxy)methyl)benzoate (725a, 12.3 mg, 0.0274 mmol, 1.0 equiv) in THF (0.2 mL) was added 1M NaOH solution (41 µL, 0.041 mmol, 1.5 equiv). The mixture was stirred at room temperature for 3 h and more 1M NaOH solution (41 µL, 0.041 mmol, 1.5 equiv) was added. The mixture was stirred at room temperature overnight, acidified with 10% citric acid, and extracted with ethyl acetate. The organic layer was washed with brine (1×), dried, and concentrated to give 725b which was used without purification.

Step 3. 4-chloro-3-((1-(4-(2-cyclopropoxyphenyl)pyridin-3-yl)cyclopropoxy)methyl)-N,N-dimethylbenzamide (I-725)

To a mixture of 4-chloro-3-((1-(4-(2-cyclopropoxyphenyl)pyridin-3-yl)cyclopropoxy)methyl)benzoic acid (725b, 0.0274 mmol, 1.0 equiv) and dimethylamine (40 wt. % in $H_2O$, 6.9 µL, 0.055 mmol, 2.0 equiv) in DMF (0.2 mL) were added N,N-diisopropylethylamine (23.2 µL, 0.137 mmol, 5.0 equiv) and HATU (20.8 mg, 0.0548 mmol, 2.0 equiv). The mixture was stirred at room temperature overnight h and purified by preparative HPLC to give 4.6 mg (29%, 2 steps) of the title compound I-725 TFA salt as a white solid. MS (ES, m/z): 463.2 [M+H]$^+$; $^1$H-NMR (400 MHz, $CD_3OD$) δ 8.93 (s, 1H), 8.74 (d, J=5.9 Hz, 1H), 7.83 (d, J=5.9 Hz, 1H), 7.49-7.34 (m, 4H), 7.30 (d, J=8.2 Hz, 1H), 7.07 (t, J=7.5 Hz, 1H), 7.02 (s, 1H), 4.45 (s, 2H), 3.57 (d, J=1.4 Hz, 1H), 3.12 (s, 3H), 2.93 (s, 3H), 1.24-1.09 (m, 4H), 0.71-0.58 (m, 2H), 0.45-0.36 (m, 2H).

Example 107: 1-(5-(4-chloro-3-((1-(4-(2-cyclopropoxyphenyl)pyridin-3-yl)cyclopropoxy) methyl)phenoxy)pentyl)-3-((2S,3R,4R,5R)-2,3,4,5,6-pentahydroxyhexyl)urea (I-726)

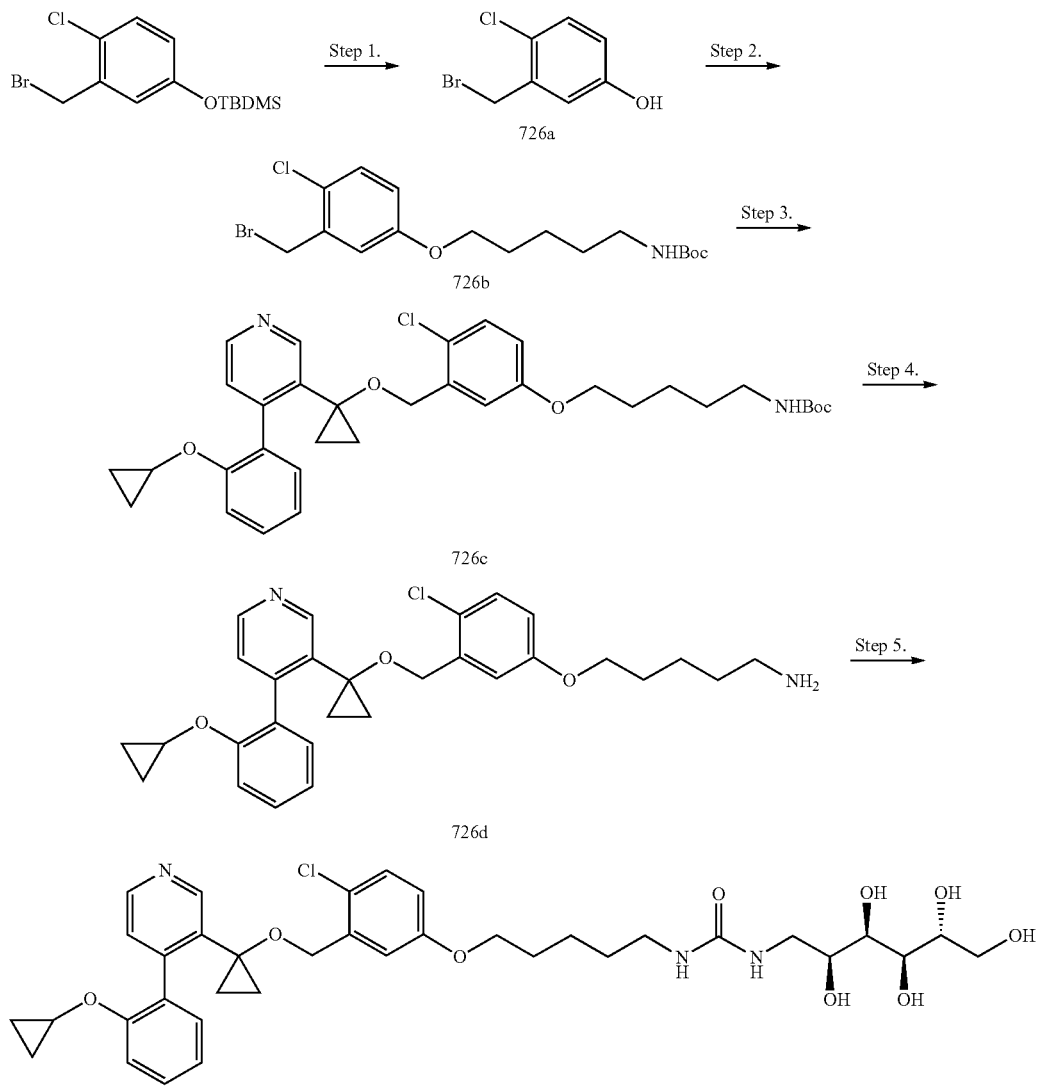

I-726

Step 1. 3-(bromomethyl)-4-chlorophenol (Intermediate 726a)

To a mixture of (3-(bromomethyl)-4-chlorophenoxy)(tert-butyl)dimethylsilane (320 mg, 0.953 mmol, 1.0 equiv) in THF (5.8 mL) at 0° C. was added 1M TBAF in THF (1.05 mL, 1.05 mmol, 1.1 equiv). The mixture was stirred at 0° C. for 10 minutes, quenched with water, and extracted with ethyl acetate. The organic layer was washed with brine (1×), dried, concentrated, and purified by flash column chromatography on silica eluting with 0-30% ethyl acetate/hexanes to give 186 mg (88%) of 726a as a white solid.

Step 2. tert-butyl (5-(3-(bromomethyl)-4-chlorophenoxy)pentyl)carbamate (Intermediate 726b)

To a solution of 3-(bromomethyl)-4-chlorophenol (726a, 127 mg, 0.575 mmol, 1.00 equiv), tert-butyl (5-hydroxypentyl)carbamate (146 mg, 0.718 mmol, 1.25 equiv), and PPh$_3$ (188 mg, 0.718 mmol, 1.25 equiv) in toluene (2 mL) at 0° C. was added DIAD (141 μL, 0.718 mmol, 1.25 equiv) dropwise. The mixture was stirred at 0° C. for 2 h, quenched with water, and extracted with ethyl acetate. The organic layer was washed with brine (1×), dried, concentrated, and purified by flash column chromatography on silica eluting with 0-40% ethyl acetate/hexanes to give 215 mg (92%) of 726b as a clear syrup.

Step 3. tert-butyl (5-(4-chloro-3-((1-(4-(2-cyclopropoxyphenyl)pyridin-3-yl)cyclopropoxy) methyl) phenoxy)pentyl)carbamate (Intermediate 726c)

To a mixture of 1-(4-(2-cyclopropoxyphenyl)pyridin-3-yl)cyclopropanol (A-23, 118 mg, 0.44 mmol, 1.0 equiv) and tert-butyl (5-(3-(bromomethyl)-4-chlorophenoxy) pentyl) carbamate (726b, 215 mg, 0.53 mmol, 1.2 equiv) in DMF (1.7 mL) at 0° C. was added NaH (60% in mineral oil, 24.7 mg, 0.62 mmol, 1.4 equiv). The mixture was stirred at 0° C. for 10 minutes and at room temperature for 1 h. The resulting mixture was quenched with saturated ammonium chloride and extracted with ethyl acetate. The organic layer was washed with water (2×) and brine (1×), dried, and concentrated, and purified by column chromatography to give 186.5 mg (71%) of 726c as an orange syrup.

Step 4. 5-(4-chloro-3-((1-(4-(2-cyclopropoxyphenyl)pyridin-3-yl)cyclopropoxy)methyl) phenoxy)pentan-1-amine (Intermediate 726d)

To a mixture of tert-butyl (5-(4-chloro-3-((1-(4-(2-cyclopropoxyphenyl)pyridin-3-yl)cyclopropoxy)methyl)phenoxy)pentyl)carbamate (726c, 186.5 mg, 0.314 mmol) in DCM (0.2 mL) was added 4.0 M HCl in dioxane (3 mL). The mixture was stirred at room temperature for 1 h and concentrated. The residue was diluted with ethyl acetate, washed with saturated NaHCO$_3$ (1×) and brine (1×), dried, and concentrated to give 726d which was used without further purification.

Step 5. 1-(5-(4-chloro-3-((1-(4-(2-cyclopropoxyphenyl)pyridin-3-yl)cyclopropoxy) methyl) phenoxy) pentyl)-3-((2S,3R,4R,5R)-2,3,4,5,6-pentahydroxyhexyl)urea (I-726)

To a mixture of 5-(4-chloro-3-((1-(4-(2-cyclopropoxyphenyl)pyridin-3-yl)cyclopropoxy)methyl)phenoxy)pentan-1-amine (726d, 0.169 mmol, 1.0 equiv) in DMF (1 mL) was added N,N'-disuccinimidyl carbonate (54.6 mg, 0.213 mmol, 1.3 equiv). The mixture was stirred at room temperature for 1 h. D-glucamine (73.5 mg, 0.406 mmol, 2.4 equiv) was added. The mixture was stirred at 60° C. overnight and purified by preparative HPLC to give 54.5 mg (46%, 2 steps) of the title compound I-726 as a white solid. MS (ES, m/z): 700.3 [M+H]$^+$. $^1$H-NMR (400 MHz, CD$_3$OD) δ.8.64 (s, 1H), 8.47 (d, J=5.1 Hz, 1H), 7.42-7.30 (m, 2H), 7.28 (d, J=7.5 Hz, 1H), 7.22 (d, J=5.1 Hz, 1H), 7.16 (d, J=8.7 Hz, 1H), 6.98 (dd, J=10.4, 4.2 Hz, 1H), 6.75 (dd, J=8.7, 2.8 Hz, 1H), 6.63 (d, J=2.7 Hz, 1H), 4.35 (s, 2H), 3.88 (t, J=6.2 Hz, 2H), 3.80-3.72 (m, 3H), 3.72-3.65 (m, 1H), 3.65-3.57 (m, 2H), 3.56-3.49 (m, 1H), 3.40 (dd, J=13.9, 4.5 Hz, 1H), 3.23-3.10 (m, 3H), 1.81-1.70 (m, 2H), 1.61-1.45 (m, 4H), 1.04-0.85 (m, 4H), 0.65-0.54 (m, 2H), 0.43-0.33 (m, 2H).

Example 108: 3-((4-chloro-3-((1-(4-(2-cyclopropoxyphenyl)pyridin-3-yl)cyclopropoxy) methyl) benzyl)oxy)-N-((2S,3R,4R,5R)-2,3,4,5,6-pentahydroxyhexyl)benzamide (I-727)

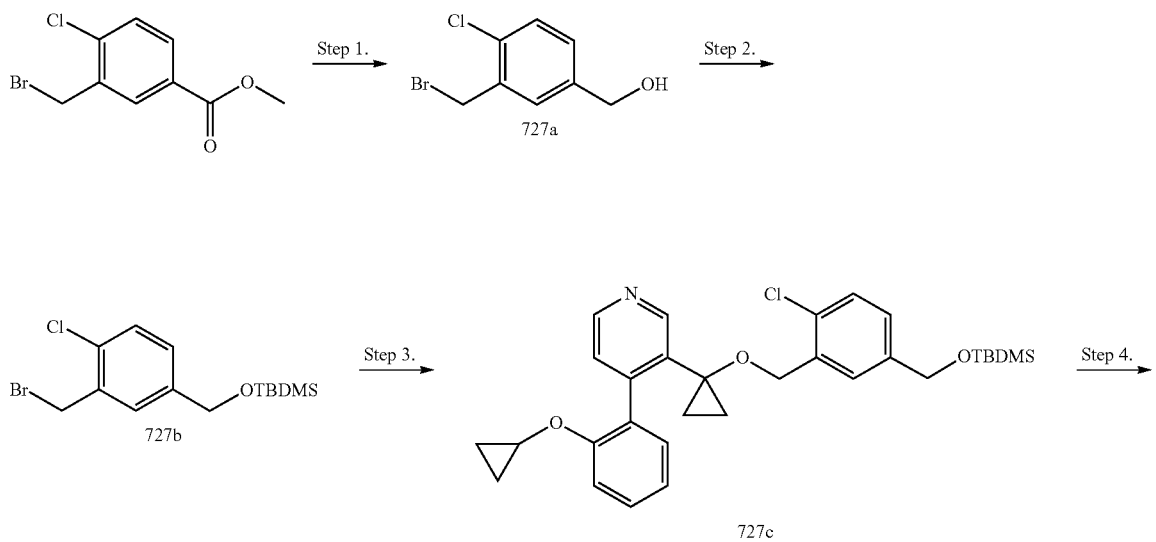

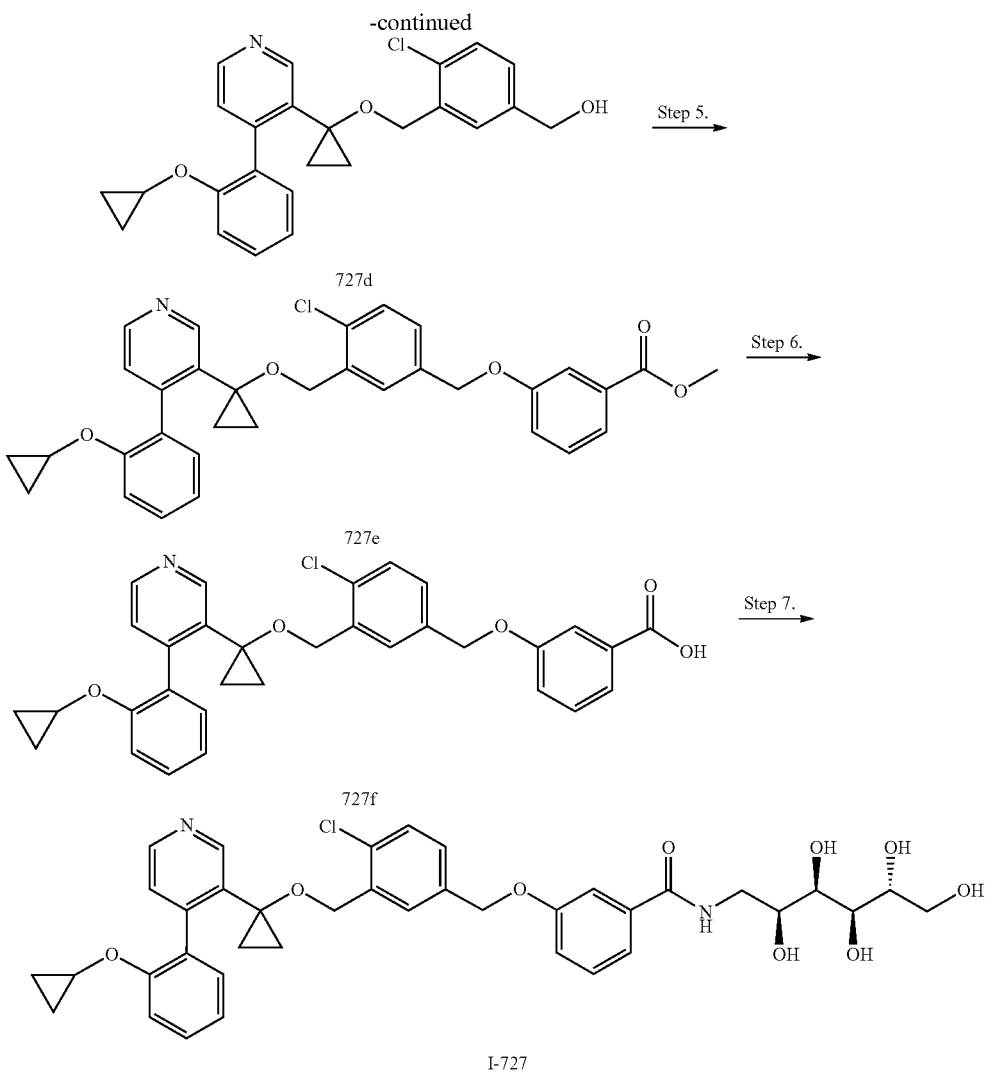

Step 1. (3-(bromomethyl)-4-chlorophenyl)methanol (Intermediate 727a)

To a mixture of methyl 3-(bromomethyl)-4-chlorobenzoate (1.570 g, 5.96 mmol, 1.0 equiv) in toluene (16 mL) at 0° C. was added DIBALH (1M in DCM, 11.9 mL, 11.9 mmol, 2.0 equiv) dropwise. The mixture was stirred at 0° C. for 2 h, quenched with 1M HCl, and extracted with ethyl acetate (2×). The combined organic layers were washed with brine (1×), dried, concentrated, and purified by flash column chromatography on silica eluting with ethyl acetate/hexanes to give 820 mg (58%) of 727a as a white solid.

Step 2. ((3-(bromomethyl)-4-chlorobenzyl)oxy)(tert-butyl)dimethylsilane (Intermediate 727b)

To a solution of (3-(bromomethyl)-4-chlorophenyl) methanol (727a, 750 mg, 3.19 mmol, 1.0 equiv) in DCM (15 mL) were added TBMDSCl (576 mg, 3.82 mmol, 1.2 equiv) and imidazole (434 mg, 6.37 mmol, 2.0 equiv). The mixture was stirred at 0° C. for 30 minutes, quenched with water, and extracted with ethyl acetate. The organic layer was washed with 1M HCl (1×), saturated NaHCO₃ (1×), and brine (1×), dried, concentrated, and purified by flash column chromatography on silica eluting with 0-10% ethyl acetate/hexanes to give 1.10 g (99%) of 727b as a clear syrup.

Step 3. 3-(1-((5-(((tert-butyldimethylsilyl)oxy) methyl)-2-chlorobenzyl)oxy)cyclopropyl)-4-(2-cyclopropoxyphenyl)pyridine (Intermediate 727c)

To a mixture of 1-(4-(2-cyclopropoxyphenyl)pyridin-3-yl)cyclopropanol (A-23, 553 mg, 2.069 mmol, 1.0 equiv) and ((3-(bromomethyl)-4-chlorobenzyl)oxy)(tert-butyl)dimethylsilane (727b, 796 mg, 2.28 mmol, 1.1 equiv) in DMF (16 mL) at 0° C. was added NaH (60% in mineral oil, 116 mg, 2.896 mmol, 1.4 equiv). The mixture was stirred at 0° C. for 40 minutes. The resulting mixture was quenched with saturated ammonium chloride and extracted with ethyl acetate. The organic layer was washed with water (2×) and brine (1×), dried, and concentrated, and purified by flash column chromatography on silica eluting with ethyl acetate/hexanes to give 882 mg (79%) of 727c as a yellow syrup.

Step 4. (4-chloro-3-((1-(4-(2-cyclopropoxyphenyl) pyridin-3-yl)cyclopropoxy) methyl) phenyl)methanol (Intermediate 727d)

To a mixture of 3-(1-((5-(((tert-butyldimethylsilyl)oxy) methyl)-2-chlorobenzyl) oxy)cyclopropyl)-4-(2-cyclopropoxyphenyl)pyridine (727c, 831 mg, 1.552 mmol, 1.0 equiv) in THF (9 mL) at 0° C. was added 1M TBAF in THF (1.71 mL, 1.71 mmol, 1.1 equiv). The mixture was stirred at 0° C. for 20 minutes, quenched with water, and extracted with ethyl acetate. The organic layer was washed with brine (1×), dried, concentrated, and purified by flash column chromatography on silica eluting with 0-60% ethyl acetate/hexanes to give 648 mg (99%) of 727d as a clear syrup.

Step 5. methyl 3-((4-chloro-3-((1-(4-(2-cyclopropoxyphenyl)pyridin-3-yl)cyclopropoxy) methyl) benzyl)oxy)benzoate (Intermediate 727e)

To a solution of (4-chloro-3-((1-(4-(2-cyclopropoxyphenyl)pyridin-3-yl)cyclopropoxy)methyl)phenyl)methanol (727d, 51 mg, 0.121 mmol, 1.00 equiv), methyl 3-hydroxybenzoate (23 mg, 0.151 mmol, 1.25 equiv), and PPh$_3$ (39.7 mg, 0.151 mmol, 1.25 equiv) in toluene (0.4 mL) at 0° C. was added DIAD (30 μL, 0.151 mmol, 1.25 equiv) dropwise. The mixture was slowly warmed to room temperature and stirred at room temperature overnight. The resulting mixture was quenched with water and extracted with ethyl acetate. The organic layer was washed with brine (1×), dried, concentrated, and purified by column chromatography to give 69.3 mg (103%) of 727e.

Step 6. 3-((4-chloro-3-((1-(4-(2-cyclopropoxyphenyl)pyridin-3-yl)cyclopropoxy) methyl)benzyl)oxy) benzoic acid (Intermediate 727f)

To a solution of methyl 3-((4-chloro-3-((1-(4-(2-cyclopropoxyphenyl)pyridin-3-yl)cyclopropoxy)methyl)benzyl) oxy)benzoate (727e, 69.3 mg, 0.124 mmol, 1.0 equiv) in THF (0.9 mL) was added 1M NaOH solution (0.187 mL, 0.187 mmol, 1.5 equiv). The mixture was stirred at room temperature overnight and more 1M NaOH solution (0.248 mL, 0.248 mmol, 2.0 equiv) was added. The mixture was stirred at room temperature for 5 h and 5M NaOH solution (50 μL, 0.25 mmol, 2.0 equiv) was added. The resulting mixture was stirred at room temperature overnight, acidified with 10% citric acid, and extracted with ethyl acetate. The organic layer was washed with brine (1×), dried, and concentrated to give 56.4 mg (84%) of 727f which was used without purification.

Step 7. 3-((4-chloro-3-((1-(4-(2-cyclopropoxyphenyl)pyridin-3-yl)cyclopropoxy)methyl) benzyl)oxy)-N-((2S,3R,4R,5R)-2,3,4,5,6-pentahydroxyhexyl) benzamide (I-727)

To a mixture of 3-((4-chloro-3-((1-(4-(2-cyclopropoxyphenyl)pyridin-3-yl)cyclopropoxy)methyl)benzyl)oxy)benzoic acid (727f, 22.9 mg, 0.0423 mmol, 1.0 equiv), and D-glucamine (10.7 mg, 0.0591 mmol, 1.4 equiv) in DMF (0.3 mL) were added N,N-diisopropylethylamine (35.9 μL, 0.212 mmol, 5.0 equiv) and HATU (22.5 mg, 0.059 mmol, 1.4 equiv). The mixture was stirred at room temperature for 1 h and purified by preparative HPLC to give 23.1 mg (77%) of the title compound I-727 as a white solid. MS (ES, m/z): 705.3 [M+H]$^+$; $^1$H-NMR (400 MHz, CD$_3$OD) δ 8.63 (s, 1H), 8.49-8.39 (m, 1H), 7.52-7.34 (m, 3H), 7.35-7.22 (m, 5H), 7.22-7.10 (m, 3H), 6.95 (t, J=7.1 Hz, 1H), 5.04 (s, 2H), 4.40 (s, 2H), 4.03-3.92 (m, 1H), 3.86-3.58 (m, 6H), 3.52-3.40 (m, 2H), 1.07-0.82 (m, 4H), 0.63-0.48 (m, 2H), 0.42-0.26 (m, 2H).

Example 109: (2S,3S,4R,5S)-2,3,4,5,6-pentahydroxy-N-[4-[N-(propan-2-yl)[4-chloro-5-([1-[4-(2-cyclopropoxyphenyl)pyridin-3-yl]cyclopropoxy] methyl)-2-fluorobenzene]sulfonamido]butyl] hexanamide (I-728)

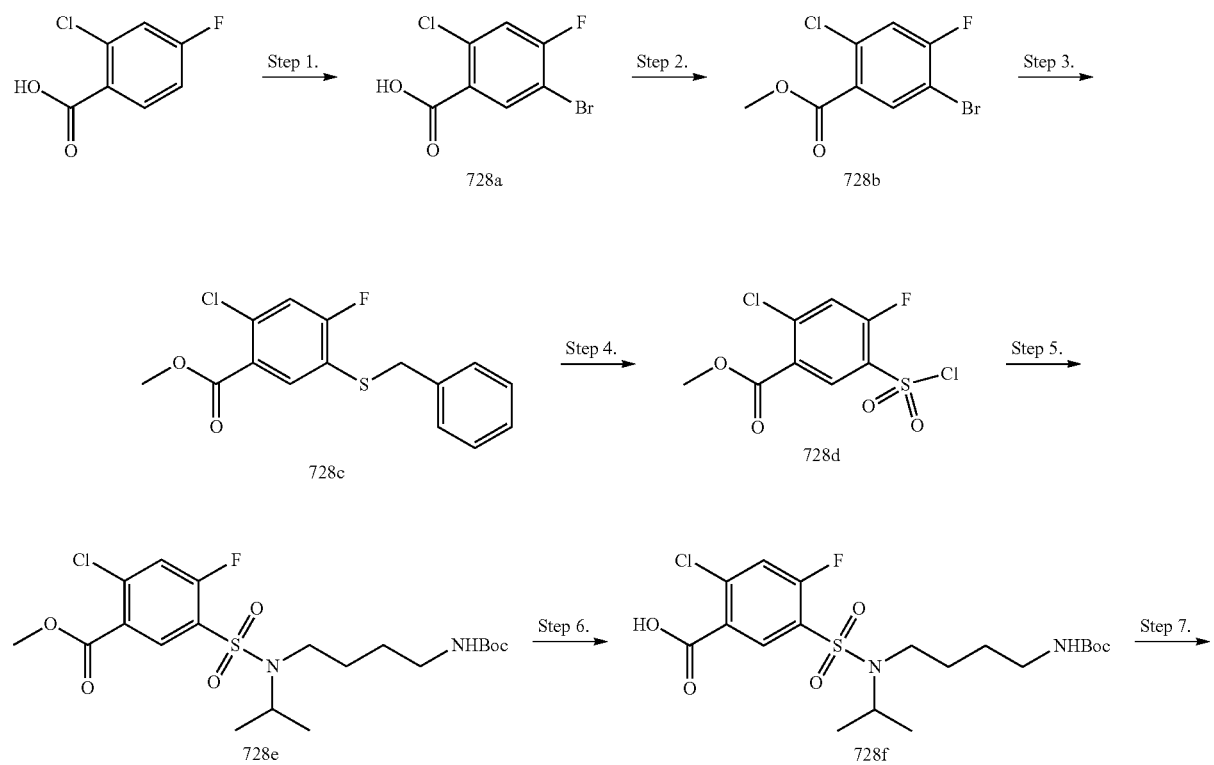

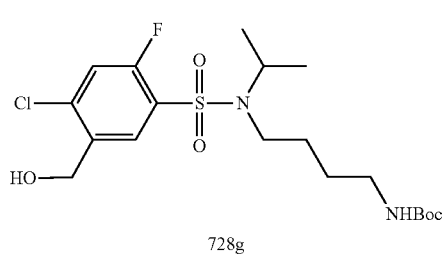

728g

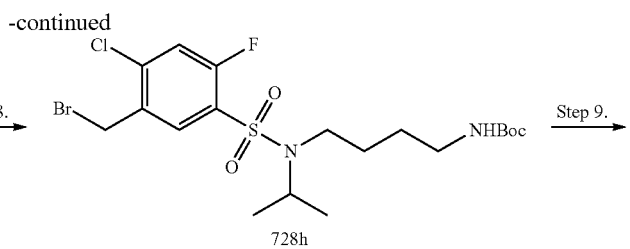

728h

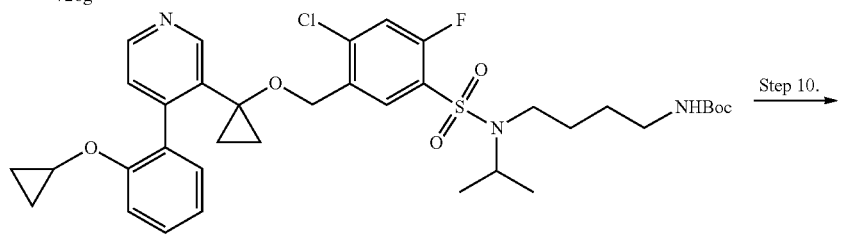

728i

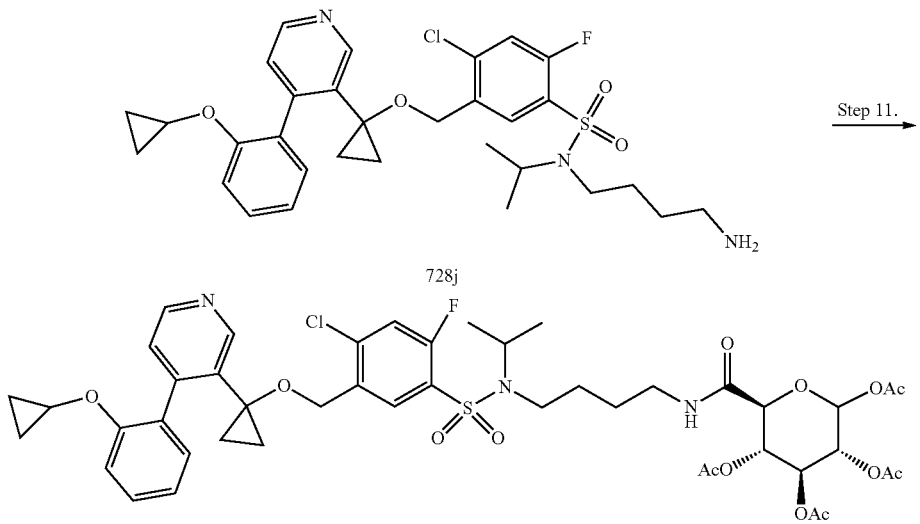

728j

728k

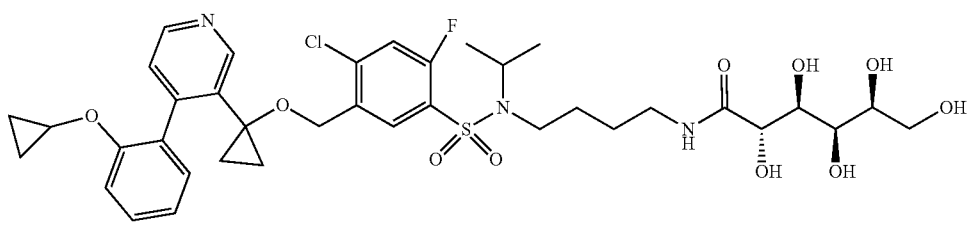

I-728

Step 1. 5-bromo-2-chloro-4-fluorobenzoic acid (Intermediate 728a)

A 100-mL 3-necked round-bottom flask was charged with a solution of 2-chloro-4-fluorobenzoic acid (15 g, 85.93 mmol, 1.0 equiv), chlorosulfonic acid (45 mL), Br$_2$ (1.52 mL), S (113 mg, 3.53 mmol, 0.04 equiv). The resulting solution was stirred overnight at 70° C. in an oil bath. The reaction was then quenched by the addition of 200 mL of water/ice. The solids were collected by filtration to provide 16 g (73%) of 5-bromo-2-chloro-4-fluorobenzoic acid 728a as a light yellow solid.

Step 2. Methyl 5-bromo-2-chloro-4-fluorobenzoate (Intermediate 728b)

A 500-mL 3-necked round-bottom flask was charged with a solution of 5-bromo-2-chloro-4-fluorobenzoic acid (728a, 16.2 g, 63.92 mmol, 1.0 equiv) in dichloromethane/CH$_3$OH (150/50 mL). This was followed by the addition of (diazomethyl)trimethylsilane (64 mL, 2M in Et$_2$O) dropwise with stirring at room temperature in 20 min. The resulting solution was stirred for 0.5 h at room temperature. The resulting mixture was concentrated under vacuum. The residue was applied onto a silica gel column with ethyl acetate/petroleum ether (1:10). This resulted in 6.83 g (40%) of methyl 5-bromo-2-chloro-4-fluorobenzoate 728b as a light yellow oil.

Step 3. Methyl
5-(benzylsulfanyl)-2-chloro-4-fluorobenzoate
(Intermediate 728c)

A 1000-mL round-bottom flask was charged with a solution of methyl 5-bromo-2-chloro-4-fluorobenzoate (728b, 6.833 g, 25.55 mmol, 1.0 equiv), phenylmethanethiol (3.1 mL), XantPhos (1.48 g, 2.56 mmol, 0.1 equiv), $Pd_2(dba)_3 \cdot CHCl_3$ (1.32 g, 1.44 mmol, 0.06 equiv) in dioxane (426 mL) and DIEA (8.6 mL). The resulting solution was stirred overnight at 80° C. in an oil bath and then concentrated under vacuum. The resulting solution was extracted with 3×300 mL of ethyl acetate and the combined organic layers were washed with 3×200 mL of brine. The mixture was dried over anhydrous sodium sulfate, filtered and concentrated in vacuo. The resulting residue was purified via silica gel column with ethyl acetate/petroleum ether (0-20%) to provide 6.8 g (86%) of methyl 5-(benzylsulfanyl)-2-chloro-4-fluorobenzoate 728c as a light yellow oil.

Step 4. Methyl
2-chloro-5-(chlorosulfonyl)-4-fluorobenzoate
(Intermediate 728d)

A 250-mL round-bottom flask was charged with a solution of methyl 5-(benzylsulfanyl)-2-chloro-4-fluorobenzoate (728c, 2.5 g, 8.04 mmol, 1.0 equiv), NCS (3.23 g, 24.2 mmol, 3.01 equiv) in AcOH (100.8 mL) and water (11.2 mL) and the resulting solution was stirred for 1.5 h at room temperature. The reaction mixture was cooled to 5-10° C. with a water/ice bath and then diluted with 200 mL of ethyl acetate. The organic layer was washed with 2×100 mL of $H_2O$ and 3×200 mL of brine, dried over anhydrous sodium sulfate, filtered, and concentrated under vacuum to provide 2.5 g (crude) of methyl 2-chloro-5-(chlorosulfonyl)-4-fluorobenzoate 728d as a light yellow oil.

Step 5. Methyl 5-[(4-[[(tert-butoxy)carbonyl]amino]
butyl)(propan-2-yl)sulfamoyl]-2-chloro-4-fluorobenzoate (Intermediate 728e)

A 25-mL round-bottom flask was charged with a solution of tert-butyl N-4-[(propan-2-yl)amino]butylcarbamate (2.8 g, 12.2 mmol, 1.51 equiv) TEA (2.25 mL), methyl 2-chloro-5-(chlorosulfonyl)-4-fluorobenzoate (728d, 2.31 g, 8.06 mmol, 1.0 equiv), dichloromethane (10 mL) and the resulting solution was stirred for 1.5 h at room temperature. The resulting mixture was diluted with ethyl acetate, washed with 2×100 mL of brine, dried over anhydrous sodium sulfate, filtered, and concentrated under vacuum. The resulting residue was purified via silica gel column eluting with ethyl acetate/petroleum ether (0 to 20%) to provide 1.5 g (39%) of methyl 5-[(4-[[(tert-butoxy)carbonyl]amino]butyl) (propan-2-yl)sulfamoyl]-2-chloro-4-fluorobenzoate 728e as a white solid.

Step 6. 5-[(4-[[(tert-butoxy)carbonyl]amino]butyl)
(propan-2-yl) sulfamoyl]-2-chloro-4-fluorobenzoic
acid (Intermediate 728f)

A 100-mL round-bottom flask purged and maintained under an inert atmosphere of nitrogen was charged with a solution of methyl 5-[(4-[[(tert-butoxy)carbonyl]amino] butyl) (propan-2-yl)sulfamoyl]-2-chloro-4-fluoro benzoate (728e, 2 g, 4.16 mmol, 1.0 equiv) in THF (20 mL, 5.0 equiv) and water (4 mL, 1.0 equiv). $LiOH \cdot H_2O$ (523.4 mg, 21.86 mmol, 3.0 equiv) was added and the resulting solution was stirred for 30 min at 60° C. in an oil bath. The pH value of the solution was then adjusted to 6 with hydrogen chloride (4 M). The resulting solution was extracted with 3×50 mL of ethyl acetate and the combined organic layers were concentrated under vacuum to provide 1.74 g (90%) of 5-[(4-[[(tert-butoxy)carbonyl]amino]butyl)(propan-2-yl)sulfamoyl]-2-chloro-4-fluorobenzoic acid 728f as a white solid.

Step 7. tert-butyl N-[4-[N-(propan-2-yl)[4-chloro-2-
fluoro-5-(hydroxymethyl)benzene]sulfonamido]
butyl]carbamate (Intermediate 728g)

A 250-mL round-bottom flask purged and maintained under an inert atmosphere of nitrogen was charged with a solution of 5-[(4-[[(tert-butoxy)carbonyl]amino]butyl)(propan-2-yl)sulfamoyl]-2-chloro-4-fluorobenzoic acid (728f, 1.74 g, 3.73 mmol, 1.0 equiv), IBCF (0.58 mL, 1.2 equiv) in THF (30 mL). TEA (0.6 mL, 1.2 equiv) was then added and the resulting mixture was stirred for 1 h at 0° C. To this was added $NaBH_4$ (564 mg, 14.91 mmol, 4.0 equiv) in ethanol (30 mL) and the resulting solution was stirred for 10 min at 0° C. in an ice/salt bath. The resulting mixture was concentrated under vacuum, extracted with 3×20 mL of ethyl acetate and the combined organic layers were concentrated in vacuo. The resulting residue was purified via silica gel column chromatography eluting with ethyl acetate/petroleum ether (0 to 30%) to provide 1.49 g (88%) of tert-butyl N-[4-[N-(propan-2-yl)[4-chloro-2-fluoro-5-(hydroxymethyl) benzene]sulfonamido]butyl]carbamate 728g as a yellow oil.

Step 8. tert-butyl N-[4-[N-(propan-2-yl)[5-(bro-
momethyl)-4-chloro-2-fluorobenzene]sulfonamido]
butyl]carbamate (Intermediate 728h)

A 100-mL 3-necked round-bottom flask purged and maintained under an inert atmosphere of nitrogen was charged with a solution of tert-butyl N-[4-[N-(propan-2-yl)[4-chloro-2-fluoro-5-(hydroxymethyl)benzene]sulfonamido] butyl]carbamate (728g, 1.485 g, 3.28 mmol, 1.0 equiv) in dichloromethane (20 mL) and tetrahydrofuran (20 mL, 1.0 equiv) and then cooled to 0° C. NBS (933.68 mg, 5.25 mmol, 1.6 equiv) and $PPh_3$ (1.29 g, 4.92 mmol, 1.5 equiv) were then added and the resulting solution was stirred for 30 min at room temperature and then concentrated under vacuum. The resulting residue was purified via silica gel column chromatography eluting with ethyl acetate/petroleum ether (0 to 20%) to provide 1.15 g (68%) of tert-butyl N-[4-[N-(propan-2-yl) [5-(bromomethyl)-4-chloro-2-fluorobenzene]sulfonamido]butyl]carbamate 728h as a white solid.

Step 9. tert-butyl N-[4-[N-(propan-2-yl)[4-chloro-5-
([1-[4-(2-cyclopropoxyphenyl)pyridin-3-yl]cyclo-
propoxy]methyl)-2-fluorobenzene]sulfonamido]
butyl]carbamate (Intermediate 728i)

A 250-mL 3-necked round-bottom flask purged and maintained under an inert atmosphere of nitrogen was charged with a solution of tert-butyl N-[4-[N-(propan-2-yl)[5-(bromomethyl)-4-chloro-2-fluorobenzene] sulfonamido]butyl] carbamate (728h, 1.15 g, 2.22 mmol, 1.0 equiv), 1-[4-(2-cyclopropoxyphenyl)pyridin-3-yl]cyclopropan-1-ol (592.6 mg, 2.22 mmol, 1.0 equiv) and DMF (70 mL). The mixture was stirred at 0° C. and NaH (106.5 mg, 4.44 mmol, 2.0 equiv) was then added in portions at 0° C. The resulting solution was stirred for 20 min at 0° C. in a water/ice bath and then quenched by the addition of 10 mL of NH$_4$Cl (sat). The resulting mixture was extracted with 3×20 mL of ethyl acetate and the combined organic layers were concentrated under vacuum. The resulting residue was purified via silica gel column eluting with ethyl acetate/petroleum ether (0 to 25%) to provide 1.32 g (85%) of tert-butyl N-[4-[N-(propan-2-yl)[4-chloro-5-([1-[4-(2-cyclopropoxyphenyl)pyridin-3-yl]cyclopropoxy] methyl)-2-fluorobenzene]sulfonamido] butyl] carbamate 728i as a white solid.

Step 10. N-(4-aminobutyl)-4-chloro-5-([1-[4-(2-cyclopropoxyphenyl)pyridin-3-yl] cyclopropoxy] methyl)-2-fluoro-N-(propan-2-yl)benzene-1-sulfonamide (Intermediate 728j)

A 100-mL round-bottom flask purged and maintained under an inert atmosphere of nitrogen was charged with a solution of tert-butyl N-[4-[N-(propan-2-yl)[4-chloro-5-([1-[4-(2-cyclopropoxyphenyl)pyridin-3-yl]cyclopropoxy] methyl)-2-fluorobenzene]sulfonamido]butyl]carbamate (728i, 1.323 g, 1.88 mmol, 1.0 equiv) in dichloromethane (3 mL, 1.0 equiv) and trifluoroacetic acid (30 mL, 10.0 equiv) and the resulting solution was stirred for 20 min at room temperature. The reaction was quenched by the addition of 10 mL of sodium bicarbonate and the resulting solution was extracted with 3×20 mL of ethyl acetate and the combined organic layers were concentrated under vacuum to provide 1.21 g (crude) of N-(4-aminobutyl)-4-chloro-5-([1-[4-(2-cyclopropoxyphenyl)pyridin-3-yl]cyclopropoxy]methyl)-2-fluoro-N-(propan-2-yl)benzene-1-sulfonamide 728j as a white solid.

Step 11. (2S,3S,4S,5R)-4,5,6-tris(acetyloxy)-2-([4-[N-(propan-2-yl)[4-chloro-5-([1-[4-(2-cyclopropoxyphenyl)pyridin-3-yl]cyclopropoxy]methyl)-2-fluorobenzene]sulfonamido] butyl]carbamoyl)oxan-3-yl acetate (Intermediate 728k)

A 25-mL round-bottom flask purged and maintained under an inert atmosphere of nitrogen was charged with a solution of N-(4-aminobutyl)-4-chloro-5-([1-[4-(2-cyclopropoxyphenyl)pyridin-3-yl]cyclopropoxy]methyl)-2-fluoro-N-(propan-2-yl)benzene-1-sulfonamide (728j, 500 mg, 0.83 mmol, 1.0 equiv), (2S,3S,4S,5R)-3,4,5,6-tetrakis(acetyloxy)oxane-2-carboxylic acid (301 mg, 0.83 mmol, 1.00 equiv), DIEA (321.9 mg, 2.49 mmol, 3.0 equiv), and HATU (473.3 mg, 1.24 mmol, 1.5 equiv) in DMF (10 mL). The resulting solution was stirred for 2 h at room temperature, diluted with water, extracted with 3×20 mL of ethyl acetate, and the combined organic layers were concentrated in vacuo. The resulting residue was purified via silica gel column chromatography eluting with ethyl acetate/petroleum ether (0 to 100%) to provide 601 mg (76%) of (2S,3S,4S,5R)-4,5,6-tris(acetyloxy)-2-([4-[N-(propan-2-yl)[4-chloro-5-([1-[4-(2-cyclopropoxyphenyl)pyridin-3-yl]cyclopropoxy]methyl)-2-fluorobenzene]sulfonamido]butyl]carbamoyl)oxan-3-yl acetate 728k as a white solid.

Step 12. (2S,3S,4R,5S)-2,3,4,5-pentahydroxy-N-[4-[N-(propan-2-yl)[4-chloro-5-([1-[4-(2-cyclopropoxyphenyl)pyridin-3-yl]cyclopropoxy]methyl)-2-fluorobenzene]sulfonamido]butyl]hexanamide (I-728)

A 8-mL vial was charged with a solution of (2S,3S,4S,5R)-4,5,6-tris(acetyloxy)-2-([4-[N-(propan-2-yl)[4-chloro-5-([1-[4-(2-cyclopropoxyphenyl)pyridin-3-yl]cyclopropoxy]methyl)-2-fluorobenzene]sulfonamido]butyl]carbamoyl)oxa3-yl acetate (728k, 200 mg, 0.21 mmol, 1.0 equiv), MeONa (1.06 mL, 0.5 equiv) in methanol (3 mL).NaBH$_4$ (16.0 mg, 0.42 mmol, 2.0 equiv) was added and the reaction mixture was stirred for 30 min at room temperature. The resulting mixture was concentrated and the resulting residue was purified by preparative HPLC using the following conditions: Column, Gemini-NX C18 AXAI Packed, 21.2×150 mm, 5um; mobile phase, Waters (0.05% NH$_4$OH) and ACN (30% ACN up to 55% in 9 min); Detector, UV 254 nm to provide 107.4 mg (65%) of (2S,3S,4R,5S)-2,3,4,5,6-pentahydroxy-N-[4-[N-(propan-2-yl)[4-chloro-5-([1-[4-(2-cyclopropoxyphenyl)pyridin-3-yl]cyclopropoxy]methyl)-2-fluorobenzene]sulfonamido]butyl]hexanamide I-728 as a white solid. (ES, m/z): [M+1]: 780
$^1$H NMR (300 MHz, Methanol-d$_4$) δ 0.43 (s, 2H), 0.64 (h, J=5.4, 4.9 Hz, 2H), 0.94-1.15 (m, 10H), 1.60 (dq, J=33.3, 7.8 Hz, 4H), 3.18-3.35 (m, 4H), 3.53-3.73 (m, 3H), 3.72-4.03 (m, 4H), 4.13 (d, J=5.9 Hz, 1H), 4.42 (s, 2H), 7.01 (t, J=7.3 Hz, 1H), 7.18-7.45 (m, 5H), 7.65 (d, J=7.7 Hz, 1H), 8.48 (d, J=5.1 Hz, 1H), 8.64 (s, 1H).

Example 110: N-[[4-chloro-3-([1-[4-(2-cyclopropoxyphenyl)pyridin-3-yl]cyclopropoxy] methyl)benzene]sulfonyl] (I-729)

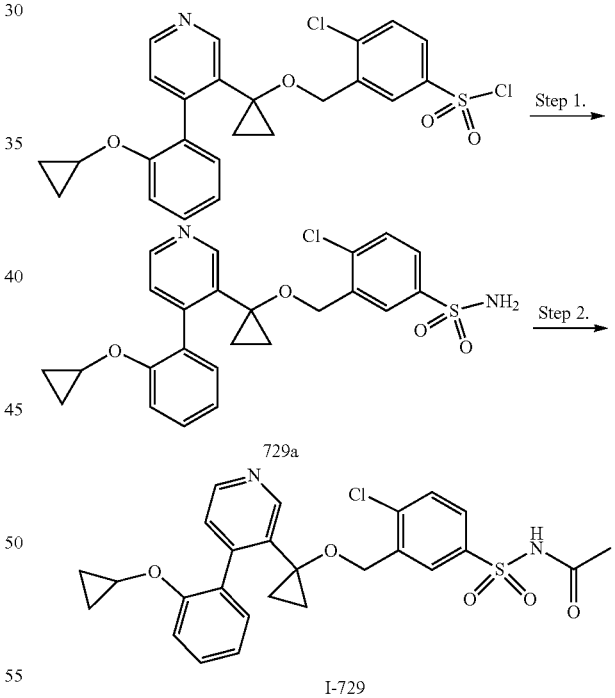

Step 1. 4-chloro-3-([1-[4-(2-cyclopropoxyphenyl) pyridin-3-yl]cyclopropoxy]methyl) benzene-1-sulfonamide (Intermediate 729a)

A 100-mL 3-necked round-bottom flask purged and maintained under an inert atmosphere of nitrogen was charged with a solution of 4-chloro-3-([1-[4-(2-cyclopropoxyphenyl) pyridin-3-yl]cyclopropoxy]methyl)benzene-1-sulfonyl chloride (200 mg, 0.41 mmol, 1.0 equiv) in dichloromethane (10 mL). To the above mixture was added NH₃ (g) and the resulting solution was stirred for 30 min at room temperature. The resulting mixture was concentrated under vacuum and the crude residue was purified via silica gel column chromatography eluting with ethyl acetate/petroleum ether (2:3) to provide 200 mg (69%) of 4-chloro-3-([1-[4-(2-cyclopropoxyphenyl)pyridin-3-yl]cyclopropoxy]methyl)benzene-1-sulfonamide 729a as a yellow solid.

Step 2. N-[[4-chloro-3-([1-[4-(2-cyclopropoxyphenyl)pyridin-3-yl]cyclopropoxy]methyl) benzene]sulfonyl]acetamide (I-729)

A 250-mL round-bottom flask was charged with a solution of 4-chloro-3-([1-[4-(2-cyclopropoxyphenyl)pyridin-3-yl]cyclopropoxy]methyl)benzene-1-sulfonamide (729a, 180 mg, 0.38 mmol, 1.0 equiv) in 50% aqueous sodium hydroxide (0.51 mL) and acetic anhydride (10 mL) and the resulting solution was stirred for 12 h at 80° C. in an oil bath. The reaction mixture was concentrated under vacuum and diluted with 100 mL of ethyl acetate. The organic layer was washed with 2×30 mL of sodium bicarbonate and 1×30 mL of water, dried, and concentrated in vacuo. The crude product was further purified by preparative HPLC with the following conditions: Column, XBridge C18 OBD Preparative Column, 19 mm×250 mm; mobile phase, water (10 mmol/L NH₄HCO₃) and ACN (15.0% to 50.0% ACN in 8 min); Detector, UV 254 nm to provide 64.0 mg (33%) of N-[[4-chloro-3-([1-[4-(2-cyclopropoxyphenyl)pyridin-3-yl]cyclopropoxy]methyl)benzene]sulfonyl] acetamide I-729 as a white solid. (ES, m/z): [M+1]: 513; ¹H NMR (300 MHz, DMSO-d₆) δ 12.17 (s, 1H), 8.71 (s, 1H), 8.53 (d, J=4.9 Hz, 1H), 7.78 (dd, J=8.3, 2.3 Hz, 1H), 7.71-7.58 (m, 2H), 7.43-7.21 (m, 3H), 7.16 (d, J=4.9 Hz, 1H), 7.07-6.96 (m, 1H), 4.40 (s, 2H), 3.61 (dt, J=6.1, 3.1 Hz, 1H), 2.08 (s, 0H), 1.89 (s, 3H), 0.91 (d, J=7.4 Hz, 4H), 0.66-0.53 (m, 2H), 0.34 (s, 2H).

Example 111: 4-chloro-5-([1-[4-(2-cyclopropoxyphenyl)pyridin-3-yl]cyclopropoxy]methyl)-2-methoxy-N,N-dimethylbenzene-1-sulfonamide (I-730)

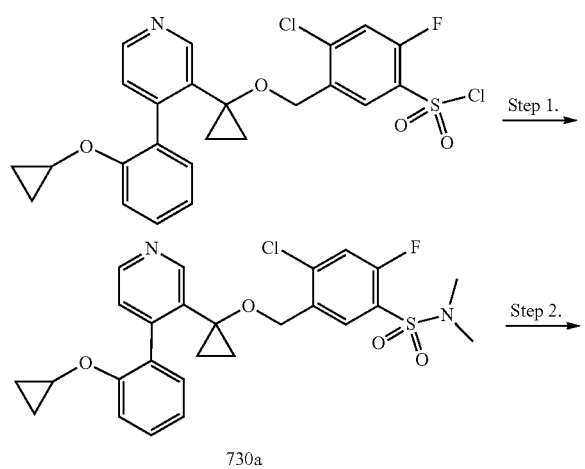

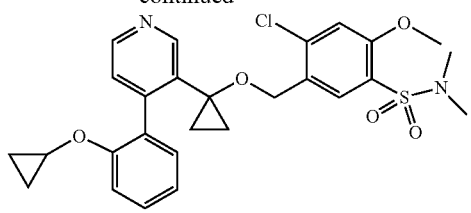

I-730

Step 1. 4-chloro-5-([1-[4-(2-cyclopropoxyphenyl)pyridin-3-yl]cyclopropoxy]methyl)-2-fluoro-N,N-dimethylbenzene-1-sulfonamide 730a A 25-mL round-bottom flask was charged with a solution of dimethylamine (2.82 mL), and 4-chloro-5-([1-[4-(2-cyclopropoxyphenyl)pyridin-3-yl]cyclopropoxy]methyl)-2-fluorobenzene-1-sulfonyl chloride (286.5 mg, 0.56 mmol, 1.0 equiv) in DCM (2 mL). The resulting solution was stirred for 1 h at 16-20° C. and then concentrated under vacuum. The resulting residue was purified via silica gel column chromatography eluting with ethyl acetate/petroleum ether (2:1) to provide 180 mg (62%) of 4-chloro-5-([1-[4-(2-cyclopropoxyphenyl)pyridin-3-yl]cyclopropoxy]methyl)-2-fluoro-N,N-dimethylbenzene-1-sulfonamide 730a as a light yellow oil.

Step 2. 4-chloro-5-([1-[4-(2-cyclopropoxyphenyl)pyridin-3-yl]cyclopropoxy]methyl)-2-methoxy-N,N-dimethylbenzene-1-sulfonamide (I-730)

A 25-mL round-bottom flask was charged with a solution of 4-chloro-5-([1-[4-(2-cyclopropoxyphenyl)pyridin-3-yl]cyclopropoxy]methyl)-2-fluoro-N,N-dimethylbenzene-1-sulfonamide (730a, 170 mg, 0.33 mmol, 1.0 equiv) in N,N-dimethylformamide (5 mL) followed by addition of sodium methoxide (53.3 mg, 0.99 mmol, 3.0 equiv). The resulting solution was stirred for 0.5 h at 16-20° C. and then quenched by the addition of 0.5 mL of water. The crude product was purified by prep-HPLC using the following conditions: Column, XBridge C18 OBD Prep Column, 19 mm×250 mm; mobile phase, waters (0.05% NH₄OH) and ACN (42% to 62% ACN in 8 min); Detector, UV 254 nm to provide 84 mg (48%) of 4-chloro-5-([1-[4-(2-cyclopropoxyphenyl)pyridin-3-yl]cyclopropoxy]methyl)-2-methoxy-N,N-dimethylbenzene-1 sulfonamide I-730 as a white solid. (ES, m/z): [M+1]⁺: 529; ¹H NMR (400 MHz, Methanol-d₄) δ 0.45 (dh, J=5.4, 3.1 Hz, 2H), 0.65 (ddd, J=7.3, 4.4, 3.1 Hz, 2H), 0.91 (s, 2H), 0.99 (d, J=5.2 Hz, 2H), 2.77 (s, 6H), 3.65 (tt, J=6.0, 2.9 Hz, 1H), 3.90 (s, 3H), 4.39 (s, 2H), 7.00 (ddd, J=7.5, 4.9, 3.6 Hz, 1H), 7.18-7.31 (m, 3H), 7.31-7.41 (m, 2H), 7.64 (s, 1H), 8.47 (d, J=5.1 Hz, 1H), 8.64 (d, J=0.8 Hz, 1H).

Example 112: 4-chloro-5-([1-[4-(2-cyclopropoxy-phenyl)pyridin-3-yl]cyclopropoxy]methyl)-2-hydroxy-N,N-dimethylbenzene-1-sulfonamide (I-731)

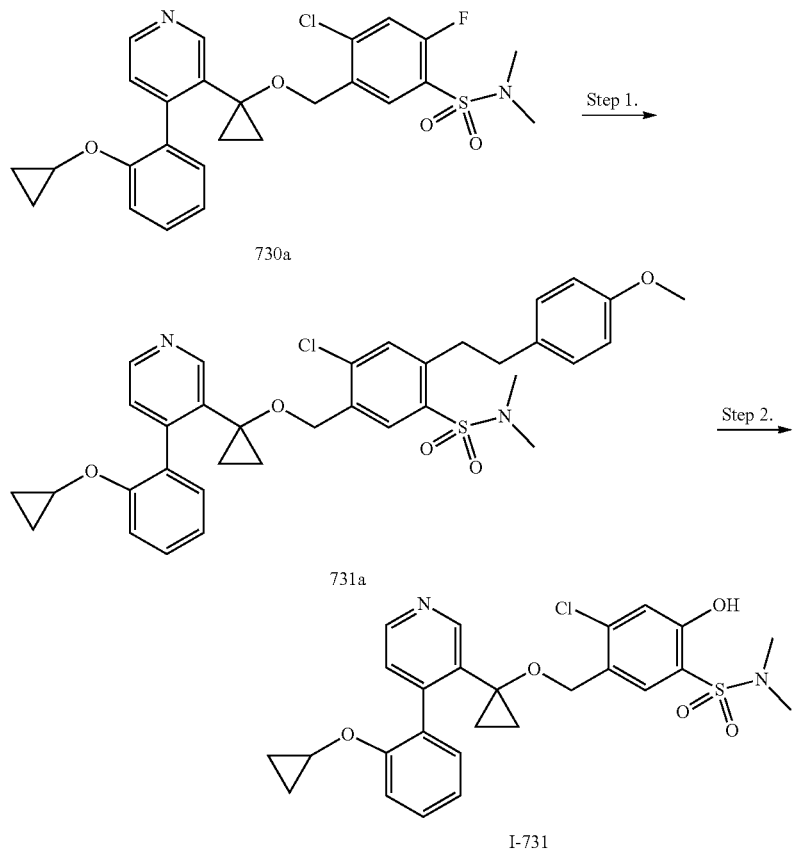

Step 1. 4-chloro-5-([1-[4-(2-cyclopropoxyphenyl)pyridin-3-yl]cyclopropoxy]methyl)-2-[(4-methoxyphenyl)methoxy]-N,N-dimethylbenzene-1-sulfonamide (Intermediate 731a)

To a solution of (4-methoxyphenyl)methanol (80 mg, 0.58 mmol, 1.2 equiv) and 730a (250 mg, 0.48 mmol, 1.0 equiv) in N,N-dimethylformamide (5 mL) was sodium hydride (35 mg, 1.46 mmol, 3.02 equiv). The resulting solution was stirred for 2 h at room temperature and then diluted with 20 mL of EtOAc. The reaction was then quenched by the addition of 20 mL of NH₄Cl. The resulting solution was extracted with 2×50 mL of ethyl acetate and the combined organic layers were washed with 3×100 mL of Brine, dried over anhydrous sodium sulfate, filtered, and concentrated under vacuum. The crude residue was purified via silica gel column chromatography eluting with ethyl acetate/petroleum ether (1:1) to provide 270 mg (88%) of 4-chloro-5-([1-[4-(2-cyclopropoxyphenyl)pyridin-3-yl]cyclopropoxy]methyl)-2-[(4-methoxyphenyl)methoxy]-N,N-dimethylbenzene-1-sulfonamide 731a as a white solid.

Step 2. 4-chloro-5-([1-[4-(2-cyclopropoxyphenyl)pyridin-3-yl]cyclopropoxy]methyl)-2-hydroxy-N,N-dimethylbenzene-1-sulfonamide (I-731)

To a solution of 4-chloro-5-([1-[4-(2-cyclopropoxyphenyl)pyridin-3-yl]cyclopropoxy]methyl)-2-[(4-methoxyphenyl)methoxy]-N,N-dimethylbenzene-1-sulfonamide (731a, 270 mg, 0.43 mmol, 1.0 equiv) in dichloromethane (10 mL) was added trifluoroacetic acid (4 mL). The resulting mixture was stirred for 30 min at room temperature and then concentrated under vacuum. The reaction mixture was diluted with 20 mL of ethyl acetate and the pH value of the solution was adjusted to 8.0 with sodium bicarbonate (100%). The resulting solution was extracted with 2×50 mL of ethyl acetate and the combined organic layers were washed with 50 mL of brine, dried over anhydrous sodium sulfate, filtered, and concentrated under vacuum. The crude product (10 mL) was purified by Prep-HPLC using the following conditions: Column, XBridge C18 OBD Prep Column, 19 mm×250 mm; mobile phase, waters (0.05% NH₄OH) and ACN (18% to 38% CAN over 8 min); Detector, UV 254 nm, to provide 90.6 mg (41%) of 4-chloro-5-([1-[4-(2-cyclopropoxyphenyl)pyridin-3-yl]cyclopropoxy]methyl)-2-hydroxy-N,N-dimethylbenzene-1-sulfonamide I-731 as a white solid. (ES, m/z): [M+1]⁺: 515; ¹H NMR (300 MHz, DMSO-d₆) δ 0.33-0.45 (m, 2H), 0.57-0.70 (m, 2H), 0.80 (d, J=17.7 Hz, 4H), 2.67 (s, 6H), 3.70 (dq, J=6.0, 3.0 Hz, 1H), 4.20 (s, 2H), 6.82 (s, 1H), 6.86-6.98 (m, 1H), 7.12 (d, J=5.0 Hz, 1H), 7.20-7.36 (m, 3H), 7.40 (s, 1H), 8.47 (d, J=5.0 Hz, 1H), 8.65 (s, 1H).

Example 113: 1-(4-[[4-chloro-3-([1-[4-(2-cyclopropoxyphenyl)pyridin-3-yl]cyclopropoxy]methyl)benzene]sulfonyl]-1,4-diazepan-1-yl)ethan-1-one (I-732)

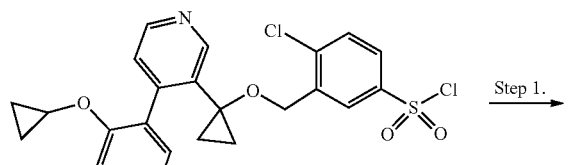

388e

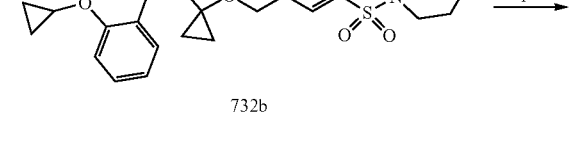

732a

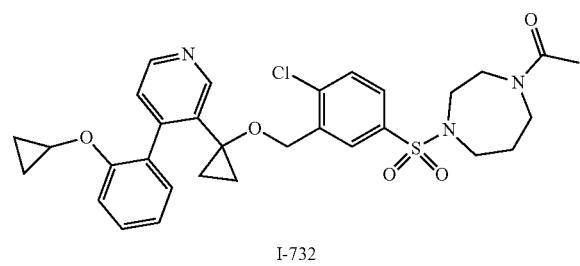

732b

I-732

Step 1. tert-butyl 4-[[4-chloro-3-([1-[4-(2-cyclopropoxyphenyl)pyridin-3-yl]cyclopropoxy] methyl)benzene]sulfonyl]-1,4-diazepane-1-carboxylate (Intermediate 732a)

A 100-mL round-bottom flask was charged with a solution of tert-butyl 1,4-diazepane-1-carboxylate (184 mg, 0.92 mmol, 1.5 equiv) in TEA (0.34 mL, 4.0 equiv) and dichloromethane (10 mL), and 4-chloro-3-([1-[4-(2-cyclopropoxyphenyl)pyridin-3-yl] cyclopropoxy]methyl)benzene-1-sulfonyl chloride (300 mg, 0.61 mmol, 1.0 equiv) and the resulting solution was stirred for 12 h at room temperature and then concentrated under vacuum. The crude residue was purified via silica gel column chromatography eluting with ethyl acetate/petroleum ether (2:1) to provide 300 mg (75%) of tert-butyl 4-[[4-chloro-3-([1-[4-(2-cyclopropoxyphenyl)pyridin-3-yl] cyclopropoxy]methyl)benzene]sulfonyl]-1,4-diazepane-1-carboxylate 732a as a yellow solid.

Step 2. 1-[[4-chloro-3-([1-[4-(2-cyclopropoxyphenyl)pyridin-3-yl]cyclopropoxy]methyl) benzene]sulfonyl]-1,4-diazepane (Intermediate 732b)

A 25-mL round-bottom flask was charged with a solution of tert-butyl 4-[[4-chloro-3-([1-[4-(2-cyclopropoxyphenyl)pyridin-3-yl]cyclopropoxy]methyl)benzene]sulfonyl]-1,4-diazepane-1-carboxylate (732a, 300 mg, 0.46 mmol, 1.0 equiv) in dichloromethane (10 mL) and trifluoroacetic acid (2 mL) and the resulting solution was stirred for 2.5 h at room temperature and then concentrated under vacuum. The resulting solution was diluted with 50 mL of ethyl acetate and the organic layer was washed with 2×20 mL of sodium bicarbonate, 1×20 mL of water, and 1×20 mL of brine, dried over anhydrous sodium sulfate, filtered, and concentrated under vacuum. This provided 198 mg (78%) of 1-[[4-chloro-3-([1-[4-(2-cyclopropoxyphenyl)pyridin-3-yl]cyclopropoxy]methyl)benzene]sulfonyl]-1,4-diazepane 732b as a white solid.

Step 3. 1-(4-[[4-chloro-3-([1-[4-(2-cyclopropoxyphenyl)pyridin-3-yl]cyclopropoxy]methyl) benzene]sulfonyl]-1,4-diazepan-1-yl)ethan-1-one (I-732)

A 100-mL round-bottom flask purged and maintained under an inert atmosphere of nitrogen was charged with a solution of 1-[[4-chloro-3-([1-[4-(2-cyclopropoxyphenyl)pyridin-3-yl]cyclopropoxy]methyl)benzene]sulfonyl]-1,4-diazepane (732b, 178 mg, 0.32 mmol, 1.0 equiv) and TEA (130 mg, 1.28 mmol, 4.0 equiv) in dichloromethane (10 mg, 0.12 mmol, 0.37 equiv). Acetyl chloride (39 mg, 0.50 mmol, 1.5 equiv) was then added dropwise with stirring and the resulting solution was stirred for 2 h at room temperature. The resulting mixture was concentrated under vacuum and diluted with 100 mL of ethyl acetate. The organic layer was washed with 30 mL of sodium bicarbonate, 30 mL of water, and 30 mL of brine, dried over anhydrous sodium sulfate, filtered, and concentrated under vacuum. The crude product was purified by Preparative HPLC using the following conditions: Column, XBridge C18 OBD Prep Column, 19 mm×250 mm; mobile phase, water (0.05% $NH_4OH$) and ACN (35% to 58% ACN over 8 min); Detector, UV 254 nm, to provide 76.2 mg (40%) of 1-(4-[[4-chloro-3-([1-[4-(2-cyclopropoxyphenyl)pyridin-3-yl]cyclopropoxy]methyl)benzene]sulfonyl]-1,4-diazepan-1-yl)ethan-1-one I-732 as a white solid. (ES, m/z): [M+1]: 596.20. $^1$H NMR (300 MHz, DMSO-$d_6$) δ 8.71 (s, 1H), 8.53 (d, J=5.0 Hz, 1H), 7.66 (dtd, J=11.3, 8.4, 2.4 Hz, 2H), 7.54 (dd, J=5.1, 2.1 Hz, 1H), 7.43-7.24 (m, 3H), 7.17 (d, J=5.0 Hz, 1H), 6.97 (t, J=7.3 Hz, 1H), 4.40 (s, 2H), 3.65 (tt, J=6.0, 3.0 Hz, 1H), 3.58-3.38 (m, 4H), 3.20 (q, J=5.5 Hz, 3H), 2.08 (s, 1H), 1.95 (s, 3H), 1.74 (dp, J=23.6, 5.9 Hz, 2H), 0.92 (d, J=7.3 Hz, 4H), 0.63 (d, J=6.2 Hz, 2H), 0.34 (s, 2H).

Example 114: 6-[[4-chloro-3-([1-[4-(2-cyclo-propoxyphenyl)pyridin-3-yl]cyclopropoxy]methyl)benzene]sulfonyl]-2-methoxy-5,6,7,8-tetrahydro-1,6-naphthyridine (I-733)

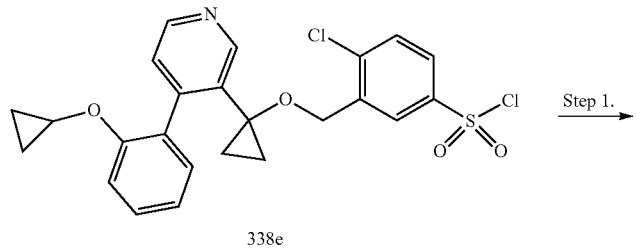

338e

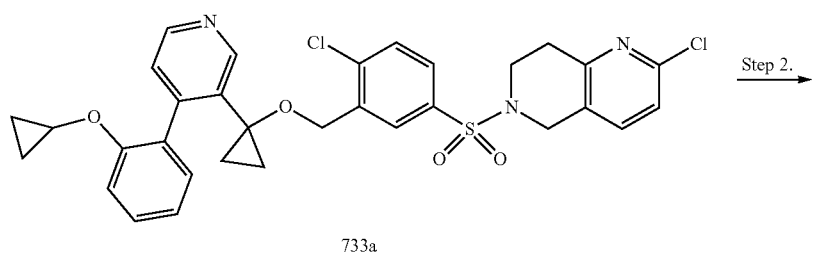

733a

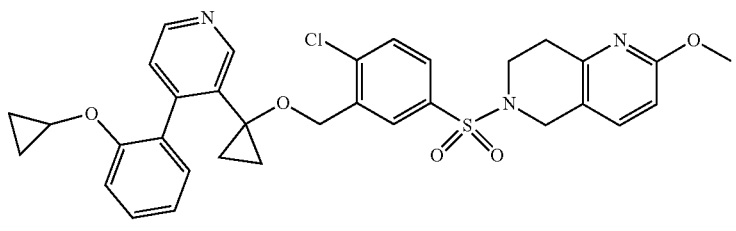

I-733

Step 1. 2-chloro-6-[[4-chloro-3-([1-[4-(2-cyclo-propoxyphenyl)pyridin-3-yl]cyclopropoxy]methyl)benzene]sulfonyl]-5,6,7,8-tetrahydro-1,6-naphthyridine (Intermediate 733a)

A 25-mL round-bottom flask purged and maintained under an inert atmosphere of nitrogen was charged with a solution of 4-chloro-3-([1-[4-(2-cyclopropoxyphenyl)pyridin-3-yl]cyclopropoxy]methyl)benzene-1-sulfonyl chloride (150 mg, 0.31 mmol, 1.0 equiv), 2-chloro-5,6,7,8-tetrahydro-1,6-naphthyridine hydrochloride (537.8 mg, 2.62 mmol, 1.5 equiv) in TEA (0.407 mL, 4.0 equiv) and dichloromethane (10 mL) and the resulting solution was stirred for 10 min at room temperature. The reaction mixture was diluted with water, extracted with 3×10 mL of ethyl acetate, and the combined layers were concentrated in vacuo. The crude product was purified via silica gel column chromatography eluting with ethyl acetate/petroleum ether to provide 275 mg of 2-chloro-6-[[4-chloro-3-([1-[4-(2-cyclopropoxyphenyl)pyridin-3-yl]cyclopropoxy]methyl)benzene]sulfonyl]-5,6,7,8-tetrahydro-1,6-naphthyridine 733a as a yellow solid.

Step 2. 6-[[4-chloro-3-([1-[4-(2-cyclopropoxyphenyl)pyridin-3-yl]cyclopropoxy]methyl) benzene]sulfonyl]-2-methoxy-5,6,7,8-tetrahydro-1,6-naphthyridine (I-733)

A 10-mL round-bottom flask purged and maintained under an inert atmosphere of nitrogen was charged with a solution of (733a, 200 mg, 0.32 mmol, 1.0 equiv) and MeONa (173.54 mg, 10.0 equiv) in dioxane (5.7 mL) and the resulting solution was stirred overnight at 115° C. in an oil bath. The crude product was purified by Preparative HPLC using the following conditions: Column, XBridge C18 OBD Prep Column, 19 mm×250 mm; mobile phase, water (0.05% $NH_4OH$) and ACN (62.0% to 80.0% ACN over 8 min); Detector, UV 254 nm, to provide 34.1 mg (17%) of 6-[[4-chloro-3-([1-[4-(2-cyclopropoxyphenyl)pyridin-3-yl]cyclopropoxy] methyl)benzene]sulfonyl]-2-methoxy-5,6,7,8-tetrahydro-1,6-naphthyridine (I-733) as a white solid. (ES, m/z): [M+1]: 618; $^1$H NMR (300 MHz, DMSO-$d_6$) δ 0.32 (s, 2H), 0.59 (d, J=6.6 Hz, 2H), 0.79-0.94 (m, 4H), 1.95 (s, 1H), 2.47 (s, 4H), 2.76 (q, J=15.4, 10.8 Hz, 2H), 3.06-3.18 (m, 1H), 3.60 (s, 1H), 3.75 (s, 3H), 4.10 (s, 2H), 4.36 (s, 2H), 6.60 (d, J=8.3 Hz, 1H), 6.93 (t, J=7.3 Hz, 1H), 7.13 (d, J=5.0 Hz, 1H), 7.29 (q, J=8.5 Hz, 3H), 7.42 (d, J=8.5 Hz, 1H), 7.54 (s, 1H), 7.66 (q, J=8.3 Hz, 2H), 8.50 (d, J=4.9 Hz, 1H), 8.68 (s, 1H).

Example 115: 6-[[4-chloro-3-([1-[4-(2-cyclopropoxyphenyl)pyridin-3-yl]cyclopropoxy]methyl)benzene]sulfonyl]-5,6,7,8-tetrahydro-1,6-naphthyridin-2-ol (I-734)

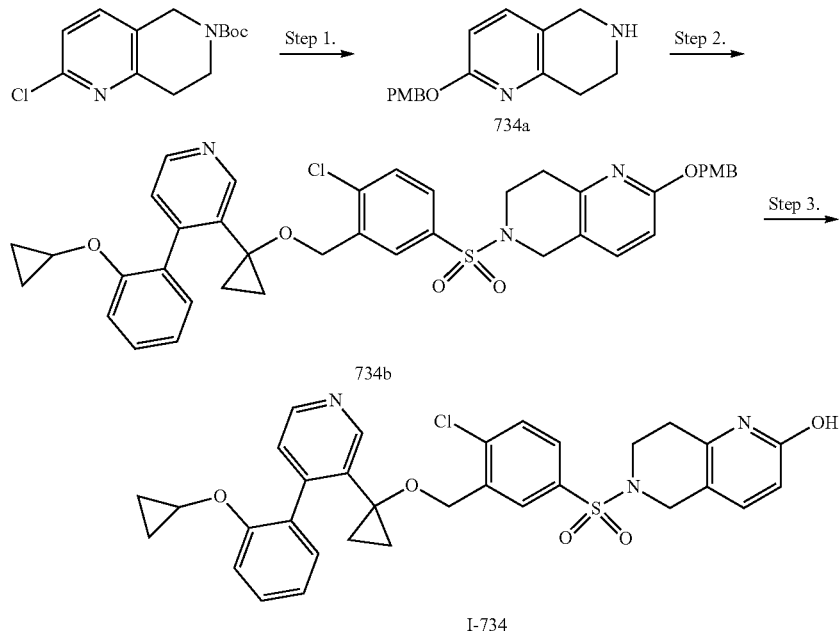

Step 1. 2-[(4-Methoxyphenyl)methoxy]-5,6,7,8-tetrahydro-1,6-naphthyridine (Intermediate 734a)

A 25-mL round-bottom flask purged and maintained under an inert atmosphere of nitrogen was charged with a solution of tert-butyl 2-chloro-5,6,7,8-tetrahydro-1,6-naphthyridine-6-carboxylate (241 mg, 0.90 mmol, 1.0 equiv) and (4-methoxyphenyl)methanol (185.9 mg, 1.35 mmol, 1.5 equiv) in dioxane (8 mL), and followed by addition of potassium tert-butoxide (251.6 mg, 2.24 mmol, 0.8 equiv) and the resulting solution was stirred for 2 h at 115° C. in an oil bath. The reaction mixture was quenched with water, extracted with 3×10 mL of ethyl acetate, and the combined organic layers were concentrated and purified via silica gel column chromatography eluting with dichloromethane/methanol (10:1) to provide 131 mg (54%) of 2-[(4-methoxyphenyl)methoxy]-5,6,7,8-tetrahydro-1,6-naphthyridine 734a as a yellow solid.

Step 2. 6-[[4-chloro-3-([1-[4-(2-cyclopropoxyphenyl)pyridin-3-yl]cyclopropoxy] methyl) benzene]sulfonyl]-2-[(4-methoxyphenyl)methoxy]-5,6,7,8-tetrahydro-1,6-naphthyridine (Intermediate 734b)

A 50-mL round-bottom flask purged and maintained under an inert atmosphere of nitrogen was charged with a solution of 2-[(4-methoxyphenyl)methoxy]-5,6,7,8-tetrahydro-1,6-naphthyridine (734a, 131 mg, 0.48 mmol, 1.0 equiv) and 4-chloro-3-([1-[4-(2-cyclopropoxyphenyl)pyridin-3-yl]cyclopropoxy]methyl)benzene-1-sulfonyl chloride (356 mg, 0.73 mmol, 1.5 equiv) in TEA (2.67 mL, 4.0 equiv) and dichloromethane (9 mL) and the resulting solution was stirred for 30 min at room temperature. The mixture was extracted with 3×10 mL of ethyl acetate and the combined organic layers were concentrated. The crude product was purified via silica gel column chromatography eluting with ethyl acetate/petroleum ether (2:1) to provide 198 mg (56%) of 6-[[4-chloro-3-([1-[4-(2-cyclopropoxyphenyl)pyridin-3-yl]cyclopropoxy]methyl)benzene]sulfonyl]-2-[(4-methoxyphenyl)methoxy]-5,6,7,8-tetrahydro-1,6-naphthyridine 734b as a yellow solid.

Step 3. 6-[[4-chloro-3-([1-[4-(2-cyclopropoxyphenyl)pyridin-3-yl]cyclopropoxy]methyl) benzene]sulfonyl]-5,6,7,8-tetrahydro-1,6-naphthyridin-2-ol (I-734)

A 25-mL round-bottom flask purged and maintained under an inert atmosphere of nitrogen was charged with a solution of 6-[[4-chloro-3-([1-[4-(2-cyclopropoxyphenyl)pyridin-3-yl]cyclopropoxy]methyl)benzene] sulfonyl]-2-[(4-methoxyphenyl)methoxy]-5,6,7,8-tetrahydro-1,6-naphthyridine (734b, 180 mg, 0.25 mmol, 1.0 equiv) in dichloromethane (9 mL, 1.0 equiv) and trifluoroacetic acid (3 mL, 3.0 equiv). The resulting solution was stirred for 30 min at room temperature. The pH value of the solution was adjusted to 8 with sodium bicarbonate (sat.). The resulting solution was extracted with 50 mL of dichloromethane and the organic layers combined and dried over sodium sulfate and concentrated under vacuum. The crude product was purified by Preparative HPLC with the following conditions: Column, XBridge C18 OBD Prep Column, 19 mm×250 mm; mobile phase, water (0.05% NH$_4$OH) and ACN (48% ACN up to 65% in 8 min); Detector, UV 254 nm, to provide 76.7 mg (51%) of 6-[[4-chloro-3-([1-[4-(2-cyclopropoxyphenyl)pyridin-3-yl]cyclopropoxy]methyl)benzene]sulfonyl]-5,6,7,8-tetrahydro-1,6-naphthyridin-2-ol I-734 as a white solid. (ES, m/z): [M+1]: 604; $^1$H NMR (300 MHz, Methanol-$d_4$) δ 0.39 (s, 2H), 0.61 (d, J=6.2 Hz, 2H), 1.01 (d, J=8.8 Hz, 4H), 2.69 (d, J=6.1 Hz, 2H), 3.35 (t, J=5.7 Hz, 2H), 3.52-3.61 (m, 1H), 4.01 (s, 2H), 4.47 (s, 2H), 6.37 (d, J=9.3 Hz, 1H), 6.96-7.08 (m, 1H), 7.18-7.41 (m, 5H), 7.57 (d, J=9.1 Hz, 2H), 7.72 (dd, J=8.3, 2.3 Hz, 1H), 8.48 (d, J=5.1 Hz, 1H), 8.66 (s, 1H).

Example 116: 1-(4-[N-methyl[4-chloro-3-([1-[4-(2-cyclopropoxyphenyl)pyridin-3-yl]cyclopropoxy]methyl)benzene]sulfonamido](d$_8$)butyl)-3-[(2S,3R,4S,5R)-1,3,4,5,6-pentahydroxyhexan-2-yl]urea (I-735)

Step 1. tert-butyl phenyl carbonate (Intermediate 735a)

A 100-mL 3-necked round-bottom flask purged and maintained under an inert atmosphere of nitrogen was charged with a solution of 2-methylpropan-2-ol (9.5 g, 128.17 mmol, 1.0 equiv) in pyridine (12.8 mL) and dichloromethane (22 mL). Phenyl chloroformate (20 g, 127.74 mmol, 1.0 equiv) was then added dropwise with stirring at room temperature over 60 min and the resulting solution was stirred for 3 h at room temperature. The reaction was then quenched by the addition of 32 mL of water and diluted with 100 mL of DCM. The resulting mixture was washed with 2×32 mL of 2M $H_2SO_4$ and 1×100 mL of brine, dried over anhydrous

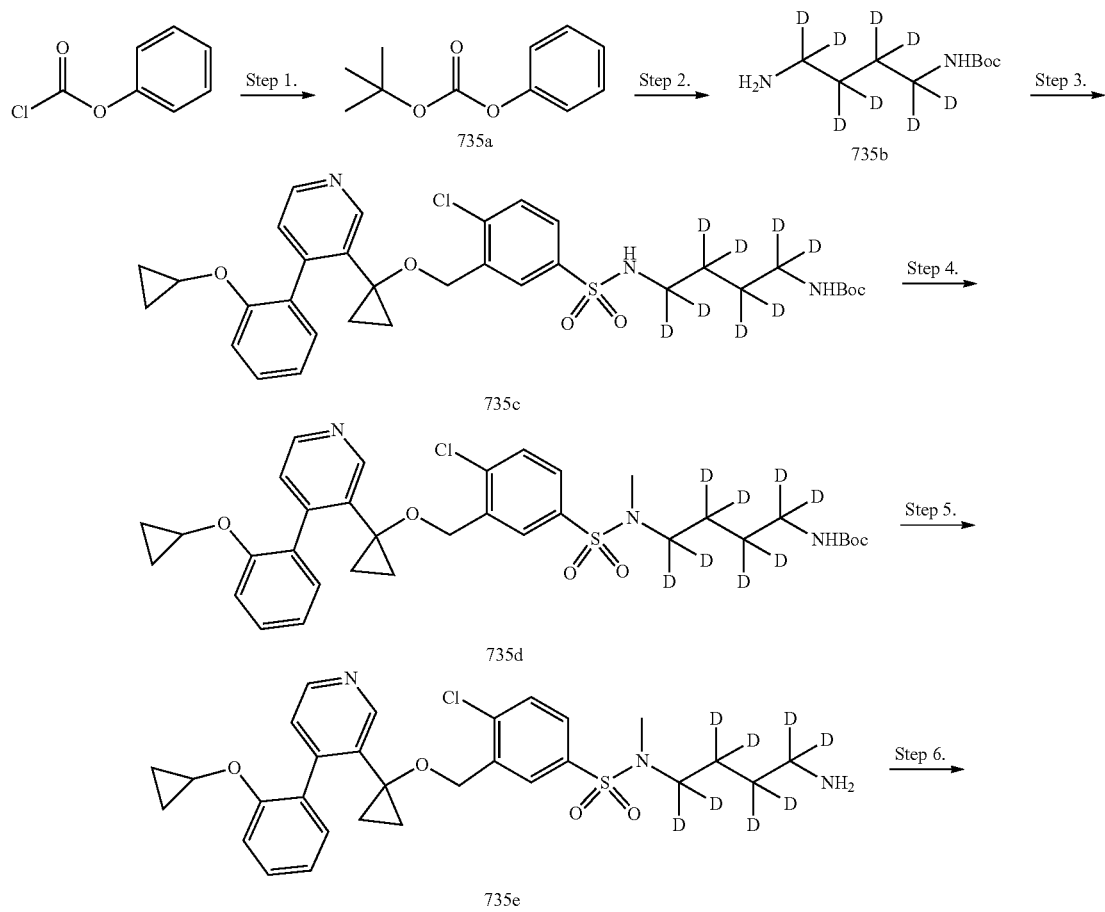

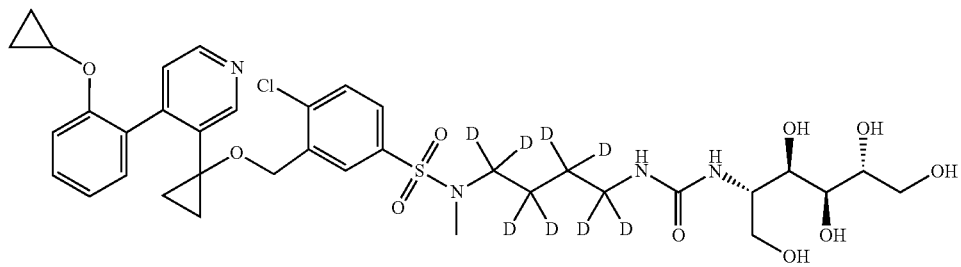

I-735 sodium sulfate, filtered, and concentrated under vacuum. The crude product was purified by distillation under reduced pressure (2 mm Hg) and the fraction collected at 90° C. provided 17 g (69%) of tert-butyl phenyl carbonate 735a as colorless oil.

Step 2. tert-butyl N-[4-amino(d$_8$)butyl]carbamate (Intermediate 735b)

A 250-mL round-bottom flask was charged with a solution of tert-butyl phenyl carbonate (735a, 574.2 mg, 2.96 mmol, 1.0 equiv), (d$_8$)-butane-1,4-diamine dihydrochloride (500 mg, 2.96 mmol, 1.0 equiv), and sodium bicarbonate (994 mg, 11.83 mmol, 4.0 equiv) in ethanol (45 mL) and the resulting solution was stirred overnight at 80° C. in an oil bath and then concentrated under vacuum. The crude residue was dissolved in 50 mL of H$_2$O and the pH value of the solution was adjusted to 3.0 with hydrogen chloride (2 mol/L). The resulting solution was washed with 4×80 mL of dichloromethane. The pH of the aqueous layer was adjusting to 11.0 using sodium hydroxide (2 mol/L) and the resulting solution was extracted with 5×100 mL of dichloromethane. The combined organic layers were dried over anhydrous sodium sulfate, filtered, and concentrated to provide 285 mg (49%) of tert-butyl N-[4-amino(d$_8$)butyl]carbamate 735b as orange oil.

Step 3. tert-butyl N-(4-[[4-chloro-3-([1-[4-(2-cyclopropoxyphenyl)pyridin-3-yl] cyclopropoxy]methyl) benzene]sulfonamido](d$_8$)butyl)carbamate (Intermediate 735c)

A 50-mL 3-necked round-bottom flask purged and maintained under an inert atmosphere of nitrogen was charged with a solution of tert-butyl N-[4-amino-(d$_8$)-butyl]carbamate (735b, 285 mg, 1.45 mmol, 1.0 equiv) in dichloromethane (20 mL) and TEA (0.821 mL). 4-chloro-3-([1-[4-(2-cyclopropoxyphenyl)pyridin-3-yl]cyclopropoxy]methyl) benzene-1-sulfonyl chloride (1.29 g, 2.63 mmol, 1.81 equiv) was then added dropwise with stirring at 15-25° C. over 15 min and the resulting solution was stirred overnight at room temperature. The reaction mixture was diluted with 20 mL of DCM, quenched by the addition of 50 mL of water, and extracted with 2×50 mL of ethyl acetate. The combined organic layers were washed with 100 mL of brine, dried over anhydrous sodium sulfate, filtered, and concentrated under vacuum. The crude residue was purified via silica gel column chromatography eluting with ethyl acetate/petroleum ether (1:1) to provide 650 mg (69%) of tert-butyl N-(4-[[4-chloro-3-([1-[4-(2-cyclopropoxyphenyl)pyridin-3-yl]cyclopropoxy]methyl) benzene]sulfonamido]-(d$_8$)-butyl) carbamate 735c as a white solid.

Step 4. tert-butyl N-(4-[N-methyl[4-chloro-3-([1-[4-(2-cyclopropoxyphenyl)pyridin-3-yl]cyclopropoxy] methyl)benzene]sulfonamido]-(d$_8$)-butyl)carbamate (Intermediate 735d)

A 25-mL 3-necked round-bottom flask purged and maintained under an inert atmosphere of nitrogen was charged with a solution of tert-butyl N-(4-[[4-chloro-3-([1-[4-(2-cyclopropoxyphenyl)pyridin-3-yl]cyclopropoxy]methyl) benzene]sulfonamido]-(d$_8$)-butyl) carbamate (780 mg, 1.20 mmol, 1.0 equiv), methanol (0.105 mL), and PPh$_3$ (680 mg, 2.59 mmol, 2.16 equiv) in tetrahydrofuran (8 mL). A solution of DEAD (0.4 mL) in toluene (0.73 ml) was then added dropwise with stirring at 0-5° C. over 20-30 min and the resulting solution was stirred overnight at room temperature and concentrated under vacuum. The crude residue was purified via silica gel column chromatography eluting with ethyl acetate/petroleum ether (1:1) to provide 770 mg (97%) of tert-butyl N-(4-[N-methyl[4-chloro-3-([1-[4-(2-cyclopropoxyphenyl) pyridin-3-yl]cyclopropoxy]methyl)benzene]sulfonamido]-(d$_8$)-butyl) carbamate 735d as white solid.

Step 5. N-[4-amino(d$_8$)butyl]-4-chloro-3-([1-[4-(2-cyclopropoxyphenyl)pyridin-3-yl] cyclopropoxy] methyl)-N-methylbenzene-1-sulfonamide (Intermediate 735e)

A 100-mL round-bottom flask was charged with a solution of tert-butyl N-(4-[N-methyl[4-chloro-3-([1-[4-(2-cyclopropoxyphenyl)pyridin-3-yl]cyclopropoxy]methyl)benzene]sulfonamido]-(d$_8$)-butyl)carbamate (735d, 770 mg, 1.16 mmol, 1.0 equiv) in TFA/DCM (5/20 mL) and the resulting solution was stirred for 1 h at room temperature. The pH value of the solution was adjusted to ~9.0-10.0 with sodium bicarbonate (100%) and the resulting solution was extracted with 3×200 mL of ethyl acetate. The combined organic layers were washed with 1×100 mL of brine, dried over anhydrous sodium sulfate, filtered, and concentrated under vacuum. The crude residue was purified via silica gel column chromatography eluting with dichloromethane/ methanol (10:1) to provide 591 mg (90%) of N-[4-amino-(d$_8$)-butyl]-4-chloro-3-([1-[4-(2-cyclopropoxyphenyl)pyridin-3-yl]cyclopropoxy]methyl)-N-methylbenzene-1-sulfonamide 735e as a white solid.

Step 6. 1-(4-[N-methyl[4-chloro-3-([1-[4-(2-cyclopropoxyphenyl)pyridin-3-yl]cyclopropoxy]methyl) benzene]sulfonamido](d$_8$)butyl)-3-[(2S,3R,4S,5R)-1, 3,4,5,6-pentahydroxyhexan-2-yl]urea (I-735)

A 100-mL round-bottom flask was charged with a solution of N-[4-amino-(d$_8$)-butyl]-4-chloro-3-([1-[4-(2-cyclopropoxyphenyl)pyridin-3-yl]cyclopropoxy]methyl)-N-methylbenzene-1-sulfonamide (735e, 1.034 g, 1.83 mmol, 1.0 equiv) in N,N-dimethylformamide (18.3 mL) and DSC (516.2 mg). The mixture was stirred at room temperature for 1 hour and then (2R,3S,4R,5S)-5-aminohexane-1,2,3,4,6-pentol (995 mg, 5.49 mmol, 3.0 equiv) was added. The resulting solution was stirred for 1 h at room temperature and then for an additional 3 h at 60° C. in an oil bath. The reaction mixture was diluted with 25 mL of H$_2$O, and extracted with 5×50 mL of ethyl acetate. The combined organic layers were dried over anhydrous sodium sulfate, filtered, and concentrated. The crude residue was purified by preparative HPLC chromatography eluting with ACN/H$_2$O (0 to 40%) to provide 0.84 g (59%) of 1-(4-[N-methyl[4-chloro-3-([1-[4-(2-cyclopropoxyphenyl)pyridin-3-yl]cyclopropoxy]methyl)benzene]sulfonamido]-(d$_8$)-butyl)-3-[(2S, 3R,4S,5R)-1,3,4,5,6-pentahydroxyhexan-2-yl]urea I-735 as a white solid. (ES, m/z): [M+1]: 771; $^1$H NMR (400 MHz, Methanol-d$_4$) δ 0.34-0.43 (m, 2H), 0.56-0.66 (m, 2H), 0.95-1.04 (m, 4H), 2.66 (s, 3H), 3.52-3.72 (m, 6H), 3.73-3.89 (m, 2H), 3.96 (dd, J=4.9, 2.8 Hz, 1H), 4.47 (s, 2H), 7.02 (td, J=7.2, 1.6 Hz, 1H), 7.20-7.30 (m, 2H), 7.31-7.43 (m, 2H), 7.49-7.59 (m, 2H), 7.64 (dd, J=8.5, 2.2 Hz, 1H), 8.49 (d, J=5.1 Hz, 1H), 8.66 (d, J=0.7 Hz, 1H).

Example 117: 3-(4-[N-methyl[4-chloro-3-([1-[4-(2-cyclopropoxyphenyl)pyridin-3-yl]cyclopropoxy]methyl)benzene]sulfonamido]butyl)-1-[2-(2-[2-[([4-[([2-[2-(2-[[(4-[N-methyl[4-chloro-3-([1-[4-(2-cyclopropoxyphenyl)pyridin-3-yl]cyclopropoxy]methyl) benzene]sulfonamido]butyl)carbamoyl]amino]ethoxy)ethoxy]ethyl]carbamoyl)amino]butyl]carbamoyl)amino]ethoxy]ethoxy)ethyl]urea (I-736)
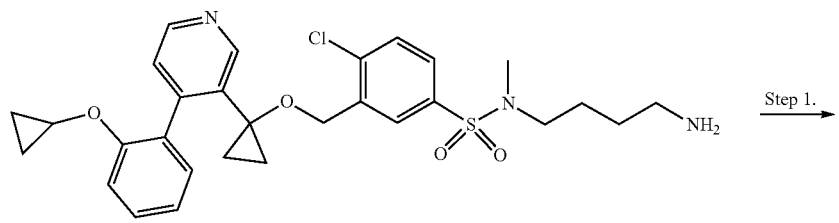
389e
Step 1.
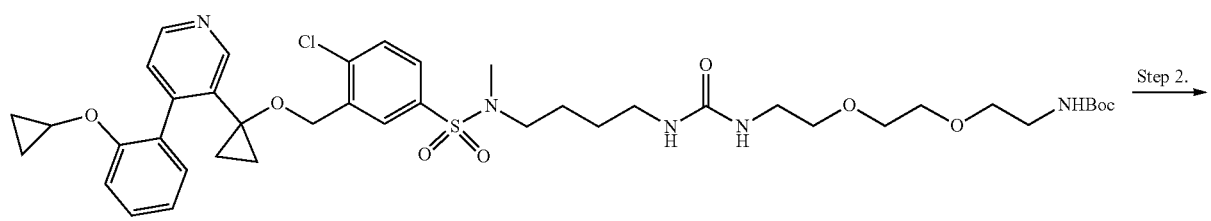
736a
Step 2.
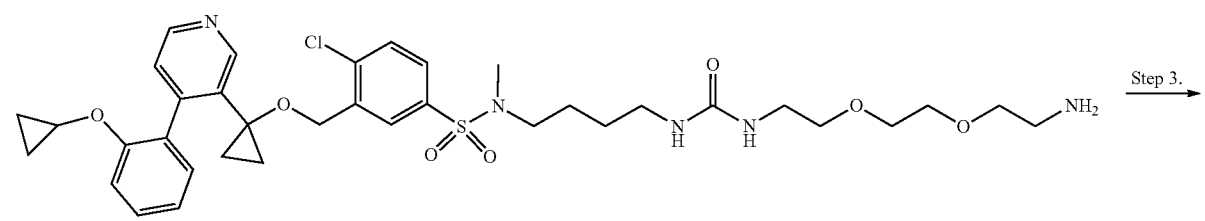
736b
Step 3.
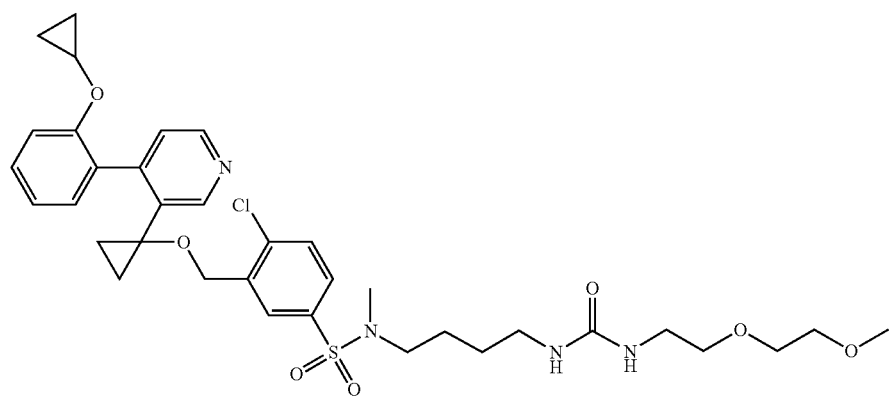

-continued

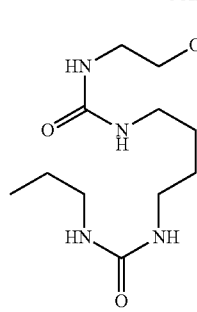
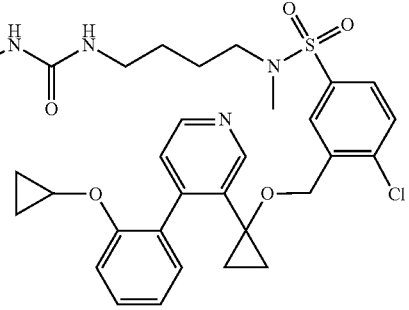

I-736

Step 1. tert-butyl N-[2-[2-(2-[[(4-[N-methyl[4-chloro-3-([1-[4-(2-cyclopropoxyphenyl)pyridin-3-yl]cyclopropoxy]methyl)benzene]sulfonamido]butyl)carbamoyl]amino]ethoxy)ethoxy]ethyl]carbamate (Intermediate 736a)

A 8-mL vial was charged with a solution of N-(4-aminobutyl)-4-chloro-3-([1-[4-(2-cyclopropoxyphenyl)pyridin-3-yl]cyclopropoxy]methyl)-N-methylbenzene-1-sulfonamide (389e, 183.2 mg, 0.33 mmol, 1.0 equiv) and DSC (93 mg, 1.1 equiv) in N,N-dimethylformamide (3.3 mL). The mixture was stirred at room temperature for 1 hour and then tert-butyl N-[2-[2-(2-aminoethoxy)ethoxy]ethyl]carbamate (270 mg, 1.09 mmol, 3.0 equiv) was added. The resulting solution was stirred for 60 minutes at 60° C. in an oil bath. The reaction was then quenched by the addition of 4.1 mL of 10% $Na_2CO_3$ and extracted with 3×20 mL of ethyl acetate and the combined organic layers were concentrated in vacuo. The crude residue was purified via silica gel column chromatography eluting with dichloromethane/methanol (5:1). This resulted in 273 mg (100%) of tert-butyl N-[2-[2-(2-[[(4-[N-methyl[4-chloro-3-([1-[4-(2-cyclopropoxyphenyl)pyridin-3-yl]cyclopropoxy]methyl) benzene]sulfonamido]butyl)carbamoyl]amino] ethoxy)ethoxy]ethyl]carbamate 736a as a yellow solid.

Step 2. 3-[2-[2-(2-aminoethoxy)ethoxy]ethyl]-1-(4-[N-methyl[4-chloro-3-([1-[4-(2-cyclopropoxyphenyl)pyridin-3-yl]cyclopropoxy]methyl)benzene]sulfonamido]butyl)urea (Intermediate 736b)

A 250-mL round-bottom flask was charged with a solution of tert-butyl N-[2-[2-(2 [[(4-[N-methyl[4-chloro-3-([1-[4-(2-cyclopropoxyphenyl)pyridin-3-yl]cyclopropoxy]methyl)benzene]sulfonamido]butyl)carbamoyl] amino]ethoxy) ethoxy]ethyl]carbamate (736a, 273 mg, 0.33 mmol, 1.0 equiv) in dichloromethane (8 mL, 10.0 equiv) and trifluoroacetic acid (0.8 mL, 1.0 equiv) and the resulting solution was stirred for 1 h at room temperature. The pH value of the solution was adjusted to ~9.0-10.0 with sodium bicarbonate and then extracted with 3×20 mL of ethyl acetate. The combined organic layers combined were concentrated in vacuo and the crude residue was a purified via silica gel column chromatography eluting with dichloromethane/methanol (5:1) to provide 164 mg (68%) of 3-[2-[2-(2-aminoethoxy) ethoxy]ethyl]-1-(4-[N-methyl[4-chloro-3-([1-[4-(2-cyclopropoxyphenyl)pyridin-3-yl]cyclopropoxy]methyl)benzene]sulfonamido]butyl)urea 736b as a yellow solid.

Step 3. 3-(4-[N-methyl[4-chloro-3-([1-[4-(2-cyclopropoxyphenyl)pyridin-3-yl]cyclopropoxy]methyl) benzene]sulfonamido]butyl)-1-[2-(2-[2-[((4-[((2-[2-(2-[[(4-[N-methyl[4-chloro-3-([1-[4-(2-cyclopropoxyphenyl)pyridin-3-yl]cyclopropoxy] methyl) benzene]sulfonamido]butyl) carbamoyl] amino]ethoxy)ethoxy]ethyl]carbamoyl)amino]butyl] carbamoyl)amino]ethoxy]ethoxy)ethyl]urea (I-736)

To a solution of 3-[2-[2-(2-aminoethoxy)ethoxy]ethyl]-1-(4-[N-methyl[4-chloro-3-([1-[4-(2-cyclopropoxyphenyl)pyridin-3-yl]cyclopropoxy]methyl) benzene]sulfonamido]butyl)urea (736b, 50 mg, 0.07 mmol, 1.0 equiv) in N,N-dimethylformamide (0.46 mL) was added 1,4-diisocyanatobutane (4.3 mg, 0.03 mmol, 0.5 equiv) and the resulting solution was stirred for 1 h at 60° C. in an oil bath. The resulting mixture was concentrated under vacuum and the crude residue was purified via silica gel column chromatography eluting with $ACN:H_2O$ (0% to 35%) to provide 30 mg (27%) of 3-(4-[N-methyl[4-chloro-3-([1-[4-(2-cyclopropoxyphenyl)pyridin-3-yl]cyclopropoxy]methyl)benzene]sulfonamido]butyl)-1-[2-(2-[2-[((4-[((2-[2-(2-[[(4-[N-methyl[4-chloro-3-([1-[4-(2-cyclopropoxyphenyl)pyridin-3-yl]cyclopropoxy]methyl)benzene]sulfonamido]butyl) carbamoyl] amino]ethoxy)ethoxy]ethyl]carbamoyl)amino] butyl]carbamoyl)amino]ethoxy]ethoxy)ethyl]urea I-736 as a white solid. (ES, m/z): [M+1]:1599; $^1$H NMR (400 MHz, Methanol-$d_4$) δ 0.39 (d, J=2.8 Hz, 2H), 0.57-0.66 (m, 2H), 0.94-1.03 (m, 4H), 1.44-1.60 (m, 6H), 2.66 (s, 3H), 2.96 (t, J=6.5 Hz, 2H), 3.08-3.17 (m, 3H), 3.24-3.35 (m, 7H), 3.47-3.63 (m, 9H), 4.47 (s, 2H), 7.01 (td, J=7.2, 1.6 Hz, 1H), 7.19-7.29 (m, 2H), 7.31-7.43 (m, 2H), 7.51-7.58 (m, 2H), 7.64 (dd, J=8.2, 2.3 Hz, 1H), 8.48 (d, J=5.0 Hz, 1H), 8.66 (s, 1H).

Example 118: 3-(4-[N-methyl[4-chloro-3-([1-[4-(2-cyclopropoxyphenyl)pyridin-3-yl]cyclopropoxy]methyl)benzene]sulfonamido]butyl)-1-[2-(2-[2-[([2-[2-(2-[[(4-[N-methyl[4-chloro-3-([1-[4-(2-cyclopropoxyphenyl)pyridin-3-yl]cyclopropoxy]methyl)benzene]sulfonamido]butyl)carbamoyl]amino]ethoxy]ethoxy]ethyl]carbamoyl)amino]ethoxy]ethoxy) ethyl]urea (I-737)
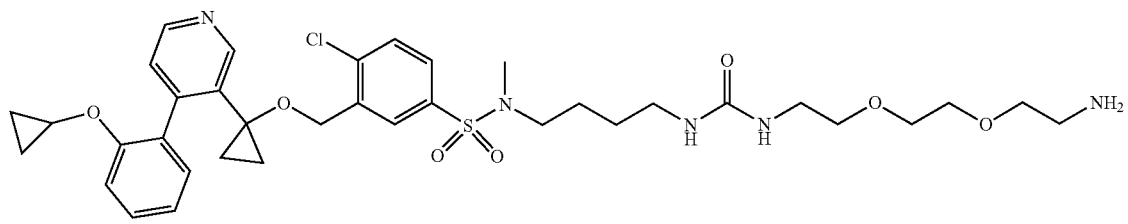
736b
Step 2.
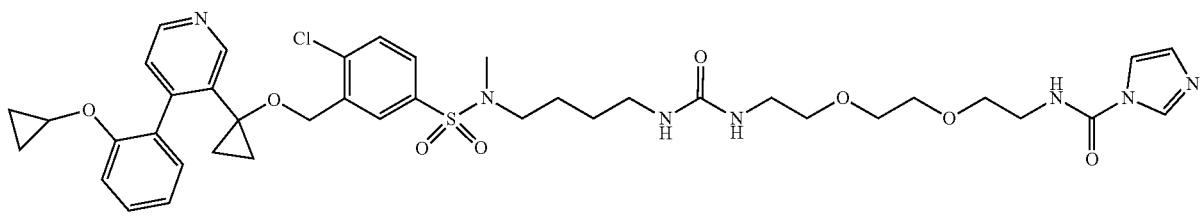
737a
Step 2.
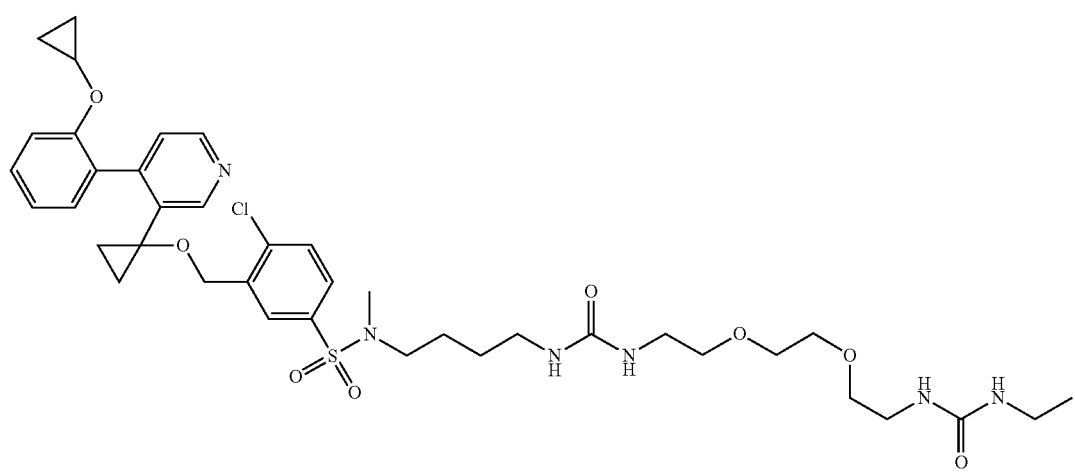

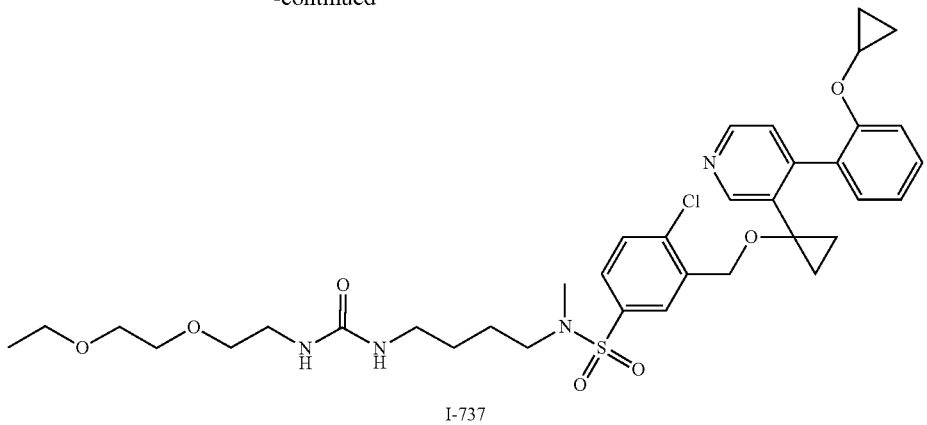

I-737

Step 1. N-[2-[2-(2-[[(4-[N-methyl[4-chloro-3-([1-[4-(2-cyclopropoxyphenyl)pyridin-3-yl]cyclopropoxy]methyl)benzene]sulfonamido]butyl)carbamoyl]amino]ethoxy)ethoxy]ethyl]-1H-imidazole-1-carboxamide (Intermediate 737a)

A 8-mL vial was charged with a solution of CDI (33.3 mg, 0.21 mmol, 3.0 equiv) and 3-[2-[2-(2-aminoethoxy)ethoxy]ethyl]-1-(4-[N-methyl[4-chloro-3-([1-[4-(2-cyclopropoxyphenyl) pyridin-3-yl]cyclopropoxy]methyl)benzene]sulfonamido]butyl)urea (736b, 50 mg, 0.07 mmol, 1.0 equiv) in tetrahydrofuran (0.45 mL) and the resulting solution was stirred for 1 h at 30° C. in an oil bath and then concentrated under vacuum. The crude residue was purified via silica gel column chromatography eluting with dichloromethane/methanol (1:5) to provide 38 mg (67%) of N-[2-[2-(2-[[(4-[N-methyl[4-chloro-3-([1-[4-(2-cyclopropoxyphenyl)pyridin-3-yl]cyclopropoxy]methyl)benzene]sulfonamido]butyl)carbamoyl]amino]ethoxy)ethoxy]ethyl]-1H-imidazole-1-carboxamide 737a as a yellow solid.

Step 2. 3-(4-[N-methyl[4-chloro-3-([1-[4-(2-cyclopropoxyphenyl)pyridin-3-yl]cyclopropoxy] methyl)benzene]sulfonamido]butyl)-1-[2-(2-[2-[(2-[2-(2-[[(4-[N-methyl[4-chloro-3-([1-[4-(2-cyclopropoxyphenyl)pyridin-3-yl]cyclopropoxy]methyl)benzene]sulfonamido]butyl) carbamoyl]amino]ethoxy)ethoxy]ethyl]carbamoyl)amino]ethoxy]ethoxy)ethyl]urea (I-737)

A 50-mL round-bottom flask purged and maintained under an inert atmosphere of nitrogen was charged with a solution of 3-[2-[2-(2-aminoethoxy)ethoxy]ethyl]-1-(4-[N-methyl[4-chloro-3-([1-[4-(2-cyclopropoxyphenyl)pyridin-3-yl]cyclopropoxy]methyl)benzene]sulfonamido]butyl)urea (736b, 38 mg, 0.05 mmol, 1.0 equiv) and N-[2-[2-(2-[[(4-[N-methyl[4-chloro-3-([1-[4-(2-cyclopropoxyphenyl)pyridin-3-yl]cyclopropoxy]methyl) benzene]sulfonamido]butyl)carbamoyl]amino]ethoxy)ethoxy]ethyl]-1H-imidazole-1-carboxamide (737a, 34 mg, 0.04 mmol, 1.0 equiv) in tetrahydrofuran (1 mL) and the resulting solution was stirred for 2 h at 70° C. in an oil bath and then concentrated under vacuum. The crude residue was purified via silica gel column chromatography eluting with ACN: $H_2O$ (0% 30%) to provide 23.7 mg (31%) of 3-(4-[N-methyl[4-chloro-3-([1-[4-(2-cyclopropoxyphenyl) pyridin-3-yl]cyclopropoxy]methyl)benzene]sulfonamido]butyl)-1-[2-(2-[2-[(([2-[2-(2-[[(4-[N-methyl[4-chloro-3-([1-[4-(2-cyclopropoxyphenyl)pyridin-3-yl]cyclopropoxy]methyl) benzene]sulfonamido]butyl)carbamoyl]amino]ethoxy) ethoxy]ethyl]carbamoyl)amino]ethoxy]eth oxy)ethyl]urea I-737 as a white solid. (ES, m/z): [M+1]$^+$: 1485; $^1$H NMR (400 MHz, Methanol-$d_4$) δ 0.34-0.43 (m, 2H), 0.56-0.66 (m, 2H), 0.94-1.05 (m, 4H), 1.31 (d, J=17.8 Hz, 1H), 1.53 (tdd, J=14.7, 7.3, 3.9 Hz, 4H), 2.66 (s, 3H), 2.96 (t, J=6.6 Hz, 2H), 3.13 (t, J=6.6 Hz, 2H), 3.29 (d, J=5.1 Hz, 1H), 3.48-3.63 (m, 9H), 4.47 (s, 2H), 4.74 (s, 1H), 7.01 (td, J=7.2, 1.6 Hz, 1H), 7.17-7.29 (m, 2H), 7.30-7.42 (m, 2H), 7.48-7.58 (m, 2H), 7.63 (dd, J=8.3, 2.4 Hz, 1H), 8.48 (d, J=5.1 Hz, 1H), 8.66 (s, 1H).

Example 119: (2R,3S,4R,5S)-5-[[(4-[N-methyl[4-chloro-3-([1-[4-(2-cyclopropoxyphenyl) pyridin-3-yl]cyclopropoxy]methyl)benzene]sulfonamido] butyl)carbamoyl]amino]-1,2,4,6-tetrakis (propanoyloxy)hexan-3-yl propanoate (I-738)

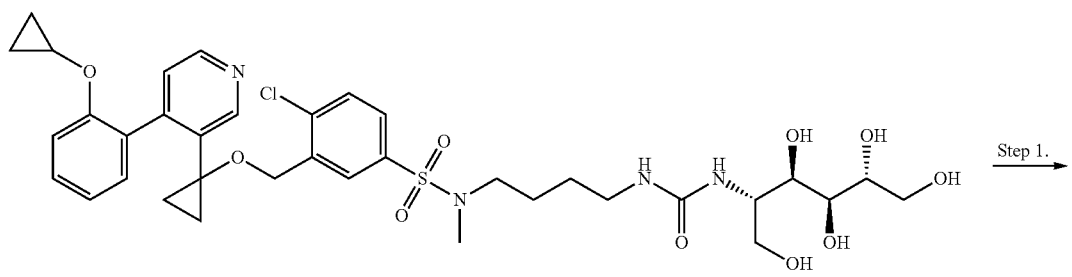

I-389

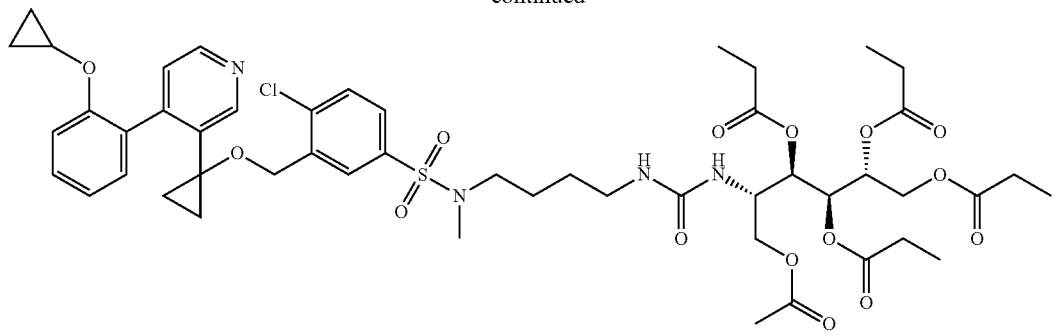

I-738

A 100-mL 3-necked round-bottom flask purged and maintained under an inert atmosphere of nitrogen was charged with a solution of 1-(4-[N-methyl[4-chloro-3-([1-[4-(2-cyclopropoxyphenyl)pyridin-3-yl]cyclopropoxy]methyl)benzene]sulfonamido]butyl)-3-[(2S,3R,4S,5R)-1,3,4,5,6-pentahydroxyhexan-2-yl]urea (I-389, 200 mg, 0.26 mmol, 1.0 equiv) in pyridine (10 mL). Propanoyl propanoate (4 mL, 3.0 equiv) was then added at 10° C. and the resulting solution was stirred overnight at room temperature and concentrated under vacuum. The crude product was purified by Preparative HPLC with the following conditions: Column, XBridge Prep C18 OBD Column 5 um, 19×150 mm; mobile phase, water (0.05% TFA) and ACN (54.0% to 74.0% ACN over 8 min); Detector, uv 220 nm, to provide 212.6 mg (78%) of (2R,3S,4R,5S)-5-[[(4-[N-methyl[4-chloro-3-([1-[4-(2-cyclopropoxyphenyl)pyridin-3-yl]cyclopropoxy]methyl)benzene]sulfonamido]butyl)carbamoyl]amino]-1,2,4,6-tetrakis(propanoyloxy)hexan-3-yl propanoate I-738 as an off-white solid. [M+1]$^+$: 1043; $^1$H NMR (400 MHz, Methanol-d$_4$) δ 8.98 (s, 1H), 8.77 (d, J=5.8 Hz, 1H), 7.84 (d, J=5.8 Hz, 1H), 7.68 (dd, J=8.4, 2.3 Hz, 1H), 7.59 (d, J=8.4 Hz, 1H), 7.55-7.36 (m, 4H), 7.11 (td, J=7.4, 1.1 Hz, 1H), 5.50 (dd, J=7.4, 4.1 Hz, 1H), 5.37 (dd, J=5.7, 4.1 Hz, 1H), 5.22-5.13 (m, 1H), 4.53 (s, 2H), 4.36-4.25 (m, 2H), 4.21-4.00 (m, 3H), 3.66 (tt, J=6.0, 2.9 Hz, 1H), 3.15 (t, J=6.6 Hz, 2H), 2.99 (t, J=6.6 Hz, 2H), 2.70 (s, 3H), 2.50-2.27 (m, 10H), 1.61-1.50 (m, 4H), 1.25-1.06 (m, 21H), 0.73-0.64 (m, 2H), 0.44 (q, J=5.4, 4.4 Hz, 2H).

Compounds I-739 to I-780 (Table 17) were prepared from commercial, known starting materials or the appropriate intermediates disclosed herein using methods from the examples specified in Table 17 and methods generally known to those skilled in the art.

TABLE 17

Compounds I-739 to I-780

| Cmpd. No.: | Synthetic Method | Compound Structure | Obs. mass [M + H]$^+$ |
|---|---|---|---|
| I-739 | Example 4 | 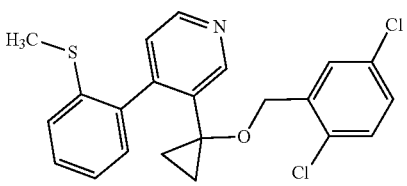 [SMILES: CSc1ccccc1-c1ccncc1C1(OCc2cc(Cl)ccc2Cl)CC1] | 416 |
| I-740 | Example 9 | 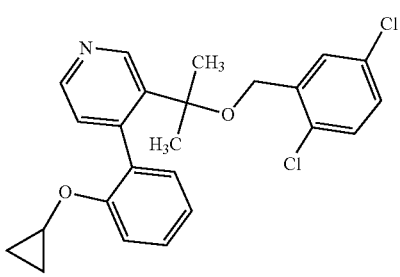 [SMILES: CC(C)(OCc1cc(Cl)ccc1Cl)c1cnccc1-c1ccccc1OC1CC1] | 428.2 |

TABLE 17-continued

Compounds I-739 to I-780

| Cmpd. No.: | Synthetic Method | Compound Structure | Obs. mass [M + H]+ |
|---|---|---|---|
| I-741 | Example 9 | 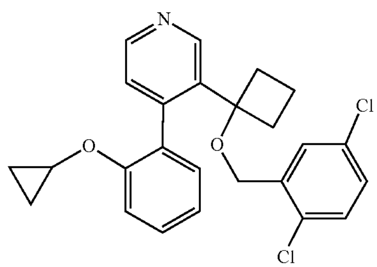 [SMILES: Clc1ccc(Cl)c(COC2(c3cnccc3-c3ccccc3OC3CC3)CCC2)c1] | 440.1 |
| I-742 | Example 9 | 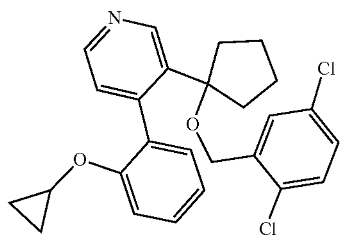 [SMILES: Clc1ccc(Cl)c(COC2(c3cnccc3-c3ccccc3OC3CC3)CCCC2)c1] | 454.2 |
| I-743 | Example 9 | 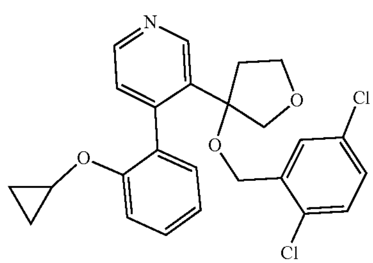 [SMILES: Clc1ccc(Cl)c(COC2(c3cnccc3-c3ccccc3OC3CC3)CCOC2)c1] | 456.1 |
| I-744 | Example 74 | 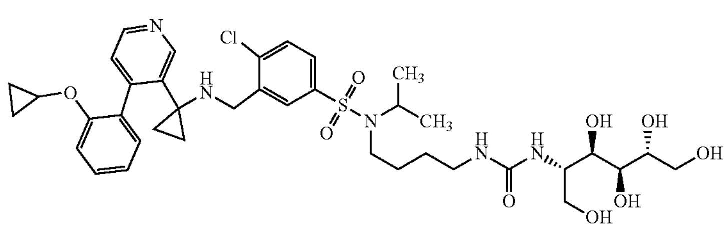 [SMILES: CC(C)N(CCCCNC(=O)N[C@@H](CO)[C@@H](O)[C@H](O)[C@H](O)CO)S(=O)(=O)c1ccc(Cl)c(CNC2(c3cnccc3-c3ccccc3OC3CC3)CC2)c1] | 790.2 |
| I-745 | Example 9 | 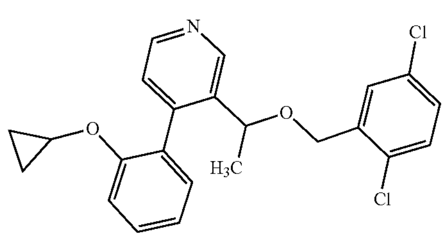 [SMILES: CC(OCc1cc(Cl)ccc1Cl)c1cnccc1-c1ccccc1OC1CC1] | 414.2 |

TABLE 17-continued

Compounds I-739 to I-780

| Cmpd. No.: | Synthetic Method | Compound Structure | Obs. mass [M + H]+ |
|---|---|---|---|
| I-746 | Example 71 | 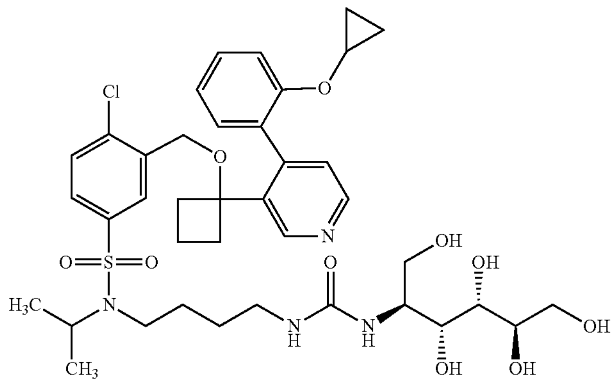 [SMILES: CC(C)N(CCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CCC2)c1] | 805.2 |
| I-747 | Example 71 | 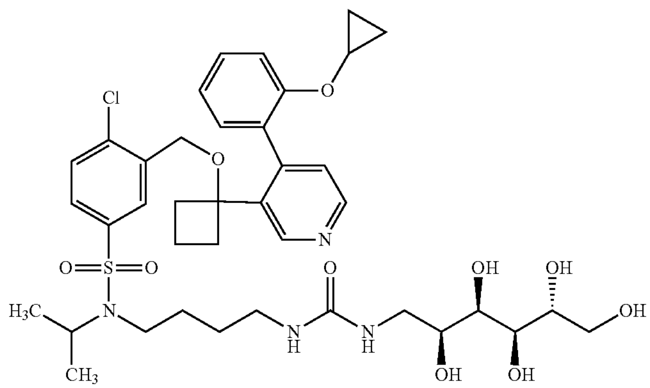 [SMILES: CC(C)N(CCCCNC(=O)NC[C@H](O)[C@@H](O)[C@H](O)[C@H](O)CO)S(=O)(=O)c1ccc(Cl)c(COC2(c3cnccc3-c3ccccc3OC3CC3)CCC2)c1] | 805.2 |
| I-748 | Example 106 | 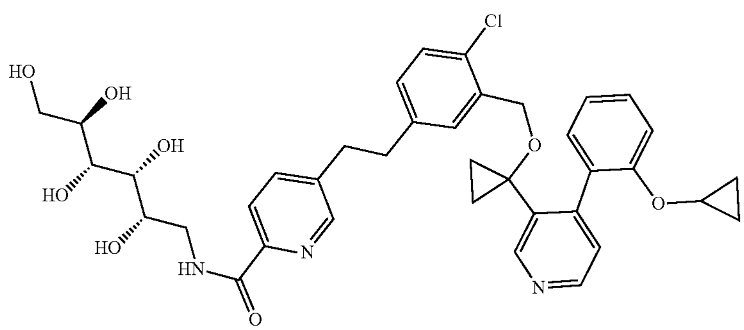 [SMILES: O=C(NC[C@H](O)[C@@H](O)[C@H](O)[C@H](O)CO)c1ccc(CCc2ccc(Cl)c(COC3(c4cnccc4-c4ccccc4OC4CC4)CC3)c2)cn1] | 704.3 |
| I-749 | Example 71 | 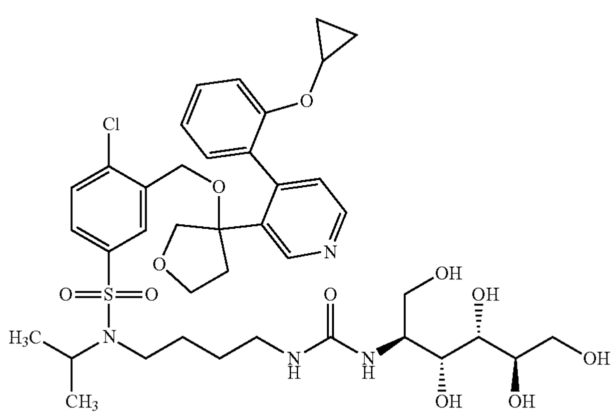 [SMILES: CC(C)N(CCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CCOC2)c1] | 821.2 |

TABLE 17-continued
Compounds I-739 to I-780
| Cmpd. No.: | Synthetic Method | Compound Structure | Obs. mass [M + H]+ |
|---|---|---|---|
| I-750 | Example 71 | 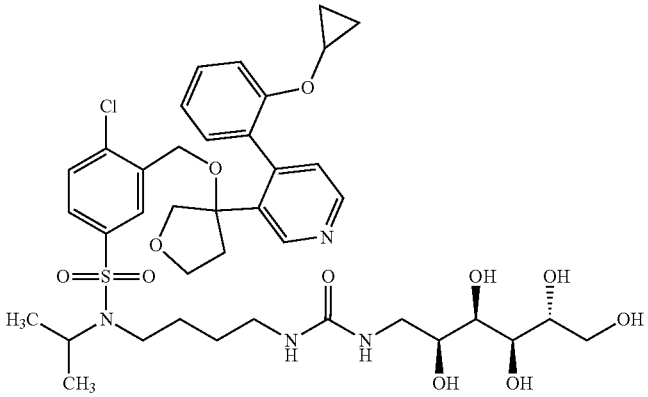 [SMILES: CC(C)N(CCCCNC(=O)NC[C@H](O)[C@@H](O)[C@H](O)[C@H](O)CO)S(=O)(=O)c1ccc(Cl)c(COC2(c3cnccc3-c3ccccc3OC3CC3)CCOC2)c1] | 821.2 |
| I-751 | Example 74 | 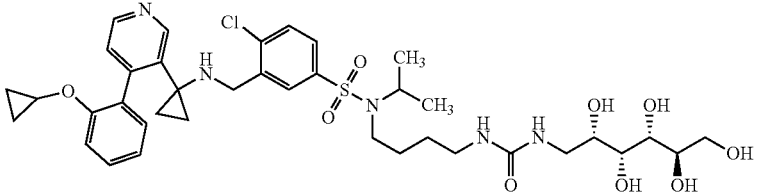 [SMILES: CC(C)N(CCCCNC(=O)NC[C@H](O)[C@@H](O)[C@H](O)[C@H](O)CO)S(=O)(=O)c1ccc(Cl)c(CNC2(c3cnccc3-c3ccccc3OC3CC3)CC2)c1] | 790.3 |
| I-752 | Example 71 | 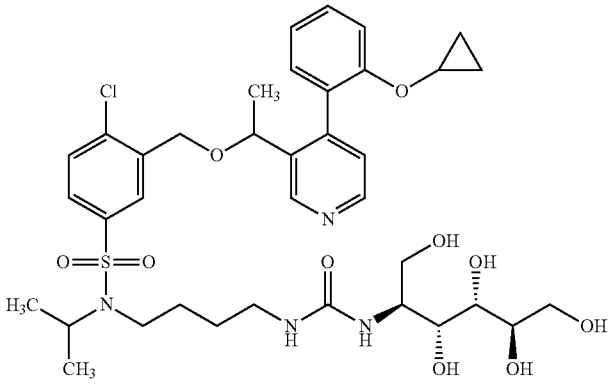 [SMILES: CC(OCc1cc(S(=O)(=O)N(CCCCNC(=O)N[C@@H](CO)[C@@H](O)[C@H](O)[C@H](O)CO)C(C)C)ccc1Cl)c1cnccc1-c1ccccc1OC1CC1] | 779.2 |
| I-753 | Example 71 | 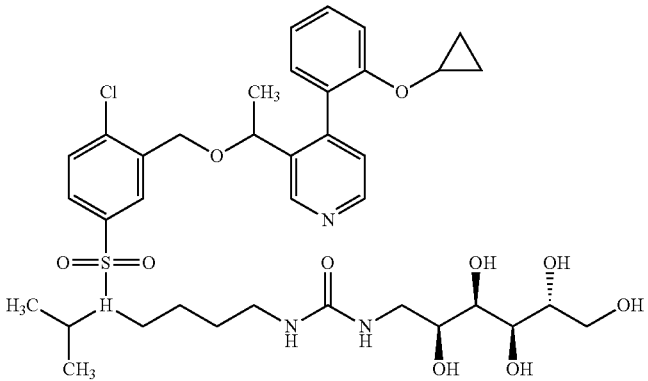 | 779.2 |

TABLE 17-continued
Compounds I-739 to I-780
| Cmpd. No.: | Synthetic Method | Compound Structure | Obs. mass [M + H]+ |
|---|---|---|---|
| I-754 | Example 74 | 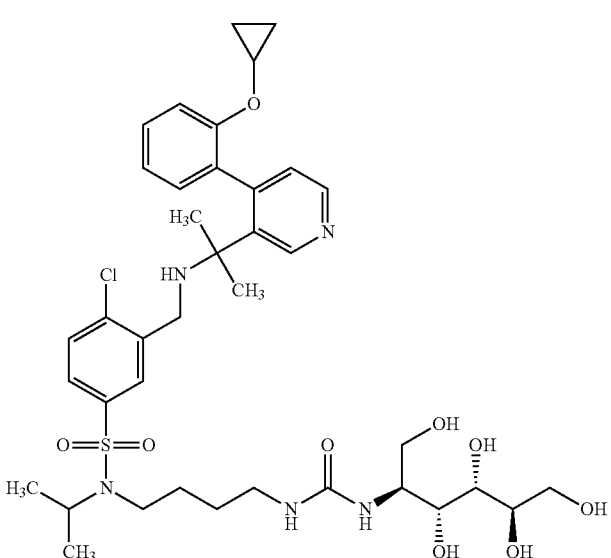 | 792.2 |
| I-755 | Example 107 | 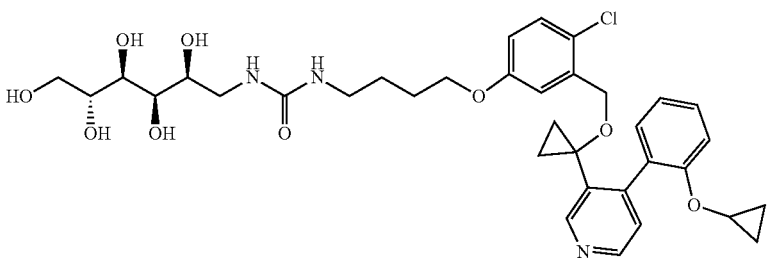 [SMILES: O=C(NCCCCOc1ccc(Cl)c(COC2(c3cnccc3-c3ccccc3OC3CC3)CC2)c1)NC[C@H](O)[C@@H](O)[C@H](O)[C@H](O)CO] | 686.3 |
| I-756 | Example 108 | 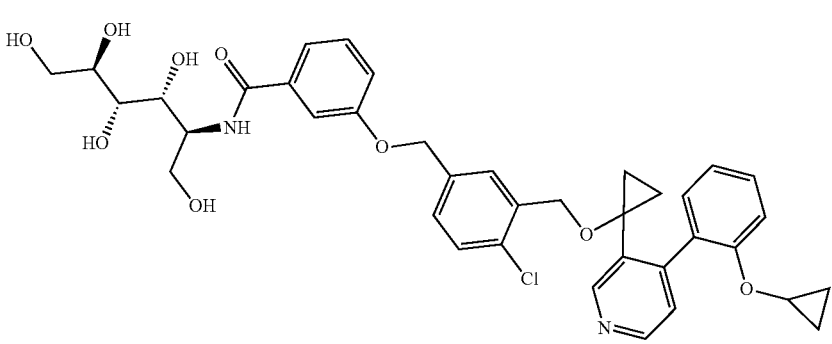 [SMILES: O=C(N[C@@H](CO)[C@@H](O)[C@H](O)[C@H](O)CO)c1cccc(OCc2ccc(Cl)c(COC3(c4cnccc4-c4ccccc4OC4CC4)CC3)c2)c1] | 705.3 |

TABLE 17-continued
Compounds I-739 to I-780
| Cmpd. No.: | Synthetic Method | Compound Structure | Obs. mass [M + H]+ |
|---|---|---|---|
| I-757 | Example 108 | 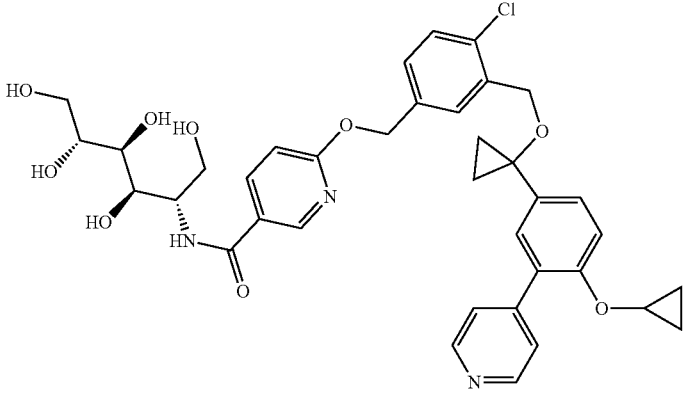 [SMILES: O=C(N[C@@H](CO)[C@@H](O)[C@H](O)[C@H](O)CO)c1ccc(OCc2ccc(Cl)c(COC3(c4ccc(OC5CC5)c(-c5ccncc5)c4)CC3)c2)nc1] | 706.3 |
| I-758 | Example 108 | 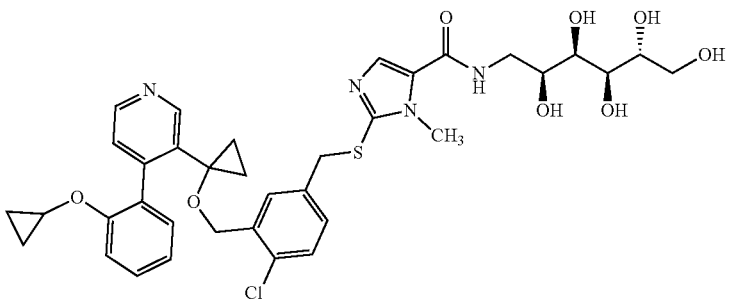 [SMILES: Cn1c(C(=O)NC[C@H](O)[C@@H](O)[C@H](O)[C@H](O)CO)cnc1SCc1ccc(Cl)c(COC2(c3cnccc3-c3ccccc3OC3CC3)CC2)c1] | 725.1 |
| I-759 | Example 108 | 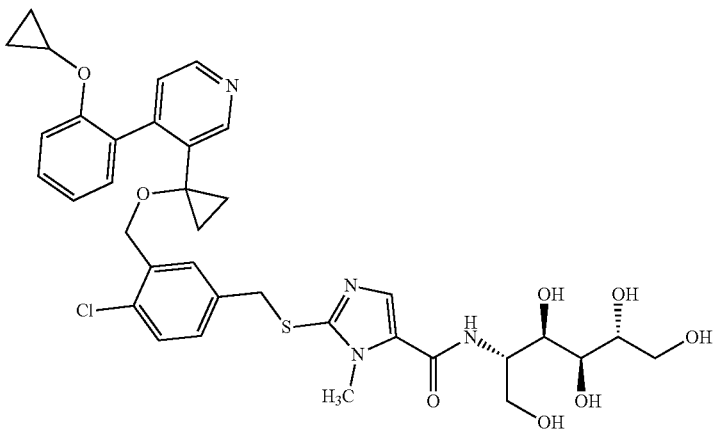 [SMILES: Cn1c(C(=O)N[C@@H](CO)[C@@H](O)[C@H](O)[C@H](O)CO)cnc1SCc1ccc(Cl)c(COC2(c3cnccc3-c3ccccc3OC3CC3)CC2)c1] | 725.1 |
| I-760 | Example 107 | 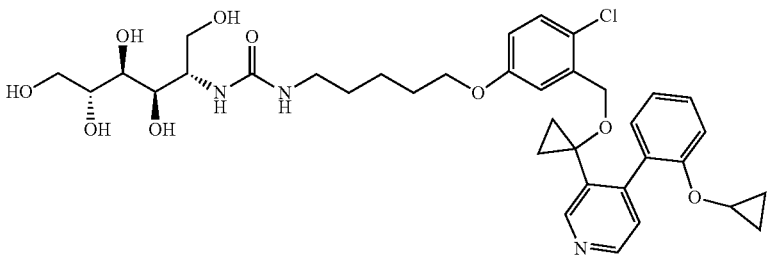 [SMILES: O=C(NCCCCCOc1ccc(Cl)c(COC2(c3cnccc3-c3ccccc3OC3CC3)CC2)c1)N[C@@H](CO)[C@@H](O)[C@H](O)[C@H](O)CO] | 700.3 |

TABLE 17-continued

Compounds I-739 to I-780

| Cmpd. No.: | Synthetic Method | Compound Structure | Obs. mass [M + H]+ |
|---|---|---|---|
| I-761 | Example 73 | 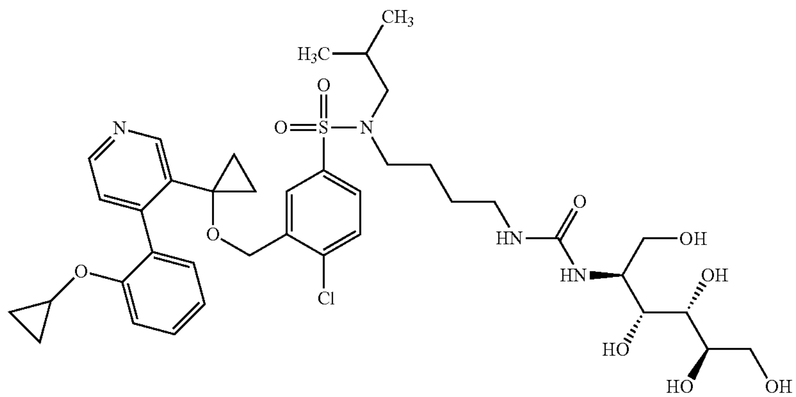 [SMILES: CC(C)CN(CCCCNC(=O)N[C@@H](CO)[C@@H](O)[C@H](O)[C@H](O)CO)S(=O)(=O)c1ccc(Cl)c(COC2(c3cnccc3-c3ccccc3OC3CC3)CC2)c1] | 805 |
| I-762 | Example 73 | 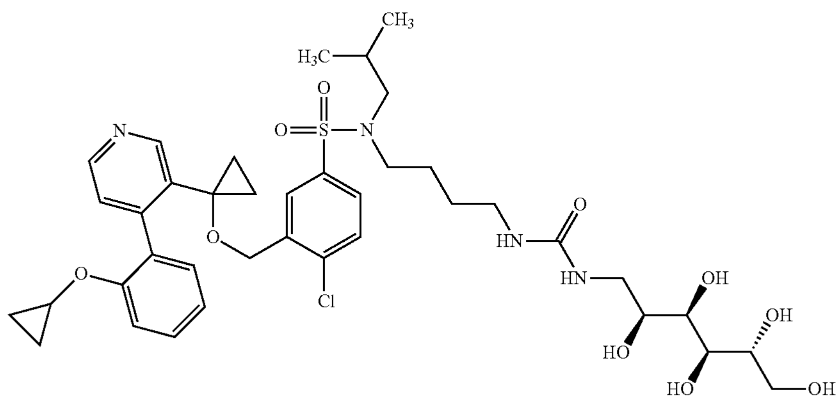 [SMILES: CC(C)CN(CCCCNC(=O)NC[C@H](O)[C@@H](O)[C@H](O)[C@H](O)CO)S(=O)(=O)c1ccc(Cl)c(COC2(c3cnccc3-c3ccccc3OC3CC3)CC2)c1] | 805 |
| I-763 | Example 73 | 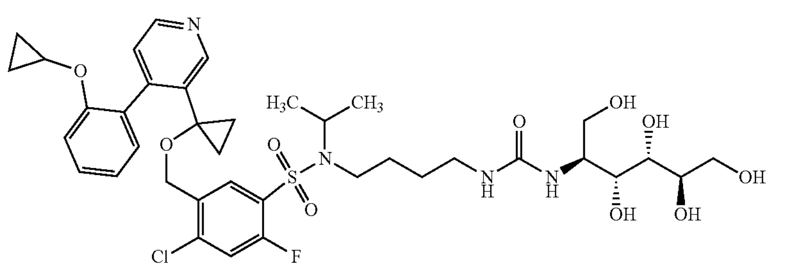 [SMILES: CC(C)N(CCCCNC(=O)N[C@@H](CO)[C@@H](O)[C@H](O)[C@H](O)CO)S(=O)(=O)c1cc(COC2(c3cnccc3-c3ccccc3OC3CC3)CC2)c(Cl)cc1F] | 809 |
| I-764 | Example 73 | 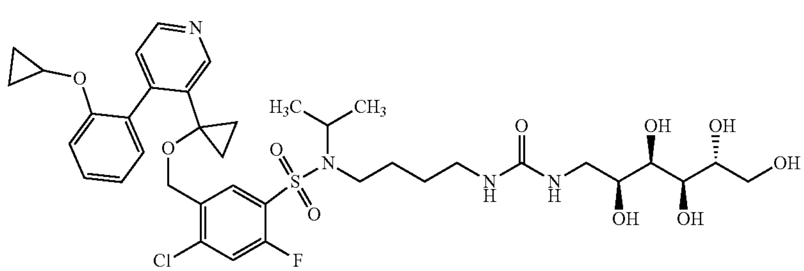 [SMILES: CC(C)N(CCCCNC(=O)NC[C@H](O)[C@@H](O)[C@H](O)[C@H](O)CO)S(=O)(=O)c1cc(COC2(c3cnccc3-c3ccccc3OC3CC3)CC2)c(Cl)cc1F] | 809 |

TABLE 17-continued

Compounds I-739 to I-780

| Cmpd. No.: | Synthetic Method | Compound Structure | Obs. mass [M + H]+ |
|---|---|---|---|
| I-765 | Example 4 | 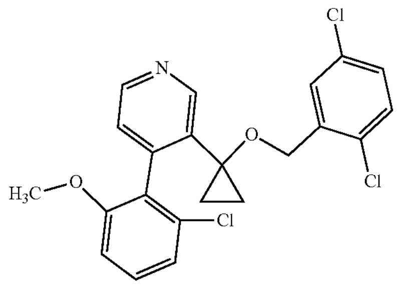 [SMILES: COc1cccc(Cl)c1-c1ccncc1C1(OCc2cc(Cl)ccc2Cl)CC1] | 434 |
| I-766 | Example 113 | 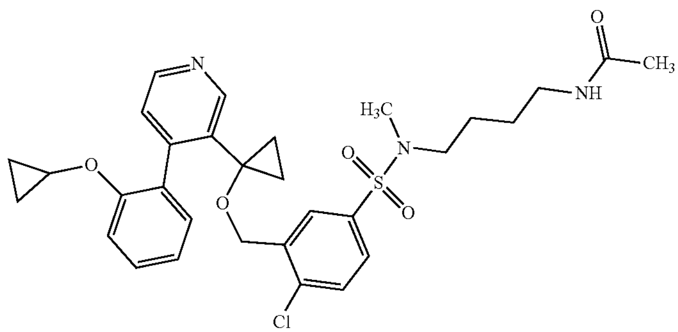 [SMILES: CC(=O)NCCCCN(C)S(=O)(=O)c1ccc(Cl)c(COC2(c3cnccc3-c3ccccc3OC3CC3)CC2)c1] | 598 |
| I-767 | Example 118 | 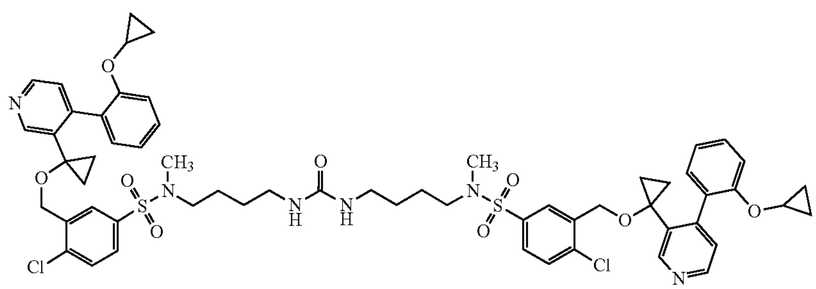 [SMILES: CN(CCCCNC(=O)NCCCCN(C)S(=O)(=O)c1ccc(Cl)c(COC2(c3cnccc3-c3ccccc3OC3CC3)CC2)c1)S(=O)(=O)c1ccc(Cl)c(COC2(c3cnccc3-c3ccccc3OC3CC3)CC2)c1] | 1137.3 |
| I-768 | Example 4 | 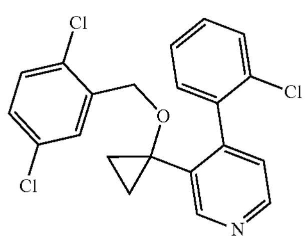 [SMILES: Clc1ccc(Cl)c(COC2(c3cnccc3-c3ccccc3Cl)CC2)c1] | 404 |
| I-769 | Example 75 | 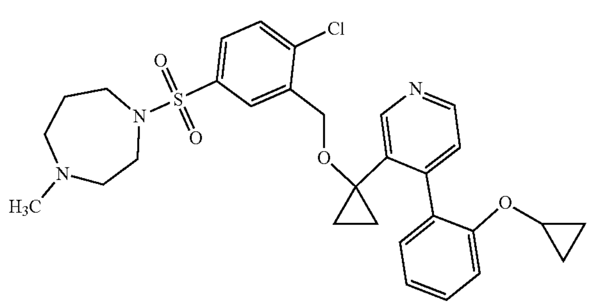 [SMILES: CN1CCCN(S(=O)(=O)c2ccc(Cl)c(COC3(c4cnccc4-c4ccccc4OC4CC4)CC3)c2)CC1] | 568 |

TABLE 17-continued

Compounds I-739 to I-780

| Cmpd. No.: | Synthetic Method | Compound Structure | Obs. mass [M + H]+ |
|---|---|---|---|
| I-770 | Example 75 | 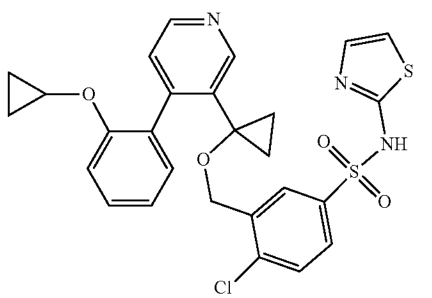 [SMILES: O=S(=O)(Nc1nccs1)c1ccc(Cl)c(COC2(c3cnccc3-c3ccccc3OC3CC3)CC2)c1] | 554 |
| I-771 | Example 75 | 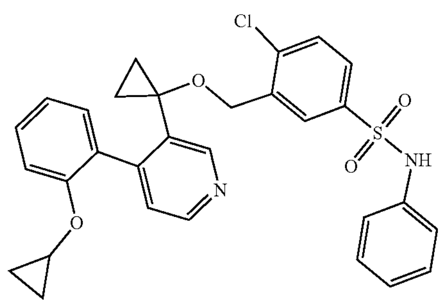 [SMILES: O=S(=O)(Nc1ccccc1)c1ccc(Cl)c(COC2(c3cnccc3-c3ccccc3OC3CC3)CC2)c1] | 547 |
| I-772 | Example 75 | 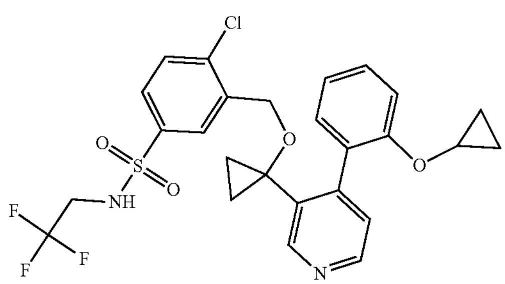 [SMILES: O=S(=O)(NCC(F)(F)F)c1ccc(Cl)c(COC2(c3cnccc3-c3ccccc3OC3CC3)CC2)c1] | 553 |
| I-773 | Example 4 | 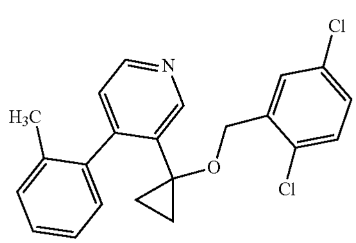 [SMILES: Cc1ccccc1-c1ccncc1C1(OCc2cc(Cl)ccc2Cl)CC1] | 384 |
| I-774 | Example 4 | 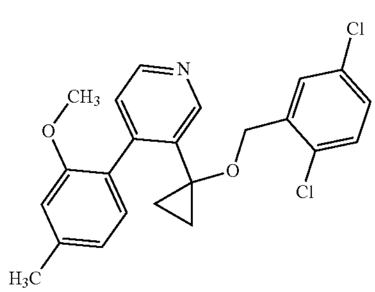 [SMILES: COc1cc(C)ccc1-c1ccncc1C1(OCc2cc(Cl)ccc2Cl)CC1] | 414 |

TABLE 17-continued

Compounds I-739 to I-780

| Cmpd. No.: | Synthetic Method | Compound Structure | Obs. mass [M + H]+ |
|---|---|---|---|
| I-775 | Example 97 | 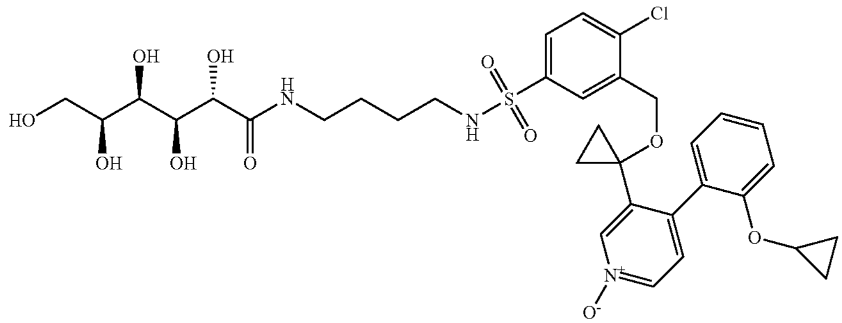 [SMILES: O=C(NCCCCNS(=O)(=O)c1ccc(Cl)c(COC2(c3c[n+]([O-])ccc3-c3ccccc3OC3CC3)CC2)c1)[C@@H](O)[C@@H](O)[C@H](O)[C@@H](O)CO] | 736 |
| I-776 | Example 71 | 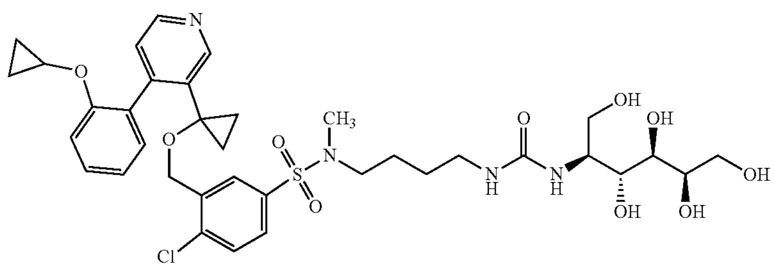 [SMILES: CN(CCCCNC(=O)N[C@@H](CO)[C@@H](O)[C@@H](O)[C@H](O)CO)S(=O)(=O)c1ccc(Cl)c(COC2(c3cnccc3-c3ccccc3OC3CC3)CC2)c1] | 763.3 |
| I-777 | Example 75 | 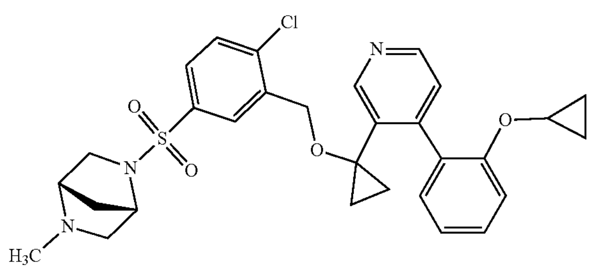 [SMILES: CN1C[C@@H]2C[C@H]1CN2S(=O)(=O)c1ccc(Cl)c(COC2(c3cnccc3-c3ccccc3OC3CC3)CC2)c1] | 566.1 |
| I-778 | Example 71 | 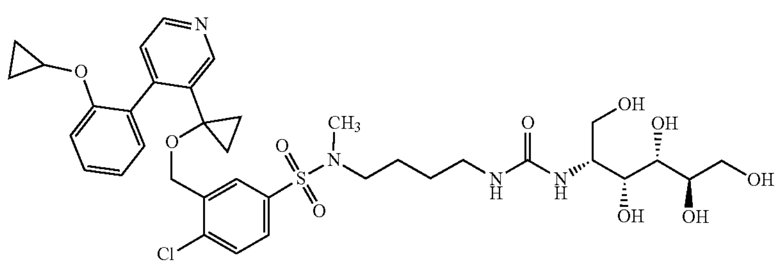 [SMILES: CN(CCCCNC(=O)N[C@H](CO)[C@@H](O)[C@H](O)[C@H](O)CO)S(=O)(=O)c1ccc(Cl)c(COC2(c3cnccc3-c3ccccc3OC3CC3)CC2)c1] | 763.3 |
| I-779 | Example 4 | 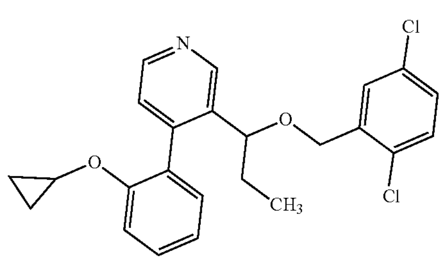 [SMILES: CCC(OCc1cc(Cl)ccc1Cl)c1cnccc1-c1ccccc1OC1CC1] | 427.1 |

TABLE 17-continued

Compounds I-739 to I-780

| Cmpd. No.: | Synthetic Method | Compound Structure | Obs. mass [M + H]+ |
|---|---|---|---|
| I-780 | Example 113 | 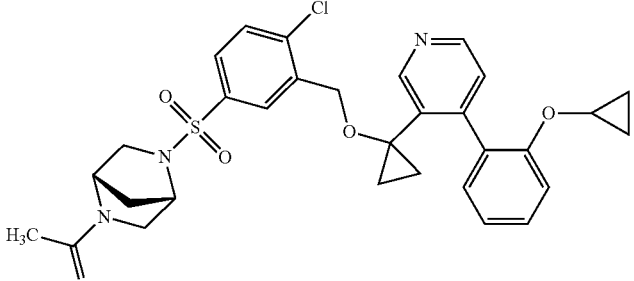 | 594.1 |

Example 120: Cell-Based TGR5 Assays

A primary cell-based assay utilized HEK293 cells stably transfected with a gene encoding human TGR5. Cells were treated with candidate TGR5 activators and assessed for increased intercellular levels of cAMP.

TGR5-mediated cAMP generation was measured using a homogeneous time resolved fluorescence (HTRF) detection method (Cisbio). Test compounds were dissolved in DMSO to a final concentration of 10 mM. Serial 3-fold dilutions of the stock solution were made in DMSO, and these solutions were diluted 100-fold into Hanks Balanced Salt Solution supplemented with 10 mM HEPES pH 7.4, 0.003% Tween 20 and 0.5 mM isobutyl methylxanthine. Five microliters of diluted test compounds were added to wells of a black 384 well plate.

Cells grown overnight at 37° C./5% $CO_2$ were harvested and resuspended in Hanks Balanced Salt Solution containing 10 mM HEPES to a concentration of 50,000 cells/mL. Five microliters (2500 cells) were dispensed into each well of the 384 well plate containing compound dilutions and incubated at 37° C. for 30 minutes. Each compound was tested in duplicate at 12 concentrations ranging from 0.05 nM to 10 µM.

Following incubation with test compounds, cAMP was detected through the successive addition of 5 µL each of cAMP labeled with the modified allophyocyanin dye d2 (cAMP-d2) and cryptate-labeled anti-cAMP in lysis buffer, and reading HTRF per the manufacturer's instructions.

A standard curve was used to convert the raw HTRF data into [cAMP]. The concentration of cAMP was plotted against log [test compound] and the resulting curves were fit to a 3-parameter logistical equation using GraphPad Prism to determine $pEC_{50}$ (the negative log of the $EC_{50}$) and the magnitude of the response. The magnitude of the maximum response was typically between 50 and 200% of the maximum response elicited by a benchmark compound that had a maximum response similar to that elicited by lithocholic acid. The results of this assay are set forth in Table 18.

TABLE 18 pEC50 Values of Representative Compounds*

| Compound No. | pEC50 Human TGR5 |
|---|---|
| I-1 | A |
| I-2 | A |
| I-3 | A |
| I-4 | B |
| I-5 | B |
| I-6 | B |
| I-7 | B |
| I-8 | B |
| I-9 | B |
| I-10 | B |
| I-11 | B |
| I-12 | B |
| I-13 | B |
| I-14 | B |
| I-15 | B |
| I-16 | C |
| I-17 | C |
| I-18 | A |
| I-19 | A |
| I-20 | B |
| I-21 | B |
| I-22 | C |
| I-23 | A |
| I-24 | A |
| I-25 | A |
| I-26 | B |
| I-27 | B |
| I-28 | B |
| I-29 | B |
| I-30 | B |
| I-31 | A |
| I-32 | A |
| I-33 | A |
| I-34 | A |
| I-35 | A |
| I-36 | B |
| I-37 | A |
| I-38 | B |
| I-39 | B |
| I-40 | A |
| I-42 | A |
| I-43 | B |
| I-44 | C |
| I-45 | A |
| I-46 | A |
| I-47 | B |
| I-48 | B |
| I-49 | A |

TABLE 18-continued pEC$_{50}$ Values of Representative Compounds*

| Compound No. | pEC$_{50}$ Human TGR5 |
|---|---|
| I-50 | C |
| I-51 | B |
| I-52 | A |
| I-53 | A |
| I-54 | A |
| I-55 | A |
| I-56 | C |
| I-57 | C |
| I-58 | C |
| I-59 | A |
| I-60 | A |
| I-61 | B |
| I-62 | B |
| I-63 | B |
| I-64 | A |
| I-65 | A |
| I-66 | B |
| I-67 | A |
| I-68 | A |
| I-69 | B |
| I-70 | B |
| I-71 | A |
| I-72 | A |
| I-73 | A |
| I-74 | B |
| I-75 | A |
| I-76 | B |
| I-77 | A |
| I-78 | A |
| I-79 | A |
| I-80 | A |
| I-81 | A |
| I-82 | A |
| I-83 | A |
| I-84 | A |
| I-85 | A |
| I-86 | A |
| I-87 | A |
| I-88 | A |
| I-89 | A |
| I-90 | B |
| I-91 | A |
| I-92 | A |
| I-93 | A |
| I-94 | A |
| I-95 | A |
| I-96 | A |
| I-97 | B |
| I-98 | A |
| I-99 | A |
| I-100 | A |
| I-101 | C |
| I-102 | B |
| I-103 | A |
| I-104 | A |
| I-105 | A |
| I-106 | A |
| I-107 | A |
| I-108 | A |
| I-109 | A |
| I-110 | A |
| I-111 | A |
| I-112 | A |
| I-113 | A |
| I-114 | A |
| I-115 | A |
| I-116 | A |
| I-117 | A |
| I-118 | A |
| I-119 | B |
| I-120 | B |
| I-121 | A |
| I-122 | A |
| I-123 | A |
| I-124 | A |
| I-125 | A |
| I-126 | B |
| I-127 | A |
| I-128 | A |
| I-129 | A |
| I-130 | A |
| I-131 | A |
| I-132 | A |
| I-133 | B |
| I-134 | B |
| I-135 | A |
| I-136 | A |
| I-137 | A |
| I-138 | A |
| I-139 | A |
| I-140 | A |
| I-141 | A |
| I-142 | A |
| I-143 | A |
| I-144 | B |
| I-145 | A |
| I-146 | A |
| I-147 | B |
| I-148 | B |
| I-149 | B |
| I-150 | A |
| I-151 | B |
| I-152 | B |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | A |
| I-164 | A |
| I-165 | A |
| I-166 | A |
| I-167 | A |
| I-168 | A |
| I-169 | B |
| I-170 | C |
| I-171 | C |
| I-172 | A |
| I-173 | A |
| I-174 | B |
| I-175 | B |
| I-176 | A |
| I-177 | A |
| I-178 | B |
| I-179 | A |
| I-180 | A |
| I-181 | A |
| I-182 | A |
| I-183 | A |
| I-184 | A |
| I-185 | A |
| I-186 | B |
| I-187 | A |
| I-188 | B |
| I-189 | A |
| I-190 | A |
| I-191 | A |
| I-192 | A |
| I-193 | A |
| I-194 | A |
| I-195 | B |
| I-196 | B |
| I-197 | B |

TABLE 18-continued pEC$_{50}$ Values of Representative Compounds*

| Compound No. | pEC$_{50}$ Human TGR5 |
|---|---|
| I-198 | A |
| I-199 | B |
| I-200 | C |
| I-201 | C |
| I-202 | A |
| I-203 | A |
| I-204 | A |
| I-205 | A |
| I-206 | A |
| I-207 | B |
| I-208 | A |
| I-209 | A |
| I-210 | A |
| I-211 | A |
| I-212 | A |
| I-213 | A |
| I-214 | A |
| I-215 | A |
| I-216 | B |
| I-217 | A |
| I-218 | A |
| I-219 | A |
| I-220 | B |
| I-221 | A |
| I-222 | A |
| I-223 | A |
| I-224 | A |
| I-225 | A |
| I-226 | A |
| I-227 | A |
| I-228 | A |
| I-229 | A |
| I-230 | A |
| I-231 | A |
| I-232 | A |
| I-233 | A |
| I-234 | A |
| I-235 | A |
| I-236 | A |
| I-237 | B |
| I-238 | B |
| I-239 | B |
| I-240 | A |
| I-241 | B |
| I-242 | A |
| I-243 | B |
| I-244 | B |
| I-245 | B |
| I-246 | B |
| I-247 | A |
| I-248 | A |
| I-249 | A |
| I-250 | A |
| I-251 | A |
| I-252 | B |
| I-253 | A |
| I-254 | A |
| I-255 | A |
| I-256 | A |
| I-257 | A |
| I-258 | A |
| I-259 | A |
| I-260 | A |
| I-261 | A |
| I-262 | A |
| I-263 | A |
| I-264 | A |
| I-265 | A |
| I-266 | A |
| I-267 | A |
| I-268 | A |
| I-269 | A |
| I-270 | A |
| I-271 | A |
| I-272 | A |
| I-273 | A |
| I-274 | A |
| I-275 | A |
| I-276 | A |
| I-277 | B |
| I-278 | A |
| I-279 | A |
| I-280 | A |
| I-281 | A |
| I-282 | A |
| I-283 | A |
| I-284 | A |
| I-285 | B |
| I-286 | A |
| I-287 | A |
| I-288 | A |
| I-289 | A |
| I-290 | A |
| I-291 | A |
| I-292 | A |
| I-293 | A |
| I-294 | A |
| I-295 | A |
| I-296 | A |
| I-297 | A |
| I-298 | A |
| I-299 | A |
| I-300 | A |
| I-301 | A |
| I-302 | A |
| I-303 | A |
| I-304 | A |
| I-305 | A |
| I-306 | A |
| I-307 | A |
| I-308 | A |
| I-309 | A |
| I-310 | A |
| I-311 | A |
| I-312 | A |
| I-313 | A |
| I-314 | A |
| I-315 | A |
| I-316 | A |
| I-317 | A |
| I-318 | A |
| I-319 | A |
| I-320 | A |
| I-321 | A |
| I-322 | A |
| I-323 | A |
| I-324 | A |
| I-325 | A |
| I-326 | A |
| I-327 | A |
| I-328 | A |
| I-329 | A |
| I-330 | A |
| I-331 | A |
| I-332 | A |
| I-333 | A |
| I-334 | A |
| I-335 | B |
| I-336 | A |
| I-337 | B |
| I-338 | A |
| I-339 | A |
| I-340 | B |
| I-341 | A |
| I-342 | A |
| I-343 | A |
| I-344 | B |
| I-345 | B |

TABLE 18-continued pEC$_{50}$ Values of Representative Compounds*

| Compound No. | pEC$_{50}$ Human TGR5 |
|---|---|
| I-346 | A |
| I-347 | A |
| I-348 | A |
| I-349 | A |
| I-350 | A |
| I-351 | A |
| I-352 | A |
| I-353 | A |
| I-354 | A |
| I-355 | A |
| I-356 | A |
| I-357 | A |
| I-358 | B |
| I-359 | B |
| I-360 | A |
| I-361 | B |
| I-362 | A |
| I-363 | A |
| I-364 | B |
| I-365 | B |
| I-366 | B |
| I-367 | A |
| I-368 | A |
| I-369 | A |
| I-370 | A |
| I-371 | A |
| I-372 | C |
| I-373 | A |
| I-374 | A |
| I-375 | A |
| I-376 | A |
| I-377 | A |
| I-378 | A |
| I-379 | B |
| I-380 | B |
| I-381 | A |
| I-382 | A |
| I-383 | A |
| I-384 | B |
| I-385 | A |
| I-386 | A |
| I-387 | B |
| I-388 | A |
| I-389 | A |
| I-390 | A |
| I-391 | A |
| I-392 | A |
| I-393 | A |
| I-394 | A |
| I-395 | A |
| I-396 | A |
| I-397 | B |
| I-398 | A |
| I-399 | B |
| I-400 | B |
| I-401 | A |
| I-402 | A |
| I-403 | A |
| I-404 | A |
| I-405 | A |
| I-406 | A |
| I-407 | A |
| I-408 | A |
| I-409 | A |
| I-410 | A |
| I-411 | A |
| I-412 | A |
| I-413 | A |
| I-414 | A |
| I-415 | A |
| I-416 | A |
| I-417 | A |
| I-418 | A |
| I-419 | A |

TABLE 18-continued pEC$_{50}$ Values of Representative Compounds*

| Compound No. | pEC$_{50}$ Human TGR5 |
|---|---|
| I-420 | A |
| I-421 | A |
| I-422 | A |
| I-423 | B |
| I-424 | A |
| I-425 | B |
| I-426 | A |
| I-427 | B |
| I-428 | B |
| I-429 | B |
| I-430 | B |
| I-431 | A |
| I-432 | A |
| I-433 | A |
| I-434 | A |
| I-435 | A |
| I-436 | A |
| I-437 | A |
| I-438 | A |
| I-439 | A |
| I-440 | B |
| I-441 | B |
| I-442 | A |
| I-443 | B |
| I-444 | A |
| I-445 | B |
| I-446 | A |
| I-447 | A |
| I-448 | A |
| I-449 | A |
| I-450 | A |
| I-451 | A |
| I-452 | A |
| I-453 | A |
| I-454 | B |
| I-455 | A |
| I-456 | A |
| I-457 | A |
| I-458 | A |
| I-459 | A |
| I-460 | A |
| I-461 | A |
| I-462 | A |
| I-463 | A |
| I-464 | A |
| I-465 | A |
| I-466 | A |
| I-467 | A |
| I-468 | B |
| I-469 | A |
| I-470 | B |
| I-471 | A |
| I-472 | A |
| I-473 | A |
| I-474 | A |
| I-475 | A |
| I-476 | B |
| I-477 | A |
| I-478 | A |
| I-479 | A |
| I-480 | A |
| I-481 | A |
| I-482 | B |
| I-483 | B |
| I-484 | A |
| I-485 | A |
| I-486 | B |
| I-487 | B |
| I-488 | A |
| I-489 | A |
| I-490 | A |
| I-491 | B |
| I-492 | A |
| I-493 | A |

TABLE 18-continued pEC$_{50}$ Values of Representative Compounds*

| Compound No. | pEC$_{50}$ Human TGR5 |
|---|---|
| I-494 | A |
| I-495 | B |
| I-496 | A |
| I-497 | B |
| I-498 | A |
| I-499 | A |
| I-500 | A |
| I-501 | A |
| I-502 | A |
| I-503 | A |
| I-504 | B |
| I-505 | A |
| I-506 | A |
| I-507 | A |
| I-508 | A |
| I-509 | A |
| I-510 | A |
| I-511 | A |
| I-512 | A |
| I-513 | A |
| I-514 | A |
| I-515 | A |
| I-516 | A |
| I-517 | A |
| I-518 | A |
| I-519 | B |
| I-520 | B |
| I-521 | B |
| I-522 | B |
| I-523 | A |
| I-524 | B |
| I-525 | B |
| I-526 | B |
| I-527 | A |
| I-528 | B |
| I-529 | B |
| I-530 | B |
| I-531 | B |
| I-532 | A |
| I-533 | A |
| I-534 | A |
| I-535 | B |
| I-536 | B |
| I-537 | B |
| I-538 | C |
| I-539 | B |
| I-540 | B |
| I-541 | B |
| I-542 | A |
| I-543 | B |
| I-544 | B |
| I-545 | B |
| I-546 | B |
| I-547 | C |
| I-548 | B |
| I-549 | A |
| I-550 | B |
| I-551 | B |
| I-552 | C |
| I-553 | B |
| I-554 | B |
| I-555 | A |
| I-556 | B |
| I-557 | B |
| I-558 | B |
| I-559 | A |
| I-560 | B |
| I-561 | B |
| I-562 | B |
| I-563 | B |
| I-564 | A |
| I-565 | B |
| I-566 | A |
| I-567 | B |
| I-568 | A |
| I-569 | B |
| I-570 | A |
| I-571 | A |
| I-572 | A |
| I-573 | B |
| I-574 | A |
| I-575 | A |
| I-576 | A |
| I-577 | A |
| I-578 | A |
| I-579 | A |
| I-580 | B |
| I-581 | A |
| I-582 | A |
| I-583 | B |
| I-584 | A |
| I-585 | A |
| I-586 | B |
| I-587 | B |
| I-588 | A |
| I-589 | B |
| I-590 | A |
| I-591 | B |
| I-592 | B |
| I-593 | A |
| I-594 | A |
| I-595 | B |
| I-596 | B |
| I-597 | B |
| I-598 | A |
| I-599 | A |
| I-600 | A |
| I-601 | A |
| I-602 | B |
| I-603 | A |
| I-604 | A |
| I-605 | A |
| I-606 | A |
| I-607 | A |
| I-608 | A |
| I-609 | A |
| I-610 | A |
| I-611 | A |
| I-612 | B |
| I-613 | A |
| I-614 | B |
| I-615 | A |
| I-617 | A |
| I-619 | A |
| I-620 | C |
| I-621 | A |
| I-622 | A |
| I-623 | A |
| I-624 | B |
| I-625 | A |
| I-626 | A |
| I-627 | A |
| I-628 | A |
| I-629 | A |
| I-630 | A |
| I-631 | A |
| I-632 | A |
| I-633 | A |
| I-634 | A |
| I-635 | A |
| I-636 | A |
| I-637 | A |
| I-638 | B |
| I-639 | A |
| I-640 | A |
| I-641 | A |
| I-642 | A |
| I-643 | A |

TABLE 18-continued pEC$_{50}$ Values of Representative Compounds*

| Compound No. | pEC$_{50}$ Human TGR5 |
|---|---|
| I-644 | A |
| I-645 | A |
| I-646 | A |
| I-647 | B |
| I-648 | A |
| I-649 | A |
| I-650 | A |
| I-651 | A |
| I-652 | A |
| I-653 | C |
| I-654 | C |
| I-655 | D |
| I-656 | D |
| I-657 | C |
| I-658 | C |
| I-659 | A |
| I-660 | B |
| I-661 | A |
| I-662 | B |
| I-663 | B |
| I-664 | A |
| I-665 | B |
| I-666 | A |
| I-667 | B |
| I-668 | A |
| I-669 | B |
| I-670 | B |
| I-671 | B |
| I-672 | B |
| I-673 | B |
| I-674 | B |
| I-675 | C |
| I-676 | A |
| I-677 | A |
| I-678 | A |
| I-679 | A |
| I-680 | B |
| I-681 | A |
| I-682 | A |
| I-683 | B |
| I-684 | B |
| I-685 | A |
| I-686 | B |
| I-687 | B |
| I-688 | B |
| I-689 | A |
| I-690 | A |
| I-691 | B |
| I-692 | B |
| I-693 | B |
| I-694 | B |
| I-695 | A |
| I-696 | A |
| I-700 | A |
| I-704 | C |
| I-705 | B |
| I-706 | C |
| I-707 | C |
| I-708 | C |
| I-709 | C |
| I-723 | A |
| I-724 | B |
| I-725 | B |
| I-726 | B |
| I-727 | B |
| I-728 | A |
| I-729 | C |
| I-730 | A |
| I-731 | A |
| I-732 | A |
| I-733 | A |
| I-734 | A |
| I-735 | A |
| I-736 | B |
| I-737 | B |
| I-738 | B |
| I-739 | B |
| I-740 | A |
| I-741 | A |
| I-742 | B |
| I-743 | A |
| I-744 | A |
| I-745 | B |
| I-746 | A |
| I-747 | A |
| I-748 | A |
| I-749 | A |
| I-750 | A |
| I-751 | A |
| I-752 | A |
| I-753 | A |
| I-754 | A |
| I-755 | B |
| I-756 | B |
| I-757 | B |
| I-758 | B |
| I-759 | B |
| I-760 | B |
| I-761 | A |
| I-762 | A |
| I-763 | A |
| I-764 | A |
| I-765 | A |
| I-766 | A |
| I-767 | B |
| I-768 | B |
| I-769 | B |
| I-770 | A |
| I-771 | A |
| I-772 | A |
| I-773 | B |
| I-774 | B |
| I-775 | B |
| I-776 | A |
| I-777 | B |
| I-778 | A |
| I-779 | C |
| I-780 | B |

*pEC$_{50}$ values are expressed as the following ranges: A is a pEC$_{50}$ of >7, B is a pEC$_{50}$ of 6 to 6.9, C is a pEC$_{50}$ of 5.0 to 5.9, D is a pEC$_{50}$ 4.3 to 4.9.

Example 121: In Vivo Measurement of Diarrhea in a Chemotherapy-Induced Diarrhea Model Four groups of adult CD-1 female mice on regular chow were dosed with the following BID starting on Day 1: 2 groups, vehicle (10% hydroxypropyl-β-cyclodextrin in PBS; PO; 5 mL/kg); 1 group, Compound I-388 at 30 mg/kg in vehicle (PO; 5 mL/kg); and 1 group, teduglutide 0.4 mg/kg (American Peptide, Sunnyvale, CA; reconstituted in PBS; SQ; 10 mL/kg) 0.4 mg/kg SQ. On Days 5-11, the groups of mice were also given QD IP injections (5 mL/kg) of the following treatments: first vehicle group, PBS and remaining groups, 5-fluorouracil (5-FU) 60 mg/kg (Fresenius Kabi USA, Lake Zurich, IL) diluted in PBS to induce mucositis with diarrhea. Body weight was measured throughout the study and fecal form was scored on Day 11-13 of the study according to the following scale: 0, normal stool; 1, slightly wet and soft stool; 2, wet and unformed stool with moderate perianal staining of the coat; 3, watery stool with severe perianal staining of the coat.

As shown in FIG. 1 (FIG. 1), I-388 significantly improved cumulative fecal form score (FFS) as did Teuduglutide in mice with 5-FU-induced diarrhea. All mice were dosed on day 1-13 with vehicle, with 0.4 mg/kg of teduglutide, or with 30 mg/kg of compound I-388 (vehicle and Cmpd. I-388: PO, 5 mg/kg and teduglutide: SQ, 10 mL/kg). PBS or 5-FU at 60 mg/kg (used to induce mucositis and diarrhea) were administered interperionally (IP; 5 mL/kg) on days 5-11. FFS were measured on days 11-13 and summed for cumulative FFS (animals that did not defecate in the 30 min observation period on each session did not receive a score and were excluded from the analysis). These data are reported as median values and were analyzed for statistical significance by Kruskal-Wallis test followed by Dunn's test.

Example 122: In Vivo Measurement of Colon Length, Weight and Inflammation in an Inflammatory Bowel Disease Model Six week old C57BL/6 female, were acclimated for 2 days. Starting on Day −2, 5 groups of mice were dosed PO (mL/kg) BID with 1) vehicle (10% HPCD); 2) vehicle; 3) vehicle; mice had sitagliptin (3.6 g/L for a dose of ~800 mg/kg/day) added to their drinking water; 4) I-389 30 mg/kg; or 5) I-389 30 mg/kg; mice had sitagliptin (3.6 g/L for a dose of 800 mg/kg/day) added to their drinking water. On Day 0, mice in groups 2-5 were put on drinking water containing 1.5% DSS to induce colitis. Note: Groups 3 & 5 were on drinking water containing both DSS and sitagliptin. On Day 7, mice were taken off of DSS treatment and received either regular drinking water (Groups 1, 2, and 4) or drinking water with sitagliptin (Groups 3 and 5). On Day 8, mice were transferred to a separate container for DAI scoring which consists of evaluation of stool consistency, blood in stool, incidence of rectal prolapse, and body condition according to the scoring system shown in Table 19. The DAI score is a summation of each individual score in each category (columns) for a single animal. Mice were euthanized, blood was collected for plasma, colons were removed for length measurement, cytokine analysis, and histological staining, pathological analysis and scoring of colonic tissue damage. Colonic tissue damage was scored according to observed microscopic changes based on the following schema: 0=no significant change, 1=minimal, 2=mild, 3=moderate and 4=severe. Parametric data for each group are presented as mean±SEM. Statistical analysis was performed using one-way ANOVA followed by Holm-Sidak's multiple comparisons test. Statistical significance versus DSS/vehicle is marked as *, $P<0.05$; , $P<0.01$, *, $P<0.001$, and ****, $P<0.0001$. Statistical significance versus DSS/I-389 is marked as †††, $P<0.001$. Non-parametric data for each group is shown as a dot blot with median (line). Statistical analysis was performed using Kruskal-Wallis test followed by Dunn's test to detect differences between groups.

TABLE 19

Disease Activity Index Scoring Schema

| Stool score | Stool blood score | Rectal prolapse | Body condition |
|---|---|---|---|
| 0 Normal | 0 No blood | 0 Negative | 0 Normal |
| 1 Moist/sticky stool | 1 Evidence of blood in stool or around anus | 1 Positive | 1 Ruffled fur or altered gait |
| 2 Soft stool | 2 Severe bleeding | | 2 Lethargic or moribund |
| 3 Diarrhea | | | |

Figure 2:
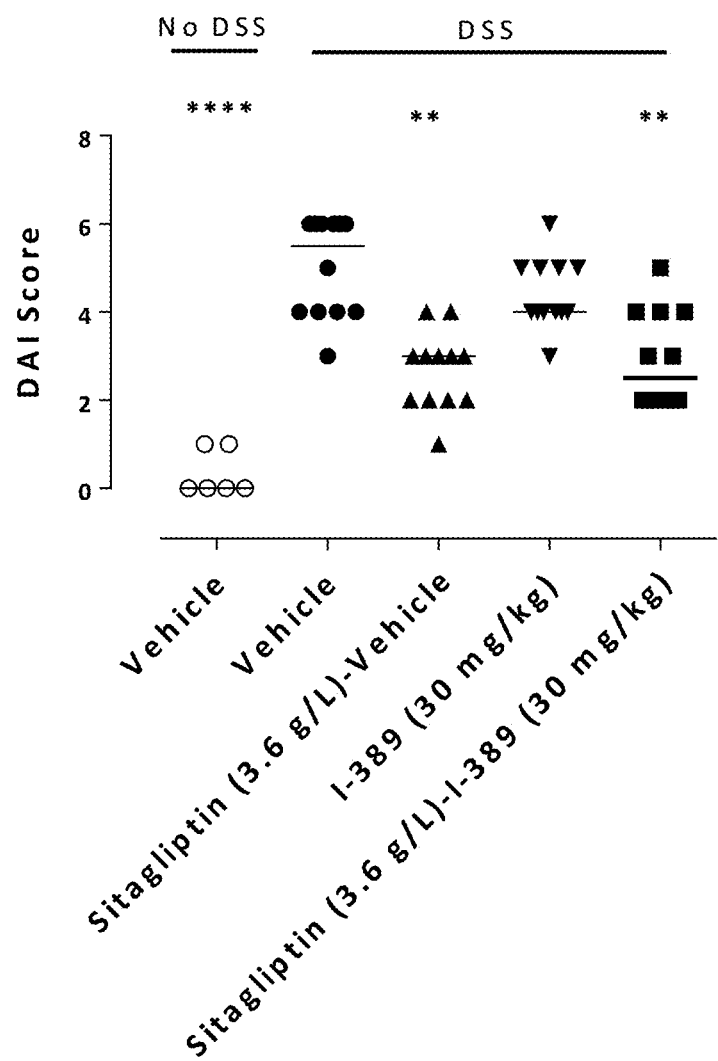
FIG. 2 shows the DAI score in a mouse Inflammatory Bowel disease model upon treatment when mice were treated with Sitagliptin at 3.6 g/L, Compound I-389 at 30 mg/kg, a combination of Sitagliptin at 3.6 g/L and Compound I-389 at 30 mg/kg, and vehicle.
Figure 3:
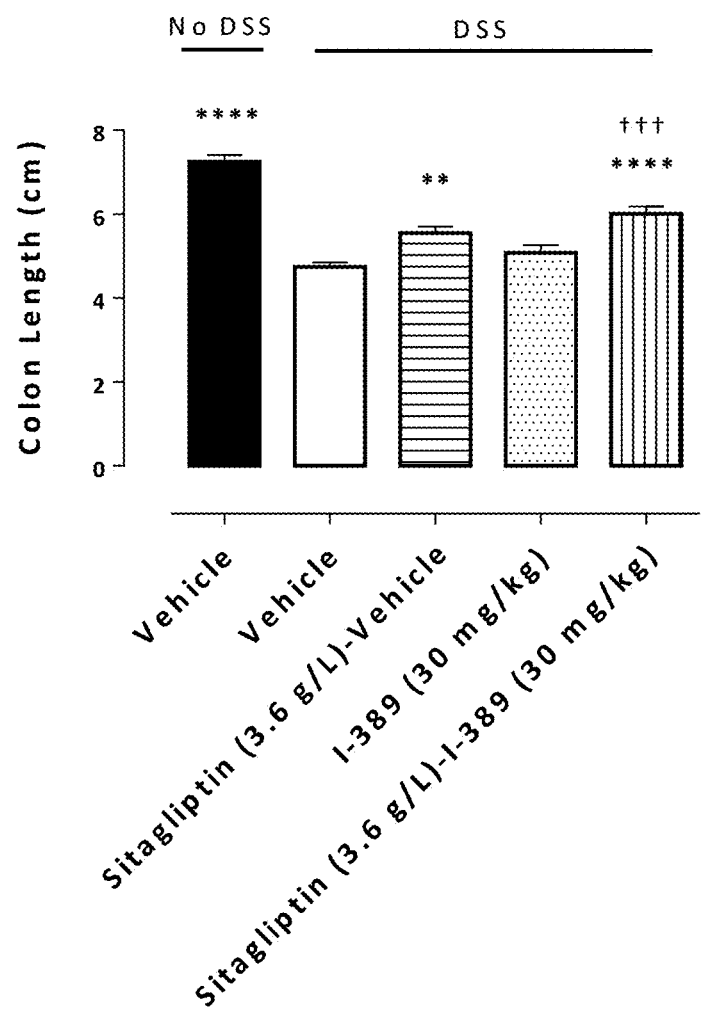
FIG. 3 shows the colon length in a mouse Inflammatory Bowel disease model upon treatment when mice were treated with Sitagliptin at 3.6 g/L, Compound I-389 at 30 mg/kg, a combination of Sitagliptin at 3.6 g/L and Compound I-389 at 30 mg/kg, and vehicle.
Figure 4:
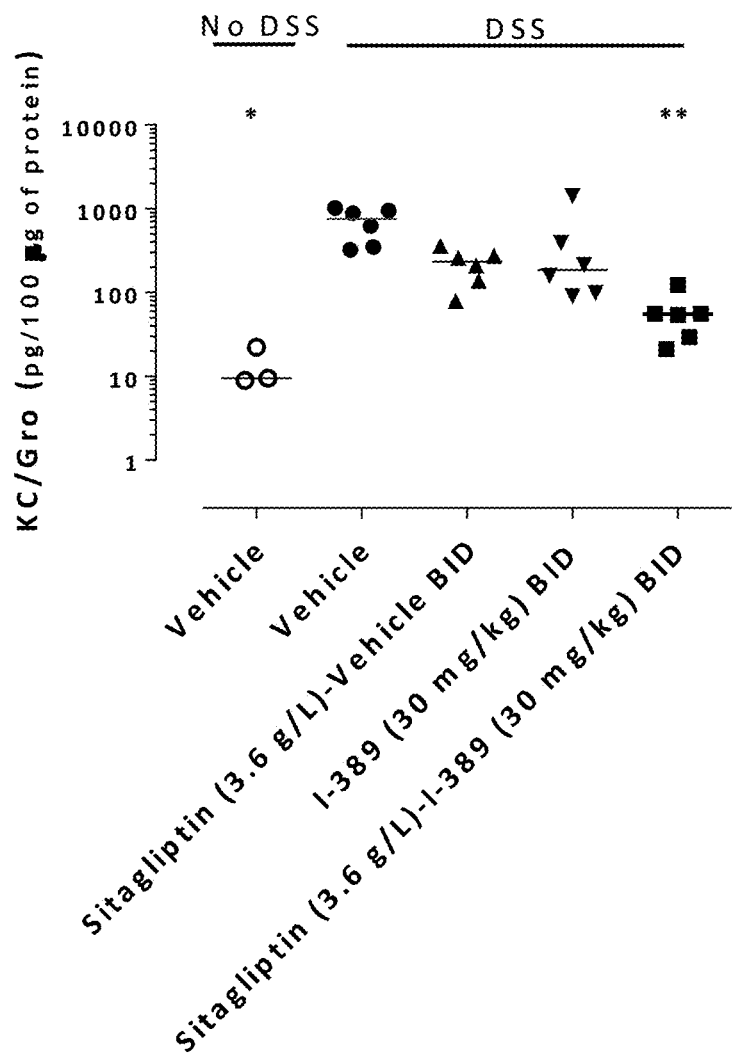
FIG. 4 shows the colon cytokine level of KC/Gro in a mouse Inflammatory Bowel disease model upon treatment when mice were treated with Sitagliptin at 3.6 g/L, Compound I 389 at 30 mg/kg, a combination of Sitagliptin at 3.6 g/L and Compound I-389 at 30 mg/kg, and vehicle.
Figure 5:
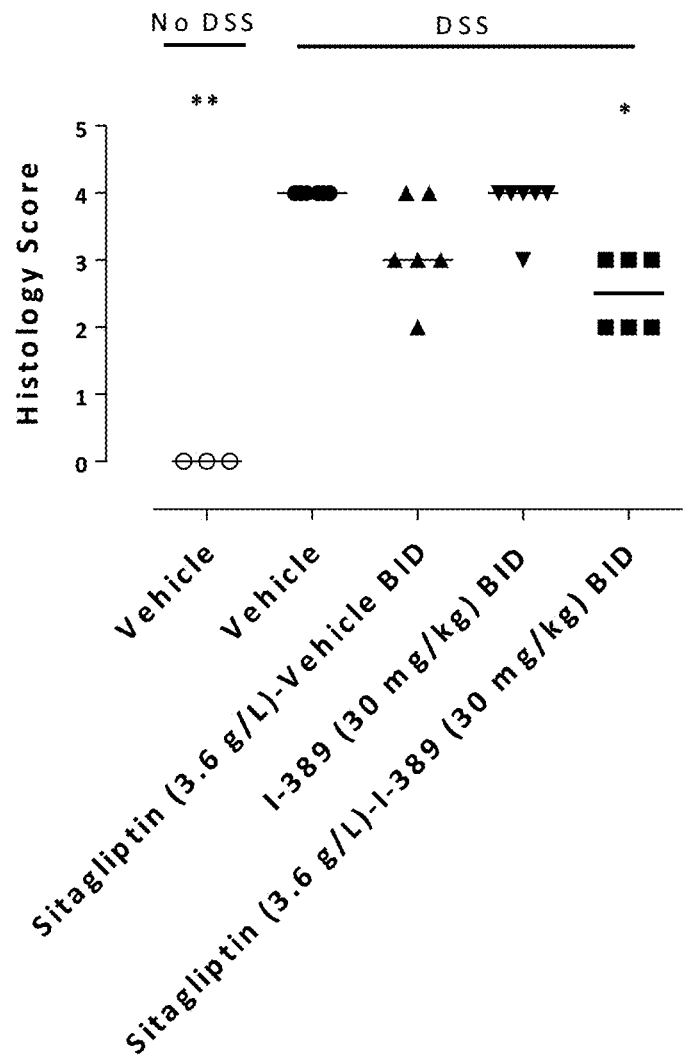
FIG. 5 shows the colon histology score in a mouse Inflammatory Bowel disease model upon treatment when mice were treated with Sitagliptin at 3.6 g/L, Compound I-389 at 30 mg/kg, a combination of Sitagliptin at 3.6 g/L and Compound I-389 at 30 mg/kg, and vehicle.

Treatment of mice with I-389 combined with sitagliptin or sitagliptin treatment alone partially abrogated DSS-induced colonic damage. Compared to the vehicle/DSS group, the I-389+sitagliptin/DSS group had a significantly lower disease activity score (5.6 versus 2.6, respectively); FIG. 2 (FIG. 2), increased colon length (4.7±0.1 versus 6.0±0.2 cm, respectively); FIG. 3 (FIG. 3), colon cytokine level of KC/Gro (56.5±14.6 versus 690.5±124.8 pg/100 µg of tissue, respectively); FIG. 4 (FIG. 4) and colon histology score (4.0 versus 2.5, respectively); FIG. 5 (FIG. 5). The sitagliptin/DDS also had a significantly decreased DAI score (3.0) and increased colon length (5.6±0.2 cm), but to a lesser degree than when it was combined with I-389.

Example 123: Pharmacodynamic Effects on Acute Phosphate Uptake in Rats

Compounds are tested for the ability to reduce the appearance of circulating radiolabeled phosphate subsequent to administration to the alimentary canal in rats. The rate of radiolabeled phosphate tracer accumulation in the blood of rats is taken as a surrogate for the intestinal absorption rate of a phosphate meal from the gastrointestinal tract. To this end, circulating radiolabeled phosphate is monitored after intragastric co-administration to rats of a phosphate tracer meal along with a compound of Formula (I') or Formula (I). However, since some of the compounds tested potentially had properties that may hinder this assay, such as having putative gastrointestinal motility effects (e.g., delaying gastric emptying) or being purposefully chemically unstable in the gastrointestinal tract, direct intraduodenal administrations of the phosphate tracer bolus is also performed at times.

Male Sprague-Dawley rats that are 8-weeks of age are purchased from Charles River Laboratories (Hollister, CA). To enable blood sampling, rats are purchased with catheters surgically implanted in the jugular vein by the vendor. For studies requiring intraduodenal administration, an additional catheter is surgically implanted by the vendor to allow for direct infusion to the lumen of the duodenum. Rats are fed a normal, grain-based chow (Harlan Teklad, Madison, WI; 2018 Teklad Global 18% Protein Rodent Diet) containing 0.65% P, 1% Ca; 1.5 IU/g Vitamin $D_3$ and given water ad libitum leading up to the study.

Following an overnight fast, rats are administered a phosphate solution containing [$^{33}$P]orthophosphate (PerkinElmer, Waltham, MA) as a tracer with or without test articles dispersed in the solution at the indicated dosage. This dosing solution typically contains 8 mM monobasic sodium phosphate (1.25 µCi [$^{33}$P]orthophosphate/µmol), 4 mM calcium chloride, 0.4% hydroxypropyl methocellulose (w/v), and 2% dimethylsulfoxide (w/v). The dosing solutions are prepared in water for intragastric gavage at 10 ml/kg and in saline if administered intraduodenally using a previously implanted catheter at 5 ml/kg as a bolus.

Blood is sampled from the jugular vein via implanted catheters from conscious rats following dosing and the radioisotope associated with the resulting plasma is determined by scintillation counting. The relative amount of phosphate uptake from the administered dose to the plasma is assessed using body weight estimation of total circulating plasma. See Bijsterbosch et al., Experientia. 37: 381-382, 1981 (The plasma volume of the Wistar rat in relation to the body weight). The comparative amount of phosphate uptake at 15 min post-dose for each group (n=6) is expressed as a percentage relative to the study vehicle group (n=6) as mean±SEM. Statistical comparisons of the means of each test group compared to the mean of the vehicle group are determined by one-way analysis of variance followed by the Dunnett's posthoc test and P<0.05 is accepted as statistically significant (ns, not significant; *, P<0.05; , P<0.01; and *, P<0.001).

Example 124: Flux Rate Measurements of Tissues Using a Ussing Chamber

Segments of duodenum and jejunum are immediately removed from anesthetized animals and opened along the mesenteric line and fixed on a Pyrex plate with the mucosal surface uppermost. Epithelial tissues are stripped off the muscle layers and mounted in computer-controlled Ussing chambers (National Physiology Instrument, California) with an exposed area of 100 mm$^2$. The tissues are incubated on both sides with 13 mL of an isotonic buffer solution (pH 6.0 or pH7.4) containing (mmol/L) NaCl 125.4, KCl 5.4, CaCl$_2$, 1.2, NaHCO$_3$, 21, Na$_2$HPO$_4$, 0.3, NaH$_2$PO$_4$, 1.2. The functional viability and the integrity of the tissues at the start and the end of flux measurements are ensured with the measurement of short-circuit current ($I_{sc}$) in response to either theophylline (10 mM serosal) or glucose (10 mM mucosal) or L-alanine (5 mM mucosal).

For calculations of unidirectional Pi flux rates ($J_{ms}$: flux from mucosal to serosal side, $J_{sm}$: flux in the opposite direction), 185 KBq [$^{33}$P]-orthophosphate (370 MBq/mL, Perkin-Elmer) and test compounds are added to one side of the tissue. Samples (0.1 ml) are taken from the labeled side 20 minutes later and subsequently in at least three 10 min intervals from the unlabeled side (0.5 mL) of the Ussing chamber. All samples taken from the unlabeled side are replaced by equal volumes of isosmotic bathing fluid. Net fluxes ($J_{net}$) are calculated as differences between $J_{ms}$ and $J_{sm}$ of paired tissues whose conductances do not differ by more than 25%. In another series of experiments flux measurements are done before and after the addition of arsenate (mucosal) or ouabain (serosal) to the bathing solution. Radioactivity measurements are measured in a TopCount (Perkin Elmer) liquid scintillation counter.

Example 125: In Vitro—Ex Vivo Assays

Segments of duodenum and jejunum (5 cm) are removed from animals anesthetized with pentobarbitone sodium, flushed with ice-cold 0.9% saline and everted on glass rods. Samples are securely mounted on the rod and then preincubated for 5 min at 37° C. in oxygenated buffer, pH 7.4 or 6.0, containing in mM: hydroxyethylpiperazine-N'-2-ethanesulfonic acid 16, glucose 10, KCl 3.5, MgSO$_4$ 10, CaCl$_2$ 1, NaCl 125, followed by 2 min incubation in the same buffer containing 100 mM $^{33}$Pi ($^{33}$Pi-specific activity 1.85 MBq/mL) and test compounds. The buffer is rapidly stirred using a magnetic flea to minimize the effects of static water layers at the mucosal surface.

Uptake is terminated by exposing the tissue for 10 minutes at room temperature to phosphate-buffered saline containing a 10-fold excess of nonradioactive phosphate. This procedure is followed by a further 10 minute wash in phosphate-buffered saline at room temperature and samples are then blotted dry and the weight recorded. Samples are digested overnight in Protosol (PerkinElmer). Scintillation counting of the digested sample and initial uptake solution permits calculation of phosphate retention of tissue (in nmol/g).

Example 126: Inhibition of Intestinal Sodium and Phosphate Absorption

To assess the ability of selected example compounds of Formula (I') or Formula (I) to inhibit the absorption of phosphate from the intestinal lumen, the intake and excretion balance of phosphate is measured in rats. Eight week old Sprague Dawley rats are purchased from Charles River Laboratories (Hollister, CA) and acclimated for at least 6 days with free access to food and water. During this time and throughout the study, rats may be fed a standard diet (Harlan Teklad, Madison, WI; 2018 Teklad Global 18% Protein Rodent Diet) or a purified egg white synthetic diet consisting of 0.6% Ca and 0.35 or 0.6% phosphorus (Harlan Teklad; TD.84122 and TD.130318, respectively).

A day prior to the initiation of the study, rats are acclimated to individual metabolic cages with free access to water and a powdered version of the diets listed above. Animals are dosed approximately 1 hour prior to the commencement to the dark phase either PO at 10 ml/kg with an effective dose of the test article or via drug-admixed food) based on the daily mass of chow rats have been determined to consume. With both dosing paradigms, each rat is given free access to water and an aliquot of powdered chow for each day they are housed in the metabolic cage that is the daily average of ad libitum consumption for that type of chow, for the same type of rats (i.e., male rats at 8 weeks of age consume an average of 18 g/d of the purified diets listed above). This is done to reduce variability and streamline subsequent 24 hour consumption and excretion measurements. Daily water and chow consumption measurements as well as daily urine and fecal collections follow from 1 to 4 consecutive days.

The phosphate, sodium, and potassium content of urine samples are determined by ion chromatography. Urine samples are processed by gravimetric volume determinations followed by acidification with 6 N HCl. Acidified samples are briefly centrifuged (3,600×g) and the supernatants are then diluted with 10 mM HCl. The diluted samples, calibration standards (Sigma/Fluka Analytical), and QC samples (standards prepared in-house) are filtered prior to injection on an ion exchange chromatography system (Dionex ICS-3000). Sodium and potassium are resolved using an isocratic method consisting of a 25 mM methanesulfonic acid mobile phase and a Dionex CS 12A cation exchange analytical column. Phosphate is resolved using an isocratic method consisting of a 35 mM potassium hydroxide mobile phase and a Dionex AS 18 anion exchange analytical column. Quantitative analysis is performed using Dionex Chromeleon software. All sample concentrations are interpolated from a calibration curve based on chromatographic peak areas.

The phosphate, sodium, calcium, and potassium content of each 24 hour fecal sample are determined by atomic emission spectroscopy. Dried fecal pellets or a representative sample from dried homogenized feces are digested with repeated additions of concentrated nitric acid and hydrogen peroxide over 2-3 hours at 65-95° C. The sample solutions are then diluted with 1% nitric acid prior to analysis with an atomic emission spectrometer (Agilent 4100 MP-AES) at the following element emission wavelengths: calcium (422.673 nm), sodium (588.995 nm), potassium (766.491 nm), and phosphorus (214.915 or 213.618 nm). A cesium solution is used as both an ionization buffer and an internal standard. Data analysis is performed using Agilent MP Expert software.

Daily urinary and fecal phosphate output relative to the P consumed in the diet for each animal on each day measured is calculated. The percentage inhibition of phosphorus absorption is expressed by determining the reduction of these ratios compared to the control group (animals with no drug in chow). This may also be done with other ions of interest. If there are multiple days tested, these may represent replicates for steady-state measurement of phosphate balance for each rat, in which case regular daily consumption by the animals is a prerequisite. Increased fecal phosphate with an approximate concomitant decrease in urinary P to maintain neutral balance in the rats is an indication of overall decreased phosphate absorption in rats treated with example compounds (i.e., compounds of Formula (I') or Formula (I)).

Example 127: Effects in a Rat Chronic Kidney Disease (CKD) Model

To assess the ability of selected example compounds of Formula (I') or Formula (I) to impact soft tissue calcification often associated with later stages of CKD, the 5/6 nephrectomy (5/6Nx) rat model is utilized to examine mineral homeostasis in a diseased state. A commonly used model to study various aspects of CKD, the 5/6Nx rat is not normally hyperphosphatemic unless challenged with dietary phosphate (see Shobeiri et. al., *Am J Nephrol.* 31:471-481, 2010, Vascular Calcification in Animal Models of CKD: A Review). Therefore, to ensure efficient and steady phosphatemic vascular calcification progression in these animals, a combination of enhanced bioavailable phosphate in the diet and Vitamin $D_3$ treatment is implemented as adapted from the protocol developed by the Lopez group (see Lopez et al., *J. Am. Soc. Nephrol.* 17: 795-804, 2006. Calcimimetic R-568 Decreases Extraosseous Calcifications in Uremic Rats Treated with Calcitriol).

Male Sprague-Dawley ⅚th nephrectomized rats are purchased from Charles River Laboratories (Hollister, CA) with surgical procedures performed by the vendor. Reduction in functional renal mass is achieved by two surgeries: sub-total nephrectomy of the left kidney followed by a 1-week recovery prior to uninephrectomy of the right kidney. After a 3 day recovery period from the second surgery, the rats are transported to the testing facility at 9 weeks of age.

Upon arrival and throughout the study, rats are fed a purified powdered diet consisting of 0.9% inorganic P (phosphorus) and 0.6% Ca (TD.10809, Harlan-Teklad, Madison, WI). Matinal serum is obtained by retroorbital or tail vein bleeding and only animals with serum creatinine levels of 0.9 to 1.2 mg/dl are enrolled to the study with groups (n=12) stratified based on serum creatinine and body weight. Enrolled rats in treatment groups are dosed drug-in-chow using the same diet as the vehicle group described above. Additionally, a regimen of calcitriol (active Vitamin $D_3$ 80 ng/kg i.p.) administration 3 times per week is initiated.

Kidney function, phosphatemic state as well as other parameters are monitored weekly with appropriate serum marker measurements via standard clinical chemistry or ELISA analysis. Rats with serum creatinine greater than 2 mg/dL or with a body weight of 80% or less of the mean cohort body weight are removed form study due to advanced diseased state. Urine markers for kidney function may also be measured by placing rats in metabolic cages to allow for the collection of excretions.

After 4 weeks, rats are euthanized and organs are collected and weighed. The mineralization of the aortic arch, heart, stomach and kidney remnant are determined. Whole tissue samples are digested with repeated additions of concentrated nitric acid and hydrogen peroxide over 2-3 hours at 65-95° C. The sample solutions are then diluted with 1% nitric acid prior to analysis with an atomic emission spectrometer (Agilent 4100 MP-AES) at the following element emission wavelengths: calcium (422.673 nm), sodium (588.995 nm), potassium (766.491 nm), and phosphorus (214.915 or 213.618 nm). A cesium solution is used as an ionization buffer and internal standard. Data analysis is performed using Agilent MP Expert software.

A reduction in vascular calcification in animals treated with test articles compared to their untreated counterparts is consistent with the reported inhibition of dietary phosphate absorption that is needed to drive the disease state in this CKD rat model.

Example 128: In Vivo Evaluation of Liver Enzymes, Triglycerides and Fibrosis in a Mouse Model of Non-Alcoholic Steatohepatitis (NASH)

NASH is established in male mice by a single subcutaneous injection of streptozotocin (Sigma, USA) after birth and feeding with a high fat diet (CLEA Japan, Japan) ad libitum after 4 weeks of age (day 28±2). Normal and NASH mice are randomized mice into 6 groups of 8-12 mice at 6 weeks of age (day 42±2). All groups are dosed BID (with vehicle or test agent; PO; 5 mL/kg) daily except the normal mice that do not receive any treatment. Groups: 1) normal mice are fed with a normal diet ad libitum without any treatment; 2) vehicle (10% hydroxypropyl-beta-cyclodextran in 10 mM PBS); 3) linagliptin 10 mg/kg QD in PM and vehicle QD in AM; 4) I-389 30 mg/kg; 5) linagliptin 10 mg/kg+I-389 30 mg/kg-QD in PM and I-389-QD in AM; and 5) telmisartan 10 mg/kg-QD in PM and vehicle-QD in AM. Individual body weight, survival, clinical signs are assessed/measured daily during the treatment period. Mice in all groups are euthanized under heavy anesthesia after up to 12 weeks of treatment. Blood and tissues are collected. From these, the following are measured: 1) liver weight (liver-to-body weight ratio are calculated); 2) plasma levels of liver enzymes; 3) liver triglycerides (quantified by Triglyceride E-test kit [Wako, Japan]); 4) NAFLD Activity score based on histological analyses of H&E-stained liver sections; and 5) fibrosis area based on histological analyses of Sirius red-stained liver sections.

Statistical tests are performed using Bonferroni Multiple Comparison (parametric data are tested by the following analyses: for more than one factor, Two-Way ANOVA followed by Bonferroni's multiple comparison post-hoc test; for one factor and more than 2 groups, One-Way ANOVA followed by Holm-Sidak's post-hoc test; and for one factor and 2 groups, Student's t-test. Non-parametric data analyses of one factor with more than 2 groups are analyzed by Kruskal-Wallis followed by Dunn's post hoc test. P values <0.05 are considered statistically significant.

Example 129: Measurement of Intestinal Motility Independent of Gastric Emptying

Seven-eight week old C57BL/6 male mice were acclimated for four days. Mice were then divided into 2 groups and fasted for 2-1/2 h, followed by a PO dose (10 mL/kg) of vehicle (10% 2-hydroxypropyl-β-cyclodextrin [HPCD] in 10 mM PBS containing 0.1% tween 80; HPCD/tween 80) or I-389 30 mg/kg. One hour later, carmine red (6% in sterile water; 100 µL/mouse) dye was infused via the duodenal catheter and mice were euthanised fifteen min after that. The entire length of the small intestine and the distance from the stomach to the dye front in the small intestine was measured and used to calculate the percentage of the small intestine the dye front had travelled during the 15 min timeframe.

Figure 6:
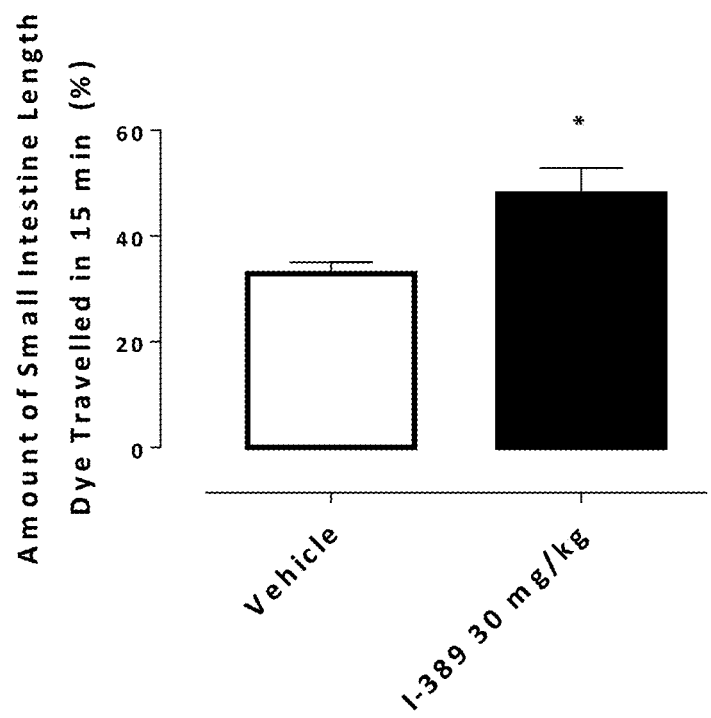
FIG. 6 shows the amount of small intestine length Dye travelled in mice when treated with Compound I-389 at 30 mg/kg and vehicle.

As shown in FIG. 6 (FIG. 6), I-389 treatment resulted in a statistically significant increase in the percentage the carmine red dye front travelled in the small intestine when compared to treatment with vehicle showing I-389 decreased intestinal transit time. These data are reported as mean±SEM values and were analyzed for statistical significance by unpaired Student's t-test, *p<0.05.

Example 130: In Vivo Evaluation of Small Intestine Length and Weight, Villus/Crypt Length in Small Intestine, and Crypt Depth in Colon in Mice Vehicle (HPCD/tween 80) or I-389, 30 or 100 mg/kg, was administered PO BID, with or without sitagliptin (a dipeptidyl peptidase 4 inhibitor [DPP-4 inhibitor] used to block the degradation of GLP-1 and GLP-2) 3.6 g/L in drinking water (dose~800 mg/kg/day) to CD-1 female mice for ten consecutive days. Tedulgutide (a GLP-2 receptor agonist; American Peptide, catalog #304076, supplied by Bachem) 50 µg/kg in I-389 was injected SC in a control group BID during the same period. Terminal plasma was collected for measurement of GLP-1 and GLP-2 concentrations. The small intestine and colon were collected, flushed with cold PBS to remove contests, patted dry, weighed and further trimmed for histological analysis. Morphometric analysis was performed to determine the villus/crypt length in the proximal jejunum and distal ileum and crypt depth (length) in the proximal colon.

Figure 7:
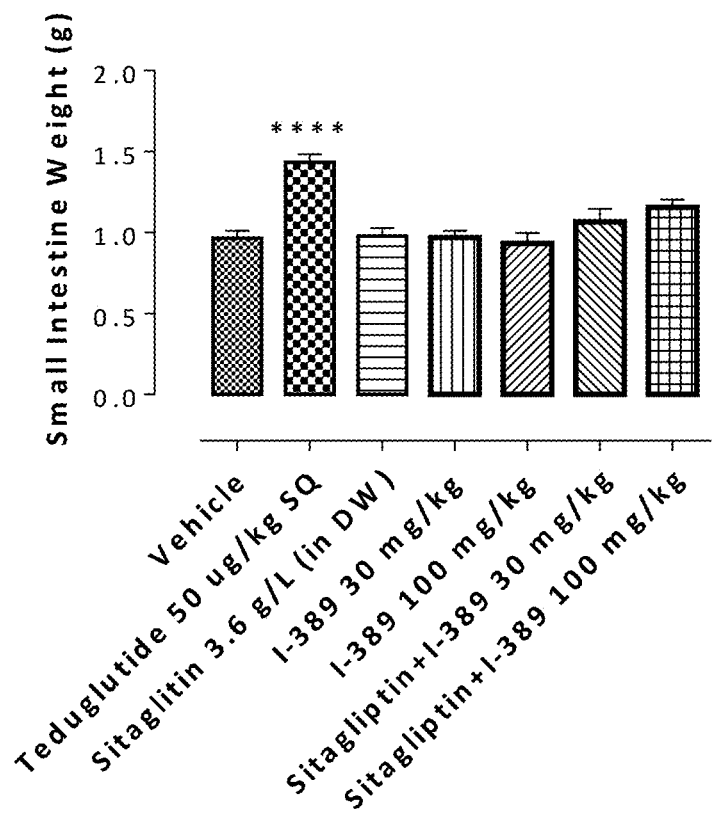
FIG. 7 shows the small intestine weight in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 8:
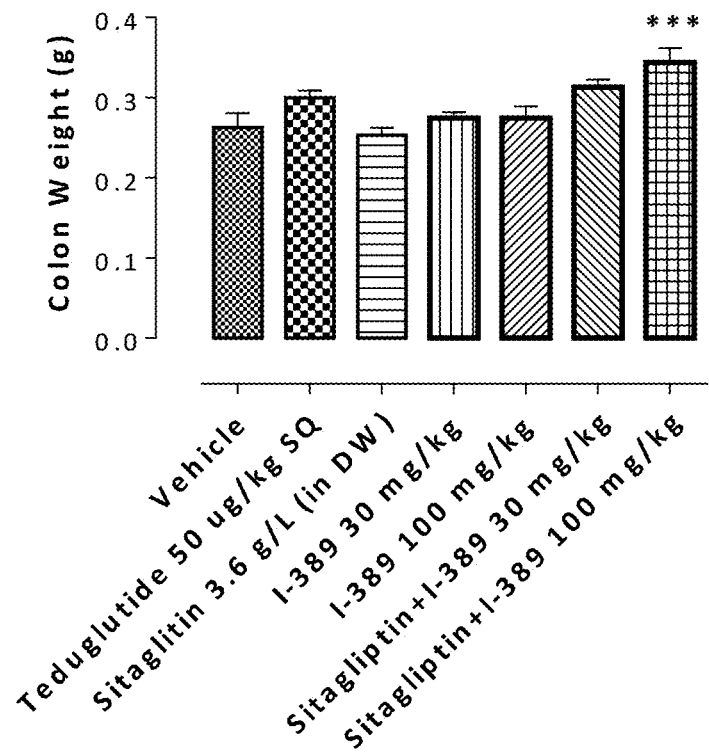
FIG. 8 shows the colon weight in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 9:
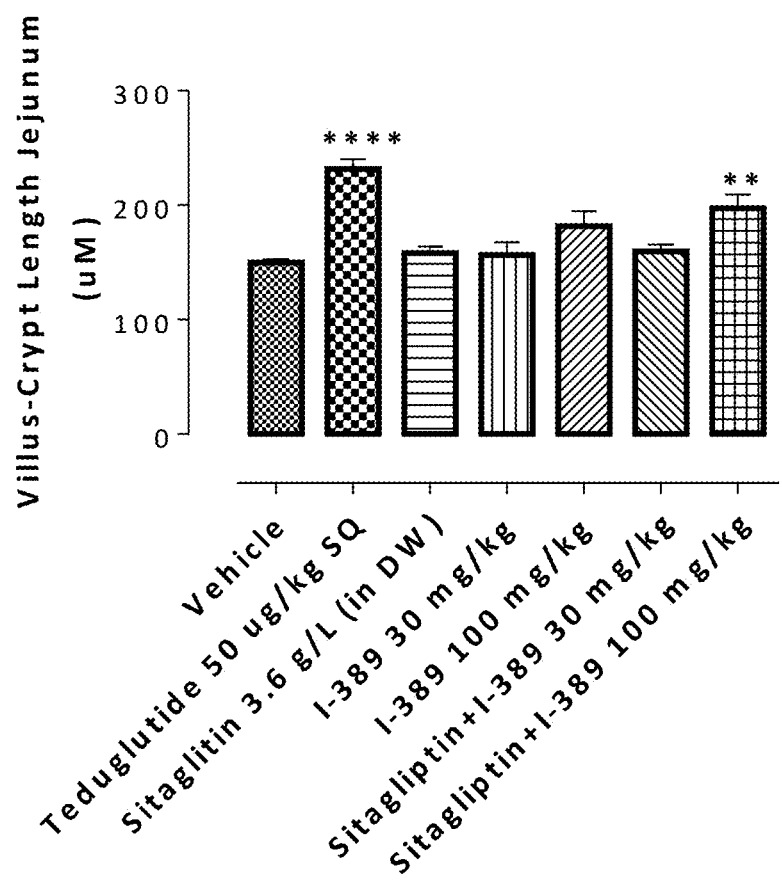
FIG. 9 shows the villus crypt length jejunum in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 10:
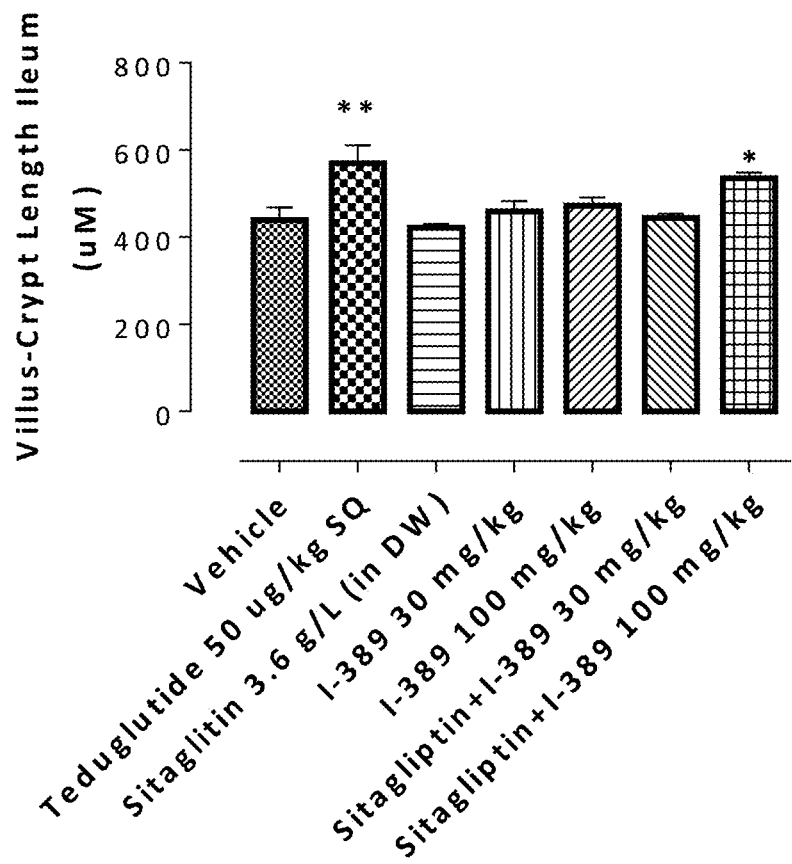
FIG. 10 shows the villus crypt length ileum in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 11:
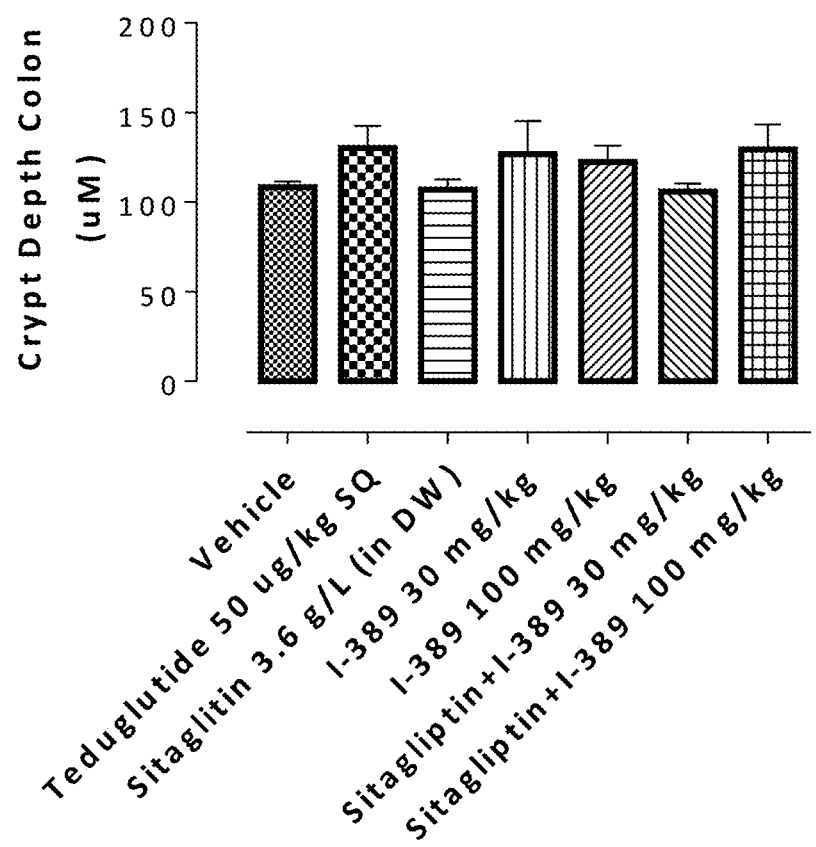
FIG. 11 shows the crypt depth of the colon in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 12:
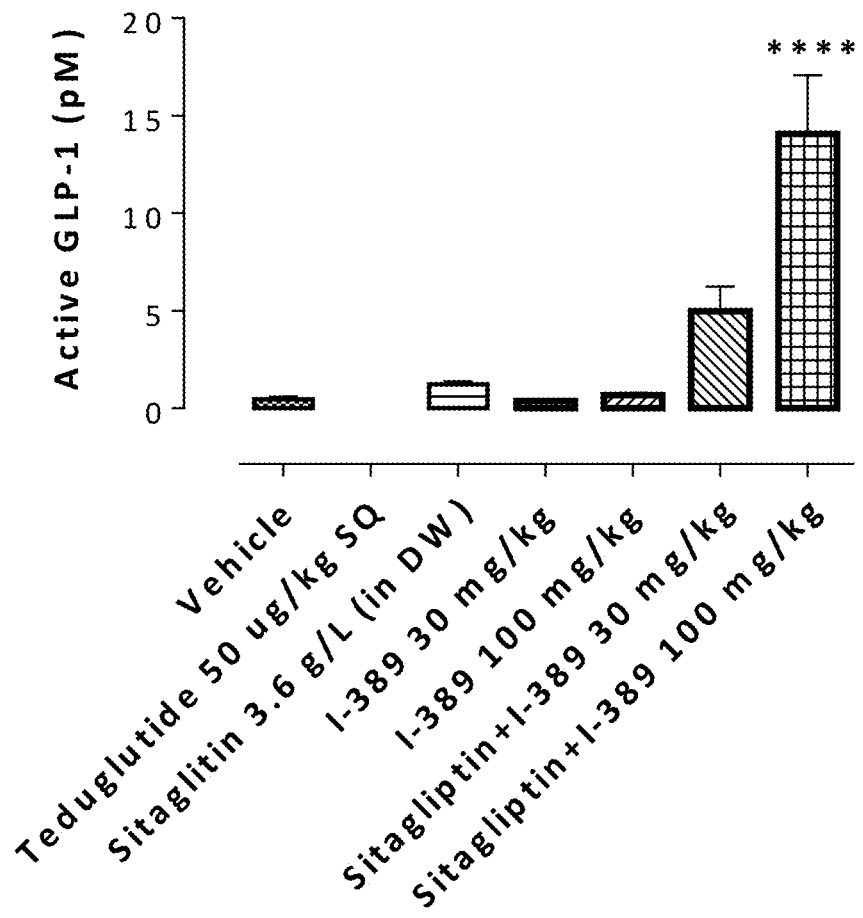
FIG. 12 shows the active GLP-1 in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.
Figure 13:
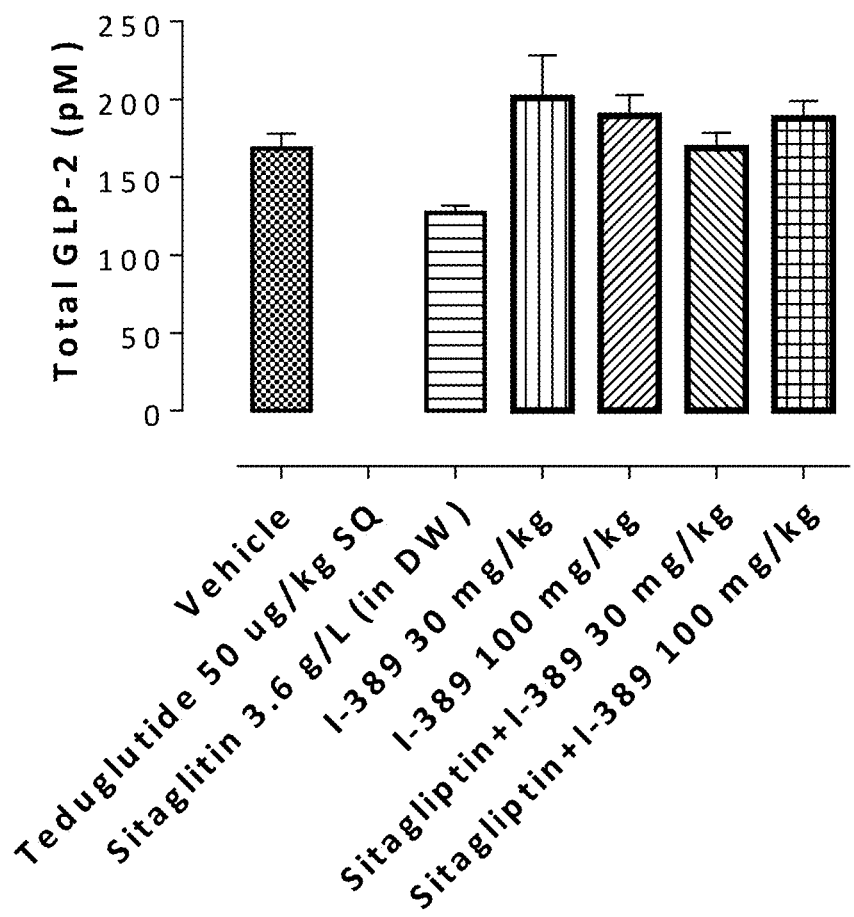
FIG. 13 shows the total GLP-2 in mice when treated with teduglutide at 0.5 mg/kg, Sitagliptin at 3.6 g/L, Compound I-389 at 30 mg/kg, Compound I-389 at 100 mg/kg, a combination of Sitagliptin at 3.6 g/L and Compound I-389 at 30 mg/kg, a combination of Sitagliptin at 3.6 g/L and Compound I-389 at 100 mg/kg, and vehicle.

Following treatments in CD-1 female mice for ten consecutive days, teduglutide significantly increased small intestine weight (48%) and showed a trend to increase colon weight (14%), FIG. 7 (FIG. 7). I-389 increased colon weight significantly at a dose of 100 mg/kg when co-dosed with sitagliptin (31%), FIG. 8 (FIG. 8). I-389 (100 mg/kg) combined with sitagliptin, like teduglutide, increased the villus-crypt length in the proximal jejunum (teduglutide: 55%, I-389 100 mg/kg+sitagliptin: 32%), FIG. 9 (FIG. 9). and distal ileum (teduglutide: 30%; I-389 100 mg/kg+ sitagliptin: 22%) FIG. 10 (FIG. 10). None of the treatments significantly affected colon crypt depth, FIG. 11 (FIG. 11). Levels of active GLP-1 were significantly increased by I-389 (100 mg/kg)+sitagliptin treatment compared to vehicle (>3000%) or either treatment alone, FIG. 12 (FIG. 12). Levels of total GLP-2 were not statistically different comparing each treatment group to vehicle, FIG. 13 (FIG. 13). Data for each group are presented as mean±SEM. Statistical analyses were performed using one-way ANOVA followed by Holm-Sidak's multiple comparisons test. Statistical significance compared to vehicle (WD) is marked as *, P<0.05; , P<0.01, *, P<0.001, and ****, P<0.0001.

Example 131: In Vivo Evaluation of Plasma Glucose and Insulin Levels and Liver Triglycerides and Total Cholesterol Levels in a Mouse Model of NAFLD and Mild Diabetes, Western Diet WD)-Fed Mice Seven week old C57BL/6 male mice were housed 5/cage. Two cages of mice were put on normal chow (Harlan Teklad 2018), and the remaining cages of mice were put on WD (Harlan Teklad, TD.88137, 62% fat/0.2% cholesterol) to induce NAFLD. After 10 weeks, mice were weighed and fasted for 4 h. Blood was collected to measure fasting glucose levels, processed to plasma for measurement of insulin, triglycerides and total cholesterol. This process was repeated on Day 29 of treatment. Based on body weight and fasted glucose and insulin levels, mice were divided into 5 treatment groups (n=10/group), Table 20. Vehicle-1 consisted of HPCD/tween 80 and was used for formulation of I-389 and linagliptin (a DPP-4 inhibitor); vehicle-2 consisted of sterile water and was used for formulation of liraglutide (a GLP-1 analogue; BACHEM, Torrance, CA). Mice were weighed twice weekly throughout the study. On the last day of the study (Day 30, 8 hours after food removal), mice were euthanized. Blood was collected in tubes with inhibitors to block DPP-4 activity and processed to plasma for measurement of liver enzymes and GLP levels using an Ace Alera clinical analyzer and the Multi-Array Assay System from Meso Scale Discovery, respectively. The entire liver was collected, weighed, and a sample was taken and weighed for measurement of triglycerides and total cholesterol.

TABLE 20

Study Group Assignment

| Treatment Group | 1 | 2 | 3 | 4 | 5 | 6 |
|---|---|---|---|---|---|---|
| Animal Number | 10 | 10 | 10 | 10 | 10 | 10 |
| Chow | Normal | WD | WD | WD | WD | WD |
| Test Article-Lot | Vehicle | Vehicle | Liraglutide | — | I-389 | I-389 |
| Vehicle | HPCD/tween 80 | HPCD/tween 80 | Sterile Water | HPCD/tween 80 | HPCD/tween 80 | HPCD/tween 80 |
| Test Article Dose (mg/kg) | — | — | 0.4 | — | 30 | 30 |
| DPP-4 Inhibitor | — | — | — | Linagliptin | ' | Linagliptin |
| DPP-4 Inhibitor Dose (mg/kg) | — | — | — | 10 | — | 10 |
| Test Article Route | PO | PO | SQ | PO | PO | PO |
| Test Article Dose Volume (mL/kg) | 10 | 10 | 10 | 10 | 10 | 10 |
| I-389 and Liraglutide Concentration (mg/mL) | — | — | 0.04 | — | 3 | 3 |
| Linagliptin Concentration (mg/mL) | — | — | — | 1 | — | 1 |
| Test Article Dosing Frequency | BID | BID | BID | QD Vehicle AM QD | BID | QD I-389 AM QD |

TABLE 20-continued

| Study Group Assignment | | | | | | |
|---|---|---|---|---|---|---|
| Treatment Group | 1 | 2 | 3 | 4 | 5 | 6 |
| | | | | Linagliptin PM | | linagliptin 10 mg/kg + I-389 30 mg/kg PM |

Figure 14:
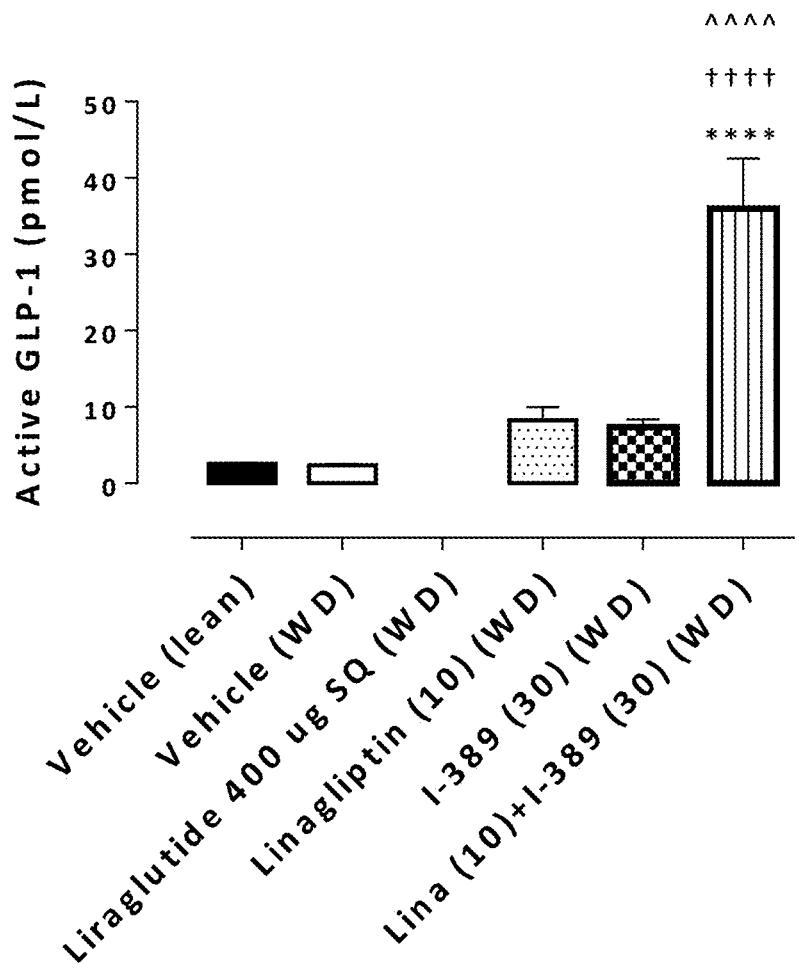
FIG. 14 shows the active GLP-1 in WD fed mice when treated with Liraglutide at 0.4 mg/kg, Linagliptin at 10 mg/kg, Compound I-389 at 30 mg/kg, a combination of Linagliptin at 10 mg/kg and Compound I-389 at 30 mg/kg, lean vehicle, and WD vehicle.
Figure 15:
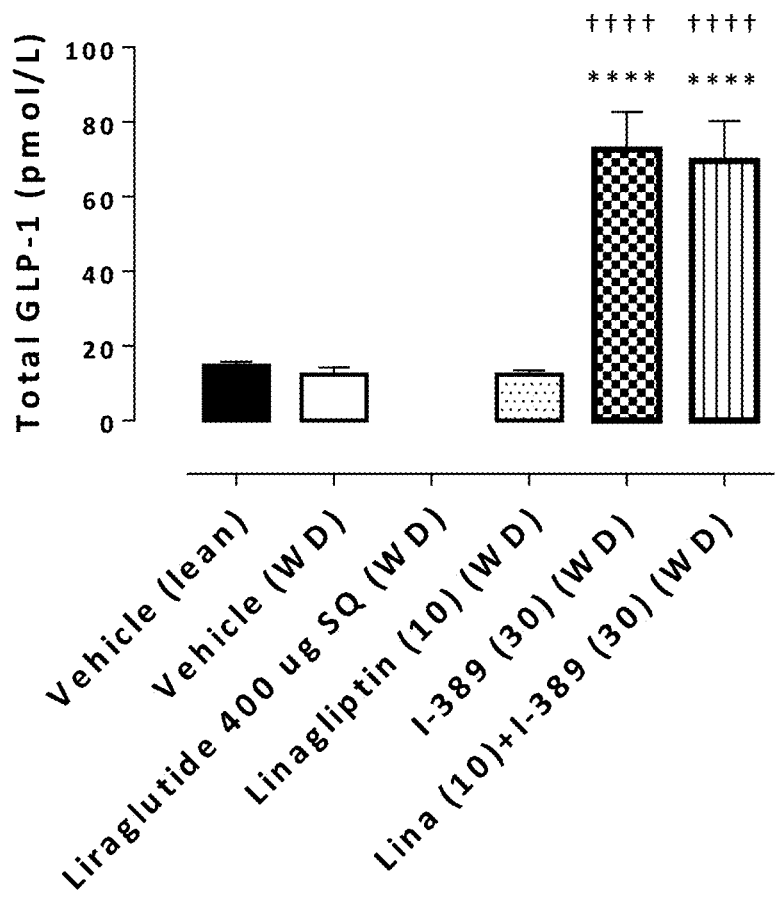
FIG. 15 shows the total GLP-1 in WD fed mice when treated with Liraglutide at 0.4 mg/kg, Linagliptin at 10 mg/kg, Compound I-389 at 30 mg/kg, a combination of Linagliptin at 10 mg/kg and Compound I-389 at 30 mg/kg, lean vehicle, and WD vehicle.

As shown in FIG. 14 (FIG. 14), I-389 was effective at inducing active GLP-1 release, total GLP-1 levels were highly elevated in both I-389 WD diet groups FIG. 15 (FIG. 15). Furthermore, the high active GLP-1 levels in the I-389 and linagliptin combo group indicates that the linagliptin dosing paradigm was sufficient to preserve the intact form of GLP-1, but that linagliptin alone did not induce GLP-1 secretion (as indicated by the low levels of active GLP-1 and total GLP-1 with this treatment). Mice on WD had significantly increased body weight, 4-hour fasted plasma glucose and insulin levels, liver weight, and liver triglyceride and total cholesterol levels in comparison to mice on normal chow (Table 21). The positive control, liraglutide, partially or completely reversed these effects. I-389, linagliptin, and the combination of both agents did not significantly affect body weight (data not shown). However, all three treatments significantly lowered fasted plasma glucose and insulin levels and liver weight. I-389 alone and combination with linagliptin lowered liver triglycerides, but only I-389 alone lowered liver total cholesterol levels. Linagliptin alone increased liver total cholesterol levels. Data for each group are presented as mean±SEM. Statistical analyses were performed using one-way ANOVA followed by Holm-Sidak's multiple comparisons test. For GLP levels, <statistical significance compared to vehicle (WD) is marked as *, P<0.05; , P<0.01, *, P<0.001, and ****, P<0.0001; of linagliptin (WD) versus I-389 alone (WD) or linaglptin+I-389 (WD) is marked as †, P<0.05; ††, P<0.01, of †††, P<0.001, and ††††, P<0.0001; and of I-389 (WD) versus linagliptin (WD)+I-389 (WD) is marked as ˆ, P<0.05; ˆˆP<0.01, ˆˆˆP, P<0.001, and ˆˆˆˆ, P<0.0001. For the remaining parameters, statistical significance compared to vehicle (WD) is marked as *, P<0.05; , P<0.01, *, P<0.001, and ****, P<0.0001.

TABLE 21

Effect of Liraglutide, I-389 and Linagliptin on Measures of Diabetes and Liver Steatosis in Mice Fed Normal or Western Diet Chow

| | Normal chow Vehicle BID (n = 10) | Western diet | | | | |
|---|---|---|---|---|---|---|
| | | Vehicle BID (n = 9) | Liraglutide 0.4 mg/kg BID (n = 10) | I-389 30 mg/kg BID (n = 9) | Linagliptin 10 mg/kg QD (n = 9) | I-389 30 mg/kg BID + Linagliptin 10 mg/kg QD (n = 10) |
| Analyte | | | | | | |
| 4-h fasted glucose (mg/dL) | 182.0 ± 9** | 239 ± 13 | 211 ± 16 | 178 ± 7** | 185 ± 6** | 165 ± 8**** |
| 4-h fasted insulin (ng/mL) | 0.55 ± 0.8**** | 2.3 ± 0.3 | 0.80 ± 0.06**** | 1.6 ± 0.2* | 1.4 ± 0.2** | 1.6 ± 0.3* |
| Liver weight (g) | 1.15 ± 0.04**** | 2.13 ± 0.14 | 1.18 ± 0.05**** | 1.77 ± 0.09* | 1.77 ± 0.11* | 1.67 ± 0.10** |
| Hepatic triglycerides (mg/g) | 8.88 ± 1.27**** | 145.40 ± 14.80 | 37.87 ± 3.13**** | 87.82 ± 13.77*** | 117.90 ± 6.76 | 85.27 ± 10.59*** |
| Hepatic cholesterol (mg/g) | 1.83 ± 0.04**** | 8.56 ± 0.25 | 4.35 ± 0.22**** | 7.24 ± 0.41** | 10.17 ± 0.21*** | 8.74 ± 0.30 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claim

The invention claimed is:
1. A compound of Formula (I'):

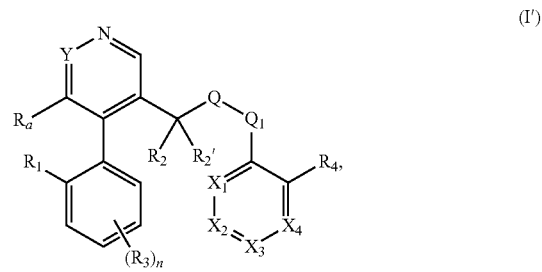

(I')

or a pharmaceutically acceptable salt, hydrate, solvate, stereoisomer, or tautomer thereof, wherein:
Q is C=(O), and $Q_1$ is $-NR_5-$;

or Q is —NR$_5$— or —O—, and Q$_1$ is —CH$_2$—;
or Q is —CH$_2$—, and Q$_1$ is —O(CH$_2$)$_{0-1}$— or —NR$_5$—;
or Q is —SO$_2$—, and Q$_1$ is —NR$_{5'}$—, —CH$_2$—, or O(CH$_2$)$_{0-1}$;

X$_1$ is CR$_6$ or N;
X$_2$ is CR$_7$ or N;
X$_3$ is CR$_8$ or N;
X$_4$ is CR$_9$ or N;
Y is CR$_b$ or N;
R$_a$ and R$_b$ are each independently H, (C$_1$-C$_6$) alkyl, (C$_1$-C$_6$) alkoxy, (C$_1$-C$_6$) haloalkyl, (C$_1$-C$_6$) haloalkoxy, or halogen; or
R$_1$ and R$_a$ together with the carbon atoms to which they are attached form a heterocycloalkyl;
R$_1$ is H, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O— heterocycloalkyl, wherein the alkyl, alkoxy, cycloalkyl, and heterocycloalkyl are optionally substituted with one or more substituents independently selected from halogen, (C$_1$-C$_4$) alkoxy, —OH, —NH$_2$, —NH(C$_1$-C$_4$) alkyl, and —N((C$_1$-C$_4$) alkyl)$_2$; or
R$_1$ and R$_3$, when on adjacent atoms, together with the carbon atoms to which they are attached form a heterocycloalkyl optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, and halogen;
R$_2$ is (C$_1$-C$_6$) alkyl, (C$_1$-C$_6$) alkoxy, (C$_1$-C$_6$) haloalkyl, or (C$_1$-C$_6$) haloalkoxy, and R$_{2'}$ is H, (C$_1$-C$_6$) alkyl, (C$_1$-C$_6$) alkoxy, (C$_1$-C$_6$) haloalkyl, or (C$_1$-C$_6$) haloalkoxy; or
R$_2$ and R$_{2'}$ together with the carbon atom to which they are attached form (C$_3$-C$_8$) cycloalkyl or heterocycloalkyl;
each R$_3$ is independently, at each occurrence, (C$_1$-C$_6$) alkyl, (C$_1$-C$_6$) alkoxy, (C$_1$-C$_6$) haloalkyl, (C$_1$-C$_6$) haloalkoxy, halogen, —S(O)$_p$(C$_1$-C$_6$) alkyl, (C$_3$-C$_8$) cycloalkyl, heterocycloalkyl, —O—(C$_3$-C$_8$) cycloalkyl, or —O-heterocycloalkyl, wherein the alkyl, alkoxy, cycloalkyl, and heterocycloalkyl are optionally substituted with one or more substituents independently selected from halogen, (C$_1$-C$_4$) alkoxy, —OH, —NH$_2$, —NH(C$_1$-C$_4$) alkyl, and —N((C$_1$-C$_4$) alkyl)$_2$; or
R$_1$ and R$_3$ together with the carbon atoms to which they are attached form a heterocycloalkyl optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, and halogen;
R$_4$ is H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_m$(C$_1$-C$_6$) alkyl, —NH(C$_1$-C$_4$) alkyl, or —N((C$_1$-C$_4$) alkyl)$_2$;
R$_5$ is H, (C$_1$-C$_6$) alkyl, —C(O)NR$_{10}$R$_{11}$, —C(O)(C$_1$-C$_6$) alkyl, or —C(O)O(C$_1$-C$_6$) alkyl;
each R$_6$ and R$_9$ is independently H, (C$_1$-C$_6$) alkyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, heterocycloalkyl, —OH, —NH$_2$, CN, —S(O)$_o$(C$_1$-C$_6$) alkyl, —NH(C$_1$-C$_4$) alkyl, or —N((C$_1$-C$_4$) alkyl)$_2$;
each R$_7$ and R$_8$ is independently H, (C$_1$-C$_8$) alkenyl, (C$_1$-C$_8$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, (C$_1$-C$_6$) aminoalkyl, halogen, (C$_3$-C$_8$) cycloalkyl, (C$_3$-C$_8$) cycloalkenyl, heterocycloalkyl, —OH, —NH$_2$, —S(O)$_q$NH$_2$, —S(O)$_q$OH, CN, or (C$_1$-C$_{18}$) alkyl, wherein 0 to 7 methylene of the (C$_1$-C$_{18}$) alkyl is optionally replaced by a moiety selected from the group consisting of —O—, —NR$_{13}$—, —S(O)$_q$—, —C(O)—, —C(CH$_2$)—, and —C(NH)—, provided that when any two methylene in the alkyl is replaced, then two —O—, two —S(O)$_q$—, or two —NR$_{13}$— and —O— and —NR$_{13}$— are not contiguous, wherein the alkyl is optionally substituted with one or more R$_{12}$, and wherein the cycloalkyl and cycloalkenyl are optionally substituted with one or more R$_{13}$;
R$_{10}$ and R$_{11}$ are each independently H or (C$_1$-C$_6$) alkyl optionally substituted with one or more substituent independently selected from —NH$_2$ and OH;
R$_{12}$ is D, —OH, halogen, —NH$_2$, —NH(C$_1$-C$_6$) alkyl, —N((C$_1$-C$_6$) alkyl)$_2$, —C(O)OH, —OC(O)(C$_1$-C$_6$) alkyl, (C$_3$-C$_8$) cycloalkyl, heterocycloalkyl, (C$_6$-C$_{10}$) aryl, heteroaryl, or R$_{17}$, wherein the cycloalkyl, heterocycloalkyl, aryl, and heteroaryl are optionally substituted with one or more substituents independently selected from —OH, —NH$_2$, —NH(C$_1$-C$_6$) alkyl, —N((C$_1$-C$_6$) alkyl)$_2$, halogen, and R$_{10}$;
R$_{13}$ is H, —OH, (C$_3$-C$_8$) cycloalkyl, heterocycloalkyl, (C$_6$-C$_{10}$) aryl, heteroaryl, or (C$_1$-C$_{12}$) alkyl, wherein 0 to 7 methylene of the (C$_1$-C$_{12}$) alkyl is optionally replaced by a moiety selected from the group consisting of —O—, —NR$_{13}$—, —S(O)$_r$—, —C(O)—, and —C(NH)—, provided that when any two methylene in the alkyl is replaced, then O and N are not contiguous and wherein the alkyl is optionally substituted with one or more R$_{15}$, and wherein the cycloalkyl, heterocycloalkyl, aryl, and heteroaryl are optionally substituted with one or more substituents independently selected from —OH, —C(O)OH, —NH$_2$, —NH(C$_1$-C$_6$) alkyl, and —N((C$_1$-C$_6$) alkyl)$_2$;
R$_{14}$ is (C$_3$-C$_8$) cycloalkyl, heterocycloalkyl, —O—(C$_3$-C$_8$) cycloalkyl, —O-heterocycloalkyl, (C$_1$-C$_{12}$) alkyl or (C$_2$-C$_{12}$) alkenyl, wherein 0 to 7 methylene of the (C$_1$-C$_{12}$) alkyl and the (C$_2$-C$_{12}$) alkenyl are optionally replaced by a moiety selected from the group consisting of —O—, —NR$_{13}$—, —S(O)$_r$—, —C(O)—, and —C(NH)—, provided that when any two methylene in the alkyl or alkenyl is replaced, then O and N are not contiguous and wherein the alkyl and alkenyl are optionally substituted with one or more R$_{15}$, and the cycloalkyl and heterocycloalkyl are optionally substituted with one or more R$_{16}$; or
when R$_{12}$ is cycloalkyl or heterocycloalkyl, two R$_{14}$ together with the atom to which they are attached form C=(O); or when R$_{12}$ is cycloalkyl or heterocycloalkyl, two R$_{14}$ together with the atoms to which they are attached form a (C$_3$-C$_8$) cycloalkyl or heterocycloalkyl optionally substituted with one or more R$_{13}$; or when R$_{12}$ is cycloalkyl or heterocycloalkyl, two R$_{14}$ together with the atom to which they are attached form a (C$_3$-C$_8$) spirocycloalkyl or a spiroheterocycloalkyl optionally substituted with one or more R$_{13}$; or when R$_{12}$ is cycloalkyl or heterocycloalkyl, two R$_{10}$ together with the atom to which they are attached form a $(C_6-C_{10})$ aryl or heteroaryl optionally substituted with one or more $R_{13}$;

$R_{15}$ is —OH, —NH$_2$, —NH(C$_1$-C$_6$) alkyl, —N((C$_1$-C$_6$) alkyl)$_2$, $(C_3-C_8)$ cycloalkyl, heterocycloalkyl, $(C_6-C_{10})$ aryl or heteroaryl, wherein the $(C_3-C_8)$ cycloalkyl and heterocycloalkyl are optionally substituted with one or more substituents independently selected from (C$_1$-C$_6$) hydroxyalkyl, (C$_1$-C$_6$) aminoalkyl, —C(O)OH, —OH, —NH$_2$, —NH(C$_1$-C$_6$) alkyl, —N((C$_1$-C$_6$) alkyl)$_2$, and oxo;

$R_{16}$ is —OH, —C(O)OH, —NH$_2$, —NH(C$_1$-C$_6$) alkyl, —N((C$_1$-C$_6$) alkyl)$_2$, (C$_1$-C$_6$) alkoxy, (C$_1$-C$_6$) hydroxyalkyl, $(C_3-C_8)$ cycloalkyl, heterocycloalkyl, —O—$(C_3-C_8)$ cycloalkyl, —O— heterocycloalkyl, $(C_6-C_{10})$ aryl or heteroaryl, wherein the $(C_3-C_8)$ cycloalkyl and heterocycloalkyl are optionally substituted with one or more substituents independently selected from (C$_1$-C$_6$) hydroxyalkyl, (C$_1$-C$_6$) aminoalkyl, —C(O)OH, —OH, —NH$_2$, —NH(C$_1$-C$_6$) alkyl, —N((C$_1$-C$_6$) alkyl)$_2$, and oxo;

$R_{17}$ is (C$_1$-C$_{18}$) alkyl or (C$_2$-C$_{18}$) alkenyl, wherein 0 to 8 methylene of the (C$_1$-C$_{18}$) alkyl and the (C$_2$-C$_{18}$) alkenyl are optionally replaced by a moiety selected from the group consisting of —O—, —NR$_{13}$—, —S(O)$_r$—, —C(O)—, and —C(NH)—, provided that when any two methylene in the alkyl or alkenyl is replaced, then O and N are not contiguous and wherein the alkyl and alkenyl are optionally substituted with one or more $R_{18}$;

$R_{18}$ is $R_{19}$, $(C_6-C_{10})$ aryl, or heteroaryl optionally substituted with one or more $R_{21}$;

$R_{19}$ is (C$_1$-C$_{18}$) alkyl wherein 0 to 8 methylene of the (C$_1$-C$_{18}$) alkyl is optionally replaced by a moiety selected from the group consisting of —O—, —NR$_{13}$—, —S(O)$_r$—, —C(O)—, and —C(NH)—, provided that when any two methylene in the alkyl or alkenyl is replaced, then O and N are not contiguous and wherein the alkyl is optionally substituted with one or more $R_{20}$;

$R_{20}$ is $(C_6-C_{10})$ aryl or heteroaryl optionally substituted with one or more $R_{21}$;

$R_{21}$ is H, (C$_1$-C$_6$) alkyl, (C$_1$-C$_6$) alkoxy, (C$_1$-C$_6$) haloalkyl, (C$_1$-C$_6$) haloalkoxy, or halogen; or two $R_{21}$ together when on adjacent atoms form a cycloalkyl or heterocycloalkyl optionally substituted with one or more $R_{22}$;

$R_{22}$ is —C(O)NH$_2$, —C(O)NH(C$_1$-C$_6$) alkyl, —C(O)N((C$_1$-C$_6$) alkyl)$_2$, —C(O) (C$_3$-C$_7$) cycloalkyl, or —C(O)heterocycloalkyl, wherein the cycloalkyl and heterocycloalkyl are optionally substituted with one or more substituents independently selected from —OH and CN;

each m, o, p, q, and r is independently, at each occurrence, 0, 1, or 2; and n is 0, 1, or 2.

2. A pharmaceutical composition comprising, a compound of claim 1, or a pharmaceutically acceptable salt, hydrate, solvate, stereoisomer, or tautomer thereof, and a pharmaceutically acceptable carrier.

3. A method of treating a disease or disorder associated with modulation of TGR5 or a side effect of chemotherapy or radiation treatment comprising, administering to a patient in need thereof an effective amount of a compound of claim 1, or a pharmaceutically acceptable salt, hydrate, solvate, stereoisomer, or tautomer thereof.

4. A method for reducing serum creatinine levels, delaying time to renal replacement therapy, reducing FGF23 levels, reducing the hyperphosphatemic effect of active vitamin D, attenuating hyperparathyroidism, reducing serum parathyroid hormone, improving endothelial dysfunction, reducing, vascular calcification, reducing urinary phosphorous, normalizing serum phosphorus levels, decreasing dietary phosphate uptake, reducing renal hypertrophy, or reducing heart hypertrophy, in a patient in need thereof; or reducing phosphate burden in an elderly patient in need thereof, comprising administering to the patient in need thereof or the elderly patient in need thereof an effective amount of a compound of claim 1, or a pharmaceutically acceptable salt, hydrate, solvate, stereoisomer, or tautomer thereof.

5. The compound of claim 1, or a pharmaceutically acceptable salt thereof.

6. The compound of claim 1, or a pharmaceutically acceptable salt, hydrate, solvate, stereoisomer, or tautomer thereof, wherein the compound is 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea.

7. The compound of claim 1, or a pharmaceutically acceptable salt, hydrate, stereoisomer, or tautomer thereof, wherein the compound is 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea.

8. The compound of claim 1, or a pharmaceutically acceptable salt or stereoisomer thereof, wherein the compound is 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea.

9. The compound of claim 1, or a pharmaceutically acceptable salt thereof, wherein the compound is 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea.

10. The pharmaceutical composition of claim 2 comprising 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea, or a pharmaceutically acceptable salt, hydrate, solvate, stereoisomer, or tautomer thereof, and a pharmaceutically acceptable carrier.

11. The pharmaceutical composition of claim 2 comprising 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea, or a pharmaceutically acceptable salt thereof, and a pharmaceutically acceptable carrier.

12. The pharmaceutical composition of claim 2 comprising 1-{4-[N-meth-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea, and a pharmaceutically acceptable carrier.

13. The method of claim 3 comprising administering to a patient in need thereof an effective amount of 1-{4-[N-methyl-4-chloro-3-({1-[4-(2-cyclopropoxyphenyl)pyridin-3-yl]cyclopropoxy}methyl)-benzenesulfonamido]butyl}-3-

[(2S,3R,4S,5R)-1,3,4,5,6-pentahydroxyhexan-2-yl]urea, or a pharmaceutically acceptable salt, hydrate, solvate, stereoisomer, or tautomer thereof.

14. The method of claim 3 comprising administering to a patient in need thereof an effective amount of 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea, or a pharmaceutically acceptable salt thereof.

15. The method of claim 14, wherein the disease or disorder associated with modulation of TGR5 or the side effect of chemotherapy or radiation treatment is diabetes.

16. The method of claim 14, wherein the disease or disorder associated with modulation of TGR5 or the side effect of chemotherapy or radiation treatment is Type II diabetes.

17. The method of claim 14, wherein the disease or disorder associated with modulation of TGR5 or the side effect of chemotherapy or radiation treatment is obesity.

18. The method of claim 14, wherein the disease or disorder associated with modulation of TGR5 or the side effect of chemotherapy or radiation treatment is fatty liver.

19. The method of claim 14, wherein the disease or disorder associated with modulation of TGR5 or the side effect of chemotherapy or radiation treatment is non-alcoholic fatty liver disease.

20. The method of claim 14, wherein the disease or disorder associated with modulation of TGR5 or the side effect of chemotherapy or radiation treatment is liver fibrosis.

21. The method of claim 14, wherein the disease or disorder associated with modulation of TGR5 or the side effect of chemotherapy or radiation treatment is non-alcoholic steatohepatitis.

22. The method of claim 3 comprising administering to a patient in need thereof an effective amount of 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea.

23. The method of claim 22, wherein the disease or disorder associated with modulation of TGR5 or the side effect of chemotherapy or radiation treatment is diabetes.

24. The method of claim 22, wherein the disease or disorder associated with modulation of TGR5 or the side effect of chemotherapy or radiation treatment is Type II diabetes.

25. The method of claim 22, wherein the disease or disorder associated with modulation of TGR5 or the side effect of chemotherapy or radiation treatment is obesity.

26. The method of claim 22, wherein the disease or disorder associated with modulation of TGR5 or the side effect of chemotherapy or radiation treatment is fatty liver.

27. The method of claim 22, wherein the disease or disorder associated with modulation of TGR5 or the side effect of chemotherapy or radiation treatment is non-alcoholic fatty liver disease.

28. The method of claim 22, wherein the disease or disorder associated with modulation of TGR5 or the side effect of chemotherapy or radiation treatment is liver fibrosis.

29. The method of claim 22, wherein the disease or disorder associated with modulation of TGR5 or the side effect of chemotherapy or radiation treatment is non-alcoholic steatohepatitis.

30. The method of claim 3, wherein the disease or disorder associated with modulation of TGR5 or the side effect of chemotherapy or radiation treatment is diabetes.

31. The method of claim 3, wherein the disease or disorder associated with modulation of TGR5 or the side effect of chemotherapy or radiation treatment is Type II diabetes.

32. The method of claim 3, wherein the disease or disorder associated with modulation of TGR5 or the side effect of chemotherapy or radiation treatment is obesity.

33. The method of claim 3, wherein the disease or disorder associated with modulation of TGR5 or the side effect of chemotherapy or radiation treatment is fatty liver.

34. The method of claim 3, wherein the disease or disorder associated with modulation of TGR5 or the side effect of chemotherapy or radiation treatment is non-alcoholic fatty liver disease.

35. The method of claim 3, wherein the disease or disorder associated with modulation of TGR5 or the side effect of chemotherapy or radiation treatment is liver fibrosis.

36. The method of claim 3, wherein the disease or disorder associated with modulation of TGR5 or the side effect of chemotherapy or radiation treatment is non-alcoholic steatohepatitis.

37. The method of claim 3, wherein the disease or disorder associated with modulation or activation of TGR5 or the side effect of chemotherapy or radiation treatment is chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia, hyperlipidemia, lipid disorder, low HDL cholesterol, high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease, psoriasis, ulcerative colitis, Crohn's disease, disorder associated with parenteral nutrition, small bowel syndrome, irritable bowel syndrome, allergy diseases, fatty liver, non-alcoholic fatty liver disease, liver fibrosis, non-alcoholic steatohepatitis, primary sclerosing cholangitis, liver cirrhosis, primary biliary cirrhosis, kidney fibrosis, anorexia nervosa, bulimia nervosa, neurological disorder, Alzheimer's disease, multiple sclerosis, schizophrenia, impaired cognition, postprandial hyperphosphatemia, renal disease, chronic kidney disease, end-stage renal disease, proteinuria, stomach and bowel-related disorder, ulcer, digestion disorder, malabsorption syndrome, short-gut syndrome, cul-de-sac syndrome, inflammatory bowel disease, celiac sprue, gluten induced enteropathy, celiac disease, tropical spree, hypogammaglobulinemic spree, enteritis, regional enteritis, small intestine damage, short bowel syndrome, radiation enteritis, infectious or post-infectious enteritis, bone marrow transplant induced enteritis, small intestinal damage due to toxic or other chemotherapeutic agents, diarrhea, abdominal cramping, vomiting, structural or functional damage of the intestinal epithelium resulting from chemotherapy treatment, diarrhea induced by an immune checkpoint inhibitor, dismotility, Parkinson's gut, cystic fibrosis gut, intestinal motility, or Gastroparesis.

38. The method of claim 14, wherein the disease or disorder associated with modulation or activation of TGR5 or the side effect of chemotherapy or radiation treatment is chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia, hyperlipidemia, lipid disorder, low HDL cholesterol, high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease, psoriasis, ulcerative colitis, Crohn's disease, disorder associated with parenteral nutrition, small bowel syndrome, irritable bowel syndrome, allergy diseases, fatty liver, non-alcoholic fatty liver disease, liver fibrosis, non-alcoholic steatohepatitis, primary sclerosing cholangitis, liver cirrhosis, primary biliary cirrhosis, kidney fibrosis, anorexia nervosa, bulimia nervosa, neurological disorder, Alzheimer's disease, multiple sclerosis, schizophrenia, impaired cognition, postprandial hyperphosphatemia, renal disease, chronic kidney disease, end-stage renal disease, proteinuria, stomach and bowel-related disorder, ulcer, digestion disorder, malabsorption syndrome, short-gut syndrome, cul-de-sac syndrome, inflammatory bowel disease, celiac sprue, gluten induced enteropathy, celiac disease, tropical spree, hypogammaglobulinemic spree, enteritis, regional enteritis, small intestine damage, short bowel syndrome, radiation enteritis, infectious or post-infectious enteritis, bone marrow transplant induced enteritis, small intestinal damage due to toxic or other chemotherapeutic agents, diarrhea, abdominal cramping, vomiting, structural or functional damage of the intestinal epithelium resulting from chemotherapy treatment, diarrhea induced by an immune checkpoint inhibitor, dismotility, Parkinson's gut, cystic fibrosis gut, intestinal motility, or Gastroparesis.

39. The method of claim 22, wherein the disease or disorder associated with modulation or activation of TGR5 or the side effect of chemotherapy or radiation treatment is chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia, hyperlipidemia, lipid disorder, low HDL cholesterol, high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease, psoriasis, ulcerative colitis, Crohn's disease, disorder associated with parenteral nutrition, small bowel syndrome, irritable bowel syndrome, allergy diseases, fatty liver, non-alcoholic fatty liver disease, liver fibrosis, non-alcoholic steatohepatitis, primary sclerosing cholangitis, liver cirrhosis, primary biliary cirrhosis, kidney fibrosis, anorexia nervosa, bulimia nervosa, neurological disorder, Alzheimer's disease, multiple sclerosis, schizophrenia, impaired cognition, postprandial hyperphosphatemia, renal disease, chronic kidney disease, end-stage renal disease, proteinuria, stomach and bowel-related disorder, ulcer, digestion disorder, malabsorption syndrome, short-gut syndrome, cul-de-sac syndrome, inflammatory bowel disease, celiac sprue, gluten induced enteropathy, celiac disease, tropical spree, hypogammaglobulinemic spree, enteritis, regional enteritis, small intestine damage, short bowel syndrome, radiation enteritis, infectious or post-infectious enteritis, bone marrow transplant induced enteritis, small intestinal damage due to toxic or other chemotherapeutic agents, diarrhea, abdominal cramping, vomiting, structural or functional damage of the intestinal epithelium resulting from chemotherapy treatment, diarrhea induced by an immune checkpoint inhibitor, dismotility, Parkinson's gut, cystic fibrosis gut, intestinal motility, or Gastroparesis.

40. The method of claim 3, wherein the disease or disorder associated with modulation or activation of TGR5 or the side effect of chemotherapy or radiation treatment is acute inflammation; alopecia areata; ankylosing spondylitis; atopy; autism spectrum disorder; chronic alcoholism; chronic constipation; chronic constipation occurring in cystic fibrosis; chronic fatigue syndrome; chronic idiopathic constipation; chronic inflammation; chronic intestinal pseudo-obstruction; cirrhosis; colonic pseudo-obstruction; congestive heart failure; constipation associated with neuropathic, metabolic or endocrine disorder; constipation associated with the use of a therapeutic agent; constipation due to the use of drugs selected from analgesics, antihypertensive, anticonvulsants, antidepressants, antispasmodics, and antipsychotics; constipation induced by calcium supplement; cystic fibrosis; diabetic kidney disease; fibromyalgia; food allergy; functional constipation; gastric ulcer; gastrointestinal disease; gastrointestinal tract disorder associated with chronic kidney disease; heart disease; heart failure; hepatic encephalopathy; idiopathic constipation; infectious diarrhea; kidney disease; leaky gut syndrome; liver disease; lupus; microscopic colitis; necrotizing enterocolitis; obesity-induced metabolic disease; opioid-induced constipation; polymyalgia rheumatica; portal hypertension; post-surgical constipation; primary biliary cholangitis; Raynaud's syndrome; Sjogren's syndrome; slow transit constipation; small intestinal bacterial overgrowth; steatosis; thyroiditis; Type 1 diabetes; urticaria; vasculitis; or vitiligo.

41. The method of claim 14, wherein the disease or disorder associated with modulation or activation of TGR5 or the side effect of chemotherapy or radiation treatment is acute inflammation; alopecia areata; ankylosing spondylitis; atopy; autism spectrum disorder; chronic alcoholism; chronic constipation; chronic constipation occurring in cystic fibrosis; chronic fatigue syndrome; chronic idiopathic constipation; chronic inflammation; chronic intestinal pseudo-obstruction; cirrhosis; colonic pseudo-obstruction; congestive heart failure; constipation associated with neuropathic, metabolic or endocrine disorder; constipation associated with the use of a therapeutic agent; constipation due to the use of drugs selected from analgesics, antihypertensive, anticonvulsants, antidepressants, antispasmodics, and antipsychotics; constipation induced by calcium supplement; cystic fibrosis; diabetic kidney disease; fibromyalgia; food allergy; functional constipation; gastric ulcer; gastrointestinal disease; gastrointestinal tract disorder associated with chronic kidney disease; heart disease; heart failure; hepatic encephalopathy; idiopathic constipation; infectious diarrhea; kidney disease; leaky gut syndrome; liver disease; lupus; microscopic colitis; necrotizing enterocolitis; obesity-induced metabolic disease; opioid-induced constipation; polymyalgia rheumatica; portal hypertension; post-surgical constipation; primary biliary cholangitis; Raynaud's syndrome; Sjogren's syndrome; slow transit constipation; small intestinal bacterial overgrowth; steatosis; thyroiditis; Type 1 diabetes; urticaria; vasculitis; or vitiligo.

42. The method of claim 22, wherein the disease or disorder associated with modulation or activation of TGR5 or the side effect of chemotherapy or radiation treatment is acute inflammation; alopecia areata; ankylosing spondylitis; atopy; autism spectrum disorder; chronic alcoholism; chronic constipation; chronic constipation occurring in cystic fibrosis; chronic fatigue syndrome; chronic idiopathic constipation; chronic inflammation; chronic intestinal pseudo-obstruction; cirrhosis; colonic pseudo-obstruction; congestive heart failure; constipation associated with neuropathic, metabolic or endocrine disorder; constipation associated with the use of a therapeutic agent; constipation due to the use of drugs selected from analgesics, antihypertensive, anticonvulsants, antidepressants, antispasmodics, and antipsychotics; constipation induced by calcium supplement; cystic fibrosis; diabetic kidney disease; fibromyalgia; food allergy; functional constipation; gastric ulcer; gastrointestinal disease; gastrointestinal tract disorder associated with chronic kidney disease; heart disease; heart failure; hepatic encephalopathy; idiopathic constipation; infectious diarrhea; kidney disease; leaky gut syndrome; liver disease; lupus; microscopic colitis; necrotizing enterocolitis; obesity-induced metabolic disease; opioid-induced constipation; polymyalgia rheumatica; portal hypertension; post-surgical constipation; primary biliary cholangitis; Raynaud's syndrome; Sjogren's syndrome; slow transit constipation; small intestinal bacterial overgrowth; steatosis; thyroiditis; Type 1 diabetes; urticaria; vasculitis; or vitiligo.

43. A method of preventing a disease or disorder associated with modulation of TGR5 or a side effect of chemotherapy or radiation treatment comprising, administering to a patient in need thereof an effective amount of a compound of claim 1, or a pharmaceutically acceptable salt, hydrate, solvate, stereoisomer, or tautomer thereof.

44. The method of claim 43, wherein the disease or disorder associated with modulation or activation of TGR5 or the side effect of chemotherapy or radiation treatment is chemotherapy-induced diarrhea, diabetes, Type II diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia, hyperlipidemia, lipid disorder, low HDL cholesterol, high LDL cholesterol, high blood pressure, angina pectoris, coronary artery disease, atherosclerosis, cardiac hypertrophy, hyperphosphatemia, rheumatoid arthritis, asthma, chronic obstructive pulmonary disease, psoriasis, ulcerative colitis, Crohn's disease, disorder associated with parenteral nutrition, small bowel syndrome, irritable bowel syndrome, allergy diseases, fatty liver, non-alcoholic fatty liver disease, liver fibrosis, non-alcoholic steatohepatitis, primary sclerosing cholangitis, liver cirrhosis, primary biliary cirrhosis, kidney fibrosis, anorexia nervosa, bulimia nervosa, neurological disorder, Alzheimer's disease, multiple sclerosis, schizophrenia, impaired cognition, postprandial hyperphatemia, renal disease, chronic kidney disease, end-stage renal disease, proteinuria, stomach and bowel-related disorder, ulcer, digestion disorder, malabsorption syndrome, short-gut syndrome, cul-de-sac syndrome, inflammatory bowel disease, celiac sprue, gluten induced enteropathy, celiac disease, tropical spree, hypogammaglobulinemic spree, enteritis, regional enteritis, small intestine damage, short bowel syndrome, radiation enteritis, infectious or post-infectious enteritis, bone marrow transplant induced enteritis, small intestinal damage due to toxic or other chemotherapeutic agents, diarrhea, abdominal cramping, vomiting, structural or functional damage of the intestinal epithelium resulting from chemotherapy treatment, diarrhea induced by an immune checkpoint inhibitor, dismotility, Parkinson's gut, cystic fibrosis gut, intestinal motility, or Gastroparesis.

45. The method of claim 43, wherein the disease or disorder associated with modulation or activation of TGR5 or the side effect of chemotherapy or radiation treatment is acute inflammation; alopecia areata; ankylosing spondylitis; atopy; autism spectrum disorder; chronic alcoholism; chronic constipation; chronic constipation occurring in cystic fibrosis; chronic fatigue syndrome; chronic idiopathic constipation; chronic inflammation; chronic intestinal pseudo-obstruction; cirrhosis; colonic pseudo-obstruction; congestive heart failure; constipation associated with neuropathic, metabolic or endocrine disorder; constipation associated with the use of a therapeutic agent; constipation due to the use of drugs selected from analgesics, antihypertensive, anticonvulsants, antidepressants, antispasmodics, and antipsychotics; constipation induced by calcium supplement; cystic fibrosis; diabetic kidney disease; fibromyalgia; food allergy; functional constipation; gastric ulcer; gastrointestinal disease; gastrointestinal tract disorder associated with chronic kidney disease; heart disease; heart failure; hepatic encephalopathy; idiopathic constipation; infectious diarrhea; kidney disease; leaky gut syndrome; liver disease; lupus; microscopic colitis; necrotizing enterocolitis; obesity-induced metabolic disease; opioid-induced constipation; polymyalgia rheumatica; portal hypertension; post-surgical constipation; primary biliary cholangitis; Raynaud's syndrome; Sjogren's syndrome; slow transit constipation; small intestinal bacterial overgrowth; steatosis; thyroiditis; Type 1 diabetes; urticaria; vasculitis; or vitiligo.

46. The compound of claim 1, or a pharmaceutically acceptable salt thereof, wherein the compound is 1-{2-[2-({4-chloro-3-[(1-{4-[2-(oxetan-3-yloxy)phenyl]pyridin-3-yl}cyclopropoxy)methyl]phenyl}sulfanyl)ethoxy]ethyl}-3-[(2S,3R,4R,5R)-2,3,4,5,6-pentahydroxyhexyl]urea.

47. The compound of claim 1, or a pharmaceutically acceptable salt thereof, wherein the compound is 4-[(4-{2,5-dichloro-4-[({1-[4-(2-cyclopropoxyphenyl)pyridin-3-yl]cyclopropyl}amino)methyl]phenyl}butyl) [(2S,3R,4R,5R)-2,3,4,5,6-pentahydroxyhexyl]carbamoyl]butanoic acid.

48. The compound of claim 1, or a pharmaceutically acceptable salt thereof, wherein the compound is 5-[2,5-dichloro-4-({1-[4-(2-cyclopropoxyphenyl)pyridin-3-yl]cyclopropoxy}methyl)phenyl]-1-{4-[(2S,3R,4S,5R)-2,3,4,5,6-pentahydroxyhexyl]piperazin-1-yl}pentan-1-one.

49. The compound of claim 1, or a pharmaceutically acceptable salt thereof, wherein the compound is 5-[2,5-dichloro-4-({1-[4-(2-cyclopropoxyphenyl)pyridin-3-yl]cyclopropoxy}methyl)phenyl]-N-(2,3-dihydroxypropyl)-N-[(2S,3R,4R,5R)-2,3,4,5,6-pentahydroxyhexyl]pentanamide.

50. The compound of claim 1, or a pharmaceutically acceptable salt thereof, wherein the compound is N-({5-[(2S)-6-aminohexan-2-yl]-2-chlorophenyl}methyl)-1-[4-(2-cyclopropoxyphenyl)pyridin-3-yl]cyclopropan-1-amine.

51. The compound of claim 1, or a pharmaceutically acceptable salt thereof, wherein the compound is (5S)-5-{4-chloro-3-[({1-[4-(2-cyclopropoxyphenyl)pyridin-3-yl]cyclopropyl}amino)methyl]phenyl}-hexanoic acid.

52. The compound of claim 1, or a pharmaceutically acceptable salt thereof, wherein the compound is 4-(4-chloro-3-((1-(4-(2-cyclopropoxyphenyl)pyridin-3-yl)cyclopropoxy)methyl)phenethyl)-N-((2S,3R,4R,5R)-2,3,4,5,6-pentahydroxyhexyl)benzamide.

53. The compound of claim 1, or a pharmaceutically acceptable salt thereof, wherein the compound is 4-chloro-3-((1-(4-(2-cyclopropoxyphenyl)pyridin-3-yl)cyclopropoxy)methyl)N,N-dimethylbenzamide.

54. The compound of claim 1, or a pharmaceutically acceptable salt thereof, wherein the compound is 6-((4-chloro-3-((1-(4-(2-cyclopropoxyphenyl)pyridin-3-yl)cyclopropoxy)methyl)phenyl) sulfonyl)-5,6,7,8-tetrahydro-1,6-naphthyridin-2-ol.

* * * * *

UNITED STATES PATENT AND TRADEMARK OFFICE
CERTIFICATE OF CORRECTION

| | | |
|---|---|---|
| PATENT NO. | : 12,084,472 B2 | |
| APPLICATION NO. | : 17/185653 | |
| DATED | : September 10, 2024 | |
| INVENTOR(S) | : Jason G. Lewis et al. | |

It is certified that error appears in the above-identified patent and that said Letters Patent is hereby corrected as shown below:

In the Claims

Column 803, Line 32, Claim 1 should read:
-- or $(C_1-C_6)$ haloalkoxy, and $R_{2'}$ is H, $(C_1-C_6)$ alkyl, --

Column 806, Lines 59-62, Claim 12 should read:
12. The pharmaceutical composition of claim 2 comprising 1-{4-[N-methyl-4-chloro-3-({1-[4-(2-cyclopropoxyphenyl)pyridin-3-yl]cyclopropoxy}methyl)-benzenesulfonamido]butyl}-3-[(2S,3R,4S,5R)-1,3,4,5,6-pentahydroxyhexan-2-yl]urea, and a pharmaceutically acceptable carrier.

Column 808, Lines 49-50, Claim 37 should read:
-- tropical sprue, hypogammaglobulinemic sprue, --

Column 809, Lines 20-21, Claim 38 should read:
-- tropical sprue, hypogammaglobulinemic sprue, --

Column 809, Lines 57-58, Claim 39 should read:
-- tropical sprue, hypogammaglobulinemic sprue, --

Column 811, Lines 50-51, Claim 44 should read:
-- tropical sprue, hypogammaglobulinemic sprue, --

Signed and Sealed this
Eighth Day of October, 2024

*Katherine Kelly Vidal*

Katherine Kelly Vidal
*Director of the United States Patent and Trademark Office*